US009815851B2

(12) United States Patent
Steeneck et al.

(10) Patent No.: US 9,815,851 B2
(45) Date of Patent: Nov. 14, 2017

(54) PYRROLO CARBOXAMIDES AS MODULATORS OF ORPHAN NUCLEAR RECEPTOR RAR-RELATED ORPHAN RECEPTOR-GAMMA (RORγ, NR1F3) ACTIVITY AND FOR THE TREATMENT OF CHRONIC INFLAMMATORY AND AUTOIMMUNE DISEASES

(71) Applicant: PHENEX PHARMACEUTICALS AG, Ludwigshafen (DE)

(72) Inventors: Christoph Steeneck, Dossenheim (DE); Olaf Kinzel, Heidelberg (DE); Christian Gege, Ehingen (DE); Gerald Kleymann, Bad Salzuflen (DE); Thomas Hoffmann, Viernheim (DE)

(73) Assignee: Phenex Pharmaceuticals AG, Ludwigshafen (DE)

( * ) Notice: Subject to any disclaimer, the term of this patent is extended or adjusted under 35 U.S.C. 154(b) by 216 days.

(21) Appl. No.: 14/359,278

(22) PCT Filed: Dec. 3, 2012

(86) PCT No.: PCT/EP2012/004977
§ 371 (c)(1),
(2) Date: May 19, 2014

(87) PCT Pub. No.: WO2013/079223
PCT Pub. Date: Jun. 6, 2013

(65) Prior Publication Data

US 2014/0349987 A1 Nov. 27, 2014

Related U.S. Application Data

(60) Provisional application No. 61/566,055, filed on Dec. 2, 2011.

(30) Foreign Application Priority Data

Dec. 2, 2011 (EP) .................................... 11009556

(51) Int. Cl.

| | |
|---|---|
| *C07D 207/34* | (2006.01) |
| *C07D 401/06* | (2006.01) |
| *C07D 513/10* | (2006.01) |
| *C07D 401/14* | (2006.01) |
| *C07D 405/14* | (2006.01) |
| *C07D 311/96* | (2006.01) |
| *C07D 403/06* | (2006.01) |
| *C07D 405/04* | (2006.01) |
| *C07D 405/12* | (2006.01) |
| *C07D 409/12* | (2006.01) |
| *C07D 409/14* | (2006.01) |

(Continued)

(52) U.S. Cl.
CPC ....... *C07D 513/10* (2013.01); *C07D 207/337* (2013.01); *C07D 207/34* (2013.01); *C07D 261/20* (2013.01); *C07D 311/96* (2013.01); *C07D 401/04* (2013.01); *C07D 401/06* (2013.01); *C07D 401/14* (2013.01); *C07D 403/04* (2013.01); *C07D 403/06* (2013.01); *C07D 405/04* (2013.01); *C07D 405/12* (2013.01); *C07D 405/14* (2013.01); *C07D 409/12* (2013.01); *C07D 409/14* (2013.01); *C07D 413/04* (2013.01); *C07D 413/12* (2013.01); *C07D 471/04* (2013.01); *C07D 498/20* (2013.01)

(58) Field of Classification Search
CPC .......................... C07D 207/337; C07D 401/04
See application file for complete search history.

(56) References Cited

U.S. PATENT DOCUMENTS

2009/0036421 A1 2/2009 Seo et al.
2012/0322837 A1 12/2012 Maeba et al.

FOREIGN PATENT DOCUMENTS

WO WO 2004/060870 A1 7/2004
WO WO 2004/060888 A1 7/2004

(Continued)

OTHER PUBLICATIONS

List of Inflammatory disease [online]. retrieved from the internet on Apr. 14, 2017. URL; http://www.progestonetherapy.com/list-of-inflammatory-diseases.html.*

(Continued)

*Primary Examiner* — Shawquia Jackson
(74) *Attorney, Agent, or Firm* — Seed IP Law Group LLP

(57) ABSTRACT

The invention provides modulators for the orphan nuclear receptor $ROR_\gamma$ and methods for treating $ROR_\gamma$ mediated diseases by administrating these novel $ROR_\gamma$ modulators to a human or a mammal in need thereof. Specifically, the present invention provides pyrrolo carboxamide compounds of Formula (1) and the enantiomers, diastereomers, N-oxides, tautomers, solvates and pharmaceutically acceptable salts thereof.

(1)

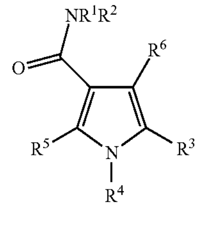

22 Claims, No Drawings

(51) Int. Cl.

| | |
|---|---|
| *C07D 413/04* | (2006.01) |
| *C07D 261/20* | (2006.01) |
| *C07D 207/337* | (2006.01) |
| *C07D 498/20* | (2006.01) |
| *C07D 401/04* | (2006.01) |
| *C07D 403/04* | (2006.01) |
| *C07D 413/12* | (2006.01) |
| *C07D 471/04* | (2006.01) |

(56) References Cited

FOREIGN PATENT DOCUMENTS

| | | |
|---|---|---|
| WO | WO 2004/103968 A1 | 12/2004 |
| WO | WO 2005/108393 A1 | 11/2005 |
| WO | WO 2006/012642 A2 | 2/2006 |
| WO | WO 2007/097276 A1 | 8/2007 |
| WO | WO 2010/049144 A2 | 5/2010 |
| WO | WO 2011/042477 A1 | 4/2011 |
| WO | WO 2011/071996 A1 | 6/2011 |
| WO | WO 2011/107248 A1 | 9/2011 |
| WO | WO 2011/112263 A1 | 9/2011 |
| WO | WO 2011/112264 A1 | 9/2011 |
| WO | WO 2011/115892 A1 | 9/2011 |
| WO | WO 2012/027965 A1 | 3/2012 |
| WO | WO 2012/028100 A1 | 3/2012 |
| WO | WO 2012/064744 A2 | 5/2012 |
| WO | WO 2012/100732 A1 | 8/2012 |
| WO | WO 2012/100734 A1 | 8/2012 |
| WO | WO 2012/106995 A1 | 8/2012 |
| WO | WO 2012/139775 A1 | 10/2012 |
| WO | WO 2012/144661 A1 | 10/2012 |
| WO | WO 2012/147916 A1 | 11/2012 |
| WO | WO 2012/158784 A2 | 11/2012 |

OTHER PUBLICATIONS

André et al., "A novel isoform of the orphan nuclear receptor RORβ is specifically expressed in pineal gland and retina," *Gene* 216: 277-283, 1998.

André et al., "Disruption of retinoid-related orphan receptor β changes circadian behavior, causes retinal degeneration and leads to *vacillans* phenotype in mice," *The EMBO Journal* 17(14): 3867-3877, 1998.

Awasthi et al., "$T_h$17 cells: from precursors to players in inflammation and infection," *International Immunology* 21(5): 489-498, 2009.

Becker-André et al., "Identification of Nuclear Receptor mRNAs by RT-PCR Amplification of Conserved Zinc-Finger Motif Sequences," *Biochemical and Biophysical Research Communications* 194(3): 1371-1379, Aug. 16, 1993.

Crome et al., "Translational Mini-Review Series on Th17 Cells: Function and regulation of human T helper 17 cells in health and disease," *Clinical and Experimental Immunology* 159: 109-119, 2009.

Dyer et al., "A Noncommercial Dual Liciferase Enzyme Assay System for Reporter Gene Analysis," *Analytical Biochemistry* 282: 158-161, 2000.

Eberl et al., "The role of the nuclear hormone receptor RORγt in the development of lymph nodes and Peyer's patches," *Immunological Reviews* 195: 81-90, 2003.

Eberl et al., "Thymic Origin of Intestinal αβ T Cells Revealed by Fate Mapping of RORγt$^{+\ Cells}$," *Science* 305: 248-251, Jul. 9, 2004.

Evans, "The Steroid and Thyroid Hormone Receptor Superfamily," *Science* 240: 889-895, May 13, 1988.

Giguère et al., "The Orphan Nuclear Receptor RORα (RORA) Maps to a Conserved Region of Homology on Human Chromosome 15q21-q22 and Mouse Chromosome 9," *Genomics* 28: 596-598, 1995.

Gu et al., "Interleukin 10 suppresses Th17 cytokines secreted by macrophages and T cells," *Eur. J. Immunol* 38: 1807-1813, 2008.

Hamilton et al., "Disruption of the nuclear hormone receptor RORα in *staggerer* mice," *Nature* 379: 736-739, Feb. 22, 1996.

He et al., "RORγt, a Novel Isoform of an Orphan Receptor, Negatively Regulates Fas Ligand Expression and IL-2 Production in T Cells," *Immunity* 9: 797-806, Dec. 1998.

He et al., "Down-Regulation of the Orphan Nuclear Receptor RORγt Is Essential for T Lymphocyte Maturation," *The Journal of Immunology* 164: 5668-5674, 2000.

Houck et al., "T0901317 is a dual LXR/FXR agonist," *Molecular Genetics and Metabolism* 83: 184-187, 2004.

Ivanov et al., "The Orphan Nuclear Receptor RORγt Directs the Differentiation Program of Proinflammatory IL-17$^{+}$ T Helper Cells," *Cell* 126: 1121-1133, Sep. 22, 2006.

Kallen et al., "X-Ray Structure of the hRORα LBD at 1.63 Å: Structural and Functional Data that Cholesterol or a Cholesterol Derivative Is the Natural Ligand of RORα," *Structure* 10: 1697-1707, Dec. 2002.

Kumar et al., "The Benzenesulfoamide T0901317 [N-(2,2,2-Trifluoroethyl)-N-[4[2,2,2-trifluoro-1-hydroxy-1-(trifluoromethyl)ethyl]phenyl]-benzenesulfonamide] Is a Novel Retinoic Acid Receptor-Related Orphan Receptor-α/γ Inverse Agonist," *Molecular Pharmacology* 77(2): 228-236, 2010.

Lau et al., "The Orphan Nuclear Receptor, RORα, Regulates Gene Expression That Controls Lipid Metabolism," *Journal of Biological Chemistry* 283(26): 18411-18421, Jun. 27, 2008.

Li et al., "A Synthesis of N-Bridged 5,6-Bicylic Pyridines via a Mild Cyclodehydration Using the Burgess Reagent and Discovery of a Novel Carbamylsulfonylation Reaction," *Organic Letters* 10(13): 2897-2900, 2008.

Mangelsdorf et al., "The Nuclear Receptor Superfamily: The Second Decade," *Cell* 83: 835-839, Dec. 15, 1995.

McKenna et al., "Nuclear Receptor Coregulators: Cellular and Molecular Biology," *Endocrine Reviews* 20(3): 321-344, 1999.

Missbach et al., "Thiazolidine Diones, Specific Ligands of the Nuclear Receptor Retinoid Z Receptor/Retinoid Acid Receptor-related Orphan Receptor α with Potent Antiarthritic Activity," *The Journal of Biological Chemistry* 271(23): 13515-13522, Jun. 7, 1996.

Murphy et al., "Meta Halogenation of 1,3-Disubstituted Arenes via Iridium-Catalyzed Arene Borylation," *J. Am. Chem. Soc.* 129: 15434-15435, 2007.

Stehlin-Gaon et al., "All-trans retinoic acid is a ligand for the orphan nuclear receptor RORβ," *Nature Structural Biology* 10(10): 820-825, Oct. 2003.

Sun et al., "Requirement for RORγ in Thymocyte Survival and Lymphoid Organ Development," *Science* 288: 2369-2373, Jun. 30, 2000.

Tesmer et al., "Th17 cells in human disease," *Immunological Reviews* 223: 87-113, 2008.

Tilley et al., "Retinoid-Related Orphan Receptor γ Controls Immunoglobulin Production and Th1/Th2 Cytokine Balance in the Adaptive Immune Response to Allergen," *The Journal of Immunology* 178: 3208-3218, 2007.

Vanacker et al., "Transcriptional Activities of the Orphan Nuclear Receptor ERRα (Estrogen Receptor-Related Receptor-α)," *Molecular Endocrinology* 13: 764-773, 1999.

Villey et al., "RORγT, a thymus-specific isoform of the orphan nuclear receptor RORγ/TOR, is up-regulated by signaling through the pre-T cell receptor and binds to the TEA promoter," *Eur. J. Immunol.* 29: 4072-4080, 1999.

Wang et al., "Modulation of Retinoic Acid Receptor-related Orphan Receptor α and γ Activity by 7-Oxygenated Sterol Ligands," *Journal of Biological Chemistry* 285(7): 5013-5025, Feb. 12, 2010.

Wiesenberg et al., "Transcriptional activation of the nuclear receptor RZRα by the pineal gland hormone melatonin and identification of CGP 52608 as a synthetic ligand," *Nucleic Acids Research* 23(3): 327-333, 1995.

Wilson et al., "The Orphan Receptors NGFI-B and Steroidogenic Factor 1 Establish Monomer Binding as a Third Paradigm of Nuclear Receptor-DNA Interaction," *Molecular and Cellular Biology* 13(9): 5794-5804, Sep. 1993.

(56) References Cited

OTHER PUBLICATIONS

Xue et al., "Crystal structure of the PXR-T1317 complex provides a scaffold to examine the potential for receptor antagonism," *Bioorg. Med. Chem.* (2007), doi:10.1016/j.bmc.2006.12.026 (11 pages).
Zhou et al., "Transcriptional regulatory networks in Th17 cell differentiation," *Curr Opin Immunol.* 21(2): 146-152, Apr. 2009.
Translation of Official Action from Patent Office of Japan, dated Jun. 30, 2015, for Patent Application No. 2014-543807, 6 pages.

* cited by examiner

PYRROLO CARBOXAMIDES AS MODULATORS OF ORPHAN NUCLEAR RECEPTOR RAR-RELATED ORPHAN RECEPTOR-GAMMA (RORγ, NR1F3) ACTIVITY AND FOR THE TREATMENT OF CHRONIC INFLAMMATORY AND AUTOIMMUNE DISEASES

CROSS-REFERENCE TO RELATED APPLICATIONS

This application is a U.S. National Phase Application of International Application No. PCT/EP2012/004977, filed Dec. 3, 2012, which claims priority to U.S. Provisional Application No. 61/566,055, filed Dec. 2, 2011, and European Patent Application No. 11009556.9, filed Dec. 2, 2011.

The invention provides pyrrolo carboxamide compounds as modulators for the orphan nuclear receptor RORγ and methods for treating RORγ mediated chronic inflammatory and autoimmune diseases by administrating these novel RORγ modulators to a human or a mammal in need thereof.

The retinoid-receptor related orphan receptors consist of three family members, namely RORα (Beckerandre et al., *Biochem. Biophys. Res. Commun.* 1993, 194:1371), RORβ (Andre et al., *Gene* 1998, 516:277) and RORγ (He et al., *Immunity* 1998, 9:797) and constitute the NR1F (ROR/RZR) subgroup of the nuclear receptor superfamily (Mangelsdorf et al., *Cell* 1995, 83:835).

The nuclear receptor superfamily shares common modular structural domains consisting of a hypervariable N-terminal domain, a conserved DNA binding domain (DBD), a hinge region and a conserved ligand-binding domain (LBD). The DBD targets the receptor to specific DNA sequences (nuclear hormone response elements or NREs) and the LBD functions in the recognition of endogenous or exogenous chemical ligands. A constitutive transcriptional activation domain is found at the N-terminus (AF1) and a ligand regulated transcriptional activation domain is embedded within the C-terminal LBD of typical NRs. The nuclear receptors can exist in a transcriptional activating or repressing state when bound to their target NREs. The basic mechanism of gene activation involves ligand dependent exchange of co-regulatory proteins, namely co-activators and co-repressors (McKenna et al., *Endocrine Rev.* 1999, 20:321). A NR in the repressing state is bound to its DNA recognition element and is associated with co-repressor proteins that recruit histone-deacetylases (HDACs). In the presence of an agonist, co-repressors are exchanged for coactivators that recruit transcription factors, which contribute to assembling of a chromatin-remodelling complex, which relieves transcriptional repression and stimulates transcriptional initiation via histone acetylation. The AF-2 domain of the LBD acts as a ligand dependant molecular switch presenting interaction surfaces for co-repressor or co-activator proteins and providing with a conserved mechanism for gene activation or repression that is shared by the members of the nuclear receptor superfamily.

The members of the NR1F family of nuclear receptors (such as RORγ) have been considered to be constitutively active transcription factors in the absence of known ligands, which is similar to the estrogen-related receptor alpha (Vanacker et al., *Mol. Endocrinol.* 1999, 13:764). Most recently, 7-oxygenated oxysterols were identified to be high affinity ligands for RORα and RORγ (Wang et al., *J. Biol. Chem.* 2010, 285:5013). 7-Hydroxycholesterol is a key metabolite during the conversion of cholesterol into bile acids, but to date it is not clear whether it is a true endogenous ligand for the RORs. In any case it can be expected that inverse agonists of RORγ should reduce the transcriptional activity of RORγ and influence the biological pathways controlled by RORγ.

The RORs are expressed as isoforms arising from differential splicing or alternative transcriptional start sites. So far, isoforms have been described that differ only in their N-terminal domain (NB-domain). In humans, four different RORα isoforms have been identified (RORα 1-4) while only two isoforms are known for both RORβ (1 and 2) and RORγ (1 and 2) (Andre et al., *Gene* 1998, 216:277; Villey et al., *Eur. J. Immunol.* 1999, 29:4072). RORγ is used herein as a term describing both, RORγ1 and/or RORγ2 (also called RORγt).

The ROR isoforms show different tissue expression patterns and regulate different target genes and physiological pathways. For example, the RORγt is highly restricted to $CD4^+CD8^+$ thymocytes and to interleukin-17 (IL-17) producing T cells while other tissues express RORγ1 (Eberl et al., *Science* 2004, 305:248, Zhou and Littmann, *Curr. Opin. Immunol.* 2009, 21:146).

RORs exhibit a structural architecture that is typical of nuclear receptors. RORs contain four major functional domains: an amino-terminal (A/B) domain, a DNA-binding domain, a hinge domain and a ligand-binding domain (Evans et al., *Science* 1988, 240:889). The DBD consists of two highly conserved zinc finger motifs involved in the recognition of ROR response elements (ROREs) which consist of the consensus motif AGGTCA preceded by an AT-rich sequence (Andre et al., *Gene* 1998, 216:277) which is similar to that of the nuclear receptors Rev-ErbAα and Rev-Erbβ (NR1D1 and D2, respectively) (Giguere et al., *Genomics* 1995, 28:596). These recognition elements do also show high similarity to those identified for the estrogen related receptors and in particular ERRα (ERRs, NR3B1, -2, -3) (Vanacker et al., *Mol. Endocrinol.* 1999, 13:764), steroidogenic factor 1 (SF-1, NR5A) and NGFI-B (NR4A1, -2, -3) (Wilson et al., *Mol. Cell. Biol.* 1993, 13:5794).

RORα is highly expressed in different brain regions and most highly in cerebellum and thalamus. RORα knock-out mice show ataxia with strong cerebellar atrophy, highly similar to the symptoms displayed in the so-called staggerer mutant mouse ($RORα^{sg/sg}$). This mouse carries mutations in RORα that results in a truncated RORα which does not contain a LBD (Hamilton et al., *Nature* 1996, 379:736).

Analysis of $RORα^{sg/sg}$ staggerer-mice have revealed a strong impact on lipid metabolism beyond the CNS defects, namely significant decreases in serum and liver triglyceride, reduced serum HDL cholesterol levels and reduced adiposity. SREBP1c and the cholesterol transporters ABCA1 and ABCG1 are reduced in livers of staggerer mice and CHIP analysis suggest that RORα is directly recruited to and regulates the SREBP1c promoter. In addition, PGC1α, PGC1β, lipin1 and β2-adrenergic receptor were found to be increased in tissues such as liver or white and brown adipose tissue, which may help to explain the observed resistance to diet-induced obesity in staggerer mice (Lau et al., *J. Biol. Chem.* 2008, 283:18411).

RORβ expression is mainly restricted to the brain and most abundantly found in the retina. RORβ knock-out mice display a duck-like gait and retinal degeneration which leads to blindness (Andre et al., *EMBO J.* 1998, 17:3867). The molecular mechanisms behind this retinal degeneration are still poorly understood.

RORγ (particularly RORγt) null-mutant mice lack lymph nodes and Peyer's patches (Eberl and Littmann, *Immunol. Rev.* 2003, 195:81) and lymphatic tissue inducer (LTi) cells are completely absent from spleen mesentery and intestine. In addition, the size of the thymus and the number of thymocytes is greatly reduced in RORγ null mice (Sun et al., *Science* 2000, 288:2369) due to a reduction in double-positive $CD4^+CD8^+$ and single positive $CD4^-CD8^+$ or $CD4^+CD8^-$ cells suggesting a very important role of RORγt in thymocyte development.

Thymocyte development follows a complex program involving coordinated cycles of proliferation, differentiation, cell death and gene recombination in cell populations dedicated by their microenvironment. Pluripotent lymphocyte progenitors migrating from fetal liver or adult bone marrow to the thymus are being committed to the T-cell lineage. They develop through a series of steps from $CD4^-CD8^-$ double negative cells to $CD4^+CD8^+$ cells and those with low affinity towards self-MHC peptides are eliminated by negative selection. These develop further into $CD4^-CD8^+$ (killer) or $CD4^+CD8^-$ (helper) T-cell lineages. RORγt is not expressed in double negative and little expressed in immature single negative thymocytes (He et al., *J. Immunol.* 2000, 164:5668), while highly upregulated in double-positive thymocytes and downregulated during differentiation in single-positive thymocytes. RORγ deficiency results in increased apoptosis in $CD4^+CD8^+$ cells and the number of peripheral blood thymocytes is decreased by 6-fold (10-fold $CD4^+$ and 3-fold $CD8^+$ thymocytes).

Recent experiments in a model of ovalbumin (OVA)-induced inflammation in mice, as a model for allergic airway disease, demonstrated a severe impairment of the development of the allergic phenotype in the RORγ KO mice with decreased numbers of $CD4^+$ cells and lower Th2 cytokine/chemokine protein and mRNA expression in the lungs after challenge with OVA (Tilley et al., *J. Immunol.* 2007, 178:3208). IFN-γ and IL-10 production were increased in splenocytes following re-stimulation with the OVA antigen compared to wt splenocytes suggesting a shift towards a Th1 type immune response on cost of a reduction of Th2 type response. This suggests that down-modulation of RORγ transcriptional activity with a ligand could result in a similar shift of the immune response towards a Th1 type response, which could be beneficial in the treatment of certain pulmonary diseases like asthma, chronic obstructive pulmonary disease (COPD) or allergic inflammatory conditions.

T-helper cells were previously considered to consist of Th1 and Th2 cells. However, a new class of Th cells, the Th17 cells, which produce IL-17, were also identified as a unique class of T-cells that are considered to be pro-inflammatory. They are recognized as key players in autoimmune and inflammatory diseases since IL-17 expression has been associated with many inflammatory diseases such as rheumatoid arthritis, systemic lupus erythematosus (SLE) and allograft rejection. (Tesmer et al., *Immunol. Rev.* 2008, 223:87).

RORγt is exclusively expressed in cells of the immune system and has been identified as a master regulator of Th17 cell differentiation. Expression of RORγt is induced by TGF-beta or IL-6 and overexpression of RORγt results in increased Th17 cell lineage and IL-17 expression. RORγt KO mice show very little Th17 cells in the intestinal lamina propria and demonstrate an attenuated response to challenges that usually lead to autoimmune disease (Ivanov et al., *Cell* 2006, 126:1121).

Inhibition of IL-17 production via inhibition of Th17 cell development may also be advantageous in atopic dermatitis and psoriasis where IL-17 is deeply involved. Interestingly, recent evidence was presented that IL-10 suppresses the expression of IL-17 secreted by both, macrophages and T-cells. In addition, the expression of the Th17 transcription factor RORγt was suppressed (Gu et al., *Eur. J. Immunol.* 2008, 38:1807). Moreover, IL-10 deficient mice provide a good model for inflammatory bowel disease (IBD) where a shift towards a Th1 type inflammatory response is frequently observed. Oral IL-10 delivery poses a potential treatment option for IBD.

The proinflammatory actions of IL-17 producing Th17 cells are counteracted by another T-helper cell type, so-called regulatory T-cells or Tregs. Naïve T-cells are differentiated into Tregs upon stimulation by TGFβ. This results in upregulation of the transcriptional modulator FoxP3 resulting in $CD4^+FoxP3^+$ Tregs. In case the naïve T-cells are co-stimulated by IL-6, FoxP3 expression is suppressed and RORγt expression is induced. These $CD4^+FoxP3^-ROR\gamma t^+$ T-helper cells then differentiate into IL-17 producing Th17 cells. (reviewed in Awasthi and Kuchroo, *Int. Immunol.* 2009, 21:489 and Zhou and Littmann, *Curr. Opin. Immunol.* 2009, 21:146). Several lines of evidence suggest that these Th17 cells are responsible for the etiology of a whole range of autoimmune diseases such as multiple sclerosis, rheumatoid arthritis, ankylosing spondylitis, psoriasis, Crohn's disease and other types of inflammatory bowel disease, lupus erythematosus and asthma. The severity of disease seems to correlate with the presence of $IL\text{-}17^+$ Th17 cells and it is believed that interception of RORγt by a small molecule inverse agonist or antagonist should result in a reduction of these $IL\text{-}17^+$ Th17 cells ultimately leading to alleviation of disease symptoms and outcome (Crome et al., *Clin. Exp. Immunol.* 2010, 159:109).

Ligands for the RORs:

It was reported that cholesterol and its sulfated derivatives might function as RORα ligands and in particular cholesterol-sulfate could restore transcriptional activity of RORα in cholesterol-depleted cells (Kallen et al., *Structure* 2002, 10:1697). Previously, melatonin (Missbach et al., *J. Biol. Chem.* 1998, 271:13515) and thiazolidinediones were suggested to bind to RORα (Wiesenberg et al., *Nucleic Acid Res.* 1995, 23:327). However, none of these have been shown to be functional ligands of RORα or of any other of the RORs. Certain retinoids including all-trans retinoid acid have been demonstrated to bind to RORβ and function as partial antagonists for RORβ but not RORα (Stehlin-Gaon et al., *Nat. Struct Biol.* 2003, 10:820).

Recently, 7-oxygenated sterols such as 7-hydroxy-cholesterol and 7-keto-cholesterol were identified as highly potent modulators of RORγ activity (Wang et al., *J. Biol. Chem.* 2010, 285:5013) in in vitro assays. The same group of investigators also found that a known LXR agonist, T0901317 ([N-(2,2,2-trifluoroethyl)-N-[4-[2,2,2-trifluoro-1-hydroxy-1-(trifluoro-methyl)ethyl]phenyl]-benzenesulfonamide]) acts as a RORγ inverse agonist at submicromolar potency (Kumar et al., *Mol. Pharmacol.* 2010, 77:228). In neither case, however, in vivo data were obtained that demonstrate a beneficial impact of these RORγ modulating compounds. In case of the 7-oxysterols their endogenous presence as metabolites naturally produced by the body itself as well as their rapid turnover and their biological activities on many cellular proteins prevent a meaningful animal study that allows drawing conclusions on the role of RORγ. In case of the T0901317 its polypharmacodynamic properties, acting on at least six different nuclear receptors (LXRα/β, FXR, PXR, RORα/γ) prevents its usefulness as a drug candidate for the development in an autoimmune disease application (Houck et al., *Mol. Genet. Metab.* 2004, 83:184; Xue et al., *Bioorg. Med. Chem.* 2007, 15:2156).

WO2004/060870 describes pyrrolo carboxamide compounds of structure (A) as modulators of the CB1 receptor useful for treating and preventing eating disorders, obesity, type II diabetes and the like, (A)

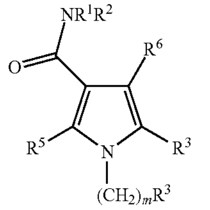

wherein $R^1$ is H or lower alkyl;

$R^2$ is limited to $C_{1-8}$-alkyl, $(CH_2)_{0\ or\ 1}$-cyclolalkyl or a $(CH_2)_{0\ or\ 1}$ connected to a 5- or 6-membered saturated heterocycle or 5- or 6-membered heteroaromatic ring, wherein the corresponding ring can be optionally substituted. Remarkably, $C_{1-8}$-alkyl can not be optionally substituted; $R^3$ is limited to optionally substituted cycloalkyl or optionally substituted phenyl; $R^4$ is limited to optionally substituted phenyl, naphthyl or a 5- or 6-membered heteroaromatic ring. Possible substitutents for $R^4$ are OH, $C_{1-8}$-alkyl, O—$C_{1-8}$-alkyl, halogen, $NO_2$, $C_{1-8}$-halogenated alkyl, O—$C_{1-8}$-halogenated alkyl, CN, $SO_2$—$C_{1-8}$-alkyl and optionally alkylated amine. Remarkably, $R^4$ can not be substituted e.g. with $C_{0-8}$-alkylene-$CONR_2$, $C_{0-8}$-alkylene-$SO_2NR_2$, $C_{0-8}$-alkylene-NRCOR or $C_{0-8}$-alkylene-$NRSO_2R$.

WO2005/108393 describes pyrrolo carboxamide compounds of structure (A) as modulators of the CB1 receptor, wherein $R^3$ is limited to a 5- or 6-membered saturated heterocyclic ring containing 1 or 2 heteroatoms independently selected from N or O, which is optionally substituted by OH, $C_{1-8}$-alkyl, O—$C_{1-8}$-alkyl, C(═O)O—$C_{1-8}$-alkyl or being condensed with a phenyl ring and $R^4$ is limited to phenyl, optionally substituted only by OH, $C_{1-8}$-alkyl, halo-$C_{1-8}$-alkyl, O—$C_{1-8}$-alkyl, O-halo-$C_{1-6}$-alkyl and halogen.

WO2004/060888 describes pyrrolo carboxamide compounds of structure (A) as modulators of the CB1 receptor, wherein $R^4$ is limited to optionally substituted 4-thiazolyl.

In none of the above mentioned publications a 4-membered heterocycle is claimed as substituent for $R^1$ or $R^2$. Furthermore there are no references, that these pyrrolo carboxamide compounds have RORγ receptor modulating activity.

US2009/0036421 (equivalent to WO2007/097276) describes pyrrolo carboxamide compounds of structure (B) as $5\text{-}HT_{2B}$ and $5\text{-}HT_7$ receptor modulators for the treatment of irritable bowel syndrome (B)

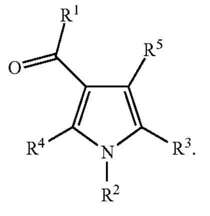

However, there is no reference, that compounds have RORγ receptor modulating activity.

In WO2006/012642 are pyrrolo-3-carboxamides described, in particular compounds wherein a $C_{1-3}$-alkylene-cycloalkyl group is connected to the pyrrolo nitrogen, e.g. structures (C) and (C').

(C)

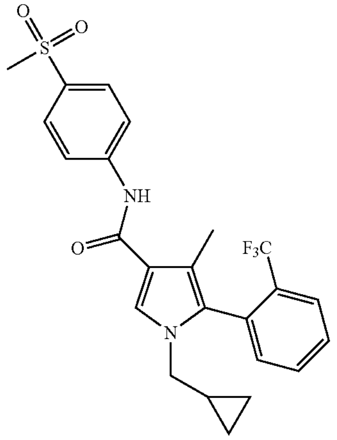

(C')

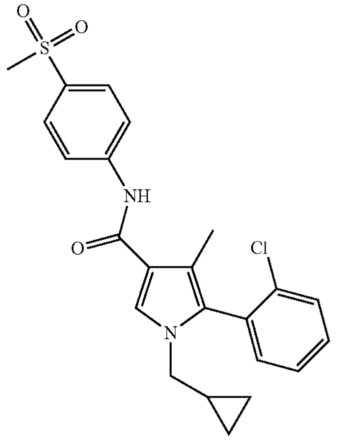

WO2004/103968 describes 2-phenylsulfopyrroles wherein the sulfonyl residue is restricted to optionally substituted phenyl.

WO2011/042477 describes substituted pyrroles and imidazoles as estrogen receptor ligands. However no pyrrolo-3-carboxamides are disclosed, which have a $C_{1-3}$-alkylene-cycloalkyl group connected to the pyrrolo nitrogen.

The Chemical Abstract database lists several pyrrolo carboxamides with no accompanying literature references, which are excluded via provisos form the presented claims, e.g.

(D)

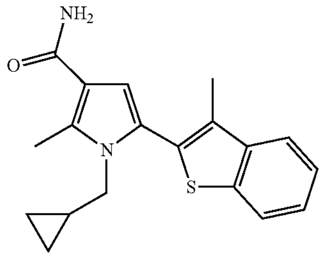

-continued (D')

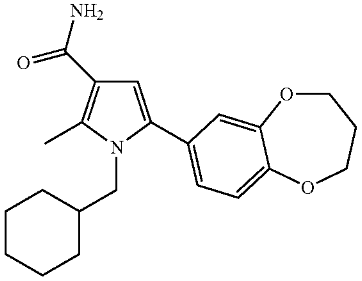

(D'')

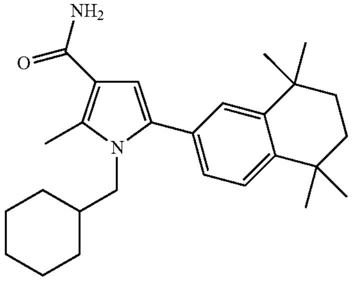

WO2012/144661 describes substituted pyrroles as TRPV4 inhibitors with a very broad coverage of various substituents. However no pyrrolo-3-carboxamides are disclosed, which fall in the scope of the present invention. In particular, no compounds with a cycloalkyl group connected via a linker (e.g. alkylene or $SO_2$) to the pyrrole nitrogen are specifically disclosed.

Modulators of the RORγ receptor were recently disclosed in WO2011/107248, WO2011/112263, WO2011/112264, WO2011/115892, WO2012/027965, WO2012/028100, WO2012/064744, WO2012/100732, WO2012/100734, WO2012/106995, WO2012/139775, WO2012/147916 and WO2012/158784, which are based upon other structural classes.

SUMMARY OF THE INVENTION

It is therefore the object of the present invention to provide compounds, which bind to the orphan nuclear receptors RORγ1 and/or RORγt and, thus, to open new methods for treating diseases associated with the modulation of RORγ, such as autoimmune diseases, inflammatory skin diseases or multiple sclerosis.

This object is solved by claims 1 to 24.

Thus, the present invention provides pyrrolo carboxamides compounds as RORγ modulators, which can be used for treating or preventing a disease or disorder associated with the inactivation or activation of the RORγ receptor.

The present invention relates to a RORγ modulator which is based on a pyrrolo carboxamide scaffold for use in the treatment or prophylaxis of a disease or disorder associated with the inhibition or activation of RORγ.

When treating the disease or disorder associated with the modulation of the RORγ receptor, the activity of said receptor is preferably reduced.

Preferably, the disease or disorder is selected from the group consisting of autoimmune diseases. Autoimmune diseases comprise a group of diseases with a similar etiology of an overshooting immune response against endogenous targets resulting in chronic inflammation and physical disabilities or other severe symptoms. Autoimmune diseases comprise e.g. rheumatoid arthritis, ankylosing spondylitis, lupus erythematosus, psoriasis, atopic eczema, inflammatory bowel diseases such as Crohn's disease, respiratory diseases such as asthma or chronic obstructive pulmonary disease (COPD), infectious diseases such as mucosal leishmaniasis, multiple sclerosis, systemic sclerosis, type 1 diabetes, Kawasaki disease, Hashimoto's thyroiditis, chronic graft-versus-host disease, acute graft-versus-host disease, Celiac Sprue, idiopathic thrombocytopenic thrombotic purpura, myasthenia gravis, Sjorgren's syndrome, scleroderma, ulcerative colitis, epidermal hyperplasia, glomerulonephritis and amyotrophic lateral sclerosis. In a preferred embodiment, the disease or disorder is rheumatoid arthritis or psoriasis.

The present invention provides novel compounds to be used in the treatment of diseases or disorders associated with the inactivation or activation of the RORγ receptor.

Moreover, the present provides a method for treating a disease or disorder associated with the modulation of the RORγ receptor, wherein the method comprises administering an effective amount of a compound according to Formula (1) to a subject in need thereof. The disease or disorder is preferably selected from the group consisting of autoimmune diseases such as rheumatoid arthritis, ankylosing spondylitis, lupus erythematosus, psoriasis, atopic eczema, inflammatory bowel diseases such as Crohn's disease, espiratory diseases such as asthma or COPD, infectious diseases such as mucosal leishmaniasis, multiple sclerosis, systemic sclerosis, type 1 diabetes, Kawasaki disease, Hashimoto's thyroiditis, chronic graft-versus-host disease, acute graft-versus-host disease, Celiac Sprue, idiopathic thrombocytopenic thrombotic purpura, myasthenia gravis, Sjorgren's syndrome, scleroderma, ulcerative colitis, epidermal hyperplasia, glomerulonephritis and amyotrophic lateral sclerosis. In a certain embodiment the disorder is rheumatoid arthritis and psoriasis.

DETAILED DESCRIPTION OF THE INVENTION

The present invention provides a compound represented by Formula (1)

(1)

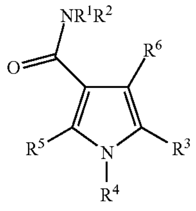

an enantiomer, diastereomer, tautomer, N-oxide, solvate, formulation and pharmaceutically acceptable salt thereof, wherein $R^1$ is selected from H, $C_{1-10}$-alkyl, $C_{2-10}$-alkenyl, $C_{2-10}$-alkynyl, $C_{3-6}$-cycloalkyl, $C_{3-6}$-heterocycloalkyl, $C_{1-10}$-alkylene-$C_{3-10}$-cycloalkyl, $C_{1-10}$-alkylene-$C_{3-10}$-heterocycloalkyl, $C_{1-10}$-alkylene-(5-membered monocyclic heteroaryl), $SO_2$—$C_{1-10}$-alkyl, wherein alkyl, alkenyl, alkynyl, alkylene, cycloalkyl, heterocycloalkyl and heteroaryl is unsubstituted or substituted with 1 to 7 substituents independently selected from oxo, CN, $OR^{11}$, O—$C_{2-6}$-alkylene-$OR^{11}$, $C_{1-6}$-alkyl, halo-$C_{1-6}$-alkyl, halogen, $CO_2R^{11}$, $CONR^{11}R^{12}$, $COR^{11}$, $SO_yR^{11}$, $SO_3H$, $SO_2NR^{11}R^{12}$, $NR^{11}COR^{11}$, $NR^{11}SO_2R^{11}$, $NR^{11}$—CO—$NR^{11}R^{12}$, $NR^{11}$—$SO_2$—$NR^{11}R^{12}$, $C_{3-6}$-cycloalkyl, O—$C_{3-6}$-cycloalkyl, $C_{3-6}$-heterocycloalkyl, O—$C_{3-6}$-heterocycloalkyl and $NR^{11}R^{12}$; and $R^3$ is pyridinone, a 6- to 10-membered mono- or bicyclic aryl, a 5- to 10-membered mono- or bicyclic heteroaryl containing 1 to 4 heteroatoms independently selected from the group consisting of N, O and S or a 6- to 12-membered partially saturated spiroheterocycle containing 1 to 4 heteroatoms independently selected from the group consisting of N, O and S, wherein pyridinone and spiroheterocycle is optionally substituted with 1 to 4 groups independently selected from halogen, $C_{1-6}$-alkyl, halo-$C_{1-6}$-alkyl, OH, O—$C_{1-6}$-alkyl, O-halo-$C_{1-6}$-alkyl, oxo, =N—$OR^{32}$, N($R^{32}$), $C_{0-6}$-alkylene-$C_{3-10}$-cycloalkyl, $C_{0-6}$-alkylene-$C_{3-10}$-heterocycloalkyl, $C_{0-6}$-alkylene-(5- or 6-membered monocyclic heteroaryl), $C_{1-6}$-alkylene-O—$R^{31}$, $C_{0-6}$-alkylene-CN, O—$C_{3-10}$-cycloalkyl, O—$C_{1-6}$-alkylene-O—$R^{32}$, O—$C_{3-10}$-heterocycloalkyl, $C_{0-6}$-alkylene-$COOR^{31}$, $C_{0-6}$-alkylene-C(O)$R^{31}$, $C_{0-6}$-alkylene-C(O)N($R^{31}$)$_2$, $C_{0-6}$-alkylene-N($R^{31}$)C(O)$R^{31}$, $C_{0-6}$-alkylene-SO—$R^{31}$, $C_{0-6}$-alkylene-$SO_2$—$R^{31}$, $C_{0-6}$-alkylene-$SO_2$—N($R^{31}$)$_2$, $C_{0-6}$-alkylene-N($R^{31}$)$SO_2$—$R^{31}$, $C_{0-6}$-alkylene-$SO_2$—$C_{3-10}$-heterocycloalkyl and $C_{0-6}$-alkylene-$SO_2$—$C_{3-10}$-heterocycloalkyl, wherein alkylene, cycloalkyl, heterocycloalkyl and heteroaryl is optionally substituted by 1 to 4 substituents independently selected from the group consisting of halogen, CN, $C_{1-3}$-alkyl, halo-$C_{1-3}$-alkyl, OH, oxo, O—$C_{1-3}$-alkyl and O-halo-$C_{1-3}$-alkyl;

wherein aryl and heteroaryl is substituted with at least one group selected from $C_{3-10}$-cycloalkyl, $C_4$-heterocycloalkyl, $C_{1-4}$-alkylene-$C_{3-10}$-cycloalkyl, $C_{1-4}$-alkylene-($C_{3-10}$-heterocycloalkyl), carbon atom linked 5- or 6-membered monocyclic heteroaryl, $C_{1-6}$-alkylene-(5- or 6-membered monocyclic heteroaryl), $C_{1-4}$-alkylene-O—$R^{31}$, $C_{1-4}$-alkylene-CN, O—$C_{3-10}$-cycloalkyl, O—$C_{1-6}$-alkylene-O—$R^{32}$, O—$C_{3-10}$-heterocycloalkyl, $C_{0-6}$-alkylene-$COOR^{31}$, $C_{0-6}$-alkylene-C(O)$R^{31}$, $C_{0-6}$-alkylene-C(O)N($R^{31}$)$_2$, $C_{0-6}$-alkylene-N($R^{31}$)C(O)$R^{31}$, $C_{0-6}$-alkylene-SO—$R^{31}$, $C_{1-6}$-alkylene-$SO_2$—$R^{31}$, $C_{0-6}$-alkylene-$SO_2$—N($R^{31}$)$_2$, $C_{0-6}$-alkylene-N($R^{31}$)$SO_2$—$R^{31}$, $SO_2$—$C_{3-10}$-heterocycloalkyl, $SO_2$—$C_{3-10}$-cycloalkyl, $C_{0-6}$-alkylene-SO—$R^{31}$ and two adjacent substituents completing a 3- to 8-membered saturated or partially unsaturated ring containing carbon atoms and optionally containing 1 to 3 heteroatoms selected from O, S or N, wherein the ring is unsubstituted or substituted with 1 to 6 substituents independently selected from halogen, $C_{1-6}$-alkyl, halo-$C_{1-6}$-alkyl, $C_{3-6}$-cycloalkyl, $C_{3-6}$-heterocycloalkyl, oxo, =N—$OR^{32}$, OH, O—$C_{1-6}$-alkyl and O-halo-$C_{1-6}$-alkyl, wherein alkylene, cycloalkyl, heterocycloalkyl and the 5- or 6-membered monocyclic heteroaryl is optionally substituted by 1 to 4 substituents independently selected from the group consisting of halogen, CN, halo-$C_{1-3}$-alkyl, OH, oxo, =N—$OR^{32}$, O—$C_{1-3}$-alkyl and O-halo-$C_{1-3}$-alkyl; and wherein aryl and heteroaryl are optionally substituted by 1 to 4 substituents independently selected from the group consisting of halogen, CN, $C_{1-3}$-alkyl, halo-$C_{1-3}$-alkyl, OH, O—$C_{1-3}$-alkyl and O-halo-$C_{1-3}$-alkyl;

or $R^1$ is selected from a 4-membered heterocycloalkyl group containing one heteroatom selected from the group consisting of N, O and S, or $C_{1-10}$-alkyl substituted with a group selected from halogen, CN, $OR^{11}$, $SO_yR^{11}$, $SO_3H$, $NR^{11}SO_2R^{11}$, $SO_2NR^{11}R^{12}$, $CO_2R^{11}$, $CONR^{11}R^{12}$, $NR^{11}$—CO—$R^{11}$, $NR^{11}$—CO—$NR^{11}R^{12}$, $NR^{11}$—$SO_2$—$NR^{11}R^{12}$, $NR^{11}R^{12}$ and a 4-membered heterocycloalkyl group containing one heteroatom selected from the group consisting of N, O and S, or $C_{0-1}$-alkylene-$C_{3-10}$-cycloalkyl substituted with a group selected from halogen, CN, $SO_yR^{11}$, $NR^{11}SO_2R^{11}$, $SO_2NR^{11}R^{12}$, $CO_2R^{11}$, $CONR^{11}R^{12}$, $NR^{11}$—CO—$R^{11}$, $NR^{11}$—CO—$NR^{11}R^{12}$, $NR^{11}$—$SO_2$—$NR^{11}R^{12}$ and $NR^{11}R^{12}$, or $C_{2-10}$-alkylene-$C_{3-10}$-cycloalkyl, $C_{2-10}$-alkylene-O—$C_{3-10}$-cycloalkyl, $C_{2-10}$-alkylene-$C_{5-10}$-heterocycloalkyl, $C_{2-10}$-alkylene-O—$C_{5-10}$-heterocycloalkyl and $SO_2$—$C_{1-10}$-alkyl, wherein alkyl, alkylene, cycloalkyl and heterocycloalkyl are optionally substituted with 1 to 7 substituents independently selected from the group consisting of OH, oxo, CN, O—$C_{1-6}$-alkyl, O-halo-$C_{1-6}$-alkyl, $C_{1-6}$-alkyl, halo-$C_{1-6}$-alkyl, halogen, $CO_2R^{11}$, $CONR^{11}R^{12}$, $COR^{11}$, $SO_2R^{11}$, $SO_2NR^{11}R^{12}$, $NR^{11}COR^{11}$, $NR^{11}SO_2R^{11}$, $C_{3-6}$-cycloalkyl, O—$C_{3-6}$-cycloalkyl, $C_{3-6}$-heterocycloalkyl, O—$C_{3-6}$-heterocycloalkyl, O—$C_{2-6}$-alkylene-$OR^{11}$ and $NR^{11}R^{12}$; and $R^3$ is pyridinone, a 6- to 10-membered mono- or bicyclic aryl, a 5- to 10-membered mono- or bicyclic heteroaryl containing 1 to 4 heteroatoms independently selected from the group consisting of N, O and S or a 6- to 12-membered partially saturated spiroheterocycle containing 1 to 4 heteroatoms independently selected from the group consisting of N, O and S, wherein pyridinone, aryl and heteroaryl and spiroheterocycle is optionally substituted with 1 to 4 groups independently selected from halogen, $C_{1-6}$-alkyl, halo-$C_{1-6}$-alkyl, OH, O—$C_{1-6}$-alkyl, O-halo-$C_{1-6}$-alkyl, oxo, =N—$OR^{32}$, N($R^{32}$), $C_{0-6}$-alkylene-$C_{3-10}$-cycloalkyl, $C_{0-6}$-alkylene-$C_{3-10}$-heterocycloalkyl, $C_{0-6}$-alkylene-(5- or 6-membered monocyclic heteroaryl), $C_{1-6}$-alkylene-O—$R^{31}$, $C_{0-6}$-alkylene-ON, O—$C_{3-10}$-cycloalkyl, O—$C_{1-6}$-alkylene-O—$R^{32}$, O—$C_{3-10}$-heterocycloalkyl, $C_{0-6}$-alkylene-$COOR^{31}$, $C_{0-6}$-alkylene-C(O)$R^{31}$, $C_{0-6}$-alkylene-C(O)N($R^{31}$)$_2$, $C_{0-6}$-alkylene-N($R^{31}$)C(O)$R^{31}$, $C_{0-6}$-alkylene-SO—$R^{31}$, $C_{0-6}$-alkylene-$SO_2$—$R^{31}$, $C_{0-6}$-alkylene-$SO_2$—N($R^{31}$)$_2$ and $C_{0-6}$-alkylene-N($R^{31}$)$SO_2$—$R^{31}$, and two adjacent substituents completing a 3- to 8-membered saturated or partially unsaturated ring containing carbon atoms and optionally containing 1 to 3 heteroatoms selected from O, S or N, wherein the ring is unsubstituted or substituted with 1 to 6 substituents independently selected from halogen, $C_{1-6}$-alkyl, halo-$C_{1-6}$-alkyl, $C_{3-6}$-cycloalkyl, $C_{3-6}$-heterocycloalkyl, oxo, =N—$OR^{32}$, OH, O—$C_{1-6}$-alkyl and O-halo-$C_{1-6}$-alkyl, wherein alkylene, cycloalkyl, heterocycloalkyl and the 5- or 6-membered monocyclic heteroaryl is optionally substituted by 1 to 4 substituents independently selected from the group consisting of halogen, CN, halo-$C_{1-3}$-alkyl, OH, oxo, =N—$OR^{32}$, O—$C_{1-3}$-alkyl and O-halo-$C_{1-3}$-alkyl;

and $R^2$ is selected from the group consisting of H, $C_{1-6}$-alkyl, halo-$C_{1-6}$-alkyl and hydroxy-$C_{1-6}$-alkyl, or $R^1$ and $R^2$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from halogen, oxo, CN, $OR^{11}$, $SO_yR^{11}$, $SO_3H$, $NR^{11}SO_2R^{11}$, $SO_2NR^{11}R^{12}$, $C_{0-6}$-alkylene-$CO_2R^{11}$, $CONR^{11}R^{12}$, $COR^{11}$, $NR^{11}$—CO—$R^{11}$, $NR^{11}$—CO—$NR^{11}R^{12}$, $NR^{11}$—$SO_2$—$NR^{11}R^{12}$, $NR^{11}R^{12}$, $C_{1-6}$-alkyl, halo-$C_{1-6}$-alkyl, hydroxy-$C_{1-6}$-alkyl, $C_{3-6}$-cycloalkyl, O—$C_{3-6}$-cycloalkyl, $C_{3-6}$-heterocycloalkyl and O—$C_{3-6}$-heterocycloalkyl, wherein cycloalkyl and heterocycloalkyl are unsubstituted or substituted with 1 to 4 substituents independently selected from halogen, $C_{1-3}$-alkyl, halo-$C_{1-3}$-alkyl and oxo;

$R^4$ is $SO_2$—$(CR^8R^8)_yR^7$, $SO_2$—$NR^{12}R^7$, $(CR^8R^8)_x$—$R^{10}$ or $C_{3-6}$-cycloalkyl, which is spirocyclic fused with $C_{3-10}$-cycloalkyl;

$R^5$ is selected from H, halo-$C_{1-6}$-alkyl, CHO, $CON(R^{52})_2$ or halogen, wherein alkyl is unsubstituted or substituted with 1 to 3 substituents independently selected from the group consisting of O—$C_{1-6}$-alkyl, O-halo-$C_{1-6}$-alkyl and OH;

$R^6$ is selected from H, halo-$C_{1-6}$-alkyl or halogen;

$R^7$ is selected from $C_{3-10}$-cycloalkyl and $C_{3-10}$-heterocycloalkyl, wherein cycloalkyl and heterocycloalkyl are unsubstituted or substituted with 1 to 3 substituents independently selected from the group consisting of halogen, OH, oxo, O—$C_{1-6}$-alkyl, O-halo-$C_{1-6}$-alkyl, $C_{1-6}$-alkyl, halo-$C_{1-6}$-alkyl, cycloalkyl and heterocycloalkyl;

$R^8$ is independently selected from H, F, $C_{1-3}$-alkyl, halo-$C_{1-3}$-alkyl or OH;

$R^{10}$ is $C_{3-10}$-cycloalkyl, wherein cycloalkyl is unsubstituted or substituted with 1 to 6 substituents independently selected from halogen, OH, oxo, O—$C_{1-6}$-alkyl, O-halo-$C_{1-6}$-alkyl, $C_{1-6}$-alkyl, halo-$C_{1-6}$-alkyl, cycloalkyl, heterocycloalkyl, and optionally two adjacent substituents together complete a 6-membered aryl ring wherein the ring is unsubstituted or substituted with 1 to 3 substituents independently selected from halogen, $C_{1-2}$-alkyl, halo-$C_{1-2}$-alkyl;

$R^{11}$ is independently selected from H, $C_{1-6}$-alkyl, $C_{0-6}$-alkylene-$C_{3-6}$-cycloalkyl, $C_{0-6}$-alkylene-$C_{3-6}$-heterocycloalkyl, wherein alkyl, alkylene, cyclolalkyl and heterocycloalkyl are unsubstituted or substituted with 1 to 6 substituents independently selected from halogen, OH, oxo, $C_{1-3}$-alkyl, halo-$C_{1-3}$-alkyl, O—$C_{1-3}$-alkyl, O-halo-$C_{1-3}$-alkyl and $SO_2$—$C_{1-3}$-alkyl;

$R^{12}$ is independently selected from H, $C_{1-6}$-alkyl and halo-$C_{1-6}$-alkyl;

$R^{31}$ is independently selected from H, $C_{1-6}$-alkyl, halo-$C_{1-6}$-alkyl, $C_{0-6}$-alkylene-$C_{3-6}$-cycloalkyl, $C_{0-6}$-alkylene-$C_{3-6}$-heterocycloalkyl, 5- or 6-membered heteroaryl and 6-membered aryl, wherein alkyl, alkylene, cyclolalkyl, heterocycloalkyl, aryl and heteroaryl are unsubstituted or substituted with 1 to 6 substituents independently selected from halogen, CN, OH, oxo, $C_{1-3}$-alkyl, halo-$C_{1-3}$-alkyl, O—$C_{1-3}$-alkyl, O-halo-$C_{1-3}$-alkyl and $SO_2$—$C_{1-3}$-alkyl;

and optionally wherein two $R^{31}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from fluoro, OH, oxo, $C_{1-4}$-alkyl and halo-$C_{1-4}$-alkyl;

$R^{32}$ is independently selected from H, $C_{1-6}$-alkyl and halo-$C_{1-6}$-alkyl;

$R^{52}$ is independently selected from H, $C_{1-3}$-alkyl and halo-$C_{1-3}$-alkyl;

x is independently selected from 1 and 2;

y is independently selected from 0, 1 and 2;

with the proviso that $R^3$ is not an unsubstituted or substituted ring selected from

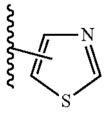
,
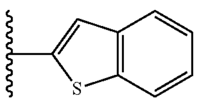
,
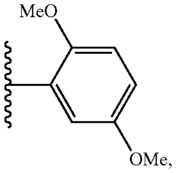

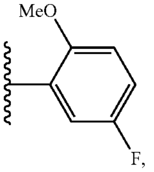

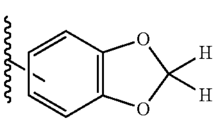
,

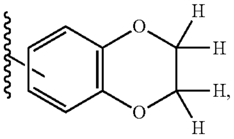

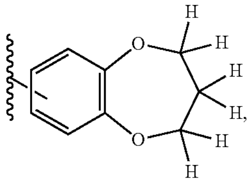

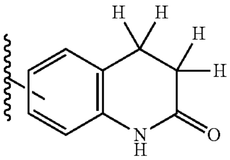
and
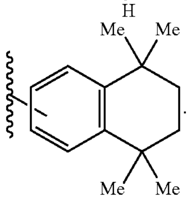

In a preferred embodiment, the present invention provides a compound of Formula (1)

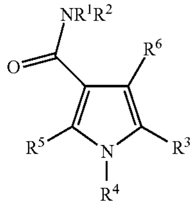
(1)

an enantiomer, diastereomer, tautomer, solvate, formulation and pharmaceutically acceptable salt thereof, wherein $R^1$ is selected from H, $C_{1-10}$-alkyl, $C_{2-10}$-alkenyl, $C_{2-10}$-alkynyl, $C_{3-6}$-cycloalkyl, $C_{3-6}$-heterocycloalkyl, $C_{1-10}$-alkylene-$C_{3-10}$-cycloalkyl, $C_{1-10}$-alkylene-$C_{3-10}$-heterocycloalkyl, $C_{1-10}$-alkylene-(5-membered monocyclic heteroaryl), $SO_2$—$C_{1-10}$-alkyl, wherein alkyl, alkenyl, alkynyl, alkylene, cycloalkyl, heterocycloalkyl and heteroaryl is unsubstituted or substituted with 1 to 7 substituents independently selected from oxo, CN, $OR^{11}$, O—$C_{2-6}$-alkylene-$OR^{11}$, $C_{1-6}$-alkyl, halo-$C_{1-6}$-alkyl, halogen, $CO_2R^{11}$, $CONR^{11}R^{12}$, $COR^{11}$, $SO_yR^{11}$, $SO_3H$, $SO_2NR^{11}R^{12}$, $NR^{11}COR^{11}$, $NR^{11}SO_2R^{11}$, $NR^{11}$—CO—$NR^{11}R^{12}$, $NR^{11}$—$SO_2$—$NR^{11}R^{12}$, $C_{3-6}$-cycloalkyl, O—$C_{3-6}$-cycloalkyl, $C_{3-6}$-heterocycloalkyl, O—$C_{3-6}$-heterocycloalkyl and $NR^{11}R^{12}$; and $R^3$ is pyridinone, a 6- to 10-membered mono- or bicyclic aryl, a 5- to 10-membered mono- or bicyclic heteroaryl containing 1 to 4 heteroatoms independently selected from the group consisting of N, O and S or a 6- to 12-membered partially saturated spiroheterocycle containing 1 to 4 heteroatoms independently selected from the group consisting of N, O and S, wherein pyridinone and spiroheterocycle is optionally substituted with a group selected from $C_{3-10}$-cycloalkyl, $C_4$-heterocycloalkyl, $C_{1-4}$-alkylene-$C_{3-10}$-cycloalkyl, $C_{1-4}$-alkylene-$C_{3-10}$-heterocycloalkyl, $C_{0-6}$-alkylene-(5-membered monocyclic heteroaryl), $C_{1-4}$-alkylene-O—$R^{31}$, $C_{1-4}$-alkylene-CN, O—$C_{3-10}$-cycloalkyl, O—$C_{1-6}$-alkylene-O—$R^{32}$, O—$C_{3-10}$-heterocycloalkyl, $C_{0-6}$-alkylene-$COOR^{31}$, $C_{0-6}$-alkylene-C(O)$R^{31}$, $C_{0-6}$-alkylene-C(O)N($R^{31}$)$_2$, $C_{0-6}$-alkylene-N($R^{31}$)C(O)$R^{31}$, $C_{0-6}$-alkylene-$SO_2$—N($R^{31}$)$_2$, $C_{0-6}$-alkylene-N($R^{31}$)$SO_2$—$R^{31}$, $C_{0-6}$-alkylene-$SO_2$—$C_{3-10}$-heterocycloalkyl and $C_{0-6}$-alkylene-SO—$R^{31}$, aryl and heteroaryl is substituted with at least one group selected from $C_{3-10}$-cycloalkyl, $C_4$-heterocycloalkyl, $C_{1-4}$-alkylene-$C_{3-10}$-cycloalkyl, $C_{1-4}$-alkylene-$C_{3-10}$-heterocycloalkyl, $C_{0-6}$-alkylene-(5-membered monocyclic heteroaryl), $C_{0-6}$-alkylene-(6-membered monocyclic heteroaryl), $C_{1-4}$-alkylene-O—$R^{31}$, $C_{1-4}$-alkylene-CN, O—$C_{3-10}$-cycloalkyl, O—$C_{1-6}$-alkylene-O—$R^{32}$, O—$C_{3-10}$-heterocycloalkyl, $C_{0-6}$-alkylene-$COOR^{31}$, $C_{0-6}$-alkylene-C(O)$R^{31}$, $C_{0-6}$-alkylene-C(O)N($R^{31}$)$_2$, $C_{0-6}$-alkylene-N($R^{31}$)C(O)$R^{31}$, $C_{0-6}$-alkylene-$SO_2$—N($R^{31}$)$_2$, $C_{0-6}$-alkylene-N($R^{31}$)$SO_2$—$R^{31}$, $C_{0-6}$-alkylene-$SO_2$—$C_{3-10}$-heterocycloalkyl, $C_{0-6}$-alkylene-SO—$R^{31}$ and two adjacent substituents completing a 3- to 8-membered saturated or partially unsaturated ring containing carbon atoms and optionally containing 1 to 3 heteroatoms selected from O, S or N, wherein the ring is unsubstituted or substituted with 1 to 6 substituents independently selected from halogen, $C_{1-6}$-alkyl, halo-$C_{1-6}$-alkyl, $C_{3-6}$-cycloalkyl, $C_{3-6}$-heterocycloalkyl, oxo, OH, O—$C_{1-6}$-alkyl and O-halo-$C_{1-6}$-alkyl, wherein pyridinone, aryl, heteroaryl, spiroheterocycle, alkyl, alkylene, cycloalkyl and heterocycloalkyl are optionally substituted by 1 to 4 substituents independently selected from the group consisting of halogen, CN, $C_{1-6}$-alkyl, halo-$C_{1-6}$-alkyl, $C_{3-6}$-cycloalkyl, $C_{3-6}$-heterocycloalkyl, OH, O—$C_{1-3}$-alkyl, O-halo-$C_{1-3}$-alkyl, O—$C_{3-6}$-cycloalkyl, O—$C_{3-6}$-heterocycloalkyl, oxo, N($R^{32}$)$_2$, COOH, CON($R^{32}$)$_2$, CN and $NR^{32}$—$COR^{32}$;

or $R^1$ is selected from a 4-membered heterocycloalkyl group containing one heteroatom selected from the group consisting of N, O and S, or $C_{1-10}$-alkyl substituted with a group selected from halogen, CN, $OR^{11}$, $SO_yR^{11}$, $SO_3H$, $NR^{11}SO_2R^{11}$, $SO_2NR^{11}R^{12}$, $CO_2R^{11}$, $CONR^{11}R^{12}$, $NR^{11}$—CO—$R^{11}$, $NR^{11}$—CO—$NR^{11}R^{12}$, $NR^{11}$—$SO_2$—$NR^{11}R^{12}$, $NR^{11}R^{12}$ and a 4-membered heterocycloalkyl group containing one heteroatom selected from the group consisting of N, O and S, or $C_{0-1}$-alkylene-$C_{3-10}$-cycloalkyl substituted with a group selected from halogen, CN, $SO_yR^{11}$, $NR^{11}SO_2R^{11}$, $SO_2NR^{11}R^{12}$, $CO_2R^{11}$, $CONR^{11}R^{12}$, $NR^{11}$—CO—$R^{11}$, $NR^{11}$—CO—$NR^{11}R^{12}$, $NR^{11}$—$SO_2$—$NR^{11}R^{12}$ and $NR^{11}R^{12}$, or $C_{2-10}$-alkylene-$C_{3-10}$-cycloalkyl, $C_{2-10}$-alkylene-O—$C_{3-10}$-cycloalkyl, $C_{2-10}$-alkylene-$C_{5-10}$-heterocycloalkyl, $C_{2-10}$-alkylene-O—$C_{5-10}$-heterocycloalkyl and $SO_2$—$C_{1-10}$-alkyl, wherein alkyl, alkylene, cycloalkyl and heterocycloalkyl are optionally substituted with 1 to 7 substituents independently selected from the group consisting of OH, oxo, CN, O—$C_{1-6}$-alkyl, O-halo-$C_{1-6}$-alkyl, $C_{1-6}$-alkyl, halo-$C_{1-6}$-alkyl, halogen, $CO_2R^{11}$, $CONR^{11}R^{12}$, $COR^{11}$, $SO_2R^{11}$, $SO_2NR^{11}R^{12}$, $NR^{11}COR^{11}$, $NR^{11}SO_2R^{11}$, $C_{3-6}$-cycloalkyl, O—$C_{3-6}$-cycloalkyl, $C_{3-6}$-heterocycloalkyl, O—$C_{3-6}$-heterocycloalkyl, O—$C_{2-6}$-alkylene-$OR^{11}$ and $NR^{11}R^{12}$; and $R^3$ is pyridinone, a 6- to 10-membered mono- or bicyclic aryl, a 5- to 10-membered mono- or bicyclic heteroaryl containing 1 to 4 heteroatoms independently selected from the group consisting of N, O and S or a 6- to 12-membered partially saturated spiroheterocycle containing 1 to 4 heteroatoms independently selected from the group consisting of N, O and S, wherein pyridinone, aryl, heteroaryl and spiroheterocycle are unsubstituted or substituted with 1 to 5 substituents independently selected from halogen, CN, $C_{1-6}$-alkyl, $C_{3-10}$-cycloalkyl, $C_{3-10}$-heterocycloalkyl, $C_{0-6}$-alkylene-(5-membered monocyclic heteroaryl), $C_{0-6}$-alkylene-(6-membered monocyclic heteroaryl), $C_{0-6}$-alkylene-O—$R^{31}$, O—$C_{1-6}$-alkylene-O—$R^{32}$, $C_{0-6}$-alkylene-$COOR^{31}$, $C_{0-6}$-alkylene-C(O)$R^{31}$, $C_{0-6}$-alkylene-C(O)N($R^{31}$)$_2$, $C_{0-6}$-alkylene-N($R^{31}$)C(O)$R^{31}$, $C_{0-6}$-alkylene-$SO_2$—N($R^{31}$)$_2$, $C_{0-6}$-alkylene-N($R^{31}$)$SO_2$—$R^{31}$, $C_{0-6}$-alkylene-$SO_2$—$R^{31}$, $C_{0-6}$-alkylene-SO—$R^{31}$ and $C_{0-6}$-alkylene-N($R^{31}$)$_2$, wherein alkyl, alkylene, cycloalkyl and heterocycloalkyl are unsubstituted or substituted by 1 to 4 substituents independently selected from the group consisting of halogen, CN, $C_{1-3}$-alkyl, halo-$C_{1-3}$-alkyl, $C_{3-6}$-cycloalkyl, $C_{3-6}$-heterocycloalkyl, OH, O—$C_{1-3}$-alkyl, O-halo-$C_{1-3}$-alkyl, O—$C_{3-6}$-cycloalkyl, O—$C_{3-6}$-heterocycloalkyl, oxo, N($R^{32}$)$_2$, COOH, CON($R^{32}$)$_2$, CN and $NR^{32}$—$COR^{32}$, and wherein optionally two adjacent substituents complete a 3- to 8-membered saturated or partially unsaturated ring containing carbon atoms and optionally containing 1 to 3 heteroatoms selected from O, S or N, wherein the ring is unsubstituted or substituted with 1 to 6 substituents independently selected from halogen, $C_{1-6}$-alkyl, halo-$C_{1-6}$-alkyl, $C_{3-6}$-cycloalkyl, $C_{3-6}$-heterocycloalkyl, oxo, OH, O—$C_{1-6}$-alkyl and O-halo-$C_{1-6}$-alkyl;

and $R^2$ is selected from the group consisting of H, $C_{1-6}$-alkyl, halo-$C_{1-6}$-alkyl and hydroxy-$C_{1-6}$-alkyl, or $R^1$ and $R^2$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from halogen, oxo, CN, $OR^{11}$, $SO_yR^{11}$, $SO_3H$, $NR^{11}SO_2R^{11}$, $SO_2NR^{11}R^{12}$, $CO_2R^{11}$, $CONR^{11}R^{12}$, $NR^{11}$—CO—$R^{11}$, $NR^{11}$—CO—$NR^{11}R^{12}$, $NR^{11}$—$SO_2$—$NR^{11}R^{12}$, $NR^{11}R^{12}$, $C_{1-6}$-alkyl, halo-$C_{1-6}$-alkyl, hydroxy-$C_{1-6}$-alkyl, $C_{3-6}$-cycloalkyl, O—$C_{3-6}$-cycloalkyl, $C_{3-6}$-heterocycloalkyl and O—$C_{3-6}$-heterocycloalkyl;

$R^4$ is $SO_2$—$(CR^8R^8)_yR^7$, $SO_2$—$NR^{12}R^7$ or $(CR^8R^8)_x$—$R^{10}$;

$R^5$ is selected from H, $C_{1-6}$-alkyl, halo-$C_{1-6}$-alkyl, CHO or halogen, wherein alkyl is unsubstituted or substituted with 1 to 3 substituents independently selected from the group consisting of O—$C_{1-6}$-alkyl, O-halo-$C_{1-6}$-alkyl and OH;

$R^6$ is selected from H, $C_{1-6}$-alkyl, halo-$C_{1-6}$-alkyl or halogen;

$R^7$ is selected from $C_{3-10}$-cycloalkyl and $C_{3-10}$-heterocycloalkyl, wherein cycloalkyl and heterocycloalkyl are unsubstituted or substituted with 1 to 3 substituents independently selected from the group consisting of halogen, OH, oxo, O—$C_{1-6}$-alkyl, O-halo-$C_{1-6}$-alkyl, $C_{1-6}$-alkyl, halo-$C_{1-6}$-alkyl, cycloalkyl and heterocycloalkyl;

$R^8$ is independently selected from H, F, $C_{1-3}$-alkyl, halo-$C_{1-3}$-alkyl or OH;

$R^{10}$ is $C_{3-10}$-cycloalkyl, wherein cycloalkyl is unsubstituted or substituted with 1 to 6 substituents independently selected from halogen, OH, oxo, O—$C_{1-6}$-alkyl, O-halo-$C_{1-6}$-alkyl, $C_{1-6}$-alkyl, cycloalkyl, heterocycloalkyl, and optionally two adjacent substituents together complete a 6-membered aryl ring wherein the ring is unsubstituted or substituted with 1 to 3 substituents independently selected from halogen, $C_{1-2}$-alkyl, halo-$C_{1-2}$-alkyl;

$R^{11}$ is independently selected from H, $C_{1-6}$-alkyl, $C_{0-6}$-alkylene-$C_{3-6}$-cycloalkyl, $C_{0-6}$-alkylene-$C_{3-6}$-heterocycloalkyl, wherein alkyl, alkylene, cyclolalkyl and heterocycloalkyl are unsubstituted or substituted with 1 to 6 substituents independently selected from halogen, OH, oxo, $C_{1-3}$-alkyl, halo-$C_{1-3}$-alkyl, O—$C_{1-3}$-alkyl, O-halo-$C_{1-3}$-alkyl and $SO_2$—$C_{1-3}$-alkyl;

$R^{12}$ is independently selected from H, $C_{1-6}$-alkyl and halo-$C_{1-6}$-alkyl;

$R^{31}$ is independently selected from H, $C_{1-6}$-alkyl, $C_{0-6}$-alkylene-$C_{3-6}$-cycloalkyl, $C_{0-6}$-alkylene-$C_{3-6}$-heterocycloalkyl, a 6-membered aryl wherein alkyl, alkylene, cyclolalkyl, heterocycloalkyl and aryl are unsubstituted or substituted with 1 to 6 substituents independently selected from halogen, OH, oxo, $C_{1-3}$-alkyl, halo-$C_{1-3}$-alkyl, O—$C_{1-3}$-alkyl, O-halo-$C_{1-3}$-alkyl and $SO_2$—$C_{1-3}$-alkyl;

$R^{32}$ is independently selected from H, $C_{1-6}$-alkyl and halo-$C_{1-6}$-alkyl;

x is independently selected from 1 and 2;

y is independently selected from 0, 1 and 2;

with the proviso that $R^3$ is not an unsubstituted or substituted ring selected from

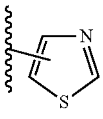
,
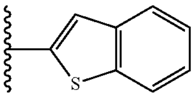
,
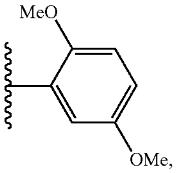

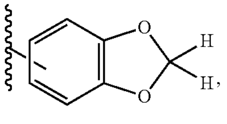
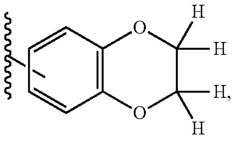

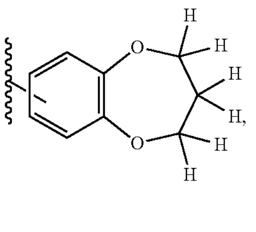

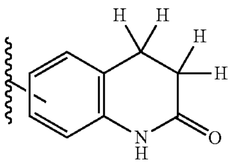
and
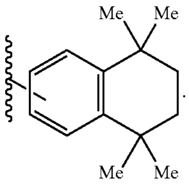
.

In a first alternative, the invention provides a compound represented by Formula (1)

(1)

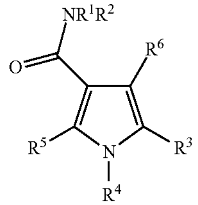

an enantiomer, diastereomer, tautomer, N-oxide, solvate, formulation and pharmaceutically acceptable salt thereof, wherein $R^1$ is selected from H, $C_{3-6}$-cycloalkyl, $C_{3-6}$-heterocycloalkyl, $C_{1-10}$-alkylene-$C_{3-10}$-cycloalkyl, $C_{1-10}$-alkylene-$C_{3-10}$-heterocycloalkyl, $C_{1-10}$-alkylene-(5-membered monocyclic heteroaryl), wherein alkyl, alkylene, cycloalkyl, heterocycloalkyl and heteroaryl is unsubstituted or substituted with 1 to 7 substituents independently selected from oxo, CN, $OR^{11}$, O—$C_{2-6}$-alkylene-$OR^{11}$, $C_{1-6}$-alkyl, halo-$C_{1-6}$-alkyl, halogen, $CO_2R^{11}$, $CONR^{11}R^{12}$, $COR^{11}$, $SO_yR^{11}$, $SO_3H$, $SO_2NR^{11}R^{12}$, $NR^{11}COR^{11}$, $NR^{11}SO_2R^{11}$, $NR^{11}$—CO—$NR^{11}R^{12}$, $NR^{11}$—$SO_2$—$NR^{11}R^{12}$, $C_{3-6}$-cycloalkyl, O—$C_{3-6}$-cycloalkyl, $C_{3-6}$-heterocycloalkyl, O—$C_{3-6}$-heterocycloalkyl and $NR^{11}R^{12}$;

$R^2$ is selected from the group consisting of H, halo-$C_{1-6}$-alkyl and hydroxy-$C_{1-6}$-alkyl, or $R^1$ and $R^2$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from halogen, oxo, CN, $OR^{11}$, $SO_yR^{11}$, $SO_3H$, $NR^{11}SO_2R^{11}$, $SO_2NR^{11}R^{12}$, $C_{0-6}$-alkylene-$CO_2R^{11}$, $CONR^{11}R^{12}$, $COR^{11}$, $NR^{11}$—CO—$R^{11}$, $NR^{11}$—CO—$NR^{11}R^{12}$, $NR^{11}$—$SO_2$—$NR^{11}R^{12}$, $NR^{11}R^{12}$, $C_{1-6}$-alkyl, halo-$C_{1-16}$-alkyl, hydroxy-$C_{1-6}$-alkyl, $C_{3-6}$-cycloalkyl, O—$C_{3-6}$-cycloalkyl, $C_{3-6}$-heterocycloalkyl and O—$C_{3-6}$-heterocycloalkyl, wherein cycloalkyl and heterocycloalkyl are unsubstituted or substituted with 1 to 4 substitutents independently selected from halogen, $C_{1-3}$-alkyl, halo-$C_{1-3}$-alkyl and oxo;

$R^3$ is a 6- or 10-membered mono- or bicyclic aryl or a 6- to 10-membered mono- or bicyclic heteroaryl containing 1 or 2 heteroatoms selected from the group consisting of N, O and S, wherein aryl and heteroaryl is substituted with at least one group selected from $C_{3-6}$-cycloalkyl, $C_4$-heterocycloalkyl, $C_{1-4}$-alkylene-$C_{3-10}$-cycloalkyl, carbon atom linked 5- or 6-membered monocyclic heteroaryl, $C_{1-4}$-alkylene-O—$R^{31}$, O—$C_{3-10}$-cycloalkyl, $C(O)R^{31}$, $C_{0-6}$-alkylene-$C(O)N(R^{31})_2$, $SO_2$—$N(R^{31})_2$, $N(R^{31})SO_2$—$R^{31}$, $SO_2$—$C_{3-10}$-heterocycloalkyl, SO—$R^{31}$ and two adjacent substituents completing a 3- to 8-membered saturated or partially unsaturated ring containing carbon atoms and optionally containing 1 to 3 heteroatoms selected from O, S or N, wherein the ring is unsubstituted or substituted with 1 to 6 substituents independently selected from halogen, $C_{1-6}$-alkyl, halo-$C_{1-6}$-alkyl, $C_{3-6}$-cycloalkyl, $C_{3-6}$-heterocycloalkyl, oxo, =N—$OR^{32}$, OH, O—$C_{1-6}$-alkyl and O-halo-$C_{1-6}$-alkyl, wherein alkylene, cycloalkyl, heterocycloalkyl and the carbon atom linked 5- or 6-membered monocyclic heteroaryl is optionally substituted by 1 to 4 substituents independently selected from the group consisting of halogen, CN, halo-$C_{1-3}$-alkyl, OH, oxo, $=N—OR^{32}$, O—$C_{1-3}$-alkyl and O-halo-$C_{1-3}$-alkyl; and wherein aryl and heteroaryl are optionally substituted by 1 to 4 substituents independently selected from the group consisting of halogen, CN, halo-$C_{1-3}$-alkyl, OH, O—$C_{1-3}$-alkyl and O-halo-$C_{1-3}$-alkyl; and $R^4$ is $SO_2—(CR^8R^8)_yR^7$, $SO_2—NR^{12}R^7$, $(CR^8R^8)_x—R^{10}$ or $C_{3-6}$-cycloalkyl, which is spirocyclic fused with $C_{3-10}$-cycloalkyl;

$R^5$ is selected from H, halo-$C_{1-6}$-alkyl, CHO, $CON(R^{52})_2$ or halogen, wherein alkyl is unsubstituted or substituted with 1 to 3 substituents independently selected from the group consisting of O—$C_{1-6}$-alkyl, O-halo-$C_{1-6}$-alkyl and OH;

$R^6$ is selected from H, $C_{1-6}$-alkyl, halo-$C_{1-6}$-alkyl or halogen;

$R^7$ is selected from $C_{3-10}$-cycloalkyl and $C_{3-10}$-heterocycloalkyl, wherein cycloalkyl and heterocycloalkyl are unsubstituted or substituted with 1 to 3 substituents independently selected from the group consisting of halogen, OH, oxo, O—$C_{1-6}$-alkyl, O-halo-$C_{1-6}$-alkyl, $C_{1-6}$-alkyl, halo-$C_{1-6}$-alkyl, cycloalkyl and heterocycloalkyl;

$R^8$ is independently selected from H, F, $C_{1-3}$-alkyl, halo-$C_{1-3}$-alkyl or OH;

$R^{10}$ is $C_{3-10}$-cycloalkyl, wherein cycloalkyl is unsubstituted or substituted with 1 to 6 substituents independently selected from halogen, OH, oxo, O—$C_{1-6}$-alkyl, O-halo-$C_{1-6}$-alkyl, $C_{1-6}$-alkyl, halo-$C_{1-6}$-alkyl, cycloalkyl, heterocycloalkyl, and optionally two adjacent substituents together complete a 6-membered aryl ring wherein the ring is unsubstituted or substituted with 1 to 3 substituents independently selected from halogen, $C_{1-2}$-alkyl, halo-$C_{1-2}$-alkyl;

$R^{11}$ is independently selected from H, $C_{1-6}$-alkyl, $C_{0-6}$-alkylene-$C_{3-6}$-cycloalkyl, $C_{0-6}$-alkylene-$C_{3-6}$-heterocycloalkyl, wherein alkyl, alkylene, cyclolalkyl and heterocycloalkyl are unsubstituted or substituted with 1 to 6 substituents independently selected from halogen, OH, oxo, $C_{1-3}$-alkyl, halo-$C_{1-3}$-alkyl, O—$C_{1-3}$-alkyl, O-halo-$C_{1-3}$-alkyl and $SO_2—C_{1-3}$-alkyl;

$R^{12}$ is independently selected from H, $C_{1-6}$-alkyl and halo-$C_{1-6}$-alkyl;

$R^{31}$ is independently selected from H, $C_{1-6}$-alkyl, halo-$C_{1-6}$-alkyl, $C_{0-6}$-alkylene-$C_{3-6}$-cycloalkyl, $C_{0-6}$-alkylene-$C_{3-6}$-heterocycloalkyl, 5- or 6-membered heteroaryl and 6-membered aryl, wherein alkyl, alkylene, cyclolalkyl, heterocycloalkyl, aryl and heteroaryl are unsubstituted or substituted with 1 to 6 substituents independently selected from halogen, CN, OH, oxo, $C_{1-3}$-alkyl, halo-$C_{1-3}$-alkyl, O—$C_{1-3}$-alkyl, O-halo-$C_{1-3}$-alkyl and $SO_2—C_{1-3}$-alkyl;

and optionally wherein two $R^{31}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from fluoro, OH, oxo, $C_{1-4}$-alkyl and halo-$C_{1-4}$-alkyl;

$R^{32}$ is independently selected from H, $C_{1-6}$-alkyl and halo-$C_{1-6}$-alkyl;

$R^{52}$ is independently selected from H, $C_{1-3}$-alkyl and halo-$C_{1-3}$-alkyl;

x is independently selected from 1 and 2;

y is independently selected from 0, 1 and 2.

In an additionally preferred embodiment in combination with any of the above or below embodiments of the first alternative $R^3$ is selected from phenyl, pyridinyl, pyrimidinyl, naphthyl, benzothiophenyl and quinolinyl, wherein phenyl, pyridinyl, pyrimidinyl, naphthyl, benzothiophenyl and quinolinyl is substituted with at least one group selected from $C_{3-4}$-cycloalkyl, carbon atom linked 5- or 6-membered monocyclic heteroaryl, $C_{1-4}$-alkylene-O—$R^{31}$, $C(O)R^{31}$, $C(O)N(R^{31})_2$, $SO_2—N(R^{31})_2$, $SO_2—C_{3-10}$-heterocycloalkyl, SO—$R^{31}$ and two adjacent substituents completing a 3- to 8-membered saturated or partially unsaturated ring containing carbon atoms and optionally containing 1 to 3 heteroatoms selected from O, S or N, wherein the ring is unsubstituted or substituted with 1 to 5 substituents independently selected from halogen, $C_{1-3}$-alkyl, halo-$C_{1-3}$-alkyl, $C_{3-4}$-cycloalkyl, $C_{3-4}$-heterocycloalkyl, oxo, OH, O—$C_{1-3}$-alkyl and O-halo-$C_{1-3}$-alkyl, wherein phenyl, pyridinyl, pyrimidinyl, naphthyl, benzothiophenyl, chinolinyl, alkyl, alkylene, cycloalkyl, heterocycloalkyl and the carbon atom linked 5- or 6-membered monocyclic heteroaryl are optionally substituted by 1 to 4 substituents independently selected from the group consisting of halogen, CN, $C_{1-3}$-alkyl, halo-$C_{1-3}$-alkyl, OH, O—$C_{1-3}$-alkyl and O-halo-$C_{1-3}$-alkyl.

In a further preferred embodiment in combination with any of the above or below embodiments of the first alternative $R^1$ is selected from $C_{1-10}$-alkyl, $C_{3-6}$-cycloalkyl, $C_{3-6}$-heterocycloalkyl, $C_{1-10}$-alkylene-$C_{3-10}$-cycloalkyl, $C_{1-10}$-alkylene-$C_{3-10}$-heterocycloalkyl, wherein alkyl, alkylene, cycloalkyl and heterocycloalkyl is unsubstituted or substituted with 1 to 7 substituents independently selected from oxo, CN, $OR^{11}$, O—$C_{2-6}$-alkylene-$OR^{11}$, $C_{1-6}$-alkyl, halo-$C_{1-6}$-alkyl, halogen, $CO_2R^{11}$, $CONR^{11}R^{12}$, $COR^{11}$, $SO_yR^{11}$, $SO_3H$, $SO_2NR^{11}R^{12}$, $NR^{11}COR^{11}$, $NR^{11}SO_2R^{11}$, $NR^{11}$—CO—$NR^{11}R^{12}$, $NR^{11}$—$SO_2$—$NR^{11}R^{12}$, $C_{3-6}$-cycloalkyl, O—$C_{3-6}$-cycloalkyl, $C_{3-6}$-heterocycloalkyl, O—$C_{3-6}$-heterocycloalkyl and $NR^{11}R^{12}$;

$R^2$ is selected from the group consisting of H, $C_{1-6}$-alkyl and halo-$C_{1-6}$-alkyl, or $R^1$ and $R^2$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from halogen, oxo, CN, $OR^{11}$, $SO_yR^{11}$, $SO_3H$, $NR^{11}SO_2R^{11}$, $SO_2NR^{11}R^{12}$, $C_{0-6}$-alkylene-$CO_2R^{11}$, $CONR^{11}R^{12}$, $COR^{11}$, $NR^{11}$—CO—$R^{11}$, $NR^{11}$—CO—$NR^{11}R^{12}$, $NR^{11}$—$SO_2$—$NR^{11}R^{12}$, $NR^{11}R^{12}$, $C_{1-6}$-alkyl, halo-$C_{1-6}$-alkyl, hydroxy-$C_{1-6}$-alkyl, $C_{3-6}$-cycloalkyl, O—$C_{3-6}$-cycloalkyl, $C_{3-6}$-heterocycloalkyl and O—$C_{3-6}$-heterocycloalkyl, wherein cycloalkyl and heterocycloalkyl are unsubstituted or substituted with 1 to 4 substitutents independently selected from halogen, $C_{1-3}$-alkyl, halo-$C_{1-3}$-alkyl and oxo.

In an additionally preferred embodiment in combination with any of the above or below embodiments of the first alternative $R^1$ is selected from $C_{1-10}$-alkyl, $C_{3-6}$-cycloalkyl, $C_{3-6}$-heterocycloalkyl, $C_{1-10}$-alkylene-$C_{3-10}$-cycloalkyl, more preferably $C_{1-3}$-alkylene-$C_{3-10}$-cycloalkyl, $C_{1-10}$-alkylene-$C_{3-6}$-heterocycloalkyl, more preferably $C_{1-3}$-alkylene-$C_{3-6}$-heterocycloalkyl, wherein alkyl, alkylene, cycloalkyl and heterocycloalkyl is unsubstituted or substituted with 1 to 7 substituents independently selected from oxo, CN, $OR^{11}$, O—$C_{2-6}$-alkylene-$OR^{11}$, $C_{1-6}$-alkyl, halo-$C_{1-6}$-alkyl, halogen, $CO_2H$, $CONR^{11}R^{12}$, $COR^{11}$, $SO_yR^{11}$, $SO_3H$, $SO_2NR^{11}R^{12}$, $NR^{11}COR^{11}$, $NR^{11}SO_2R^{11}$, $NR^{11}$—CO—$NR^{11}R^{12}$, $NR^{11}$—$SO_2$—$NR^{11}R^{12}$, $C_{3-6}$-cycloalkyl, O—$C_{3-6}$-cycloalkyl, $C_{3-6}$-heterocycloalkyl, O—$C_{3-6}$-heterocycloalkyl and $NR^{11}R^{12}$;

$R^2$ is selected from the group consisting of H, $C_{1-6}$-alkyl and halo-$C_{1-6}$-alkyl, more preferably $R^2$ is hydrogen;

or $R^1$ and $R^2$ when taken together with the nitrogen to which they are attached complete a 3- to 6-membered ring containing carbon atoms and optionally containing 1 or 2 heteroatoms selected from O, S or N, wherein the ring is unsubstituted or substituted with 1 to 4 substitutents independently selected from halogen, oxo, CN, $OR^{11}$, $SO_yR^{11}$, $SO_3H$, $NR^{11}SO_2R^{11}$, $SO_2NR^{11}R^{12}$, $CMe_2CO_2H$, $CONR^{11}R^{12}$, $COR^{11}$, $NR^{11}$—CO—$R^{11}$, $NR^{11}$—CO—$NR^{11}R^{12}$, $NR^{11}$—$SO_2$—$NR^{11}R^{12}$, $NR^{11}R^{12}$, $C_{1-6}$-alkyl, halo-$C_{1-6}$-alkyl, hydroxy-$C_{1-6}$-alkyl, $C_{3-6}$-cycloalkyl, O—$C_{3-6}$-cycloalkyl, $C_{3-6}$-heterocycloalkyl and O—$C_{3-6}$-heterocycloalkyl, wherein cycloalkyl and heterocycloalkyl are unsubstituted or substituted with 1 to 4 substitutents independently selected from halogen, $C_{1-3}$-alkyl, halo-$C_{1-3}$-alkyl and oxo.

In an additionally preferred embodiment in combination with any of the above or below embodiments of the first alternative $R^1$ contains

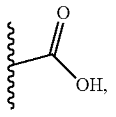 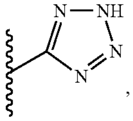, 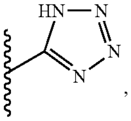,

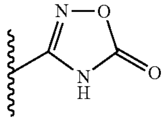 or 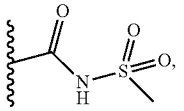

more preferred $R^1$ contains a carboxylic acid moiety and even more preferred $R^1$ contains a secondary or tertiary carboxylic acid moiety.

In a preferred embodiment in combination with any of the above or below embodiments of the first alternative $NR^1R^2$ is selected from $NH_2$, NHMe, NHEt, $NH^iPr$, $NH^tBu$, $NHCH_2CONH_2$, $NHCH_2CONMe_2$, $NHCH_2CH_2OH$, $NHCH_2CH(CF_3)OH$, $NHCH_2C(CF_3)_2OH$, $NHCH_2CH_2OMe$, $NHCH_2CH_2SO_2Me$, $NHCH_2CH_2SO_2NH_2$, $NH(CH_2)_3OH$, $NH(CH_2)_3OMe$, $NH(CH_2)_4OH$, $NH(CH_2)_4OMe$, $NH(CH_2)_5OH$, $NH(CH_2)_2CO_2H$, $NH(CH_2)_3CO_2H$, $NH(CH_2)_4CO_2H$, $NH(CH_2)_5CO_2H$, $NHCH_2CMe_2OH$, $NHCH(Me)CMe_2OH$, $NHCH_2CMe_2OMe$, $NHCH_2CMe_2CO_2H$, $NHCH_2CMe_2CONH_2$, $NHCH_2CMe_2CONHMe$, $NHCH_2CMe_2CONMe_2$, $NHCH_2CMe_2NHSO_2Me$, $NH(CH_2)_3SOMe$, $NH(CH_2)_5SO_2Me$, $NH(CH_2)_5SO_2NH_2$, $NH(CH_2)_3NHSO_2Me$, $NH(CH_2)_2O(CH_2)_2OH$, $NHCH_2CHMeOH$, $NH(CH_2)_5SOMe$, $NH(CH_2)_3SO_2Me$, 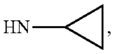, 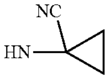,

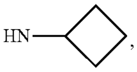, 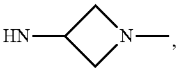, 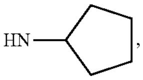,

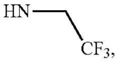 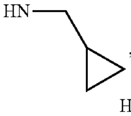, 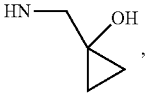,

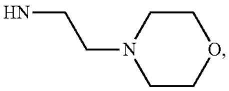 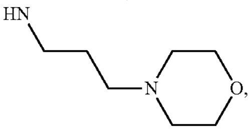

-continued

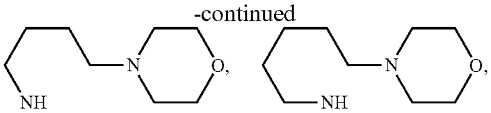

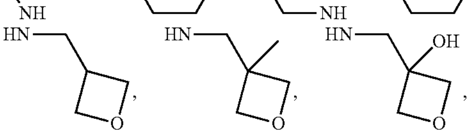

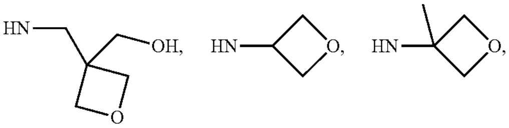

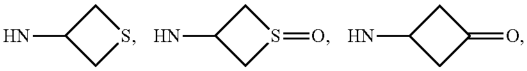

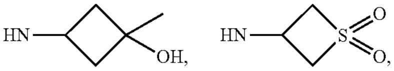

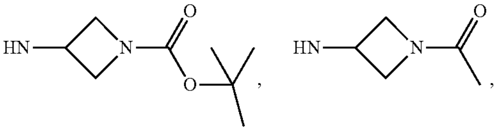

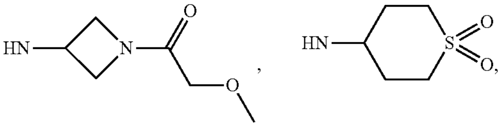

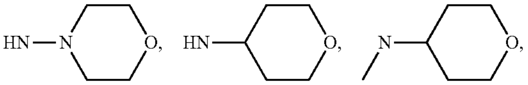

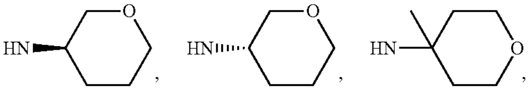

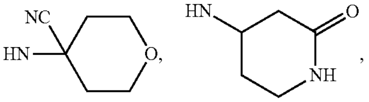

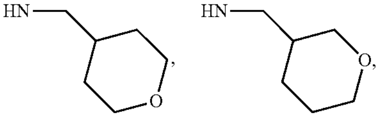

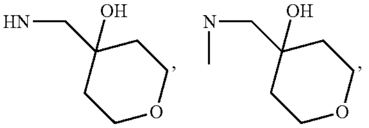

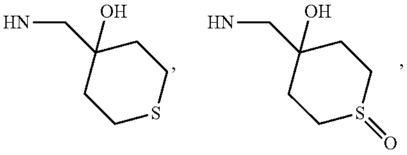

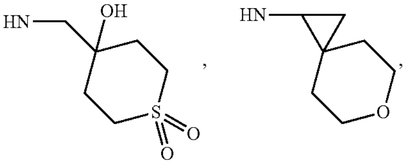

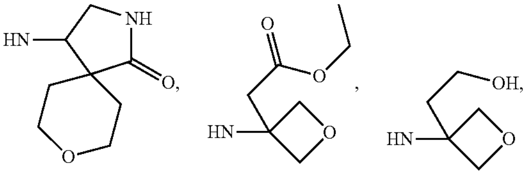

-continued
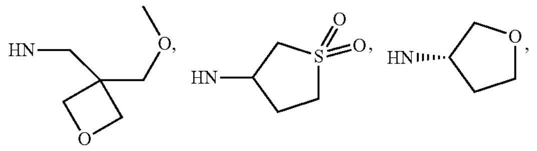
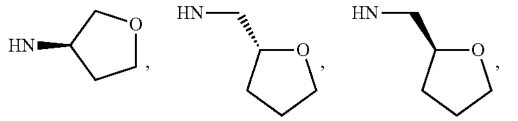
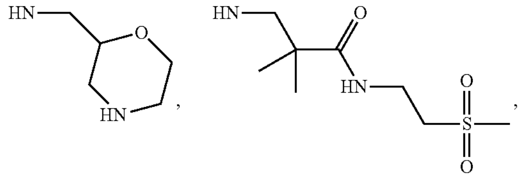
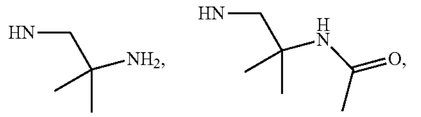
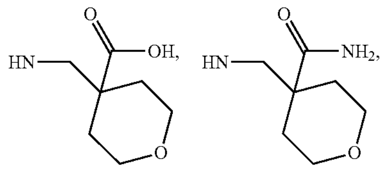
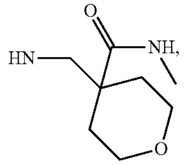
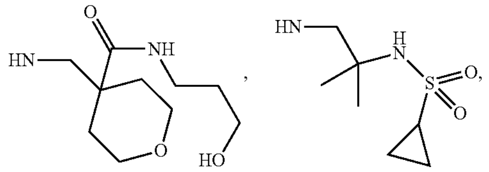
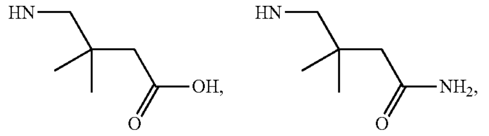
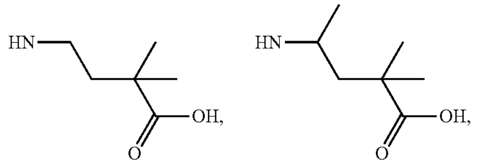
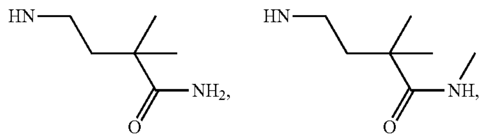
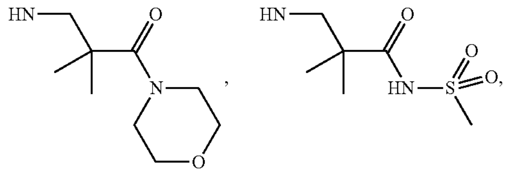
-continued
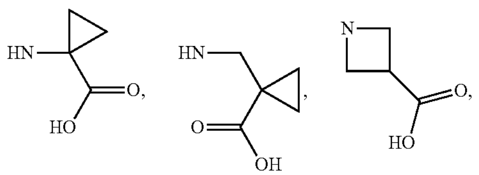
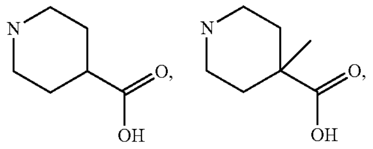
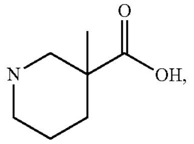
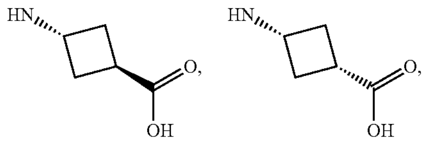
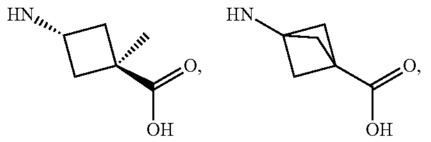
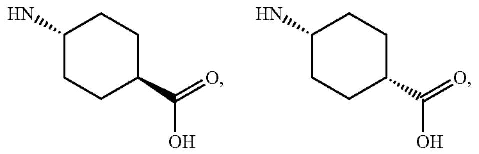
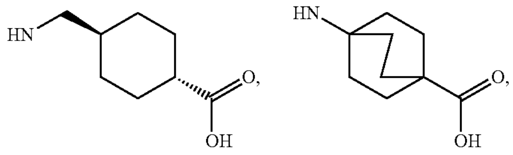
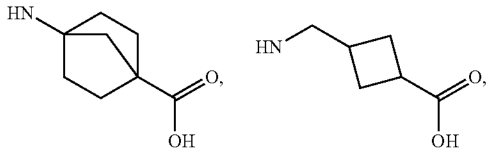
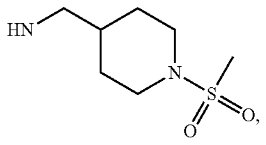
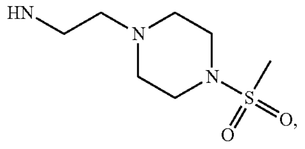
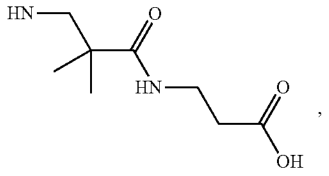

-continued

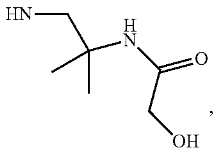

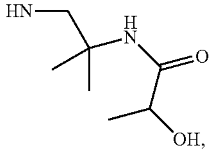

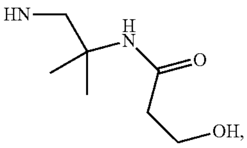

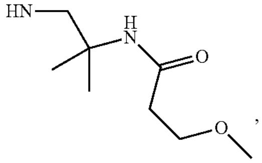

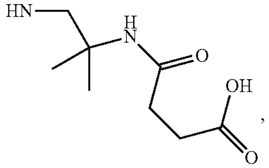

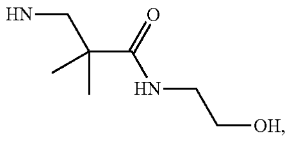

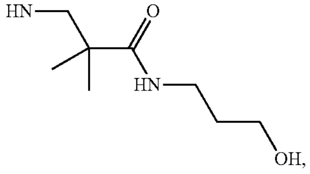

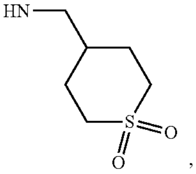

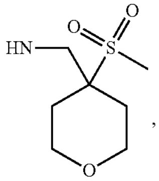

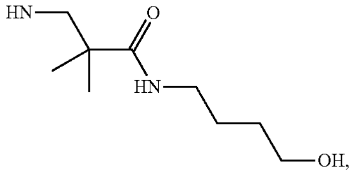

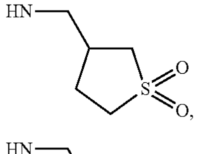

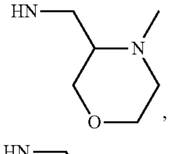

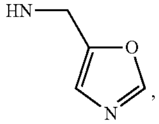

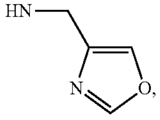

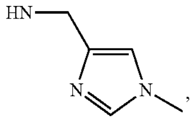

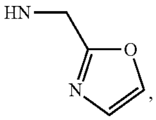

-continued

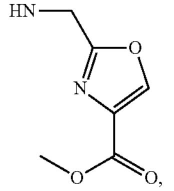

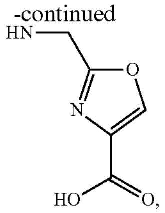

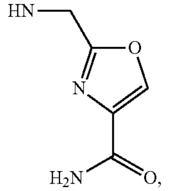

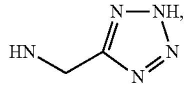

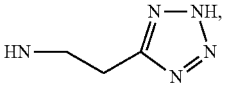

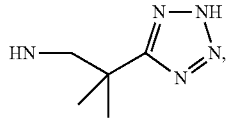

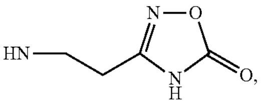

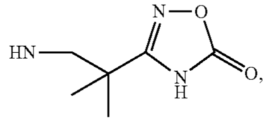

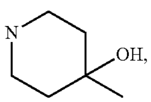

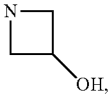

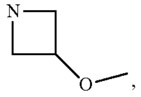

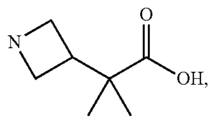

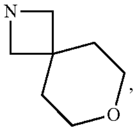

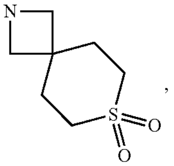

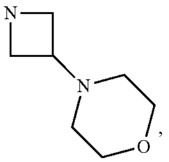

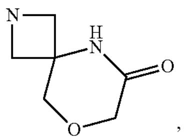

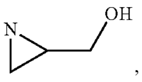

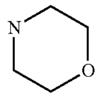

and

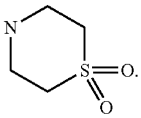

In a further preferred embodiment in combination with any of the above or below embodiments of the first alternative $NR^1R^2$ is selected from $NH_2$, NHMe, NHEt, $NH^iPr$, $NH^tBu$, $NHCH_2CONH_2$, $NHCH_2CONMe_2$, $NHCH_2CH_2OH$, $NHCH_2CH(CF_3)OH$, $NHCH_2C(CF_3)_2OH$, $NHCH_2CH_2OMe$, $NHCH_2CH_2SO_2Me$, $NHCH_2CH_2SO_2NH_2$, $NH(CH_2)_3OH$, $NH(CH_2)_3OMe$, $NH(CH_2)_4OH$, $NH(CH_2)_4OMe$, $NH(CH_2)_5OH$, $NH(CH_2)_2CO_2H$, $NH(CH_2)_3CO_2H$, $NH(CH_2)_4CO_2H$, $NH(CH_2)_5CO_2H$, $NHCH_2CMe_2OH$, $NHCH(Me)CMe_2OH$, $NHCH_2CMe_2OMe$, $NHCH_2CMe_2CO_2H$, $NHCH_2CMe_2CONH_2$, $NHCH_2CMe_2CONHMe$, $NHCH_2CMe_2CONMe_2$, $NHCH_2CMe_2NHSO_2Me$, $NH(CH_2)_3SOMe$, $NH(CH_2)_5SO_2Me$, $NH(CH_2)_3NHSO_2Me$, $NH(CH_2)_2O(CH_2)_2OH$, $NHCH_2CHMeOH$,

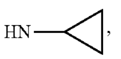

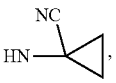

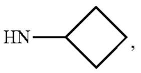

-continued
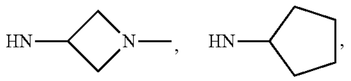
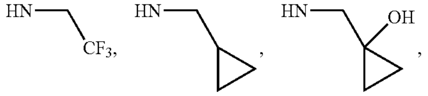
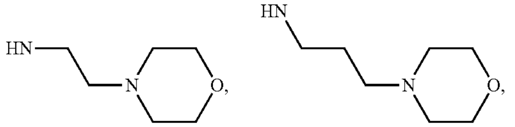
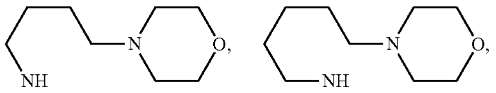
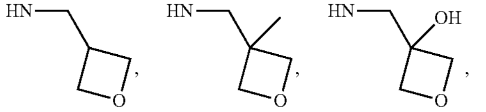
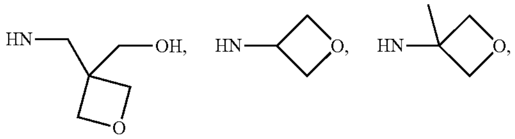
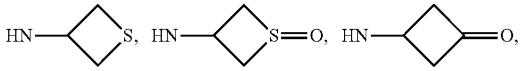
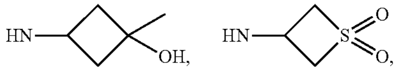
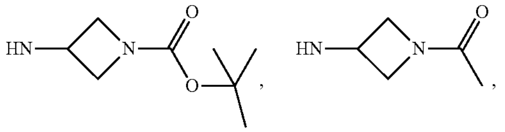
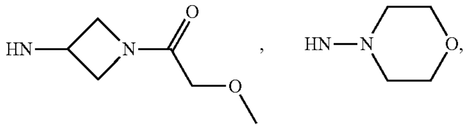
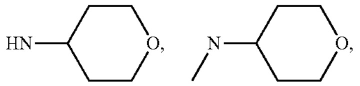
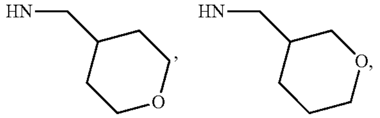
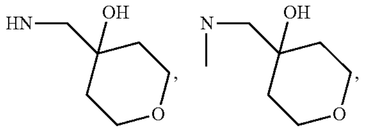
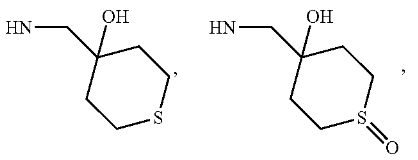
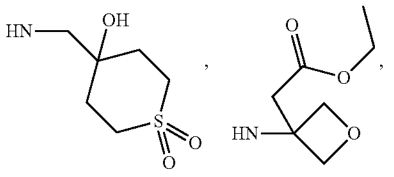
-continued
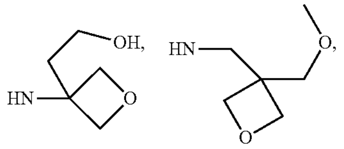
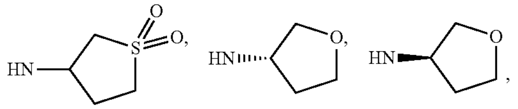
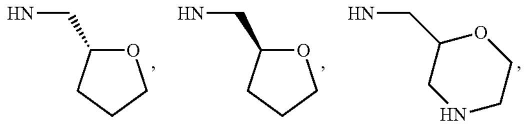
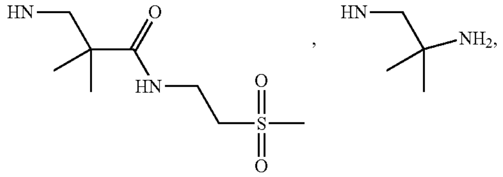
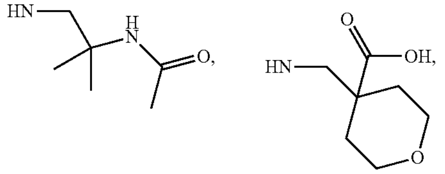
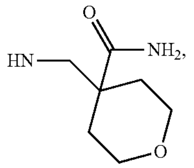
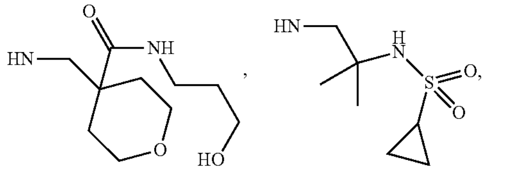
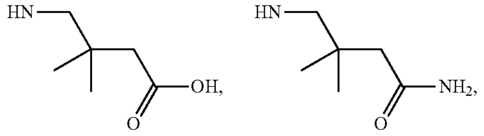
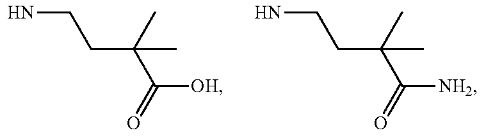
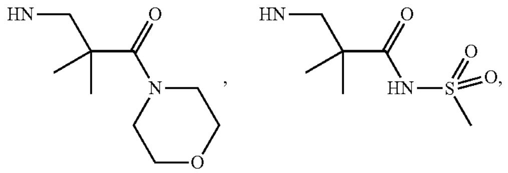
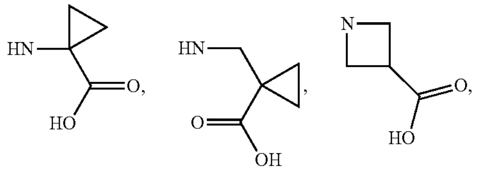

-continued
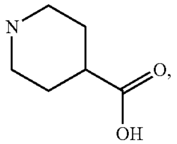,
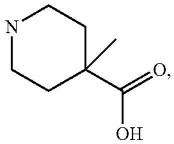,
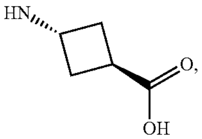,
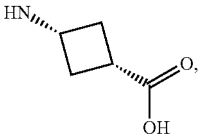,
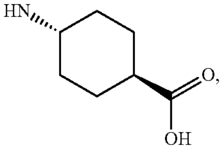,
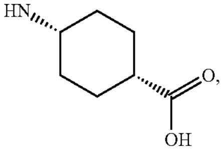,
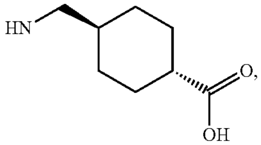,
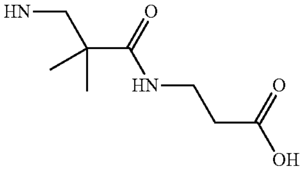,
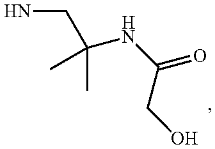,
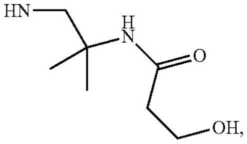,
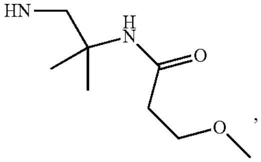,
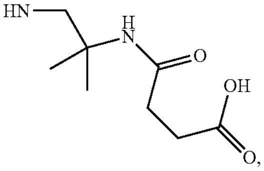,
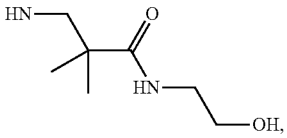,
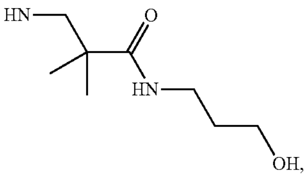,
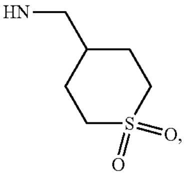,
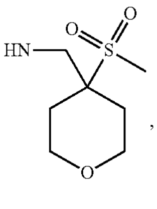,
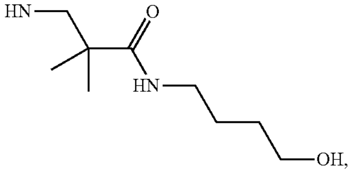,
-continued
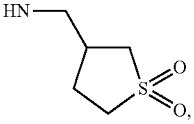,
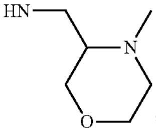,
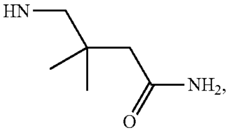,
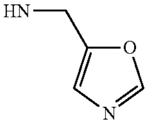,
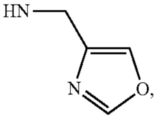,
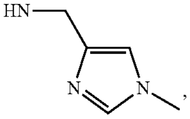,
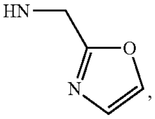,
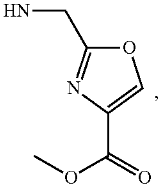,
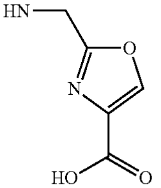,
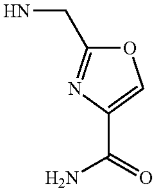,
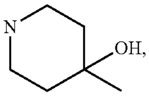,
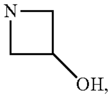,
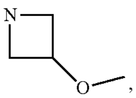,
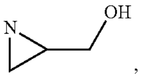,
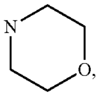, and
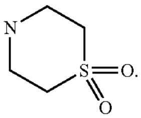.
In a more preferred embodiment in combination with any of the above or below embodiments of the first alternative $NR^1R^2$ is selected from
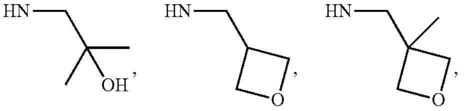
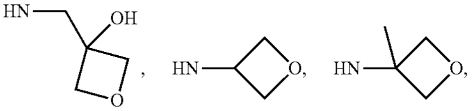
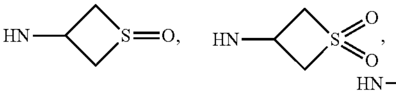
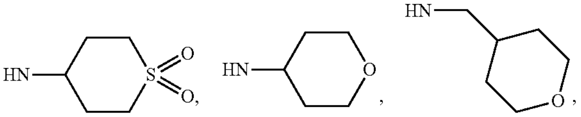
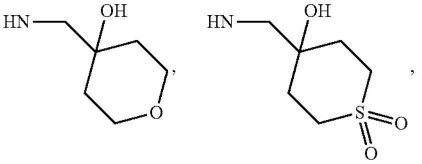

-continued
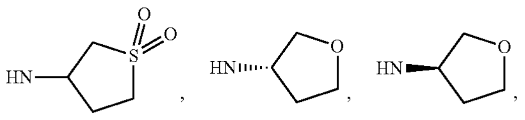
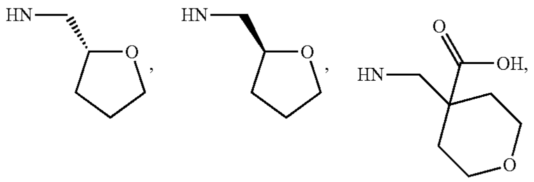
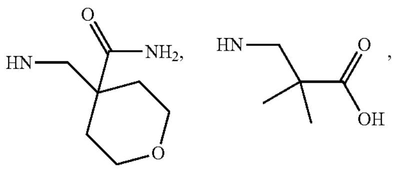
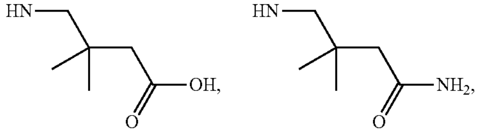
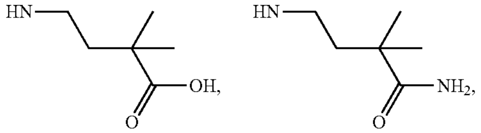
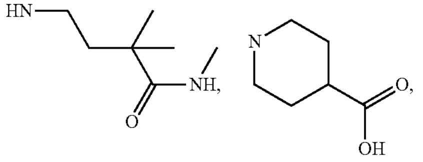
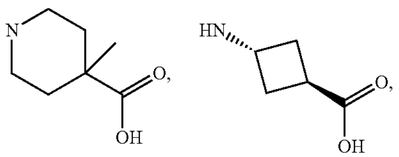
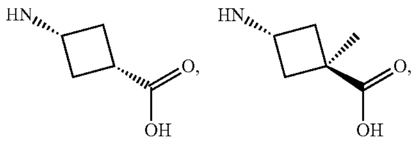
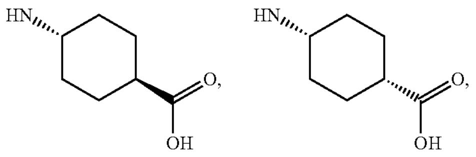
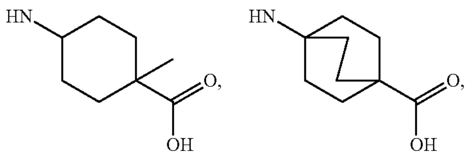
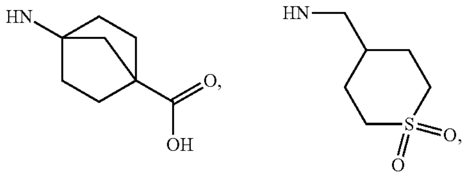
-continued
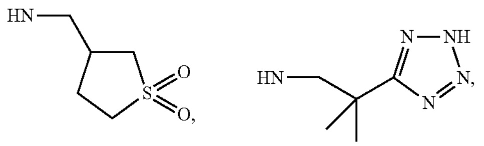
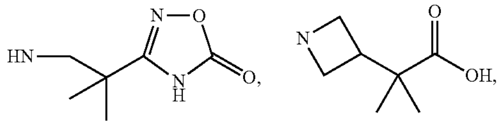
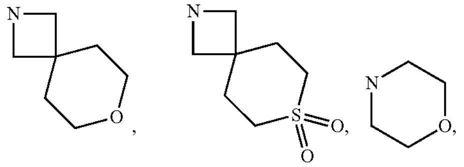
and
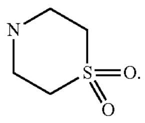
In an even more preferred embodiment in combination with any of the above or below embodiments of the first alternative $NR^1R^2$ is selected from
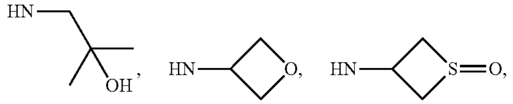
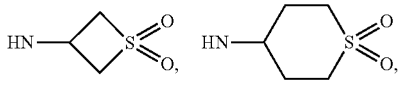
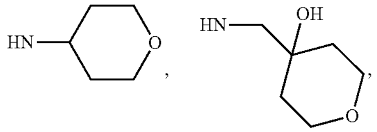
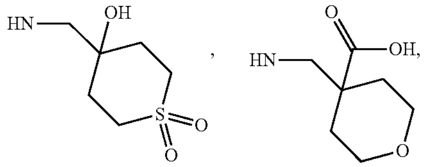
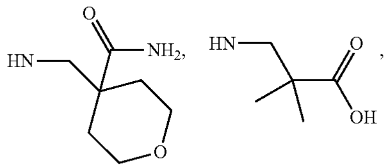
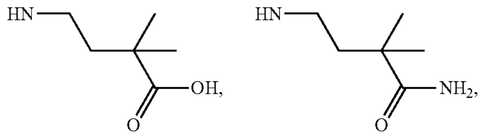
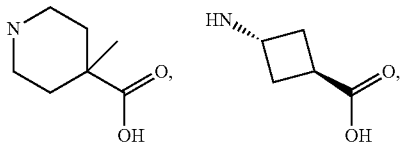

-continued

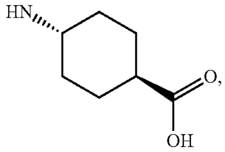,
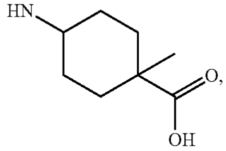,
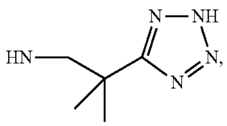,
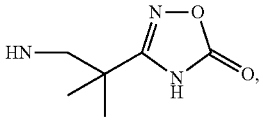,
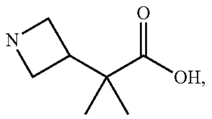,
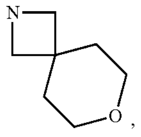,
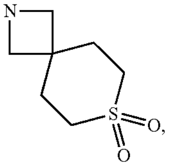,
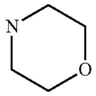 and 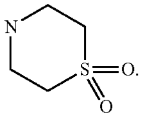.

In a most preferred embodiment in combination with any of the above or below embodiments of the first alternative $NR^1R^2$ is selected from

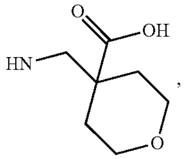,
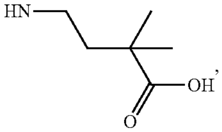,
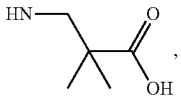,
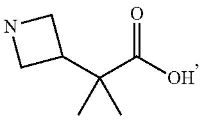,
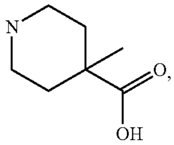,
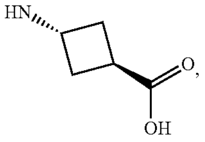,
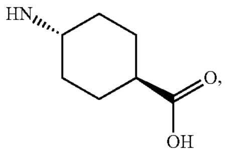,
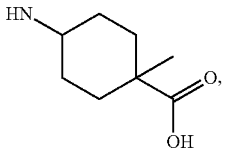,
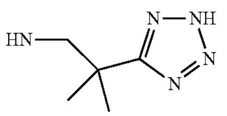 and 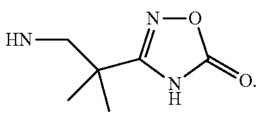.

In another preferred embodiment in combination with any of the above or below embodiments of the first alternative $R^3$ is selected from

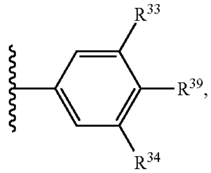,
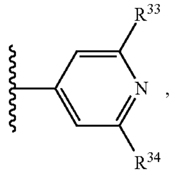,
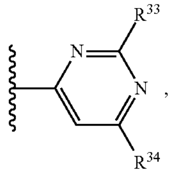,
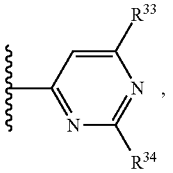,
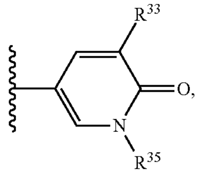,
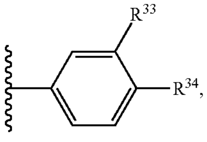,
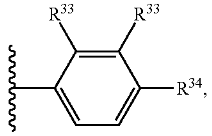,
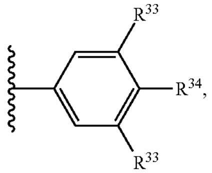,
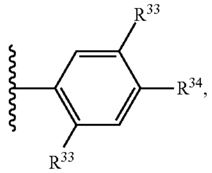,
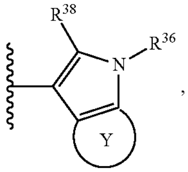,
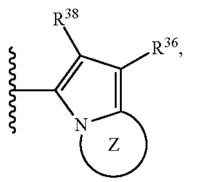,
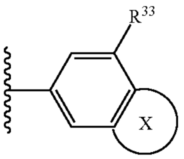 and
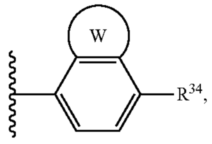, wherein $R^{33}$ is independently selected from H, halogen, CN, $C_{1-6}$-alkyl, fluoro-$C_{1-6}$-alkyl, $C_{1-4}$-alkylene-OH, $C_{1-4}$-alkylene-O—$C_{1-3}$-alkyl, $C_{1-4}$-alkylene-O-fluoro-$C_{1-3}$-alkyl, O—$C_{1-6}$-alkyl, O-fluoro-$C_{1-6}$-alkyl, NH—$C_{1-6}$-alkyl, NH-fluoro-$C_{1-6}$-alkyl, $C_{3-10}$-cycloalkyl, $C(O)N(R^{37})_2$, wherein alkylene is unsubstituted or substituted with 1 to 3 substituents selected from F, and cycloalkyl is unsubstituted or substituted with 1 to 3 substituents independently selected from F, $C_{1-3}$-alkyl and fluoro-$C_{1-3}$-alkyl;

$R^{34}$ is independently selected from $C_{1-4}$-alkylene-OH, $C_{1-4}$-alkylene-O—$C_{1-3}$-alkyl, $C_{1-4}$-alkylene-O-fluoro-$C_{1-3}$-alkyl, $C_{3-10}$-cycloalkyl, $C(O)N(R^{37})_2$, $SO_2N(R^{37})_2$, wherein alkylene is unsubstituted or substituted with 1 to 3 substituents selected from F, and cycloalkyl is unsubstituted or substituted with 1 to 3 substituents independently selected from F, $C_{1-3}$-alkyl and fluoro-$C_{1-3}$-alkyl;

$R^{35}$ is $C_{1-6}$-alkyl or fluoro-$C_{1-6}$-alkyl;

$R^{36}$ is independently selected from $C_{1-6}$-alkyl, fluoro-$C_{1-6}$-alkyl, $C(O)N(R^{37})_2$ and $SO_2N(R^{37})_2$;

$R^{37}$ is independently selected from H, $C_{1-6}$-alkyl, halo-$C_{1-6}$-alkyl, $C_{0-4}$-alkylene-$C_{3-6}$-cycloalkyl, $C_{0-4}$-alkylene-$C_{3-6}$-heterocycloalkyl, wherein alkyl and alkylene is unsubstituted or substituted with a substituent selected from halogen, OH, O—$C_{1-3}$-alkyl, CN; and cycloalkyl or heterocycloalkyl is unsubstituted or substituted with 1 to 3 substituents independently selected from F, CN, OH, oxo, $C_{1-3}$-alkyl and fluoro-$C_{1-3}$-alkyl;

or wherein two $R^{37}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from fluoro, OH, oxo, $C_{1-4}$-alkyl and halo-$C_{1-4}$-alkyl;

$R^{38}$ is independently selected from H, $C_{1-3}$-alkyl and fluoro-$C_{1-3}$-alkyl;

$R^{39}$ is H, F, OH, O—$C_{1-3}$-alkyl, O-halo-$C_{1-3}$-alkyl;

W is an annelated $C_{5-8}$-cycloalkyl, an annelated 6-membered aryl or an annelated 5- to 6-membered heteroaryl, wherein cycloalkyl, aryl and heteroaryl is unsubstituted or substituted with 1 to 2 substituents selected from halogen, methyl and $CF_3$, more preferably, W is an annelated aryl, unsubstituted or substituted with 1 to 2 substituents selected from fluoro, methyl and $CF_3$;

X is an annelated saturated heterocycle selected from the group consisting of

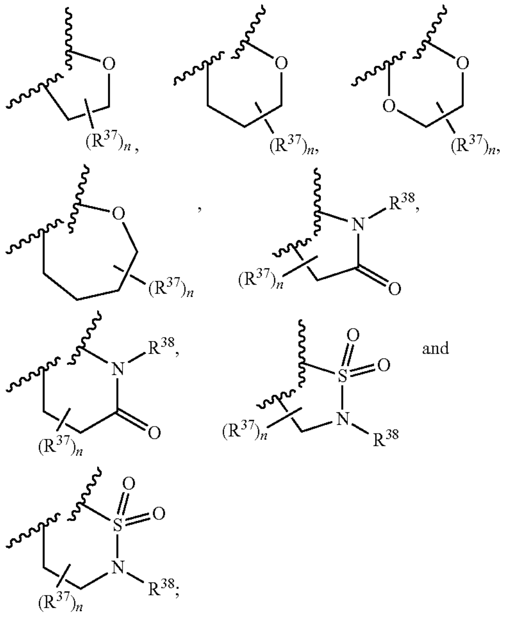

and

Y is an annelated 5- or 6-membered carbocycle, an annelated 6-membered aryl or an annelated 6-membered heteroaryl containing 1 to 2 nitrogen atoms, wherein the carbocycle, aryl or heteroaryl is unsubstituted or substituted with 1 to 3 substituents selected from fluoro, $C_{1-3}$-alkyl and fluoro-$C_{1-3}$-alkyl;

Z is an annelated 6-membered cycle forming a heteroaryl containing 1 to 2 nitrogen atoms, wherein the heteroaryl is unsubstituted or substituted with 1 to 3 substituents selected from fluoro, $C_{1-3}$-alkyl and fluoro-$C_{1-3}$-alkyl;

n is independently selected from 1 to 4.

In a more preferred embodiment in combination with any of the above or below embodiments of the first alternative $R^3$ is selected from

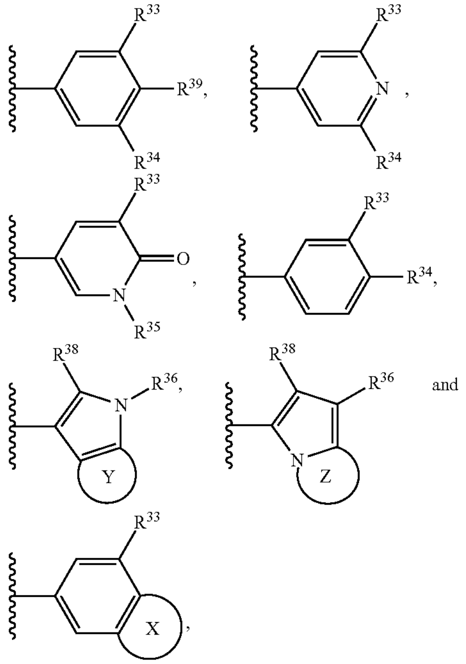

and wherein $R^{33}$ is selected from $C_{1-6}$-alkyl, fluoro-$C_{1-6}$-alkyl, $C_{1-4}$-alkylene-OH, $C_{1-4}$-alkylene-O—$C_{1-3}$-alkyl, $C_{1-4}$-alkylene-O-fluoro-$C_{1-3}$-alkyl, O—$C_{1-6}$-alkyl, O-fluoro-$C_{1-6}$-alkyl, $C_{3-10}$-cycloalkyl, $C(O)N(R^{37})_2$, wherein alkylene is unsubstituted or substituted with 1 to 3 substituents selected from F, and cycloalkyl is unsubstituted or substituted with 1 to 3 substituents independently selected from F, $C_{1-3}$-alkyl and fluoro-$C_{1-3}$-alkyl, more preferably $R^{33}$ is selected from fluoro, chloro, $CF_3$, $CHF_2$, $OCF_3$, $OCHF_2$, methyl, $^t$butyl and $CMe_2OH$, 1-methylcyclopropyl;

$R^{34}$ is selected from $C_{1-4}$-alkylene-OH, $C_{1-4}$-alkylene-O—$C_{1-3}$-alkyl, $C_{1-4}$-alkylene-O-fluoro-$C_{1-3}$-alkyl, $C_{3-10}$-cycloalkyl, $C(O)N(R^{37})_2$, $S(O_2)N(R^{37})_2$, wherein alkylene is unsubstituted or substituted with 1 to 3 substituents selected from F, and cycloalkyl is unsubstituted or substituted with 1 to 3 substituents independently selected from F, $C_{1-3}$-alkyl and fluoro-$C_{1-3}$-alkyl;

$R^{35}$ is selected from $C_{1-6}$-alkyl and fluoro-$C_{1-6}$-alkyl;

$R^{36}$ is selected from $C_{1-6}$-alkyl, fluoro-$C_{1-6}$-alkyl, $C(O)N(R^{37})_2$, $S(O_2)N(R^{37})_2$;

$R^{37}$ is independently selected from H, $C_{1-6}$-alkyl, halo-$C_{1-6}$-alkyl, $C_{1-6}$-cycloalkyl, wherein cycloalkyl is unsubstituted or substituted with 1 to 3 substituents independently selected from F, $C_{1-3}$-alkyl and fluoro-$C_{1-3}$-alkyl, or wherein two $R^{37}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from fluoro, oxo, $C_{1-4}$-alkyl and halo-$C_{1-4}$-alkyl;

$R^{38}$ is selected from H, $C_{1-3}$-alkyl and fluoro-$C_{1-3}$-alkyl;

$R^{39}$ is selected from H, F or OH;

X is an annelated saturated heterocycle selected from the group consisting of

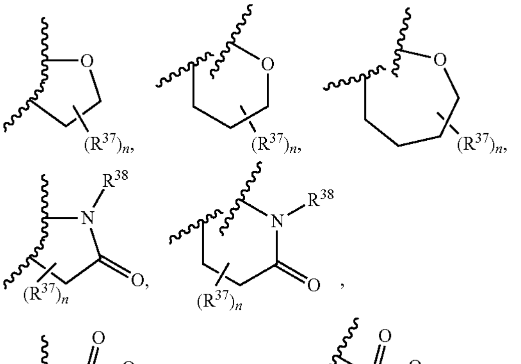

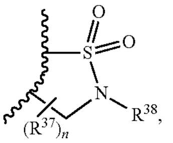

and

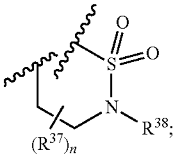

Y is an annelated 5- or 6-membered carbocycle, an annelated 6-membered aryl or an annelated 6-membered heteroaryl containing 1 to 2 nitrogen atoms, wherein the carbocycle, aryl or heteroaryl is unsubstituted or substituted with 1 to 3 substituents selected from fluoro, $C_{1-3}$-alkyl and fluoro-$C_{1-3}$-alkyl;

Z is an annelated 6-membered cycle forming a heteroaryl containing 1 to 2 nitrogen atoms, wherein the heteroaryl is unsubstituted or substituted with 1 to 3 substituents selected from fluoro, $C_{1-3}$-alkyl and fluoro-$C_{1-3}$-alkyl; and n is selected from 1 to 4.

In an equally more preferred embodiment in combination with any of the above or below embodiments of the first alternative $R^3$ is selected from

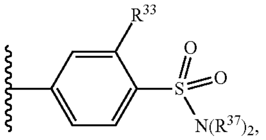

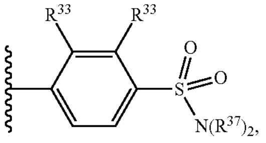

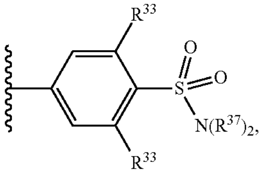

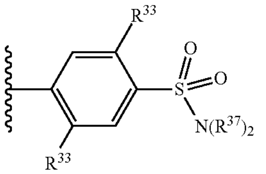

and

-continued

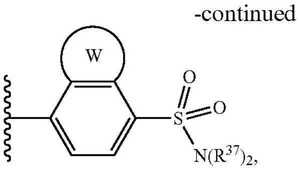

wherein $R^{33}$ is independently selected from H, halogen, $C_{1-6}$-alkyl, fluoro-$C_{1-6}$-alkyl, $C_{1-4}$-alkylene-OH, $C_{1-4}$-alkylene-O—$C_{1-3}$-alkyl, O—$C_{1-6}$-alkyl, O-fluoro-$C_{1-6}$-alkyl and $C_{3-10}$-cycloalkyl, more preferably $R^{33}$ is independently selected from fluoro, chloro, $CF_3$, $CHF_2$, $OCF_3$, $OCHF_2$, methyl, $^t$butyl and $CMe_2OH$, 1-methylcyclopropyl;

one $R^{37}$ is selected from H, $C_{1-6}$-alkyl, halo-$C_{1-6}$-alkyl and the other $R^{37}$ is selected from $C_{1-6}$-alkyl, halo-$C_{1-6}$-alkyl, $C_{0-4}$-alkylene-$C_{3-6}$-cycloalkyl, $C_{0-4}$-alkylene-$C_{3-6}$-heterocycloalkyl, wherein, wherein alkyl and alkylene is unsubstituted or substituted with a substituent selected from halogen, OH, O—$C_{1-3}$-alkyl, CN; and cycloalkyl or heterocycloalkyl is unsubstituted or substituted with 1 to 3 substituents independently selected from F, CN, OH, oxo, $C_{1-3}$-alkyl and fluoro-$C_{1-3}$-alkyl;

or wherein two $R^{37}$ when taken together with the nitrogen to which they are attached may complete a 3- to 8-membered ring containing carbon atoms and optionally containing 1 or 2 heteroatoms selected from O, S or N, wherein the ring is unsubstituted or substituted with 1 to 4 substitutents independently selected from fluoro, OH, oxo, $C_{1-4}$-alkyl and halo-$C_{1-4}$-alkyl;

W is selected from an annelated $C_{5-8}$-cycloakyl, an annelated 6-membered aryl or an annelated 5- to 6-membered heteroaryl, wherein cycloalkyl, aryl and heteroaryl is unsubstituted or substituted with 1 to 2 substituents selected from halogen, methyl and $CF_3$, more preferably, W is an annelated aryl, unsubstituted or substituted with 1 to 2 substituents selected from fluoro, methyl and $CF_3$.

In a more preferred embodiment in combination with any of the above or below embodiments of the first alternative $R^3$ is selected from

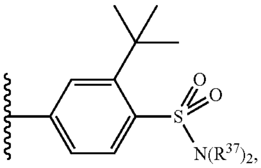

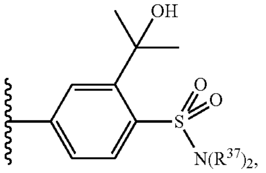

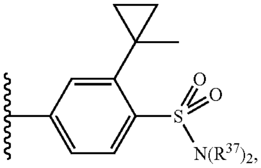

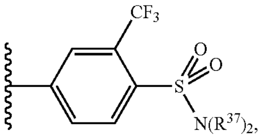

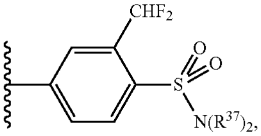

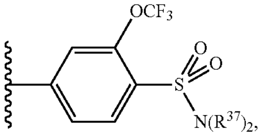

-continued

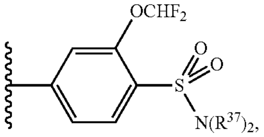
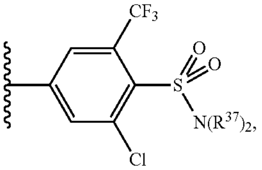
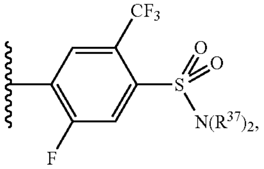
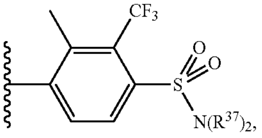
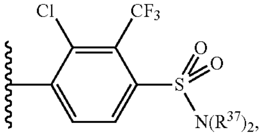
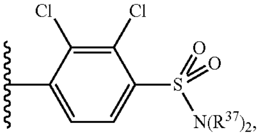
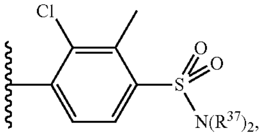
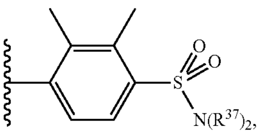
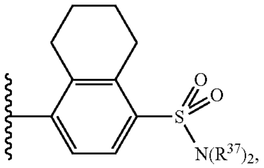
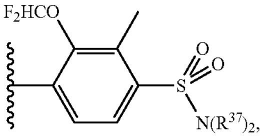
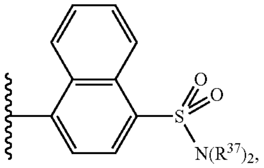
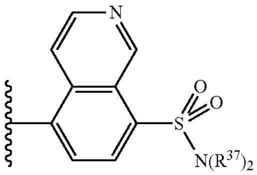
and
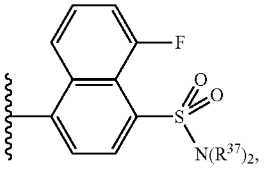

wherein $N(R^{37})_2$ is selected from

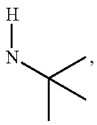
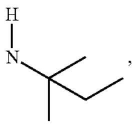
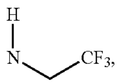
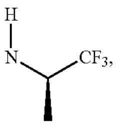
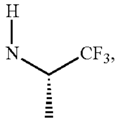
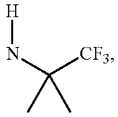
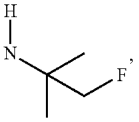

-continued

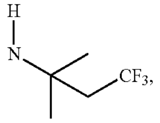
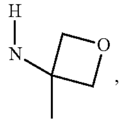
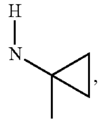
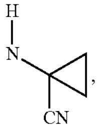
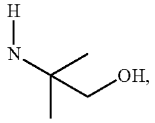
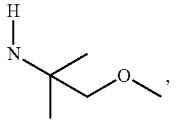
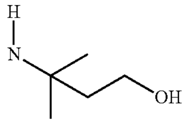
and
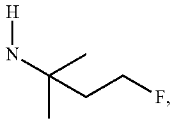

more preferably $N(R^{37})_2$ is selected from

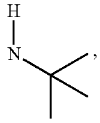
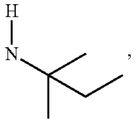
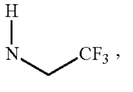
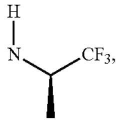
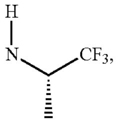
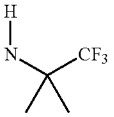
and
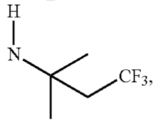

and most preferred $N(R^{37})_2$ is NH$^t$Bu.

In an equally more preferred embodiment in combination with any of the above or below embodiments of the first alternative $R^3$ is selected from

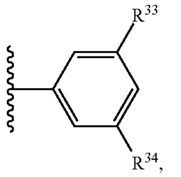
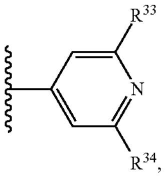
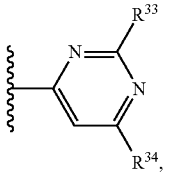
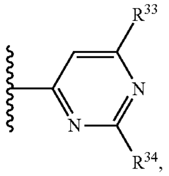

wherein $R^{33}$ is selected from fluoro, chloro, $CHMe_2$, $CMe_3$, cyclopropyl, 1-methylcyclopropyl, $CF_3$, $CHF_2$, $CMe_2OH$, $CMe_2OMe$, O—$CH_2CMe_3$, O—$CH_2CHMe_3$, $OCF_3$ and $OCHF_2$;

$R^{34}$ is selected from $C_{1-4}$-alkylene-OH, $C_{1-4}$-alkylene-O—$C_{1-3}$-alkyl, $C_{3-10}$-cycloalkyl, $C(O)N(R^{37})_2$, $SO_2N(R^{37})_2$, wherein alkylene is unsubstituted or substituted with 1 to 3 substituents selected from F, and cycloalkyl is unsubstituted or substituted with 1 to 3 substituents independently selected from F, methyl and $CF_3$; and $R^{37}$ is independently selected from H, $C_{1-6}$-alkyl, halo-$C_{1-6}$-alkyl.

In an equally more preferred embodiment in combination with any of the above or below embodiments of the first alternative $R^3$ is selected from
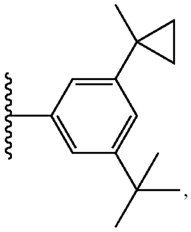,
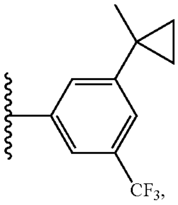
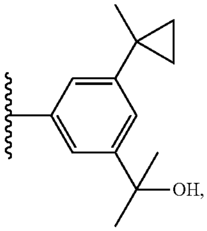
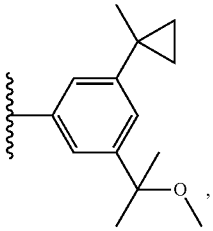,
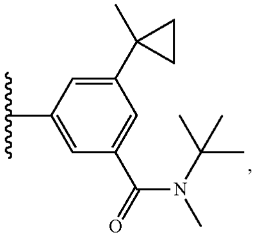,
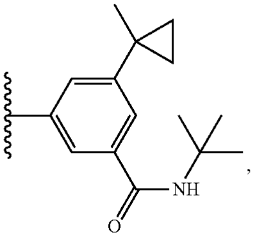,
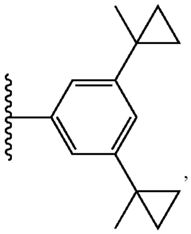,
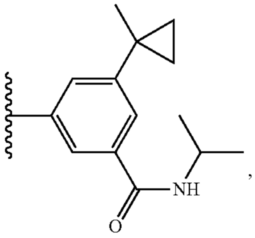,
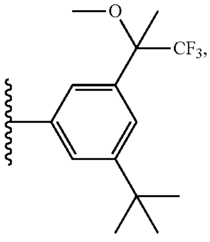
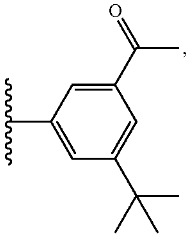,
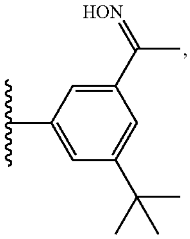,
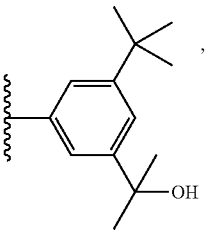,
-continued
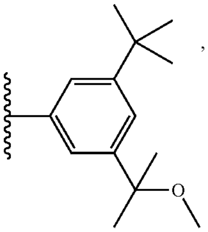,
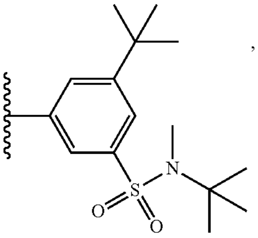,
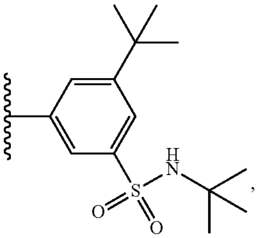,
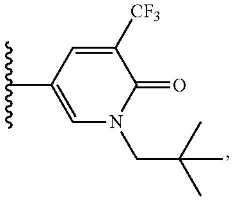
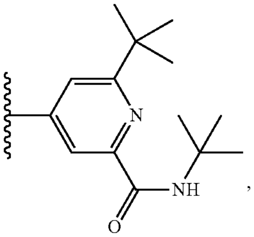,
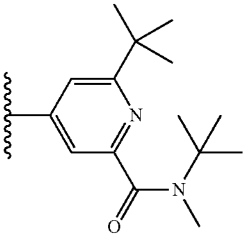,
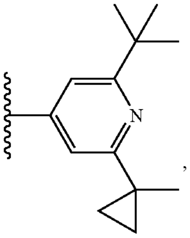,
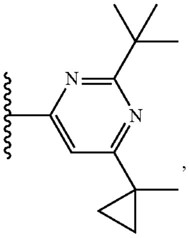,
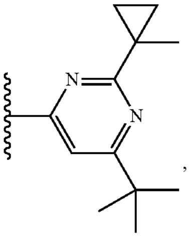,
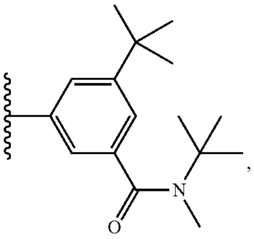,
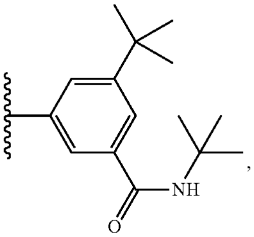,
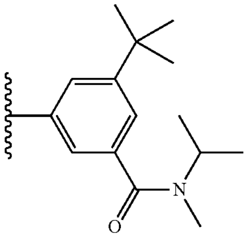,
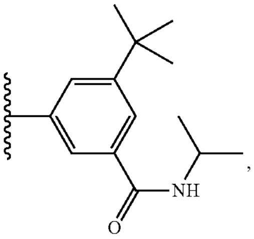,
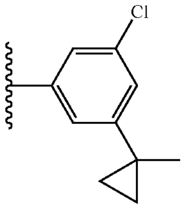, -continued
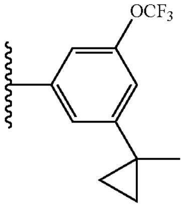,
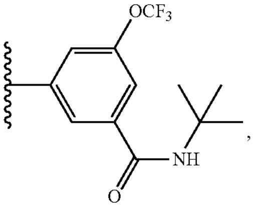,
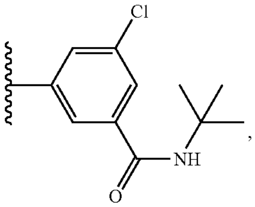,
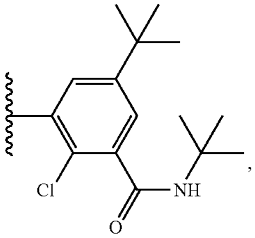,
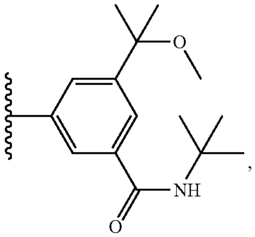,
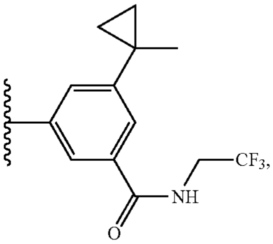
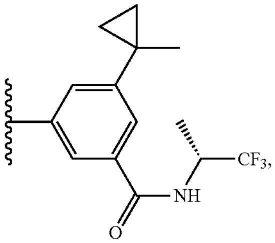
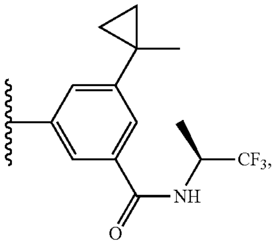
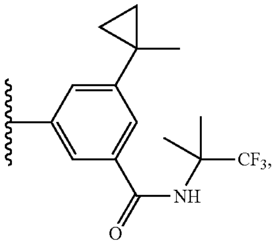
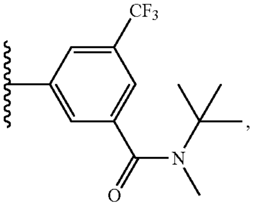,
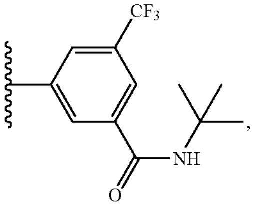,
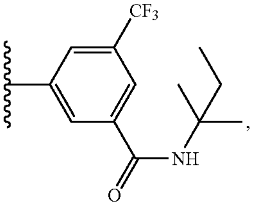,
-continued
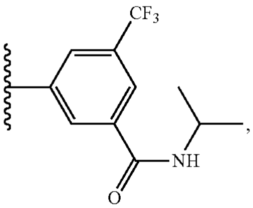,
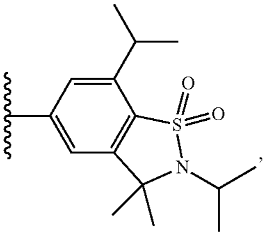,
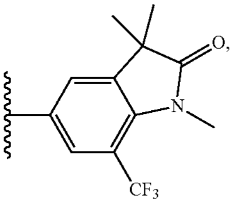
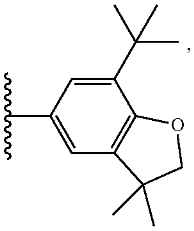,
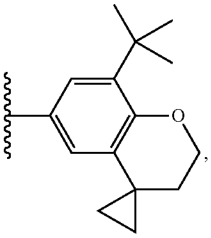,
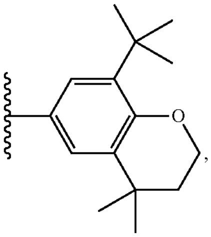,
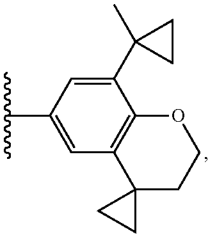,
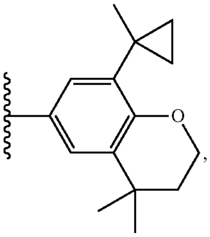,
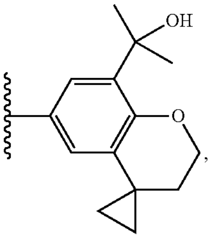,
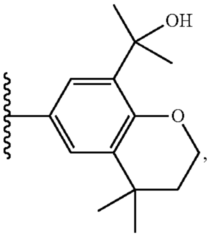,
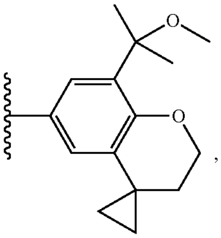,
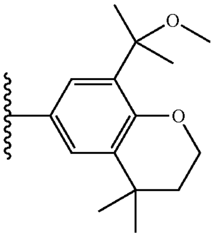,
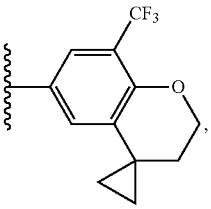,
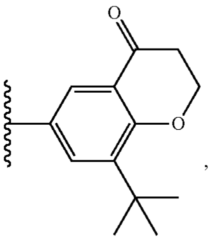, -continued
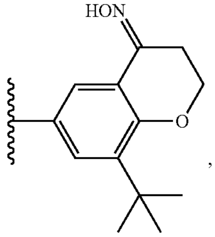
,
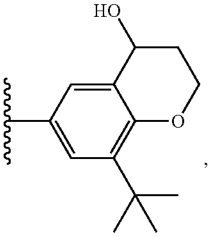
,
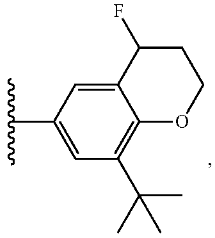
,
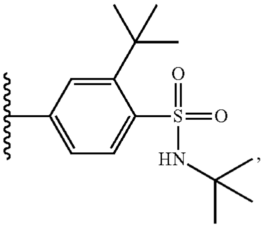
,
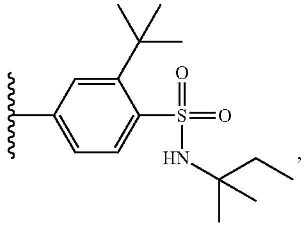
,
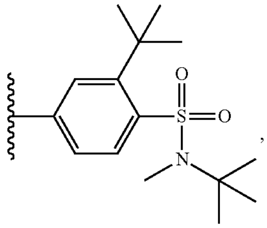
,
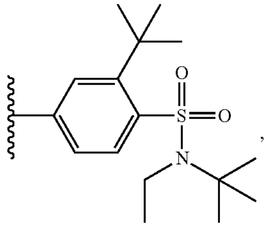
,
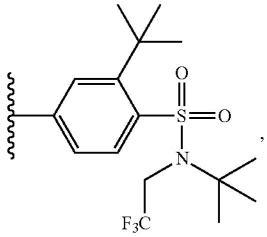
,
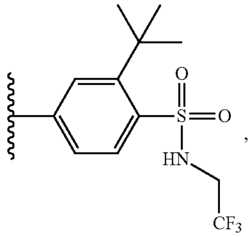
,
-continued
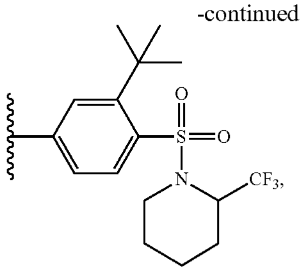
,
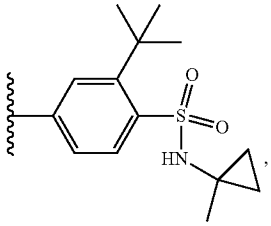
,
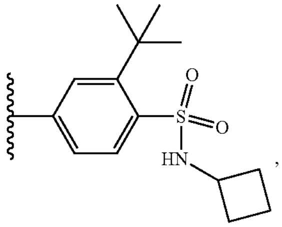
,
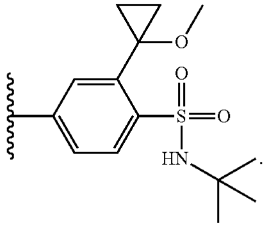
.
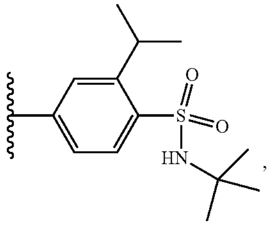
,
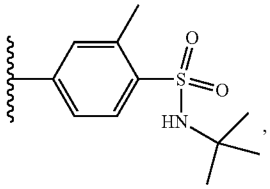
,
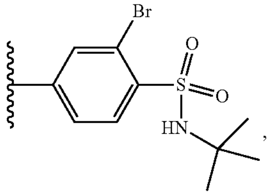
,
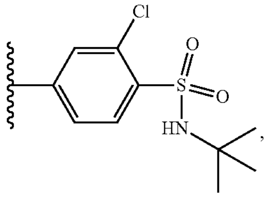
, -continued
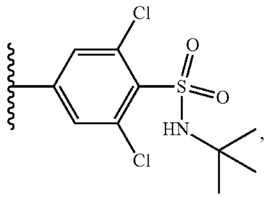
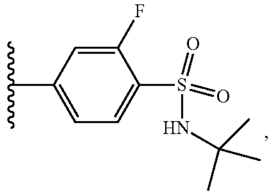
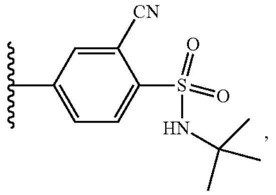
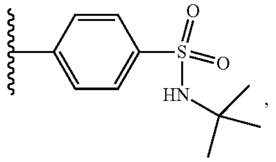
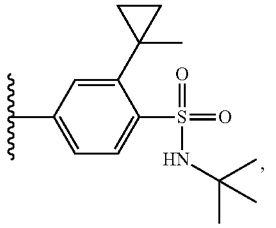
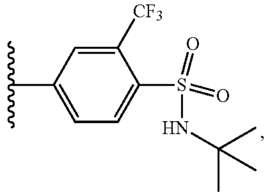
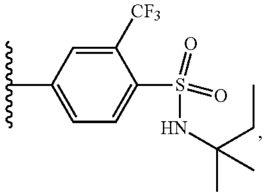
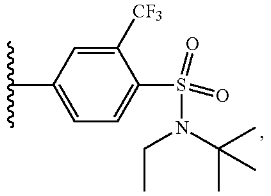
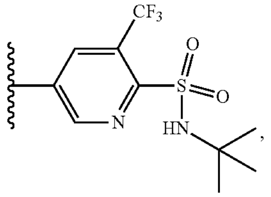
-continued
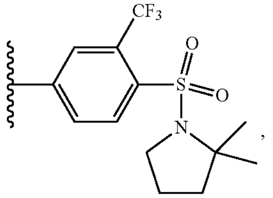
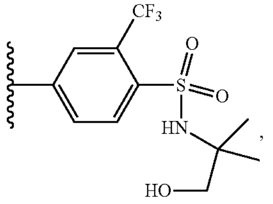
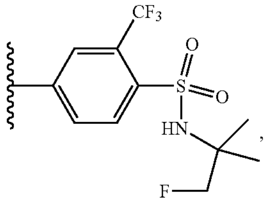
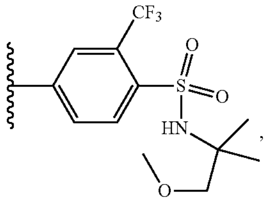
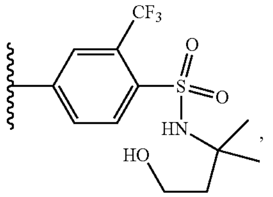
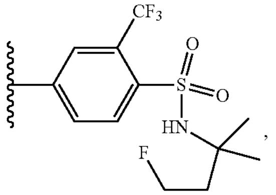
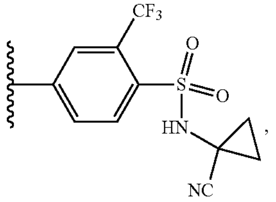
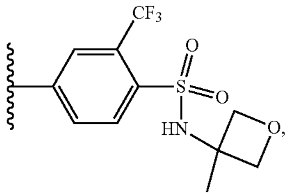

-continued
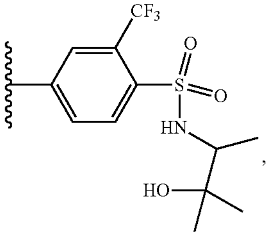
,
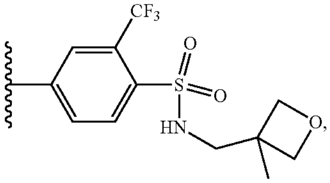
,
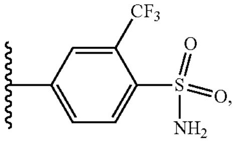
,
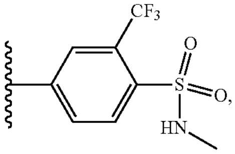
,
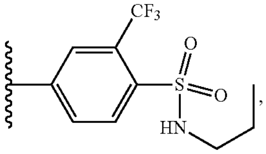
,
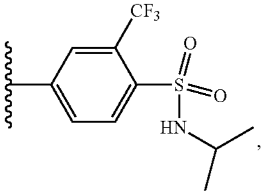
,
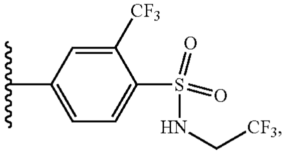
,
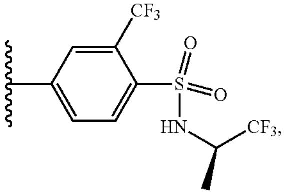
,
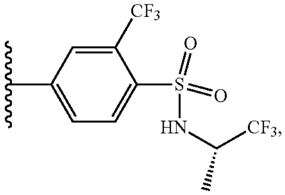
,
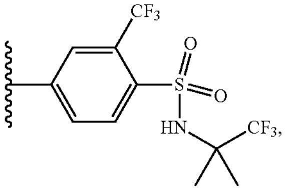
,
-continued
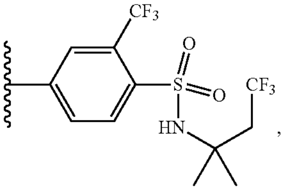
,
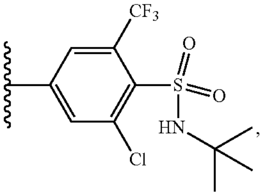
,
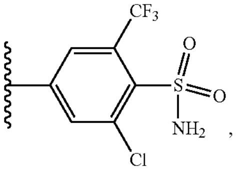
,
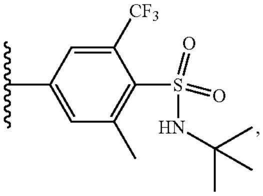
,
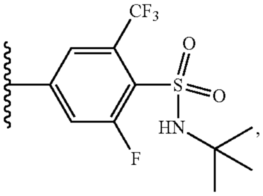
,
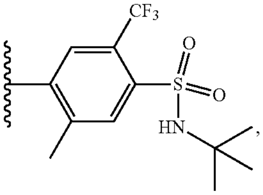
,
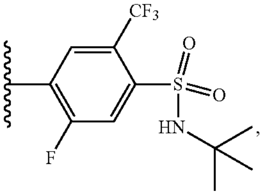
,
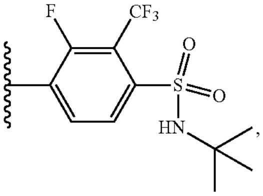
,
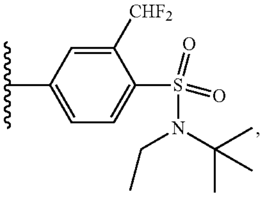
, -continued
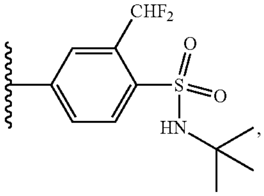
,
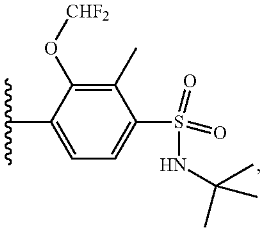
,
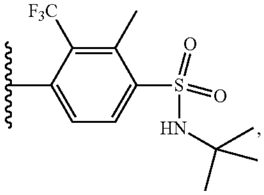
,
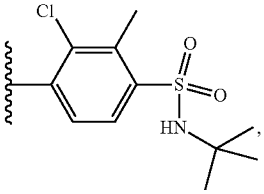
,
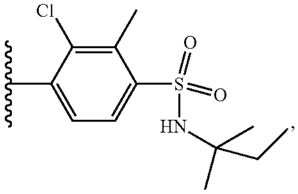
,
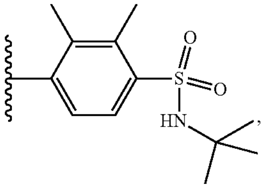
,
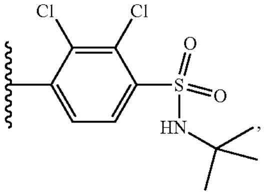
,
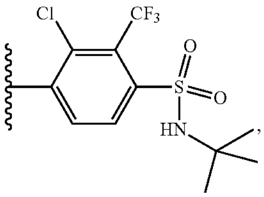
,
-continued
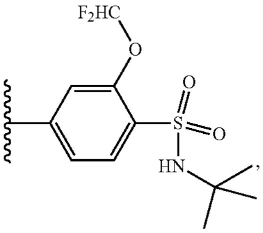
,
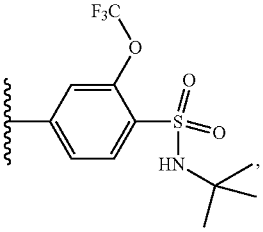
,
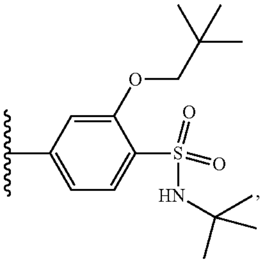
,
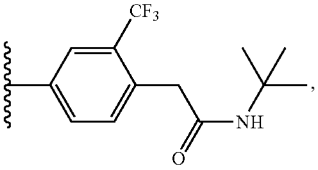
,
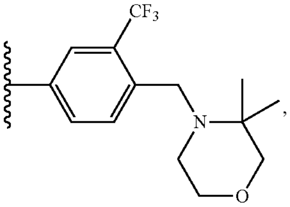
,
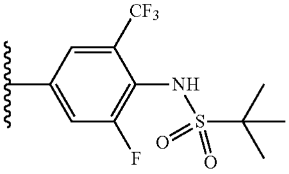
,
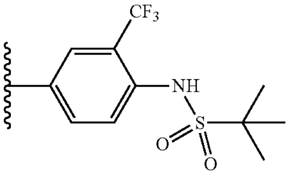
,
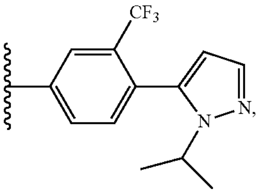
, -continued
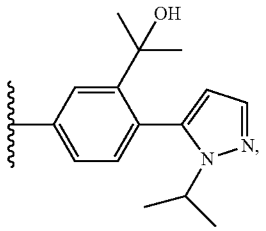
,
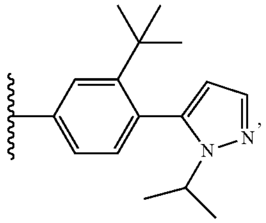
,
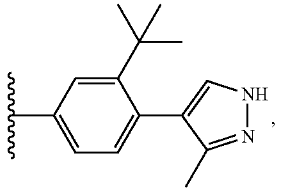
,
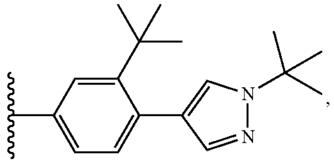
,
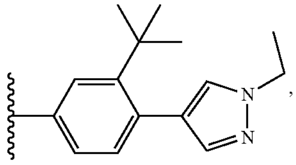
,
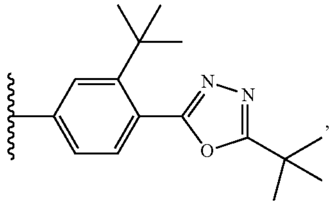
,
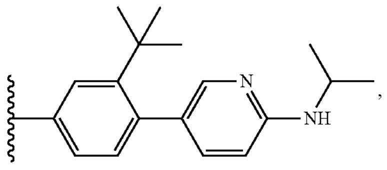
,
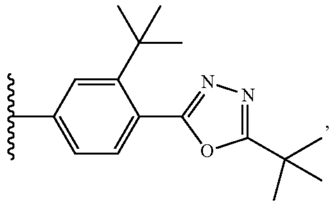
,
-continued
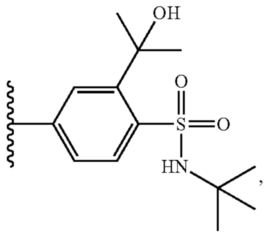
,
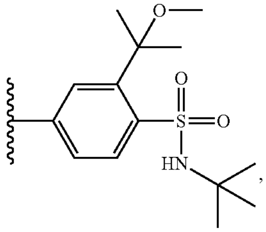
,
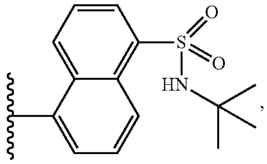
,
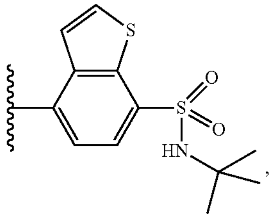
,
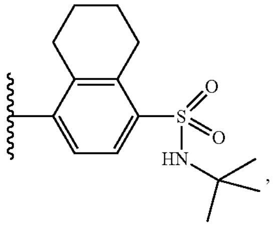
,
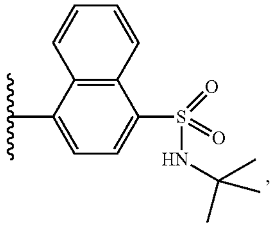
,
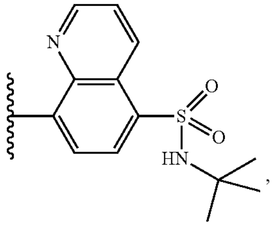
, -continued
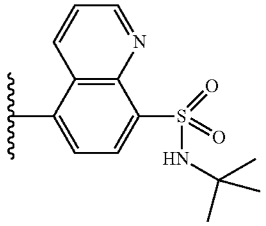
,
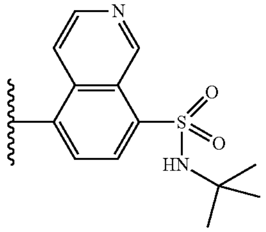
,
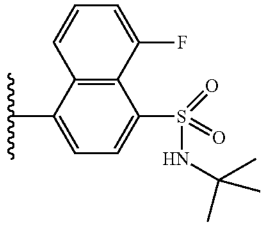
,
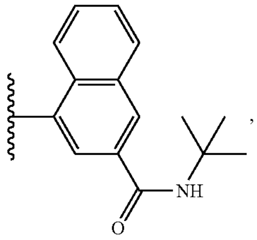
,
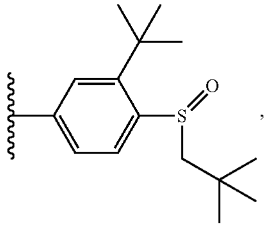
,
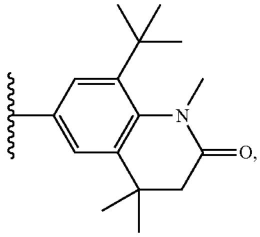
,
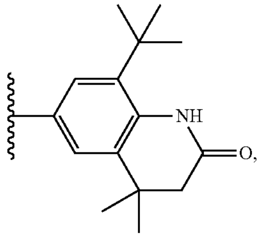
,
-continued
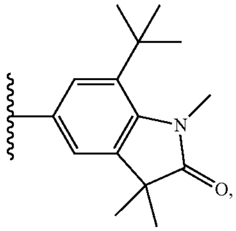
,
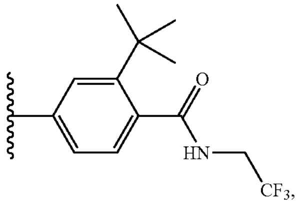
,
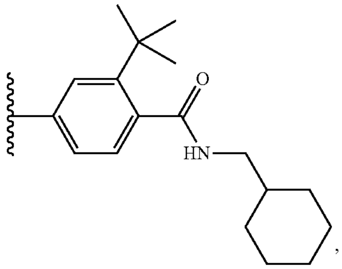
,
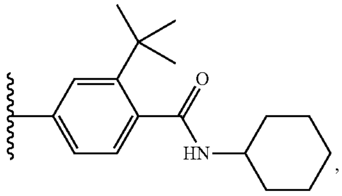
,
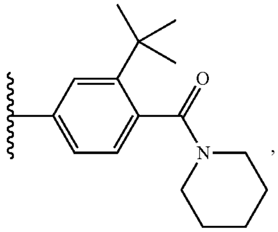
,
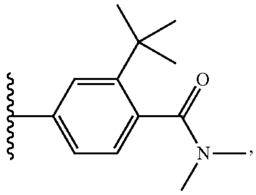
,
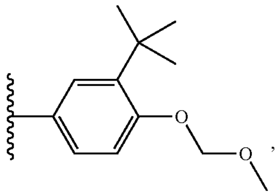
, -continued
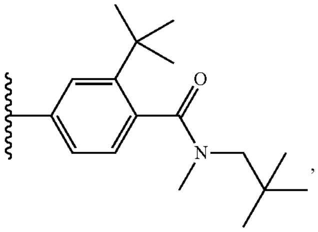
,
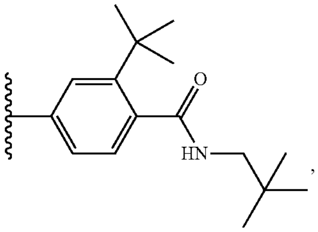
,
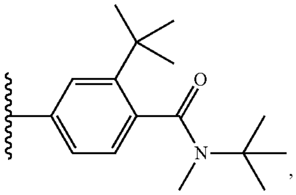
,
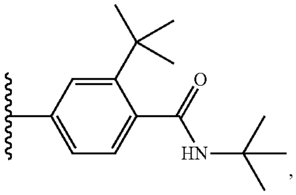
,
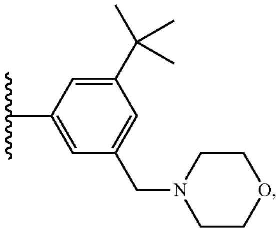
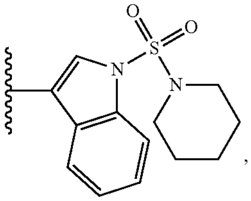
,
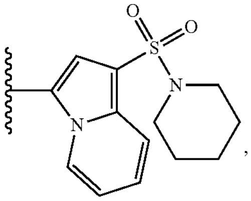
,
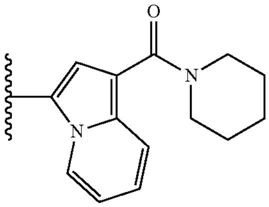
and
-continued
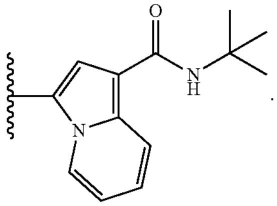
.
In a further preferred embodiment in combination with any of the above or below embodiments of the first alternative $R^3$ is selected from
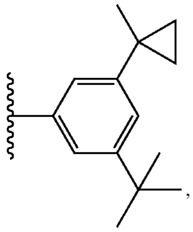
,
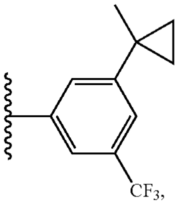
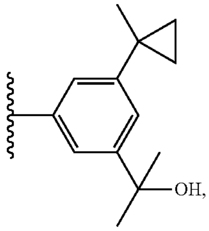
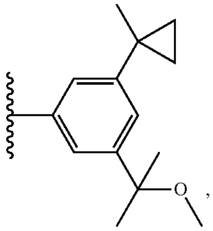
,
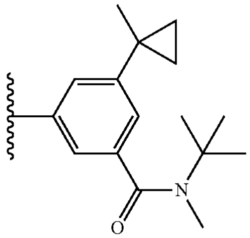
,
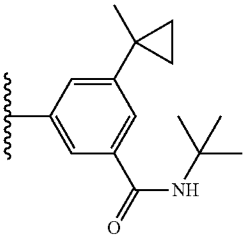
,
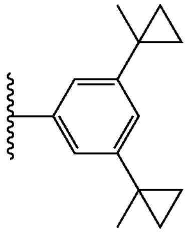
,
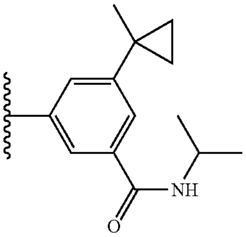
,
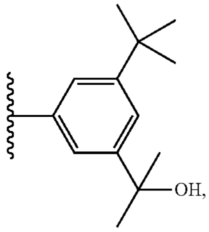
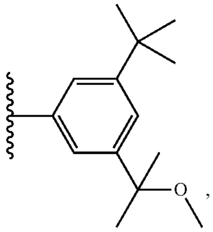
, -continued
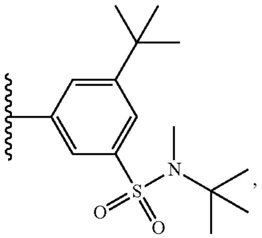
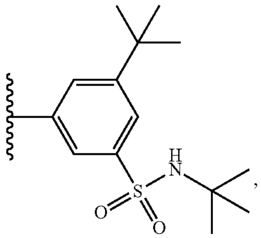
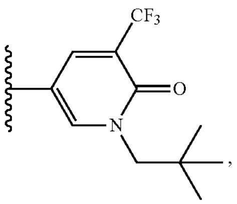
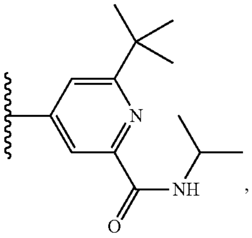
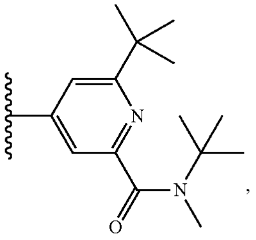
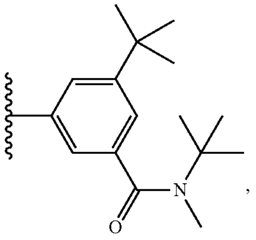
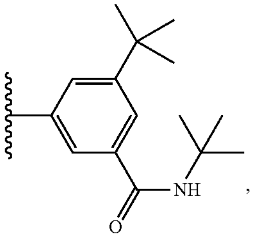
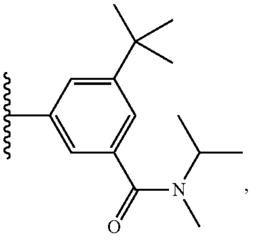
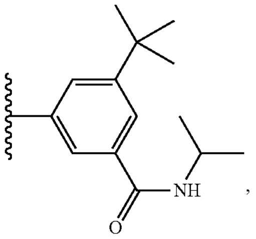
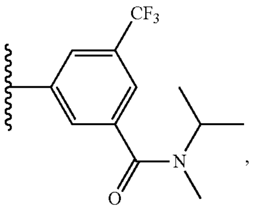
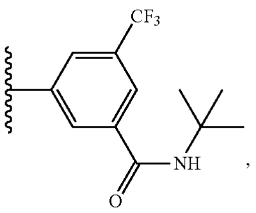
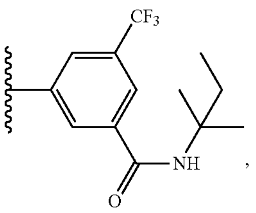
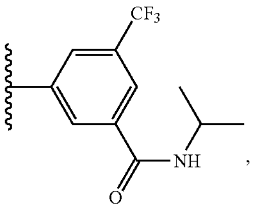
-continued
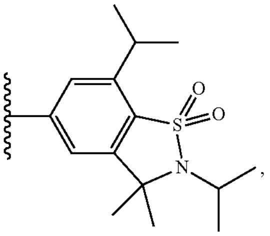
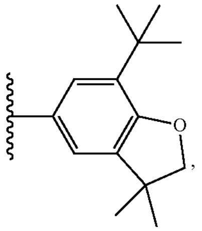
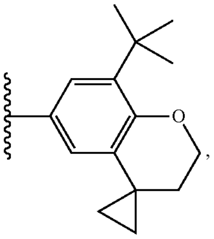
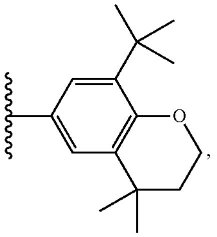
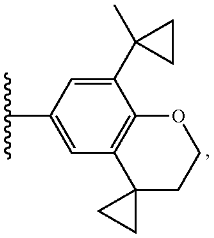
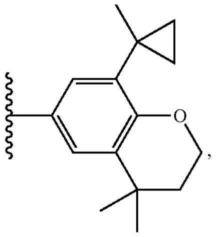
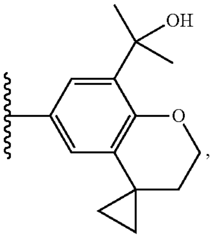
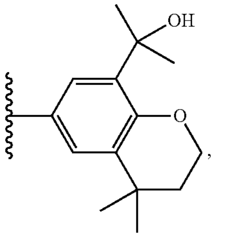
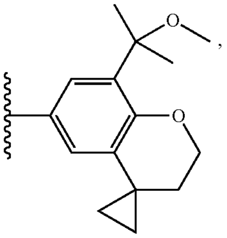
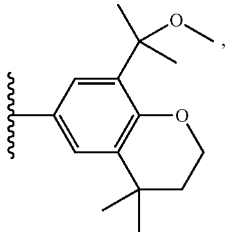
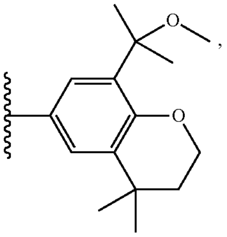
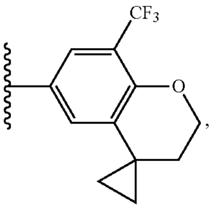
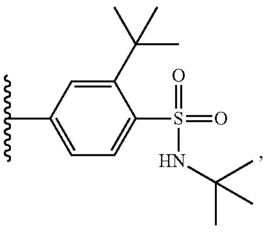

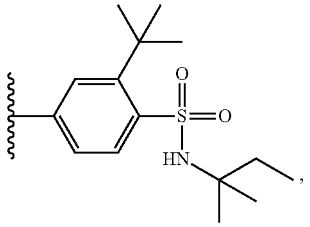
,
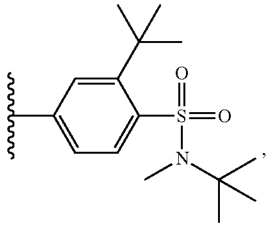
,
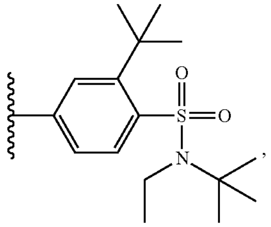
,
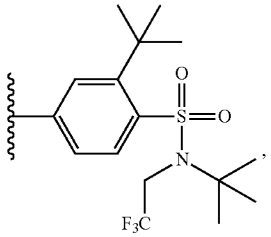
,
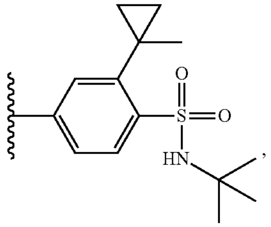
,
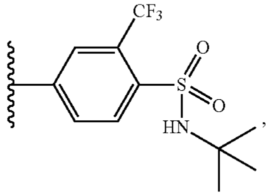
,
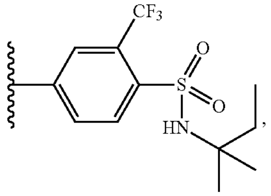
,
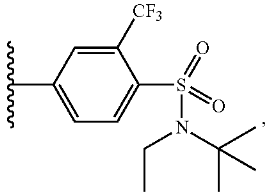
,
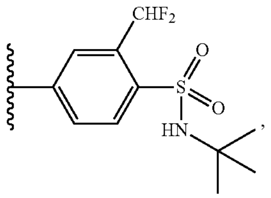
,
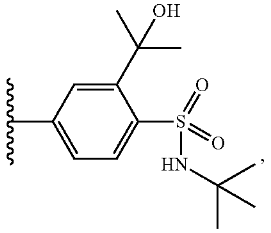
,
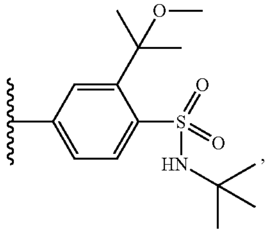
,
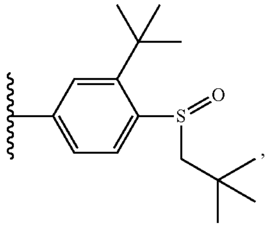
,
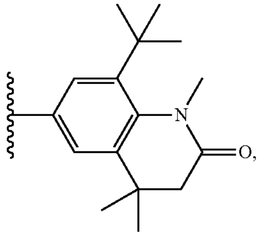
,
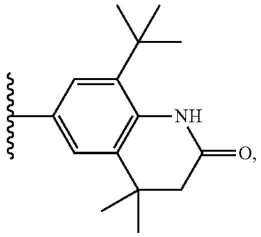
,
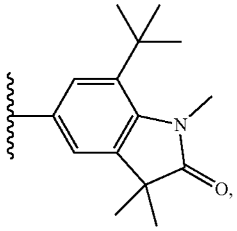
, -continued
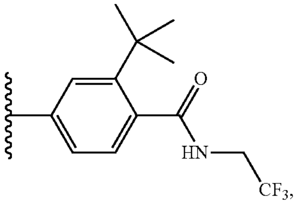
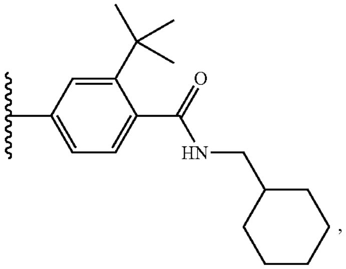
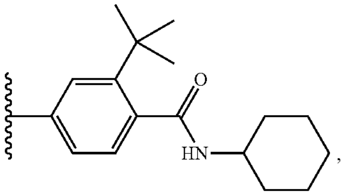
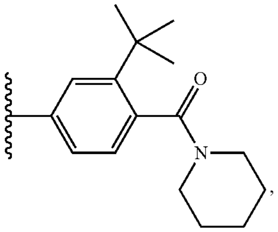
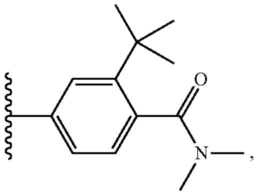
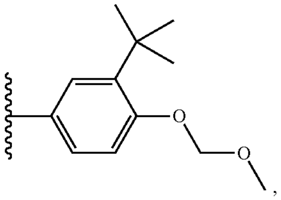
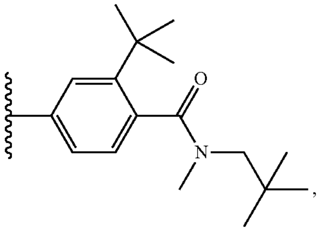
-continued
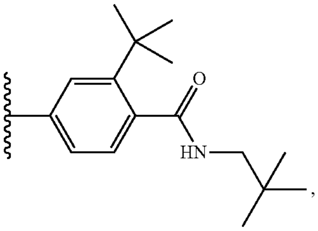
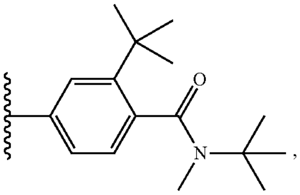
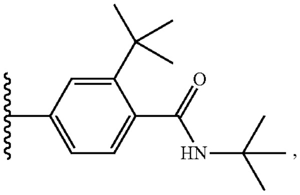
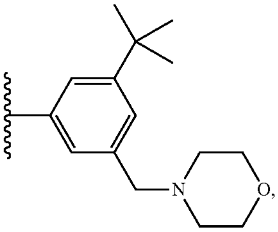
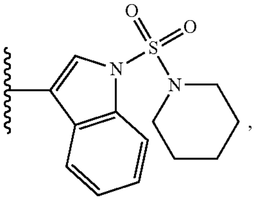
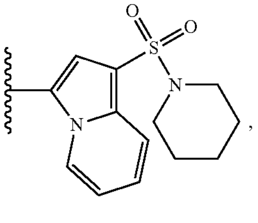
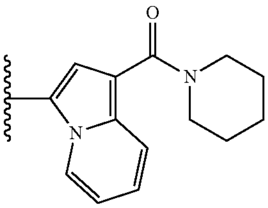
and
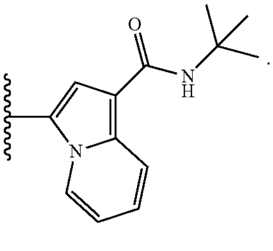

More preferably, $R^3$ is selected from
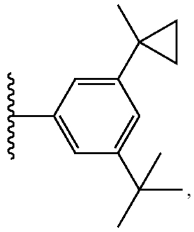,
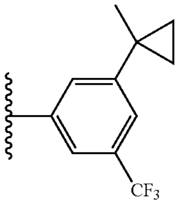,
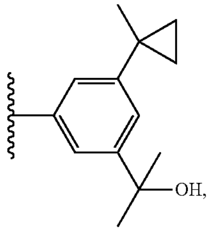
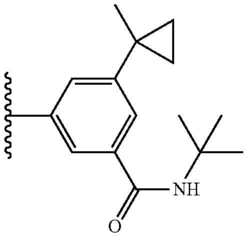,
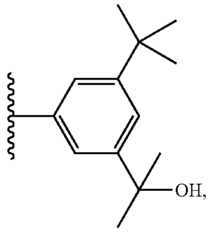
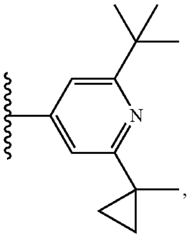
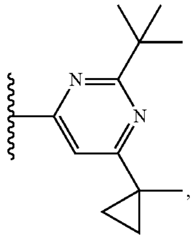
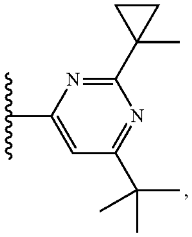
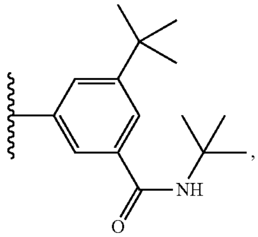
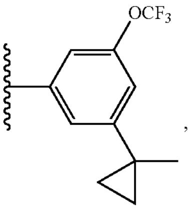,
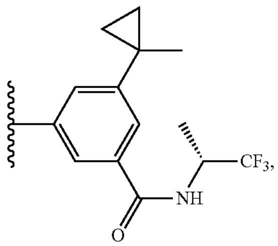
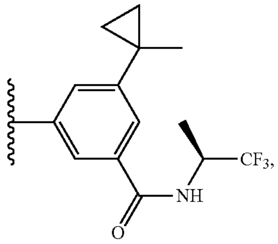
-continued
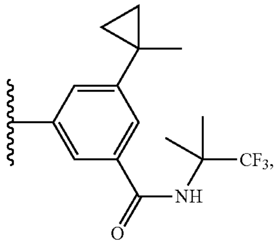
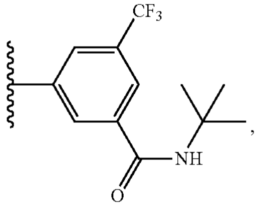
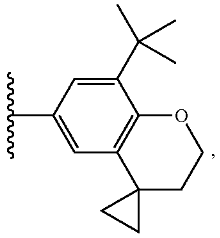
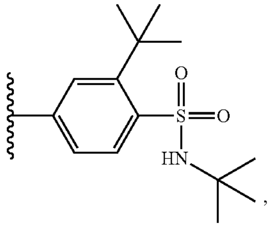
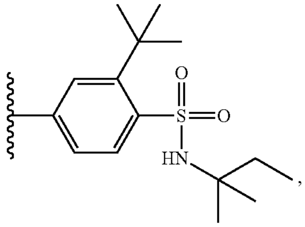
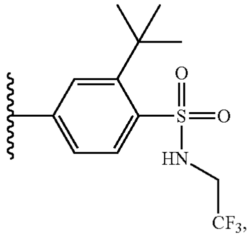
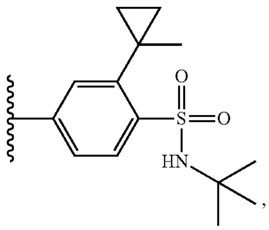

-continued
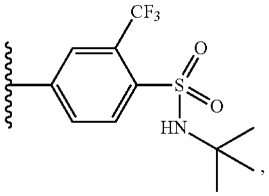
,
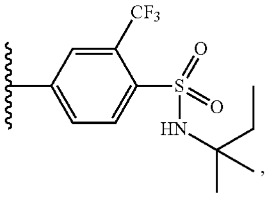
,
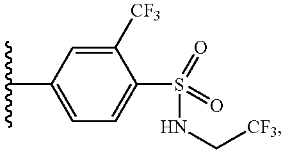
,
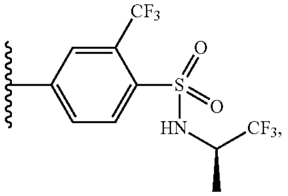
,
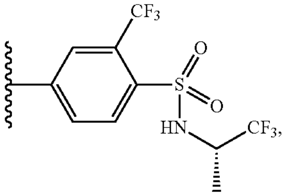
,
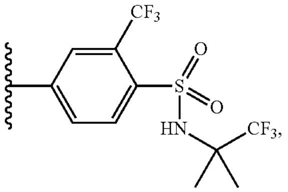
,
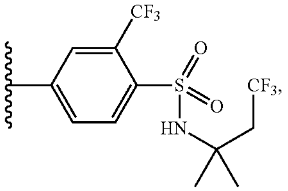
,
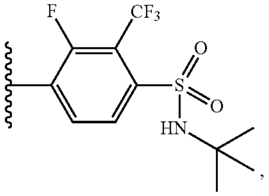
,
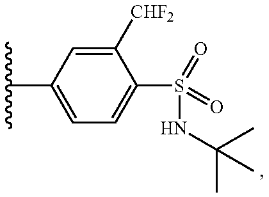
,
-continued
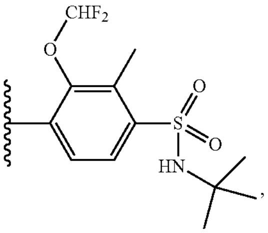
,
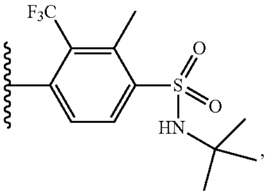
,
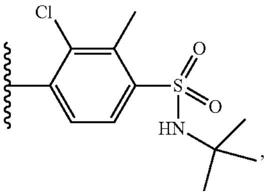
,
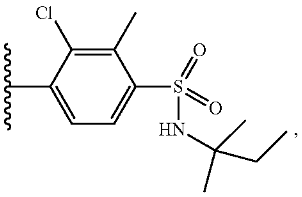
,
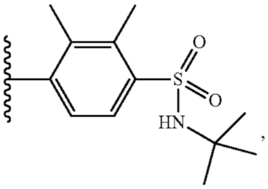
,
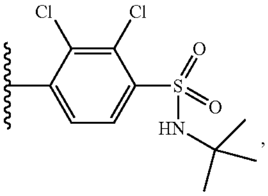
,
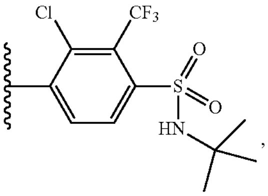
,
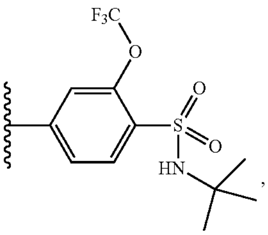
, -continued
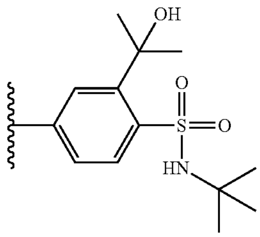
,
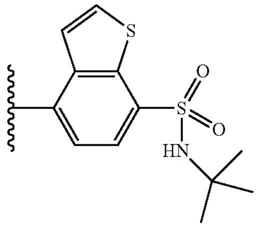
,
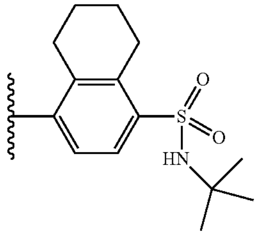
,
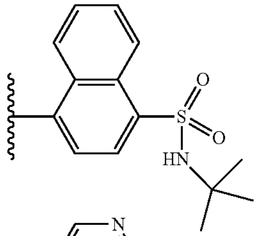
,
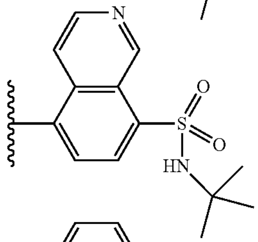
and
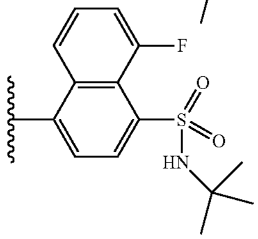
.
Most preferred, $R^3$ is selected from
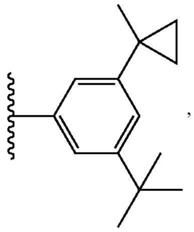
,
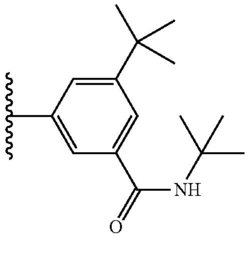
,
-continued
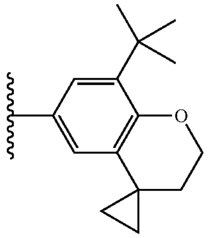
,
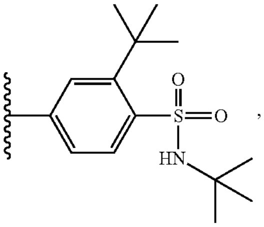
,
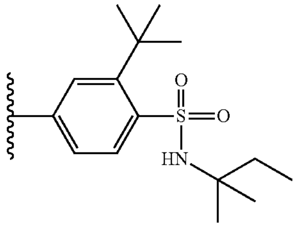
,
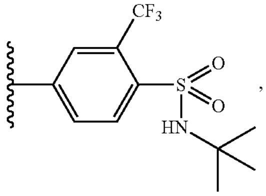
,
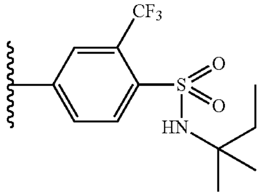
,
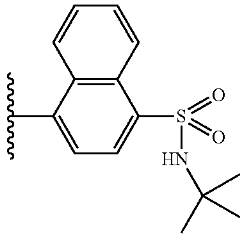
,
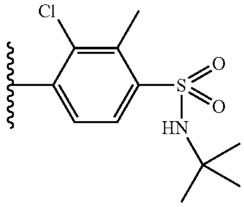
,
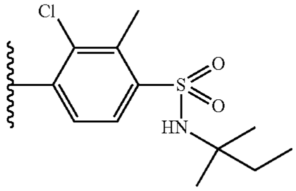
and
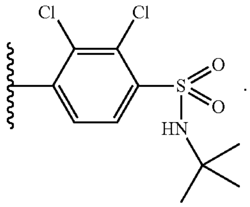
.

In a preferred embodiment in combination with any of the above or below embodiments of the first alternative $R^5$ is selected from H, $C_{1-6}$-alkyl, halo-$C_{1-6}$-alkyl or halogen, wherein alkyl is unsubstituted or substituted with 1 to 3 substituents independently selected from the group consisting of O—$C_{1-6}$-alkyl, O-halo-$C_{1-6}$-alkyl and OH; and $R^6$ is selected from H or halogen.

More preferably, $R^5$ is selected from H, $C_{1-3}$-alkyl, fluoro or chloro, even more preferred $R^5$ is selected from H, methyl, fluoro or chloro. Most preferably, $R^5$ is methyl.

In a preferred embodiment in combination with any of the above or below embodiments of the first alternative $R^6$ is selected from H, fluoro or chloro, more preferably $R^6$ is hydrogen.

In a further preferred embodiment in combination with any of the above or below embodiments of the first alternative $R^4$ is $CR^8R^8$—$R^{10}$; $R^8$ is independently selected from H, F, $C_{1-3}$-alkyl or halo-$C_{1-3}$-alkyl; $R^{10}$ is $C_{3-10}$-cycloalkyl, wherein cycloalkyl is unsubstituted or substituted with 1 to 6 substituents independently selected from halogen, $C_{1-6}$-alkyl, halo-$C_{1-6}$-alkyl and cycloalkyl.

In a preferred embodiment in combination with any of the above or below embodiments of the first alternative $R^4$ is selected from

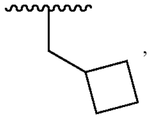,
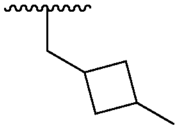,
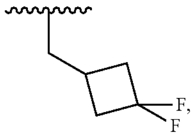
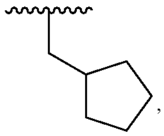,
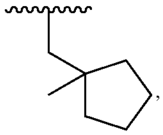,
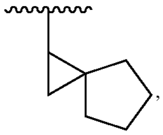,
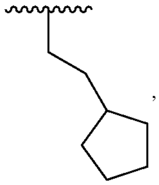,
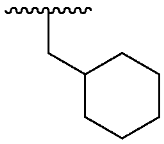,
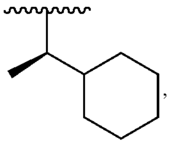,
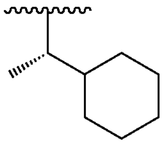,
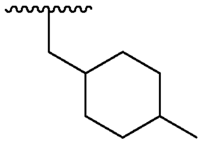,
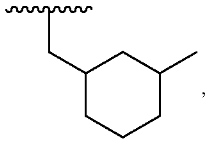,
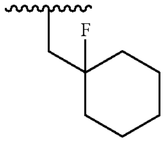,
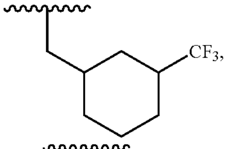
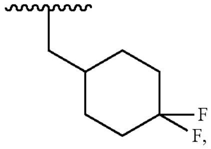
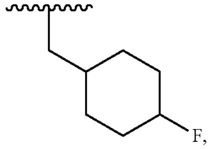

-continued

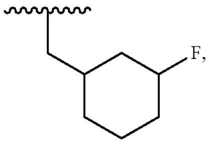
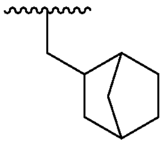
and
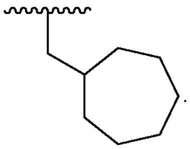.

In an equally preferred embodiment in combination with any of the above or below embodiments of the first alternative $R^4$ is $CH_2$—($C_{4-7}$-cycloalkyl), wherein $C_{4-7}$-cycloalkyl is unsubstituted or substituted with 1 to 4 substituents independently selected from fluoro or methyl.

In a more preferred embodiment in combination with any of the above or below embodiments of the first alternative $R^4$ is

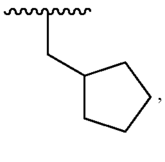,
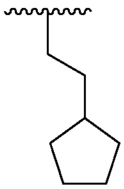,
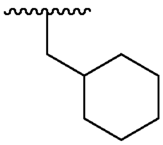,
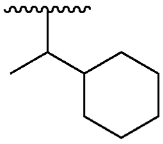,
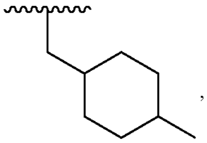,
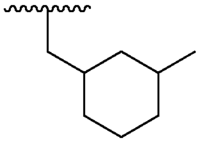,
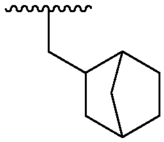
and
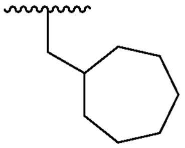.

Even more preferred, $R^4$ is

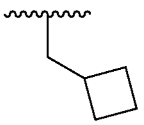,
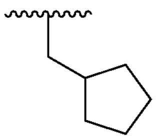,
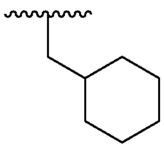,
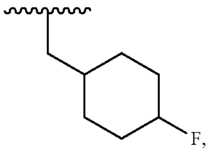
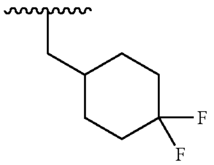,

-continued
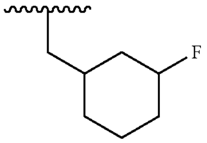
and
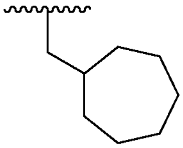
,
and most preferred, $R^4$ is $CH_2$-cyclohexyl.
In another preferred embodiment in combination with any of the above or below embodiments of the first alternative the compound of Formula (1) is selected from the group consisting of
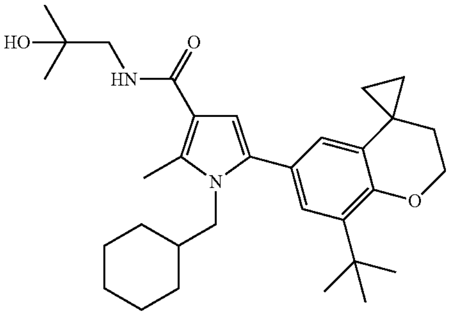
,
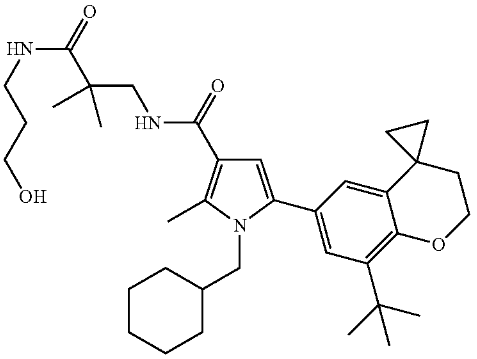
,
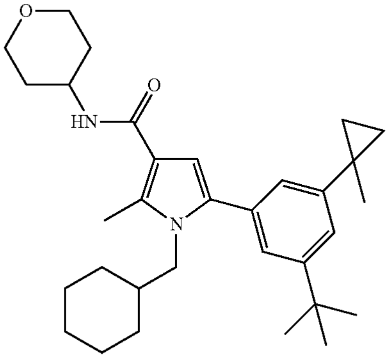
,
-continued
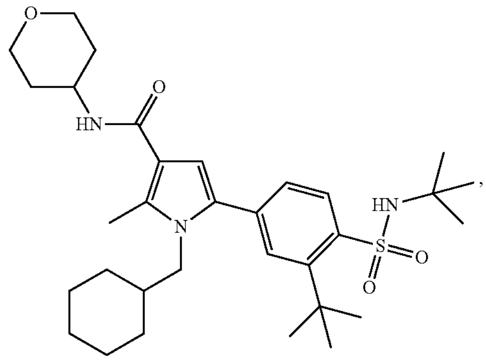
,
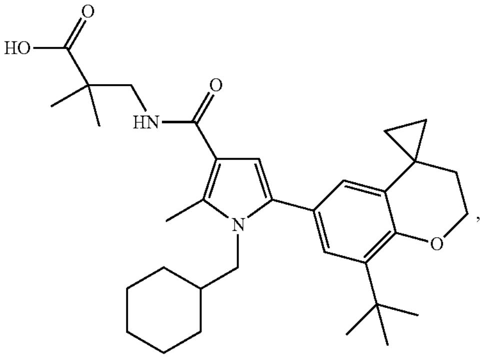
,
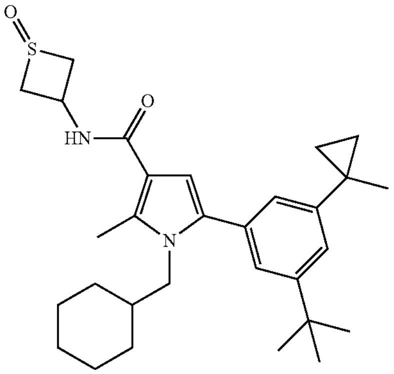
,
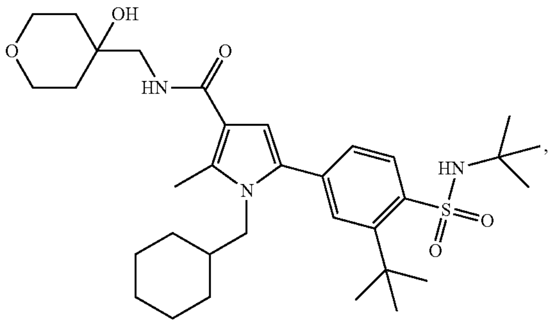
, -continued
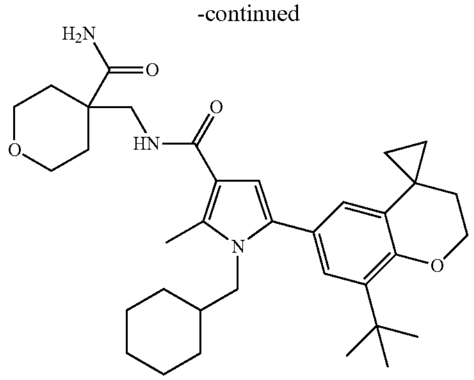
,
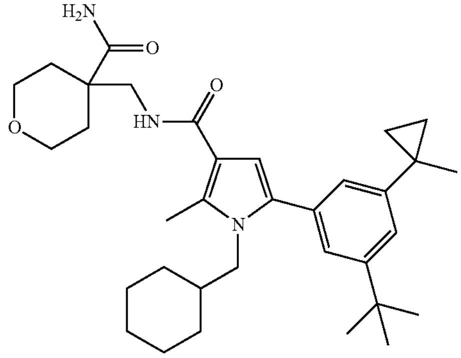
,
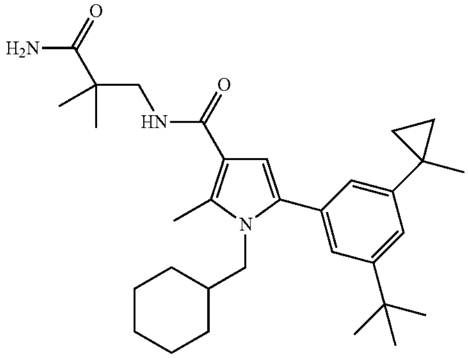
,
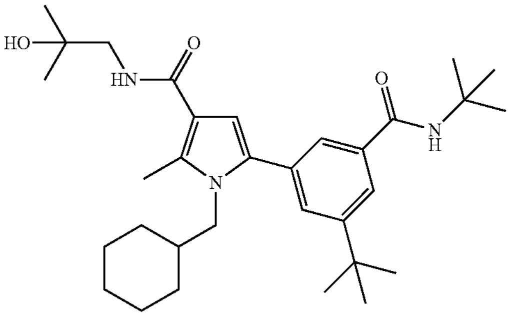
,
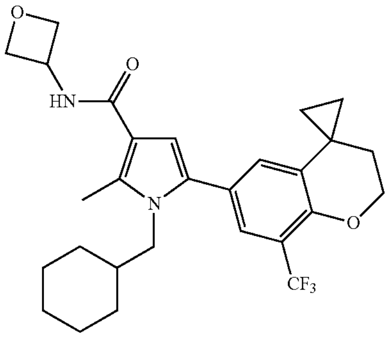
,
-continued
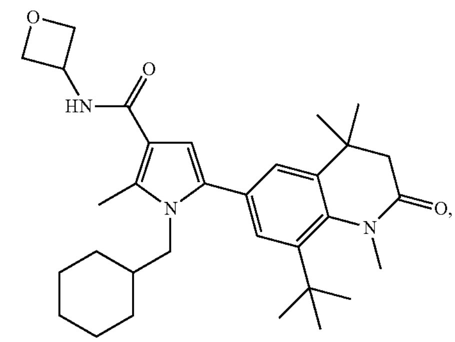
,
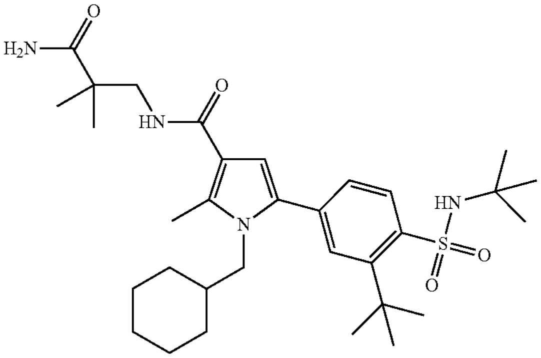
,
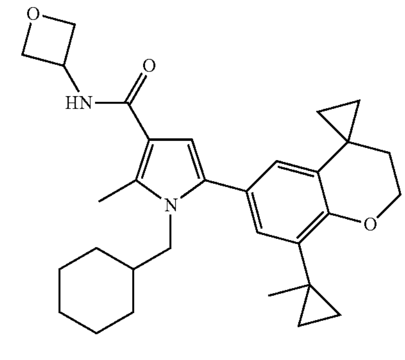
,
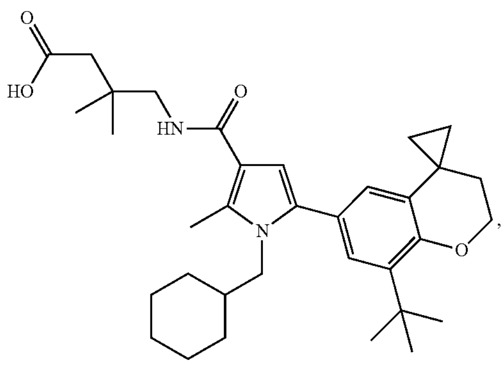
, -continued
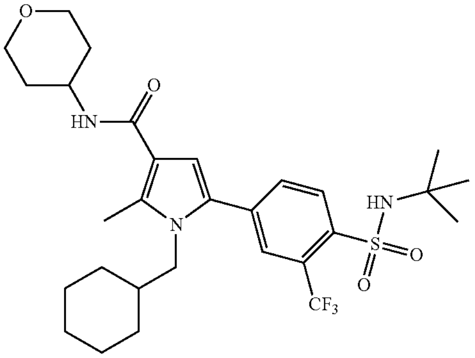
,
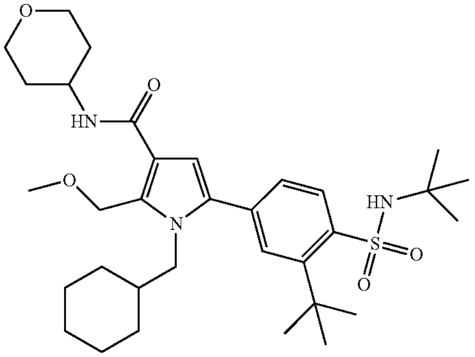
,
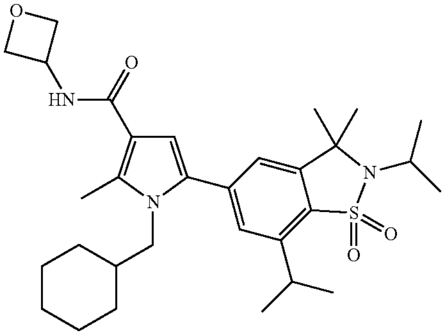
,
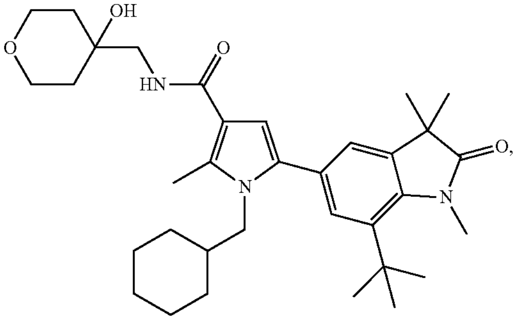
,
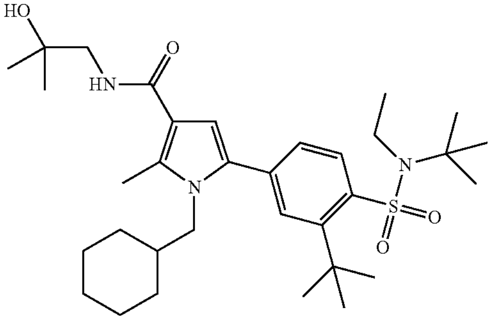
,
-continued
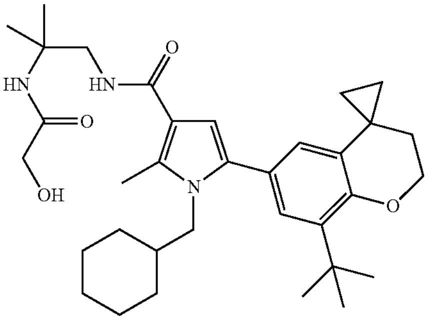
,
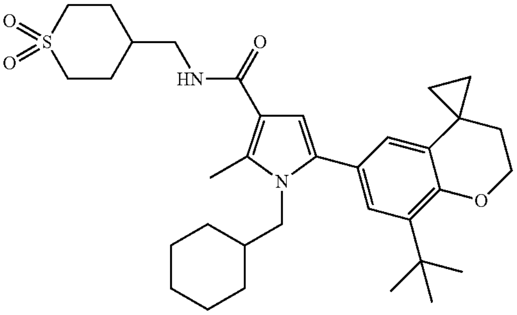
,
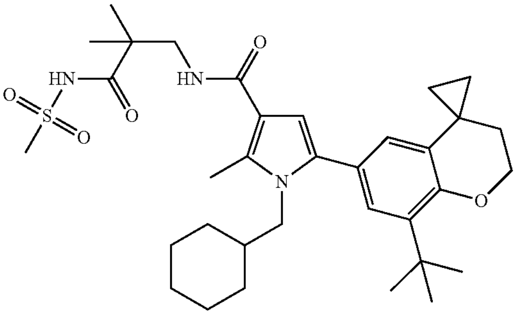
,
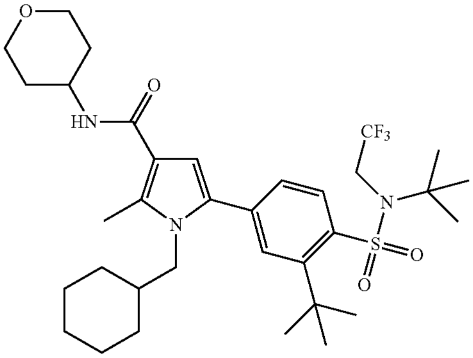
,
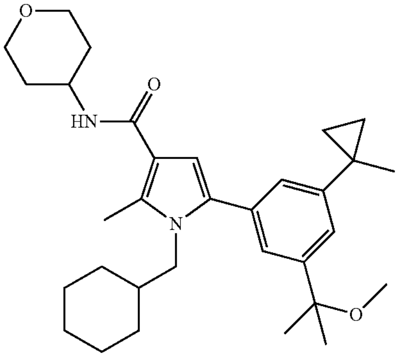
, -continued
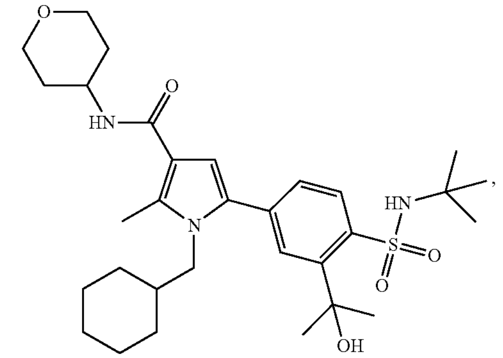
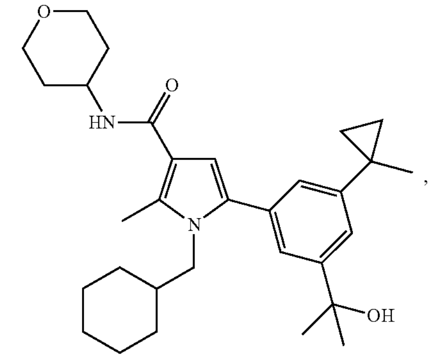
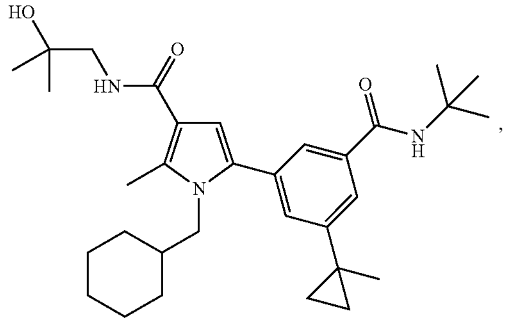
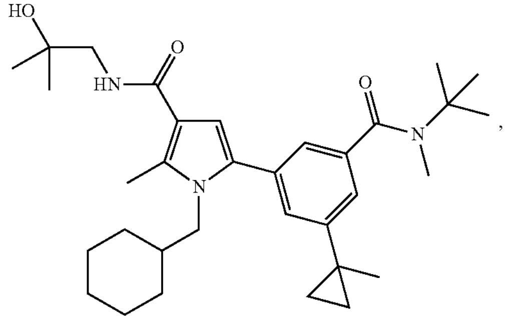
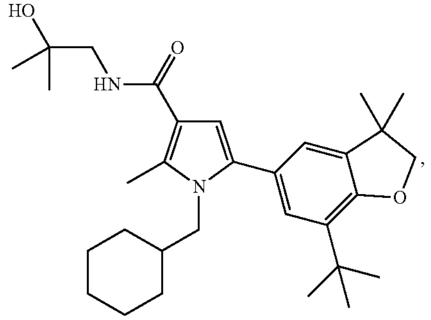
-continued
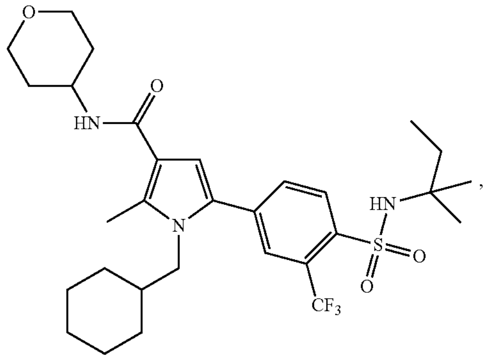
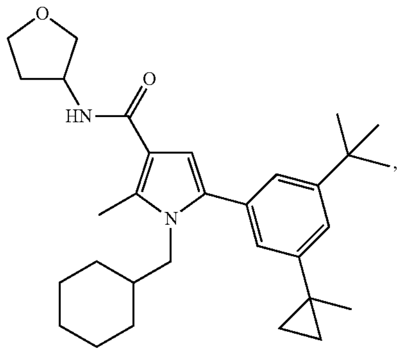
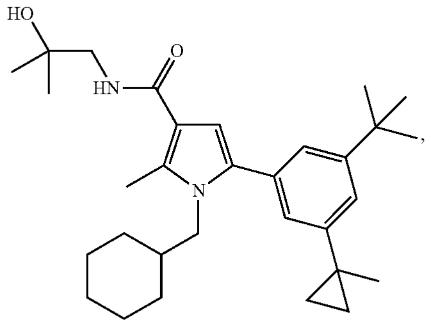
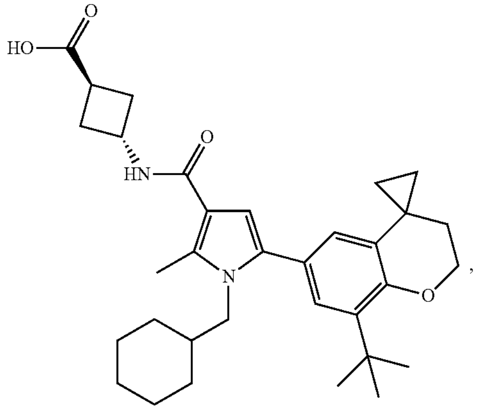

-continued
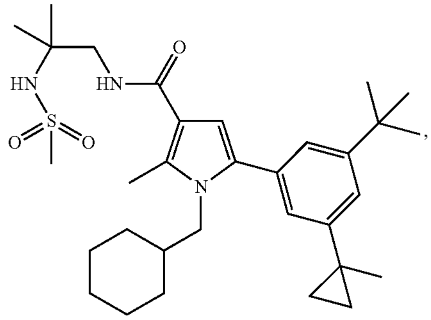
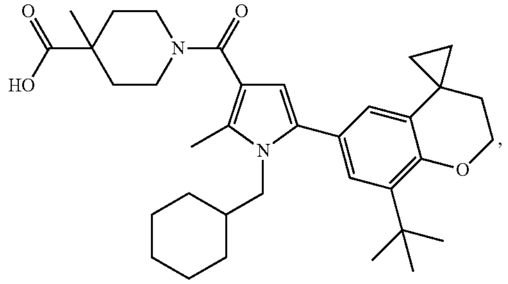
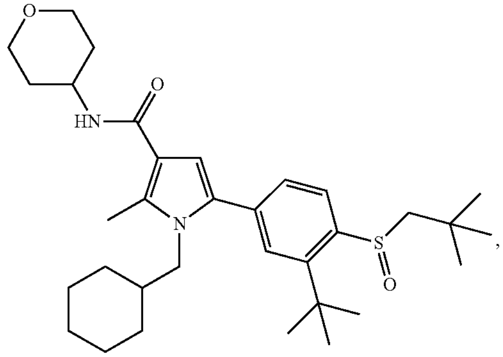
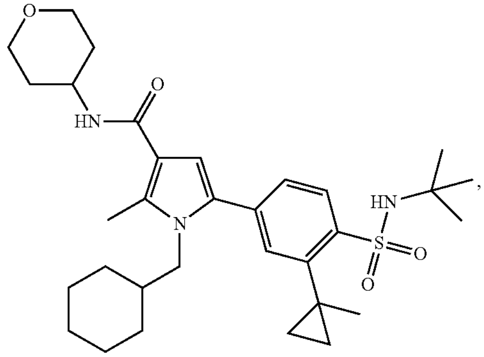
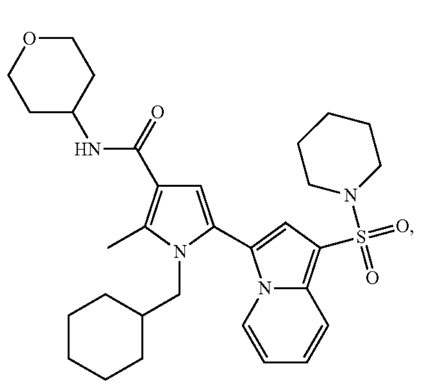
-continued
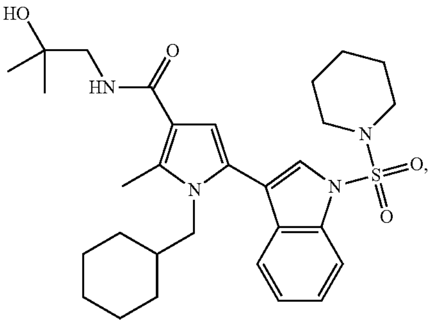
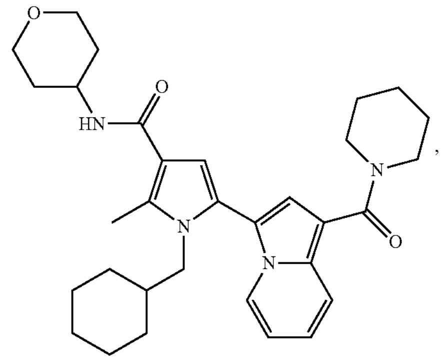
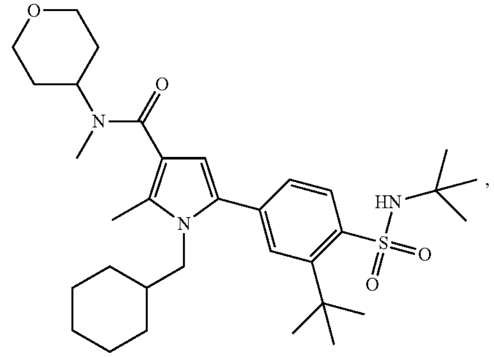
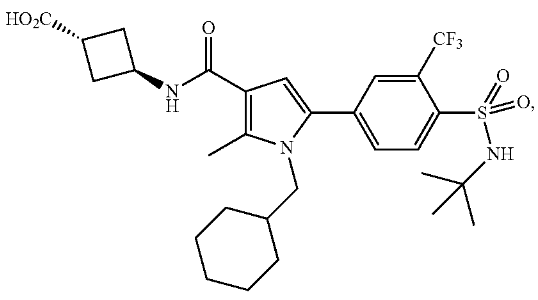
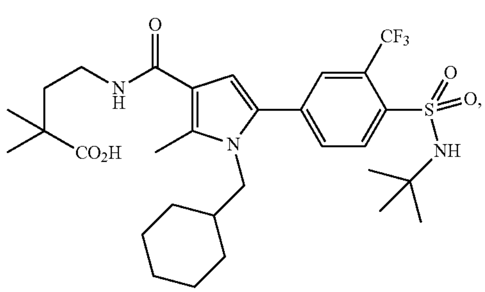

-continued
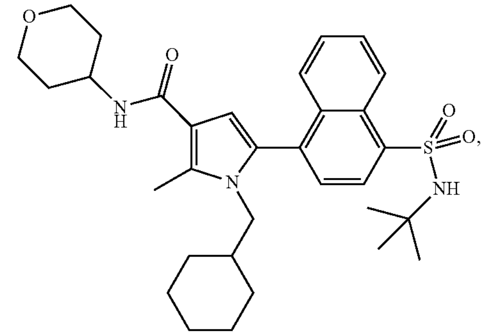
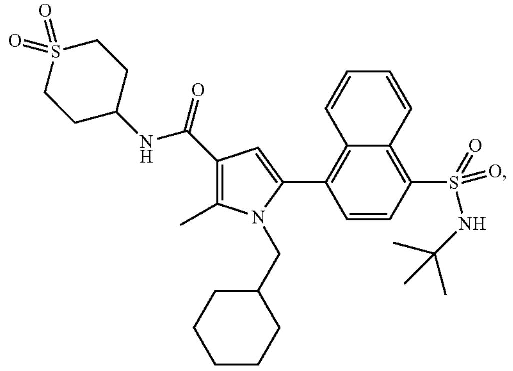
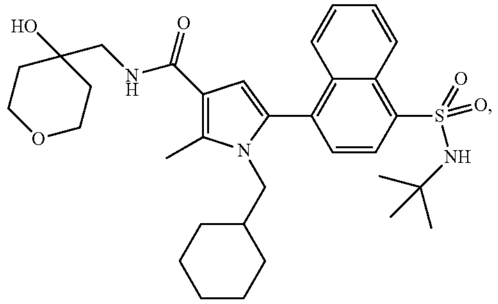
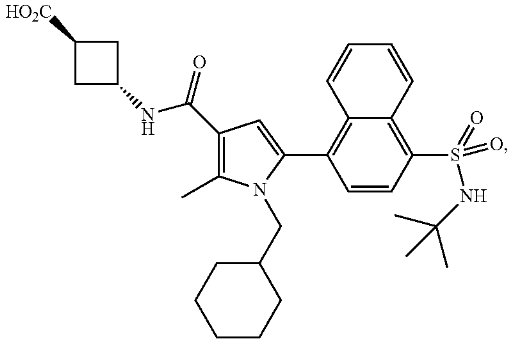
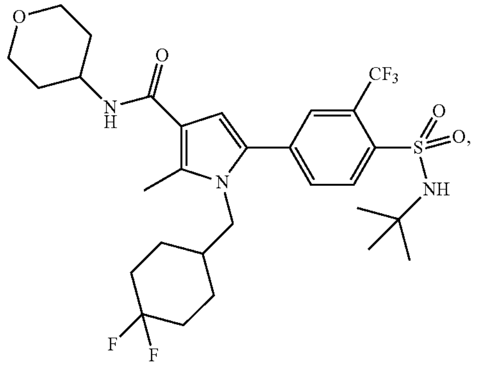
-continued
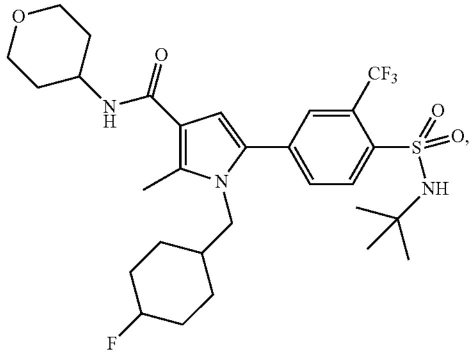
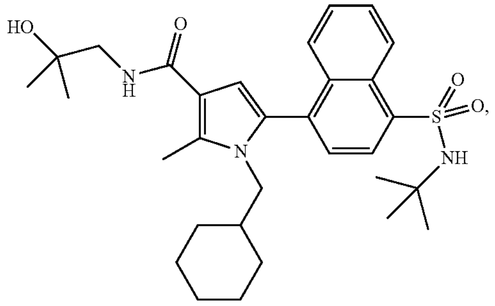
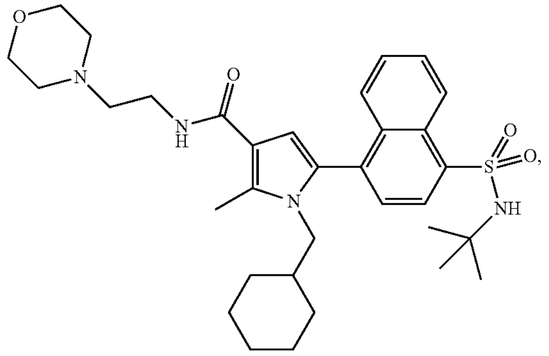
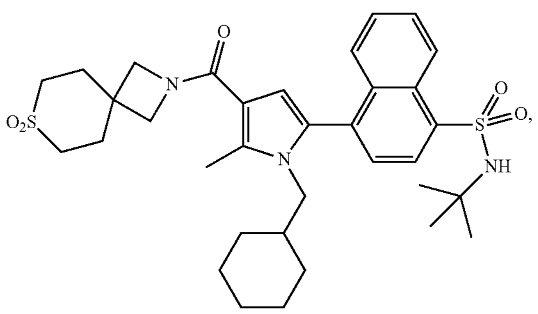
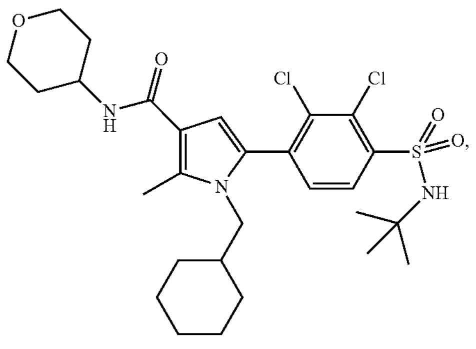

-continued
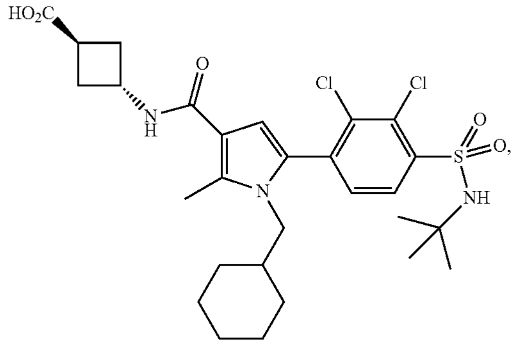
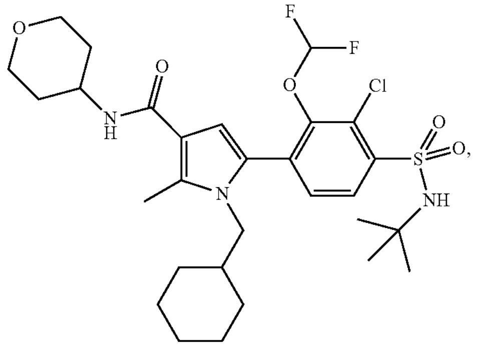
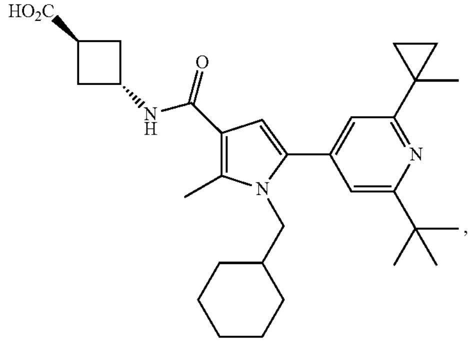
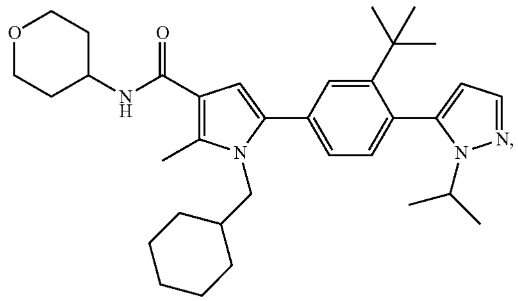
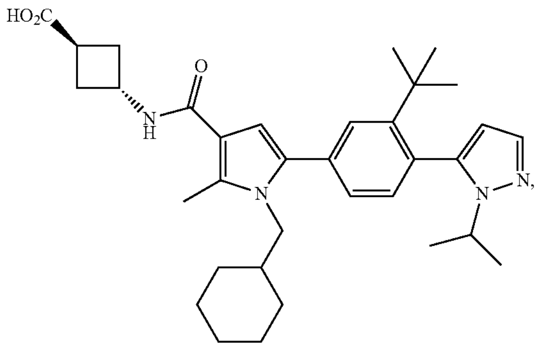
-continued
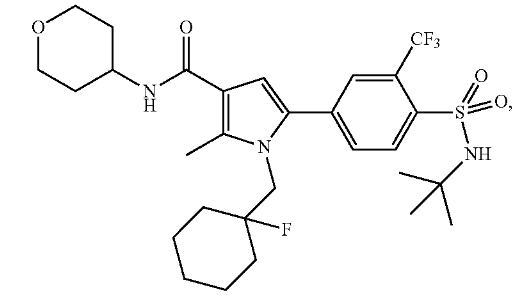
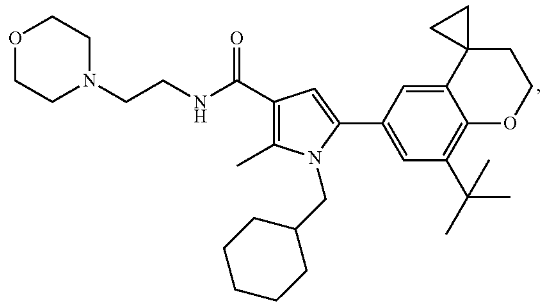
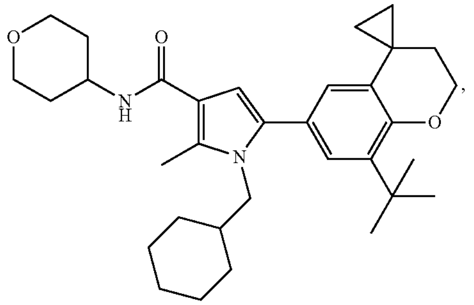
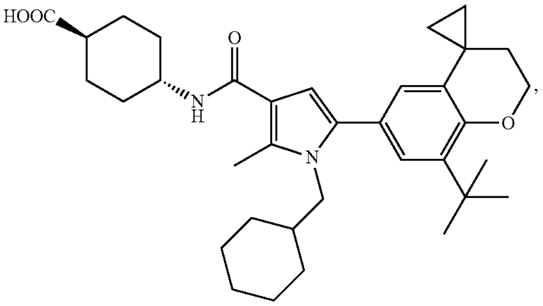
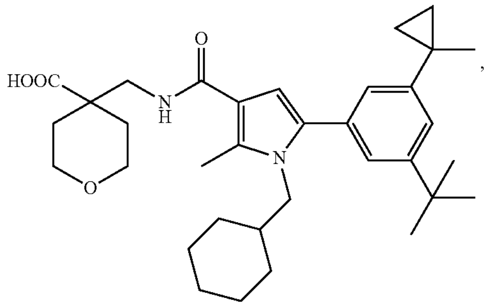

-continued
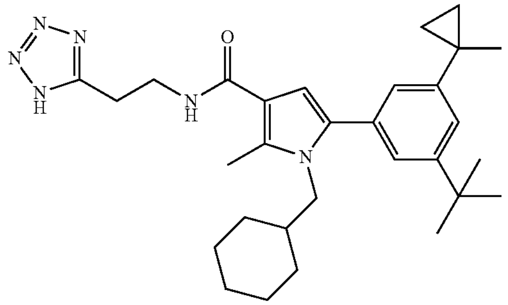
,
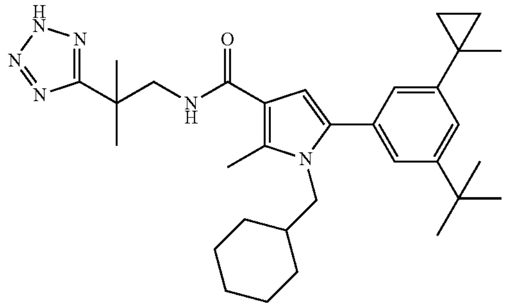
,
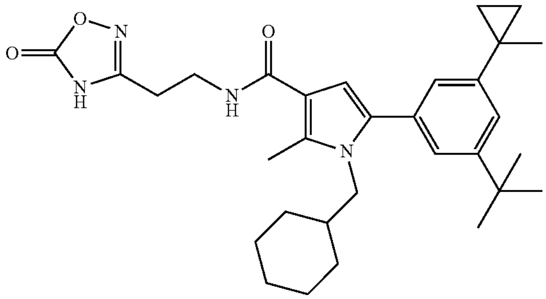
,
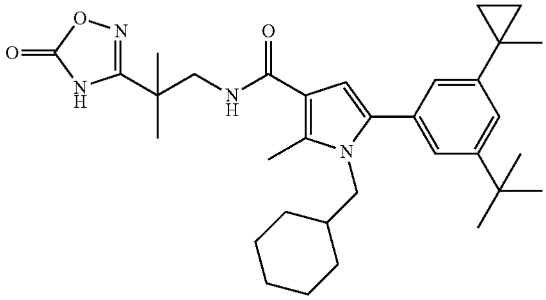
,
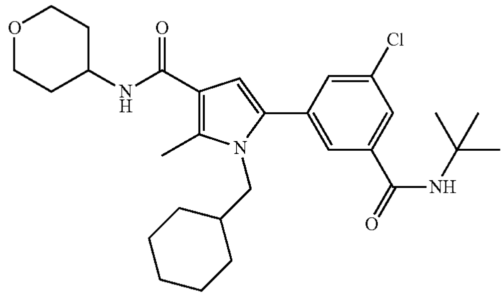
,
-continued
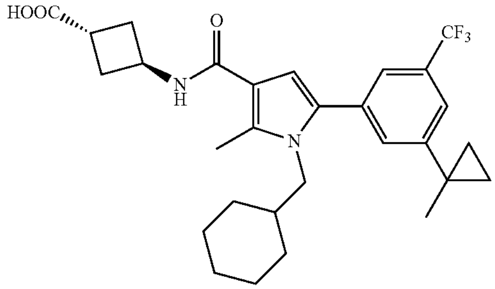
,
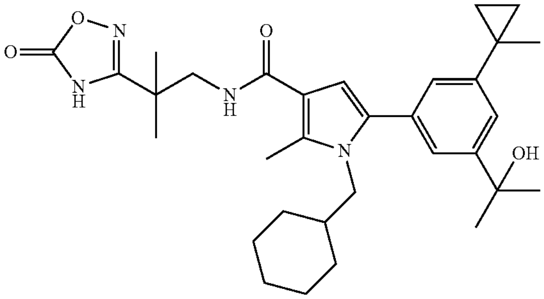
,
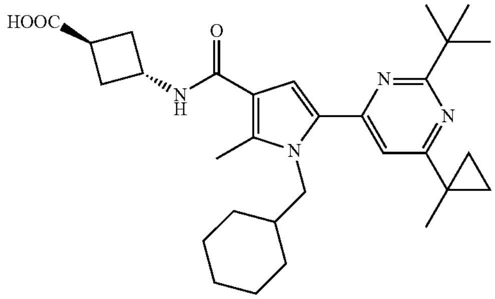
,
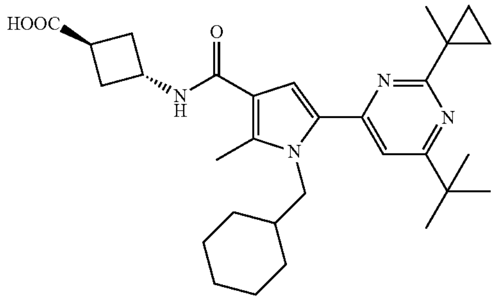
,
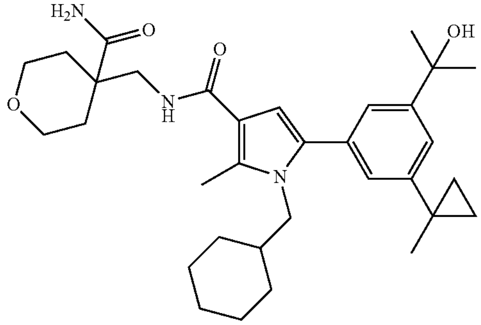
, -continued
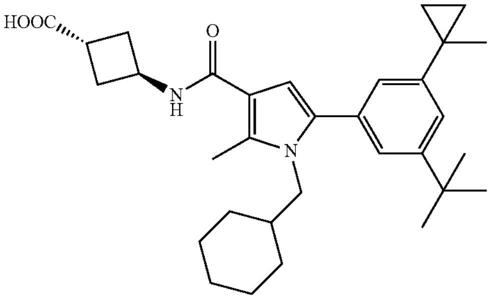
,
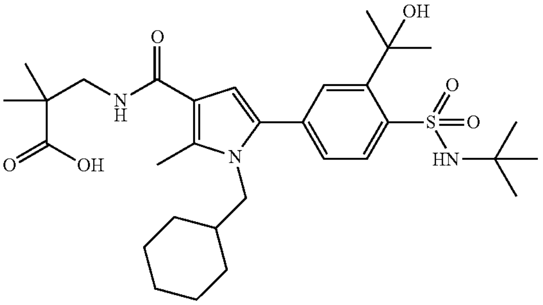
,
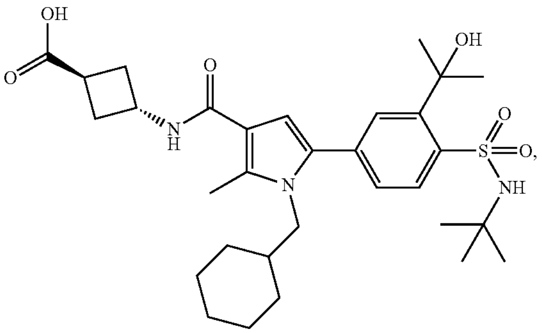
,
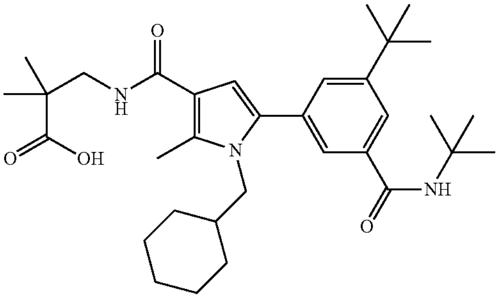
,
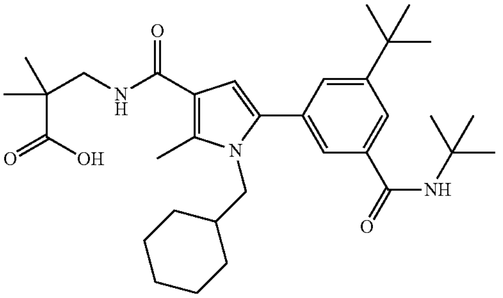
,
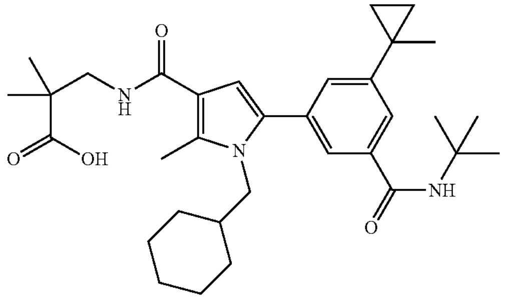
,
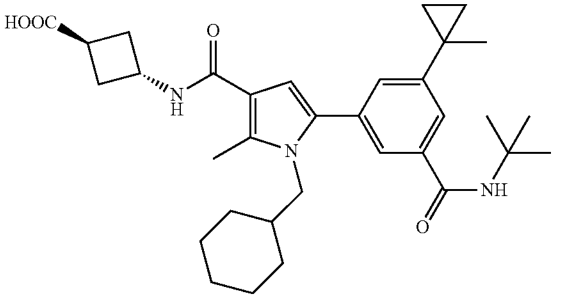
,
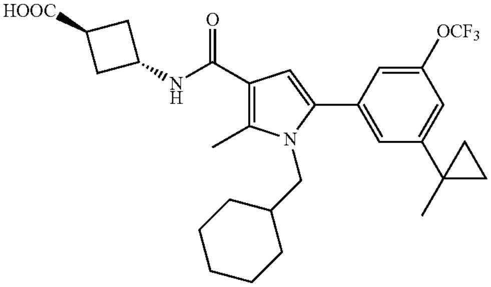
,
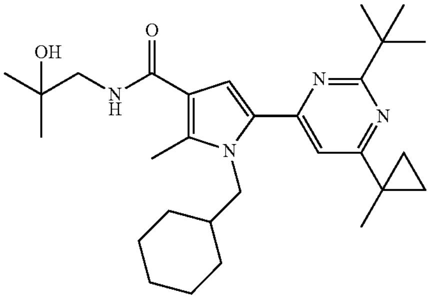
,
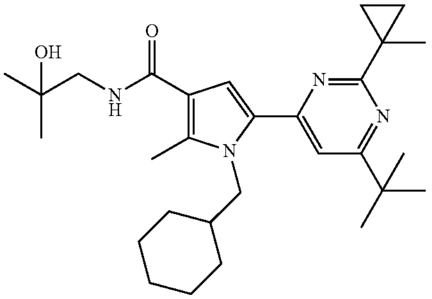
, -continued
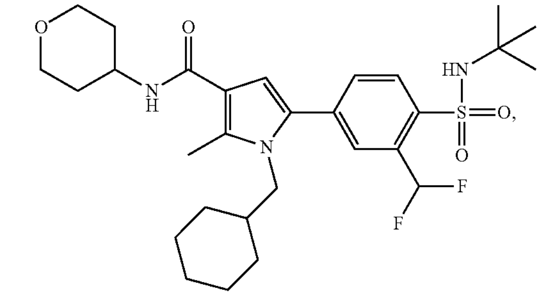,
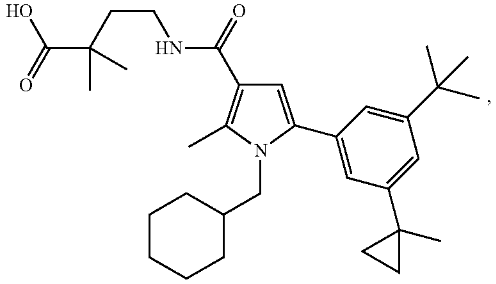,
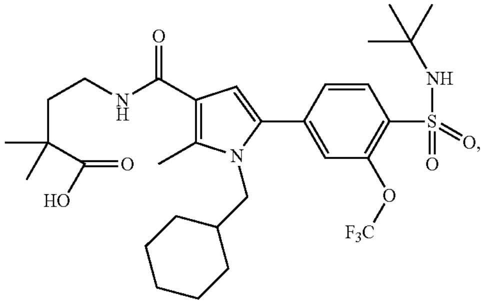,
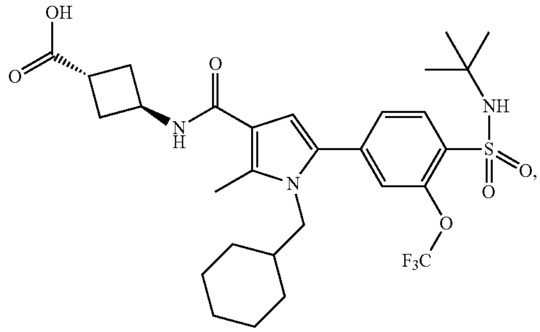,
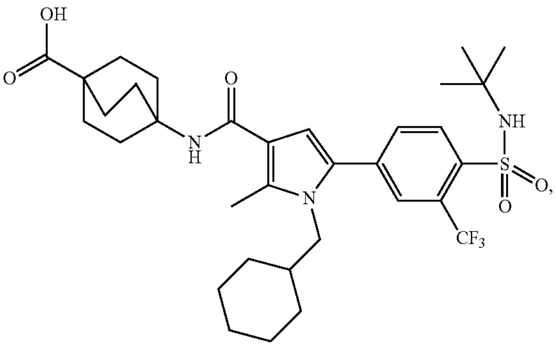,
-continued
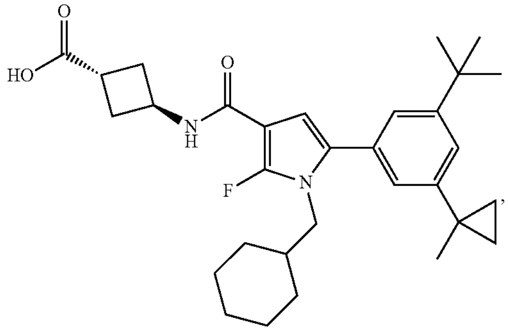,
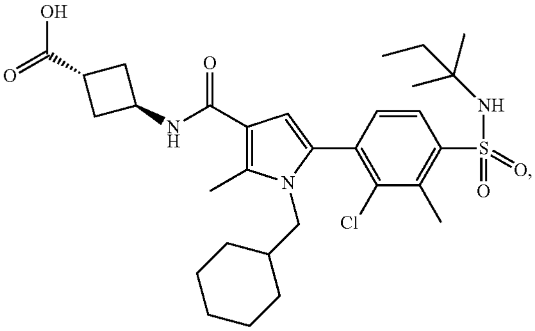,
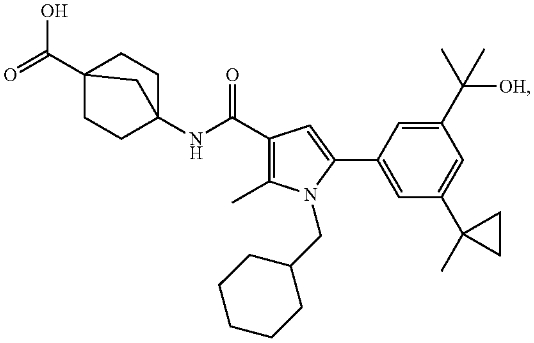,
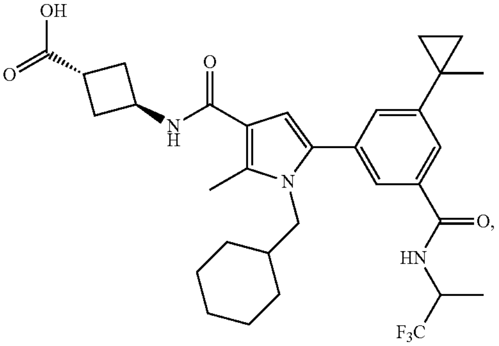,
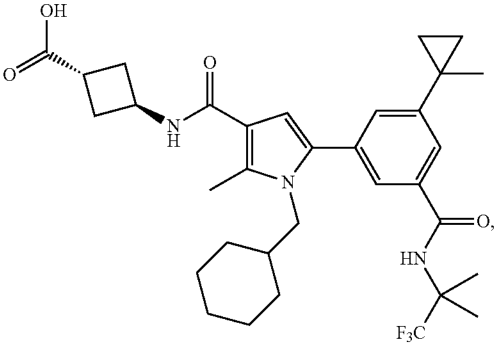, -continued
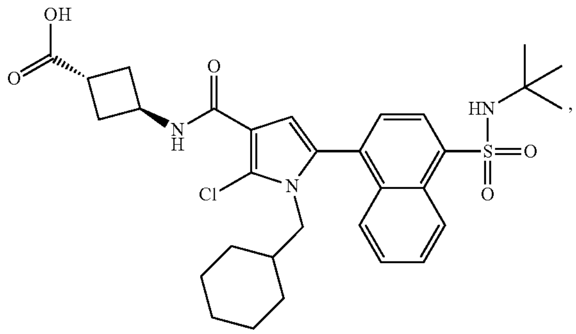
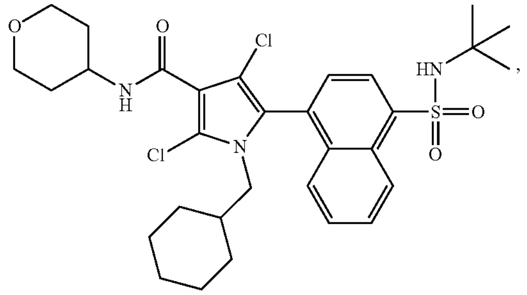
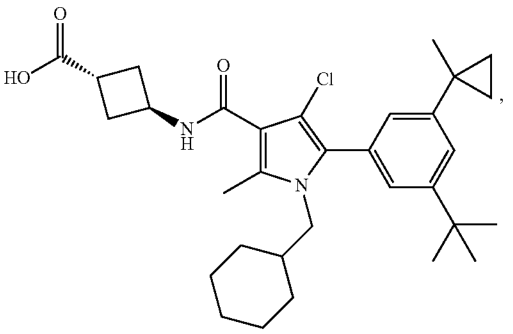
and an enantiomer, diastereomer, tautomer, N-oxide, solvate and pharmaceutically acceptable salt thereof.
In a more preferred embodiment in combination with any of the above or below embodiments of the first alternative the compound of Formula (1) is selected from the group consisting of
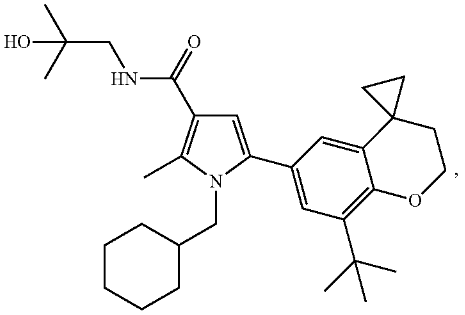
-continued
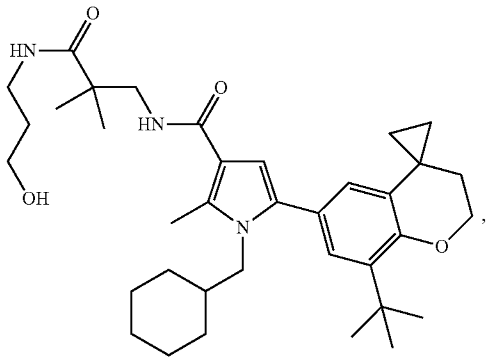
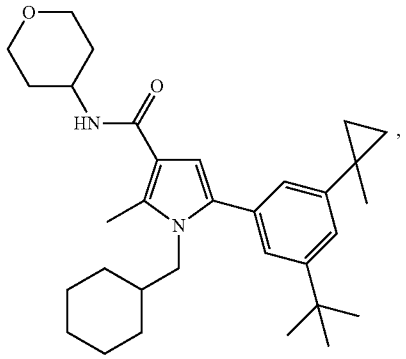
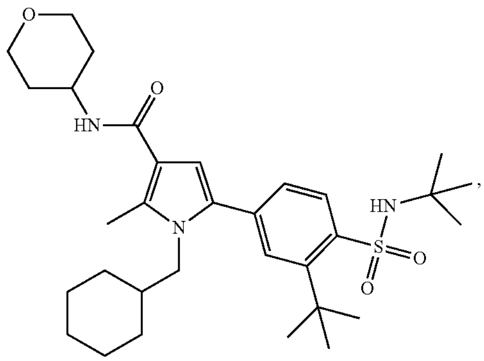
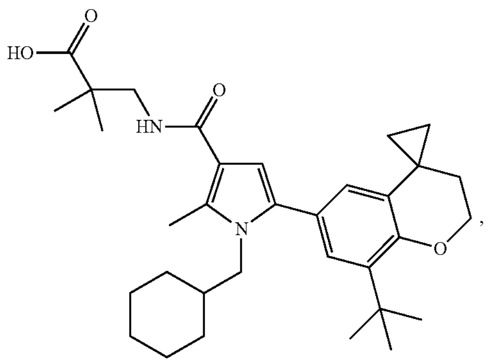

-continued
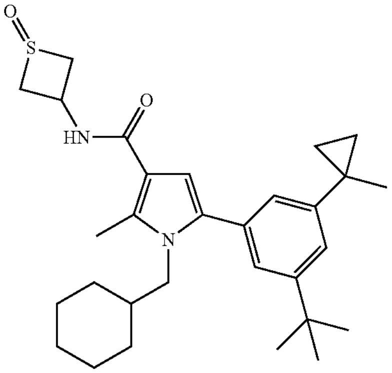
,
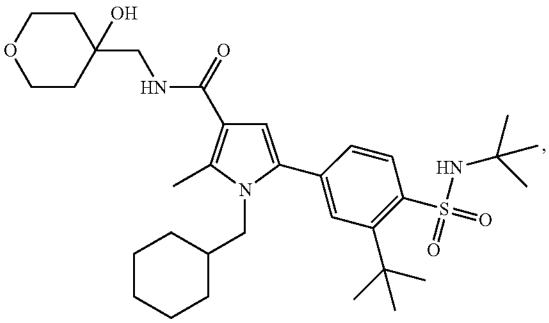
,
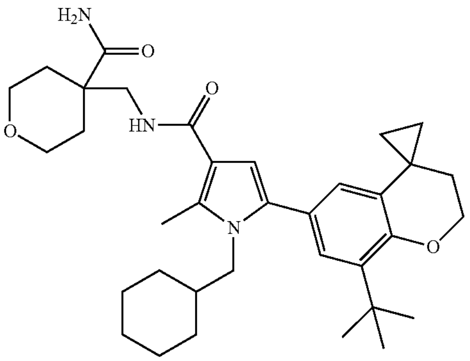
,
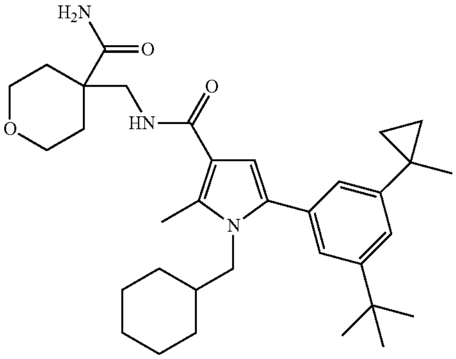
,
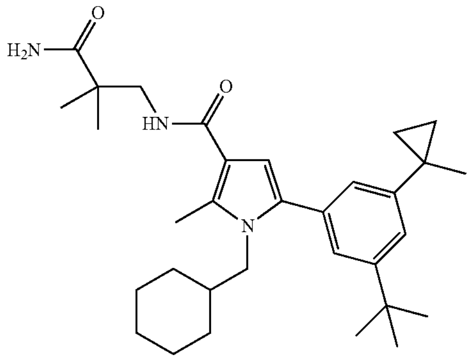
,
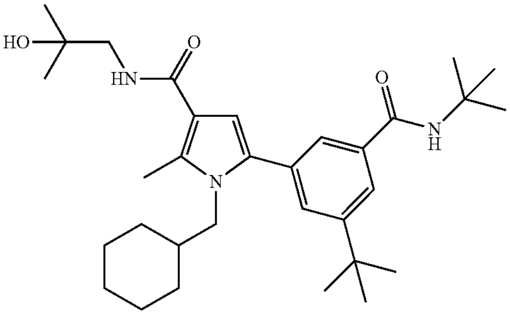
,
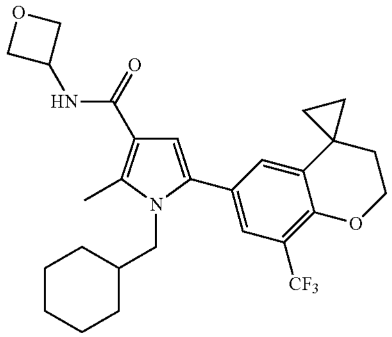
,
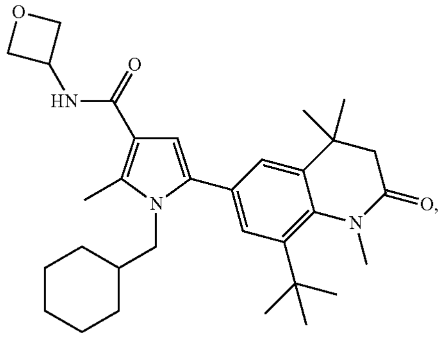
,
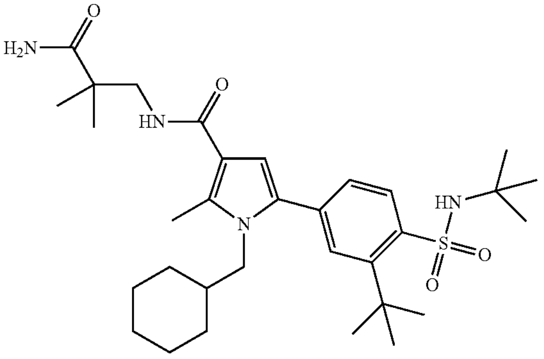
, -continued
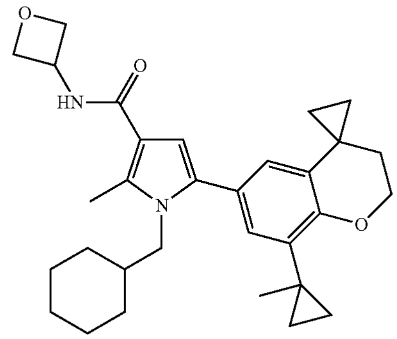
,
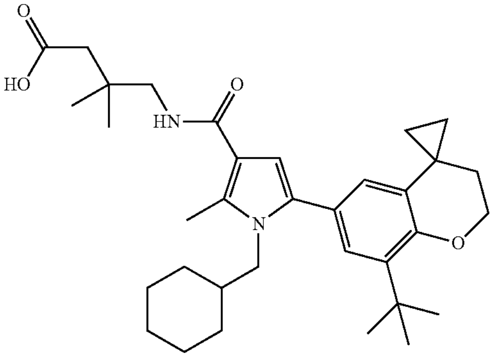
,
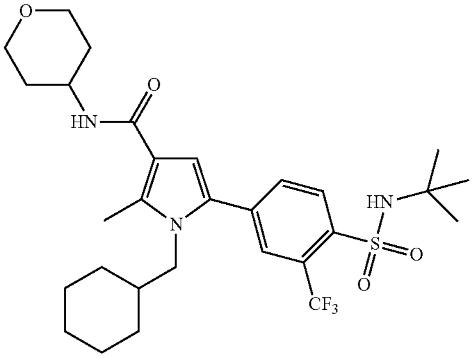
,
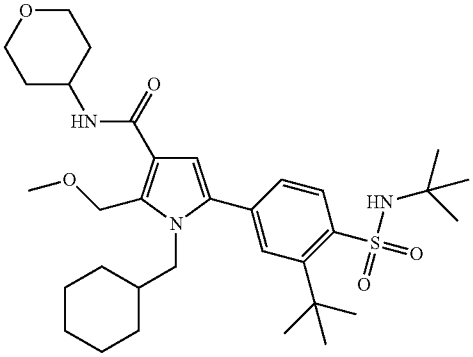
,
-continued
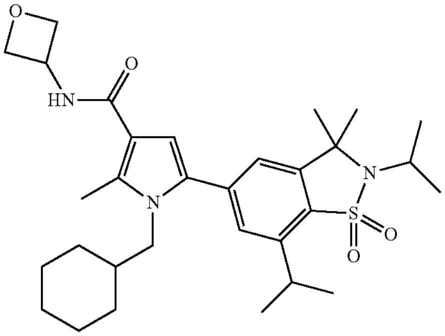
,
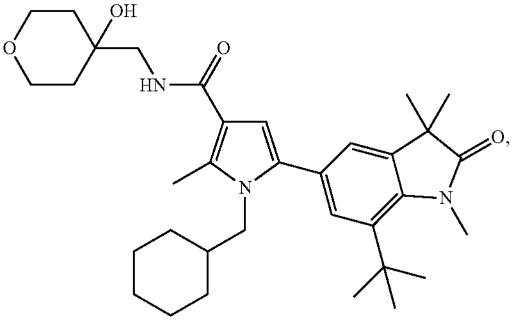
,
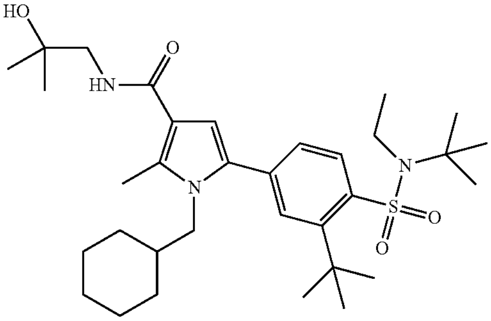
,
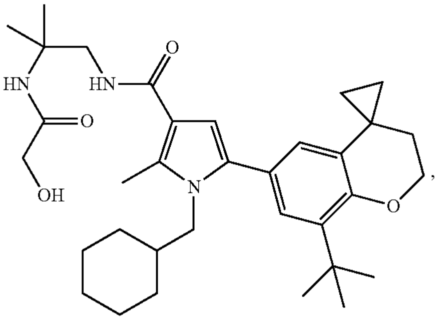
,
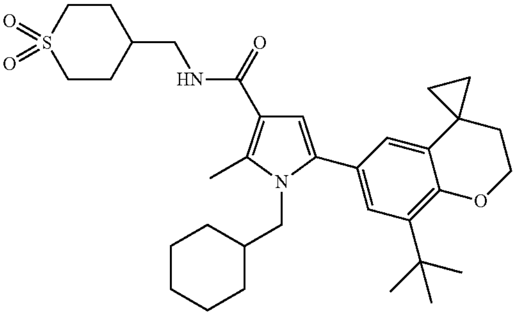
, -continued
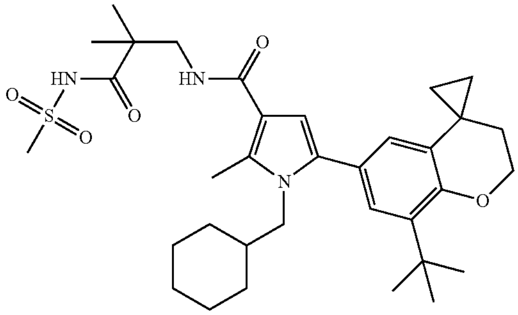
,
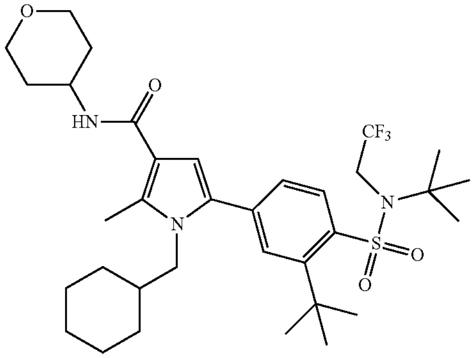
,
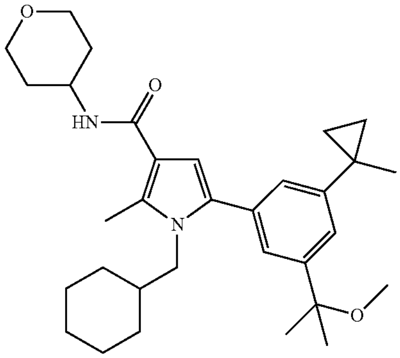
,
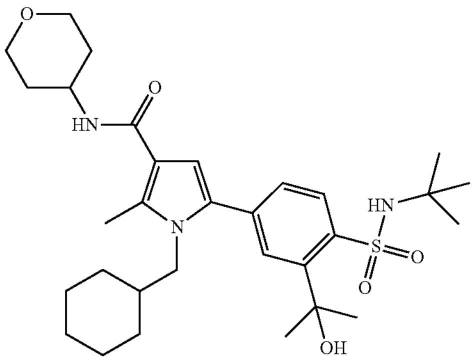
,
-continued
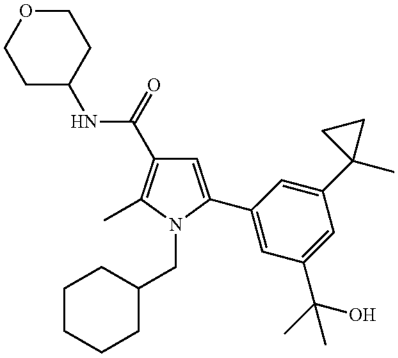
,
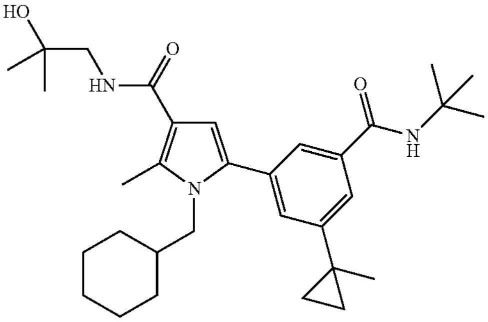
,
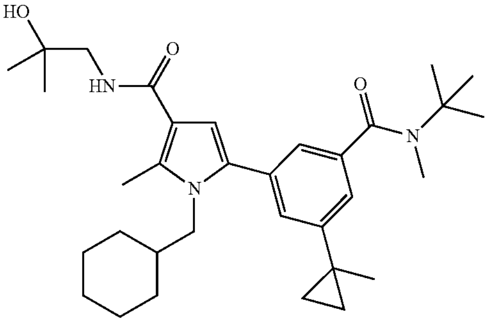
,
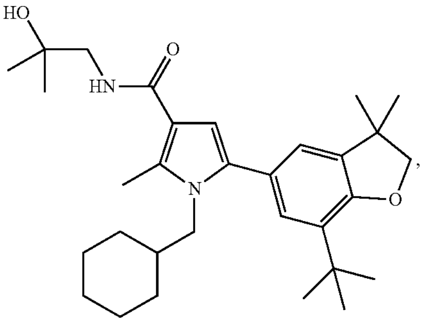
,
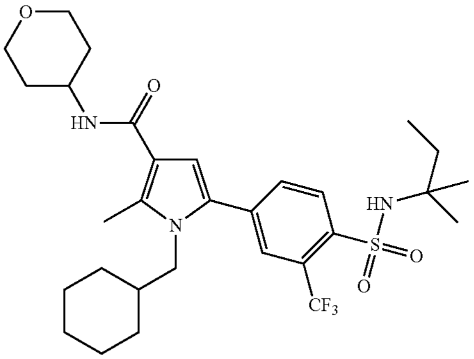
, -continued
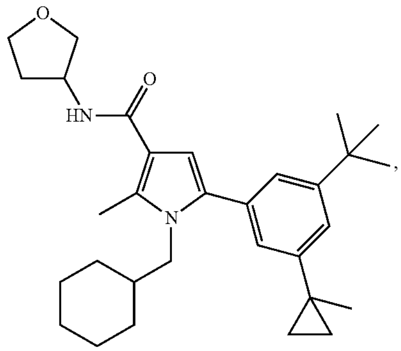
,
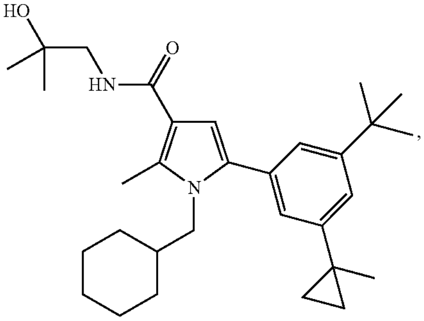
,
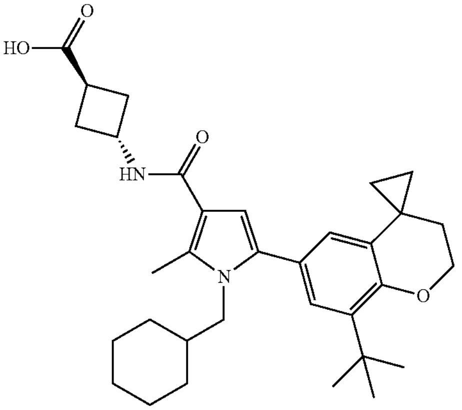
,
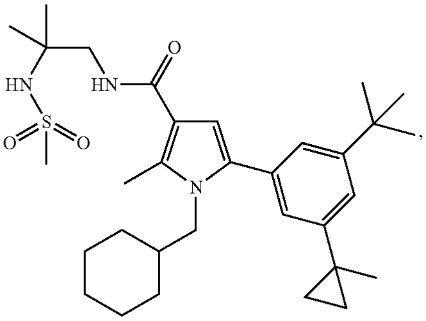
,
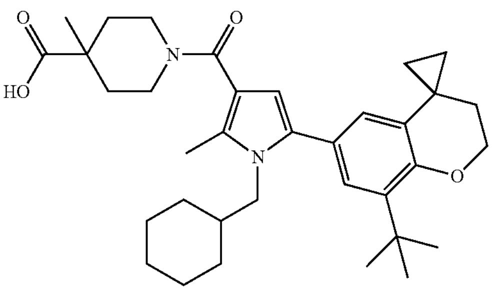
,
-continued
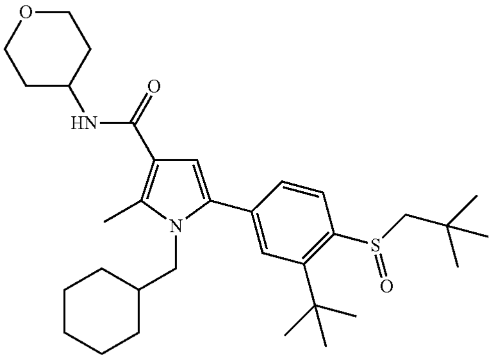
,
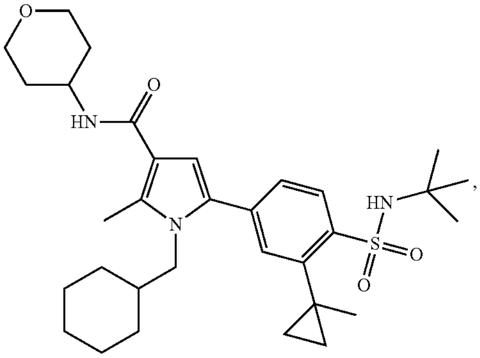
,
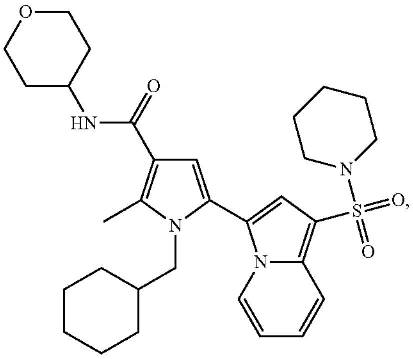
,
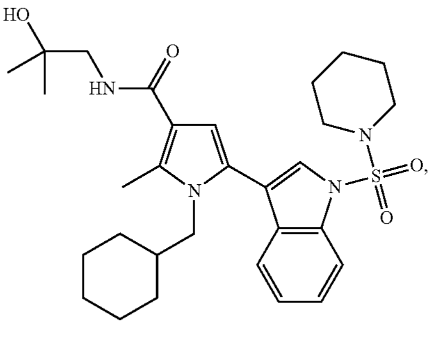
, -continued

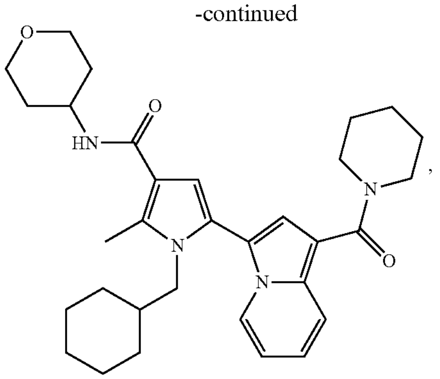

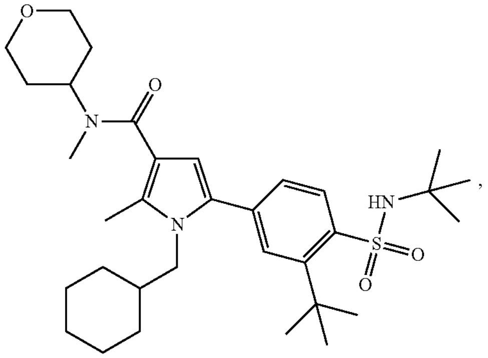

and an enantiomer, diastereomer, tautomer, solvate and pharmaceutically acceptable salt thereof.

In a second alternative, the present invention provides a compound of Formula (1)

(1)

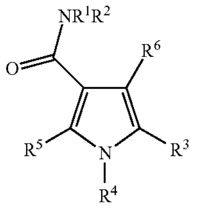

an enantiomer, diastereomer, tautomer, N-oxide, solvate, formulation and pharmaceutically acceptable salt thereof, wherein $R^1$ is selected from a 4-membered heterocycloalkyl group containing one heteroatom selected from the group consisting of N, O and S, or $C_{1-10}$-alkyl substituted with a group selected from halogen, CN, $OR^{11}$, $SO_yR^{11}$, $SO_3H$, $NR^{11}SO_2R^{11}$, $SO_2NR^{11}R^{12}$, $CO_2R^{11}$, $COR^{11}$, $CONR^{11}R^{12}$, $NR^{11}$—CO—$R^{11}$, $NR^{11}$—CO—$NR^{11}R^{12}$, $NR^{11}$—$SO_2$—$NR^{11}R^{12}$, $NR^{11}R^{12}$ and a 4-membered heterocycloalkyl group containing one heteroatom selected from the group consisting of N, O and S, or $C_{0-1}$-alkylene-$C_{3-10}$-cycloalkyl substituted with a group selected from halogen, CN, $SO_yR^{11}$, $NR^{11}SO_2R^{11}$, $SO_2NR^{11}R^{12}$, $CO_{2R}^{11}$, $CONR^{11}R^{12}$, $NR^{11}$—CO—$R^{11}$, $NR^{11}$—CO—$NR^{11}R^{12}$, $NR^{11}$—$SO_2$—$NR^{11}R^{12}$ and $NR^{11}R^{12}$, or $C_{2-10}$-alkylene-$C_{3-10}$-cycloalkyl, $C_{2-10}$-alkylene-O—$C_{3-10}$-cycloalkyl, $C_{2-10}$-alkylene-$C_{5-10}$-heterocycloalkyl and $C_{2-10}$-alkylene-O—$C_{5-10}$-heterocycloalkyl, wherein alkyl, alkylene, cycloalkyl and heterocycloalkyl are optionally substituted with 1 to 7 substituents independently selected from the group consisting of OH, oxo, CN, O—$C_{1-6}$-alkyl, O-halo-$C_{1-6}$-alkyl, $C_{1-6}$-alkyl, halo-$C_{1-6}$-alkyl, halogen, $CO_2R^{11}$, $CONR^{11}R^{12}$, $SO_2R^{11}$, $SO_2NR^{11}R^{12}$, $NR^{11}COR^{11}$, $NR^{11}SO_2R^{11}$, $C_{3-6}$-cycloalkyl, O—$C_{3-6}$-cycloalkyl, $C_{3-6}$-heterocycloalkyl, O—$C_{3-6}$-heterocycloalkyl, O—$C_{2-6}$-alkylene-$OR^{11}$ and $NR^{11}R^{12}$;

$R^2$ is selected from the group consisting of H, $C_{1-6}$-alkyl, halo-$C_{1-6}$-alkyl and hydroxy-$C_{1-6}$-alkyl;

or $R^1$ and $R^2$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from halogen, oxo, CN, $OR^{11}$, $SO_yR^{11}$, $SO_3H$, $NR^{11}SO_2R^{11}$, $SO_2NR^{11}R^{12}$, $C_{0-6}$-alkylene-$CO_2R^{11}$, $CONR^{11}R^{12}$, $COR^{11}$, $NR^{11}$—CO—$R^{11}$, $NR^{11}$—CO—$NR^{11}R^{12}$, $NR^{11}$—$SO_2$—$NR^{11}R^{12}$, $NR^{11}R^{12}$, $C_{1-6}$-alkyl, halo-$C_{1-6}$-alkyl, hydroxy-$C_{1-6}$-alkyl, $C_{3-6}$-cycloalkyl, O—$C_{3-6}$-cycloalkyl, $C_{3-6}$-heterocycloalkyl and O—$C_{3-6}$-heterocycloalkyl, wherein cycloalkyl and heterocycloalkyl are unsubstituted or substituted with 1 to 4 substitutents independently selected from halogen, $C_{1-3}$-alkyl, halo-$C_{1-3}$-alkyl and oxo;

$R^3$ is a 6- or 10-membered mono- or bicyclic aryl or a 6- to 10-membered mono- or bicyclic heteroaryl containing 1 or 2 heteroatom selected from the group consisting of N, O and S, wherein aryl and heteroaryl are unsubstituted or substituted with 1 to 5 substituents independently selected from halogen, CN, $C_{1-6}$-alkyl, $C_{3-10}$-cycloalkyl, $C_{0-6}$-alkylene-$C_{3-10}$-heterocycloalkyl, $C_{0-6}$-alkylene-O—$R^{31}$, $C_{0-6}$-alkylene-$COOR^{31}$, $C_{0-6}$-alkylene-$C(O)R^{31}$, $C_{0-6}$-alkylene-C(O)$N(R^{31})_2$, $C_{0-6}$-alkylene-$N(R^{31})C(O)R^{31}$, $C_{0-6}$-alkylene-$SO_2$—$N(R^{31})_2$, $C_{0-6}$-alkylene-$N(R^{31})SO_2$—$R^{31}$, $C_{0-6}$-alkylene-$SO_2$—$R^{31}$, $C_{0-6}$-alkylene-SO—$R^{31}$ and $C_{0-6}$-alkylene-$N(R^{31})_2$, wherein alkyl, alkylene, cycloalkyl and heterocycloalkyl are unsubstituted or substituted by 1 to 4 substituents independently selected from the group consisting of halogen, CN, $C_{1-3}$-alkyl, $C_{3-6}$-cycloalkyl, $C_{3-6}$-heterocycloalkyl, OH, O—$C_{1-3}$-alkyl, O-halo-$C_{1-3}$-alkyl, O—$C_{3-6}$-cycloalkyl, O—$C_{3-6}$-heterocycloalkyl, oxo, $N(R^{32})_2$, COOH, $CON(R^{32})_2$, CN and $NR^{32}$—$COR^{32}$, and wherein optionally two adjacent substituents complete a 3- to 8-membered saturated or partially unsaturated ring containing carbon atoms and optionally containing 1 to 3 heteroatoms selected from O, S or N, wherein the ring is unsubstituted or substituted with 1 to 6 substituents independently selected from halogen, $C_{1-6}$-alkyl, halo-$C_{1-6}$-alkyl, $C_{3-6}$-cycloalkyl, $C_{3-6}$-heterocycloalkyl, oxo, OH, O—$C_{1-6}$-alkyl and O-halo-$C_{1-6}$-alkyl;

$R^4$ is $SO_2$—$(CR^8R^8)_yR^7$, $SO_2$—$NR^{12}R^7$, $(CR^8R^8)_x$—$R^{10}$ or $C_{3-6}$-cycloalkyl, which is spirocyclic fused with $C_{3-10}$-cycloalkyl;

$R^5$ is selected from H, halo-$C_{1-6}$-alkyl, CHO, $CON(R^{52})_2$ or halogen, wherein alkyl is unsubstituted or substituted with 1 to 3 substituents independently selected from the group consisting of O—$C_{1-6}$-alkyl, O-halo-$C_{1-6}$-alkyl and OH;

$R^6$ is selected from H, $C_{1-6}$-alkyl, halo-$C_{1-6}$-alkyl or halogen;

$R^7$ is selected from $C_{3-10}$-cycloalkyl and $C_{3-10}$-heterocycloalkyl, wherein cycloalkyl and heterocycloalkyl are unsubstituted or substituted with 1 to 3 substituents independently selected from the group consisting of halogen, OH, oxo, O-$C_{1-6}$-alkyl, O-halo-$C_{1-6}$-alkyl, $C_{1-6}$-alkyl, halo-$C_{1-6}$-alkyl, cycloalkyl and heterocycloalkyl;

$R^8$ is independently selected from H, F, $C_{1-3}$-alkyl, halo-$C_{1-3}$-alkyl or OH;

$R^{10}$ is $C_{3-10}$-cycloalkyl, wherein cycloalkyl is unsubstituted or substituted with 1 to 6 substituents independently selected from halogen, OH, oxo, O—$C_{1-6}$-alkyl, O-halo-$C_{1-6}$-alkyl, $C_{1-6}$-alkyl, halo-$C_{1-6}$-alkyl, cycloalkyl, heterocycloalkyl, and optionally two adjacent substituents together complete a 6-membered aryl ring wherein the ring is unsubstituted or substituted with 1 to 3 substituents independently selected from halogen, $C_{1-2}$-alkyl, halo-$C_{1-2}$-alkyl;

$R^{11}$ is independently selected from H, $C_{1-6}$-alkyl, $C_{0-6}$-alkylene-$C_{3-6}$-cycloalkyl, $C_{0-6}$-alkylene-$C_{3-6}$-heterocycloalkyl, wherein alkyl, alkylene, cyclolalkyl and heterocycloalkyl are unsubstituted or substituted with 1 to 6 substituents independently selected from halogen, OH, oxo, $C_{1-3}$-alkyl, halo-$C_{1-3}$-alkyl, O-halo-$C_{1-3}$-alkyl and $SO_2$—$C_{1-3}$-alkyl;

$R^{12}$ is independently selected from H, $C_{1-6}$-alkyl and halo-$C_{1-6}$-alkyl;

$R^{31}$ is independently selected from H, $C_{1-6}$-alkyl, $C_{0-6}$-alkylene-$C_{3-6}$-cycloalkyl, $C_{0-6}$-alkylene-$C_{3-6}$-heterocycloalkyl, 5- or 6-membered heteroaryl and 6-membered aryl, wherein alkyl, alkylene, cyclolalkyl, heterocycloalkyl, aryl and heteroaryl are unsubstituted or substituted with 1 to 6 substituents independently selected from halogen, CN, OH, oxo, $C_{1-3}$-alkyl, halo-$C_{1-3}$-alkyl, O—$C_{1-3}$-alkyl, O-halo-$C_{1-3}$-alkyl and $SO_2$—$C_{1-3}$-alkyl;

and optionally wherein two $R^{31}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from fluoro, OH, oxo, $C_{1-4}$-alkyl and halo-$C_{1-4}$-alkyl;

$R^{32}$ is independently selected from H, $C_{1-6}$-alkyl and halo-$C_{1-6}$-alkyl;

$R^{52}$ is independently selected from H, $C_{1-3}$-alkyl and halo-$C_{1-3}$-alkyl;

x is independently selected from 1 and 2;

y is independently selected from 0, 1 and 2.

In a further preferred embodiment in combination with any one of the above or below embodiments of the second alternative $NR^1R^2$ is selected from $NHCH_2CONH_2$, $NHCH_2CONMe_2$, $NHCH_2CH_2OH$, $NHCH_2CH(CF_3)OH$, $NHCH_2C(CF_3)_2OH$, $NHCH_2CH_2OMe$, $NHCH_2CH_2SO_2Me$, $NHCH_2CH_2SO_2NH_2$, $NH(CH_2)_3OH$, $NH(CH_2)_3OMe$, $NH(CH_2)_4OH$, $NH(CH_2)_4OMe$, $NH(CH_2)_5OH$, $NH(CH_2)_2CO_2H$, $NH(CH_2)_3CO_2H$, $NH(CH_2)_4CO_2H$, $NH(CH_2)_5CO_2H$, $NHCH_2CMe_2OH$, $NHCH(Me)CMe_2OH$, $NHCH_2CMe_2OMe$, $NHCH_2CMe_2CO_2H$, $NHCH_2CMe_2CONH_2$, $NHCH_2CMe_2CONHMe$, $NHCH_2CMe_2CONMe_2$, $NHCH_2CMe_2NHSO_2Me$, $NH(CH_2)_3SOMe$, $NH(CH_2)_5SO_2Me$, $NH(CH_2)_5SO_2NH_2$, $NH(CH_2)_3NHSO_2Me$, $NH(CH_2)_2O(CH_2)_2OH$, $NHCH_2CHMeOH$, $NH(CH_2)_5SOMe$, $NH(CH_2)_3SO_2Me$, 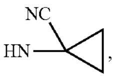, 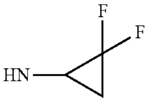, -continued

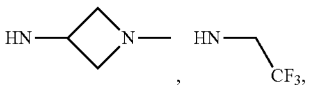

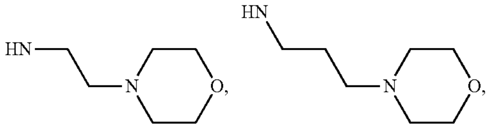

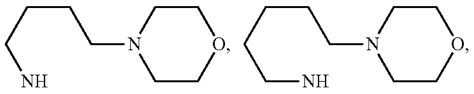

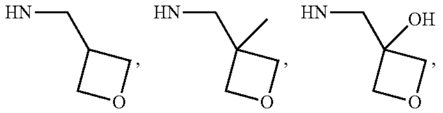

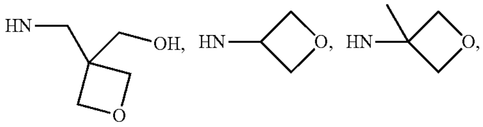

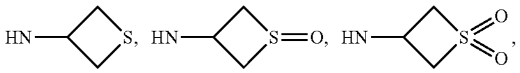

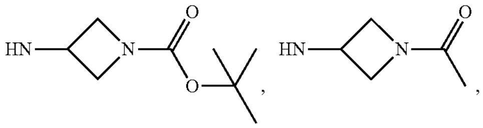

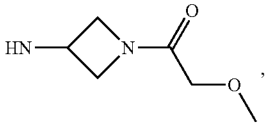

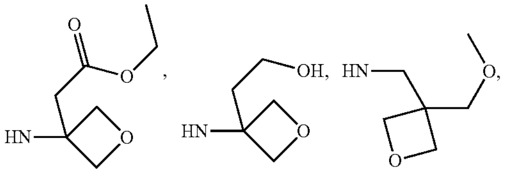

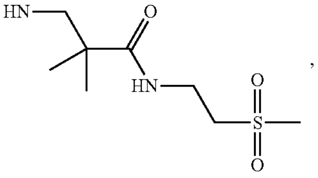

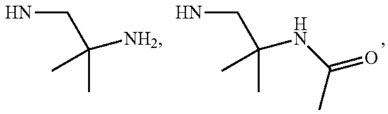

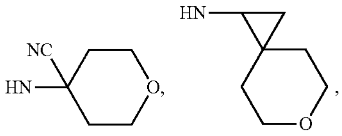

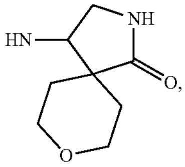

-continued
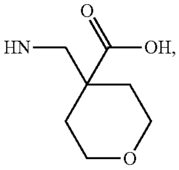
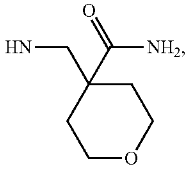
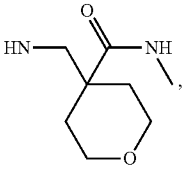
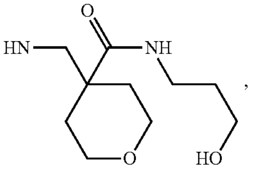
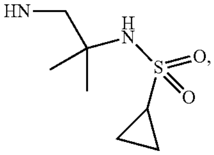
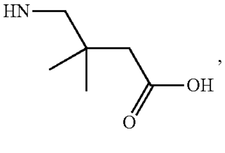
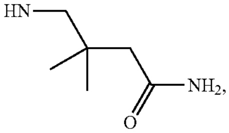
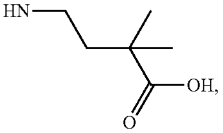
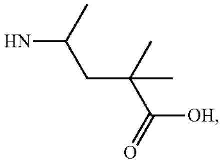
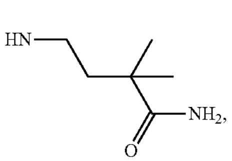
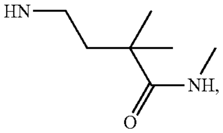
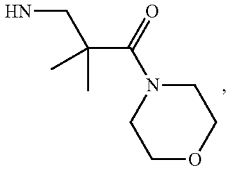
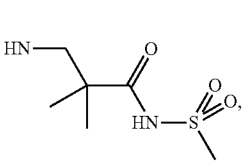
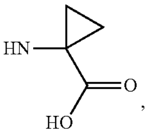
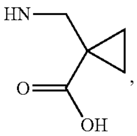
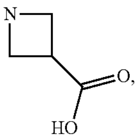
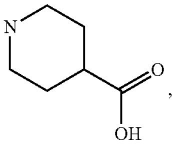
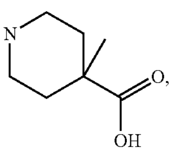
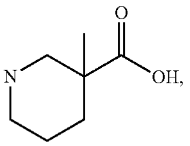
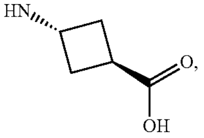
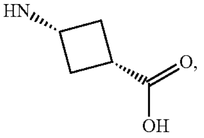
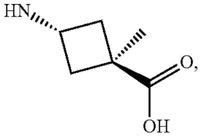
-continued
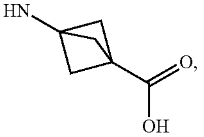
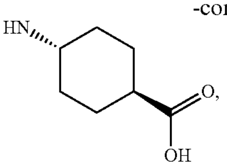
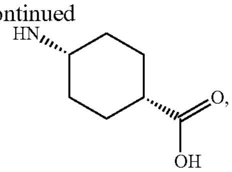
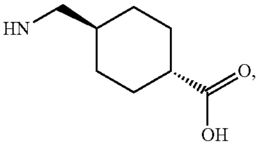
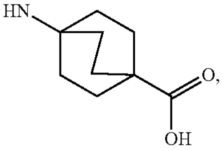
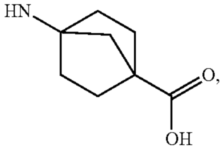
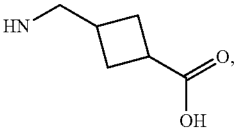
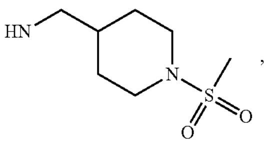
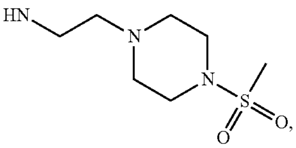
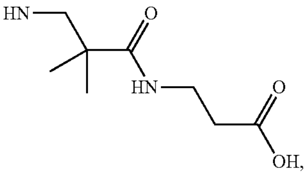
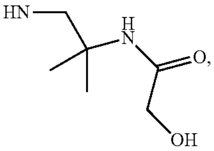
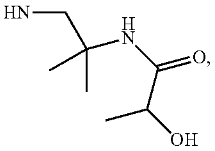
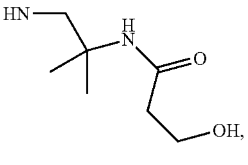
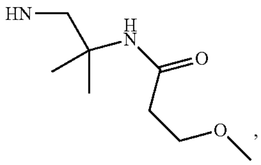
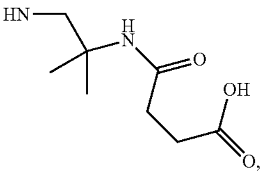
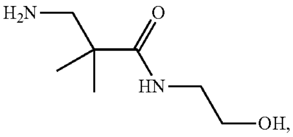

-continued

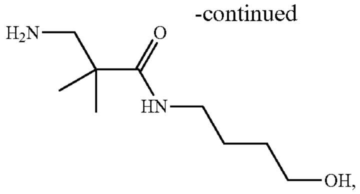

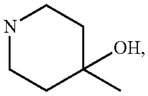

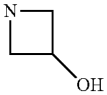

,

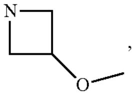

,

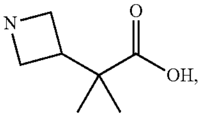

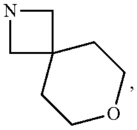

,

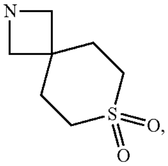

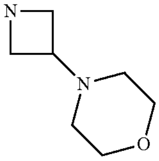

,

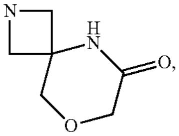

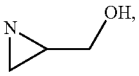

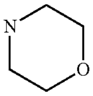

and

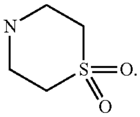

In a more preferred embodiment in combination with any one of the above or below embodiments of the second alternative $NR^1R^2$ is selected from $NHCH_2CONH_2$, $NHCH_2CONMe_2$, $NHCH_2CH_2OH$, $NHCH_2CH(CF_3)OH$, $NHCH_2C(CF_3)_2OH$, $NHCH_2CH_2OMe$, $NHCH_2CH_2SO_2Me$, $NHCH_2CH_2SO_2NH_2$, $NH(CH_2)_3OH$, $NH(CH_2)_3OMe$, $NH(CH_2)_4OH$, $NH(CH_2)_4OMe$, $NH(CH_2)_5OH$, $NH(CH_2)_2CO_2H$, $NH(CH_2)_3CO_2H$, $NH(CH_2)_4CO_2H$, $NH(CH_2)_5CO_2H$, $NHCH_2CMe_2OH$, $NHCH(Me)CMe_2OH$, $NHCH_2CMe_2OMe$, $NHCH_2CMe_2CO_2H$, $NHCH_2CMe_2CONH_2$, $NHCH_2CMe_2CONHMe$, $NHCH_2CMe_2CONMe_2$, $NHCH_2CMe_2NHSO_2Me$, $NH(CH_2)_3SOMe$, $NH(CH_2)_5SO_2Me$, $NH(CH_2)_3NHSO_2Me$, $NH(CH_2)_2O(CH_2)_2OH$, $NHCH_2CHMeOH$,

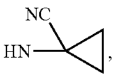

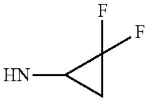

,

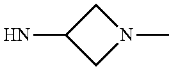

,

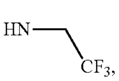

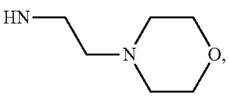

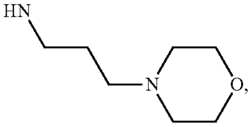

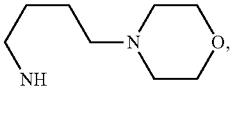

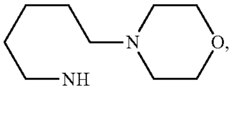

-continued

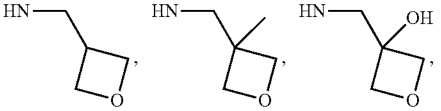

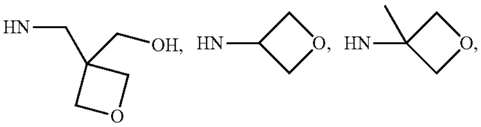

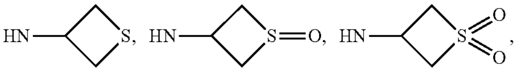

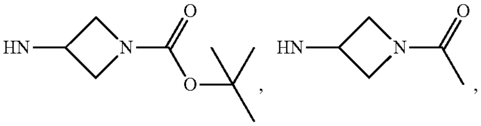

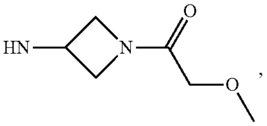

,

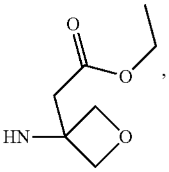

,

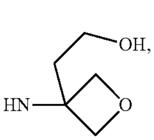

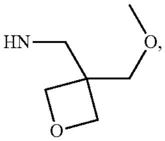

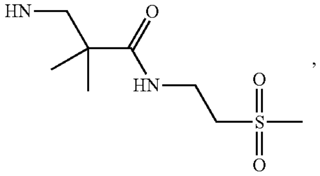

,

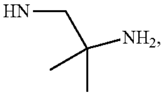

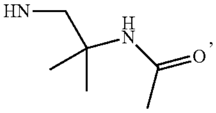

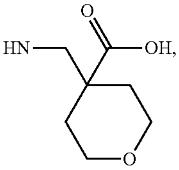

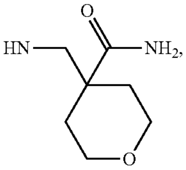

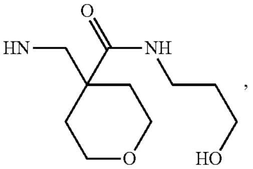

,

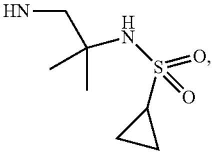

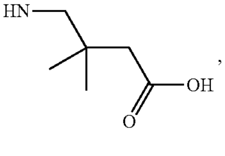

,

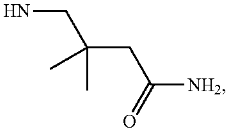

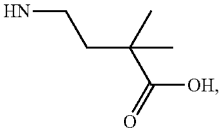

-continued
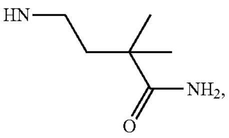,
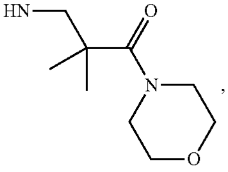,
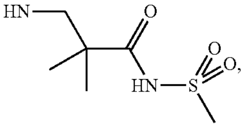, 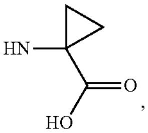,
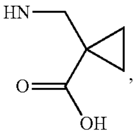, 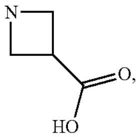, 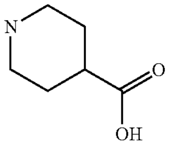,
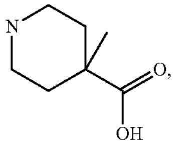,
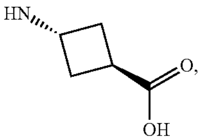 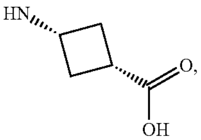
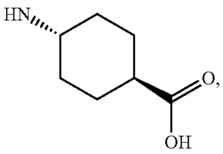 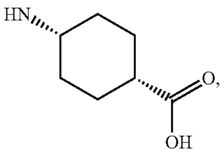
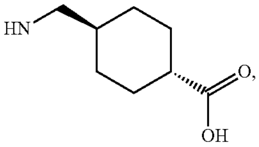
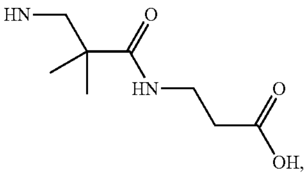
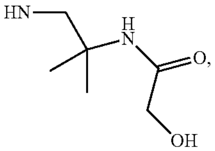
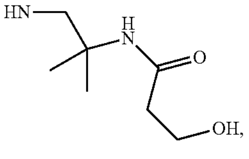 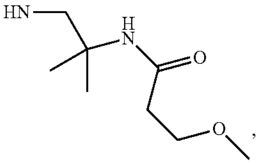,
-continued
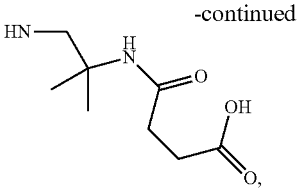
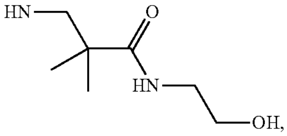
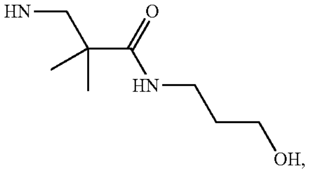 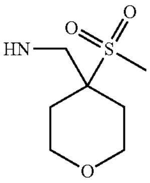,
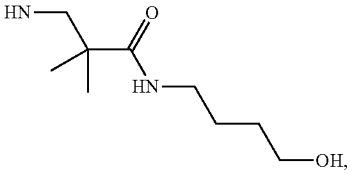
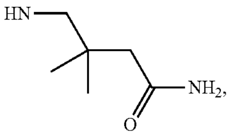
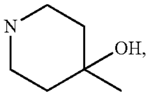 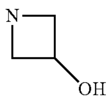, 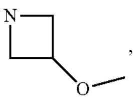,
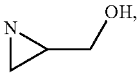
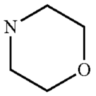 and 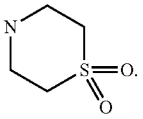
More preferably, $NR^1R^2$ is selected from
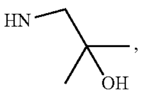, 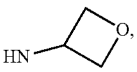 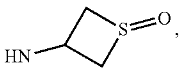
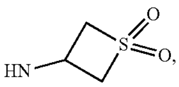 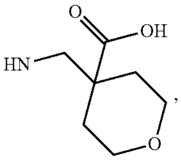,
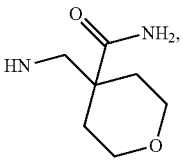 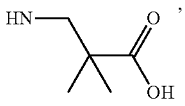,
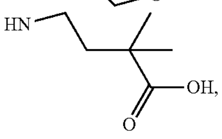 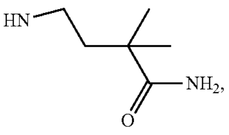

-continued

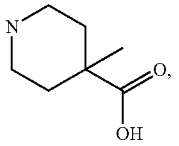
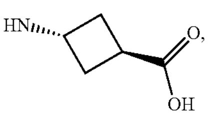
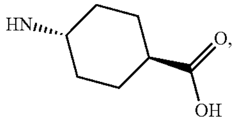
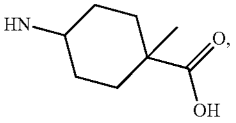
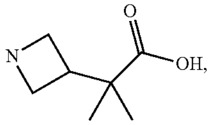
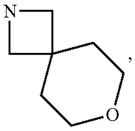,
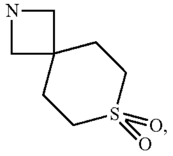
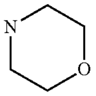
and
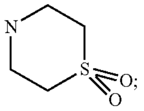

and most preferred $NR^1R^2$ is

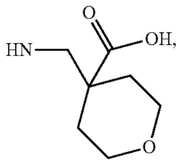
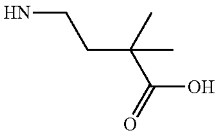,
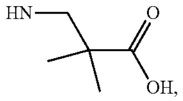
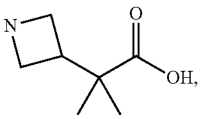
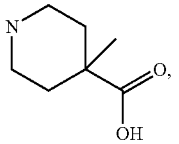
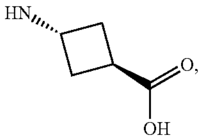
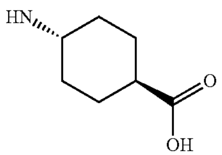
and
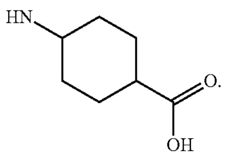

In another preferred embodiment in combination with any one of the above or below embodiments of the second alternative $R^3$ is

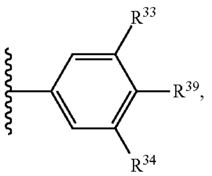
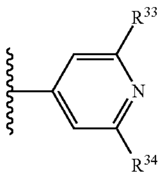,

-continued

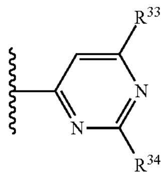
and
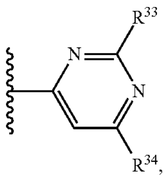

wherein $R^{33}$ is independently selected from $C_{1-6}$-alkyl and fluoro-$C_{1-6}$-alkyl;

$R^{34}$ is independently selected from halogen, $C_{1-6}$-alkyl, fluoro-$C_{1-6}$-alkyl, O—$C_{1-6}$-alkyl, O-fluoro-$C_{1-6}$-alkyl, NH—$C_{1-6}$-alkyl and NH-fluoro-$C_{1-6}$-alkyl;

$R^{39}$ is selected from H, F and OH.

In yet another preferred embodiment in combination with any one of the above or below embodiments of the second alternative $R^3$ is selected from

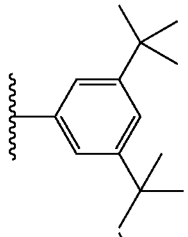,
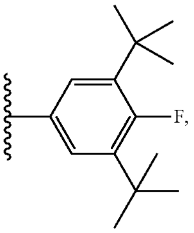
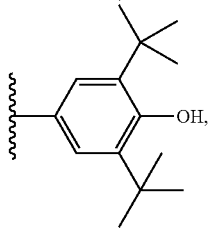
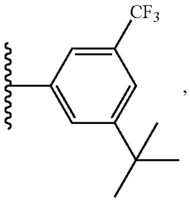,
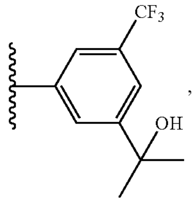,
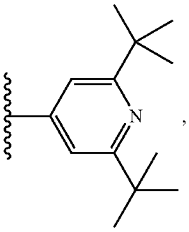,
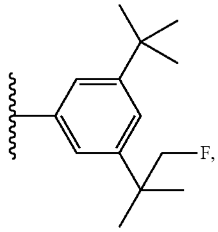
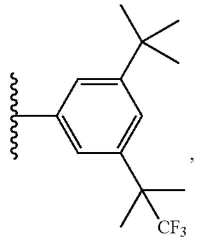,
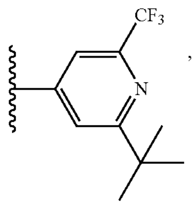,
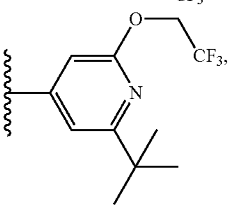

-continued
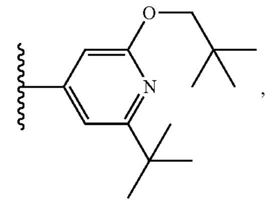,
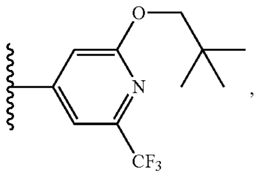,
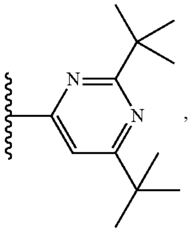,
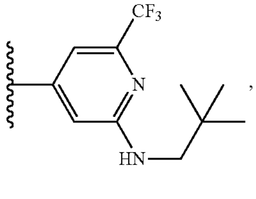,
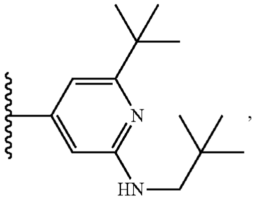,
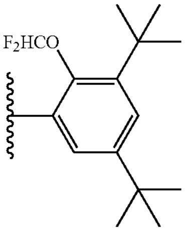
and
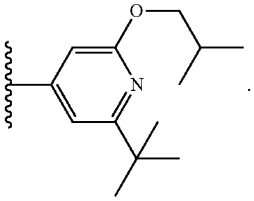.
More preferably, $R^3$ is
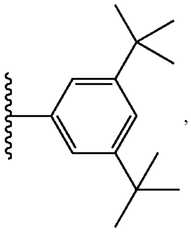,
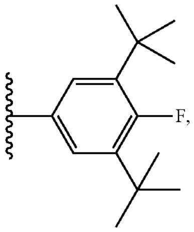
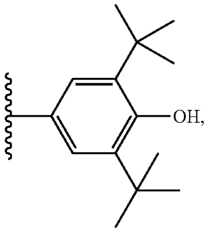
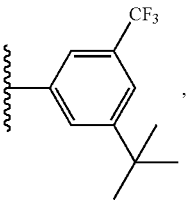,
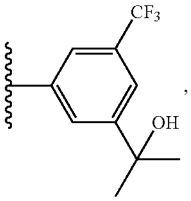,
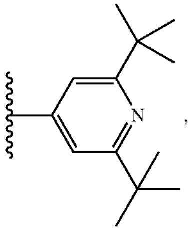,
-continued
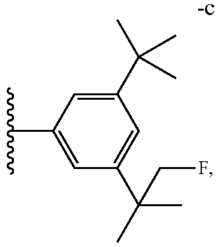
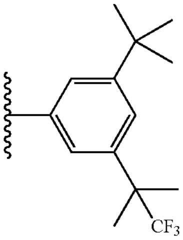,
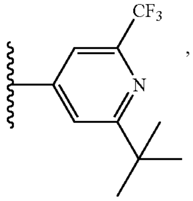,
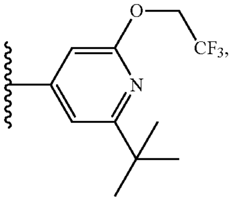
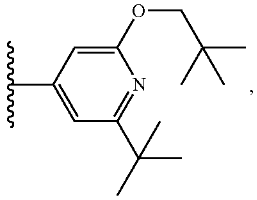,
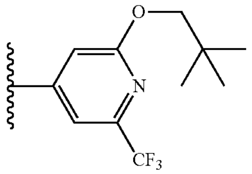
and
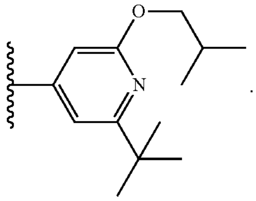.
Even more preferably, $R^3$ is
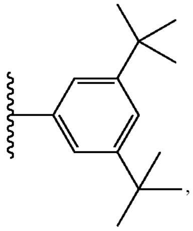
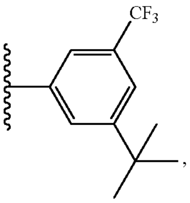
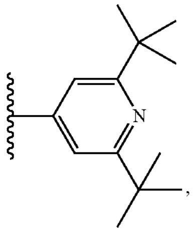
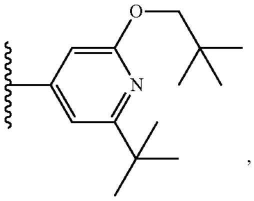, -continued

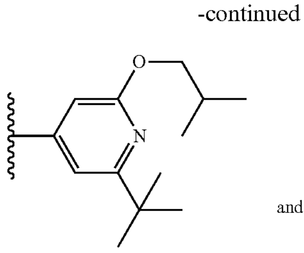

and

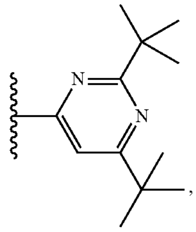,

In a further preferred embodiment in combination with any one of the above or below embodiments of the second alternative $R^5$ is selected from H, $C_{1-6}$-alkyl, halo-$C_{1-6}$-alkyl or halogen, wherein alkyl is unsubstituted or substituted with 1 to 3 substituents independently selected from the group consisting of O—$C_{1-6}$-alkyl, O-halo-$C_{1-6}$-alkyl and OH.

More preferably, $R^5$ is selected from H, $C_{1-3}$-alkyl, fluoro or chloro, even more preferred $R^5$ is selected from H, methyl, fluoro or chloro. Most preferably, $R^5$ is methyl.

In a preferred embodiment in combination with any of the above or below embodiments of the second alternative $R^6$ is selected from H, fluoro or chloro, more preferably $R^6$ is hydrogen.

In another preferred embodiment in combination with any one of the above or below embodiments of the second alternative $R^4$ is $SO_2$—$R^7$, $SO_2$—$NR^{12}R^7$, $CHR^8$—$R^{10}$ and $(CH)_2R^{10}$;

$R^7$ is independently selected from $C_{3-10}$-cycloalkyl and $C_{3-10}$-heterocycloalkyl, wherein cycloalkyl and heterocycloalkyl are unsubstituted or substituted with 1 to 3 substituents independently selected from the group consisting of fluoro, OH, $C_{1-6}$-alkyl, halo-$C_{1-6}$-alkyl and cycloalkyl;

$R^8$ is H, F, $C_{1-3}$-alkyl or halo-$C_{1-3}$-alkyl;

$R^{10}$ is $C_{3-10}$-cycloalkyl, wherein cycloalkyl is unsubstituted or substituted with 1 to 6 substituents independently selected from halogen, $C_{1-6}$-alkyl, halo-$C_{1-6}$-alkyl and cycloalkyl.

In a further preferred embodiment in combination with any one of the above or below embodiments of the second alternative $R^4$ is selected from

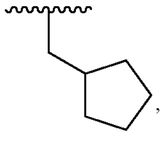,
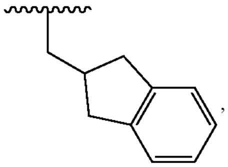,
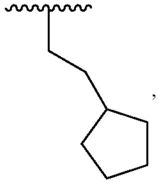,
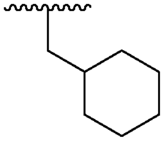,
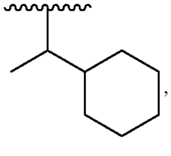,
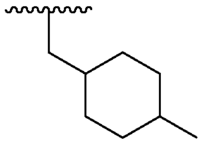,
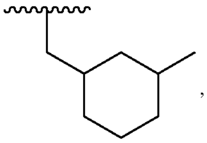, -continued

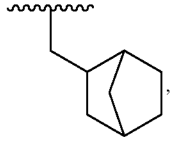,
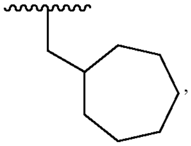,
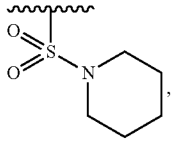,
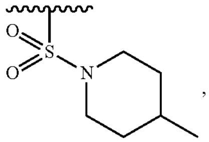,
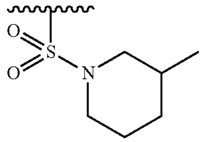,
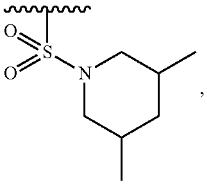,
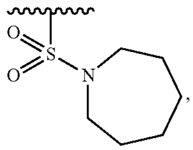,
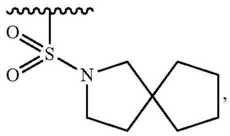,
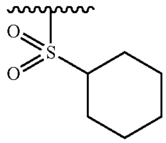

or

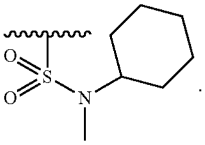.

More preferably, $R^4$ is $CH_2$—$C_{4-7}$-cycloalkyl, most preferably, $R^4$ is $CH_2$-cyclohexyl.

In yet another preferred embodiment in combination with any of the above or below embodiments of the second alternative, the compound of Formula (1) is selected from the group consisting of

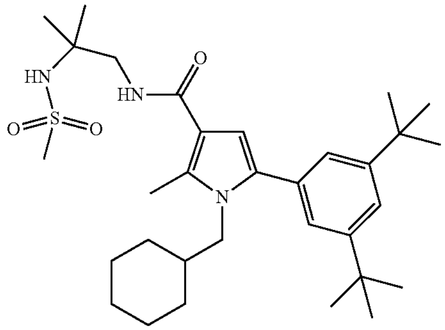,

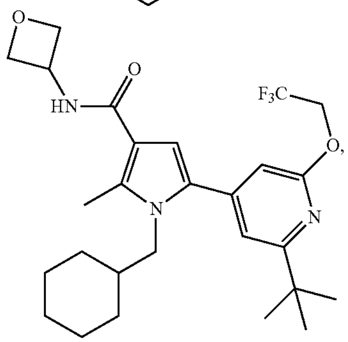

-continued
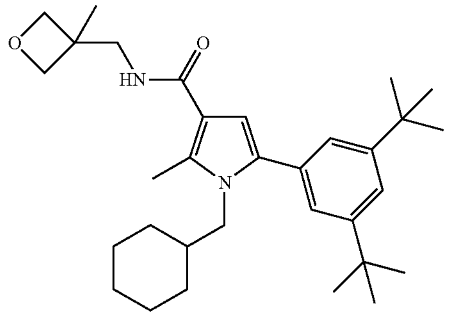
,
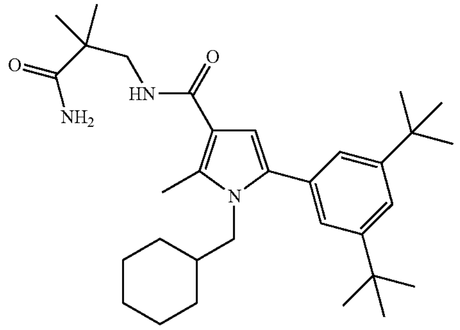
,
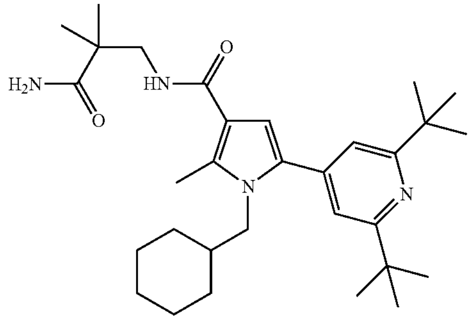
,
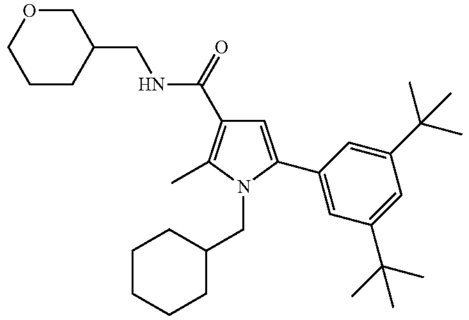
,
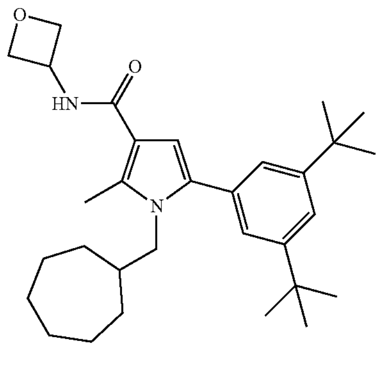
,
-continued
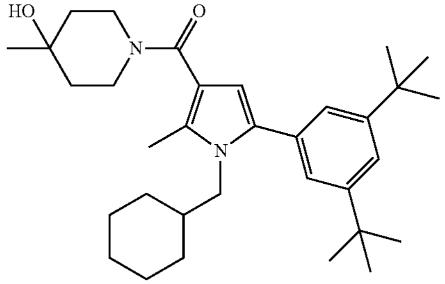
,
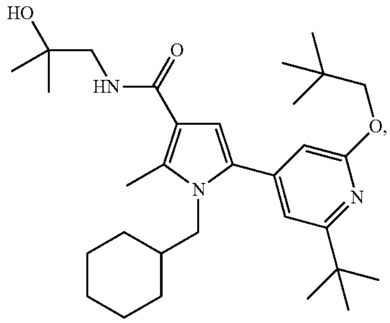
,
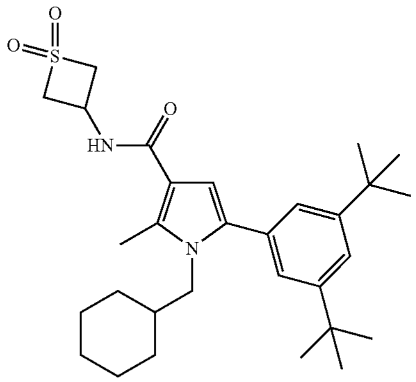
,
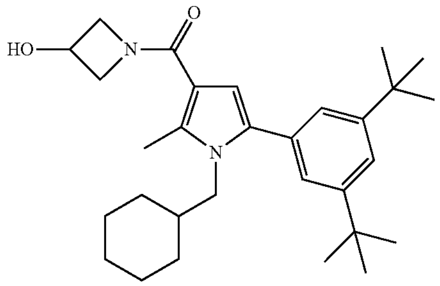
,
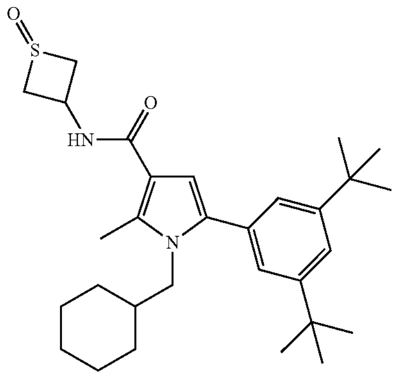
, -continued
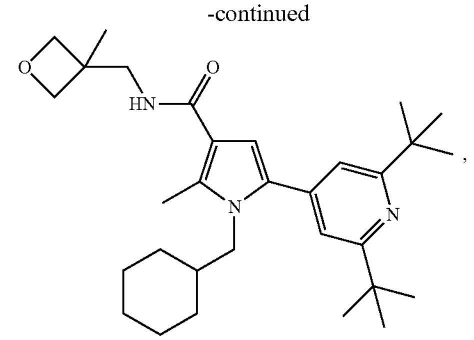
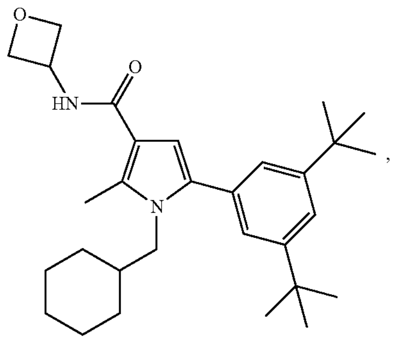
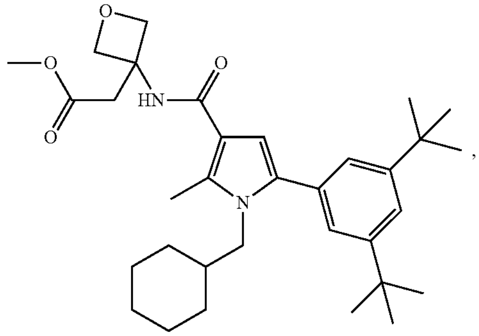
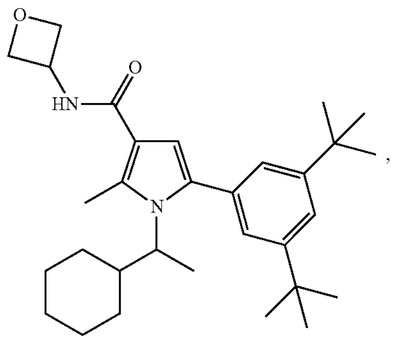
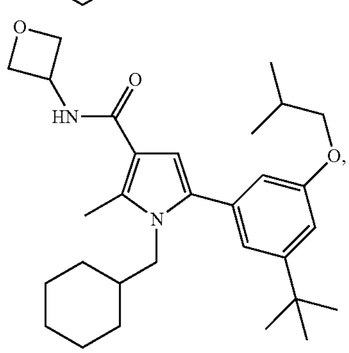
-continued
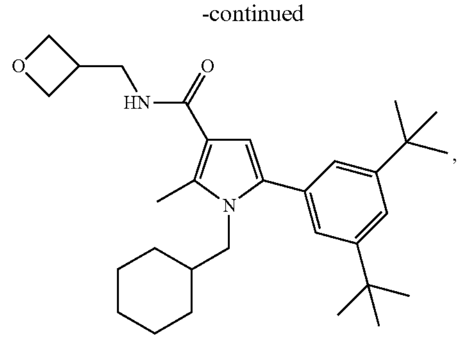
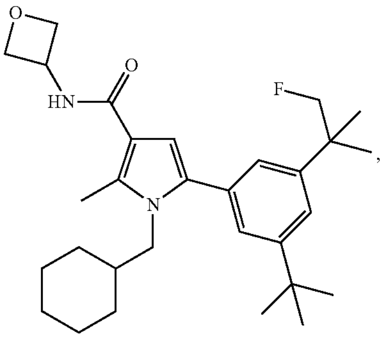
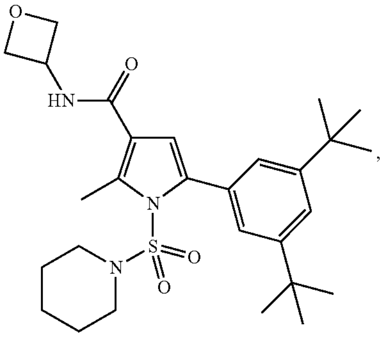
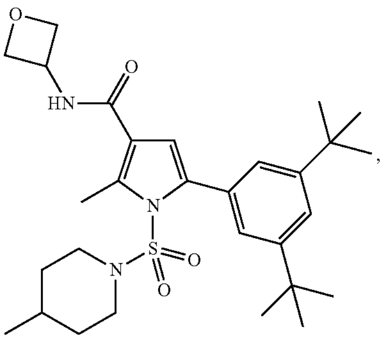
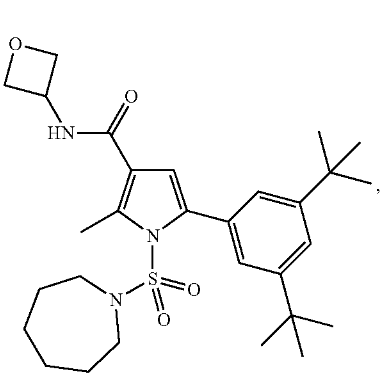

-continued
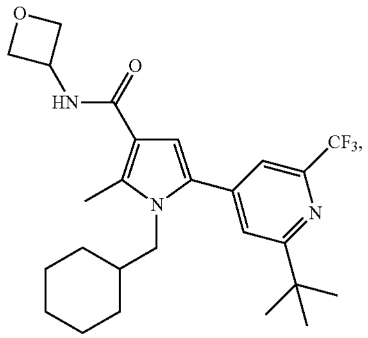
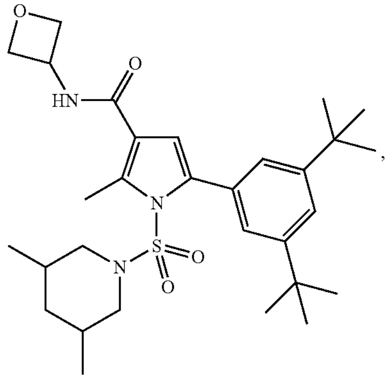
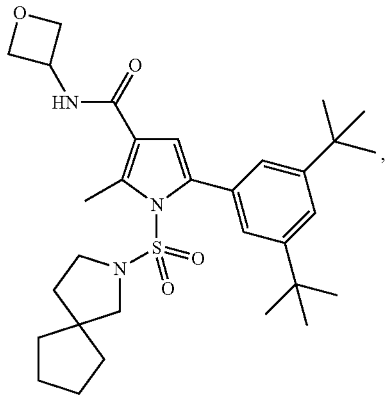
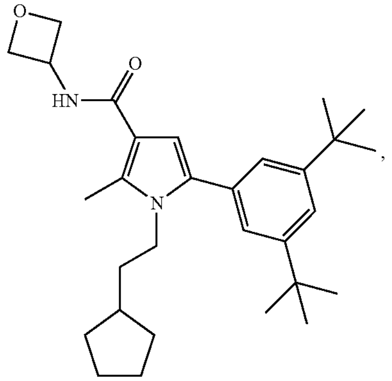
-continued
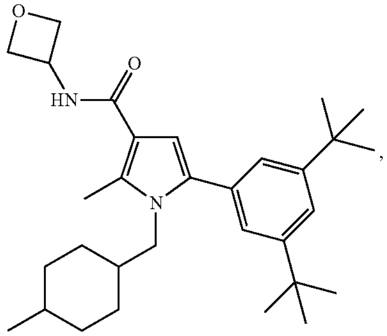
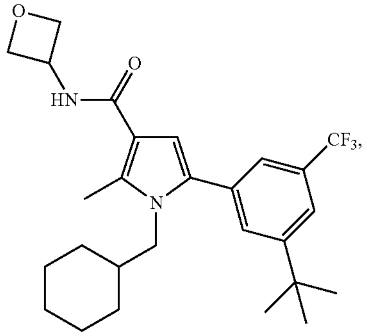
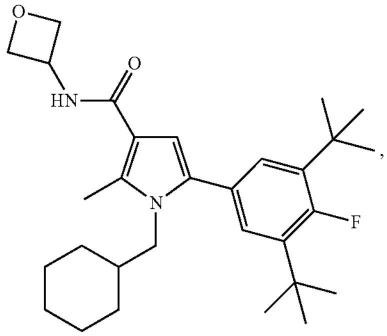
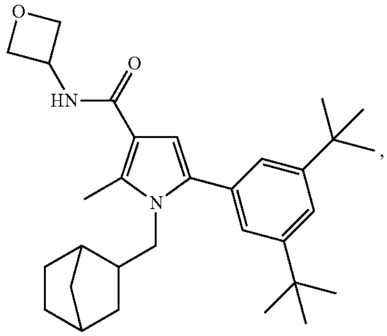
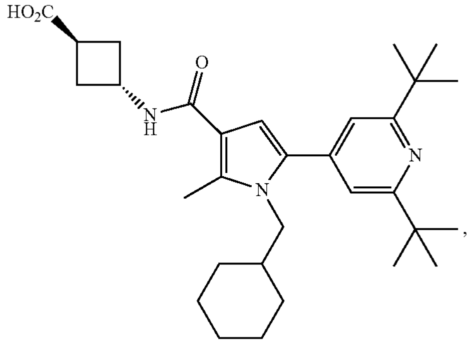

-continued
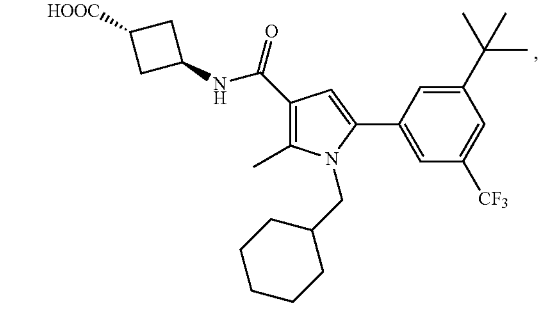
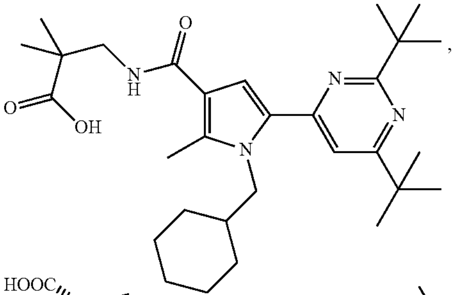
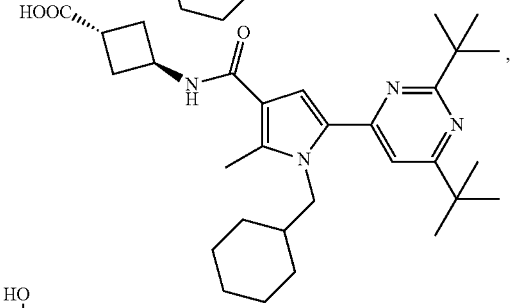
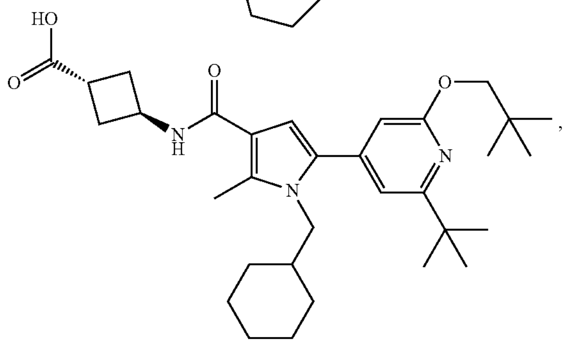
and an enantiomer, diastereomer, tautomer, N-oxide, solvate and pharmaceutically acceptable salt thereof.
More preferred are compounds of Formula (1) selected from the group consisting of
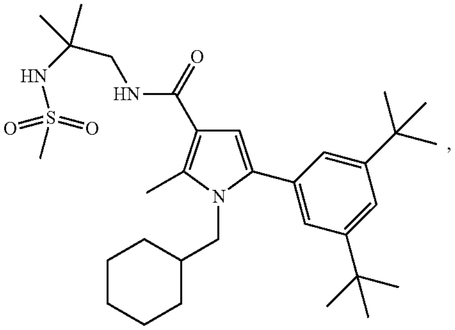
-continued
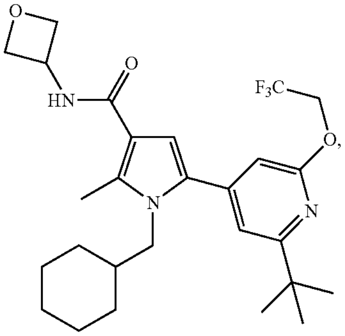
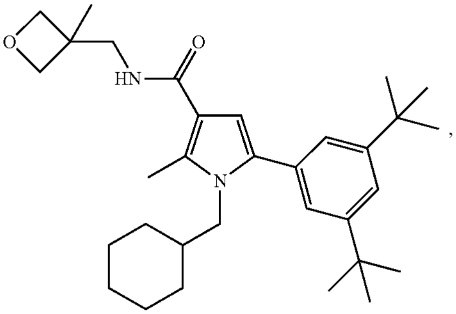
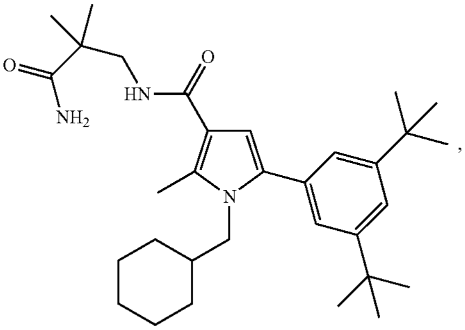
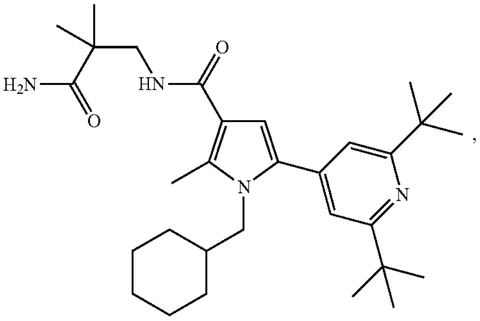
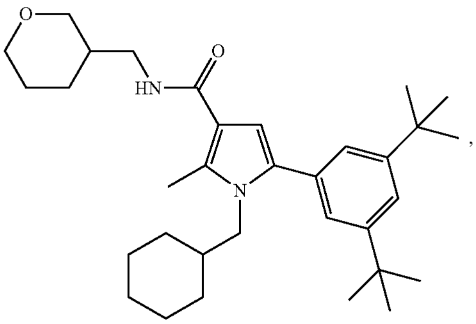

-continued
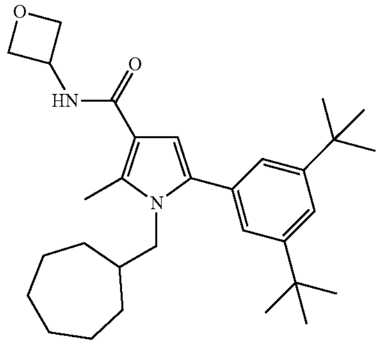
,
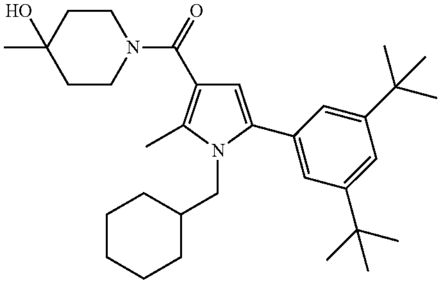
,
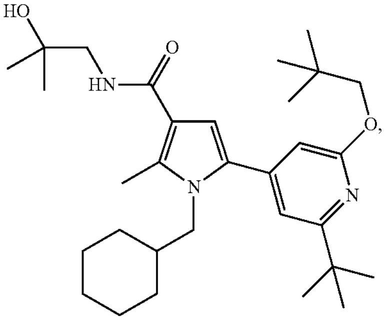
,
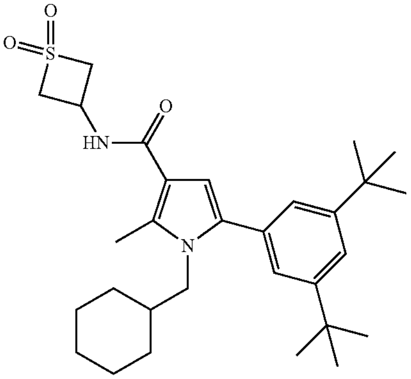
,
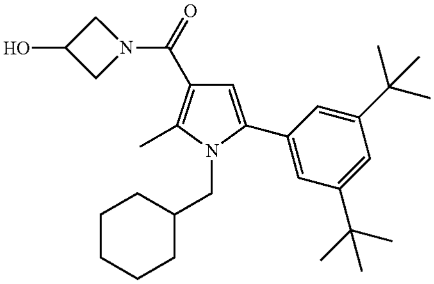
,
-continued
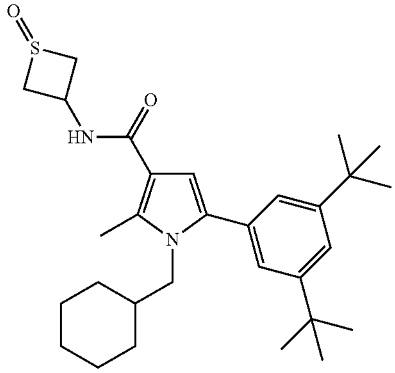
,
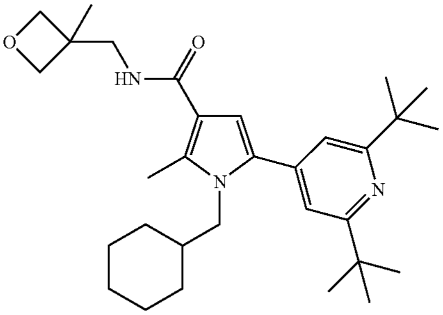
,
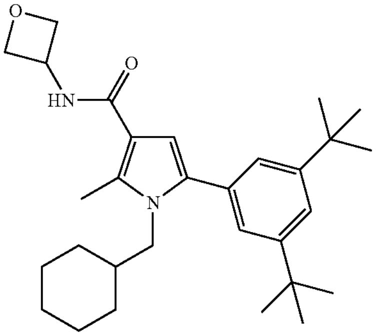
,
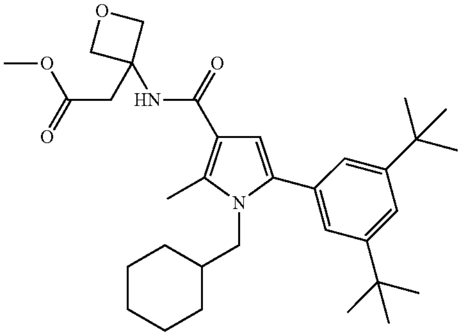
,
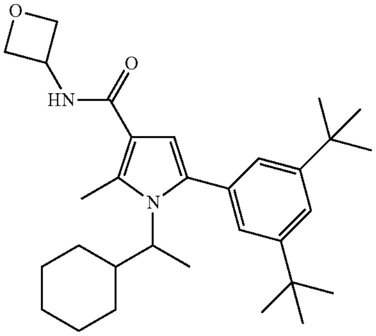
, -continued
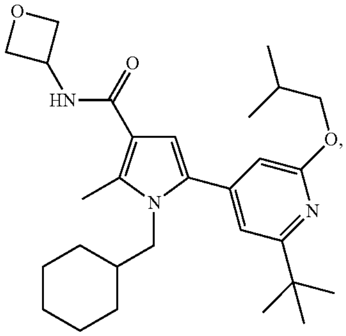
,
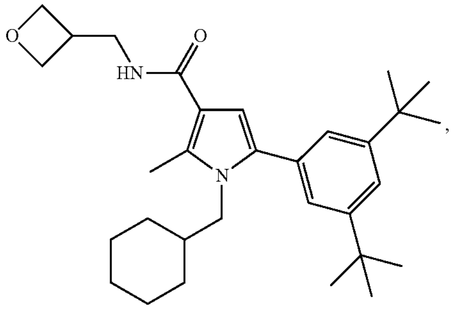
,
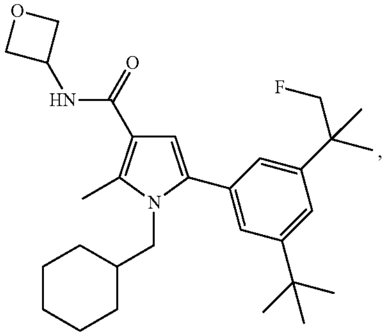
,
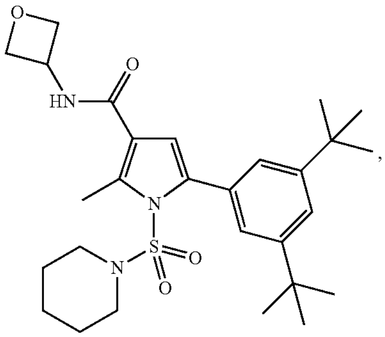
,
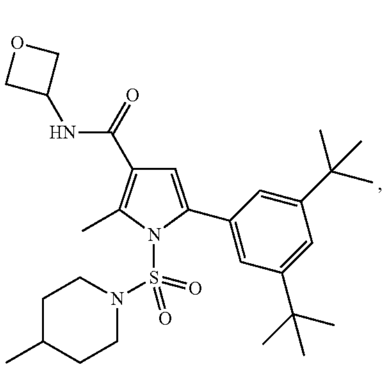
,
-continued
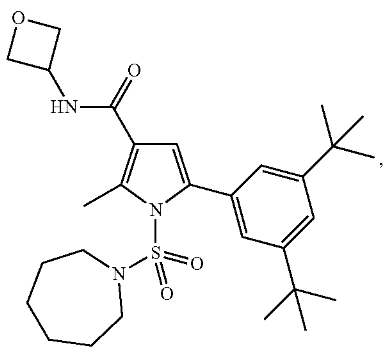
,
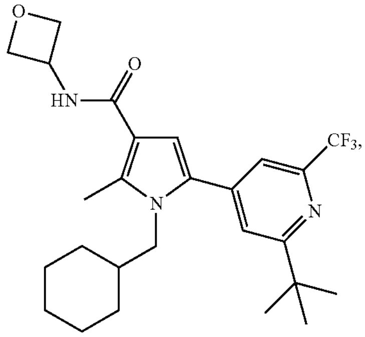
,
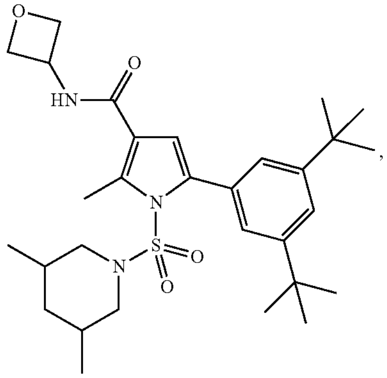
,
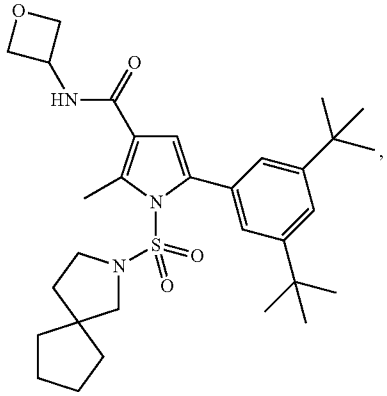
, -continued

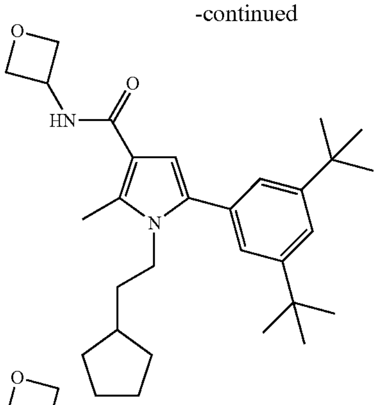

,

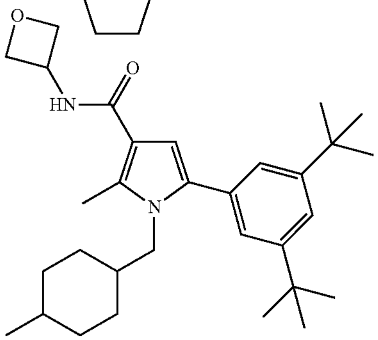

,

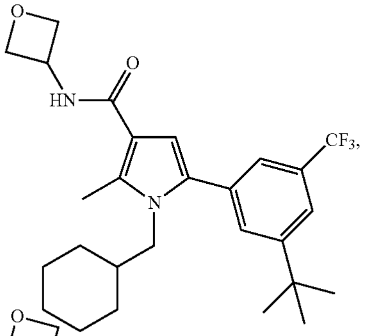

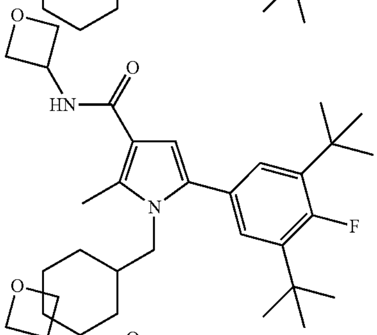

and

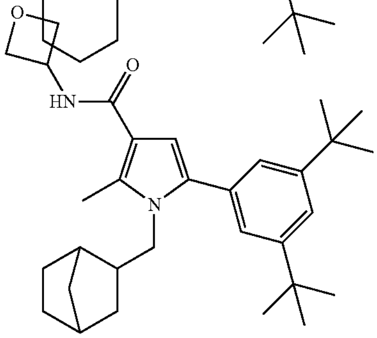

.

The invention also provides the compound of the invention for use as a medicament.

Also provided is the compound of the invention for use in treating RORγ mediated inflammatory and autoimmune diseases.

Preferably, the disease is selected from the group consisting of rheumatoid arthritis, ankylosing spondylitis, lupus erythematosus, psoriasis, psoriatic arthritis, atopic eczema, inflammatory bowel diseases such as Crohn's disease, asthma, mucosal leishmaniasis, multiple sclerosis, systemic sclerosis, type 1 diabetes, Kawasaki disease, Hashimoto's thyroiditis, chronic graft-versus-host disease, acute graft-versus-host disease, Celiac Sprue, idiopathic thrombocytopenic thromobotic purpura, myasthenia gravis, Sjorgren's syndrome, scleroderma, ulcerative colitis, epidermal hyperplasia, glomerulonephritis, chronic obstructive pulmonary disease and amyotrophic lateral sclerosis. More preferably, the disease is selected from the group consisting of rheumatoid arthritis, ankylosing spondylitis, lupus erythematosus, psoriasis, psoriatic arthritis, atopic eczema, inflammatory bowel diseases such as Crohn's disease, asthma, multiple sclerosis, type 1 diabetes, chronic obstructive pulmonary disease and amyotrophic lateral sclerosis. Most preferred, the disease is rheumatoid arthritis or psoriasis.

Also provided is a pharmaceutical composition comprising the compound of the invention and a pharmaceutically acceptable carrier.

In the context of the present invention $C_{1-12}$-alkyl means a saturated hydrocarbon chain having 1, 2, 3, 4, 5, 6, 7, 8, 9, 10, 11 or 12 carbon atoms, which may be straight chained or branched. Examples thereof include methyl, ethyl, propyl, isopropyl, n-butyl, isobutyl, tert-butyl, n-pentyl, isopentyl, neopentyl, hexyl, heptyl, octyl, nonyl, decyl, undecyl and dodecyl.

The term "halo-$C_{1-12}$-alkyl" means that one or more hydrogen atoms in the alkyl chain are replaced by a halogen. A subset of this term is "fluoro-$C_{1-4}$-alkyl", wherein one or more hydrogen atoms in the alkyl chain are replaced by a fluorine atom. Preferred examples thereof are $CF_3$, $CH_2CF_3$ and $CH_2CH_2F$.

$C_{2-12}$-alkenyl means a hydrocarbon chain having 2, 3, 4, 5, 6, 7, 8, 9, 10, 11 or 12 carbon atoms, which may be straight chained or branched, containing at least one carbon to carbon double bond. Examples thereof include ethenyl, propenyl, dodecenyl, 2-methylenehexyl and (2E,4E)-hexa-2,4-dienyl.

$C_{2-12}$-alkynyl means a hydrocarbon chain having 2, 3, 4, 5, 6, 7, 8, 9, 10, 11 or 12 carbon atoms, which may be straight chained or branched, containing at least one carbon to carbon triple bond. Examples thereof include ethynyl, propynyl and dodecynyl.

A "$C_{0-6}$-alkylene" means that the respective group is divalent and connects the attached residue with the remaining part of the molecule. Moreover, in the context of the present invention, "$C_0$-alkylene" is meant to represent a bond.

A $C_{3-10}$-cycloalkyl group means a saturated mono-, bi- or multicyclic ring system comprising 3, 4, 5, 6, 7, 8, 9 or 10 carbon atoms. Examples include cyclopropyl, cyclobutyl, cyclopentyl, cyclohexyl, bicyclo[2.2.2]octyl, bicyclo[2.2.1]heptyl, pentacyclo[$4.2.0.0^{2,5}.0^{3,8}.0^{4,7}$]octyl and adamantyl.

A $C_{3-10}$-heterocycloalkyl group means a saturated or partially unsaturated 3, 4, 5, 6, 7, 8, 9 or 10-membered carbon mono-, bi- or multicyclic ring wherein 1, 2 or 3 carbon atoms are replaced by 1, 2 or 3 heteroatoms, respectively, wherein the heteroatoms are independently selected from N, O and S. Examples thereof include epoxidyl, oxetanyl, pyrrolidinyl, tetrahydrofuranyl, piperidinyl, piperazinyl, tetrahydropyranyl, 1,4-dioxanyl, morpholinyl, 4-quinuclidinyl, 1,4-dihydropyridinyl and 3,6-dihydro-2H-thiopyranyl. The $C_{3-10}$-heterocycloalkyl group can be connected via a carbon or nitrogen atom, if not stated otherwise.

A 5- to 10-membered mono- or bicyclic heteroaryl system containing up to 4 heteroatoms means a monocyclic heteroaromatic ring such as pyrrolyl, imidazolyl, furanyl, thiophenyl, pyridinyl, pyrimidinyl, pyrazinyl, pyrazolyl, oxazolyl, isoxazolyl, triazolyl, oxadiazolyl and thiadiazolyl. It further means a bicyclic ring system wherein the heteroatom(s) may be present in one or both rings including the bridgehead atoms. Examples thereof include quinolinyl, isoquinolinyl, quinoxalinyl, benzimidazolyl, benzisoxazolyl, benzodioxanyl, benzofuranyl, benzoxazolyl, indolyl, indolizinyl and pyrazolo[1,5-a]pyrimidinyl. The nitrogen or sulphur atom of the heteroaryl system may also be optionally oxidized to the corresponding N-oxide, S-oxide or S,S-dioxide. If not stated otherwise, the heteroaryl system can be connected via a carbon or nitrogen atom. Examples for N-linked heterocycles are

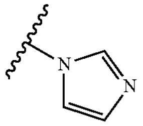

and

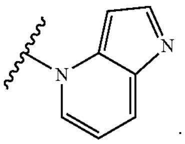

.

A 6- to 10-membered mono- or bicyclic aryl system means an aromatic carbon cycle such as phenyl or naphthalenyl.

The term "N-oxide" denotes compounds, there the nitrogen in the heteroaromatic system (preferably pyridinyl) is oxidized. Such compounds can be obtained in a known manner by reacting a compound of the present invention (such as in a pyridinyl group) with $H_2O_2$ or a peracid in an inert solvent.

Halogen is selected from fluorine, chlorine, bromine and iodine. The preferred halogen is fluorine.

Furthermore, the compounds of the present invention are partly subject to tautomerism. For example, if a heteroaromatic group containing a nitrogen atom in the ring is substituted with a hydroxy group on the carbon atom adjacent to the nitrogen atom, the following tautomerism can appear:

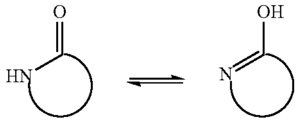

When a substitution of a residue with cycloalkyl or heterocycloalkyl is described, it is understood that the substitution can be connected straight and, when the connecting carbon atom is $sp^3$-hybridized, in addition spirocyclic. For example, when cyclohexan is substituted with the heterocycloalkyl group oxetan-3-yl, the following structures are possible:

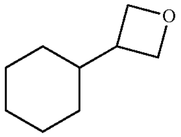

and

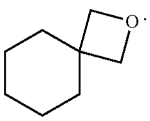

.

It will be appreciated by the skilled person that when lists of alternative substituents include members which, because of their valency requirements or other reasons, cannot be used to substitute a particular group, the list is intended to be read with the knowledge of the skilled person to include only those members of the list which are suitable for substituting the particular group.

The compounds used in the present invention can be in the form of a pharmaceutically acceptable salt or a solvate. The term "pharmaceutically acceptable salts" refers to salts prepared from pharmaceutically acceptable non-toxic bases or acids, including inorganic bases or acids and organic bases or acids. In case the compounds of the present invention contain one or more acidic or basic groups, the invention also comprises their corresponding pharmaceutically or toxicologically acceptable salts, in particular their pharmaceutically utilizable salts. Thus, the compounds of the present invention which contain acidic groups can be used according to the invention, for example, as alkali metal salts, alkaline earth metal salts or ammonium salts. More precise examples of such salts include sodium salts, potassium salts, calcium salts, magnesium salts or salts with ammonia or organic amines such as, for example, ethylamine, ethanolamine, triethanolamine or amino acids. The compounds of the present invention which contain one or more basic groups, i.e. groups which can be protonated, can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid and other acids known to the person skilled in the art. If the compounds of the present invention simultaneously contain acidic and basic groups in the molecule, the invention also includes, in addition to the salt forms mentioned, inner salts or betaines (zwitterions). The respective salts can be obtained by customary methods which are known to the person skilled in the art like, for example, by contacting these with an organic or inorganic acid or base in a solvent or dispersant, or by anion exchange or cation exchange with other salts. The present invention also includes all salts of the compounds of the present invention which, owing to low physiological compatibility, are not directly suitable for use in pharmaceuticals but which can be used, for example, as intermediates for chemical reactions or for the preparation of pharmaceutically acceptable salts.

In practical use, the compounds used in the present invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or non-aqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

The compounds used in the present invention may also be administered parenterally. Solutions or suspensions of these active compounds can be prepared in water suitably mixed with a surfactant such as hydroxy-propylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Any suitable route of administration may be employed for providing a mammal, especially a human, with an effective dose of a compound of the present invention. For example, oral, rectal, topical, parenteral (including intravenous), ocular, pulmonary, nasal and the like may be employed. Dosage forms include tablets, troches, dispersions, suspensions, solutions, capsules, creams, ointments, aerosols and the like. Preferably compounds of the present invention are administered orally.

The effective dosage of active ingredient employed may vary depending on the particular compound employed, the mode of administration, the condition being treated and the severity of the condition being treated. Such dosage may be ascertained readily by a person skilled in the art.

When treating or preventing RORγ-mediated conditions for which compounds of Formula (1) are indicated, generally satisfactory results are obtained when the compounds are administered at a daily dosage of from about 0.1 milligram to about 100 milligram per kilogram of mammal body weight, preferably given as a single daily dose or in divided doses two to six times a day, or in sustained release form. For most large mammals, the total daily dosage is from about 1.0 milligram to about 1000 milligrams, preferably from about 1 milligram to about 50 milligrams. In the case of a 70 kg adult human, the total daily dose will generally be from about 7 milligrams to about 350 milligrams. This dosage regimen may be adjusted to provide the optimal therapeutic response.

The present invention describes modulators, in the following also referred to as ligands, which bind to the RORγ receptor. Surprisingly, it has been found that compounds of Formula (1) act as modulators of the RORγ receptor.

The RORγ receptor is considered to be involved in thymocyte development, thus the modulators described herein may be useful in the treatment of inflammatory skin diseases such as atopic eczema and psoriasis. It is further suggested that down-modulation of RORγ transcriptional activity with a ligand could result in a shift of the immune response towards a Th2 type response which could be beneficial in the treatment of certain allergic inflammatory conditions such as rheumatoid arthritis, systemic lupus erythomatosis, inflammatory bowel disease (Crohn's Disease) and multiple sclerosis (Tesmer et. al., *Immunol. Rev.* 2008, 223:97).

The compounds of Formula (1) show antagonistic activity, with respect to the dose dependent modulation of the constitutive interaction of the RORγ ligand binding domain with peptides derived from the co-activators such as SRC-1, TRAP 220 or TIF-2.

It has been surprisingly found that the interaction between RORγ ligand binding domain and the peptides can be determined by a homogenous FRET based ligand-sensing assays. Even more surprising was the identification of compounds of Formula (1) as ligands for RORγ.

The identification of high affinity ligands for RORγ with agonistic and antagonistic properties is the basis to enable experts knowledgeable in the field to establish assays for the identification of novel agonistic and antagonistic RORγ ligands from libraries of small molecules. The identification of ligands which bind to and modulate the activity of RORγ1 and RORγt is the first mandatory step to develop new small molecule based medicines with a potential to be developed for the treatment of diseases which are directly or indirectly controlled by the activity of RORγ1 or RORγt. Such diseases include but are not restricted to inflammatory diseases, asthma, rheumatoid arthritis, autoimmune diseases or diseases with an autoimmune component such as systemic lupus erythomatosis, inflammatory bowel disease (Crohn's disease), ulcerative colitis, inflammatory skin diseases such as atopic eczema or psoriasis, multiple sclerosis or similar diseases.

The compounds of the present invention can be prepared by a combination of methods known in the art including the procedures described in Schemes I to III below. Pyrrole-3-esters of general structure A (Scheme I) can be N-derivatized by alkylation with alkyl halides, by reaction with sulfonyl chlorides or sulfamoyl chlorides in the presence of appropriate bases in appropriate solvents. The introduction of an aromatic or heteroaromatic substituents in the 5-position of intermediates B (Scheme I) can be achieved either by bromination with N-bromosuccinimide (NBS) and subsequent Suzuki cross coupling with boronic esters or boronic acids or by an Ir-catalyzed direct borylation (as described in *J. Am. Chem. Soc.* 2007, 129:15434) of intermediate B (Scheme I), followed by boronic ester hydrolysis and Suzuki cross coupling with halo-aromatics or halo-heteroaromatics. The order of alkylation and bromination to prepare intermediates C can be inverted as depicted in Scheme I. The common intermediate E (Scheme I) can be further transformed into carboxamides by ester hydrolysis and amide formation using methods known to those skilled in the art.

Scheme I

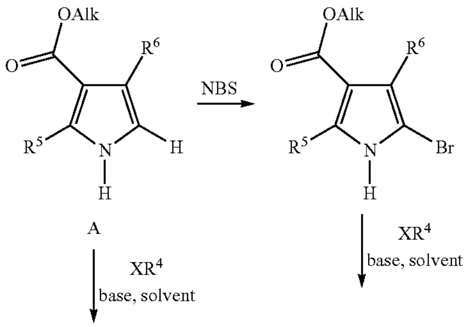

-continued

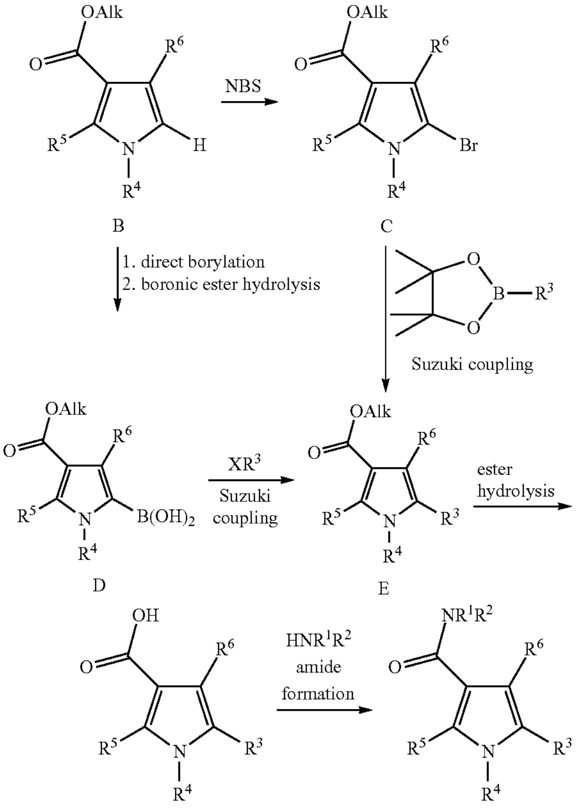

Alk = alkyl

Alternatively, for purposes of tailored late stage derivatization, the formation of the amide can be performed first, followed by bromination and Suzuki cross-coupling as final step, as depicted in Scheme II.

Scheme II

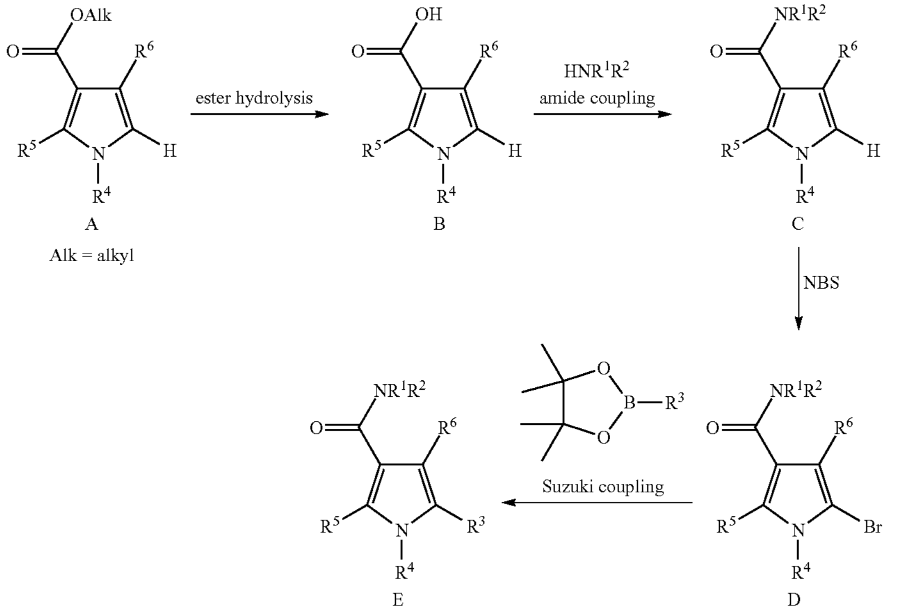

Alk = alkyl

In alternative to Pd-catalyzed cross coupling reactions the 2-position of pyrrole A (Scheme III) can be acylated and the resulting ketone intermediate B (Scheme III) can be further transformed into heteroaromatics containing analogues of the general formula C in Scheme III, using methods described in *Org. Lett.* 2008, 10:2897. Again, intermediate C (Scheme III) can be further transformed into carboxamides by ester hydrolysis and amide formation using methods known to those skilled in the art.

Scheme III

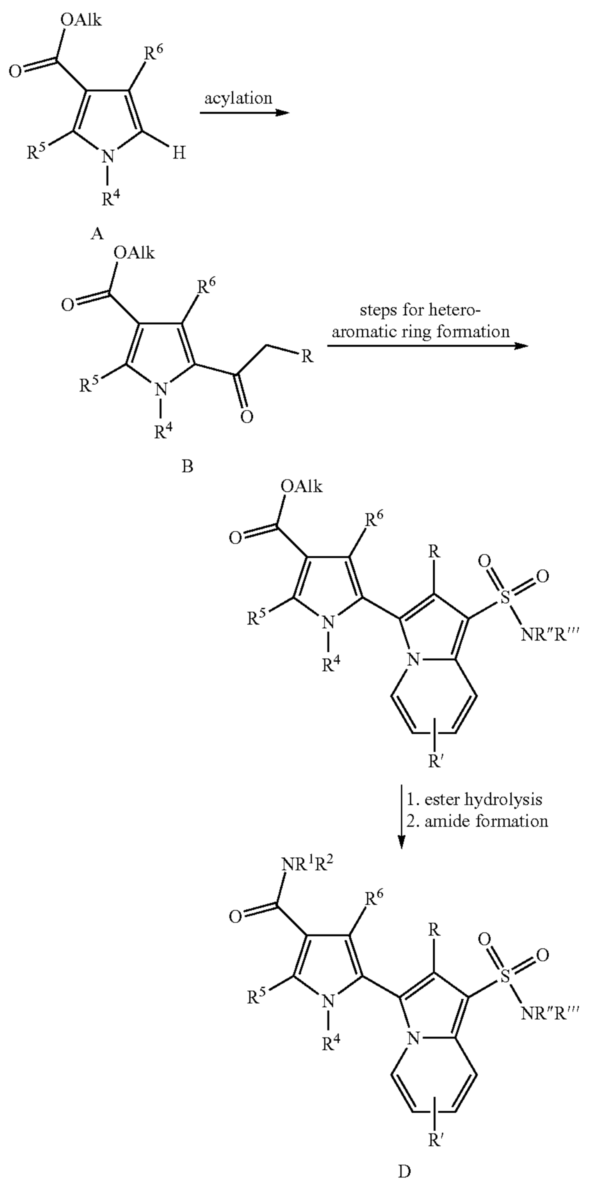

Alk = alkyl
R, R′, R″, R‴ = additional substituents

ABBREVIATIONS

Ac acetyl
ACN acetonitrile
aq. aqueous $B_2Pin_2$ 4,4,4',4',5,5,5',5'-octamethyl-2,2'-bi-1,3,2-dioxaborolane
CC flash chromatography on silica gel
COD cyclooctadiene
Cy cyclohexyl
dba dibenzylideneacetone
DCE 1,2-dichiroroethane
DCM dichloromethane
DIPEA diisopropylethylamine
DMAP 4-Dimethylaminopyridine
DMF N,N-dimethylformamide
dppf 1,1'-bis(diphenylphosphino)ferrocene
dppp 1,3-bis(diphenylphosphino)propane
dtbpy 4,4'-di-tert-butyl-2,2'-bipyridine
EA ethyl acetate
HATU O-(7-azabenzotriazole-1-yl)-N,N,N',N'-tetramethyluronium hexafluorophosphate
MOM methoxymethyl
MTBE tert-butylmethylether
NBS N-bromosuccinimide
NCS N-chlorosuccinimide
Pin pinacolato ($OCMe_2CMe_2O$)
PE petroleum ether
prep. preparative
rt room temperature
TBAB tertabutylammonium bromide
Tf trifluoromethanesulfonyl
TEA triethylamine
TFA trifluoroacetic acid
THF tetrahydrofuran
TLC thin layer chromatography

EXPERIMENTAL SECTION

Preparative Examples

The synthesis of the following Preparative Examples is described in WO2012/139775:

P1

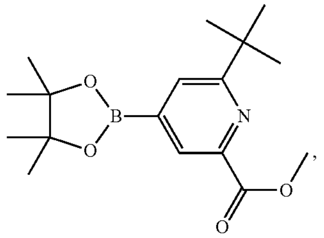

P2

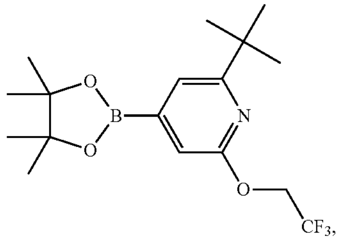

P3

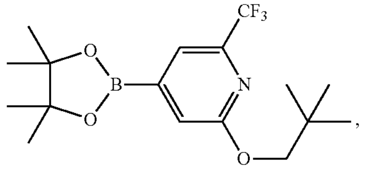

-continued
P4
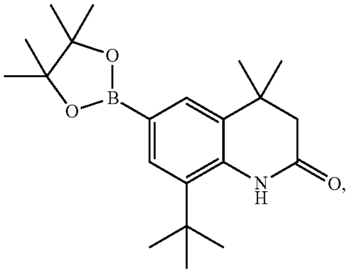,
P5
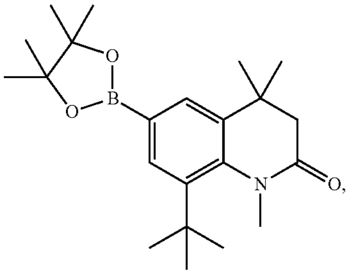,
P6
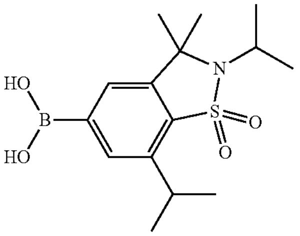,
P10
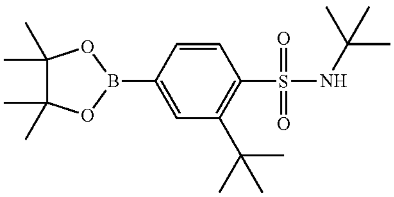,
P11
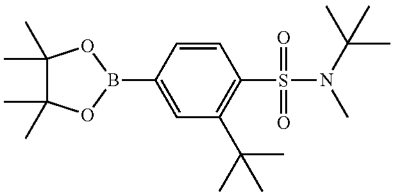,
P12
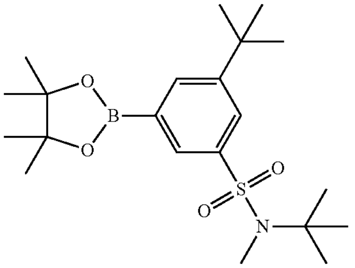,
-continued
P13
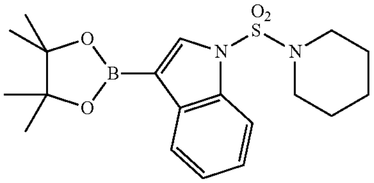,
P14
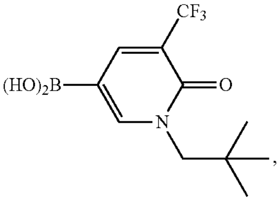,
P15
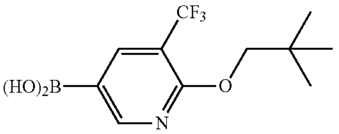,
P16
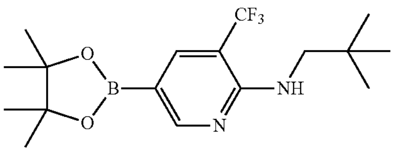,
P17
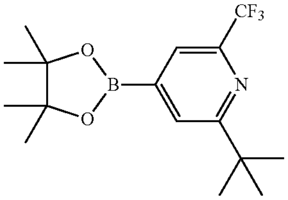,
P20
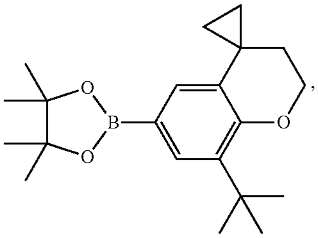,
P21
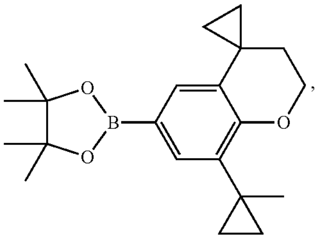,
P22
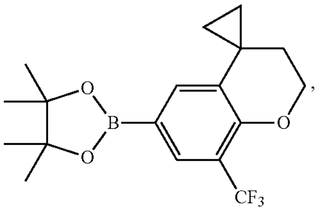, -continued
P24
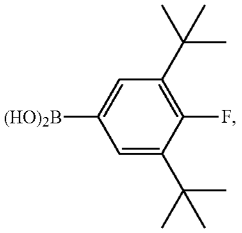
P25
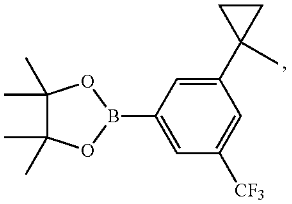
P26
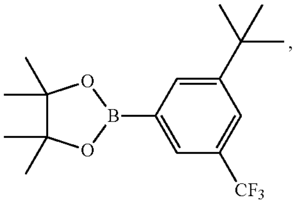
P27
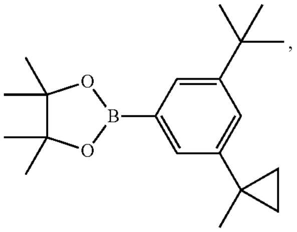
P28
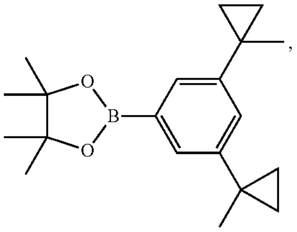
P29
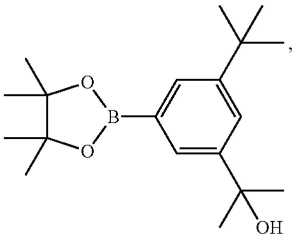
P34
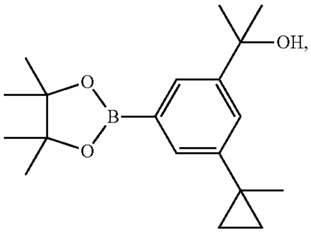
-continued
P35
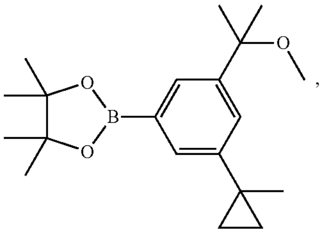
P37
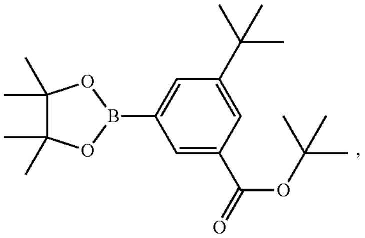
P39
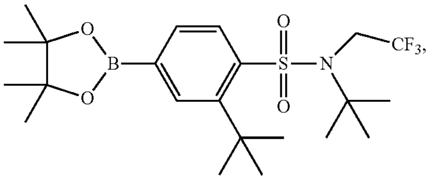
P40
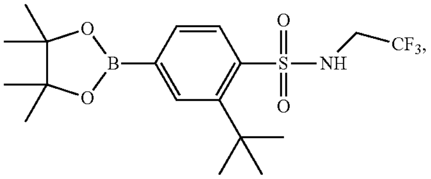
P41
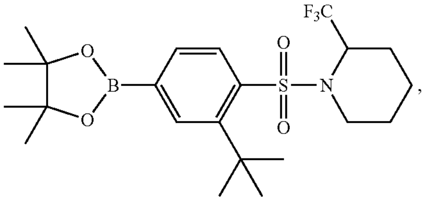
P42
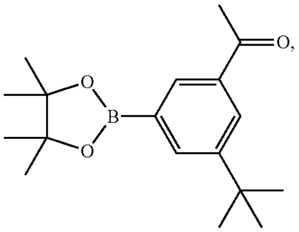
P43
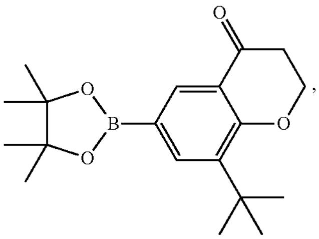

-continued

P44

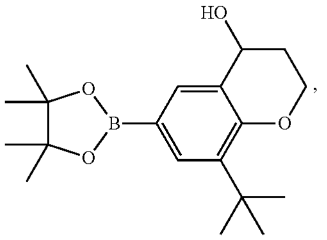

P46

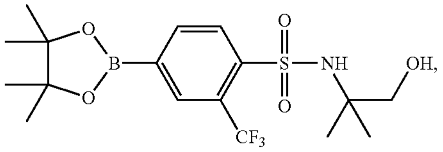

P47

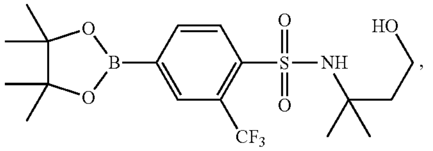

P48

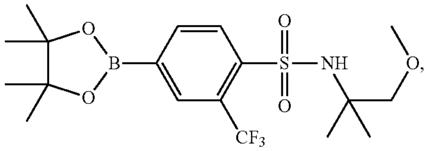

P52

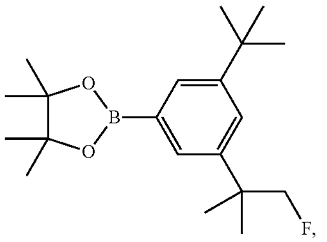

P68

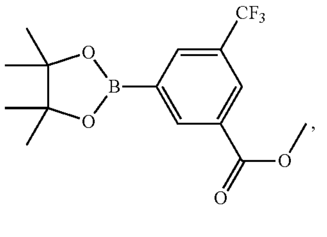

P88

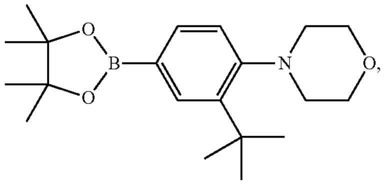

-continued

P98

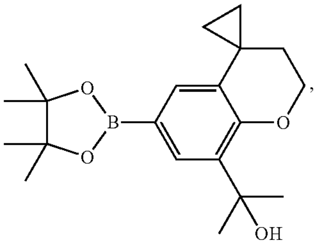

P99

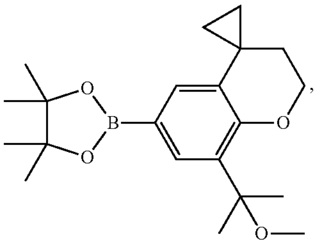

Preparative Example P7

P7

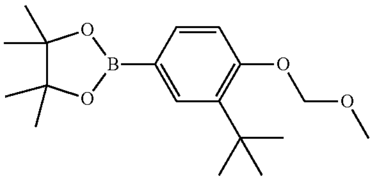

Step 1: 4-Bromo-2-(tert-butyl)phenol (P7a)

To a solution of 2-(tert-butyl)phenol (30.0 g, 200 mmol) in $CHCl_3$ (600 mL) was added tetra-n-butyl ammonium tribromide (121 g, 250 mmol) and the solution was stirred for 2 h at rt, concentrated and the crude product was partitioned between $Et_2O$ and water. The organic layer was washed sequentially with 1M HCl twice and brine twice. The organic layer was separated and dried over $MgSO_4$, concentrated and purified by CC (PE/EA=7/1) to give compound P7a (39.9 g, 89%) as a colorless solid.

Step 2: 4-Bromo-2-(tert-butyl)-1-(methoxymethoxy)benzene (P7b)

NaH (4.40 g, 110 mmol) and MOMCl (9.60 g, 120 mmol) were gradually added to a solution of compound P7a (22.8 g, 100 mol) in dry DMF (300 mL) while cooling on ice and the mixture was stirred at 0° C. overnight, poured into ice water and extracted with EA (3×). The combined organic layer was washed with water (3×) and brine consecutively, dried over $Na_2SO_4$, concentrated and purified by CC (PE/EA=100/1) to give compound P7b (24.9 g, 92%) as a light yellow oil.

Step 3: 2-(3-(tert-Butyl)-4-(methoxymethoxy)phenyl)-4,4,5,5-tetramethyl-1,3,2-dioxaborolane (P7)

A solution of compound P7b (24.2 g, 89.0 mmol), $B_2Pin_2$ (24.1 g, 95.0 mmol), KOAc (9.31 g, 95.0 mmol) and Pd(dppf)$Cl_2$ (4.00 g) in dry DMF (500 mL) was heated at 90° C. overnight under $N_2$, concentrated and the residue was partitioned between water and EA. The aq. layer was extracted with EA and the combined organic layers were washed with water twice and brine consecutively. The organic layer was dried over $Na_2SO_4$, filtered, concentrated and purified by CC (PE/EA=5/1) to give compound P7 (15.4 g, 54%) as a colorless solid.

Preparative Example P8

P8

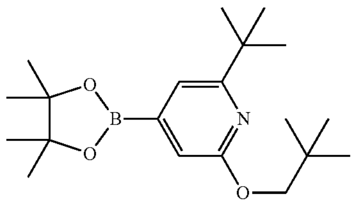

Step 1: 6-tert-Butyl-4-hydroxypyridin-2(1H)-one (P8a)

A mixture of 6-tert-butyl-4-hydroxy-2H-pyran-2-one (38 g, 168 mmol) and aq. $NH_4OH$ (150 mL, 30%) in dry toluene (200 mL) was heated at reflux for 1 h, concentrated and purified by CC (PE/EA=5/1) to give compound P8a (22.5 g, 80%) as a colorless solid.

Step 2: 4-Bromo-6-tert-butylpyridin-2(1H)-one (P8b)

To a solution of compound P8a (9.7 g, 60 mmol) in DMF (100 mL) was added $POBr_3$ (17.2 g, 60 mmol) and the mixture was heated at 90° C. for 2 h, was concentrated, diluted with water and extracted with EA. The organic layer was washed with brine (3×), concentrated and purified by CC (PE/EA=5/1) to give compound P8b (22.5 g, 80%) as a yellow solid.

Step 3: 4-Bromo-2-tert-butyl-6-(neopentyloxy)pyridine (P8c)

To a solution of compound P8b (2.0 g, 8.66 mmol) in dry DMF (20 mL) was added NaH (0.62 g, 26.0 mmol) under $N_2$ and the mixture was stirred at rt for 1 h. Then 1-bromo-2,2-dimethylpropane (2.37 g, 15.7 mmol) was added and the resulting mixture was heated at 80° C. overnight, quenched with water (10 mL) and extracted with EA twice. The combined organic layers were washed with brine (3×), concentrated and purified by CC (PE/EA=50/1) to give compound P8c (0.5 g, 20%) as an oil.

Step 4: 2-tert-Butyl-6-(neopentyloxy)-4-(4,4,5,5-tetramethyl-1,3,2-dioxaborolan-2-yl)pyridine (P8)

A mixture of compound P8c (2.2 g, 7.72 mmol), $B_2Pin_2$ (2.94 g, 11.6 mmol), KOAc (1.13 g, 11.6 mmol) and Pd(dppf)$Cl_2$ (200 mg) in dry DMF (20 mL) was heated at 90° C. under $N_2$ overnight, quenched with water and extracted with EA twice. The combined organic layers were washed with brine (3×), concentrated and purified by CC (PE/EA=50/1) to give compound P8 (2.5 g, 97%) as an oil.

Preparative Example P9

P9

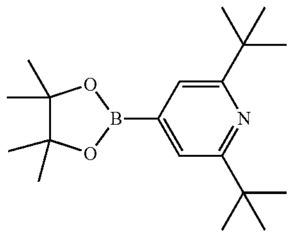

2,6-Di-tert-butyl-4-(4,4,5,5-tetramethyl-1,3,2-dioxaborolan-2-yl)pyridine (P9)

Under $N_2$ a catalyst stock solution was prepared by weighing [(COD)Ir(μ-OMe)]$_2$ (104 mg, 0.312 mmol Ir), dtbpy (84 mg, 0.312 mmol) and $B_2Pin_2$ (2.64 g, 10.4 mmol) into a vial followed by the volumetric addition of degassed MTBE to make up a 25 mL solution which upon shaking developed a deep red color. The solution was transferred to a vial and sealed with a rubber septum. Under $N_2$, a vial was charged with 2,6-di-tert-butylpyridine (1.91 g, 10.0 mmol) followed by 25 mL of the catalyst stock solution. The reaction was heated at 80° C. for 2 h, concentrated and purified by CC (PE/EA=8/1) to give compound P9 (1.89 g, 60%) as a colorless solid.

Preparative Example P18a and Preparative Example P18

P18a

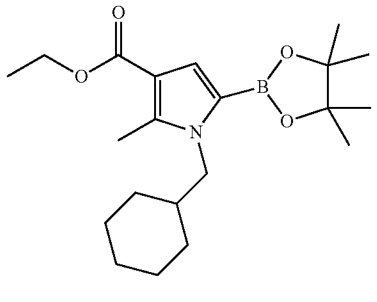

P18

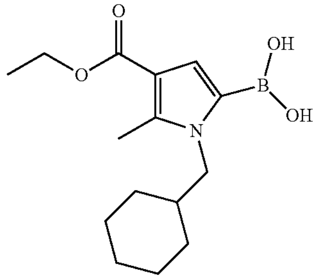

Step 1: Ethyl 1-(cyclohexylmethyl)-2-methyl-5-(4,4,5,5-tetramethyl-1,3,2-dioxaborolan-2-yl)-1H-pyrrole-3-carboxylate (P18a)

To a solution of 1-(cyclohexylmethyl)-2-ethyl-1H-pyrrole-3-carboxylate (prepared according to Example 1d, 2.12 g, 8.51 mmol) in THF (20 mL) was added $[(COD)Ir(\mu\text{-}OMe)]_2$ (167 mg, 0.25 mmol), dtbpy (137 mg, 0.51 mmol) and $B_2Pin_2$ (2.38 g, 9.37 mmol) and the solution was stirred overnight at 100° C. under $N_2$, concentrated and purified by CC (PE/EA=50/1) to give compound P18a (2.24 g, 70%) as a colorless solid.

Step 2: 1-(Cyclohexylmethyl)-4-(ethoxycarbonyl)-5-methyl-1H-pyrrol-2-ylboronic acid (P18)

To a solution of P18a (1.50 g, 4.00 mmol) in a mixture of acetone (15 mL) and water (15 mL) was added sodium periodate (2.55 g, 12.0 mmol) and ammonium acetate (1.00 g, 13 mmol) at rt and the solution was stirred at reflux for 2 d, concentrated and extracted with EA. The organic layer was washed with 0.1M HCl and brine consecutively, dried over $Na_2SO_4$, filtered and concentrated to give intermediate P18 (1.17 g, quant.) as a colorless solid.

Preparative Example P19

P19

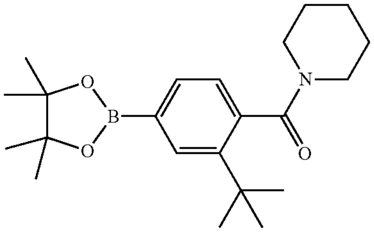

Step 1: 2-(tert-Butyl)-4-chlorophenol (P19a)

To a mixture of 4-chlorophenol (50 g, 0.39 mol) and t-BuOH (57.6 g, 0.78 mol) was added conc. $H_2SO_4$ (40 mL) and the solution was stirred at rt for 48 h, poured into ice-water and extracted with EA twice. The combined organic layers were washed with water (3×) and brine consecutively, dried over $Na_2SO_4$, filtered, concentrated and purified by CC (PE/EA=40/1) to give compound P19a (48.5 g, 68%) as a colorless solid.

Step 2: 2-(tert-Butyl)-4-chlorophenyl trifluoromethanesulfonate (P19b)

To a solution of compound P19a (32.0 g, 174 mmol) and pyridine (22.5 mL, 278 mmol) in dry DCM (500 mL) was added a solution of $Tf_2O$ (35.5 mL, 209 mmol) in dry DCM (150 mL) under ice cooling and the solution was stirred for 4 h at rt, poured into 1M HCl and extracted with DCM. The organic layer was washed with brine, dried over $Na_2SO_4$, filtered, concentrated and purified by CC (PE/EA=10/1) to give compound P19b (40.0 g, 82%) as a pale yellow solid.

Step 3: Methyl 2-(tert-butyl)-4-chlorobenzoate (P19c)

A solution of compound P19b (40.0 g, 142 mmol), dppp (5.0 g, 12 mmol), $Pd(OAc)_2$ (2.7 g, 12 mmol) and $NEt_3$ (150 mL, 1.1 mol) in a mixture of MeOH (300 mL) and DMSO (400 mL) was stirred overnight at 55° C. under an atmosphere of CO. Water and EA were added and the organic layer was separated, washed with water twice and brine, dried over $Na_2SO_4$, filtered, concentrated and purified by CC (PE/EA=8/1) to give compound P19c (27.1 g, 84%) as a colorless solid.

Step 4: 2-(tert-Butyl)-4-chlorobenzoic acid (P19d)

To a stirred solution of compound P19c (542 mg, 2.40 mmol) in a mixture of DMSO (6 mL) and $H_2O$ (2 drops) was added t-BuOK (538 mg, 4.8 mmol) and this mixture was stirred at 85° C. for 4 h, adjusted to pH=2~3 with 1N HCl and then extracted with EA (3×). The combined organic layers were washed with water (3×) and brine consecutively, dried over $Na_2SO_4$, filtered, concentrated and purified by CC (PE/EA=2/1) to give compound P19d (404 mg, 80%) as a yellow solid.

Step 4: (2-(tert-Butyl)-4-chlorophenyl)(piperidin-1-yl)methanone (P19e)

A solution of compound P19d (404 mg, 1.91 mmol), piperidine (244 mg, 2.87 mmol), HATU (870 mg, 2.29 mmol) and DIPEA (616 mg, 4.78 mmol) in DMF (5 mL) was stirred at rt for 20 min, quenched with water and extracted with EA twice. The combined organic layers were washed with water (3×) and brine consecutively, dried over $Na_2SO_4$, filtered, concentrated and purified by prep. TLC (PE/EA=1/1) to give compound P19e (550 mg, 97%) as a yellow solid.

Step 5: (2-(tert-Butyl)-4-(4,4,5,5-tetramethyl-1,3,2-dioxaborolan-2-yl)phenyl)(piperidin-1-yl)methanone (P19)

A stirred solution of $PCy_3$ (100 mg, 0.35 mmol) and $Pd(dba)_2$ (200 mg, 0.35 mmol) in 1,4-dioxane (20 mL) was stirred at rt for 30 min, then compound P19e (550 mg, 1.97 mmol), $P_2Bin_2$ (767 mg, 2.17 mmol) and KOAc (546 mg, 1.90 mmol) was added and the solution was heated at 90° C. for 3 h, diluted with water and extracted with EA. The organic layer was washed with brine, dried over $Na_2SO_4$, filtered and concentrated to give compound P19 (159 mg, 22%) as a colorless solid.

Preparative Example P23

P23

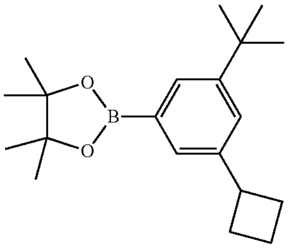

Step 1: 1-(3-Bromo-5-(tert-butyl)phenyl)cyclobutanol (P23a)

To an oven dried 100 mL 3-neck flask was added 1,3-dibromo-5-(tert-butyl)benzene (500 mg, 1.72 mmol) in dry THF (30 mL) under $N_2$ and the mixture was cooled to −78° C. n-BuLi (2.5M, 1 mL) was added and the mixture was stirred at −78° C. for 1 h. Then cyclobutanone (181 mg, 2.58 mmol) was added. After the reaction was complete (monitored by LC-MS) the mixture was quenched with aq. $NH_4Cl$ and extracted with EA. The organic layer was dried over $MgSO_4$, filtered and evaporated to give compound P23a (243 mg, 50%) as a yellow solid.

Step 2: 1-Bromo-3-(tert-butyl)-5-cyclobutylbenzene (P23b)

To the mixture of compound P23a (243 mg, 0.86 mmol) in DCM (20 mL) was added TFA (3 mL) and the mixture was stirred at rt. Triethylsilane (200 mg, 1.72 mmol) was added and the mixture was stirred overnight, diluted with water (20 mL) and extracted with EA (3×20 mL). The organic layer was washed with brine, dried over $Na_2SO_4$ and concentrated to give compound P23b (150 mg, 66%) as a colorless solid.

Step 3: 2-(3-(tert-Butyl)-5-cyclobutylphenyl)-4,4,5,5-tetramethyl-1,3,2-dioxaborolane (P23)

To a mixture of compound P23b (133 mg, 0.50 mmol), $B_2Pin_2$ (152 mg, 0.60 mmol) and KOAc (98 mg, 1.00 mmol) in 1,4-dioxane (10 mL) under Ar was added $Pd(dppf)Cl_2$ (0.03 eq) and the mixture was heated at 80° C. overnight, diluted with water (20 mL) and extracted with EA (3×20 mL). The organic layer was washed with brine, dried over $Na_2SO_4$, concentrated and purified by CC (hexane/EA=20/1) to give compound P23 (110 mg, 70%) as colorless solid.

Preparative Example P30

P30

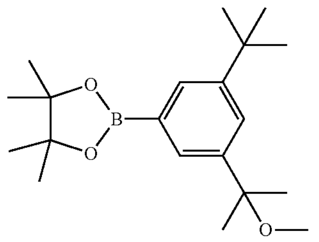

Step 1: 1-Bromo-3-(tert-butyl)-5-(2-methoxypropan-2-yl)benzene (P30a)

To a mixture of 2-(3-Bromo-5-(tert-butyl)phenyl)propan-2-ol [synthesis described in WO2012/139775] (190 mg, 0.7 mmol) in DMF (10 mL) was added NaH (60%, 20 mg, 1.2 mmol) and the mixture was stirred at rt for 10 min. Then MeI (423 mg, 3.0 mmol) was added and the mixture was stirred overnight, diluted with water (50 mL) and extracted with EA (3×50 mL). The organic layer was washed with brine, dried over $Na_2SO_4$, concentrated and purified by CC (hexane/EA=10/1) to give compound P30a (125 mg, 64%) as a colorless solid.

Step 2: 2-(3-(tert-Butyl)-5-(2-methoxypropan-2-yl)-phenyl)-4,4,5,5-tetramethyl-1,3,2-dioxaborolane (P30)

To a mixture of compound P30a (128 mg, 0.45 mmol), $B_2Pin_2$ (137 mg, 0.54 mmol) and KOAc (88 mg, 0.9 mmol) in 1,4-dioxane (25 mL) was added $Pd(dppf)Cl_2$ (0.03 eq) under Ar and the mixture was heated at 80° C. overnight, diluted with water (50 mL) and extracted with EA (3×50 mL). The organic layer was washed with brine, dried over $Na_2SO_4$, concentrated and purified by CC (hexane/EA=5/1) to give compound P30 (78 mg, 52%) as a colorless solid.

Preparative Example P31

P31

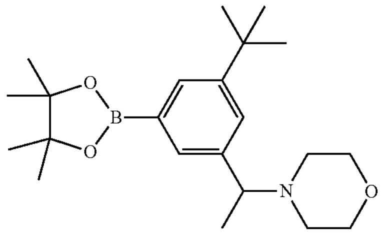

Step 1: 4-(1-(3-Bromo-5-(tert-butyl)phenyl)ethyl)morpholine (P31a)

A mixture of 1-(3-Bromo-5-(tert-butyl)phenyl)ethanone [synthesis as described in WO2012/139775] (510 mg, 2.0 mmol) and morpholine (208 mg, 2.4 mmol) in DCE (30 mL) was stirred at 0° C. for 1 h. Then $NaBH(OAc)_3$ (845 mg, 4.0 mmol) was added at this temperature and the mixture was stirred overnight, diluted with aq. $NH_4Cl$ (50 mL) and extracted with EA (3×50 mL). The organic layer was washed with brine, dried over $Na_2SO_4$, concentrated and purified by CC (hexane/EA=8/1) to give compound P31a (172 mg, 26%) as a colorless solid.

Step 2: 4-(1-(3-(tert-Butyl)-5-(4,4,5,5-tetramethyl-1,3,2-dioxaborolan-2-yl)phenyl)ethyl)morpholine (P31)

To a mixture of compound P31a (163 mg, 0.5 mmol), $B_2Pin_2$ (152 mg, 0.6 mmol) and KOAc (98 mg, 1.0 mmol) in 1,4-dioxane (25 mL) under Ar was added $Pd(dppf)Cl_2$ (0.03 eq). The mixture was heated at 80° C. overnight, diluted with water (50 mL) and extracted with EA (3×50 mL). The organic layer was washed with brine, dried over $Na_2SO_4$, concentrated and purified by CC (hexane/EA=5/1) to give compound P31 (78 mg, 42%) as a colorless solid.

Preparative Example P32

P32

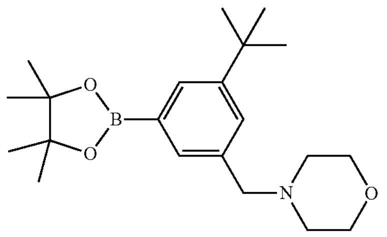

Step 1: 3-Bromo-5-(tert-butyl)benzaldehyde (P32a)

To a mixture of 1,3-dibromo-5-(tert-butyl)benzene (876 mg, 3.0 mmol) in THF (10 mL) was added tert-BuLi (2.5 M, 2.4 mL, 6.0 mmol) at −78° C. and the mixture was stirred for 1 h at this temperature. Then DMF (222 mg, 3.0 mmol) was added at this temperature and stirred for 2 h., diluted with aq. $NH_4Cl$ (50 mL) and extracted with EA (3×50 mL). The organic layer was washed with brine, dried over $Na_2SO_4$, concentrated and purified by CC (hexane/EA=5/1) to give compound P32a (452 mg, 63%) as a colorless solid.

Step 2: 4-(3-Bromo-5-(tert-butyl)benzyl)morpholine (P32b)

A mixture of compound P32a (450 mg, 1.87 mmol) and morpholine (194 mg, 2.24 mmol) in DCE (30 mL) was stirred at 0° C. for 1 h. Then $NaBH(OAc)_3$ (561 mg, 2.66 mmol) was added at this temperature and then stirred overnight, diluted with aq. $NH_4Cl$ (50 mL) and extracted with EA (3×50 mL). The organic layer was washed with brine, dried over $Na_2SO_4$, concentrated and purified by prep. TLC to give compound P32b (142 mg, 28%) as a colorless solid.

Step 3: 4-(3-(tert-Butyl)-5-(4,4,5,5-tetramethyl-1,3,2-dioxaborolan-2-yl)benzyl)morpholine (P32)

To a mixture of compound P32b (145 mg, 0.46 mmol) and $B_2Pin_2$ (152 mg, 0.6 mmol) and KOAc (98 mg, 1.0 mmol) in 1,4-dioxane (25 mL) was added $Pd(dppf)Cl_2$ (0.03 eq) under Ar and the mixture was heated at 80° C. overnight, diluted with water (50 mL) and extracted with EA (3×50 mL). The organic layer was washed with brine, dried over $Na_2SO_4$, concentrated and purified by prep. HPLC to give P32 (80 mg, 54%) as a colorless solid.

Preparative Example P33

P33

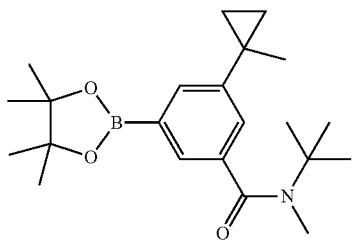

Step 1: Methyl 3-bromo-5-(prop-1-en-2-yl)benzoate (P33a)

To a solution of methyl 3-bromo-5-iodobenzoate (3.40 g, 10 mmol) in 1,4-dioxane (20 mL) was added $Pd(PPh_3)_4$ (300 mg, 0.26 mmol), prop-1-en-2-yl boronic acid (1.0 g, 12 mmol), $K_2CO_3$ (2.8 g, 20 mmol) and $H_2O$ (1 mL) under $N_2$. The mixture was stirred overnight at 90° C., concentrated and purified by CC (PE/EA=6/1) to give compound P33a (1.9 g, 71%) as a solid.

Step 2: Methyl 3-bromo-5-(1-methylcyclopropyl)benzoate (P33b)

To a solution of $Et_2Zn$ (4 mL of 1.0M solution in hexanes, 4.0 mmol) in dry DCM (4 mL) at 0° C. was added freshly distilled TFA (0.36 mL, 4.0 mmol) in DCM (4 mL) very slowly (ca. 30 min). The gray mixture was stirred at 0° C. for 20 min at which time $CH_2I_2$ (0.4 mL, 4.0 mmol) dissolved in DCM (4 mL) was introduced by cannulation. The resulting slurry was stirred for 20 min before the addition of compound P33a (0.53 g, 2.0 mmol) dissolved in DCM (3 mL). The slurry was allowed to warm to rt over 30 min, quenched by the addition of sat. aq. $NH_4Cl$ (5 mL) and the layers were separated. The aq. layer was extracted with hexane (2×) and dried over $MgSO_4$. Evaporation and purification by CC (PE/EA=7/1) afforded compound P33b (300 mg, 46%) as a colorless oil.

Step 3: 3-Bromo-5-(1-methylcyclopropyl)benzoic acid (P33c)

Compound P33b (270 mg, 1.0 mmol) and LiOH (50 mg, 2.0 mmol) were mixed in THF (3 mL) and $H_2O$ (3 mL). The mixture was stirred for 10 h, then the pH was adjusted to pH 3 with aq. HCl and extracted with EA (3×10 mL). The organic layer was dried and concentrated to afford the crude product P33c (250 mg, quant.).

Step 4: 3-Bromo-N-(tert-butyl)-N-methyl-5-(1-methylcyclopropyl)benzamide (P33d)

To a solution of compound P33c (250 mg, 1.0 mmol) in DMF (5 mL) was added HATU (380 mg, 1.0 mmol), MeNH$^t$Bu (174 mg, 2.0 mmol) and $Et_3N$ (202 mg, 2.0 mmol) and the mixture was stirred overnight. After removal of the solvents the crude product was purified with prep. HPLC to afford compound P33d (300 mg, 95%).

Step 5: N-(tert-Butyl)-N-methyl-3-(1-methylcyclopropyl)-5-(4,4,5,5-tetramethyl-1,3,2-dioxaborolan-2-yl)benzamide (P33)

To a suspension of compound P33d (323 mg, 1.0 mmol), $B_2Pin_2$ (380 mg, 1.5 mmol), KOAc (290 mg, 3.0 mmol) in 1,4-dioxane (5 mL) was added $Pd(dppf)Cl_2$ (20 mg) under $N_2$. The mixture was heated to 100° C. for 16 h, concentrated and purified by CC (PE/EA=4/1) to afford compound P33 (200 mg, 68%) as a colorless solid.

Preparative Example P33/1 to P33/2

Using similar procedures as described in Preparative Example P33, the following compounds were prepared:

| # | Structure |
|---|---|
| P33/1 | 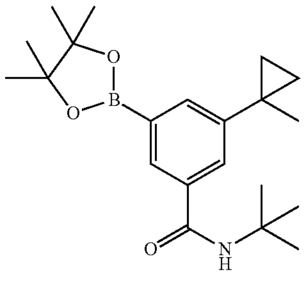 [SMILES: CC(C)(C)NC(=O)c1cc(B2OC(C)(C)C(C)(C)O2)cc(C2(C)CC2)c1] |

-continued

| # | Structure |
|---|---|
| P33/2 | 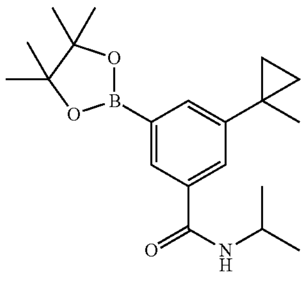 [SMILES: CC(C)NC(=O)c1cc(B2OC(C)(C)C(C)(C)O2)cc(C2(C)CC2)c1] |

Preparative Example P36

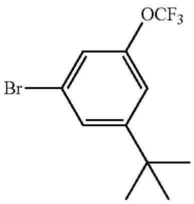

P36

Step 1: 1-(3-Bromo-5-(trifluoromethoxy)phenyl)ethanone (P36a)

To the solution of 1,3-dibromo-5-(trifluoromethoxy)benzene (654 mg, 2.06 mmol) in toluene (6 mL) were added tri-n-butyl-1-ethoxyvinyl tin (969 mg, 2.68 mmol) and $Pd(PPh_3)_2Cl_2$ (147 mg 0.21 mmol) under $N_2$. The mixture was stirred at 95° C. for 3 h, concentrated and dissolved in 1,4-dioxane and 2M HCl. The mixture was stirred rapidly at 25° C. for 1 h and then extracted with EA (3×20 mL). The organic layer was washed with brine, dried over $Na_2SO_4$, concentrated and purified by CC to give compound P36a (580 mg, 55%).

Step 2: 1-Bromo-3-(tert-butyl)-5-(trifluoromethoxy) benzene (P36)

An oven dried flask was charged with DCM (5 mL) and $TiCl_4$ (763 mg, 4.06 mmol), $Zn(CH_3)_2$ (1M, 4 mL) was added and the solution was cooled to −30° C. and stirred at constant temperature for 0.5 h. Then a solution of compound P36a (572 mg, 2.03 mmol) in DCM was added dropwise and the mixture was allowed to warm to 0° C. over a period of 40 min, stirred at rt for 2 h, 45 min at 45° C. and 40° C. overnight, diluted with water (20 mL) and extracted with EA (3×20 mL). The organic layer was washed with brine, dried over $Na_2SO_4$ and concentrated to give product P36 (180 mg, 30%) as a yellow oil.

Preparative Example P38

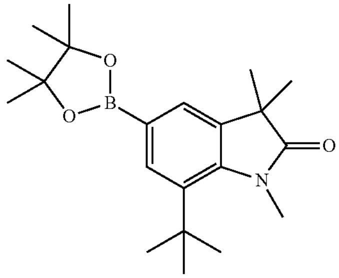

P38

Step 1: 4-Bromo-2-(tert-butyl)aniline (P38a)

To a solution of 2-(tert-butyl)aniline (14.9 g, 100 mmol) was added a solution of NBS (17.8 g, 100 mmol) in DMF at rt. The mixture was stirred overnight at rt, diluted with water (30 mL) and extracted with $Et_2O$ (3×250 mL). The organic layer was washed with brine, dried over $Na_2SO_4$, concentrated and purified by CC to give compound P38a (19 g, 83%).

Step 2: N-(4-Bromo-2-(tert-butyl)phenyl)-2-(hydroxyimino)acetamide (P38b)

To a solution of compound P38a (5.0 g, 21.9 mmol), hydroxylamine hydrochloride (5.48 g, 78.9 mmol) and sodium sulfate (24.9 g, 175 mmol) in $H_2O$ (150 mL) and 2M HCl (7.4 mL) at rt under $N_2$ was added chloral hydrate (3.88 g, 26.3 mmol). The resulting solution was stirred at 55° C. for 18 h, cooled to rt, diluted with water (100 mL) and extracted with EA (3×50 mL). The combined organic layers were concentrated to give P38b (5 g) as a viscous oil.

Step 3: 5-Bromo-7-(tert-butyl)indoline-2,3-dione (P38c)

A solution of compound P38b (5 g, 16.7 mmol) in conc. $H_2SO_4$ (30 mL) was stirred at 80° C. for 1 h, cooled to rt, poured onto crushed ice (200 mL) and allowed to stand for 30 min. The precipitate was collected by filtration, washed with water (3×) and dried under vacuum to yield compound P38c (2 g) as a yellow solid.

Step 4: 5-Bromo-7-(tert-butyl)indolin-2-one (P38d)

KOH (796 mg, 14.2 mmol) was added into a mixture of compound P38c (2 g, 7.1 mmol), ethyleneglycol (20 mL) and hydrazine hydrate (0.5 g, 9.93 mmol). The mixture was stirred at 80° C. for 3 h, cooled to rt and poured into ice cold water. The pH of the mixture was adjusted to pH 1-2 with 12M HCl and the mixture was stirred at rt for 12 h and extracted with EA. The organic phase was evaporated to give compound P38d (1.5 g) as a yellow solid.

Step 5: 5-Bromo-7-(tert-butyl)-1,3,3-trimethylindolin-2-one (P38e)

To a solution of compound P38d (1.0 g, 3.73 mmol) in DMF (20 mL) was added a solution of $CH_3I$ (0.93 mL) in DMF at 0° C. The mixture was stirred overnight at rt, diluted with water (100 mL) and extracted with $Et_2O$ (3×100 mL). The organic layer was washed with brine, dried over $Na_2SO_4$, concentrated and purified by CC to give compound P38e (500 mg, 43% over 4 steps) as a light yellow solid.

Step 6: 7-(tert-Butyl)-1,3,3-trimethyl-5-(4,4,5,5-tetramethyl-1,3,2-dioxaborolan-2-yl)indolin-2-one (P38)

A solution of compound P38e (760 mg, 2.45 mmol) was treated as described for Example P33, Step 5 to give compound P38 (750 mg, 86%) as a colorless solid.

Preparative Example P45

P45

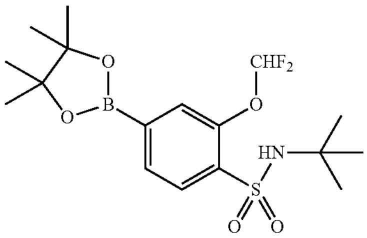

Step 1: 4-Bromo-2-(difluoromethoxy)benzene-1-sulfonyl chloride (P45a)

To a solution of 4-bromo-2-(difluoromethoxy)aniline (4.50 g, 18.9 mmol) in AcOH (20 mL) was added conc. HCl (10 mL) at rt and the solution was cooled to 5° C. Then a solution of $NaNO_2$ (1.45 g, 21.0 mmol) in $H_2O$ (15 mL) was added and the solution was stirred at 0° C. for 1 h. The resulting diazonium salt was added to a mixture of saturated solution of $SO_2$ in AcOH (100 mL) and $CuCl_2$.2HO (3.61 g, 21.0 mmol) in $H_2O$ (50 mL) at rt and the solution was stirred at rt for 30 min, poured into water and extracted with DCM twice. The combined organic layers were purified by CC (PE) to give compound P45a (2.1 g, 35%) as an oil.

Step 2: 4-Bromo-N-(tert-butyl)-2-(difluoromethoxy)benzenesulfonamide (P45b)

To a solution of compound P45a (2.10 g, 6.53 mmol) and pyridine (1.19 g, 15.1 mmol) in $CH_2Cl_2$ (20 mL) was added tert-butylamine (511 mg, 7.00 mmol) at rt and the mixture was stirred for 1 h, then washed with water and brine, dried over $Na_2SO_4$, filtered, concentrated and purified by CC (PE/EA=4/1) to give compound P45b (2.16 g, 92%) as a colorless solid.

Step 3: N-(tert-Butyl)-2-(difluoromethoxy)-4-(4,4,5,5-tetramethyl-1,3,2-dioxaborolan-2-yl)benzenesulfonamide (P45)

A solution of compound P45b (2.16 g, 6.03 mmol) was treated as described for Example P33, Step 5 to give compound P45 (1.25 g, 51%) as a colorless solid.

Preparative Example P45/1 to P45/17

Using similar procedures as described in Preparative Example P45, the following compounds were prepared:

| # | Structure |
|---|---|
| P45/1 | 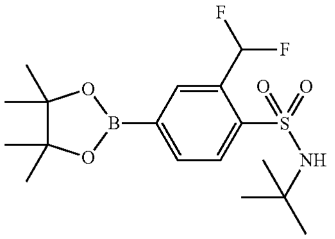 [SMILES: CC(C)(C)NS(=O)(=O)c1ccc(B2OC(C)(C)C(C)(C)O2)cc1C(F)F] |
| P45/2 | 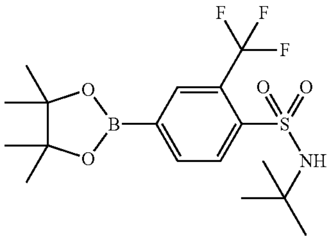 [SMILES: CC(C)(C)NS(=O)(=O)c1ccc(B2OC(C)(C)C(C)(C)O2)cc1C(F)(F)F] |
| P45/3 | 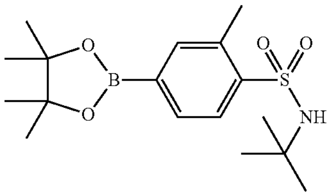 [SMILES: Cc1cc(B2OC(C)(C)C(C)(C)O2)ccc1S(=O)(=O)NC(C)(C)C] |
| P45/4 | 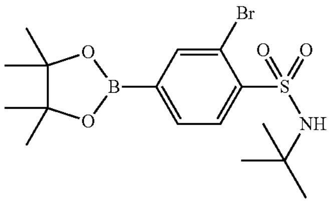 [SMILES: CC(C)(C)NS(=O)(=O)c1ccc(B2OC(C)(C)C(C)(C)O2)cc1Br] |
| P45/5 | 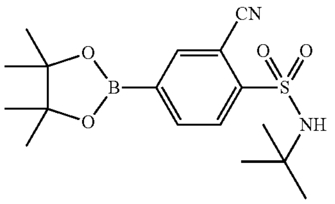 [SMILES: CC(C)(C)NS(=O)(=O)c1ccc(B2OC(C)(C)C(C)(C)O2)cc1C#N] |
| P45/6 | 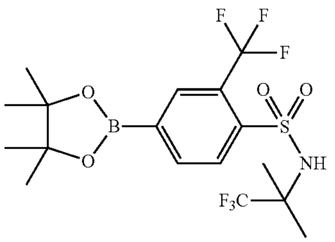 [SMILES: CC(C)(NS(=O)(=O)c1ccc(B2OC(C)(C)C(C)(C)O2)cc1C(F)(F)F)C(F)(F)F] |

-continued
| # | Structure |
|---|---|
| P45/7 | 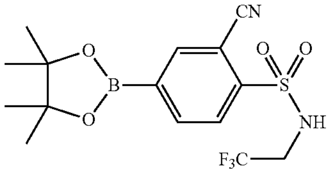 [SMILES: CC1(C)OB(c2ccc(S(=O)(=O)NCC(F)(F)F)c(C#N)c2)OC1(C)C] |
| P45/8 | 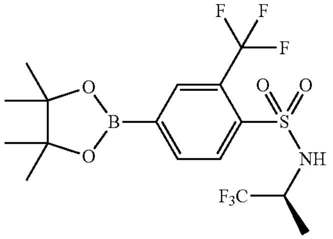 [SMILES: C[C@H](NS(=O)(=O)c1ccc(B2OC(C)(C)C(C)(C)O2)cc1C(F)(F)F)C(F)(F)F] |
| P45/9 | 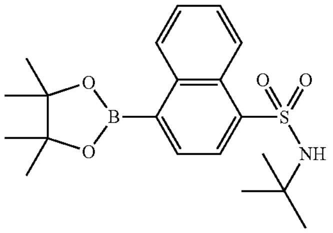 [SMILES: CC(C)(C)NS(=O)(=O)c1ccc(B2OC(C)(C)C(C)(C)O2)c2ccccc12] |
| P45/10 | 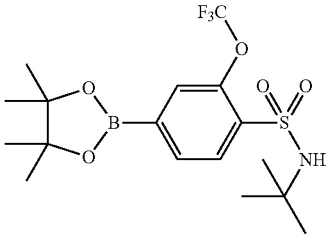 [SMILES: CC(C)(C)NS(=O)(=O)c1ccc(B2OC(C)(C)C(C)(C)O2)cc1OC(F)(F)F] |
| P45/11 | 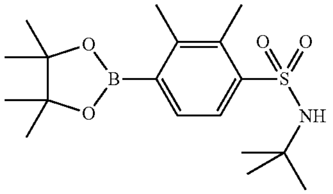 [SMILES: Cc1c(B2OC(C)(C)C(C)(C)O2)ccc(S(=O)(=O)NC(C)(C)C)c1C] |
| P45/12 | 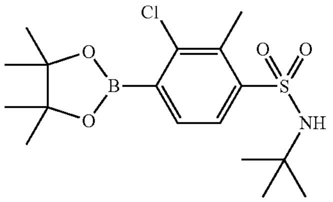 [SMILES: Cc1c(S(=O)(=O)NC(C)(C)C)ccc(B2OC(C)(C)C(C)(C)O2)c1Cl] |
| P45/13 | 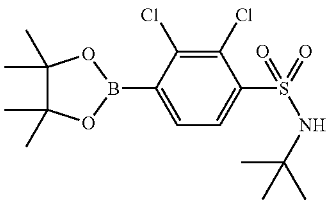 [SMILES: CC(C)(C)NS(=O)(=O)c1ccc(B2OC(C)(C)C(C)(C)O2)c(Cl)c1Cl] |
-continued
| # | Structure |
|---|---|
| P45/14 | 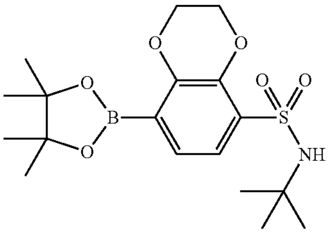 [SMILES: CC(C)(C)NS(=O)(=O)c1ccc(B2OC(C)(C)C(C)(C)O2)c2c1OCCO2] |
| P45/15 | 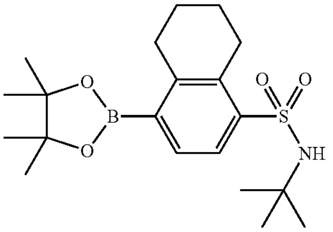 [SMILES: CC(C)(C)NS(=O)(=O)c1ccc(B2OC(C)(C)C(C)(C)O2)c2c1CCCC2] |
| P45/16 | 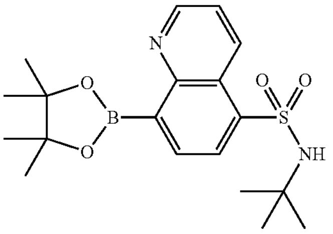 [SMILES: CC(C)(C)NS(=O)(=O)c1ccc(B2OC(C)(C)C(C)(C)O2)c2ncccc12] |
| P45/17 | 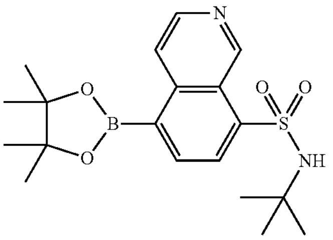 [SMILES: CC(C)(C)NS(=O)(=O)c1ccc(B2OC(C)(C)C(C)(C)O2)c2ccncc12] |
Preparative Example P49
P49
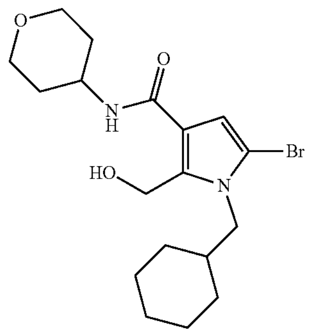
Step 1: Methyl 5-bromo-1-(cyclohexylmethyl)-2-formyl-1H-pyrrole-3-carboxylate (P49a)
To a solution of methyl 5-bromo-1-(cyclohexylmethyl)-1H-pyrrole-3-carboxylate (1.8 g, 6.0 mmol) (prepared similar as described in Example 1) and DMF (3 mL) in 1,2-dichloroethane (50 mL) was added $POCl_3$ (1.38 g, 9.0 mmol) and the solution was stirred for 1 h, then warmed to 80° C. overnight, diluted with water (50 mL), basified with 2M $NaHCO_3$ and extracted with EA (3×50 mL). The combined organic layer was washed with brine, dried over $Na_2SO_4$, filtered, evaporated and purified by CC (EA/PE=1/10) to give compound P49a (1.1 g, 58%).

Step 2: Methyl 5-bromo-1-(cyclohexylmethyl)-2-(hydroxymethyl)-1H-pyrrole-3-carboxylate (P49b)

To a solution of P49a (1.1 g, 3.5 mmol) in MeOH (3 mL) at rt was added $NaBH_4$ (152 mg, 4 mmol) and the resulting solution was stirred at this temperature for 20 min, diluted with water (50 mL) and extracted with EA (3×50 mL). The combined layer was concentrated to give compound P49b (1.03 g, 89%).

Step 3: 5-Bromo-1-(cyclohexylmethyl)-2-(hydroxymethyl)-N-(tetrahydro-2H-pyran-4-yl)-1H-pyrrole-3-carboxamide (P49)

Compound P49b (200 mg, 0.61 mmol) was saponified and then coupled with tetrahydro-2H-pyran-4-amine similar as described in Example 1 (Step 7 and 8) to give compound P49 (210 mg, 86%) as a colorless solid.

Preparative Example P50

P50

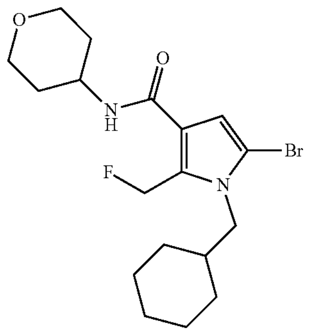

Step 1: Methyl 5-bromo-1-(cyclohexylmethyl)-2-(fluoromethyl)-1H-pyrrole-3-carboxylate (P50a)

To a solution of compound P49b (600 mg, 1.82 mmol) in $CH_2Cl_2$ at −70° C. was added bis(2-methoxyethyl)aminosulfur trifluoride (400 mg, 1.82 mmol) and the resulting solution was stirred at this temperature for 1 h, then warmed to rt for additional 1 h, diluted with water (50 mL) and extracted with EA (3×50 mL). The combined organic layer was concentrated and purified by CC (EA/PE=1/10) to give compound P50a (90 mg, 15%).

Step 2: 5-Bromo-1-(cyclohexylmethyl)-2-(fluoromethyl)-N-(tetrahydro-2H-pyran-4-yl)-1H-pyrrole-3-carboxamide (P50)

Compound P50a (90 mg, 0.61 mmol) was saponified and then coupled with tetrahydro-2H-pyran-4-amine similar as described in Example 1 (Step 7 and 8) to give compound P50 (82 mg, 77%) as a colorless solid.

Preparative Example P51

P51

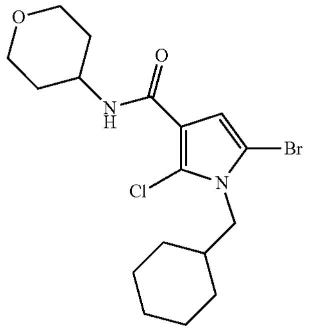

5-Bromo-2-chloro-1-(cyclohexylmethyl)-N-(tetrahydro-2H-pyran-4-yl)-1H-pyrrole-3-carboxamide (P51)

To a solution of methyl 5-bromo-1-(cyclohexylmethyl)-1H-pyrrole-3-carboxylate (600 mg, 1.63 mmol) (prepared similar as described in Example 1) in dry THF (50 mL) was added NCS (250 mg, 1.87 mmol) at rt under nitrogen. The reaction was stirred at 55° C. for overnight and quenched with a cold aq. solution of $NH_4Cl$. The organic layer was separated and the aqueous layer extracted repeatedly with EA. The combined organic layer was washed with brine, dried over $Na_2SO_4$, filtered, evaporated and purified by CC (EA/PE=1/3) to give compound P51 (510 mg, 80%).

Preparative Example P53

953

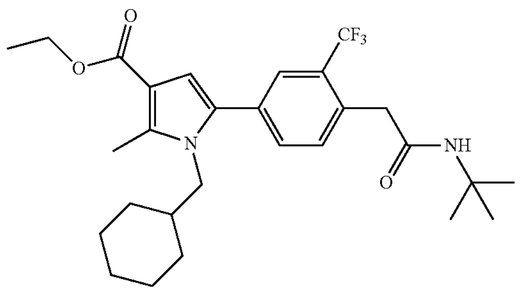

Step 1: 2-(4-Iodo-2-(trifluoromethyl)phenyl)acetyl chloride (P53a)

To a solution of 2-(4-iodo-2-(trifluoromethyl)phenyl)acetic acid (2.00 g, 6.06 mmol) in DCM (20 mL) were added $(COCl)_2$ (1.54 g, 12.1 mmol) and DMF (1 drop) in one portion at rt and the mixture was stirred at rt for 1 h and concentrated to give compound P53a (2.00 g, 95%) as a colorless oil.

Step 2: N-(tert-Butyl)-2-(4-iodo-2-(trifluoromethyl) phenyl)acetamide (P53b)

To a solution of tert-butylamine (876 mg, 12.0 mmol) in DCM (10 mL) was added TEA (2.54 g, 24.0 mmol) and the mixture was stirred at rt for 30 min, then compound P53a (2.00 g, 5.85 mmol) in DCM (10 mL) was added and the mixture was stirred at rt overnight, concentrated and purified by CC (PE/EA=1/5) to give compound P53b (1.20 g, 52%) as a yellow solid.

Step 3: Ethyl 5-(4-(2-(tert-butylamino)-2-oxoethyl)-3-(trifluoromethyl)phenyl)-1-(cyclohexylmethyl)-2-methyl-1H-pyrrole-3-carboxylate (P53)

A solution of compound P53b (500 mg, 1.30 mmol), compound Ma (535 mg, 1.40 mmol) $K_2CO_3$ (450 mg, 3.38 mmol), TBAB (10 mg) and $Pd(PPh_3)_2Cl_2$ (10 mg) in a mixture of 1,4-dioxane (10 mL) and water (5 mL) in a sealed tube was irradiated by microwaves at 100° C. for 100 min, concentrated and purified by CC (PE/EA=1/10) to afford compound P53 (100 mg, 15%) as a colorless solid.

Preparative Example P54

P54

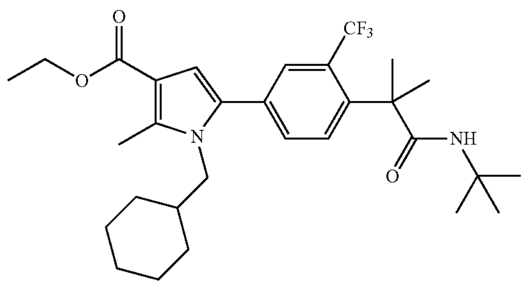

Step 1: Benzyl 2-(4-iodo-2-(trifluoromethyl)phenyl)acetate (P54a)

To a solution of BnOH (2.16 g, 20.0 mmol) in DCM (20 mL) was added TEA (3.54 g, 35.0 mmol) and the mixture was stirred at rt for 30 min. Then a solution of compound P53a (3.48 g, 10.0 mmol) in DCM (15 mL) was added and the mixture was stirred at rt overnight, concentrated and purified by CC (PE/EA=1/15) to give compound P54a (2.65 g, 79%) as a yellow oil.

Step 2: Benzyl 2-(4-iodo-2-(trifluoromethyl)phenyl)-2-methylpropanoate (P54b)

To a solution of NaH (880 mg, 22.1 mmol) in THF (30 mL) was added compound P54a (2.65 g, 6.30 mmol) and the mixture was stirred at rt for 30 min. Then MeI (3.10 g, 22.1 mmol) was added and the mixture was stirred at rt overnight, quenched with water and extracted with EA. The organic layer was dried with $MgSO_4$, filtered, concentrated and purified by CC (PE/EA=1/15) to give compound P54b (900 mg, 32%) as a yellow oil.

Step 3: Ethyl 5-(4-(1-(benzyloxy)-2-methyl-1-oxopropan-2-yl)-3-(trifluoromethyl)phenyl)-1-(cyclohexylmethyl)-2-methyl-1H-pyrrole-3-carboxylate (P54c)

A solution of compound P54b (900 mg, 2.00 mmol), compound P18a (750 mg, 2.00 mmol) $K_2CO_3$ (690 mg, 5.00 mmol), TBAB (10 mg) and $Pd(PPh_3)_2Cl_2$ (10 mg) in a mixture of dioxane (10 mL) and water (5 mL) in a sealed tube was irradiated with microwaves at 100° C. for 100 min, concentrated and purified by CC (PE/EA=1/8) to afford compound P54c (400 mg, 36%) as a colorless solid.

Step 4: 2-(4-(1-(Cyclohexylmethyl)-4-(ethoxycarbonyl)-5-methyl-1H-pyrrol-2-yl)-2-(trifluoromethyl) phenyl)-2-methylpropanoic acid (P54d)

To a solution of compound P54c (400 mg, 0.75 mmol) in EtOH (10 mL) was added Pd/C (10%, 40 mg) in one portion at rt and the mixture was stirred under $H_2$ (50 psi) for 5 h, filtered; concentrated and purified by CC (PE/EA=5/1) to give compound P54d (300 g, 90%) as a colorless solid.

Step 5: Ethyl 5-(4-(1-chloro-2-methyl-1-oxopropan-2-yl)-3-(trifluoromethyl)phenyl)-1-(cyclohexylmethyl)-2-methyl-1H-pyrrole-3-carboxylate (P54e)

To a solution of compound P54d (300 mg, 0.63 mmol) in DCM (10 mL) were added $(COCl)_2$ (159 mg, 1.25 mmol) and DMF (1 drop) in one portion at rt and the mixture was stirred for 1 h and concentrated to give compound P54e (300 mg, 95%) as a colorless oil.

Step 6: Ethyl 5-(4-(1-(tert-butylamino)-2-methyl-1-oxopropan-2-yl)-3-(trifluoromethyl)phenyl)-1-(cyclohexylmethyl)-2-methyl-1H-pyrrole-3-carboxylate (P54)

To a solution of tert-butylamine (91 mg, 1.25 mmol) in DCM (5 mL) was added TEA (190 mg, 1.88 mmol) and the mixture was stirred at rt for 30 min. Then a solution of compound P54e (300 mg, 0.63 mmol) in DCM (5 mL) was added and the mixture was stirred at rt overnight, concentrated and purified by CC (PE/EA=1/5) to give compound P54 (100 mg, 30%) as a yellow solid.

P55

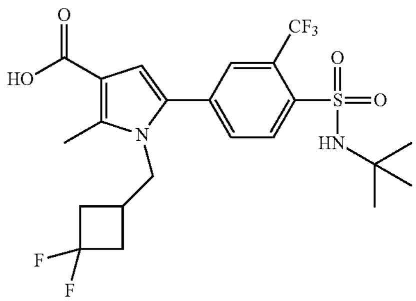

Preparative Example P55

Step 1: 4-Acetyl-N-(tert-butyl)-2-(trifluoromethyl) benzenesulfonamide (P55a)

To a solution of 4-bromo-N-(tert-butyl)-2-(trifluoromethyl)benzenesulfonamide (10.5 g, 29.2 mmol) in dry THF (100 mL) was added n-BuLi (2.5M in hexane, 12.0 mL, 30.0 mmol) drop-wise over 10 min at −78° C. under $N_2$, then the resulting solution was stirred at −78° C. for 1 h. N-Methoxy-N-methylacetamide (4.63 g, 45 mmol) was added, after stirring for a further 10 min, the cooling bath was removed and the mixture was allowed to warm to rt and then stirred at rt for 2 h, quenched with 1M HCl and extracted with EA (3×60 mL). The combined organic phase was washed with brine, dried over $Na_2SO_4$, filtered, concentrated and purified by CC (PE/EA=3/1) to give compound P55a (3.7 g, 39%) as a colorless solid.

Step 2: 4-(2-Bromoacetyl)-N-(tert-butyl)-2-(trifluoromethyl)benzenesulfonamide (P55b)

To a solution of compound P55a (3.7 g, 11.5 mmol) in dry THF (100 mL) was added $PhNMe_3Br_3$ (4.32 g, 11.5 mmol) dropwise at 0° C. and the solution was stirred for 4 h at rt, partially concentrated, washed with water twice and brine consecutively, dried over $Na_2SO_4$, filtered, concentrated and purified by CC (PE/EA=2/1) to give compound P55b (2.9 g, 63%) as yellow oil.

Step 3: Benzyl 5-(4-(N-(tert-butyl)sulfamoyl)-3-(trifluoromethyl)phenyl)-1-((3,3-difluorocyclobutyl)methyl)-2-methyl-1H-pyrrole-3-carboxylate (P55c)

A solution of 3,3-difluorocyclobutylmethylamine (0.40 g, 2.5 mmol), phenylmethyl 3-oxobutanoate (1.05 g, 5.5 mmol), DIEA (0.71 g, 5.5 mmol) in DMF (5 mL) was placed in a sealed tube in a hot oil bath (150° C.) and then stirred for 15 min. A solution of compound P55b (1.21 g, 3.0 mmol) in DMF (2 mL) was added to the hot resulting solution at 100° C. The solution was heated to 180° C. quickly and stirred for another 15 min at 180° C., cooled to rt, diluted with water and extracted with EA. The organic layer was washed with water and brine, dried over $Na_2SO_4$, filtered, concentrated and purified by CC (PE/EA=5/1) to give compound P55c (140 mg, 9%) as a brown oil.

Step 4: 5-(4-(N-(tert-Butyl)sulfamoyl)-3-(trifluoromethyl)phenyl)-1-((3,3-difluorocyclobutyl)methyl)-2-methyl-1H-pyrrole-3-carboxylic acid (P55)

A suspension of compound P55c (130 mg, 0.22 mmol) and 10% Pd/C (50 mg) in MeOH (15 mL) was stirred under 1 atmosphere of $H_2$ at rt for 2 h, filtered, concentrated and purified by CC (DCM/MeOH=15/1) to give compound P55 (65 mg, 59%) as a colorless solid.

Preparative Example P55/1 to P55/3

Using similar procedures at those described in Preparative Example P55, the following compounds were prepared:

| # | Structure |
|---|---|
| P55/1 | 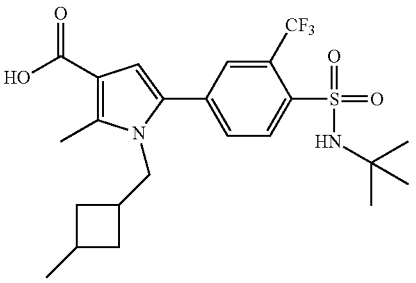 [SMILES: Cc1c(C(=O)O)cc(-c2ccc(S(=O)(=O)NC(C)(C)C)c(C(F)(F)F)c2)n1CC1CC(C)C1] |

-continued

| # | Structure |
|---|---|
| P55/2 | 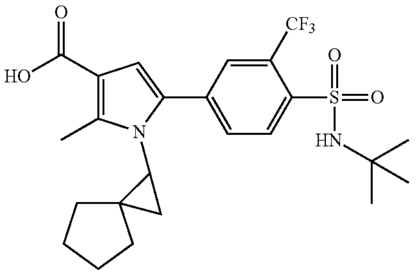 [SMILES: Cc1c(C(=O)O)cc(-c2ccc(S(=O)(=O)NC(C)(C)C)c(C(F)(F)F)c2)n1C1CC12CCCC2] |
| P55/3 | 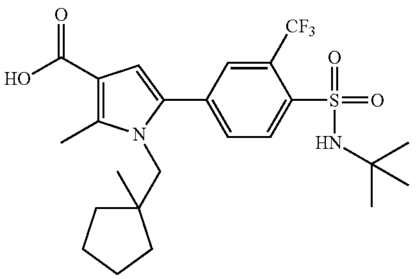 [SMILES: Cc1c(C(=O)O)cc(-c2ccc(S(=O)(=O)NC(C)(C)C)c(C(F)(F)F)c2)n1CC1(C)CCCC1] |

Preparative Example P56

P56

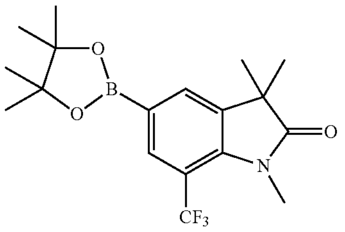

Step 1: N-(4-Bromo-2-(trifluoromethyl)phenyl)-2-(hydroxyimino)acetamide (P56a)

To a solution of 4-bromo-2-(trifluoromethyl)aniline (50 g, 22 mmol), hydroxylamine hydrochloride (5.48 g, 78.9 mmol) and sodium sulfate (24.9 g, 175 mmol) in $H_2O$ (150 mL) and 2M HCl (7.4 mL) at rt under $N_2$ was added chloral hydrate (3.88 g, 26.3 mmol) and the solution was stirred at 55° C. for 18 h, cooled to rt, diluted with water (100 mL) and extracted with EA (3×50 mL). The combined layer was concentrated to give compound P56a (5.0 g) as a viscous oil.

Step 2: 5-Bromo-7-(trifluoromethyl)indoline-2,3-dione (P56b)

A solution of P56a (5.0 g, 16.7 mmol) in conc. $H_2SO_4$ (30 mL) was stirred at 80° C. for 1 h, cooled to rt, poured into crushed ice (200 mL) and allowed to stand for 30 min. The precipitate was collected by filtration, washed with water (3×) and dried to yield compound P56b (2.0 g) as a yellow solid.

Step 3: 5-Bromo-7-(trifluoromethyl)indolin-2-one (P56c)

KOH (796 mg, 14.2 mmol) was added into a mixture of P56b (2.0 g, 7.09 mmol), ethyleneglycol (20 mL) and hydrazine hydrate (98%, 0.5 g, 10 mmol), stirred at 80° C. for 3 h, cooled to rt and poured into ice cold water. The pH of the mixture was adjusted to pH 1-2 with 12M HCl and stirred at rt for 12 h and extracted with EA. The organic phase was collected and evaporated to give compound P56c (1.5 g) as a yellow solid.

Step 4: 5-Bromo-1,3,3-trimethyl-7-(trifluoromethyl) indolin-2-one (P56d)

To a solution of compound P56c (1.0 g, 3.7 mmol) in DMF (20 mL) was added a solution of $CH_3I$ (0.93 mL) in DMF at 0° C. The mixture was stirred at rt overnight, diluted with water (100 mL) and extracted with $Et_2O$ (3×100 mL). The organic layer was washed with brine, dried over $Na_2SO_4$, concentrated and purified by CC to give compound P56d (500 mg, 43%) as a light yellow solid.

Step 5: 1,3,3-Trimethyl-5-(4,4,5,5-tetramethyl-1,3,2-dioxaborolan-2-yl)-7-(trifluoromethyl)indolin-2-one (P56)

A solution of compound P56d (760 mg, 2.45 mmol) was treated as described for Example P33, Step 5 to give compound P56 (750 mg, 86%) as a colorless solid.

Preparative Example P57

P57

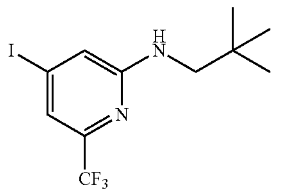

4-Iodo-N-neopentyl-6-(trifluoromethyl)pyridin-2-amine (P57)

A solution of 2-fluoro-4-iodo-6-(trifluoromethyl)pyridine (100 mg, 0.34 mmol) and neopentyl amine (150 mg, 1.70 mmol) in MeCN (1 mL) in a sealed tube was irradiated by microwaves at 130° C. for 30 min, cooled, diluted with water and extracted with EA. The organic layer was washed with brine, dried, concentrated and purified by CC (PE/EA=20/1) to give compound P57 (100 mg, 83%) as a colorless solid.

Preparative Example P58

P58

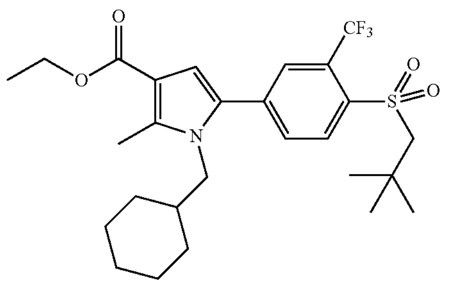

Step 1: Neopentyl(2-(trifluoromethyl)phenyl)sulfane (P58a)

To a solution of NaOEt in EtOH (prepared from sodium (1.29 g, 56.1 mmol) and EtOH (40 mmol)) was added 2-(trifluoromethyl)benzene-1-thiol (5.0 g, 28.1 mmol) and neopentyl 4-methylbenzenesulfonate (6.80 g, 28.1 mmol) and the solution was stirred at reflux under $N_2$ for 20 h, cooled to rt and the formed solid was filtered off. The cake was washed with $Et_2O$ and the combined filtrate was concentrated and diluted with water and ether consecutively. The organic phase was washed with water, dried over $Na_2SO_4$, filtered, concentrated and purified by CC (petroleum) to give compound P58a (4.55 g, 65%) as a colorless solid.

Step 2: (4-Bromo-2-(trifluoromethyl)phenyl)(neopentyl)sulfane (P58b)

To a solution of compound P58a (1.0 g, 4.0 mmol) in dry DCM (15 mL) was added $Br_2$ (640 mg, 4.0 mmol) at rt and the solution was stirred for 2 h, washed with water, sat. sodium thiosulfate and brine consecutively, dried and concentrated to give compound P58b (1.27 g, 97%) as a colorless solid.

Step 3: 4-Bromo-1-(neopentylsulfonyl)-2-(trifluoromethyl)benzene (P58c)

To a solution of compound P58b (1.27 g, 3.9 mmol) in DCM (20 mL) was added 3-chloroperoxybenzoic acid (3.0 g, 11.7 mmol) at −10° C. and the solution was stirred at rt overnight, diluted with DCM and water and the two layers were separated. The organic layer was washed with sat. $NaHCO_3$ twice and brine consecutively, dried over $Na_2SO_4$, filtered, concentrated and purified by CC (PE/EA=25/1) to give compound P58c (700 mg, 47%) as a colorless solid.

Step 4: Ethyl 1-(cyclohexylmethyl)-2-methyl-5-(4-(neopentylsulfonyl)-3-(trifluoromethyl)phenyl)-1H-pyrrole-3-carboxylate (P58)

Compound P58c (359 mg, 1.0 mmol) was treated similar as described in Preparative Example P54, Step 3 to give compound P58 (500 mg, 95%) as a yellow oil.

Preparative Example P59

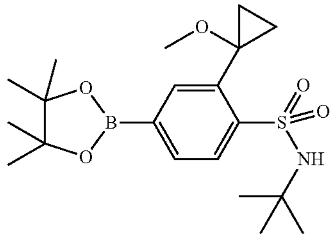

P59

Step 1: 2-(Dibenzylamino)benzoic acid (P59a)

To a solution of bisbenzylamine (140 g, 0.70 mol) in THF (1.0 L) was added n-BuLi (2.5M, 280 mL, 0.7 mol) dropwise under $N_2$ at −30° C., then the reaction solution was stirred at this temperature for 10 min. 2-Fluorobenzoic acid (50 g, 0.35 mol) in THF (500 mL) was added dropwise at −30° C. and the solution was heated to 0° C. for 2 h, quenched with water (100 mL), concentrated, treated with conc. HCl until pH 1 and extracted with DCM (3×500 mL). The organic layer was concentrated and recrystallized from $Et_2O$ to give compound P59a (40 g, 36%) as colorless solid. $^1$H-NMR (300 MHz, $CDCl_3$) δ: 4.16 (s, 4H), 7.15-7.61 (m, 13H), 8.15-8.18 (m, 1H).

Step 2: Methyl 2-(dibenzylamino)benzoate (P59b)

The solution of compound P59a (20 g, 63 mmol), $K_2CO_3$ (26 g, 189 mmol), $CH_3I$ (14 g, 94 mmol) and DMF (200 mL) was stirred at rt for 2 h, diluted with $Et_2O$ (1 L) and the organic phase was washed with water (3×500 mL) and brine consecutively, dried over $Na_2SO_4$, filtered and concentrated to give compound P59b (20 g, 96%) as colorless oil. $^1$H-NMR (300 MHz, $CDCl_3$) δ: 3.89 (s, 3H), 4.25 (s, 4H), 6.94-6.99 (m, 2H), 7.21-7.37 (m, 11H), 7.69-7.72 (m, 1H).

Step 3: 1-(2-(Dibenzylamino)phenyl)cyclopropanol (P59c)

To a solution of $Ti(Oi-Pr)_4$ (99.6 g, 0.36 mol) in dry $Et_2O$ (1.0 L) was added EtMgBr (2M in THF, 540 mL, 1.08 mol) dropwise at −68° C. under $N_2$ and the solution was stirred at this temperature for 1.5 h. To the reaction solution was added compound P59b (60.0 g, 0.18 mol) in dry $Et_2O$ (0.5 L) at −68° C. and then the solution was stirred overnight at rt, quenched carefully with 1M HCl (500 mL) at 0° C. and separated. The aq. layer was extracted with $Et_2O$ (3×300 mL). The combined organic layers were washed with brine, dried over $Na_2SO_4$, filtered, concentrated and purified by CC (PE/EA=100/1) to give compound P59c (9.0 g, 15%) as colorless oil. $^1$H-NMR (400 MHz, $CDCl_3$) δ: 0.96-0.99 (m, 2H), 1.11-1.15 (m, 2H), 4.18 (s, 4H), 6.98-7.31 (m, 14H), 7.96 (s, 1H).

Step 4: N,N-Dibenzyl-2-(1-methoxycyclopropyl)aniline (P59d)

To a solution of compound P59c (5.8 g, 17.6 mmol), $CH_3I$ (3.7 g, 26.4 mmol) in dry THF (20 mL) was added NaH (60%, 1.0 g, 26.4 mmol) in portions at 0° C. under $N_2$ and the solution was stirred at rt overnight, quenched with water (50 mL) and extracted with EA (3×150 mL). The combined organic layers were washed with brine, dried over $Na_2SO_4$, filtered, concentrated and purified by CC (PE/EA=100/1) to give compound P59d (5.0 g, 83%) as colorless oil. $^1$H-NMR (300 MHz, $CDCl_3$) δ: 0.95-0.99 (m, 2H), 1.22-1.26 (m, 2H), 3.24 (s, 3H), 4.32 (s, 4H), 6.96-7.45 (m, 14H).

Step 5: 2-(1-Methoxycyclopropyl)aniline (P59e)

A solution of compound P59d (4.0 g, 11.6 mmol), $HCO_2NH_4$ (7.3 g, 116 mmol), Pd/C (0.5 g) in MeOH (20 mL) was heated to 45° C. for 5 h, cooled to rt, filtered and the filtrate was concentrated. The residue was dissolved in EA (200 mL) and washed with water (3×100 mL). The organic layer was washed with brine, dried over $Na_2SO_4$, filtered and concentrated to give crude product P59e (1.5 g, 75%) as colorless oil. $^1$H-NMR (300 MHz, $CDCl_3$) δ: 0.90-0.93 (m, 2H), 1.09-1.13 (m, 2H), 3.16 (s, 3H), 6.66-6.69 (m, 2H), 7.10-7.14 (m, 2H).

Step 5: 4-Bromo-2-(1-methoxycyclopropyl)aniline (P59f)

To a solution of compound P59e (2.0 g, 12.3 mmol) in MeCN (10 mL) was added NBS (2.18 g, 12.3 mmol) in three portions at 0° C. under $N_2$ and the solution was stirred at rt overnight, concentrated and purified by CC (PE/EA=100/1) to give compound P59f (2.0 g, 70%) as yellow oil. $^1$H-NMR (400 MHz, $CDCl_3$) δ: 0.87-0.90 (m, 2H), 1.07-1.11 (m, 2H), 3.14 (s, 3H), 4.32 (br s, 2H), 6.55-6.57 (d, J=8.0 Hz, 1H), 7.16-7.20 (m, 2H).

Step 6: 4-Bromo-2-(1-methoxycyclopropyl)benzene-1-sulfonyl chloride (P59g)

A solution of compound P59f (1.0 g, 4.0 mmol) in MeCN (40 mL) was cooled to 0-5° C., AcOH (4.0 mL) and conc. HCl (2.0 mL) were added consecutively and then $NaNO_2$ (304 mg, 4.4 mmol) in water (3 mL) over 10 min at 0-5° C. After stirring 20 min, $SO_2$ was bubbled in over 40 min while keeping the temperature below 7° C. A solution of $CuCl_2.2H_2O$ (818 mg, 2.4 mmol) in water (3 mL) was added and the solution was allowed to warm to rt and stirred for 1 h, extracted with EA, washed with aq. $NaHCO_3$ (2×100 mL) and water (2×100 mL) consecutively, dried over $Na_2SO_4$, filtered and concentrated to give product P59g (800 mg, 50%) as yellow solid.

Step 7: 4-Bromo-N-(tert-butyl)-2-(1-methoxycyclopropyl)benzenesulfonamide (P59h)

A solution of compound P59g (800 mg, 2.46 mmol), 2-methylprop-2-ylamine (269 mg, 3.69 mmol), $Et_3N$ (497 mg, 4.92 mmol) and MeCN (5 mL) was stirred at rt overnight, concentrated and purified by CC (PE/EA=80/1) to give compound P59h (400 mg, 46%) as yellow solid. $^1$H-NMR (300 MHz, $CDCl_3$) δ: 1.15-1.23 (m, 2H), 1.25 (s, 9H), 1.28-1.33 (m, 2H), 3.22 (s, 3H), 5.87 (s, 1H), 7.59 (s, 1H), 7.61-7.62 (m, 2H), 8.01-8.04 (d, J=12.0 Hz, 1H).

Step 8: N-(tert-Butyl)-2-(1-methoxycyclopropyl)-4-(4,4,5,5-tetramethyl-1,3,2-dioxaborolan-2-yl)benzenesulfonamide (P59)

Compound P59h (200 mg, 0.55 mmol) was treated similar as described for Example P33, Step 5 to give compound P59

(150 mg, 67%) as colorless solid. $^1$H-NMR (400 MHz, $CDCl_3$) δ: 1.18-1.21 (m, 2H), 1.23 (s, 9H), 1.26-1.27 (m, 2H), 1.36 (s, 12H), 3.19 (s, 3H), 5.97 (s, 1H), 7.81 (s, 1H), 7.86-7.88 (d, J=8.0 Hz, 1H), 8.12-8.14 (d, J=8.0 Hz, 1H).

Preparative Example P60

P60

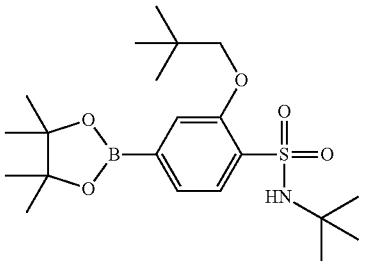

Step 1: 4-Bromo-2-fluorobenzene-1-sulfonyl chloride (P60a)

To the solution of 4-bromo-2-fluoroaniline (6.0 g, 31.6 mmol), AcOH (9 mL) and conc. HCl (5 mL) in MeCN (180 mL) was added $NaNO_2$ (2.6 g, 37.9 mmol) over 10 min at <5° C. and the solution was stirred for 30 min at this temperature. $SO_2$ gas was bubbled in over 30 min. Then a solution of $CuCl_2.H_2O$ (6.4 g, 37.9 mmol) in $H_2O$ (5 mL) was added and the solution was stirred for additional 2 h at rt, concentrated and diluted with EA. The organic layer was washed with water and brine consecutively, dried over $Na_2SO_4$, filtered, concentrated and purified by CC (PE/EA=40/1) to give compound P60a (3.7 g, 43%) as colorless oil.

Step 2: 4-Bromo-N-(tert-butyl)-2-fluorobenzenesulfonamide (P60b)

To a solution of compound P60a (3.7 g, 13.6 mmol) and pyridine (2 mL) in DCM (40 mL) was added 2-methylprop-2-ylamine (3.0 g, 40.7 mmol) at 0° C. and the solution was stirred at this temperature for 1 h, concentrated and purified by CC (PE/EA=40/1) to give compound P60b (2.2 g, 53%) as a colorless solid.

Step 3: 4-Bromo-N-(tert-butyl)-2-(neopentyloxy) benzenesulfonamide (P60c)

To a solution of 2,2-dimethylpropan-1-ol (1.14 g, 12.9 mmol) in dry DMF (15 mL) was added NaH (60% in oil, 413 mg, 10.3 mmol) at 0° C. under $N_2$ and the solution was stirred at this temperature for 40 min. Then compound P60b (800 mg, 2.58 mmol) was added and the solution was stirred at 90° C. for additional 2 h, diluted with water and extracted with EA (3×). The combined organic layers were washed with water (3×) and brine consecutively, dried over $Na_2SO_4$, filtered, concentrated and purified by CC (PE/EA=10/1) to give compound P60c (925 mg, 95%) as a colorless solid.

Step 4: N-(tert-Butyl)-2-(neopentyloxy)-4-(4,4,5,5-tetramethyl-1,3,2-dioxaborolan-2-yl)benzenesulfonamide (P60)

A solution of compound P60c (600 mg, 1.59 mmol) was treated as described for Example P33, Step 5 to give compound P60 (380 mg, 60%) as a colorless solid.

Preparative Example P61

P61

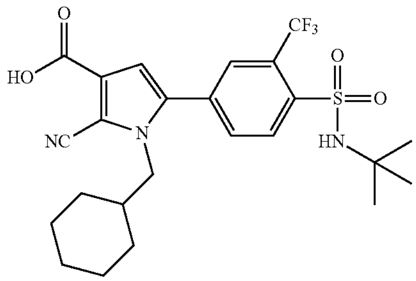

Step 1: Ethyl 2-bromo-5-(4-(N-(tert-butyl)sulfamoyl)-3-(trifluoromethyl)phenyl)-1-(cyclohexylmethyl)-1H-pyrrole-3-carboxylate (P61a)

To a solution of ethyl 5-(4-(N-(tert-butyl)sulfamoyl)-3-(trifluoromethyl)phenyl)-1-(cyclohexylmethyl)-1H-pyrrole-3-carboxylate (2.6 g, 5.06 mmol) in dry THF (25 mL) was added a solution of NBS (0.9 g, 5.06 mmol) in dry THF (10 mL) at −78° C. and the solution was stirred at −55° C. for 2 h, quenched with water and extracted with EA. The organic layer was washed with brine, dried over $Na_2SO_4$, filtered, concentrated and carefully purified by CC (PE/EA=5/1) to give compound P61a (1.08 g, 36%) as a colorless solid.

Step 2: Ethyl 5-(4-(N-(tert-butyl)sulfamoyl)-3-(trifluoromethyl)phenyl)-2-cyano-1-(cyclohexylmethyl)-1H-pyrrole-3-carboxylate (P61b)

A solution of compound P61a (800 mg, 1.35 mmol), CuCN (145 mg, 1.62 mmol) and KI (10 mg) in DMF (10 mL) was stirred at 120° C. overnight under $N_2$, cooled to rt and diluted with 27% $NH_4OH$ (2 mL). The resulting solution was filtered and the filtrate was extracted with EA. The organic layer was washed with brine, dried over $Na_2SO_4$, filtered, concentrated and purified by CC (PE/EA=3/1) to give compound P61b (496 mg, 68%) as a colorless solid.

Step 3: 5-(4-(N-(tert-Butyl)sulfamoyl)-3-(trifluoromethyl)phenyl)-2-cyano-1-(cyclohexylmethyl)-1H-pyrrole-3-carboxylic acid (P61)

A mixture of compound P61b (100 mg, 0.19 mmol) and t-BuOK (38 mg, 0.40 mmol) in a mixture of DMSO and $H_2O$ (10/1, 2 mL) was stirred at 90° C. for 1 h, cooled, diluted with water, acidified with 1M HCl to pH=6 and extracted with EA. The organic layer was washed with water and brine consecutively, dried over $Na_2SO_4$, filtered and concentrated to give compound P61 (67 mg, 70%) as a colorless solid.

Preparative Example P62

P62

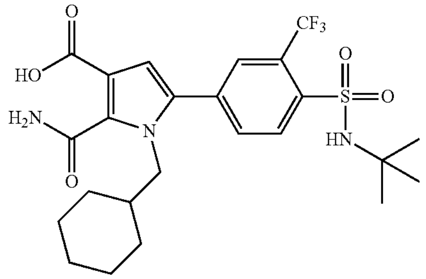

Step 1: Ethyl 5-(4-(N-(tert-Butyl)sulfamoyl)-3-(trifluoromethyl)phenyl)-2-carbamoyl-1-(cyclohexylmethyl)-1H-pyrrole-3-carboxylate (P62a)

To a cooled (ice bath) solution of compound P61b (257 mg, 0.48 mmol) in DMSO (5 mL) was added 30% $H_2O_2$ (0.07 mL) and $K_2CO_3$ (197 mg, 1.43 mmol) and the solution was stirred overnight at rt, quenched with water and extracted with EA. The organic layer was washed with brine, dried over $Na_2SO_4$, filtered, concentrated and purified by CC (PE/EA=1/1) to give compound P62a (145 mg, 54%) as a colorless solid.

Step 2: 5-(4-(N-(tert-Butyl)sulfamoyl)-3-(trifluoromethyl)phenyl)-2-carbamoyl-1-(cyclohexylmethyl)-1H-pyrrole-3-carboxylic acid (P62)

A mixture of compound P62a (145 mg, 0.26 mmol) and t-BuOK (89 mg, 0.79 mmol) in a mixture of DMSO and $H_2O$ (10/1, 2 mL) was stirred at 85° C. for 1 h, cooled, diluted with water, acidified with 1M HCl to pH=6 and extracted with EA. The organic layer was washed with water and brine consecutively, dried over $Na_2SO_4$, filtered and concentrated to give crude compound P62 (162 mg) as a colorless solid.

Preparative Example P63

P63

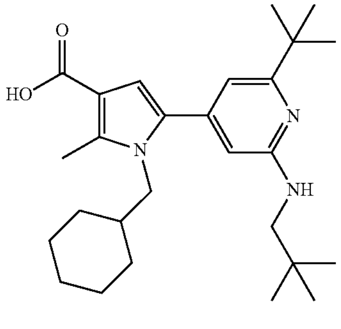

Step 1: 2-(Benzyloxy)-4-bromo-6-(tert-butyl)pyridine (P63a)

To a mixture of 4-bromo-6-(tert-butyl)pyridin-2(1H)-one (1.15 g, 5.0 mmol) in benzene (65 mL) was added BnBr (855 mg, 5.0 mmol) and $Ag_2CO_3$ (689 mg, 2.5 mmol) successively and the mixture was stirred at 60° C. overnight, cooled to rt and the solid was filtered off. The filtrate was washed with sat. $NaHCO_3$, dried over $Na_2SO_4$, concentrated and purified by CC (PE/EA=10/1) to give compound P63a (1.39 g, 86%) as a colorless oil.

Step 2: 2-(Benzyloxy)-6-(tert-butyl)-4-(4,4,5,5-tetramethyl-1,3,2-dioxaborolan-2-yl)pyridine compound (P63b)

A solution of compound P63a (320 mg, 1.0 mmol), $B_2Pin_2$ (508 mg, 2.0 mmol), KOAc (294 mg, 3.0 mmol) and $Pd(dppf)Cl_2$ (73.2 mg, 0.10 mmol) in a mixture of 1,4-dioxane and DMSO (50/1, 15 mL) was stirred at 80° C. under $N_2$ for 1 h, cooled to rt and diluted with $H_2O$ (15 mL), extracted with EA (3×). The combined organic layers were washed with brine twice, dried over $Na_2SO_4$, filtered, concentrated and purified by CC (PE/EA=10/1) to give crude compound P63b (380 mg, quant.) as a colorless solid.

Step 3: Ethyl 5-(2-(benzyloxy)-6-(tert-butyl)pyridin-4-yl)-1-(cyclohexylmethyl)-2-methyl-1H-pyrrole-3-carboxylate (P63c)

A solution of compound P63b (141 mg, 0.38 mmol), ethyl 5-bromo-1-(cyclohexylmethyl)-2-methyl-1H-pyrrole-3-carboxylate (189 mg, 0.58 mmol), $Cs_2CO_3$ (375 mg, 1.15 mmol) and $Pd(dppf)Cl_2$ (73.2 mg, 0.1 mmol) in a mixture of 1,4-dioxane and $H_2O$ (4/1, 5 mL) was stirred at 100° C. under $N_2$ for 2 h, diluted with $H_2O$ (15 mL) and extracted with EA (3×). The combined organic layers were washed with water and brine, dried over $Na_2SO_4$, filtered, concentrated and purified by CC (PE/EA=50/1) to give compound P63c (78 mg, 42%) as a colorless solid.

Step 4: Ethyl 5-(2-(tert-butyl)-6-hydroxypyridin-4-yl)-1-(cyclohexylmethyl)-2-methyl-1H-pyrrole-3-carboxylate (P63d)

To a solution of compound P63c (700 mg, 1.43 mmol) in dry DCM (30 mL) at 5° C. was added anhydrous $FeCl_3$ (1.93 g, 7.15 mmol) and the mixture was stirred at rt for 5 h under $N_2$, diluted with water and extracted with EA twice. The combined organic layers were washed with brine, dried over $Na_2SO_4$, filtered, concentrated and purified by CC (PE/EA=10/1) to give compound P63d (470 mg, 82%) as a colorless oil.

Step 4: Ethyl 5-(2-(tert-butyl)-6-(((trifluoromethyl)sulfonyl)oxy)pyridin-4-yl)-1-(cyclohexylmethyl)-2-methyl-1H-pyrrole-3-carboxylate (P63e)

To a solution of compound P63d (470 mg, 1.18 mmol) and pyridine (186 mg, 2.36 mmol) in DCM (10 mL) was added $Tf_2O$ (499 mg, 1.77 mmol) and the solution was stirred at rt for 2 h under $N_2$, diluted with water and extracted with DCM. The organic layer was washed with brine, dried over $Na_2SO_4$, filtered, concentrated and purified by prep. TLC (PE/EA=50/1) to give compound P63e (250 mg, 41%) as a colorless oil.

Step 5: Ethyl 5-(2-(tert-butyl)-6-(neopentylamino)pyridin-4-yl)-1-(cyclohexylmethyl)-2-methyl-1H-pyrrole-3-carboxylate (P63f)

A solution of compound P63e (250 mg, 0.48 mmol), 2,2-dimethylpropylamine (202 mg, 2.32 mmol), t-BuONa (178 mg, 1.86 mmol), $Pd(OAc)_2$ (21 mg, 0.09 mmol) and 2-dicyclohexylphosphino-2'-(N,N-dimethylamino)biphenyl (73 mg, 0.18 mmol) in toluene (10 mL) was stirred at 110° C. under $N_2$ for 2 h, diluted with $H_2O$ and extracted with EA (3×). The combined organic layers were washed with water and brine, dried over $Na_2SO_4$, filtered, concentrated and purified by CC (PE/EA=50/1) to give compound P63f (240 mg, quant.) as a brown solid.

Step 6: 5-(2-(tert-Butyl)-6-(neopentylamino)pyridin-4-yl)-1-(cyclohexylmethyl)-2-methyl-1H-pyrrole-3-carboxylic acid (P63)

To a solution of compound P63f (240 mg) in a mixture of DMSO and $H_2O$ (10/1, 11 mL) was added t-BuOK (288 mg, 2.57 mmol) and the solution was stirred at 90° C. for 4 h, cooled to rt, acidified with sat. citric acid to pH=3 and extracted with EA. The solution was dried over $Na_2SO_4$, filtered, concentrated and purified by prep. TLC to give compound P63 (200 mg, 89%) as a yellow oil.

Preparative Example P64

P64

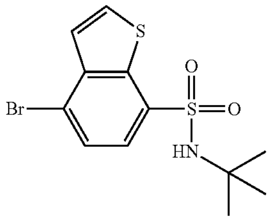

Step 1: 4-Bromobenzo[b]thiophen-7-amine (P64a)

To a solution of benzo[b]thiophen-7-amine (4.65 g, 30 mmol) in DCM (100 mL) was added a solution of $Br_2$ (4.99 g, 0.03 mL) in DCM (120 mL) at −78° C. and the solution was stirred for 1.5 h at −78° C., quenched with water and extracted with DCM (3×). The combined organic layers were washed with water and brine, dried over $Na_2SO_4$, filtered, concentrated and purified by CC (PE/EA=30/1) to give of compound P64a (2.38 g, 34%) as a colorless solid. $^1$H-NMR (400 MHz, $CD_3OD$) δ: 6.62 (d, J=8.0 Hz, 1H), 7.30 (d, J=8.4 Hz, 1H), 7.40 (d, J=5.2 Hz, 1H), 7.62 (d, J=6.0 Hz, 1H).

Step 2: 4-Bromobenzo[b]thiophene-7-sulfonyl chloride (P64b)

To a solution of compound P64a (2.38 g, 10.5 mmol) in AcOH (8 mL) was added conc. HCl (24 mL) at rt and the solution was cooled to −5° C. Then a solution of $NaNO_2$ (1.08 g, 15.7 mmol) in $H_2O$ (8 mL) was added and the solution was stirred at 0° C. for 1 h. The resulting diazonium salt was added to a premixed solution of $SO_2$ in AcOH (sat., 30 mL) and $CuCl_2.H_2O$ (1.34 g, 7.86 mmol) in $H_2O$ (20 mL) at rt and the solution was stirred at rt for 2 h, poured into water and extracted with DCM twice. The combined organic layers were concentrated and purified by CC (PE/EA=30/1) to give compound P64b (3.26 g, quant.) as a colorless oil.

Step 3: 4-Bromo-N-(tert-butyl)benzo[b]thiophene-7-sulfonamide (P64)

The solution of compound P64b (3.26 g, 10.5 mmol), tert-butyl amine (2.5 mL) and pyridine (30 mL) in dry DCM (100 mL) was stirred for 1 h at rt, washed with water twice and brine consecutively, dried over $Na_2SO_4$, filtered, concentrated and purified by CC (PE/EA=10/1) to give compound P64 (2.6 g, 71%) as a colorless solid. $^1$H-NMR (400 MHz, $CDCl_3$) δ: 1.19 (s, 9H), 7.59 (d, J=6.4 Hz, 1H), 7.67 (d, J=6.4 Hz, 1H), 7.68 (d, J=8.0 Hz, 1H), 7.82 (d, J=8.0 Hz, 1H).

Preparative Example P65

P65

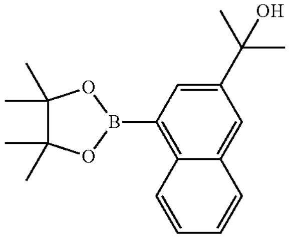

Step 1: Ethyl 4-(((trifluoromethyl)sulfonyl)oxy)-2-naphthoate (P65a)

To a solution of ethyl 4-hydroxy-2-naphthoate (15.0 g, 58.1 mmol) and $NEt_3$ (11.7 g, 116 mmol) in dry DCM (300 mL) was added a solution of $Tf_2O$ (24.5 g, 87.1 mmol) in DCM (50 mL) at 0° C. and the solution was stirred for 4 h at rt, washed with $H_2O$ and brine, dried over $Na_2SO_4$, filtered, concentrated and purified by CC (PE/EA=8/1) to give compound P65a (18.0 g, 89%) as a colorless solid.

Step 2: 3-(2-Hydroxypropan-2-yl)naphthalen-1-yl trifluoromethanesulfonate (P65b)

To a solution of compound P65a (13.2 g, 42.4 mmol) in dry THF (150 mL) was added MeMgBr (1M in THF, 51 mL, 51 mmol) dropwise at 0° C. and the solution was stirred at 25° C. for 1 h, diluted with sat. $NH_4Cl$ and extracted with DCM twice. The combined organic layers were washed with water and brine, dried over $Na_2SO_4$, filtered, concentrated and purified by CC (PE/EA=2/1) to give compound P65b (16.7 g, quant.) as a yellow oil.

Step 3: 2-(4-(4,4,5,5-Tetramethyl-1,3,2-dioxaborolan-2-yl)naphthalen-2-yl)propan-2-ol (P65)

A suspension of compound P65b (1.6 g, 4.8 mmol), KOAc (1.5 g, 14.4 mmol), $B_2Pin_2$ (1.5 g, 5.7 mmol) and $Pd(dppf)Cl_2$ (176 mg, 0.24 mmol) in 1,4-dioxane (10 mL) was stirred at 80° C. under $N_2$ overnight, concentrated and purified by CC (PE/EA=4/1) to give compound P65 (1.2 g, 80%) as a colorless solid. $^1$H-NMR (400 MHz, $CDCl_3$) δ: 1.42 (s. 3H), 1.69 (s, 6H), 1.89 (br s, 1H), 7.45-7.50 (m, 2H), 7.82 (dd, J=8.0, 1.6 Hz, 1H), 8.02 (d, J=2.0 Hz, 1H), 8.18 (d, J=2.0 Hz, 1H), 8.72 (d, J=8.0 Hz, 1H).

Preparative Example P66

P66

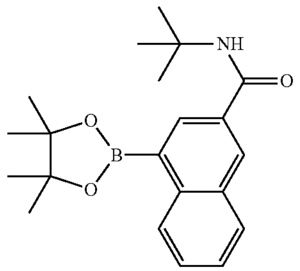

Step 1: N-(tert-Butyl)-4-hydroxy-2-naphthamide (P66a)

A solution of 4-hydroxy-2-naphthoic acid (2.0 g, 10.8 mmol), t-Bu$NH_2$ (1.5 g, 20.0 mmol), HATU (4.9 g, 13.0 mmol) and DIEA (1.4 g, 10.8 mmol) in DMF (10 mL) was stirred at 60° C. for 1.5 h, cooled to rt, diluted with water and extracted with EA (3×). The combined organic layers were washed with water and brine, dried over $Na_2SO_4$, filtered, concentrated and purified by CC (PE/EA=1/1) to give compound P66a (2.1 g, 81%) as a colorless solid. $^1$H-NMR (400 MHz, $CDCl_3$) δ: 1.56 (s, 9H), 7.26 (br s, 1H), 7.62 (d, J=1.6 Hz, 1H), 7.76-7.85 (m, 2H), 8.01 (d, J=8.4 Hz, 1H), 8.15 (d, J=8.4 Hz, 1H), 8.28 (s, 1H).

Step 2: 3-(tert-Butylcarbamoyl)naphthalen-1-yl trifluoromethanesulfonate (P66b)

To a solution of compound P66a (3.80 g, 15.6 mmol) and TEA (4.73 g, 46.8 mmol) in DCM (20 mL) was added $Tf_2O$ (6.60 g, 23.4 mmol) and the solution was stirred at rt for 2 h, diluted with DCM, washed with brine, dried over $Na_2SO_4$, filtered, concentrated and purified by CC (PE/EA=4/1) to give compound P66b (5.0 g, 85%) as a colorless solid. $^1$H-NMR (400 MHz, $CDCl_3$) δ: 1.55 (s, 9H), 7.23 (br s, 1H), 7.58 (d, J=1.8 Hz, 1H), 7.66-7.75 (m, 2H), 8.00 (d, J=8.2 Hz, 1H), 8.15 (d, J=8.2 Hz, 1H).

Step 3: N-(tert-Butyl)-4-(4,4,5,5-tetramethyl-1,3,2-dioxaborolan-2-yl)-2-naphthamide (P66)

Compound P66b (1.2 g, 3.2 mmol) was treated as described above in Example P65, Step 3 to give compound P66 (0.9 g, 80%) as a colorless solid. $^1$H-NMR (400 MHz, $CDCl_3$) δ: 1.42 (s, 12H), 1.53 (s, 9H), 1.88 (br s, 1H), 7.45-7.50 (m, 2H), 7.82 (dd, J=8.4 Hz, 1.6 Hz, 1H), 8.02 (d, J=1.6 Hz, 1H), 8.18 (d, J=1.6 Hz, 1H), 8.72 (d, J=8.4 Hz, 1H).

Preparative Example P67

P67

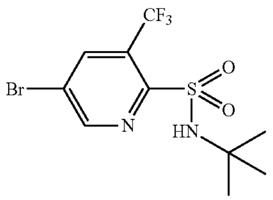

Step 1: 5-Bromo-3-(trifluoromethyl)pyridine-2(1H)-thione (P67a)

The mixture of 5-bromo-3-(trifluoromethyl)pyridin-2-ol (2.0 g, 8.26 mmol) and Lawesson's reagent (2.3 g, 5.79 mmol) in toluene (30 mL) was refluxed overnight, concentrated and purified by CC (PE/EA=20/1) to give compound P67a (1.5 g, 70%) as a yellow solid.

Step 2: 5-Bromo-N-(tert-butyl)-3-(trifluoromethyl) pyridine-2-sulfonamide (P67)

The mixture of compound P67a (0.60 g, 2.33 mmol) and NCS (1.24 g, 9.30 mmol) in DCM (30 mL) was stirred at 15° C. for 2.5 h, washed with water, dried over $Na_2SO_4$ and filtered. DIEA (0.60 g, 4.65 mmol) and tert-butylamine (0.20 g, 2.79 mmol) were added to the filtrate and the mixture was stirred at rt for 1 h, concentrated and purified by CC (PE/EA=10/1) to give compound P67 (0.10 g, 12%) as a pale brown solid.

P69

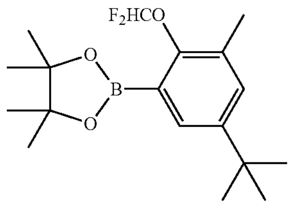

Preparative Example P69

Step 1: 2-Bromo-4-(tert-butyl)-6-methylphenol (P69a)

To a solution of 4-(tert-butyl)-2-methylphenol (10.6 g, 64.6 mmol) in dry $CCl_4$ (100 mL) was added $Br_2$ (10.9 g, 67.8 mmol) slowly and the solution was stirred at rt for 2 h, poured into sat. $Na_2S_2O_3$ and extracted with MTBE twice. The combined organic layers were washed with water and brine, dried over $Na_2SO_4$, filtered, concentrated and purified by CC (EA/PE=1/100) to give compound P69a (15 g, 96%) as colorless oil.

Step 2: 1-Bromo-5-(tert-butyl)-2-(difluoromethoxy)-3-methylbenzene (P69b)

To a solution of compound P69a (10.0 g, 41.1 mmol) in isopropanol (120 mL) was added aq. NaOH solution (20%, 120 mL) at −78° C., then $CHClF_2$ was bubbled into the solution and the solution was heated overnight at 40° C., cooled to rt, diluted with water and extracted with EA twice. The combined organic layers were washed with water and brine, dried over $Na_2SO_4$, filtered, concentrated and purified by CC (EA/PE=1/50) to give compound P69b (5.1 g, 42%) as a colorless oil.

Step 3: 2-(5-(tert-Butyl)-2-(difluoromethoxy)-3-methylphenyl)-4,4,5,5-tetramethyl-1,3,2-dioxaborolane (P69)

Compound P69b (4.8 g, 16.4 mmol) was treated as described above in Example P65, Step 3 to give compound P69 (3.2 g, 57%) as a colorless solid.

Preparative Example P70

P70

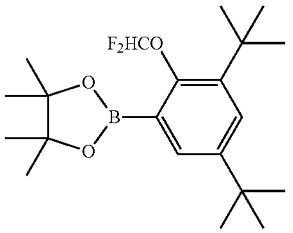

2-(3,5-Di-tert-butyl-2-(difluoromethoxy)phenyl)-4,4,5,5-tetramethyl-1,3,2-dioxaborolane (P70)

Compound P70 was prepared starting from 2-bromo-4,6-di-tert-butylphenol similar as described above in Example P69, Step 2 and 3.

Preparative Example P71

P71

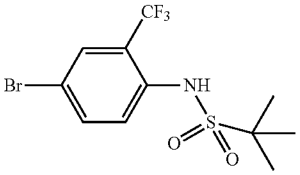

N-(4-Bromo-2-(trifluoromethyl)phenyl)-2-methyl-propane-2-sulfonamide (P71)

To a solution of 2-methylpropane-2-sulfonamide (1.00 g, 7.30 mmol) in DMF (10 mL) was added NaH (60% w/t in mineral oil, 350 mg, 8.80 mmol) at 0° C. and the solution was stirred for 30 min. Then a solution of 4-bromo-1-fluoro-2-(trifluoromethyl)benzene (1.80 g, 7.30 mmol) in DMF (10 mL) was added and the solution was stirred at 120° C. overnight, cooled, diluted with $H_2O$ and extracted with EA (3×20 mL). The combined organic phases were dried over $Na_2SO_4$, filtered, concentrated and purified by CC (PE/EA=8/1) to afford compound P71 (800 mg, 31%) as a colorless solid.

Preparative Example P72

P72

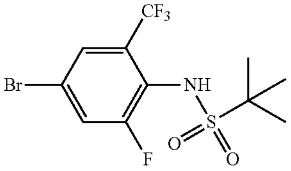

-continued

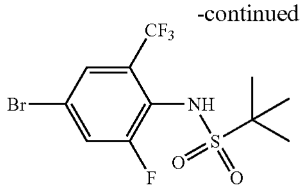

N-(4-Bromo-2-fluoro-6-(trifluoromethyl)phenyl)-2-methylpropane-2-sulfonamide (P72)

To a solution of 2-methylpropane-2-sulfonamide (173 mg, 1.15 mmol) in DMF (10 mL) was added NaH (60% w/t in mineral oil, 56 mg, 1.39 mmol) at 0° C. and the solution was stirred for 30 min. Then a solution of 5-bromo-1,2-difluoro-3-(trifluoromethyl)benzene (300 mg, 1.15 mmol) in DMF (5 mL) was added and the solution was stirred at 120° C. for 2 h, cooled, quenched with $H_2O$ and extracted with EA (3×20 mL). The combined organic phases were dried over $Na_2SO_4$, filtered, concentrated and purified by CC (PE/EA=10/1) to afford compound P72 (130 mg, 31%) as a colorless solid.

Preparative Example P73

P73

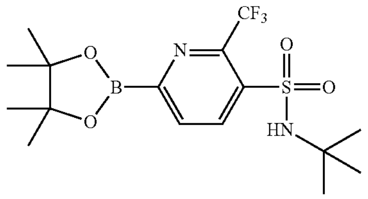

Step 1: 6-Chloro-3-nitro-2-(trifluoromethyl)pyridine (P73a)

A mixture of 5-nitro-6-(trifluoromethyl)pyridin-2(1H)-one (3.54 g, 17.0 mmol), DMF (4.96 g, 68 mmol) and $POCl_3$ (20.9 g, 136 mmol) was heated at 90° C. for 16 h, evaporated, poured into ice-water (200 mL), neutralized to pH 5 with $Na_2CO_3$ and extracted with EA (3×100 mL). The combined organic layers were dried over $Na_2SO_4$, filtered, concentrated and purified by CC (EA/PE=1/20) to give compound P73a (2.77 g, 72%) as a yellow solid. $^1H$-NMR ($CDCl_3$, 300 MHz) δ: 7.74 (1H, d, J=8.4 Hz), 8.22 (1H, d, J=8.4 Hz).

Step 2: 6-Chloro-2-(trifluoromethyl)pyridin-3-amine (P73b)

To a round bottom flask fitted with a centrally mounted stirrer, carrying a reflux condenser and a dropping funnel, was charged successively iron powder (2.18 g, 39 mmol) and ammonium chloride solution (65 mL, 1M, 65 mmol). A solution of compound P73a (2.95 g, 13 mmol) in MeOH (65 mL) was allowed to drop into the stirred slurry of iron powder-ammonium chloride solution over a duration of 10 min at rt. The mixture was stirred under reflux for 2 h, filtered hot followed by hot methanol wash (2×30 mL) and the combined washings were concentrated to leave the product precipitating out from the solution. Re-crystallization from MeOH/DCM gave compound P62b (2.0 g, 79%) as yellow solid. $^1$H-NMR ($CDCl_3$, 300 MHz) δ: 4.27 (2H, br s), 7.09 (1H, d, J=8.4 Hz), 7.25 (1H, d, J=8.4 Hz).

Step 3: 6-Chloro-2-(trifluoromethyl)pyridine-3-sulfonyl chloride (P73c)

Step (a): Thionyl chloride (42 mL) was added dropwise under ice cooling over 60 min to water (250 mL) maintaining the temperature of the mixture at 0-7° C. The solution was allowed to warm to 18° C. and stirring was continued for 3 d. CuCl (151 mg) was added to the mixture and the resultant yellow-green solution was cooled to −3° C. using an acetone/ice bath. Step (b): Hydrochloric acid (36% w/w, 12.2 mL) was added with agitation to compound P73b (1.65 g, 8.4 mmol), maintaining the temperature of the mixture below 30° C. with ice cooling. The mixture was cooled to −5° C. using an ice/acetone bath and a solution of sodium nitrite (0.68 g, 9.8 mmol) in water (2.8 mL) was added dropwise over 30 min maintaining the temperature of the mixture between −5 to 0° C. The resultant slurry was cooled to −2° C. and stirred for 10 min. Step (c): The slurry from step (b) was cooled to −5° C. and added to the solution obtained from step (a) over 95 min, maintaining the temperature of the mixture between −3 to 0° C. (the slurry from step (b) was maintained at −5° C. throughout the addition). As the reaction proceeded, a solid began to precipitate. When the addition was complete, the mixture was agitated at 0° C. for 75 min. The solid was collected by vacuum filtration, washed with ice-cooled water (2×25 mL) and dried under vacuum at below 25° C. to give compound P73c (1.53 g, 66%) as yellow solid. $^1$H-NMR ($CDCl_3$, 300 MHz) δ: 7.81 (1H, d, J=8.4 Hz), 8.57 (1H, d, J=8.4 Hz).

Step 4: N-(tert-Butyl)-6-chloro-2-(trifluoromethyl) pyridine-3-sulfonamide (P73d)

To a solution of 2-methylprop-2-ylamine (5 mL) in DCM (20 mL) was added a solution of compound P73c (1.53 g, 5.5 mmol) in DCM (10 mL) dropwise at 0° C. and the solution was stirred at rt for 1 h, washed with water (3×50 mL) and brine, dried over $Na_2SO_4$, filtered and concentrated to give compound P73d (1.2 g, 69%) as a yellow solid. $^1$H-NMR ($CDCl_3$, 300 MHz) δ: 1.26 (9H, s), 4.87 (1H, s), 7.65 (1H, d, J=8.4 Hz), 8.53 (1H, d, J=8.4 Hz).

Step 5: N-(tert-butyl)-6-(4,4,5,5-tetramethyl-1,3,2-dioxaborolan-2-yl)-2-(trifluoromethyl)pyridine-3-sulfonamide (P73)

A solution of compound P73d (317 mg, 1.0 mmol), $B_2Pin_2$ (280 mg, 1.1 mmol), potassium acetate (294 mg, 3.0 mol) in 1,2-dimethoxyethane (5 mL) was sparged for 5 min with $N_2$ and then Pd(dppf)$Cl_2$ (82 mg, 0.1 mmol) was added. The mixture was heated under reflux for 12 h, diluted with EA (20 mL) and concentrated to dryness. The residue was taken up in EA (30 mL) and water (20 mL). The organic layer was washed with water (30 mL) and brine (30 mL), dried over $Na_2SO_4$, filtered, concentrated and re-crystallized from EA/PE=1/8 to given compound P73 (200 mg, 46%) as a tan solid. $^1$H-NMR ($CDCl_3$, 400 MHz) δ: 1.24 (9H, s), 1.40 (12H, s), 4.83 (1H, s), 8.11 (1H, d, J=8.0 Hz), 8.54 (1H, d, J=8.0 Hz).

Preparative Example P74

74

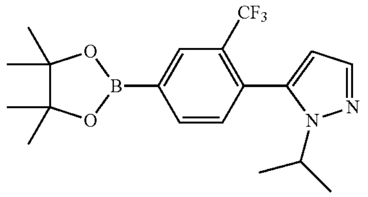

Step 1: 3-(4-Hydroxy-2-(trifluoromethyl)phenyl)-3-oxopropanal (P74a)

NaOMe (5.4 g, 0.10 mol) was suspended in THF (100 mL) and treated at rt with ethyl formate (7.4 g, 0.10 mol) followed by dropwise addition of a solution 1-(4-hydroxy-2-(trifluoromethyl)phenyl)ethanone (16.3 g, 0.08 mol) in THF. The mixture was stirred for 2.5 h at rt, quenched with $H_2O$ (300 mL) and extracted with $Et_2O$ (100 mL). The extracts were discarded. The aqueous phase was acidified with 6M $H_2SO_4$ (18 mL) and extracted with $Et_2O$ (2×100 mL). This extract was washed with water and brine, dried over $Na_2SO_4$, filtered and concentrated to afford compound P74a (12.5 g, 67%) as a yellow solid.

Step 2: 4-(1-Isopropyl-1H-pyrazol-5-yl)-3-(trifluoromethyl)phenol (P74b)

A mixture of compound P74a (5.0 g, 22 mmol) and isopropylhydrazine hydrochloride (3.63 g, 33 mmol) in ethanol (80 mL) was stirred at 80° C. for 2.5 h, concentrated and purified by CC (PE/EA=10/1) to afford compound P74b (4.8 g, 81%) as a pale solid.

Step 3: 4-(1-Isopropyl-1H-pyrazol-5-yl)-3-(trifluoromethyl)phenyl trifluoromethanesulfonate (P74c)

To a P74b (4.0 g, 14.8 mmol) in DCM (80 mL) was added TEA (3.0 g, 29.6 mmol) and $Tf_2O$ (6.26 g, 22.2 mmol). The mixture was stirred at rt for 3.5 h and washed with water (30 mL). The organic phase was dried over $Na_2SO_4$, concentrated and purified by CC (PE/EA=40/1) to afford product P74c (4.5 g, 76%) as a pale solid.

Step 4: 1-Isopropyl-5-(4-(4,4,5,5-tetramethyl-1,3,2-dioxaborolan-2-yl)-2-(trifluoromethyl)-phenyl)-1H-pyrazole (P74)

A mixture of P74c (2.0 g, 5.00 mmol), Pd(dppf)$_2$$Cl_2$ (0.2 g, 0.25 mmol), $B_2Pin_2$ (1.9 g, 7.50 mmol) and KOAc (1.47 g, 15.0 mmol) in 1,4-dioxane (200 mL) was stirred at 90° C. under $N_2$ for 3 h, washed with water (400 mL) and extracted with EA (3×100 mL). The combined organic phase was dried over $Na_2SO_4$ and evaporated to obtain product P74 (1.8 g, 95%).

Preparative Example P75

75

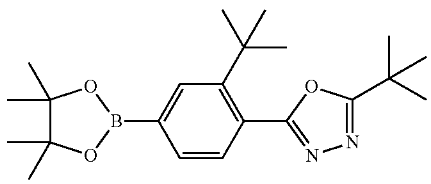

Step 1: 2-(tert-Butyl)-4-chlorophenyl trifluoromethanesulfonate (P75a)

To a solution of 2-(tert-butyl)-4-chlorophenol (30 g, 0.163 mol) and pyridine (21 mL, 0.26 mol) in dry DCM (500 mL) was added a solution of $Tf_2O$ (33 ml, 0.19 mol) in dry DCM (150 mL) at 0° C. and the solution was stirred for 4 h at rt, poured into 1M HCl and extracted with DCM. The organic layer was washed with brine, dried over $Na_2SO_4$, filtered, concentrated and purified by CC (PE/EA=10/1) to give P75a (39 g, 87%) as a colorless liquid.

Step 2: Methyl 2-(tert-butyl)-4-chlorobenzoate (P75b)

A solution of P75a (36 g, 0.13 mol), dppp (4.5 g, 11 mmol), $Pd(OAc)_2$ (2.4 g, 11 mmol) and $NEt_3$ (135 mL, 1.0 mol) in a mixture of MeOH (300 mL) and DMSO (400 mL) was stirred overnight at 55° C. under an atmosphere of CO. Water and EA were added and the organic layer was separated, washed with water twice and brine, dried over $Na_2SO_4$, filtered, concentrated and purified by CC (PE/EA=8/1) to give compound P75b (25.7 g, 89%) as a colorless solid.

Step 3: 2-(tert-Butyl)-4-chlorobenzoic acid (P75c)

To a solution of P75b (4.5 g, 20 mmol) in MeOH (30 mL) was added 3M NaOH (7 mL) and the mixture was refluxed for 12 h, concentrated and poured into water (50 mL), adjusted to pH 3 by adding 3M HCl and extracted with EA (3×30 mL). The combined organic layers were dried over $Na_2SO_4$, filtered and concentrated to dryness to obtain crude product P75c (4.0 g, 95%).

Step 4: 2-(tert-Butyl)-4-chloro-N'-pivalovlbenzohydrazide (P75d)

A solution of P75c (2.1 g, 10 mmol), HATU (5.7 g, 15 mmol) and DIPEA (3.2 g, 25 mmol) in DMF (15 mL) was stirred at rt for 30 min. Then pivalohydrazide (1.7 g, 15 mmol) was added and the mixture was stirred for 12 h under rt, poured into $H_2O$ (50 mL) and extracted with EA (3×50 mL). The combined organic layer were dried over $Na_2SO_4$, filtered, concentrated and purified by prep. HPLC to afford compound P75d (2.5 g, 80%).

Step 5: 2-(tert-Butyl)-5-(2-(tert-butyl)-4-chlorophenyl)-1,3,4-oxadiazole (P75e)

To a slurry of compound P75d (1.2 g, 3.8 mmol) in DCM (15 mL) was added pyridine (0.6 g, 7.6 mmol). The mixture was cooled to −10° C. and $Tf_2O$ (2.2 g, 7.6 mmol) was added dropwise. The mixture was stirred at −10° C. for 1 h, at 0° C. for 1 h and then warmed slowly to rt and stirred for 2 h, poured into $H_2O$ (50 mL) and extracted with EA (3×50 mL). The combined organic layers were dried over $Na_2SO_4$, filtered, concentrated and purified by CC to afford compound P75e (660 mg, 60%).

Step 6: 2-(tert-Butyl)-5-(2-(tert-butyl)-4-(4,4,5,5-tetramethyl-1,3,2-dioxaborolan-2-yl)phenyl)-1,3,4-oxadiazole (P75)

Compound P75e was treated as described above in Example P65, Step 3 to give compound P75 as a colorless solid.

Preparative Example P76

76

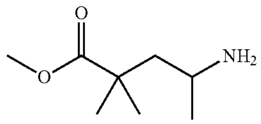

Step 1: Methyl 2,2-dimethyl-4-oxopentanoate (P76a)

A solution of 4-methoxy-3,3-dimethyl-4-oxobutanoic acid (180 mg, 1.12 mmol) in $SOCl_2$ (6 mL) was stirred at rt for 2 h and concentrated. CuI (628 mg, 3.3 mmol) and $Et_2O$ (8 mL) in a separate flask was treated with MeLi (22 mL, 3M) and the solution was stirred for 5 min. Then the resulting solution was cooled to −78° C. The acid chloride was added as a solution in $Et_2O$ (1 mL) and the solution was stirred for additional 30 min, quenched by MeOH and warmed to rt over 2 h. Aq. $NHCl_4$ was added and the mixture was extracted with EA. The organic layer was concentrated to give compound P76a (60 mg, 33%) as a colorless oil.

Step 2: 1-Benzyl-3,3,6-trimethylpiperidin-2-one (P76b)

To a solution of compound P76a (100 mg, 0.63 mmol) in DCM (10 mL) was added $BnNH_2$ (67 mg, 0.63 mmol), $NaBH(AcO)_3$ (186 mg, 0.88 mmol) and AcOH (0.04 mL) at 0° C. The mixture was allowed to reach rt and stirred overnight. Aq. NaOH (1 mL, 10%) was added dropwise and the mixture was extracted with DCM. The organic layer was concentrated and purified by CC (PE/EA=5/1) to give compound P76b (40 mg, 30%) as a colorless oil.

Step 3: 3,3,6-Trimethylpiperidin-2-one (P76c)

Na (0.3 g, 13 mmol) was added to ammonia (10 mL) at −78° C., resulting in a dark blue solution. A solution of compound P76b (60 mg, 0.27 mmol) in THF (1 mL) was added and the solution was stirred at −40° C. for 2 h, quenched with $NHCl_4$ and concentrated. The residue was diluted with water (5 mL) and extracted with EA. The organic layer was concentrated and purified CC (PE/EA=2/1) to give compound P76c (30 mg, 87%) as a colorless solid.

Step 4: Methyl 5-amino-2,2-dimethylhexanoate (P76)

A mixture of compound P76c (400 mg, 3.14 mmol) in conc. HCl (10 mL) was stirred at 120° C. in a sealed tube for 48 h and concentrated. The obtained residue (300 mg, 1.63 mmol) was dissolved in MeOH (10 mL) and TMSCl (708 mg, 6.5 mmol) was added. The solution was stirred at rt for 24 h and concentrated to give compound P76 (350 mg, 57%) as an off-white solid.

Preparative Example P77

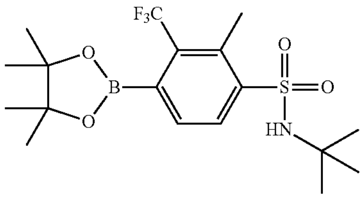

P77

Step 1: N-(2-Methyl-3-(trifluoromethyl)phenyl)acetamide (P77a)

2-Methyl-3-(trifluoromethyl)aniline (1.95 g, 11.1 mmol) was dissolved in $(Ac)_2O$ (10 mL) and the mixture was stirred at rt overnight, partitioned between DCM (20 mL) and aq. $NaHCO_3$ (20 mL) and the aq. phase was extracted again with DCM (3×20 mL). The combined organic layers were dried over $Na_2SO_4$, filtered, concentrated and purified by CC to afford compound P77a (2.08 g, 86%).

Step 2: N-(4-Bromo-2-methyl-3-(trifluoromethyl)phenyl)acetamide (P77b)

To a solution of compound P77a (2.08 g, 9.6 mmol) in HOAc (20 mL) was added under water-cooling a solution of bromine (1.8 mL) in HOAc (10 mL). The mixture was stirred at rt overnight and at 50° C. for 2 h. Additional bromine (1.5 mL) was added under water-cooling and the mixture was stirred and heated to 50° C. for 4 d, cooled to rt and poured into ice water. EA was added, followed by neutralization with $K_2CO_3$. The organic layer was separated, washed with aq. $Na_2S_2O_3$ and brine, dried over $Na_2SO_4$ and concentrated to afford compound P77b (388 mg, 16%).

Step 3: 4-Bromo-2-methyl-3-(trifluoromethyl)aniline (P77c)

To a solution of compound P77b (338 mg, 1.33 mmol) in EtOH (20 mL) was added 4M KOH (1 mL). The mixture was heated to reflux overnight, cooled to rt, concentrated, adjusted to pH~4 with 4M HCl and extracted with EA. The organic layer was washed with brine and dried over $Na_2SO_4$, filtered, concentrated and purified by prep. HPLC to give compound P77c (186 mg, 56%) as colorless solid.

Step 4: N-(tert-Butyl)-2-methyl-4-(4,4,5,5-tetramethyl-1,3,2-dioxaborolan-2-yl)-3-(trifluoro-methyl)benzenesulfonamide (P77)

Compound P77 was prepared from P77c similar as described for compound P45.

Preparative Example P77/1 to P77/2

Using similar procedures at that described in Preparative Example P77, the following compounds were prepared:

| # | Structure |
|---|---|
| P77/1 | 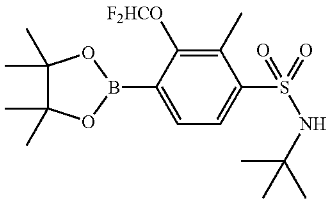 [SMILES: Cc1c(S(=O)(=O)NC(C)(C)C)ccc(B2OC(C)(C)C(C)(C)O2)c1OC(F)F] |
| P77/2 | 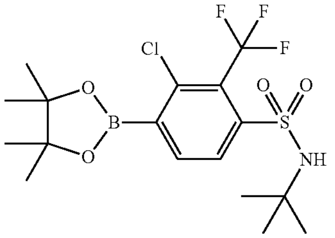 [SMILES: CC(C)(C)NS(=O)(=O)c1ccc(B2OC(C)(C)C(C)(C)O2)c(Cl)c1C(F)(F)F] |

Preparative Example P78

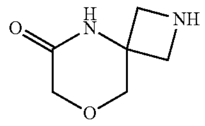

P78

Step 1: tert-Butyl 3-amino-3-(hydroxymethyl)azetidine-1-carboxylate (P78a)

To a solution of 1-tert-butyl 3-ethyl 3-aminoazetidine-1,3-dicarboxylate (366 mg, 1.50 mmol) in THF (10 mL) was added $LiBH_4$ (67 mg; 3 mmol) and the solution was refluxed for 20 min, quenched with $H_2O$, acidified with 2M aq. HCl, neutralized again with 2M aq. $Na_2CO_3$ and extracted with EA (3×). The combined organic layers were washed with water, dried over $Na_2SO_4$, filtered and concentrated to give compound P78a (300 mg, 99%) as a yellow oil.

Step 2: tert-Butyl 6-oxo-8-oxa-2,5-diazaspiro[3.5]nonane-2-carboxylate (P78b)

To a solution of compound P78a (400 mg, 1.98 mmol) and $NEt_3$ (404 mg, 4.00 mmol) in DCM (10 mL) was added 2-chloroacetyl chloride (222 mg, 1.98 mmol) at 0° C. and the solution was refluxed for 2 h, cooled to rt, washed with water and brine, dried over $Na_2SO_4$, filtered, concentrated and purified by CC (PE/EA=5/1) to give of compound P78b (145 mg, 30%) as a colourless oil.

Step 3: 8-oxa-2,5-diazaspiro[3.5]nonan-6-one (P78)

A solution of compound P78b (145 mg, 0.60 mmol) and TFA (10 mL) was stirred for 6 h at rt and concentrated to give intermediate 78 (200 mg crude) as a TFA salt. $^1$H-NMR (300 MHz, DMSO-$d_6$) δ: 3.98-3.95 (m, 1H), 4.12-4.08 (m, 5H), 4.53 (s, 2H), 8.54 (m, 3H). MS: 143 $[M+1]^+$.

P79

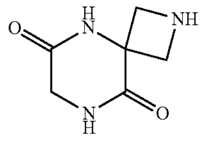

Preparative Example P79

Step 1: 1-tert-Butyl 3-ethyl 3-(2-((tert-butoxycarbonyl)amino)acetamido)azetidine-1,3-dicarboxylate (P79a)

The solution of 1-tert-butyl 3-ethyl 3-aminoazetidine-1,3-dicarboxylate (400 mg, 1.64 mmol), 2-[(tert-butoxy)carbonylamino]acetic acid (431 mg, 2.46 mmol), HOBT (332 mg, 2.46 mmol), EDCI (707 mg, 3.69 mmol) and DIEA (1 mL) in THF (20 mL) was stirred overnight at rt, washed with water and brine, dried over $Na_2SO_4$, filtered, concentrated and purified by CC (PE/EA=2/1) to give compound P79a (500 mg, 76%) as a colorless solid.

Step 2: 2,5,8-Triazaspiro[3.5]nonane-6,9-dione (P79)

A solution of compound P79a (500 mg, 1.25 mmol) and HCl in MeOH (3M, 10 mL) was stirred at rt for 1 h and then refluxed overnight, concentrated and diluted with $Et_2O$. The formed solid was collected by filtration, washed with $Et_2O$ and dried in vacuum to give compound P79 (200 mg, 84%) as a mono HCl salt. $^1$H-NMR (300 MHz, $D_2O$) δ: 4.69-4.65 (m, 2H), 4.51-4.47 (m, 2H), 4.19 (s, 2H). MS: 156 $[M+1]^+$.

Preparative Example P80

P80

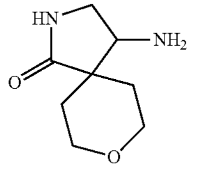

Step 1: Methyl 4-acetyltetrahydro-2H-pyran-4-carboxylate (P80a)

To a suspension of 2,2'-dichloroethyl ether (14.3 g, 100 mmol), $K_2CO_3$ (27.6 g, 200 mmol), KI (1.0 g, 6.00 mmol) in DMF (60 mL) was added methyl 3-oxobutanoate (13.9 g, 120 mmol) and the solution was stirred for 8 h at 80° C., diluted with water and extracted with EA (6×). The combined organic layers were dried over $Na_2SO_4$, filtered and the filtrate was distilled under reduced pressure (Kp 125 to 127° C., 1.3 kPa) to give compound P80a (8.0 g, 43%) as a pale yellow liquid.

Step 2: Methyl 4-(2-bromoacetyl)tetrahydro-2H-pyran-4-carboxylate (P80b)

A suspension of compound P80a (8.0 g, 43 mmol) and $CuBr_2$ (9.63 g, 43 mmol) in EA (100 mL) was stirred overnight at 40° C., filtered and the filtrate was concentrated and purified by CC (PE/EA=20/1) to give compound P80b (2.0 g, 18%) as a colorless solid.

Step 3: 8-Oxa-2-azaspiro[4.5]decane-1,4-dione (P80c)

A solution of compound P80b (2.0 g, 7.5 mmol) in $MeOH/NH_3$ (10M, 100 mL) was stirred overnight at 50° C. in a sealed tube, cooled to rt, concentrated and purified by CC (PE/EA=8/1) to give compound P80c (800 mg, 63%) as a colorless solid.

Step 4: 4-amino-8-oxa-2-azaspiro[4.5]decan-1-one (P80)

A suspension of compound P80c (800 mg, 4.7 mmol), $K_2CO_3$ (1.19 g, 8.6 mmol) and $NH_2OH.HCl$ (598 mg, 8.6 mmol) in EtOH (30 mL) was stirred for 6 h at rt and concentrated. EtOH (15 mL) and Raney-Ni (1 g) were added consecutively and the suspension was stirred under 50 psi of $H_2$ atmosphere for 3 h at 65° C., filtered and the filtrate was concentrated and purified by CC (PE/EA=1/5) to give intermediate P80 (200 mg, 25%) as a colorless solid. $^1$H-NMR (300 MHz, DMSO-$d_6$+$D_2O$) δ: 3.87-3.81 (m, 1H), 3.75-3.69 (m, 1H), 3.59-3.48 (m, 2H), 3.42-3.36 (m, 1H), 3.29-3.26 (m, 1H), 2.86-2.81 (m, 1H), 1.58-1.43 (m, 4H). MS: 171 $[M+1]^+$.

Preparative Example P81

P81

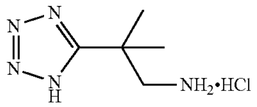

Step 1: tert-Butyl (2-methyl-2-(1H-tetrazol-5-yl)propyl)carbamate (P81a)

To a solution of tert-butyl (2-cyano-2-methylpropyl)carbamate (915 mg, 4.62 mmol) in DMF (25 mL) was added $NaN_3$ (450 mg, 6.93 mmol) and $NH_4Cl$ (367 mg, 6.93 mmol). The reaction mixture was stirred at 110° C. for 24 h, cooled, diluted with EA (20 mL) and washed with water (100 mL). The combined organic extracts were dried over $Na_2SO_4$, evaporated and purified by prep. HPLC to give compound P81a (345 mg, 31%) as a colorless solid.

Step 2: 2-Methyl-2-(1H-tetrazol-5-yl)propan-1-amine hydrochloride (P81)

A mixture of compound P81a (345 mg, 1.43 mmol) in HCl/MeOH (4M, 30 mL) was stirred at rt overnight and evaporated to give compound P81 (241 mg, 95%) as a colorless solid.

Preparative Example 82

P82

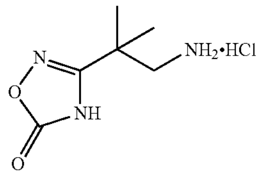

Step 1: tert-Butyl (3-(hydroxyamino)-3-imino-2,2-dimethylpropyl)carbamate (P82a)

A mixture of tert-butyl (2-cyano-2-methylpropyl)carbamate (1.75 g, 8.85 mmol), $NH_2OH$.HCl (584 mg, 17.7 mmol) and EtONa (1.80 g, 26.6 mmol) in EtOH (50 mL) was stirred at 60° C. overnight, poured into water and extracted with EA. The organic extracts were dried over $Na_2SO_4$ and evaporated to give compound P82a (1.53 g, 75%) as yellow oil.

Step 2: tert-Butyl (2-methyl-2-(5-oxo-4,5-dihydro-1,2,4-oxadiazol-3-yl)propyl)carbamate (P82b)

A mixture of P82a (1.53 g, 6.64 mmol), dimethyl carbonate (1.32 g, 13.3 mmol), EtONa (903 mg, 13.3 mmol) in EtOH (50 mL) was stirred at 60° C. overnight, poured into water and extracted with EA. The combined organic layers were dried and evaporated to afford compound P82b (700 mg, 41%) as yellow solid.

Step 3: 3-(1-Amino-2-methylpropan-2-yl)-1,2,4-oxadiazol-5(4H)-one hydrochloride (P82)

A mixture of compound P82b (700 mg, 2.73 mmol) in HCl/MeOH (4M, 30 mL) was stirred at rt overnight and evaporated to give compound P82 (420 mg, 98%) as a colorless solid.

Preparative Example P83

P83

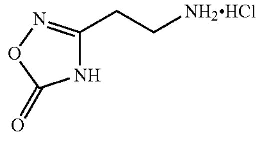

Step 1: tert-Butyl (3-(hydroxyamino)-3-iminopropyl)carbamate (P83a)

A mixture of tert-butyl (2-cyanoethyl)carbamate (763 mg, 4.49 mmol), $NH_2OH$.HCl (296 mg, 8.98 mmol) and EtONa (916 mg, 13.5 mmol) in EtOH (50 mL) was stirred at 60° C. overnight, poured into water and extracted with EA. The combined organic extracts were dried over $Na_2SO_4$ and evaporated to give compound P83a (775 mg, 85%) as yellow oil.

Step 2: tert-Butyl (2-(5-oxo-4,5-dihydro-1,2,4-oxadiazol-3-yl)ethyl)carbamate (P83b)

A mixture of compound P83a (772 mg, 3.80 mmol), 1,1'-carbonyldiimidazole (1.23 g, 7.61 mmol), EtONa (518 mg, 7.61 mmol) in EtOH (50 mL) was stirred at 60° C. overnight, poured into water and extracted with EA. The combined organic layers were dried and evaporated to afford compound P83b (540 mg, 62%) as yellow solid.

Step 3: 3-(2-Aminoethyl)-1,2,4-oxadiazol-5(4H)-one hydrochloride (P83)

A mixture of compound P83b (540 mg, 2.36 mmol) in HCl/MeOH (4M, 30 mL) was stirred at rt overnight and evaporated to give compound P83 (301 mg, 99%) as a colorless solid.

Preparative Example P84

P84

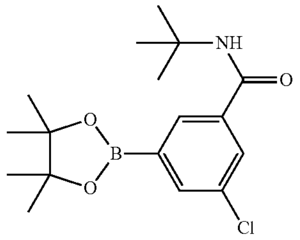

Step 1: 3-Bromo-N-(tert-butyl)-5-chlorobenzamide (P84a)

A mixture of 3-bromo-5-chlorobenzoic acid (2.3 g, 10 mmol), HATU (3.7 g, 10 mmol) and DIPEA (2 g, 15 mmol) in DMF (30 mL) was stirred at rt for 30 min. Then 2-methylbutan-2-amine (1.0 g, 10 mmol) was added and the mixture was stirred for 12 h under rt, poured into water (100 mL) and extracted with EA (3×50 mL). The combined organic layer was dried over $Na_2SO_4$, filtered, evaporated and purified by CC to give compound P84a (2.3 g, 80%).

Step 2: N-(tert-Butyl)-3-chloro-5-(4,4,5,5-tetramethyl-1,3,2-dioxaborolan-2-yl)benzamide (P84)

The mixture of compound P84a (2.0 g, 6.0 mmol), $B_2Pin_2$ (2.0 g, 8.5 mmol), KOAc (1.0 g, 10.5 mmol) and Pd(dppf)$Cl_2$ (100 mg) in 1,4-dioxane (50 mL) was stirred at 90° C. under $N_2$ for 12 h, concentrated, poured into water (50 mL) and extracted with EA (3×50 mL). The combined organic layer was dried over $Na_2SO_4$, filtered, evaporated and purified by CC to give compound P84 (1.1 g, 53%).

Preparative Example P85

P85

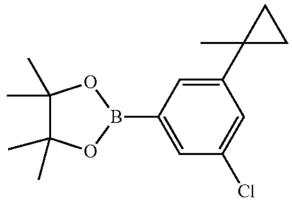

Compound P85 was prepared using similar procedures as described in WO2012/139775, Preparative Example P28, starting with 1,3-dibromo-5-chlorobenzene.

Preparative Example P86

P86

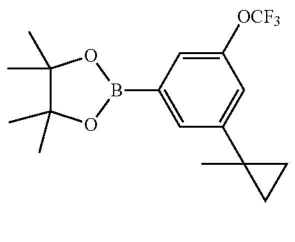

Step 1: 3-Bromo-N-methoxy-N-methyl-5-(trifluoromethoxy)benzamide (P86a)

To a solution of 3-bromo-5-(trifluoromethoxy)benzoic acid (5.00 g, 17.5 mmol), N,O-dimethylhydroxylamine.HCl (4.20 g, 43.9 mmol), HATU (14.7 g, 38.7 mmol) in DMF (50 mL) was added TEA (9.8 mL, 70.2 mmol) in portions at 0° C. and the solution was stirred overnight at rt, diluted with water and extracted with EA. The organic layer was washed with brine, dried over $Na_2SO_4$, filtered and concentrated to give compound P86a (5.5 g, 96%) as a yellow oil. $^1$H-NMR (400 MHz, $CDCl_3$) δ: 3.37 (s, 3H), 3.56 (s, 3H), 7.48 (s, 1H), 7.52 (s, 1H), 7.80 (s, 1H).

Step 2: 1-(3-Bromo-5-(trifluoromethoxy)phenyl)ethanone (P86b)

To a solution of compound P86a (4.5 g, 13.7 mmol) in dry THF (50 mL) was added $CH_3MgBr$ (3M in $Et_2O$, 9.2 mL, 27.6 mmol) in portions at −15° C. and the solution was stirred for 15 min at this temperature and then at rt for 1 h, diluted with 1M HCl and extracted with EA. The organic layer was washed with brine, dried over $Na_2SO_4$, filtered and concentrated to give compound P86b (3.5 g, 90%) as a yellow oil. $^1$H-NMR (400 MHz, $CDCl_3$) δ: 2.62 (s, 3H), 7.60 (s, 1H), 7.74 (s, 1H), 8.02 (m, 1H).

Step 3: 1-Bromo-3-(prop-1-en-2-yl)-5-(trifluoromethoxy)benzene (P86c)

To a suspension of methyltriphenylphosphonium bromide (7.60 g, 21.2 mmol) in dry THF (150 mL) was added NaHMDS (1M in THF, 10.6 mL, 10.6 mmol) at −15° C. and the solution was stirred further for 30 min. A solution of compound P86b (3.0 g, 10.6 mmol) in THF (5 mL) was added at −15° C. and the mixture was stirred at rt for 1 h, diluted with water and extracted with EA. The organic layer was washed with brine, dried over $Na_2SO_4$, filtered, concentrated and purified by CC (PE) to give compound P86c (2.4 g, 81%) as a yellow oil. $^1$H-NMR (400 MHz, $CDCl_3$) δ: 2.11 (d, J=1.6 Hz, 3H), 5.19 (s, 1H), 5.38 (s, 1H), 7.22 (s, 1H), 7.29 (s, 1H), 7.52 (m, 1H).

Step 4: 1-Bromo-3-(1-methylcyclopropyl)-5-(trifluoromethoxy)benzene (P86d)

To a suspension of $Pd(OAc)_2$ (1.0 g, 4.45 mmol) and compound P86c (3.0 g, 10.7 mmol) was added a solution of $CH_2N_2$ in $Et_2O$ (1M, 20 mL, 20 mmol) at −10° C. and the solution was stirred for 30 min, filtered and the filtrate was concentrated to give compound P86d (1.9 g, 60%) as a yellow oil. $^1$H-NMR (400 MHz, $CDCl_3$) δ: 0.78-0.81 (m, 2H), 0.84-0.88 (m, 2H), 1.39 (s, 3H), 7.00 (s, 1H), 7.18 (s, 1H), 7.30 (m, 1H).

Step 5: 4,4,5,5-Tetramethyl-2-(3-(1-methylcyclopropyl)-5-(trifluoromethoxy)phenyl)-1,3,2-dioxaborolane (P86)

To a suspension of compound P86d (1.0 g, 3.4 mmol), KOAc (1.40 g, 13.8 mmol) and $B_2Pin_2$ (1.80 g, 7.08 mmol) in 1,4-dioxane (40 mL) was added $Pd(dppf)Cl_2$ (250 mg, 356 μmol) at rt under $N_2$ and the solution was heated overnight at 80° C., cooled to rt and filtered. The filtrate was concentrated and purified by CC (PE/EA=50/1) to give compound P86 (1.0 g, 91%) as yellow oil. $^1$H-NMR (300 MHz, $CDCl_3$) δ: 0.73-0.76 (m, 2H), 0.86-0.90 (m, 2H), 1.34 (s, 12H), 1.41 (s, 3H), 7.17 (s, 1H), 7.43 (s, 1H), 7.60 (s, 1H).

Preparative Example P87

P87

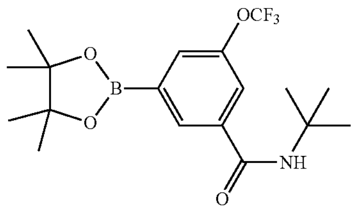

Compound P87 was prepared using similar procedures as described in Preparative Example P84.

Preparative Example P89

P89

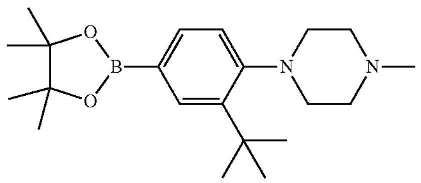

Step 1: 1-(2-(tert-Butyl)phenyl)-4-methylpiperazine (P89a)

A mixture of 2-(tert-butyl)aniline (1.0 g, 6.71 mmol), NaI (3.0 g, 20.1 mmol), $K_2CO_3$ (2.78 g, 20.1 mmol) and 2-chloro-N-(2-chloroethyl)-N-methylethanamine (1.04 g, 6.71 mmol) in diglyme (150 mL) was stirred at 170° C. for 24 h, poured into water and extracted with EA. The organic layers were dried over $Na_2SO_4$, evaporated and purified by CC (DCM/MeOH=19/1) to afford compound P89a (500 mg, 32%).

Step 2: 1-(4-Bromo-2-(tert-butyl)phenyl)-4-methylpiperazine (P89b)

Compound P89a (200 mg, 0.86 mmol) and NaOAc (210 mg, 2.58 mmol) were dissolved in AcOH (5 mL) and the mixture was stirred at it Bromine (165 mg, 1.03 mmol) was added dropwise and the mixture was stirred for 2 h at rt, diluted with 2M NaOH (150 mL) and extracted with EA. The combined organic phases were dried over $Na_2SO_4$, filtered, concentrated and purified by prep. HPLC to afford compound P89b (40 mg, 15%).

Step 3: 1-(2-(tert-Butyl)-4-(4,4,5,5-tetramethyl-1,3,2-dioxaborolan-2-yl)phenyl)-4-methylpiperazine (P89)

This compound was prepared using a similar procedure as described in Preparative Example P86, Step 5.

Preparative Example P90

P90

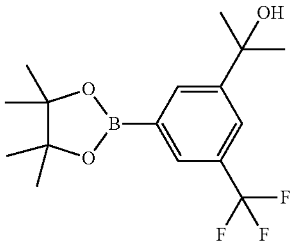

Step 1: 2-(3-Bromo-5-(trifluoromethyl)phenyl)propan-2-ol (P90a)

A mixture of 1-(3-bromo-5-(trifluoromethyl)phenyl)ethanone (0.5 g, 1.8 mmol) in THF (10 mL) was cooled to 0° C. and treated dropwise with MeMgBr (1M in $Et_2O$, 10 mmol, 10 mL). Upon completion of addition, the resulting suspension was allowed to warm to rt and was stirred for 5 h, slowly diluted with saturated aq. $NH_4Cl$ (10 mL) and EA (10 mL). The layers were separated and the aq. layer was extracted with EA (3×30 mL). The combined organic layers were dried over $MgSO_4$, evaporated and purified by CC to afford compound P90a (0.47 g, 93%).

Step 2: 2-(3-(4,4,5,5-Tetramethyl-1,3,2-dioxaborolan-2-yl)-5-(trifluoromethyl)phenyl)propan-2-ol (P90)

Compound P90 was prepared using a similar procedure as described in Preparative Example P86, Step 5.

Preparative Example P91

P91

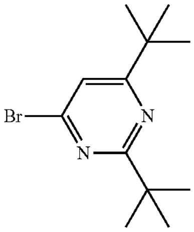

Step 1: 2,6-Di-tert-butylpyrimidin-4-ol (P91a)

To a mixture of pivalimidamide (586 mg, 5.86 mmol) and ethyl 4,4-dimethyl-3-oxopentanoate (1.21 g, 7.03 mmol) in MeOH (30 mL) was added NaOMe (623 mg, 11.7 mmol) under Ar. The mixture was refluxed at 75° C. overnight, diluted with water (20 mL) and extracted with EA (3×20 mL). The organic layer was washed with brine, dried over $Na_2SO_4$ and concentrated to give compound P91a (1.04 g, 85%) as colorless solid.

Step 2: 4-Bromo-2,6-di-tert-butylpyrimidine (P91)

Compound P91a (1.04 g, 4.99 mmol) and $POBr_3$ (10 g) was stirred at 65° C. for 1 h, poured into ice/water and extracted with EA. The organic layer was dried over $MgSO_4$, filtered and concentrated to give compound P91 (1.20 g, 89%) as a yellow oil.

Preparative Example P92

P92

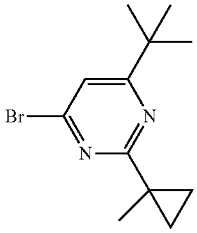

Step 1: 1-Methylcyclopropanecarboximidamide (P92a)

$NH_4Cl$ (129 mg, 2.43 mmol) was suspended in toluene (10 mL) and the slurry cooled to 0° C. $AlMe_3$ (2M in toluene, 2.43 mmol) was added at 0° C. and the mixture was allowed to warm to rt and stirred until gas evolution had ceased. Methyl 1-methylcyclopropanecarboxylate (114 mg, 1.62 mmol) was added and the mixture stirred at 80° C. overnight, cooled to rt, diluted with MeOH and stirred at rt for 1 h. The solution was filtered, the solids washed with MeOH and the solvent was removed in vacuo to afford the compound P92a (100 mg, 63%).

Step 2: 6-(tert-Butyl)-2-(1-methylcyclopropyl)pyrimidin-4-ol (P92b)

To a mixture of compound P92a (63 mg, 0.64 mmol) and methyl 4,4-dimethyl-3-oxopentanoate (121 mg, 0.77 mmol) in MeOH (30 mL) was added NaOMe (86 mg, 1.61 mmol) under Ar. The mixture was refluxed at 75° C. overnight, diluted with water (20 mL) and extracted with EA (3×20 mL). The combined organic layer was washed with brine, dried over $Na_2SO_4$ and concentrated to give compound P92b (112 mg, 85%) as a colorless solid.

Step 3: 4-Bromo-6-(tert-butyl)-2-(1-methylcyclopropyl)pyrimidine (P92)

Compound P92b (105 mg, 0.51 mmol) and $POBr_3$ (200 mg) was stirred without solvent at 65° C. for 1 h, poured into ice/water and extracted with EA. The organic layer was dried over $MgSO_4$, filtered and concentrated to give compound P92 (121 mg, 89%) as yellow oil.

Preparative Example P93

P93

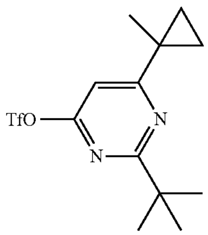

Step 1: Methyl 3-(1-methylcyclopropyl)-3-oxopropanoate (P93a)

To a solution of 1-(1-methylcyclopropyl)ethanone (328 mg, 3.35 mmol) in THF (90 mL) was added LiHMDS (1M in THF, 2.5 mL) at −78° C. The cooling bath was removed and the mixture was stirred at rt for 30 min. Dimethyl carbonate (452 mg, 5.03 mmol) was added and the mixture stirred at rt overnight, evaporated, diluted with water and EA, acidified with AcOH and extracted with EA. The organic layer was dried over $MgSO_4$, filtered, concentrated and purified by CC (EA/PE=1/9) to give compound P93a (68 mg, 13%) as a yellow oil.

Step 2: 2-(tert-Butyl)-6-(1-methylcyclopropyl)pyrimidin-4-ol (P93b)

To a mixture of compound P93a (60 mg, 0.38 mmol) and pivalimidamide (46 mg, 0.46 mmol) in MeOH (30 mL) was added NaOMe (51 mg, 0.95 mmol) under Ar. The mixture was refluxed at 75° C. overnight, diluted with water (20 mL) and extracted with EA (3×20 mL). The organic layer was washed with brine, dried over $Na_2SO_4$ and concentrated to give compound P93b (63 mg, 80%) as a colorless solid.

Step 3: 2-(tert-Butyl)-6-(1-methylcyclopropyl)pyrimidin-4-yl trifluoromethanesulfonate (P93)

To a mixture of compound P93b (57 mg, 0.28 mmol) in DCM (10 mL) was added $Tf_2O$ (118 mg, 0.42 mmol) and TEA (71 mg, 0.70 mmol) and the mixture was stirred at rt overnight, poured into water and extracted with DCM. The organic layer was dried over $MgSO_4$, filtered and concentrated to afford compound P93 (81 mg, 86%) as a yellow oil.

Preparative Example P94

P94

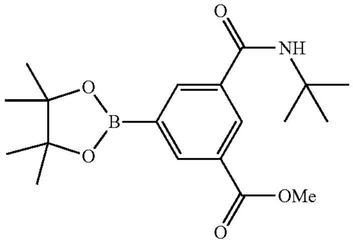

Step 1: 3-Bromo-5-(methoxycarbonyl)benzoic acid (P94a)

To a solution of dimethyl 5-bromoisophthalate (5.0 g, 18.3 mmol) in a mixture of THF (25 mL) and MeOH (25 mL) was added NaOH (740 mg, 18.4 mmol) and the mixture was stirred at rt overnight, concentrated, diluted with 2M HCl (20 mL) and extracted with EA. The combined organic layers were dried over $MgSO_4$, filtered and concentrated. The crude product was washed with a mixture of PE/EA (10:1, 10 mL) to give compound P94a (4.2 g, 88%) as a colorless solid.

Step 2: Methyl 3-bromo-5-(tert-butylcarbamoyl)benzoate (P94b)

A solution of compound P94a (400 mg, 1.54 mmol) in $SOCl_2$ (10 mL) was heated at reflux for 2 h, concentrated and coevaporated with toluene twice. The residue was dissolved in dry DCM (6 mL). TEA (0.2 mL) and tert-butylamine (0.15 mL) were added and the solution was stirred for further 40 min, concentrated and purified by CC (PE/EA=10:1) to give compound P94b (360 mg, 76%) as a colorless oil.

Step 3: Methyl 3-(tert-butylcarbamoyl)-5-(4,4,5,5-tetramethyl-1,3,2-dioxaborolan-2-yl)benzoate (P94)

A flask was charged with compound P94b (360 mg, 1.15 mmol), $B_2Pin_2$ (1.57 g, 5.4 mmol), KOAc (0.72 g, 7.3 mmol), Pd(dppf)$Cl_2$ (60 mg) and DMF (10 mL) and the mixture was stirred at 90° C. for 12 h, cooled, concentrated and purified by CC (PE/EA=10/1) to give compound P94 (315 mg, 76%) as a colorless solid.

Preparative Example P95

P95

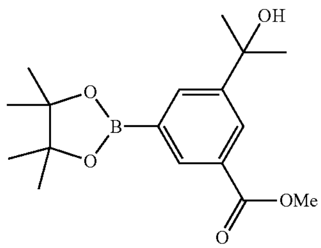

Step 1: Methyl 3-bromo-5-(methoxy(methyl)carbamoyl)benzoate (P95a)

A solution of compound P94a (3.8 g, 14.7 mmol) in $SOCl_2$ (40 mL) was heated at reflux for 2 h, concentrated and diluted with dry DCM (200 mL). Then the solution was added to a stirring solution of N,O-dimethylhydroxylamine hydrochloride (1.69 g, 17.6 mmol) and $NEt_3$ (6 mL) in dry DCM (60 mL) slowly at 0° C. and the solution was stirred for 1 h at rt, poured into water. The organic layer was separated, washed with water and brine, dried over $Na_2SO_4$, filtered and concentrated to give crude compound P95a (4.2 g, 94%) as a light brown oil.

Step 2: Methyl 3-acetyl-5-bromobenzoate (P95b)

To a solution of compound P95a (4.2 g, 14.0 mmol) in dry THF (120 mL) was added MeMgBr (3M in $Et_2O$, 5.5 mL, 16.7 mmol) dropwise at 0° C. and the solution was stirred for 4 h at rt, quenched with aq. $NHCl_4$ and extracted with EA twice. The combined organic layers were washed with water and brine consecutively, dried over $Na_2SO_4$, filtered and concentrated to give crude compound P95b (2.5 g) which contains 15% compound P95c (based on LCMS) as a colorless oil Step 3: Methyl 3-bromo-5-(2-hydroxypropan-2-yl)benzoate (P95c)

To a solution of crude compound P95b (2.5 g, 9.7 mmol) in dry THF (50 mL) was added MeMgBr (3M in $Et_2O$, 3.7 mL, 11.1 mmol) dropwise at 0° C. and the solution was stirred for 4 h at rt, quenched with aq. $NHCl_4$ and extracted with EA twice. The combined organic layers were washed with water and brine consecutively, dried over $Na_2SO_4$, filtered and concentrated to give crude compound P95c (2.1 g, 79% over two steps) as pale yellow oil.

Step 4: Methyl 3-(2-hydroxypropan-2-yl)-5-(4,4,5,5-tetramethyl-1,3,2-dioxaborolan-2-yl)-benzoate (P95)

A flask was charged with compound P95c (900 mg, 3.3 mmol), $B_2Pin_2$ (4.5 g, 17.8 mmol), KOAc (2.3 g, 23.1 mmol), $Pd(dppf)Cl_2$ (100 mg) and DMF (200 mL) and the solution was stirred at 100° C. for 12 h, concentrated and purified by CC (PE/EA=10/1) to give compound P95 (650 mg, 62%) as a colorless solid.

Preparative Example P96

P96

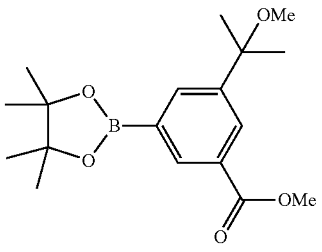

Step 1: Methyl 3-bromo-5-(2-methoxypropan-2-yl)benzoate (P96a)

To a solution of compound P95c (1.1 g, 4.0 mmol) in dry THF (20 mL) was added NaH (195 mg, 8.0 mmol) under $N_2$ and the suspension was stirred for 1 h at rt. Then MeI (1.72 g, 12.0 mmol) was added and the solution was stirred at 70° C. in a sealed tube overnight, poured into water and extracted with $Et_2O$. The organic layer was washed with water and brine, dried over $Na_2SO_4$, filtered, concentrated and purified by CC (PE) to give compound P96a (600 mg, 52%) as a colorless oil.

Step 2: Methyl 3-(2-methoxypropan-2-yl)-5-(4,4,5,5-tetramethyl-1,3,2-dioxaborolan-2-yl)benzoate (P96)

A flask was charged with compound P96a (600 mg, 2.1 mmol), $B_2Pin_2$ (1.07 g, 4.2 mmol), KOAc (1.44 g, 14.7 mmol), $Pd(dppf)Cl_2$ (60 mg) and DMF (10 mL) and the solution was stirred at 100° C. for 12 h, cooled, concentrated and purified by CC (PE/EA=20/1) to give compound P96 (400 mg, 57%) as a colorless solid.

P97

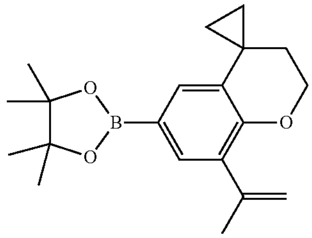

Preparative Example P97

Step 1: 6-Bromo-8-(prop-1-en-2-yl)spiro[chroman-4,1'-cyclopropane] (P97a)

To a solution of 2-(spiro[chroman-4,1'-cyclopropan]-8-yl)propan-2-ol (prepared as described in WO2012/139775, Preparative Example P39) (1.0 g, 4.58 mmol) in dry THF (10 mL) was added NBS (980 mg, 5.5 mmol) and the mixture was heated at reflux overnight, cooled, poured into water and extracted with EA twice. The combined organic layers were washed with brine, dried over $Na_2SO_4$, filtered, concentrated and purified by CC (PE/EA=100/1) to give 2-(6-bromospiro[chroman-4,1'-cyclopropan]-8-yl)propan-2-ol (180 mg, 14%) and compound P97a (300 mg, 24%) as a colorless oil.

Step 2: 4,4,5,5-tetramethyl-2-(8-(prop-1-en-2-yl)spiro[chroman-4,1'-cyclopropan]-6-yl)-1,3,2-dioxaborolane (P97)

A mixture of compound P97a (300 mg, 1.08 mmol), $Pin_2B_2$ (386 mg, 1.52 mmol), $Pd(dppf)Cl_2$ (30 mg) and KOAc (150 mg, 1.52 mmol) in DMF (5 mL) under $N_2$ atmosphere was stirred at 95° C. overnight, concentrated and purified by CC (PE/EA=10/1) to give compound P97 (128 mg, 36%) as a colorless solid.

Example 1

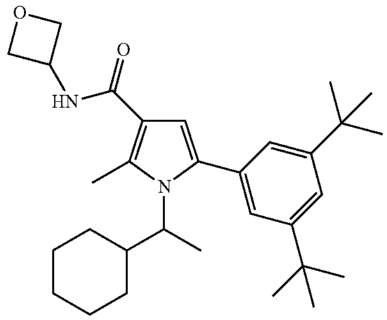

Step 1: 1-Cyclohexylethyl methanesulfonate (1a)

A solution of 1-cyclohexylethanol (1.28 g, 10 mmol) in DCM (50 mL), mesylchloride (15 mmol), $Et_3N$ (30 mmol) was added under 0° C. The mixture was stirred for additional 2 h, quenched with ice water and extracted with EA. The organic layer was separated, washed with brine and dried over $Na_2SO_4$. After filtration, the filtrate was evaporated and the crude intermediate 1a was used in the next step.

Step 2: 1,2-Dibromoethyl acetate (1b)

Under $N_2$, vinyl acetate (86 g, 1.0 mol) was dissolved in dry $CCl_4$ (200 mL) and bromine (160 g, 1 mol) in dry $CCl_4$ (100 mL) was added dropwise over 2 h with vigorous stirring in an ice-water bath below 10° C. The mixture was stirred for additional 30 min and solvent was removed to give crude product 1b, which was used for the next step without further purification.

Step 3: Ethyl 2-methyl-1H-pyrrole-3-carboxylate (1c)

$NH_3$ (gas) was bubbled to a stirred solution of compound 1b (24.6 g, 10 mmol) and ethyl 3-oxobutanoate (13.0 g, 0.1 mol) in dry THF for 15 min. The solid was filtered off and solvent was removed to give crude product 1c.

Step 4: Ethyl 1-(1-cyclohexylethyl)-2-methyl-1H-pyrrole-3-carboxylate (1d)

To a solution of compound 1c (1.53 g, 10 mmol) in dry DMF (10 mL) was added NaH (60% in mineral oil, 1.2 g, 0.03 mol) in an ice-water bath below 0° C. The mixture was stirred for 30 min and then compound 1a (3.09 g, 15 mmol) was added to the mixture. The mixture was stirred for additional 12 h, quenched with ice water and extracted with EA. The organic layer was separated and washed with brine and dried over $Na_2SO_4$. After filtration, the filtrate was evaporated and purified by CC (EA/PE=1/60) to give compound 1d (1.63 g, 62%) as a pale yellow oil.

Step 5: Ethyl 5-bromo-1-(1-cyclohexylethyl)-2-methyl-1H-pyrrole-3-carboxylate (1e)

To a solution of compound 1d (1.32 g, 5.0 mmol) in dry THF (25 mL) was added NBS (0.89 g, 5 mmol) at −78° C. under $N_2$. The reaction was stirred 5 min (monitored by TLC) and quenched with cold aq. $NH_4Cl$. The organic layer was separated and the aq. layer extracted repeatedly with EA. The combined organic layer was washed with brine and dried over $Na_2SO_4$. After filtration, the filtrate was evaporated and purified by CC (EA/PE=1/60) to give compound 1e (1.57 g, 92%).

Step 6: Ethyl 1-(1-cyclohexylethyl)-5-(3,5-di-tert-butylphenyl)-2-methyl-1H-pyrrole-3-carboxylate (1f)

A suspension of compound 1e (1.71 g, 5 mmol), $Cs_2CO_3$ (3.25 g 10 mmol), 2-(3,5-di-tert-butylphenyl)-4,4,5,5-tetramethyl-1,3,2-dioxaborolane (2.37 g, 7.5 mmol), Pd(dppf)$Cl_2$ (30 mg) in 1,4-dioxane/$H_2O$ (10:1, 50 mL) was heated overnight under $N_2$ at 90° C. After cooling, the mixture was concentrated and extracted with EA. The organic layer was washed with brine, dried over magnesium sulfate, filtered, concentrated and purified by CC (EA/PE=1/50) to give compound 1f (903 mg, 40%).

Step 7: 1-(1-Cyclohexylethyl)-5-(3,5-di-tert-butylphenyl)-2-methyl-1H-pyrrole-3-carboxylic acid (1g)

To a solution of compound 1f (902 mg, 2 mmol) in EtOH (20 mL) was added 5M KOH (10 mL). The mixture was refluxed overnight, the solvent was removed under reduced pressure and the residue was adjusted to pH<2 with 4M HCl. The mixture was extracted with EA three times and the combined organic layer was washed with brine and dried over $Na_2SO_4$. After filtration, the filtrate was evaporated and purified by prep. HPLC to give pure product 1g as a colorless solid.

Step 8: 1-(1-Cyclohexylethyl)-5-(3,5-di-tert-butylphenyl)-2-methyl-N-(oxetan-3-yl)-1H-pyrrole-3-carboxamide (1)

To a solution of compound 1g (85 mg, 0.2 mmol) in DMF (5 mL) was added HATU (152 mg, 0.4 mmol) and DIPEA (129 mg, 1 mmol). The mixture was stirred for 60 min and then oxetan-3-amine (110 mg, 1.5 mmol) was added to the mixture. The mixture was stirred overnight and quenched with ice water and extracted with EA. The organic layer was separated washed with brine and dried over $Na_2SO_4$. After filtration, the filtrate was evaporated and purified by prep. HPLC to give compound 1 (40 mg, 42%) as a colorless solid. $^1$H-NMR (500 MHz, DMSO-$d_6$) δ: 0.63 (m, 2H), 1.01 (m, 4H), 1.13-1.31 (m, 20H), 1.47 (m, 6H), 2.57 (s, 3H), 3.86 (m, 1H), 4.52 (m, 2H), 4.70 (m, 2H), 4.95 (m, 1H), 6.50 (s, 1H), 7.09 (s, 2H), 7.39 (s, 1H), 8.19 (d, 1H). MS: 479.4 (M+1).

Example 1/1 to 1/132

The following Examples were prepared similar as in Example 1:

| # | Structure | Analytical data |
|---|---|---|
| 1/1 | 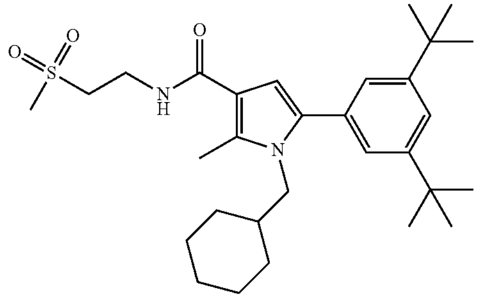 [SMILES: Cc1c(C(=O)NCCS(C)(=O)=O)cc(-c2cc(C(C)(C)C)cc(C(C)(C)C)c2)n1CC1CCCCC1] | $^1$H-NMR (400 MHz, DMSO-$d_6$) δ: 7.88 (t, J = 5.6 Hz, 1H), 7.36 (s, 1H), 7.15 (d, J = 1.6 Hz, 1H), 6.46 (s, 1H), 3.77 (d, J = 7.2 Hz, 2H), 3.60-3.55 (m, 2H), 3.31 (t, J = 7.0 Hz, 2H), 3.01 (s, 3H), 2.53 (s, 3H), 1.46-1.43 (m, 3H), 1.31-1.21 (m, 21H), 0.93-0.88 (m, 3H), 0.68-0.62 (m, 2H). MS: 515.1 (M + 1). |
| 1/2 | 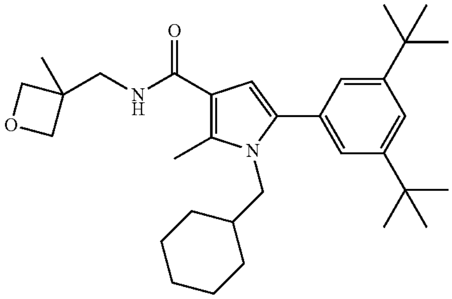 [SMILES: Cc1c(C(=O)NCC2(C)COC2)cc(-c2cc(C(C)(C)C)cc(C(C)(C)C)c2)n1CC1CCCCC1] | $^1$H-NMR (400 MHz, DMSO-$d_6$) δ: 7.80 (t, J = 6.0 Hz, 1H), 7.36 (t, J = 1.8 Hz, 1H), 7.16 (d, J = 1.6 Hz, 2H), 6.53 (s, 1H), 4.47 (d, J = 5.6 Hz, 2H), 4.15 (d, J = 5.6 Hz, 2H), 3.76 (d, J = 7.2 Hz, 2H), 3.34 (d, J = 6.0 Hz, 2H), 2.52 (s, 3H), 1.46-1.44 (m, 3H), 1.34-1.23 (m, 24H), 0.95-0.89 (m, 3H), 0.66-0.60 (m, 2H). MS: 493.4 (M + 1). |
| 1/3 | 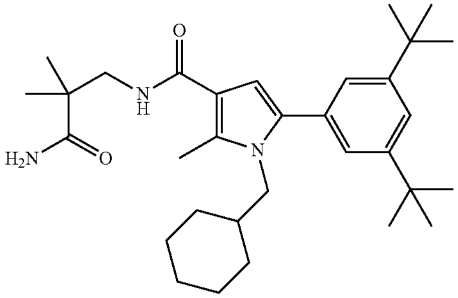 [SMILES: Cc1c(C(=O)NCC(C)(C)C(N)=O)cc(-c2cc(C(C)(C)C)cc(C(C)(C)C)c2)n1CC1CCCCC1] | $^1$H-NMR (400 MHz, DMSO-$d_6$) δ: 7.36-7.31 (m, 2H), 7.20 (s, 1H), 7.15 (d, J = 1.6 Hz, 2H), 6.84 (s, 1H), 6.42 (s, 1H), 3.75 (d, J = 7.2 Hz, 2H), 3.29 (s, 2H), 2.51 (s, 3H), 1.46-1.43 (m, 3H), 1.32-1.22 (m, 21H), 1.07 (s, 6H), 0.95-0.89 (m, 3H), 0.67-0.60 (m, 2H). MS: 508.2 (M + 1). |
| 1/4 | 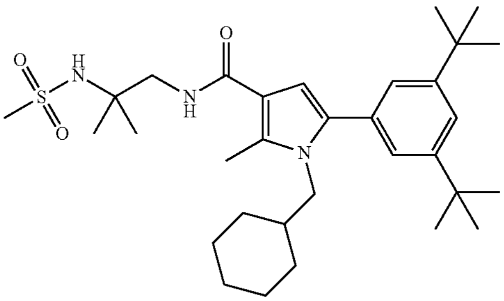 [SMILES: Cc1c(C(=O)NCC(C)(C)NS(C)(=O)=O)cc(-c2cc(C(C)(C)C)cc(C(C)(C)C)c2)n1CC1CCCCC1] | $^1$H-NMR (400 MHz, DMSO-$d_6$) δ: 7.65 (t, J = 6.2 Hz, 1H), 7.36 (s, 1H), 7.16 (d, J = 1.6 Hz, 2H), 7.04 (s, 1H), 6.50 (s, 1H), 3.76 (d, J = 7.2 Hz, 2H), 3.28 (d, J = 6.4 Hz, 2H), 2.95 (s, 3H), 2.52 (s, 3H), 1.46-1.43 (m, 3H), 1.31-1.15 (m, 27H), 0.95-0.87 (m, 3H), 0.68-0.59 (m, 2H), MS: 558.1 (M + 1). |

-continued

| # | Structure | Analytical data |
|---|---|---|
| 1/5 | 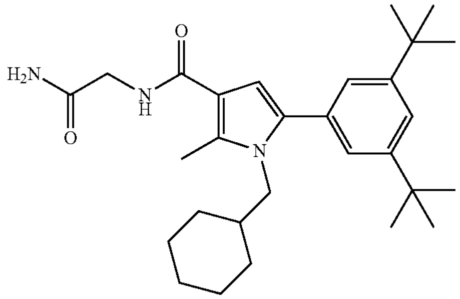 [SMILES: Cc1c(C(=O)NCC(N)=O)cc(-c2cc(C(C)(C)C)cc(C(C)(C)C)c2)n1CC1CCCCC1] | $^1$H-NMR (400 MHz, DMSO-$d_6$) δ: 7.81 (t, J = 5.8 Hz, 1H), 7.36 (s, 1H), 7.22 (s, 1H), 7.17 (d, J = 1.6 Hz, 1H), 6.96 (s, 1H), 6.53 (s, 1H), 3.78 (d, J = 7.2 Hz, 2H), 3.72 (d, J = 5.6 Hz, 2H), 2.53 (s, 3H), 1.46-1.43 (m, 3H), 1.31-1.15 (m, 21H), 0.93-0.86 (m, 3H), 0.69-0.61 (m, 2H). MS: 466.1 (M + 1). |
| 1/6 | 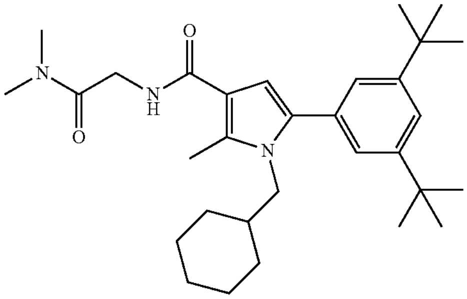 [SMILES: Cc1c(C(=O)NCC(=O)N(C)C)cc(-c2cc(C(C)(C)C)cc(C(C)(C)C)c2)n1CC1CCCCC1] | $^1$H-NMR (400 MHz, DMSO-$d_6$) δ: 7.65 (t, 1H), 7.36 (s, 1H), 7.17 (d, J = 1.6 Hz, 2H), 6.51 (s, 1H), 3.99 (d, J = 5.2 Hz, 2H), 3.77 (d, J = 7.2 Hz, 2H), 3.00 (s, 3H), 2.84 (s, 3H), 2.52 (s, 3H), 1.46-1.43 (m, 3H), 1.35-1.23 (m, 21H), 0.94-0.85 (m, 3H), 0.67-0.61 (m, 2H). MS: 494.2 (M + 1). |
| 1/7 | 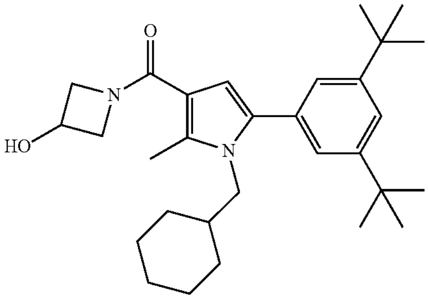 [SMILES: Cc1c(C(=O)N2CC(O)C2)cc(-c2cc(C(C)(C)C)cc(C(C)(C)C)c2)n1CC1CCCCC1] | $^1$H-NMR (400 MHz, DMSO-$d_6$) δ: 7.35 (t, J = 2.0 Hz, 1H), 7.15 (d, J = 2.0 Hz, 2H), 6.18 (s, 1H), 4.47-3.68 (m, 8H), 2.46 (s, 3H), 1.46-1.43 (m, 3H), 1.31-1.21 (m, 21H), 0.98-0.85 (m, 3H), 0.68-0.60 (m, 2H). MS: 465.1 (M + 1). |
| 1/8 | 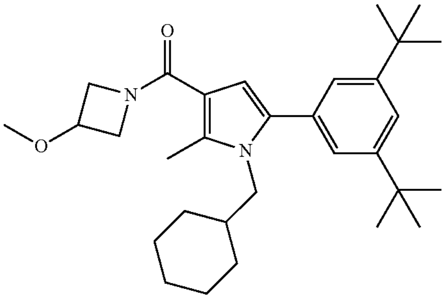 [SMILES: COC1CN(C(=O)c2cc(-c3cc(C(C)(C)C)cc(C(C)(C)C)c3)n(CC3CCCCC3)c2C)C1] | $^1$H-NMR (400 MHz, DMSO-$d_6$) δ: 7.36 (t, J = 1.6 Hz, 1H), 7.15 (d, J = 1.6 Hz, 2H), 6.21 (s, 1H), 4.43-3.69 (m, 7H), 3.21 (s, 3H), 2.47 (s, 3H), 1.46-1.35 (m, 3H), 1.31-1.15 (m, 21H), 1.00-0.85 (m, 3H), 0.68-0.60 (m, 2H). MS: 479.1 (M + 1). |
| 1/9 | 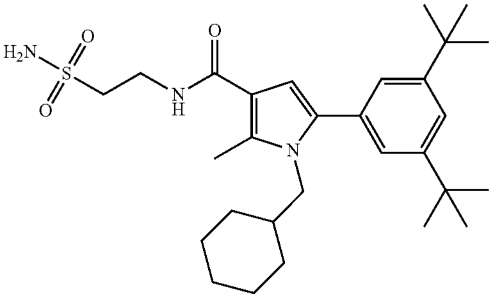 [SMILES: Cc1c(C(=O)NCCS(N)(=O)=O)cc(-c2cc(C(C)(C)C)cc(C(C)(C)C)c2)n1CC1CCCCC1] | $^1$H-NMR (400 MHz, DMSO-$d_6$) δ: 7.80 (t, J = 5.8 Hz, 1H), 7.36 (s, 1H), 7.15 (d, J = 1.6 Hz, 2H), 6.92 (s, 2H), 6.44 (s, 1H), 3.76 (d, J = 7.2 Hz, 2H), 3.56 (q, 2H), 3.18 (t, J = 7.4 Hz, 2H), 2.53 (s, 3H), 1.46-1.43 (m, 3H), 1.31-1.21 (m, 21H), 0.94-0.88 (m, 3H), 0.68-0.60 (m, 2H). MS: 516.1 (M + 1). |

-continued

| # | Structure | Analytical data |
|---|---|---|
| 1/10 | 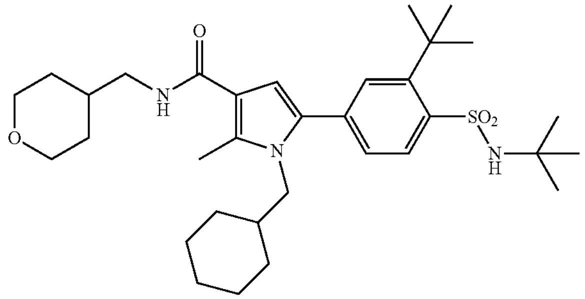 [SMILES: Cc1c(C(=O)NCC2CCOCC2)cc(-c2ccc(S(=O)(=O)NC(C)(C)C)c(C(C)(C)C)c2)n1CC1CCCCC1] | $^1$H-NMR (400 MHz, $CDCl_3$) δ: 8.18 (d, J = 8.4 Hz, 1H), 7.59 (s, 1H), 7.26 (d, J = 8.4 Hz, 1H), 6.26 (s, 1H), 5.89 (m, 1H), 4.56 (s, 1H), 4.00 (m, 2H), 3.77 (d, J = 7.2 Hz, 2H), 3.38 (m, 2H), 3.30 (m, 2H), 2.63 (s, 3H), 1.86 (m, 1H), 1.66 (m, 11H), 1.55-1.51 (m, 3H), 1.42-1.24 (m, 14H), 1.01-0.92 (m, 3H), 0.60 (m, 2H). MS: 586.1 $(M + 1)^+$. |
| 1/11 | 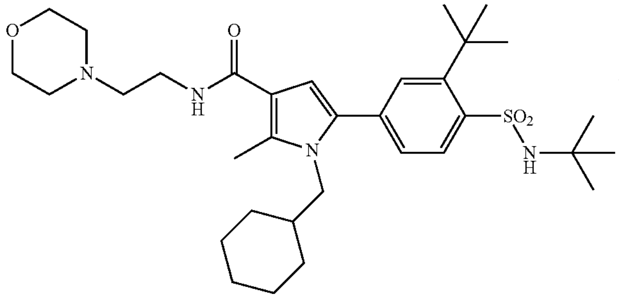 [SMILES: Cc1c(C(=O)NCCN2CCOCC2)cc(-c2ccc(S(=O)(=O)NC(C)(C)C)c(C(C)(C)C)c2)n1CC1CCCCC1] | $^1$H-NMR (400 MHz, DMSO-$d_6$) δ: 8.12 (d, J = 8.4 Hz, 1H), 7.74 (s, 1H), 7.63 (m, 1H), 7.52 (s, 1H), 7.40 (m, 1H), 6.62 (s, 1H), 3.84 (m, 2H), 3.56 (m, 4H), 3.27 (m, 2H), 2.52 (s, 3H), 2.38 (m, 6H), 1.54 (s, 9H), 1.43 (m, 3H), 1.22-1.12 (m, 12H), 0.99-0.82 (m, 3H), 0.59 (m, 2H). MS: 601.1 $(M + 1)^+$. |
| 1/12 | 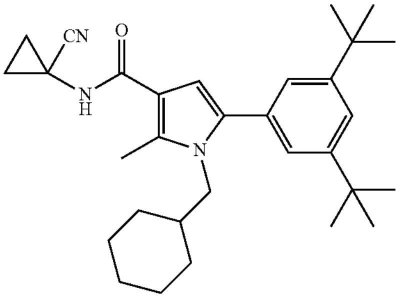 [SMILES: Cc1c(C(=O)NC2(C#N)CC2)cc(-c2cc(C(C)(C)C)cc(C(C)(C)C)c2)n1CC1CCCCC1] | $^1$H-NMR (400 MHz, DMSO-$d_6$) δ: 8.45 (s, 1H), 7.36 (t, J = 1.6 Hz, 1H), 7.15 (d, J = 1.6 Hz, 2H), 6.48 (s, 1H), 3.77 (d, J = 6.8 Hz, 2H), 2.54 (s, 3H), 1.50-1.43 (m, 5H), 1.30-1.14 (m, 22H), 0.94-0.86 (m, 3H), 0.67-0.60 (m, 2H). MS: 474.1 (M + 1). |
| 1/13 | 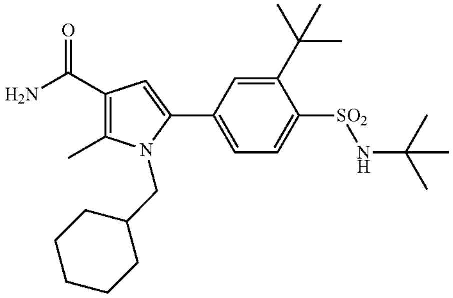 [SMILES: Cc1c(C(N)=O)cc(-c2ccc(S(=O)(=O)NC(C)(C)C)c(C(C)(C)C)c2)n1CC1CCCCC1] | $^1$H-NMR (400 MHz, $CDCl_3$) δ: 8.21 (d, J = 8.4 Hz, 1H), 7.59 (s, 1H), 7.27 (d, J = 8.4 Hz, 1H), 6.31 (s, 1H), 5.52 (br s, 2H), 4.67 (s, 1H), 3.80 (d, J = 6.8 Hz, 2H), 2.63 (s, 3H), 1.62 (s, 9H), 1.53 (m, 3H), 1.35-1.29 (m, 12H), 1.02-0.95 (m, 3H), 0.61 (m, 2H). MS Found: 488.5 $(M + 1)^+$. |
| 1/14 | 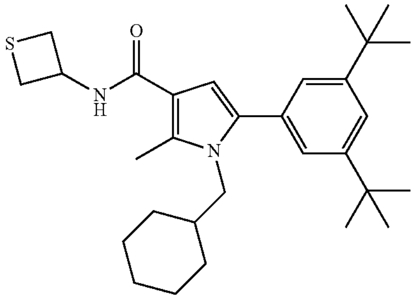 [SMILES: Cc1c(C(=O)NC2CSC2)cc(-c2cc(C(C)(C)C)cc(C(C)(C)C)c2)n1CC1CCCCC1] | $^1$H-NMR (400 MHz, DMSO-$d_6$) δ: 8.19 (d, J = 8.0 Hz, 1H), 7.36 (s, 1H), 7.16 (d, J = 1.6 Hz, 2H), 6.53 (s, 1H), 5.22-5.16 (m, 1H), 3.76 (d, J = 6.8 Hz, 2H), 3.50 (t, J = 9.0 Hz, 2H), 3.19 (t, J = 10.4 Hz, 2H), 2.43 (s, 3H), 1.45-1.40 (m, 3H), 1.31-1.15 (m, 21H), 0.97-0.87 (m, 3H), 0.67-0.58 (m, 2H). MS: 481.1 (M + 1). |

-continued

| # | Structure | Analytical data |
|---|---|---|
| 1/15 | 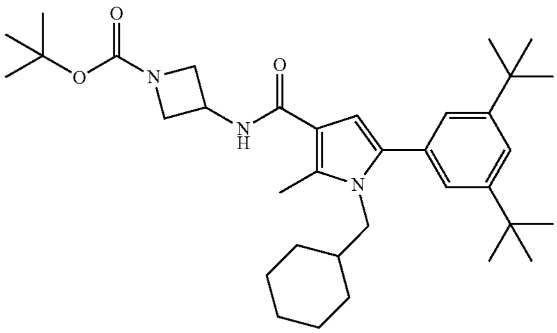 [SMILES: Cc1c(C(=O)NC2CN(C(=O)OC(C)(C)C)C2)cc(-c2cc(C(C)(C)C)cc(C(C)(C)C)c2)n1CC1CCCCC1] | $^1$H-NMR (400 MHz, DMSO-$d_6$) δ: 8.12 (d, J = 7.2 Hz, 1H), 7.36 (t, J = 1.6 Hz, 1H), 7.16 (d, J = 1.6 Hz, 2H), 6.56 (s, 1H), 4.63-4.58 (m, 1H), 4.06-4.02 (m, 2H), 3.81-3.76 (m, 4H), 2.51 (s, 3H), 1.45-1.43 (m, 3H), 1.38 (s, 9H), 1.31 (s, 18H), 1.27-1.15 (m, 3H), 0.92-0.84 (m, 3H), 0.67-0.59 (m, 2H). MS: 564.2 (M + 1). |
| 1/16 | 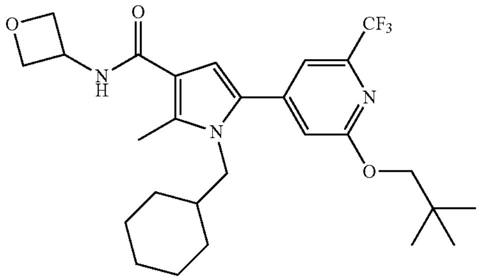 [SMILES: Cc1c(C(=O)NC2COC2)cc(-c2cc(OCC(C)(C)C)nc(C(F)(F)F)c2)n1CC1CCCCC1] | $^1$H-NMR (300 MHz, $CDCl_3$) δ: 0.66-0.72 (m, 2H), 0.97-1.04 (m, 9H), 1.25-1.43 (m, 4H), 1.58-1.63 (m, 4H), 2.60 (s, 3H), 3.85 (d, J = 7.2 Hz, 2H), 4.07 (s, 2H), 4.57 (t, J = 6.6 Hz, 2H), 4.98 (t, J = 7.2 Hz, 2H), 5.15-5.23 (m, 1H), 6.23-6.25 (m, 1H), 6.45 (s, 1H), 6.86 (s, 1H), 7.21 (s, 1H). MS: 508 $(M + 1)^+$. |
| 1/17 | 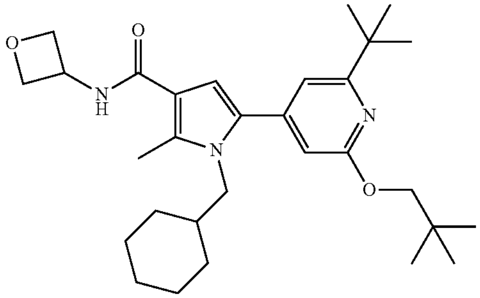 | $^1$H-NMR (300 MHz, $CDCl_3$) δ: 0.66-0.72 (m, 2H), 0.98-1.06 (m, 3H), 1.23-1.40 (m, 12H), 1.51-1.58 (m, 3H), 2.59 (s, 3H), 3.83 (d, J = 7.2 Hz, 2H), 4.57 (t, J = 6.6 Hz, 2H), 4.82 (q, J = 8.7 Hz, 2H), 4.99 (t, J = 7.2 Hz, 2H), 5.15-5.23 (m, 1H), 6.19 (d, J = 7.2 Hz, 2H), 6.35 (s, 1H), 6.62 (d, J = 0.9 Hz, 1H), 6.93 (d, J = 0.9 Hz, 1H). MS: 508 $(M + 1)^+$. |
| 1/18 | 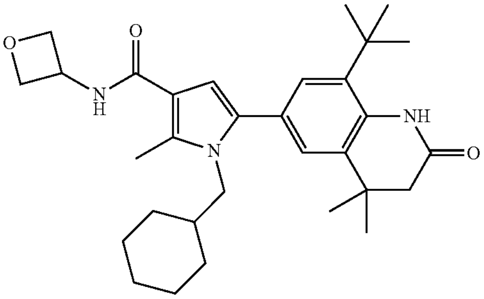 [SMILES: Cc1c(C(=O)NC2COC2)cc(-c2cc(C(C)(C)C)c3c(c2)C(C)(C)CC(=O)N3)n1CC1CCCCC1] | $^1$H-NMR (400 MHz, DMSO-$d_6$) δ: 8.23-8.20 m (2H), 7.18 (s, 1H), 7.17 (s, 1H), 6.57 (s, 1H), 4.97-4.92 (m, 1H), 4.71 (t, 2H), 4.54 (t, 2H), 3.75 (d, 2H), 2.42 (s, 3H), 1.48-1.46 (m, 3H), 1.41 (s, 9H), 1.36-1.24 (m, 9H), 0.97-0.92 (m, 3H), 0.73-0.64 (m, 2H). MS: 506.3 (M + 1). |
| 1/19 | 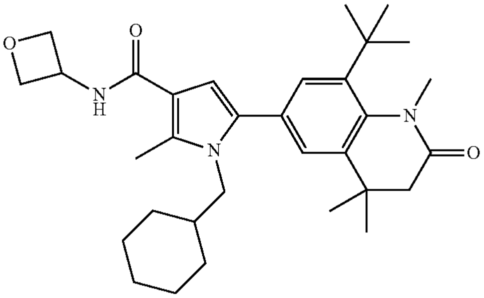 [SMILES: Cc1c(C(=O)NC2COC2)cc(-c2cc(C(C)(C)C)c3c(c2)C(C)(C)CC(=O)N3C)n1CC1CCCCC1] | $^1$H-NMR (400 MHz, $CDCl_3$) δ: 7.32 (d, 1H), 7.04 (d, 1H), 6.23 (s, 1H), 6.20 (d, J = 7.2 Hz, 2H), 5.23-5.20 (m, 1H), 5.00 (t, 2H), 4.57 (t, 2H), 3.74 (d, J = 6.8 Hz, 2H), 3.29 (s, 3H), 2.60 (s, 3H), 2.50 (br s, 2H), 1.56-1.54 (m, 3H), 1.45 (s, 9H), 1.42-1.18 (m, 9H), 1.02-1.00 (d, 3H), 0.69-0.65 (m, 2H). MS: 520.3 (M + 1). |

-continued
| # | Structure | Analytical data |
|---|---|---|
| 1/20 | 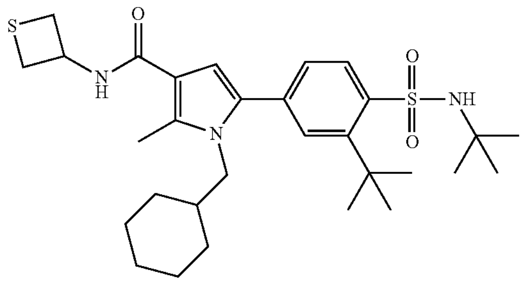 [SMILES: Cc1c(C(=O)NC2CSC2)cc(-c2ccc(S(=O)(=O)NC(C)(C)C)c(C(C)(C)C)c2)n1CC1CCCCC1] | n.d. |
| 1/21 | 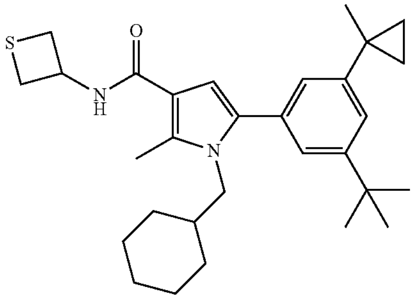 [SMILES: Cc1c(C(=O)NC2CSC2)cc(-c2cc(C(C)(C)C)cc(C3(C)CC3)c2)n1CC1CCCCC1] | n.d. |
| 1/22 | 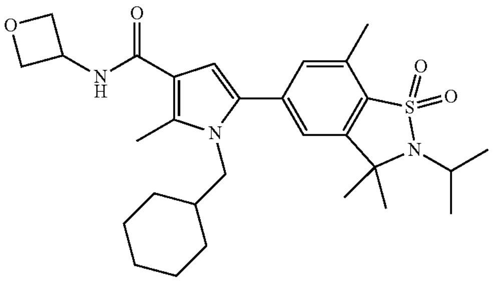 | $^1$H-NMR (300 MHz, DMSO-$d_6$) δ: 8.31 (d, J = 6.6 Hz, 1H), 7.58 (s, 1H), 7.46 (s, 1H), 6.78 (s, 1H), 4.98-4.92 (m, 1H), 4.73 (t, J = 6.8 Hz, 2H), 4.55 (t, J = 6.2 Hz, 2H), 3.94-3.84 (m, 3H), 3.58-3.51 (m, 1H), 2.53 (s, 3H), 1.54-1.44 (m, 15H), 1.31-1.20 (m, 9H), 0.95-0.88 (m, 3H), 0.70-0.62 (m, 2H). MS: 556.4 (M + 1). |
| 1/23 | 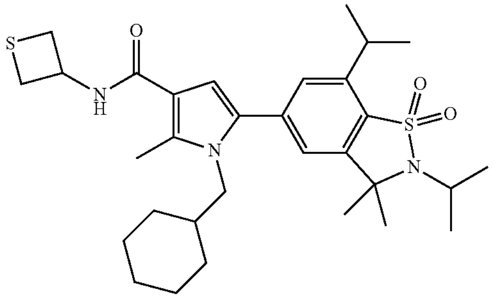 [SMILES: Cc1c(C(=O)NC2CSC2)cc(-c2cc(C(C)C)c3c(c2)C(C)(C)N(C(C)C)S3(=O)=O)n1CC1CCCCC1] | n.d. |
| 1/24 | 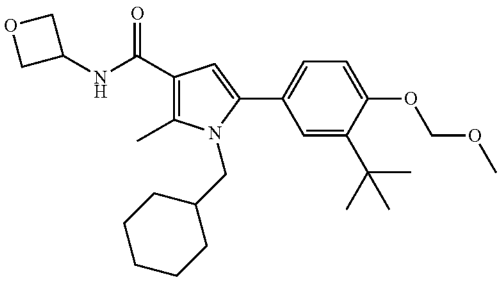 [SMILES: COCOc1ccc(-c2cc(C(=O)NC3COC3)c(C)n2CC2CCCCC2)cc1C(C)(C)C] | $^1$H-NMR (400 MHz, $CDCl_3$,) δ: 7.26 (s, 1H), 7.22 (d, 1H, J = 2.0 Hz), 7.10 (t, 1H, J = 2.0 Hz), 6.16 (s, 1H), 6.15 (s, 1H), 5.28 (s, 2H), 5.18-5.23 (m, 1H), 4.98 (t, 2H, J = 9.6 Hz), 4.57 (t, 2H, J = 8.8 Hz), 3.70 (d, 2H, J = 7.2 Hz), 3.54 (s, 3H), 2.60 (s, 3H), 1.55-1.51 (m, 3H), 1.45-1.31 (m, 12H), 1.03-0.97 (m, 3H), 0.68-0.64 (m, 2H). MS: 469 (M + 1). |

-continued

| # | Structure | Analytical data |
|---|---|---|
| 1/25 | 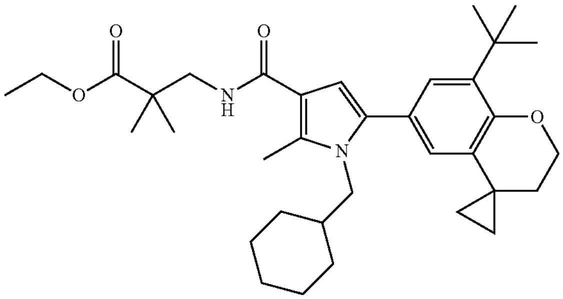 [SMILES: CCOC(=O)C(C)(C)CNC(=O)c1cc(-c2cc(C(C)(C)C)c3c(c2)C2(CCO3)CC2)n(CC2CCCCC2)c1C] | n.d. |
| 1/26 | 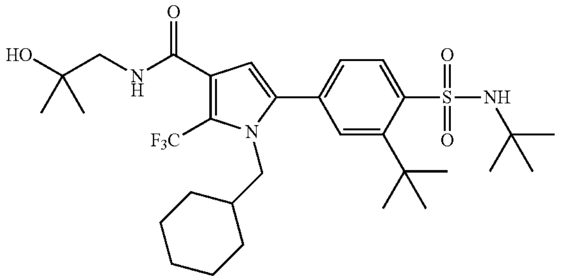 [SMILES: CC(C)(O)CNC(=O)c1cc(-c2ccc(S(=O)(=O)NC(C)(C)C)c(C(C)(C)C)c2)n(CC2CCCCC2)c1C(F)(F)F] | $^1$H-NMR (500 MHz, $CDCl_3$) δ: 8.14 (d, J = 8.5 Hz, 1H), 7.71 (d, J = 2.0 Hz, 1H), 7.36 (dd, J = 8.5, 2.0 Hz, 1H), 6.44 (s, 1H), 6.89 (s, 1H), 6.02 (t, J = 6.0 Hz, 1H), 4.53 (s, 1H), 3.86 (d, J = 7.5 Hz, 2H), 3.34 (d, J = 6.0 Hz, 2H), 1.71 (m, 6H), 1.61 (s, 9H), 1.31 (s, 9H), 1.26 (m, 3H), 1.17 (s, 6H), 0.97 (m, 2H). MS: 614.2 (M + 1). |
| 1/27 | 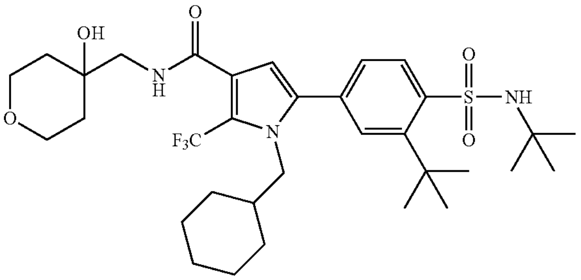 [SMILES: CC(C)(C)NS(=O)(=O)c1ccc(-c2cc(C(=O)NCC3(O)CCOCC3)c(C(F)(F)F)n2CC2CCCCC2)cc1C(C)(C)C] | $^1$H-NMR (500 MHz, $CDCl_3$) δ: 8.13 (d, J = 8.0 Hz, 1H), 7.68 (d, J = 2.0 Hz, 1H), 7.35 (dd, J = 8.0, 2.0 Hz, 1H), 6.89 (s, 1H), 6.89 (s, 1H), 5.97 (t, J = 6.0 Hz, 1H), 4.46 (s, 1H), 3.87 (d, J = 7.5 Hz, 2H), 3.74 (dd, J = 7.4, 3.0 Hz, 4H), 3.38 (d, J = 6.0 Hz, 2H), 1.78 (m, 5H), 1.60 (s, 9H), 1.57 (m, 4H), 1.47 (m, 2H), 1.33 (s, 9H), 1.29 (m, 4H), 1.00 (m, 2H). MS: 656.2 (M + 1). |
| 1/28 | 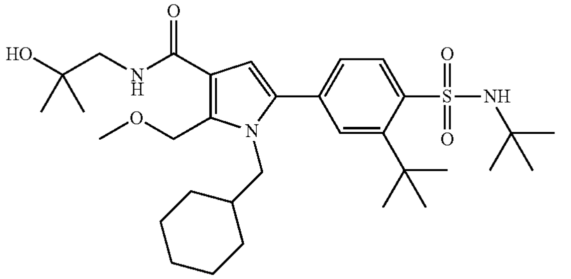 | $^1$H-NMR (500 MHz, $CDCl_3$) δ: 8.21 (d, J = 8.0 Hz, 1H), 7.63 (d, J = 2.0 Hz, 1H), 7.29 (dd, J = 8.0, 2.0 Hz, 1H), 6.88 (s, 1H), 6.49 (s, 1H), 4.80 (s, 2H), 4.63 (s, 1H), 3.92 (d, J = 6.0 Hz, 2H), 3.46 (m, 5H), 1.62 (s, 9H), 1.56 (m, 3H), 1.29 (m, 21H), 0.98 (m, 3H), 0.65 (m, 2H). MS: 558.3 $(M - OCH_3)^+$. |
| 1/29 | 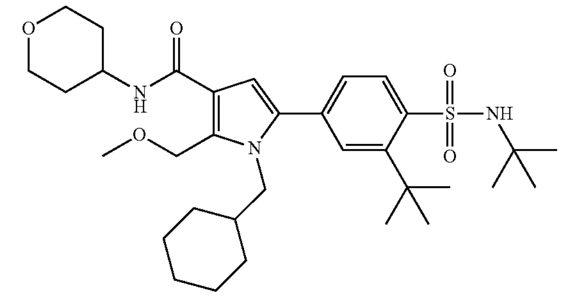 | $^1$H-NMR (500 MHz, $CDCl_3$) δ: 8.21 (d, J = 8.0 Hz, 1H), 7.62 (d, J = 2.0 Hz, 1H), 7.29 (d, 2.0 Hz, 1H), 6.53 (d, J = 8.0, 1H), 6.49 (s, 1H), 4.72 (s, 3H), 4.19 (m, 1H), 4.00 (m, 2H), 3.90 (d, J = 6.0 Hz, 2H), 3.57 (t, J = 6.0 Hz, 2H), 2.03 (d, J = 12.5 Hz, 2H), 1.75 (s, 2H), 1.62 (s, 9H), 1.58 (m, 5H), 1.30 (m, 13H), 0.99 (m, 3H), 0.64 (m, 2H). MS: 570.3 $(M - OCH_3)^+$. |

-continued

| # | Structure | Analytical data |
|---|---|---|
| 1/30 | 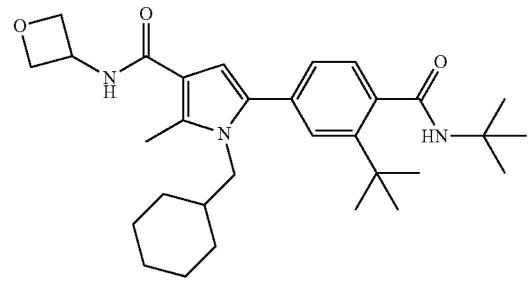 [SMILES: Cc1c(C(=O)NC2COC2)cc(-c2ccc(C(=O)NC(C)(C)C)c(C(C)(C)C)c2)n1CC1CCCCC1] | $^1$H-NMR ($CDCl_3$, 300 MHz) δ: 7.40 (d, 1H, J = 1.5 Hz), 7.25 (d, 1H, J = 7.5 Hz), 7.13 (dd, 1H, J = 7.5 Hz, 1.5 Hz), 6.19-6.16 (m, 2H), 5.57 (s, 1H), 5.22-5.17 (m, 1H), 4.99 (t, 2H, J = 6.6 Hz), 4.58 (t, 2H, J = 6.6 Hz), 3.75 (d, 2H, J = 7.2 Hz), 2.59 (s, 3H), 1.55-1.51 (m, 3H), 1.50-1.47 (m, 18H), 1.43-1.33 (m, 3H), 1.02-0.93 (m, 12H), 0.68-0.64 (m, 2H). MS: 508 (M + 1) |
| 1/31 | 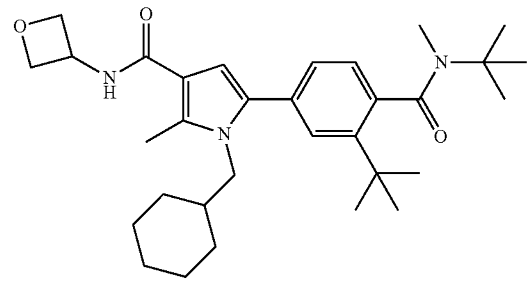 [SMILES: Cc1c(C(=O)NC2COC2)cc(-c2ccc(C(=O)N(C)C(C)(C)C)c(C(C)(C)C)c2)n1CC1CCCCC1] | $^1$H-NMR ($CDCl_3$, 400 MHz) δ: 7.40 (d, 1H, J = 2.4 Hz), 7.14 (dd, 1H, J = 10.0 Hz, 2.0 Hz), 7.04 (1H, d, J = 10.0 Hz), 6.22 (s, 1H), 6.20-6.18 (m, 1H), 5.23-5.19 (m, 1H), 4.99 (t, 2H, J = 6.8 Hz), 4.57 (t, 2H, J = 6.4 Hz), 3.75 (d, 2H, J = 6.0 Hz), 2.76 (s, 3H), 2.59 (s, 3H), 1.57-1.52 (m, 12 H), 1.41 (s, 9H), 1.36-1.25 (m, 3H), 1.03-0.97 (m, 3H), 0.68-0.64 (m, 2H). MS: 522 (M + 1). |
| 1/32 | 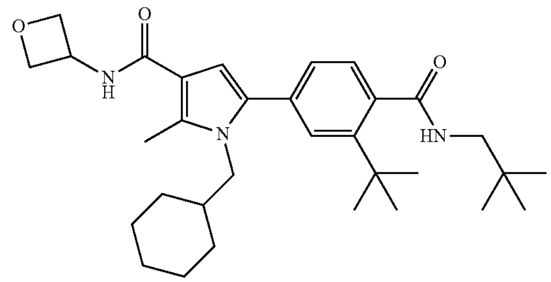 [SMILES: Cc1c(C(=O)NC2COC2)cc(-c2ccc(C(=O)NCC(C)(C)C)c(C(C)(C)C)c2)n1CC1CCCCC1] | $^1$H-NMR ($CDCl_3$, 400 MHz) δ: 7.43 (d, 1H, J = 1.2 Hz), 7.29 (d, 1H, J = 8.0 Hz), 7.16 (dd, 1H, J = 7.6 Hz, 1.6 Hz), 6.21-6.19 (m, 2H), 5.82-5.79 (m, 1H), 5.20-5.19 (m, 1H), 4.99 (t, 2H, J = 6.8 Hz), 4.58 (t, 2H, J = 6.4 Hz), 3.76 (d, 2H, J = 7.2 Hz), 3.28 (d, 2H, J = 6.4 Hz), 2.60 (s, 3H), 1.59-1.56 (m, 3H), 1.44 (s, 9H), 1.42-1.33 (m, 3H), 1.02-0.93 (m, 12H), 0.68-0.64 (m, 2H). MS: 522 (M + 1) |
| 1/33 | 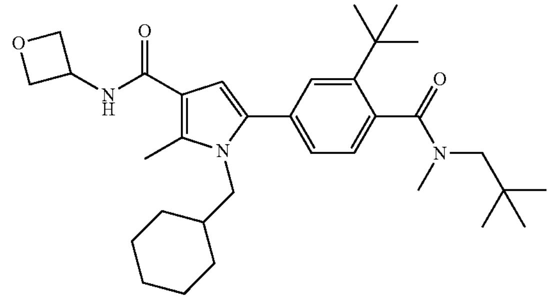 [SMILES: Cc1c(C(=O)NC2COC2)cc(-c2ccc(C(=O)N(C)CC(C)(C)C)c(C(C)(C)C)c2)n1CC1CCCCC1] | $^1$H-NMR ($CDCl_3$, 400 MHz) δ: 7.43 (d, 1H, J = 1.6 Hz), 7.17-7.10 (m, 2H), 6.24-6.17 (m, 2H), 5.24-5.19 (m, 1H), 4.99 (t, 2H, J = 6.8 Hz), 4.57 (t, 2H, J = 6.4 Hz), 4.20 (d, 1H, J = 14.0 Hz), 3.75 (d, 2H, J = 6.0 Hz), 3.14 (s, 3H), 2.63 (d, 1H, J = 14.4 Hz), 2.60 (s, 3H), 1.57-1.52 (m, 3H), 1.43-1.31 (m, 12H), 1.08 (s, 9H), 1.03-0.97 (m, 3H), 0.68-0.64 (m, 2H). MS: 536 (M + 1). |
| 1/34 | 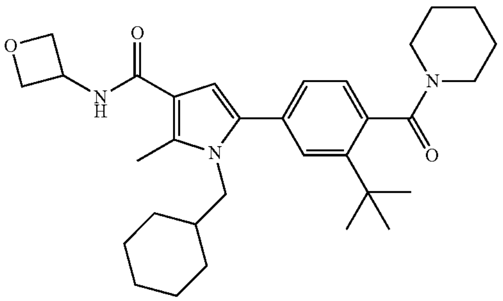 [SMILES: Cc1c(C(=O)NC2COC2)cc(-c2ccc(C(=O)N3CCCCC3)c(C(C)(C)C)c2)n1CC1CCCCC1] | $^1$H-NMR ($CDCl_3$, 400 MHz) δ: 7.43 (s, 1H), 7.16 (d, 1H, J = 8.0 Hz), 7.09 (1H, d, J = 7.6 Hz), 6.24 (s, 1H), 6.19 (d, 1H, J = 7.6 Hz), 5.23-5.19 (m, 1H), 4.99 (t, 2H, J = 6.8 Hz), 4.57 (t, 2H, J = 6.4 Hz), 4.12 (m, 1H), 3.75 (d, 2H, J = 6.0 Hz), 3.38-3.35 (m, 1H), 3.27-3.23 (m, 1H), 3.07-3.05 (m, 1H), 2.60 (s, 3H), 1.76-1.67 (m, 4H), 1.63-1.45 (m, 5H), 1.41 (s, 9H), 1.36-1.25 (m, 3H), 1.03-0.97 (m, 3H), 0.68-0.64 (m, 2H). MS: 520 (M + 1). |

-continued

| # | Structure | Analytical data |
|---|---|---|
| 1/35 | 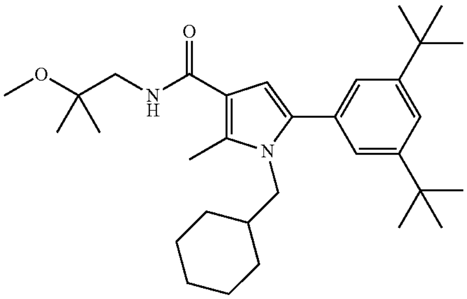 [SMILES: COC(C)(C)CNC(=O)c1cc(-c2cc(C(C)(C)C)cc(C(C)(C)C)c2)n(CC2CCCCC2)c1C] | $^1$H-NMR (400 MHz, DMSO-$d_6$) δ: 7.35 (s, 1H), 7.32-7.28 (t, J = 6.2 Hz, 1H), 7.16-7.15 (d, J = 1.6 Hz, 2H), 6.53 (s, 1H), 3.77-3.74 (d, J = 7.2 Hz, 2H), 3.25-3.23 (d, J = 6.0 Hz, 2H), 3.13 (s, 3H), 2.52 (s, 3H), 1.46-1.43 (d, J = 10.4 Hz, 3H), 1.31-1.22 (m, 21H), 1.08 (s, 6H), 0.99-0.86 (m, 3H), 0.68-0.60 (m, 2H). MS: 495.2 (M + 1). |
| 1/36 | 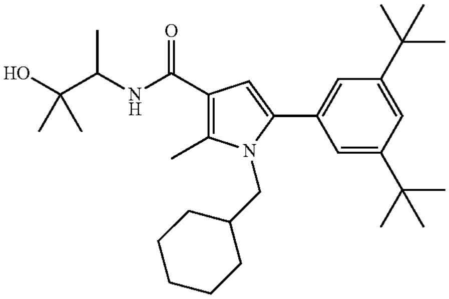 [SMILES: Cc1c(C(=O)NC(C)C(C)(C)O)cc(-c2cc(C(C)(C)C)cc(C(C)(C)C)c2)n1CC1CCCCC1] | $^1$H-NMR (400 MHz, $CDCl_3$) δ: 7.36-7.34 (t, J = 1.6 Hz, 1H), 7.15-7.14 (d, J = 2.0 Hz, 2H), 7.01-6.98 (d, J = 8.8 Hz, 1H), 6.50 (s, 1H), 4.37 (s, 1H), 3.93-3.89 (m, 1H), 3.76-3.73 (d, J = 7.2 Hz, 2H), 2.51 (s, 3H), 1.46-1.44 (t, J = 4.6 Hz, 3H), 1.31-1.23 (m, 21H), 1.09-1.07 (t, J = 3.8 Hz, 3H), 0.95-0.89 (m, 3H), 0.66-0.60 (m, 2H). MS: 495.2 (M + 1). |
| 1/37 | 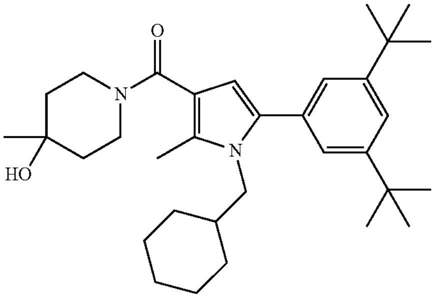 [SMILES: Cc1c(C(=O)N2CCC(C)(O)CC2)cc(-c2cc(C(C)(C)C)cc(C(C)(C)C)c2)n1CC1CCCCC1] | $^1$H-NMR (400 MHz, DMSO-$d_6$) δ: 7.34-7.33 (d, J = 1.6 Hz, 1H), 7.16-7.15 (d, J = 2.0 Hz, 2H), 6.04 (s, 1H), 3.77-3.29 (m, 7H), 2.26 (d, 3H), 1.46-1.40 (m, 7H), 1.30-1.22 (m, 18H), 1.14 (s, 3H), 0.94-0.88 (m, 3H), 0.66-0.63 (m, 2H). MS: 507.2 (M + 1). |
| 1/38 | 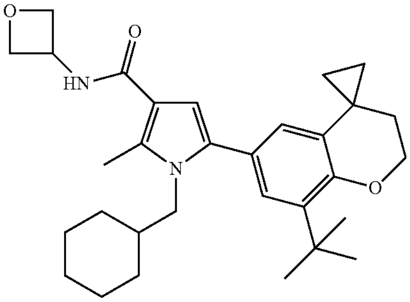 | $^1$H-NMR ($CDCl_3$, 400 MHz) δ: 0.70 (2H, m), 0.86 (2H, m), 1.02 (5H, m), 1.39 (12H, s), 1.57 (3H, m), 1.91 (2H, t, J = 4.8 Hz), 2.57 (3H, s), 3.64 (2H, d, J = 7.2 Hz), 4.34 (2H, t, J = 4.8 Hz), 4.57 (2H, t, J = 6.4 Hz), 4.98 (2H, t, J = 7.2 Hz), 5.21-5.24 (1H, m), 6.11 (1H, s), 6.15 (1H, d, J = 7.2 Hz), 6.43 (1H, d, J = 2.0 Hz), 6.97 (1H, d, J = 1.6 Hz). MS: 491 (M + 1). |
| 1/39 | 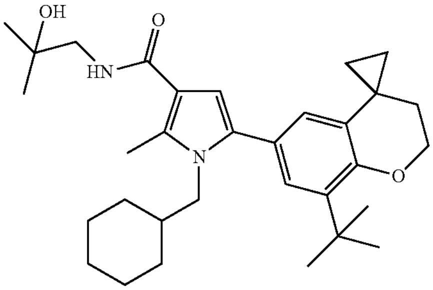 [SMILES: Cc1c(C(=O)NCC(C)(C)O)cc(-c2cc(C(C)(C)C)c3c(c2)C2(CCO3)CC2)n1CC1CCCCC1] | $^1$H-NMR ($CDCl_3$, 400 MHz) δ: 0.70 (2H, m), 0.85 (2H, m), 1.01 (5H, m), 1.23 (7H, s), 1.38 (12H, s), 1.56 (3H, m), 1.90 (2H, t, J = 5.2 Hz), 2.59 (3H, s), 3.28 (1H, s), 3.38 (2H, d, J = 6.0 Hz), 3.64 (2H, d, J = 7.2 Hz), 4.33 (2H, t, J = 5.2 Hz), 6.11-6.13 (2H, m), 6.43 (1H, d, J = 1.6 Hz), 6.97 (1H, d, J = 1.6 Hz). MS: 507 (M + 1). |

-continued

| # | Structure | Analytical data |
|---|---|---|
| 1/40 | 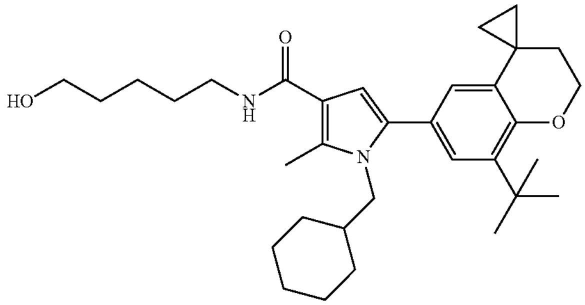 [SMILES: Cc1c(C(=O)NCCCCCO)cc(-c2cc(C(C)(C)C)c3c(c2)C2(CCO3)CC2)n1CC1CCCCC1] | $^1$H-NMR ($CDCl_3$, 400 MHz) δ: 0.64-0.72 (2H, m), 0.83-0.88 (2H, m), 0.98-1.03 (5H, m), 1.35-1.49 (12H, s), 1.57-1.65 (12H, m), 1.90 (2H, t, J = 5.2 Hz), 2.59 (3H, s), 3.39 (2H, d, J = 6.8 Hz), 3.63 (4H, d, J = 7.2 Hz), 4.33 (2H, t, J = 4.8 Hz), 5.75 (1H, t, J = 6.0 Hz), 6.06 (1H, s), 6.43 (1H, d, J = 2.0 Hz), 6.97 (1H, d, J = 2.0 Hz). MS: 521 (M + 1). |
| 1/41 | 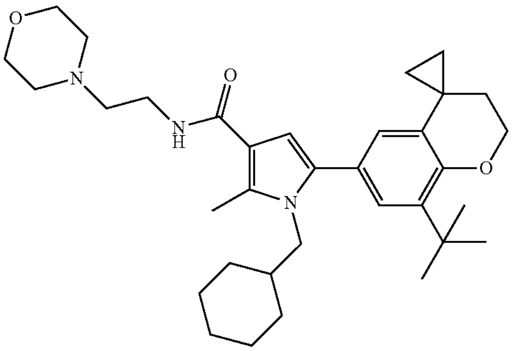 [SMILES: Cc1c(C(=O)NCCN2CCOCC2)cc(-c2cc(C(C)(C)C)c3c(c2)C2(CCO3)CC2)n1CC1CCCCC1] | $^1$H-NMR ($CDCl_3$, 400 MHz) δ: 0.68-0.70 (2H, m), 0.84-0.87 (2H, m), 1.00-1.03 (5H, m), 1.39 (12H, s), 1.59 (9H, s), 1.90 (2H, t, J = 5.6 Hz), 2.48 (2H, d, J = 4.0 Hz), 2.55 (2H, t, J = 6.0 Hz), 2.60 (3H, s), 3.48 (2H, d, J = 5.6 Hz), 3.63 (2H, d, J = 7.6 Hz), 3.70 (4H, t, J = 4.4 Hz), 4.34 (2H, t, J = 5.2 Hz), 6.11 (1H, s), 6.30 (1H, d, J = 3.6 Hz), 6.45 (1H, d, J = 2.0 Hz), 6.99 (1H, d, J = 2.0 Hz). MS: 548 (M + 1). |
| 1/42 | 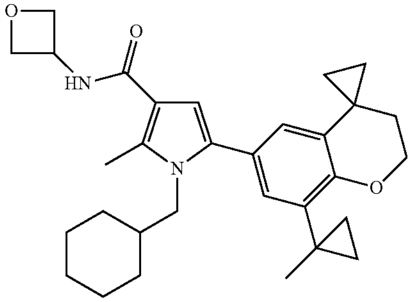 [SMILES: Cc1c(C(=O)NC2COC2)cc(-c2cc(C3(C)CC3)c3c(c2)C2(CCO3)CC2)n1CC1CCCCC1] | $^1$H-NMR ($CDCl_3$, 400 MHz) δ: 0.64-0.74 (6H, m), 0.85-0.88 (2H, m), 1.00-1.03 (5H, m), 1.33-1.42 (6H, m), 1.56 (3H, m), 1.90-1.92 (2H, t, J = 10.0 Hz), 2.57 (3H, s), 3.64-3.66 (2H, d, J = 7.2 Hz), 4.38-4.40 (2H, t, J = 10.4 Hz), 4.55-4.58 (2H, t, J = 13.2 Hz), 4.96-5.00 (2H, t, J = 14.4 Hz), 5.20-5.22 (1H, m), 6.10 (1H, s), 6.13-6.15 (1H, m), 6.43 (1H, s), 6.97 (1H, s). MS: 489 $(M + 1)^+$. |
| 1/43 | 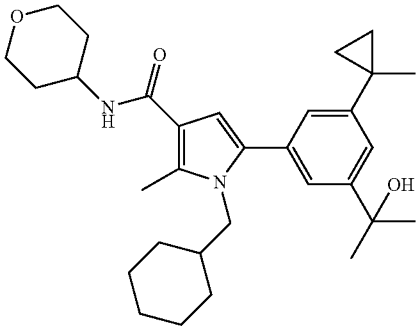 [SMILES: Cc1c(C(=O)NC2CCOCC2)cc(-c2cc(C(C)(C)O)cc(C3(C)CC3)c2)n1CC1CCCCC1] | $^1$H-NMR ($CDCl_3$, 400 MHz) δ: 0.63-0.66 (m, 2H), 0.76-0.77 (m, 2H), 0.86-0.89 (m, 2H), 0.98-0.99 (m, 3H), 1.33-1.43 (m, 3H), 1.47 (s, 3H), 1.52-1.56 (m, 5H), 1.58 (s, 6H), 1.75 (s, 2H), 2.61 (s, 3H), 3.49-3.55 (t, 2H, J = 12.0 Hz), 3.72-3.74 (d, 2H, J = 8.0 Hz), 3.96-3.99 (m, 2H), 4.15-4.17 (m, 1H), 5.60-5.62 (d, 1H, J = 8.0 Hz), 6.17 (s, 1H), 7.07 (s, 1H), 7.20 (s, 1H), 7.39 (s, 1H). MS: 493 (M + 1). |

-continued
| # | Structure | Analytical data |
|---|---|---|
| 1/44 | 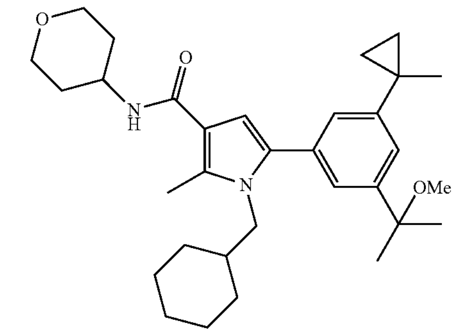 [SMILES: COC(C)(C)c1cc(-c2cc(C(=O)NC3CCOCC3)c(C)n2CC2CCCCC2)cc(C2(C)CC2)c1] | $^1$H-NMR ($CDCl_3$, 400 MHz) δ: 0.61-0.64 (m, 2H), 0.75-0.77 (m, 2H), 0.86-0.89 (m, 2H), 0.98-0.99 (m, 3H), 1.32-1.37 (m, 3H), 1.43 (s, 3H), 1.47-1.53 (m, 11H), 1.96-2.00 (m, 2H), 2.61 (s, 3H), 3.08 (s, 1H), 3.49-3.55 (t, 2H, J = 12.0 Hz), 3.73-3.75 (d, 2H, J = 8.0 Hz), 3.96-3.99 (m, 2H), 4.15-4.17 (m, 1H), 5.60-5.62 (d, 1H, J = 8.0 Hz), 6.17 (s, 1H), 7.07 (s, 1H), 7.15 (s, 1H), 7.26 (s, 1H). MS: 507 (M + 1). |
| 1/45 | 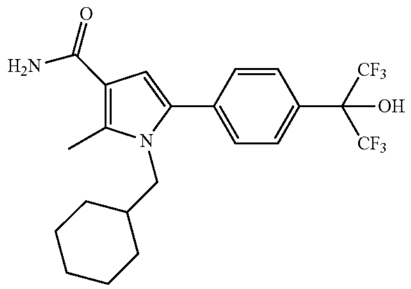 [SMILES: Cc1c(C(N)=O)cc(-c2ccc(C(O)(C(F)(F)F)C(F)(F)F)cc2)n1CC1CCCCC1] | $^1$H-NMR (DMSO-$d_6$, 400 MHz) δ: 8.74 (s, 1H), 7.72 (d, 2H), 7.52 (d, 2H), 7.17 (m, 1H), 6.66 (m, 1H), 6.60 (s, 1H), 3.85 (m, 2H), 2.53 (s, 3H), 1.55-1.40 (m, 3H), 1.35-1.20 (m, 3H), 1.00-0.80 (m, 3H), 0.70-0.55 (m, 2H). MS: 463 (M + 1). |
| 1/46 | 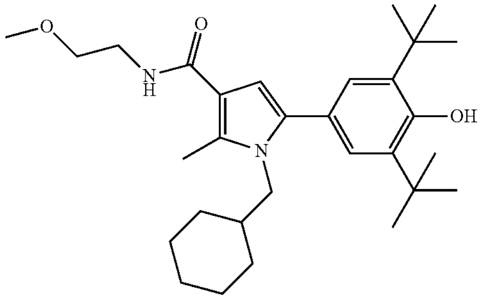 [SMILES: COCCNC(=O)c1cc(-c2cc(C(C)(C)C)c(O)c(C(C)(C)C)c2)n(CC2CCCCC2)c1C] | $^1$H-NMR ($CDCl_3$, 400 MHz) δ: 7.09 (s, 2H), 6.16 (s, 1H), 6.12 (m, 1H), 5.26 (s, 1H), 3.68-3.62 (m, 2H), 3.61-3.56 (m, 2H), 3.54-3.51 (m, 2H), 3.36 (s, 3H), 2.61 (s, 3H), 1.65-1.50 (m, 3H), 1.45 (s, 18H), 1.40-1.30 (m, 3H), 1.05-0.95 (m, 3H), 0.75-0.60 (m, 2H). MS: 483 (M + 1). |
| 1/47 | 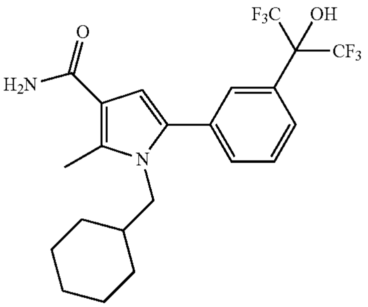 [SMILES: Cc1c(C(N)=O)cc(-c2cccc(C(O)(C(F)(F)F)C(F)(F)F)c2)n1CC1CCCCC1] | $^1$H-NMR ($CDCl_3$, 400 MHz) δ: 7.75-7.70 (m, 2H), 7.51 (m, 1H), 7.44-7.42 (m, 1H), 6.25 (s, 1H), 5.40 (br s, 2H), 3.74 (d, 2H), 2.60 (s, 3H), 1.60-1.45 (m, 3H), 1.35-1.20 (m, 3H), 1.00-0.90 (m, 3H), 0.65-0.50 (m, 2H). MS: 463 (M + 1). |
| 1/48 | 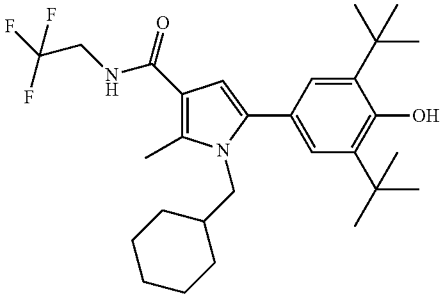 [SMILES: Cc1c(C(=O)NCC(F)(F)F)cc(-c2cc(C(C)(C)C)c(O)c(C(C)(C)C)c2)n1CC1CCCCC1] | $^1$H-NMR (400 MHz, $CDCl_3$) δ: 7.08 (s, 2H), 6.15 (s, 1H), 5.88-5.92 (t, 1H), 5.28 (s, 1H), 4.01-4.08 (m, 2H), 3.65-3.67 (d, 2H, J = 8.0 Hz), 2.60 (s, 3H), 1.52-1.56 (m, 4H), 1.45 (s, 18H), 1.34-1.37 (m, 2H), 0.96-1.03 (m, 3H), 0.67-0.73 (m, 2H). MS: 507 (M + 1). |

-continued

| # | Structure | Analytical data |
|---|---|---|
| 1/49 | 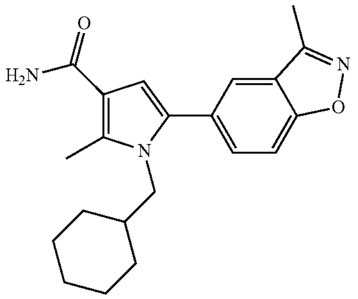 [SMILES: Cc1noc2ccc(-c3cc(C(N)=O)c(C)n3CC3CCCCC3)cc12] | $^1$H-NMR (400 MHz, $CDCl_3$) δ: 7.57-7.59 (d, 2H, J = 8.0 Hz), 7.48-7.50 (d, 1H, J = 8.0 Hz), 6.24 (s, 1H), 5.39-5.43 (m, 2H), 3.74-3.76 (d, 2H, J = 8.0 Hz), 2.56-2.63 (m, 6H), 1.54-1.57 (m, 4H), 1.25-1.39 (m, 2H), 1.28 (t, 3H), 0.83-1.05 (m, 3H), 0.58-0.64 (m, 2H). MS: 352 (M + 1). |
| 1/50 | 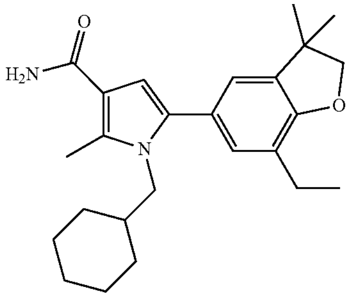 [SMILES: CCc1cc(-c2cc(C(N)=O)c(C)n2CC2CCCCC2)cc2c1OCC2(C)C] | $^1$H-NMR (400 MHz, $CDCl_3$) δ: 6.91-6.93 (d, 1H, J = 8.0 Hz), 6.87-6.89 (d, 1H, J = 8.0 Hz), 6.15 (s, 1H), 5.36-5.39 (m, 2H), 4.28 (s, 2H), 3.68-3.70 (d, 2H, J = 8.0 Hz), 2.61-2.65 (q, 2H), 2.60 (s, 3H), 1.50-1.59 (m, 4H), 1.40-1.45 (m, 2H), 1.38 (s, 6H), 1.28 (m, 3H), 0.98-1.18 (m, 3H), 0.60-0.69 (m, 2H). MS: 395 (M + 1). |
| 1/51 | 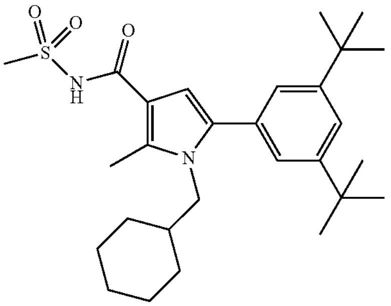 [SMILES: Cc1c(C(=O)NS(C)(=O)=O)cc(-c2cc(C(C)(C)C)cc(C(C)(C)C)c2)n1CC1CCCCC1] | $^1$H-NMR (400 MHz, $CDCl_3$) δ: 7.90 (s, 1H), 7.40 (m, 1H), 7.10 (m, 1H), 6.18 (s, 1H), 3.70 (d, 1H), 3.38 (s, 3H), 2.60 (s, 3H), 1.57-1.50 (m, 3H), 1.38-1.25 (m, 21H), 1.00-0.90 (m, 3H), 0.70-0.60 (m, 2H). MS (m/z): 487 (M + 1). |
| 1/52 | 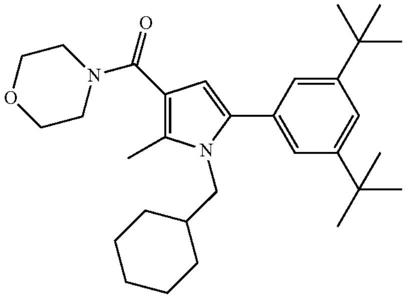 [SMILES: Cc1c(C(=O)N2CCOCC2)cc(-c2cc(C(C)(C)C)cc(C(C)(C)C)c2)n1CC1CCCCC1] | $^1$H-NMR (400 MHz, $CDCl_3$) δ: 7.30 (s, 1H), 7.08 (m, 2H), 6.04 (s, 1H), 3.63 (m, 10H), 2.32 (s, 3H), 1.75 (m, 1H), 1.45 (m, 3H), 1.26 (s, 21H), 0.93 (m, 3H), 0.57 (m, 2H). MS (m/z): 479.2 (M + 1). |
| 1/53 | 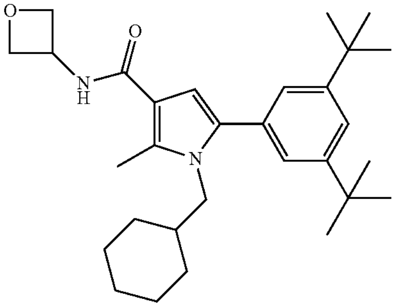 [SMILES: Cc1c(C(=O)NC2COC2)cc(-c2cc(C(C)(C)C)cc(C(C)(C)C)c2)n1CC1CCCCC1] | $^1$H-NMR (500 MHz, $CDCl_3$) δ: 7.33 (s, 1H), 7.07 (m, 2H), 6.16 (s, 1H), 6.13 (m, 1H), 5.15 (m, 1H), 4.91 (t, J = 7.0 Hz, 2H), 4.51 (t, J = 6.5 Hz, 2H), 3.64 (d, J = 7.0 Hz, 2H), 2.53 (s, 3H), 1.45 (m, 3H), 1.28 (s, 21H), 0.92 (m, 3H), 0.57 (m, 2H). MS (m/z): 465.2 (M + 1). |

-continued

| # | Structure | Analytical data |
|---|---|---|
| 1/54 | 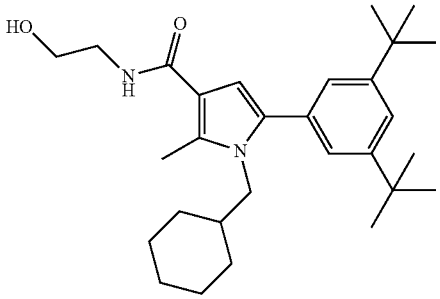 [SMILES: Cc1c(C(=O)NCCO)cc(-c2cc(C(C)(C)C)cc(C(C)(C)C)c2)n1CC1CCCCC1] | $^1$H-NMR (500 MHz, $CDCl_3$) δ: 7.31 (s, 1H), 7.07 (m, 2H), 6.18 (m, 1H), 6.15 (s, 1H), 3.71 (m, 2H), 3.64 (d, J = 7.0 Hz, 2H), 3.48 (m, 2H), 2.54 (s, 3H), 1.45 (m, 3H), 1.27 (s, 21H), 0.92 (m, 3H), 0.57 (m, 2H). MS (m/z): 453.2 (M + 1). |
| 1/55 | 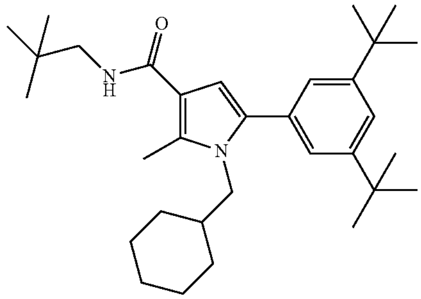 [SMILES: Cc1c(C(=O)NCC(C)(C)C)cc(-c2cc(C(C)(C)C)cc(C(C)(C)C)c2)n1CC1CCCCC1] | $^1$H-NMR (400 MHz, $CDCl_3$) δ: 7.31 (s, 1H), 7.07 (m, 2H), 6.16 (m, 2H), 3.64 (d, J = 7.2 Hz, 2H), 3.32 (d, J = 6.0 Hz, 2H), 2.54 (s, 3H), 1.45 (m, 3H), 1.27 (s, 21H), 1.18 (s, 6H), 0.92 (m, 3H), 0.57 (m, 2H). MS (m/z): 481.2 (M + 1). |
| 1/56 | 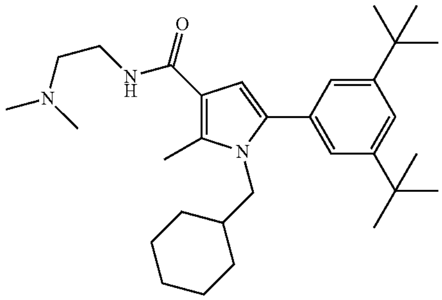 [SMILES: Cc1c(C(=O)NCCN(C)C)cc(-c2cc(C(C)(C)C)cc(C(C)(C)C)c2)n1CC1CCCCC1] | $^1$H-NMR (500 MHz, $CDCl_3$) δ: 7.38 (m, 1H), 7.14 (m, 2H), 6.87 (br s, 1H), 6.35 (s, 1H), 3.70 (d, J = 7.5 Hz, 2H), 3.60 (m, 2H), 3.01 (m, 2H), 2.67 (s, 6H), 2.57 (s, 3H), 1.52 (m, 3H), 1.33 (s, 21H), 0.98 (m, 3H), 0.64 (m, 2H). MS (m/z): 480.2 (M + 1). |
| 1/57 | 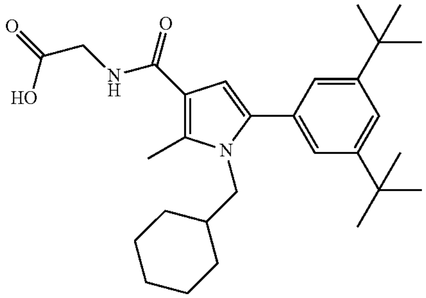 [SMILES: Cc1c(C(=O)NCC(=O)O)cc(-c2cc(C(C)(C)C)cc(C(C)(C)C)c2)n1CC1CCCCC1] | $^1$H-NMR (500 MHz, $CDCl_3$) δ: 7.26 (s, 1H), 7.01 (m, 2H), 6.26 (br s, 1H), 6.14 (s, 1H), 4.05 (m, 2H), 3.58 (d, J = 7.5 Hz, 2H), 2.47 (s, 3H), 1.40 (m, 3H), 1.20 (s, 21H), 0.87 (m, 3H), 0.52 (m, 2H). MS (m/z): 467.2 (M + 1). |
| 1/58 | 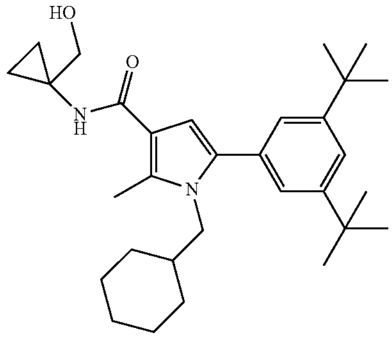 [SMILES: Cc1c(C(=O)NC2(CO)CC2)cc(-c2cc(C(C)(C)C)cc(C(C)(C)C)c2)n1CC1CCCCC1] | $^1$H-NMR (400 MHz, $CDCl_3$) δ: 7.32 (s, 1H), 7.05 (m, 2H), 6.25 (br s, 1H), 6.05 (s, 1H), 5.18 (br s, 1H), 3.64 (d, J = 6.8 Hz, 4H), 2.54 (s, 3H), 1.45 (m, 3H), 1.24 (s, 21H), 0.92 (m, 7H), 0.57 (m, 2H). MS (m/z): 479.2 (M + 1). |

-continued

| # | Structure | Analytical data |
|---|---|---|
| 1/59 | 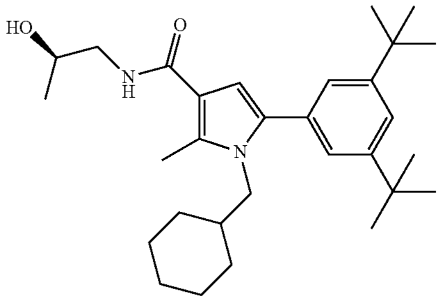 [SMILES: Cc1c(C(=O)NC[C@@H](C)O)cc(-c2cc(C(C)(C)C)cc(C(C)(C)C)c2)n1CC1CCCCC1] | $^1$H-NMR (400 MHz, $CDCl_3$) δ: 7.32 (s, 1H), 7.07 (m, 2H), 6.15 (m, 2H), 3.64 (d, J = 6.8 Hz, 2H), 3.28-3.48 (m, 4H), 2.54 (s, 3H), 1.45 (m, 3H), 1.24 (m, 24H), 0.92 (m, 3H), 0.57 (m, 2H). MS (m/z): 467.2 (M + 1). |
| 1/60 | 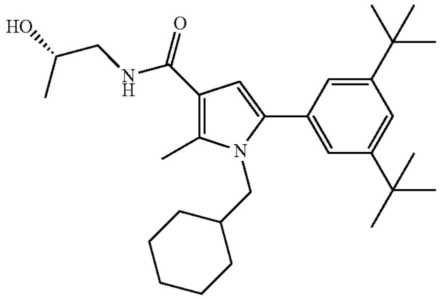 [SMILES: Cc1c(C(=O)NC[C@H](C)O)cc(-c2cc(C(C)(C)C)cc(C(C)(C)C)c2)n1CC1CCCCC1] | $^1$H-NMR (400 MHz, $CDCl_3$) δ: 7.31 (s, 1H), 7.07 (m, 2H), 6.20 (br s, 1H), 6.15 (s, 1H), 3.93 (m, 1H), 3.64 (d, J = 7.2 Hz, 2H), 3.45 (m, 2H), 3.22 (m, 1H), 2.53 (s, 3H), 1.45 (m, 3H), 1.27 (s, 21H), 1.14 (m, 3H), 0.91 (m, 3H), 0.55 (m, 2H). MS (m/z): 467.2 (M + 1). |
| 1/61 | 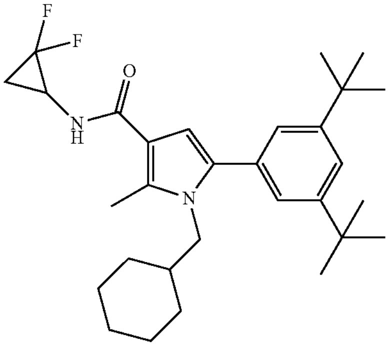 | $^1$H-NMR (400 MHz, $CDCl_3$) δ: 7.40 (m, 1H), 7.12 (m, 2H), 6.18 (s, 1H), 6.10 (br s, 1H), 3.71 (d, J = 7.2 Hz, 2H), 3.47 (m, 1H), 2.59 (s, 3H), 1.86 (m, 1H), 1.52 (m, 3H), 1.30 (s, 22H), 0.98 (m, 3H), 0.64 (m, 2H). MS (m/z): 585.2 (M + 1). |
| 1/62 | 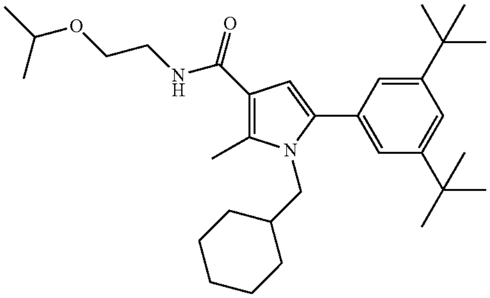 [SMILES: Cc1c(C(=O)NCCOC(C)C)cc(-c2cc(C(C)(C)C)cc(C(C)(C)C)c2)n1CC1CCCCC1] | $^1$H-NMR (400 MHz, DMSO-$d_6$) δ: 7.72-7.69 (t, J = 5.4 Hz, 1H), 7.47 (s, 1H), 7.23 (s, 2H), 6.57 (s, 1H), 3.85-3.83 (d, J = 6.8 Hz, 2H), 3.65-3.62 (t, J = 6.0 Hz, 1H), 3.51-3.48 (t, J = 6.0 Hz, 2H), 3.39-3.36 (t, J = 6.0 Hz, 2H), 2.60 (s, 3H), 1.54-1.51 (d, J = 8.8 Hz, 3H), 1.39-1.29 (m, 21H), 1.17-1.16 (d, J = 6.0 Hz, 6H), 0.99-0.96 (d, J = 12.4 Hz, 3H), 0.76-0.70 (t, J = 10.6 Hz, 2H). MS (m/z): 495 (M + 1). |
| 1/63 | 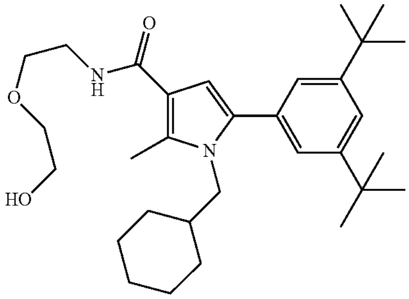 [SMILES: Cc1c(C(=O)NCCOCCO)cc(-c2cc(C(C)(C)C)cc(C(C)(C)C)c2)n1CC1CCCCC1] | $^1$H-NMR (400 MHz, DMSO-$d_6$) δ: 7.65-7.62 (t, J = 4.8 Hz, 1H), 7.34 (s, 1H), 7.15 (s, 2H), 6.49 (s, 1H), 4.61-4.59 (t, J = 5.0 Hz, 1H), 3.76-3.74 (d, J = 6.4 Hz, 2H), 3.51-3.43 (m, 6H), 3.34 (s, 2H), 2.52 (s, 3H), 1.44-1.42 (d, J = 4.4 Hz, 3H), 1.30 (s, 18H), 1.24-1.21 (d, J = 13.2 Hz, 3H), 0.93-0.87 (t, J = 10.4 Hz, 3H), 0.64-0.61 (d, J = 10.8 Hz, 2H). MS (m/z): 497 (M + 1). |

-continued

| # | Structure | Analytical data |
|---|---|---|
| 1/64 | 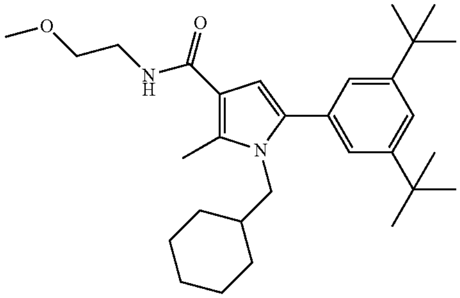 [SMILES: COCCNC(=O)c1cc(-c2cc(C(C)(C)C)cc(C(C)(C)C)c2)n(CC2CCCCC2)c1C] | $^1$H-NMR (400 MHz, DMSO-$d_6$) δ: 7.67-7.64 (t, J = 5.2 Hz, 1H), 7.35 (s, 1H), 7.16 (s, 2H), 6.51 (s, 1H), 3.77-3.76 (d, J = 6.8 Hz, 2H), 3.42-3.39 (t, J = 5.6 Hz, 2H), 3.35 (s, 2H), 3.26 (s, 3H), 2.53 (s, 3H), 1.45-1.43 (d, J = 8.8 Hz, 3H), 1.31 (s, 18H), 1.25-1.22 (d, J = 13.2 Hz, 3H), 0.94-0.89 (t, J = 10.6 Hz, 3H), 0.68-0.60 (m, 2H). MS (m/z): 467 (M + 1). |
| 1/65 | 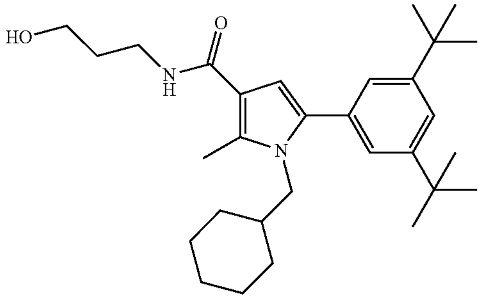 [SMILES: Cc1c(C(=O)NCCCO)cc(-c2cc(C(C)(C)C)cc(C(C)(C)C)c2)n1CC1CCCCC1] | $^1$H-NMR (400 MHz, DMSO-$d_6$) δ: 7.70-7.68 (d, J = 4.8 Hz, 1H), 7.42 (s, 1H), 7.23 (s, 2H), 6.60 (s, 1H), 4.57-4.54 (t, J = 5.0 Hz, 1H), 3.84-3.82 (d, J = 7.2 Hz, 2H), 3.54-3.49 (m, 2H), 3.32-3.28 (m, 2H), 2.58 (s, 3H), 1.71-1.68 (t, J = 6.4 Hz, 2H), 1.53-1.51 (d, J = 9.6 Hz, 3H), 1.38-1.29 (m, 21H), 1.01-0.96 (t, J = 10.0 Hz, 3H), 0.75-0.70 (t, J = 10.4 Hz, 2H). MS (m/z): 467 (M + 1). |
| 1/66 | 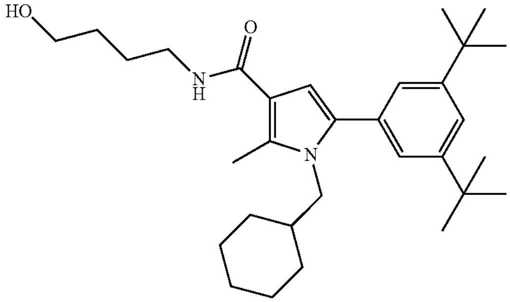 [SMILES: Cc1c(C(=O)NCCCCO)cc(-c2cc(C(C)(C)C)cc(C(C)(C)C)c2)n1CC1CCCCC1] | $^1$H-NMR (400 MHz, DMSO-$d_6$) δ: 7.60-7.58 (d, J = 5.2 Hz, 1H), 7.35 (s, 1H), 7.15 (s, 2H), 6.48 (s, 1H), 4.39-4.37 (t, J = 5.2 Hz, 1H), 3.77-3.75 (d, J = 7.2 Hz, 2H), 3.43-3.38 (m, 2H), 3.18-3.14 (m, 2H), 2.52 (s, 3H), 1.48-1.43 (t, J = 10.0 Hz, 7H), 1.31-1.21 (m, 21H), 0.94-0.89 (t, J = 10.4 Hz, 3H), 0.65-0.62 (d, J = 11.2 Hz, 2H). MS (m/z): 481 (M + 1). |
| 1/67 | 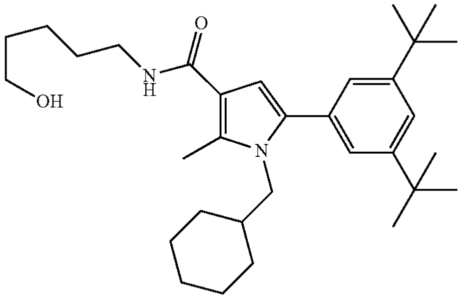 [SMILES: Cc1c(C(=O)NCCCCCO)cc(-c2cc(C(C)(C)C)cc(C(C)(C)C)c2)n1CC1CCCCC1] | $^1$H-NMR (400 MHz, DMSO-$d_6$) δ: 7.58 (s, 1H), 7.33 (s, 1H), 7.14 (s, 2H), 6.48 (s, 1H), 4.34 (s, 1H), 3.75-3.74 (d, J = 6.0 Hz, 2H), 3.39-3.38 (d, J = 5.2 Hz, 2H), 3.12-3.14 (d, J = 6.0 Hz, 2H), 2.51 (s, 3H), 1.45-1.43 (d, J = 5.6 Hz, 7H), 1.30 (s, 20H), 1.24-1.21 (d, J = 12.4 Hz, 3H), 0.91-0.88 (d, J = 11.2 Hz, 3H), 0.64-0.61 (d, J = 10.4 Hz, 2H). MS (m/z): 495 (M + 1). |
| 1/68 | 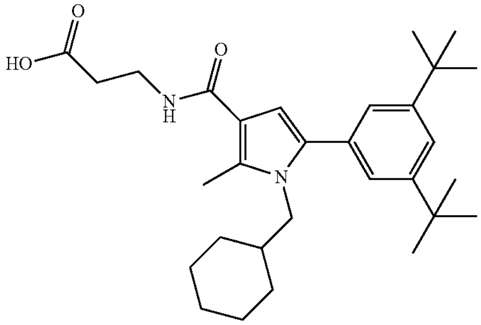 [SMILES: Cc1c(C(=O)NCCC(=O)O)cc(-c2cc(C(C)(C)C)cc(C(C)(C)C)c2)n1CC1CCCCC1] | $^1$H-NMR (400 MHz, DMSO-$d_6$) δ: 12.13 (s, 1H), 7.70-7.67 (t, J = 5.2 Hz, 1H), 7.35 (s, 1H), 7.15 (s, 2H), 6.47 (s, 1H), 3.77-3.75 (d, J = 6.8 Hz, 2H), 3.38-3.35 (t, J = 6.0 Hz, 2H), 2.52-2.45 (m, 5H), 1.46-1.43 (d, J = 4.6 Hz, 3H), 1.31-1.21 (t, J = 9.8 Hz, 21H), 0.94-0.89 (t, J = 5.0 Hz, 3H), 0.65-0.62 (d, J = 10.8 Hz, 2H). MS (m/z): 481 (M + 1). |

-continued

| # | Structure | Analytical data |
|---|---|---|
| 1/69 | 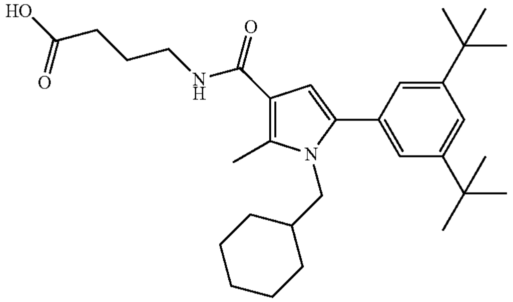 [SMILES: Cc1c(C(=O)NCCCC(=O)O)cc(-c2cc(C(C)(C)C)cc(C(C)(C)C)c2)n1CC1CCCCC1] | $^1$H-NMR (400 MHz, DMSO-$d_6$) δ: 12.03 (s, 1H), 7.66-7.63 (t, J = 5.2 Hz, 1H), 7.35 (s, 1H), 7.15 (s, 2H), 6.49 (s, 1H), 3.77-3.75 (d, J = 6.8 Hz, 2H), 3.20-3.15 (m, 2H), 2.52-2.50 (d, J = 6.8 Hz, 3H), 2.26-2.23 (t, J = 7.2 Hz, 2H), 1.73-1.66 (m, 2H), 1.46-1.44 (d, J = 4.4 Hz, 3H), 1.31-1.15 (m, 21H), 0.98-0.89 (m, 3H), 0.65-0.62 (m, 2H). MS (m/z): 495 (M + 1). |
| 1/70 | 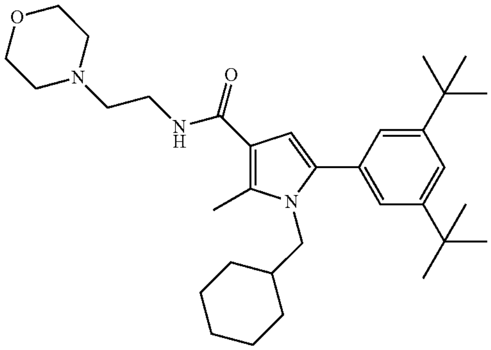 [SMILES: Cc1c(C(=O)NCCN2CCOCC2)cc(-c2cc(C(C)(C)C)cc(C(C)(C)C)c2)n1CC1CCCCC1] | $^1$H-NMR (400 MHz, DMSO-$d_6$) δ: 7.60 (s, 1H), 7.35 (s, 1H), 7.15 (s, 2H), 6.46 (s, 1H), 3.77-3.75 (d, J = 7.2 Hz, 2H), 3.60 (s, 4H), 3.32 (s, 4H), 2.52-2.40 (t, 7H), 1.46-1.44 (d, J = 9.2 Hz, 3H), 1.31 (s, 18H), 1.24-1.21 (d, J = 13.6 Hz, 3H), 0.91-0.88 (m, 3H), 0.68-0.60 (m, 2H). MS (m/z): 522 (M + 1). |
| 1/71 | 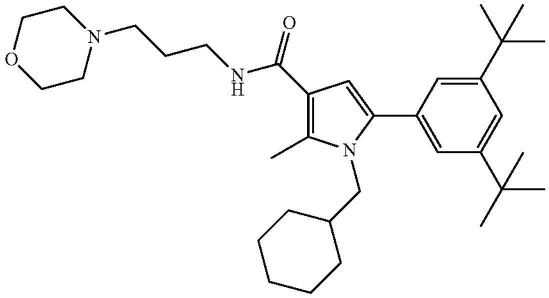 [SMILES: Cc1c(C(=O)NCCCN2CCOCC2)cc(-c2cc(C(C)(C)C)cc(C(C)(C)C)c2)n1CC1CCCCC1] | $^1$H-NMR (400 MHz, DMSO-$d_6$) δ: 7.68-7.66 (t, J = 5.4 Hz, 1H), 7.35 (s, 1H), 7.15 (s, 2H), 6.46 (s, 1H), 3.77-3.75 (d, J = 6.8 Hz, 2H), 3.58-3.57 (d, J = 4.0 Hz, 4H), 3.22-3.18 (m, 2H), 2.52-2.50 (d, J = 6.0 Hz, 3H), 2.39-2.34 (t, J = 10.6 Hz, 6H), 1.66-1.62 (t, J = 6.6 Hz, 2H), 1.46-1.43 (d, J = 9.2 Hz, 3H), 1.31-1.21 (m, 21H), 0.91-0.88 (d, J = 12.0 Hz, 3H), 0.67-0.62 (t, J = 10.8 Hz, 2H). MS (m/z): 536 (M + 1). |
| 1/72 | 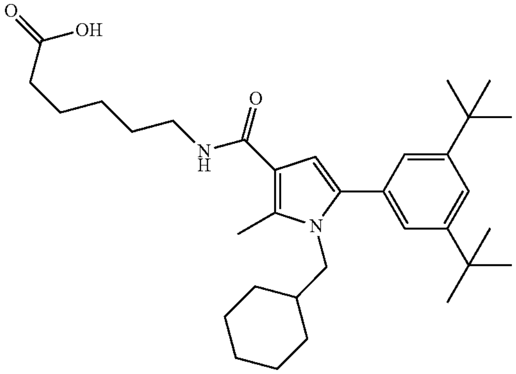 [SMILES: Cc1c(C(=O)NCCCCCC(=O)O)cc(-c2cc(C(C)(C)C)cc(C(C)(C)C)c2)n1CC1CCCCC1] | $^1$H-NMR (400 MHz, DMSO-$d_6$) δ: 11.97 (s, 1H), 7.63-7.60 (t, J = 5.6 Hz, 1H), 7.37 (s, 1H), 7.18-7.17 (d, J = 1.2 Hz, 2H), 6.50 (s, 1H), 3.79-3.77 (d, J = 7.2 Hz, 2H), 3.19-3.15 (m, 2H), 2.54-2.52 (m, 3H), 2.25-2.21 (t, J = 7.4 Hz, 2H), 1.56-1.46 (m, 7H), 1.33-1.24 (m, 23H), 0.96-0.88 (m, 3H), 0.69-0.67 (m, 2H). MS (m/z): 523 (M + 1). |

-continued

| # | Structure | Analytical data |
|---|---|---|
| 1/73 | 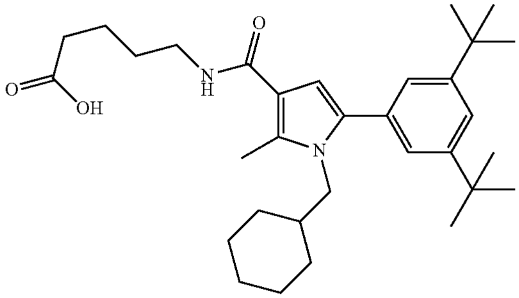 [SMILES: Cc1c(C(=O)NCCCCC(=O)O)cc(-c2cc(C(C)(C)C)cc(C(C)(C)C)c2)n1CC1CCCCC1] | $^1$H-NMR (400 MHz, DMSO-d$_6$) δ: 12.01 (s, 1H), 7.63-7.60 (t, J = 5.6 Hz, 1H), 7.35 (s, 1H), 7.16-7.15 (d, J = 1.2 Hz, 2H), 6.48 (s, 1H), 3.77-3.75 (d, J = 6.8 Hz, 2H), 3.18-3.15 (t, J = 6.2 Hz, 2H), 2.52-2.51 (d, J = 4.8 Hz, 3H), 2.25-2.21 (t, J = 6.8 Hz, 2H), 1.50-1.43 (m, 7H), 1.31-1.25 (m, 21H), 0.94-0.85 (m, 3H), 0.63-0.60 (m, 2H). MS (m/z): 509 (M + 1). |
| 1/74 | 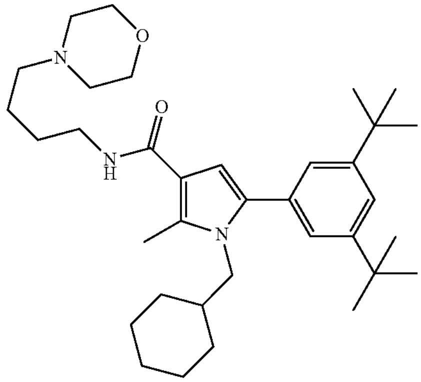 [SMILES: Cc1c(C(=O)NCCCCN2CCOCC2)cc(-c2cc(C(C)(C)C)cc(C(C)(C)C)c2)n1CC1CCCCC1] | $^1$H-NMR (400 MHz, DMSO-d$_6$) δ: 7.67 (s, 1H), 7.39 (s, 1H), 7.20 (s, 2H), 6.54 (s, 1H), 3.81-3.80 (d, J = 6.0 Hz, 2H), 3.62 (s, 4H), 3.23 (s, 2H), 2.57 (s, 3H), 2.45 (s, 4H), 2.39 (s, 2H), 1.52 (s, 7H), 1.35-1.26 (m, 21H), 0.96 (s, 3H), 0.69-0.67 (d, J = 10.4 Hz, 2H). MS (m/z): 550 (M + 1). |
| 1/75 | 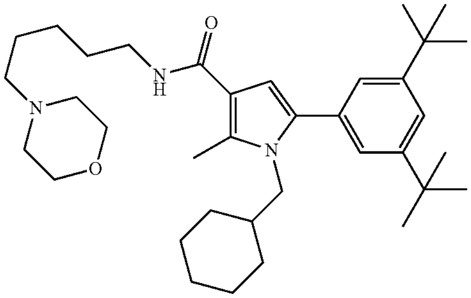 [SMILES: Cc1c(C(=O)NCCCCCN2CCOCC2)cc(-c2cc(C(C)(C)C)cc(C(C)(C)C)c2)n1CC1CCCCC1] | $^1$H-NMR (400 MHz, DMSO-d$_6$) δ: 7.61-7.58 (t, J = 5.8 Hz, 1H), 7.35 (s, 1H), 7.15-7.15 (d, J = 1.6 Hz, 2H), 6.48 (s, 1H), 3.77-3.75 (d, J = 6.8 Hz, 2H), 3.55-3.54 (d, J = 4.4 Hz, 4H), 3.18-3.13 (m, 2H), 2.51-2.51 (d, J = 3.2 Hz, 3H), 2.33 (s, 4H), 2.28-2.24 (t, J = 7.2 Hz, 2H), 1.49-1.40 (m, 7H), 1.31-1.21 (m, 23H), 0.92-0.88 (d, J = 12.8 Hz, 3H), 0.67-0.62 (t, J = 10.4 Hz, 2H). MS (m/z): 564 (M + 1). |
| 1/76 | 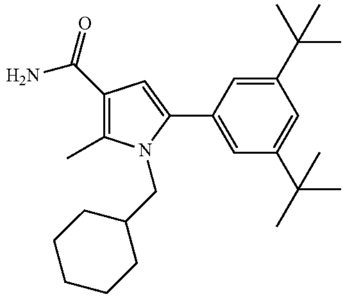 [SMILES: Cc1c(C(N)=O)cc(-c2cc(C(C)(C)C)cc(C(C)(C)C)c2)n1CC1CCCCC1] | $^1$H-NMR (500 MHz, CDCl$_3$) δ: 0.59 (m, 2H), 0.80 (m, 3H), 1.11 (m, 14H), 1.47 (m, 3H), 1.80-2.54 (m, 8H), 3.67 (d, 2H), 5.40 (br s, 2H), 6.14 (s, 1H), 6.94 (s, 1H), 7.08 (m, 2H). MS (m/z): 407 (M + 1). |
| 1/77 | 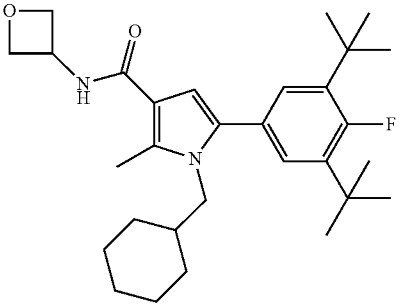 [SMILES: Cc1c(C(=O)NC2COC2)cc(-c2cc(C(C)(C)C)c(F)c(C(C)(C)C)c2)n1CC1CCCCC1] | $^1$H-NMR (300 MHz, DMSO-d$_6$) δ: 8.22 (d, J = 6.6 Hz, 1H), 7.14 (d, J = 7.5 Hz, 2H), 6.59 (s, 1H), 4.96 (m, 1H), 4.74 (m, 2H), 4.56 (m, 2H), 3.74 (d, J = 6.6 Hz, 2H), 2.50 (s, 3H), 1.49 (m, 24H), 0.98 (m, 3H), 0.71 (m, 2H). MS (m/z): 483 (M + 1). |

-continued

| # | Structure | Analytical data |
|---|---|---|
| 1/78 | 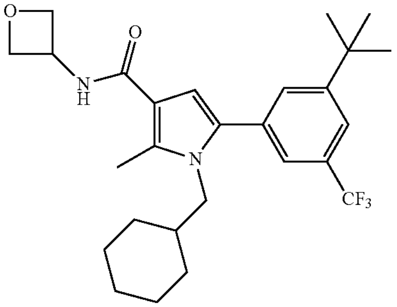 [SMILES: Cc1c(C(=O)NC2COC2)cc(-c2cc(C(C)(C)C)cc(C(F)(F)F)c2)n1CC1CCCCC1] | $^1$H-NMR (400 MHz, $CDCl_3$) δ: 7.60 (s, 1H), 7.53 (s, 1H), 7.41 (s, 1H), 6.28 (s, 1H), 6.17 (d, 1H), 5.23 (m, 1H), 4.99 (m, 2H), 4.58 (t, 2H), 3.73 (d, 2H), 2.61 (s, 3H), 1.56 (s, 6H), 1.32 (m, 9H), 1.00 (m, 3H), 0.63 (m, 2H). MS (m/z): 477 (M + 1). |
| 1/79 | 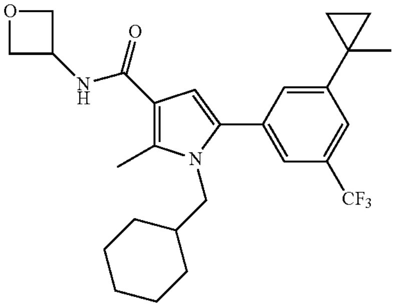 [SMILES: Cc1c(C(=O)NC2COC2)cc(-c2cc(C(F)(F)F)cc(C3(C)CC3)c2)n1CC1CCCCC1] | $^1$H-NMR (400 MHz, $CDCl_3$) δ: 7.47 (s, 1H), 7.37 (s, 2H), 6.27 (s, 1H), 6.16 (d, 1H), 5.21 (m, 1H), 4.99 (m, 2H), 4.58 (m, 2H), 3.73 (d, 2H), 2.60 (s, 3H), 1.54 (m, 4H), 1.46 (s, 3H), 1.33 (m, 3H), 1.01 (m, 2H), 1.00 (m, 2H), 0.84 (m, 2H), 0.66 (m, 2H). MS (m/z): 475 (M + 1). |
| 1/80 | 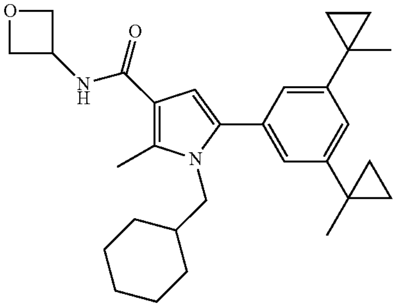 [SMILES: Cc1c(C(=O)NC2COC2)cc(-c2cc(C3(C)CC3)cc(C3(C)CC3)c2)n1CC1CCCCC1] | $^1$H-NMR ($CDCl_3$, 300 MHz) δ: 7.07 (s, 1H), 6.92 (d, J = 1.5 Hz, 2H), 6.10 (m, 2H), 5.15 (m, 1H), 4.91 (t, 2H), 4.50 (t, 2H), 3.64 (d, J = 6.9 Hz, 2H), 2.52 (s, 3H), 1.47 (m, 3H), 1.18-1.46 (m, 9H), 0.94 (m, 3H), 0.76-0.81 (m, 10H). MS (m/z): 461 (M + 1). |
| 1/81 | 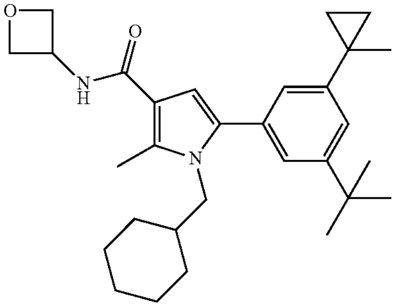 [SMILES: Cc1c(C(=O)NC2COC2)cc(-c2cc(C(C)(C)C)cc(C3(C)CC3)c2)n1CC1CCCCC1] | $^1$H-NMR (DMSO-$d_6$, 400 MHz) δ: 8.22 (d, 1H), 7.20 (s, 1H), 7.16 (s, 1H), 6.99 (s, 1H), 6.59 (s, 1H), 4.93 (m, 1H), 4.72 (t, 2H), 4.55 (t, 2H), 3.76 (t, 2H), 2.50 (s, 3H), 1.45 (m, 3H), 1.40 (s, 3H), 1.31 (s, 9H), 1.23 (m, 3H), 0.95 (m, 3H), 0.84 (m, 2H), 0.76 (m, 2H), 0.65 (m, 2H). MS (m/z): 463 (M + 1). |
| 1/82 | 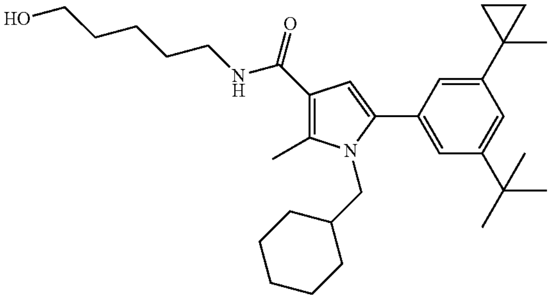 [SMILES: Cc1c(C(=O)NCCCCCO)cc(-c2cc(C(C)(C)C)cc(C3(C)CC3)c2)n1CC1CCCCC1] | $^1$H-NMR (400 MHz, DMSO-$d_6$) δ: 7.58 (t, 1H), 7.19 (s, 1H), 7.14 (s, 1H), 6.97 (s, 1H), 6.48 (s, 1H), 4.34 (t, 1H), 3.75 (d, 2H), 3.69 (m, 2H), 3.15 (m, 2H), 2.50 (m, 3H), 1.40-1.48 (m, 10H), 1.27 (m, 14H), 0.77-0.96 (m, 9H). MS (m/z): 493 (M + 1). |

-continued
| # | Structure | Analytical data |
|---|---|---|
| 1/83 | 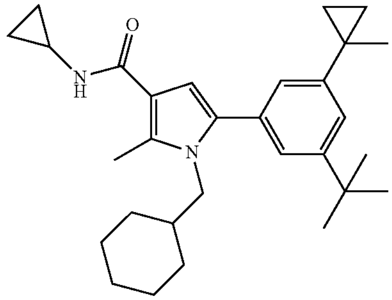 [SMILES: Cc1c(C(=O)NC2CC2)cc(-c2cc(C(C)(C)C)cc(C3(C)CC3)c2)n1CC1CCCCC1] | $^1$H-NMR (400 MHz, DMSO-$d_6$) δ: 7.57 (t, 1H), 7.19 (s, 1H), 7.13 (s, 1H), 6.96 (s, 1H), 6.46 (s, 1H), 3.75 (d, 2H), 2.73 (m, 1H), 2.50 (m, 3H), 1.21-1.47 (m, 18H), 0.74-0.95 (m, 13H). MS (m/z): 447 (M + 1). |
| 1/84 | 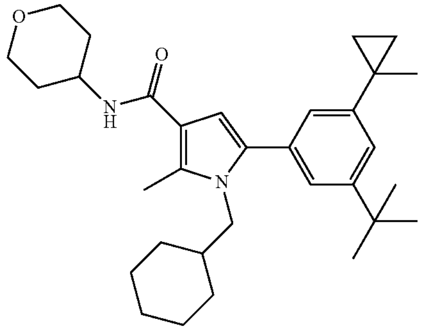 [SMILES: Cc1c(C(=O)NC2CCOCC2)cc(-c2cc(C(C)(C)C)cc(C3(C)CC3)c2)n1CC1CCCCC1] | $^1$H-NMR (400 MHz, DMSO-$d_6$) δ: 7.41 (d, 1H), 7.20 (s, 1H), 7.14 (s, 1H), 6.97 (s, 1H), 6.53 (s, 1H), 3.95 (m, 1H), 3.87 (d, 2H), 3.85 (d, 2H), 3.35 (d, 2H), 2.56 (m, 3H), 1.71 (d, 2H), 1.45-1.68 (m, 8H), 1.22-1.30 (m, 12H), 0.59-0.96 (m, 9H). MS (m/z): 491 (M + 1). |
| 1/85 | 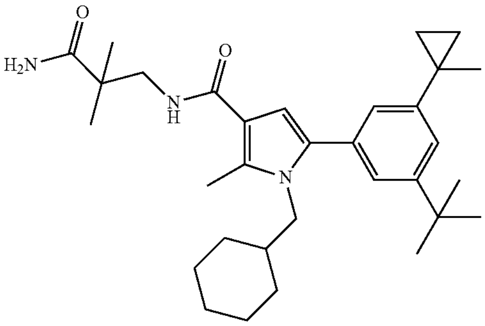 [SMILES: Cc1c(C(=O)NCC(C)(C)C(N)=O)cc(-c2cc(C(C)(C)C)cc(C3(C)CC3)c2)n1CC1CCCCC1] | $^1$H-NMR (400 MHz, DMSO-$d_6$) δ: 7.33 (t, 1H), 7.19 (d, 2H), 7.13 (s, 1H), 6.96 (s, 1H), 6.85 (s, 1H), 6.41 (s, 1H), 3.74 (d, 2H), 3.28 (d, 2H), 2.50 (m, 3H), 1.22-1.46 (m, 18H), 0.75-0.95 (m, 15H). MS (m/z): 506 (M + 1). |
| 1/86 | 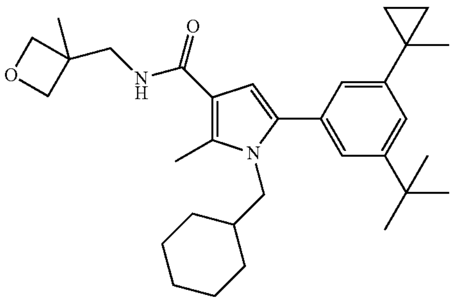 [SMILES: Cc1c(C(=O)NCC2(C)COC2)cc(-c2cc(C(C)(C)C)cc(C3(C)CC3)c2)n1CC1CCCCC1] | $^1$H-NMR (400 MHz, DMSO-$d_6$) δ: 7.80 (t, 1H), 7.20 (d, 2H), 6.98 (s, 1H), 6.53 (s, 1H), 4.47 (d, 2H), 4.15 (d, 2H), 3.75 (d, 2H), 3.33 (s, 2H), 2.50 (m, 3H), 1.23-1.47 (m, 21H), 0.63-0.96 (m, 9H). MS (m/z): 491 (M + 1). |
| 1/87 | 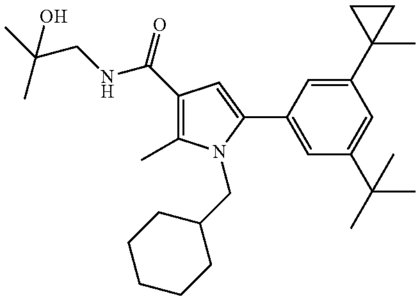 [SMILES: Cc1c(C(=O)NCC(C)(C)O)cc(-c2cc(C(C)(C)C)cc(C3(C)CC3)c2)n1CC1CCCCC1] | $^1$H-NMR (400 MHz, DMSO-$d_6$) δ: 7.46 (t, 1H), 7.19 (d, 2H), 6.98 (s, 1H), 6.53 (s, 1H), 4.66 (s, 1H), 3.76 (d, 2H), 3.16 (d, 2H), 2.51 (m, 3H), 1.24-1.47 (m, 18H), 0.63-1.08 (m, 15H). MS (m/z): 479 (M + 1). |

-continued
| # | Structure | Analytical data |
|---|---|---|
| 1/88 | 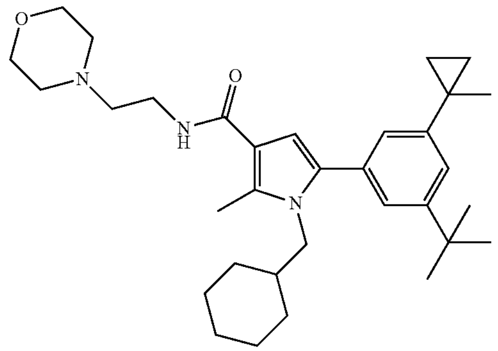 [SMILES: Cc1c(C(=O)NCCN2CCOCC2)cc(-c2cc(C(C)(C)C)cc(C3(C)CC3)c2)n1CC1CCCCC1] | $^1$H-NMR (400 MHz, DMSO-$d_6$) δ: 7.56 (t, 1H), 7.19 (d, 2H), 6.97 (s, 1H), 6.45 (s, 1H), 3.75 (d, 2H), 3.57 (m, 4H), 3.28 (m, 2H), 2.50 (m, 3H), 2.40 (m, 6H), 1.22-1.47 (m, 18H), 0.75-0.96 (m, 9H). MS (m/z): 520 (M + 1). |
| 1/89 | 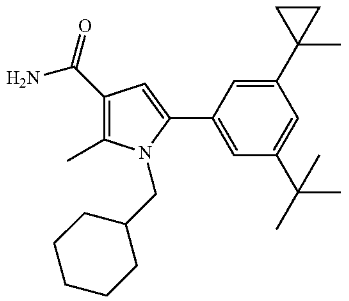 [SMILES: Cc1c(C(N)=O)cc(-c2cc(C(C)(C)C)cc(C3(C)CC3)c2)n1CC1CCCCC1] | $^1$H-NMR (400 MHz, DMSO-$d_6$) δ: 7.14 (m, 3H), 6.97 (s, 1H), 6.49 (d, 2H), 3.77 (d, 2H), 2.50 (m, 3H), 1.23-1.48 (m, 18H), 0.66-0.96 (m, 9H). MS (m/z): 407 (M + 1). |
| 1/90 | 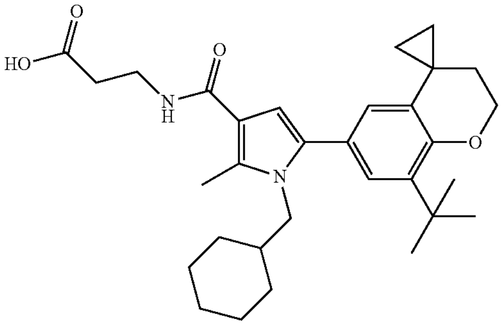 [SMILES: Cc1c(C(=O)NCCC(=O)O)cc(-c2cc(C(C)(C)C)c3c(c2)C2(CCO3)CC2)n1CC1CCCCC1] | $^1$H-NMR (400 MHz, $CDCl_3$) δ: 6.96 (s, 1H), 6.42 (s, 1H), 6.32 (m, 1H), 6.07 (s, 1H), 4.34 (t, 2H), 3.67 (m, 4H), 2.72 (t, 2H), 2.58 (s, 3H), 1.91 (t, 2H), 1.53 (m, 3H), 1.44 (m, 12H), 1.02 (m, 5H), 0.84 (m, 2H), 0.67 (m, 2H). MS (m/z): 507 (M + 1). |
| 1/91 | 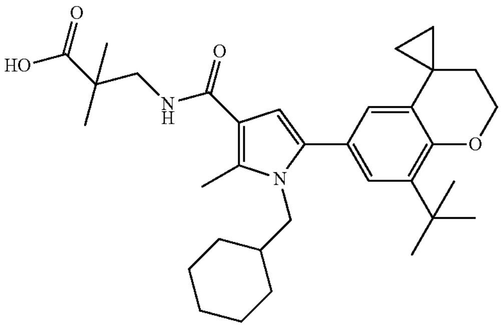 [SMILES: Cc1c(C(=O)NCC(C)(C)C(=O)O)cc(-c2cc(C(C)(C)C)c3c(c2)C2(CCO3)CC2)n1CC1CCCCC1] | $^1$H-NMR (400 MHz, $CDCl_3$) δ: 6.97 (s, 1H), 6.43 (s, 1H), 6.29 (m, 1H), 6.09 (s, 1H), 4.34 (t, 2H), 3.63 (d, 2H), 3.52 (d, 2H), 2.59 (s, 3H), 1.90 (t, 2H), 1.57 (m, 3H), 1.38 (m, 12H), 1.25 (m, 6H), 1.01 (m, 5H), 0.83 (m, 2H), 0.67 (m, 2H). MS (m/z): 534 (M + 1). |

-continued

| # | Structure | Analytical data |
| --- | --- | --- |
| 1/92 | 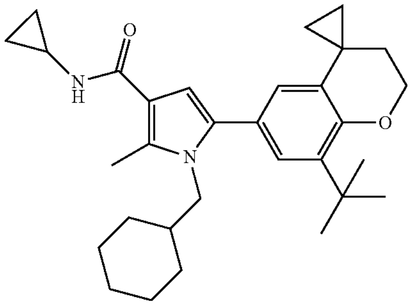 [SMILES: Cc1c(C(=O)NC2CC2)cc(-c2cc(C(C)(C)C)c3c(c2)C2(CCO3)CC2)n1CC1CCCCC1] | $^1$H-NMR (400 MHz, $CDCl_3$) δ: 6.96 (s, 1H), 6.42 (s, 1H), 6.00 (s, 1H), 5.83 (br s, 1H), 4.33 (t, 2H), 3.64 (d, 2H), 2.81 (s, 1H), 2.60 (s, 3H), 1.91 (t, 2H), 1.57 (m, 3H), 1.39 (m, 12H), 1.02 (m, 5H), 0.85 (m, 4H), 0.77 (m, 2H), 0.57 (m, 2H). MS (m/z): 475 (M + 1). |
| 1/93 | 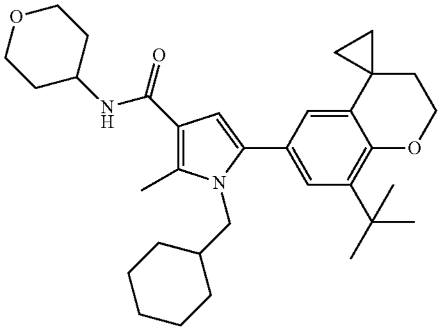 [SMILES: Cc1c(C(=O)NC2CCOCC2)cc(-c2cc(C(C)(C)C)c3c(c2)C2(CCO3)CC2)n1CC1CCCCC1] | $^1$H-NMR (400 MHz, $CDCl_3$) δ: 6.97 (s, 1H), 6.43 (s, 1H), 6.06 (s, 1H), 5.57 (d, 1H), 4.34 (t, 2H), 4.17 (s, 1H), 3.96 (m, 2H), 3.63 (d, 2H), 3.49 (t, 2H), 2.59 (s, 3H), 1.99 (d, 2H), 1.95 (t, 2H), 1.52 (m, 5H), 1.38 (m, 12H), 1.02 (m, 5H), 0.86 (m, 2H), 0.64 (m, 2H). MS (m/z): 519 (M + 1). |
| 1/94 | 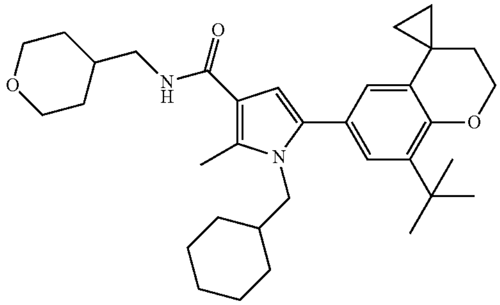 [SMILES: Cc1c(C(=O)NCC2CCOCC2)cc(-c2cc(C(C)(C)C)c3c(c2)C2(CCO3)CC2)n1CC1CCCCC1] | $^1$H-NMR (400 MHz, $CDCl_3$) δ: 6.97 (s, 1H), 6.43 (s, 1H), 6.05 (s, 1H), 5.83 (s, 1H), 4.34 (t, 2H), 3.99 (d, 2H), 3.64 (d, 2H), 3.37 (t, 2H), 3.26 (t, 2H), 2.59 (s, 3H), 1.91 (t, 3H), 1.84 (m, 2H), 1.57 (m, 3H), 1.34 (m, 12H), 1.02 (m, 5H), 0.86 (m, 2H), 0.69 (m, 2H). MS (m/z): 533 (M + 1). |
| 1/95 | 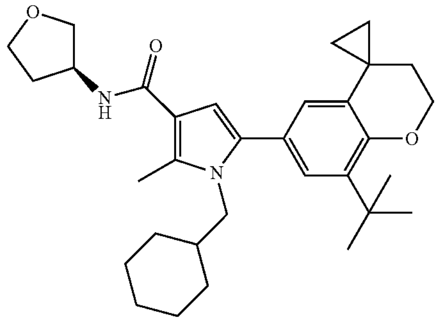 [SMILES: Cc1c(C(=O)N[C@H]2CCOC2)cc(-c2cc(C(C)(C)C)c3c(c2)C2(CCO3)CC2)n1CC1CCCCC1] | $^1$H-NMR (400 MHz, $CDCl_3$) δ: 6.96 (s, 1H), 6.42 (s, 1H), 6.06 (s, 1H), 5.85 (d, 1H), 4.69 (s, 1H), 4.34 (t, 2H), 3.94 (m, 2H), 3.84 (m, 2H), 3.71 (d, 2H), 2.58 (s, 3H), 2.31 (m, 1H), 1.90 (m, 3H), 1.56 (m, 3H), 1.38 (m, 12H), 1.02 (m, 5H), 0.84 (m, 2H), 0.65 (m, 2H). MS (m/z): 505 (M + 1). |
| 1/96 | 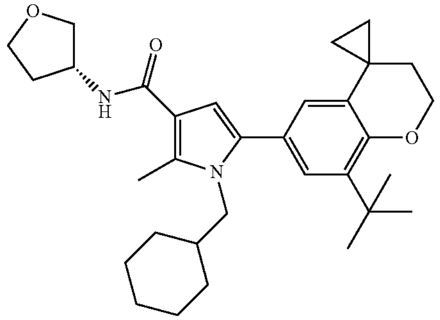 [SMILES: Cc1c(C(=O)N[C@@H]2CCOC2)cc(-c2cc(C(C)(C)C)c3c(c2)C2(CCO3)CC2)n1CC1CCCCC1] | $^1$H-NMR (400 MHz, $CDCl_3$) δ: 6.96 (s, 1H), 6.43 (s, 1H), 6.06 (s, 1H), 5.85 (d, 1H), 4.69 (s, 1H), 4.34 (t, 2H), 3.94 (m, 2H), 3.84 (m, 2H), 3.71 (d, 2H), 2.58 (s, 3H), 2.31 (m, 1H), 1.90 (m, 3H), 1.56 (m, 3H), 1.38 (m, 12H), 1.02 (m, 5H), 0.84 (m, 2H), 0.64 (m, 2H). MS (m/z): 505 (M + 1). |

-continued

| # | Structure | Analytical data |
|---|---|---|
| 1/97 | 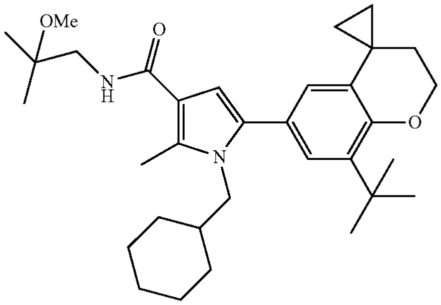 [SMILES: COC(C)(C)CNC(=O)c1cc(-c2cc(C(C)(C)C)c3c(c2)C2(CCO3)CC2)n(CC2CCCCC2)c1C] | $^1$H-NMR (400 MHz, $CDCl_3$) δ: 6.91 (s, 1H), 6.38 (s, 1H), 6.06 (s, 1H), 5.97 (d, 1H), 4.27 (t, 2H), 3.57 (d, 2H), 3.35 (d, 2H), 3.71 (d, 2H), 3.13 (s, 3H), 2.52 (s, 3H), 1.84 (m, 2H), 1.50 (m, 3H), 1.36 (m, 12H), 1.19 (s, 6H), 0.95 (m, 5H), 0.78 (m, 2H), 0.63 (m, 2H). MS (m/z): 521 (M + 1). |
| 1/98 | 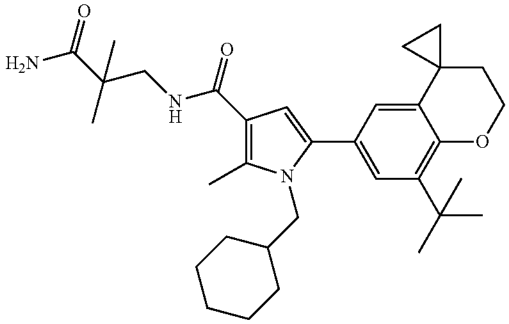 [SMILES: Cc1c(C(=O)NCC(C)(C)C(N)=O)cc(-c2cc(C(C)(C)C)c3c(c2)C2(CCO3)CC2)n1CC1CCCCC1] | $^1$H-NMR (400 MHz, $CDCl_3$) δ: 6.89 (s, 1H), 6.31 (m, 3H), 6.03 (s, 1H), 5.19 (s, 1H), 4.26 (t, 2H), 3.55 (d, 2H), 3.45 (d, 2H), 2.51 (s, 3H), 1.84 (t, 2H), 1.50 (m, 3H), 1.37 (m, 12H), 1.25 (s, 6H), 0.96 (m, 5H), 0.79 (m, 2H), 0.60 (m, 2H). MS (m/z): 534 (M + 1). |
| 1/99 | 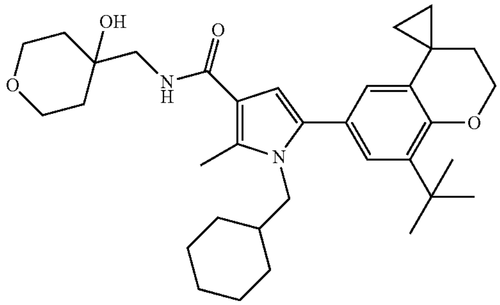 [SMILES: Cc1c(C(=O)NCC2(O)CCOCC2)cc(-c2cc(C(C)(C)C)c3c(c2)C2(CCO3)CC2)n1CC1CCCCC1] | $^1$H-NMR (400 MHz, $CDCl_3$) δ: 6.97 (s, 1H), 6.43 (s, 1H), 6.08 (d, 2H), 4.35 (t, 2H), 3.85 (m, 4H), 3.77 (d, 2H), 3.44 (s, 2H), 2.59 (s, 3H), 1.90 (t, 2H), 1.63 (m, 7H), 1.44 (m, 12H), 1.02 (m, 5H), 1.00 (m, 2H), 0.72 (m, 2H). MS (m/z): 549 (M + 1). |
| 1/100 | 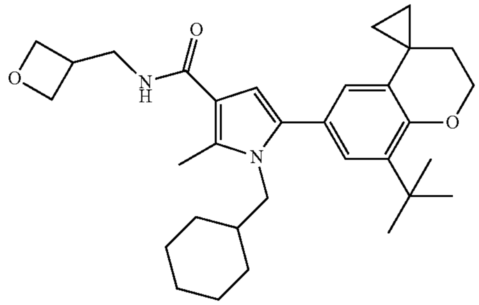 [SMILES: Cc1c(C(=O)NCC2COC2)cc(-c2cc(C(C)(C)C)c3c(c2)C2(CCO3)CC2)n1CC1CCCCC1] | $^1$H-NMR (400 MHz, $CDCl_3$) δ: 6.89 (s, 1H), 6.36 (s, 1H), 5.99 (s, 1H), 5.84 (t, 1H), 4.73 (t, 2H), 4.40 (t, 2H), 4.25 (t, 2H), 3.58 (m, 4H), 3.20 (m, 1H), 2.51 (s, 3H), 1.83 (m, 2H), 1.51 (m, 3H), 1.33 (m, 12H), 0.95 (m, 5H), 0.79 (m, 2H), 0.60 (m, 2H). MS (m/z): (M + 1). |
| 1/101 | 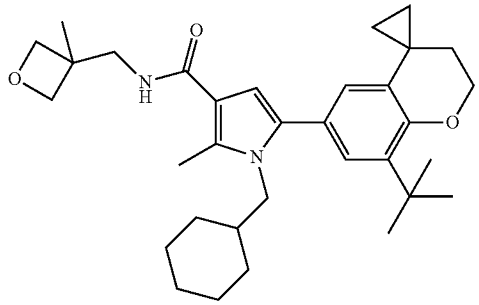 [SMILES: Cc1c(C(=O)NCC2(C)COC2)cc(-c2cc(C(C)(C)C)c3c(c2)C2(CCO3)CC2)n1CC1CCCCC1] | $^1$H-NMR (400 MHz, $CDCl_3$) δ: 6.97 (s, 1H), 6.43 (s, 1H), 6.10 (s, 1H), 6.00 (t, 1H), 4.54 (d, 2H), 4.38 (d, 2H), 4.32 (t, 2H), 3.63 (d, 2H), 3.55 (d, 2H), 2.59 (s, 3H), 1.90 (m, 2H), 1.56 (m, 3H), 1.26 (m, 15H), 1.01 (m, 5H), 0.85 (m, 2H), 0.68 (m, 2H). MS (m/z): 519 (M + 1). |

-continued

| # | Structure | Analytical data |
| --- | --- | --- |
| 1/102 | 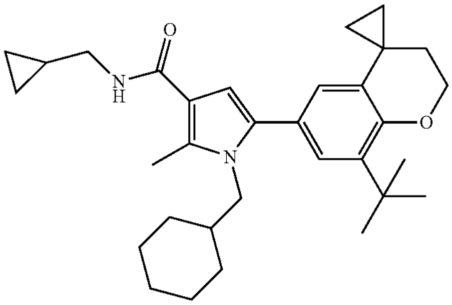 [SMILES: Cc1c(C(=O)NCC2CC2)cc(-c2cc(C(C)(C)C)c3c(c2)C2(CCO3)CC2)n1CC1CCCCC1] | $^1$H-NMR (400 MHz, $CDCl_3$) δ: 6.98 (s, 1H), 6.44 (s, 1H), 6.10 (s, 1H), 5.81 (s, 1H), 4.33 (t, 2H), 3.63 (d, 2H), 3.24 (d, 2H), 2.59 (s, 3H), 1.91 (m, 2H), 1.58 (m, 3H), 1.37 (m, 12H), 1.01 (m, 6H), 0.85 (m, 2H), 0.67 (m, 2H), 0.25 (m, 2H), 0.21 (m, 2H). MS (m/z): 489 (M + 1). |
| 1/103 | 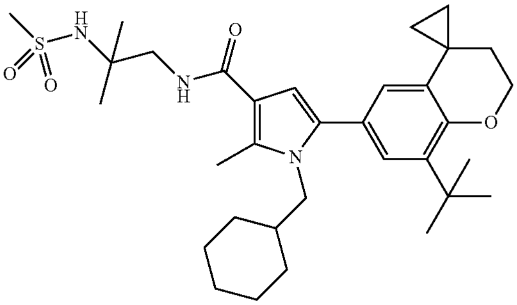 [SMILES: Cc1c(C(=O)NCC(C)(C)NS(C)(=O)=O)cc(-c2cc(C(C)(C)C)c3c(c2)C2(CCO3)CC2)n1CC1CCCCC1] | $^1$H-NMR (400 MHz, $CDCl_3$) δ: 6.90 (s, 1H), 6.37 (s, 1H), 6.21 (t, 1H), 6.06 (s, 1H), 5.56 (s, 1H), 4.25 (t, 2H), 3.56 (d, 2H), 3.38 (d, 2H), 2.94 (s, 3H), 2.51 (s, 3H), 1.83 (m, 2H), 1.50 (m, 3H), 1.33 (m, 18H), 0.96 (m, 5H), 0.78 (m, 2H), 0.61 (m, 2H). MS (m/z): 584 (M + 1). |
| 1/104 | 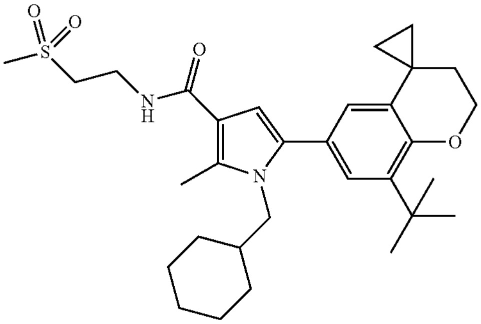 [SMILES: Cc1c(C(=O)NCCS(C)(=O)=O)cc(-c2cc(C(C)(C)C)c3c(c2)C2(CCO3)CC2)n1CC1CCCCC1] | $^1$H-NMR (400 MHz, $CDCl_3$) δ: 6.89 (s, 1H), 6.35 (m, 2H), 6.03 (s, 1H), 4.27 (t, 2H), 3.84 (m, 2H), 3.57 (d, 2H), 3.27 (t, 2H), 2.90 (s, 3H), 2.51 (s, 3H), 1.84 (m, 2H), 1.58 (m, 3H), 1.30 (m, 12H), 0.97 (m, 5H), 0.78 (m, 2H), 0.61 (m, 2H). MS (m/z): 541 (M + 1). |
| 1/105 | 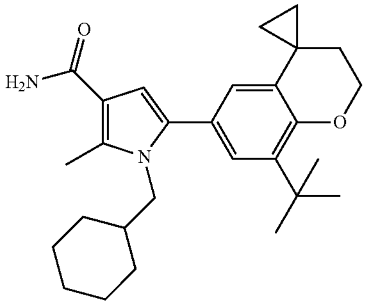 [SMILES: Cc1c(C(N)=O)cc(-c2cc(C(C)(C)C)c3c(c2)C2(CCO3)CC2)n1CC1CCCCC1] | $^1$H-NMR (400 MHz, $CDCl_3$) δ: 6.91 (s, 1H), 6.37 (s, 1H), 6.04 (t, 1H), 5.45 (s, 2H), 4.27 (t, 2H), 3.37 (d, 2H), 2.52 (s, 3H), 1.84 (m, 2H), 1.51 (m, 3H), 1.29 (m, 12H), 0.94 (m, 5H), 0.79 (m, 2H), 0.61 (m, 2H). MS (m/z): 435 (M + 1). |
| 1/106 | 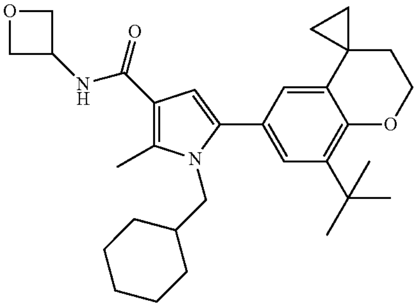 | $^1$H-NMR (400 MHz, DMSO-$d_6$) δ: 8.22 (d, 1H), 7.49 (s, 1H), 7.18 (d, 2H), 6.59 (s, 1H), 5.05 (s, 1H), 4.94 (m, 1H), 4.71 (t, 2H), 4.55 (t, 2H), 3.77 (d, 2H), 2.50 (s, 3H), 1.44 (s, 9H), 1.31 (s, 9H), 1.21 (m, 3H), 0.92 (m, 3H), 0.59 (m, 2H). MS (m/z): 467 (M + 1). |

-continued

| # | Structure | Analytical data |
|---|---|---|
| 1/107 | 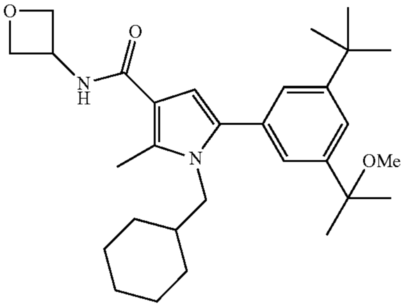 [SMILES: COC(C)(C)c1cc(-c2cc(C(=O)NC3COC3)c(C)n2CC2CCCCC2)cc(C(C)(C)C)c1] | $^1$H-NMR (400 MHz, $CDCl_3$) δ: 7.42 (s, 1H), 7.23 (s, 1H), 7.10 (s, 1H), 6.25 (s, 1H), 6.18 (d, 1H), 5.24 (m, 1H), 4.97 (t, 2H), 4.56 (t, 2H), 3.73 (d, 2H), 3.09 (s, 3H), 2.60 (s, 3H), 1.53 (m, 9H), 1.37 (m, 12H), 0.97 (m, 3H), 0.61 (m, 2H). MS (m/z): 481 (M + 1). |
| 1/108 | 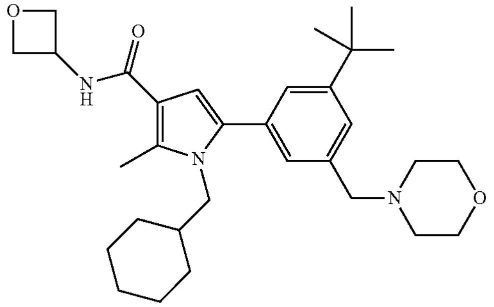 [SMILES: Cc1c(C(=O)NC2COC2)cc(-c2cc(CN3CCOCC3)cc(C(C)(C)C)c2)n1CC1CCCCC1] | $^1$H-NMR (400 MHz, DMSO-$d_6$) δ: 8.22 (d, 1H), 7.26 (s, 2H), 7.13 (s, 1H), 6.61 (s, 1H), 4.98 (m, 1H), 4.73 (t, 2H), 4.53 (t, 2H), 3.78 (d, 2H), 3.57 (t, 3H), 3.51 (s, 2H), 2.36 (s, 4H), 1.45 (d, 3H), 1.24 (m, 12H), 086 (m, 3H), 0.56 (m, 2H). MS (m/z): 508 (M + 1). |
| 1/109 | 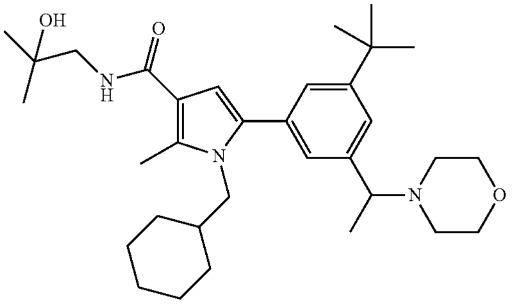 [SMILES: Cc1c(C(=O)NCC(C)(C)O)cc(-c2cc(C(C)N3CCOCC3)cc(C(C)(C)C)c2)n1CC1CCCCC1] | $^1$H-NMR (400 MHz, DMSO-$d_6$) δ: 7.48 (t, 1H), 7.24 (s, 2H), 7.10 (s, 1H), 6.54 (s, 1H), 4.64 (m, 1H), 3.78 (t, 2H), 3.55 (m, 4H), 3.40 (m, 1H), 3.16 (d, 2H), 2.52 (s, 3H), 2.29 (m, 2H), 2.26 (m, 2H), 1.45 (m, 3H), 1.31 (m, 12H), 1.23 (m, 3H), 1.08 (s, 6H), 0.92 (m, 3H), 0.59 (m, 2H). MS (m/z): 538 (M + 1). |
| 1/110 | 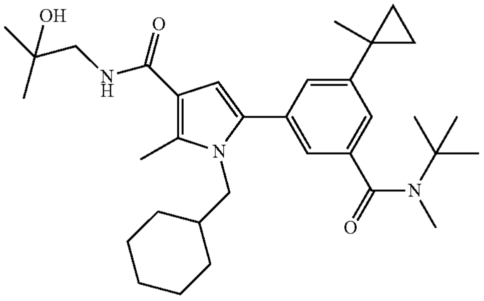 [SMILES: Cc1c(C(=O)NCC(C)(C)O)cc(-c2cc(C(=O)N(C)C(C)(C)C)cc(C3(C)CC3)c2)n1CC1CCCCC1] | $^1$H-NMR (400 MHz, DMSO-$d_6$) δ: 7.47 (t, 1H), 7.23 (s, 1H), 7.16 (s, 1H), 7.11 (s, 1H), 6.61 (s, 1H), 3.81 (d, 2H), 3.17 (d, 2H), 2.81 (s, 3H), 2.50 (s, 3H), 1.41 (m, 15H), 1.24 (m, 3H), 1.07 (s, 6H), 0.63-0.89 (m, 8H). MS (m/z): 536 (M + 1). |
| 1/111 | 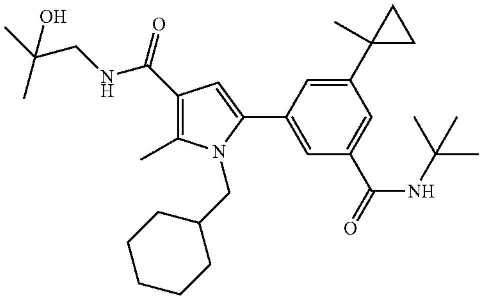 [SMILES: Cc1c(C(=O)NCC(C)(C)O)cc(-c2cc(C(=O)NC(C)(C)C)cc(C3(C)CC3)c2)n1CC1CCCCC1] | $^1$H-NMR (400 MHz, DMSO-$d_6$) δ: 7.82 (s, 1H), 7.64 (s, 1H), 7.59 (s, 1H), 7.47 (m, 1H), 7.32 (s, 1H), 6.62 (s, 1H), 4.64 (s, 1H), 3.82 (d, 2H), 3.16 (d, 2H), 2.54 (s, 3H), 1.46 (m, 15H), 1.30 (m, 3H), 1.11 (s, 6H), 0.63-0.97 (m, 8H). MS (m/z): 522 (M + 1). |

-continued

| # | Structure | Analytical data |
|---|---|---|
| 1/112 | 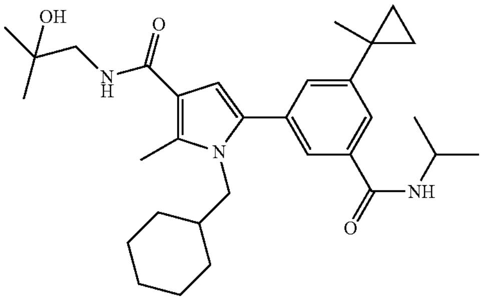 [SMILES: Cc1c(C(=O)NCC(C)(C)O)cc(-c2cc(C(=O)NC(C)C)cc(C3(C)CC3)c2)n1CC1CCCCC1] | $^1$H-NMR (400 MHz, DMSO-$d_6$) δ: 8.28 (d, 1H), 7.68 (d, 2H), 7.48 (t, 1H), 7.34 (s, 2H), 6.63 (s, 1H), 4.64 (s, 1H), 4.13 (m, 1H), 3.83 (d, 2H), 3.16 (d, 2H), 2.49 (s, 3H), 1.17-1.48 (m, 15H), 1.08 (s, 6H), 0.63-0.90 (m, 9H). MS (m/z): 508 (M + 1). |
| 1/113 | 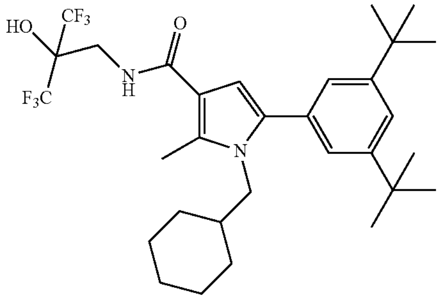 [SMILES: Cc1c(C(=O)NCC(O)(C(F)(F)F)C(F)(F)F)cc(-c2cc(C(C)(C)C)cc(C(C)(C)C)c2)n1CC1CCCCC1] | $^1$H-NMR (400 MHz, $CDCl_3$) δ: 8.05 (s, 1H), 7.43 (s, 1H), 7.16 (s, 2H), 6.25 (t, J = 5.6 Hz, 1H), 6.23 (s, 1H), 3.93 (d, J = 6.0 Hz, 2H), 3.74 (d, J = 7.2 Hz, 2H), 2.61 (s, 3H), 1.56-1.51 (m, 4H), 1.36 (s, 18H), 1.40-1.25 (m, 4H), 1.02-0.87 (m, 3H), 0.67-0.64 (m, 2H). MS: 589 (M + 1). |
| 1/114 | 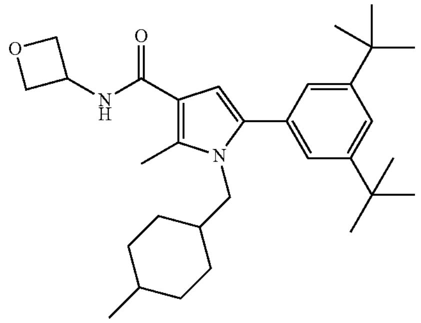 [SMILES: Cc1c(C(=O)NC2COC2)cc(-c2cc(C(C)(C)C)cc(C(C)(C)C)c2)n1CC1CCC(C)CC1] | $^1$H-NMR (400 MHz, $CD_3OD$) δ: 7.34 (s, 1H), 7.10 (m, 2H), 6.41 (s, 1H), 4.96 (m, 1H), 4.62 (m, 2H), 4.58 (t, J = 6.8 Hz, 2H), 3.93-3.70 (m, 2H), 2.44 (m, 3H), 1.47-1.26 (m, 1H), 1.26-1.02 (m, 24H), 0.70-0.42 (m, 6H). MS: 479.4 $(M + 1)^+$. |
| 1/115 | 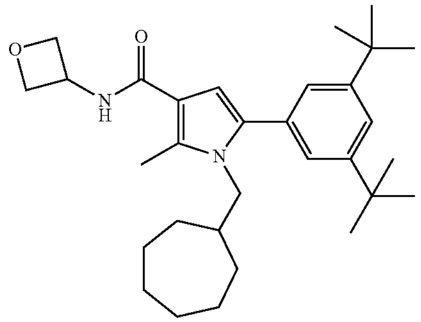 [SMILES: Cc1c(C(=O)NC2COC2)cc(-c2cc(C(C)(C)C)cc(C(C)(C)C)c2)n1CC1CCCCCC1] | $^1$H-NMR (400 MHz, $CDCl_3$) δ: 7.42 (s, 1H), 7.18 (s, 2H), 6.29-6.26 (m, 2H), 5.26 (m, 1H), 5.01 (t, J = 6.8 Hz, 2H), 4.61 (t, J = 6.4 Hz, 2H), 3.73 (d, J = 7.6 Hz, 2H), 2.62 (s, 3H), 1.27-1.55 (m, 27H), 0.89-1.21 (m, 4H). MS: 479.4 $(M + 1)^+$. |
| 1/116 | 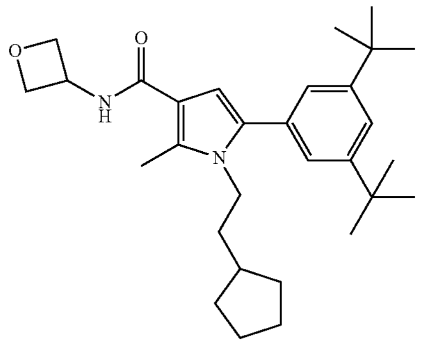 [SMILES: Cc1c(C(=O)NC2COC2)cc(-c2cc(C(C)(C)C)cc(C(C)(C)C)c2)n1CCC1CCCC1] | $^1$H-NMR (400 MHz, DMSO-$d_6$) δ: 8.23 (d, J = 5.2 Hz, 1H), 7.40 (s, 1H), 7.17 (s, 2H), 6.58 (s, 1H), 4.97 (m, 1H), 4.72 (t, J = 6.8 Hz, 2H), 4.55 (t, J = 6.4 Hz, 2H), 3.84 (m, 2H), 2.53 (m, 3H), 1.35-1.56 (m, 27H), 0.84 (m, 2H). MS: 465.4 $(M + 1)^+$. |

-continued
| # | Structure | Analytical data |
|---|---|---|
| 1/117 | 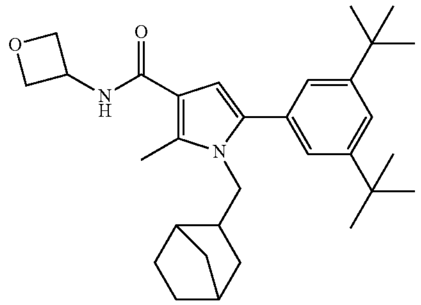 [SMILES: Cc1c(C(=O)NC2COC2)cc(-c2cc(C(C)(C)C)cc(C(C)(C)C)c2)n1CC1CC2CCC1C2] | $^1$H-NMR (400 MHz, $CDCl_3$) δ: 7.29 (s, 1H), 7.05 (s, 2H), 6.26 (m, 1H), 6.16 (m, 1H), 5.10 (m, 1H), 4.85 (t, J = 6.8 Hz, 2H), 4.47 (m, 2H), 3.53-3.84 (m, 2H), 2.50 (m, 3H), 1.12-1.89 (m, 23H), 0.27-0.85 (m, 6H). MS: 477.1 $(M + 1)^+$. |
| 1/118 | 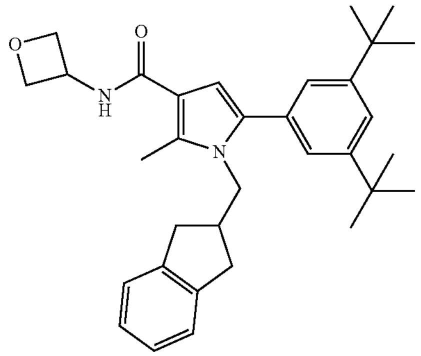 [SMILES: Cc1c(C(=O)NC2COC2)cc(-c2cc(C(C)(C)C)cc(C(C)(C)C)c2)n1CC1Cc2ccccc2C1] | $^1$H-NMR (400 MHz, $CDCl_3$) δ: 7.28 (m, 1H), 7.09 (m, 2H), 6.95 (m, 4H), 6.22-6.18 (m, 2H), 5.18 (m, 1H), 4.93 (t, J = 6.8 Hz, 2H), 4.51 (t, J = 6.8 Hz, 2H), 3.94 (d, J = 7.6 Hz, 2H), 2.65 (m, 2H), 2.56-2.48 (m, 4H), 2.29 (m, 2H), 1.24 (s, 18H). MS: 499.4 $(M + 1)^+$. |
| 1/119 | 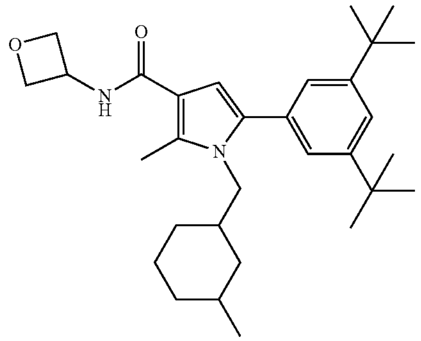 [SMILES: Cc1c(C(=O)NC2COC2)cc(-c2cc(C(C)(C)C)cc(C(C)(C)C)c2)n1CC1CCCC(C)C1] | $^1$H-NMR (400 MHz, $CDCl_3$) δ: 7.40 (m, 1H), 7.17 (m, 2H), 6.20 (m, 2H), 5.24 (m, 1H), 4.99 (t, J = 6.8 Hz, 2H), 4.58 (m, 2H), 3.70-3.91 (m, 2H), 2.60 (s, 3H), 1.31-1.62 (m, 22H), 0.23-0.98 (m, 9H). MS: 479.6 $(M + 1)^+$. |
| 1/120 | 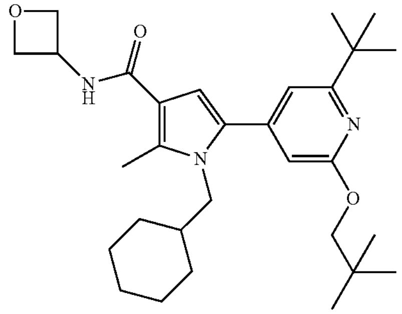 [SMILES: Cc1c(C(=O)NC2COC2)cc(-c2cc(OCC(C)(C)C)nc(C(C)(C)C)c2)n1CC1CCCCC1] | $^1$H-NMR ($CDCl_3$, 300 MHz) δ: 0.67-0.68 (2H, m), 0.87-1.03 (12H, m), 1.33-1.36 (12H, m), 1.56-1.57 (2H, m), 2.59 (3H, s), 3.82-3.84 (2H, d, J = 7.2 Hz), 4.06 (2H, s), 4.57 (2H, t, J = 6.6 Hz), 5.20 (2H, t, J = 6.6 Hz), 5.18-5.23 (1H, m), 6.17-6.19 (1H, m), 6.32 (1H, s), 6.50 (1H, s), 6.80 (1H, s). MS: 496.5 (M + 1). |

-continued

| # | Structure | Analytical data |
|---|---|---|
| 1/121 | 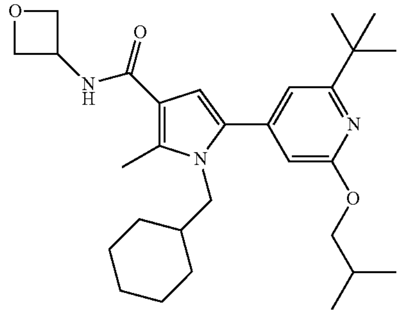 [SMILES: Cc1c(C(=O)NC2COC2)cc(-c2cc(OCC(C)C)nc(C(C)(C)C)c2)n1CC1CCCCC1] | $^1$H-NMR ($CDCl_3$, 300 MHz) δ: 0.65-0.74 (2H, m), 0.97-1.06 (6H, m), 1.29-1.34 (9H, m), 1.53-1.58 (4H, m), 1.96-2.00 (2H, m), 2.06-2.13 (1H, m), 2.61 (3H, s), 3.48-3.56 (2H, m), 3.82 (2H, d, J = 9.9 Hz), 3.99-4.01 (2H, m), 4.11-4.17 (3H, m), 5.58-5.61 (1H, m), 6.26 (1H, s), 6.48 (1H, s), 6.80 (1H, s). MS: 482.5 (M + 1). |
| 1/122 | 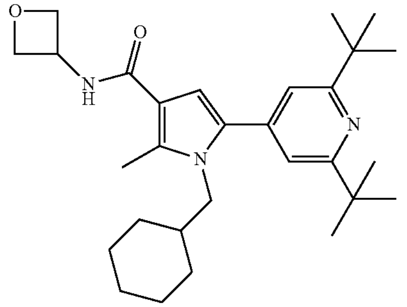 [SMILES: Cc1c(C(=O)NC2COC2)cc(-c2cc(C(C)(C)C)nc(C(C)(C)C)c2)n1CC1CCCCC1] | $^1$H-NMR ($CDCl_3$, 400 MHz) δ: 0.67-0.69 (2H, m), 0.98-1.02 (3H, m), 1.36 (18H, m), 1.57 (6H, m), 2.60 (3H, s), 3.78-3.80 (2H, d, J = 7.2 Hz), 4.58 (2H, t, J = 6.8 Hz), 4.99 (2H, t, J = 6.8 Hz), 5.21-5.23 (1H, m), 6.19-6.21 (1H, m), 6.32 (1H, s), 7.05 (2H, s). MS: 466.2 (M + 1). |
| 1/123 | 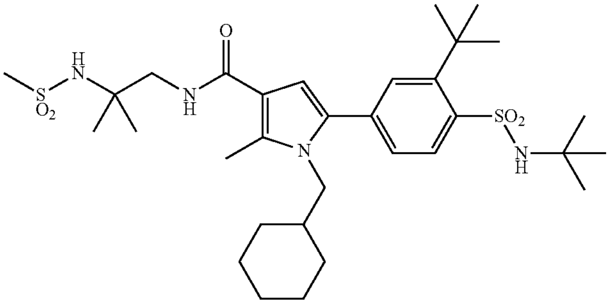 [SMILES: Cc1c(C(=O)NCC(C)(C)NS(C)(=O)=O)cc(-c2ccc(S(=O)(=O)NC(C)(C)C)c(C(C)(C)C)c2)n1CC1CCCCC1] | $^1$H-NMR (400 MHz, $CDCl_3$) δ: 8.18 (d, J = 8.4 Hz, 1H), 7.59 (s, 1H), 7.27 (m, 1H), 6.43 (m, 1H), 6.35 (s, 1H), 4.52 (s, 1H), 3.79 (d, J = 7.2 Hz, 2H), 3.49 (d, J = 6.4 Hz, 2H), 3.04 (s, 3H), 2.62 (s, 3H), 1.62 (m, 9H), 1.54 (m, 3H), 1.46 (m, 6H), 1.26 (m, 12H), 0.97 (m, 3H), 0.60 (m, 2H). MS: 637.3 (M + 1). |
| 1/124 | 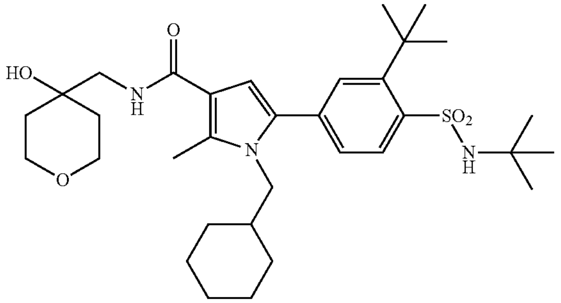 [SMILES: Cc1c(C(=O)NCC2(O)CCOCC2)cc(-c2ccc(S(=O)(=O)NC(C)(C)C)c(C(C)(C)C)c2)n1CC1CCCCC1] | $^1$H-NMR (400 MHz, $CDCl_3$) δ: 8.18 (d, J = 8.0 Hz, 1H), 7.58 (s, 1H), 7.24 (m, 1H), 6.30 (s, 1H), 6.17 (m, 1H), 4.49 (s, 1H), 3.86-3.72 (m, 6H), 3.45 (m, 2H), 2.62 (s, 3H), 1.53-1.70 (m, 16H), 1.34-1.31 (m, 12H), 0.98 (m, 3H), 0.60 (m, 2H). MS: 602.3 (M + 1). |
| 1/125 | 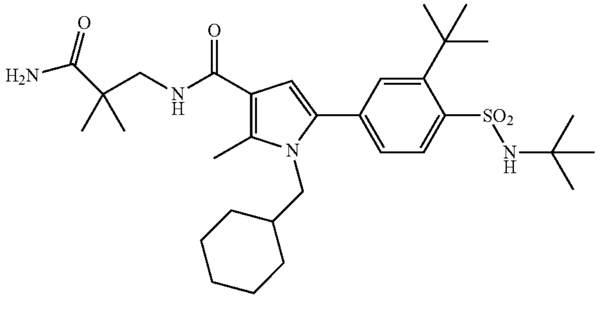 [SMILES: Cc1c(C(=O)NCC(C)(C)C(N)=O)cc(-c2ccc(S(=O)(=O)NC(C)(C)C)c(C(C)(C)C)c2)n1CC1CCCCC1] | $^1$H-NMR (400 MHz, $CDCl_3$) δ: 8.17 (d, J = 8.4 Hz, 1H), 7.58 (s, 1H), 7.24 (m, 1H), 6.52 (m, 1H), 6.30 (s, 1H), 6.17 (br s, 1H), 5.28 (br s, 1H), 4.54 (m, 1H), 3.76 (m, 2H), 3.54 (m, 2H), 2.61 (s, 3H), 1.45-1.62 (m, 12H), 1.35-1.31 (m, 18H), 0.98 (m, 3H), 0.60 (m, 2H). MS: 587.4 (M + 1). |

-continued

| # | Structure | Analytical data |
| --- | --- | --- |
| 1/126 | 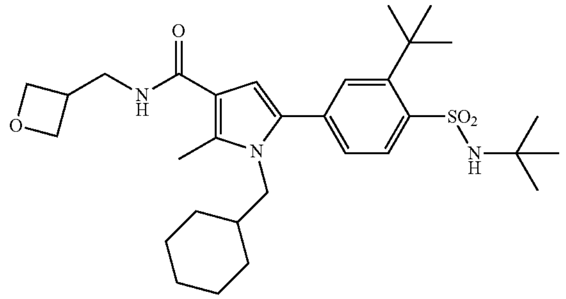 [SMILES: Cc1c(C(=O)NCC2COC2)cc(-c2ccc(S(=O)(=O)NC(C)(C)C)c(C(C)(C)C)c2)n1CC1CCCCC1] | $^1$H-NMR (400 MHz, DMSO-$d_6$) δ: 8.14 (d, J = 8.0 Hz, 1H), 7.85 (m, 1H), 7.82 (s, 1H), 7.52 (s, 1H), 7.42 (m, 1H), 6.64 (s, 1H), 4.60 (m, 2H), 4.32 (t, J = 6.0 Hz, 2H), 3.82 (m, 2H), 3.42 (m, 2H), 3.10 (m, 1H), 2.52 (s, 3H), 1.54 (s, 9H), 1.43 (m, 3H), 1.18 (m, 12H), 0.88 (m, 3H), 0.59 (m, 2H). MS: 558.7 (M + 1). |
| 1/127 | 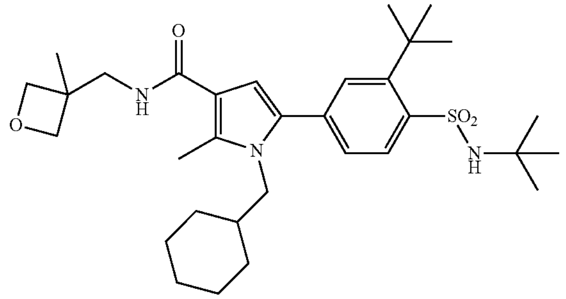 [SMILES: Cc1c(C(=O)NCC2(C)COC2)cc(-c2ccc(S(=O)(=O)NC(C)(C)C)c(C(C)(C)C)c2)n1CC1CCCCC1] | $^1$H-NMR (400 MHz, DMSO-$d_6$) δ: 8.17 (d, J = 8.4 Hz, 1H), 7.89 (m, 1H), 7.86 (s, 1H), 7.56 (s, 1H), 7.46 (m, 1H), 6.73 (s, 1H), 4.50 (d, J = 5.6 Hz, 2H), 4.18 (d, J = 5.6 Hz, 2H), 3.87 (m, 2H), 3.39 (m, 2H), 2.58-2.54 (m, 3H), 1.58 (s, 9H), 1.46 (m, 3H), 1.26-1.22 (m, 6H), 1.23 (s, 9H), 0.89 (m, 3H), 0.66 (m, 2H). MS: 572.2 $(M + 1)^+$. |
| 1/128 | 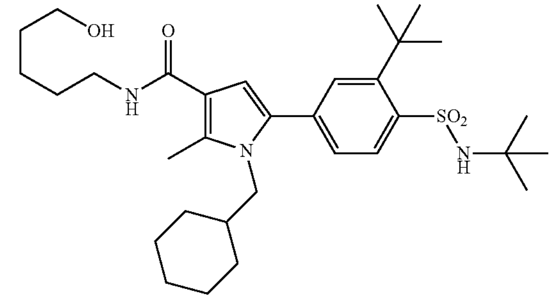 [SMILES: Cc1c(C(=O)NCCCCCO)cc(-c2ccc(S(=O)(=O)NC(C)(C)C)c(C(C)(C)C)c2)n1CC1CCCCC1] | $^1$H-NMR (400 MHz, DMSO-$d_6$) δ: 8.13 (d, J = 8.4 Hz, 1H), 7.73 (s, 1H), 7.65 (m, 1H), 7.52 (s, 1H), 7.40 (m, 1H), 6.65 (s, 1H), 4.34 (m, 1H), 3.82 (m, 2H), 3.37 (m, 2H), 3.12 (m, 2H), 2.52 (s, 3H), 1.54 (s, 9H), 1.51-1.38 (m, 7H), 1.31 (m, 2H), 1.22-1.06 (m, 12H), 0.89 (m, 3H), 0.65 (m, 2H). MS: 574.1 $(M + 1)^+$. |
| 1/129 | 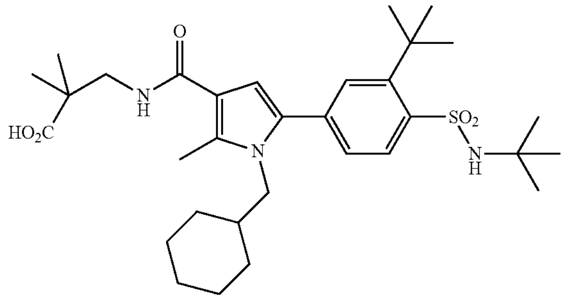 [SMILES: Cc1c(C(=O)NCC(C)(C)C(=O)O)cc(-c2ccc(S(=O)(=O)NC(C)(C)C)c(C(C)(C)C)c2)n1CC1CCCCC1] | $^1$H-NMR (400 MHz, $CDCl_3$) δ: 8.16 (d, J = 8.4 Hz, 1H), 7.57 (s, 1H), 7.25 (m, 1H), 6.39 (m, 1H), 6.27 (s, 1H), 4.83 (s, 1H), 3.77 (m, 2H), 3.53 (m, 2H), 2.60 (s, 3H), 1.61 (s, 9H), 1.58 (m, 3H), 1.29 (m, 18H), 0.98 (m, 3H), 0.59 (m, 2H). MS: 588.3 $(M + 1)^+$. |
| 1/130 | 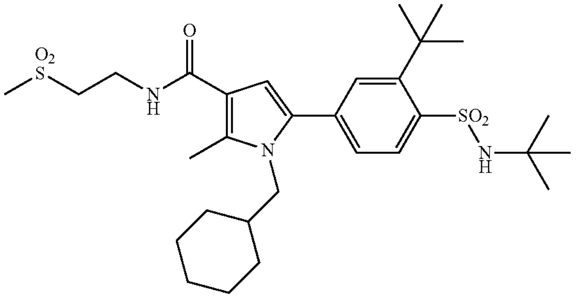 [SMILES: Cc1c(C(=O)NCCS(C)(=O)=O)cc(-c2ccc(S(=O)(=O)NC(C)(C)C)c(C(C)(C)C)c2)n1CC1CCCCC1] | $^1$H-NMR (400 MHz, DMSO-$d_6$) δ: 8.12 (d, J = 8.4 Hz, 1H), 7.95 (m, 1H), 7.74 (s, 1H), 7.52 (s, 1H), 7.40 (m, 1H), 6.62 (s, 1H), 3.85 (m, 2H), 3.59 (m, 2H), 3.29 (m, 2H), 3.01 (s, 3H), 2.53 (s, 3H), 1.54 (s, 9H), 1.45 (m, 3H), 1.16 (m, 12H), 0.87 (m, 3H), 0.56 (m, 2H). MS: 594.0 $(M + 1)^+$. |

-continued

| # | Structure | Analytical data |
|---|---|---|
| 1/131 | 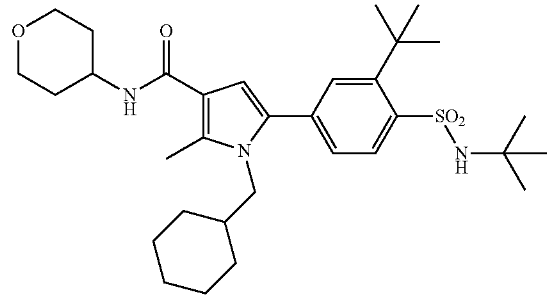 [SMILES: Cc1c(C(=O)NC2CCOCC2)cc(-c2ccc(S(=O)(=O)NC(C)(C)C)c(C(C)(C)C)c2)n1CC1CCCCC1] | $^1$H-NMR (400 MHz, DMSO-$d_6$) δ: 8.14 (d, J = 8.4 Hz, 1H), 7.74 (s, 1H), 7.52 (s, 1H), 7.46 (m, 1H), 7.40 (m, 1H), 6.69 (s, 1H), 4.01-3.81 (m, 5H), 3.35 (m, 2H), 2.52 (s, 3H), 1.71 (m, 2H), 1.60-1.40 (m, 14H), 1.25-1.05 (m, 12H), 0.92-0.81 (m, 3H), 0.59 (m, 2H). MS: 572.1 $(M + 1)^+$. |
| 1/132 | 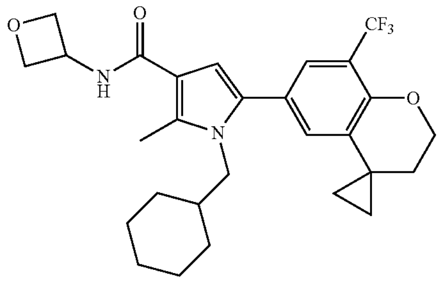 [SMILES: Cc1c(C(=O)NC2COC2)cc(-c2cc(C(F)(F)F)c3c(c2)C2(CCO3)CC2)n1CC1CCCCC1] | $^1$H-NMR ($CDCl_3$, 300 MHz) δ: 0.68-0.69 (2H, m), 0.85-0.96 (2H, m), 0.99-1.08 (3H, m), 1.20-1.42 (5H, m), 1.59-1.62 (3H, m), 1.94 (2H, t, J = 5.1 Hz), 2.57 (3H, s), 3.65 (2H, d, J = 7.2 Hz), 4.44 (2H, t, J = 5.1 Hz), 4.56 (2H, t, J = 6.9 Hz), 4.98 (2H, t, J = 6.9 Hz), 5.20 (1H, m), 6.14-6.15 (2H, m), 6.73 (1H, d, J = 1.8 Hz), 7.28 (1H, d, J = 1.8 Hz). MS: 503 $(M + 1)^+$. |

Example 2

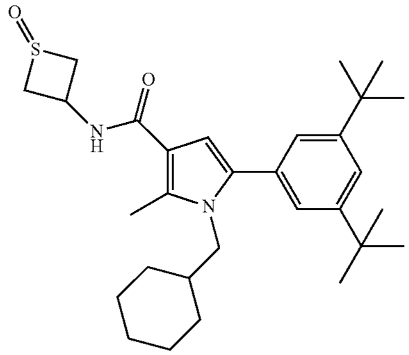

2

Step 1: 1-(Cyclohexylmethyl)-5-(3,5-di-tert-butylphenyl)-2-methyl-N-(1-oxidothietan-3-yl)-1H-pyrrole-3-carboxamide (2)

A solution of compound of Example 1/14 (96 mg, 0.2 mmol) in DCM (6 mL) was treated with m-chloroperoxybenzoic acid (99 mg, 0.4 mmol) in an ice-bath for 1 h and then allowed to warm to rt and stirred for 3 h. The mixture was quenched with aq. $Na_2SO_3$ and extracted with EA (3×30 mL). The organic layer was separated and washed with brine and dried over $Na_2SO_4$. After filtration, the filtrate was evaporated and purified by prep. HPLC to give the target compound 2 (38 mg, 40%). $^1$H-NMR (400 MHz, DMSO-$d_6$) δ: 8.15 (d, J=8.0 Hz, 1H), 7.36 (s, 1H), 7.16 (d, J=1.6 Hz, 2H), 6.53 (s, 1H), 4.40-4.33 (m, 1H), 4.04-3.99 (m, 2H), 3.77 (d, J=6.8 Hz, 2H), 3.30-3.27 (m, 2H), 2.50 (s, 3H), 1.45-1.38 (m, 3H), 1.31-1.16 (m, 21H), 0.97-0.85 (m, 3H), 0.67-0.57 (m, 2H). MS: 497.1 (M+1).

Examples 2/1 to 2/3

The following Examples were prepared from the corresponding thioether similar as described in Example 2:

| # | Structure | Analytical data |
|---|---|---|
| 2/1 | 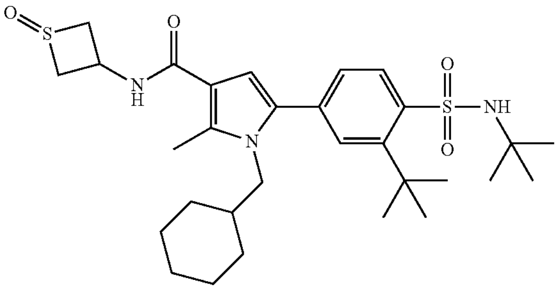 [SMILES: Cc1c(C(=O)NC2CS(=O)C2)cc(-c2ccc(S(=O)(=O)NC(C)(C)C)c(C(C)(C)C)c2)n1CC1CCCCC1] | $^1$H-NMR (400 MHz, $CDCl_3$) δ: 8.19 (d, J = 8.4 Hz, 1H), 7.58 (d, 1H), 7.24 (d, 1H), 6.37-6.34 (m, 2H), 4.74-4.67 (m, 2H), 4.21-4.16 (m, 2H), 3.78 (d, J = 6.8 Hz, 2H), 3.35-3.30 (m, 2H), 2.60 (s, 3H), 1.61 (s, 9H), 1.58-1.53 (m, 3H), 1.34-1.25 (m, 12H), 0.99-0.96 (d, 3H), 0.68-0.60 (m, 2H). MS: 576.0 (M + 1). |

-continued

| # | Structure | Analytical data |
| --- | --- | --- |
| 2/2 | 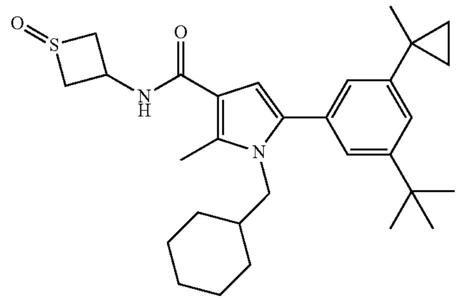 | $^1$H-NMR (400 MHz, $CDCl_3$) δ: 7.28-7.27 (m, 1H), 7.13 (t, 1H), 7.00 (t, 1H), 6.18 (s, 1H), 6.02 (d, J = 7.2 Hz, 1H), 4.66-4.59 (m, 1H), 4.19-4.13 (m, 2H), 3.72 (d, J = 7.2 Hz, 2H), 3.22-3.16 (m, 2H), 2.59 (s, 3H), 1.53 (m, 3H), 1.42 (m, 3H), 1.41-1.31 (m, 12H), 1.00-0.98 (m, 3H), 0.89-0.86 (m, 2H), 0.77-0.74 (m, 2H), 0.66-0.63 (m, 2H). MS: 595.0 (M + 1). |
| 2/3 | 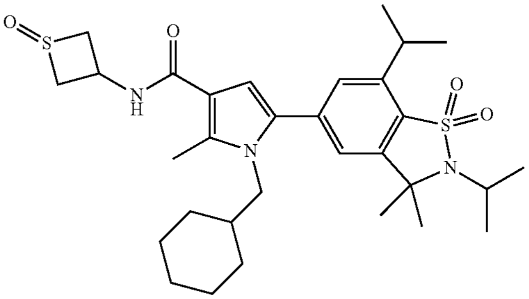 [SMILES: Cc1c(C(=O)NC2CS(=O)C2)cc(-c2cc(C(C)C)c3c(c2)C(C)(C)N(C(C)C)S3(=O)=O)n1CC1CCCCC1] | $^1$H-NMR (400 MHz, $CDCl_3$) δ: 7.31 (s, 1H), 7.10 (s, 1H), 6.31 (s, 1H), 6.26 (d, J = 8.0 Hz, 1H), 4.69-4.63 (m, 1H), 4.19-4.14 (m, 2H), 3.80-3.73 (m, 4H), 3.28-3.22 (m, 2H), 2.60 (s, 3H), 1.66-1.55 (m, 15H), 1.38-1.30 (m, 9H), 1.02-0.98 (m, 3H), 0.65-0.61 (m, 2H). MS: 588.3 (M + 1). |

Example 3

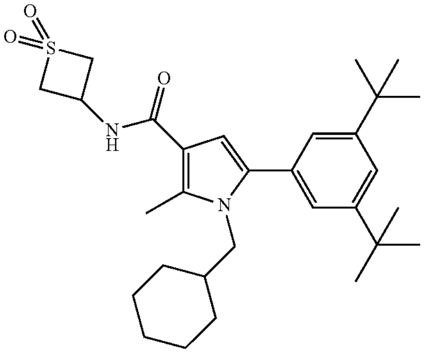

3

Step 1: 1-(Cyclohexylmethyl)-5-(3,5-di-tert-butylphenyl)-N-(1,1-dioxidothietan-3-yl)-2-methyl-1H-pyrrole-3-carboxamide (3)

To a solution of compound 2 (67 mg, 0.14 mmol) in DCM (2 mL), cooled to 0° C., was added titanium isopropoxide (42 μL, 0.14 mmol) followed by hydrogen peroxide (58 μL, 0.56 mmol) and the solution was stirred at 0° C. for 15 min. The ice-bath was removed and stirring was continued at rt for 1 h. The mixture was diluted with DCM (10 mL) and quenched by addition of $H_2O$ (10 mL). The organic layers was separated and washed with brine and dried over $Na_2SO_4$. After filtration, the filtrate was evaporated and purified by prep. HPLC to give the target compound 3 (40 mg, 56%). $^1$H-NMR (400 MHz, DMSO-$d_6$) δ: 8.20 (d, J=3.6 Hz, 1H), 7.37 (s, 1H), 7.16 (d, J=1.6 Hz, 2H), 6.55 (s, 1H), 4.53-4.47 (m, 3H), 4.28-4.23 (m, 2H), 3.77 (d, J=7.2 Hz, 2H), 2.52 (s, 3H), 1.45-1.43 (m, 3H), 1.31-1.20 (m, 21H), 0.94-0.86 (m, 3H), 0.66-0.61 (m, 2H). MS: 513.3 (M+1).

Example 4

4

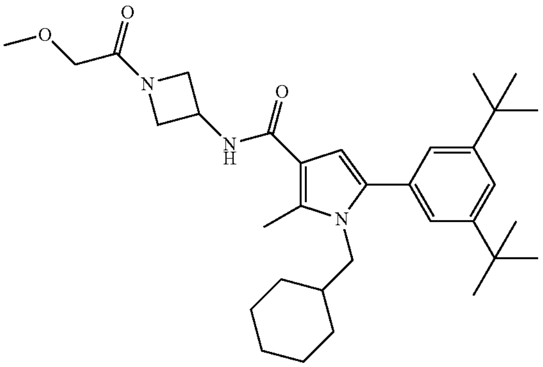

Step 1: N-(Azetidin-3-yl)-1-(cyclohexylmethyl)-5-(3,5-di-tert-butylphenyl)-2-methyl-1H-pyrrole-3-carboxamide hydrochloride (4a)

Compound of Example 1/15 (400 mg, 0.71 mmol) was treated with $HCl/CH_3OH$ (20 mL) at rt for 18 h. The solvent was evaporated to give intermediate 4a (355 mg, 100%) as a colorless solid, which was used without further purification.

Step 2: 1-(Cyclohexylmethyl)-5-(3,5-di-tert-butylphenyl)-N-(1-(2-methoxyacetyl)azetidin-3-yl)-2-methyl-1H-pyrrole-3-carboxamide (4)

To a mixture of compound 4a (100 mg, 0.2 mmol) and DIPEA (78 mg, 0.6 mmol) in DCM (15 mL) was added 2-methoxyacetyl chloride (26 mg, 0.24 mmol) at 0° C. and the mixture was stirred for 2 h. Then it was quenched with $H_2O$ (20 mL) and extracted with DCM (3×20 mL). The organic layer was separated and washed with brine and dried over $Na_2SO_4$. After filtration, the filtrate was evaporated and purified by prep. HPLC to give the target compound 4 (56 mg, 52%). $^1H$-NMR (400 MHz, $CDCl_3$) δ: 7.38 (t, J=1.8 Hz, 1H), 7.17 (d, J=1.6 Hz, 2H), 6.96 (br s, 1H), 6.50 (s, 1H), 4.39 (br s, 2H), 4.04 (s, 1H), 3.96-3.87 (m, 2H), 3.73 (d, J=7.2 Hz, 2H), 3.66-3.63 (m, 1H), 3.48-3.43 (m, 1H), 3.38 (s, 3H), 2.58 (s, 3H), 1.53-1.49 (m, 3H), 1.37-1.28 (m, 21H), 0.99-0.95 (m, 3H), 0.68-0.61 (m, 2H). MS: 536.2 (M+1).

Example 5

5

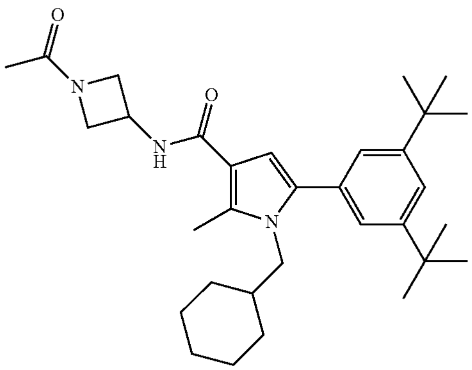

Step 1: N-(1-Acetylazetidin-3-yl)-1-(cyclohexylmethyl)-5-(3,5-di-tert-butylphenyl)-2-methyl-1H-pyrrole-3-carboxamide (5)

To a mixture of compound 4a (100 mg, 0.2 mmol) and DIPEA (78 mg, 0.6 mmol) in DCM (15 mL) was added acetyl chloride (19 mg, 0.24 mmol) at 0° C. and the mixtures was stirred for 2 h. Then it was quenched with $H_2O$ (20 mL) and extracted with DCM (3×20 mL). The organic layer was separated and washed with brine and dried over $Na_2SO_4$. After filtration, the filtrate was evaporated and purified by prep. HPLC to give the target compound 5 (59 mg, 54%). $^1H$-NMR (400 MHz, DMSO-$d_6$) δ: 7.98 (t, J=5.6 Hz, 1H), 7.36 (t, J=1.6 Hz, 1H), 7.15 (d, J=1.6 Hz, 2H), 6.29 (s, 1H), 4.27-4.18 (m, 2H), 3.99-3.96 (m, 1H), 3.79 (d, J=7.2 Hz, 2H), 3.31-3.27 (m, 1H), 3.10-3.03 (m, 1H), 2.53 (s, 3H), 1.83 (s, 3H), 1.46-1.43 (m, 3H), 1.30 (s, 18H), 1.24-1.15 (m, 3H), 0.97-0.85 (m, 3H), 0.68-0.60 (m, 2H). MS: 506.1 (M+1).

Example 6

6

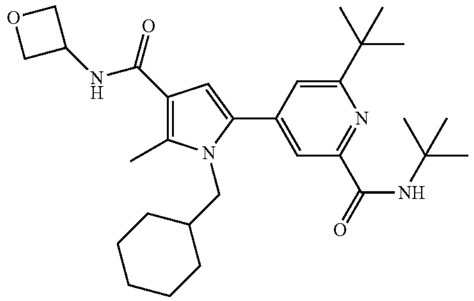

Step 1: Methyl 6-(tert-butyl)-4-(1-(cyclohexylmethyl)-5-methyl-4-(oxetan-3-ylcarbamoyl)-1H-pyrrol-2-yl) picolinate (6a)

To a mixture of compound P1 (3.0 g, 9.4 mmol), 5-bromo-1-(cyclohexylmethyl)-2-methyl-N-(oxetan-3-yl)-1H-pyrrole-3-carboxamide (similar prepared as in Example 1) (4.3 g, 10.6 mmol), $K_2CO_3$ (3.12 g, 22.6 mmol) and TBAB (180 mg, 0.54 mmol) in 1,4-dioxane (10 mL) and $H_2O$ (4 mL) was added $Ph(PPh_3)_2Cl_2$ (180 mg, 0.24 mmol) under $N_2$. Under microwave conditions, the solution was heated at 100° C. for 1.5 h. Water was added and the solution was extracted with EA. The organic layer was washed with brine, dried over $NaSO_4$, filtered, concentrated and purified by CC (PE/EA=3/1) to give compound 6a (1.8 g, 41%) as a colorless solid.

Step 2: 6-(tert-Butyl)-4-(1-(cyclohexylmethyl)-5-methyl-4-(oxetan-3-ylcarbamoyl)-1H-pyrrol-2-yl) picolinic acid (6b)

To a stirred solution of compound 6a (1.65 g, 3.54 mmol) in a mixture of THF (15 mL) and $H_2O$ (5 mL) was added $LiOH.H_2O$ (300 mg, 5.64 mmol) and this mixture was stirred at 60° C. for 3 h. The solution was adjusted to pH=2-3 with 1M HCl. Then the mixture was extracted with EA. The organic layer was washed with brine, dried over $Na_2SO_4$, concentrated and purified by CC (PE/EA=2/1) to give compound 6b (1.3 g, 81%) as a colorless powder.

Step 3: N,6-Di-tert-butyl-4-(1-(cyclohexylmethyl)-5-methyl-4-(oxetan-3-ylcarbamoyl)-1H-pyrrol-2-yl) picolinamide (6)

A mixture of compound 6b (150 mg, 0.33 mmol), tert-butylamine (36 mg, 0.48 mmol), HATU (207 mg, 0.54 mmol) and DIPEA (146 mg, 1.14 mmol) in DMF (5 mL) was stirred at rt for 20 min. The mixture was washed with water and extracted with EA. The organic layer was washed with brine, dried over $Na_2SO_4$, concentrated and purified by CC (PE/EA=2/1) to give compound 6 (42 mg, 30%) as a colorless powder. $^1H$-NMR ($CDCl_3$, 300 MHz) δ: 8.19 (s, 1H), 7.94 (s, 1H), 7.39 (s, 1H), 6.45 (s, 1H), 6.38 (d, J=6.9 Hz, 1H), 5.20 (q, J=6.9 Hz, 1H), 4.97 (t, J=6.9 Hz, 2H), 4.60 (t, J=6.9 Hz, 2H), 3.84 (d, J=6.9 Hz, 2H), 2.60 (s, 3H), 1.66 (m, 2H), 1.51 (s, 9H), 1.40 (s, 9H), 1.38-1.29 (m, 3H), 1.03-0.97 (m, 3H), 0.68-0.61 (m, 2H). MS: 509 (M+1).

Examples 6/1 to 6/9

The following Examples were prepared similar as in Example 6:

| # | Structure | Analytical data |
|---|---|---|
| 6/1 | 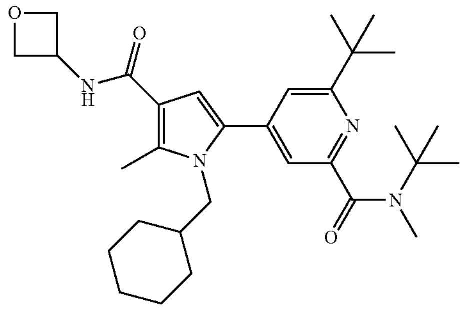 [SMILES: Cc1c(C(=O)NC2COC2)cc(-c2cc(C(=O)N(C)C(C)(C)C)nc(C(C)(C)C)c2)n1CC1CCCCC1] | $^1$H-NMR ($CDCl_3$, 300 MHz) δ: 7.33 (s, 1H), 7.26 (s, 1H), 6.42 (s, 1H), 6.33 (d, J = 6.9 Hz, 1H), 5.20 (q, J = 6.9 Hz, 1H), 4.96 (t, J = 6.9 Hz, 2H), 4.58 (t, J = 6.9 Hz, 2H), 3.84 (d, J = 6.9 Hz, 2H), 2.92 (s, 3H), 2.59 (s, 3H), 1.73-1.62 (m, 2H), 1.53 (s, 9H), 1.43 (s, 9H), 1.38-1.30 (m, 4H), 1.03-0.97 (m, 3H), 0.72-0.63 (m, 2H). MS: 523 (M + 1). |
| 6/2 | 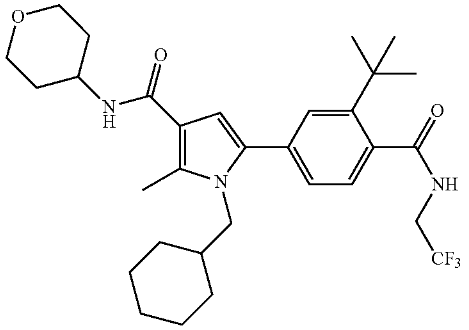 [SMILES: Cc1c(C(=O)NC2CCOCC2)cc(-c2ccc(C(=O)NCC(F)(F)F)c(C(C)(C)C)c2)n1CC1CCCCC1] | $^1$H-NMR ($CDCl_3$, 400 MHz) δ: 7.44 (d, 1H, J = 1.6 Hz), 7.25 (d, 1H, J = 8.0 Hz), 7.16 (dd, 1H, J = 8.0 Hz, 1.6 Hz), 6.17 (s, 1H), 6.09-6.07 (m, 1H), 5.60 (d, 1H, J = 8.0 Hz), 4.18-4.09 (m, 3H), 3.99-3.96 (m, 2H), 3.75 (d, 2H, J = 7.2 Hz), 3.55-3.49 (m, 2H), 3.29 (t, 2H, J = 6.4 Hz), 2.62 (s, 3H), 2.00-1.96 (m, 2H), 1.58-1.47 (m, 5H), 1.44 (s, 9H), 1.41-1.33 (m, 3H), 1.06-1.00 (m, 3H), 0.67-0.62 (m, 2H). MS: 562 (M + 1). |
| 6/3 | 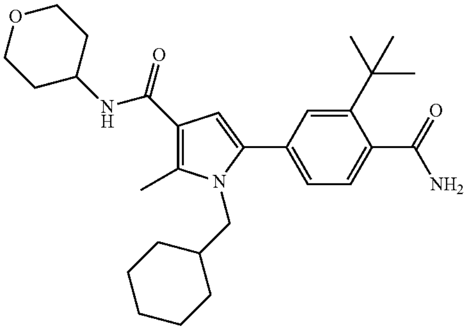 [SMILES: Cc1c(C(=O)NC2CCOCC2)cc(-c2ccc(C(N)=O)c(C(C)(C)C)c2)n1CC1CCCCC1] | $^1$H-NMR ($CDCl_3$, 400 MHz) δ: 7.43 (d, 1H, J = 1.6 Hz), 7.33 (d, 1H, J = 7.6 Hz), 7.16 (dd, 1H, J = 7.6 Hz, 1.6 Hz), 6.17 (s, 1H), 5.75 (m, 2H), 5.60 (t, 2H, J = 7.2 Hz), 4.19-4.14 (m, 1H), 3.99-3.96 (m, 2H), 3.75 (d, 2H, J = 7.6 Hz), 3.55-3.48 (m, 2H), 2.61 (s, 3H), 2.04-1.96 (m, 5H), 1.54-1.46 (m, 5H), 1.44 (s, 9H), 1.41-1.36 (m, 3H), 1.03-1.05 (m, 3H), 0.67-0.62 (m, 2H). MS: 480 (M + 1). |
| 6/4 | 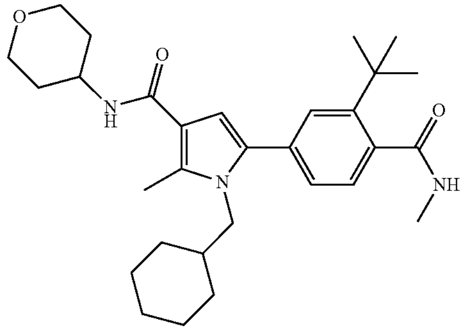 [SMILES: CNC(=O)c1ccc(-c2cc(C(=O)NC3CCOCC3)c(C)n2CC2CCCCC2)cc1C(C)(C)C] | $^1$H-NMR ($CDCl_3$, 400 MHz) δ: 7.40 (d, 1H, J = 1.2 Hz), 7.24 (d, 1H, J = 7.6 Hz), 7.13 (dd, 1H, J = 8.0 Hz, 1.2 Hz), 6.15 (s, 1H), 5.74 (d, 1H, J = 4.8 Hz), 5.60 (d, 1H, J = 7.2 Hz), 4.18-4.15 (m, 1H), 3.99-3.96 (m, 2H), 3.75 (d, 2H, J = 7.2 Hz), 3.55-3.49 (m, 2H), 3.01-3.00 (d, 3H, J = 4.8 Hz), 2.61 (s, 3H), 1.56-1.53 (m, 5H), 1.47 (s, 9H), 1.41-1.36 (m, 3H), 1.01-0.99 (m, 3H), 0.62-0.87 (m, 2H). MS: 494 (M + 1). |

-continued

| # | Structure | Analytical data |
| --- | --- | --- |
| 6/5 | 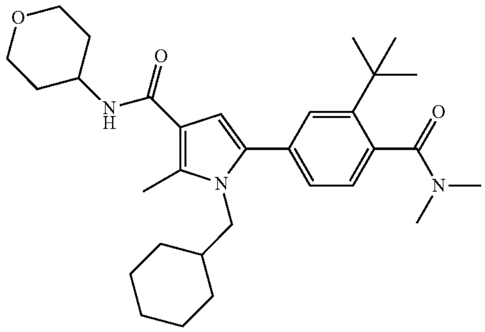 [SMILES: Cc1c(C(=O)NC2CCOCC2)cc(-c2ccc(C(=O)N(C)C)c(C(C)(C)C)c2)n1CC1CCCCC1] | $^1$H-NMR ($CDCl_3$, 400 MHz) δ: 7.43 (d, 1H, J = 1.6 Hz), 7.24 (dd, 1H, J = 8.0 Hz, 1.6 Hz), 7.08 (d, 1H, J = 8.0 Hz), 6.18 (s, 1H), 5.61 (t, 2H, J = 7.2 Hz), 4.18-4.14 (m, 1H), 3.99-3.96 (m, 2H), 3.75 (d, 2H, J = 8.0 Hz), 3.55-3.49 (m, 2H), 3.12 (s, 3H), 2.82 (s, 3H), 2.61 (s, 3H), 1.99-1.96 (m, 2H), 1.53-1.48 (m, 5H), 1.42-1.23 (m, 12H), 1.01-1.00 (m, 3H), 0.64-0.61 (m, 2H). MS: 508 (M + 1). |
| 6/6 | 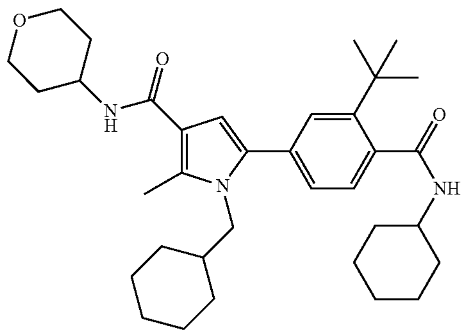 [SMILES: Cc1c(C(=O)NC2CCOCC2)cc(-c2ccc(C(=O)NC3CCCCC3)c(C(C)(C)C)c2)n1CC1CCCCC1] | $^1$H-NMR ($CDCl_3$, 400 MHz) δ: 7.40 (d, 1H, J = 1.2 Hz), 7.22 (d, 1H, J = 8.0 Hz), 7.13 (dd, 1H, J = 8.0 hz, 1.2 Hz), 6.14 (s, 1H), 5.60 (t, 2H, J = 7.2 Hz), 4.18-4.14 (m, 1H), 4.00-3.96 (m, 3H), 3.73 (d, 2H, J = 7.2 Hz), 3.55-3.48 (m, 2H), 2.61 (s, 3H), 2.09-1.96 (m, 5H), 1.78-1.74 (m, 2H), 1.68-1.65 (m, 1H), 1.56-1.53 (m, 4H), 1.51-1.43 (m, 12H), 1.41-1.36 (m, 3H), 1.29-1.19 (m, 4H), 1.03-1.05 (m, 3H), 0.66-0.69 (m, 2H). MS: 562 (M + H). |
| 6/7 | 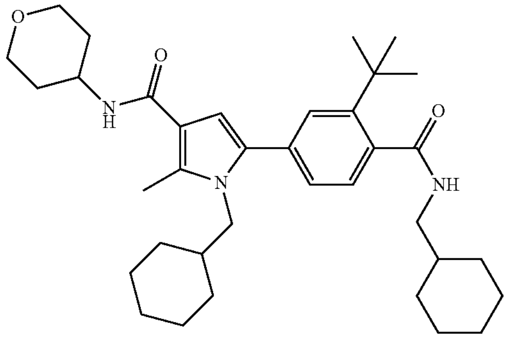 [SMILES: Cc1c(C(=O)NC2CCOCC2)cc(-c2ccc(C(=O)NCC3CCCCC3)c(C(C)(C)C)c2)n1CC1CCCCC1] | $^1$H-NMR ($CDCl_3$, 400 MHz) δ: 7.41 (d, 1H, J = 1.6 Hz), 7.25 (d, 1H, J = 8.0 Hz), 7.14 (dd, 1H, J = 8.0 Hz, 1.6 Hz), 6.15 (s, 1H), 5.79 (t, 2H, J = 6.0 Hz), 5.60 (d, 1H, J = 8.0 Hz), 4.18-4.15 (m, 1H), 4.00-3.95 (m, 2H), 3.75 (d, 2H, J = 7.6 Hz), 3.55-3.49 (m, 2H), 3.29 (t, 2H, J = 6.4 Hz), 2.61 (s, 3H), 2.00-1.96 (m, 2H), 1.82-1.74 (m, 4H), 1.71-1.67 (m, 4H), 1.51-1.43 (m, 12H), 1.41-1.32 (m, 6H), 1.19-1.05 (m, 5H), 0.66-0.69 (m, 2H). MS: 576 (M + 1). |
| 6/8 | 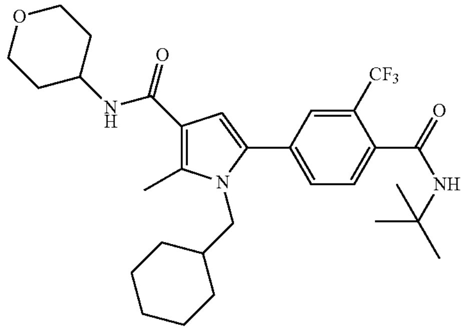 [SMILES: Cc1c(C(=O)NC2CCOCC2)cc(-c2ccc(C(=O)NC(C)(C)C)c(C(F)(F)F)c2)n1CC1CCCCC1] | $^1$H-NMR (400 MHz, DMSO-$d_6$) δ: 8.14 (s, 1H), 7.80-7.67 (m, 2H), 7.55-7.49 (m, 2H), 6.72 (s, 1H), 4.01-3.82 (m, 5H), 3.35 (m, 2H), 2.55 (s, 3H), 1.75-1.67 (m, 2H), 1.59-1.44 (m, 5H), 1.36 (s, 9H), 1.34-1.24 (m, 3H), 0.98 (m, 3H), 0.63 (m, 2H). MS: 548.3 $(M + 1)^+$. |

-continued

| # | Structure | Analytical data |
|---|---|---|
| 6/9 | 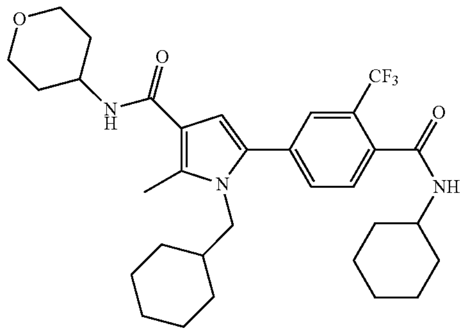 [SMILES: Cc1c(C(=O)NC2CCOCC2)cc(-c2ccc(C(=O)NC3CCCCC3)c(C(F)(F)F)c2)n1CC1CCCCC1] | $^1$H-NMR (400 MHz, DMSO-$d_6$): δ: 8.41 (d, J = 8.0 Hz, 1H), 7.80-7.67 (m, 2 H), 7.52 (d, J = 8.0 Hz, 2H), 6.73 (s, 1H), 3.99-3.83 (m, 5H), 3.72 (m, 1H), 3.40-3.32 (m, 2H), 2.55 (s, 3H), 1.86-1.80 (m, 2H), 1.76-1.67 (m, 4H), 1.62-1.47 (m, 6H), 1.40-1.10 (m, 8H), 0.98 (s, 3H), 0.65 (m, 2H). MS: 574.3 $(M + 1)^+$. |

Example 7

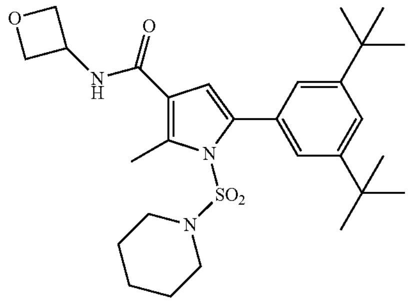

7

Step 1: Ethyl 2-methyl-1-(piperidin-1-ylsulfonyl)-1H-pyrrole-3-carboxylate (7a)

To a solution of ethyl 2-methyl-1H-pyrrole-3-carboxylate (1.0 g, 6.52 mmol) in dry DMF (10 mL) was added NaH (172 mg, 7.17 mmol) in portions and the resulting mixture was stirred at rt for 30 min. A solution of piperidine-1-sulfonyl chloride (1.32 g, 7.17 mmol) in dry DMF (4 mL) was added and the resulting mixture was stirred at rt for 3 h. The mixture was quenched with aq. $NH_4Cl$ and diluted with EA. The organic phase was washed with water and brine and dried over $Na_2SO_4$. After filtration the organic phase was concentrated and purified by CC (PE/EA=10/1) to give 7a as a colorless solid (1.7 g).

Step 2: Ethyl 5-bromo-2-methyl-1-(piperidin-1-ylsulfonyl)-1H-pyrrole-3-carboxylate (7b)

To a solution of compound 7a (600 mg, 2 mmol) in dry DMF (8 mL) was added NBS (409 mg, 2.3 mmol) in portions at 0° C. and this mixture was stirred at rt for 3 h. The mixture was diluted with EA and washed with water and brine. The organic phase was dried over $Na_2SO_4$, concentrated and purified by CC (PE/EA=15/1) to give compound 7b (700 mg) as a pale-yellow solid.

Step 3: Ethyl 5-(3,5-di-tert-butylphenyl)-2-methyl-1-(piperidin-1-ylsulfonyl)-1H-pyrrole-3-carboxylate (7c)

A mixture of compound 7b (700 mg, 1.85 mmol), 2-(3,5-di-tert-butylphenyl)-4,4,5,5-tetramethyl-1,3,2-dioxaborolane (519 mg, 2.22 mmol) and $Pd(PPh_3)_4$ (107 mg) in degassed 1,2-dimethoxyethane (5 mL) and 2M $Na_2CO_3$ (8 mL) was heated to 100° C. for 30 min under microwave irradiation. The mixture was cooled and diluted with EA and washed with water and brine. The organic phase was dried over $Na_2SO_4$, concentrated and purified by CC (PE/EA=100/1 to 80/1) to give compound 7c as a colorless solid (500 mg).

Step 4: 5-(3,5-Di-tert-butylphenyl)-2-methyl-1-(piperidin-1-ylsulfonyl)-1H-pyrrole-3-carboxylic acid (7d)

A mixture of compound 7c (300 mg, 0.614 mmol), $LiOH.H_2O$ (503 mg, 12.3 mmol) and NaOH (125 mg) in 1,4-dioxane (5 mL) and water (3 mL) was stirred and heated to 120° C. for 25 min under microwave irradiation. The mixture was cooled and acidified by 2M HCl to pH~2 and then extracted with EA. The combined extracts were washed with water and brine, dried over $Na_2SO_4$, concentrated and purified by CC (PE/EA=10/1 to 2/1) to give compound 7d (250 mg) as a colorless solid.

Step 5: 5-(3,5-Di-tert-butylphenyl)-2-methyl-N-(oxetan-3-yl)-1-(piperidin-1-ylsulfonyl)-1H-pyrrole-3-carboxamide (7)

To a solution of compound 7d (100 mg, 217 μmol), oxetan-3-amine (18 mg, 238 μmol) and HATU (124 mg, 326 μmol) in dry DMF (2 mL) at 0° C. was added DIPEA (42 mg, 326 μmol) and the resulting mixture was stirred at rt overnight. The mixture was diluted with water, extracted with EA and the combined extracts were washed with water and brine. The organic phase was dried over $Na_2SO_4$, concentrated and purified by CC (PE/EA=3/1 to 2/1) to give compound 7 (80 mg, 72%) as a colorless solid. $^1$H-NMR (400 MHz, $CDCl_3$) δ: 7.41 (1H, s), 7.28 (2H, s), 6.22 (1H, s), 6.19 (1H, d, J=7.2 Hz), 5.23-5.17 (1H, m), 4.99 (2H, t, J=6.8 Hz), 4.55 (2H, t, J=6.4 Hz), 2.81 (3H, s), 2.74 (4H, m), 1.34 (23H, m), 0.85 (1H, m). MS: 516.4 $(M+1)^+$.

Examples 7/1 to 7/8

The following Examples were prepared similar as in Example 7:

| # | Structure | Analytical data |
|---|---|---|
| 7/1 | 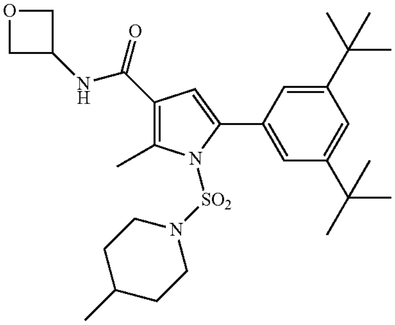 [SMILES: Cc1c(C(=O)NC2COC2)cc(-c2cc(C(C)(C)C)cc(C(C)(C)C)c2)n1S(=O)(=O)N1CCC(C)CC1] | $^1$H-NMR (400 MHz, $CDCl_3$) δ: 7.41 (1H, s), 7.26 (2H, s), 6.22 (1H, s), 6.20 (1H, d, J = 8.0 Hz), 5.21-5.18 (1H, m), 4.99 (2H, t, J = 7.2 Hz), 4.55 (2H, t, J = 6.4 Hz), 3.28 (2 H, m), 2.81 (3H, s), 2.20 (2H, m), 1.42 (2H, m), 1.34 (18H, s), 1.23 (1H, m), 0.95 (2H, m), 0.83 (3H, d, J = 6.8 Hz). MS: 530.3 $(M + 1)^+$. |
| 7/2 | 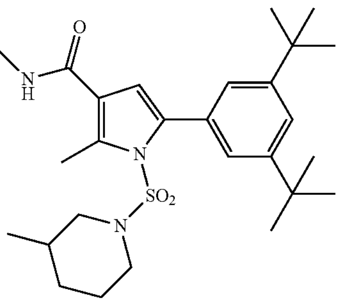 | $^1$H-NMR (400 MHz, $CDCl_3$) δ: 7.42 (1H, s), 7.28 (2H, m), 6.22 (1H, s), 6.19 (1H, m), 5.21-5.17 (1H, m), 4.99 (2H, t, J = 6.8 Hz), 4.55 (2H, t, J = 6.4 Hz), 3.23 (1H, m), 3.14 (1H, m), 2.81 (3H, s), 2.15 (1H, m), 1.68 (1H, m), 1.61-1.57 (1H, m), 1.50-1.45 (1H, m), 1.34 (20H, s), 0.90 (1H, m), 0.69 (3H, d, J = 6.4 Hz). MS: 530.3 $(M + 1)^+$. |
| 7/3 | 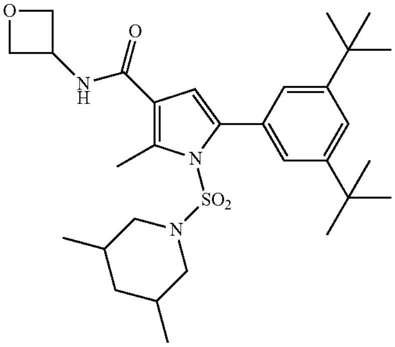 [SMILES: Cc1c(C(=O)NC2COC2)cc(-c2cc(C(C)(C)C)cc(C(C)(C)C)c2)n1S(=O)(=O)N1CC(C)CC(C)C1] | $^1$H-NMR (400 MHz, DMSO-$d_6$) δ: 8.53 (1H, d, J = 6.4 Hz), 7.42 (1H, s), 7.24 (2H, s), 6.56 (1H, s), 4.98-4.92 (1H, m), 4.72 (1H, t, J = 6.8 Hz), 4.53 (1H, t, J = 6.4 Hz), 3.13 (2H, m), 2.71 (3H, s), 1.68-1.49 (3H, m), 1.34-1.20 (19H, m), 0.68 (6H, m), 0.40-0.36 (1H, m). MS: 544.4 $(M + 1)^+$. |
| 7/4 | 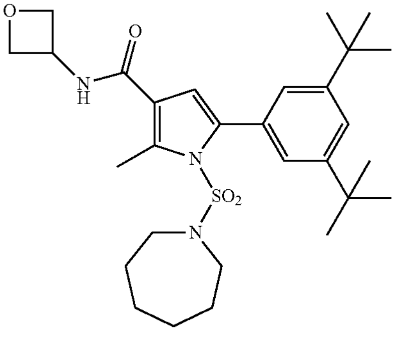 [SMILES: Cc1c(C(=O)NC2COC2)cc(-c2cc(C(C)(C)C)cc(C(C)(C)C)c2)n1S(=O)(=O)N1CCCCCC1] | $^1$H-NMR (400 MHz, DMSO-$d_6$) δ: 8.50 (1H, d, J = 6.4 Hz), 7.41 (1H, s), 7.21 (2H, s), 6.63 (1H, s), 4.95-4.91 (1H, m), 4.72 (1H, t, J = 6.8 Hz), 4.52 (1H, t, J = 6.4 Hz), 2.71-2.69 (7H, m), 1.40 (8H, s), 1.34 (18H, s). MS: 530.3 $(M + 1)^+$. |

-continued
| # | Structure | Analytical data |
|---|---|---|
| 7/5 | 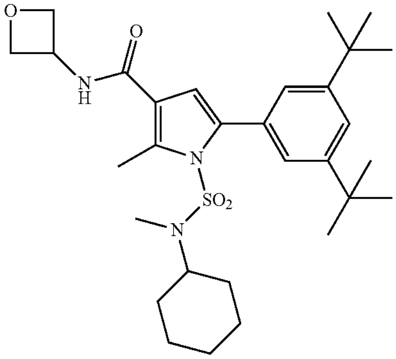 [SMILES: Cc1c(C(=O)NC2COC2)cc(-c2cc(C(C)(C)C)cc(C(C)(C)C)c2)n1S(=O)(=O)N(C)C1CCCCC1] | $^1$H-NMR (400 MHz, DMSO-$d_6$) δ: 8.53 (1H, d, J = 6.4 Hz), 7.41 (1H, s), 7.23 (2H, s), 6.65 (1H, s), 4.98-4.92 (1H, m), 4.73 (1H, t, J = 6.4 Hz), 4.53 (1H, t, J = 6.4 Hz), 3.11 (1H, m), 2.71 (3H, s), 2.36 (3H, s), 1.63 (2H, m), 1.48 (1H, m), 1.32 (18H, s), 1.27-0.95 (5H, m). MS: 544.4 $(M + 1)^+$. |
| 7/6 | 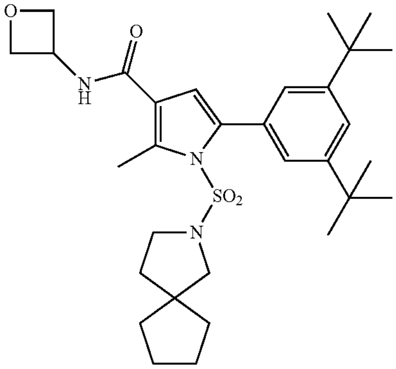 [SMILES: Cc1c(C(=O)NC2COC2)cc(-c2cc(C(C)(C)C)cc(C(C)(C)C)c2)n1S(=O)(=O)N1CCC2(CCCC2)C1] | $^1$H-NMR (400 MHz, $CDCl_3$) δ: 8.52 (1H, d, J = 6.8 Hz), 7.42 (1H, s), 7.25 (2H, s), 6.66 (1H, s), 4.94 (1H, m), 4.72 (2H, t, J = 6.8 Hz), 4.53 (2H, t, J = 6.4 Hz), 2.93 (2H, t, J = 6.8 Hz), 2.71 (3H, s), 2.62 (2H, s), 1.52-1.40 (6H, m), 1.31 (22H, m). MS: 556.5 $(M + 1)^+$. |
| 7/7 | 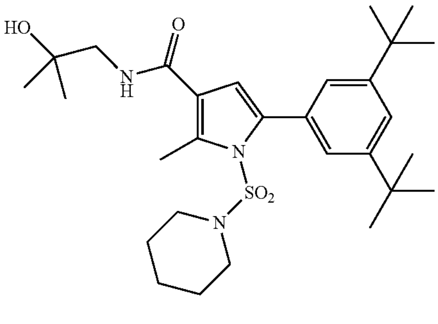 [SMILES: Cc1c(C(=O)NCC(C)(C)O)cc(-c2cc(C(C)(C)C)cc(C(C)(C)C)c2)n1S(=O)(=O)N1CCCCC1] | $^1$H-NMR (400 MHz, DMSO-$d_6$): δ 7.75 (1H, t, J = 6.4 Hz), 7.39 (1H, s), 7.24 (2H, s), 6.62 (1H, s), 4.50 (1H, br s), 3.17 (2H, d, J = 6.0 Hz), 2.77-2.68 (7H, m), 1.30 (19H, m), 1.21 (5H, m), 1.07 (6H, s). MS: 532.4 $(M + 1)^+$. |
| 7/8 | 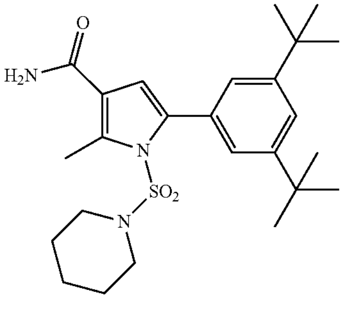 [SMILES: Cc1c(C(N)=O)cc(-c2cc(C(C)(C)C)cc(C(C)(C)C)c2)n1S(=O)(=O)N1CCCCC1] | $^1$H-NMR (400 MHz, $CDCl_3$): δ 7.41 (s, 1H), 7.28 (s, 2H), 6.22 (s, 1H), 5.59 (br s, 2H), 2.84 (s, 3H), 2.76-2.73 (m, 4H), 1.34 (s, 18H), 1.26 (m, 6H). MS: 460.2 $(M + 1)^+$. |

Example 8

8

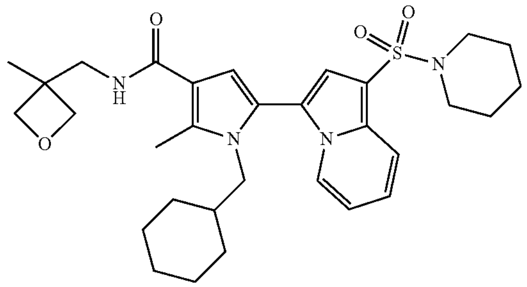

Step 1: Ethyl 5-acetyl-1-(cyclohexylmethyl)-2-methyl-1H-pyrrole-3-carboxylate (8a)

To a stirred solution of ethyl 1-(cyclohexylmethyl)-2-methyl-1H-pyrrole-3-carboxylate (8.0 g, 32.1 mmol, prepared according to Example 1d) and 1-methylvinyl acetate (6.4 g, 64.2 mmol) in 1,2-dichloroethane (100 mL) was added p-toluenesulfonic acid monohydrate (250 mg, 1.45 mmol) under $N_2$ and the mixture was stirred and heated to reflux overnight. After cooling rt the mixture was diluted with water and extracted with DCM twice. The combined organic layers were dried over $Na_2SO_4$, filtered, concentrated and purified by CC (PE/EA=30/1) to give compound 8a (5.7 g, 61%) as a yellow solid.

Step 2: (E)-Ethyl 1-(cyclohexylmethyl)-2-methyl-5-(3-(pyridin-2-yl)acryloyl)-1H-pyrrole-3-carboxylate (8b)

To a solution of compound 8a (5.4 g, 18.5 mmol) and picolinaldehyde (4.0 g, 37.4 mmol) in THF (60 mL) was added DBU (3.1 g, 20.4 mmol) and the solution was stirred at rt for 3 d. The solution was quenched with aq. $NH_4Cl$ and extracted with EA twice. The combined organic layers were washed with brine and dried over $Na_2SO_4$, filtered, concentrated and purified by CC (PE/EA=20/1) to give compound 8b (3.8 g, 54%) as a yellow solid.

Step 3: Ethyl 1-(cyclohexylmethyl)-2-methyl-5-(3-(pyridin-2-yl)propanoyl)-1H-pyrrole-3-carboxylate (8c)

To a solution of compound 8b (3.7 g, 9.7 mmol) in MeOH (100 mL) was added Pd/C (370 mg) and the mixture was stirred at rt under $H_2$ (15 psi) overnight. The solution was filtered, concentrated and purified by CC (PE/EA=20/1) to give compound 8c (3.2 g, 86%) as a colorless solid.

Step 4: Ethyl 1-(cyclohexylmethyl)-5-(1-(N-(methoxycarbonyl)sulfamoyl)indolizin-3-yl)-2-methyl-1H-pyrrole-3-carboxylate (8d)

A solution of compound 8c (3.0 g, 7.8 mmol) in dry toluene (50 mL) was refluxed with a Dean-Stark tube to remove water under $N_2$ for 10 min and then (methoxycarbonyl-sulfamoyl)triethylammonium hydroxide inner salt (Burgess reagent, 3.8 g, 15.9 mmol) was added to the mixture. The mixture was heated to reflux for further 30 min and cooled to rt. The solution was quenched with aq. $NH_4Cl$ and extracted with EA twice. The combined organic layers were washed with brine and dried over $Na_2SO_4$, filtered, concentrated and purified by CC (PE/EA=3/1) to give compound 8d (2.1 g) as a yellow solid.

Step 5: Ethyl 1-(cyclohexylmethyl)-2-methyl-5-(1-(piperidin-1-ylsulfonyl)indolizin-3-yl)-1H-pyrrole-3-carboxylate (8e)

To a solution of compound 8d (700 mg, 1.4 mmol) in ACN (20 mL) was added 1,5-dibromopentane (383 mg, 1.68 mmol) and $K_2CO_3$ (483 mg, 3.5 mmol) and the mixture was stirred overnight at reflux. The resulting solution was cooled to rt and further $K_2CO_3$ (483 mg, 3.5 mmol) was added. The solution was stirred again overnight at reflux. After cooling to rt the mixture was diluted with water and extracted with EA twice. The combined organic layers were washed brine, dried over $Na_2SO_4$, filtered and concentrated to dryness. CC (PE/EA=10/1) afforded compound 8e (610 mg, 85%) as an oil.

Step 6: 1-(Cyclohexylmethyl)-2-methyl-5-(1-(piperidin-1-ylsulfonyl)indolizin-3-yl)-1H-pyrrole-3-carboxylic acid (8f)

To a stirred solution of compound 8e (600 mg, 1.17 mmol) in a mixture of DMSO (15 mL) and $H_2O$ (2 drops) was added KOtBu (655 mg, 5.85 mmol) and the mixture was stirred at 85° C. for 4 h. After cooling to rt the pH was adjusted to pH 2-3 with 1M HCl and then the mixture was extracted with EA. The organic layer was washed with water and brine, dried over $Na_2SO_4$, concentrated and purified by CC (PE/EA=2/1) to give compound 8f (450 mg, 80%) as a yellow solid.

Step 7: 1-(Cyclohexylmethyl)-2-methyl-N-((3-methyloxetan-3-yl)methyl)-5-(1-(piperidin-1-ylsulfonyl)indolizin-3-yl)-1H-pyrrole-3-carboxamide (8)

A mixture of compound 8f (150 mg, 0.31 mmol), (3-methyloxetan-3-yl)methanamine (62 mg, 0.62 mmol), HATU (207 mg, 0.54 mmol) and DIPEA (146 mg, 1.14 mmol) in DMF (5 mL) was stirred at rt for 20 min. The resulting solution was diluted with water and extracted with EA twice. The combined organic layers were washed with water three times and brine consecutively, dried over $Na_2SO_4$, concentrated and purified by prep. TLC (PE/EA=1/1) to give compound 8 (30 mg, 16%) as a pale yellow powder. $^1H$-NMR ($CDCl_3$, 400 MHz) δ: 8.05 (d, 1H, J=9.2 Hz), 7.81 (d, 1H, J=6.8 Hz), 7.10-7.05 (m, 2H), 6.77-6.73 (m, 1H), 6.47 (s, 1H), 6.10 (t, 1H, J=6.0 Hz), 4.55 (d, 2H, J=6.0 Hz), 4.42 (d, 2H, J=6.0 Hz), 3.56 (d, 2H, J=6.0 Hz), 3.52 (d, 2H, J=7.2 Hz), 3.00 (m, 4H), 2.64 (s, 3H), 1.67-1.62 (m, 4H), 1.57-1.53 (m, 5H), 1.37-1.25 (m, 6H), 0.99-0.95 (m, 3H), 0.61-0.57 (m, 2H). MS: 567.1 $(M+1)^+$.

Examples 8/1 to 8/2

The following Examples were prepared similar as in Example 8:

| # | Structure | Analytical data |
|---|---|---|
| 8/1 | 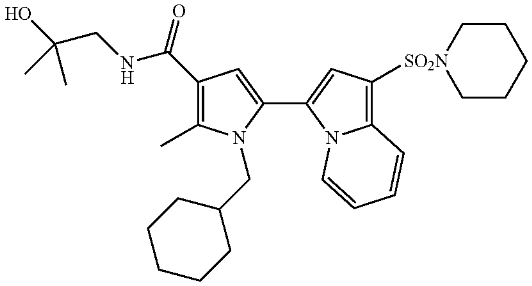 | $^1$H-NMR ($CDCl_3$, 400 MHz) δ: 8.06 (d, 1H, J = 8.8 Hz), 7.82 (d, 1H, J = 6.8 Hz), 7.10-7.05 (m, 2H), 6.77-6.73 (m, 1H), 6.48 (s, 1H), 6.20 (m, 1H), 3.52 (d, 2H, J = 7.2 Hz), 3.41 (d, 2H, J = 6.0 Hz), 3.00 (m, 4H), 2.63 (s, 3H), 1.67-1.63 (m, 4H), 1.60-1.53 (m, 3H), 1.44-1.37 (m, 15H), 0.99-0.95 (m, 3H), 0.61-0.57 (m, 2H). MS: 555.1 $(M + 1)^+$. |
| 8/2 | 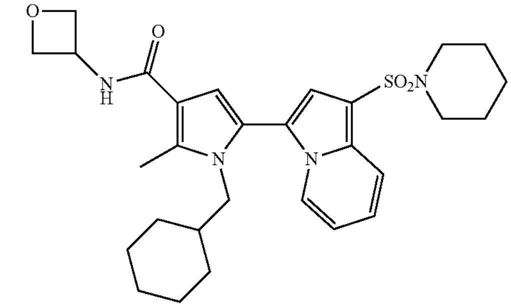 | $^1$H-NMR ($CDCl_3$, 400 MHz) δ: 8.06 (d, 1H, J = 8.8 Hz), 7.82 (d, 1H, J = 6.8 Hz), 7.11-7.06 (m, 2H), 6.76 (t, 1H, J = 5.4 Hz), 6.49 (s, 1H), 6.22 (d, 1H, J = 7.2 Hz), 5.24-5.19 (m, 1H), 5.00 (t, 1H, J = 7.2 Hz), 4.57 (t, 1H, J = 7.2 Hz), 3.52 (d, 2H, J = 7.2 Hz), 3.00 (m, 4H), 2.62 (s, 3H), 1.67-1.52 (m, 9H), 1.39-1.24 (m, 4H), 0.99-0.95 (m, 3H), 0.61-0.57 (m, 2H). MS: 539.1 $(M + 1)^+$. |

Example 9

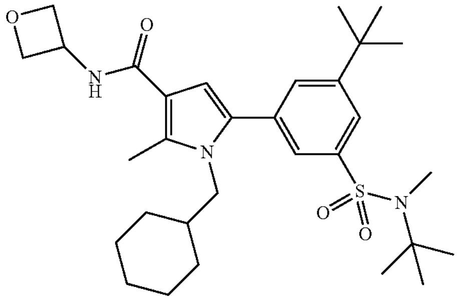

9

Step 1: 1-(Cyclohexylmethyl)-2-methyl-1H-pyrrole-3-carboxylic acid (9a)

To a solution of 1-(cyclohexylmethyl)-2-ethyl-1H-pyrrole-3-carboxylate (prepared according to Example 1d, 875 mg, 3.5 mmol) in EtOH (50 mL) was added 5M KOH (10 mL). The mixture was stirred and heated to reflux overnight. After cooling to rt the solvent was concentrated and the pH of the remaining aq. mixture was adjusted to <2 with 4M HCl. The mixture was extracted with EA three times and the combined organic layers were washed with brine and dried over $Na_2SO_4$. After filtration, the filtrate was evaporated and purified by prep. HPLC to give pure product 9a as a colorless solid.

Step 2: 1-(Cyclohexylmethyl)-2-methyl-N-(oxetan-3-yl)-1H-pyrrole-3-carboxamide (9b)

To a solution of 9a (505 mg, 2.29 mmol) in DMF (15 mL) was added HATU (1.74 mg, 4.58 mmol) and DIPEA (1.48 mg, 11.5 mmol). The mixture was stirred for 60 min and then oxetan-3-amine (185 mg, 2.52 mmol) was added. The mixture was stirred for additional 18 h, quenched with ice water and extracted with EA. The organic layer was separated, washed with brine and dried over $Na_2SO_4$. After filtration, the filtrate was evaporated and purified by prep. HPLC to give 9b (398 mg, 63%) as a colorless solid.

Step 3: 5-Bromo-1-(cyclohexylmethyl)-2-methyl-N-(oxetan-3-yl)-1H-pyrrole-3-carboxamide To a solution of 9b (555 mg, 2 mmol) in dry THF (10 mL) was added NBS (374 mg, 2.1 mmol) at −78° C. under $N_2$. The mixture was stirred for 5 min and quenched with a cold aq. solution of $NH_4Cl$. The organic layer was separated and the aq. layer extracted repeatedly with EA. The combined organic layers were washed with brine and dried over $Na_2SO_4$. After filtration, the filtrate was evaporated and purified by CC (EA/PE=1/60) to give compound 9c (630 mg, 89%).

Step 4: 5-(3-tert-Butyl-5-(N-tert-butyl-N-methylsulfamoyl)phenyl)-1-(cyclohexylmethyl)-2-methyl-N-(oxetan-3-yl)-1H-pyrrole-3-carboxamide (9)

Compound 9c (86 mg, 244 μmol), compound P12 (100 mg, 244 μmol) and $Cs_2CO_3$ (238 mg, 732 μmol) in 1,4-dioxane/water (10:1, 2.2 mL) were stirred at rt. $Pd(PPh_3)_4$ (0.03 eq) was added under $N_2$ and the mixture was stirred and heated under microwave irradiation to 120° C. for 2 h. The mixture was cooled to rt, filtered and purified by prep. HPLC to give target 9 (81.5 mg, 60%) as a colorless solid. $^1$H-NMR (400 MHz, DMSO-$d_6$) δ: 8.32-8.30 (d, J=6.4 Hz, 1H), 7.69 (m, 2H), 7.54-7.53 (t, J=1.4 Hz, 1H), 6.75 (s, 1H), 4.96 (m, 1H), 4.74-4.70 (t, J=7.0 Hz, 1H), 4.57-4.53 (t, J=6.2 Hz, 1H), 3.85-3.82 (m, 1H), 2.97 (s, 3H), 2.53 (s, 3H), 1.48-1.45 (m, 3H), 1.35 (s, 9H), 1.24-1.20 (m, 12H), 0.92 (m, 3H), 0.61 (m, 2H). MS: 558.3 $(M+1)^+$.

Examples 9/1 to 9/15

The following Examples were prepared similar as in Example 9, using the corresponding borononic ester building blocks prepared as or similar as described above:

| # | Structure | Analytical data |
|---|---|---|
| 9/1 | 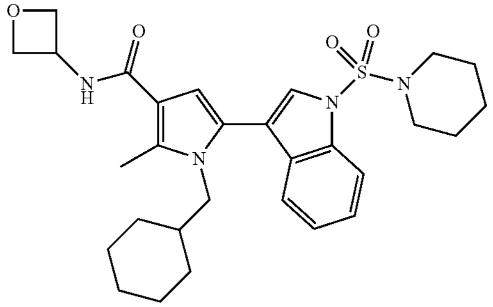 [SMILES: Cc1c(C(=O)NC2COC2)cc(-c2cn(S(=O)(=O)N3CCCCC3)c3ccccc23)n1CC1CCCCC1] | $^1$H-NMR (400 MHz, DMSO-$d_6$) δ: 8.33 (d, J = 6.8 Hz, 1H), 7.96 (d, J = 8.4 Hz, 1H), 7.51 (s, 1H), 7.76 (s, 1H), 7.65 (d, J = 7.6 Hz, 1H), 7.42 (d, J = 3.8 Hz, 1H), 7.36 (d, J = 7.2 Hz, 1H), 4.98 (d, J = 6.8 Hz, 1H), 4.75-4.71 (t, J = 7.0 Hz, 2H), 4.58-4.54 (t, J = 6.6 Hz, 2H), 3.85 (d, J = 7.2 Hz, 2H), 3.19-3.16 (m, 4H), 2.54 (s, 3H), 1.46 (s, 7H), 1.35 (m, 5H), 0.92 (d, J = 5.2 Hz, 3H), 0.64-0.60 (t, J = 6.6 Hz, 2H). MS: 539.2 $(M + 1)^+$. |
| 9/2 | 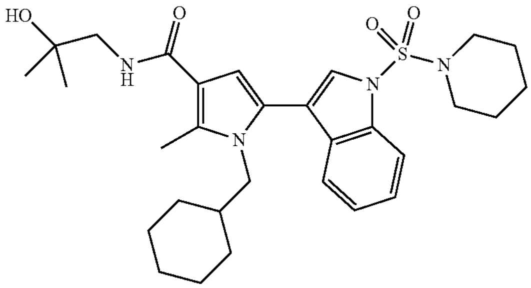 [SMILES: Cc1c(C(=O)NCC(C)(C)O)cc(-c2cn(S(=O)(=O)N3CCCCC3)c3ccccc23)n1CC1CCCCC1] | $^1$H-NMR (400 MHz, DMSO-$d_6$) δ: 7.95 (d, J = 8.0 Hz, 1H), 7.75 (s, 1H), 7.63-7.61 (m, 1H), 7.56 (s, 1H), 7.41-7.39 (m, 1H), 7.35-7.33 (m, 1H), 6.73 (s, 1H), 3.84-3.82 (d, J = 7.6 Hz, 2H), 3.59 (br s, 1H), 3.19-3.17 (m, 6H), 2.56 (s, 3H), 1.46 (s, 7H), 1.35 (m, 5H), 1.08 (s, 6H), 0.91 (m, 3H), 0.64-0.61 (m, 2H). MS: 555.1 $(M + 1)^+$. |
| 9/3 | 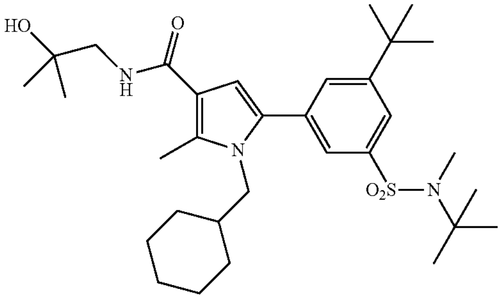 [SMILES: Cc1c(C(=O)NCC(C)(C)O)cc(-c2cc(C(C)(C)C)cc(S(=O)(=O)N(C)C(C)(C)C)c2)n1CC1CCCCC1] | $^1$H-NMR (400 MHz, DMSO-$d_6$) δ: 7.68 (m, 2H), 7.55 (m, 2H), 6.69 (s, 1H), 3.99 (s, 1H), 3.84-3.82 (d, J = 6.8 Hz, 2H), 3.17-3.16 (d, J = 6.0 Hz, 2H), 2.96 (s, 3H), 2.54 (s, 3H), 1.48-1.46 (m, 3H), 1.34 (s, 9H), 1.24 (s, 12H), 1.08 (s, 6H), 0.93 (m, 3H), 0.62 (m, 2H). MS: 574.2 $(M + 1)^+$. |
| 9/4 | 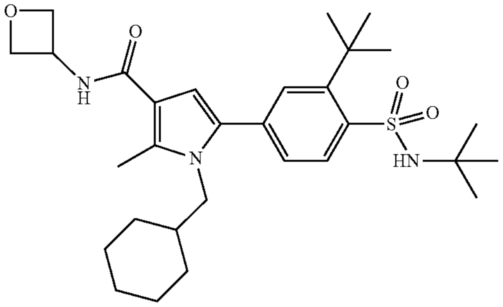 [SMILES: Cc1c(C(=O)NC2COC2)cc(-c2ccc(S(=O)(=O)NC(C)(C)C)c(C(C)(C)C)c2)n1CC1CCCCC1] | $^1$H-NMR (400 MHz, DMSO-$d_6$) δ: 8.36 (d, J = 6.4 Hz, 1H), 8.22 (d, J = 8.4 Hz, 1H), 7.84 (s, 1H), 7.61 (s, 1H), 7.51 (m, 1H), 6.83 (s, 1H), 5.03 (m, 1H), 4.79 (m, 2H), 4.61 (m, 2H), 3.90 (m, 2H), 2.58 (s, 3H), 1.62 (s, 9H), 1.50 (m, 3H), 1.30-1.20 (m, 12H), 0.95 (m, 3H), 0.67 (m, 2H). MS: 544.2 $(M + 1)^+$. |

-continued

| # | Structure | Analytical data |
|---|---|---|
| 9/5 | 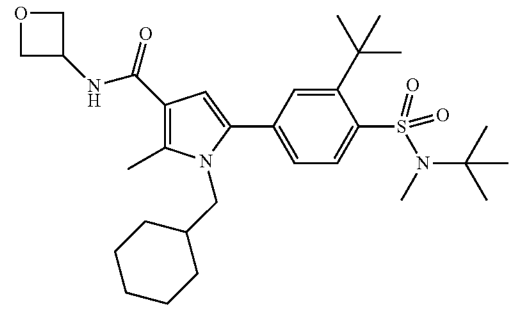 [SMILES: Cc1c(C(=O)NC2COC2)cc(-c2ccc(S(=O)(=O)N(C)C(C)(C)C)c(C(C)(C)C)c2)n1CC1CCCCC1] | $^1$H-NMR (400 MHz, DMSO-$d_6$) δ: 8.31 (d, J = 7.2 Htz, 1H), 7.79 (d, J = 8.4 Hz, 1H), 7.57 (s, 1H), 7.43 (m, 1H), 6.76 (s, 1H), 4.98 (m, 1H), 4.73 (m, 2H), 4.56 (m, 2H), 3.84 (m, 2H), 3.09 (s, 3H), 2.51 (s, 3H), 1.54 (s, 9H), 1.43 (m, 3H), 1.21 (s, 9H), 0.91 (m, 3H), 0.89 (m, 3H), 0.61 (m, 2H). MS: 558 $(M + 1)^+$. |
| 9/6 | 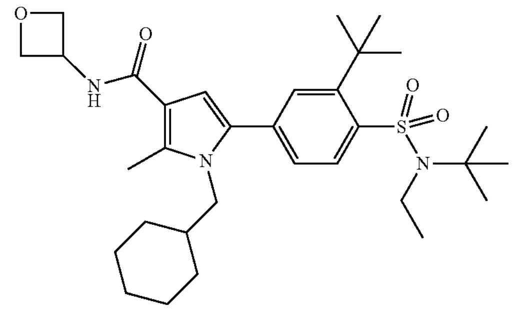 [SMILES: CCN(C(C)(C)C)S(=O)(=O)c1ccc(-c2cc(C(=O)NC3COC3)c(C)n2CC2CCCCC2)cc1C(C)(C)C] | $^1$H-NMR (400 MHz, DMSO-$d_6$) δ: 8.31 (d, J = 6.4 Hz, 1H), 7.81 (d, J = 8.0 Hz, 1H), 7.58 (s, 1H), 7.43 (m, 1H), 6.76 (s, 1H), 4.96 (m, 1H), 4.72 (m, 2H), 4.54 (m, 2H), 3.83 (d, 2H), 3.59 (m, 2H), 2.51 (s, 3H), 1.55 (s, 9H), 1.43 (m, 3H), 1.27 (m, 12H), 1.18 (m, 3H), 0.88 (m, 3H), 0.60 (m, 2H). MS: 572.3 $(M + 1)^+$. |
| 9/7 | 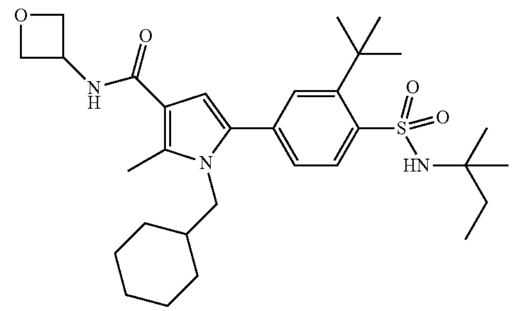 [SMILES: CCC(C)(C)NS(=O)(=O)c1ccc(-c2cc(C(=O)NC3COC3)c(C)n2CC2CCCCC2)cc1C(C)(C)C] | $^1$H-NMR (400 MHz, DMSO-$d_6$) δ: 8.30 (d, J = 6.4 Hz, 1H), 8.17 (d, J = 8.0 Hz, 1H), 7.62 (s, 1H), 7.54 (s, 1H), 7.42 (m, 1H), 6.77 (s, 1H), 4.97 (m, 1H), 4.74 (m, 2H), 4.55 (m, 2H), 3.84 (d, 2H), 2.52 (s, 3H), 1.55 (m, 11H), 1.44 (m, 3H), 1.19 (d, 3H), 1.08 (s, 6H), 0.89 (m, 6H), 0.63 (m, 2H). MS: 558.3 $(M + 1)^+$. |
| 9/8 | 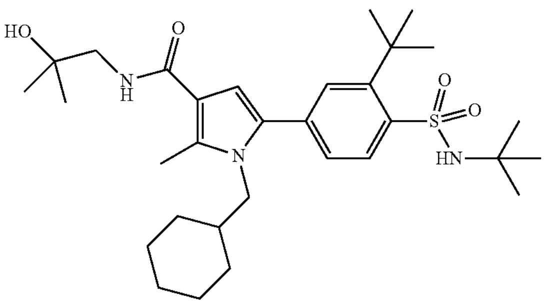 [SMILES: Cc1c(C(=O)NCC(C)(C)O)cc(-c2ccc(S(=O)(=O)NC(C)(C)C)c(C(C)(C)C)c2)n1CC1CCCCC1] | $^1$H-NMR (400 MHz, DMSO-$d_6$) δ: 8.14 (d, J = 8.4 Hz, 1H), 7.75 (s, 1H), 7.55-7.45 (m, 2H), 7.42 (m, 1H), 6.71 (s, 1H), 4.61 (s, 1H), 3.85 (m, 2H), 3.15 (m, 2H), 2.52 (s, 3H), 1.54 (s, 9H), 1.45-1.40 (m, 3H), 1.20-1.06 (m, 12H), 1.07 (s, 6H), 0.92-0.80 (m, 3H), 0.56 (m, 2H). MS: 560.3 $(M + 1)^+$. |
| 9/9 | 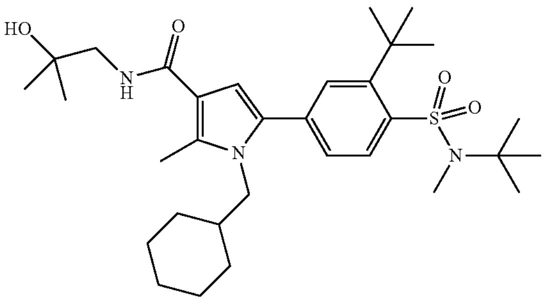 [SMILES: Cc1c(C(=O)NCC(C)(C)O)cc(-c2ccc(S(=O)(=O)N(C)C(C)(C)C)c(C(C)(C)C)c2)n1CC1CCCCC1] | $^1$H-NMR (400 MHz, DMSO-$d_6$) δ: 7.78 (d, J = 8.4 Hz, 1H), 7.60-7.45 (m, 2H), 7.41 (m, 1H), 6.71 (s, 1H), 4.61 (s, 1H), 3.84 (m, 2H), 3.17 (m, 2H), 3.08 (s, 3H), 2.53 (s, 3H), 1.54 (s, 9H), 1.46-1.40 (m, 3H), 1.22 (s, 9H), 1.27-1.18 (m, 3H), 1.04 (s, 6H), 0.93-0.80 (m, 3H), 0.62 (m, 2H). MS: 574.3 $(M + 1)^+$. |

-continued

| # | Structure | Analytical data |
|---|---|---|
| 9/10 | 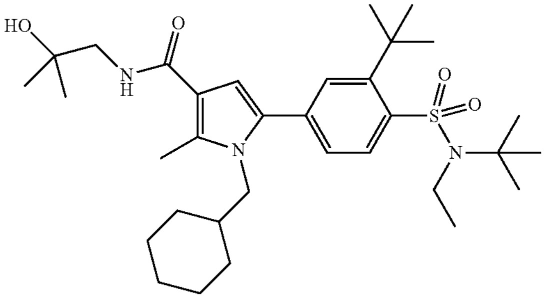 [SMILES: CCN(C(C)(C)C)S(=O)(=O)c1ccc(-c2cc(C(=O)NCC(C)(C)O)c(C)n2CC2CCCCC2)cc1C(C)(C)C] | $^1$H-NMR (400 MHz, DMSO-$d_6$) δ: 7.80 (d, J = 8.4 Hz, 1H), 7.62-7.44 (m, 2H), 7.41 (m, 1H), 6.71 (s, 1H), 4.61 (s, 1H), 3.84 (m, 2H), 3.62 (m, 2H), 3.15 (m, 2H), 2.52 (s, 3H), 1.54 (s, 9H), 1.45-1.41 (m, 3H), 1.35-1.16 (m, 15H), 1.07 (s, 6H), 0.96-0.80 (m, 3H), 0.63 (m, 2H). MS: 588.3 (M + 1)$^+$. |
| 9/11 | 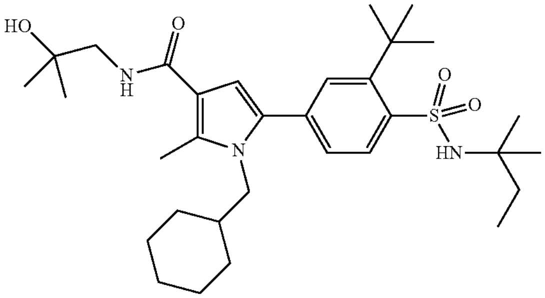 [SMILES: CCC(C)(C)NS(=O)(=O)c1ccc(-c2cc(C(=O)NCC(C)(C)O)c(C)n2CC2CCCCC2)cc1C(C)(C)C] | $^1$H-NMR (400 MHz, DMSO-$d_6$) δ: 8.14 (d, J = 8.4 Hz, 1H), 7.62 (s, 1H), 7.54-7.50 (m, 2H), 7.42 (m, 1H), 6.72 (s, 1H), 4.61 (s, 1H), 3.86 (m, 2H), 3.18 (m, 2H), 2.53 (s, 3H), 1.560-1.50 (m, 11H), 1.49-1.40 (m, 3H), 1.25-1.21 (m, 3H), 1.08 (s, 12H), 0.93-0.81 (s, 6H), 0.61 (m, 2H). MS: 574.1 (M + 1)$^+$. |
| 9/12 | 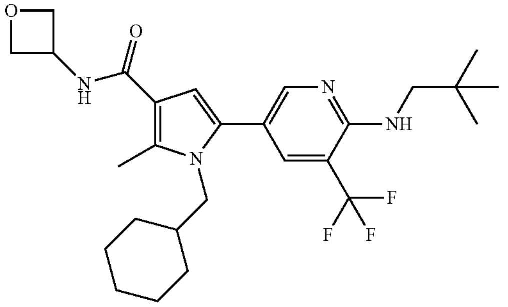 [SMILES: Cc1c(C(=O)NC2COC2)cc(-c2cnc(NCC(C)(C)C)c(C(F)(F)F)c2)n1CC1CCCCC1] | $^1$H-NMR (400 MHz, $CDCl_3$) δ: 0.68-0.71 (2H, m), 1.01-1.07 (12H, m), 1.37-1.45 (3H, m), 1.58 (3H, m), 2.58 (3H, s), 3.41 (2H, d, J = 5.6 Hz), 3.65 (2H, d, J = 7.2 Hz), 4.57 (2H, t, J = 6.4 Hz), 4.97-5.00 (2H, t, J = 6.4 Hz), 5.04 (1H, s), 5.20-5.22 (1H, m), 6.17 (2H, d, J = 7.6 Hz), 6.20 (1H, s), 7.58 (1H, d, J = 2.4 Hz), 8.20 (1H, d, J = 2.0 Hz). MS: 507.1 (M + 1)$^+$. |
| 9/13 | 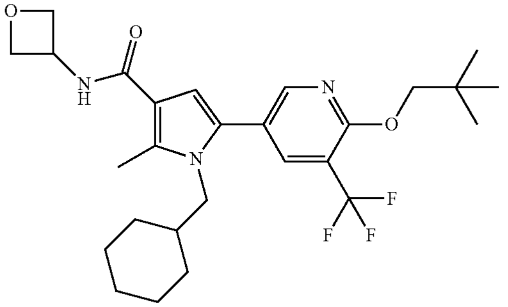 [SMILES: Cc1c(C(=O)NC2COC2)cc(-c2cnc(OCC(C)(C)C)c(C(F)(F)F)c2)n1CC1CCCCC1] | $^1$H-NMR (400 MHz, DMSO-$d_6$) δ: 0.67-0.69 (2H, m), 0.86-1.02 (12H, m), 1.29-1.36 (3H, m), 1.51-1.53 (3H, m), 2.45 (3H, s), 3.76 (2H, m), 4.12 (2H, s), 4.54 (2H, m), 4.72 (2H, m), 4.94 (1H, m), 6.72 (1H, s), 8.07 (1H, m), 8.28 (1H, m), 8.45 (1H, m). MS: 508.1 (M + 1)$^+$. |
| 9/14 | 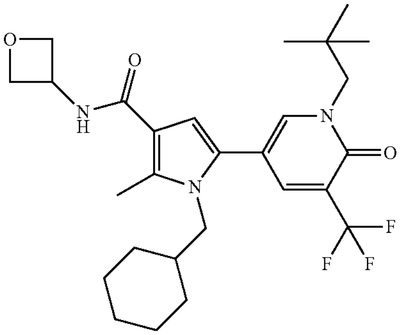 [SMILES: Cc1c(C(=O)NC2COC2)cc(-c2cc(C(F)(F)F)c(=O)n(CC(C)(C)C)c2)n1CC1CCCCC1] | $^1$H-NMR (400 MHz, DMSO-$d_6$) δ: 8.24 (m, 1H), 8.03 (m, 1H), 7.92 (m, 1H), 6.64 (s, 1H), 4.94 (m, 1H), 4.71 (m, 2H), 4.53 (m, 2H), 3.94 (s, 2H), 3.71 (m, 2H), 2.49 (s, 3H, partial overlay with solvent signal), 1.59-1.52 (m, 2H), 1.50-1.25 (m, 4H), 1.10-1.00 (m, 2H), 0.94 (s, 9H), 0.76 (m, 2H); MS: 508.1 (M + 1)$^+$. |

-continued

| # | Structure | Analytical data |
| --- | --- | --- |
| 9/15 | 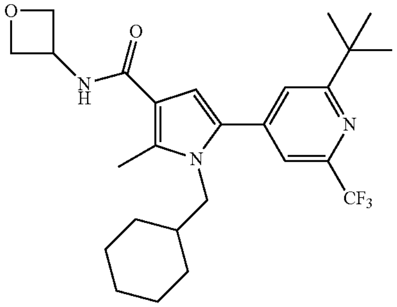 [SMILES: Cc1c(C(=O)NC2COC2)cc(-c2cc(C(C)(C)C)nc(C(F)(F)F)c2)n1CC1CCCCC1] | $^1$H-NMR (300 MHz, $CDCl_3$) δ: 7.45-7.42 (m, 2H), 6.43 (s, 1H), 6.35 (d, 1H, J = 6.9 Hz), 5.20 (m, 1H), 4.99 (t, 2H, J = 6.9 Hz), 4.58 (t, 2H, J = 6.9 Hz), 3.84 (d, 2H, J = 6.9 Hz), 2.61 (s, 3H), 1.66 (m, 3H), 1.41 (s, 9H), 1.30-1.38 (m, 3H), 0.97-1.03 (m, 3H), 0.63 (m, 2H). MS: 478.2 (M + 1). |

Example 10

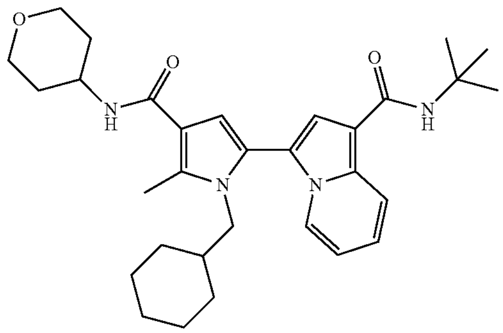

Step 1: Indolizine-1-carboxylic acid (10a)

A solution of ethyl indolizine-1-carboxylate (1.3 g, 6.88 mmol, prepared according J. Org. Chem. 1999, 64:7618) and 10% aq. NaOH (120 mL) in THF (10 mL) was heated to 50° C. overnight. The resulting solution was concentrated and adjusted to pH 1 by conc. HCl. The solution was extracted twice with EA. The combined organic layers were washed with brine, dried with $Na_2SO_4$, filtered and concentrated to give intermediate 10a (0.50 g, 45%) as a colorless solid.

Step 2: N-tert-Butylindolizine-1-carboxamide (10b)

A solution of intermediate 10a (500 mg, 3.11 mmol), HATU (1.42 g, 3.73 mmol) and DIPEA (1.2 g, 9.33 mmol) in DMF (10 mL) was stirred at rt for 30 min, then tert-butylamine (273 mg, 3.73 mmol) was added and the solution was stirred for another 0.5 h. The mixture was quenched with water and extracted three times with EA. The combined organic layers were washed with water and brine consecutively, dried over $Na_2SO_4$, filtered, concentrated and purified by CC (PE/EA=5/1) to give intermediate 10b (410 mg, 61%) as a colorless solid.

Step 3: 3-Bromo-N-tert-butylindolizine-1-carboxamide (10c)

A solution of intermediate 10b (100 mg, 463 μmol) and $CuBr_2.2H_2O$ (124 mg, 556 μmol) in ACN (10 mL) was stirred at rt for 1.5 h. The mixture was quenched with sat. aq. $NH_4Cl$ and extracted twice with EA. The combined organic layers were washed with brine, dried over $Na_2SO_4$, filtered, concentrated and purified by CC (PE/EA=20/1) to give intermediate 10c (50 mg, 37%) as a yellow solid.

Step 4: Ethyl 5-(1-(tert-butylcarbamoyl)indolizin-3-yl)-1-(cyclohexylmethyl)-2-methyl-1H-pyrrole-3-carboxylate (10d)

To a solution of intermediate 10c (50 mg, 169 μmol), P18 (59.5 mg, 203 μmol), $K_2CO_3$ (58 mg, 423 μmol) and TBAB (10 mg) in a mixture of 1,4-dioxane (1 mL) and water (0.5 mL) was added $Pd(PPh_3)_2Cl_2$ (10 mg) under $N_2$ and the solution was heated to 85° C. for 1 h under microwave irradiation (120 W). After cooling to rt the resulting solution was poured into a mixture of water and EA and the aq. phase was extracted twice with EA. The combined organic layers were washed with water and brine, dried over $Na_2SO_4$, filtered, concentrated and purified by CC (PE/EA=5/1) to give intermediate 10d (30 mg, 38%) as a colorless solid.

Step 5: 5-(1-(tert-Butylcarbamoyl)indolizin-3-yl)-1-(cyclohexylmethyl)-2-methyl-1H-pyrrole-3-carboxylic acid (10e)

To a solution of intermediate 10d (156 mg, 337 μmol) in a mixture of DMSO (1.5 mL) and water (one drop) was added KOtBu (76 mg, 674 μmol) and the solution was stirred at 80° C. overnight. The mixture was quenched with water, the pH was adjusted to 5 with 1M HCl and extracted twice with DCM. The combined organic layers were washed with water three times and brine consecutively, dried over $Na_2SO_4$, filtered and concentrated to give intermediate 10e (143 mg, 98%) as a colorless solid.

Step 6: N-tert-Butyl-3-(1-(cyclohexylmethyl)-5-methyl-4-(tetrahydro-2H-pyran-4-ylcarbamoyl)-1H-pyrrol-2-yl)indolizine-1-carboxamide (10)

A solution of intermediate 10e (143 mg, 329 μmol), HATU (150 mg, 394 μmol) and DIPEA (127 mg, 986 μmol) in dry DMF (2 mL) was stirred for 30 min at rt, then 4-aminotetrahydropyran (40 mg, 394 μmol) was added and the solution was stirred for another 0.5 h. The mixture was quenched with water and extracted twice with EA. The combined organic layers were washed with water three times and brine consecutively, dried over $Na_2SO_4$, filtered, concentrated and purified by prep. HPLC to give 10 (25 mg, 15%) as a colorless solid. $^1$H-NMR ($CDCl_3$, 400 MHz) δ: 0.54-0.60 (2H, m), 0.96-0.98 (3H, m), 1.25-1.28 (4H, m), 1.44-1.51 (13H, m), 1.97-2.01 (2H, m), 2.64 (3H, s), 3.50-3.55 (4H, m), 3.97-3.99 (2H, m), 4.15-4.4.19 (1H, m), 5.58-5.60 (1H, d, J=8.0 Hz), 5.67 (1H, s), 6.35 (1H, s), 6.63-6.67 (1H, m), 6.83 (1H, s), 6.99-7.03 (1H, m), 7.73 (1H, d, J=7.6 Hz), 8.37 (1H, d, J=9.2 Hz). MS: 519.2 (M+1).

Example 10/1

The following Example was prepared similar as in Example 10:

| # | Structure | Analytical data |
| --- | --- | --- |
| 10/1 | 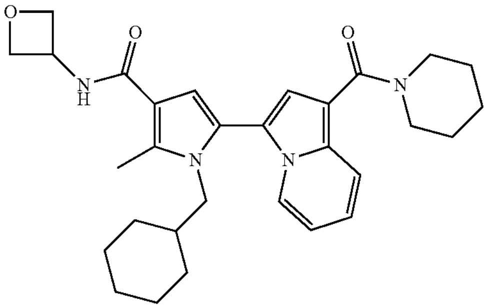 [SMILES: Cc1c(C(=O)NC2COC2)cc(-c2cc(C(=O)N3CCCCC3)c3ccccn23)n1CC1CCCCC1] | $^1$H-NMR ($CDCl_3$, 400 MHz) δ: 0.61-0.63 (2H, m), 0.96-0.98 (3H, m), 1.34-1.36 (4H, m), 1.53-1.55 (2H, m), 1.64-1.72 (6H, m), 2.62 (3H, s), 3.51-3.53 (2H, d, J = 7.2 Hz), 3.70-3.73 (4H, m), 4.56-4.59 (2H, m), 4.98-5.01 (2H, m), 5.20-5.22 (1H, m), 6.21-6.22 (1H, m), 6.43 (1H, s), 6.60-6.64 (1H, m), 6.87 (1H, s), 6.93-6.97 (1H, m), 7.70-7.72 (1H, m), 7.90-7.92 (1H, m). MS: 503.1 $(M + 1)^+$. |

Example 11

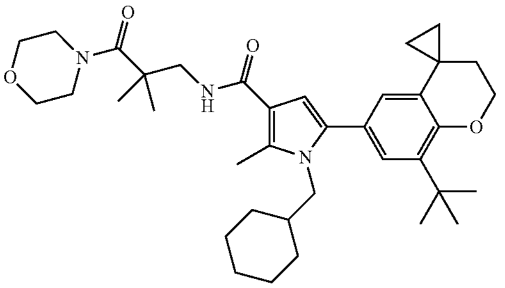

11

5(8-(tert-Butyl)spiro[chroman-4,1'-cyclopropan]-6-yl)-1-(cyclohexylmethyl)-N-(2,2-dimethyl-3-morpholino-3-oxopropyl)-2-methyl-1H-pyrrole-3-carboxamide (11)

To a solution of Example 1/91 (106 mg, 0.2 mmol) in DMF (5 mL) was added HATU (152 mg, 0.4 mmol) and DIPEA (129 mg, 1 mmol). The mixture was stirred for 60 min and then morpholine (87 mg, 1 mmol) was added into the mixture. The mixture was stirred overnight and quenched with ice water and extracted with EA. The organic layer was separated and washed with brine and dried over $Na_2SO_4$. After filtration, the filtrate was evaporated and purified by prep. HPLC to give compound 11 (54 mg, 45%) as a colorless solid. $^1$H-NMR (400 MHz, DMSO-$d_6$) δ: 7.26 (t, 1H), 6.89 (s, 1H), 6.48 (s, 1H), 6.26 (s, 1H), 4.28 (t, 2H), 3.65 (d, 2H), 3.57 (s, 8H), 3.37 (m, 2H), 2.47 (s, 3H), 1.84 (t, 2H), 1.51 (m, 3H), 1.26 (m, 12H), 1.17 (s, 6H), 0.98 (m, 5H), 0.71 (m, 2H), 0.66 (m, 2H). MS: 604.3 (M+1).

Example 11/1 to 11/7

The following Examples were prepared similar as in Example 11:

| # | Structure | Analytical data |
| --- | --- | --- |
| 11/1 | 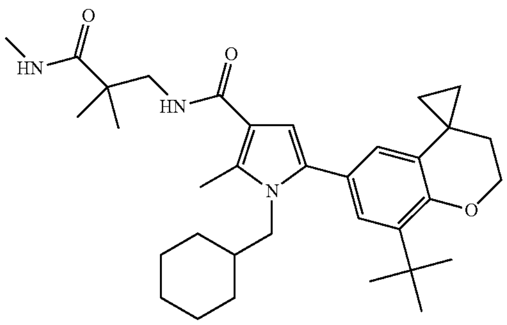 [SMILES: CNC(=O)C(C)(C)CNC(=O)c1cc(-c2cc(C(C)(C)C)c3c(c2)C2(CCO3)CC2)n(CC2CCCCC2)c1C] | $^1$H-NMR (400 MHz, DMSO-$d_6$) δ: 7.60 (t, 1H), 7.29 (t, 1H), 6.90 (s, 1H), 6.48 (s, 1H), 6.30 (s, 1H), 4.29 (t, 2H), 3.65 (d, 2H), 3.27 (d, 2H), 3.56 (s, 3H), 2.47 (s, 3H), 1.84 (t, 2H), 1.50 (m, 3H), 1.29 (m, 12H), 1.07 (s, 6H), 0.95 (m, 5H), 0.88 (m, 2H), 0.67 (m, 2H). MS: 548.4 (M + 1). |

-continued
| # | Structure | Analytical data |
|---|---|---|
| 11/2 | 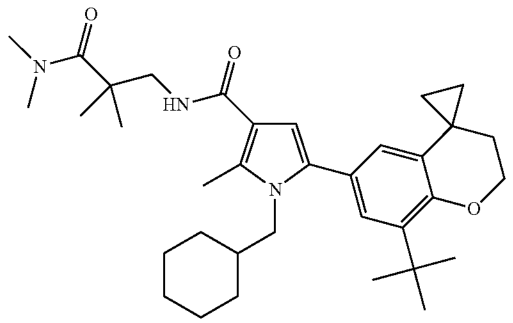 [SMILES: Cc1c(C(=O)NCC(C)(C)C(=O)N(C)C)cc(-c2cc(C(C)(C)C)c3c(c2)C2(CCO3)CC2)n1CC1CCCCC1] | $^1$H-NMR (400 MHz, $CDCl_3$) δ: 6.96 (s, 1H), 6.87 (s, 1H), 6.43 (s, 1H), 6.14 (s, 1H), 4.32 (t, 2H), 3.63 (d, 2H), 3.52 (d, 2H), 3.02 (s, 6H), 2.58 (s, 3H), 1.91 (t, 2H), 1.57 (m, 3H), 1.37 (m, 12H), 1.29 (s, 6H), 1.02 (m, 5H), 0.82 (m, 2H), 0.66 (m, 2H). MS: 562.8 (M + 1). |
| 11/3 | 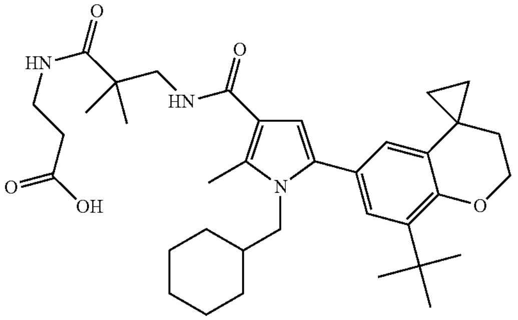 [SMILES: Cc1c(C(=O)NCC(C)(C)C(=O)NCCC(=O)O)cc(-c2cc(C(C)(C)C)c3c(c2)C2(CCO3)CC2)n1CC1CCCCC1] | $^1$H-NMR (400 MHz, $CDCl_3$) δ: 7.00 (m, 2H), 6.42 (m, 2H), 6.11 (s, 1H), 4.33 (t, 2H), 3.61 (d, 2H), 3.50 (m, 4H), 2.56 (m, 5H), 1.91 (t, 2H), 1.56 (m, 3H), 1.32 (m, 12H), 1.26 (s, 6H), 1.00 (m, 5H), 0.84 (m, 2H), 0.65 (m, 2H). MS: 606.4 (M + 1). |
| 11/4 | 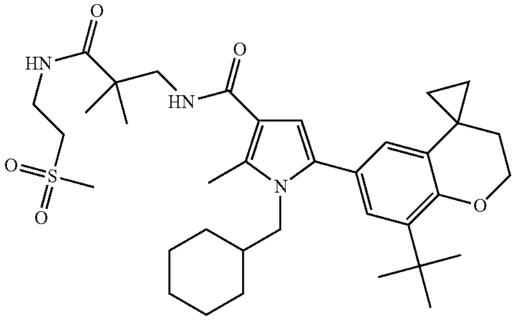 [SMILES: Cc1c(C(=O)NCC(C)(C)C(=O)NCCS(C)(=O)=O)cc(-c2cc(C(C)(C)C)c3c(c2)C2(CCO3)CC2)n1CC1CCCCC1] | $^1$H-NMR (400 MHz, DMSO-$d_6$) δ: 7.87 (t, 1H), 7.31 (t, 1H), 6.90 (s, 1H), 6.48 (s, 1H), 6.33 (s, 1H), 4.28 (t, 2H), 3.67 (d, 2H), 3.46 (m, 2H), 3.29 (m, 2H), 3.23 (m, 2H), 2.97 (s, 3H), 2.48 (s, 3H), 1.86 (t, 2H), 1.84 (m, 3H), 1.27 (m, 12H), 1.03 (s, 6H), 0.98 (m, 5H), 0.87 (m, 2H), 0.66 (m, 2H). MS: 640.4 (M + 1). |
| 11/5 | 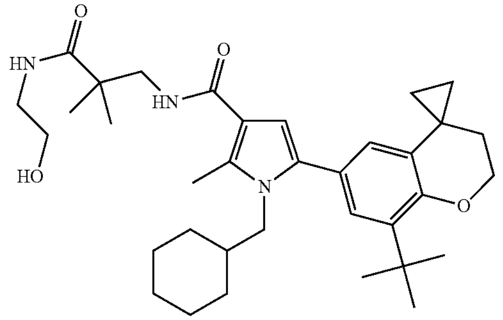 [SMILES: Cc1c(C(=O)NCC(C)(C)C(=O)NCCO)cc(-c2cc(C(C)(C)C)c3c(c2)C2(CCO3)CC2)n1CC1CCCCC1] | $^1$H-NMR (400 MHz, DMSO-$d_6$) δ: 7.60 (t, 1H), 7.29 (t, 1H), 6.90 (s, 1H), 6.48 (s, 1H), 6.31 (s, 1H), 4.64 (t, 1H), 4.29 (t, 2H), 3.66 (d, 2H), 3.39 (m, 2H), 3.33 (m, 2H), 3.11 (m, 2H), 2.47 (s, 3H), 1.84 (t, 2H), 1.50 (m, 3H), 1.26 (m, 12H), 1.02 (s, 6H), 0.94 (m, 5H), 0.87 (m, 2H), 0.67 (m, 2H). MS: 578.4 (M + 1). |

-continued

| # | Structure | Analytical data |
|---|---|---|
| 11/6 | 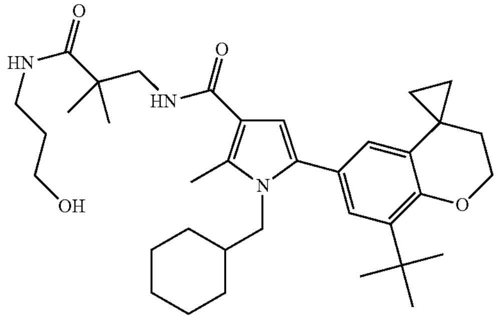 [SMILES: Cc1c(C(=O)NCC(C)(C)C(=O)NCCCO)cc(-c2cc(C(C)(C)C)c3c(c2)C2(CCO3)CC2)n1CC1CCCCC1] | $^1$H-NMR (400 MHz, DMSO-$d_6$) δ: 7.66 (t, 1H), 7.30 (t, 1H), 6.90 (s, 1H), 6.48 (s, 1H), 6.30 (s, 1H), 4.42 (t, 1H), 4.28 (t, 2H), 3.66 (d, 2H), 3.37 (m, 2H), 3.29 (d, 2H), 3.09 (m, 2H), 2.48 (s, 3H), 1.84 (t, 2H), 1.52 (m, 5H), 1.29 (m, 12H), 1.06 (s, 6H), 0.98 (m, 5H), 0.88 (m, 2H), 0.67 (m, 2H). MS: 592.5 (M + 1). |
| 11/7 | 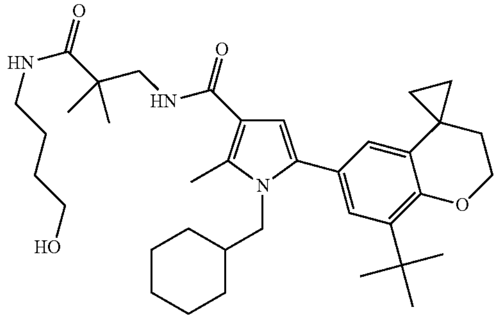 [SMILES: Cc1c(C(=O)NCC(C)(C)C(=O)NCCCCO)cc(-c2cc(C(C)(C)C)c3c(c2)C2(CCO3)CC2)n1CC1CCCCC1] | $^1$H-NMR (400 MHz, DMSO-$d_6$) δ: 7.66 (t, 1H), 7.29 (t, 1H), 6.90 (s, 1H), 6.48 (s, 1H), 6.29 (s, 1H), 4.36 (t, 1H), 4.28 (t, 2H), 3.67 (d, 2H), 3.29 (m, 4H), 3.03 (m, 2H), 2.48 (s, 3H), 1.86 (t, 2H), 1.51 (m, 3H), 1.41 (m, 16H), 0.99 (s, 6H), 0.89 (m, 5H), 0.88 (m, 2H), 0.66 (m, 2H). MS: 606.5 (M + 1). |

Example 12

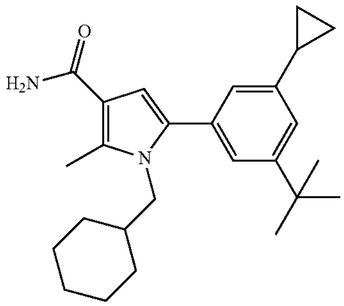

12

Step 1: Ethyl 5-(3-bromo-5-(tert-butyl)phenyl)-1-(cyclohexylmethyl)-2-methyl-1H-pyrrole-3-carboxylate (12a)

To a solution of compound P18a (643 mg, 1.71 mmol) in 1,4-dioxane/$H_2O$ (3 mL/0.8 mL) 1,3-dibromo-5-(tert-butyl) benzene (595 mg, 2.05 mmol), $Cs_2CO_3$ (1.11 g, 3.42 mmol) and $Pd(PPh_3)_4$ (66 mg, 0.17 mmol) were added under $N_2$. The mixture was stirred under microwave at about 110° C. for 2.5 h. Removal of the solvents and purification by prep. TLC (PE/EA=20/1) yielded compound 12a (275 mg, 35%) as yellow solid.

Step 2: Ethyl 5-(3-(tert-butyl)-5-cyclopropylphenyl)-1-(cyclohexylmethyl)-2-methyl-1H-pyrrole-3-carboxylate (12b)

To a solution of compound 12a (275 mg, 0.60 mmol) in toluene/$H_2O$ (2 mL/0.1 mL) cyclopropylboronic acid (154 mg, 1.80 mmol), tricyclohexylphosphine (17 mg, 0.06 mmol), $K_3PO_4$ (505 mg, 2.11 mmol) and $Pd(OAc)_2$ (7 mg, 0.03 mmol) were added under $N_2$. The mixture was stirred at 100° C. for 3 h, then concentrated and purified by prep. TLC (PE/EA=20/1) to yield compound 12b (150 mg, 60%) as a colorless solid.

Step 3: 5-(3-(tert-Butyl)-5-cyclopropylphenyl)-1-(cyclohexylmethyl)-2-methyl-1H-pyrrole-3-carboxylic acid (12c)

To a solution of 10% NaOH in water/MeOH (10 mL, 1:1) was added compound 12b (150 mg, 0.36 mmol) and the mixture was stirred at 70° C. for 3 h. Then 2M HCl was added to adjust the pH to 4. The mixture was extracted with EA and removal of the organic solvents gave the crude compound 12c (100 mg, 90%).

Step 4: 5-(3-(tert-Butyl)-5-cyclopropylphenyl)-1-(cyclohexylmethyl)-2-methyl-1H-pyrrole-3-carboxamide (12)

To a solution of compound 12c (50 mg, 0.125 mmol) in DCM (5 mL) was added $(COCl)_2$ (160 mg, 1.25 mmol) dropwise and then a drop of DMF under $N_2$. The mixture was stirred at rt for 1 h and then concentrated. Then $NH_3$ in THF was added and the mixture was stirred for 1 min, concentrated and purified by prep. HPLC to afford compound 12 (15 mg, 35%) as a colorless solid. $^1$H-NMR (500 MHz, $CDCl_3$) δ: 0.63-0.66 (m, 4H), 0.91-1.00 (m, 5H), 1.34-1.38 (m, 12H), 1.54 (m, 3H), 1.93 (m, 1H), 2.62 (s, 3H), 3.72 (d, 2H), 5.44 (br s, 2H), 6.19 (s, 1H), 6.75 (s, 1H), 7.11-7.14 (m, 2H). MS (m/z): 393 (M+1).

Example 13 to Example 15

13

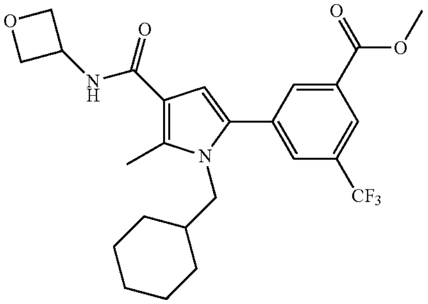

14

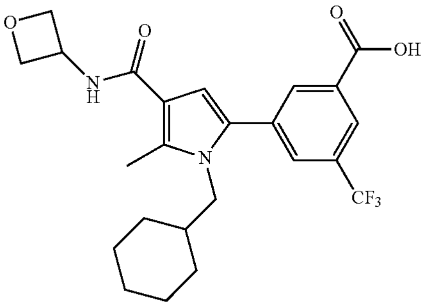

15

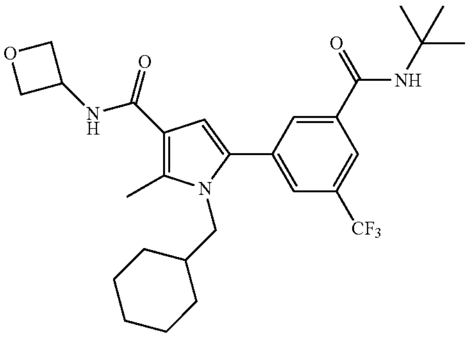

Step 1: Methyl 3-(1-(cyclohexylmethyl)-5-methyl-4-(oxetan-3-ylcarbamoyl)-1H-pyrrol-2-yl)-5-(trifluoromethyl)benzoate (13)

A mixture of 5-bromo-1-(cyclohexylmethyl)-2-methyl-N-(oxetan-3-yl)-1H-pyrrole-3-carboxamide (1.54 g, 4.66 mmol), compound P68 (1.50 g, 4.24 mmol), $K_2CO_3$ (1.46 g, 10.6 mmol) and TBAB (60 mg, 0.18 mmol) in 1,4-dioxane/$H_2O$ (10 mL/5 mL) was added $Ph(PPh_3)_2Cl_2$ (300 mg) under $N_2$. The solution was heated under microwave conditions at 100° C. for 1.5 h. Water was added and the solution was extracted with EA. The organic layer was washed with brine, dried over $NaSO_4$, filtered, concentrated and purified by CC (PE/EA=5/1) to give compound 13 (1.12 g, 63%) as a colorless solid.

Step 2: 3-(1-(Cyclohexylmethyl)-5-methyl-4-(oxetan-3-ylcarbamoyl)-1H-pyrrol-2-yl)-5-(trifluoromethyl)benzoic acid (14)

To a stirred solution of compound 13 (680 mg, 1.42 mmol) in a mixture of THF (10 mL) and $H_2O$ (3 mL) was added $LiOH.H_2O$ (420 mg, 10 mmol) and this mixture was stirred at 60° C. for 3 h. The mixture was adjusted to pH=2-3 with 1M HCl and then extracted with EA. The organic layer was washed with brine, dried over $Na_2SO_4$, concentrated and purified by CC (PE/EA=2/1) to give compound 14 (640 mg, 97%) as a colorless powder.

Step 3: 5-(3-(tert-Butylcarbamoyl)-5-(trifluoromethyl)phenyl)-1-(cyclohexylmethyl)-2-methyl-N-(oxetan-3-yl)-1H-pyrrole-3-carboxamide (15)

A mixture of compound 14 (160 mg, 0.34 mmol), tert-butylamine (26 mg, 0.36 mmol), HATU (94.2 mg, 0.36 mmol) and DIPEA (97.4 mg, 0.76 mmol) in DMF (5 mL) was stirred at rt for 20 min. The mixture was diluted with EA and the organic layer was washed with brine, dried over $Na_2SO_4$, concentrated and purified by prep. TLC to give compound 15 (46 mg, 26%) as a colorless powder. $^1H$-NMR ($CDCl_3$, 300 MHz) δ: 7.89 (m, 2H), 7.69 (s, 1H), 6.35 (s, 1H), 6.25 (d, 1H, J=7.2 Hz), 5.99 (s, 1H), 5.20 (m, 1H), 4.99 (t, 2H, J=7.2 Hz), 4.58 (t, 2H, J=7.2 Hz), 3.77 (d, 2H, J=6.9 Hz), 2.60 (s, 3H), 1.61 (m, 3H), 1.50 (s, 9H), 1.33-1.38 (m, 3H), 0.99-1.03 (m, 3H), 0.63 (m, 2H). MS: 520 (M+1).

Examples 15/1 to 15/9

Using similar procedures as described in Example 15 the following Examples have been prepared:

| # | Structure | Analytical data |
|---|---|---|
| 15/1 | 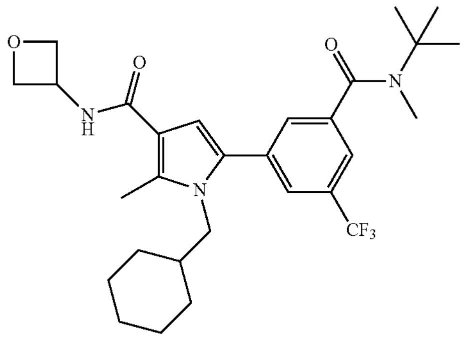 [SMILES: Cc1c(C(=O)NC2COC2)cc(-c2cc(C(=O)N(C)C(C)(C)C)cc(C(F)(F)F)c2)n1CC1CCCCC1] | $^1H$-NMR ($CDCl_3$, 300 MHz) δ: 7.65 (s, 1H), 7.60 (s, 1H), 7.59 (s, 1H), 6.32 (s, 1H), 6.21 (d, 1H, J = 6.9 Hz), 5.20 (q, 1H, J = 7.2 Hz), 4.99 (t, 2H, J = 7.2 Hz), 4.57 (t, 2H, J = 7.2 Hz), 3.77 (d, 2H, J = 6.9 Hz), 2.87 (s, 3H), 2.60 (s, 3H), 1.61 (m, 3H), 1.53 (s, 9H), 1.33-1.38 (m, 3H), 0.99-1.03 (m, 3H), 0.65 (m, 2H). MS: 534 (M + 1). |

-continued

| # | Structure | Analytical data |
|---|---|---|
| 15/2 | 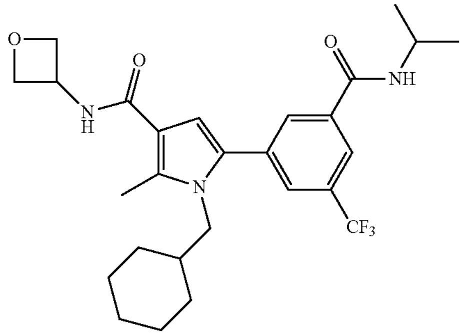 [SMILES: Cc1c(C(=O)NC2COC2)cc(-c2cc(C(=O)NC(C)C)cc(C(F)(F)F)c2)n1CC1CCCCC1] | $^1$H-NMR (DMSO-$d_6$, 400 MHz ) δ: 8.65 (d, 1H, J = 7.5 Hz), 8.32 (d, 1H, J = 6.9 Hz), 8.19 (d, 2H, J = 12.3 Hz), 7.87 (s, 1H), 6.85 (s, 1H), 4.95 (q, 1H, J = 7.2 Hz), 4.72 (t, 2H, J = 7.2 Hz), 4.54 (t, 2H, J = 7.2 Hz), 4.14 (q, 1H, J = 6.9 Hz), 3.87 (d, 2H, J = 7.2 Hz), 2.54 (s, 3H), 1.51 (m, 3H), 1.35-1.19 (m, 9H), 1.33-1.38 (m, 3H), 0.98-0.94 (m, 3H), 0.68 (m, 2H). MS: 506 (M + 1). |
| 15/3 | 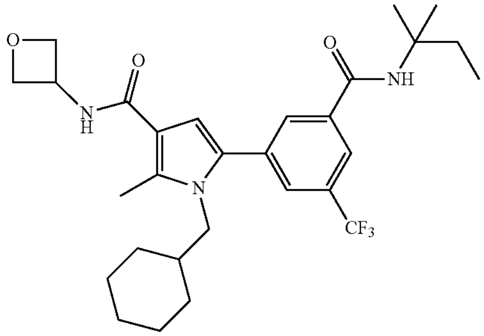 [SMILES: CCC(C)(C)NC(=O)c1cc(-c2cc(C(=O)NC3COC3)c(C)n2CC2CCCCC2)cc(C(F)(F)F)c1] | $^1$H-NMR ($CDCl_3$, 300 MHz) δ: 7.88 (s, 2H), 7.69 (s, 1H),<br>6.29 (s, 1H), 6.21 (d, 1H, J = 6.9 Hz), 5.20 (q, 1H, J = 7.2<br>Hz), 4.99 (t, 2H, J = 7.2 Hz), 4.59 (t, 2H, J = 7.2 Hz), 3.76<br>(d, 2H, J = 6.9 Hz), 2.87 (s, 3H), 2.60 (s, 3H), 1.85 (q, 2H,<br>J = 7.5 Hz), 1.57 (m, 3H), 1.43 (s, 6H), 1.28 (m, 3H), 0.95<br>(t, 3H, J = 7.5 Hz), 0.68 (m, 2H). MS: 534 (M + 1). |
| 15/4 | 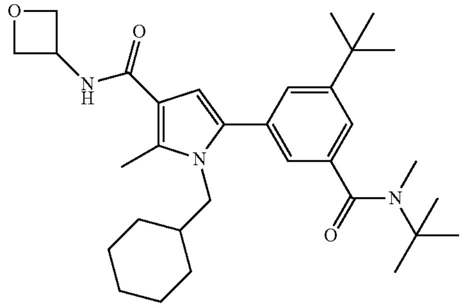 [SMILES: Cc1c(C(=O)NC2COC2)cc(-c2cc(C(=O)N(C)C(C)(C)C)cc(C(C)(C)C)c2)n1CC1CCCCC1] | $^1$H-NMR (400 MHz, DMSO-$d_6$) δ: 8.26 (d, J = 6.8 Hz, 1H), 7.45 (s, 1H), 7.32 (s, 1H), 7.14 (s, 1H), 6.68 (s, 1H), 4.98-4.93 (m, 1H), 4.73-4.70 (t, J = 7.0 Hz, 2H), 4.56-4.53 (t, J = 6.6 Hz, 2H), 3.83 (d, J = 7.2 Hz, 2H), 2.83 (s, 3H), 2.52 (s, 3H), 1.45 (s, 12H), 1.40 (s, 9H), 1.27-1.20 (m, 3H), 0.97-0.89 (m, 3H), 0.66-0.60 (m, 2H). MS: 522 (M + 1). |
| 15/5 | 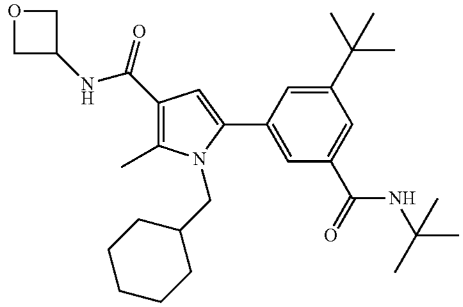 [SMILES: Cc1c(C(=O)NC2COC2)cc(-c2cc(C(=O)NC(C)(C)C)cc(C(C)(C)C)c2)n1CC1CCCCC1] | $^1$H-NMR (400 MHz, DMSO-$d_6$) δ: 8.28 (d, 1H), 7.83 (s, 1H), 7.76 (s, 1H), 7.70 (s, 1H), 7.51 (d, 1H), 6.96 (s, 1H),<br>4.98-4.94 (d, 1H), 4.73-4.71 (t, 2H), 4.56-4.54 (t, 2H), 3.82-3.81 (d, 2H), 2.52 (s, 3H), 1.50-1.40 (m, 3H), 1.40 (s, 9H), 1.34 (s, 9H), 1.29-1.15 (d, 3H), 0.96-0.93 (m, 3H), 0.66-0.61 (m, 2H). MS: 508 (M + 1). |

-continued
| # | Structure | Analytical data |
|---|---|---|
| 15/6 | 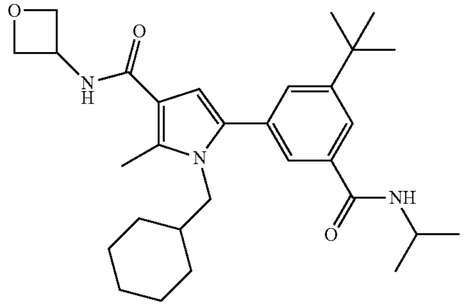 [SMILES: Cc1c(C(=O)NC2COC2)cc(-c2cc(C(=O)NC(C)C)cc(C(C)(C)C)c2)n1CC1CCCCC1] | $^1$H-NMR (400 MHz, DMSO-$d_6$) δ: 8.30-8.27 (t, 2H), 7.83 (s, 1H), 7.72 (s, 1H), 7.53 (s, 1H), 6.70 (s, 1H), 4.98-4.94 (d, 1H), 4.73-4.71 (t, 2H), 4.56-4.54 (t, 2H), 4.15-4.11 (m, 1H), 3.83-3.81 (d, 2H), 2.53 (s, 3H), 1.47 (m, 3H), 1.34 (s, 9H), 1.31-1.26 (m, 3H), 1.19-1.18 (d, 6H), 0.96-0.91 (m, 3H), 0.65-0.63 (m, 2H). MS: 494 (M + 1). |
| 15/7 | 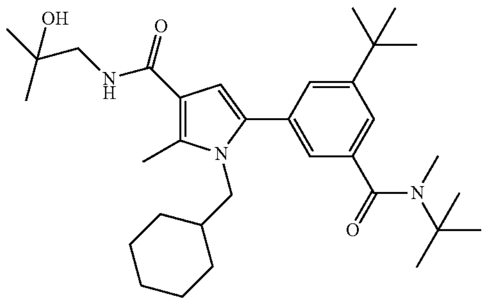 [SMILES: Cc1c(C(=O)NCC(C)(C)O)cc(-c2cc(C(=O)N(C)C(C)(C)C)cc(C(C)(C)C)c2)n1CC1CCCCC1] | $^1$H-NMR (400 MHz, DMSO-$d_6$) δ: 7.48-7.46 (t, 2H), 7.44 (s, 1H), 7.31 (s, 1H), 7.14 (s, 1H), 6.61 (s, 1H), 3.82-3.81 (d, 2H), 3.17-3.16 (d, 2H), 2.82 (s, 3H), 2.53 (s, 3H), 1.47-1.45 (m, 12H), 1.29-1.20 (m, 12H), 1.08 (s, 6H), 0.98-0.87 (m, 3H), 0.67-0.61 (m, 2H). MS: 538 (M + 1). |
| 15/8 | 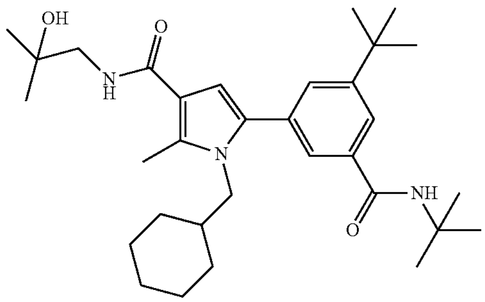 [SMILES: Cc1c(C(=O)NCC(C)(C)O)cc(-c2cc(C(=O)NC(C)(C)C)cc(C(C)(C)C)c2)n1CC1CCCCC1] | $^1$H-NMR (400 MHz, DMSO-$d_6$) δ: 7.81 (s, 1H), 7.75 (s, 1H), 7.68 (s, 1H), 7.50 (s, 1H), 7.47-7.45 (m, 1H), 6.62 (s, 1H), 4.63 (s, 1H), 3.82-3.80 (d, 2H), 3.18-3.16 (d, 2H), 2.54 (s, 3H), 1.50-1.48 (m, 3H), 1.39 (s, 9H), 1.34 (s, 9H), 1.29-1.17 (m, 3H), 1.08 (s, 6H), 1.00-0.95 (m, 3H), 0.70-0.63 (m, 2H). MS: 524 (M + 1). |
| 15/9 | 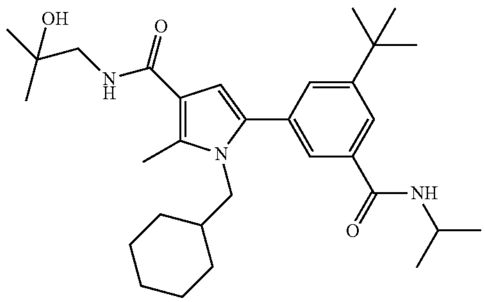 [SMILES: Cc1c(C(=O)NCC(C)(C)O)cc(-c2cc(C(=O)NC(C)C)cc(C(C)(C)C)c2)n1CC1CCCCC1] | $^1$H-NMR (400 MHz, DMSO-$d_6$) δ: 8.29-8.28 (d, 1H), 7.82 (s, 1H), 7.71 (s, 1H), 7.52 (s, 1H), 7.49-7.47 (m, 1H), 6.62 (s, 1H), 4.63 (m, 1H), 4.16-4.11 (m, 1H), 3.82-3.81 (d, 2H), 3.18-3.16 (d, 2H), 2.54 (s, 3H), 1.49-1.47 (m, 3H), 1.34 (s, 12H), 1.31-1.17 (m, 6H), 1.08 (s, 6H), 0.96-0.92 (m, 3H), 0.66-0.64 (m, 2H). MS: 510 (M + 1). |

Example 16

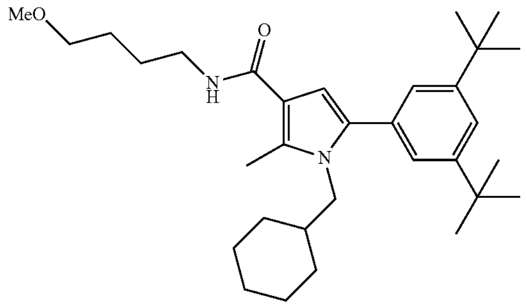

16

Step 1: 1-(Cyclohexylmethyl)-5-(3,5-di-tert-butylphenyl)-2-methyl-1H-pyrrole-3-carboxamide (16a)

To a solution of 1-(cyclohexylmethyl)-5-(3,5-di-tert-butylphenyl)-2-methyl-1H-pyrrole-3-carboxylic acid (410 mg, 1.0 mmol) in DMF (25 mL) was added HATU (456 mg, 1.2 mmol) in an ice-water bath below 10° C. The mixture was stirred for 60 min and then $NH_4Cl$ (81 mg, 1.5 mmol) was added to the mixture. The mixture was stirred for additional 12 h, quenched with ice water and extracted with EA. The organic layer was separated and washed with brine, dried over $Na_2SO_4$, filtered, evaporated and purified by prep. HPLC to give compound 16a as a colorless solid.

Step 2: 1-(Cyclohexylmethyl)-5-(3,5-di-tert-butylphenyl)-N-(4-methoxybutyl)-2-methyl-1H-pyrrole-3-carboxamide (16)

A mixture of compound 16a (82 mg, 0.2 mmol) and 1-chloro-4-methoxybutane (27 mg, 0.22 mmol) in DMF (5 mL) was added NaH (60%, 24 mg, 0.6 mmol) at 0° C. and the mixture was stirred overnight under Ar at 90° C., quenched with ice water and extracted with EA. The organic layer was separated, washed with brine, dried over $Na_2SO_4$, filtered, evaporated and purified by prep. HPLC to give compound 16 (16 mg, 16%) as a colorless solid. $^1$H-NMR (400 MHz, DMSO-$d_6$) δ: 7.63-7.60 (t, J=5.8 Hz, 1H), 7.35 (s, 1H), 7.16-7.15 (d, J=1.6 Hz, 2H), 6.49 (s, 1H), 3.77-3.75 (d, J=6.8 Hz, 2H), 3.34-3.31 (t, J=5.8 Hz, 2H), 3.22 (s, 3H), 3.17-3.16 (d, J=6.0 Hz, 3H), 2.52 (s, 3H), 1.51-1.50 (t, J=3.0 Hz, 4H), 1.46-1.43 (d, J=9.2 Hz, 3H), 1.31 (s, 18H), 1.27-1.21 (t, J=11.2 Hz, 3H), 0.94-0.89 (t, J=10.8 Hz, 3H), 0.65-0.62 (d, J=11.2 Hz, 2H). MS: 495 (M+1).

Example 17/1 to 17/374

The following Examples were prepared similar as described above:

| # | Structure | Analytical data |
|---|---|---|
| 17/1 | 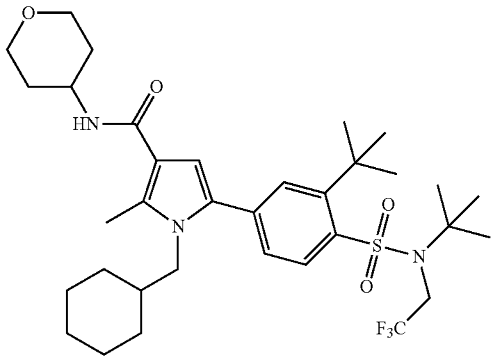 [SMILES: Cc1c(C(=O)NC2CCOCC2)cc(-c2ccc(S(=O)(=O)N(CC(F)(F)F)C(C)(C)C)c(C(C)(C)C)c2)n1CC1CCCCC1] | $^1$H-NMR ($CDCl_3$, 500 MHz) δ: 7.82 (d, 1H), 7.61 (d, 1H), 7.24 (d, 1H), 6.27 (s, 1H), 5.61 (d, 1H), 4.24-4.15 (m, 3H), 3.98 (d, 2H), 3.78 (d, 2H), 3.52 (dd, 2H), 2.62 (s, 3H), 1.98 (dd, 2H), 1.66-1.51 (m, 16H), 1.43-1.30 (m, 12H), 1.00-0.97 (m, 3H), 0.66-0.60 (m, 2H). MS: 654.3 (M + 1). |
| 17/2 | 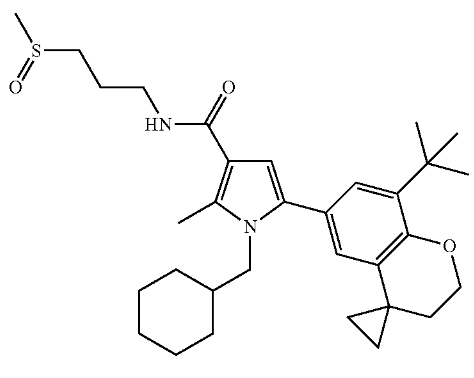 [SMILES: Cc1c(C(=O)NCCCS(C)=O)cc(-c2cc(C(C)(C)C)c3c(c2)C2(CCO3)CC2)n1CC1CCCCC1] | $^1$H-NMR (400 MHz, $CDCl_3$) δ: 6.97 (d, 1H), 6.43 (d, 1H), 6.12 (s, 2H), 4.33 (t, 2H), 3.65-3.59 (m, 4H), 3.17-2.82 (m, 2H), 2.64-2.60 (m, 6H), 2.12 (br s, 2H), 1.90 (t, 2H), 1.58-1.56 (m, 3H), 1.45-1.28 (m, 12H), 1.03-1.00 (m, 5H), 0.88-0.84 (m, 2H), 0.72-0.66 (m, 2H). MS: 539.3 [M + 1]$^+$. |

-continued
| # | Structure | Analytical data |
|---|---|---|
| 17/3 | 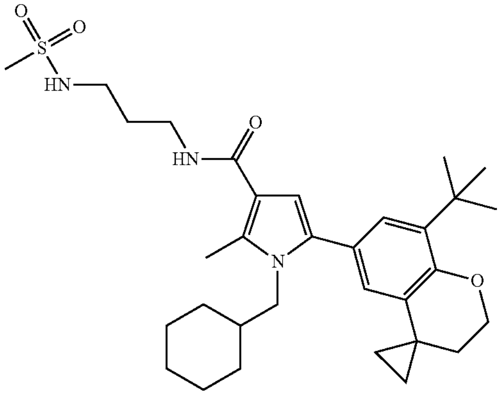 [SMILES: Cc1c(C(=O)NCCCNS(C)(=O)=O)cc(-c2cc(C(C)(C)C)c3c(c2)C2(CCO3)CC2)n1CC1CCCCC1] | $^1$H-NMR (400 MHz, DMSO-$d_6$) δ: 7.58 (t, 1H), 6.97 (t, 1H), 6.90 (d, 1H), 6.49 (d, 1H), 6.34 (s, 1H), 4.28 (t, 2H), 3.67 (d, 2H), 3.20 (q, 2H), 2.96 (q, 2H), 2.88 (s, 3H), 2.49 (s, 3H), 1.85 (t, 2H), 1.69-1.62 (m, 2H), 1.51-1.49 (m, 3H), 1.35-1.25 (m, 12H), 0.99-0.87 (m, 7H), 0.72-0.63 (m, 2H). MS: 570.4 [M + 1]$^+$. |
| 17/4 | 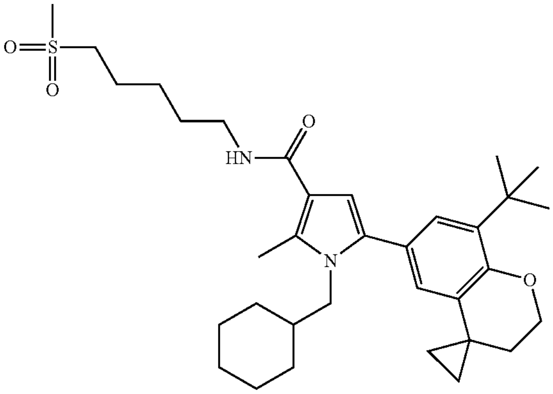 [SMILES: Cc1c(C(=O)NCCCCCS(C)(=O)=O)cc(-c2cc(C(C)(C)C)c3c(c2)C2(CCO3)CC2)n1CC1CCCCC1] | $^1$H-NMR (400 MHz, $CDCl_3$) δ: 6.97 (d, 1H), 6.43 (d, 1H), 6.06 (s, 1H), 5.77 (t, 1H), 4.33 (t, 2H), 3.64 (d, 2H), 3.39 (q, 2H), 3.02 (t, 2H), 2.90 (s, 3H), 2.59 (s, 3H), 1.94-1.86 (m, 4H), 1.69-1.50 (m, 7H), 1.46-1.35 (m, 12H), 1.03-1.00 (m, 5H), 0.87-0.84 (m, 2H), 0.72-0.64 (m, 2H). MS: 583.3 [M + 1]$^+$. |
| 17/5 | 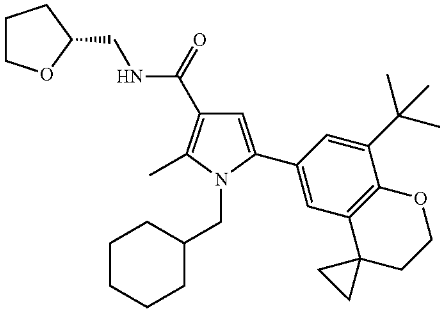 [SMILES: Cc1c(C(=O)NC[C@H]2CCCO2)cc(-c2cc(C(C)(C)C)c3c(c2)C2(CCO3)CC2)n1CC1CCCCC1] | $^1$H-NMR (400 MHz, $CDCl_3$) δ: 6.97 (d, 1H), 6.43 (d, 1H), 6.11 (d, 1H), 4.33 (t, 2H), 4.06-4.00 (m, 1H), 3.89-3.83 (m, 1H), 3.78-3.63 (m, 4H), 3.36-3.31 (m, 1H), 2.59 (s, 3H), 2.01-1.89 (m, 5H), 1.60-1.56 (m, 4H), 1.38-1.34 (m, 12H), 1.03-1.00 (m, 5H), 0.86-0.85 (m, 2H), 0.69-0.63 (m, 2H). MS: 519.3 (M + 1). |
| 17/6 | 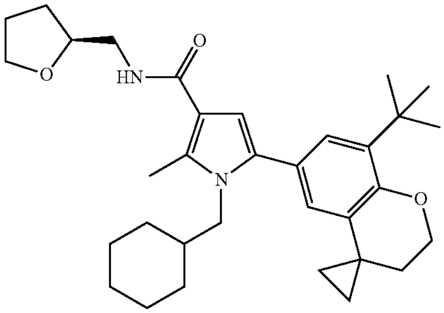 [SMILES: Cc1c(C(=O)NC[C@@H]2CCCO2)cc(-c2cc(C(C)(C)C)c3c(c2)C2(CCO3)CC2)n1CC1CCCCC1] | $^1$H-NMR (400 MHz, $CDCl_3$) δ: 6.97 (d, 1H), 6.43 (d, 1H), 6.11 (d, 1H), 4.33 (t, 2H), 4.06-4.00 (m, 1H), 3.89-3.83 (m, 1H), 3.78-3.63 (m, 4H), 3.36-3.31 (m, 1H), 2.59 (s, 3H), 2.01-1.89 (m, 5H), 1.60-1.56 (m, 4H), 1.38-1.34 (m, 12H), 1.03-1.00 (m, 5H), 0.86-0.85 (m, 2H), 0.69-0.63 (m, 2H). MS: 519.3 (M + 1) |

-continued
| # | Structure | Analytical data |
|---|---|---|
| 17/7 | 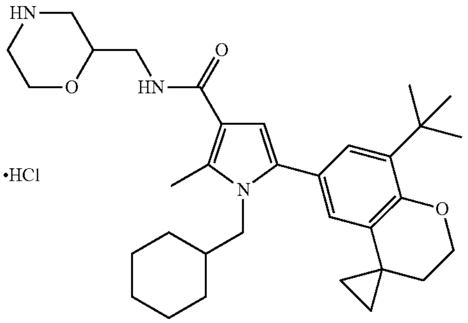 [SMILES: Cl ; Cc1c(C(=O)NCC2CNCCO2)cc(-c2cc(C(C)(C)C)c3c(c2)C2(CCO3)CC2)n1CC1CCCCC1] •HCl | $^1$H-NMR (400 MHz, $CDCl_3$) δ: 10.04 (s, 2H), 6.97 (s, 1H), 6.44 (s, 1H), 6.17 (br s, 1H), 6.11 (s, 1H), 4.33 (t, 2H), 4.11-4.02 (m, 3H), 3.64 (d, 2H), 3.60-3.34 (s, 4H), 3.05-2.87 (m, 2H), 2.57 (s, 3H), 1.90 (t, 3H), 1.56-1.52 (m, 3H), 1.38-1.35 (m, 12H), 1.04-1.02 (m, 5H), 0.86-0.85 (m, 2H), 0.672-0.65 (m, 2H). MS: 534.4 $(M - Cl)^+$. |
| 17/8 | 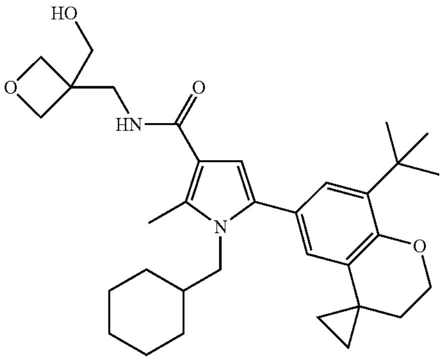 [SMILES: Cc1c(C(=O)NCC2(CO)COC2)cc(-c2cc(C(C)(C)C)c3c(c2)C2(CCO3)CC2)n1CC1CCCCC1] | $^1$H-NMR (400 MHz, $CDCl_3$) δ: 6.96 (d, 1H), 6.42 (d, 1H), 6.08-6.03 (m, 2H), 4.66 (t, 1H), 4.42 (dd, 4H), 4.33 (t, 2H), 3.80-3.78 (m, 4H), 3.64 (d, 2H), 2.57 (s, 3H), 1.90 (t, 2H), 1.56 (s, 3H), 1.42-1.35 (m, 12H), 1.04-0.99 (m, 5H), 0.87-0.84 (m, 2H), 0.72-0.66 (m, 2H). MS: 535.3 (M + 1). |
| 17/9 | 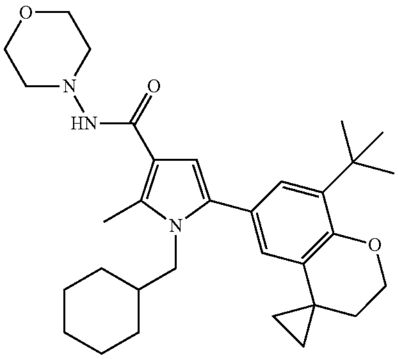 [SMILES: Cc1c(C(=O)NN2CCOCC2)cc(-c2cc(C(C)(C)C)c3c(c2)C2(CCO3)CC2)n1CC1CCCCC1] | $^1$H-NMR (400 MHz, $CDCl_3$) δ: 6.96 (d, 1H), 6.84 (br s, 1H), 6.42 (d, 1H), 6.09 (br d, 1H), 4.33 (t, 2H), 3.86-3.84 (m, 4H), 3.63 (d, 2H), 2.99 (br s, 4H), 2.58 (s, 3H), 1.90 (t, 2H), 1.58-1.56 (m, 3H), 1.45-1.32 (m, 12H), 1.04-0.96 (m, 5H), 0.87-0.84 (m, 2H), 0.70-0.65 (m, 2H). MS: 520.1 (M + 1). |
| 17/10 | 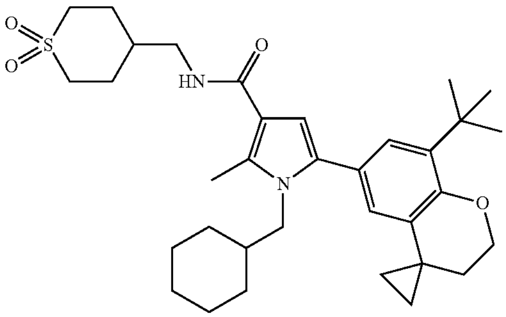 [SMILES: Cc1c(C(=O)NCC2CCS(=O)(=O)CC2)cc(-c2cc(C(C)(C)C)c3c(c2)C2(CCO3)CC2)n1CC1CCCCC1] | $^1$H-NMR (400 MHz, $CDCl_3$) δ: 6.96 (d, 1H), 6.42 (d, 1H), 6.05 (s, 1H), 5.92 (t, 1H), 4.34 (t, 2H), 3.64 (d, 2H), 3.31 (t, 2H), 3.09-3.06 (m, 2H), 2.96 (td, 2H), 2.58 (s, 3H), 2.18 (d, 2H), 1.91-1.84 (m, 5H), 1.59-1.56 (m, 3H), 1.38-1.35 (m, 12H), 1.04-0.99 (m, 5H), 0.87-0.84 (m, 2H), 0.73-0.65 (m, 2H). MS: 581.4 (M + 1). |

-continued
| # | Structure | Analytical data |
|---|---|---|
| 17/11 | 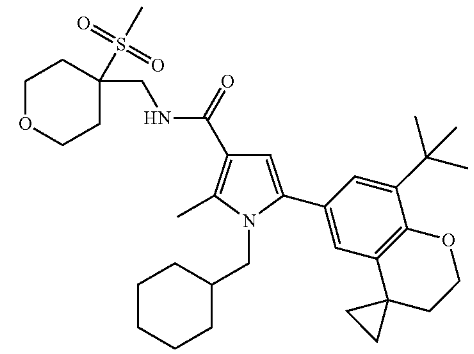 [SMILES: Cc1c(C(=O)NCC2(S(C)(=O)=O)CCOCC2)cc(-c2cc(C(C)(C)C)c3c(c2)C2(CCO3)CC2)n1CC1CCCCC1] | $^1$H-NMR (400 MHz, $CDCl_3$) δ: 6.95 (d, 1H), 6.72 (t, 1H), 6.42 (d, 1H), 6.15 (s, 1H), 4.33 (t, 2H), 4.11 (d, 2H), 3.95 (dd, 2H), 3.77 (td, 2H), 3.63 (d, 2H), 2.87 (s, 3H), 2.59 (s, 3H), 2.15-2.08 (m, 2H), 1.89 (t, 2H), 1.79 (d, 2H), 1.60-1.53 (m, 3H), 1.46-1.38 (m, 12H), 1.04-1.00 (m, 5H), 0.86-0.83 (m, 2H), 0.73-0.65 (m, 2H). MS: 611.3 (M + 1). |
| 17/12 | 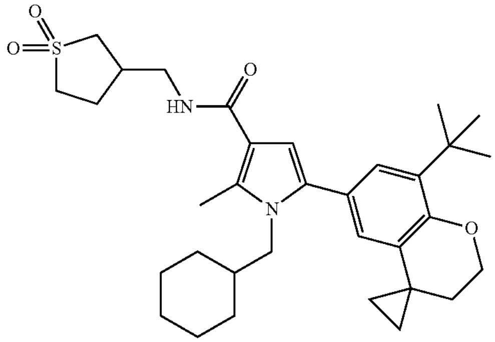 [SMILES: Cc1c(C(=O)NCC2CCS(=O)(=O)C2)cc(-c2cc(C(C)(C)C)c3c(c2)C2(CCO3)CC2)n1CC1CCCCC1] | $^1$H-NMR (400 MHz, $CDCl_3$) δ: 6.97 (d, 1H), 6.43 (d, 1H), 6.05 (s, 1H), 5.91 (t, 1H), 4.34 (t, 2H), 3.64 (d, 2H), 3.58-3.44 (m, 2H), 3.28-3.19 (m, 2H), 3.09-3.01 (m, 1H), 2.90-2.80 (m, 2H), 2.58 (s, 3H), 2.38-2.33 (m, 1H), 2.01-1.96 (m, 1H), 1.90 (t, 2H), 1.59-1.54 (m, 3H), 1.44-1.35 (m, 12H), 1.04-1.00 (m, 5H), 0.87-0.64 (m, 4H). MS: 567.3 (M + 1). |
| 17/13 | 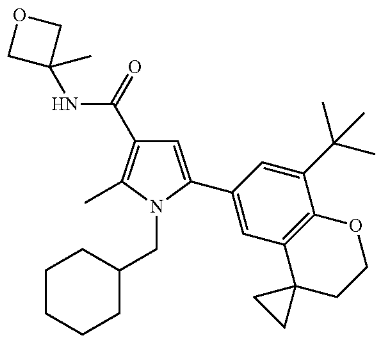 [SMILES: Cc1c(C(=O)NC2(C)COC2)cc(-c2cc(C(C)(C)C)c3c(c2)C2(CCO3)CC2)n1CC1CCCCC1] | $^1$H-NMR (400 MHz, $CDCl_3$) δ: 6.96 (d, 1H), 6.42 (d, 1H), 6.06 (s, 1H), 5.93 (s, 1H), 4.83 (d, 2H), 4.53 (d, 2H), 4.33 (t, 2H), 3.64 (d, 2H), 2.58 (s, 3H), 1.90 (t, 2H), 1.74 (s, 3H), 1.59 (br s, 3H), 1.38-1.35 (m, 12H), 1.04-1.00 (m, 5H), 0.87-0.84 (m, 2H), 0.69-0.66 (m, 2H). MS: 505.3 (M + 1). |
| 17/14 | 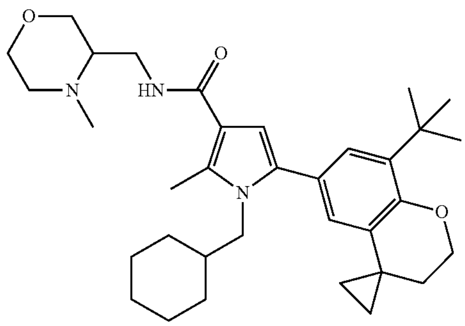 [SMILES: Cc1c(C(=O)NCC2COCCN2C)cc(-c2cc(C(C)(C)C)c3c(c2)C2(CCO3)CC2)n1CC1CCCCC1] | $^1$H-NMR (400 MHz, $CDCl_3$) δ: 6.95 (d, 1H), 6.89 (br s, 1H), 6.42 (d, 1H), 6.24 (br s, 1H), 4.33 (t, 2H), 4.14 (br s, 2H), 3.96-3.86 (m, 4H), 3.64-3.52 (m, 4H), 3.36 (br s, 1H), 3.01 (br s, 3H), 2.58 (s, 3H), 1.90 (t, 2H), 1.57 (br s, 3H), 1.43-1.26 (m, 12H), 1.03-1.02 (m, 5H), 0.88-0.83 (m, 2H), 0.69-0.66 (m, 2H). MS: 548.4 (M + 1). |

-continued
| # | Structure | Analytical data |
|---|---|---|
| 17/15 | 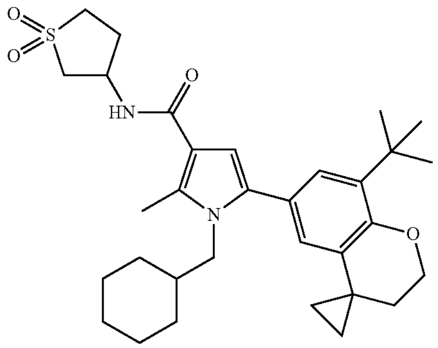 [SMILES: Cc1c(C(=O)NC2CCS(=O)(=O)C2)cc(-c2cc(C(C)(C)C)c3c(c2)C2(CCO3)CC2)n1CC1CCCCC1] | $^{1}$H-NMR (400 MHz, $CDCl_3$) δ: 6.88 (d, 1H), 6.35 (d, 1H), 6.12 (d, 1H), 6.02 (s, 1H), 4.89-4.85 (m, 1H), 4.26 (t, 2H), 3.57 (d, 2H), 3.38 (m, 1H), 3.20-3.15 (m, 1H), 3.10-3.02 (m, 1H), 2.97 (dd, 1H), 2.52-2.46 (m, 4H), 2.31-2.26 (m, 1H), 1.84-1.82 (m, 2H), 1.52-1.50 (m, 3H), 1.37-1.26 (m, 12H), 0.96-0.93 (m, 5H), 0.80-0.77 (m, 2H), 0.65-0.59 (m, 2H). MS: 553.3 (M + 1). |
| 17/16 | 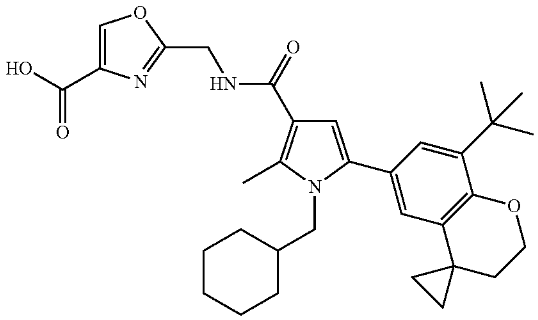 [SMILES: Cc1c(C(=O)NCc2nc(C(=O)O)co2)cc(-c2cc(C(C)(C)C)c3c(c2)C2(CCO3)CC2)n1CC1CCCCC1] | $^{1}$H-NMR (400 MHz, $CDCl_3$) δ: 7.98 (s, 1H), 6.95 (d, 1H), 6.82 (br s, 1H), 6.41 (d, 1H), 6.23 (s, 1H), 4.63 (d, 2H), 4.30 (t, 2H), 3.61 (d, 2H), 2.56 (s, 3H), 1.86 (t, 2H), 1.56-1.51 (m, 3H), 1.42-1.36 (m, 12H), 1.02-0.96 (m, 5H), 0.82-0.79 (m, 2H), 0.70-0.63 (m, 2H). MS: 559.3 $(M)^+$, 418.2 $(M - C_6H_{10}N_2O_3)^+$. |
| 17/17 | 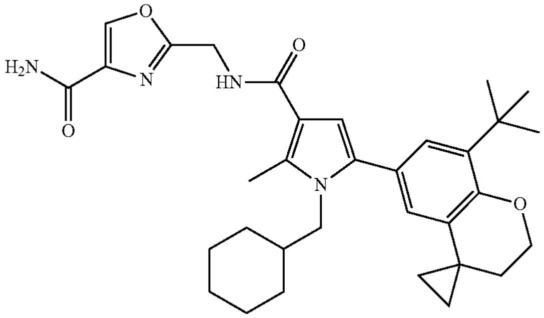 [SMILES: Cc1c(C(=O)NCc2nc(C(N)=O)co2)cc(-c2cc(C(C)(C)C)c3c(c2)C2(CCO3)CC2)n1CC1CCCCC1] | $^{1}$H-NMR (400 MHz, $CDCl_3$) δ: 8.18 (s, 1H), 6.98 (d, 1H), 6.80 (br s, 1H), 6.44 (d, 1H), 6.25 (br s, 1H), 6.15 (s, 1H), 5.68 (br s, 1H), 4.72 (d, 2H), 4.34 (t, 2H), 3.65 (d, 2H), 2.60 (s, 3H), 1.90 (t, 2H), 1.58-1.55 (m, 3H), 1.38-1.35 (m, 12H), 1.04-0.99 (m, 5H), 0.87-0.84 (m, 2H), 0.73-0.66 (m, 2H). MS: 559.3 (M + 1). |
| 17/18 | 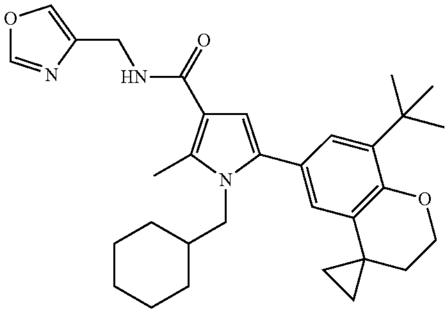 [SMILES: Cc1c(C(=O)NCc2cocn2)cc(-c2cc(C(C)(C)C)c3c(c2)C2(CCO3)CC2)n1CC1CCCCC1] | $^{1}$H-NMR (400 MHz, DMSO-$d_6$) δ: 8.29 (s, 1H), 8.01 (t, 1H), 7.87 (d, 1H), 6.91 (d, 1H), 6.48 (d, 1H), 6.42 (s, 1H) 4.29-4.26 (m, 4H), 3.68 (d, 2H), 2.50 (s, 3H), 1.85 (t, 2H), 1.51-1.49 (m, 3H), 1.35-1.25 (m, 12H), 0.99-0.94 (m, 5H), 0.90-0.64 (m, 9H). MS: 516.3 (M + 1). |

-continued
| # | Structure | Analytical data |
|---|---|---|
| 17/19 | 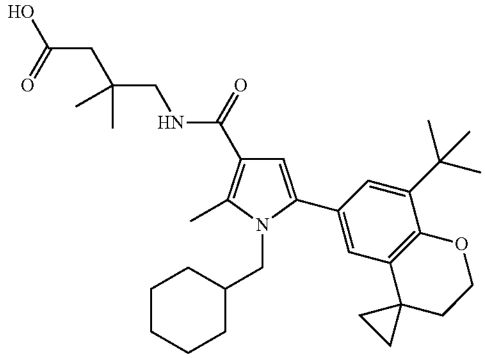 [SMILES: Cc1c(C(=O)NCC(C)(C)CC(=O)O)cc(-c2cc(C(C)(C)C)c3c(c2)C2(CCO3)CC2)n1CC1CCCCC1] | $^1$H-NMR (400 MHz, DMSO-$d_6$) δ: 12.17 (s, 1H), 7.53 (t, 1H), 6.91 (d, 1H), 6.49 (d, 1H), 6.42 (s, 1H), 4.28 (t, 2H), 3.67 (d, 2H), 3.12 (d, 2H), 2.49 (s, 3H), 2.12 (d, 2H), 1.85 (t, 2H), 1.52-1.50 (m, 3H), 1.35-1.24 (m, 12H), 1.00-0.87 (m, 13H), 0.72-0.65 (m, 2H). MS: 549.1 (M + 1). |
| 17/20 | 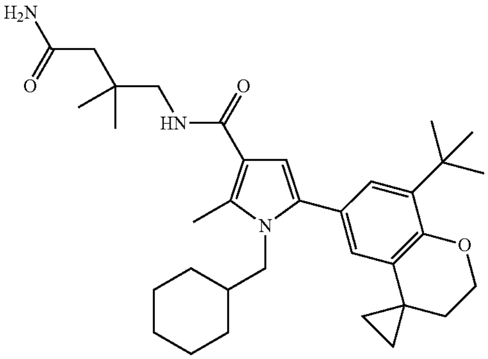 [SMILES: Cc1c(C(=O)NCC(C)(C)CC(N)=O)cc(-c2cc(C(C)(C)C)c3c(c2)C2(CCO3)CC2)n1CC1CCCCC1] | $^1$H-NMR (400 MHz, DMSO-$d_6$) δ: 7.66 (t, 1H), 7.54 (br s, 1H), 6.89 (d, 1H), 6.82 (s, 1H), 6.48 (d, 1H), 6.37 (s, 1H), 4.27 (t, 2H), 3.65 (d, 2H), 3.11 (d, 1H), 2.46 (s, 3H), 1.97 (s, 2H), 1.84 (t, 2H), 1.51-1.49 (m, 3H), 1.34-1.26 (m, 12H), 0.99-0.88 (m, 13H), 0.70-0.62 (m, 2H). MS: 548.3 (M + 1). |
| 17/21 | 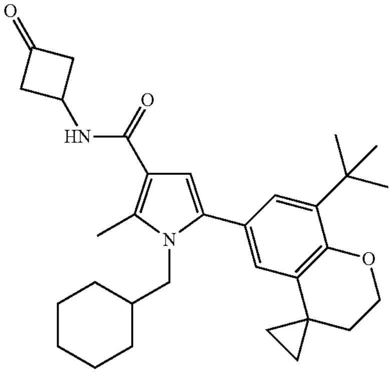 [SMILES: Cc1c(C(=O)NC2CC(=O)C2)cc(-c2cc(C(C)(C)C)c3c(c2)C2(CCO3)CC2)n1CC1CCCCC1] | $^1$H-NMR (400 MHz, $CDCl_3$) δ: 6.97 (d, 1H), 6.43 (d, 1H), 6.08 (s, 1H), 6.00 (d, 1H), 4.64-4.60 (m, 1H), 4.34 (t, 2H), 3.65 (d, 2H), 3.54-3.48 (m, 2H), 3.14-3.09 (m, 2H), 2.59 (s, 3H), 1.90 (t, 2H), 1.59-1.53 (m, 3H), 1.45-1.34 (m, 12H), 1.04-1.00 (m, 5H), 0.87-0.84 (m, 2H), 0.73-0.62 (m, 2H). MS: 503.4 (M + 1). |
| 17/22 | 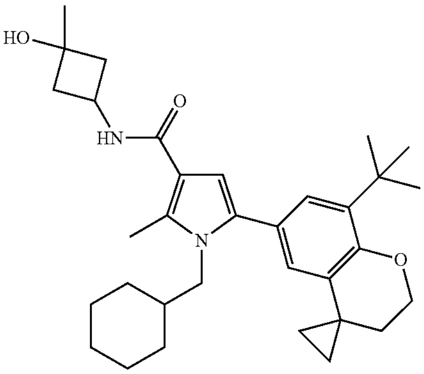 [SMILES: Cc1c(C(=O)NC2CC(C)(O)C2)cc(-c2cc(C(C)(C)C)c3c(c2)C2(CCO3)CC2)n1CC1CCCCC1] | $^1$H-NMR (400 MHz, $CDCl_3$) δ: 6.96 (d, 1H), 6.42 (d, 1H), 6.05 (s, 1H), 5.89 (d, 1H), 4.85-4.84 (m, 1H), 4.62-4.58 (m, 1H), 4.35-4.29 (m, 3H), 3.65 (d, 2H), 2.96-2.89 (m, 1H), 2.58-2.50 (m, 4H), 1.90 (t, 2H), 1.57 (m, 6H), 1.42-1.25 (m, 12H), 1.03-1.00 (m, 5H), 0.88-0.84 (m, 2H), 0.72-0.66 (m, 2H). MS: 519.3 (M + 1). |

-continued
| # | Structure | Analytical data |
|---|---|---|
| 17/23 | 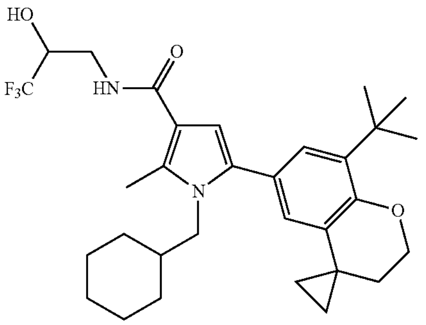 [SMILES: Cc1c(C(=O)NCC(O)C(F)(F)F)cc(-c2cc(C(C)(C)C)c3c(c2)C2(CCO3)CC2)n1CC1CCCCC1] | $^1$H-NMR (400 MHz, $CDCl_3$) δ: 6.96 (d, 1H), 6.42 (d, 1H), 6.13 (t, 1H), 6.08 (s, 1H), 4.34 (t, 2H), 4.14-4.10 (m, 1H), 3.75-3.63 (m, 4H), 2.58 (s, 3H), 1.90 (t, 2H), 1.59-1.54 (m, 3H), 1.45-1.35 (m, 12H), 1.04-0.99 (m, 5H), 0.87-0.84 (m, 2H), 0.72-0.65 (m, 2H). MS: 547.3 (M + 1). |
| 17/24 | 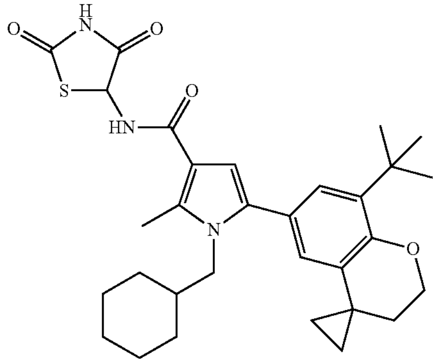 [SMILES: Cc1c(C(=O)NC2SC(=O)NC2=O)cc(-c2cc(C(C)(C)C)c3c(c2)C2(CCO3)CC2)n1CC1CCCCC1] | $^1$H-NMR (400 MHz, $CDCl_3$) δ: 7.96 (s, 1H), 6.95 (d, 1H), 6.45 (d, 1H), 6.41 (d, 1H), 6.14 (d, 1H), 6.11 (s, 1H), 4.34 (t, 2H), 3.64 (d, 2H), 2.58 (s, 3H), 1.90 (t, 2H), 1.57 (br s, 3H), 1.49-1.34 (m, 12H), 1.04-0.99 (m, 5H), 0.87-0.85 (m, 2H), 0.72-0.65 (m, 2H). MS: 550.2 (M + 1). |
| 17/25 | 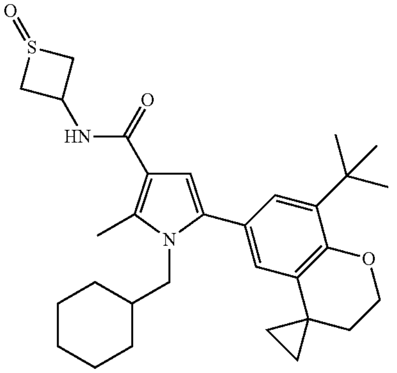 [SMILES: Cc1c(C(=O)NC2CS(=O)C2)cc(-c2cc(C(C)(C)C)c3c(c2)C2(CCO3)CC2)n1CC1CCCCC1] | $^1$H-NMR (400 MHz, $CDCl_3$) δ: 6.97 (d, 1H), 6.43 (d, 1H), 6.08 (s, 1H), 6.02 (d, 1H), 4.65-4.58 (m, 1H), 4.34 (t, 2H), 4.18-4.13 (m, 2H), 3.64 (d, 2H), 3.22-3.17 (m, 2H), 2.57 (s, 3H), 1.91 (t, 2H), 1.57 (br s, 3H), 1.37-1.34 (m, 12H), 1.03-1.00 (m, 5H), 0.88-0.85 (m, 2H), 0.72-0.64 (m, 2H). MS: 523.2 (M + 1). |
| 17/26 | 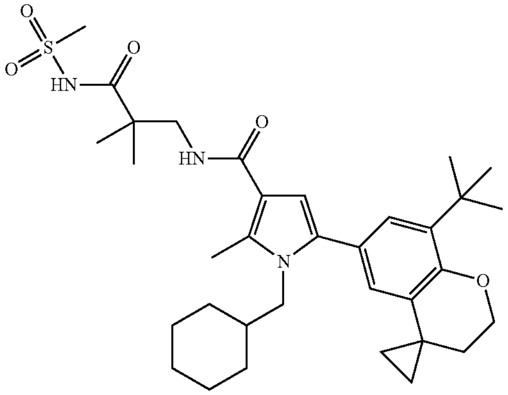 [SMILES: Cc1c(C(=O)NCC(C)(C)C(=O)NS(C)(=O)=O)cc(-c2cc(C(C)(C)C)c3c(c2)C2(CCO3)CC2)n1CC1CCCCC1] | $^1$H-NMR (400 MHz, DMSO-$d_6$) δ: 11.45 (s, 1H), 7.59 (br s, 1H), 6.90 (d, 1H), 6.48 (d, 1H), 6.35 (s, 1H), 4.28 (t, 2H), 3.66 (d, 2H), 3.37 (s, 2H), 3.17-3.14 (m, 3H), 2.46 (s, 2H), 1.85 (t, 2H), 1.51-1.49 (m, 3H), 1.34-1.25 (m, 12H), 1.10 (s, 6H), 0.98-0.95 (m, 5H), 0.88-0.86 (m, 2H), 0.68-0.62 (m, 2H). MS: 612.3 (M + 1). |

-continued

| # | Structure | Analytical data |
|---|---|---|
| 17/27 | 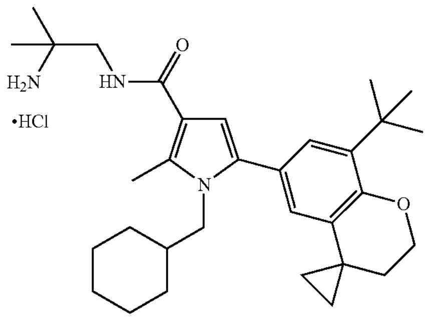 [SMILES: Cc1c(C(=O)NCC(C)(C)N)cc(-c2cc(C(C)(C)C)c3c(c2)C2(CCO3)CC2)n1CC1CCCCC1 ; Cl] | $^{1}$H-NMR (400 MHz, DMSO-$d_6$) δ: 7.41 (br s, 1H), 6.91 (d, 1H), 6.49 (d, 1H), 6.45 (s, 1H), 4.28 (t, 2H), 3.67 (d, 2H, J = 6.8 Hz), 3.09 (d, 2H, J = 6.4 Hz), 2.49 (s, 3H), 2.01-1.84 (m, 4H), 1.52-1.49 (m, 3H), 1.35-1.23 (m, 12H), 1.00-0.94 (m, 11H), 0.89-0.87 (m, 2H), 0.70-0.65 (m, 2H). MS: 506.2 [(M − Cl)]$^+$. |
| 17/28 | 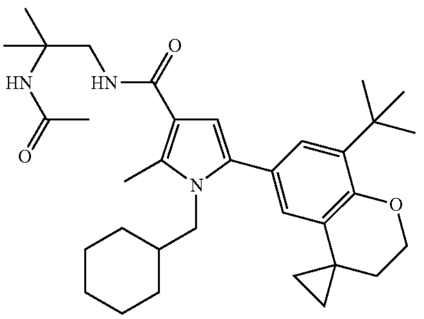 [SMILES: CC(=O)NC(C)(C)CNC(=O)c1cc(-c2cc(C(C)(C)C)c3c(c2)C2(CCO3)CC2)n(CC2CCCCC2)c1C] | $^{1}$H-NMR (400 MHz, DMSO-$d_6$) δ: 7.77 (t, 1H), 7.66 (s, 1H), 6.90 (d, 1H, J = 2.0 Hz), 6.49 (d, 1H, J = 2.0 Hz), 6.37 (s, 1H), 4.28 (t, 2H), 3.66 (d, 2H, J = 6.8 Hz), 3.29 (d, 2H), 2.49 (s, 3H), 1.85 (t, 2H), 1.76 (s, 3H), 1.52-1.50 (m, 3H), 1.35-1.22 (m, 18H), 0.99-0.87 (m, 7H), 0.71-0.65 (m, 2H). MS: 548.4 (M + 1). |
| 17/29 | 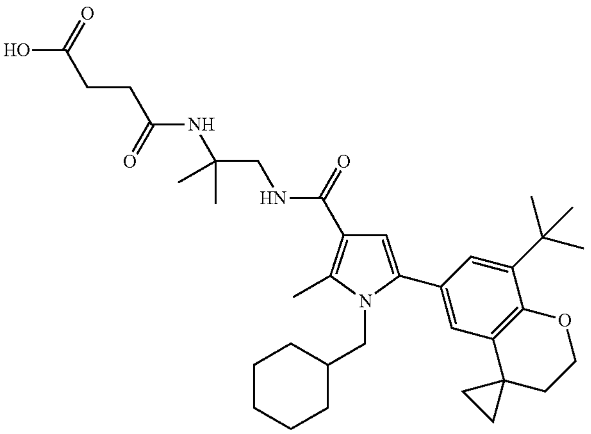 [SMILES: Cc1c(C(=O)NCC(C)(C)NC(=O)CCC(=O)O)cc(-c2cc(C(C)(C)C)c3c(c2)C2(CCO3)CC2)n1CC1CCCCC1] | $^{1}$H-NMR (400 MHz, DMSO-$d_6$) δ: 7.68-7.63 (m, 2H), 6.91 (d, 1H, J = 2.4 Hz), 6.49 (d, 1H, J = 2.0 Hz), 6.39 (s, 1H), 4.28 (t, 2H), 3.68 (d, 2H, J = 6.8 Hz), 3.32 (d, 2H, J = 6.0 Hz), 2.49 (s, 3H), 2.40 (t, 2H), 2.27 (t, 2H), 1.85 (t, 2H), 1.52-1.50 (m, 3H), 1.34-1.23 (m, 12H), 1.21 (s, 6H), 0.99-0.97 (m, 5H), 0.89-0.87 (m, 2H), 0.71-0.65 (m, 2H). MS: 606.4 (M + 1). |
| 17/30 | 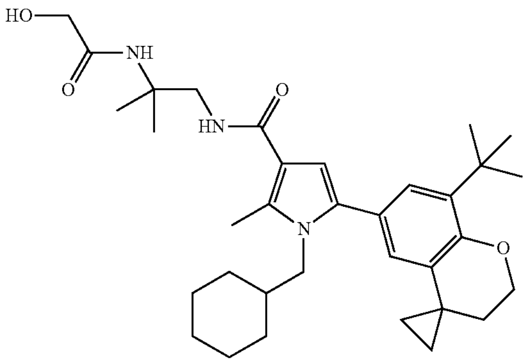 [SMILES: Cc1c(C(=O)NCC(C)(C)NC(=O)CO)cc(-c2cc(C(C)(C)C)c3c(c2)C2(CCO3)CC2)n1CC1CCCCC1] | $^{1}$H-NMR (400 MHz, $CDCl_3$) δ: 7.48 (s, 2H), 6.97 (d, 1H, J = 2.0 Hz), 6.54 (t, 1H), 6.43 (d, 1H, J = 2.4 Hz), 6.13 (s, 1H), 4.33 (t, 2H), 3.97 (s, 2H), 3.63 (d, 2H, J = 7.6 Hz), 3.45 (d, 2H, J = 6.8 Hz), 2.58 (s, 3H), 1.90 (t, 2H), 1.58 (br s, 3H), 1.49-1.28 (m, 18H), 1.04-1.00 (m, 5H), 0.86-0.84 (m, 2H), 0.73-0.65 (m, 2H). |

-continued

| # | Structure | Analytical data |
| --- | --- | --- |
| 17/31 | 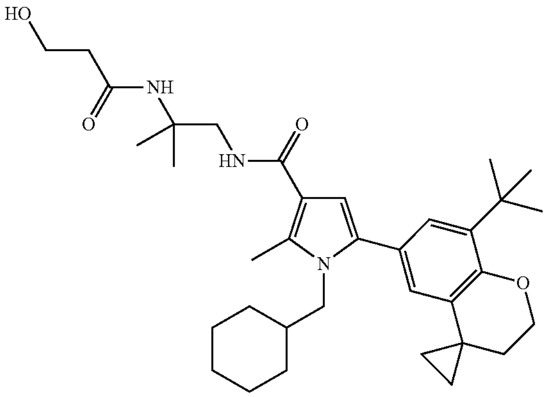 [SMILES: Cc1c(C(=O)NCC(C)(C)NC(=O)CCO)cc(-c2cc(C(C)(C)C)c3c(c2)C2(CCO3)CC2)n1CC1CCCCC1] | $^1$H-NMR (400 MHz, $CDCl_3$) δ: 7.32 (s, 1H), 6.97 (d, 1H, J = 1.6 Hz), 6.43 (d, 1H, J = 2.0 Hz), 6.40 (t, 1H), 6.12 (s, 1H), 4.34 (t, 2H), 3.88 (br s, 2H), 3.64 (d, 2H, J = 7.2 Hz), 3.42 (d, 2H, J = 6.4 Hz), 2.58 (s, 3H), 2.37 (br s, 2H), 1.90 (t, 2H), 1.57-1.54 (m, 3H), 1.46-1.38 (m, 18H), 1.05-1.00 (m, 5H), 0.87-0.84 (m, 2H), 0.73-0.68 (m, 2H). MS: 578.3 (M + 1). |
| 17/32 | 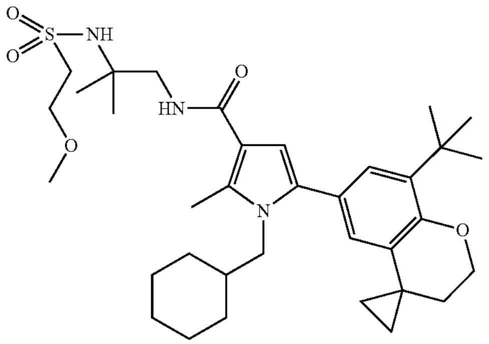 [SMILES: COCCS(=O)(=O)NC(C)(C)CNC(=O)c1cc(-c2cc(C(C)(C)C)c3c(c2)C2(CCO3)CC2)n(CC2CCCCC2)c1C] | $^1$H-NMR (400 MHz, DMSO-$d_6$) δ: 7.68 (t, 1H), 7.09 (s, 1H), 6.91 (d, 1H, J = 1.6 Hz), 6.49 (d, 1H, J = 1.6 Hz), 6.38 (s, 1H), 4.28 (t, 2H), 3.68 (d, 2H, J = 7.2 Hz), 3.62 (t, 2H), 3.25 (t, 4H), 3.17 (s, 3H), 2.50 (s, 3H), 1.85 (t, 2H), 1.51-1.49 (m, 3H), 1.35 (s, 9H), 1.31-1.28 (m, 9H), 0.99-0.87 (m, 7H), 0.71-0.64 (m, 2H). MS: 628.3 (M + 1). |
| 17/33 | 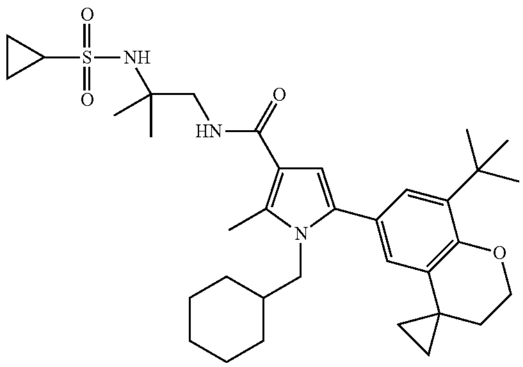 [SMILES: Cc1c(C(=O)NCC(C)(C)NS(=O)(=O)C2CC2)cc(-c2cc(C(C)(C)C)c3c(c2)C2(CCO3)CC2)n1CC1CCCCC1] | $^1$H-NMR (400 MHz, $CDCl_3$) δ: 6.97 (d, 1H, J = 2.0 Hz), 6.43 (d, 1H, J = 2.0 Hz), 6.33 (t, 1H), 6.13 (s, 1H), 5.34 (br s, 1H), 4.33 (t, 2H), 3.64 (d, 2H, J = 7.2 Hz), 3.48 (d, 2H, J = 6.4 Hz), 2.58 (s, 3H), 2.47-2.42 (m, 1H), 1.90 (m, 2H), 1.58-1.54 (m, 3H), 1.46-1.33 (m, 18H), 1.21-1.17 (m, 2H), 1.04-0.94 (m, 7H), 0.86-0.84 (m, 2H), 0.73-0.65 (m, 2H). MS: 610.5 (M + 1). |
| 17/34 | 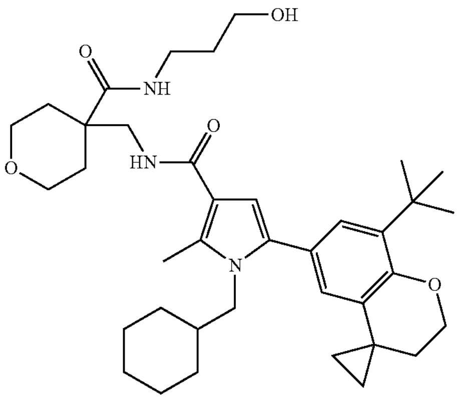 [SMILES: Cc1c(C(=O)NCC2(C(=O)NCCCO)CCOCC2)cc(-c2cc(C(C)(C)C)c3c(c2)C2(CCO3)CC2)n1CC1CCCCC1] | $^1$H-NMR (400 MHz, $CDCl_3$) δ: 6.95 (d, 1H), 6.66 (br t, 1H), 6.42 (d, 1H), 6.21 (m, 1H), 6.08 (s, 1H), 4.33 (m, 2H), 3.87-3.82 (m, 2H), 3.68-3.56 (m, 8H), 3.46-3.44 (m, 2H), 2.56 (s, 3H), 1.99-1.95 (m, 2H), 1.90 (t, 2H), 1.70-1.57 (m, 7H), 1.43-1.32 (m, 12H), 1.03-1.00 (m, 5H), 0.87-0.84 (m, 2H), 0.71-0.65 (m, 2H). MS: 634.3 (M + 1). |

-continued
| # | Structure | Analytical data |
|---|---|---|
| 17/35 | 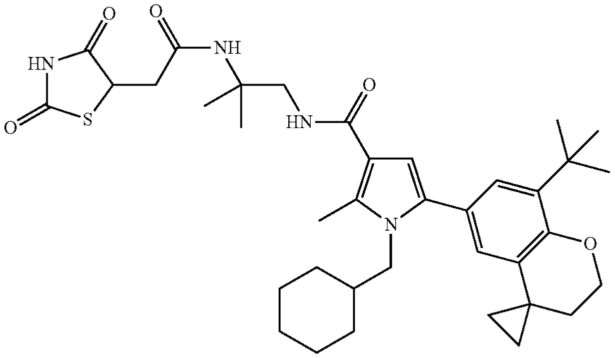 [SMILES: Cc1c(C(=O)NCC(C)(C)NC(=O)CC2SC(=O)NC2=O)cc(-c2cc(C(C)(C)C)c3c(c2)C2(CCO3)CC2)n1CC1CCCCC1] | $^1$H-NMR (400 MHz, $CDCl_3$) δ: 8.31-8.25 (m, 1H), 7.87 (s, 1H), 6.97 (d, 1H, J = 2.0 Hz), 6.44 (d, 1H, J = 2.0 Hz), 6.29 (t, J = 6.6 Hz, 1H), 6.11 (s, 1H), 4.53 (dd, 1H), 4.34 (t, 2H), 3.65 (d, 2H, J = 6.8 Hz), 3.35 (d, 2H, J = 6.4 Hz), 3.06 (dd, J = 4.0, J = 16.0 Hz, 1H), 2.79 (dd, J = 6.0, J = 16.0 Hz, 1H), 2.58 (s, 3H), 1.85 (t, 2H), 1.59-1.54 (m, 3H), 1.47-1.38 (m, 18H), 1.05-1.00 (m, 5H), 0.88-0.84 (m, 2H), 0.74-0.69 (m, 2H). MS: 663.1 (M + 1). |
| 17/36 | 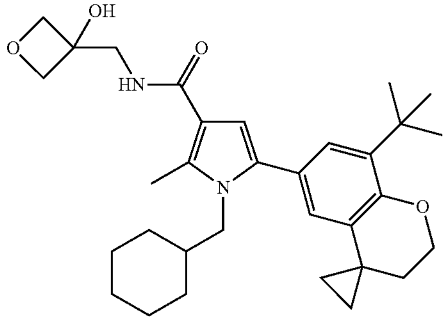 [SMILES: Cc1c(C(=O)NCC2(O)COC2)cc(-c2cc(C(C)(C)C)c3c(c2)C2(CCO3)CC2)n1CC1CCCCC1] | $^1$H-NMR (400 MHz, $CDCl_3$) δ: 6.96 (d, 1H), 6.42 (d, 1H), 6.30 (t, 1H), 6.18 (s, 1H), 6.09 (s, 1H), 4.65 (d, 2H), 4.42 (d, 2H), 4.34 (t, 2H), 3.82 (d, 2H), 3.64 (d, 2H), 2.57 (s, 3H), 1.90 (t, 2H), 1.57 (s, 3H), 1.38-1.34 (m, 12H), 1.04-0.99 (m, 5H), 0.87-0.85 (m, 2H), 0.72-0.66 (m, 2H). MS: 521.3 (M + 1). |
| 17/37 | 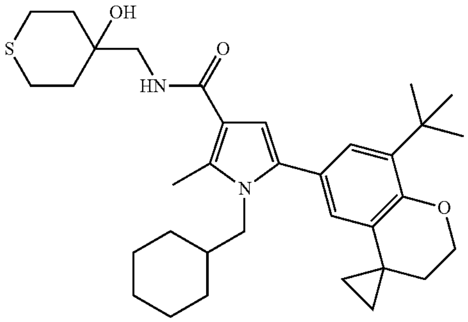 [SMILES: Cc1c(C(=O)NCC2(O)CCSCC2)cc(-c2cc(C(C)(C)C)c3c(c2)C2(CCO3)CC2)n1CC1CCCCC1] | $^1$H-NMR (400 MHz, $CDCl_3$) δ: 6.96 (d, 1H), 6.42 (d, 1H), 6.08-6.05 (m, 2H), 4.33 (t, 2H), 3.64 (d, 2H), 3.36 (d, 2H), 3.02 (t, 3H), 2.58 (s, 3H), 2.44 (d, 2H), 1.98-1.89 (m, 4H), 1.84-1.57 (m, 4H), 1.43-1.35 (m, 12H), 1.04-0.99 (m, 5H), 0.87-0.84 (m, 2H), 0.72-0.64 (m, 2H). MS: 565.3 (M + 1). |
| 17/38 | 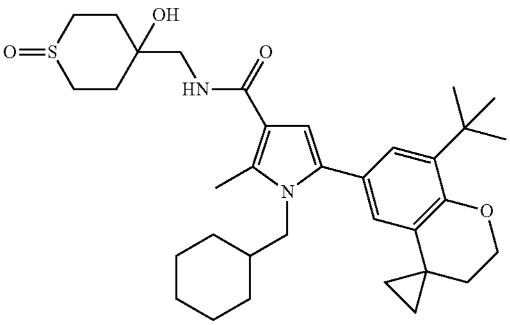 [SMILES: Cc1c(C(=O)NCC2(O)CCS(=O)CC2)cc(-c2cc(C(C)(C)C)c3c(c2)C2(CCO3)CC2)n1CC1CCCCC1] | $^1$H-NMR (400 MHz, $CDCl_3$) δ: 6.96 (d, 1H), 6.42 (d, 1H), 6.19 (t, 1H), 6.11 (s, 1H), 4.34 (t, 2H), 3.64 (d, 2H), 3.41 (d, 2H), 2.98-2.83 (m, 4H), 2.58 (s, 3H), 2.25 (td, 2H), 1.90 (t, 2H), 1.77-1.74 (m, 2H), 1.59-1.54 (m, 3H), 1.44-1.38 (m, 12H), 1.04-0.99 (m, 5H), 0.87-0.84 (m, 2H), 0.72-0.66 (m, 2H). MS: 581.3 (M + 1). |

-continued
| # | Structure | Analytical data |
| --- | --- | --- |
| 17/39 | 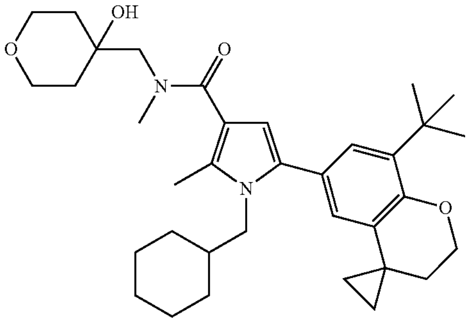 [SMILES: Cc1c(C(=O)N(C)CC2(O)CCOCC2)cc(-c2cc(C(C)(C)C)c3c(c2)C2(CCO3)CC2)n1CC1CCCCC1] | $^1$H-NMR (400 MHz, $CDCl_3$) δ: 6.97 (d, 1H), 6.43 (d, 1H), 6.08 (s, 1H), 4.33 (t, 2H), 3.85-3.77 (m, 4H), 3.63 (d, 2H), 3.54 (s, 2H), 3.26 (s, 3H), 2.39 (s, 3H), 1.90 (m, 2H), 1.67-1.57 (m, 7H), 1.38-1.34 (m, 12H), 1.04-1.00 (m, 5H), 0.86-0.84 (m, 2H), 0.72-0.65 (m, 2H). MS: 563.3 (M + 1). |
| 17/40 | 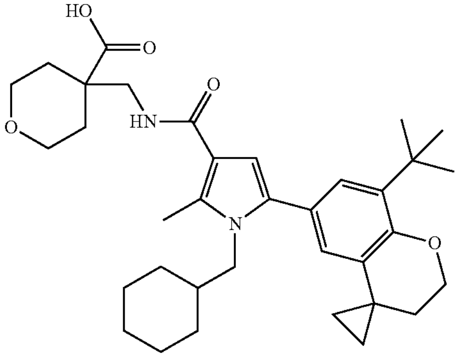 [SMILES: Cc1c(C(=O)NCC2(C(=O)O)CCOCC2)cc(-c2cc(C(C)(C)C)c3c(c2)C2(CCO3)CC2)n1CC1CCCCC1] | $^1$H-NMR (400 MHz, DMSO-$d_6$) δ: 12.49 (br s, 1H), 7.46 (t, 1H), 6.90 (d, 1H), 6.48 (d, 1H), 6.36 (s, 1H), 4.28 (t, 2H), 3.74 (dd, 2H), 3.66 (d, 2H), 3.36-3.27 (m, 4H), 2.47 (s, 3H), 1.86-1.84 (m, 4H), 1.51-1.45 (m, 5H), 1.35-1.23 (m, 12H), 1.00-0.87 (m, 7H), 0.71-0.64 (m, 2H). |
| 17/41 | 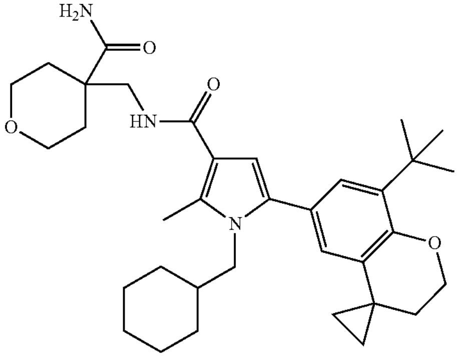 [SMILES: Cc1c(C(=O)NCC2(C(N)=O)CCOCC2)cc(-c2cc(C(C)(C)C)c3c(c2)C2(CCO3)CC2)n1CC1CCCCC1] | $^1$H-NMR (400 MHz, DMSO-$d_6$) δ: 7.28-7.24 (m, 2H), 7.03 (br s, 1H), 6.90 (d, 1H), 6.48 (d, 1H), 6.34 (s, 1H), 4.28 (m, 2H), 3.70-3.65 (m, 4H), 3.32-3.30 (m, 4H), 2.48 (s, 3H), 1.93-1.84 (m, 4H), 1.51-1.42 (m, 5H), 1.35-1.24 (m, 12H), 1.00-0.85 (m, 7H), 0.71-0.63 (m, 2H). MS: 576.1 (M + 1). |
| 17/42 | 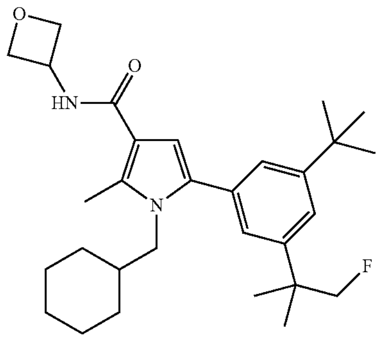 [SMILES: Cc1c(C(=O)NC2COC2)cc(-c2cc(C(C)(C)C)cc(C(C)(C)CF)c2)n1CC1CCCCC1] | $^1$H-NMR (300 MHz, $CDCl_3$) δ: 7.22 (d, J = 7.8 Hz, 1H), 7.01 (s, 1H), 6.23 (s, 1H), 6.19 (d, J = 5.4 Hz, 1H), 5.26-5.20 (m, 1H), 4.99 (t, J = 5.1 Hz, 2H), 4.58 (t, J = 4.8 Hz, 2H), 3.76 (d, J = 5.4 Hz, 2H), 2.96 (d, J = 15.9 Hz, 2H), 2.60 (s, 3H), 1.57-1.51 (m, 3H), 1.37--1.25 (m, 19H), 0.98-0.96 (m, 4H), 0.64-0.58 (m, 2H). MS: 483.4 (M + 1). |

-continued

| # | Structure | Analytical data |
|---|---|---|
| 17/43 | 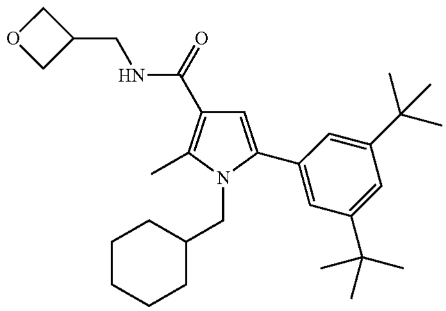 [SMILES: Cc1c(C(=O)NCC2COC2)cc(-c2cc(C(C)(C)C)cc(C(C)(C)C)c2)n1CC1CCCCC1] | $^{1}$H-NMR (400 MHz, DMSO-$d_6$) δ: 7.78 (t, 1H), 7.35 (t, 1H), 7.15 (d, 2H), 6.47 (s, 1H), 4.60 (dd, 2H), 4.33 (t, 2H), 3.75 (d, 2H), 3.43 (t, 2H), 3.14-3.06 (m, 1H), 1.52 (s, 3H), 1.46-1.43 (m, 3H), 1.31-1.21 (m, 21H), 0.94-0.83 (m, 3H), 0.67-0.60 (m, 2H). MS: 479.4 (M + 1). |
| 17/44 | 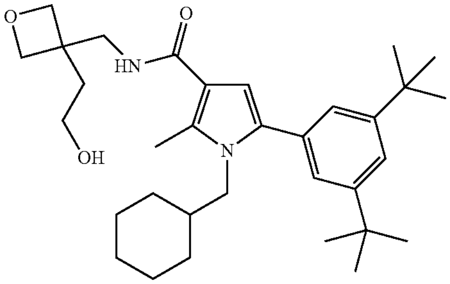 [SMILES: Cc1c(C(=O)NCC2(CCO)COC2)cc(-c2cc(C(C)(C)C)cc(C(C)(C)C)c2)n1CC1CCCCC1] | $^{1}$H-NMR (400 MHz, DMSO-$d_6$) δ: 7.74 (t, 1H), 7.36 (s, 1H), 7.15 (d, 2H), 6.51 (s, 1H), 4.49 (t, 1H), 4.40 (d, 2H), 4.30 (d, 2H), 3.75 (d, 2H), 3.55 (dd 2H), 3.46 (d, 2H), 2.52 (s, 3H), 1.80 (t, 2H), 1.45 (d, 3H), 1.31-1.19 (m, 21H), 0.95-0.90 (m, 3H), 0.67-0.59 (m, 2H). MS: 523.4 (M + 1). |
| 17/45 | 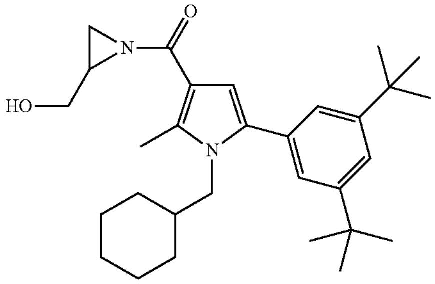 [SMILES: Cc1c(C(=O)N2CC2CO)cc(-c2cc(C(C)(C)C)cc(C(C)(C)C)c2)n1CC1CCCCC1] | $^{1}$H-NMR (400 MHz, DMSO-$d_6$) δ: 7.35 (t, 1H), 7.15 (d, 2H), 6.28 (s, 1H), 4.76 (t, 1H), 4.27-4.02 (m, 3H), 3.79 (d, 2H), 3.60-3.57 (m, 1H), 3.34 (in solvent signal, 1H), 2.53 (s, 3H), 1.46-1.43 (m, 3H), 1.30-1.21 (m, 21H), 0.95-0.85 (m, 3H), 0.68-0.60 (m, 2H). MS: 465.1 (M + 1). |
| 17/46 | 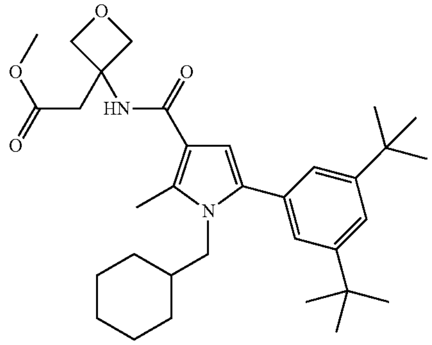 [SMILES: COC(=O)CC1(NC(=O)c2cc(-c3cc(C(C)(C)C)cc(C(C)(C)C)c3)n(CC3CCCCC3)c2C)COC1] | $^{1}$H-NMR (400 MHz, DMSO-$d_6$) δ: 8.16 (s, 1H), 7.49 (d, 1H), 7.36 (m, 2H), 7.15 (d, 1H), 4.66 (d, 2H), 4.54 (d, 2H), 3.76 (d, 2H), 3.57 (s, 3H), 3.14 (s, 2H), 2.50 (s, 3H), 1.45 (d, 3H), 1.31-1.13 (m, 21H), 0.95-0.84 (m, 3H), 0.68-0.60 (m, 2H). MS: 537.4 (M + 1). |
| 17/47 | 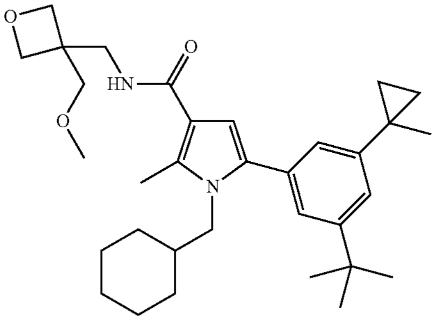 [SMILES: COCC1(CNC(=O)c2cc(-c3cc(C(C)(C)C)cc(C4(C)CC4)c3)n(CC3CCCCC3)c2C)COC1] | $^{1}$H-NMR (400 MHz, DMSO-$d_6$) δ: 7.81 (t, 1H), 7.20 (t, 1H), 7.15 (s, 1H), 6.98 (s, 1H), 6.53 (s, 1H), 4.41 (d, 2H), 4.27 (d, 2H), 3.76 (d, 2H), 3.48 (s, 2H), 3.41 (d, 2H), 3.32 (s, 3H), 2.52 (s, 3H), 1.46 (br d, 3H), 1.40 (s, 3H), 1.33-1.24 (m, 12H), 0.96-0.61 (m, 9H). MS: 521.3 (M + 1). |

-continued
| # | Structure | Analytical data |
|---|---|---|
| 17/48 | 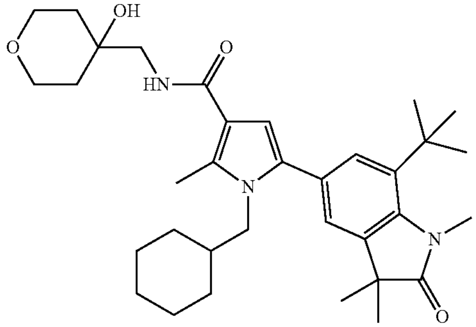 [SMILES: Cc1c(C(=O)NCC2(O)CCOCC2)cc(-c2cc(C(C)(C)C)c3c(c2)C(C)(C)C(=O)N3C)n1CC1CCCCC1] | $^1$H-NMR (500 MHz, $CDCl_3$) δ: 7.26 (d, J = 1.5 Hz, 1H), 7.01 (d, J = 1.0 Hz, 1H), 6.22 (s 2H), 4.08 (br s, 1H), 3.83-3.74 (m, 4H), 3.71 (d, J = 7.5 Hz, 2H), 3.66 (s, 3H), 3.45 (d, J = 6.0 Hz, 2H), 2.61 (s, 3H), 1.82-1.80 (m, 1H), 1.66-1.53 (m, 15H), 1.41-1.36 (m, 9H), 1.03-1.01 (m, 3H), 0.70-0.64 (m, 2H). MS: 564.3 (M + 1). |
| 17/49 | 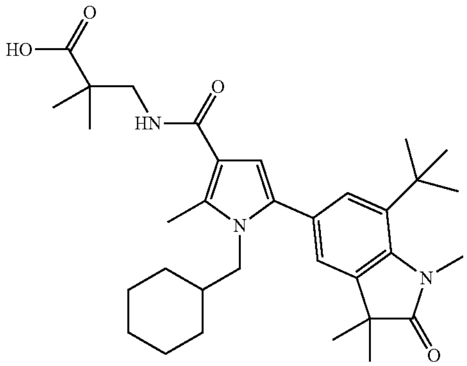 [SMILES: Cc1c(C(=O)NCC(C)(C)C(=O)O)cc(-c2cc(C(C)(C)C)c3c(c2)C(C)(C)C(=O)N3C)n1CC1CCCCC1] | $^1$H-NMR (500 MHz, $CDCl_3$) δ: 7.27 (d, J = 1.5 Hz, 1H), 7.03 (d, J = 1.5 Hz, 1H), 6.40 (t, J = 6.5 Hz, 1H), 6.20 (s, 1H), 3.70 (d, J = 7.0 Hz, 2H), 3.67 (s, 3H), 3.66 (d, J = 6.5 Hz, 2H), 2.60 (s, 3H), 1.57-1.54 (m, 12H), 1.38 (s, 9H), 1.31 (s, 6H), 1.03-1.01 (m, 3H), 0.71-0.65 (m, 2H). MS: 550.4 (M + 1). |
| 17/50 | 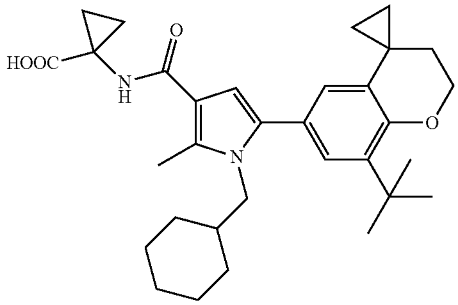 [SMILES: Cc1c(C(=O)NC2(C(=O)O)CC2)cc(-c2cc(C(C)(C)C)c3c(c2)C2(CCO3)CC2)n1CC1CCCCC1] | $^1$H-NMR (400 MHz, DMSO-$d_6$) δ: 12.20 (s, 1H), 8.05 (s, 1H), 6.90 (d, 1H), 6.47 (d, 1H), 6.40 (s, 1H), 4.27-4.29 (t, 2H), 3.66-3.67 (d, 2H), 2.49-2.51 (m, 3H), 1.84-1.87 (t, 2H), 1.50-1.52 (t, 3H), 1.25-1.35 (m, 14H), 0.96-1.03 (m, 7H), 0.66-0.69 (d, 2H), 0.64 (d, 2H). MS: 519.2 (M + 1). |
| 17/51 | 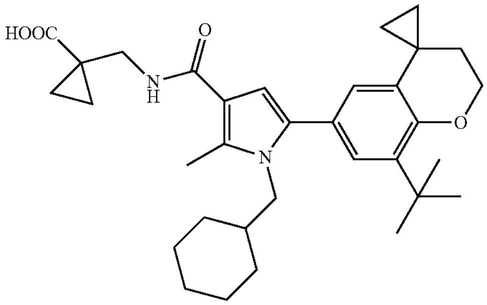 [SMILES: Cc1c(C(=O)NCC2(C(=O)O)CC2)cc(-c2cc(C(C)(C)C)c3c(c2)C2(CCO3)CC2)n1CC1CCCCC1] | $^1$H-NMR (400 MHz, DMSO-$d_6$) δ: 12.32 (s, 1H), 7.40-7.43 (t, 1H), 6.90 (d, 1H), 6.48 (d, 1H), 6.35 (s, 1H), 4.27-4.29 (t, 2H), 3.65-3.67 (d, 2H), 3.46-3.47 (d, 2H), 2.48 (s, 3H), 1.83-1.86 (t, 2H), 1.49-1.51 (m, 3H), 1.25-1.35 (m, 12H), 0.93-1.00 (m, 7H), 0.87-0.89 (m, 4H), 0.66-0.69 (m, 2H). MS: 533.3 $(M + 1)^+$. |

-continued

| # | Structure | Analytical data |
|---|---|---|
| 17/52 | 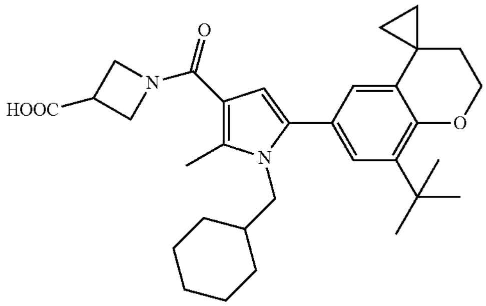 [SMILES: Cc1c(C(=O)N2CC(C(=O)O)C2)cc(-c2cc(C(C)(C)C)c3c(c2)C2(CCO3)CC2)n1CC1CCCCC1] | $^1$H-NMR (400 MHz, DMSO-$d_6$) δ: 12.66 (s, 1H), 6.90-6.90 (d, 1H), 6.49 (d, 1H), 6.09 (s, 1H), 3.96-4.42 (m, 6H), 3.67-3.69 (d, 2H), 3.38 (s, 1H), 2.45 (s, 3H), 1.83-1.86 (t, 2H), 1.50-1.51 (m, 3H), 1.25-1.34 (m, 12H), 0.98-1.02 (m, 5H), 0.87 (m, 2H), 0.65-0.68 (m, 2H). MS: 519.1 (M + 1). |
| 17/53 | 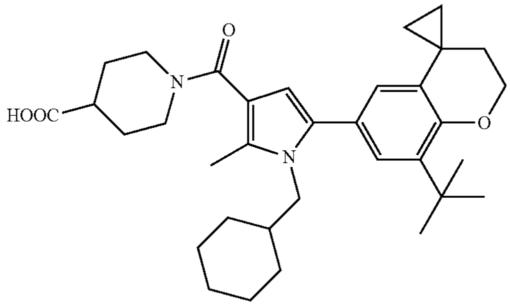 [SMILES: Cc1c(C(=O)N2CCC(C(=O)O)CC2)cc(-c2cc(C(C)(C)C)c3c(c2)C2(CCO3)CC2)n1CC1CCCCC1] | $^1$H-NMR (400 MHz, DMSO-$d_6$) δ: 12.26 (s, 1H), 6.91 (d, 1H), 6.50 (d, 1H), 5.95 (s, 1H), 4.27 (t, 2H), 4.09-4.11 (m, 2H), 3.68 (d, 2H), 2.95 (m, 2H), 2.46-2.51 (m, 1H), 2.24 (s, 3H), 1.81-1.86 (m, 4H), 1.23-1.52 (m, 17H), 0.96-1.05 (m, 5H), 0.85-0.87 (m, 2H), 0.65-0.73 (m, 2H). MS: 547.3 $(M + 1)^+$. |
| 17/54 | 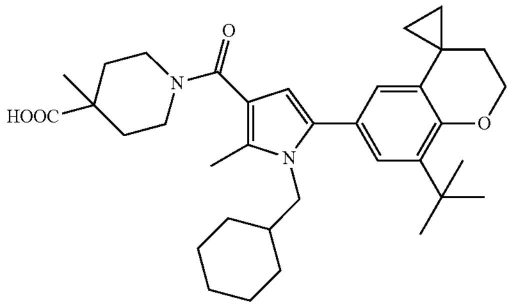 [SMILES: Cc1c(C(=O)N2CCC(C)(C(=O)O)CC2)cc(-c2cc(C(C)(C)C)c3c(c2)C2(CCO3)CC2)n1CC1CCCCC1] | $^1$H-NMR (400 MHz, DMSO-$d_6$) δ: 12.42 (s, 1H), 6.91 (d, 1H), 6.49 (d, 1H), 5.94 (s, 1H), 4.27 (t, 2H), 3.84 (m, 2H), 3.67 (d, 2H), 3.13 (s, 2H), 2.24 (s, 3H), 1.92 (d, 2H), 1.84 (t, 2H), 1.50-1.52 (m, 3H), 1.23-1.34 (m, 14H), 1.16 (m, 3H), 0.96-1.01 (m, 5H), 0.86-0.88 (m, 2H), 0.68-0.70 (m, 2H). MS: 561.4 $(M + 1)^+$. |
| 17/55 | 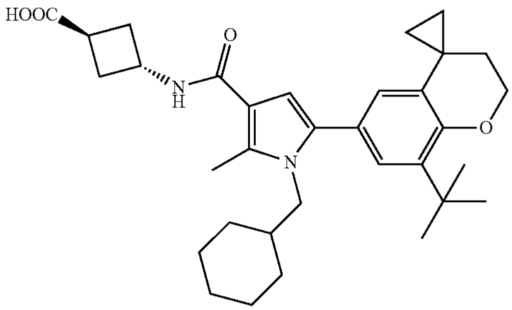 [SMILES: Cc1c(C(=O)N[C@H]2C[C@H](C(=O)O)C2)cc(-c2cc(C(C)(C)C)c3c(c2)C2(CCO3)CC2)n1CC1CCCCC1] | $^1$H-NMR (400 MHz, DMSO-$d_6$) δ: 12.15 (s, 1H), 7.76 (d, 1H), 6.91 (d, 1H), 6.49 (d, 1H), 6.42 (s, 1H), 4.47-4.53 (m, 1H), 4.28 (t, 2H), 3.67 (d, 2H), 2.88-2.92 (d, 1H), 2.47 (s, 3H), 2.24-2.40 (m, 4H), 1.84-1.87 (m, 2H), 1.49-1.51 (m, 3H), 1.24-1.35 (m, 12H), 0.94-0.98 (m, 5H), 0.87-0.89 (m, 2H), 0.62-0.68 (m, 2H). MS: 533.3 $(M + 1)^+$. |
| 17/56 | 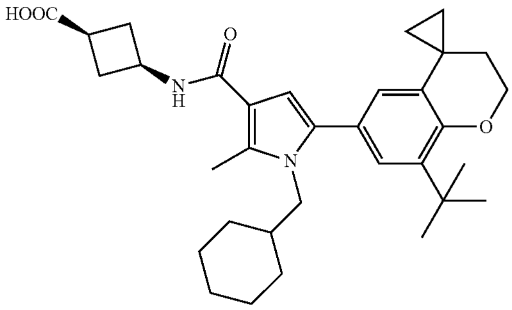 [SMILES: Cc1c(C(=O)N[C@H]2C[C@@H](C(=O)O)C2)cc(-c2cc(C(C)(C)C)c3c(c2)C2(CCO3)CC2)n1CC1CCCCC1] | $^1$H-NMR (400 MHz, DMSO-$d_6$) δ: 12.07 (s, 1H), 7.75 (d, 1H), 6.91 (d, 1H), 6.49 (d, 1H), 6.43 (s, 1H), 4.27-4.31 (m, 3H), 3.68 (d, 2H), 2.71 (t, 1H), 2.48 (s, 3H), 2.38-2.41 (m, 2H), 2.34-2.37 (m, 2H), 2.16-2.19 (m, 2H), 1.48-1.50 (m, 3H), 1.23-1.35 (m, 12H), 0.93-0.98 (m, 5H), 0.87-0.90 (m, 2H), 0.65-0.68 (m, 2H). MS: 533.3 $(M + 1)^+$. |

-continued
| # | Structure | Analytical data |
|---|---|---|
| 17/57 | 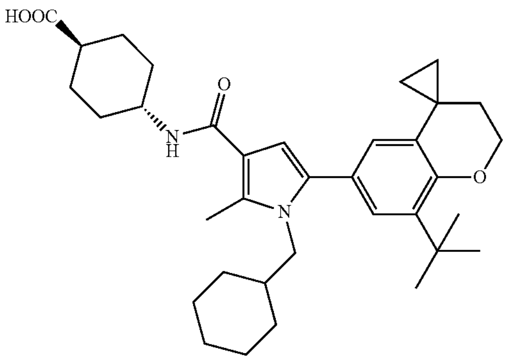 [SMILES: Cc1c(C(=O)N[C@H]2CC[C@H](C(=O)O)CC2)cc(-c2cc(C(C)(C)C)c3c(c2)C2(CCO3)CC2)n1CC1CCCCC1] | $^1$H-NMR (400 MHz, DMSO-$d_6$) δ: 12.06 (s, 1H), 7.28 (d, 1H), 6.90 (d, 1H), 6.47 (d, 1H), 6.38 (s, 1H), 4.28 (t, 2H), 3.66 (d, 3H), 2.48 (s, 3H), 2.09-2.14 (m, 1H), 1.90-1.94 (m, 2H), 1.84-1.86 (m, 4H), 1.49-1.51 (m, 3H), 1.24-1.39 (m, 16H), 0.97-1.00 (m, 5H), 0.91-0.94 (m, 2H), 0.62-0.70 (m, 2H). MS: 561 $(M + 1)^+$. |
| 17/58 | 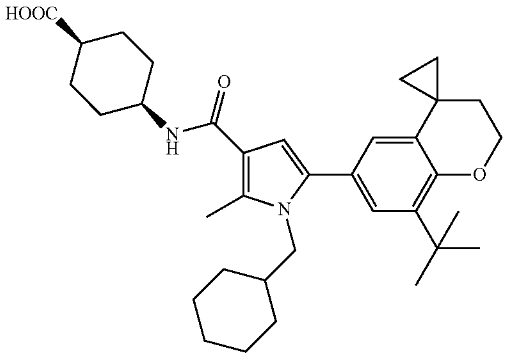 [SMILES: Cc1c(C(=O)N[C@H]2CC[C@@H](C(=O)O)CC2)cc(-c2cc(C(C)(C)C)c3c(c2)C2(CCO3)CC2)n1CC1CCCCC1] | $^1$H-NMR (400 MHz, $CD_3OD$) δ: 6.98 (s, 1H), 6.50 (d, 1H), 6.32 (s, 1H), 4.33 (t, 2H), 3.92 (m, 1H), 3.73 (d, 2H), 2.58 (m, 1H), 2.52 (s, 3H), 2.09 (m, 2H), 1.91 (m, 2H), 1.56-1.77 (m, 9H), 1.30-1.42 (m, 12H), 1.01-1.07 (m, 5H), 0.88-0.90 (m, 2H), 0.67-0.76 (m, 2H). MS: 561 $(M + 1)^+$. |
| 17/59 | 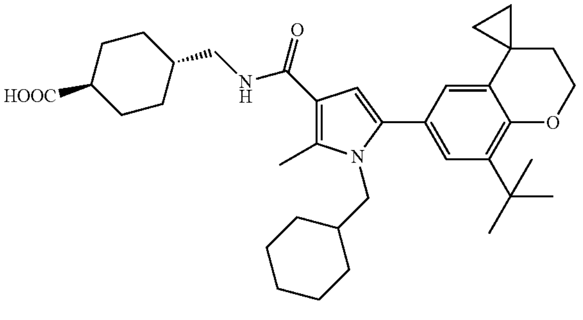 [SMILES: Cc1c(C(=O)NC[C@H]2CC[C@H](C(=O)O)CC2)cc(-c2cc(C(C)(C)C)c3c(c2)C2(CCO3)CC2)n1CC1CCCCC1] | $^1$H-NMR (400 MHz, $CDCl_3$) δ: 6.97 (s, 1H), 6.43 (d, 1H), 6.06 (s, 1H), 5.80 (s, 1H), 4.33 (m, 2H), 3.63 (d, 2H), 3.25 (m, 2H), 2.59 (s, 3H), 2.25-2.32 (m, 1H), 2.01-2.06 (m, 2H), 1.89-1.91 (m, 4H), 1.52-1.56 (m, 4H), 1.42-1.48 (m, 2H), 1.25-1.38 (m, 12H), 1.00-1.07 (m, 7H), 0.84-0.86 (m, 2H), 0.67-0.73 (m, 2H). MS: 575.5 $(M + 1)^+$. |
| 17/60 | 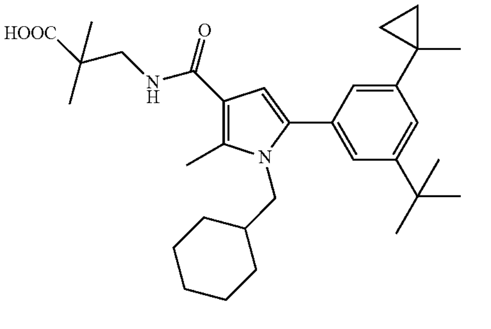 [SMILES: Cc1c(C(=O)NCC(C)(C)C(=O)O)cc(-c2cc(C(C)(C)C)cc(C3(C)CC3)c2)n1CC1CCCCC1] | $^1$H-NMR (400 MHz, DMSO-$d_6$) δ: 12.22 (s, 1H), 7.42 (m, 1H), 7.19 (s, 1H), 7.15 (s, 1H), 6.97 (s, 1H), 6.49 (s, 1H), 3.76 (d, 2H), 3.36 (s, 2H), 2.50 (s, 3H), 1.47 (d, 3H), 1.40 (s, 3H), 1.30-1.23 (m, 12H), 1.08 (s, 6H), 0.93 (m, 3H), 0.84 (m, 2H), 0.76 (m, 2H), 0.64 (m, 2H). MS: 507.3 $(M + 1)^+$. |

-continued

| # | Structure | Analytical data |
|---|---|---|
| 17/61 | 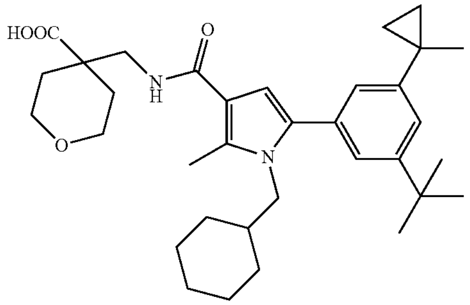 [SMILES: Cc1c(C(=O)NCC2(C(=O)O)CCOCC2)cc(-c2cc(C(C)(C)C)cc(C3(C)CC3)c2)n1CC1CCCCC1] | $^1$H-NMR (400 MHz, DMSO-$d_6$) δ: 12.48 (s, 1H), 7.56 (m, 1H), 7.19 (s, 1H), 7.15 (s, 1H), 6.97 (s, 1H), 6.49 (s, 1H), 3.73-3.77 (m, 4H), 3.27-3.32 (m, 4H), 2.50 (s, 3H), 1.85 (d, 2H), 1.45-1.50 (m, 5H), 1.40 (s, 3H), 1.30-1.23 (m, 12H), 0.95 (m, 3H), 0.84 (m, 2H) 0.76 (m, 2H), 0.64 (m, 2H). MS: 549 $(M + 1)^+$ |
| 17/62 | 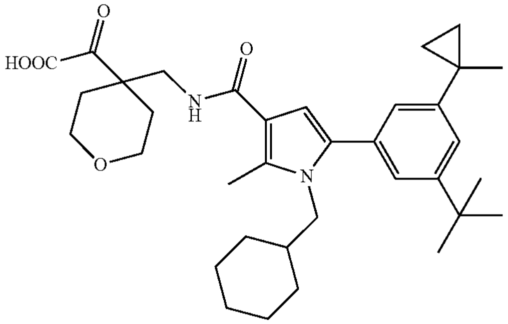 | $^1$H-NMR (400 MHz, DMSO-$d_6$) δ: 7.34 (m, 1H), 7.29 (s, 1H), 7.19 (s, 1H), 7.14 (s, 1H), 7.04 (s, 1H), 6.97 (s, 1H), 6.47 (s, 1H), 3.76 (d, 2H), 3.65 (m, 2H), 3.34-3.28 (m 4H), 2.51 (s, 3H), 1.91 (d, 2H), 1.45-1.50 (m, 4H), 1.40 (s, 3H), 1.30-1.20 (m, 12H), 0.92 (m, 3H), 0.83 (m, 2H), 0.76 (m, 2H), 0.64 (m, 2H). MS: 548.3 $(M + 1)^+$ |
| 17/63 | 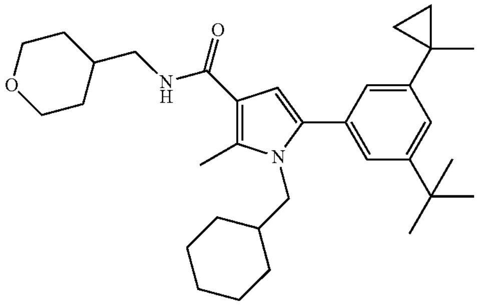 [SMILES: Cc1c(C(=O)NCC2CCOCC2)cc(-c2cc(C(C)(C)C)cc(C3(C)CC3)c2)n1CC1CCCCC1] | $^1$H-NMR (400 MHz, $CDCl_3$) δ: 7.25 (s, 1H), 7.13 (m, 1H), 7.00 (m, 1H), 6.15 (s, 1H), 5.86 (m, 1H), 3.98 (m, 2H), 3.71 (d, 2H), 3.38 (m, 2H), 3.29 (m, 2H), 2.62 (s, 3H), 1.85 (m, 1H), 1.68 (m, 2H), 1.53 (m, 3H), 1.40 (s, 3H), 1.38-1.33 (m, 14H), 1.00 (m, 3H), 0.87 (m, 2H), 0.75 (m, 2H), 0.64 (m, 2H). MS: 505.4 $(M + 1)^+$. |
| 17/64 | 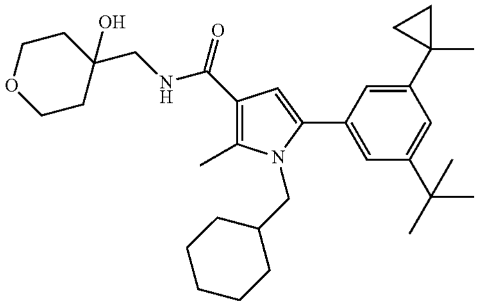 [SMILES: Cc1c(C(=O)NCC2(O)CCOCC2)cc(-c2cc(C(C)(C)C)cc(C3(C)CC3)c2)n1CC1CCCCC1] | $^1$H-NMR (400 MHz, DMSO-$d_6$) δ: 7.54 (m, 1H), 7.20 (s, 1H), 7.15 (s, 1H), 6.98 (s, 1H), 6.53 (s, 1H), 4.78 (s, 2H), 3.77 (d, 2H), 3.59 (m, 4H), 3.22 (d, 2H), 2.52 (s, 3H), 1.60-1.45 (m, 4H), 1.40-1.34 (m, 5H), 1.30-1.23 (m, 12H), 0.93 (m, 3H), 0.83 (m, 2H), 0.76 (m, 2H), 0.64 (m, 2H). MS: 521.3 $(M + 1)^+$. |
| 17/65 | 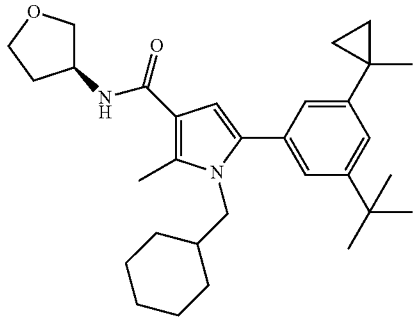 [SMILES: Cc1c(C(=O)N[C@H]2CCOC2)cc(-c2cc(C(C)(C)C)cc(C3(C)CC3)c2)n1CC1CCCCC1] | $^1$H-NMR (400 MHz, $CDCl_3$) δ: 7.25 (s, 1H), 7.12 (s, 1H), 7.00 (s, 1H), 6.15 (s, 1H), 5.89 (d, 1H), 4.69 (m, 1H), 4.00-3.90 (m, 2H), 3.82 (m, 1H), 3.75-3.70 (m, 3H), 2.61 (s, 3H), 2.31 (m, 1H), 1.88 (m, 1H), 1.56 (m, 3H), 1.42 (m, 3H), 1.41-1.33 (m, 12H), 1.00 (m, 3H), 0.88 (m, 2H), 0.75 (m, 2H), 0.65 (m, 2H). MS: 477.4 $(M + 1)^+$. |

-continued
| # | Structure | Analytical data |
|---|---|---|
| 17/66 | 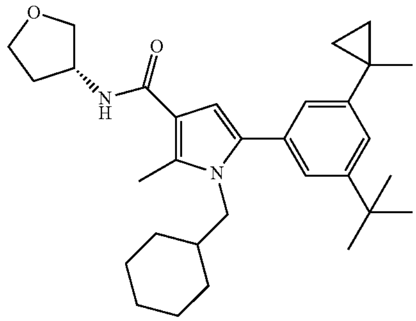 [SMILES: Cc1c(C(=O)N[C@@H]2CCOC2)cc(-c2cc(C(C)(C)C)cc(C3(C)CC3)c2)n1CC1CCCCC1] | $^1$H-NMR (400 MHz, $CDCl_3$) δ: 7.25 (s, 1H), 7.12 (s, 1H), 7.00 (s, 1H), 6.15 (s, 1H), 5.89 (d, 1H), 4.00-3.91 (m, 2H), 3.83 (m, 1H), 3.75-3.71 (m, 3H), 2.61 (s, 3H), 2.31 (m, 1H), 1.88 (m, 1H), 1.53 (m, 3H), 1.42 (m, 3H), 1.41-1.33 (m, 12H), 1.00 (m, 3H), 0.87 (m, 2H), 0.75 (m, 2H), 0.65 (m, 2H). MS: 477.2 $(M + 1)^+$. |
| 17/67 | 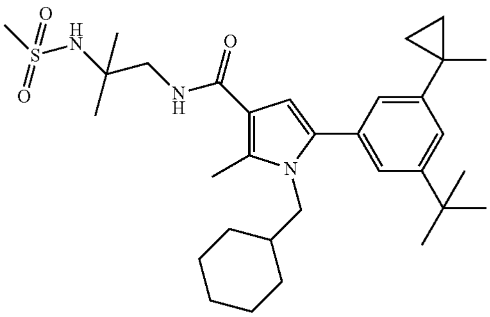 [SMILES: Cc1c(C(=O)NCC(C)(C)NS(C)(=O)=O)cc(-c2cc(C(C)(C)C)cc(C3(C)CC3)c2)n1CC1CCCCC1] | $^1$H-NMR (400 MHz, $CDCl_3$) δ: 7.26 (s, 1H), 7.13 (m, 1H), 7.01 (s, 1H), 6.30 (m, 1H), 6.22 (s, 1H), 3.71 (d, 2H), 3.47 (d, 2H), 3.02 (s, 3H), 2.61 (s, 3H), 1.54 (m, 3H), 1.43 (s, 9H), 1.39-1.26 (m, 12H), 0.99 (m, 3H), 0.87 (m, 2H) 0.75 (m, 2H), 0.65 (m, 2H). MS: 556.3 $(M + 1)^+$. |
| 17/68 | 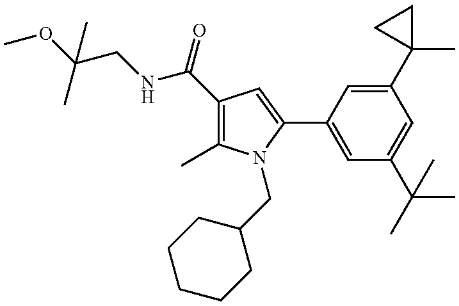 [SMILES: COC(C)(C)CNC(=O)c1cc(-c2cc(C(C)(C)C)cc(C3(C)CC3)c2)n(CC2CCCCC2)c1C] | $^1$H-NMR (400 MHz, $CDCl_3$) δ: 7.26 (m, 1H), 7.14 (m, 1H), 7.02 (m, 1H), 6.22 (m, 1H), 6.06 (m, 1H), 3.71 (d, 2H), 3.43 (d, 2H), 3.21 (s, 3H), 2.61 (s, 3H), 1.53 (m, 3H), 1.49 (s, 3H), 1.42-1.33 (m, 12H), 1.20 (s, 6H), 0.99 (m, 3H), 0.87 (m, 2H), 0.74 (m, 2H), 0.65 (m, 2H). MS: 493.5 $(M + 1)^+$. |
| 17/69 | 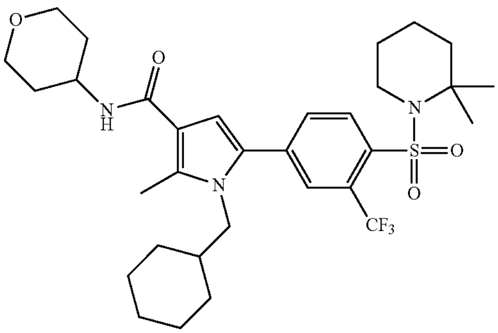 [SMILES: Cc1c(C(=O)NC2CCOCC2)cc(-c2ccc(S(=O)(=O)N3CCCCC3(C)C)c(C(F)(F)F)c2)n1CC1CCCCC1] | $^1$H-NMR (400 MHz, DMSO-$d_6$) δ: 8.20 (d, 1H, J = 8.0 Hz), 7.93-7.90 (m, 2 H), 7.58 (d, 1H, J = 8.0 Hz), 6.91 (s, 1H), 3.95-3.85 (m, 5H), 3.51-3.50 (m, 2H), 3.38-3.34 (m, 2H), 2.55-2.50 (m, 3H), 1.72-1.62 (m, 2 H), 1.56 (m, 4 H), 1.55-1.45 (m, 7H), 1.23 (m, 9 H), 0.95-0.86 (m, 3H), 0.67-0.64 (m, 2H). MS: 624.3 $(M + H)^+$. |

-continued
| # | Structure | Analytical data |
|---|---|---|
| 17/70 | 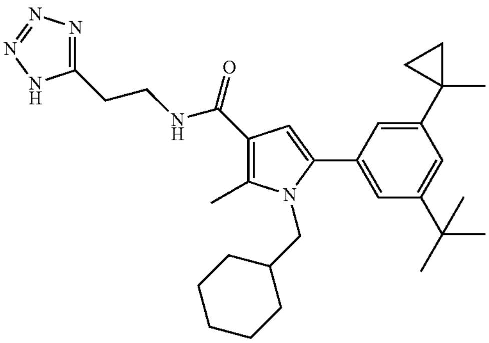 [SMILES: Cc1c(C(=O)NCCc2nnn[nH]2)cc(-c2cc(C(C)(C)C)cc(C3(C)CC3)c2)n1CC1CCCCC1] | $^1$H-NMR (400 MHz, DMSO-$d_6$) δ: 7.85 (m, 1H), 7.19 (m, 1H), 7.14 (m, 1H), 6.96 (m, 1H), 6.43 (s, 1H), 3.76 (d, 2H), 3.52 (m, 2H), 3.07 (m, 2H), 2.50 (s, 3H), 1.46 (m, 2H), 1.39 (s, 3H), 1.29-1.22 (m, 12H), 0.96-0.91 (m, 3H), 0.85-0.81 (m, 2H), 0.77-0.75 (m, 2H), 0.65-0.62 (m, 2H). MS: 503.2 $(M + 1)^+$. |
| 17/71 | 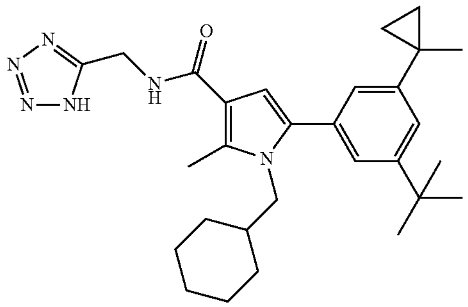 [SMILES: Cc1c(C(=O)NCc2nnn[nH]2)cc(-c2cc(C(C)(C)C)cc(C3(C)CC3)c2)n1CC1CCCCC1] | $^1$H-NMR (400 MHz, DMSO-$d_6$) δ: 8.27 (m, 1H), 7.19 (s, 1H), 7.15 (s, 1H), 6.98 (s, 1H), 6.56 (s, 1H), 4.61 (d, 2H), 3.79 (d, 2H), 2.53 (s, 3H), 1.46 (m, 3H), 1.40 (s, 3H), 1.30-1.22 (m, 12H), 0.96-0.90 (m, 3H), 0.85-0.79 (m, 2H), 0.78-0.75 (m, 2H), 0.68-0.60 (m, 2H). MS: 489.2 $(M + 1)^+$. |
| 17/72 | 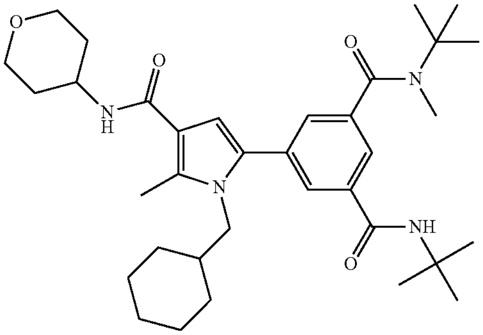 | $^1$H-NMR (400 MHz, DMSO-$d_6$) δ: 8.10 (d, 1H), 7.56 (s, 1H), 7.49 (d, 1H), 7.43 (d, 1H), 7.35 (s, 1H), 6.72 (s, 1H), 6.03 (s, 1H), 3.84-3.94 (m, 5H), 3.36 (m, 2H), 2.53 (s, 3H), 1.67-1.70 (m, 8H), 1.53 (m, 2H), 1.45 (m, 3H), 1.23 (m, 3H), 1.12 (s, 9H), 0.88 (m, 3H), 0.60 (m, 2H). MS: 574.3 $(M + 1)^+$. |
| 17/73 | 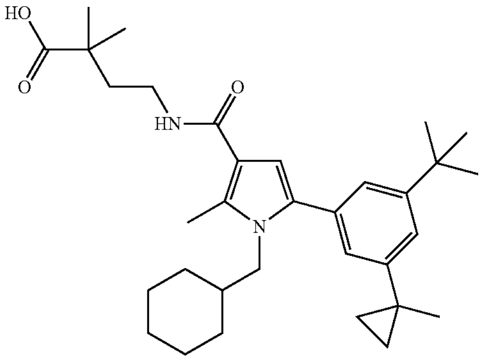 [SMILES: Cc1c(C(=O)NCCC(C)(C)C(=O)O)cc(-c2cc(C(C)(C)C)cc(C3(C)CC3)c2)n1CC1CCCCC1] | $^1$H-NMR (400 MHz, DMSO-$d_6$) δ: 11.93 (s, 1H), 7.61 (d, 1H), 7.18 (t, 1H), 7.14 (d, 1H), 6.97 (s, 1H), 6.47 (s, 1H), 3.76 (d, 2H), 3.17-3.12 (m, 2H), 2.51 (s, 3H), 1.70-1.66 (m, 2H), 1.46 (d, 3H), 1.40 (s, 3H), 1.30-1.13 (m, 12H), 0.95-0.62 (m, 9H). MS: 521.2 (M + 1). |

-continued
| # | Structure | Analytical data |
|---|---|---|
| 17/74 | 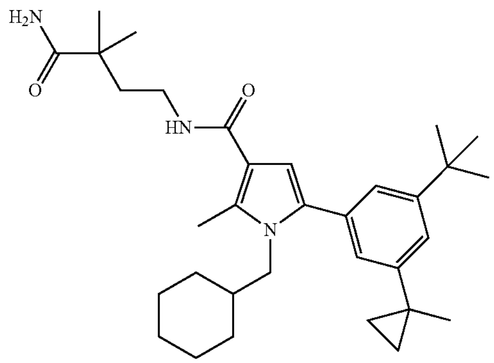 [SMILES: Cc1c(C(=O)NCCC(C)(C)C(N)=O)cc(-c2cc(C(C)(C)C)cc(C3(C)CC3)c2)n1CC1CCCCC1] | $^1$H-NMR (400 MHz, DMSO-$d_6$) δ: 7.61 (t, 1H), 7.18 (d, 1H), 7.15 (d, 1H), 6.97 (s, 1H), 6.86 (s, 1H), 6.47 (s, 1H), 3.76 (d, 2H), 3.114-3.09 (m, 2H), 2.51 (s, 3H), 1.67-1.63 (m, 2H), 1.46 (d, 3H), 1.40 (s, 3H), 1.30-1.21 (m, 12H), 1.09 (s, 6H), 0.95-0.62 (m, 9H). MS: 520.4 (M + 1). |
| 17/75 | 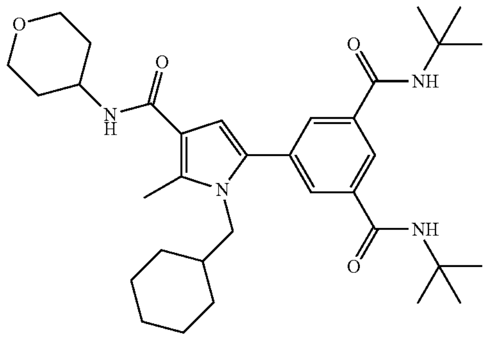 [SMILES: Cc1c(C(=O)NC2CCOCC2)cc(-c2cc(C(=O)NC(C)(C)C)cc(C(=O)NC(C)(C)C)c2)n1CC1CCCCC1] | $^1$H-NMR ($CDCl_3$, 300 MHz) δ: 7.99 (s, 1H), 7.76 (s, 2H), 6.28 (s, 1H), 6.10 (s, 1H), 5.68 (d, 1H, J = 8.0 Hz), 4.16 (m, 1H), 3.98 (m, 2H), 3.79 (d, 2H, J = 7.2 Hz), 3.53 (m, 2H), 2.62 (s, 3H), 1.98 (m, 2H), 1.58-1.52 (m, 5H), 1.49 (s, 18H), 1.40-1.33 (m, 3H), 1.00 (m, 3H), 0.64 (m, 2H). MS: 579.2 $(M + 1)^+$. |
| 17/76 | 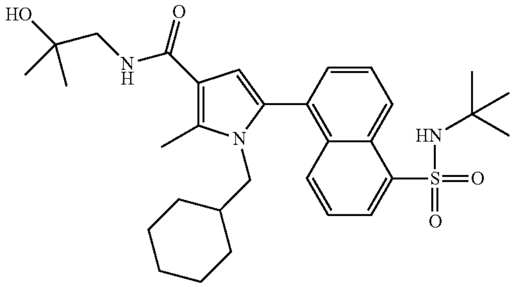 [SMILES: Cc1c(C(=O)NCC(C)(C)O)cc(-c2cccc3c(S(=O)(=O)NC(C)(C)C)cccc23)n1CC1CCCCC1] | $^1$H-NMR (400 MHz, $CDCl_3$) δ: 8.67 (d, 1H, J = 8.8 Hz), 8.33 (d, 1H, J = 7.2 Hz), 7.90 (d, 1H, J = 8.8 Hz), 7.72-7.68 (m, 1H), 7.55-7.47 (m, 2H), 6.34 (s, 1H), 6.19 (t, 1H, J = 6.0 Hz), 4.62 (s, 1H), 3.68-3.63 (m, 1H), 3.42 (d, 2H, J = 6.0 Hz), 3.31-3.26 (m, 1H), 2.676 (s, 3H), 1.48 (br s, 3H), 1.28 (s, 6H), 1.26 (s, 3H), 1.21 (s, 9H), 0.94-0.86 (m, 3H), 0.52-0.47 (m, 2H). MS: 554.3 (M + 1). |
| 17/77 | 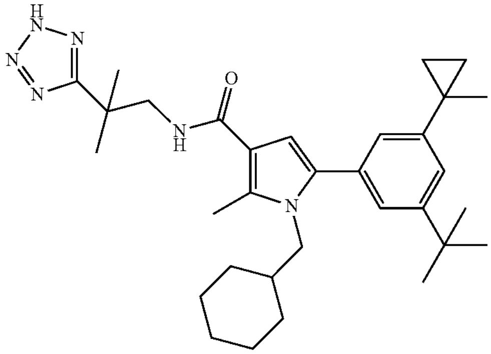 [SMILES: Cc1c(C(=O)NCC(C)(C)c2nn[nH]n2)cc(-c2cc(C(C)(C)C)cc(C3(C)CC3)c2)n1CC1CCCCC1] | $^1$H-NMR (400 MHz, $CDCl_3$) δ: 7.27 (m, 1H), 7.09 (m, 1H), 6.98 (m, 1H), 6.29 (m, 1H), 6.15 (s, 1H), 3.76 (d, 2H, J = 7.6 Hz), 3.71 (d, 2H, J = 7.2 Hz), 2.64 (s, 3H), 1.55-1.52 (m, 9H), 1.48 (s, 3H), 1.41-1.24 (m, 12H), 1.00 (m, 3H), 0.86 (m, 2H), 0.74 (m, 2H), 0.66 (m, 2 H). MS: 531.4 $(M + 1)^+$. |

-continued
| # | Structure | Analytical data |
|---|---|---|
| 17/78 | 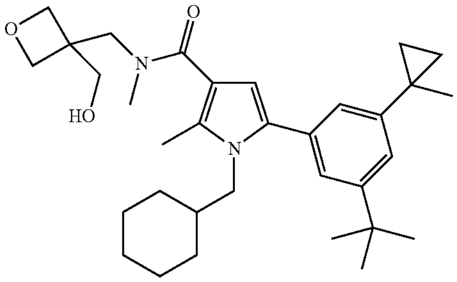 [SMILES: Cc1c(C(=O)N(C)CC2(CO)COC2)cc(-c2cc(C(C)(C)C)cc(C3(C)CC3)c2)n1CC1CCCCC1] | $^{1}$H-NMR (400 MHz, $CDCl_3$) δ: 7.26 (t, 1H), 7.13 (t, 1H), 7.00 (t, 1H), 6.13 (s, 1H), 4.93 (br s, 1H), 4.61 (d, 2H), 4.47 (d, 2H), 3.91 (s, 2H), 3.82 (d, 2H), 3.71 (d, 2H), 3.12 (s, 3H), 2.38 (s, 3H), 1.58-1.53 (m, 3H), 1.42 (s, 3H), 1.36-1.25 (m, 12H), 1.01-0.98 (m, 3H), 0.86 (dd, 2H), 0.74 (dd, 2H), 0.68-0.60 (m, 2H). MS: 521.3 (M + 1). |
| 17/79 | 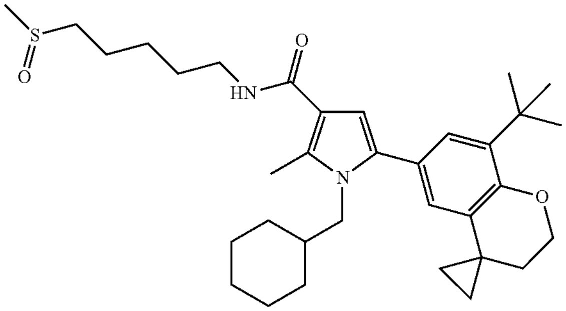 [SMILES: Cc1c(C(=O)NCCCCCS(C)=O)cc(-c2cc(C(C)(C)C)c3c(c2)C2(CCO3)CC2)n1CC1CCCCC1] | $^{1}$H-NMR (400 MHz, $CDCl_3$) δ: 6.97 (d, 1H), 6.43 (d, 1H), 6.06 (s, 1H), 5.76 (t, 1H), 4.33 (t, 2H), 3.64 (d, 2H), 3.39 (q, 2H), 2.75-2.65 (m, 2H), 2.59 (s, 3H), 2.56 (s, 3H), 1.90 (t, 2H), 1.83-1.79 (m, 2H), 1.57-1.51 (m, 7H), 1.45-1.33 (m, 12H), 1.03-1.00 (m, 5H), 0.87-0.84 (m, 2H), 0.71-0.65 (m, 2H). MS: 567.3 $[M + 1]^+$. |
| 17/80 | 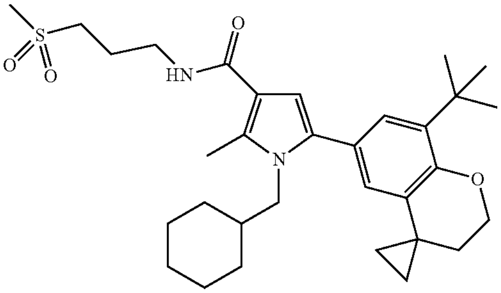 [SMILES: Cc1c(C(=O)NCCCS(C)(=O)=O)cc(-c2cc(C(C)(C)C)c3c(c2)C2(CCO3)CC2)n1CC1CCCCC1] | $^{1}$H-NMR (400 MHz, $CDCl_3$) δ: 6.97 (d, 1H), 6.43 (d, 1H), 6.08 (s, 1H), 5.99 (t, 1H), 4.34 (t, 2H), 3.64 (d, 2H), 3.59-3.54 (m, 2H), 3.14 (t, 2H), 2.92 (s, 3H), 2.58 (s, 3H), 2.19-2.12 (m, 2H), 1.90 (t, 2H), 1.57 (br s, 3H), 1.44-1.36 (m, 12H), 1.04-1.00 (m, 5H), 0.87-0.84 (m, 2H), 0.72-0.65 (m, 2H). MS: 555.3 $[M + 1]^+$. |
| 17/81 | 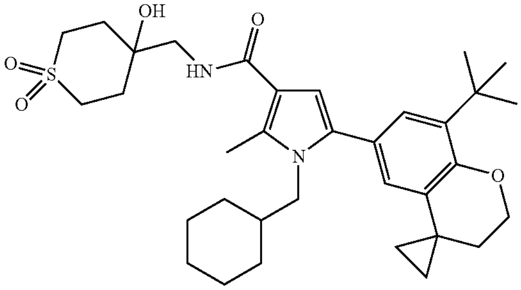 [SMILES: Cc1c(C(=O)NCC2(O)CCS(=O)(=O)CC2)cc(-c2cc(C(C)(C)C)c3c(c2)C2(CCO3)CC2)n1CC1CCCCC1] | $^{1}$H-NMR (400 MHz, $CDCl_3$) δ: 6.95 (d, 1H), 6.42 (d, 1H), 6.13 (t, 1H), 6.08 (s, 1H), 4.34 (t, 2H), 3.64 (d, 2H), 3.50 (dt, 2H), 3.41 (d, 2H), 2.86 (dd, 2H), 2.58 (s, 3H), 2.14-1.99 (m, 4H), 1.90 (m, 2H), 1.59-1.41 (m, 3H), 1.38-1.28 (m, 12H), 1.04-0.99 (m, 5H), 0.88-0.85 (m, 2H), 0.73-0.65 (m, 2H). MS: 597.4 (M + 1). |
| 17/82 | 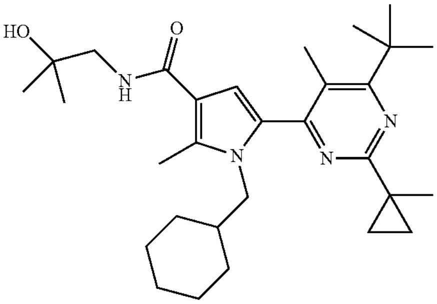 [SMILES: Cc1c(-c2cc(C(=O)NCC(C)(C)O)c(C)n2CC2CCCCC2)nc(C2(C)CC2)nc1C(C)(C)C] | MS: 495.3 $(M + H)^+$. |

-continued
| # | Structure | Analytical data |
|---|---|---|
| 17/83 | 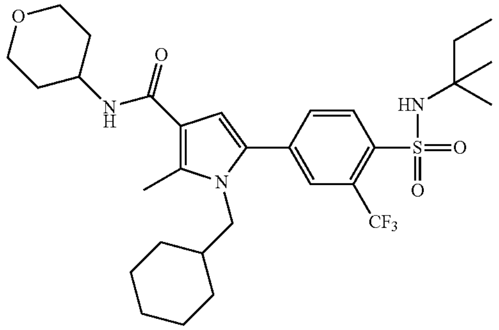 [SMILES: CCC(C)(C)NS(=O)(=O)c1ccc(-c2cc(C(=O)NC3CCOCC3)c(C)n2CC2CCCCC2)cc1C(F)(F)F] | $^1$H-NMR (400 MHz, DMSO-$d_6$) δ: 8.23 (d, 1H, J = 8.0 Hz), 7.96-7.71 (m, 3H), 7.57 (d, 1H, J = 8.0 Hz), 6.88 (s, 1H), 3.95-3.85 (m, 5H), 3.38-3.32 (m, 2H), 2.55 (m, 3H), 1.72-1.68 (m, 2H), 1.56-1.45 (m, 7H), 1.24-1.21 (m, 3H), 1.08 (m, 6H), 0.93-0.88 (m, 3H), 0.79-0.75 (m, 3H), 0.68-0.59 (m, 2H). MS: 598.3 $(M + H)^+$. |
| 17/84 | 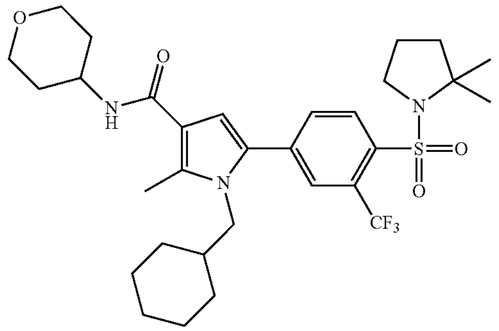 [SMILES: Cc1c(C(=O)NC2CCOCC2)cc(-c2ccc(S(=O)(=O)N3CCCC3(C)C)c(C(F)(F)F)c2)n1CC1CCCCC1] | $^1$H-NMR (400 MHz, DMSO-$d_6$) δ: 8.06-8.04 (m, 1H), 7.89-7.88 (m, 2H), 7.57 (d, 1H, J = 8.0 Hz), 6.88 (s, 1H), 3.95-3.88 (m, 6H), 3.56-3.52 (m, 2H), 2.38-3.33 (m, 2H), 2.56 (m, 3H), 1.95-1.92 (m, 4H), 1.72-1.69 (m, 2H), 1.56-1.46 (m, 5H), 1.33 (m, 6H), 1.26-1.23 (m, 3H), 0.94-0.91 (m, 3H), 0.67-0.64 (m, 2H). MS: 610.3 $(M + H)^+$. |
| 17/85 | 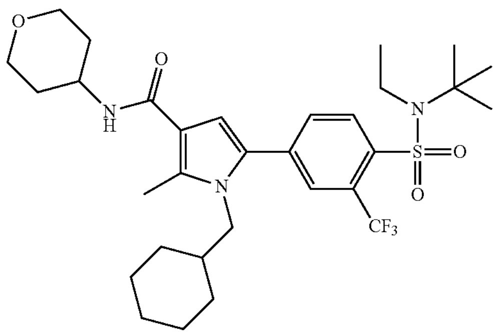 [SMILES: CCN(C(C)(C)C)S(=O)(=O)c1ccc(-c2cc(C(=O)NC3CCOCC3)c(C)n2CC2CCCCC2)cc1C(F)(F)F] | $^1$H-NMR (400 MHz, DMSO-$d_6$) δ: 7.99 (d, 1H, J = 8.4 Hz), 7.90-7.88 (m, 2H), 7.56 (d, 1H, J = 8.0 Hz), 6.88 (s, 1H), 3.95-3.85 (m, 5H), 3.63-3.58 (m, 2H), 3.38-3.32 (m, 2H), 2.55 (m, 3H), 1.72-1.68 (m, 2H), 1.55-1.46 (m, 5H), 1.34-0.95 (m, 15H), 0.92-0.89 (m, 3H), 0.66-0.64 (m, 2H). MS: 612.3 $(M + 1)^+$. |
| 17/86 | 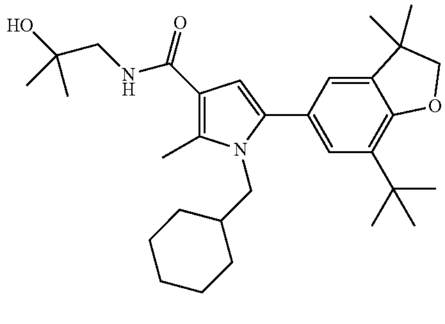 [SMILES: Cc1c(C(=O)NCC(C)(C)O)cc(-c2cc(C(C)(C)C)c3c(c2)C(C)(C)CO3)n1CC1CCCCC1] | $^1$H-NMR (300 MHz, $CDCl_3$) δ: 6.99 (s, 1H), 6.89 (s, 1H), 6.18 (s, 1H), 6.15 (m, 1H), 4.27 (s, 2H), 3.67 (d, J = 7.2 Hz, 2H), 3.39 (d, J = 5.7 Hz, 2H), 2.60 (s, 3H), 1.59-1.53 (m, 3H), 1.36-1.33 (m, 18H), 1.25 (m, 8H), 1.01 (m, 3H), 0.67-0.66 (m, 2H). MS: 495.4 $(M + 1)^+$. |

-continued

| # | Structure | Analytical data |
|---|---|---|
| 17/87 | 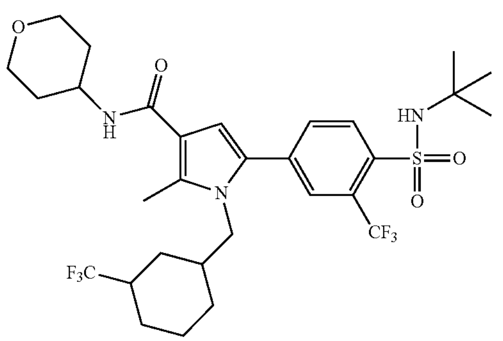 [SMILES: Cc1c(C(=O)NC2CCOCC2)cc(-c2ccc(S(=O)(=O)NC(C)(C)C)c(C(F)(F)F)c2)n1CC1CCCC(C(F)(F)F)C1] | $^1$H-NMR (400 MHz, $CDCl_3$) δ: 0.55-0.64 (m, 2H), 0.83-0.89 (m, 2H), 1.02-1.10 (m, 2H), 1.26 (s, 9H), 1.35-1.44 (m, 2H), 1.53-1.61 (m, 2H), 1.75-1.84 (m, 3H), 1.97-2.00 (m, 2H), 2.64 (s, 3H), 3.53 (t, J = 11.6 Hz, 2H), 3.85-3.88 (m, 2H), 3.98-4.01 (m, 2H), 4.12-4.21 (m, 1H), 4.74 (s, 1H), 5.65 (d, J = 7.6 Hz, 1H), 6.38 (s, 1H), 7.60 (d, J = 8.4 Hz, 1H), 7.79 (s, 1H), 8.33 (d, J = 8.4 Hz, 1H). MS: 652.2 $[M + 1]^+$. |
| 17/88 | 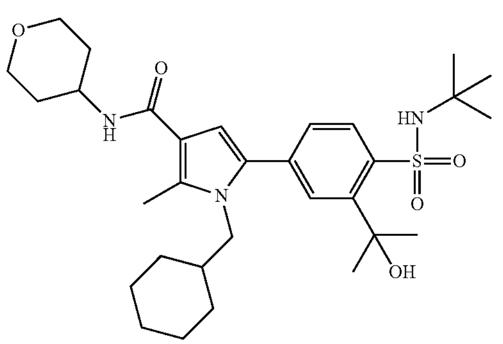 | $^1$H-NMR (400 MHz, DMSO-$d_6$) δ: 8.10 (d, 1H), 7.56 (s, 1H), 7.49 (d, 1H), 7.43 (d, 1H), 7.35 (s, 1H), 6.72 (s, 1H), 6.03 (s, 1H), 3.84-3.94 (m, 5H), 3.36 (m, 2H), 2.53 (s, 3H), 1.67-1.70 (m, 8H), 1.53 (m, 2H), 1.45 (m, 3H), 1.23 (m, 3H), 1.12 (s, 9H), 0.88 (m, 3H), 0.60 (m, 2H). MS: 574.3 $(M + 1)^+$. |
| 17/89 | 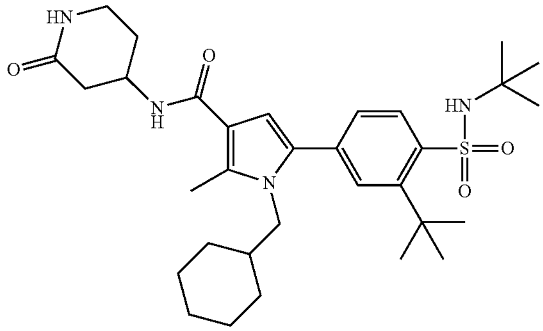 [SMILES: Cc1c(C(=O)NC2CCNC(=O)C2)cc(-c2ccc(S(=O)(=O)NC(C)(C)C)c(C(C)(C)C)c2)n1CC1CCCCC1] | $^1$H-NMR (400 MHz, DMSO-$d_6$) δ: 8.13 (d, J = 8.4 Hz, 1H), 7.78 (s, 1H), 7.63 (d, J = 8.4 Hz, 1H), 7.54 (m, 2H), 7.42 (m, 1H), 6.71 (s, 1H), 4.13 (m, 1H), 3.84 (m, 2H), 3.31 (m, 2H), 2.53 (s, 3H), 2.39 (m, 1H), 2.21 (m, 1H), 1.89 (d, 1H), 1.66 (m, 1H), 1.55 (s, 9H), 1.45 (m, 3H), 1.32-1.21 (m, 12H), 0.84 (m, 3H), 0.60 (m, 2H). MS: 585.3 $(M + 1)^+$. |
| 17/90 | 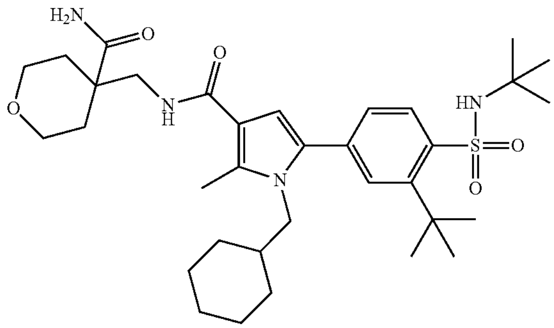 [SMILES: Cc1c(C(=O)NCC2(C(N)=O)CCOCC2)cc(-c2ccc(S(=O)(=O)NC(C)(C)C)c(C(C)(C)C)c2)n1CC1CCCCC1] | $^1$H-NMR (400 MHz, DMSO-$d_6$) δ: 8.13 (d, J = 8.4 Hz, 1H), 7.76 (s, 1H), 7.53 (s, 1H), 7.43 (m, 2H), 7.30 (s, 1H), 7.04 (s, 1H), 6.67 (s, 1H), 3.84 (m, 2H), 3.69 (m, 2H), 3.37-3.30 (m, 4H), 2.52 (s, 3H), 1.92 (m, 2H), 1.55-1.44 (m, 14H), 1.22-1.16 (m, 12H), 0.96-0.82 (m, 3H), 0.62 (m, 2H). MS: 629.3 $(M + 1)^+$. |

-continued
| # | Structure | Analytical data |
|---|---|---|
| 17/91 | 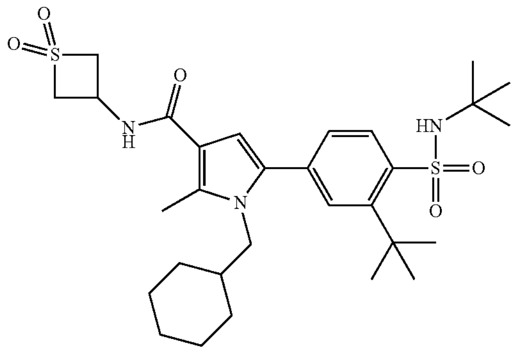 [SMILES: Cc1c(C(=O)NC2CS(=O)(=O)C2)cc(-c2ccc(S(=O)(=O)NC(C)(C)C)c(C(C)(C)C)c2)n1CC1CCCCC1] | $^1$H-NMR (400 MHz, DMSO-$d_6$) δ: 8.29 (m, 1H), 8.15 (d, J = 8.4 Hz, 1H), 7.78 (s, 1H), 7.54 (s, 1H), 7.43 (m, 1H), 6.73 (s, 1H), 4.54-4.48 (m, 3H), 4.28-4.21 (m, 2H), 3.85 (m, 2H), 2.53 (s, 3H), 1.55 (s, 9H), 1.44 (m, 3H), 1.20-1.16 (m, 12H), 0.95-0.80 (m, 3H), 0.64 (m, 2H). MS: 592.3 $(M + 1)^+$. |
| 17/92 | 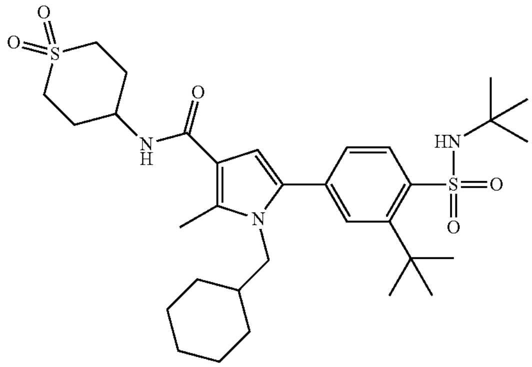 [SMILES: Cc1c(C(=O)NC2CCS(=O)(=O)CC2)cc(-c2ccc(S(=O)(=O)NC(C)(C)C)c(C(C)(C)C)c2)n1CC1CCCCC1] | $^1$H-NMR (400 MHz, DMSO-$d_6$) δ: 8.13 (d, J = 8.4 Hz, 1H), 7.78 (s, 1H), 7.63 (m, 1H), 7.52 (s, 1H), 7.41 (m, 1H), 6.72 (s, 1H), 4.14 (m, 1H), 3.84 (m, 2H), 3.31-3.22 (m, 1H), 3.13-3.08 (m, 2H), 2.53 (s, 3H), 2.11-2.00 (m, 4H), 1.55 (s, 9H), 1.45 (m, 3H), 1.21-1.16 (m, 12H), 0.95-0.88 (m, 3H), 0.61 (m, 2H). MS: 620.3 $(M + 1)^+$. |
| 17/93 | 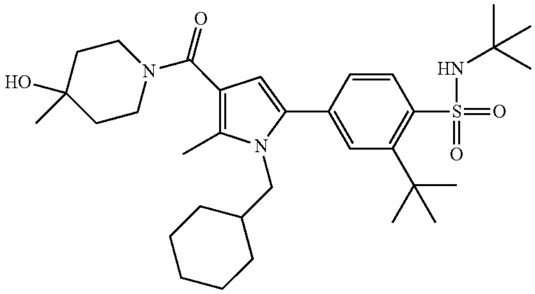 [SMILES: Cc1c(C(=O)N2CCC(C)(O)CC2)cc(-c2ccc(S(=O)(=O)NC(C)(C)C)c(C(C)(C)C)c2)n1CC1CCCCC1] | $^1$H-NMR (400 MHz, DMSO-$d_6$) δ: 8.12 (d, J = 8.4 Hz, 1H), 7.77 (s, 1H), 7.53 (s, 1H), 7.44 (m, 1H), 6.23 (s, 1H), 4.39 (s, 1H), 3.86-3.78 (m, 4H), 3.27 (m, 2H), 2.27 (s, 3H), 1.55 (s, 9H), 1.45-1.38 (m, 7H), 1.22-1.17 (m, 12H), 1.14 (s, 3H), 0.93-0.82 (m, 3H), 0.64 (m, 2H). MS: 586.4 $(M + 1)^+$. |
| 17/94 | 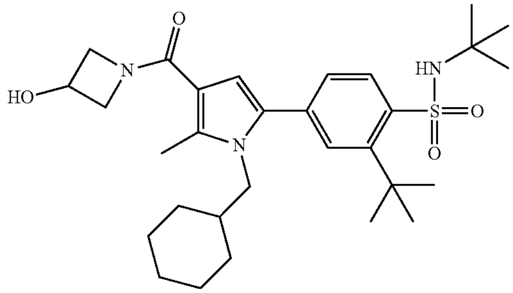 [SMILES: Cc1c(C(=O)N2CC(O)C2)cc(-c2ccc(S(=O)(=O)NC(C)(C)C)c(C(C)(C)C)c2)n1CC1CCCCC1] | $^1$H-NMR (400 MHz, $CDCl_3$) δ: 8.17 (d, J = 8.4 Hz, 1H), 7.57 (s, 1H), 7.22 (m, 1H), 6.24 (s, 1H), 4.70 (m, 1H), 4.55-4.48 (m, 3H), 4.12 (m, 2H), 3.77 (m, 2H), 2.57 (s, 3H), 1.62 (s, 9H), 1.54 (m, 3H), 1.34-1.28 (m, 12H), 1.01-0.92 (m, 3H), 0.62 (m, 2H). MS: 544.3 $(M + 1)^+$. |

-continued

| # | Structure | Analytical data |
|---|---|---|
| 17/95 | 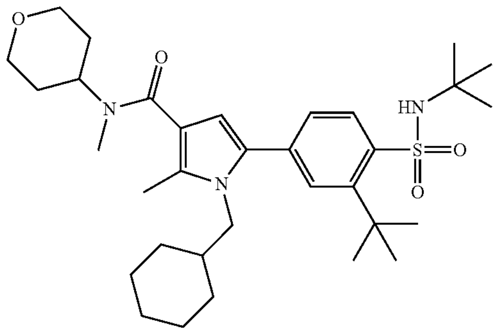 [SMILES: Cc1c(C(=O)N(C)C2CCOCC2)cc(-c2ccc(S(=O)(=O)NC(C)(C)C)c(C(C)(C)C)c2)n1CC1CCCCC1] | $^1$H-NMR (400 MHz, DMSO-$d_6$) δ: 8.12 (d, J = 8.8 Hz, 1H), 7.77 (s, 1H), 7.53 (s, 1H), 7.45 (m, 1H), 6.27 (s, 1H), 4.32 (s, br, 1H), 3.95-3.80 (m, 4H), 3.29 (m, 2H), 2.87 (s, 3H), 2.26 (s, 3H), 1.78 (m, 2H), 1.59-1.44 (m, 14H), 1.22-1.012 (m, 12H), 0.96-0.91 (m, 3H), 0.63 (m, 2H). MS: 586.4 $(M + 1)^+$. |
| 17/96 | 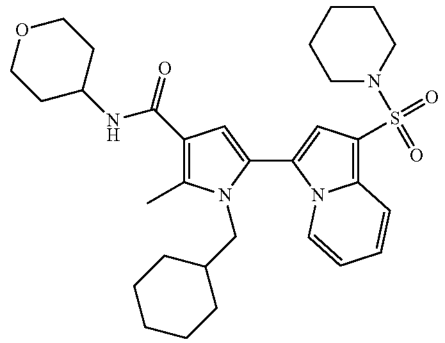 [SMILES: Cc1c(C(=O)NC2CCOCC2)cc(-c2cc(S(=O)(=O)N3CCCCC3)c3ccccn23)n1CC1CCCCC1] | $^1$H-NMR ($CDCl_3$, 400 MHz) δ: 8.07 (d, 1H, J = 8.8 Hz), 7.82 (d, 1H, J = 7.2 Hz), 7.10-7.05 (m, 2H), 6.76 (t, 1H, J = 6.0 Hz), 6.43 (s, 1H), 5.60 (d, 1H, J = 7.6 Hz), 4.19-4.15 (m, 1H), 3.99-3.96 (m, 2H), 3.55-3.50 (m, 4H), 3.01 (t, 4H, J = 5.6 Hz), 2.63 (s, 3H), 2.00-1.97 (m, 2H), 1.67-1.63 (m, 4H), 1.51-1.48 (m, 4H), 1.38-1.26 (m, 6H), 0.99-0.95 (m, 3H), 0.60-0.56 (m, 2H). MS: 567.1 $(M + 1)^+$. |
| 17/97 | 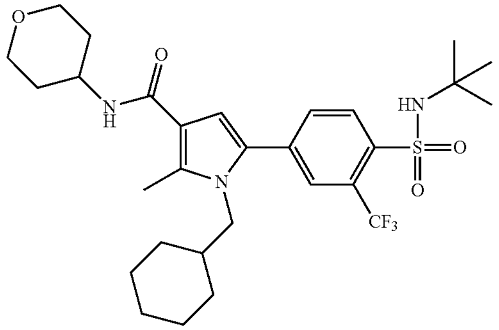 | $^1$H-NMR (400 MHz, DMSO-$d_6$) δ: 8.23 (d, 1H, J = 8.0 Hz), 7.94-7.91 (m, 1H), 7.86 (s, 1H), 6.56 (d, 1H, J = 8.0 Hz), 6.88 (s, 1H), 3.94-3.85 (m, 5H), 3.38-3.31 (m, 2H), 1.78 (m, 3H), 1.72-1.68 (m, 2H), 1.55-1.45 (m, 5H), 1.23-1.21 (m, 3H), 1.15 (m, 9H), 0.93-0.88 (m, 3H), 0.65-0.62 (m, 2H). MS: 584.2 $(M + 1)^+$. |
| 17/98 | 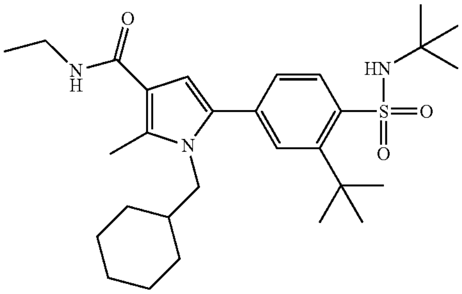 [SMILES: CCNC(=O)c1cc(-c2ccc(S(=O)(=O)NC(C)(C)C)c(C(C)(C)C)c2)n(CC2CCCCC2)c1C] | $^1$H-NMR (400 MHz, DMSO-$d_6$) δ: 8.13 (d, J = 8.4 Hz, 1H), 7.74 (s, 1H), 7.67 (t, J = 5.6 Hz, 1H), 7.53 (s, 1H), 7.42 (m, 1H), 6.65 (s, 1H), 3.84 (m, 2H), 3.19 (m, 2H), 2.53 (s, 3H), 1.55 (s, 9H), 1.44 (m, 3H), 1.24-1.16 (m, 12H), 1.07 (t, J = 6.8 Hz, 3H), 0.97-0.82 (m, 3H), 0.63 (m, 2H). MS: 516.3 $(M + 1)^+$. |

-continued

| # | Structure | Analytical data |
|---|---|---|
| 17/99 | 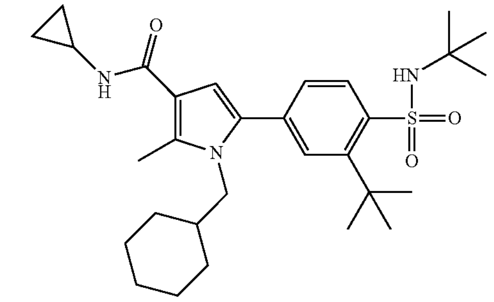 [SMILES: Cc1c(C(=O)NC2CC2)cc(-c2ccc(S(=O)(=O)NC(C)(C)C)c(C(C)(C)C)c2)n1CC1CCCCC1] | $^1$H-NMR (400 MHz, DMSO-$d_6$) δ: 8.12 (d, J = 8.4 Hz, 1H), 7.74 (s, 1H), 7.64 (m, 1H), 7.51 (s, 1H), 7.40 (m, 1H), 6.63 (s, 1H), 3.83 (m, 2H), 2.75 (m, 1H), 2.72 (s, 3H), 1.54 (s, 9H), 1.44 (m, 3H), 1.24-1.16 (m, 12H), 0.92-0.82 (m, 3H), 0.62 (m, 4H), 0.49 (m, 2H). MS: 528.3 (M + 1)$^+$. |
| 17/100 | 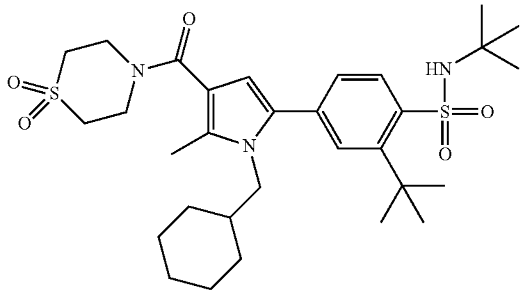 [SMILES: Cc1c(C(=O)N2CCS(=O)(=O)CC2)cc(-c2ccc(S(=O)(=O)NC(C)(C)C)c(C(C)(C)C)c2)n1CC1CCCCC1] | $^1$H-NMR (400 MHz, $CDCl_3$) δ: 8.20 (d, J = 8.8 Hz, 1H), 7.58 (s, 1H), 7.24 (m, 1H), 6.17 (s, 1H), 4.49 (s, br, 1H), 4.19 (m, 4H), 3.78 (m, 2H), 3.07 (m, 4H), 2.41 (s, 3H), 1.62 (s, 9H), 1.55 (m, 3H), 1.34-1.26 (m, 12H), 1.02-0.93 (m, 3H), 0.63 (m, 2H). MS: 606.3 (M + 1)$^+$. |
| 17/101 | 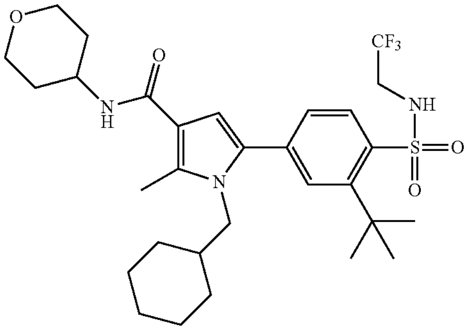 [SMILES: Cc1c(C(=O)NC2CCOCC2)cc(-c2ccc(S(=O)(=O)NCC(F)(F)F)c(C(C)(C)C)c2)n1CC1CCCCC1] | $^1$H-NMR ($CDCl_3$, 500 MHz) δ: 8.05 (d, 1H), 7.56 (d, 1H), 7.22 (dd, 1H), 6.21 (s, 1H), 5.54 (d, 1H), 4.95 (t, 1H), 4.12-4.08 (m, 1H), 3.92 (d, 2H), 3.72-3.65 (m, 4H), 3.46 (dt, 2H), 2.56 (s, 3H), 1.94-1.90 (m, 2H), 1.54 (s, 9H), 1.48-1.42 (m, 9H), 1.31-1.23 (m, 4H), 0.94-0.90 (m, 3H), 0.57-0.52 (m, 2H). MS: 598.2 (M + 1). |
| 17/102 | 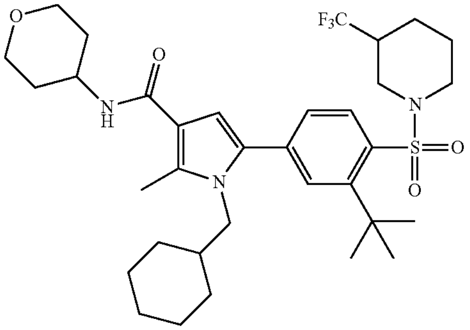 [SMILES: Cc1c(C(=O)NC2CCOCC2)cc(-c2ccc(S(=O)(=O)N3CCCC(C(F)(F)F)C3)c(C(C)(C)C)c2)n1CC1CCCCC1] | $^1$H-NMR ($CDCl_3$, 500 MHz) δ: 7.77 (d, 1H), 7.63 (d, 1H), 7.27-7.25 (m, 1H), 6.26 (s, 1H), 5.60 (d, 1H), 4.20-4.16 (m, 1H), 4.02-3.97 (m, 3H), 3.92-3.88 (m, 1H), 3.78 (d, 2H), 3.52 (t, 2H), 2.82-2.76 (m, 2H), 2.63 (s, 3H), 2.13-2.11 (s, 1H), 1.98 (dd, 2H), 1.89-1.87 (d, 1H), 1.63-1.32 (m, 19H), 1.35-0.60 (m, 11H). MS: 652.2 (M + 1). |
| 17/103 | 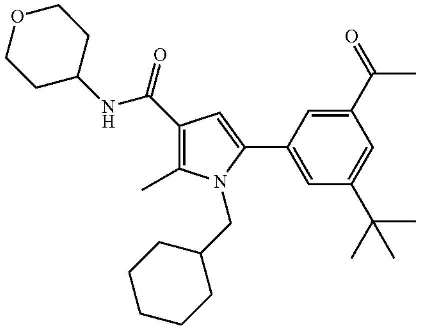 [SMILES: CC(=O)c1cc(-c2cc(C(=O)NC3CCOCC3)c(C)n2CC2CCCCC2)cc(C(C)(C)C)c1] | $^1$H-NMR ($CDCl_3$, 400 MHz) δ: 7.97 (s, 1H), 7.72 (s, 1H), 7.56 (s, 1H), 6.25 (s, 1H), 5.65 (d, 1H, J = 8.0 Hz), 4.16-4.18 (m, 1H), 3.98 (d, 2H, J = 11.2 Hz), 3.74 (d, 2H, J = 6.8 Hz), 3.52 (t, 2H, J = 11.2 Hz), 2.63 (s, 6H), 1.98 (d, 2H, J = 11.6 Hz), 1.48-1.55 (m, 5H), 1.33-1.38 (m, 12H), 0.99 (br s, 3H), 0.59-0.66 (m, 2H). MS: 479.3 (M + 1)$^+$. |

-continued

| # | Structure | Analytical data |
|---|---|---|
| 17/104 | 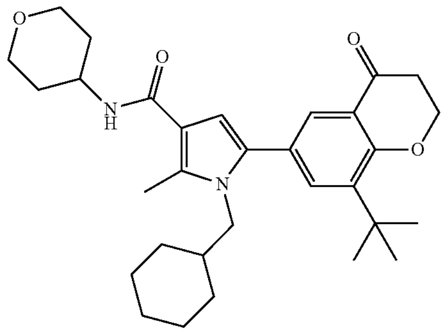 [SMILES: Cc1c(C(=O)NC2CCOCC2)cc(-c2cc3c(c(C(C)(C)C)c2)OCCC3=O)n1CC1CCCCC1] | $^1$H-NMR ($CDCl_3$, 400 MHz) δ: 7.76 (d, 1H), 7.42 (d, 1H), 6.16 (s, 1H), 5.60 (d, 1H, J = 7.6 Hz), 4.61 (t, 2H, J = 6.4 Hz), 4.14-4.17 (m, 1H), 3.96-3.99 (m, 2H), 3.71 (d, 2H, J = 6.8 Hz), 3.53 (dd, 2H), 2.86 (t, 2H, J = 6.4 Hz), 2.61 (s, 3H), 1.97-1.99 (m, 2H), 1.47-1.55 (m, 5H), 1.35-1.47 (m, 12H), 0.98-1.02 (m, 3H), 0.62-0.68 (m, 2H). MS: 507.3 $(M + 1)^+$. |
| 17/105 | 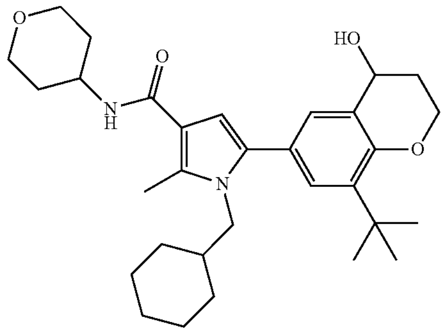 [SMILES: Cc1c(C(=O)NC2CCOCC2)cc(-c2cc3c(c(C(C)(C)C)c2)OCCC3O)n1CC1CCCCC1] | $^1$H-NMR ($CDCl_3$, 400 MHz) δ: 7.14 (d, 2H, J = 5.6 Hz), 6.11 (s, 1H), 5.59 (d, 1H, J = 8.0 Hz), 4.81 (d, 1H, J = 3.2 Hz), 4.29-4.39 (m, 2H), 4.14-4.18 (m, 1H), 3.97 (d, 2H, J = 11.2 Hz), 3.70 (d, 2H, J = 7.2 Hz), 3.49-3.55 (m, 2H), 2.60 (s, 3H), 1.96-2.18 (m, 4H), 1.83 (d, 2H, J = 4.4 Hz), 1.37-1.58 (m, 17H), 1.03-1.05 (m, 3H), 0.67-0.70 (m, 2H). MS: 509.3 $(M + 1)^+$. |
| 17/106 | 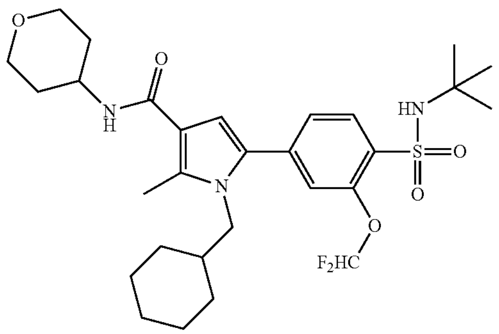 | $^1$H-NMR (DMSO-$d_6$, 400 MHz) δ: 7.92 (d, 1H, J = 8.0 Hz), 7.57 (s, 1H), 7.55 (s, 0.25H), 7.45 (s, 1H), 7.41 (s, 0.5H), 7.38 (d, 1H, J = 8.0 Hz), 7.21 (s, 0.25H), 6.78 (s, 1H), 3.85-3.94 (m, 5H), 3.33-3.38 (m, 2H), 2.54 (s, 3H), 1.68-1.71 (m, 2H), 1.46-1.55 (m, 5H), 1.21-1.26 (m, 3H), 1.11 (s, 9H), 0.89-0.94 (m, 3H), 0.60-0.67 (m, 2H). MS: 582.3 $(M + 1)^+$. |
| 17/107 | 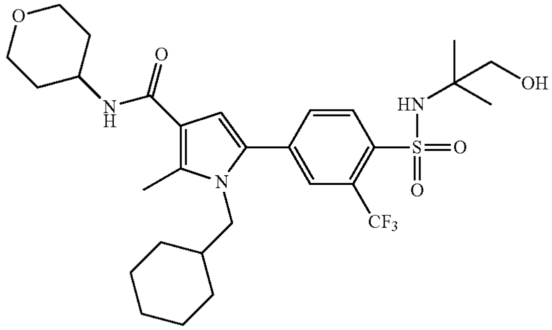 [SMILES: Cc1c(C(=O)NC2CCOCC2)cc(-c2ccc(S(=O)(=O)NC(C)(C)CO)c(C(F)(F)F)c2)n1CC1CCCCC1] | $^1$H-NMR ($CDCl_3$, 400 MHz) δ: 8.31 (d, 1H, J = 11.2 Hz), 7.82 (s, 1H), 7.63 (d, 1H, J = 11.2 Hz), 6.39 (s, 1H), 5.66 (d, 1H, J = 10.4 Hz), 5.10 (s, 1H), 4.12-4.19 (m, 1H), 3.98-4.01 (m, 2H), 3.82 (d, 2H), 3.49-3.57 (m, 4H), 2.63 (s, 3H), 2.31-2.34 (m, 1H), 1.97-2.01 (m, 2H), 1.55-1.64 (m, 3H), 1.22-1.34 (m, 3H), 1.17 (s, 6H), 0.56-1.03 (m, 7H). MS: 600.3 $(M + 1)^+$. |

-continued

| # | Structure | Analytical data |
|---|---|---|
| 17/108 | 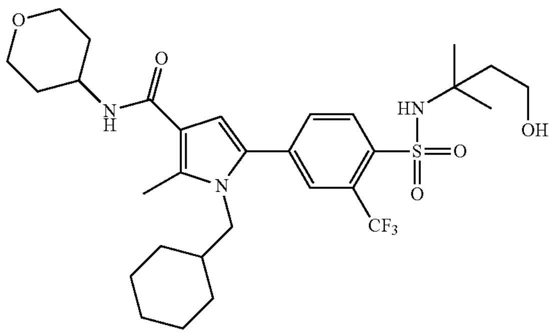 [SMILES: Cc1c(C(=O)NC2CCOCC2)cc(-c2ccc(S(=O)(=O)NC(C)(C)CCO)c(C(F)(F)F)c2)n1CC1CCCCC1] | $^1$H-NMR ($CDCl_3$, 400 MHz) δ: 8.29 (d, 1H, J = 8.4 Hz), 7.79 (s, 1H), 7.60 (d, 1H, J = 8.4 Hz), 6.39 (s, 1H), 6.33 (s, 1H), 5.70 (d, 1H, J = 7.6 Hz), 4.14-4.21 (m, 1H), 3.98-4.01 (m, 2H), 3.90-3.93 (m, 2H), 3.81 (d, 2H), 3.50-3.56 (m, 2H), 2.63 (s, 3H), 1.97-2.00 (m, 2H), 1.97 (br s, 1H), 1.78 (t, 2H), 1.50-1.60 (m, 5H), 1.24-1.37 (m, 9H), 1.00 (br s, 3H), 0.57-0.64 (m, 2H). MS: 614.4 $(M + 1)^+$. |
| 17/109 | 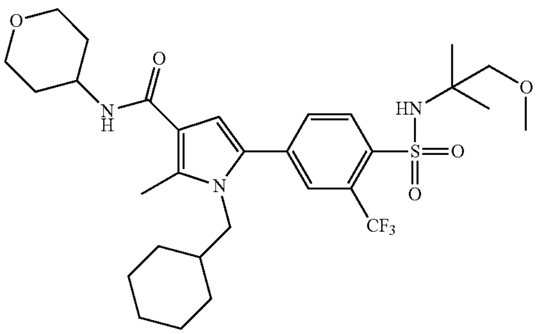 | $^1$H-NMR ($CDCl_3$, 400 MHz) δ: 8.29 (d, 1H, J = 8.4 Hz), 7.80 (d, J = 1.2 Hz, 1H), 7.61 (dd, J = 1.6 Hz, J = 8.4 Hz, 1H), 6.36 (s, 1H), 5.60-5.62 (d, J = 8.0 Hz, 1H), 5.29 (s, 1H), 4.13-4.18 (m, 1H), 3.97-4.00 (m, 2H), 3.81 (d, J = 6.8 Hz, 2H), 3.49-3.56 (m, 2H), 3.27 (s, 3H), 3.17 (s, 2H), 2.63 (s, 3H), 1.97-2.00 (m, 1H), 1.48-1.57 (m, 4H), 1.31-1.38 (m, 3H), 1.23 (s, 6H), 0.97-1.00 (m, 3H), 0.57-0.64 (m, 2H). MS: 614.4 $(M + 1)^+$. |
| 17/110 | 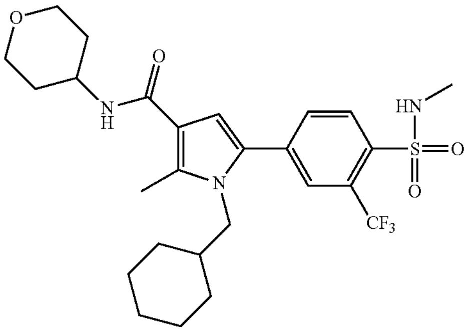 [SMILES: CNS(=O)(=O)c1ccc(-c2cc(C(=O)NC3CCOCC3)c(C)n2CC2CCCCC2)cc1C(F)(F)F] | $^1$H-NMR (300 MHz, $CDCl_3$) δ: 0.60-0.68 (2H, m), 1.00-1.04 (3H, m), 1.27-1.61 (9H, m), 1.98-2.02 (2H, m), 2.65 (3H, s), 2.74 (3H, d, J = 5.1 Hz), 3.54 (2H, dt), 3.83 (2H, d, J = 7.2 Hz), 3.99-4.02 (2H, m), 4.13-4.23 (1H, m), 4.64-4.69 (1H, m), 5.63 (1H, d, J = 2.1 Hz), 6.38 (1H, s), 7.65 (1H, d, J = 8.1 Hz), 7.85 (1H, s), 8.26 (1H, d, J = 8.1 Hz). MS: 542.2 $(M + 1)^+$. |
| 17/111 | 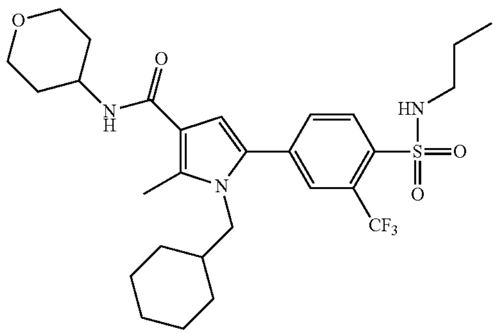 [SMILES: CCCNS(=O)(=O)c1ccc(-c2cc(C(=O)NC3CCOCC3)c(C)n2CC2CCCCC2)cc1C(F)(F)F] | $^1$H-NMR (300 MHz, $CDCl_3$) δ: 0.57-0.69 (2H, m), 0.87 (t, 3H, J = 7.5 Hz), 1.02 (3H, br s), 1.23-1.57 (10H, d), 1.96-2.02 (2H, m), 2.64 (3H, s), 3.00 (q, 2H, J = 6.6 Hz), 3.53 (2H, t, J = 11.1 Hz), 3.82 (2H, d, J = 7.2 Hz), 3.98-4.03 (2H, m), 4.11-4.22 (1H, m), 4.78 (1H, t, J = 5.9 Hz), 5.68 (1H, d, J = 8.1 Hz), 6.39 (1H, s), 7.64 (1H, d, J = 8.1 Hz), 7.83 (1H, s), 8.24 (1H, d, J = 8.1 Hz). MS: 570.3 $[M + 1]^+$. |

-continued

| # | Structure | Analytical data |
|---|---|---|
| 17/112 | 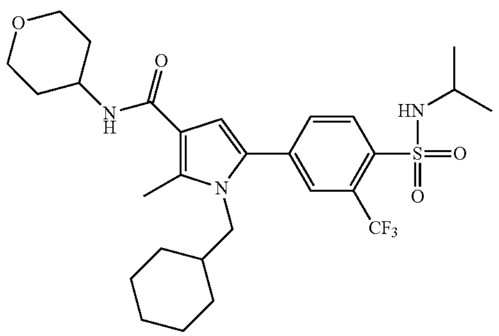 [SMILES: Cc1c(C(=O)NC2CCOCC2)cc(-c2ccc(S(=O)(=O)NC(C)C)c(C(F)(F)F)c2)n1CC1CCCCC1] | $^1$H-NMR (300 MHz, $CDCl_3$) δ: 0.57-0.69 (2H, m), 0.98.101 (3H, m), 1.10 (6H, d, J = 8.1 Hz), 1.32-1.40 (3H, m), 1.48-1.62 (5H, m), 1.97-2.02 (2H, m), 2.65 (3H, s), 3.50-3.63 (3H, m), 3.82 (2H, d, J = 7.2 Hz), 3.98-4.03 (2H, m), 4.13-4.23 (1H, m), 4.53-4.55 (2H, m), 5.64 (1H, d, J = 7.8 Hz), 6.39 (1H, s), 7.64 (1H, dd, J = 8.4, 1.5 Hz), 7.84 (1H, d, J = 1.2 Hz), 8.29 (1H, d, J = 8.4 Hz). MS: 570.3 $[M + 1]^+$. |
| 17/113 | 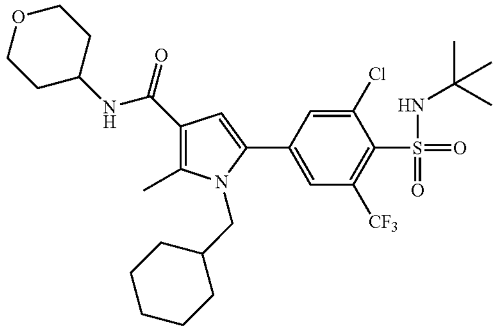 [SMILES: Cc1c(C(=O)NC2CCOCC2)cc(-c2cc(Cl)c(S(=O)(=O)NC(C)(C)C)c(C(F)(F)F)c2)n1CC1CCCCC1] | $^1$H-NMR (300 MHz, $CDCl_3$) δ: 0.65-0.69 (2H, m), 1.03 (3H, br s), 1.26 (9H, s), 1.33-1.37 (3H, m), 1.48-1.61 (7H, m), 2.00 (2H, dd, J = 12.6, 2.1 Hz), 2.64 (3H, s), 3.53 (2H, dt, J = 11.6, 1.8 Hz), 3.83 (2H, d, J = 7.2 Hz), 3.99-4.03 (2H, m), 4.16-4.19 (1H, m), 5.52 (1H, s), 5.63 (1H, d, J = 7.8 Hz), 6.43 (1H, s), 7.71 (1H, d, J = 1.8 Hz), 7.82 (1H, d, J = 1.5 Hz). MS: 618.3 $[M + 1]^+$. |
| 17/114 | 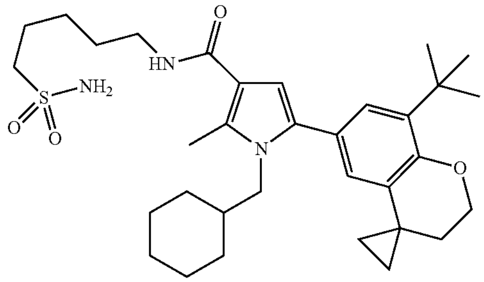 [SMILES: Cc1c(C(=O)NCCCCCS(N)(=O)=O)cc(-c2cc(C(C)(C)C)c3c(c2)C2(CCO3)CC2)n1CC1CCCCC1] | $^1$H-NMR (400 MHz, $CDCl_3$) δ: 6.97 (d, 1H), 6.43 (d, 1H), 6.06 (s, 1H), 5.79 (br s, 1H), 4.88 (s, 2H), 4.33 (t, 2H), 3.63 (d, 2H), 3.40-3.44 (m, 2H), 3.13 (t, 2H), 2.58 (s, 3H), 1.99-1.89 (m, 4H), 1.63-1.56 (m, 7H), 1.45-1.32 (m, 12H), 1.04-1.00 (m, 5H), 0.87-0.84 (m, 2H), 0.72-0.65 (m, 2H). MS: 584.3 $[M + 1]^+$. |
| 17/115 | 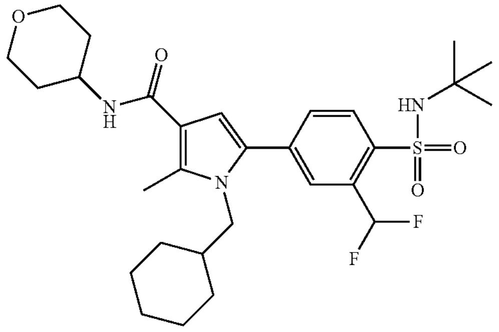 [SMILES: Cc1c(C(=O)NC2CCOCC2)cc(-c2ccc(S(=O)(=O)NC(C)(C)C)c(C(F)F)c2)n1CC1CCCCC1] | $^1$H-NMR (400 MHz, DMSO-$d_6$) δ: 8.03 (d, 1H), 7.95 (s, 1H), 7.82-7.69 (m, 3H), 7.57-7.55 (m, 1H), 6.86 (s, 1H), 3.94-3.85 (m 5H), 3.38-3.30 (m, 2H), 2.55 (s, 1H), 1.72-1.69 (m, 2H), 1.54-1.45 (m, 5H), 1.24-1.20 (m, 3H), 1.10 (s, 9H), 0.93-0.87 (m, 3H), 0.66-0.59 (m, 2H). MS: 566.2 $[M + 1]^+$. |

-continued

| # | Structure | Analytical data |
|---|---|---|
| 17/116 | 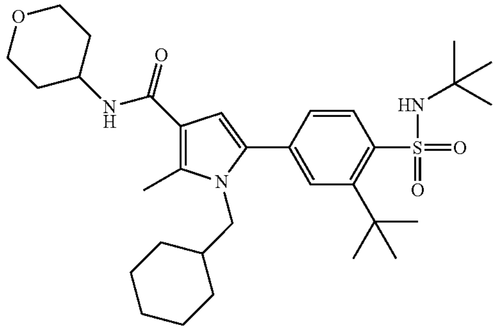 | $^1$H-NMR (400 MHz, $CDCl_3$) δ: 8.20 (d, 1H), 7.61 (d, 1H), 7.34 (d, 1H), 7.29 (d, 1H), 6.42 (d, 1H), 5.65 (d, 1H), 4.51 (s, 1H), 4.21-4.17 (m, 1H), 4.00-3.97 (m, 1H), 3.76 (d, 2H), 3.56-3.49 (m, 2H), 2.01-1.98 (m, 2H), 1.62-1.44 (m, 16H), 1.31 (s, 9H), 1.07-1.05 (m, 3H), 0.80-0.75 (m, 2H). MS: 558.3 $[M + 1]^+$. |
| 17/117 | 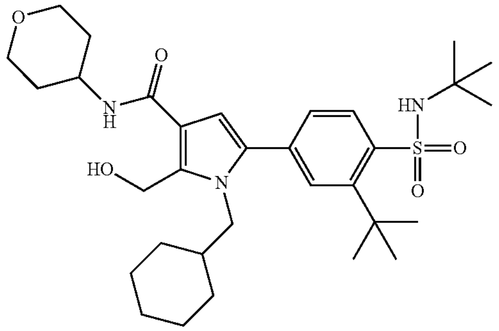 [SMILES: CC(C)(C)NS(=O)(=O)c1ccc(-c2cc(C(=O)NC3CCOCC3)c(CO)n2CC2CCCCC2)cc1C(C)(C)C] | $^1$H-NMR (400 MHz, $CDCl_3$) δ: 8.21 (d, J = 8.0 Hz, 1H), 7.58 (d, J = 1.6 Hz, 1H), 7.25 (dd, J = 8.0 Hz, J = 1.6 Hz, 1H), 6.30 (s, 1H), 5.85 (d, J = 8.0 Hz, 1H), 4.73 (s, 2H), 4.58 (s, 1H), 4.21-4.14 (m, 1H), 4.00 (dd, J = 10.0 Hz, J = 2.0 Hz, 2H), 3.83 (d, J = 7.2 Hz, 2H), 3.53 (td, 2H), 2.02 (dd, J = 12.4 Hz, J = 2.0 Hz, 2H), 1.62-1.52 (m, 14H), 1.38-1.36 (m, 12H), 1.04-0.96 (m, 3H), 0.65-0.56 (m, 2H). MS: 570.3 ($[M - OH]^+$). |
| 17/118 | 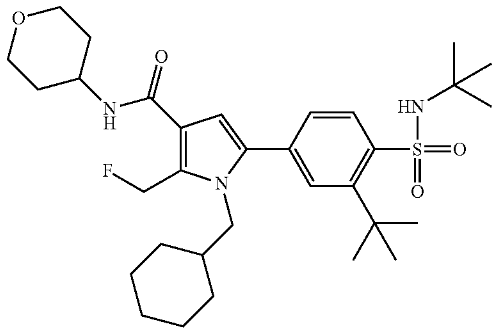 | $^1$H-NMR (400 MHz, $CDCl_3$) δ: 8.17 (d, J = 8.4 Hz, 1H), 7.57 (s, 1H), 7.23 (d, J = 8.4 Hz, 1H), 6.45 (s, 1H), 6.35 (d, J = 7.6 Hz, 1H), 5.03 (s, 2H), 4.56 (s, 1H), 4.19-4.17 (m, 1H), 3.97 (d, J = 11.6 Hz, 2H), 3.83 (d, J = 6.8 Hz, 2H), 3.54 (t, J = 11.2 Hz, 2H), 1.98 (d, J = 12.0 Hz, 2H), 1.62-1.49 (m, 14H), 1.30-1.22 (m, 12H), 0.93-0.88 (m, 3H), 0.59-0.53 (m, 2H). MS: 570.2 ($[M - F]^+$). |
| 17/119 | 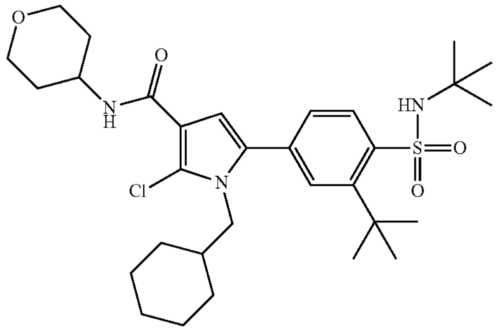 | $^1$H-NMR (400 MHz, $CDCl_3$) δ: 8.21 (d, J = 8.4 Hz, 1H), 7.59 (d, J = 1.6 Hz, 1H), 7.28-7.25 (m, 1H), 6.68 (s, 1H), 6.21 (d, J = 8.0 Hz, 1H), 4.55 (s, 1H), 4.24-4.21 (m, 1H), 4.01-3.98 (m, 2H), 3.87 (d, J = 7.2 Hz, 2H), 3.55 (td, J = 11.6 Hz, J = 1.6 Hz, 2H), 2.04-2.01 (d, 2H), 1.61-1.54 (s, 13H), 1.48-1.25 (m, 13H), 0.99 (br s, 3H), 0.69-0.64 (m, 2H). MS: 592.3 $[M + 1]^+$. |

-continued

| # | Structure | Analytical data |
|---|---|---|
| 17/120 | 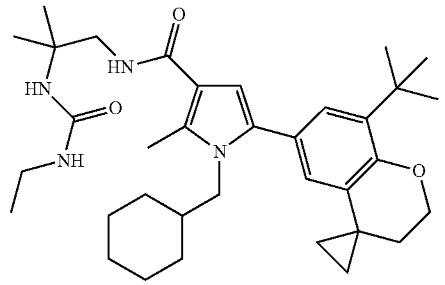 [SMILES: CCNC(=O)NC(C)(C)CNC(=O)c1cc(-c2cc(C(C)(C)C)c3c(c2)C2(CCO3)CC2)n(CC2CCCCC2)c1C] | $^1$H-NMR (400 MHz, $CD_3OD$) δ: 6.96 (d, 1H, J = 1.6 Hz), 6.48 (d, 1H, J = 2.0 Hz), 6.29 (s, 1H), 4.30 (t, 2H), 3.71 (d, 2H, J = 7.6 Hz), 3.42 (s, 2H), 3.08 (q, 2H), 2.52 (s, 3H), 1.88 (t, 2H), 1.57-1.54 (m, 3H), 1.37-1.27 (m, 18H), 1.07-0.98 (m, 8H), 0.86 (dd, 2H), 0.72-0.67 (m, 2H). MS: 577.5 $[M + 1]^+$. |
| 17/121 | 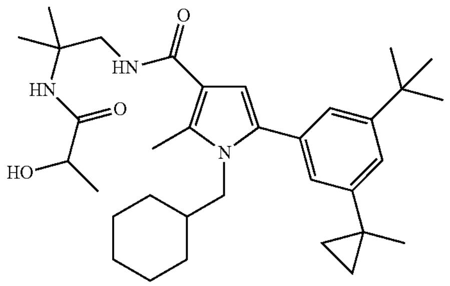 [SMILES: Cc1c(C(=O)NCC(C)(C)NC(=O)C(C)O)cc(-c2cc(C(C)(C)C)cc(C3(C)CC3)c2)n1CC1CCCCC1] | $^1$H-NMR (400 MHz, $CDCl_3$) δ: 7.57 (br s, 1H), 7.27 (d, 1H), 7.13 (t, 1H), 7.01 (t, 1H), 6.88 (t, 1H), 6.25 (s, 1H), 4.15 (q, 1H), 3.71 (d, 2H, J = 7.2 Hz), 3.54-3.41 (m, 2H), 2.59 (s, 3H), 1.55-1.53 (m, 3H), 1.42-1.30 (m, 24H), 1.03 (br s, 3H), 0.88-0.86 (m, 2H), 0.76-0.73 (m, 2H), 0.68-0.62 (m, 2H). MS: 550.4 $[M + 1]^+$. |
| 17/122 | 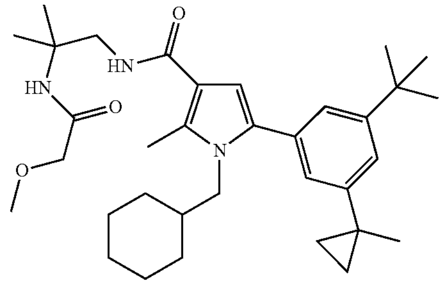 [SMILES: COCC(=O)NC(C)(C)CNC(=O)c1cc(-c2cc(C(C)(C)C)cc(C3(C)CC3)c2)n(CC2CCCCC2)c1C] | $^1$H-NMR (400 MHz, $CDCl_3$) δ: 7.26 (s, 1H), 7.13 (s, 1H), 7.01-6.95 (m, 3H), 6.27 (s, 1H), 3.81 (s, 2H), 3.70 (d, 2H, J = 6.8 Hz), 3.59 (d, 2H, J = 6.0 Hz), 3.40 (s, 3H), 2.62 (s, 3H), 1.58-1.52 (m, 3H), 1.47-1.24 (m, 21H), 1.00 (br s, 3H), 0.88-0.84 (m, 2H), 0.75-0.72 (m, 2H), 0.66-0.62 (m, 2H). MS: 550.4 $[M + 1]^+$. |
| 17/123 | 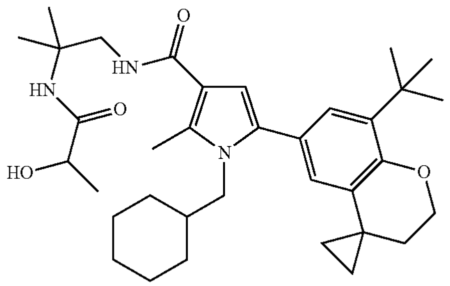 [SMILES: Cc1c(C(=O)NCC(C)(C)NC(=O)C(C)O)cc(-c2cc(C(C)(C)C)c3c(c2)C2(CCO3)CC2)n1CC1CCCCC1] | $^1$H-NMR (400 MHz, $CD_3OD$) δ: 6.87 (d, 1H), 6.39 (d, 1H), 6.20 (s, 1H), 4.22 (t, 2H), 3.96-3.91 (m, 1H), 3.62 (d, 2H), 3.37 (q, 2H), 2.44 (s, 3H), 1.80 (t, 3H), 1.49-1.46 (m, 3H), 1.33-1.19 (m, 23H), 1.00-0.86 (m, 5H), 0.80-0.77 (m, 2H), 0.66-0.62 (m, 2H). MS: 578.4 $[M + 1]^+$. |
| 17/124 | 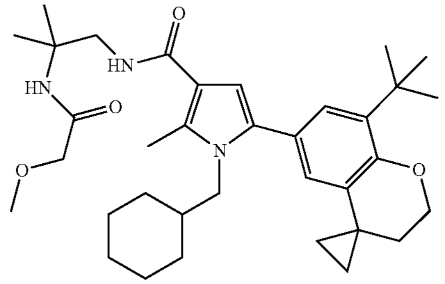 [SMILES: COCC(=O)NC(C)(C)CNC(=O)c1cc(-c2cc(C(C)(C)C)c3c(c2)C2(CCO3)CC2)n(CC2CCCCC2)c1C] | $^1$H-NMR (400 MHz, $CD_3OD$) δ: 6.88 (d, 1H), 6.39 (d, 1H), 6.21 (s, 1H), 4.22 (t, 2H), 3.68 (s, 2H), 3.62 (d, 2H), 3.33 (s, 2H), 3.28 (s, 3H), 2.45 (s, 3H), 1.79 (t, 3H), 1.48-1.46 (m, 3H), 1.32-1.19 (m, 21H), 0.97-0.90 (m, 5H), 0.80-0.77 (m, 2H), 0.66-0.62 (m, 2H). MS: 578.4 $[M + 1]^+$. |

-continued

| # | Structure | Analytical data |
|---|---|---|
| 17/125 | 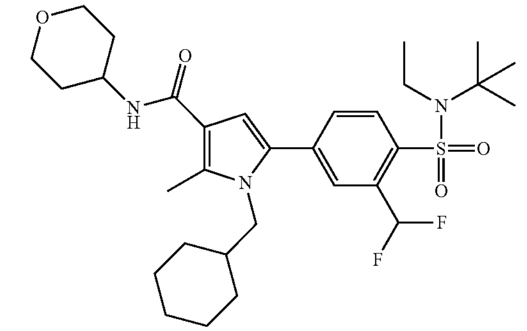 [SMILES: CCN(C(C)(C)C)S(=O)(=O)c1ccc(-c2cc(C(=O)NC3CCOCC3)c(C)n2CC2CCCCC2)cc1C(F)F] | $^1$H-NMR (400 MHz, DMSO-$d_6$) δ: 7.92 (d, 1H), 7.81-7.78 (m, 2H), 7.59 (t, 1H, J = 55.2 Hz), 7.57 (d, 1H, J = 8.0 Hz), 6.86 (s, 1H), 3.94-3.85 (m, 5H), 3.54 (q, 2H), 3.36 (t, 2H), 2.58 (s, 3H), 1.72-1.69 (m, 2H), 1.54-1.45 (m, 5H), 1.33 (s, 9H), 1.29-1.20 (m, 6H), 0.94-0.86 (m, 3H), 0.67-0.61 (m, 2H). MS: 594.3 $[M + 1]^+$. |
| 17/126 | 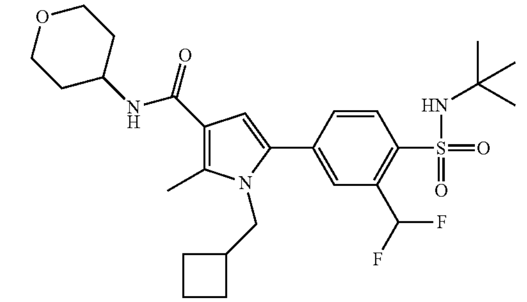 [SMILES: Cc1c(C(=O)NC2CCOCC2)cc(-c2ccc(S(=O)(=O)NC(C)(C)C)c(C(F)F)c2)n1CC1CCC1] | $^1$H-NMR (400 MHz, DMSO-$d_6$) δ: 8.04 (d, 1H), 7.96 (s, 1H), 7.82-7.55 (m, 4H), 6.84 (s, 1H), 4.07 (d, 2H), 3.94-3.84 (m, 3H), 3.35 (dd, 2H), 2.55 (s, 3H), 2.32-2.28 (m, 1H), 1.74-1.24 (m, 10H), 1.11 (s, 9H). MS: 538.2 $[M + 1]^+$. |
| 17/127 | 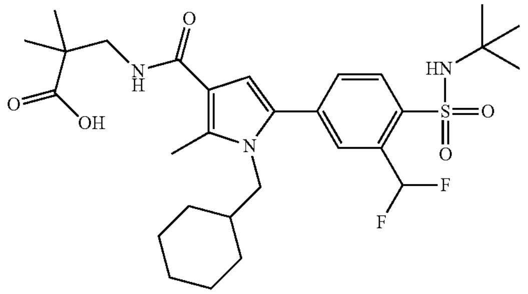 [SMILES: Cc1c(C(=O)NCC(C)(C)C(=O)O)cc(-c2ccc(S(=O)(=O)NC(C)(C)C)c(C(F)F)c2)n1CC1CCCCC1] | $^1$H-NMR (400 MHz, DMSO-$d_6$) δ: 8.03 (d, 1H), 7.93 (s, 1H), 7.82-7.53 (m, 4H), 6.83 (s, 1H), 3.89 (d, 2H), 3.36 (d, 2H), 2.54 (s, 3H), 1.47-1.45 (m, 3H), 1.24-1.21 (m, 3H), 1.10-1.09 (m, 15H), 0.93-0.85 (m, 3H), 0.66-0.60 (m, 2H). MS: 582.2 $[M + 1]^+$. |
| 17/128 | 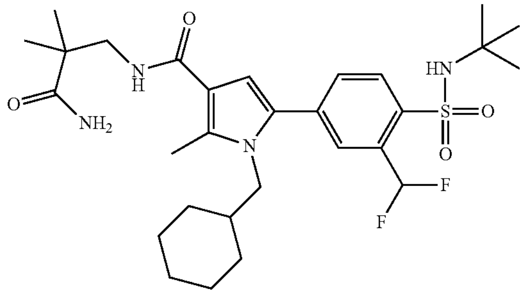 [SMILES: Cc1c(C(=O)NCC(C)(C)C(N)=O)cc(-c2ccc(S(=O)(=O)NC(C)(C)C)c(C(F)F)c2)n1CC1CCCCC1] | $^1$H-NMR (400 MHz, DMSO-$d_6$) δ: 8.02 (d, 1H), 7.95 (s, 1H), 7.82-7.56 (m, 3H), 7.48 (t, 1H), 7.19 (br s, 1H), 6.85 (br s, 1H), 6.78 (s, 1H), 3.89 (d, 2H), 3.31 (d, 2H), 2.54 (s, 3H), 1.47-1.45 (m, 3H), 1.28-1.21 (m, 3H), 1.10 (s, 9H), 1.07 (m, 6H), 0.93-0.86 (m, 3H), 0.66-0.59 (m, 2H). MS: 581.3 $[M + 1]^+$. |
| 17/129 | 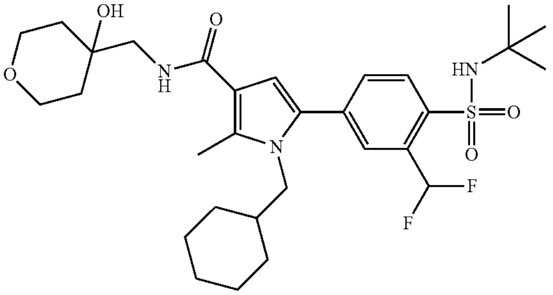 [SMILES: Cc1c(C(=O)NCC2(O)CCOCC2)cc(-c2ccc(S(=O)(=O)NC(C)(C)C)c(C(F)F)c2)n1CC1CCCCC1] | $^1$H-NMR (400 MHz, DMSO-$d_6$) δ: 8.03 (m, 1H), 7.94 (s, 1H), 7.81-7.55 (m, 4H), 6.86 (s, 1H), 3.90 (d, 2H), 3.60 (dd, 4H), 3.22 (d, 2H), 2.55 (s, 3H), 1.58-1.45 (m, 5H), 1.38-1.35 (m, 2H), 1.28-1.21 (m, 3H), 1.10 (s, 9H), 0.93-0.85 (m, 3H), 0.67-0.59 (m, 2H). MS: 596.3 $[M + 1]^+$. |

-continued

| # | Structure | Analytical data |
|---|---|---|
| 17/130 | 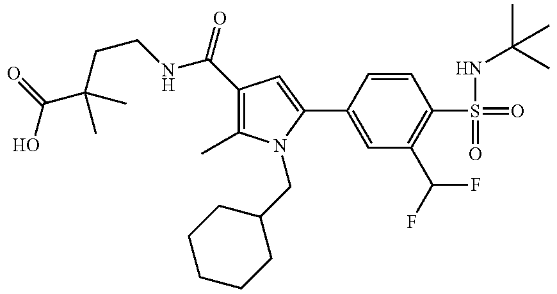 [SMILES: Cc1c(C(=O)NCCC(C)(C)C(=O)O)cc(-c2ccc(S(=O)(=O)NC(C)(C)C)c(C(F)F)c2)n1CC1CCCCC1] | $^1$H-NMR (400 MHz, DMSO-d$_6$) δ: 8.02 (d, 1H), 7.93 (s, 1H), 7.82-7.55 (m, 4H), 6.79 (s, 1H), 3.89 (d, 2H, J = 6.8 Hz), 3.19-3.15 (m, 2H), 2.54 (s, 3H), 1.72-1.68 (m, 2H), 1.47-1.44 (m, 3H), 1.23-1.20 (m, 3H), 1.13 (s, 6H), 1.10 (s, 9H), 0.94-0.87 (m, 3H), 0.66-0.60 (m, 2H). MS: 596.3 [M + 1]$^+$. |
| 17/131 | 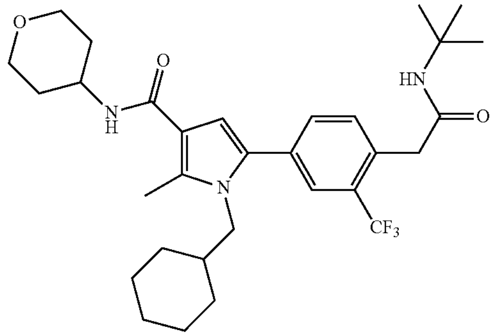 [SMILES: Cc1c(C(=O)NC2CCOCC2)cc(-c2ccc(CC(=O)NC(C)(C)C)c(C(F)(F)F)c2)n1CC1CCCCC1] | $^1$H-NMR (CDCl$_3$, 400 MHz) δ: 7.62 (s, 1H), 7.47-7.53 (m, 1H), 6.23 (s, 1H), 5.61 (d, J = 7.6 Hz, 1H), 5.22 (s, 1H), 4.14-4.19 (m, 1H), 3.98 (d, J = 10.4 Hz, 2H), 3.76 (d, J = 7.2 Hz, 2H), 3.66 (s, 2H), 3.52 (t, J = 10.0 Hz, 2H), 2.62 (s, 3H), 1.96-2.00 (m, 2H), 1.47-1.59 (m, 5H), 1.31-1.43 (m, 12H), 0.96-1.03 (m, 3H), 0.61-0.67 (m, 2H). MS: 562.3 (M + 1)$^+$. |
| 17/132 | 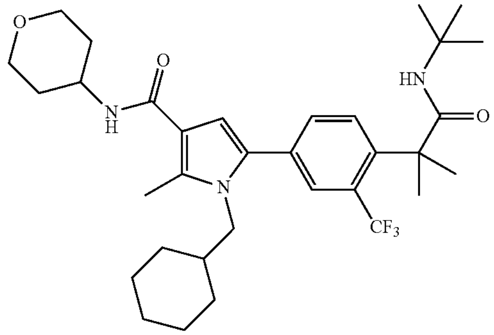 [SMILES: Cc1c(C(=O)NC2CCOCC2)cc(-c2ccc(C(C)(C)C(=O)NC(C)(C)C)c(C(F)(F)F)c2)n1CC1CCCCC1] | $^1$H-NMR (CDCl$_3$, 400 MHz) δ: 7.65-7.70 (m, 2H), 7.51 (d, J = 7.6 Hz, 1H), 6.28 (s, 1H), 5.61 (d, J = 8.0 Hz, 1H), 4.74 (s, 1H), 4.15-4.19 (m, 1H), 3.98 (d, J = 12.0 Hz, 2H), 3.78 (d, J = 6.8 Hz, 2H), 3.52 (t, J = 11.2 Hz, 2H), 2.63 (s, 3H), 1.99 (d, J = 11.2 Hz, 1H), 1.64 (s, 6H), 1.47-1.58 (m, 5H), 1.34-1.39 (m, 3H), 1.25 (s, 9H), 0.98-1.03 (m, 3H), 0.61-0.67 (m, 3H). MS: 590.3 (M + 1)$^+$. |
| 17/133 | 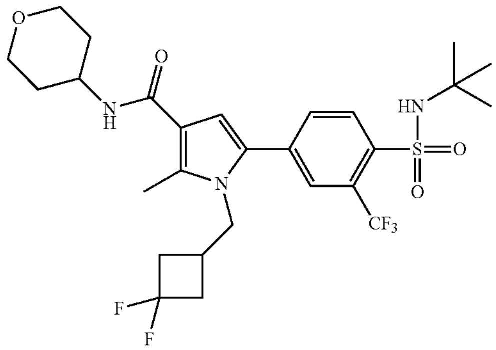 [SMILES: Cc1c(C(=O)NC2CCOCC2)cc(-c2ccc(S(=O)(=O)NC(C)(C)C)c(C(F)(F)F)c2)n1CC1CC(F)(F)C1] | $^1$H-NMR (CDCl$_3$, 400 MHz) δ: 0.79-0.88 (m, 2H), 1.26 (s, 9H), 1.49-1.58 (m, 2H), 1.89-2.00 (m, 4H), 2.17-2.26 (m, 1H), 2.40-2.51 (m, 2H), 2.66 (s, 3H), 3.52 (t, J = 12.0 Hz, 2H), 3.99 (d, J = 12.0 Hz, 2H), 4.13-4.15 (m, 3H), 4.71 (s, 1H), 5.62 (d, J = 8.0 Hz, 1H), 6.39 (s, 1H), 7.62 (d, J = 8.4 Hz, 1H), 7.80 (s, 1H), 8.35 (d, J = 8.4 Hz, 1H). MS: 592.2 (M + 1)$^+$. |

-continued

| # | Structure | Analytical data |
|---|---|---|
| 17/134 | 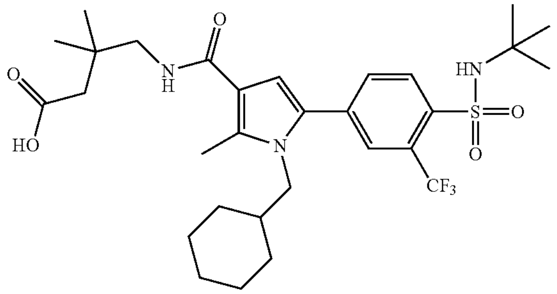 [SMILES: Cc1c(C(=O)NCC(C)(C)CC(=O)O)cc(-c2ccc(S(=O)(=O)NC(C)(C)C)c(C(F)(F)F)c2)n1CC1CCCCC1] | $^1$H-NMR (400 MHz, $CDCl_3$) δ: 8.33 (d, 1H, J = 8.4 Hz), 7.80 (s, 1H), 7.63 (d, 1H, J = 8.4 Hz), 6.42 (s, 1H), 6.37 (t, 1H), 4.74 (s, 1H), 3.81 (d, 2H, J = 6.8 Hz), 3.33 (d, 2H, J = 6.4 Hz), 2.63 (s, 3H), 2.31 (s, 2H), 1.58-1.56 (m, 3H), 1.35-1.32 (m, 3H), 1.26 (s, 9H), 1.10-1.01 (m, 9H), 0.67-0.60 (m, 2H). MS: 614.3 $(M + 1)^+$. |
| 17/135 | 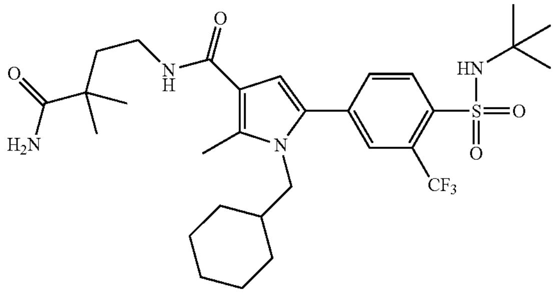 [SMILES: Cc1c(C(=O)NCCC(C)(C)C(N)=O)cc(-c2ccc(S(=O)(=O)NC(C)(C)C)c(C(F)(F)F)c2)n1CC1CCCCC1] | $^1$H-NMR (400 MHz, $CDCl_3$) δ: 8.31 (d, 1H, J = 8.4 Hz), 7.79 (s, 1H), 7.61 (d, 1H, J = 8.4 Hz), 6.89 (s, 1H), 6.39 (s, 1H), 6.30-6.24 (m, 2H), 4.72 (s, 1H), 3.79 (d, 2H, J = 6.8 Hz), 3.45-3.44 (m, 2H), 2.61 (s, 3H), 1.90 (t, 2H), 1.57-1.52 (m, 3H), 1.33-1.27 (m, 18H), 0.99 (s, 3H), 0.64-0.58 (m, 2H). MS: 613.3 $(M + 1)^+$. |
| 17/136 | 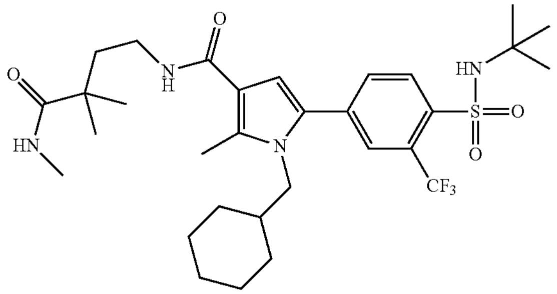 [SMILES: CNC(=O)C(C)(C)CCNC(=O)c1cc(-c2ccc(S(=O)(=O)NC(C)(C)C)c(C(F)(F)F)c2)n(CC2CCCCC2)c1C] | $^1$H-NMR (400 MHz, DMSO-$d_6$) δ: 8.23 (d, 1H, J = 8.4 Hz), 7.91 (d, 1H, J = 8.8 Hz), 7.84 (m, 2H), 7.66 (t, 1H), 7.51 (d, 1H), 6.81 (s, 1H), 3.90 (d, 2H, J = 6.8 Hz), 3.11-3.06 (m, 2H), 2.57 (d, 3H, J = 4.4 Hz), 2.54 (s, 3H), 1.68-1.64 (m, 2H), 1.47-1.45 (m, 3H), 1.23-1.20 (m, 3H), 1.15 (s, 9H), 1.10 (s, 6H), 0.92-0.84 (m, 3H), 0.68-0.60 (m, 2H). MS: 627.3 $(M + 1)^+$. |
| 17/137 | 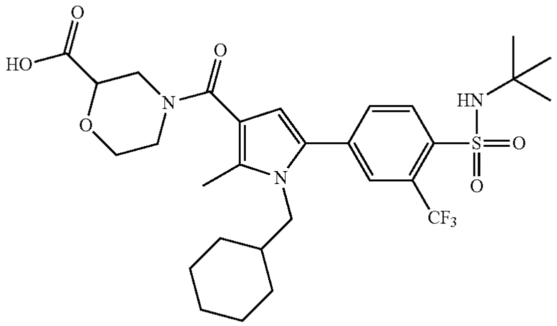 [SMILES: Cc1c(C(=O)N2CCOC(C(=O)O)C2)cc(-c2ccc(S(=O)(=O)NC(C)(C)C)c(C(F)(F)F)c2)n1CC1CCCCC1] | $^1$H-NMR (400 MHz, $CDCl_3$) δ: 8.31 (d, 1H, J = 8.4 Hz), 7.80 (s, 1H), 7.62 (d, 1H, J = 8.4 Hz), 6.29 (s, 1H), 4.72 (s, 1H), 4.55-4.50 (m, 1H), 4.29-4.24 (m, 1H), 4.16-4.09 (m, 2H), 3.80 (d, 2H, J = 7.2 Hz), 3.74-3.69 (m, 1H), 3.29-3.26 (m, 2H), 2.41 (s, 3H), 1.55 (br s, 3H), 1.34-1.32 (m, 3H), 1.27 (s, 9H), 1.00 (br s, 3H), 0.65-0.61 (m, 2H). MS: 614.2 $(M + 1)^+$. |
| 17/138 | 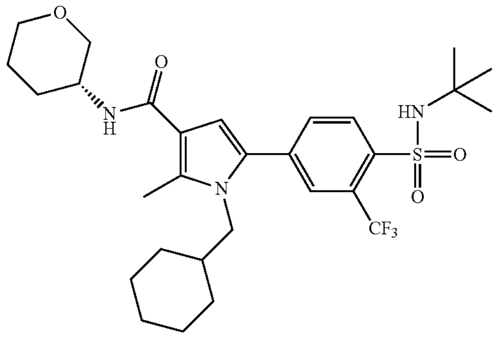 [SMILES: Cc1c(C(=O)N[C@@H]2CCCOC2)cc(-c2ccc(S(=O)(=O)NC(C)(C)C)c(C(F)(F)F)c2)n1CC1CCCCC1] | $^1$H-NMR (400 MHz, $CDCl_3$) δ: 8.32 (d, 1H, J = 8.0 Hz), 7.81 (s, 1H), 7.62 (d, 1H, J = 8.0 Hz), 6.42 (s, 1H), 6.16 (d, 1H, J = 8.8 Hz), 4.72 (s, 1H), 4.17 (br s, 1H), 3.84-3.74 (m, 4H), 3.66-3.57 (m, 2H), 2.62 (s, 3H), 1.91-1.81 (m, 3H), 1.62-1.55 (m, 4H), 1.37-1.31 (m, 3H), 1.26 (s, 9H), 1.00 (br s, 3H), 0.64-0.58 (m, 2H). MS: 584.2 $(M + 1)^+$. |

-continued

| # | Structure | Analytical data |
|---|---|---|
| 17/139 | 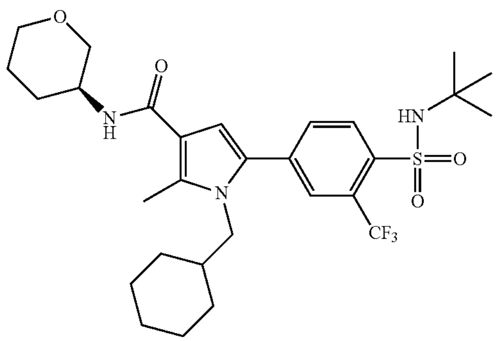 [SMILES: Cc1c(C(=O)N[C@H]2CCCOC2)cc(-c2ccc(S(=O)(=O)NC(C)(C)C)c(C(F)(F)F)c2)n1CC1CCCCC1] | $^1$H-NMR (400 MHz, $CDCl_3$) δ: 8.32 (d, 1H, J = 8.0 Hz), 7.81 (s, 1H), 7.62 (d, 1H, J = 8.0 Hz), 6.42 (s, 1H), 6.18 (d, 1H, J = 8.8 Hz), 4.71 (s, 1H), 4.17 (br s, 1H), 3.84-3.74 (m, 4H), 3.65-3.58 (m, 2H), 2.62 (s, 3H), 1.91-1.81 (m, 3H), 1.62-1.55 (m, 4H), 1.37-1.31 (m, 3H), 1.26 (s, 9H), 1.00-0.96 (m, 3H), 0.67-0.59 (m, 2H). MS: 584.2 $(M + 1)^+$. |
| 17/140 | 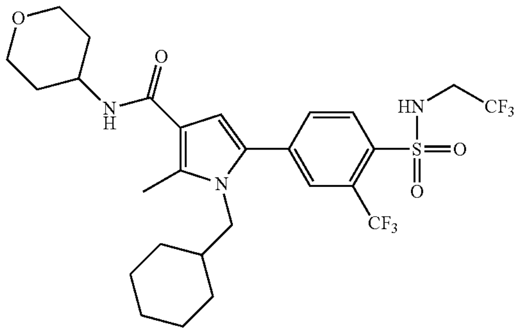 [SMILES: Cc1c(C(=O)NC2CCOCC2)cc(-c2ccc(S(=O)(=O)NCC(F)(F)F)c(C(F)(F)F)c2)n1CC1CCCCC1] | $^1$H-NMR (400 MHz, $CD_3OD$) δ: 8.25 (d, 1H, J = 8.0 Hz), 7.94 (s, 1H), 7.83 (d, 1H, J = 8.4 Hz), 6.75 (s, 1H), 4.08-3.95 (m, 5H), 3.84 (dd, 2H), 3.53 (t, 2H), 2.60 (s, 3H), 1.90-1.87 (m, 2H), 1.70-1.58 (m, 5H), 1.36-1.33 (m, 3H), 1.06-1.02 (m, 3H), 0.73-0.67 (m, 2H). MS: 610.2 $(M + 1)^+$. |
| 17/141 | 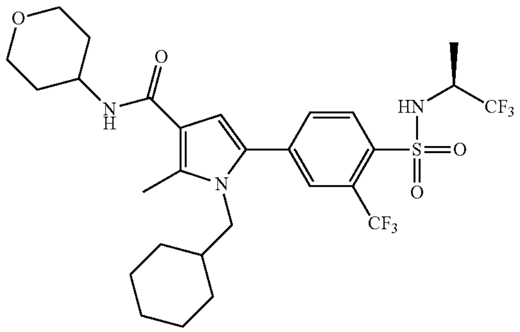 [SMILES: Cc1c(C(=O)NC2CCOCC2)cc(-c2ccc(S(=O)(=O)N[C@@H](C)C(F)(F)F)c(C(F)(F)F)c2)n1CC1CCCCC1] | $^1$H-NMR (400 MHz, DMSO-$d_6$) δ: 8.92 (d, 1H, J = 8.8 Hz), 8.20 (d, 1H, J = 8.0 Hz), 7.93 (d, 1H, J = 8.4 Hz), 7.90 (s, 1H), 7.56 (d, 1H, J = 8.0 Hz), 6.90 (s, 1H), 4.15-4.10 (m, 1H), 3.95-3.85 (m, 5H), 3.39-3.36 (m, 2H), 2.55 (s, 3H), 1.71 (dd, 2H), 1.57-1.47 (m, 5H), 1.23-1.21 (m, 6H), 0.95-0.87 (m, 3H), 0.68-0.61 (m, 2H). MS: 624.2 $(M + 1)^+$. |
| 17/142 | 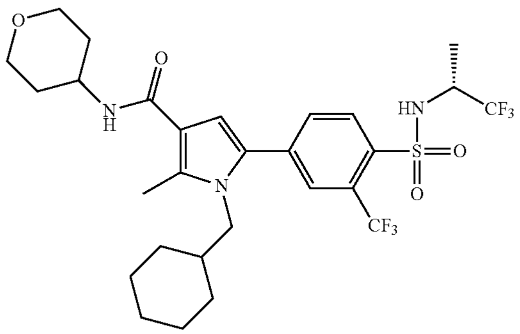 [SMILES: Cc1c(C(=O)NC2CCOCC2)cc(-c2ccc(S(=O)(=O)N[C@H](C)C(F)(F)F)c(C(F)(F)F)c2)n1CC1CCCCC1] | $^1$H-NMR (400 MHz, DMSO-$d_6$) δ: 8.92 (d, 1H, J = 8.8 Hz), 8.20 (d, 1H, J = 8.0 Hz), 7.93 (d, 1H, J = 8.4 Hz), 7.90 (s, 1H), 7.56 (d, 1H, J = 8.0 Hz), 6.90 (s, 1H), 4.15-4.10 (m, 1H), 3.95-3.85 (m, 5H), 3.93-3.36 (m, 2H), 2.55 (s, 3H), 1.71 (dd, 2H), 1.57-1.47 (m, 5H), 1.23-1.21 (m, 6H), 0.95-0.87 (m, 3H), 0.68-0.61 (m, 2H). MS: 624.2 $(M + 1)^+$. |

-continued

| # | Structure | Analytical data |
|---|---|---|
| 17/143 | 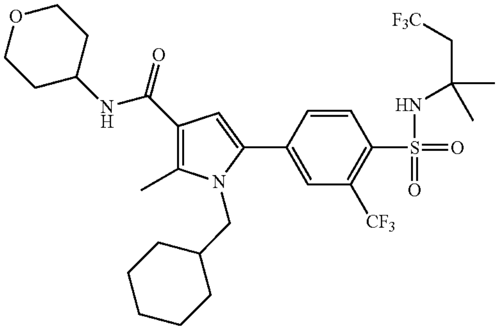 [SMILES: Cc1c(C(=O)NC2CCOCC2)cc(-c2ccc(S(=O)(=O)NC(C)(C)CC(F)(F)F)c(C(F)(F)F)c2)n1CC1CCCCC1] | $^1$H-NMR (400 MHz, $CDCl_3$) δ: 8.29 (d, 1H, J = 8.4 Hz), 7.82 (s, 1H), 7.63 (d, 1H, J = 9.6 Hz), 6.38 (s, 1H), 5.61 (d, 1H, J = 8.0 Hz), 4.89 (s, 1H), 4.19-4.15 (m, 1H), 4.00-3.98 (m, 2H), 3.81 (d, 2H, J = 9.2 Hz), 3.55-3.49 (m, 2H), 2.65-2.57 (m, 5H), 1.98 (dd, 2H), 1.58-1.48 (m, 5H), 1.36-1.31 (m, 9H), 1.00-0.99 (m, 3H), 0.66-0.60 (m, 2H). MS: 652.3 $(M + 1)^+$. |
| 17/144 | 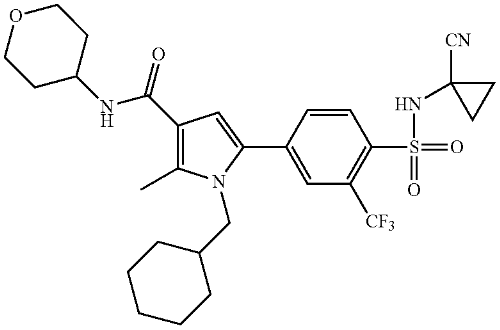 [SMILES: Cc1c(C(=O)NC2CCOCC2)cc(-c2ccc(S(=O)(=O)NC3(C#N)CC3)c(C(F)(F)F)c2)n1CC1CCCCC1] | $^1$H-NMR (400 MHz, DMSO-$d_6$) δ: 9.34 (s, 1H), 8.25 (d, 1H, J = 8.4 Hz), 7.98 (d, 1H, J = 9.2 Hz), 7.94 (s, 1H), 7.58 (d, 1H, J = 7.6 Hz), 6.92 (s, 1H), 3.97-3.85 (m, 5H), 3.36 (t, 2H), 2.56 (s, 3H), 1.72-1.70 (m, 2H), 1.57-1.45 (m, 7H), 1.32-1.19 (m, 5H), 0.93 (br s, 3H), 0.69-0.64 (m, 2H). MS: 593.3 $(M + 1)^+$. |
| 17/145 | 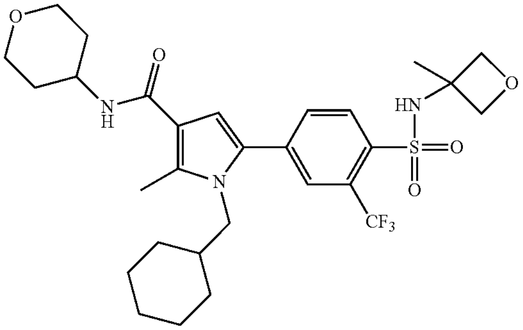 | $^1$H-NMR (400 MHz, $CDCl_3$) δ: 8.34 (br s, 1H), 8.19 (d, 1H, J = 8.4 Hz), 7.94 (d, 1H, J = 8.8 Hz), 7.90 (s, 1H), 7.56 (d, 1H, J = 8.0 Hz), 6.90 (s, 1H), 4.62 (d, 2H, J = 6.0 Hz), 4.19 (d, 2H, J = 6.4 Hz), 4.20-3.85 (m, 5H), 3.38-3.36 (m, 2H), 2.55 (s, 3H), 1.72-1.69 (m, 2H), 1.56-1.42 (m, 8H), 1.235-1.22 (m, 3H), 0.98-0.86 (m, 3H), 0.69-0.61 (m, 2H). MS: 698.3 $(M + 1)^+$. |
| 17/146 | 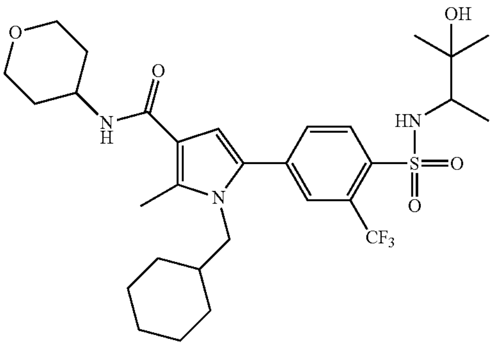 [SMILES: Cc1c(C(=O)NC2CCOCC2)cc(-c2ccc(S(=O)(=O)NC(C)C(C)(C)O)c(C(F)(F)F)c2)n1CC1CCCCC1] | $^1$H-NMR (400 MHz, DMSO-$d_6$) δ: 8.22 (d, 1H, J = 8.0 Hz), 7.92 (d, 1H, J = 8.0 Hz), 7.88 (s, 1H), 7.55 (d, 1H, J = 7.6 Hz), 7.41 (d, 1H, J = 9.2 Hz), 6.88 (s, 1H), 3.95-3.85 (m, 5H), 3.36 (t, 2H), 3.13-3.09 (m, 1H), 2.55 (s, 3H), 1.72-1.69 (m, 2H), 1.57-1.47 (m, 5H), 1.24-1.22 (m, 3H), 0.96-0.89 (m, 12H), 0.64-0.58 (m, 2H). MS: 614.3 $(M + 1)^+$. |

-continued

| # | Structure | Analytical data |
|---|---|---|
| 17/147 | 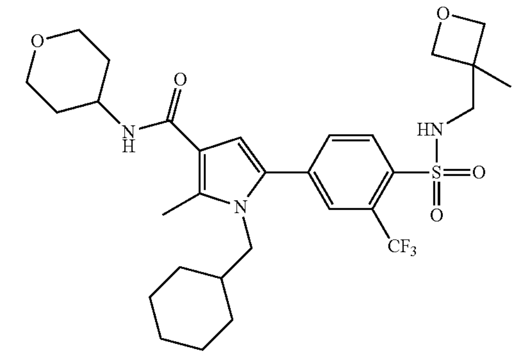 [SMILES: Cc1c(C(=O)NC2CCOCC2)cc(-c2ccc(S(=O)(=O)NCC3(C)COC3)c(C(F)(F)F)c2)n1CC1CCCCC1] | $^1$H-NMR (400 MHz, $CDCl_3$) δ: 8.26 (d, 1H, J = 8.0 Hz), 7.85 (s, 1H), 7.65 (dd, 1H, J = 8.4 Hz, J = 1.2 Hz), 6.38 (s, 1H), 5.63 (d, 1H, J = 8.0 Hz), 4.98 (m, 1H), 4.39-4.35 (m, 4H), 4.21-4.14 (m, 1H), 4.00-3.98 (m, 2H), 3.82 (d, 2H, J = 7.2 Hz), 3.53 (td, 2H), 3.22 (d, 2H, J = 6.4 Hz), 2.64 (s, 3H), 2.01-1.97 (m, 2H), 1.63-1.33 (m, 8H), 1.30 (s, 3H), 1.01-0.98 (m, 3H), 0.69-0.63 (m, 2H). MS: 612.3 $(M + 1)^+$. |
| 17/148 | 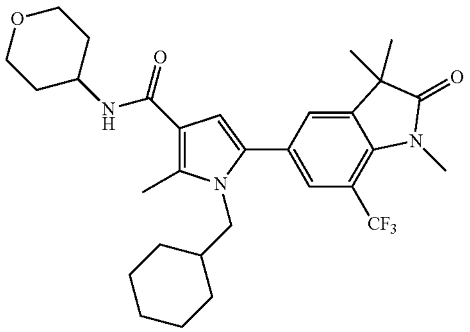 [SMILES: Cc1c(C(=O)NC2CCOCC2)cc(-c2cc(C(F)(F)F)c3c(c2)C(C)(C)C(=O)N3C)n1CC1CCCCC1] | $^1$H-NMR (400 MHz, DMSO-$d_6$) δ: 7.80 (d, J = 1.2 Hz, 1H), 7.51 (d, J = 1.2 Hz, 1H), 7.46 (d, J = 8.0 Hz, 1H), 6.67 (s, 1H), 3.95-3.80 (m, 5H), 3.78.3.35 (m, 5H), 2.54 (s, 3H), 1.71-1.67 (m, 2H), 1.57-1.47 (m, 5H), 1.34-1.25 (m, 9H), 0.97-0.91 (m, 3H), 0.71-0.63 (m, 2H). MS: 546.8 $(M + 1)^+$. |
| 17/149 | 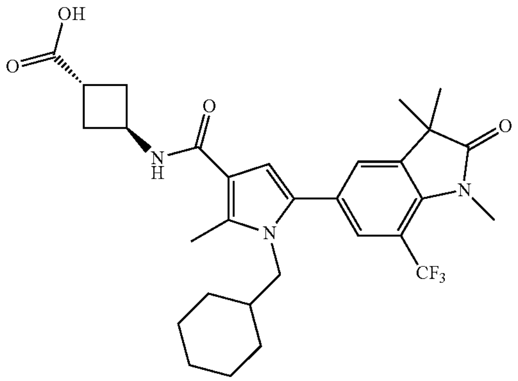 [SMILES: Cc1c(C(=O)N[C@H]2C[C@H](C(=O)O)C2)cc(-c2cc(C(F)(F)F)c3c(c2)C(C)(C)C(=O)N3C)n1CC1CCCCC1] | $^1$H-NMR (400 MHz, $CDCl_3$) δ: 7.50 (d, J = 1.2 Hz, 1H), 7.31 (d, J = 1.6 Hz, 1H), 6.22 (s, 1H), 5.97 (br s, 1H), 4.76-4.78 (m, 1H), 3.71 (d, J = 7.2 Hz, 2H), 3.46 (d, J = 2.0 Hz, 3H), 3.10-3.15 (m, 1H), 2.76-2.83 (m, 2H), 2.59 (s, 3H), 2.28-2.36 (m, 2H), 1.54-1.60 (m, 3H), 1.41 (s, 6H), 1.34-1.37 (m, 3H), 0.98-1.04 (m, 3H), 0.63-0.70 (m, 2H). MS: 560.3 $(M + 1)^+$. |
| 17/150 | 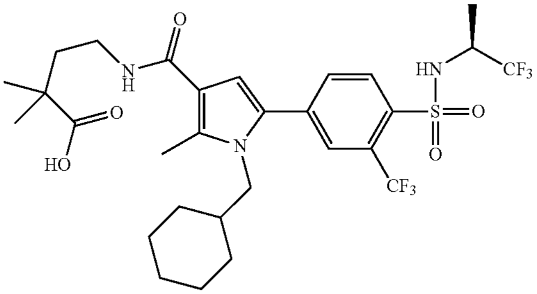 [SMILES: Cc1c(C(=O)NCCC(C)(C)C(=O)O)cc(-c2ccc(S(=O)(=O)N[C@@H](C)C(F)(F)F)c(C(F)(F)F)c2)n1CC1CCCCC1] | $^1$H-NMR (400 MHz, $CDCl_3$) δ: 8.21 (d, 1H, J = 8.4 Hz), 7.82 (s, 1H), 7.63 (d, 1H, J = 8.0 Hz), 6.39 (s, 1H), 6.12 (br s, 1H), 5.17 (d, 1H, J = 10.0 Hz), 4.14-4.06 (m, 1H), 3.80 (d, 2H, J = 7.2 Hz), 3.43 (br s, 1H), 2.60 (s, 3H), 1.86 (t, 2H), 1.56-1.54 (m, 3H), 1.38 (d, 3H, J = 6.4 Hz), 1.31-1.24 (m, 9H), 0.98 (s, 3H), 0.62-0.54 (m, 2H). MS: 654.2 $(M + 1)^+$. |

-continued

| # | Structure | Analytical data |
| --- | --- | --- |
| 17/151 | 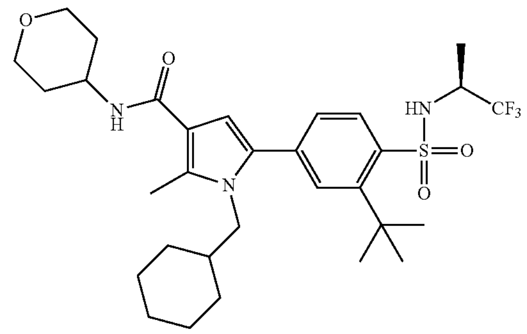 [SMILES: Cc1c(C(=O)NC2CCOCC2)cc(-c2ccc(S(=O)(=O)N[C@@H](C)C(F)(F)F)c(C(C)(C)C)c2)n1CC1CCCCC1] | $^1$H-NMR (400 MHz, $CDCl_3$) δ: 8.18 (d, 1H, J = 8.0 Hz), 7.61 (d, 1H), 7.30 (d, 1H), 6.29 (s, 1H), 5.67 (d, 1H, J = 8.0 Hz), 4.81 (d, 1H, J = 9.6 Hz), 4.19-4.16 (m, 1H), 4.05-3.98 (m, 3H), 3.78 (d, 2H, J = 7.2 Hz), 3.56-3.50 (m, 2H), 2.62 (s, 3H), 2.00-1.97 (m, 2H), 1.60-1.49 (m, 14H), 1.38-1.29 (m, 6H), 0.98 (m, 3H), 0.62-0.57 (m, 2H). MS: 612.3 $(M + 1)^+$. |
| 17/152 | 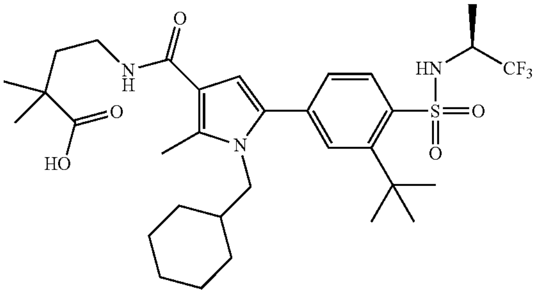 [SMILES: Cc1c(C(=O)NCCC(C)(C)C(=O)O)cc(-c2ccc(S(=O)(=O)N[C@@H](C)C(F)(F)F)c(C(C)(C)C)c2)n1CC1CCCCC1] | $^1$H-NMR (400 MHz, $CDCl_3$) δ: 8.16 (d, 1H, J = 8.4 Hz), 7.60 (d, 1H), 7.28 (d, 1H), 6.27 (s, 1H), 6.12 (br s, 1H), 5.25 (d, 1H, J = 16.0 Hz), 4.08-4.00 (m, 1H), 3.77 (d, 2H, J = 7.2 Hz), 3.43 (br s, 2H), 2.60 (s, 3H), 1.87-1.83 (m, 2H), 1.60-1.52 (m, 12H), 1.38 (d, 3H, J = 6.8 Hz), 1.33-1.21 (m, 9H), 0.97 (s, 3H), 0.63-0.58 (m, 2H). MS: 642.3 $(M + 1)^+$. |
| 17/153 | 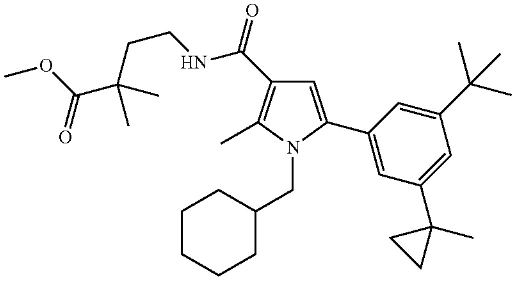 [SMILES: COC(=O)C(C)(C)CCNC(=O)c1cc(-c2cc(C(C)(C)C)cc(C3(C)CC3)c2)n(CC2CCCCC2)c1C] | $^1$H-NMR ($CDCl_3$, 400 MHz) δ: 0.60-0.67 (m, 2H), 0.73-0.76 (m, 2H), 0.86-0.88 (m, 2H), 0.96-0.99 (m, 3H), 1.24 (s, 6H), 1.27-1.40 (m, 12H), 1.42 (s, 3H), 1.49-1.59 (m, 3H), 1.86 (t, J = 7.2 Hz, 2H), 2.61 (s, 3H), 3.38-3.43 (m, 2H), 3.64 (s, 3H), 3.71 (d, J = 7.2 Hz, 2H), 5.84-5.86 (m, 1H), 6.15 (s, 1H), 7.00 (s, 1H), 7.13 (s, 1H), 7.25 (s, 1H). MS: 535.4 $(M + 1)^+$. |
| 17/154 | 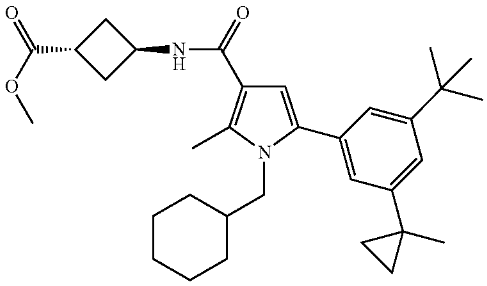 [SMILES: COC(=O)[C@H]1C[C@H](NC(=O)c2cc(-c3cc(C(C)(C)C)cc(C4(C)CC4)c3)n(CC3CCCCC3)c2C)C1] | $^1$H-NMR ($CDCl_3$, 400 MHz) δ: 0.58-0.67 (m, 2H), 0.73-0.76 (m, 2H), 0.86-0.88 (m, 2H), 0.93-0.99 (m, 3H), 1.28-1.38 (m, 12H), 1.42 (s, 3H), 1.49-1.56 (m, 3H), 2.26-2.31 (m, 2H), 2.60 (s, 3H), 2.70-2.76 (m, 2H), 3.05-3.11 (m, 1H), 3.70-3.72 (m, 5H), 4.66-4.76 (m, 1H), 5.87 (d, J = 6.8 Hz, 1H), 6.16 (s, 1H), 7.00 (s, 1H), 7.13 (s, 1H), 7.25 (s, 1H). MS: 519.3 $(M + 1)^+$. |
| 17/155 | 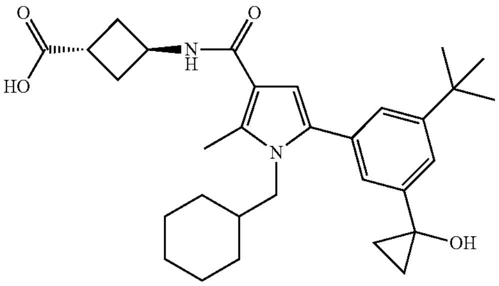 [SMILES: Cc1c(C(=O)N[C@H]2C[C@H](C(=O)O)C2)cc(-c2cc(C(C)(C)C)cc(C3(O)CC3)c2)n1CC1CCCCC1] | $^1$H-NMR (400 MHz, $CDCl_3$) δ: 7.39 (s, 1H), 7.20 (s, 1H), 7.08 (s, 1H), 6.19 (s, 1H), 5.97-6.00 (m, 1H), 4.74-4.84 (m, 1H), 3.73 (d, 2H, J = 6.8 Hz), 3.06-3.11 (m, 1H), 2.76-2.81 (m, 2H), 2.60 (s, 3H), 2.25-2.33 (m, 2H), 1.54 (d, 2H, J = 6.4 Hz), 1.43 (s, 3H), 1.32-1.35 (m, 3H), 0.99-1.06 (m, 3H), 0.87-0.90 (m, 2H), 0.75-0.77 (m, 2H), 0.59-0.68 (m, 2H). MS: 507.3 $[M + 1]^+$. |

-continued

| # | Structure | Analytical data |
|---|---|---|
| 17/156 | 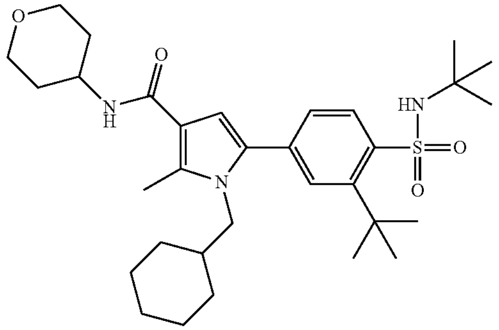 | $^1$H-NMR ($CDCl_3$, 400 MHz) δ: 0.59-0.65 (2H, m), 0.97-0.99 (3H, m), 1.23 (9H, s), 1.29-1.33 (3H, m), 1.49-1.58 (6H, m), 1.96-1.99 (2H, m), 2.62 (3H, s), 2.69 (3H, s), 3.52 (2H, dt, J = 9.6, J = 1.2 Hz), 3.80 (2H, d, J = 6.8 Hz), 3.98 (2H, d, J = 10.8 Hz), 4.11-4.21 (1H, m), 4.45 (1H, s), 5.61 (1H, d, J = 8.0 Hz), 6.27 (1H, s), 7.25 (1H, s), 8.05 (1H, d, J = 8.8 Hz). MS: 530.3 $(M + 1)^+$. |
| 17/157 | 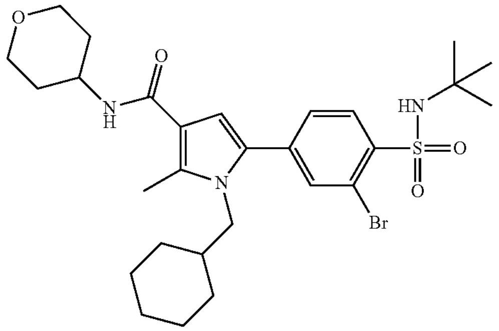 [SMILES: Cc1c(C(=O)NC2CCOCC2)cc(-c2ccc(S(=O)(=O)NC(C)(C)C)c(Br)c2)n1CC1CCCCC1] | $^1$H-NMR ($CDCl_3$, 400 MHz) δ: 0.60-0.66 (2H, m), 0.97-1.00 (3H, m), 1.20-1.25 (11H, s), 1.32-1.37 (m, 3H), 1.47-1.49 (m, 6H), 1.97 (2H, dd, J = 12.0, 2.0 Hz), 2.62 (3H, s), 3.52 (2H, td, J = 10.0, 1.6 Hz), 3.80 (2H, d, J = 6.8 Hz), 3.98 (2H, d, J = 11.2 Hz), 4.15-4.17 (m, 1H), 5.11 (1H, s), 5.61 (1H, d, J = 8.0 Hz), 6.32 (1H, s), 7.40 (1H, dd, J = 8.4, 1.6 Hz), 7.70 (1H, d, J = 1.2 Hz), 8.17 (1H, d, J = 8.4 Hz). MS: 594.6/596.2 $(M + 1)^+$. |
| 17/158 | 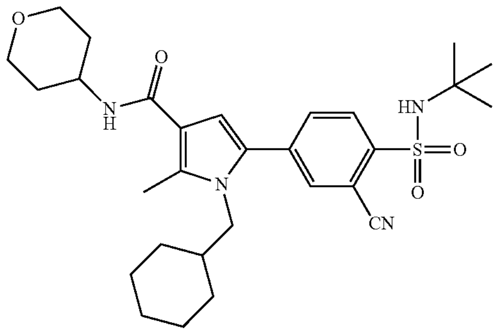 [SMILES: Cc1c(C(=O)NC2CCOCC2)cc(-c2ccc(S(=O)(=O)NC(C)(C)C)c(C#N)c2)n1CC1CCCCC1] | $^1$H-NMR ($CDCl_3$, 400 MHz) δ: 0.57-0.65 (2H, m), 0.97-1.00 (3H, m), 1.27 (9H, s), 1.29-1.33 (3H, m), 1.49-1.58 (6H, m), 1.96-2.00 (2H, m), 2.63 (3H, s), 3.53 (2H, td, J = 11.6, 1.2 Hz), 3.81 (2H, d, J = 7.2 Hz), 4.00 (2H, d, J = 10.8 Hz), 4.14-4.18 (1H, m), 5.13 (1H, s), 5.64 (1H, d, J = 8.0 Hz), 6.38 (1H, s), 7.65 (1H, dd, J = 8.0, 1.6 Hz), 7.79 (1H, d, J = 1.6 Hz), 8.16 (1H, d, J = 8.4 Hz). MS: 541.3 $(M + 1)^+$. |
| 17/159 | 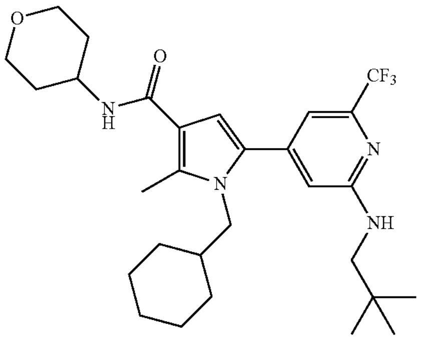 [SMILES: Cc1c(C(=O)NC2CCOCC2)cc(-c2cc(NCC(C)(C)C)nc(C(F)(F)F)c2)n1CC1CCCCC1] | $^1$H-NMR ($CDCl_3$, 400 MHz) δ: 6.87 (s, 1H), 6.47 (s, 1H), 6.32 (s, 1H), 6.60 (d, J = 8.0 Hz, 1H), 4.95 (t, J = 6.0 Hz, 1H), 4.14-4.18 (m, 1H), 3.98 (d, J = 11.2 Hz, 2H), 3.82 (d, J = 7.6 Hz, 2H), 3.52 (t, J = 11.2 Hz, 2H), 3.11 (d, J = 6.0 Hz, 1H), 2.61 (s, 3H), 1.98 (d, J = 11.2 Hz, 2H), 1.46-1.58 (m, 6H), 1.27-1.36 (m, 2H), 1.01-1.04 (m, 12H), 0.69-0.74 (m, 2H). MS: 535.3 $(M + 1)^+$. |

-continued

| # | Structure | Analytical data |
|---|---|---|
| 17/160 | 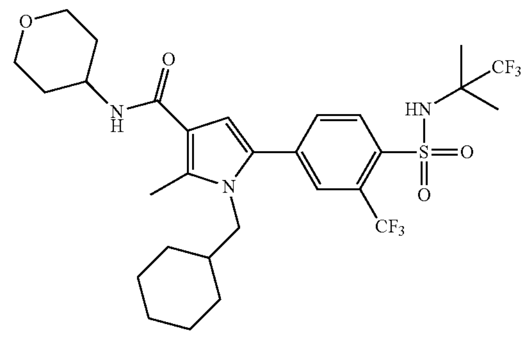 [SMILES: Cc1c(C(=O)NC2CCOCC2)cc(-c2ccc(S(=O)(=O)NC(C)(C)C(F)(F)F)c(C(F)(F)F)c2)n1CC1CCCCC1] | $^1$H-NMR ($CDCl_3$, 400 MHz) δ: 0.59-0.67 (m, 2H), 0.93-1.00 (m, 3H), 1.26-1.37 (m, 4H), 1.49 (s, 6H), 1.52-1.65 (m, 5H), 1.99 (d, 2H, J = 13.6 Hz), 2.63 (s, 3H), 3.53 (t, 2H, J = 11.2 Hz), 3.81 (d, 2H, J = 6.8 Hz), 3.99 (d, 2H, J = 11.2 Hz), 4.12-4.20 (m, 1H), 5.07 (s, 1H), 5.63 (d, 1H, J = 7.6 Hz), 6.39 (s, 1H), 7.63 (d, 1H, J = 8.4 Hz), 7.83 (s, 1H), 8.25 (d, 1H, J = 8.4 Hz). MS: 638.2 $(M + 1)^+$. |
| 17/161 | 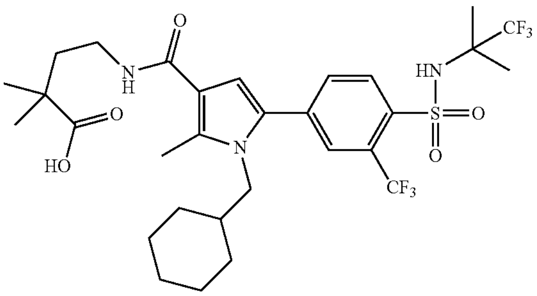 [SMILES: Cc1c(C(=O)NCCC(C)(C)C(=O)O)cc(-c2ccc(S(=O)(=O)NC(C)(C)C(F)(F)F)c(C(F)(F)F)c2)n1CC1CCCCC1] | $^1$H-NMR ($CDCl_3$, 400 MHz) δ: 0.58-0.65 (m, 2H), 0.91-1.00 (m, 3H), 1.16-1.34 (m, 10H), 1.44 (s, 6H), 1.57 (d, 1H, J = 8.0 Hz), 1.88 (t, 2H, J = 10.0 Hz), 2.63 (s, 3H), 3.41-3.48 (m, 2H), 3.81 (d, 2H, J = 8.8 Hz), 5.14 (s, 1H), 5.99 (t, 1H, J = 7.6 Hz), 6.40 (s, 1H), 7.65 (d, 1H, J = 11.2 Hz), 7.84 (s, 1H), 8.25 (d, 1H, J = 11.2 Hz). MS: 668.3 $(M + 1)^+$. |
| 17/162 | 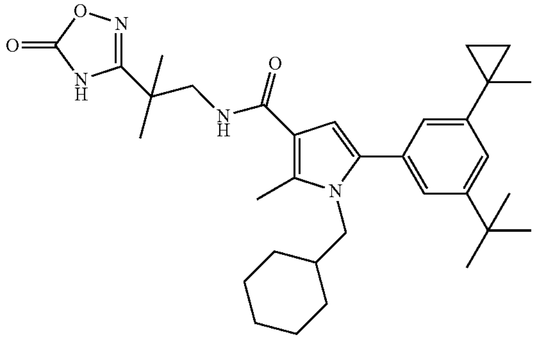 [SMILES: Cc1c(C(=O)NCC(C)(C)c2noc(=O)[nH]2)cc(-c2cc(C(C)(C)C)cc(C3(C)CC3)c2)n1CC1CCCCC1] | $^1$H-NMR (400 MHz, $CDCl_3$) δ: 7.28 (m, 1H), 7.11 (m, 1H), 6.99 (m, 1H), 6.19 (m, 1H), 6.14 (s, 1H), 3.71 (d, 2H, J = 7.2 Hz), 3.58 (d, 2H, J = 7.2 Hz), 2.59 (s, 3H), 1.62 (m, 3H), 1.55-1.46 (m, 9H), 1.42-1.26 (m, 12H), 1.00 (m, 3H), 0.86 (m, 2H), 0.74 (m, 2H), 0.65 (m, 2 H). MS: 547.4 $(M + 1)^+$. |
| 17/163 | 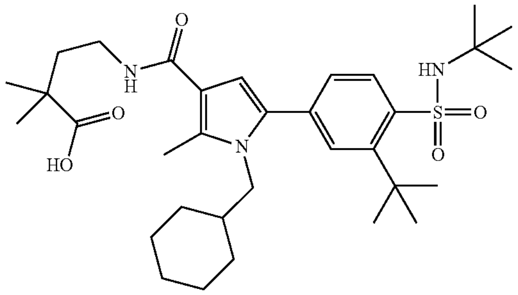 [SMILES: Cc1c(C(=O)NCCC(C)(C)C(=O)O)cc(-c2ccc(S(=O)(=O)NC(C)(C)C)c(C(C)(C)C)c2)n1CC1CCCCC1] | $^1$H-NMR ($CDCl_3$, 400 MHz) δ: 0.57-0.66 (m, 2H), 0.97-1.01 (m, 3H), 1.25 (s, 6H), 1.30 (s, 12H), 1.50-1.54 (m, 3H), 1.62 (s, 9H), 1.86 (t, J = 7.4 Hz, 2H), 2.61 (s, 3H), 3.41-3.46 (m, 2H), 3.77 (d, J = 7.2 Hz, 2H), 4.71 (s, 1H), 5.96-5.98 (m, 1H), 6.26 (s, 1H), 7.24 (s, 1H), 7.58 (s, 1H), 8.17 (d, J = 8.8 Hz, 1H). MS: 602.3 $(M + 1)^+$. |

-continued

| # | Structure | Analytical data |
| --- | --- | --- |
| 17/164 | 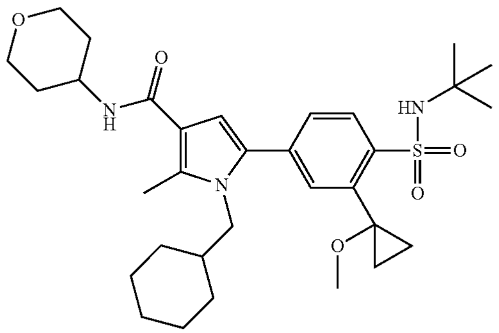 [SMILES: COC1(c2cc(-c3cc(C(=O)NC4CCOCC4)c(C)n3CC3CCCCC3)ccc2S(=O)(=O)NC(C)(C)C)CC1] | $^1$H-NMR (400 MHz, $CDCl_3$) δ: 0.53-0.63 (m, 2H), 0.96-0.98 (m, 3H), 1.15-1.19 (m, 2H), 1.25 (s, 9H), 1.28-1.33 (m, 5H), 1.47-1.54 (m, 5H), 1.97-2.00 (m, 2H), 2.62 (s, 3H), 3.21 (s, 3H), 3.50-3.56 (m, 2H), 3.78-3.80 (m, 2H), 3.97-4.00 (m, 2H), 4.20 (br s, 1H), 5.62 (d, J = 8.0 Hz, 1H), 5.89 (s, 1H), 6.29 (s, 1H), 7.39-7.42 (m, 2H), 8.18 (d, J = 8.0 Hz, 1H). MS: 586.4 ([M + H]$^+$). |
| 17/165 | 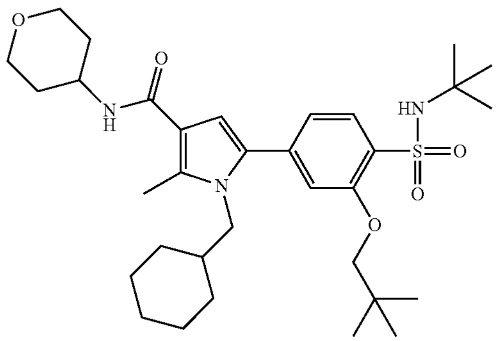 [SMILES: Cc1c(C(=O)NC2CCOCC2)cc(-c2ccc(S(=O)(=O)NC(C)(C)C)c(OCC(C)(C)C)c2)n1CC1CCCCC1] | $^1$H-NMR ($CDCl_3$, 400 MHz) δ: 0.58-0.70 (m, 2H), 0.86-1.11 (m, 3H), 1.17 (s, 9H), 1.21 (s, 9H), 1.23-1.34 (m, 5H), 1.38-1.57 (m, 3H), 1.96-2.00 (m, 2H), 2.62 (s, 3H), 3.48-3.56 (m, 2H), 3.79-3.81 (m, 4H), 3.97-4.00 (m, 2H), 4.13-4.19 (m, 1H), 4.88 (s, 1H), 5.61 (d, J = 8.0 Hz, 1H), 6.28 (s, 1H), 6.93 (s, 1H), 6.99 (d, J = 8.0 Hz, 1H), 7.93 (d, J = 8.0 Hz, 1H). MS: 602.2 (M + 1)$^+$. |
| 17/166 | 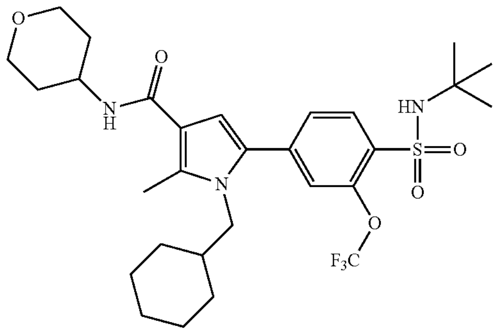 [SMILES: Cc1c(C(=O)NC2CCOCC2)cc(-c2ccc(S(=O)(=O)NC(C)(C)C)c(OC(F)(F)F)c2)n1CC1CCCCC1] | $^1$H-NMR ($CDCl_3$, 400 MHz) δ: 0.58-0.67 (m, 2H), 0.93-0.99 (m, 3H), 1.24 (s, 9H), 1.30-1.33 (m, 3H), 1.51-1.58 (m, 5H), 1.97-2.01 (m, 2H), 2.62 (s, 3H), 3.53 (t, J = 11.2 Hz, 2H), 3.79 (d, J = 7.2 Hz, 2H), 3.99 (d, J = 11.2 Hz, 2H), 4.11-4.21 (m, 1H), 4.69 (s, 1H), 5.61 (d, J = 7.6 Hz, 1H), 6.34 (s, 1H), 7.33-7.34 (m, 2H), 8.06 (d, J = 8.0 Hz, 1H), MS: 600.3 (M + 1)$^+$. |
| 17/167 | 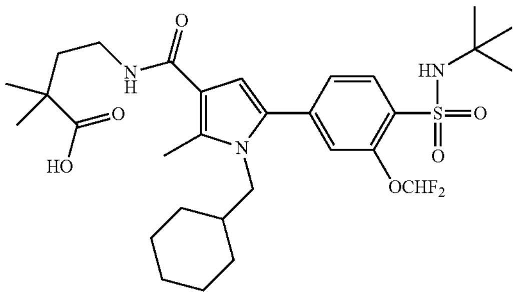 [SMILES: Cc1c(C(=O)NCCC(C)(C)C(=O)O)cc(-c2ccc(S(=O)(=O)NC(C)(C)C)c(OC(F)F)c2)n1CC1CCCCC1] | $^1$H-NMR ($CDCl_3$, 400 MHz) δ: 0.58-0.66 (m, 2H), 0.93-1.04 (m, 3H), 1.23 (s, 9H), 1.27-1.32 (s, 9H), 1.54-1.56 (m, 3H), 1.88 (t, J = 7.6 Hz, 2H), 2.60 (s, 3H), 3.43 (t, J = 6.0 Hz, 2H), 3.79 (d, J = 6.8 Hz, 2H), 4.79 (s, 1H), 5.96 (d, J = 8.0 Hz, 1H), 6.32 (s, 1H), 6.64 (t, J = 73.6 Hz, 1H), 7.26 (s, 1H), 7.30 (d, J = 8.4 Hz, 1H), 8.00 (d, J = 8.4 Hz, 1H). MS: 612.3 (M + 1)$^+$. |
| 17/168 | 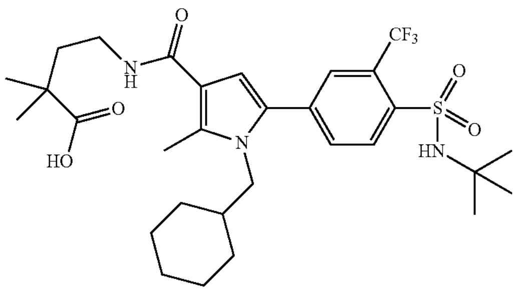 | $^1$H-NMR ($CDCl_3$, 400 MHz) δ: 0.72-0.78 (m, 2H), 1.03-1.07 (m, 3H), 1.22-1.28 (m, 15H), 1.34-1.37 (m, 2H), 1.49-1.59 (m, 4H), 1.89 (t, J = 7.2 Hz, 2H), 3.48-3.53 (m, 2H), 4.00 (d, J = 7.6 Hz, 2H), 4.77 (s, 1H), 6.31 (t, J = 5.6 Hz, 1H), 6.64 (s, 1H), 7.71 (dd, J = 8.4 Hz, 1.6 Hz, 1H), 7.85 (d, J = 0.8 Hz, 1H), 8.40 (d, J = 8.0 Hz, 1H). MS: 625.2 (M + 1)$^+$. |

-continued

| # | Structure | Analytical data |
| --- | --- | --- |
| 17/169 | 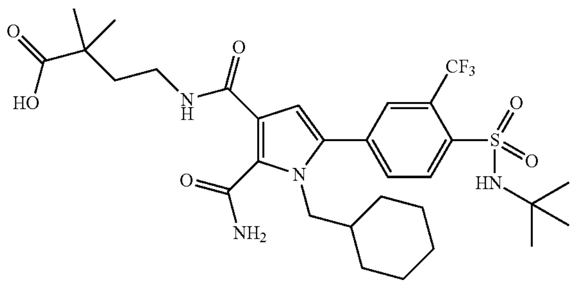 [SMILES: CC(C)(C)NS(=O)(=O)c1ccc(-c2cc(C(=O)NCCC(C)(C)C(=O)O)c(C(N)=O)n2CC2CCCCC2)cc1C(F)(F)F] | $^1$H-NMR ($CD_3OD$, 400 MHz) δ: 0.57-0.64 (m, 2H), 0.99-1.03 (m, 3H), 1.24 (s, 6H), 1.25 (s, 9H), 1.27-1.44 (m, 3H), 1.51-1.53 (m, 3H), 1.86 (t, J = 7.6 Hz, 2H), 3.38 (t, J = 7.6 Hz, 2H), 4.31 (d, J = 7.6 Hz, 2H), 6.67 (s, 1H), 7.86 (dd, J = 8.4 Hz, 1.6 Hz, 1H), 7.93 (s, 1H), 8.36 (d, J = 8.4 Hz, 1H). MS: 643.2 $(M + 1)^+$. |
| 17/170 | 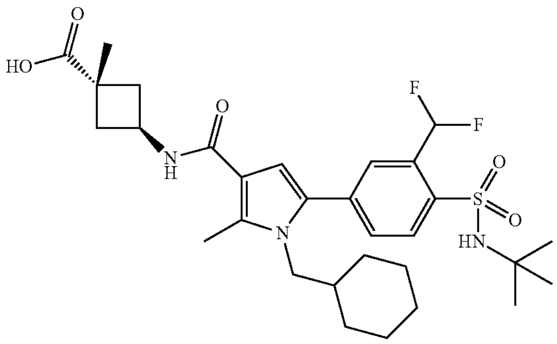 [SMILES: Cc1c(C(=O)N[C@H]2C[C@](C)(C(=O)O)C2)cc(-c2ccc(S(=O)(=O)NC(C)(C)C)c(C(F)F)c2)n1CC1CCCCC1] | $^1$H-NMR (400 MHz, $CDCl_3$) δ: 8.11 (d, 1H, J = 8.4 Hz), 7.81 (s, 1H), 7.55-5.53 (m, 1H), 7.42-7.39 (m, 1H), 6.37 (s, 1H), 6.11 (d, 1H, J = 8.4 Hz), 4.62 (s, 2H), 3.81 (d, 2H, J = 6.8 Hz), 2.61-2.53 (m, 5H), 2.43-2.38 (m, 2H), 1.56-1.54 (m, 3H), 1.48 (s, 3H), 1.38-1.25 (m, 3H), 1.23 (s, 9H), 0.98-0.88 (m, 3H), 0.65-0.58 (m, 2H). MS: 594.2 $(M + 1)^+$. |
| 17/171 | 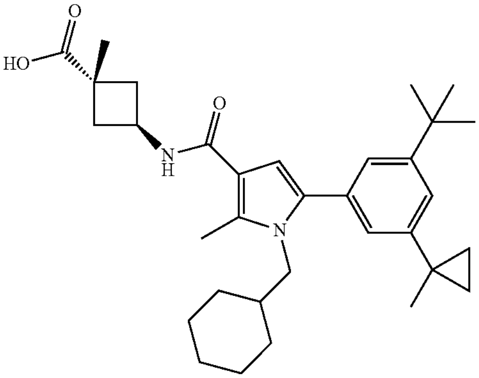 [SMILES: Cc1c(C(=O)N[C@H]2C[C@](C)(C(=O)O)C2)cc(-c2cc(C(C)(C)C)cc(C3(C)CC3)c2)n1CC1CCCCC1] | $^1$H-NMR (400 MHz, DMSO-$d_6$) δ: 12.14 (s, 1H), 7.79 (d, 1H, J = 8.0 Hz), 7.19 (t, 1H, J = 1.6 Hz), 7.14 (t, 1H, J = 1.6 Hz), 6.97 (t, 1H, J = 2.0 Hz), 6.55 (s, 1H), 4.47-4.42 (m, 1H), 3.76 (d, 2H, J = 7.2 Hz), 2.51 (s, 3H), 2.42-2.37 (m, 2H), 2.10-2.05 (m, 2H), 1.45-1.47 (m, 3H), 1.40-1.21 (m, 18H), 0.95-0.72 (m, 10H). MS: 519.3 $(M + 1)^+$. |
| 17/172 | 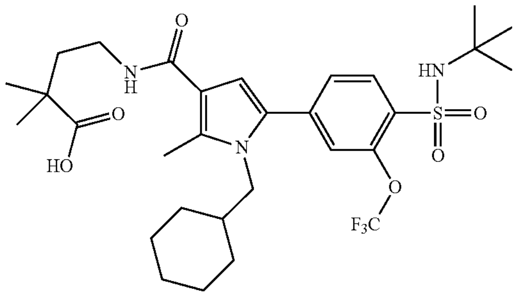 [SMILES: Cc1c(C(=O)NCCC(C)(C)C(=O)O)cc(-c2ccc(S(=O)(=O)NC(C)(C)C)c(OC(F)(F)F)c2)n1CC1CCCCC1] | $^1$H-NMR (400 MHz, $CD_3OD$) δ: 0.56-0.63 (m, 2H), 0.87-0.93 (m, 3H), 1.12 (s, 9H), 1.14 (s, 6H), 1.20-1.23 (m, 3H), 1.44-1.47 (m, 3H), 1.75 (br s, 2H), 2.47 (s, 3H), 3.26 (br s, 2H), 3.81 (d, J = 7.2 Hz, 2H), 6.51 (s, 1H), 7.36 (s, 1H), 7.40 (d, J = 8.8 Hz, 1H), 7.96 (d, J = 8.0 Hz, 1H). MS: 630.3 $[M + 1]^+$. |

-continued

| # | Structure | Analytical data |
|---|---|---|
| 17/173 | 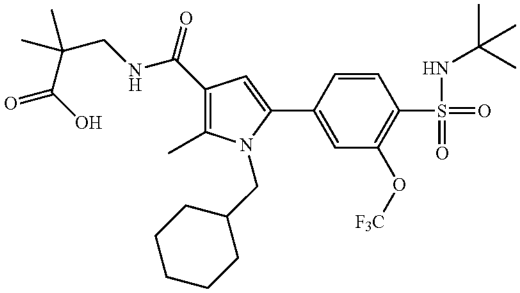 [SMILES: Cc1c(C(=O)NCC(C)(C)C(=O)O)cc(-c2ccc(S(=O)(=O)NC(C)(C)C)c(OC(F)(F)F)c2)n1CC1CCCCC1] | $^{1}$H-NMR (400 MHz, DMSO-$d_6$) δ: 0.60-0.67 (m, 2H), 0.88-0.97 (m, 3H), 1.09 (s, 6H), 1.14 (s, 9H), 1.21-1.23 (m, 3H), 1.45-1.48 (m, 3H), 2.53 (s, 3H), 3.34-3.36 (m, 2H), 3.87 (d, J = 6.8 Hz, 2H), 6.79 (s, 1H), 7.48-7.58 (m, 3H), 7.72 (s, 1H), 8.00 (d, J = 8.0 Hz, 1H), 12.19 (br s, 1H). MS: 616.2 [M + 1]$^+$. |
| 17/174 | 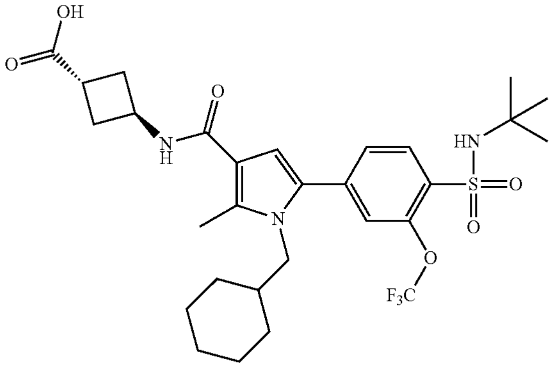 [SMILES: Cc1c(C(=O)N[C@H]2C[C@H](C(=O)O)C2)cc(-c2ccc(S(=O)(=O)NC(C)(C)C)c(OC(F)(F)F)c2)n1CC1CCCCC1] | $^{1}$H-NMR (400 MHz, DMSO-$d_6$) δ: 0.59-0.66 (m, 2H), 0.90-0.94 (m, 3H), 1.13 (s, 9H), 1.19-1.22 (m, 3H), 1.45-1.48 (m, 3H), 2.25-2.40 (m, 4H), 2.52 (s, 3H), 2.85-2.95 (m, 1H), 3.87 (d, J = 6.8 Hz, 1H), 4.48-4.54 (m, 1H), 6.81 (s, 1H), 7.48 (s, 1H), 7.58 (dd, J = 8.0, J = 1.6 Hz, 1H), 7.72 (s, 1H), 7.94 (d, J = 8.0 Hz, 1H), 8.01 (d, J = 8.0 Hz, 1H), 12.15 (s, 1H). MS: 614.2 [M + 1]$^+$. |
| 17/175 | 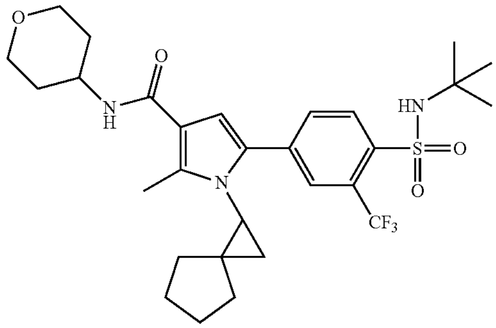 [SMILES: Cc1c(C(=O)NC2CCOCC2)cc(-c2ccc(S(=O)(=O)NC(C)(C)C)c(C(F)(F)F)c2)n1C1CC12CCCC2] | $^{1}$H-NMR (400 MHz, $CDCl_3$) δ: 1.05-1.10 (m, 3H), 1.26 (s, 12H), 1.49-1.80 (m, 7H), 1.97-2.00 (m, 2H), 2.65 (s, 3H), 3.30 (br s, 1H), 3.53 (t, J = 11.2 Hz, 2H), 3.99 (dd, J = 10.4 Hz, 1.6 Hz, 2H), 4.10-4.23 (m, 1H), 4.68 (s, 1H), 5.62 (d, J = 8.0 Hz, 1H), 6.42 (s, 1H), 7.69 (d, J = 8.4 Hz, 1H), 7.89 (s, 1H), 8.27 (d, J = 8.4 Hz, 1H). MS: 582.2 [M + 1]$^+$. |
| 17/176 | 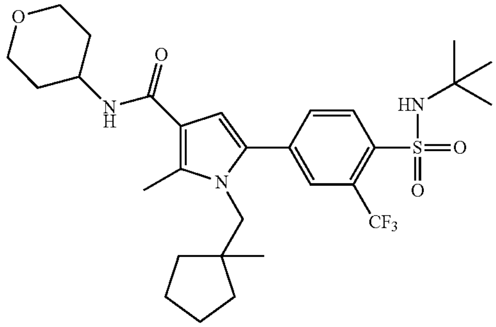 [SMILES: Cc1c(C(=O)NC2CCOCC2)cc(-c2ccc(S(=O)(=O)NC(C)(C)C)c(C(F)(F)F)c2)n1CC1(C)CCCC1] | $^{1}$H-NMR (400 MHz, $CDCl_3$) δ: 0.64 (s, 3H), 0.99-1.07 (m, 4H), 1.25 (s, 9H), 1.32-1.39 (m, 2H), 1.46-1.54 (m, 4H), 1.98 (dd, J = 12.4 Hz, 2.0 Hz, 2H), 2.65 (s, 3H), 3.53 (td, J = 11.2 Hz, 2.0 Hz, 2H), 3.99 (dd, J = 11.2 Hz, 2.0 Hz, 2H), 4.04 (s, 2H), 4.12-4.21 (m, 1H), 4.70 (s, 1H), 5.63 (d, J = 7.2 Hz, 1H), 6.38 (s, 1H), 7.25 (s, 1H), 7.62 (d, J = 8.4 Hz, 1H), 7.81 (s, 1H), 8.31 (d, J = 8.4 Hz, 1H). MS: 584.3 [M + 1]$^+$. |

-continued

| # | Structure | Analytical data |
|---|---|---|
| 17/177 | 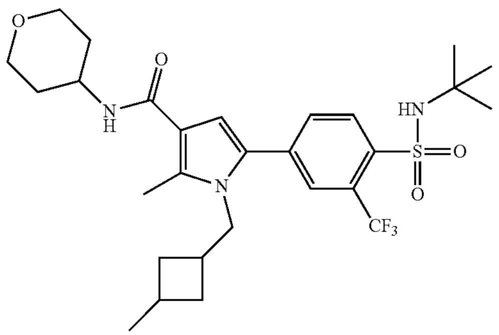 [SMILES: Cc1c(C(=O)NC2CCOCC2)cc(-c2ccc(S(=O)(=O)NC(C)(C)C)c(C(F)(F)F)c2)n1CC1CC(C)C1] | $^1$H-NMR (400 MHz, $CDCl_3$) δ: 0.86 (d, J = 6.4 Hz, 2H), 0.96-0.99 (m, 2H), 1.26 (d, J = 2.0 Hz, 9H), 1.49-1.55 (m, 4H), 1.96-2.01 (m, 5H), 2.62-2.64 (m, 3H), 3.52 (td, J = 11.2 Hz, 2.0 Hz, 2H), 3.92 (d, J = 6.4 Hz, 1H), 3.99 (dd, J = 8.4 Hz, 2.4 Hz, 2H), 4.04 (d, J = 7.2 Hz, 1H), 4.11-4.23 (m, 1H), 4.71 (s, 1H), 5.61 (d, J = 7.2 Hz, 1H), 6.36 (s, 1H), 7.61 (dd, J = 8.0 Hz, 1.6 Hz, 1H), 7.80 (br s, 1H), 8.32 (d, J = 8.0 Hz, 1H). MS: 570.2 $[M + 1]^+$. |
| 17/178 | 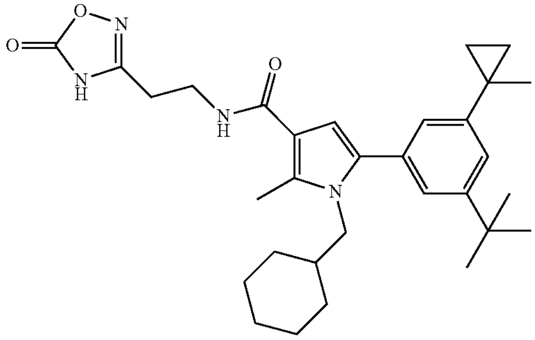 [SMILES: Cc1c(C(=O)NCCc2noc(=O)[nH]2)cc(-c2cc(C(C)(C)C)cc(C3(C)CC3)c2)n1CC1CCCCC1] | $^1$H-NMR (400 MHz, $CDCl_3$) δ: 7.28 (s, 1H), 7.11 (m, 1H), 6.99 (m, 1H), 6.25 (m, 1H), 6.15 (s, 1H), 3.72 (m, 4H), 2.92 (m, 2H), 2.61 (s, 3H), 1.54 (m, 3H), 1.42 (s, 3H), 1.40-1.25 (m, 12H), 1.00 (m, 3H), 0.86 (m, 2H), 0.75 (m, 2H), 0.65 (m, 2 H). MS: 519 $(M + 1)^+$. |
| 17/179 | 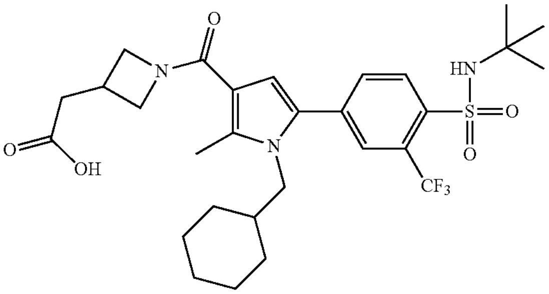 [SMILES: Cc1c(C(=O)N2CC(CC(=O)O)C2)cc(-c2ccc(S(=O)(=O)NC(C)(C)C)c(C(F)(F)F)c2)n1CC1CCCCC1] | $^1$H-NMR ($CDCl_3$, 400 MHz) δ: 0.58-0.65 (m, 2H), 0.98-0.99 (m, 3H), 1.26 (s, 9H), 1.29-1.32 (m, 2H), 1.55-1.56 (m, 4H), 2.59 (s, 3H), 2.73 (d, J =7.6 Hz, 1H), 2.99-3.05 (m, 1H), 3.80 (d, J = 7.6 Hz, 2H), 3.88-4.58 (m, 4H), 4.74 (s, 1H), 6.33 (s, 1H), 7.60 (dd, J = 8.4 Hz, 1.6 Hz, 1H), 7.77 (s, 1H). 8.31 (d, J = 8.4 Hz, 1H). MS: 598.2 $(M + 1)^+$. |
| 17/180 | 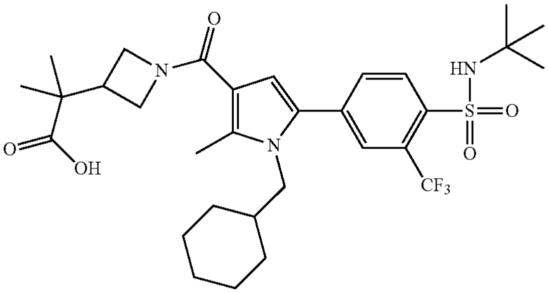 [SMILES: Cc1c(C(=O)N2CC(C(C)(C)C(=O)O)C2)cc(-c2ccc(S(=O)(=O)NC(C)(C)C)c(C(F)(F)F)c2)n1CC1CCCCC1] | $^1$H-NMR ($CDCl_3$, 400 MHz) δ: 0.60-0.63 (m, 2H), 0.99 (br s, 3H), 1.24 (s, 6H), 1.27 (s, 9H), 1.30-1.36 (m, 3H), 1.54-1.56 (m, 3H), 2.58 (s, 3H), 2.93-2.98 (m, 1H), 3.79 (d, J = 6.8 Hz, 2H), 3.88-4.48 (m, 4H), 4.84 (s, 1H), 6.35 (s, 1H), 7.61 (dd, J = 8.4 Hz, 1.6 Hz, 1H), 7.78 (d, J = 1.6 Hz, 1H), 8.31 (d, J = 8.4 Hz, 1H). MS: 626.3 $(M + 1)^+$. |

-continued

| # | Structure | Analytical data |
|---|---|---|
| 17/181 | 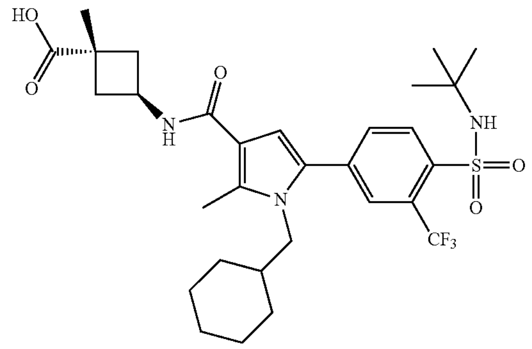 | $^1$H-NMR (400 MHz, DMSO-$d_6$) δ: 12.21 (s, 1H), 8.23 (d, 1H, J = 8.4 Hz), 7.92 (d, 2H, J = 8.0 Hz), 7.84 (d, 2H, J = 8.4 Hz), 6.91 (s, 1H), 4.47-4.44 (m, 1H), 3.89 (d, 2H, J = 6.8 Hz), 2.54 (s, 3H), 2.42-2.37 (m, 2H), 2.11-2.06 (m, 2H), 1.47-1.45 (m, 3H), 1.36-1.32 (m, 3H), 1.23-1.20 (m, 3H), 1.15 (s, 9H), 0.93-0.85 (m, 3H), 0.66-0.61 (m, 2H). MS: 626.3 (M + 1)$^+$. |
| 17/182 | 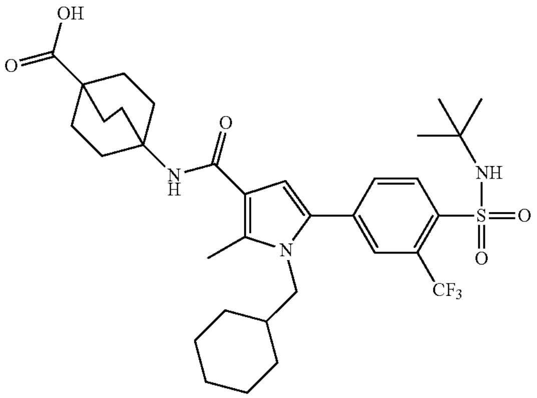 [SMILES: Cc1c(C(=O)NC23CCC(C(=O)O)(CC2)CC3)cc(-c2ccc(S(=O)(=O)NC(C)(C)C)c(C(F)(F)F)c2)n1CC1CCCCC1] | $^1$H-NMR (400 MHz, $CDCl_3$) δ: 8.31 (d, 1H, J = 8.4 Hz), 7.78 (s, 1H), 7.60 (d, 1H, J = 8.4 Hz), 6.29 (s, 1H), 5.44 (s, 1H), 4.71 (s, 1H), 3.79 (d, 1H, J = 7.2 Hz), 2.60 (s, 9H), 2.06-1.94 (m, 12H), 1.56-1.54 (m, 3H), 1.42-1.26 (m, 12H), 0.99 (br s, 3H), 0.64-0.57 (m, 2H). MS: 652.2 (M + 1)$^+$. |
| 17/183 | 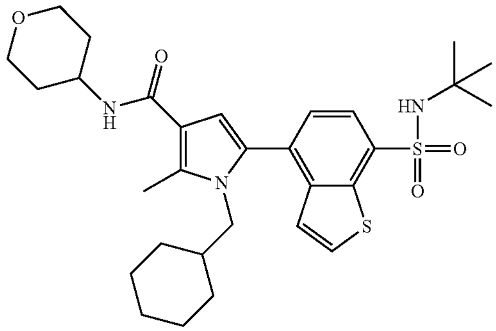 [SMILES: Cc1c(C(=O)NC2CCOCC2)cc(-c2ccc(S(=O)(=O)NC(C)(C)C)c3sccc23)n1CC1CCCCC1] | $^1$H-NMR (400 MHz, $CDCl_3$) δ: 0.47-0.50 (m, 2H), 0.85-0.90 (m, 3H), 1.20 (s, 9H), 1.24-1.30 (m, 3H), 1.47-1.55 (m, 5H), 1.97-2.00 (m, 2H), 2.66 (s, 3H), 3.50-3.55 (m, 2H), 3.63-3.65 (m, 2H), 3.96-3.99 (m, 2H), 4.17 (s, 1H), 4.76 (s, 1H), 5.62 (s, 1H), 6.34 (s, 1H), 7.30 (d, J = 6.4 Hz, 1H), 7.38 (d, J = 8.0 Hz, 1H), 7.59 (d, J = 6.4 Hz, 1H), 8.01 (d, J = 8.0 Hz, 1H). MS: 572.2 (M + 1)$^+$. |
| 17/184 | 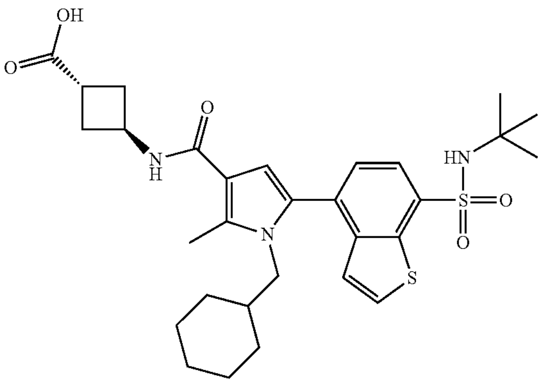 [SMILES: Cc1c(C(=O)N[C@H]2C[C@H](C(=O)O)C2)cc(-c2ccc(S(=O)(=O)NC(C)(C)C)c3sccc23)n1CC1CCCCC1] | $^1$H-NMR (400 MHz, $CD_3OD$) δ: 0.55-0.59 (m, 2H), 0.87-0.94 (m, 3H), 1.18-1.27 (m, 13H), 1.48-1.49 (m, 2H), 2.41 (q, J = 10.0 Hz, 2H), 2.62-2.65 (s, 5H), 3.06 (br s, 1H), 3.77 (d, J = 4.2 Hz, 2H), 4.72 (t, J = 6.8 Hz, 1H), 6.70 (s, 1H), 7.41 (d, J = 4.8 Hz, 1H), 7.51 (d, J = 7.6 Hz, 1H), 7.82 (d, J = 5.6 Hz, 1H), 8.03 (d, J = 7.6 Hz, 1H). MS: 586.2 (M + 1)$^+$. |

-continued
| # | Structure | Analytical data |
|---|---|---|
| 17/185 | 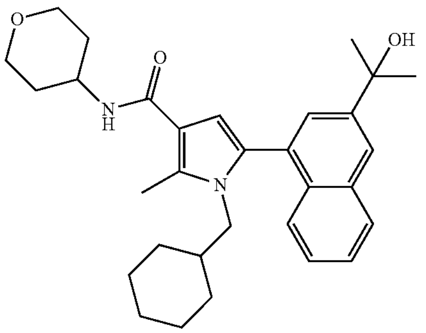 [SMILES: Cc1c(C(=O)NC2CCOCC2)cc(-c2cc(C(C)(C)O)cc3ccccc23)n1CC1CCCCC1] | $^1$H-NMR (400 MHz, $CDCl_3$) δ: 0.50-1.46 (m, 11H), 1.62 (s, 6H), 1.93 (d, J = 12.4 Hz, 2H), 2.60 (s, 3H), 2.41 (d, J = 7.6 Hz, 2H), 3.22 (m, 1H), 3.45 (m, 2H), 3.59 (m, 1H), 3.92 (m, 1H, m, 4.12 (m, 1H), 5.57 (br s, 1H), 6.21 (s, 1H), 7.33-7.50 (m, 4H), 7.82 (d, J = 8.0 Hz, 1H), 7.93 (d, J = 8.0 Hz, 1H). MS: 489.3 $(M + 1)^+$. |
| 17/186 | 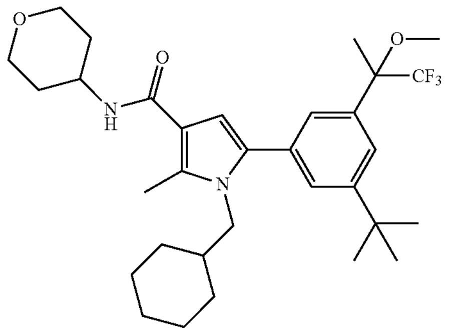 [SMILES: COC(C)(c1cc(-c2cc(C(=O)NC3CCOCC3)c(C)n2CC2CCCCC2)cc(C(C)(C)C)c1)C(F)(F)F] | MS: 563.3 $(M + 1)^+$. |
| 17/187 | 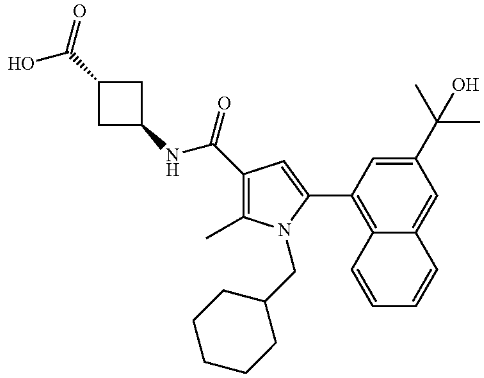 [SMILES: Cc1c(C(=O)N[C@H]2C[C@H](C(=O)O)C2)cc(-c2cc(C(C)(C)O)cc3ccccc23)n1CC1CCCCC1] | $^1$H-NMR (400 MHz, $CD_3OD$) δ: 0.45-1.39 (m, 11H), 1.55-1.56 (m, 6H), 2.25-2.33 (m, 2H), 2.50 (s, 3H), 2.52-2.56 (m, 2H), 2.91-2.96 (m, 1H), 3.20-3.23 (m, 1H), 3.63-3.66 (m, 1H), 4.57-3.65 (m, 1H), 6.46 (s, 1H), 7.31-7.41 (m, 2H), 7.49-7.52 (m, 2H), 7.82 (d, J = 8.2 Hz, 1H), 7.92 (d, J = 1.2 Hz, 1H). MS: 503.2 $(M + 1)^+$. |
| 17/188 | 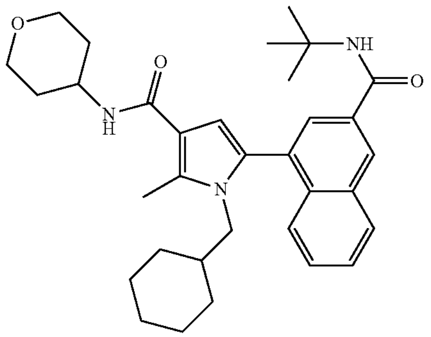 [SMILES: Cc1c(C(=O)NC2CCOCC2)cc(-c2cc(C(=O)NC(C)(C)C)cc3ccccc23)n1CC1CCCCC1] | $^1$H-NMR (400 MHz, $CDCl_3$) δ: 0.45-0.54 (m, 2H), 0.85-0.90 (m, 4H), 1.24-1.30 (m, 5H), 1.24-1.50 (m, 4H), 1.53 (s, 9H), 1.98-2.04 (m, 2H), 2.68 (s, 3H), 3.37-3.41 (m, 1H), 3.53 (td, J = 11.6, J = 2.2 Hz, 2H), 3.67-3.71 (m, 1H), 3.97 (d, J = 11.6 Hz, 1H), 4.18 (br s, 1H), 5.63 (d, J = 6.8 Hz, 1H), 6.06 (s, 1H), 6.29 (s, 1H), 7.52-7.57 (m. 2H), 7.68 (d, J = 8.0 Hz, 1H), 7.71 (d, J = 1.2 Hz, 1H), 7.97 (dd, J= 8.0, J = 1.2 Hz, 1H), 8.27 (d, J = 1.2 Hz, 1H). MS: 530.3 $(M + 1)^+$. |

-continued

| # | Structure | Analytical data |
|---|---|---|
| 17/189 | 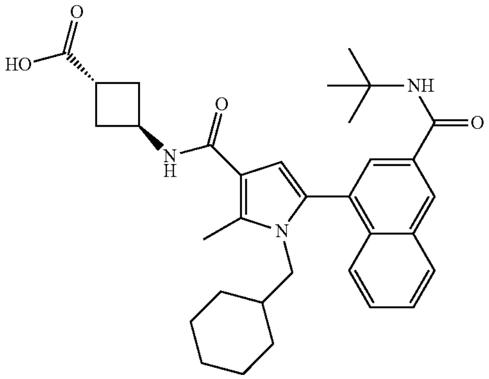 [SMILES: Cc1c(C(=O)N[C@H]2C[C@H](C(=O)O)C2)cc(-c2cc(C(=O)NC(C)(C)C)cc3ccccc23)n1CC1CCCCC1] | $^1$H-NMR (400 MHz, $CD_3OD$) δ: 0.40-1.37 (m, 11H), 1.40 (s, 9H), 2.23-2.31 (m, 2H), 2.47-2.53 (s, 5H), 2.89-2.93 (m, 1H), 3.32-3.36 (m, 1H), 3.69-3.69 (m, 1H), 4.58 (t, J = 8.0 Hz, 1H), 6.47 (s, 1H), 7.43-7.49 (m, 2H), 7.63 (d, J = 8.4 Hz, 1H), 7.68 (d, J = 1.6 Hz, 1H), 7.86 (br s, 1H), 7.93 (dd, J = 8.4, J = 1.6 Hz, 1H), 8.23 (s, 1H). MS: 544.3 $(M + 1)^+$. |
| 17/190 | 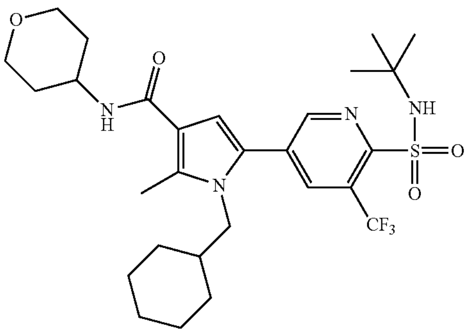 [SMILES: Cc1c(C(=O)NC2CCOCC2)cc(-c2cnc(S(=O)(=O)NC(C)(C)C)c(C(F)(F)F)c2)n1CC1CCCCC1] | $^1$H-NMR ($CDCl_3$, 400 MHz) δ: 0.62-0.69 (m, 2H), 1.02 (br s, 3H), 1.28 (s, 9H), 1.34-1.39 (m, 3H), 1.49-1.64 (m, 5H), 1.97-2.00 (m, 2H), 2.65 (s, 3H), 3.53 (t, J = 11.4 Hz, 2H), 3.82 (d, J = 7.2 Hz, 2H), 3.98-4.01 (m, 2H), 4.13-4.19 (m, 1H), 5.24 (s, 1H), 5.54 (d, J =7.6 Hz, 1H), 6.46 (s, 1H), 8.11 (s, 1H), 8.78 (s, 1H). MS: 585.2 $(M + 1)^+$. |
| 17/191 | 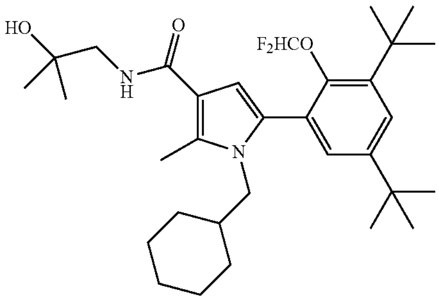 [SMILES: Cc1c(C(=O)NCC(C)(C)O)cc(-c2cc(C(C)(C)C)cc(C(C)(C)C)c2OC(F)F)n1CC1CCCCC1] | $^1$H-NMR (400 MHz, $CD_3OD$) δ: 0.50-0.77 (m, 2H), 1.00-1.10 (m, 3H), 1.26 (s, 6H), 1.37 (s, 9H), 1.49 (s, 9H), 1.18-1.64 (m, 6H), 2.58 (s, 3H), 3.34-3.39 (m, 2H), 3.57-3.73 (m, 2H), 6.16 (t, J = 74.8 Hz, 1H), 6.56 (s, 1H), 7.27 (d, J = 2.4 Hz, 1H), 7.56 (d, J = 2.4 Hz, 1H). MS: 547.3 $[M + 1]^+$. |
| 17/192 | 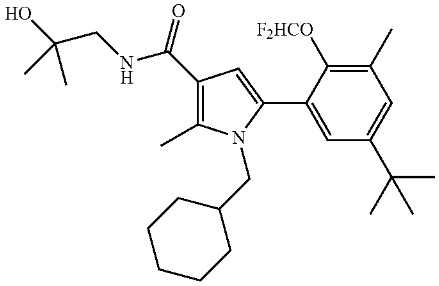 [SMILES: Cc1cc(C(C)(C)C)cc(-c2cc(C(=O)NCC(C)(C)O)c(C)n2CC2CCCCC2)c1OC(F)F] | $^1$H-NMR (400 MHz, $CD_3OD$) δ: 0.63-0.65 (m, 2H), 0.98-1.01 (m, 3H), 1.22 (s, 6H), 1.28-1.29 (m, 3H), 1.33 (s, 9H), 1.54-1.55 (m, 3H), 2.35 (s, 3H), 2.55 (s, 3H), 3.33 (s, 2H), 3.62 (d, J = 6.8 Hz, 2H), 6.10 (t, J = 75.6 Hz, 1H), 6.46 (s, 1H), 7.22 (d, J = 2.8 Hz, 1H), 7.36 (d, J = 2.0 Hz, 1H). MS: 505.4 $[M + 1]^+$. |

-continued
| # | Structure | Analytical data |
|---|---|---|
| 17/193 | 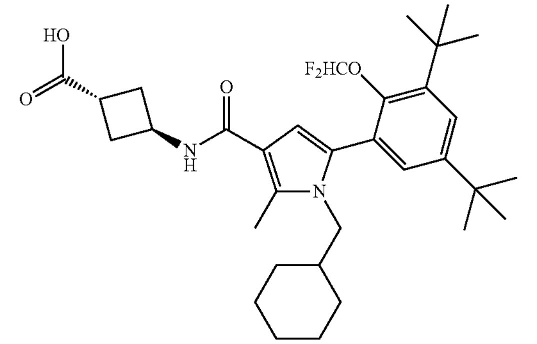 [SMILES: Cc1c(C(=O)N[C@H]2C[C@H](C(=O)O)C2)cc(-c2cc(C(C)(C)C)cc(C(C)(C)C)c2OC(F)F)n1CC1CCCCC1] | $^1$H-NMR (400 MHz, $CD_3OD$) δ: 0.45-0.75 (m, 2H), 0.87-1.00 (m, 3H), 1.33 (s, 9H), 1.45 (s, 9H), 1.14-1.61 (m, 6H), 2.34-2.42 (m, 2H), 2.52 (s, 3H), 2.58-2.64 (m, 2H), 3.00-3.07 (m, 1H), 3.53-3.70 (m, 2H), 4.84-4.69 (m, 1H), 6.10 (t, J = 75.2 Hz, 1H), 6.54 (s, 1H), 7.23 (d, J = 2.4 Hz, 1H), 7.52 (d J = 2.4 Hz, 1H). MS: 573.4 [M + 1]$^+$. |
| 17/194 | 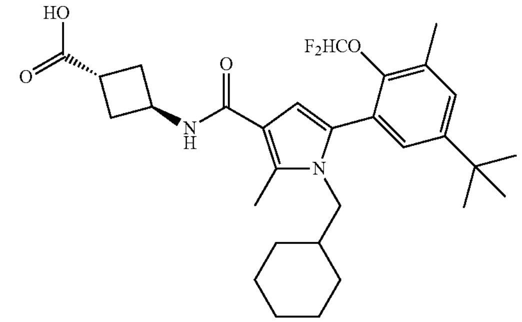 [SMILES: Cc1cc(C(C)(C)C)cc(-c2cc(C(=O)N[C@H]3C[C@H](C(=O)O)C3)c(C)n2CC2CCCCC2)c1OC(F)F] | $^1$H-NMR (400 MHz, $CD_3OD$) δ: 0.62-0.65 (m, 2H), 0.96-1.01 (m, 3H), 1.28-1.31 (m, 3H), 1.33 (s, 9H), 1.53-1.55 (m, 3H), 2.34 (s, 3H), 2.35-2.41 (m, 2H), 2.53 (s, 3H), 2.58-2.63 (m, 2H), 3.01-3.05 (m, 1H), 3.61 (d, J = 6.8 Hz, 2H), 4.66 (m, 1H), 6.08 (t, J = 75.6 Hz, 1H), 6.48 (s, 1H), 7.21 (d, J = 2.4 Hz, 1H), 7.36 (d, J = 2.0 Hz, 1H). MS: 531.3 [M + 1]$^+$. |
| 17/195 | 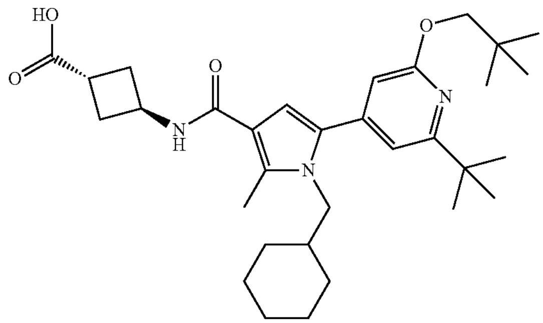 [SMILES: Cc1c(C(=O)N[C@H]2C[C@H](C(=O)O)C2)cc(-c2cc(OCC(C)(C)C)nc(C(C)(C)C)c2)n1CC1CCCCC1] | $^1$H-NMR (300 MHz, $CDCl_3$) δ: 0.67-0.72 (m, 2H), 0.86-0.90 (m, 1H), 0.98-1.03 (m, 12H), 1.26-1.36 (m, 14H), 1.55-1.57 (m, 3H), 2.28-2.35 (m, 2H), 2.60 (s, 3H), 2.75-2.82 (m, 2H), 3.09 (br s, 1H), 3.82 (d, J = 7.5 Hz, 2H), 4.06 (s, 2H), 4.75-4.83 (m, 1H), 5.94 (d, J = 6.9 Hz, 1H), 6.28 (s, 1H), 6.49 (d, J = 0.9 Hz, 1H), 6.79 (s, 1H). MS: 538.3 (M + 1)$^+$. |
| 17/196 | 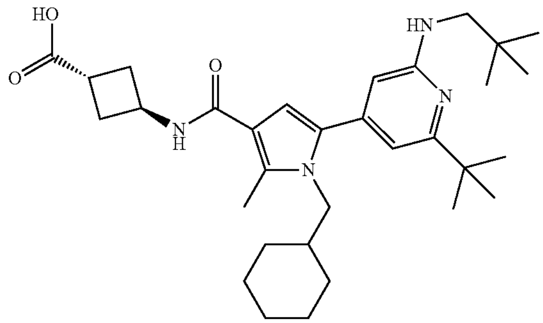 [SMILES: Cc1c(C(=O)N[C@H]2C[C@H](C(=O)O)C2)cc(-c2cc(NCC(C)(C)C)nc(C(C)(C)C)c2)n1CC1CCCCC1] | $^1$H-NMR (400 MHz, $CD_3OD$) δ: 0.80-0.89 (m, 2H), 1.06-1.10 (m, 12H), 1.27-1.42 (m, 15H), 1.59-1.62 (m, 3H), 2.36-2.43 (m, 2H), 2.57-2.64 (m, 5H), 3.02-3.07 (m, 1H), 3.23 (s, 2H), 4.01 (d, 2H), 4.63-4.68 (m, 1H), 6.78 (s, 1H), 6.80 (s, 1H), 6.96 (s, 1H). MS: 537.4 (M + 1)$^+$. |

-continued

| # | Structure | Analytical data |
|---|---|---|
| 17/197 | 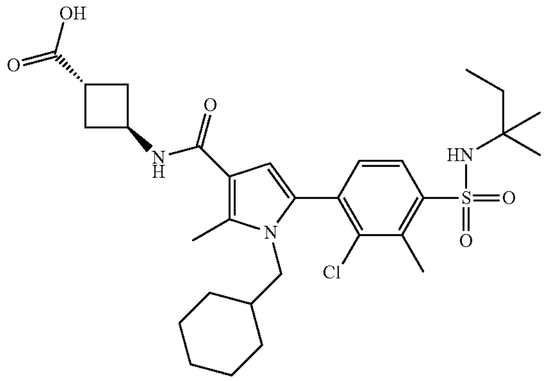 [SMILES: CCC(C)(C)NS(=O)(=O)c1ccc(-c2cc(C(=O)N[C@H]3C[C@H](C(=O)O)C3)c(C)n2CC2CCCCC2)c(Cl)c1C] | $^1$H-NMR (300 MHz, $CDCl_3$) δ: 0.60 (br s, 2H), 0.86 (t, J = 7.5 Hz, 3H), 0.98-1.04 (m, 3H), 1.17 (s, 6H), 1.20-1.38 (m, 4H), 1.54-1.61 (m, 6H), 2.27-2.34 (m, 2H), 2.60 (s, 3H), 2.77 (s, 5H), 3.05-3.10 (m, 1H), 3.53 (br s, 2H), 4.59 (s, 1H), 4.78-4.82 (m, 1H), 6.04 (d, J = 6.6 Hz, 1H), 6.24 (s, 1H), 7.27 (d, J = 8.4 Hz, 1H), 8.03 (d, J = 8.4 Hz, 1H). MS: 592.3 $(M + 1)^+$. |
| 17/198 | 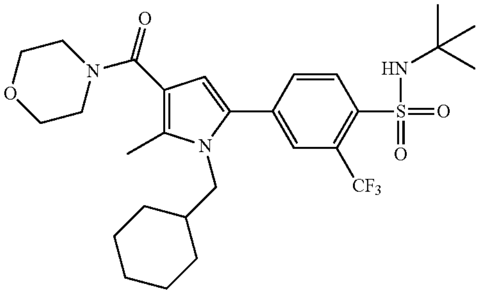 [SMILES: Cc1c(C(=O)N2CCOCC2)cc(-c2ccc(S(=O)(=O)NC(C)(C)C)c(C(F)(F)F)c2)n1CC1CCCCC1] | $^1$H-NMR (400 MHz, $CDCl_3$) δ: 8.31 (d, 1H, J = 8.4 Hz), 7.79 (s, 1H), 7.61 (m, 1H), 6.27 (d, 1H), 4.71 (s, 1H), 3.79 (m, 2H), 3.71 (m, 8H), 2.40 (s, 3H), 1.56 (m, 3H), 1.35-1.26 (m, 12H), 1.00 (m, 3H), 0.63 (m, 2H). MS: 570.3 $(M + 1)^+$. |
| 17/199 | 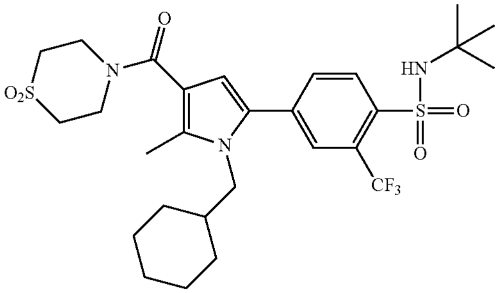 [SMILES: Cc1c(C(=O)N2CCS(=O)(=O)CC2)cc(-c2ccc(S(=O)(=O)NC(C)(C)C)c(C(F)(F)F)c2)n1CC1CCCCC1] | $^1$H-NMR (400 MHz, $CDCl_3$) δ: 8.32 (d, 1H, J = 8.4 Hz), 7.79 (s, 1H), 7.61 (m, 1H), 6.26 (s, 1H), 4.73 (s, 1H), 4.17 (m, 4H), 3.80 (m, 2H), 3.07 (m, 4H), 2.41 (s, 3H), 1.57 (m, 3H), 1.34-1.27 (m, 12H), 1.00 (m, 3H), 0.64 (m, 2H). MS: 618.2 $(M + 1)^+$. |
| 17/200 | 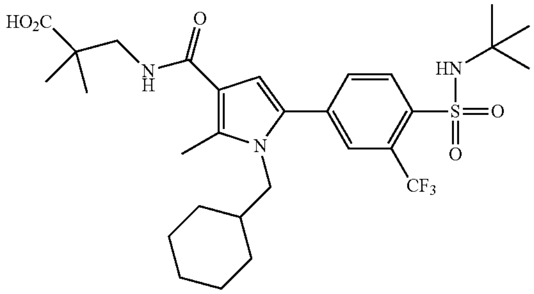 [SMILES: Cc1c(C(=O)NCC(C)(C)C(=O)O)cc(-c2ccc(S(=O)(=O)NC(C)(C)C)c(C(F)(F)F)c2)n1CC1CCCCC1] | $^1$H-NMR (400 MHz, DMSO-$d_6$) δ; 12.19 (s, 1H), 8.22 (d, 1H, J = 8.4 Hz), 7.92 (d, 1H, J = 8.4 Hz), 7.85 (d, 2H, J = 8.8 Hz), 7.52 (t, J = 6.4 Hz, 1H), 6.86 (s, 1H), 3.90 (d, 1H, J = 6.8 Hz), 3.35 (m, 2H), 2.54 (s, 3H), 1.46 (m, 3H), 1.22 (m, 3H), 1.09 (s, 9H), 1.06 (s, 6H), 0.95-0.85 (m, 3H), 0.62 (m, 2H). MS: 600.3 $(M + 1)^+$. |
| 17/201 | 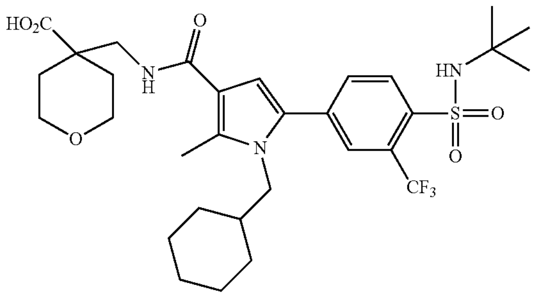 [SMILES: Cc1c(C(=O)NCC2(C(=O)O)CCOCC2)cc(-c2ccc(S(=O)(=O)NC(C)(C)C)c(C(F)(F)F)c2)n1CC1CCCCC1] | $^1$H-NMR (400 MHz, $CDCl_3$) δ: 8.31 (d, 1H, J = 8.0 Hz), 7.78 (s, 1H), 7.60 (m, 1H), 6.39 (s, 1H), 6.35 (m, 1H), 4.87 (s, 1H), 3.88 (m, 2H), 3.78 (m, 2H), 3.64 (m, 2H), 3.53 (m, 2H), 2.56 (s, 3H), 2.13 (m, 2H), 1.64-1.55 (m, 5H), 1.32-1.26 (m, 12H), 0.99 (m, 3H), 0.61 (m, 2H). MS: 642.3 $(M + 1)^+$. |

-continued
| # | Structure | Analytical data |
|---|---|---|
| 17/202 | 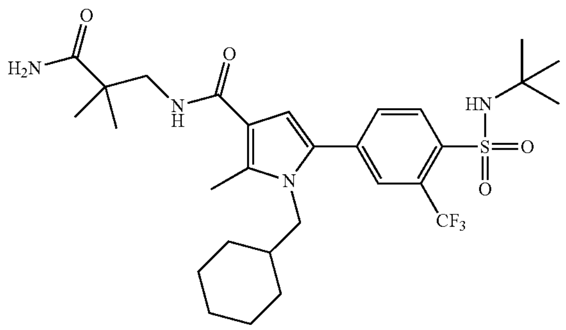 [SMILES: Cc1c(C(=O)NCC(C)(C)C(N)=O)cc(-c2ccc(S(=O)(=O)NC(C)(C)C)c(C(F)(F)F)c2)n1CC1CCCCC1] | $^1$H-NMR (400 MHz, $CDCl_3$) δ: 8.31 (d, 1H, J = 8.4 Hz), 7.79 (s, 1H), 7.61 (m, 1H), 6.59 (m, 1H), 6.39 (s, 1H), 6.12 (m, 1H), 5.40 (m, 1H), 4.74 (s, 1H), 3.79 (m, 2H), 3.53 (m, 2H), 2.62 (s, 3H), 1.55 (m, 3H), 1.34-1.10 (m, 18H), 1.00 (m, 3H), 0.63 (m, 2H). MS: 599.3 $(M + 1)^+$. |
| 17/203 | 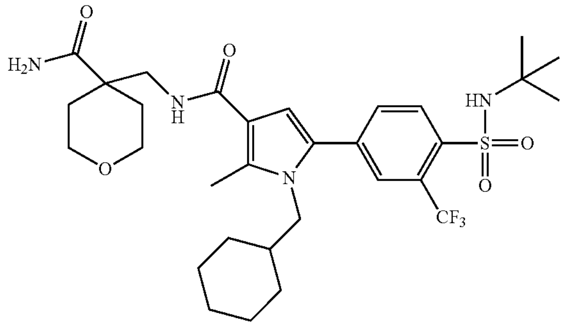 [SMILES: Cc1c(C(=O)NCC2(C(N)=O)CCOCC2)cc(-c2ccc(S(=O)(=O)NC(C)(C)C)c(C(F)(F)F)c2)n1CC1CCCCC1] | $^1$H-NMR (400 MHz, $CDCl_3$) δ: 8.31 (d, 1H, J = 8.4 Hz), 7.78 (s, 1H), 7.60 (m, 1H), 6.36 (m, 2H), 6.11 (s, br, 1H), 5.98 (s, br, 1H), 4.77 (s, 1H), 3.86 (m, 2H), 3.79 (m, 2H), 2.60 (s, 3H), 1.97 (m, 2H), 1.73 (m, 2H), 1.55 (m, 2H), 1.33-1.24 (m, 12H), 1.00 (m, 3H), 0.62 (m, 2H). MS: 641.3 $(M + 1)^+$. |
| 17/204 | 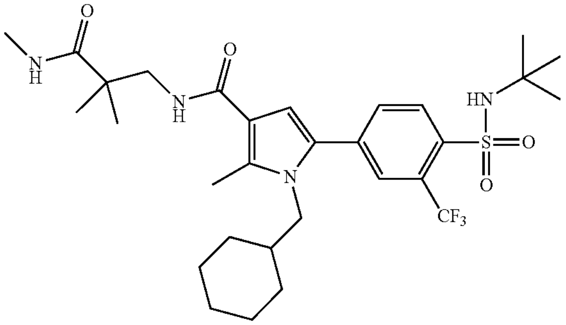 [SMILES: CNC(=O)C(C)(C)CNC(=O)c1cc(-c2ccc(S(=O)(=O)NC(C)(C)C)c(C(F)(F)F)c2)n(CC2CCCCC2)c1C] | $^1$H-NMR (400 MHz, $CDCl_3$) δ: 8.31 (d, 1H, J = 8.4 Hz), 7.79 (s, 1H), 7.62 (d, 1H, J = 8.4 Hz), 7.00 (m, 1H), 6.44 (s, 1H), 6.09 (m, 1H), 4.71 (s, 1H), 3.77 (m, 2H), 3.49 (m, 2H), 2.82 (d, 3H, J = 4.8 Hz), 2.61 (s, 3H), 1.56 (m, 3H), 1.36-1.22 (m, 18H), 0.99 (m, 3H), 0.61 (m, 2H). MS: 613.3 $(M + 1)^+$. |
| 17/205 | 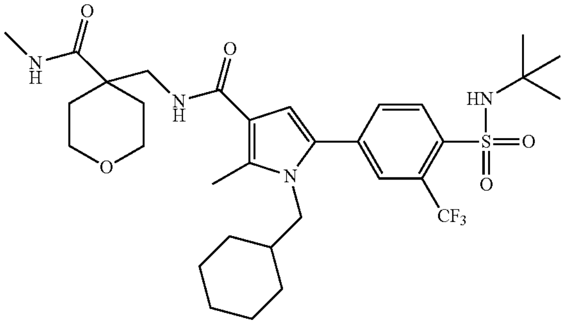 [SMILES: CNC(=O)C1(CNC(=O)c2cc(-c3ccc(S(=O)(=O)NC(C)(C)C)c(C(F)(F)F)c3)n(CC3CCCCC3)c2C)CCOCC1] | $^1$H-NMR (400 MHz, $CDCl_3$) δ: 8.31 (d, 1H, J = 8.0 Hz), 7.78 (s, 1H), 7.61 (m, 1H), 6.58 (m, 1H), 6.40 (s, 1H), 5.98 (m, 1H), 4.72 (s, 1H), 3.82 (m, 4H), 3.66 (m, 4H), 2.86 (d, 3H, J = 4.8 Hz), 2.60 (s, 3H), 1.95 (m, 2H), 1.72 (m, 2H), 1.56 (m, 3H), 1.36-1.24 (m, 12H), 1.00 (m, 3H), 0.60 (m, 2H). MS: 655.3 $(M + 1)^+$. |

-continued
| # | Structure | Analytical data |
| --- | --- | --- |
| 17/206 | 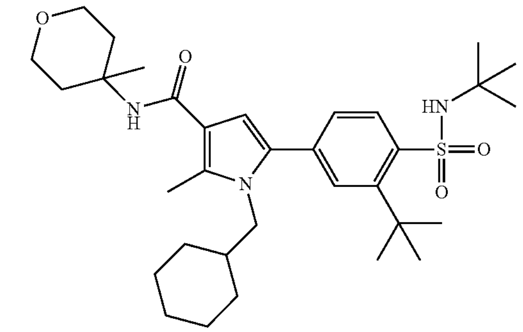 [SMILES: Cc1c(C(=O)NC2(C)CCOCC2)cc(-c2ccc(S(=O)(=O)NC(C)(C)C)c(C(C)(C)C)c2)n1CC1CCCCC1] | $^1$H-NMR (400 MHz, $CDCl_3$) δ: 8.20 (d, 1H, J = 8.4 Hz), 7.58 (s, 1H), 7.27-7.25 (m, 1H), 6.24 (s, 1H), 5.53 (s, 1H), 4.48 (s, 1H), 3.78-3.68 (m, 6H), 2.59 (s, 3H), 2.14 (m, 2H), 1.81-1.74 (m, 2H), 1.62 (s, 9H), 1.54 (s, 6H), 1.32 (m, 12H), 0.98 (m, 3H), 0.61 (m, 2H). MS: 586.3 $(M + 1)^+$. |
| 17/207 | 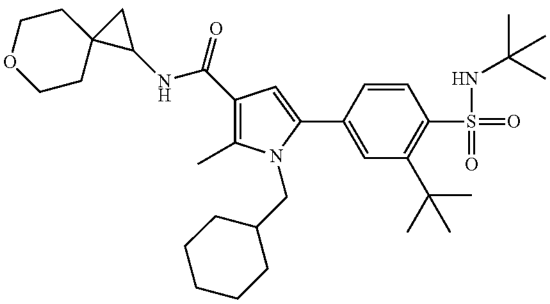 [SMILES: Cc1c(C(=O)NC2CC23CCOCC3)cc(-c2ccc(S(=O)(=O)NC(C)(C)C)c(C(C)(C)C)c2)n1CC1CCCCC1] | $^1$H-NMR (400 MHz, $CDCl_3$) δ: 8.19 (d, 1H, J = 8.4 Hz), 7.57 (s, 1H), 7.24 (m, 1H), 6.20 (s, 1H), 5.79 (s, 1H), 4.48 (s, 1H), 3.92 (m, 1H), 4.48-3.78 (m, 3H), 3.73-3.66 (m, 2H), 2.78-2.75 (m, 1H), 2.62 (s, 3H), 1.62-1.53 (m, 16H), 1.49-1.33 (m, 12H), 0.98 (m, 3H), 0.91-0.89 (m, 1H), 0.62 (m, 2H), 0.48 (m, 1H). MS: 598.3 $(M + 1)^+$. |
| 17/208 | 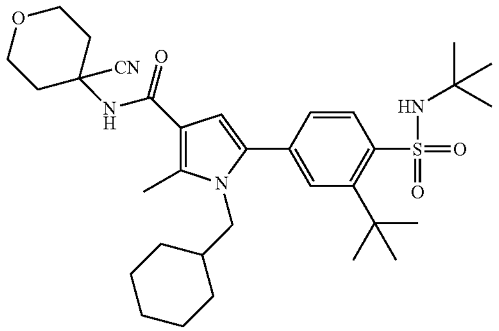 | $^1$H-NMR (400 MHz, DMSO-$d_6$) δ: 8.15 (d, 1H, J = 8.4 Hz), 7.91 (s, 1H), 7.76 (s, 1H), 7.53 (s, 1H), 7.43 (d, 1H, J = 6.8 Hz), 6.77 (s, 1H), 3.85 (s, 4H), 3.61-3.55 (m, 2H), 2.54 (s, 3H), 2.30 (m, 2H), 2.00-1.96 (m, 2H), 1.55 (s, 9H), 1.50-1.44 (m, 3H), 1.23-1.19 (m, 3H), 1.16 (s, 9H), 0.90-0.85 (m, 3H), 0.63 (m, 2H). MS: 597.3 $(M + 1)^+$. |
| 17/209 | 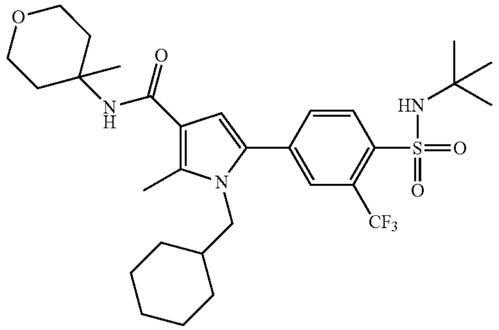 [SMILES: Cc1c(C(=O)NC2(C)CCOCC2)cc(-c2ccc(S(=O)(=O)NC(C)(C)C)c(C(F)(F)F)c2)n1CC1CCCCC1] | $^1$H-NMR (400 MHz, $CDCl_3$) δ: 8.32 (d, 1H, J = 8.4 Hz), 7.80 (s, 1H), 7.62 (d, 1H, J = 6.4 Hz), 6.33 (s, 1H), 5.50 (s, 1H), 4.71 (s, 1H), 3.81-3.67 (m, 6H), 2.61 (s, 3H), 2.14 (m, 2H), 1.81-1.74 (m, 2H), 1.56 (m, 6H), 1.33 (m, 3H), 1.23-1.19 (m, 3H), 1.26 (s, 9H), 0.99 (m, 3H), 0.62 (m, 2H). MS: 598.3 $(M + 1)^+$. |

-continued

| # | Structure | Analytical data |
|---|---|---|
| 17/210 | 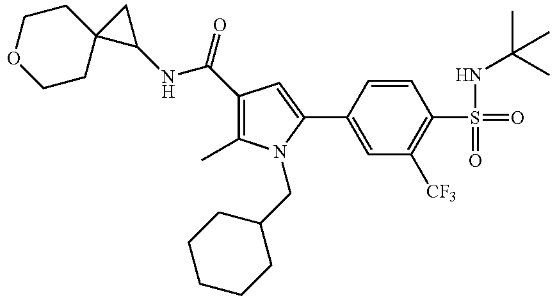 [SMILES: Cc1c(C(=O)NC2CC23CCOCC3)cc(-c2ccc(S(=O)(=O)NC(C)(C)C)c(C(F)(F)F)c2)n1CC1CCCCC1] | $^1$H-NMR (400 MHz, $CDCl_3$) δ: 8.31 (d, 1H, J = 8.4 Hz), 7.79 (s, 1H), 7.60 (d, 1H, J = 6.4 Hz), 6.30 (s, 1H), 5.75 (s, 1H), 4.71 (s, 1H), 3.93-3.88 (m, 1H), 3.80-3.78 (m, 3H), 3.73-3.70 (m, 2H), 2.77-2.74 (m, 1H), 2.62 (s, 3H), 1.56-1.41 (m, 7H), 1.37-1.31 (m, 3H), 1.26 (s, 9H), 0.99 (m, 3H), 0.90-0.87 (m, 1H), 0.62 (m, 2H), 0.46 (m, 1H). MS: 610.3 $(M + 1)^+$. |
| 17/211 | 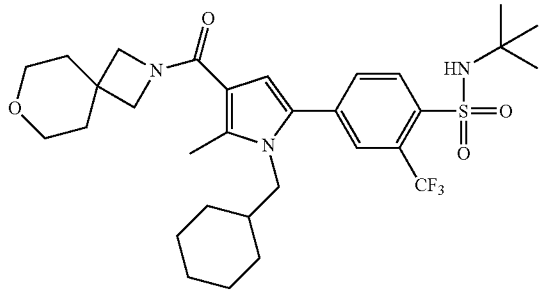 [SMILES: Cc1c(C(=O)N2CC3(CCOCC3)C2)cc(-c2ccc(S(=O)(=O)NC(C)(C)C)c(C(F)(F)F)c2)n1CC1CCCCC1] | $^1$H-NMR (400 MHz, $CDCl_3$) δ: 8.32 (d, 1H, J = 8.0 Hz), 7.78 (s, 1H), 7.61 (m, 1H), 6.35 (s, 1H), 4.71 (s, 1H), 3.99 (m, 4H), 3.80 (m, 2H), 3.64 (m, 4H), 2.60 (s, 3H), 1.82-1.80 (m, 4H), 1.56 (m, 3H), 1.31 (m, 3H), 1.27 (s, 9H), 0.99 (m, 3H), 0.63 (m, 2H). MS: 610.3 $(M + H)^+$. |
| 17/212 | 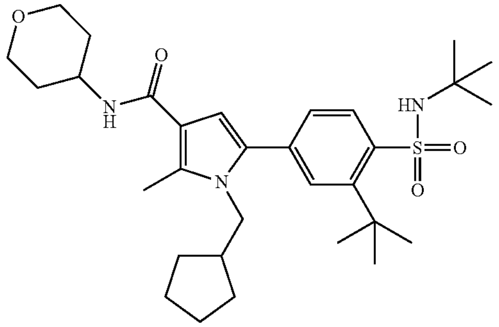 [SMILES: Cc1c(C(=O)NC2CCOCC2)cc(-c2ccc(S(=O)(=O)NC(C)(C)C)c(C(C)(C)C)c2)n1CC1CCCC1] | 1H-NMR (400 MHz, $CDCl_3$) δ: 8.19 (d, J = 8.4 Hz, 1H), 7.60 (s, 1H), 7.26 (m, 1H), 6.27 (s, 1H), 5.62 (d, J = 7.6 Hz, 1H), 4.47 (s, 1H), 4.17 (m, 1H), 3.99 (m, 2H), 3.89 (m, 2H), 3.53 (m, 2H), 2.65 (s, 3H), 2.01-1.92 (m, 3H), 1.61 (s, 9H), 1.55-1.49 (m, 4H), 1.46-1.34 (m, 4H), 1.31 (s, 9H), 0.90 (m, 2H). MS: 558.1 $(M + 1)^+$. |
| 17/213 | 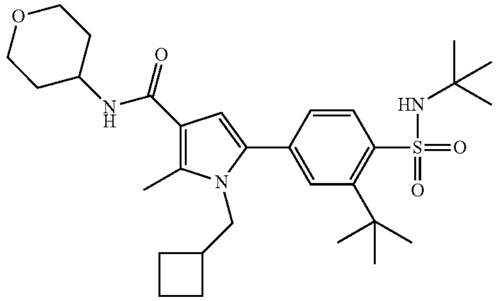 [SMILES: Cc1c(C(=O)NC2CCOCC2)cc(-c2ccc(S(=O)(=O)NC(C)(C)C)c(C(C)(C)C)c2)n1CC1CCC1] | $^1$H-NMR (400 MHz, $CDCl_3$) δ: 8.20 (d, J = 8.4 Hz, 1H), 7.59 (s, 1H), 7.26 (m, 1H), 6.26 (s, 1H), 5.61 (d, J = 7.6 Hz, 1H), 4.46 (s, 1H), 4.17 (m, 1H), 4.01-3.90 (m, 4H), 3.52 (m, 2H), 2.63 (s, 3H), 2.36 (m, 1H), 1.98 (m, 2H), 1.86 (m, 3H), 1.69 (s, 9H), 1.66-1.37 (m, 5H), 1.29 (s, 9H). MS: 544.1 $(M + 1)^+$. |
| 17/214 | 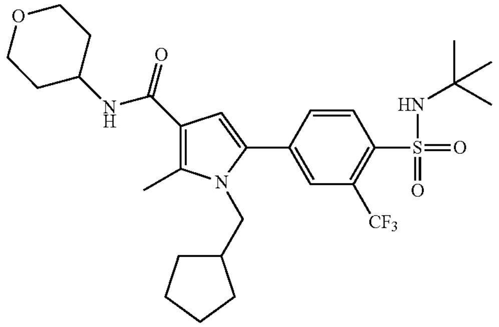 [SMILES: Cc1c(C(=O)NC2CCOCC2)cc(-c2ccc(S(=O)(=O)NC(C)(C)C)c(C(F)(F)F)c2)n1CC1CCCC1] | $^1$H-NMR (400 MHz, DMSO-$d_6$) δ: 8.23 (d, J = 8.4 Hz, 1H), 7.92 (m, 1H), 7.86 (m, 1H), 7.84 (s, 1H), 7.55 (m, 1H), 6.87 (s, 1H), 3.99-3.85 (m, 5H), 3.34 (m, 2H), 2.57 (s, 3H), 1.87 (m, 1H), 1.71 (m, 2H), 1.53 (m, 2H), 1.34-1.25 (m, 6H), 1.15 (s, 9H), 0.88 (m, 2H). MS: 570.0 $(M + 1)^+$. |

-continued
| # | Structure | Analytical data |
|---|---|---|
| 17/215 | 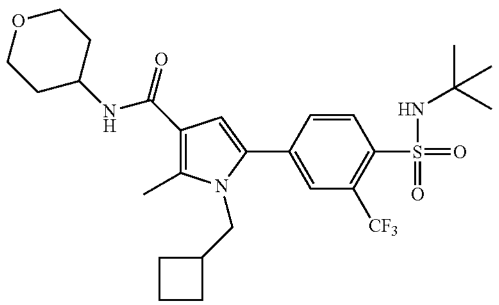 [SMILES: Cc1c(C(=O)NC2CCOCC2)cc(-c2ccc(S(=O)(=O)NC(C)(C)C)c(C(F)(F)F)c2)n1CC1CCC1] | $^1$H-NMR (400 MHz, $CDCl_3$) δ: 8.32 (d, J = 8.4 Hz, 1H), 7.80 (s, 1H), 7.62 (m, 1H), 6.36 (s, 1H), 5.61 (d, J = 8.0 Hz, 1H), 4.70 (s, 1H), 4.16 (m, 1H), 4.01-3.97 (m, 4H), 3.52 (m, 2H), 2.63 (s, 3H), 2.37 (m, 1H), 1.98 (m, 2H), 1.80-1.62 (m, 4H), 1.58-1.41 (m, 4H), 1.27 (s, 9H). MS: 556.0 $(M + 1)^+$. |
| 17/216 | 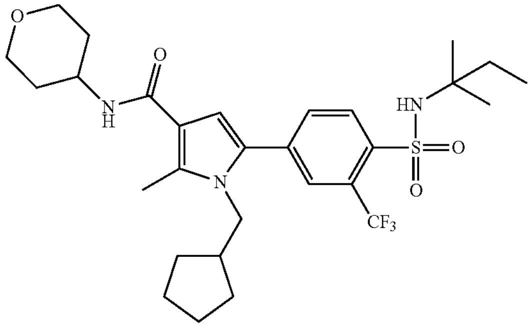 [SMILES: CCC(C)(C)NS(=O)(=O)c1ccc(-c2cc(C(=O)NC3CCOCC3)c(C)n2CC2CCCC2)cc1C(F)(F)F] | $^1$H-NMR (400 MHz, $CDCl_3$) δ: 8.30 (d, J = 8.4 Hz, 1H), 7.81 (s, 1H), 7.62 (m, 1H), 6.37 (s, 1H), 5.62 (d, J = 8.4 Hz, 1H), 4.61 (s, 1H), 4.16 (m, 1H), 4.01-3.96 (m, 2H), 3.92 (m, 2H), 3.53 (m, 2H), 2.65 (s, 3H), 2.01-1.90 (m, 3H), 1.62-1.51 (m, 2H), 1.49-1.35 (m, 5H), 1.22 (m, 8H), 0.87 (m, 6H). MS: 584.0 $(M + 1)^+$. |
| 17/217 | 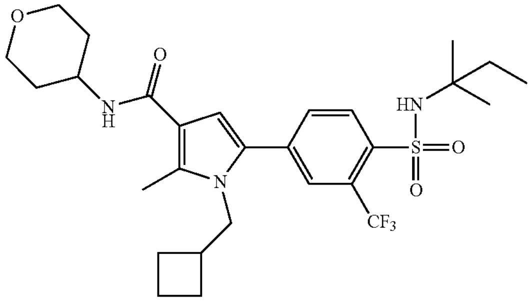 [SMILES: CCC(C)(C)NS(=O)(=O)c1ccc(-c2cc(C(=O)NC3CCOCC3)c(C)n2CC2CCC2)cc1C(F)(F)F] | $^1$H-NMR (400 MHz, $CDCl_3$) δ: 8.31 (d, J = 8.4 Hz, 1H), 7.80 (s, 1H), 7.62 (m, 1H), 6.36 (s, 1H), 5.61 (d, J = 7.6 Hz, 1H), 4.62 (s, 1H), 4.17 (m, 1H), 4.01-3.95 (m, 4H), 3.52 (m, 2H), 2.63 (s, 3H), 2.37 (m, 1H), 1.97 (d, 2H), 1.89-1.65 (m, 3H), 1.63-1.50 (m, 5H), 1.49 (m, 2H), 1.41 (s, 6H), 0.85 (t, J = 7.6 Hz, 3H). MS: 570.1 $(M + 1)^+$. |
| 17/218 | 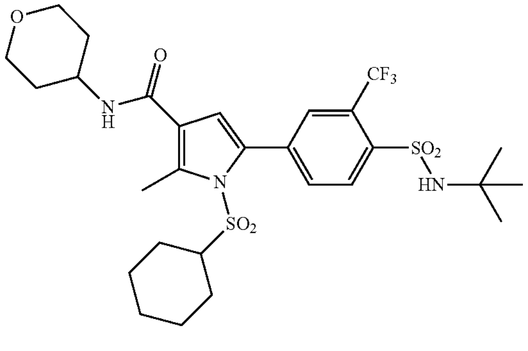 [SMILES: Cc1c(C(=O)NC2CCOCC2)cc(-c2ccc(S(=O)(=O)NC(C)(C)C)c(C(F)(F)F)c2)n1S(=O)(=O)C1CCCCC1] | $^1$H-NMR (400 MHz, $CDCl_3$) δ: 8.19-8.18 (m, 1H), 7.90-7.86 (m, 4H), 6.92 (s, 1H), 3.96-3.86 (m, 1H), 3.86-3.83 (m, 2H), 3.38-3.33 (m, 2H), 2.79 (s, 3H), 1.73-1.69 (m, 4H), 1.58-1.47 (m, 5H), 1.28-1.20 (m, 4H), 1.17 (m, 9H), 1.06 (m, 2H). MS: 634.2 $(M + H)^+$. |

-continued
| # | Structure | Analytical data |
| --- | --- | --- |
| 17/219 | 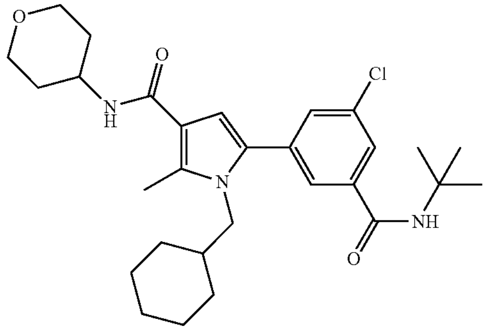 [SMILES: Cc1c(C(=O)NC2CCOCC2)cc(-c2cc(Cl)cc(C(=O)NC(C)(C)C)c2)n1CC1CCCCC1] | $^1$H-NMR (400 MHz, DMSO-$d_6$) δ: 7.99 (s, 1 H), 7.82 (m, 2 H), 7.59 (s, 1 H), 7.50 (d, 1 H, J = 8 Hz), 6.76 (s, 1 H), 3.92 (m, 5 H), 3.35 (m, 2 H), 2.54 (s, 3 H), 1.71 (m, 2 H), 1.53 (m, 5 H), 1.48 (s, 9 H), 1.36 (m, 3 H), 0.98 (m, 3 H), 0.66 (m, 2 H). MS: 514.2 $(M + 1)^+$. |
| 17/220 | 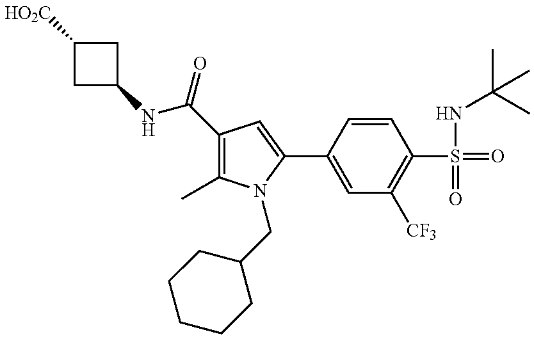 [SMILES: Cc1c(C(=O)N[C@H]2C[C@H](C(=O)O)C2)cc(-c2ccc(S(=O)(=O)NC(C)(C)C)c(C(F)(F)F)c2)n1CC1CCCCC1] | $^1$H-NMR (DMSO-$d_6$, 500 MHz) δ: 12.18 (s, 1H), 8.24 (m, 1H), 7.92-7.97 (m, 2H), 7.85-7.87 (m, 2H), 6.87 (s, 1H), 4.49-4.54 (m, 1H), 3.89-3.91 (m, 2H), 2.89-2.95 (m, 1H), 2.42 (s, 3H), 2.31-2.40 (m, 2H), 2.24-2.29 (m, 2H), 1.45-1.47 (m, 3H), 1.20-1.23 (m, 3H), 1.15 (s, 9H), 0.87-0.99 (m, 3H), 0.60-0.68 (m, 2H). MS: 598.2 $(M + 1)^+$. |
| 17/221 | 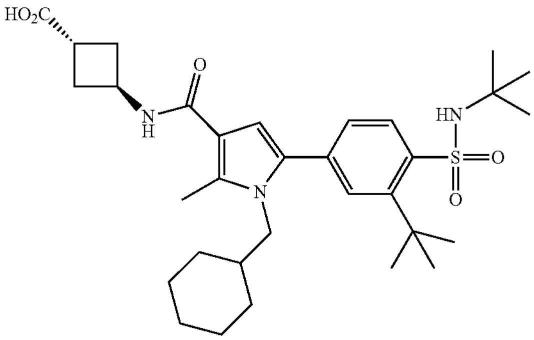 [SMILES: Cc1c(C(=O)N[C@H]2C[C@H](C(=O)O)C2)cc(-c2ccc(S(=O)(=O)NC(C)(C)C)c(C(C)(C)C)c2)n1CC1CCCCC1] | $^1$H-NMR ($CDCl_3$, 500 MHz) δ: 8.18-8.20 (m, 1H), 7.58 (s, 1H), 7.24-7.25 (m, 1H), 6.28 (s, 1H), 5.99-6.01 (m, 1H), 4.76-4.82 (m, 1H), 4.56 (s, 1H), 3.77-3.79 (m, 2H), 3.07-3.12 (m, 1H), 2.77-2.81 (m, 2H), 2.76 (s, 3H), 2.27-2.35 (m, 2H), 1.62 (s, 9H), 1.53-1.54 (m, 3H), 1.25-1.34 (m, 12H), 0.93-0.97 (m, 3H), 0.60-0.62 (m, 2H). MS: 586.1 $(M + 1)^+$. |
| 17/222 | 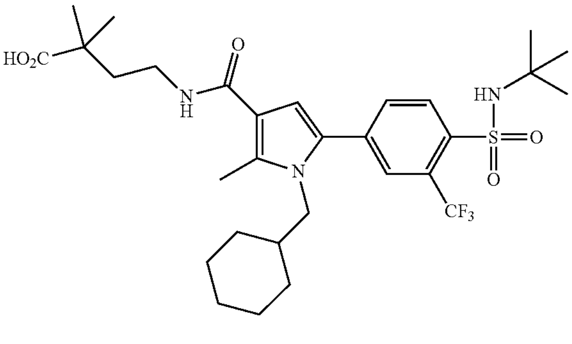 [SMILES: Cc1c(C(=O)NCCC(C)(C)C(=O)O)cc(-c2ccc(S(=O)(=O)NC(C)(C)C)c(C(F)(F)F)c2)n1CC1CCCCC1] | $^1$H-NMR (400 MHz, $CDCl_3$) δ: 8.31 (d, 1H, J = 8.0 Hz), 7.79 (s, 1H), 7.61 (m, 1H), 6.36 (s, 1H), 6.07 (s, br, 1H), 4.72 (s, 1H), 3.79 (m, 2H), 3.44 (m, 2H), 2.60 (s, 3H), 1.88 (m, 2H), 1.55 (m, 3H), 1.32-1.26 (m, 18H), 0.93 (m, 3H), 0.63 (m, 2H). MS: 614.3 $(M + H)^+$. |

-continued
| # | Structure | Analytical data |
|---|---|---|
| 17/223 | 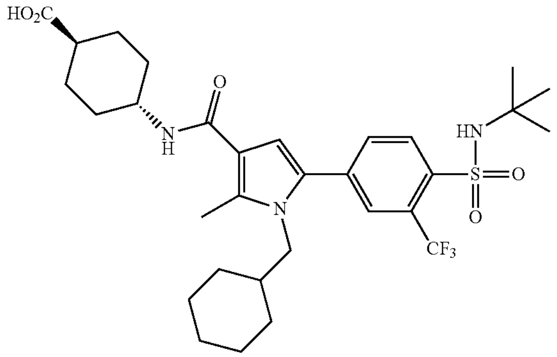 [SMILES: Cc1c(C(=O)N[C@H]2CC[C@H](C(=O)O)CC2)cc(-c2ccc(S(=O)(=O)NC(C)(C)C)c(C(F)(F)F)c2)n1CC1CCCCC1] | $^1$H-NMR (400 MHz, $CD_3OD$) δ: 8.31 (d, 1H, J = 8.4 Hz), 7.90 (s, 1H), 7.81 (m, 1H), 6.71 (s, 1H), 3.94 (m, 1H), 3.82 (m, 1H), 2.59 (s, 3H), 2.27 (m, 1H), 2.05 (s, 4H), 1.61-1.52 (m, 5H), 1.45-1.31 (m, 5H), 1.25 (s, 9H), 1.01 (m, 3H), 0.71 (m, 2H). MS: 626.3 $(M + 1)^+$. |
| 17/224 | 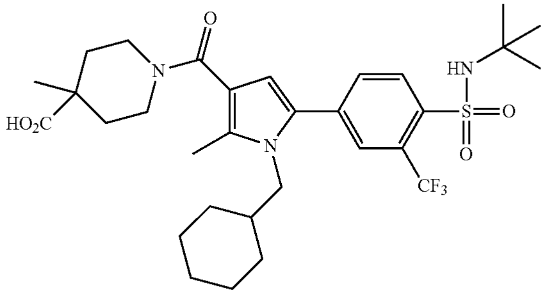 [SMILES: Cc1c(C(=O)N2CCC(C)(C(=O)O)CC2)cc(-c2ccc(S(=O)(=O)NC(C)(C)C)c(C(F)(F)F)c2)n1CC1CCCCC1] | $^1$H-NMR (400 MHz, $CDCl_3$) δ: 8.29 (d, 1H, J = 8.4 Hz), 7.80 (s, 1H), 7.61 (m, 1H), 6.28 (s, 1H), 4.72 (s, 1H), 3.79 (m, 2H), 3.25 (m, 2H), 2.37 (s, 3H), 2.17 (m, 2H), 1.78-1.71 (m, 5H), 1.62-1.47 (m, 8H), 1.35-1.22 (m, 9H), 0.88 (m, 3H), 0.62 (m, 2H). MS: 626.3 $(M + 1)^+$. |
| 17/225 | 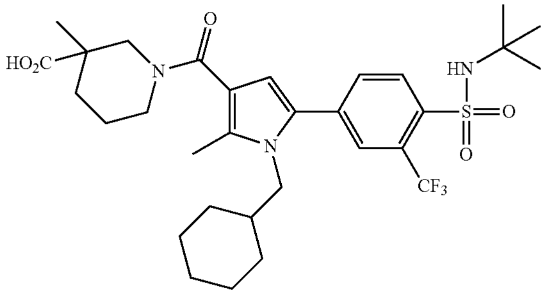 [SMILES: Cc1c(C(=O)N2CCCC(C)(C(=O)O)C2)cc(-c2ccc(S(=O)(=O)NC(C)(C)C)c(C(F)(F)F)c2)n1CC1CCCCC1] | $^1$H-NMR (400 MHz, $CDCl_3$) δ: 8.30 (d, 1H, J = 8.0 Hz), 7.79 (s, 1H), 7.61 (m, 1H), 6.30 (s, 1H), 4.72 (s, 1H), 4.38 (m, 1H), 3.90 (m, 1H), 3.79 (m, 2H), 3.36 (m, 1H), 3.11 (m, 1H), 2.39 (s, 3H), 2.28 (m, 1H), 1.57-1.47 (m, 6H), 1.45-1.26 (m, 15H), 1.00 (m, 3H), 0.63 (m, 2H). MS: 626.3 $(M + 1)^+$. |
| 17/226 | 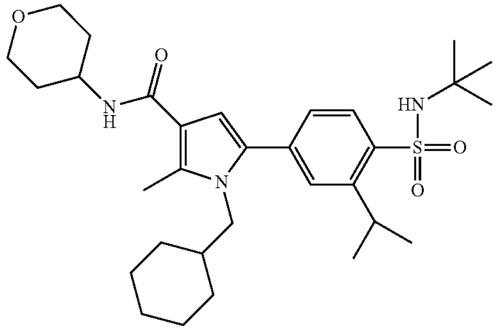 [SMILES: Cc1c(C(=O)NC2CCOCC2)cc(-c2ccc(S(=O)(=O)NC(C)(C)C)c(C(C)C)c2)n1CC1CCCCC1] | $^1$H-NMR ($CDCl_3$, 400 MHz) δ: 8.05 (d, J = 8.0 Hz, 1H), 7.41 (s, 1H), 7.22 (m, 1H), 6.28 (s, 1H), 5.62 (m, 1H), 4.38 (s, 1H), 4.23-4.12 (m, 1H), 4.02-3.95 (m, 2H), 3.86 (h, J = 6.8 Hz, 1H), 3.78 (m, 2H), 3.53 (m, 2H), 2.62 (s, 3H), 2.02-1.95 (m, 2H), 1.60-1.48 (m, 5H), 1.32 (d, J = 6.8 Hz, 6H), 1.30-1.21 (m, 12H), 1.02-0.94 (m, 3H), 0.59 (m, 2H). MS: 558.3 $(M + 1)^+$. |

-continued

| # | Structure | Analytical data |
|---|---|---|
| 17/227 | 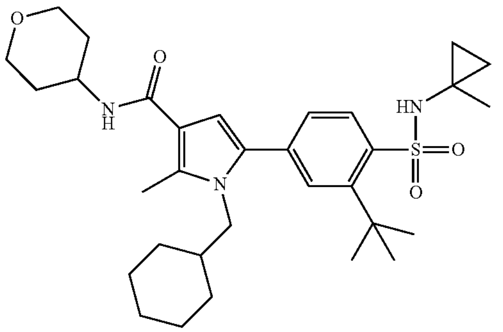 [SMILES: Cc1c(C(=O)NC2CCOCC2)cc(-c2ccc(S(=O)(=O)NC3(C)CC3)c(C(C)(C)C)c2)n1CC1CCCCC1] | $^1H$-NMR (400 MHz, $CDCl_3$) δ: 8.21 (d, 1H, J = 8.4 Hz), 7.59 (s, 1H), 7.30-7.26 (m, 1H), 6.29 (s, 1H), 5.64 (d, 1H, J = 8.0 Hz), 4.92 (s, 1H), 4.18-4.16 (m, 1H), 4.00-3.97 (m, 2H), 3.79 (m, 2H), 3.56-3.49 (m, 2H), 2.62 (s, 1H), 2.00-1.97 (m, 2H), 1.68-1.53 (m, 14H), 1.35-1.30 (m, 3H), 1.19 (s, 3H), 0.97 (m, 3H), 0.83-0.81 (m, 2H), 0.63-0.60 (m, 2H), 0.50-0.47 (m, 2H). MS: 570.1 $(M + 1)^+$. |
| 17/228 | 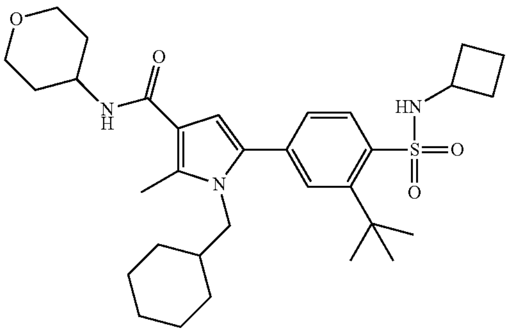 [SMILES: Cc1c(C(=O)NC2CCOCC2)cc(-c2ccc(S(=O)(=O)NC3CCC3)c(C(C)(C)C)c2)n1CC1CCCCC1] | $^1H$-NMR (400 MHz, DMSO-$d_6$) δ: 8.19 (d, 1H, J = 8.4 Hz), 7.99 (d, 1H, J = 8.0 Hz), 7.54-7.41 (m, 3H), 6.71 (s, 1H), 3.95-3.84 (m, 5H), 3.68-3.62 (m, 1H), 3.37-3.33 (m, 2H), 2.53 (s, 3H), 1.95-1.88 (m, 4H), 1.72-1.68 (m, 2H), 1.57-1.45 (m, 16H), 1.23-1.20 (m, 3H), 0.93-0.88 (m, 3H), 0.66-0.61 (m, 2H). MS: 570.1 $(M + 1)^+$. |
| 17/229 | 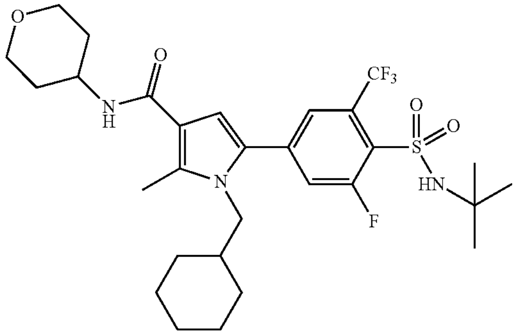 [SMILES: Cc1c(C(=O)NC2CCOCC2)cc(-c2cc(F)c(S(=O)(=O)NC(C)(C)C)c(C(F)(F)F)c2)n1CC1CCCCC1] | $^1H$-NMR (400 MHz, $CDCl_3$) δ: 7.65 (s, 1H), 7.37 (d, 1H, J = 10.4 Hz), 6.41 (s, 1H), 5.62 (d, 1H, J = 8.0 Hz), 5.07 (s, 1H), 4.16 (m, 1H), 3.99 (m, 2H), 3.83 (m, 2H), 3.53 (m, 2H), 2.63 (s, 3H), 1.98 (m, 2H), 1.58-1.49 (m, 5H), 1.38-1.26 (m, 12H), 1.02 (m, 3H), 0.67 (m, 2H). MS: 602.2 $(M + H)^+$. |
| 17/230 | 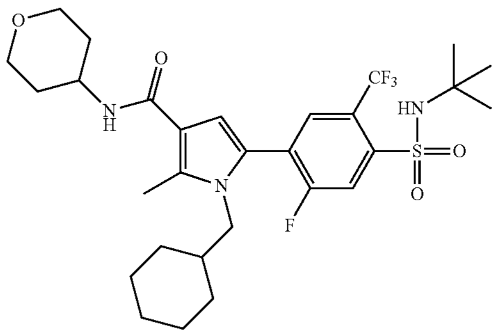 [SMILES: Cc1c(C(=O)NC2CCOCC2)cc(-c2cc(C(F)(F)F)c(S(=O)(=O)NC(C)(C)C)cc2F)n1CC1CCCCC1] | $^1H$-NMR (400 MHz, $CDCl_3$) δ: 8.09 (d, 1H, J = 9.6 Hz), 7.79 (d, 1H, J = 6.4 Hz), 6.38 (s, 1H), 5.61 (d, 1H, J = 8.0 Hz), 4.76 (s, 1H), 4.16 (m, 1H), 3.98 (m, 2H), 3.66 (d, 2H, J = 6.8 Hz), 3.52 (m, 2H), 2.63 (s, 3H), 1.98 (m, 2H), 1.59-1.47 (m, 5H), 1.35-1.24 (m, 12H), 1.00 (m, 3H), 0.58 (m, 2H). MS: 602.3 $(M + H)^+$. |

-continued
| # | Structure | Analytical data |
|---|---|---|
| 17/231 | 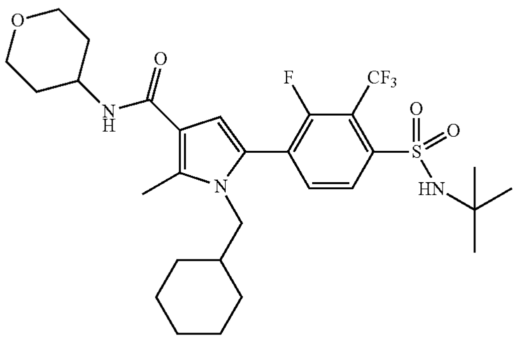 [SMILES: Cc1c(C(=O)NC2CCOCC2)cc(-c2ccc(S(=O)(=O)NC(C)(C)C)c(C(F)(F)F)c2F)n1CC1CCCCC1] | $^1$H-NMR (400 MHz, $CDCl_3$) δ: 8.18 (d, 1H, J = 8.4 Hz), 7.60 (m, 1H), 6.36 (s, 1H), 5.59 (d, 1H, J = 8.0 Hz), 4.79 (s, 1H), 4.16 (m, 1H), 3.98 (m, 2H), 3.64 (d, 2H, J = 6.8 Hz), 3.52 (m, 2H), 2.62 (s, 3H), 1.97 (m, 2H), 1.55-1.47 (m, 5H), 1.34-1.28 (m, 12H), 1.01 (m, 3H), 0.62 (m, 2H). MS: 602.2 $(M + H)^+$. |
| 17/232 | 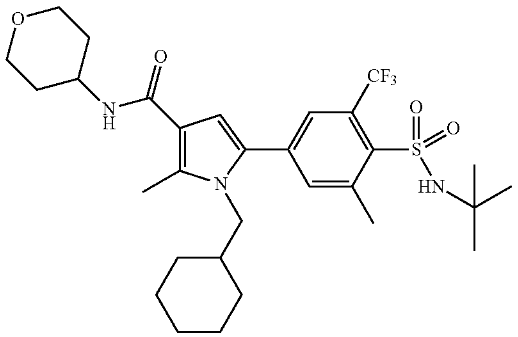 [SMILES: Cc1cc(-c2cc(C(=O)NC3CCOCC3)c(C)n2CC2CCCCC2)cc(C(F)(F)F)c1S(=O)(=O)NC(C)(C)C] | $^1$H-NMR (400 MHz, $CDCl_3$) δ: 7.70 (s, 1H), 7.47 (s, 1H), 6.35 (s, 1H), 5.61 (d, 1H, J = 8.4 Hz), 4.65 (s, 1H), 4.17 (m, 1H), 3.98 (m, 2H), 3.80 (d, 2H, J = 7.2 Hz), 3.53 (m, 2H), 2.82 (s, 3H), 2.62 (s, 3H), 1.99 (m, 2H), 1.77-1.63 (m, 5H), 1.58-1.20 (m, 12H), 1.00 (m, 3H), 0.64 (m, 2H). MS: 598.3 $(M + H)^+$. |
| 17/233 | 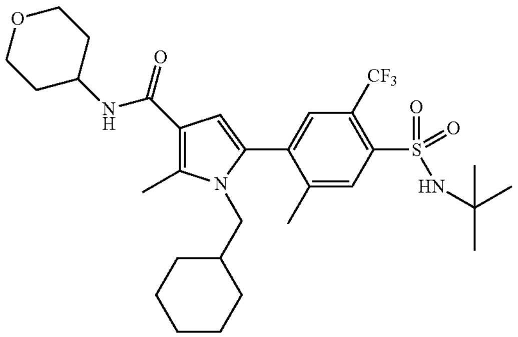 [SMILES: Cc1cc(S(=O)(=O)NC(C)(C)C)c(C(F)(F)F)cc1-c1cc(C(=O)NC2CCOCC2)c(C)n1CC1CCCCC1] | $^1$H-NMR (400 MHz, $CDCl_3$) δ: 8.13 (s, 1H), 7.58 (s, 1H), 6.15 (s, 1H), 5.52 (d, 1H, J = 7.6 Hz), 4.65 (s, 1H), 4.13-4.06 (m, 1H), 3.93-3.90 (m, 2H), 3.48-3.41 (m, 4H), 2.55 (s, 3H), 2.24 (s, 3H), 1.94-1.90 (m, 2H), 1.53-1.40 (m, 5H), 1.35-1.19 (m, 12H), 0.93 (m, 3H), 0.57-0.51 (m, 2H). MS: 598.3 $(M + H)^+$. |
| 17/234 | 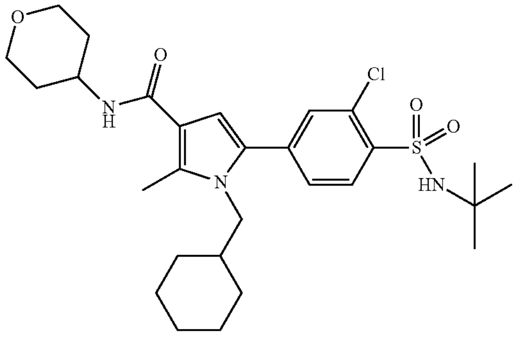 [SMILES: Cc1c(C(=O)NC2CCOCC2)cc(-c2ccc(S(=O)(=O)NC(C)(C)C)c(Cl)c2)n1CC1CCCCC1] | $^1$H-NMR (400 MHz, $CDCl_3$) δ: 8.06 (d, 1H, J = 8.0 Hz), 7.42 (s, 1H), 7.28 (d, 1H, J = 8.4 Hz), 6.26 (s, 1H), 5.54-5.52 (m, 1H), 4.90 (s, 1H), 4.10 (m, 1H), 3.92 (m, 2H), 3.74 (m, 2H), 3.46 (m, 2H), 2.55 (s, 3H), 1.91 (m, 2H), 1.50-1.32 (m, 5H), 1.27-1.17 (m, 12H), 0.93 (m, 3H), 0.55 (m, 2H). MS: 550.2 $(M + H)^+$. |

-continued

| # | Structure | Analytical data |
|---|---|---|
| 17/235 | 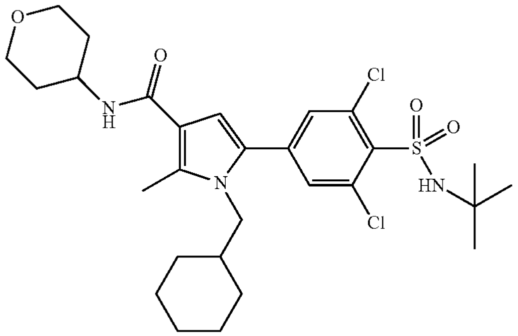 [SMILES: Cc1c(C(=O)NC2CCOCC2)cc(-c2cc(Cl)c(S(=O)(=O)NC(C)(C)C)c(Cl)c2)n1CC1CCCCC1] | $^1$H-NMR (400 MHz, $CDCl_3$) δ: 7.44 (s, 2H), 6.36 (s, 1H), 5.59 (d, 1H, J = 6.4 Hz), 5.32 (s, 1H), 4.16 (m, 1H), 3.99 (m, 2H), 3.81 (m, 2H), 3.53 (m, 2H), 2.62 (s, 3H), 1.98 (m, 2H), 1.59-1.41 (m, 5H), 1.39-1.45 (m, 12H), 1.03 (m, 3H), 0.69 (m, 2H). MS: 584.2 $(M + H)^+$. |
| 17/236 | 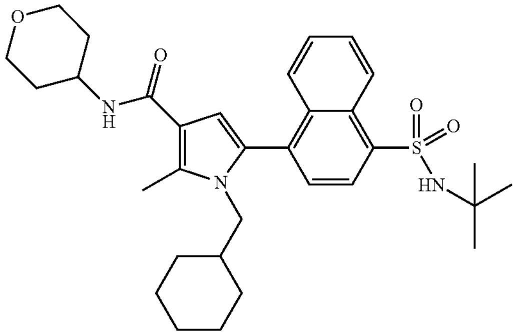 [SMILES: Cc1c(C(=O)NC2CCOCC2)cc(-c2ccc(S(=O)(=O)NC(C)(C)C)c3ccccc23)n1CC1CCCCC1] | $^1$H-NMR (400 MHz, $CDCl_3$) δ: 8.64 (d, 1H, J = 8.4 Hz), 8.35 (m, 1H), 7.77-7.67 (m, 2H), 7.58-7.48 (m, 2H), 6.34 (s, 1H), 5.64 (d, 1H, J = 7.6 Hz), 4.63 (s, 1H), 4.21-4.17 (m, 1H), 4.00-3.97 (m, 2H), 3.71-3.66 (m, 1H), 3.56-3.50 (m, 2H), 3.33-3.27 (m, 1H), 2.68 (s, 3H), 2.01-1.98 (m, 2H), 1.57-1.45 (m, 5H), 1.30-1.17 (m, 12H), 0.90-0.84 (m, 3H), 0.51-0.43 (m, 2H). MS: 566.3 $(M + H)^+$. |
| 17/237 | 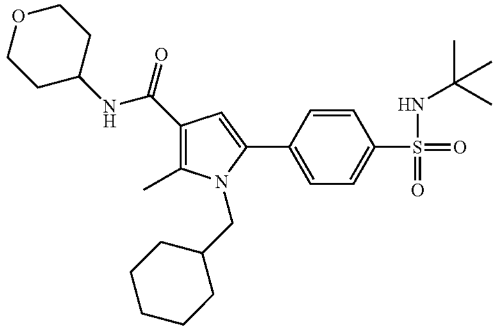 [SMILES: Cc1c(C(=O)NC2CCOCC2)cc(-c2ccc(S(=O)(=O)NC(C)(C)C)cc2)n1CC1CCCCC1] | $^1$H-NMR (400 MHz, $CDCl_3$) δ: 7.91 (d, 2H, J = 8.4 Hz), 7.44 (d, 2H, J = 8.4 Hz), 6.29 (s, 1H), 5.61 (d, 1H, J = 7.6 Hz), 4.49 (s, 1H), 4.17 (m, 1H), 3.98 (m, 2H), 3.80 (m, 2H), 3.52 (m, 2H), 2.62 (s, 3H), 1.98 (m, 2H), 1.59-1.47 (m, 5H), 1.36-1.25 (m, 12H), 0.96 (m, 3H), 0.65 (m, 2H). MS: 516.3 $(M + H)^+$. |
| 17/238 | 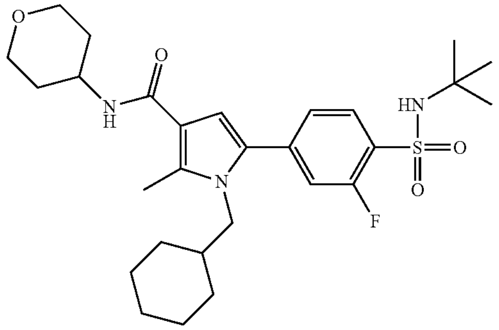 [SMILES: Cc1c(C(=O)NC2CCOCC2)cc(-c2ccc(S(=O)(=O)NC(C)(C)C)c(F)c2)n1CC1CCCCC1] | $^1$H-NMR (400 MHz, $CDCl_3$) δ: 7.92 (t, J = 8.0 Hz, 1H), 7.21 (d, 1H, J = 6.8 Hz), 7.16 (d, 1H, J = 10.0 Hz), 6.32 (s, 1H), 5.55 (d, 1H, J = 8.0 Hz), 4.74 (s, 1H), 4.16 (m, 1H), 3.98 (m, 2H), 3.81 (m, 2H), 3.52 (m, 2H), 2.62 (s, 3H), 1.98 (m, 2H), 1.56-1.47 (m, 5H), 1.37-1.21 (m, 12H), 0.99 (m, 3H), 0.63 (m, 2H). MS: 534.2 $(M + H)^+$. |

-continued

| # | Structure | Analytical data |
|---|---|---|
| 17/239 | 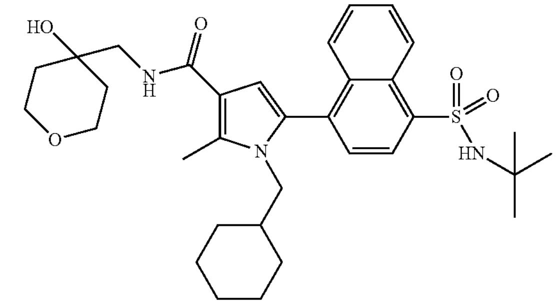 [SMILES: Cc1c(C(=O)NCC2(O)CCOCC2)cc(-c2ccc(S(=O)(=O)NC(C)(C)C)c3ccccc23)n1CC1CCCCC1] | $^1$H-NMR (400 MHz, $CDCl_3$) δ: 8.58 (d, J = 8.4 Hz, 1H), 8.26 (d, J = 7.6 Hz, 1H), 7.67-7.59 (m, 2H), 7.50-7.38 (m, 2H), 6.31-6.23 (m, 1H), 4.66 (s, 1H), 3.76-3.70 (m, 3H), 3.63-3.58 (m, 1H), 3.41 (m, 2H), 3.25-3.19 (m, 1H), 2.59 (s, 3H), 1.60 (m, 4H), 1.42-1.41 (m, 3H), 1.37-1.35 (m, 3H), 1.31-1.10 (m, 9H), 0.87-0.81 (m, 3H), 0.44-0.38 (m, 2H). MS: 596.3 $(M + H)^+$. |
| 17/240 | 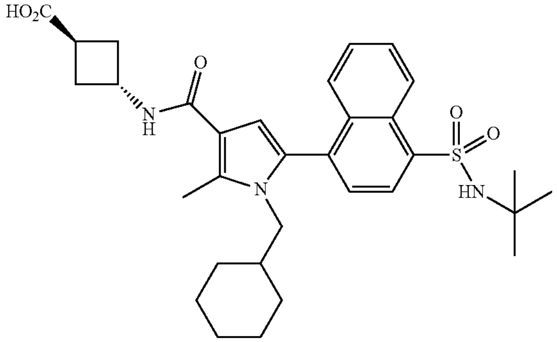 [SMILES: Cc1c(C(=O)N[C@H]2C[C@H](C(=O)O)C2)cc(-c2ccc(S(=O)(=O)NC(C)(C)C)c3ccccc23)n1CC1CCCCC1] | $^1$H-NMR (400 MHz, DMSO-$d_6$) δ: 8.77 (d, J = 8.4 Hz, 1H), 8.24 (d, J = 7.6 Hz, 1H), 7.93-7.91 (m, 1H), 7.85-7.80 (m, 2H), 7.75-7.69 (m, 2H), 7.67-7.59 (m, 1H), 6.75 (s, 1H), 4.56-4.50 (m, 1H), 3.75-3.74 (m, 1H), 3.38 (m, 1H), 2.92-2.87 (m, 1H), 2.58 (s, 3H), 2.41-2.36 (m, 2H), 2.28-2.26 (m, 2H), 1.39-1.34 (m, 3H), 1.17-1.01 (m, 9H), 0.87-0.85 (m, 3H), 0.82-0.74 (m, 3H), 0.50-0.42 (m, 2H). MS: 580.3 $(M + H)^+$. |
| 17/241 | 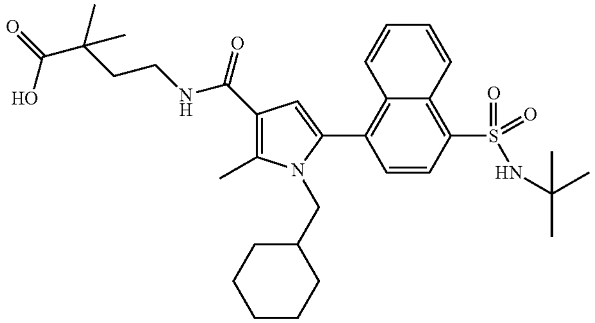 [SMILES: Cc1c(C(=O)NCCC(C)(C)C(=O)O)cc(-c2ccc(S(=O)(=O)NC(C)(C)C)c3ccccc23)n1CC1CCCCC1] | $^1$H-NMR (400 MHz, $CDCl_3$) δ: 8.57 (d, J = 8.4 Hz, 1H), 8.25 (d, J = 7.6 Hz, 1H), 7.68-7.66 (m, 1H), 7.61-7.57 (m, 1H), 7.49-7.45 (m, 1H), 7.39 (d, J = 7.6 Hz, 1H), 6.26 (s, 1H), 6.11 (s, br, 1H), 4.73 (s, 1H), 3.61-3.57 (m, 1H), 3.37 (m, 2H), 3.24-3.18 (m, 1H), 2.56 (s, 3H), 1.79-1.76 (m, 2H), 1.40 (m, 3H), 1.18-1.10 (m, 18H), 0.85-0.79 (m, 3H), 0.42-0.40 (m, 2H). MS: 596.3 $(M + 1)^+$. |
| 17/242 | 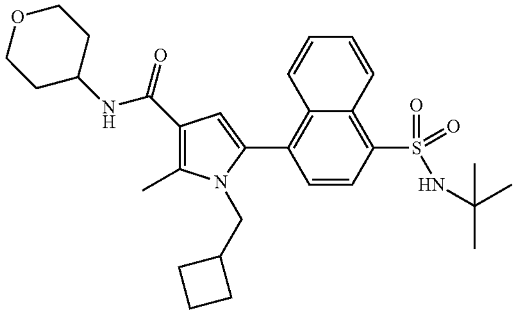 [SMILES: Cc1c(C(=O)NC2CCOCC2)cc(-c2ccc(S(=O)(=O)NC(C)(C)C)c3ccccc23)n1CC1CCC1] | $^1$H-NMR (400 MHz, $CDCl_3$) δ: 8.66 (d, J = 8.4 Hz, 1H), 8.35 (d, J = 7.6 Hz, 1H), 7.77-7.67 (m, 1H), 7.58-7.54 (m, 2H), 7.53-7.51 (m, 1H), 7.50 (d, J = 7.6 Hz, 1H), 6.32 (s, 1H), 5.65-5.63 (m, 1H), 4.69 (s, 1H), 4.21-4.17 (m, 1H), 3.99-3.96 (m, 2H), 3.88-3.82 (m, 1H), 3.56-3.50 (m, 3H), 2.68 (s, 3H), 2.29-2.25 (m, 1H), 2.01-1.97 (m, 2H), 1.77-1.46 (m, 6H), 1.26-1.20 (m, 12H). MS: 538.3 $(M + H)^+$. |
| 17/243 | 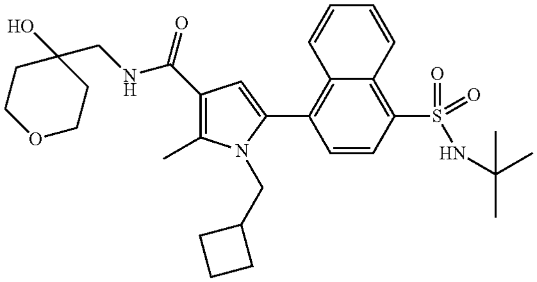 [SMILES: Cc1c(C(=O)NCC2(O)CCOCC2)cc(-c2ccc(S(=O)(=O)NC(C)(C)C)c3ccccc23)n1CC1CCC1] | $^1$H-NMR (400 MHz, $CDCl_3$) δ: 8.66 (d, J = 8.4 Hz, 1H), 8.34 (d, J = 7.6 Hz, 1H), 7.74-7.67 (m, 2H), 7.58-7.47 (m, 2H), 6.36 (s, 1H), 6.23 (m, 1H), 4.68 (s, 1H), 3.87-3.76 (m, 5H), 3.53-3.46 (m, 3H), 2.67 (s, 3H), 2.28-2.24 (m, 1H), 1.72-1.58 (m, 6H), 1.48-1.45 (m, 1H), 1.24 (s, 12H). MS: 568.2 $(M + H)^+$. |

-continued

| # | Structure | Analytical data |
|---|---|---|
| 17/244 | 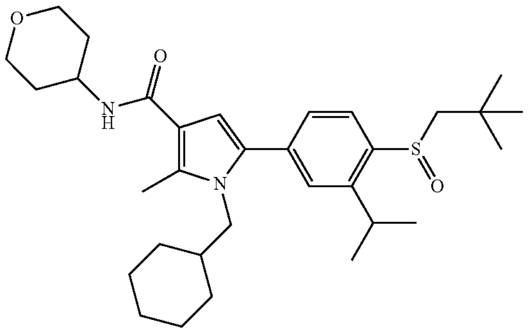 | $^1$H-NMR (400 MHz, $CDCl_3$) δ: 8.21 (d, 1H, J = 8.0 Hz), 7.39 (d, 1H, J = 8.0 Hz), 7.34 (s, 1H), 6.22 (s, 1H), 5.63 (d, 1H, J = 7.2 Hz), 4.18-4.16 (m, 1H), 3.98 (m, 2H), 3.77 (m, 2H), 3.55-3.50 (m, 2H), 2.76-2.63 (m, 5H), 2.01-1.97 (m, 2H), 1.71-1.51 (m, 5H), 1.48 (s, 9H), 1.43-1.32 (m, 3H), 1.24 (s, 9H), 1.04-0.98 (m, 3H), 0.70-0.61 (m, 2H). MS found: 555.0 $(M + 1)^+$. |
| 17/245 | 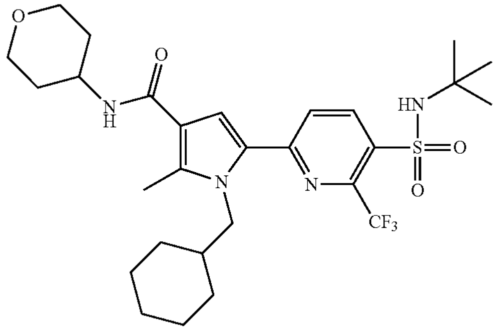 | $^1$H-NMR ($CDCl_3$, 300 MHz) δ: 0.82-0.84 (2H, m), 1.01-1.09 (3H, m), 1.22-1.32 (12H, m), 1.44-1.65 (5H, m), 1.97-2.03 (2H, m), 2.63 (3H, s), 3.53 (2H, m), 3.98-4.03 (2H, m), 4.14-4.21 (1H, m), 4.43-4.49 (2H, m), 4.79 (1H, s), 5.63 (1H, d, J = 7.5 Hz), 6.92 (1H, m), 7.78 (1H, d, J = 9.0 Hz), 8.44 (1H, d, J = 9.0 Hz). MS: 585.2 $(M + 1)^+$. |
| 17/246 | 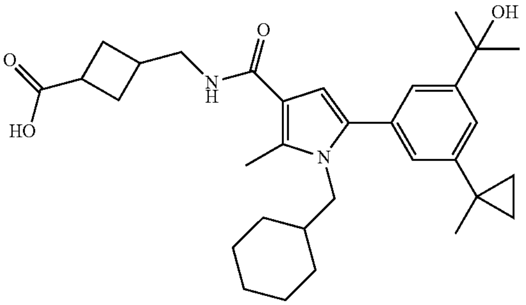 [SMILES: Cc1c(C(=O)NCC2CC(C(=O)O)C2)cc(-c2cc(C(C)(C)O)cc(C3(C)CC3)c2)n1CC1CCCCC1] | $^1$H-NMR (300 MHz, $CD_3OD$) δ: 0.64-0.89 (m, 9H), 1.03-1.10 (m, 3H), 1.30 (s, 3H), 1.54-1.66 (m, 9H), 1.96-2.10 (m, 2H), 2.25-2.33 (m, 2H), 2.49-2.64 (m, 4H), 2.92-3.19 (m, 1H), 3.30-3.43 (m, 2H), 3.81-3.83 (m. 2H), 6.40 (s, 1H), 7.09 (s, 1H), 7.23 (s, 1H), 7.40-7.41 (m, 1H), 7.73-7.76 (m, 1H). MS: 521.3 $(M + 1)^+$. |
| 17/247 | 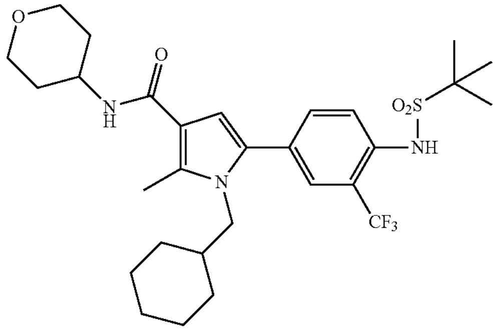 [SMILES: Cc1c(C(=O)NC2CCOCC2)cc(-c2ccc(NS(=O)(=O)C(C)(C)C)c(C(F)(F)F)c2)n1CC1CCCCC1] | $^1$H-NMR ($CDCl_3$, 400 MHz) δ: 8.11 (d, J = 12.0 Hz, 1H), 7.56 (s, 1H), 7.47 (d, J = 12.0 Hz, 1H), 6.50 (s, 1H), 6.23 (s, 1H), 5.60 (d, J = 9.6 Hz, 1H), 4.14-4.20 (m, 1H), 3.97-4.01 (m, 2H), 3.73-3.76 (m, 2H), 3.49-3.57 (m, 2H), 2.62 (s, 3H), 1.97-2.01 (m, 2H), 1.50-1.59 (m, 5H), 1.46 (s, 9H), 1.26-1.39 (m, 3H), 0.72-1.01 (m, 3H), 0.59-0.72 (m, 2H). MS: 584.3 $(M + 1)^+$. |

-continued
| # | Structure | Analytical data |
|---|---|---|
| 17/248 | 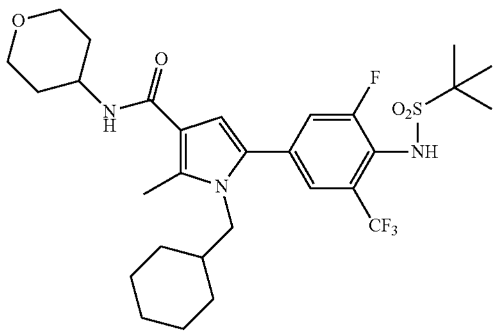 [SMILES: Cc1c(C(=O)NC2CCOCC2)cc(-c2cc(F)c(NS(=O)(=O)C(C)(C)C)c(C(F)(F)F)c2)n1CC1CCCCC1] | $^1$H-NMR ($CDCl_3$, 400 MHz) δ: 7.45 (s, 1H), 7.31 (d, J = 9.6 Hz, 1H), 6.27 (s, 1H), 5.68 (s, 1H), 5.60 (d, J = 7.6 Hz, 1H), 4.13-4.18 (m, 1H), 3.98 (d, J = 11.6 Hz, 2H), 3.77 (d, J = 7.2 Hz, 2H), 3.52 (m, 2H), 2.61 (s, 3H), 1.96-2.00 (m, 2H), 1.53-1.55 (m, 15H), 1.40-1.44 (m, 2H), 1.01-1.03 (m, 3H), 0.66-0.71 (m, 2H). MS: 602.2 $(M + 1)^+$. |
| 17/249 | 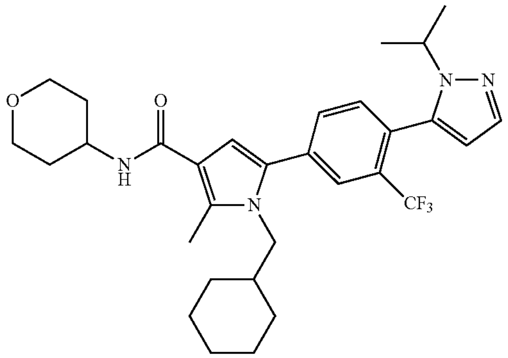 [SMILES: Cc1c(C(=O)NC2CCOCC2)cc(-c2ccc(-c3ccnn3C(C)C)c(C(F)(F)F)c2)n1CC1CCCCC1] | $^1$H-NMR (400 MHz, $CDCl_3$) δ: 7.77 (s, 1H), 7.64 (s, 1H), 7.61-7.55 (m, 1H), 7.38 (d, J = 8.0 Hz, 1H), 6.35-6.30 (m, 2H), 5.64 (d, 1H, J = 7.6 Hz), 4.23-4.05 (m, 2H), 4.02-3.96 (m, 2H), 3.83 (d, 2H, J = 7.2 Hz), 3.58-3.48 (m, 2H), 2.64 (s, 3H), 2.03-1.96 (m, 2H), 1.62-1.36 (m, 14H), 1.07-1.00 (m, 3H), 0.76-0.63 (m, 2H). MS: 557.3 $(M + H)^+$. |
| 17/250 | 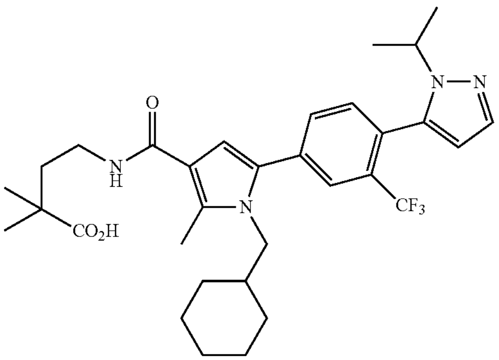 [SMILES: Cc1c(C(=O)NCCC(C)(C)C(=O)O)cc(-c2ccc(-c3ccnn3C(C)C)c(C(F)(F)F)c2)n1CC1CCCCC1] | $^1$H-NMR (400 MHz, $CDCl_3$) δ: 7.76 (s, 1H), 7.65 (s, 1H), 7.56 (d, 1H, J = 8.0 Hz), 7.35 (d, 1H, J = 7.6 Hz), 6.34-6.26 (m, 2H), 6.07 (br s, 1H), 4.15-4.08 (m, 1H), 3.82 (m, 2H), 3.48 (br s, 2H), 2.63 (s, 3H), 1.93-1.86 (m, 2H), 1.62-1.53 (m, 3H), 1.46-1.34 (m, 9H), 1.28 (m, 6H), 1.24-0.96 (m, 3H), 1.71-0.66 (m, 2H). MS: 587.3 $(M + H)^+$. |
| 17/251 | 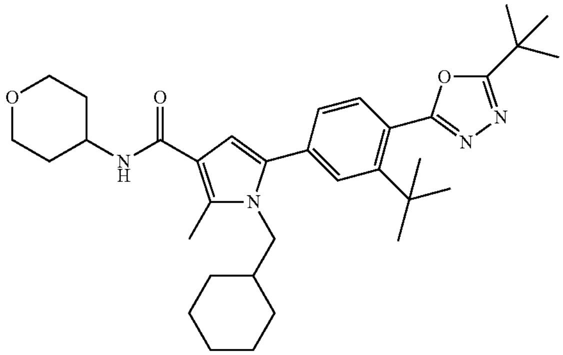 [SMILES: Cc1c(C(=O)NC2CCOCC2)cc(-c2ccc(-c3nnc(C(C)(C)C)o3)c(C(C)(C)C)c2)n1CC1CCCCC1] | $^1$H-NMR (400 MHz, DMSO-$d_6$) δ: 7.59 (s, 1H), 7.53-7.49 (m, 2H), 7.42-7.37 (m, 1H), 6.69 (s, 1H), 4.01-3.82 (m, 5H), 3.35 (m, 2H), 2.54 (s, 3H), 1.74-1.70 (m, 2H), 1.58-1.43 (m, 5H), 1.42 (s, 9H), 1.31-1.20 (m, 12H), 1.02-0.92 (m, 3H), 0.67 (m, 2H). MS: 561.3 $(M + 1)^+$. |

-continued

| # | Structure | Analytical data |
|---|---|---|
| 17/252 | 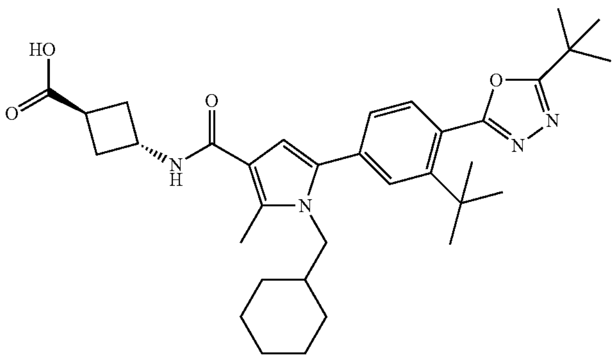 [SMILES: Cc1c(C(=O)N[C@H]2C[C@H](C(=O)O)C2)cc(-c2ccc(-c3nnc(C(C)(C)C)o3)c(C(C)(C)C)c2)n1CC1CCCCC1] | $^1$H-NMR (400 MHz, $CDCl_3$) δ: 7.53 (s, 1H), 7.44 (d, 1H, J = 7.6 Hz), 7.25-7.21 (m, 1H), 6.26 (s, 1H), 6.05 (br s, 1H), 4.79 (br s, 1H), 3.77 (m, 1H), 3.15-3.05 (m, 1H), 2.81-2.72 (m, 2H), 2.60 (s, 3H), 2.33-2.28 (m, 2H), 1.60-1.43 (m, 12H), 1.38-1.22 (m, 12H), 1.05-0.96 (m, 3H), 0.62 (m, 2H). MS: 574.8 $(M + 1)^+$. |
| 17/253 | 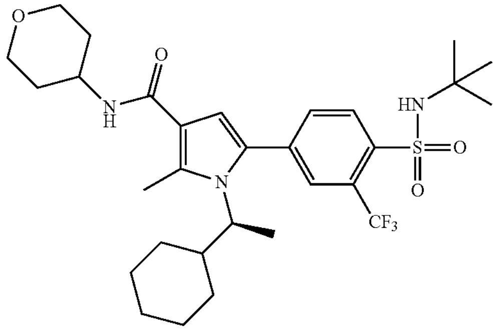 [SMILES: Cc1c(C(=O)NC2CCOCC2)cc(-c2ccc(S(=O)(=O)NC(C)(C)C)c(C(F)(F)F)c2)n1[C@@H](C)C1CCCCC1] | $^1$H-NMR (400 MHz, $CDCl_3$) δ: 0.35-0.50 (m, 1H), 0.65-0.76 (m, 1H), 1.02-1.03 (m, 3H), 1.28 (s, 9H), 1.47-1.53 (m, 5H), 1.58-1.65 (m, 3H), 1.68-1.83 (m, 3H), 1.98 (m, 2H), 2.71 (s, 3H), 3.52 (m, 2H), 3.80-3.84 (m, 1H), 3.97-4.00 (m, 2H), 4.11-4.20 (m, 1H), 4.71 (s, 1H), 5.61 (d, J = 7.2 Hz, 1H), 6.27 (s, 1H), 7.52-7.57 (m, 1H), 7.74 (s, 1H), 8.31 (d, J = 8.4 Hz, 1H). MS: 598.3 $(M + 1)^+$. |
| 17/254 | 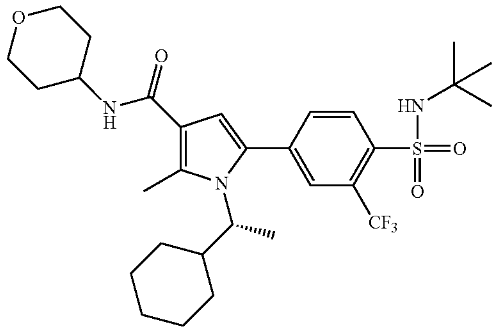 [SMILES: Cc1c(C(=O)NC2CCOCC2)cc(-c2ccc(S(=O)(=O)NC(C)(C)C)c(C(F)(F)F)c2)n1[C@H](C)C1CCCCC1] | $^1$H-NMR (400 MHz, $CDCl_3$) δ: 0.33-0.48 (m, 1H), 0.66-0.75 (m, 1H), 0.98-1.06 (m, 3H), 1.28 (s, 9H), 1.47-1.53 (m, 5H), 1.58-1.65 (m, 3H), 1.68-1.83 (m, 3H), 1.98 (m, 2H), 2.71 (s, 3H), 3.53 (m, 2H), 3.79-3.84 (m, 1H), 3.97-4.00 (m, 2H), 4.14-4.18 (m, 1H), 4.71 (s, 1H), 5.61 (d, J = 7.2 Hz, 1H), 6.27 (s, 1H), 7.52-7.57 (m, 1H), 7.75 (s, 1H), 8.31 (d, J = 8.4 Hz, 1H). MS: 598.3 $(M + 1)^+$. |
| 17/255 | 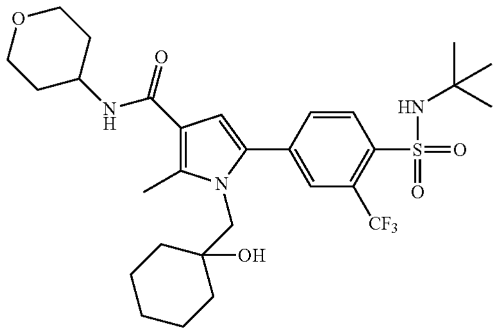 [SMILES: Cc1c(C(=O)NC2CCOCC2)cc(-c2ccc(S(=O)(=O)NC(C)(C)C)c(C(F)(F)F)c2)n1CC1(O)CCCCC1] | $^1$H-NMR (400 MHz, $CDCl_3$) δ: 0.96-1.06 (m, 2H), 1.26 (s, 11H), 1.29-1.40 (m, 4H), 1.47-1.56 (m, 3H), 2.01-1.96 (m, 2H), 2.70 (s, 3H), 3.49-3.55 (m, 3H), 4.02-3.96 (m, 2H), 4.03 (s, 2H), 4.13-4.21 (m, 1H), 4.69 (s, 1H), 5.62 (d, J = 8.0 Hz, 1H), 6.40 (s, 1H), 7.61 (d, J = 8.0 Hz, 1H), 7.80 (s, 1H), 8.31 (d, J = 8.0 Hz, 1H). MS: 600.3 $(M + 1)^+$. |

-continued

| # | Structure | Analytical data |
|---|---|---|
| 17/256 | 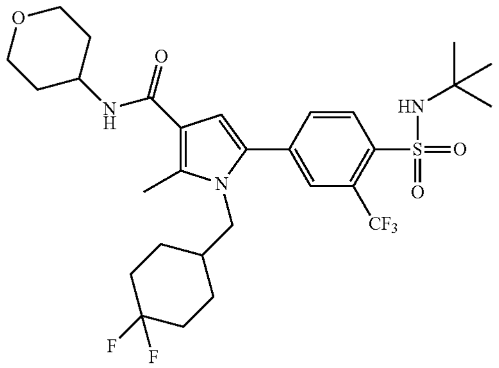 [SMILES: Cc1c(C(=O)NC2CCOCC2)cc(-c2ccc(S(=O)(=O)NC(C)(C)C)c(C(F)(F)F)c2)n1CC1CCC(F)(F)CC1] | $^1$H-NMR (300 MHz, $CDCl_3$) δ: 0.99-1.02 (m, 13H), 1.26 (s, 9H), 1.28-1.47 (m, 4H), 1.48-1.57 (m, 2H), 1.94-2.00 (m, 4H), 2.64 (s, 3H), 3.52 (m, 2.0 Hz, 2H), 3.90 (m, 2H), 3.97-4.02 (m, 2H), 4.14-4.17 (m, 1H), 4.72 (s, 1H), 5.62 (d, J = 7.6 Hz, 1H), 6.39 (s, 1H), 7.62 (dd, J = 8.0 Hz, 1.6 Hz, 1H), 7.79 (d, J = 1.2 Hz, 1H), 8.34 (d, J = 8.0 Hz, 1H). MS: 620.3 $(M + 1)^+$. |
| 17/257 | 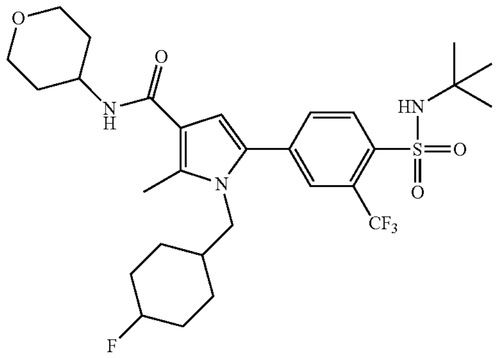 [SMILES: Cc1c(C(=O)NC2CCOCC2)cc(-c2ccc(S(=O)(=O)NC(C)(C)C)c(C(F)(F)F)c2)n1CC1CCC(F)CC1] | $^1$H-NMR (300 MHz, $CDCl_3$) δ: 0.68-0.77 (m, 2H), 0.88-1.30 (m, 13H), 1.35-1.48 (m, 3H), 1.51-1.58 (m, 2H), 1.88-2.04 (m, 4H), 2.63-2.64 (m, 3H), 3.52 (m, 2H), 3.83-3.88 (m, 2H), 4.02-3.96 (m, 2H), 4.11-4.44 (m, 2H), 4.80-4.70 (m, 1H), 5.63 (d, J = 7.6 Hz, 1H), 6.39 (s, 1H), 7.60-7.63 (m, 1H), 7.79-7.80 (m, 1H), 8.32 (d, J = 8.0 Hz, 1H). MS: 602.3 $(M + 1)^+$. |
| 17/258 | 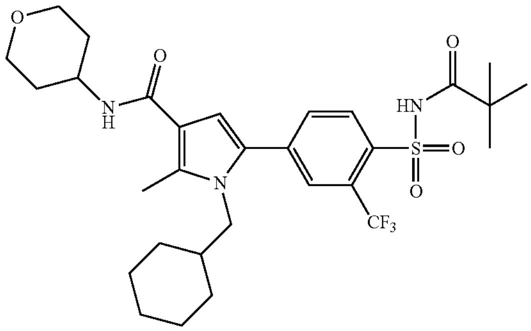 [SMILES: Cc1c(C(=O)NC2CCOCC2)cc(-c2ccc(S(=O)(=O)NC(=O)C(C)(C)C)c(C(F)(F)F)c2)n1CC1CCCCC1] | $^1$H-NMR (400 MHz, $CDCl_3$) δ: 8.45 (d, J = 8.4 Hz, 1H), 8.18 (s, 1H), 7.74 (s, 1H), 7.65-7.60 (m, 1H), 6.33 (s, 1H), 5.57 (d, 1H, J = 8.0 Hz), 4.12-4.02 (m, 1H), 3.95-3.89 (m, 2H), 3.76 (d, 2H, J = 6.8 Hz), 3.49-3.43 (m, 2H), 2.56 (s, 3H), 1.94-1.90 (m, 2H), 1.51-1.45 (m, 5H), 1.28-1.25 (m, 3H), 1.10 (s, 9H), 0.94-0.93 (m, 3H), 0.59 (m, 2H). MS: 612.3 $(M + H)^+$. |
| 17/259 | 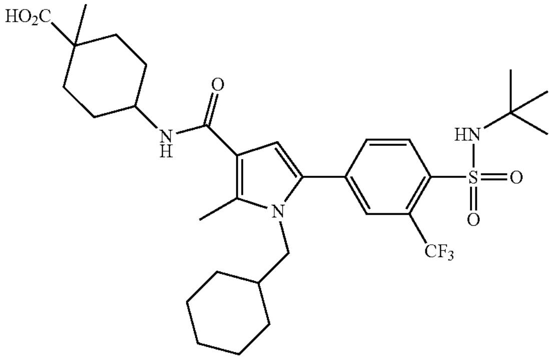 [SMILES: Cc1c(C(=O)NC2CCC(C)(C(=O)O)CC2)cc(-c2ccc(S(=O)(=O)NC(C)(C)C)c(C(F)(F)F)c2)n1CC1CCCCC1] | $^1$H-NMR ($CDCl_3$, 400 MHz) δ: 0.56-0.65 (m, 2H), 0.96-1.03 (m, 3H), 1.25 (s, 14H), 1.27-1.42 (m, 8H), 1.62-1.64 (m, 2H), 1.98-2.02 (m, 2H), 2.22-2.24 (m, 2H), 2.62 (s, 3H), 3.80 (d, J = 7.2 Hz, 2H), 3.91-3.95 (m, 1H), 4.81 (s, 1H), 5.57 (d, J = 8.4 Hz, 1H), 6.33 (s, 1H), 7.60 (dd, J = 8.4 Hz, 1.6 Hz, 1H), 7.79 (s, 1H), 8.30 (d, J = 8.4 Hz, 1H). MS: 640.3 $(M + 1)^+$. |

-continued

| # | Structure | Analytical data |
|---|---|---|
| 17/260 | 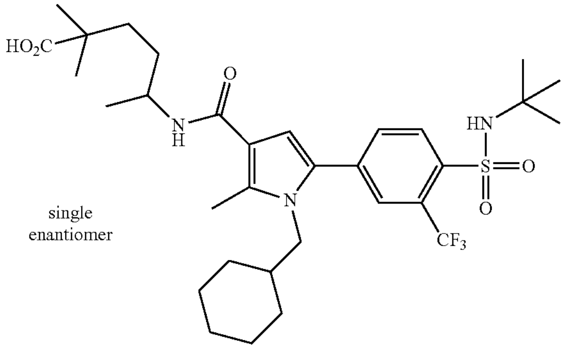 single enantiomer | $^1$H-NMR ($CDCl_3$, 400 MHz) δ: 0.59-0.67 (m, 3H), 0.94-1.03 (m, 5H), 1.14-1.37 (m, 21H), 1.60-1.62 (m, 2H), 2.04-2.12 (m, 1H), 2.63 (s, 3H), 3.80 (d, 2H, J = 6.6 Hz), 4.33 (m, 1H), 4.74 (s, 1H), 5.81 (d, 1H, J = 8.4 Hz), 6.35 (s, 1H), 7.63 (d, 1H, J = 8.4 Hz), 7.80 (s, 1H), 8.30 (d, 1H, J = 8.4 Hz). MS: 628.3 $(M + 1)^+$. Chiral HPLC (hexane/ethanol/$NHEt_2$ = 70/30/0.2 on Chiralpak IC 5 μm 4.6 × 250 mm, 1 mL/min, T = 30° C.): $R_t$ = 7.646 min (2nd eluting enantiomer). |
| 17/261 | 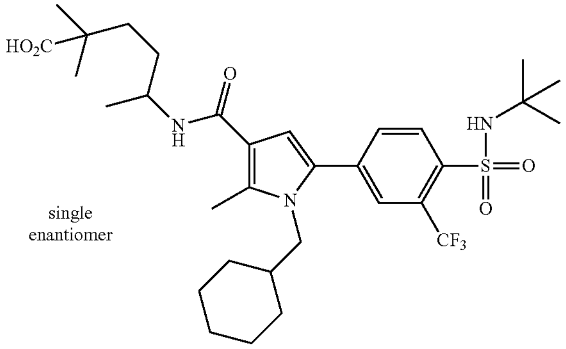 single enantiomer | $^1$H-NMR ($CDCl_3$, 400 MHz) δ: 0.59-0.67 (m, 3H), 0.94-1.03 (m, 5H), 1.14-1.37 (m, 21H), 1.60-1.62 (m, 2H), 2.04-2.12 (m, 1H), 2.63 (s, 3H), 3.80 (d, 2H, J = 6.6 Hz), 4.33 (m, 1H), 4.74 (s, 1H), 5.81 (d, 1H, J = 8.4 Hz), 6.35 (s, 1H), 7.63 (d, 1H, J = 8.4 Hz), 7.80 (s, 1H), 8.30 (d, 1H, J = 8.4 Hz). MS: 628.3 $(M + 1)^+$. Chiral HPLC (hexane/ethanol/$NHEt_2$ = 70/30/0.2 on Chiralpak IC 5 μm 4.6 × 250 mm, 1 mL/min, T = 30° C.): $R_t$ = 6.256 min (1st eluting enantiomer). |
| 17/262 | 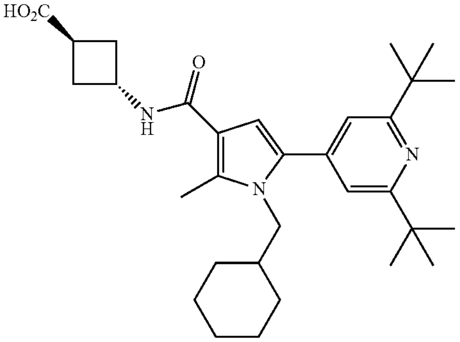 [SMILES: Cc1c(C(=O)N[C@H]2C[C@H](C(=O)O)C2)cc(-c2cc(C(C)(C)C)nc(C(C)(C)C)c2)n1CC1CCCCC1] | $^1$H-NMR ($CDCl_3$, 400 MHz) δ: 7.04 (s, 2H), 6.29 (s, 1H), 6.00 (d, J = 7.6 Hz, 1H), 4.82-4.75 (m, 1H), 3.78 (d, J = 7.2 Hz, 2H), 3.11-3.06 (m, 1H), 2.84-2.75 (m, 1H), 2.60 (s, 3H), 2.35-2.24 (m, 2H), 1.57-1.51 (m, 2H), 1.37 (s, 18H), 1.33-1.25 (m, 4H), 1.02-0.84 (m, 3H), 0.69-0.64 (m, 2H). MS: 508.3 (M + 1)+; |
| 17/263 | 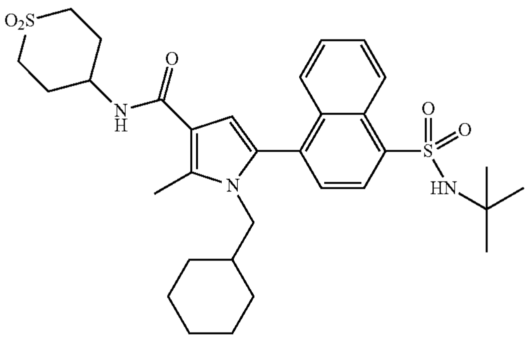 [SMILES: Cc1c(C(=O)NC2CCS(=O)(=O)CC2)cc(-c2ccc(S(=O)(=O)NC(C)(C)C)c3ccccc23)n1CC1CCCCC1] | $^1$H-NMR (400 MHz, $CDCl_3$) δ: 8.64 (d, 1H, J = 8.4 Hz), 8.33 (d, 1H, J = 7.6 Hz), 7.74-7.64 (m, 2H), 7.60-7.50 (m, 2H), 6.37 (s, 1H), 5.89 (d, 1H, J = 8.0 Hz), 4.85 (s, 1H), 4.35-4.29 (m, 1H), 3.72-3.63 (m, 1H), 3.33-3.24 (m, 1H), 3.20-3.13 (m, 4H), 2.66 (s, 3H), 2.42-2.38 (m, 2H), 2.22-2.18 (m, 2H), 1.52-1.45 (m, 3H), 1.30-1.13 (m, 12H), 0.91-0.86 (m, 3H), 0.52-0.42 (m, 2H). MS: 614.2 $(M + 1)^+$. |

-continued

| # | Structure | Analytical data |
|---|---|---|
| 17/264 | 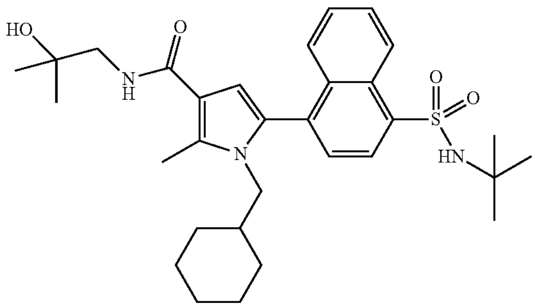 [SMILES: Cc1c(C(=O)NCC(C)(C)O)cc(-c2ccc(S(=O)(=O)NC(C)(C)C)c3ccccc23)n1CC1CCCCC1] | $^1$H-NMR (400 MHz, $CDCl_3$) δ: 8.65 (d, 1H, J = 8.4 Hz), 8.34 (d, 1H, J = 7.6 Hz), 7.78-7.74 (m, 1H), 7.71-7.66 (m, 1H), 7.59-7.52 (m, 1H), 7.49 (d, J = 7.6 Hz, 1H), 6.38 (s, 1H), 6.24 (br s, 1H), 4.63 (s, 1H), 3.70-3.66 (m, 1H), 3.45-3.40 (m, 2H), 3.33-3.26 (m, 1H), 2.67 (s, 3H), 1.52-1.47 (m, 3H), 1.33-1.12 (m, 18H), 0.91-0.87 (m, 3H), 0.53-0.45 (m, 2H). MS: 554.3 $(M + 1)^+$. |
| 17/265 | 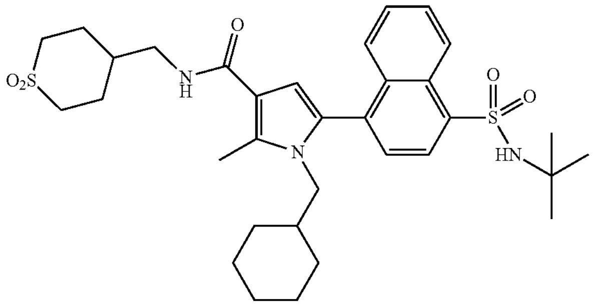 [SMILES: Cc1c(C(=O)NCC2CCS(=O)(=O)CC2)cc(-c2ccc(S(=O)(=O)NC(C)(C)C)c3ccccc23)n1CC1CCCCC1] | $^1$H-NMR (400 MHz, $CDCl_3$) δ: 8.65 (d, 1H, J = 8.4 Hz), 8.34 (d, 1H, J = 7.6 Hz), 7.75-7.68 (m, 2H), 7.58-7.52 (m, 1H), 7.48 (d, J = 7.6 Hz, 1H), 6.33 (s, 1H), 6.04-5.98 (m, 1H), 4.64 (s, 1H), 3.70-3.66 (m, 1H), 3.32-3.25 (m, 3H), 3.12-2.92 (m, 4H), 2.66 (s, 3H), 2.21-1.89 (m, 5H), 1.48 (m, 3H), 1.30-1.11 (m, 12H), 0.90 (m, 3H), 0.49 (m, 2H). MS: 628.3 $(M + 1)^+$. |
| 17/266 | 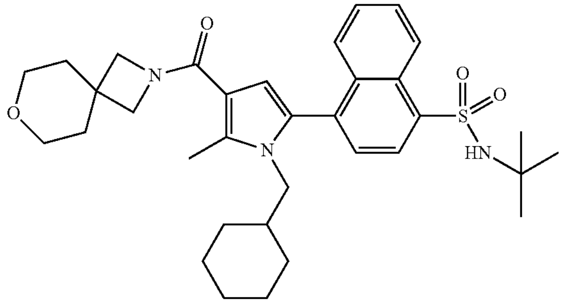 [SMILES: Cc1c(C(=O)N2CC3(CCOCC3)C2)cc(-c2ccc(S(=O)(=O)NC(C)(C)C)c3ccccc23)n1CC1CCCCC1] | $^1$H-NMR (400 MHz, $CDCl_3$) δ: 8.64 (d, 1H, J = 8.8 Hz), 8.34 (d, 1H, J = 7.6 Hz), 7.77-7.65 (m, 2H), 7.59-7.46 (m, 2H), 6.35 (s, 1H), 4.63 (s, 1H), 4.01 (s, 4H), 3.73-3.56 (m, 5H), 3.29 (m, 1H), 2.65 (s, 3H), 1.80 (m, 4H), 1.78 (m, 3H), 1.28-1.18 (m, 12H), 0.88 (m, 3H), 0.47 (m, 2H). MS: 592.3 $(M + 1)^+$. |
| 17/267 | 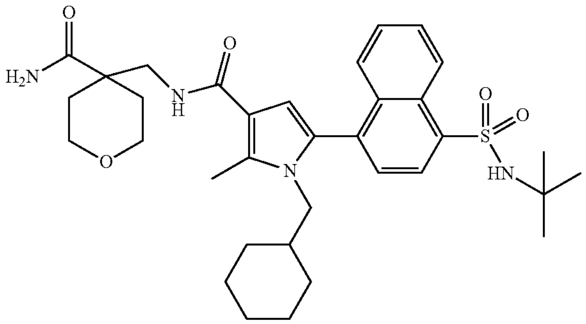 [SMILES: Cc1c(C(=O)NCC2(C(N)=O)CCOCC2)cc(-c2ccc(S(=O)(=O)NC(C)(C)C)c3ccccc23)n1CC1CCCCC1] | $^1$H-NMR (400 MHz, DMSO-$d_6$) δ: 8.77 (d, 1H, J = 8.8 Hz), 8.24 (d, 1H, J = 7.6 Hz), 7.86 (s, 1H), 7.81-7.59 (m, 4H), 7.45 (m, 1H), 7.30 (s, 1H), 7.02 (s, 1H), 6.69 (s, 1H), 3.79-3.66 (m, 3H), 3.38-3.22 (m, 5H), 2.58 (s, 3H), 1.92 (d, 2H, J = 15.6 Hz), 1.50-1.37 (m, 5H), 1.19-1.13 (m, 3H), 1.02 (s, 9H), 0.82-0.73 (m, 3H), 0.45 (m, 2H). MS: 623.3 $(M + 1)^+$. |
| 17/268 | 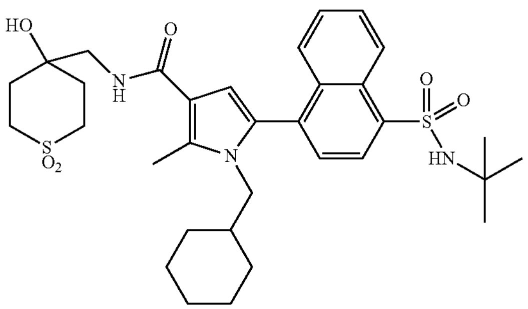 [SMILES: Cc1c(C(=O)NCC2(O)CCS(=O)(=O)CC2)cc(-c2ccc(S(=O)(=O)NC(C)(C)C)c3ccccc23)n1CC1CCCCC1] | $^1$H-NMR (400 MHz, DMSO-$d_6$) δ: 8.65 (d, 1H, J = 8.8 Hz), 8.33 (d, 1H, J = 7.6 Hz), 7.69 (m, 2H), 7.56 (m, 1H), 7.46 (d, 1H, J = 7.6 Hz), 6.39-6.31 (m, 2H), 4.70 (s, 1H), 3.68-3.64 (m, 1H), 3.54-3.42 (m, 4H), 3.30 (m, 1H), 2.87 (m, 2H), 2.66 (s, 3H), 2.18-2.00 (m, 4H), 1.48 (m, 3H), 1.25-1.21 (m, 3H), 1.17 (s, 9H), 0.89 (m, 3H), 0.54 (m, 2H). MS: 644.2 $(M + 1)^+$. |

-continued

| # | Structure | Analytical data |
|---|---|---|
| 17/269 | 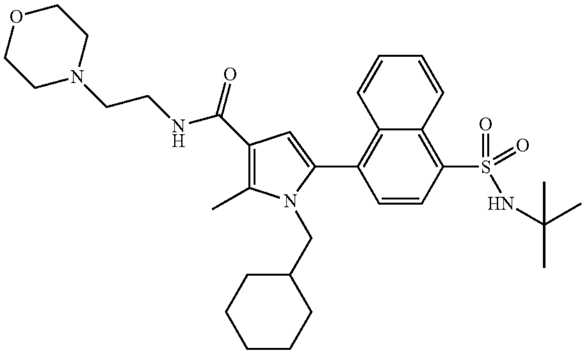 [SMILES: Cc1c(C(=O)NCCN2CCOCC2)cc(-c2ccc(S(=O)(=O)NC(C)(C)C)c3ccccc23)n1CC1CCCCC1] | $^1$H-NMR (400 MHz, $CDCl_3$) δ: 8.63 (d, 1H, J = 8.4 Hz), 8.32 (d, 1H, J = 7.6 Hz), 7.73-7.62 (m, 2H), 7.52 (m, 1H), 7.48-7.38 (m, 2H), 6.45 (s, 1H), 4.85 (s, 1H), 3.99-3.63 (m, 9H), 3.35-3.24 (m, 3H), 2.91 (m, 2H), 2.64 (s, 3H), 1.49-1.45 (m, 3H), 1.29-1.13 (m, 12H), 0.88 (m, 3H), 0.47 (m, 2H). MS: 595.5 $(M + 1)^+$. |
| 17/270 | 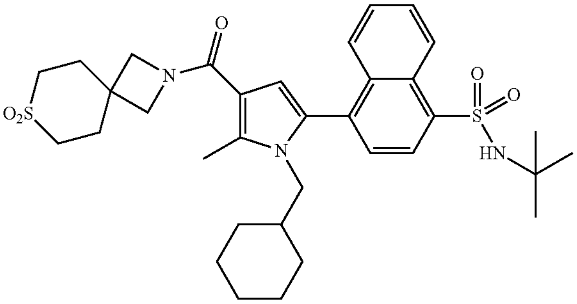 [SMILES: Cc1c(C(=O)N2CC3(CCS(=O)(=O)CC3)C2)cc(-c2ccc(S(=O)(=O)NC(C)(C)C)c3ccccc23)n1CC1CCCCC1] | $^1$H-NMR (400 MHz, $CDCl_3$) δ: 8.65 (d, 1H, J = 8.4 Hz), 8.35 (d, 1H, J = 7.6 Hz), 7.69 (m, 2H), 7.58 (m, 1H), 7.49 (m, 1H), 6.30 (s, 1H), 4.76 (s, 1H), 4.06 (m, 4H), 3.69 (m, 1H), 3.30 (m, 1H), 3.02 (m, 4H), 2.65 (s, 3H), 2.39-2.35 (m, 4H), 1.48 (m, 3H), 1.29-1.18 (m, 12H), 0.88 (m, 3H), 0.48 (m, 2H). MS: 640.4 $(M + 1)^+$. |
| 17/271 | 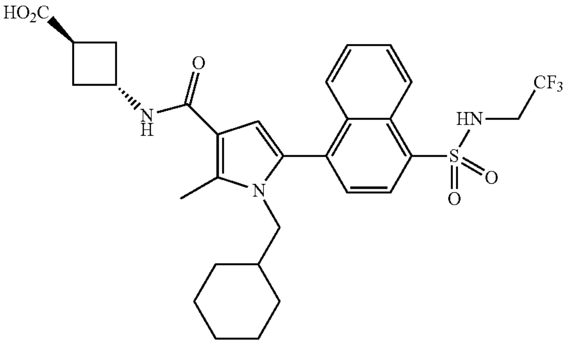 [SMILES: Cc1c(C(=O)N[C@H]2C[C@H](C(=O)O)C2)cc(-c2ccc(S(=O)(=O)NCC(F)(F)F)c3ccccc23)n1CC1CCCCC1] | $^1$H-NMR ($CDCl_3$, 400 MHz) δ: 8.64 (d, J = 8.4 Hz, 1H), 8.30 (d, J = 7.6 Hz, 1H), 7.80 (m, 1H), 7.74 (m, 1H), 7.59 (m, 1H), 7.49 (d, J = 8.4 Hz, 1H), 6.35 (s, 1H), 5.99 (m, 1H), 5.31 (m, 1H), 4.80 (m, 1H), 3.75-3.60 (n, 3H), 3.30 (m, 1H), 3.08 (m, 1H), 2.82-2.75 (m, 2H), 2.67 (s, 3H), 2.25 (m, 2H), 1.56-1.46 (m, 3H), 1.27-1.17 (m, 6H), 0.95-0.75 (m, 4H), 0.45 (m, 2H). MS: 606.2 (M + 1)+; |
| 17/272 | 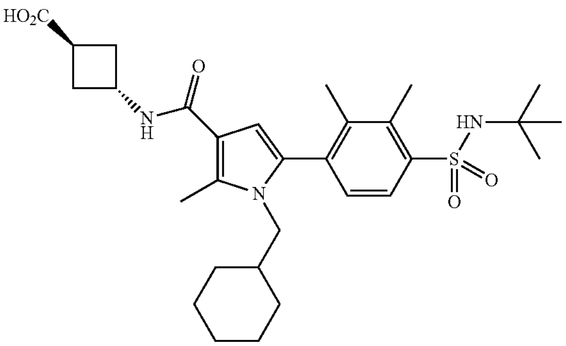 [SMILES: Cc1c(-c2cc(C(=O)N[C@H]3C[C@H](C(=O)O)C3)c(C)n2CC2CCCCC2)ccc(S(=O)(=O)NC(C)(C)C)c1C] | $^1$H-NMR (400 MHz, $CD_3OD$) δ: 0.50-0.58 (m, 2H), 0.88-0.92 (m, 3H), 1.08 (s, 9H), 1.19-1.26 (m, 4H), 1.45-1.46 (m, 3H), 2.06 (s, 3H), 2.24-2.32 (m, 2H), 2.44 (s, 3H), 2.48-2.52 (m, 2H), 2.53 (s, 3H), 2.93 (m, 1H), 3.20-3.25 (m, 2H), 3.50-3.61 (m, 1H), 4.58 (m, 1H), 6.33 (s, 1H), 7.12 (d, J = 8.0 Hz, 1H), 7.81 (d, J = 8.0 Hz, 1H). MS: 558.2 $[M + 1]^+$. |

-continued

| # | Structure | Analytical data |
|---|---|---|
| 17/273 | 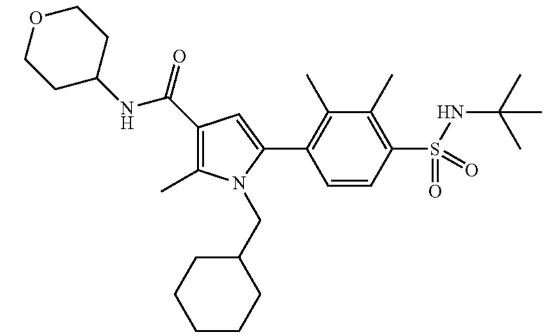 [SMILES: Cc1c(-c2cc(C(=O)NC3CCOCC3)c(C)n2CC2CCCCC2)ccc(S(=O)(=O)NC(C)(C)C)c1C] | $^1$H-NMR (400 MHz, $CDCl_3$) δ: 0.54-0.64 (m, 2H), 0.98-1.00 (m, 3H), 1.07 (s, 9H), 1.18-1.38 (m, 3H), 1.46-1.56 (m, 3H), 1.96-2.00 (m, 2H), 2.12 (s, 3H), 2.62 (m, 6H), 3.26 (br s, 1H), 3.49-3.63 (m, 3H), 3.96-3.99 (m, 2H), 4.14-4.18 (m, 1H), 4.47 (s, 1H), 5.60 (d, J = 8.0 Hz, 1H), 6.12 (s, 1H), 7.18 (d, J = 8.0 Hz, 1H), 7.96 (d, J = 8.0 Hz, 1H). MS: 544.3 $[M + 1]^+$. |
| 17/274 | 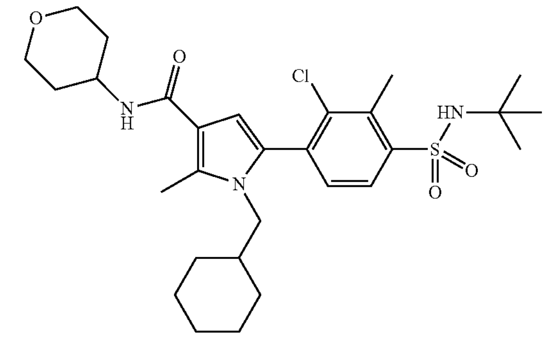 [SMILES: Cc1c(S(=O)(=O)NC(C)(C)C)ccc(-c2cc(C(=O)NC3CCOCC3)c(C)n2CC2CCCCC2)c1Cl] | $^1$H-NMR (400 MHz, $CDCl_3$) δ: 0.57-0.63 (m, 2H), 0.96-1.04 (m, 3H), 1.25 (s, 9H), 1.34-1.42 (m, 3H), 1.46-1.58 (m, 5H), 1.97-2.00 (m, 2H), 2.62 (s, 3H), 2.77 (s, 3H), 3.49-3.55 (m, 3H), 3.98 (m, 2H), 4.11-4.18 (m, 1H), 4.51 (s, 1H), 5.60 (d, J = 7.6 Hz, 1H), 6.21 (s, 1H), 7.28 (d, J = 8.0 Hz, 1H), 8.03 (d, J = 8.0 Hz, 1H), MS: 564.2 $[M + 1]^+$. |
| 17/275 | 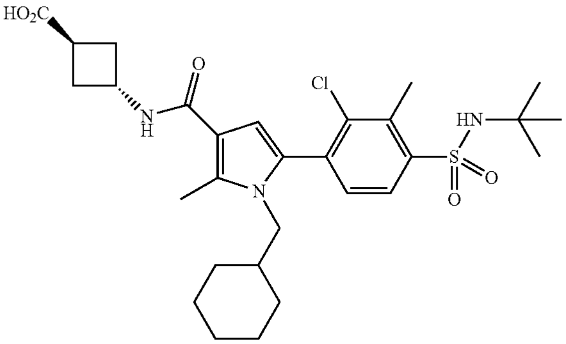 | $^1$H-NMR (400 MHz, $CDCl_3$) δ: 0.57-0.61 (m, 2H), 0.98-1.00 (m, 3H), 1.25 (s, 9H), 1.33-1.35 (m, 3H), 1.51-1.59 (m, 3H), 2.26-2.33 (m, 2H), 2.60 (s, 3H), 2.77-2.80 (m, 5H), 3.05-3.13 (m, 1H), 3.51-3.55 (m, 1H), 4.53 (s, 1H), 4.73-4.81 (m, 1H), 5.94-5.95 (m, 1H), 6.23 (s, 1H), 7.27 (d, J = 8.0 Hz, 1H). 8.04 (d, J = 8.0 Hz, 1H). MS: 578.2 $[M + 1]^+$. |
| 17/276 | 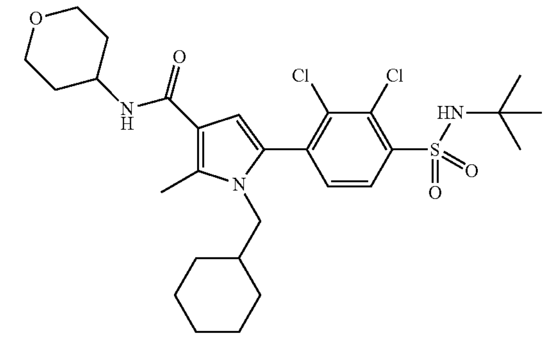 [SMILES: Cc1c(C(=O)NC2CCOCC2)cc(-c2ccc(S(=O)(=O)NC(C)(C)C)c(Cl)c2Cl)n1CC1CCCCC1] | $^1$H-NMR (400 MHz, $CDCl_3$) δ: 0.59-0.61 (m, 2H), 0.99-1.04 (m, 3H), 1.19 (s, 9H), 1.23-1.36 (m, 5H), 1.46-1.53 (m, 3H), 1.98 (m, 2H), 2.62 (s, 3H), 3.47-3.55 (m, 4H), 3.96-3.99 (m, 2H), 4.15-4.18 (m, 1H), 5.07 (s, 1H), 5.59 (d, J = 7.6 Hz, 1H), 6.26 (s, 1H), 7.37 (d, J = 8.4 Hz, 1H), 8.10 (d, J = 8.4 Hz, 1H). MS: 584.2 $[M + 1]^+$. |

-continued

| # | Structure | Analytical data |
|---|---|---|
| 17/277 | 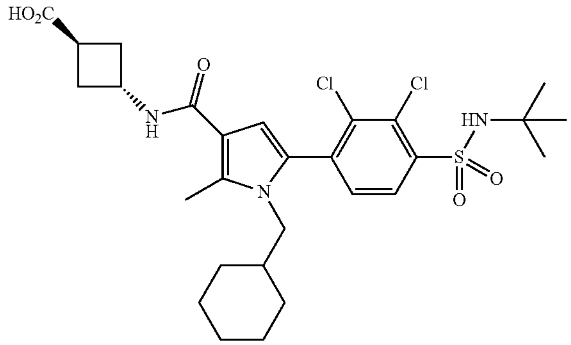 [SMILES: Cc1c(C(=O)N[C@H]2C[C@H](C(=O)O)C2)cc(-c2ccc(S(=O)(=O)NC(C)(C)C)c(Cl)c2Cl)n1CC1CCCCC1] | $^1$H-NMR (400 MHz, $CDCl_3$ + $D_2O$) δ: 0.58-0.60 (m, 2H), 0.88-0.89 (m, 3H), 1.29 (s, 9H), 1.32-1.35 (m, 3H), 1.51-1.77 (m, 2H), 2.30 (br s, 2H), 2.60 (s, 3H), 2.73-2.78 (m, 2H), 3.07-3.10 (m, 1H), 3.47-3.54 (m, 3H), 4.73-4.76 (m, 1H), 6.28 (s, 1H), 7.36 (d, J = 8.4 Hz, 1H), 8.10 (d, J = 8.4 Hz, 1H). MS: 598.2 $[M + 1]^+$. |
| 17/278 | 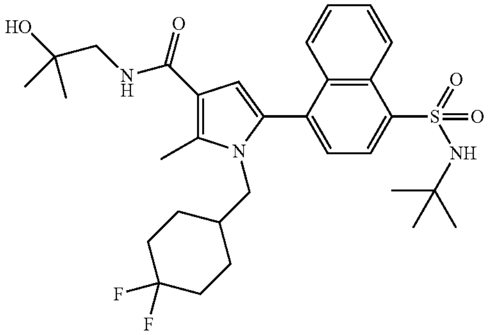 [SMILES: Cc1c(C(=O)NCC(C)(C)O)cc(-c2ccc(S(=O)(=O)NC(C)(C)C)c3ccccc23)n1CC1CCC(F)(F)CC1] | $^1$H-NMR (300 MHz, $CDCl_3$) δ: 8.67 (d, J = 8.4 Hz, 1H), 8.35 (d, J = 8.4 Hz, 1H), 7.77-7.45 (m, 4H), 6.42 (s, 1H), 6.21 (t, J = 6.3 Hz, 1H), 4.66 (s, 1H), 3.82-3.74 (m, 1H), 3.46-3.34 (m, 3H), 2.68 (s, 3H), 1.93-1.82 (m, 2H), 1.48-1.18 (m, 20H), 0.90-0.80 (m, 3H). MS: 590.3 $[M + 1]^+$. |
| 17/279 | 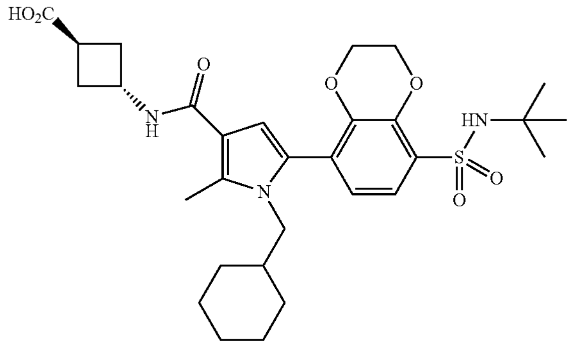 [SMILES: Cc1c(C(=O)N[C@H]2C[C@H](C(=O)O)C2)cc(-c2ccc(S(=O)(=O)NC(C)(C)C)c3c2OCCO3)n1CC1CCCCC1] | $^1$H-NMR (400 MHz, $CD_3OD$) δ: 0.63-0.68 (m, 2H), 0.95-0.99 (m, 3H), 1.14 (s, 9H), 1.25-1.32 (m, 3H), 1.51-1.53 (m, 3H), 2.30-2.38 (m, 2H), 2.48 (s, 3H), 2.54-2.60 (m, 2H), 2.97-3.02 (m, 1H), 3.26-3.28 (m, 3H), 3.66 (d, J = 6.8 Hz, 2H), 4.26-4.28 (m, 2H), 4.38-4.40 (m, 2H), 4.63 (t, J = 8.0 Hz, 1H), 6.44 (s, 1H), 6.89 (d, J = 8.4 Hz, 1H), 7.40 (d, J = 8.4 Hz, 1H). MS: 588.3 $[M + 1]^+$. |
| 17/280 | 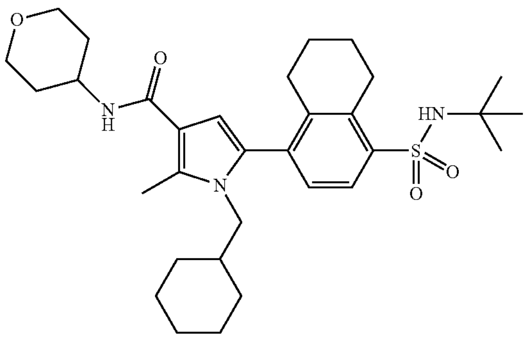 [SMILES: Cc1c(C(=O)NC2CCOCC2)cc(-c2ccc(S(=O)(=O)NC(C)(C)C)c3c2CCCC3)n1CC1CCCCC1] | $^1$H-NMR (400 MHz, $CDCl_3$) δ: 0.57-0.67 (m, 2H), 0.86-1.00 (m, 3H), 1.24 (s, 9H), 1.25-1.43 (m, 5H), 1.46-1.53 (m, 3H), 1.68-1.71 (m, 2H), 1.80-1.85 (m, 2H), 1.95-2.00 (m, 2H), 2.44-2.58 (m, 2H), 2.60 (s, 3H), 3.21 (m, 3H), 3.49-3.65 (m, 3H), 3.96-3.99 (m, 2H), 4.14-4.18 (m, 1H), 4.41 (s, 1H), 5.80 (d, J = 8.0 Hz, 1H), 6.11 (s, 1H), 7.15 (d, J = 8.4 Hz, 1H), 7.96 (d, J = 8.4 Hz, 1H). MS: 570.3 $[M + 1]^+$. |

-continued

| # | Structure | Analytical data |
|---|---|---|
| 17/281 | 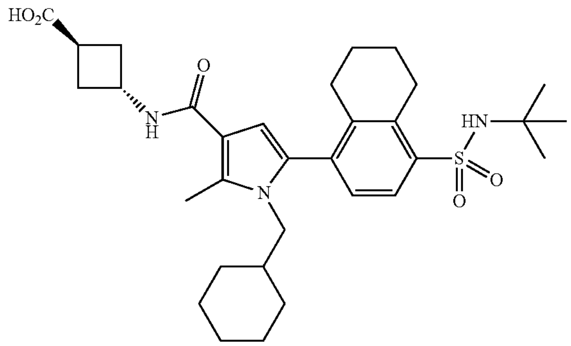 [SMILES: Cc1c(C(=O)N[C@H]2C[C@H](C(=O)O)C2)cc(-c2ccc(S(=O)(=O)NC(C)(C)C)c3c2CCCC3)n1CC1CCCCC1] | $^1$H-NMR (400 MHz, $CDCl_3$ + $D_2O$) δ: 0.57-0.67 (m, 5H), 1.19-1.31 (m, 14H), 1.57-1.70 (m, 4H), 1.8-1.84 (m, 2H), 2.26-2.33 (m, 2H), 2.42-2.59 (m, 2H), 2.77 (s, 3H), 3.08-3.10 (m, 2H), 3.19-3.25 (m, 4H), 3.60-3.65 (m, 2H), 6.12 (s, 1H), 7.15 (d, J = 8.0 Hz, 1H), 7.96 (d, J = 8.0 Hz, 1H). MS: 584.3 $[M + 1]^+$. |
| 17/282 | 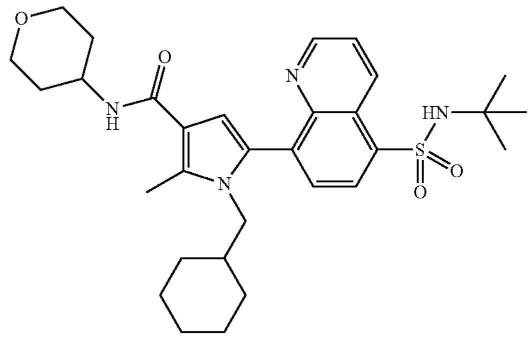 [SMILES: Cc1c(C(=O)NC2CCOCC2)cc(-c2ccc(S(=O)(=O)NC(C)(C)C)c3cccnc23)n1CC1CCCCC1] | $^1$H-NMR (400 MHz, $CDCl_3$) δ: 9.10 (d, J = 8.8 Hz, 1H), 9.05-9.03 (m, 1H), 8.39 (d, J = 7.6 Hz, 1H), 7.77 (d, J = 7.6 Hz, 1H), 7.67-7.62 (m, 1H), 6.42 (s, 1H), 5.81-5.79 (m, 1H), 4.70 (s, 1H), 4.19-4.17 (m, 1H), 4.00-3.97 (m, 2H), 3.58-3.50 (m, 4H), 2.64 (s, 3H), 1.99-1.95 (m, 2H), 1.57-1.48 (m, 5H), 1.27-1.22 (m, 12H), 0.94-0.89 (m, 3H), 0.45-0.43 (m, 2H). MS: 567.5 $(M + H)^+$. |
| 17/283 | 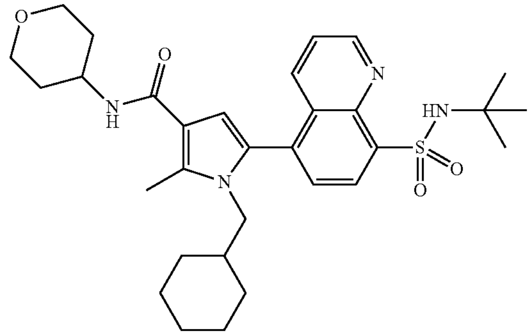 [SMILES: Cc1c(C(=O)NC2CCOCC2)cc(-c2ccc(S(=O)(=O)NC(C)(C)C)c3ncccc23)n1CC1CCCCC1] | $^1$H-NMR (400 MHz, $CDCl_3$) δ: 9.07-9.04 (m, 1H), 8.47 (d, J = 7.6 Hz, 1H), 8.21 (m, 1H), 7.61-7.50 (m, 2H), 6.46-6.36 (m, 2H), 5.70-5.69 (m, 1H), 4.20-4.16 (m, 1H), 4.01-3.98 (m, 2H), 3.74-3.70 (m, 1H), 3.56-3.51 (m, 2H), 3.38-3.32 (m, 1H), 2.67 (s, 3H), 2.20-1.95 (m, 2H), 1.58-1.48 (m, 5H), 1.30-1.18 (m, 12H), 0.89-0.84 (m, 3H), 0.50-0.47 (m, 2H). MS: 567.4 $(M + H)^+$. |
| 17/284 | 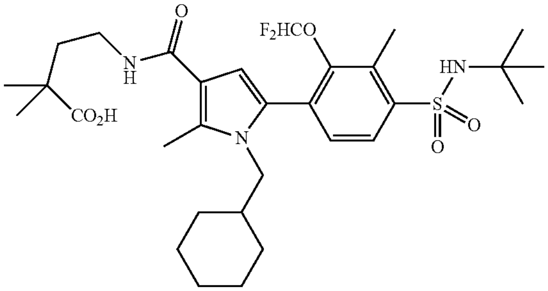 [SMILES: Cc1c(S(=O)(=O)NC(C)(C)C)ccc(-c2cc(C(=O)NCCC(C)(C)C(=O)O)c(C)n2CC2CCCCC2)c1OC(F)F] | $^1$H-NMR (400 MHz, $CDCl_3$) δ: 8.02 (d, J = 8.0 Hz, 1H), 7.31 (d, J = 8.0 Hz, 1H), 6.29 (s, 1H), 6.05-5.99 (m, 1H), 5.87 (t, J = 75.2 Hz, 1H), 4.57 (s, 1H), 3.62-3.58 (m, 1H), 3.44-3.40 (m, 2H), 2.66 (s, 3H), 2.60 (s, 3H), 1.87 (m, 2H), 1.57-1.53 (m, 3H), 1.30-1.20 (m, 18H), 0.98-0.96 (m, 3H), 0.57-0.54 (m, 2H). MS: 625.8 $(M + H)^+$. |

-continued

| # | Structure | Analytical data |
|---|---|---|
| 17/285 | 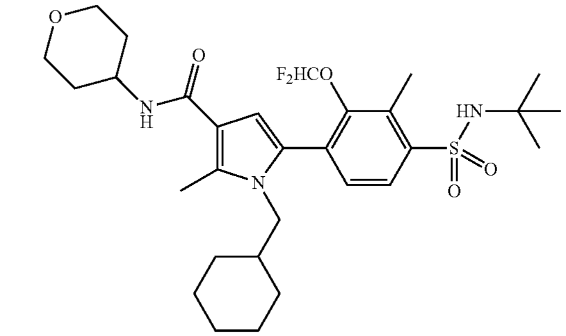 [SMILES: Cc1c(S(=O)(=O)NC(C)(C)C)ccc(-c2cc(C(=O)NC3CCOCC3)c(C)n2CC2CCCCC2)c1OC(F)F] | $^1$H-NMR (400 MHz, $CDCl_3$) δ: 8.03 (d, J = 8.0 Hz, 1H), 7.32 (d, 1H, J = 8.0 Hz), 6.29 (s, 1H), 5.86 (t, J = 75.2 Hz, 1H), 5.58 (m, 1H), 4.47 (s, 1H), 4.17-4.15 (m, 1H), 4.01-3.97 (m, 2H), 3.63-3.61 (m, 2H), 3.56-3.50 (m, 2H), 2.67 (s, 3H), 2.62 (s, 3H), 2.01-1.98 (m, 2H), 1.53-1.49 (m, 5H), 1.34-1.30 (m, 3H), 1.31 (s, 9H), 1.28-1.20 (m, 3H), 1.01-0.94 (m, 3H), 0.58-0.55 (m, 2H). MS: 595.8 $(M + H)^+$. |
| 17/286 | 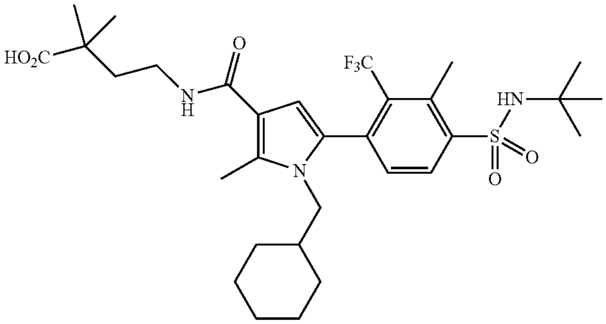 [SMILES: Cc1c(S(=O)(=O)NC(C)(C)C)ccc(-c2cc(C(=O)NCCC(C)(C)C(=O)O)c(C)n2CC2CCCCC2)c1C(F)(F)F] | $^1$H-NMR (400 MHz, $CDCl_3$) δ: 8.26 (d, J = 8.4 Hz, 1H), 7.30 (d, J = 8.4 Hz, 1H), 6.14 (s, 1H), 5.98 (br s, 1H), 4.69 (s, 1H), 3.68-3.63 (m, 1H), 3.42 (m, 2H), 3.33-3.27 (m, 1H), 2.84 (s, 3H), 2.57 (s, 3H), 1.87-1.84 (m, 2H), 1.63-1.52 (m, 3H), 1.43-1.40 (m, 18H), 1.05-0.92 (m, 3H), 0.73-0.70 (m, 1H), 0.48-0.46 (m, 1H). MS: 627.8 $(M + H)^+$. |
| 17/287 | 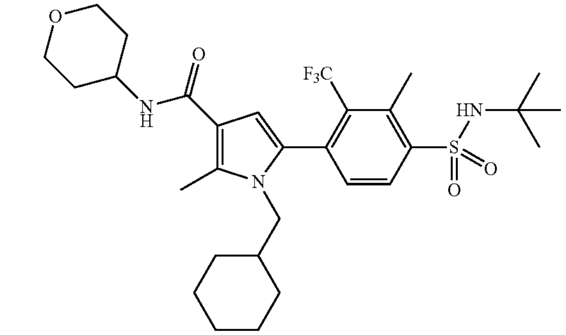 [SMILES: Cc1c(S(=O)(=O)NC(C)(C)C)ccc(-c2cc(C(=O)NC3CCOCC3)c(C)n2CC2CCCCC2)c1C(F)(F)F] | $^1$H-NMR (400 MHz, $CDCl_3$) δ: 8.28 (d, J = 8.4 Hz, 1H), 7.32 (d, J = 8.4 Hz, 1H), 6.15 (s, 1H), 5.63-5.61 (m, 1H), 4.56 (s, 1H), 4.16-4.12 (m, 1H), 4.00-3.97 (m, 2H), 3.70-3.65 (m, 1H), 3.55-3.50 (m, 2H), 3.34-3.28 (m, 1H), 2.85 (s, 3H), 2.59 (s, 3H), 2.02-1.97 (m, 2H), 1.64-1.50 (m, 5H), 1.49-1.23 (m, 12H), 1.09-0.93 (m, 3H), 0.72-0.71 (m, 1H), 0.48-0.45 (m, 1H). MS: 597.8 $(M + H)^+$. |
| 17/288 | 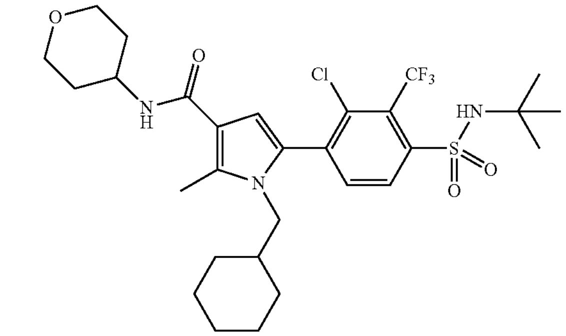 [SMILES: Cc1c(C(=O)NC2CCOCC2)cc(-c2ccc(S(=O)(=O)NC(C)(C)C)c(C(F)(F)F)c2Cl)n1CC1CCCCC1] | $^1$H-NMR (400 MHz, $CDCl_3$) δ: 8.35 (d, J = 8.4 Hz, 1H), 7.60 (d, J = 8.4 Hz, 1H), 6.27 (s, 1H), 5.61-5.60 (m, 1H), 4.86 (s, 1H), 4.21-4.13 (m, 1H), 4.00-3.97 (m, 2H), 3.55-3.50 (m, 4H), 2.62 (s, 3H), 2.00-1.96 (m, 2H), 1.75-1.70 (m, 5H), 1.58-1.22 (m, 12H), 1.10-0.98 (m, 3H), 0.60 (m, 2H). MS: 618.0 $(M + H)^+$. |

-continued

| # | Structure | Analytical data |
|---|---|---|
| 17/289 | 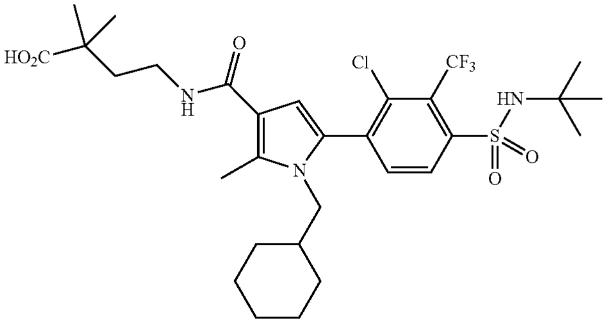 [SMILES: Cc1c(C(=O)NCCC(C)(C)C(=O)O)cc(-c2ccc(S(=O)(=O)NC(C)(C)C)c(C(F)(F)F)c2Cl)n1CC1CCCCC1] | $^1$H-NMR (400 MHz, $CDCl_3$) δ: 8.34 (d, J = 8.4 Hz, 1H), 7.60 (d, J = 8.4 Hz, 1H), 6.27 (s, 1H), 6.10 (br s, 1H), 4.89 (s, 1H), 4.85-4.43 (br s, 1H), 3.62-3.42 (m, 4H), 2.59 (s, 3H), 1.88-1.84 (m, 2H), 1.58-1.54 (m, 3H), 1.38-1.20 (m, 18H), 1.03-0.97 (m, 3H), 0.59 (m, 2H). MS: 648.0 $(M + H)^+$. |
| 17/290 | 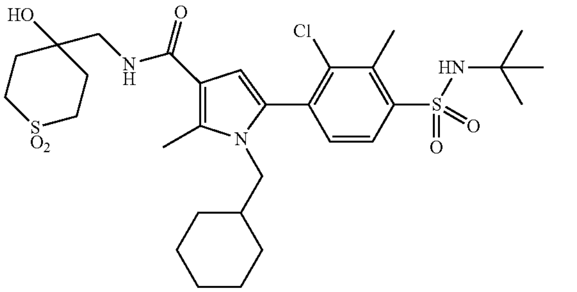 [SMILES: Cc1c(S(=O)(=O)NC(C)(C)C)ccc(-c2cc(C(=O)NCC3(O)CCS(=O)(=O)CC3)c(C)n2CC2CCCCC2)c1Cl] | $^1$H-NMR (300 MHz, $CDCl_3$) δ: 0.52-0.68 (m, 2H), 0.92-1.10 (m, 3H), 1.24 (s, 9H), 1.30-1.42 (m, 3H), 1.52-1.62 (m, 3H), 1.97-2.2.0 (m, 4H), 2.60 (s, 3H), 2.76 (s, 3H), 2.82-2.93 (m, 2H), 3.40-3.58 (m, 5H), 4.54 (s, 1H), 6.20-6.25 (m, 2H), 7.26 (d, J = 8.1 Hz, 1H), 8.03 (d, J = 8.1 Hz, 1H). MS: 642.2 $(M + 1)^+$. |
| 17/291 | 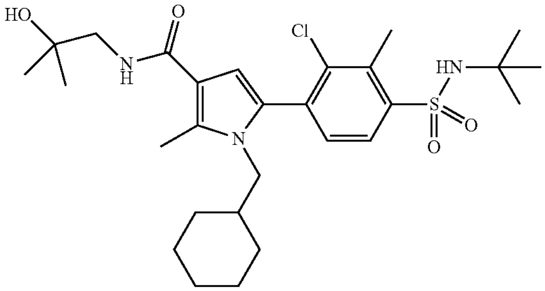 [SMILES: Cc1c(S(=O)(=O)NC(C)(C)C)ccc(-c2cc(C(=O)NCC(C)(C)O)c(C)n2CC2CCCCC2)c1Cl] | $^1$H-NMR (300 MHz, $CDCl_3$) δ: 8.03 (d, J = 8.4 Hz, 1H), 7.28 (d, J = 8.4 Hz, 1H), 6.25 (s, 1H), 6.20 (m, 1H), 4.47 (s, 1H), 3.52 (br s, 2H), 3.39 (m, 2H), 2.96 (s, 1H), 2.77 (s, 3H), 3.25 (s, 3H), 1.40-1.30 (m, 4H), 1.26 (s, 6H), 1.25 (s, 9H), 1.10-0.91 (m, 4H), 0.62 (m, 2H). MS: 552.3 $(M + 1)^+$. |
| 17/292 | 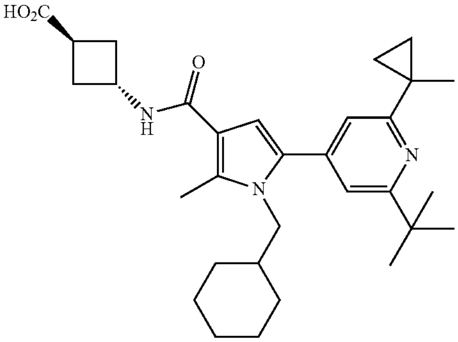 [SMILES: Cc1c(C(=O)N[C@H]2C[C@H](C(=O)O)C2)cc(-c2cc(C(C)(C)C)nc(C3(C)CC3)c2)n1CC1CCCCC1] | $^1$H-NMR ($CD_3OD$, 400 MHz) δ: 7.14 (s, 2H), 6.67 (s, 1H), 4.70 (m, 1H), 3.95 (d, J = 7.2 Hz, 2H), 3.06 (m, 1H), 2.68-2.59 (m, 2H), 2.58 (s, 3H), 2.41 (m, 2H), 1.63-1.50 (m, 6H), 1.48-1.30 (m, 14H), 1.20-0.98 (m, 3H), 0.76-0.65 (m, 4H). MS: 506.3 $(M + 1)^+$. |
| 17/293 | 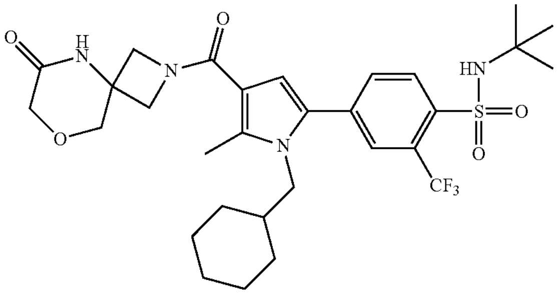 [SMILES: Cc1c(C(=O)N2CC3(COCC(=O)N3)C2)cc(-c2ccc(S(=O)(=O)NC(C)(C)C)c(C(F)(F)F)c2)n1CC1CCCCC1] | $^1$H-NMR ($CDCl_3$, 300 MHz) δ: 0.59-0.63 (m, 2H), 0.95-1.02 (m, 3H), 1.25 (s, 9H), 1.30-1.40 (m, 2H), 1.54-1.56 (m, 3H), 2.00 (s, 1H), 2.58 (s, 3H), 3.79 (m, 2H), 3.94 (s, 3H), 4.16 (s, 2H), 4.21-4.30 (m, 3H), 5.00 (s, 1H), 6.29 (s, 1H), 7.48 (br s, 1H), 7.59 (d, J = 8.1 Hz, 1H), 7.76 (s, 1H), 8.30 (d, J = 8.1 Hz, 1H). MS: 625.3 $(M + 1)^+$. |

-continued

| # | Structure | Analytical data |
|---|---|---|
| 17/294 | 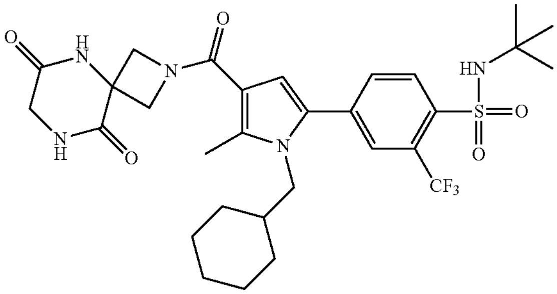 [SMILES: Cc1c(C(=O)N2CC3(C2)NC(=O)CNC3=O)cc(-c2ccc(S(=O)(=O)NC(C)(C)C)c(C(F)(F)F)c2)n1CC1CCCCC1] | $^1$H-NMR ($CD_3OD$, 400 MHz) δ: 0.66-0.74 (m, 2H), 0.95-1.03 (m, 3H), 1.24 (s, 10H), 1.30-1.38 (m, 5H), 1.53-1.58 (m, 3H), 2.55 (s, 3H), 3.93-3.97 (m, 4H), 4.10-4.13 (m, 1H), 4.40-4.42 (m, 1H), 4.57-4.60 (m, 1H), 6.49 (s, 1H), 7.81 (d, J = 8.0 Hz, 1H), 7.88 (s, 1H), 8.31 (d, J = 8.0 Hz, 1H). MS: 638.3 $(M + 1)^+$. |
| 17/295 | 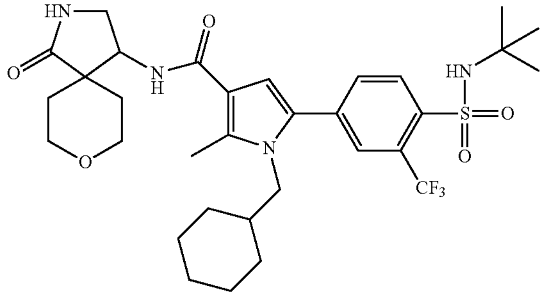 [SMILES: Cc1c(C(=O)NC2CNC(=O)C23CCOCC3)cc(-c2ccc(S(=O)(=O)NC(C)(C)C)c(C(F)(F)F)c2)n1CC1CCCCC1] | $^1$H-NMR ($CDCl_3$, 300 MHz) δ: 0.61-0.68 (m, 2H), 0.98-1.00 (m, 3H), 1.27-1.35 (m, 14H), 1.52-1.56 (m, 2H), 1.71-1.75 (m, 2H), 1.84-1.97 (m, 2H), 2.63 (s, 3H), 3.21 (m, 1H), 3.61-3.69 (m, 1H), 3.76-3.82 (m, 4H), 3.98-4.05 (m, 2H), 4.93-4.98 (m, 1H), 5.26 (s, 1H), 5.66 (s, 1H), 6.32 (d, J = 10.2 Hz, 1H), 6.48 (s, 1H), 7.63 (d, J = 8.4 Hz, 1H), 7.75 (s, 1H), 8.30 (d, J = 8.4 Hz, 1H). MS: 653.3 $(M + 1)^+$. |
| 17/296 | 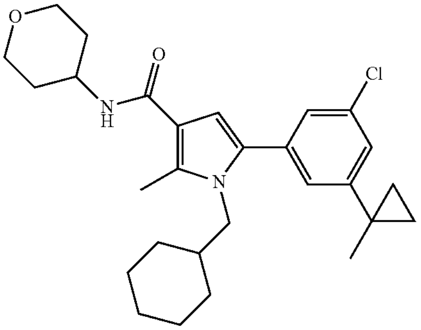 [SMILES: Cc1c(C(=O)NC2CCOCC2)cc(-c2cc(Cl)cc(C3(C)CC3)c2)n1CC1CCCCC1] | $^1$H-NMR (400 MHz, $CDCl_3$) δ: 7.19 (m, 1 H), 7.11 (s, 1 H), 7.06 (s, 1 H), 6.18 (s, 1 H), 5.63 (d, 1 H, J = 7.6 Hz), 4.16 (m, 1 H), 3.98 (m, 2 H), 3.74 (d, 2 H, J = 7.2 Hz), 3.53 (m, 2 H), 2.60 (s, 3 H), 1.97 (m, 2 H), 1.54 (m, 5 H), 1.47 (s, 3 H), 1.36 (m, 3 H), 1.02 (m, 3 H), 0.86 (m, 2 H), 0.78 (m, 2 H), 0.66 (m, 2 H). MS: 469.2 $(M + 1)^+$. |
| 17/297 | 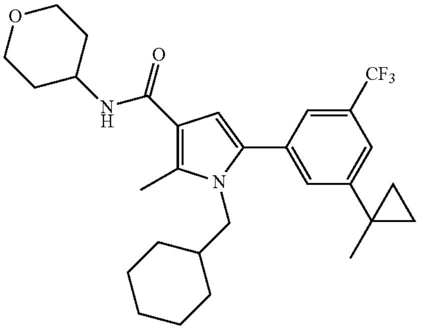 | $^1$H-NMR (400 MHz, $CDCl_3$) δ: 7.46 (s, 1 H), 7.37 (m, 2 H), 6.22 (s, 1 H), 5.61 (d, 1 H, J = 8 Hz), 4.16 (m, 1 H), 3.98 (m, 2 H), 3.74 (d, 2 H, J = 7.2 Hz), 3.53 (m, 2 H), 2.62 (s, 3 H), 1.97 (m, 2 H), 1.54 (m, 5 H), 1.45 (s, 3 H), 1.37 (m, 3 H), 1.01 (m, 3 H), 0.86 (m, 2 H), 0.83 (m, 2 H), 0.66 (m, 2 H). MS: 503.3 $(M + 1)^+$. |
| 17/298 | 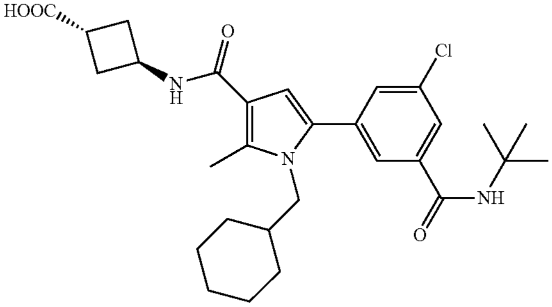 [SMILES: Cc1c(C(=O)N[C@H]2C[C@H](C(=O)O)C2)cc(-c2cc(Cl)cc(C(=O)NC(C)(C)C)c2)n1CC1CCCCC1] | $^1$H-NMR (400 MHz, DMSO-$d_6$) δ: 7.99 (s, 1 H), 7.89 (d, 1 H, J = 7.6 Hz), 7.82 (m, 2 H), 7.59 (1 H), 6.75 (s, 1 H), 4.50 (m, 1 H), 3.86 (d, 2 H, J = 7.2 Hz), 2.88 (m, 2 H), 2.38 (m, 2 H), 2.24 (m, 2 H), 1.50 (m, 3 H), 1.39 (s, 9 H), 1.30 (m, 3 H), 0.98 (m, 3 H), 0.66 (m, 2 H). MS: 528.2 $(M + 1)^+$. |

-continued
| # | Structure | Analytical data |
|---|---|---|
| 17/299 | 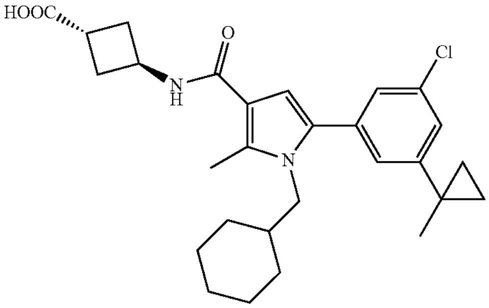 [SMILES: Cc1c(C(=O)N[C@H]2C[C@H](C(=O)O)C2)cc(-c2cc(Cl)cc(C3(C)CC3)c2)n1CC1CCCCC1] | $^1$H-NMR (400 MHz, $CDCl_3$) δ: 7.20 (s, 1 H), 7.10 (s, 1 H), 7.06 (s, 1 H), 6.20 (s, 1 H), 6.03 (d, 1 H, J = 6.8 Hz), 4.80 (m, 1 H), 3.74 (d, 2 H, J = 7.2 Hz), 3.09 (m, 1 H), 2.78 (m, 2 H), 2.59 (s, 3 H), 2.30 (m, 2 H), 1.56 (m, 3 H), 1.41 (s, 3 H), 1.33 (m, 3 H), 1.02 (m, 3 H), 0.86 (m, 2 H), 0.78 (m, 2 H), 0.65 (m, 2 H). MS: 483.3 $(M + 1)^+$. |
| 17/300 | 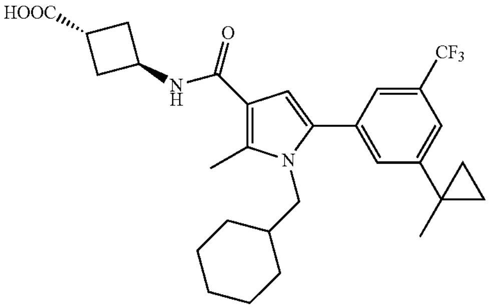 [SMILES: Cc1c(C(=O)N[C@H]2C[C@H](C(=O)O)C2)cc(-c2cc(C(F)(F)F)cc(C3(C)CC3)c2)n1CC1CCCCC1] | $^1$H-NMR (400 MHz, $CDCl_3$) δ: 7.46 (s, 1 H), 7.36 (m, 2 H), 6.23 (s, 1 H), 5.98 (m, 1 H, J = 3.6 Hz), 4.80 (m, 1 H), 3.73 (d, 2 H, J = 6.8 Hz), 3.07 (m, 1 H), 2.78 (m, 2 H), 2.60 (s, 3 H), 2.30 (m, 2 H), 1.54 (m, 3 H), 1.46 (s, 3 H), 1.33 (m, 3 H), 1.00 (m, 3 H), 0.89 (m, 2 H), 0.83 (m, 2 H), 0.64 (m, 2 H). MS: 517.3 $(M + 1)^+$. |
| 17/301 | 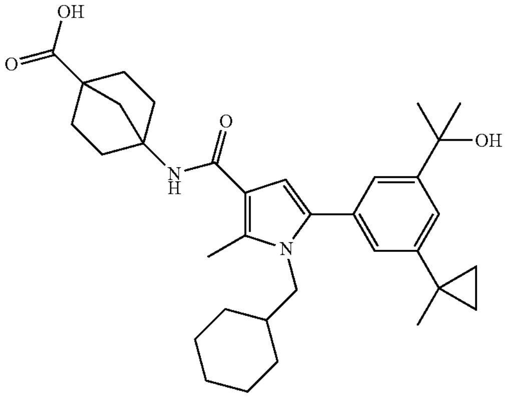 [SMILES: Cc1c(C(=O)NC23CCC(C(=O)O)(CC2)C3)cc(-c2cc(C(C)(C)O)cc(C3(C)CC3)c2)n1CC1CCCCC1] | $^1$H-NMR (300 MHz, $CD_3OD$) δ: 0.74-1.03 (m, 8H), 1.29-1.42 (m, 9H), 1.54-1.73 (m, 11H), 1.97-2.09 (m, 9H), 2.53 (s, 3H), 3.81 (d, J = 7.2 Hz, 2H), 6.41 (s, 1H), 7.09 (s, 1H), 7.23 (s, 1H), 7.41 (s, 1H). MS: 547.3 $(M + 1)^+$. |
| 17/302 | 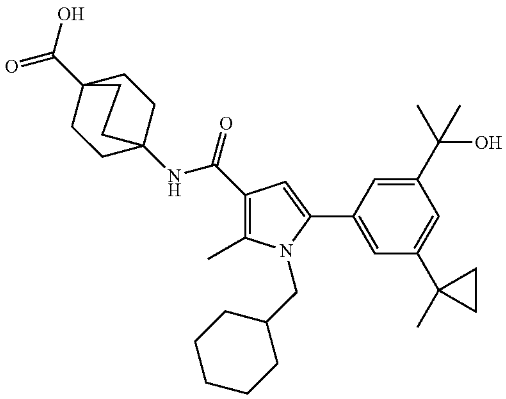 [SMILES: Cc1c(C(=O)NC23CCC(C(=O)O)(CC2)CC3)cc(-c2cc(C(C)(C)O)cc(C3(C)CC3)c2)n1CC1CCCCC1] | $^1$H-NMR (300 MHz, $CDCl_3$) δ: 0.70-0.76 (m, 3H), 0.86-0.87 (m, 3H), 0.98-1.00 (m, 3H), 1.25-1.32 (m, 3H), 1.36 (s, 3H), 1.42-1.55 (m, 3H), 1.59 (s, 6H), 1.90-2.11 (m, 12H), 2.58 (s, 3H), 3.70-3.73 (m, 2H), 5.45 (s, 1H), 6.10 (s, 1H), 7.06 (s, 1H), 7.18 (s, 1H), 7.38 (s, 1H). MS: 561.4 $(M + 1)^+$. |

-continued
| # | Structure | Analytical data |
| --- | --- | --- |
| 17/303 | 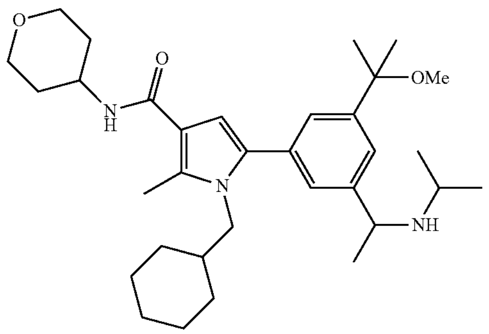 [SMILES: COC(C)(C)c1cc(-c2cc(C(=O)NC3CCOCC3)c(C)n2CC2CCCCC2)cc(C(C)NC(C)C)c1] | $^1$H-NMR ($CDCl_3$, 300 MHz): δ: 7.76 (s, 1H), 7.60 (s, 1H), 7.54 (d, 1H), 6.27 (s, 1H), 6.11 (m, 1H), 5.73 (m, 1H), 4.31 (m, 1H), 4.15 (m, 1H), 3.98 (d, 2H, J = 11.2 Hz), 3.77 (d, 2H, J = 6.8 Hz), 3.51 (m, 2H), 3.10 (s, 3H), 2.62 (s, 3H), 1.97 (m, 2H), 1.87-1.80 (m, 3H), 1.57 (s, 6H), 1.55-1.49 (m, 2H), 1.40-1.35 (m, 3H), 1.29 (d, 6H, J = 6.4 Hz), 0.98 (m, 3H), 0.61 (m, 2H). MS: 538.2 $(M + 1)^+$. |
| 17/304 | 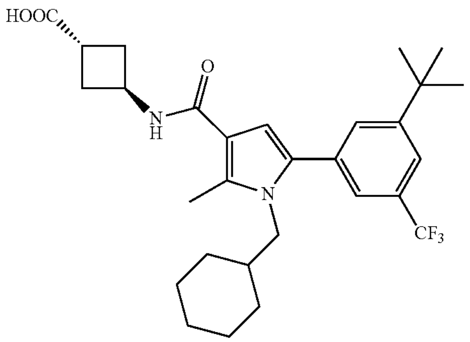 [SMILES: Cc1c(C(=O)N[C@H]2C[C@H](C(=O)O)C2)cc(-c2cc(C(C)(C)C)cc(C(F)(F)F)c2)n1CC1CCCCC1] | $^1$H-NMR (400 MHz, $CDCl_3$) δ: 7.60 (s, 1H), 7.52 (s, 1H), 7.40 (s, 1H), 6.24 (s, 1H), 5.96 (d, 1H, J = 7.2 Hz), 4.80 (m, 1H), 3.73 (d, 2H, J = 6.8 Hz), 3.08 (m, 1H), 2.80 (m, 2H), 2.62 (s, 3H), 2.30 (m, 2H), 1.57-1.52 (m, 3H), 1.40-1.31 (m, 12H), 1.00 (m, 3H), 0.62 (m, 2H). MS: 519.2 $(M + 1)^+$. |
| 17/305 | 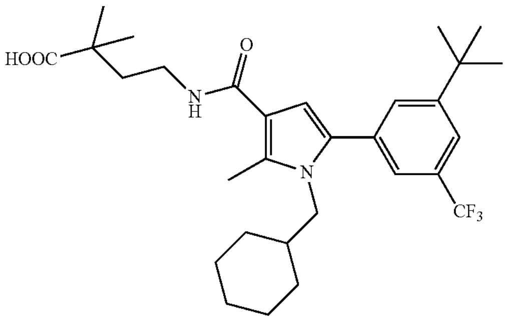 [SMILES: Cc1c(C(=O)NCCC(C)(C)C(=O)O)cc(-c2cc(C(C)(C)C)cc(C(F)(F)F)c2)n1CC1CCCCC1] | $^1$H-NMR (400 MHz, $CDCl_3$) δ: 7.58 (s, 1H), 7.51 (s, 1H), 7.39 (s, 1H), 6.21 (s, 1H), 5.89 (m, 1H), 3.72 (d, 2H, J =7.2 Hz), 3.44 (m, 2H), 2.62 (s, 3H), 1.87 (m, 2H), 1.57-1.51 (m, 3H), 1.39-1.30 (m, 12H), 1.31 (s, 6H), 1.00 (m, 3H), 0.62 (m, 2H). MS: 535.3 $(M + 1)^+$. |
| 17/306 | 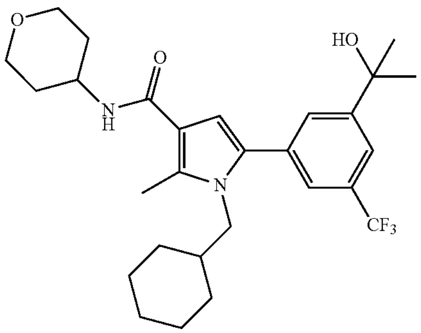 [SMILES: Cc1c(C(=O)NC2CCOCC2)cc(-c2cc(C(C)(C)O)cc(C(F)(F)F)c2)n1CC1CCCCC1] | $^1$H-NMR (400 MHz, $CDCl_3$) δ: 7.74 (s, 1H), 7.63 (s, 1H), 7.47 (s, 1H), 6.26 (s, 1H), 5.67 (d, 1H, J = 7.6 Hz), 4.18 (m, 1H), 3.99 (m, 2H), 3.75 (d, 2H, J = 6.8 Hz), 3.52 (m, 2H), 2.60 (s, 3H), 1.99 (m, 2H), 1.63-1.46 (m, 11H), 1.40-1.33 (m, 3H), 1.00 (m, 3H), 0.62 (m, 2H). MS: 507.2 $(M + 1)^+$. |

-continued
| # | Structure | Analytical data |
|---|---|---|
| 17/307 | 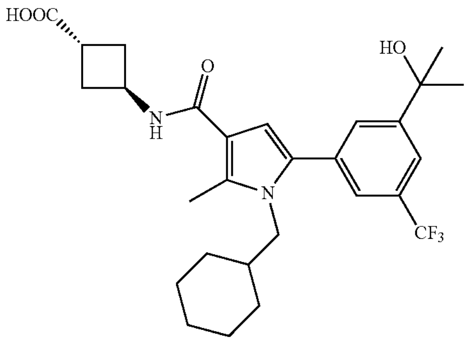 [SMILES: Cc1c(C(=O)N[C@H]2C[C@H](C(=O)O)C2)cc(-c2cc(C(C)(C)O)cc(C(F)(F)F)c2)n1CC1CCCCC1] | $^1$H-NMR (400 MHz, $CDCl_3$) δ: 7.73 (s, 1H), 7.63 (s, 1H), 7.46 (s, 1H), 6.27 (s, 1H), 6.04 (d, 1H, J = 7.2 Hz), 4.78 (m, 1H), 3.74 (d, 2H, J = 7.2 Hz), 3.08 (m, 1H), 2.78 (m, 2H), 2.59 (s, 3H), 2.29 (m, 2H), 1.63 (s, 6H), 1.57-1.52 (m, 3H), 1.39-1.30 (m, 3H), 1.00 (m, 3H), 0.62 (m, 2H). MS: 521.2 $(M + 1)^+$. |
| 17/308 | 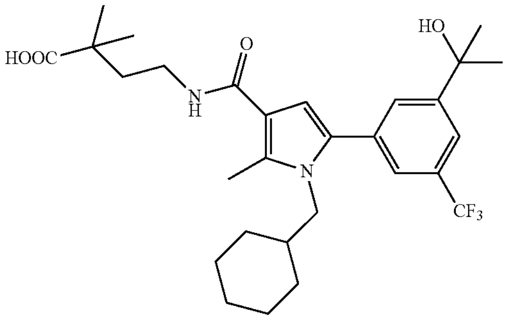 [SMILES: Cc1c(C(=O)NCCC(C)(C)C(=O)O)cc(-c2cc(C(C)(C)O)cc(C(F)(F)F)c2)n1CC1CCCCC1] | $^1$H-NMR (400 MHz, $CDCl_3$) δ: 7.69 (s, 1H), 7.65 (s, 1H), 7.45 (s, 1H), 6.18 (s, 1H), 6.02 (m, 1H), 3.72 (d, 2H, J = 6.8 Hz), 3.36 (m, 2H), 2.56 (s, 3H), 1.81 (m, 2H), 1.67 (s, 6H), 1.56-1.50 (m, 3H), 1.38-1.28 (m, 3H), 1.21 (s, 6H), 0.99 (m, 3H), 0.62 (m, 2H). MS: 537.3 $(M + 1)^+$. |
| 17/309 | 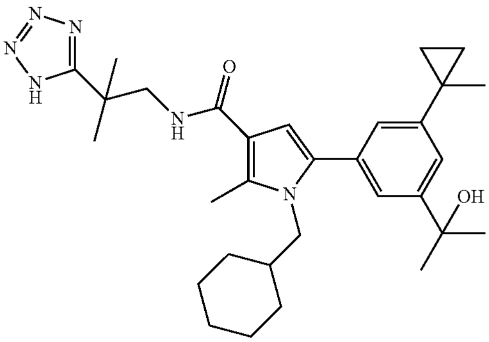 [SMILES: Cc1c(C(=O)NCC(C)(C)c2nnn[nH]2)cc(-c2cc(C(C)(C)O)cc(C3(C)CC3)c2)n1CC1CCCCC1] | $^1$H-NMR (400 MHz, DMSO-$d_6$) δ: 7.61 (m, 1H), 7.32 (s, 1H), 7.18 (s, 1H), 6.97 (s, 1H), 6.45 (s, 1H), 3.76 (d, 2H, J = 6.8 Hz), 3.46 (d, 2H, J = 6.0 Hz), 2.46 (s, 3H), 1.47-1.31 (m, 9H), 1.30 (s, 3H), 1.29 (s, 6H), 1.27-1.23 (m, 3H), 0.94 (m, 3H), 0.82 (m, 2H), 0.75 (m, 2H), 0.64 (m, 2H). MS: 533.3 $(M + 1)^+$. |
| 17/310 | 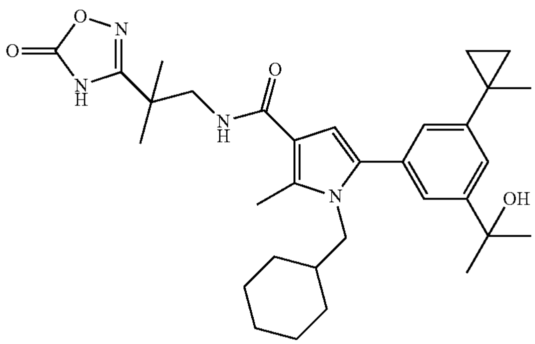 [SMILES: Cc1c(C(=O)NCC(C)(C)c2noc(=O)[nH]2)cc(-c2cc(C(C)(C)O)cc(C3(C)CC3)c2)n1CC1CCCCC1] | $^1$H-NMR (400 MHz, $CDCl_3$) δ: 7.40 (m, 1H), 7.20 (m, 1H), 7.07 (m, 1H), 6.20 (m, 1H), 6.16 (s, 1H), 3.72 (d, 2H, J = 7.2 Hz), 3.58 (d, 2H, J = 7.2 Hz), 2.59 (s, 3H), 1.59-1.48 (m, 9H), 1.43-1.25 (m, 12H), 1.00 (m, 3H), 0.87 (m, 2H), 0.75 (m, 2H), 0.62 (m, 2H). MS: 549.4 $(M + 1)^+$. |

-continued
| # | Structure | Analytical data |
|---|---|---|
| 17/311 | 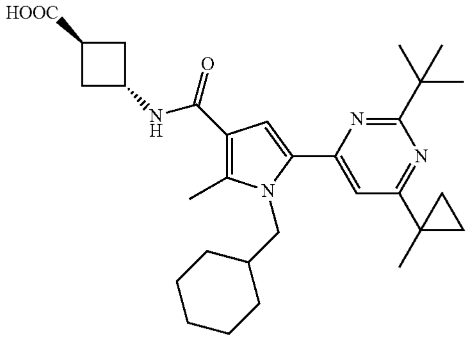 [SMILES: Cc1c(C(=O)N[C@H]2C[C@H](C(=O)O)C2)cc(-c2cc(C3(C)CC3)nc(C(C)(C)C)n2)n1CC1CCCCC1] | $^1$H-NMR (400 MHz, $CDCl_3$) δ: 7.23 (s, 1H), 6.86 (s, 1H), 6.16 (m, 1H), 4.78 (m, 1H), 4.52 (m, 2H), 3.13 (m, 1H), 2.79 (m, 2H), 2.59 (s, 3H), 2.36 (m, 2H), 1.64-1.58 (m, 3H), 1.54 (m, 3H), 1.50-1.37 (m, 14H), 1.02 (m, 3H), 0.83 (m, 4H). MS: 507.1 $(M + 1)^+$. |
| 17/312 | 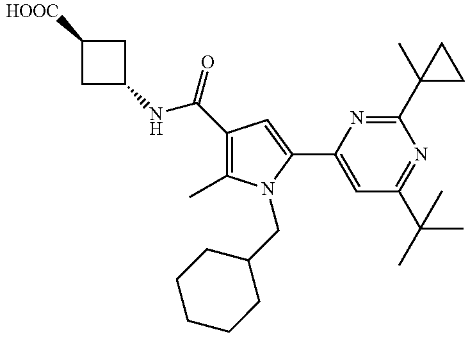 [SMILES: Cc1c(C(=O)N[C@H]2C[C@H](C(=O)O)C2)cc(-c2cc(C(C)(C)C)nc(C3(C)CC3)n2)n1CC1CCCCC1] | $^1$H-NMR (400 MHz, $CDCl_3$) δ: 7.17 (s, 1H), 6.78 (s, 1H), 6.00 (d, 1H, J = 7.2 Hz), 4.79 (m, 1H), 4.52 (m, 2H), 3.11 (m, 1H), 2.81 (m, 2H), 2.60 (s, 3H), 2.35 (m, 2H), 1.63-1.53 (m, 6H), 1.44-1.35 (m, 14H), 1.07 (m, 3H), 0.85 (m, 4H). MS: 507.1 $(M + 1)^+$. |
| 17/313 | 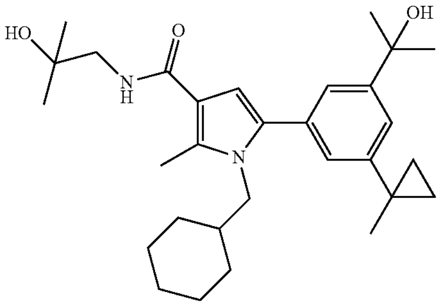 [SMILES: Cc1c(C(=O)NCC(C)(C)O)cc(-c2cc(C(C)(C)O)cc(C3(C)CC3)c2)n1CC1CCCCC1] | $^1$H-NMR (400 MHz, $CDCl_3$) δ: 7.40 (s, 1H), 7.21 (s, 1H), 7.08 (s, 1H), 6.22 (s, 2H), 3.73 (d, 2H, J = 7.2 Hz), 3.40 (m, 2H), 2.59 (s, 3H), 1.59-1.53 (m, 9H), 1.43-1.31 (m, 6H), 1.27 (s, 6H), 1.02-0.96 (m, 3H), 0.89-0.87 (m, 2H), 0.77-0.75 (m, 2H), 0.68-0.61 (m, 2H). MS: 481.3 $(M + 1)^+$. |
| 17/314 | 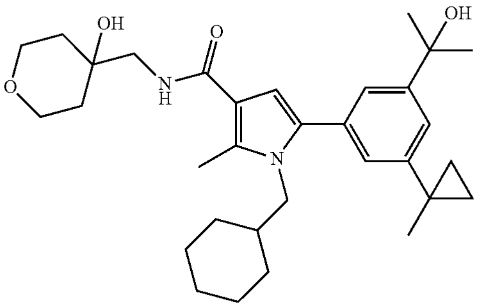 [SMILES: Cc1c(C(=O)NCC2(O)CCOCC2)cc(-c2cc(C(C)(C)O)cc(C3(C)CC3)c2)n1CC1CCCCC1] | $^1$H-NMR (400 MHz, $CDCl_3$) δ: 7.40 (s, 1H), 7.20 (s, 1H), 7.07 (s, 1H), 6.20-6.18 (m, 2H), 3.81-3.72 (m, 6H), 3.43 (m, 2H), 2.59 (s, 3H), 1.66-1.53 (m, 13H), 1.43-1.33 (m, 6H), 1.00 (m, 3H), 0.87 (m, 2H), 0.77-0.75 (m, 2H), 0.68-0.61 (m, 2 H). MS: 523.3 $(M + 1)^+$. |

-continued
| # | Structure | Analytical data |
|---|---|---|
| 17/315 | 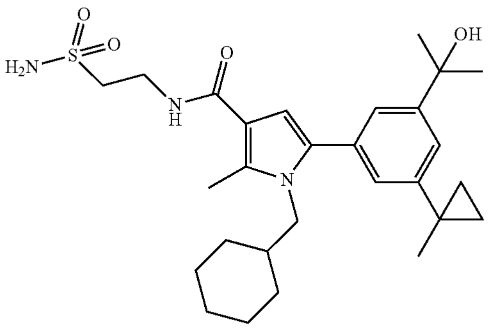 [SMILES: Cc1c(C(=O)NCCS(N)(=O)=O)cc(-c2cc(C(C)(C)O)cc(C3(C)CC3)c2)n1CC1CCCCC1] | $^1$H-NMR (400 MHz, $CDCl_3$) δ: 7.35 (s, 1H), 7.21 (s, 1H), 7.06 (s, 1H), 6.55 (s, 1H), 6.21 (s, 1H), 5.23 (m, 2H), 3.85 (m, 2H), 3.71 (d, 2H, J = 6.8 Hz), 3.34 (m, 2H), 2.54 (s, 3H), 1.58-1.52 (m, 9H), 1.42-1.31 (m, 6H), 0.99 (m, 3H), 0.86 (m, 2H), 0.80-0.74 (m, 2H), 0.67-0.60 (m, 2 H). MS: 516.2 $(M + 1)^+$. |
| 17/316 | 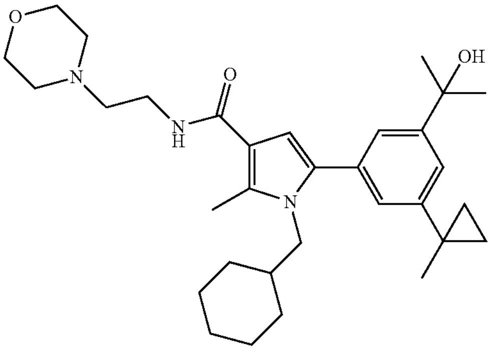 [SMILES: Cc1c(C(=O)NCCN2CCOCC2)cc(-c2cc(C(C)(C)O)cc(C3(C)CC3)c2)n1CC1CCCCC1] | $^1$H-NMR (400 MHz, $CDCl_3$) δ: 7.38 (s, 1H), 7.26 (s, 1H), 7.19 (s, 1H), 7.07 (s, 1H), 6.31 (s, 1H), 3.96-3.93 (m, 4H), 3.80 (s, 2H), 3.72 (d, 2H, J = 6.8 Hz), 3.63-3.59 (m, 2H), 3.30 (s, 2H), 2.93-2.89 (m, 2H), 2.58 (s, 3H), 1.59-1.49 (m, 9H), 1.42-1.32 (m, 6H), 0.99-0.95 (m, 3H), 0.87 (t, 2H, J = 5.2 Hz), 0.78-0.73 (m, 2H), 0.67-0.59 (m, 2 H). MS: 522.3 $(M + 1)^+$. |
| 17/317 | 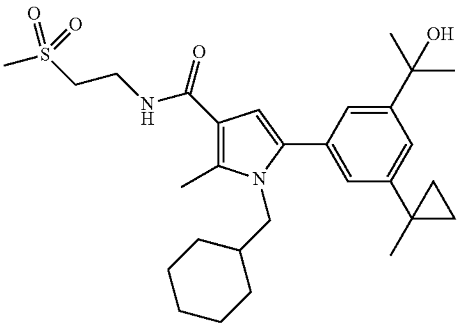 [SMILES: Cc1c(C(=O)NCCS(C)(=O)=O)cc(-c2cc(C(C)(C)O)cc(C3(C)CC3)c2)n1CC1CCCCC1] | $^1$H-NMR (400 MHz, $CDCl_3$) δ: 7.40 (s, 1H), 7.19 (s, 1H), 7.07 (s, 1H), 6.45 (s, 1H), 6.20 (s, 1H), 3.92-3.88 (m, 2H), 3.73 (d, 2H, J = 6.8 Hz), 3.34 (m, 2H), 2.97 (s, 3H), 2.60 (s, 3H), 1.59-1.53 (m, 9H), 1.43-1.32 (m, 6H), 1.00 (m, 3H), 0.88 (m, 2H), 0.77-0.74 (m, 2H), 0.68-0.61 (m, 2H). MS: 515.2 $(M + 1)^+$. |
| 17/318 | 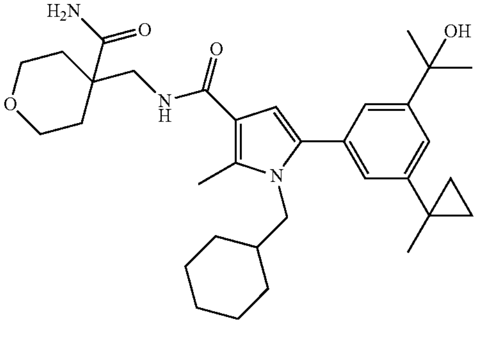 [SMILES: Cc1c(C(=O)NCC2(C(N)=O)CCOCC2)cc(-c2cc(C(C)(C)O)cc(C3(C)CC3)c2)n1CC1CCCCC1] | $^1$H-NMR (400 MHz, $CDCl_3$) δ: 7.39 (s, 1H), 7.19 (s, 1H), 7.07 (s, 1H), 6.38-6.25 (m, 3H), 6.18 (s, 1H), 3.86-3.83 (m, 2H), 3.73-3.57 (m, 6H), 2.56 (s, 3H), 2.01-1.97 (m, 2H), 1.73-1.69 (m, 2H), 1.59-1.53 (m, 9H), 1.43 (s, 3H), 1.40-1.32 (m, 3H), 1.00 (s, 3H), 0.87 (m, 2H), 0.77-0.75 (m, 2H), 0.65-0.63 (m, 2H). MS: 550.3 $(M + 1)^+$. |

-continued

| # | Structure | Analytical data |
|---|---|---|
| 17/319 | 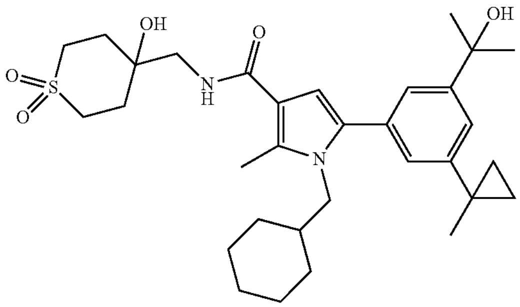 [SMILES: Cc1c(C(=O)NCC2(O)CCS(=O)(=O)CC2)cc(-c2cc(C(C)(C)O)cc(C3(C)CC3)c2)n1CC1CCCCC1] | $^1$H-NMR (400 MHz, $CDCl_3$) δ: 7.40 (s, 1H), 7.20 (s, 1H), 7.07 (s, 1H), 6.22 (m, 1H), 6.20 (s, 1H), 3.74 (d, 2H, J = 6.8 Hz), 3.53-3.42 (m, 4H), 2.93-2.85 (m, 2H), 2.59 (s, 3H), 2.14-2.01 (m, 4H), 1.60-1.54 (m, 9H), 1.43-1.33 (m, 6H), 1.00 (m, 3H), 0.87 (m, 2H), 0.78-0.76 (m, 2H), 0.69-0.62 (m, 2H). MS: 571.3 $(M + 1)^+$. |
| 17/320 | 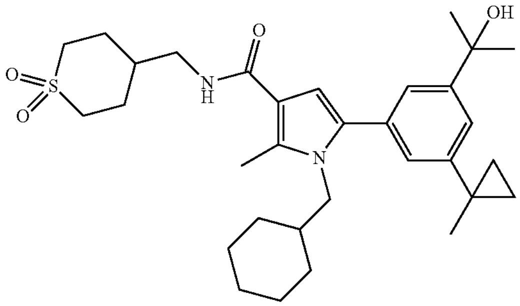 [SMILES: Cc1c(C(=O)NCC2CCS(=O)(=O)CC2)cc(-c2cc(C(C)(C)O)cc(C3(C)CC3)c2)n1CC1CCCCC1] | $^1$H-NMR (400 MHz, $CDCl_3$) δ: 7.39 (s, 1H), 7.21 (s, 1H), 7.07 (s, 1H), 6.17 (s, 1H), 5.97 (m, 1H), 3.73 (d, 2H, J = 6.8 Hz), 3.32 (m, 2H), 3.09-2.92 (m, 4H), 2.60 (s, 3H), 2.20-2.17 (m, 2H), 2.01-1.87 (m, 3H), 1.59-1.53 (m, 9H), 1.43-1.33 (m, 6H), 1.00 (s, 3H), 0.87 (m, 2H), 0.77-0.75 (m, 2H), 0.68-0.61 (m, 2H). MS: 555.3 $(M + 1)^+$. |
| 17/321 | 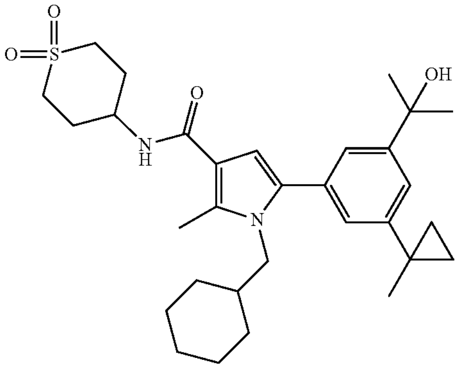 [SMILES: Cc1c(C(=O)NC2CCS(=O)(=O)CC2)cc(-c2cc(C(C)(C)O)cc(C3(C)CC3)c2)n1CC1CCCCC1] | $^1$H-NMR (400 MHz, $CDCl_3$) δ: 7.39 (s, 1H), 7.21 (s, 1H), 7.07 (s, 1H), 6.17 (s, 1H), 5.69 (d, 1H, J = 7.6 Hz), 5.25-4.23 (m, 1H), 3.74 (d, 2H, J = 7.2 Hz), 3.14-3.06 (m, 4H), 2.60 (s, 3H), 2.39-2.36 (m, 2H), 2.21-2.15 (m, 2H), 1.59-1.54 (m, 9H), 1.43-1.33 (m, 6H), 1.00 (m, 3H), 0.87 (m, 2H), 0.78-0.75 (m, 2H), 0.68-0.60 (m, 2H). MS: 541.3 $(M + 1)^+$. |
| 17/322 | 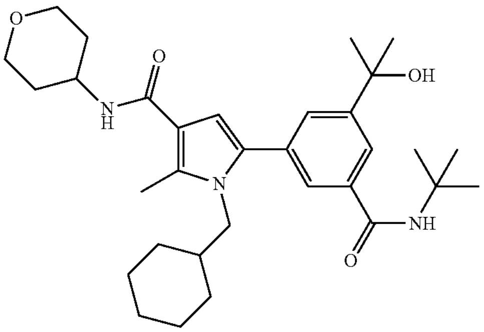 [SMILES: Cc1c(C(=O)NC2CCOCC2)cc(-c2cc(C(=O)NC(C)(C)C)cc(C(C)(C)O)c2)n1CC1CCCCC1] | $^1$H-NMR ($CDCl_3$, 300 MHz) δ: 7.85 (s, 1H), 7.55 (s, 1H), 7.53 (s, 1H), 6.24 (s, 1H), 6.00 (s, 1H), 5.65 (d, 1H, J = 7.6 Hz), 4.16 (m, 1H), 3.98 (d, 2H, J = 11.6 Hz), 3.76 (d, 2H, J = 7.6 Hz), 3.52 (m, 2H), 2.62 (s, 3H), 1.98 (m, 2H), 1.89 (s, 1H), 1.61 (s, 6H), 1.58-1.51 (m, 5H), 1.49 (s, 9H), 1.36 (m, 3H), 1.00 (m, 3H), 0.63 (m, 2H). MS: 538.2 $(M + 1)^+$. |

-continued

| # | Structure | Analytical data |
|---|---|---|
| 17/323 | 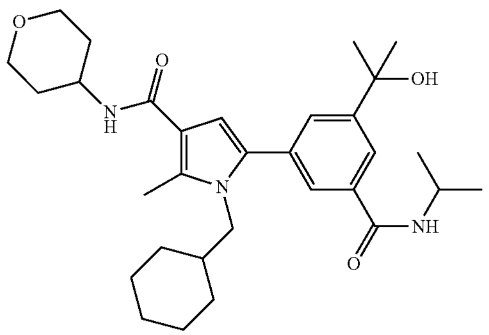 [SMILES: Cc1c(C(=O)NC2CCOCC2)cc(-c2cc(C(=O)NC(C)C)cc(C(C)(C)O)c2)n1CC1CCCCC1] | $^1$H-NMR ($CDCl_3$, 300 MHz) δ: 7.87 (s, 1H), 7.58 (s, 1H), 7.56 (s, 1H), 6.25 (s, 1H), 6.01 (d, 1H, J = 7.6 Hz), 5.65 (d, 1H, J = 8.0 Hz), 4.31 (m, 1H), 4.16 (m, 2H), 3.98 (d, 2H, J = 11.2 Hz), 3.76 (d, 2H, J = 7.2 Hz), 3.52 (m, 2H), 2.62 (s, 3H), 1.98 (m, 2H), 1.91 (s, 1H), 1.63 (s, 6H), 1.58-1.48 (m, 5H), 1.40-1.33 (m, 3H), 1.29 (d, 6H, J = 6.4 Hz), 0.99 (m, 3H), 0.63 (m, 2H). MS: 524.2 $(M + 1)^+$. |
| 17/324 | 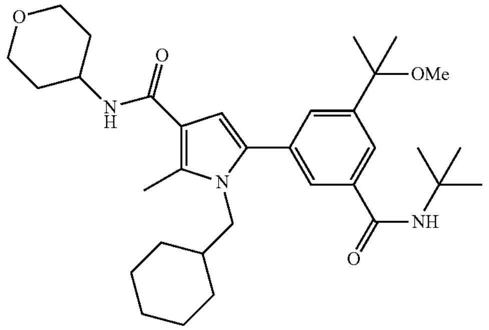 [SMILES: COC(C)(C)c1cc(C(=O)NC(C)(C)C)cc(-c2cc(C(=O)NC3CCOCC3)c(C)n2CC2CCCCC2)c1] | $^1$H-NMR ($CDCl_3$, 300 MHz) δ: 7.74 (s, 1H), 7.53 (s, 2H), 6.26 (s, 1H), 5.99 (s, 1H), 5.66 (d, 1H, J = 7.6 Hz), 4.17 (m, 1H), 3.98 (d, 2H, J = 11.2 Hz), 3.78 (d, 2H, J = 7.2 Hz), 3.53 (m, 2H), 3.10 (s, 3H), 2.62 (s, 3H), 1.97 (m, 2H), 1.57 (s, 6H), 1.51-1.50 (m, 5H), 1.47 (s, 9H), 1.34-1.32 (m, 3H), 0.91 (m, 3H), 0.62 (m, 2H). MS: 552 $(M + 1)^+$. |
| 17/325 | 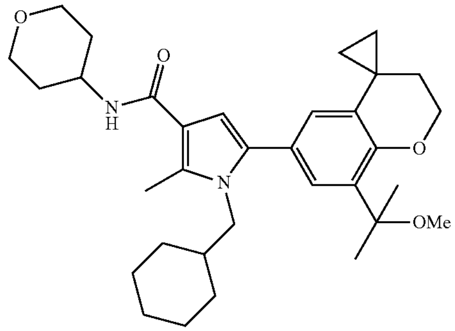 [SMILES: COC(C)(C)c1cc(-c2cc(C(=O)NC3CCOCC3)c(C)n2CC2CCCCC2)cc2c1OCCC21CC1] | $^1$H-NMR ($CDCl_3$, 300 MHz) δ: 0.61-0.69 (2H, m), 0.72-0.74 (2H, m), 0.88-0.98 (5H, m), 1.33-1.40 (3H, m), 1.51-1.62 (7H, m), 1.89-2.01 (4H, m), 2.61 (1H, s), 3.21 (3H, s), 3.53 (2H, t, J = 11.7 Hz), 3.68 (2H, d, J = 6.3 Hz), 3.97-4.01 (2H, m), 4.14-4.19 (1H, m), 4.33-4.36 (2H, m), 5.59-5.62 (1H, m), 6.09 (1H, s), 6.50 (1H, s), 7.13 (1H, s). MS: 535.4 $(M + 1)^+$. |
| 17/326 | 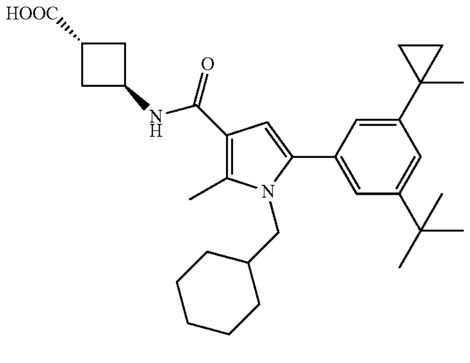 [SMILES: Cc1c(C(=O)N[C@H]2C[C@H](C(=O)O)C2)cc(-c2cc(C(C)(C)C)cc(C3(C)CC3)c2)n1CC1CCCCC1] | $^1$H-NMR (400 MHz, DMSO-$d_6$) δ: 0.60-0.67 (m, 2H), 0.75-0.77 (m, 2H), 0.83-0.86 (m, 2H), 0.90-0.95 (m, 3H), 1.21-1.24 (m, 3H), 1.30 (s, 9H), 1.40 (s, 3H), 1.45-1.47 (m, 3H), 2.27-2.32 (m, 2H), 2.36-2.41 (m, 2H), 2.50 (s, 3H), 2.80-2.94 (m, 1H), 3.76 (d, J = 6.8 Hz, 2H), 4.52 (m, 1H), 6.53 (s, 1H), 6.98 (s, 1H), 7.15 (s, 1H), 7.19 (s, 1H), 7.82 (d, J = 7.6 Hz, 1H), 12.08 (br s, 1H). MS: 505.3 $(M + 1)^+$. |

-continued
| # | Structure | Analytical data |
|---|---|---|
| 17/327 | 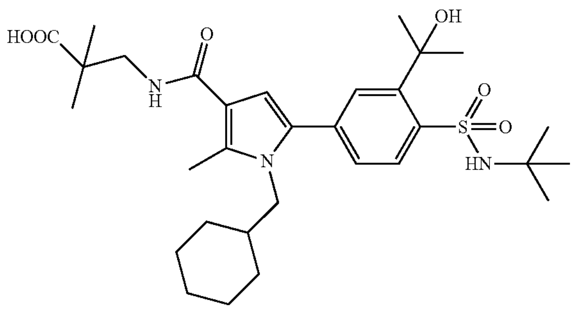 [SMILES: Cc1c(C(=O)NCC(C)(C)C(=O)O)cc(-c2ccc(S(=O)(=O)NC(C)(C)C)c(C(C)(C)O)c2)n1CC1CCCCC1] | $^1$H-NMR (400 MHz, $CDCl_3$) δ: 8.20 (d, 1H, J = 8.8 Hz), 7.29 (s, 2H), 6.44 (m, 1H), 6.29 (s, 1H), 3.75 (d, 2H, J = 7.2 Hz), 3.55 (d, 2H, J = 6.0 Hz), 2.58 (s, 3H), 1.70 (s, 6 H), 1.53 (m, 3H), 1.30-1.22 (m, 18H), 0.97 (m, 3H), 0.57 (m, 2H). MS: 590.3 $(M + 1)^+$. |
| 17/328 | 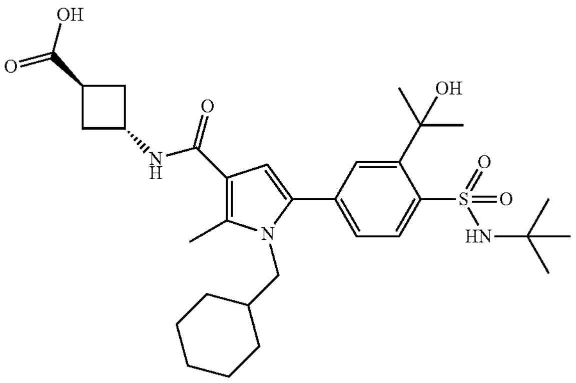 [SMILES: Cc1c(C(=O)N[C@H]2C[C@H](C(=O)O)C2)cc(-c2ccc(S(=O)(=O)NC(C)(C)C)c(C(C)(C)O)c2)n1CC1CCCCC1] | $^1$H-NMR (400 MHz, $CDCl_3$) δ: 8.21 (d, 1H, J = 8.0 Hz), 7.30 (s, 1H), 6.32 (s, 1H), 6.14 (m, 1H), 4.79 (s, 1H), 3.76 (d, 2H, J = 6.4 Hz), 3.10 (m, 1H), 2.79 (m, 2H), 2.59 (s, 3H), 2.34 (s, 2H), 1.71 (s, 6H), 1.54 (m, 3H), 1.30-1.21 (m, 12H), 0.97 (m, 3 H), 0.59 (m, 2 H). MS: 588.3 $(M + 1)^+$. |
| 17/329 | 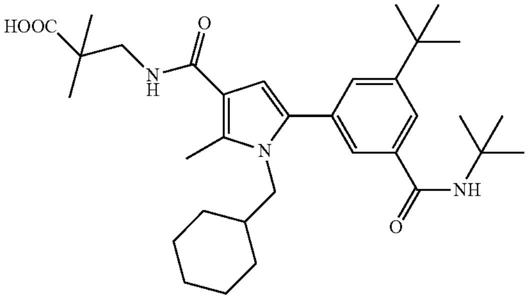 [SMILES: Cc1c(C(=O)NCC(C)(C)C(=O)O)cc(-c2cc(C(=O)NC(C)(C)C)cc(C(C)(C)C)c2)n1CC1CCCCC1] | $^1$H-NMR (400 MHz, $CD_3OD$) δ: 7.67 (s, 1H), 7.44 (m, 2H), 6.31 (s, 1H), 3.75 (d, 2H, J = 6.8 Hz), 3.39 (s, 2H), 2.46 (s, 3H), 1.44 (m, 3H), 1.37 (m, 9H), 1.31-1.19 (m, 12H), 1.13 (m, 6H), 0.92 (m, 3H), 0.60-0.58 (m, 2H). MS: 552.4 $(M + 1)^+$. |
| 17/330 | 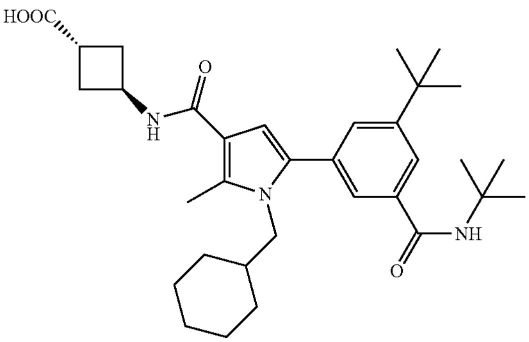 [SMILES: Cc1c(C(=O)N[C@H]2C[C@H](C(=O)O)C2)cc(-c2cc(C(=O)NC(C)(C)C)cc(C(C)(C)C)c2)n1CC1CCCCC1] | $^1$H-NMR (400 MHz, DMSO-$d_6$) δ: 7.88 (d, 1H, J = 7.6 Hz), 7.83 (s, 1H), 7.75 (s, 1H), 7.69 (s, 1H), 7.50 (s, 1H), 6.64 (s, 1H), 4.52 (m, 1H), 3.81 (d, 2H, J = 6.8 Hz), 2.92-2.90 (m, 1H), 2.53 (s, 3H), 2.42-2.36 (m, 2H), 2.32-2.27 (m, 2H), 1.49-1.47 (m, 3H), 1.40 (s, 9H), 1.34-1.24 (m, 12H), 0.96-0.92 (m, 3H), 0.66-0.63 (m, 2H). MS: 550.3 $(M + 1)^+$. |

-continued
| # | Structure | Analytical data |
|---|---|---|
| 17/331 | 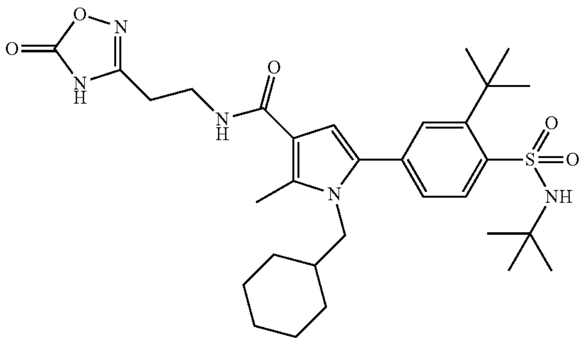 [SMILES: Cc1c(C(=O)NCCc2noc(=O)[nH]2)cc(-c2ccc(S(=O)(=O)NC(C)(C)C)c(C(C)(C)C)c2)n1CC1CCCCC1] | $^1$H-NMR (400 MHz, $CDCl_3$) δ: 11.02 (s, 1H), 8.19 (d, 1H, J = 8.4 Hz), 7.57 (s, 1H), 7.22 (m, 1H), 6.35 (m, 1H), 6.27 (s, 1H), 4.55 (s, 1H), 3.76-3.70 (m, 4H), 2.92 (m, 2H), 2.60 (s, 3H), 1.61-1.46 (m, 12H), 1.35-1.25 (m, 12H), 0.96 (m, 3H), 0.58 (m, 2H). MS: 600.3 $(M + 1)^+$ |
| 17/332 | 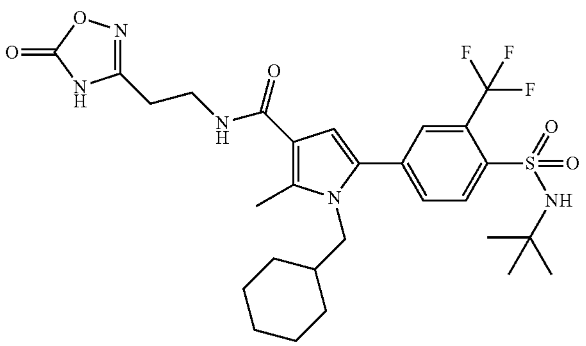 [SMILES: Cc1c(C(=O)NCCc2noc(=O)[nH]2)cc(-c2ccc(S(=O)(=O)NC(C)(C)C)c(C(F)(F)F)c2)n1CC1CCCCC1] | $^1$H-NMR (400 MHz, $CDCl_3$) δ: 10.82 (s, 1H), 8.33 (d, 1H, J = 8.0 Hz), 7.78 (s, 1H), 7.61 (d, 1H, J = 8.0 Hz), 6.36 (s, 1H), 6.33 (m, 1H), 4.74 (s, 1H), 3.83-3.72 (m, 4H), 2.93 (m, 2H), 2.61 (s, 3H), 1.56 (m, 3H), 1.32 (m, 3H), 1.24 (s, 9H), 1.00 (m, 3H), 0.62 (m, 2H). MS: 612.2 $(M + 1)^+$. |
| 17/333 | 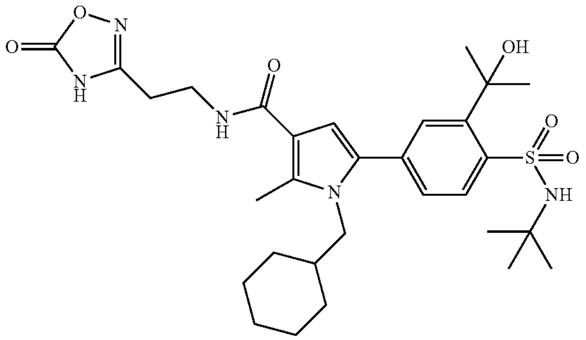 [SMILES: Cc1c(C(=O)NCCc2noc(=O)[nH]2)cc(-c2ccc(S(=O)(=O)NC(C)(C)C)c(C(C)(C)O)c2)n1CC1CCCCC1] | $^1$H-NMR (400 MHz, $CDCl_3$) δ: 10.86 (s, 1H), 8.21 (d, 1H, J = 8.4 Hz), 7.28 (s, 2H), 6.30 (m, 1H), 6.27 (s, 1H), 3.78-3.70 (m, 4H), 2.93 (m, 2H), 2.60 (s, 3H), 1.70 (s, 6H), 1.55 (m, 3H), 1.31-1.26 (m, 12H), 0.98 (m, 3H), 0.58 (m, 2H). MS: 602 $(M + 1)^+$ |
| 17/334 | 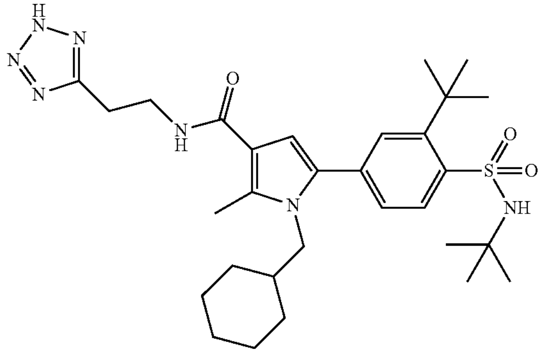 [SMILES: Cc1c(C(=O)NCCc2nn[nH]n2)cc(-c2ccc(S(=O)(=O)NC(C)(C)C)c(C(C)(C)C)c2)n1CC1CCCCC1] | $^1$H-NMR (400 MHz, $CDCl_3$) δ: 8.19 (d, 1H, J = 8.4 Hz), 7.56 (s, 1H), 7.21 (d, 1H, J = 7.6 Hz), 6.52 (m, 1H), 6.26 (s, 1H), 4.57 (m, 1H), 3.97 (m, 2H), 3.77 (d, 2H, J = 6.8 Hz), 3.40 (m, 2H), 2.61 (s, 3H), 1.58 (s, 9H), 1.54 (m, 3H), 1.33-1.24 (m, 12H), 0.98 (m, 3H), 0.59 (m, 2 H). MS: 584.4 $(M + 1)^+$. |

-continued
| # | Structure | Analytical data |
|---|---|---|
| 17/335 | 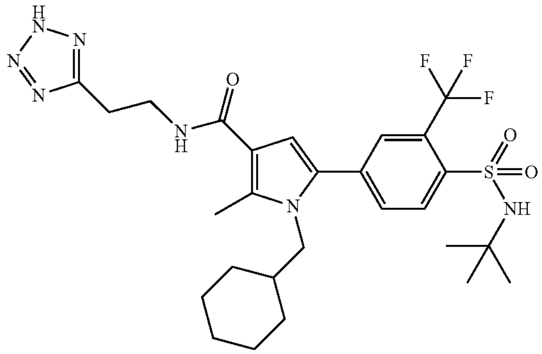 [SMILES: Cc1c(C(=O)NCCc2nn[nH]n2)cc(-c2ccc(S(=O)(=O)NC(C)(C)C)c(C(F)(F)F)c2)n1CC1CCCCC1] | $^1$H-NMR (400 MHz, $CD_3OD$) δ: 8.31 (d, 1H, J = 8.4 Hz), 7.89 (s, 1H), 7.81 (d, 1H, J = 8.4 Hz), 6.63 (s, 1H), 3.94 (d, 2H, J = 6.8 Hz), 3.74 (m, 2H), 3.24 (m, 2H), 2.58 (s, 3H), 1.56 (m, 3H), 1.32 (m, 3H), 1.26 (s, 9H), 1.02 (m, 3 H), 0.71 (m, 2 H). MS: 596.2 (M + 1)$^+$. |
| 17/336 | 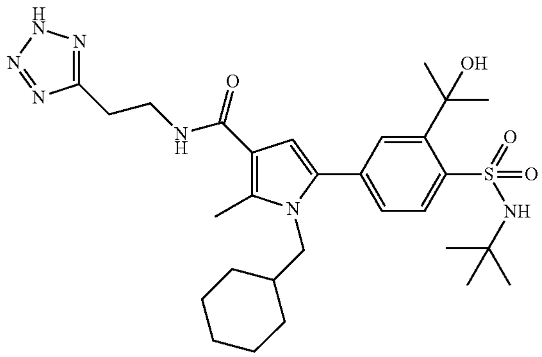 [SMILES: Cc1c(C(=O)NCCc2nn[nH]n2)cc(-c2ccc(S(=O)(=O)NC(C)(C)C)c(C(C)(C)O)c2)n1CC1CCCCC1] | $^1$H-NMR (400 MHz, $CDCl_3$) δ: 8.21 (d, 1H, J = 8.4 Hz), 7.24 (s, 2H), 6.49 (s, 1H), 6.28 (s, 1H), 3.97 (m, 2H), 3.76 (d, 2H, J = 7.2 Hz), 3.36 (m, 2H), 2.62 (s, 3H), 1.69 (s, 6H), 1.54 (m, 3H), 1.30-1.24 (m, 12H), 0.96 (m, 3H), 0.59 (m, 2H). MS: 586.3 (M + 1)$^+$ |
| 17/337 | 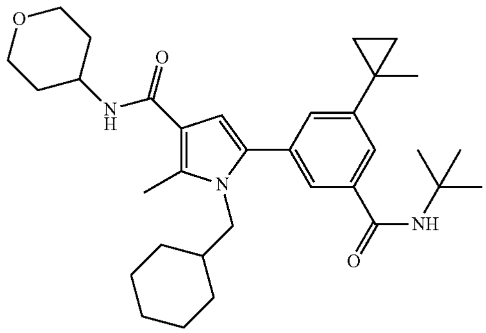 [SMILES: Cc1c(C(=O)NC2CCOCC2)cc(-c2cc(C(=O)NC(C)(C)C)cc(C3(C)CC3)c2)n1CC1CCCCC1] | $^1$H-NMR (400 MHz, $CDCl_3$) δ: 7.61 (m, 1H), 7.39 (m, 1H), 7.32 (m, 1H), 6.21 (s, 1H), 5.92 (s, 1H), 5.62 (d, 1H, J = 8.0 Hz), 4.16 (m, 1H), 3.98 (m, 2H), 3.75 (d, 2H, J = 7.2 Hz), 3.52 (m, 2H), 2.62 (s, 3H), 1.99 (m, 2H), 1.57-1.46 (m, 3H), 1.44-1.42 (m, 15H), 1.40 (m, 3H), 1.26 (m, 3H), 1.01 (m, 3H), 0.89 (m, 2H), 0.79 (m, 2H), 0.62 (m, 2H). MS: 534.3 (M + 1)$^+$. |
| 17/338 | 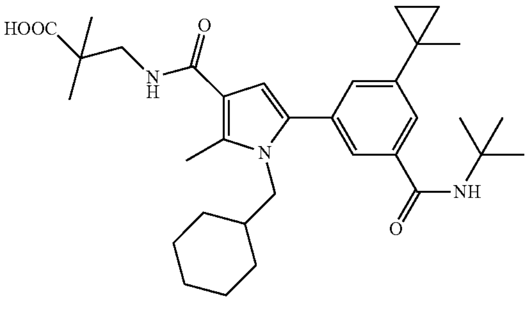 [SMILES: Cc1c(C(=O)NCC(C)(C)C(=O)O)cc(-c2cc(C(=O)NC(C)(C)C)cc(C3(C)CC3)c2)n1CC1CCCCC1] | $^1$H-NMR (400 MHz, $CDCl_3$) δ: 7.62 (s, 1H), 7.38 (s, 1H), 7.31 (s, 1H), 6.34 (m, 1H), 6.22 (s, 1H), 5.95 (s, 1H), 3.72 (d, 2H, J = 7.2 Hz), 3.53 (d, 2H, J = 6.0 Hz), 2.60 (s, 3H), 1.55 (m, 3H), 1.48 (s, 9H), 1.43 (s, 3H), 1.30 (m, 9H), 1.00 (m, 3H), 0.89 (m, 2H), 0.78 (m, 2H), 0.62 (m, 2H). MS: 550.3 (M + 1)$^+$. |

-continued

| # | Structure | Analytical data |
|---|---|---|
| 17/339 | 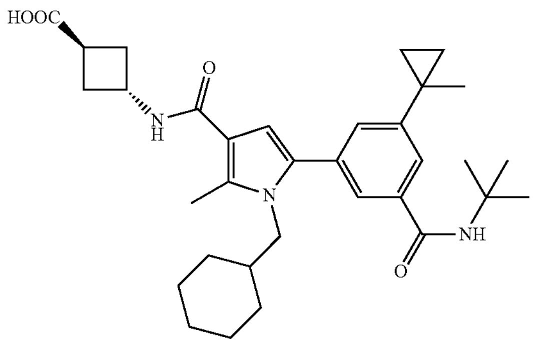 [SMILES: Cc1c(C(=O)N[C@H]2C[C@H](C(=O)O)C2)cc(-c2cc(C(=O)NC(C)(C)C)cc(C3(C)CC3)c2)n1CC1CCCCC1] | $^1$H-NMR (400 MHz, $CDCl_3$) δ: 7.61 (m, 1H), 7.39 (m, 1H), 7.32 (m, 1H), 6.23 (s, 1H), 6.00 (m. 1H), 5.96 (s, 1H), 4.78 (m, 1H), 3.74 (d, 2H, J = 7.2 Hz), 3.10 (m, 1H), 2.80 (m, 2H), 2.59 (s, 3H), 2.32 (m, 2H), 1.58-1.53 (m, 3H), 1.49 (s, 9H), 1.44 (s, 3H), 1.38 (m, 3H), 1.01 (m, 3H), 0.89 (m, 2H), 0.79 (m, 2H), 0.62 (m, 2H). MS: 548.3 $(M + 1)^+$. |
| 17/340 | 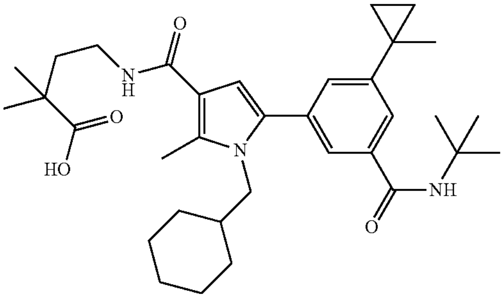 [SMILES: Cc1c(C(=O)NCCC(C)(C)C(=O)O)cc(-c2cc(C(=O)NC(C)(C)C)cc(C3(C)CC3)c2)n1CC1CCCCC1] | $^1$H-NMR (400 MHz, $CDCl_3$) δ: 7.62 (s, 1H), 7.42 (s, 1H), 7.30 (s, 1H), 6.23 (s, 1H), 6.16 (s, 1H), 6.02 (m, 1H), 3.72 (d, 2H, J = 7.2 Hz), 3.39 (m, 2H), 2.59 (s, 3H), 1.82 (m, 2H), 1.57-1.52 (m, 3H), 1.49 (s, 9H), 1.43 (s, 3H), 1.32 (m, 3H), 1.22 (s, 6H), 1.00 (m, 3H), 0.89 (m, 2H), 0.78 (m, 2H), 0.62 (m, 2H). MS: 564.3 $(M + 1)^+$. |
| 17/341 | 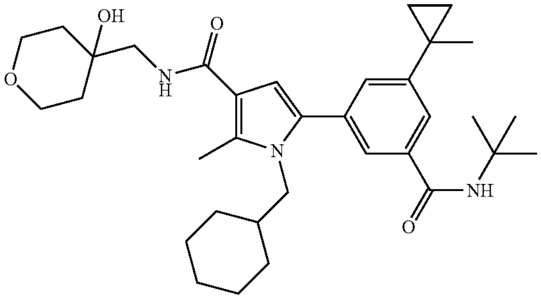 [SMILES: Cc1c(C(=O)NCC2(O)CCOCC2)cc(-c2cc(C(=O)NC(C)(C)C)cc(C3(C)CC3)c2)n1CC1CCCCC1] | $^1$H-NMR (400 MHz, $CDCl_3$) δ: 7.61 (m, 1H), 7.40 (m, 1H), 7.31 (m, 1H), 6.23 (s, 1H), 6.21 (m, 1H), 5.98 (s, 1H), 3.74-3.73 (m, 6H), 3.44 (d, 2H, J = 6.0 Hz), 2.61 (s, 3H), 1.69-1.53 (m, 6H), 1.49 (s, 9H), 1.43 (s, 3H), 1.32 (m, 3H), 1.00 (m, 3H), 0.89 (m, 2H), 0.78 (m, 2H), 0.62 (m, 2H). MS: 564.3 $(M + 1)^+$. |
| 17/342 | 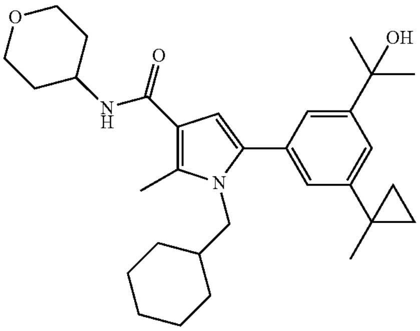 [SMILES: Cc1c(C(=O)NC2CCOCC2)cc(-c2cc(C(C)(C)O)cc(C3(C)CC3)c2)n1CC1CCCCC1] | $^1$H-NMR ($CDCl_3$, 400 MHz) δ: 0.63-0.66 (m, 2H), 0.76-0.77 (m, 2H), 0.86-0.89 (m, 2H), 0.98-0.99 (m, 3H), 1.33-1.43 (m, 3H), 1.47 (s, 3H), 1.52-1.56 (m, 5H), 1.58 (s, 6H), 1.73 (s, 2H), 2.61 (s, 3H), 3.52 (t, 2H, J = 12.0 Hz), 3.73 (d, 2H, J = 8.0 Hz), 3.96-3.99 (m, 2H), 4.15-4.17 (m, 1 H), 5.61 (d, 1H, J = 8.0 Hz), 6.17 (s, 1H), 7.07 (s, 1H), 7.20 (s, 1H), 7.39 (s, 1H). MS: 493.2 $(M + 1)^+$. |

-continued

| # | Structure | Analytical data |
|---|---|---|
| 17/343 | 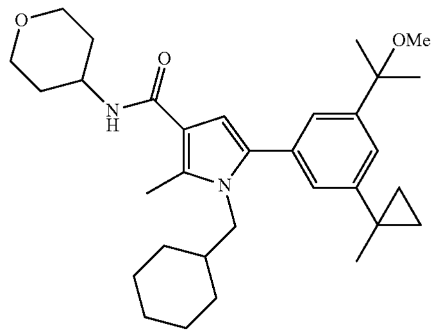 [SMILES: COC(C)(C)c1cc(-c2cc(C(=O)NC3CCOCC3)c(C)n2CC2CCCCC2)cc(C2(C)CC2)c1] | $^1$H-NMR ($CDCl_3$, 400 MHz) δ: 0.61-0.64 (m, 2H), 0.75-0.77 (m, 2H), 0.86-0.89 (m, 2H), 0.98-0.99 (m, 3H), 1.32-1.37 (m, 3H), 1.43 (s, 3H), 1.47-1.53 (m, 11H), 1.96-2.00 (m, 2H), 2.61 (s, 3H), 3.08 (s, 1H), 3.53 (t, 2H, J = 12.0 Hz), 3.74 (d, 2H, J = 8.0 Hz), 3.96-3.99 (m, 2H), 4.15-4.17 (m, 1 H), 5.61 (d, 1H, J = 8.0 Hz), 6.18 (s, 1H), 7.08 (s, 1H), 7.16 (s, 1H), 7.26 (s, 1H). MS 507.2 $(M + 1)^+$. |
| 17/344 | 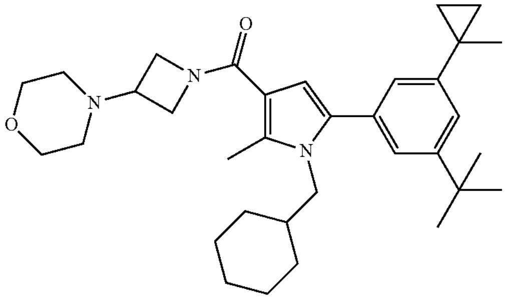 [SMILES: Cc1c(C(=O)N2CC(N3CCOCC3)C2)cc(-c2cc(C(C)(C)C)cc(C3(C)CC3)c2)n1CC1CCCCC1] | $^1$H-NMR ($CDCl_3$, 400 MHz) δ: 0.62-0.68 (m, 2H), 0.73-0.75 (m, 2H), 0.85-0.88 (m, 2H), 0.99 (m, 3H), 1.26-1.28 (m, 1H), 1.33 (s, 9H), 1.37-1.39 (m, 2H), 1.42 (s, 3H), 1.52-1.54 (m, 3H), 2.39 (m, 4H), 2.57 (s, 3H), 3.14-3.19 (m, 1H), 3.70-3.74 (m, 6H), 3.98-4.32 (m, 4H), 6.17 (s, 1H), 7.00 (m, 1H), 7.12 (m, 1H), 7.25 (m, 1H). MS: 532.4 $(M + 1)^+$. |
| 17/345 | 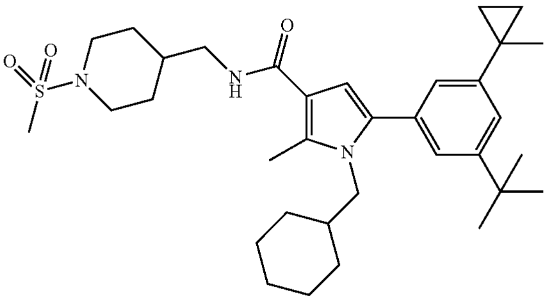 [SMILES: Cc1c(C(=O)NCC2CCN(S(C)(=O)=O)CC2)cc(-c2cc(C(C)(C)C)cc(C3(C)CC3)c2)n1CC1CCCCC1] | $^1$H-NMR ($CDCl_3$, 400 MHz) δ: 0.63-0.66 (m, 2H), 0.73-0.76 (m, 2H), 0.85-0.88 (m, 2H), 0.99 (m, 3H), 1.33 (s, 9H), 1.36-1.39 (m, 4H), 1.42 (s, 3H), 1.53-1.55 (m, 4H), 1.70-1.80 (m, 1H), 1.88 (d, J = 13.2 Hz, 2H), 2.61 (s, 3H), 2.66 (m, 2H), 2.76 (s, 3H), 3.30 (m, 2H), 3.71 (d, J = 7.2 Hz, 2H), 3.80 (m, 2H), 5.89 (m, 1H), 6.15 (s, 1H), 7.00 (m, 1H), 7.12 (m, 1H), 7.25 (m, 1H). MS: 582.4 $(M + 1)^+$. |
| 17/346 | 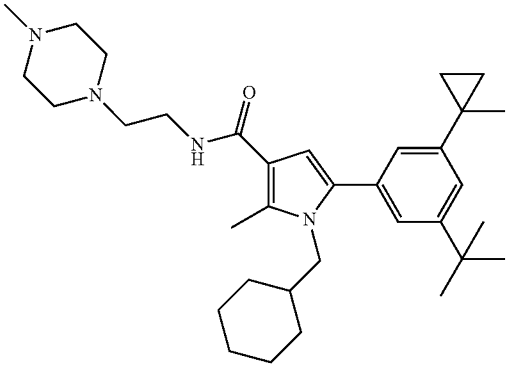 [SMILES: Cc1c(C(=O)NCCN2CCN(C)CC2)cc(-c2cc(C(C)(C)C)cc(C3(C)CC3)c2)n1CC1CCCCC1] | $^1$H-NMR ($CDCl_3$, 400 MHz) δ: 0.64-0.67 (m, 2H), 0.73-0.75 (m, 2H), 0.86-0.88 (m, 2H), 1.00 (m, 3H), 1.33 (s, 9H), 1.34-1.38 (m, 2H), 1.42 (s, 3H), 1.61-1.63 (m, 5H), 2.53 (s, 3H), 2.57 (s, 3H), 2.60-3.00 (m, 3H), 3.10-3.30 (m, 5H), 3.67-3.68 (m, 2H), 3.71-3.73 (m, 2H), 6.28 (s, 1H), 7.00 (m, 1H), 7.12 (m, 1H), 7.27 (m, 1H). MS: 533.4 $(M + 1)^+$. |

-continued
| # | Structure | Analytical data |
|---|---|---|
| 17/347 | 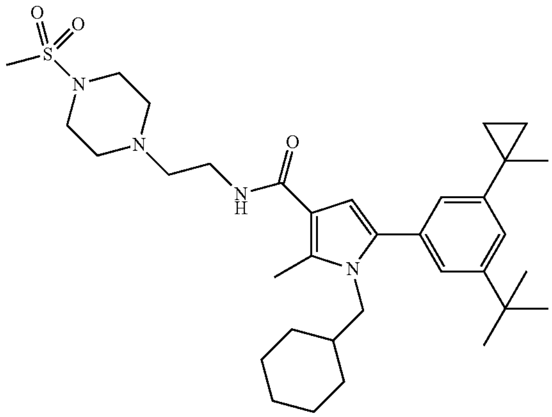 [SMILES: Cc1c(C(=O)NCCN2CCN(S(C)(=O)=O)CC2)cc(-c2cc(C(C)(C)C)cc(C3(C)CC3)c2)n1CC1CCCCC1] | $^1$H-NMR ($CDCl_3$, 400 MHz) δ: 0.62-0.68 (m, 2H), 0.75-0.77 (m, 2H), 0.85-0.87 (m, 2H), 1.00 (m, 3H), 1.33 (s, 9H), 1.35-1.38 (m, 2H), 1.43 (s, 3H), 1.53-1.56 (m, 4H), 2.58-2.64 (m, 9H), 2.77 (s, 3H), 3.24 (m, 4H), 3.50-3.52 (m, 2H), 3.70 (d, J = 7.2 Hz, 2H), 6.17 (s, 1H), 7.02 (m, 1H), 7.14 (m, 1H), 7.28 (m, 1H). MS: 597.4 $(M + 1)^+$. |
| 17/348 | 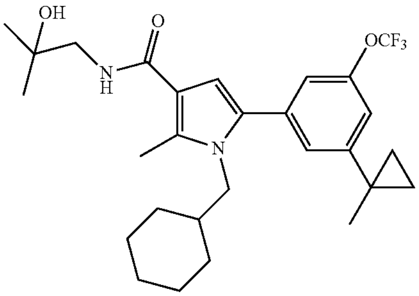 [SMILES: Cc1c(C(=O)NCC(C)(C)O)cc(-c2cc(OC(F)(F)F)cc(C3(C)CC3)c2)n1CC1CCCCC1] | $^1$H-NMR (400 MHz, $CD_3OD$) δ: 0.65-0.74 (m, 2H), 0.82-0.86 (m, 2H), 0.88-0.82 (m, 2H), 0.99-1.04 (m, 3H), 1.21 (s, 6H), 1.28-1.39 (m, 3H), 1.43 (s, 3H), 1.53-1.56 (m, 3H), 2.56 (s, 3H), 3.32 (s, 2H), 3.84 (d, J = 7.2 Hz, 2H), 6.51 (s, 1H), 7.07 (m, 1H), 7.11 (m, 1H), 7.23 (m, 1H). MS: 507.3 $(M + 1)^+$. |
| 17/349 | 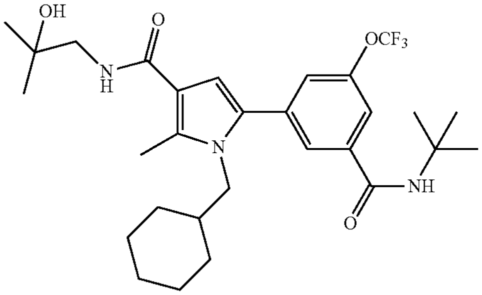 [SMILES: Cc1c(C(=O)NCC(C)(C)O)cc(-c2cc(OC(F)(F)F)cc(C(=O)NC(C)(C)C)c2)n1CC1CCCCC1] | $^1$H-NMR (400 MHz, $CD_3OD$) δ: 0.70-0.73 (m, 2H), 1.01-1.05 (m, 3H), 1.22 (s, 6H), 1.33-1.36 (m, 3H), 1.46 (s, 9H), 1.55-1.58 (m, 3H), 2.58 (s, 3H), 3.33 (s, 2H), 3.90 (d, J = 7.6 Hz, 2H), 6.60 (s, 1H), 7.45 (s, 1H), 7.64 (s, 1H), 7.77 (m, 1H). MS: 552.3 $(M + 1)^+$. |
| 17/350 | 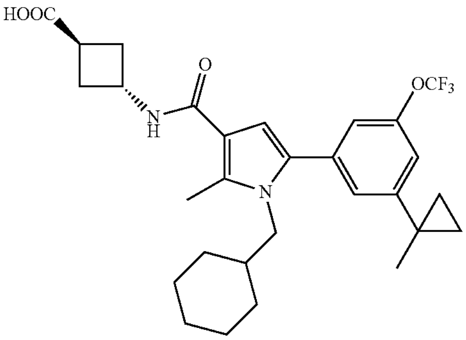 [SMILES: Cc1c(C(=O)N[C@H]2C[C@H](C(=O)O)C2)cc(-c2cc(OC(F)(F)F)cc(C3(C)CC3)c2)n1CC1CCCCC1] | $^1$H-NMR (400 MHz, $CD_3OD$) δ: 0.71-0.74 (m, 2H), 0.86-0.89 (m, 2H), 0.93-0.95 (m, 2H), 1.02-1.07 (m, 3H), 1.33-1.36 (m, 3H), 1.47 (s, 3H), 1.57-1.60 (m, 3H), 2.37-2.47 (m, 2H), 2.58 (s, 3H), 2.61-2.67 (m, 2H), 3.05-3.07 (m, 1H), 3.87 (d, J = 6.8 Hz, 2H), 4.66-4.73 (m, 1H), 6.57 (s, 1H), 7.10 (s, 1H), 7.14 (s, 1H), 7.27 (s, 1H). MS: 533.2 $(M + 1)^+$. |

-continued
| # | Structure | Analytical data |
|---|---|---|
| 17/351 | 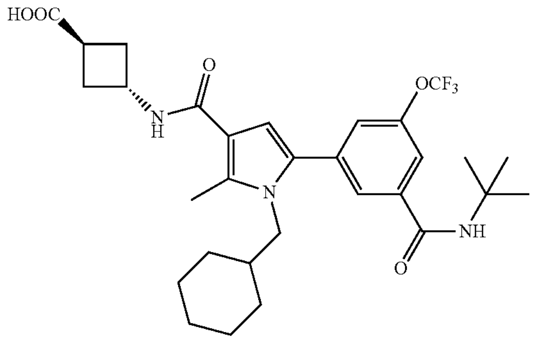 [SMILES: Cc1c(C(=O)N[C@H]2C[C@H](C(=O)O)C2)cc(-c2cc(OC(F)(F)F)cc(C(=O)NC(C)(C)C)c2)n1CC1CCCCC1] | $^1$H-NMR (400 MHz, $CD_3OD$) δ: 0.69-0.72 (m, 2H), 0.99-1.04 (m, 3H), 1.28-1.35 (m, 3H), 1.46 (s, 9H), 1.55-1.57 (m, 3H), 2.33-2.41 (m, 2H), 2.55 (s, 3H), 2.57-2.64 (m, 2H), 3.00-3.05 (m, 1H), 3.89 (d, J = 7.2 Hz, 2H), 4.64-4.68 (m, 1H), 6.61 (s, 1H), 7.44 (s, 1H), 7.63 (s, 1H), 7.76 (s, 1H). MS: 578.3 $(M + 1)^+$. |
| 17/352 | 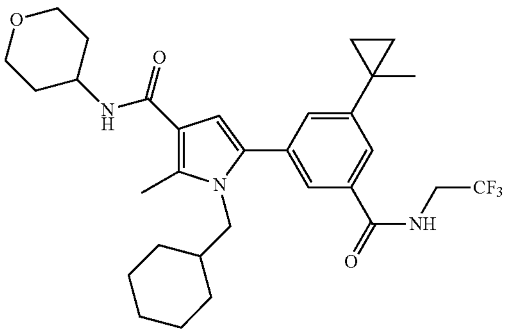 [SMILES: Cc1c(C(=O)NC2CCOCC2)cc(-c2cc(C(=O)NCC(F)(F)F)cc(C3(C)CC3)c2)n1CC1CCCCC1] | $^1$H-NMR (400 MHz, $CDCl_3$) δ: 0.58-0.60 (m, 2H), 0.63-1.02 (m, 4H), 1.23-1.68 (m, 12H), 1.94-1.98 (m, 2H), 2.62 (s, 3H), 3.48 (t, J = 7.2 Hz, 2H), 3.76 (d, J = 8.0 Hz, 2H), 3.98 (d, J = 12.4 Hz, 2H), 4.09-4.16 (m, 3H), 5.64-5.66 (m, 1H), 6.24 (s, 1H), 6.69 (s, 1H), 7.40 (s, 1H), 7.57 (s, 1H), 7.70 (s, 1H). MS: 560.3 $(M + 1)^+$. |
| 17/353 | 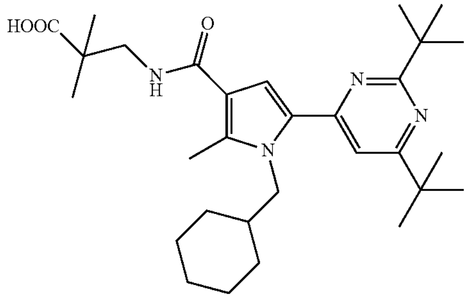 [SMILES: Cc1c(C(=O)NCC(C)(C)C(=O)O)cc(-c2cc(C(C)(C)C)nc(C(C)(C)C)n2)n1CC1CCCCC1] | $^1$H-NMR (400 MHz, $CDCl_3$) δ: 7.20 (s, 1H), 6.77 (s, 1H), 6.36 (m, 1H), 4.57 (m, 2H), 3.56 (d, 2H, J = 6.4 Hz), 2.60 (s, 3H), 1.59 (m, 3H), 1.54-1.20 (m, 27H), 1.01 (m, 3H), 0.81 (m, 2H). MS: 511.3 $(M + 1)^+$. |
| 17/354 | 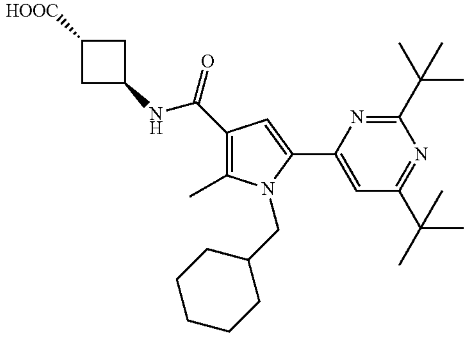 [SMILES: Cc1c(C(=O)N[C@H]2C[C@H](C(=O)O)C2)cc(-c2cc(C(C)(C)C)nc(C(C)(C)C)n2)n1CC1CCCCC1] | $^1$H-NMR (400 MHz, $CDCl_3$) δ: 7.21 (s, 1H), 6.79 (s, 1H), 6.03 (d, 1H, J = 6.8 Hz), 4.82 (m, 1H), 4.58 (s, 2H), 3.11 (m, 1H), 2.81 (m, 2H), 2.61 (s, 3H), 2.36 (m, 2H), 1.60 (m, 3H), 1.55-1.37 (m, 21H), 1.05 (m, 3H), 0.83 (m, 2 H). MS: 509.3 $(M + 1)^+$. |

-continued
| # | Structure | Analytical data |
|---|---|---|
| 17/355 | 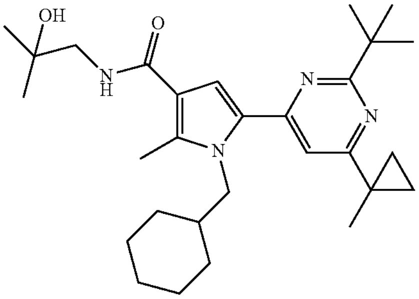 [SMILES: Cc1c(C(=O)NCC(C)(C)O)cc(-c2cc(C3(C)CC3)nc(C(C)(C)C)n2)n1CC1CCCCC1] | $^1$H-NMR (400 MHz, $CDCl_3$) δ: 7.22 (s, 1H), 6.84 (s, 1H), 6.22 (m, 1H), 4.59 (m, 2H), 3.42 (d, 2H, J = 6.0 Hz), 2.62 (s, 3H), 1.61 (m, 3H), 1.53-1.42 (m, 8H), 1.36 (s, 9H), 1.28 (s, 6H), 1.04 (m, 3H), 0.87-0.79 (m, 4H). MS: 481.4 $(M + 1)^+$. |
| 17/356 | 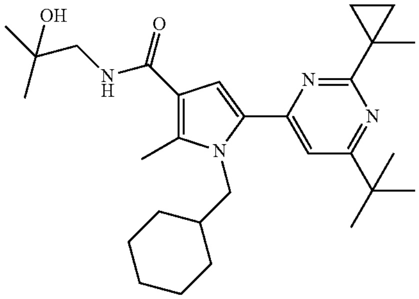 [SMILES: Cc1c(C(=O)NCC(C)(C)O)cc(-c2cc(C(C)(C)C)nc(C3(C)CC3)n2)n1CC1CCCCC1] | $^1$H-NMR (400 MHz, $CDCl_3$) δ: 7.17 (s, 1H), 6.83 (s, 1H), 6.24 (m, 1H), 4.54 (m, 2H), 3.42 (d, 2H, J = 5.6 Hz), 2.61 (s, 3H), 1.63-1.54 (m, 6H), 1.45-1.34 (m, 14H), 1.29 (s, 6H), 1.07 (m, 3H), 0.88-0.84 (m, 4H). MS: 481.3 $(M + 1)^+$. |
| 17/357 | 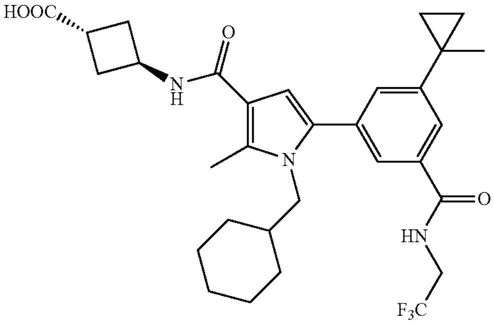 [SMILES: Cc1c(C(=O)N[C@H]2C[C@H](C(=O)O)C2)cc(-c2cc(C(=O)NCC(F)(F)F)cc(C3(C)CC3)c2)n1CC1CCCCC1] | $^1$H-NMR (400 MHz, $CD_3OD$) δ: 0.59-0.65 (m, 2H), 0.78 (s, 2H), 0.89-0.96 (m, 5H), 1.22-1.29 (m, 5H), 1.41 (s, 3H), 1.45-1.48 (m, 2H), 2.30-2.32 (m, 2H), 2.49 (s, 3H), 2.54-2.56 (m, 2H), 2.96-2.99 (m, 2H), 3.80 (d, J = 6.8 Hz, 2H), 4.04 (dd, J = 14.4, 7.2 Hz, 2H), 4.60 (br s, 1H), 6.48 (s, 1H), 7.41 (s, 1H), 7.60 (s, 1H), 7.69 (s, 1H). MS: 574.3 $(M + 1)^+$. |
| 17/358 | 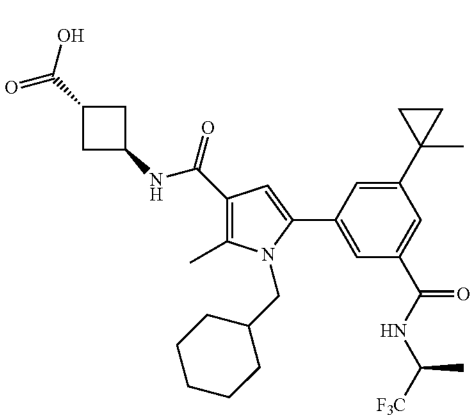 [SMILES: Cc1c(C(=O)N[C@H]2C[C@H](C(=O)O)C2)cc(-c2cc(C(=O)N[C@@H](C)C(F)(F)F)cc(C3(C)CC3)c2)n1CC1CCCCC1] | $^1$H-NMR (400 MHz, $CD_3OD$) δ: 0.57-0.61 (m, 2H), 0.72-0.75 (m, 2H), 0.84-0.86 (m, 2H), 0.92-0.97 (m, 3H), 1.20-1.28 (m, 3H), 1.33-1.37 (m, 6H), 144-1.47 (m, 3H), 2.12-2.19 (m, 2H), 2.44 (s, 3H), 2.45-2.54 (m, 2H), 2.84-2.88 (m, 1H), 3.76 (d, J = 6.8 Hz, 2H), 4.46-4.50 (m, 1H), 4.78-4.84 (m, 1H), 6.45 (s, 1H), 7.37 (s, 1H), 7.56 (s, 1H), 7.63 (s, 1H). MS: 588.4 $(M + 1)^+$. |

-continued
| # | Structure | Analytical data |
| --- | --- | --- |
| 17/359 | 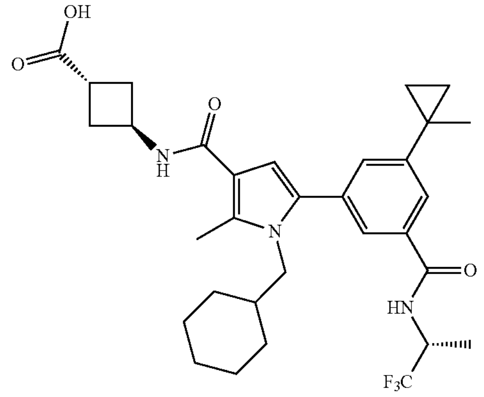 [SMILES: Cc1c(C(=O)N[C@H]2C[C@H](C(=O)O)C2)cc(-c2cc(C(=O)N[C@H](C)C(F)(F)F)cc(C3(C)CC3)c2)n1CC1CCCCC1] | $^1$H-NMR (400 MHz, $CD_3OD$) δ: 0.57-0.61 (m, 2H), 0.72-0.75 (m, 2H), 0.84-0.86 (m, 2H), 0.92-0.97 (m, 3H), 1.20-1.28 (m, 3H), 1.33-1.37 (m, 6H), 144-1.47 (m, 3H), 2.12-2.19 (m, 2H), 2.44 (s, 3H), 2.45-2.54 (m, 2H), 2.84-2.88 (m, 1H), 3.76 (d, J = 6.8 Hz, 2H), 4.46-4.50 (m, 1H), 4.78-4.84 (m, 1H), 6.45 (s, 1H), 7.37 (s, 1H), 7.56 (s, 1H), 7.63 (s, 1H). MS: 588.3 $(M + 1)^+$. |
| 17/360 | 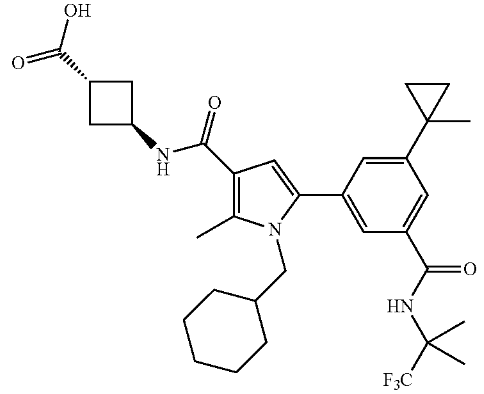 [SMILES: Cc1c(C(=O)N[C@H]2C[C@H](C(=O)O)C2)cc(-c2cc(C(=O)NC(C)(C)C(F)(F)F)cc(C3(C)CC3)c2)n1CC1CCCCC1] | $^1$H-NMR (400 MHz, $CD_3OD$) δ: 0.58-0.61 (m, 2H), 0.71-0.74 (m, 2H), 0.83-0.85 (m, 2H), 0.92 (s, 3H), 1.23-1.30 (m, 3H), 1.37 (d, J = 7.2 Hz, 3H), 1.45-1.47 (m, 3H), 1.59 (s, 6H), 2.12-2.20 (m, 2H), 2.44 (d, J = 5.6 Hz, 3H), 2.48-2.55 (m, 2H), 2.86-2.88 (m, 1H), 3.75 (d, J = 6.8 Hz, 2H), 4.48 (t, J = 7.6 Hz, 1H), 6.44 (s, 1H), 7.34 (t, J = 1.6 Hz, 1H), 7.43 (t, J = 1.6 Hz, 1H), 7.50 (t, J = 1.6 Hz, 1H). MS: 602.4 $(M + 1)^+$. |
| 17/361 | 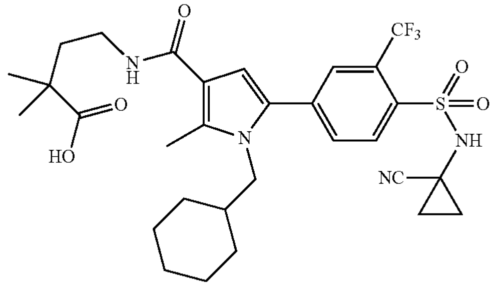 [SMILES: Cc1c(C(=O)NCCC(C)(C)C(=O)O)cc(-c2ccc(S(=O)(=O)NC3(C#N)CC3)c(C(F)(F)F)c2)n1CC1CCCCC1] | MS: 623.3 $(M + 1)^+$. |
| 17/362 | 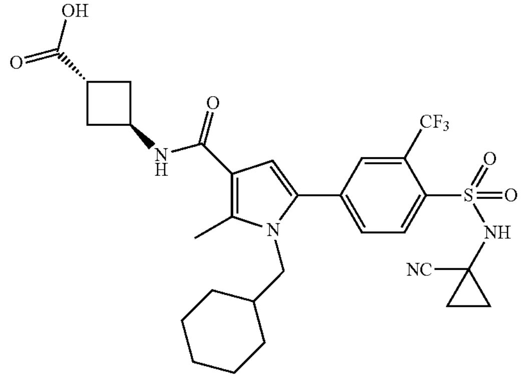 [SMILES: Cc1c(C(=O)N[C@H]2C[C@H](C(=O)O)C2)cc(-c2ccc(S(=O)(=O)NC3(C#N)CC3)c(C(F)(F)F)c2)n1CC1CCCCC1] | MS: 607.2 $(M + 1)^+$. |

-continued
| # | Structure | Analytical data |
|---|---|---|
| 17/363 | 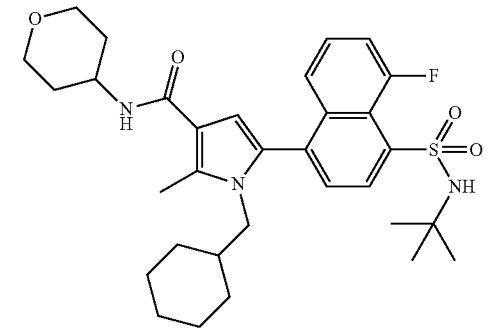 [SMILES: Cc1c(C(=O)NC2CCOCC2)cc(-c2ccc(S(=O)(=O)NC(C)(C)C)c3c(F)cccc23)n1CC1CCCCC1] | MS: 584.3 $(M + 1)^+$. |
| 17/364 | 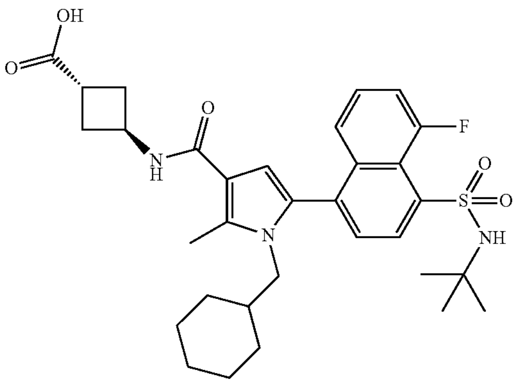 [SMILES: Cc1c(C(=O)N[C@H]2C[C@H](C(=O)O)C2)cc(-c2ccc(S(=O)(=O)NC(C)(C)C)c3c(F)cccc23)n1CC1CCCCC1] | MS: 598.3 $(M + 1)^+$. |
| 17/365 | 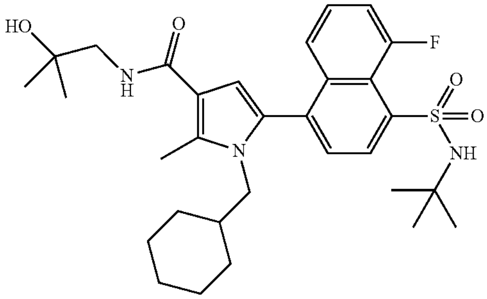 [SMILES: Cc1c(C(=O)NCC(C)(C)O)cc(-c2ccc(S(=O)(=O)NC(C)(C)C)c3c(F)cccc23)n1CC1CCCCC1] | MS: 572.3 $(M + 1)^+$. |
| 17/366 | 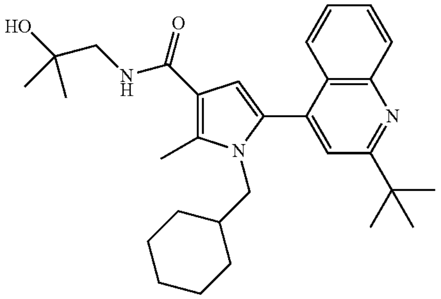 [SMILES: Cc1c(C(=O)NCC(C)(C)O)cc(-c2cc(C(C)(C)C)nc3ccccc23)n1CC1CCCCC1] | $^1$H-NMR (400 MHz, $CDCl_3$) δ: 8.68 (s, 1H), 8.08 (d, 1H, J = 8.8 Hz), 7.95 (d, 1H, J = 5.6 Hz), 7.78 (t, 1H, J = 7.6 Hz), 7.58 (s, 1H), 6.75 (d, 1H, J = 6.8 Hz), 6.54-6.46 (m, 1H), 3.75 (s, 2H), 3.44 (d, 2H, J = 4.4 Hz), 2.72 (s, 3H), 1.63 (s, 9H), 1.52 (d, 3H, J = 6.8 Hz), 1.33-1.28 (m, 9H), 0.98-0.89 (m, 3H), 0.54-0.48 (m, 2H). MS: 476.3 $(M + 1)^+$. |

-continued

| # | Structure | Analytical data |
|---|---|---|
| 17/367 | 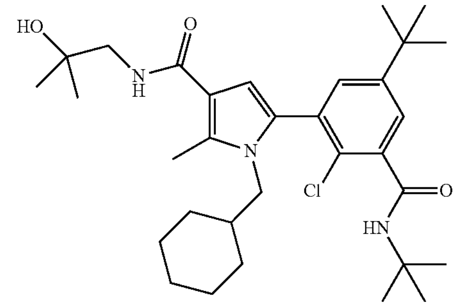 [SMILES: Cc1c(C(=O)NCC(C)(C)O)cc(-c2cc(C(C)(C)C)cc(C(=O)NC(C)(C)C)c2Cl)n1CC1CCCCC1] | $^1$H-NMR (400 MHz, $CDCl_3$) δ: 8.08 (s, 1H), 7.47 (t, 1H, J = 6.0 Hz), 7.38 (d, 1H, J = 2.4 Hz), 7.29 (d, 1H, J = 2.4 Hz), 6.99 (s, 1H), 3.16 (d, 2H, J = 6.0 Hz), 2.52 (s, 3H), 1.52-1.51 (m, 3H), 1.36-1.25 (m, 21H), 1.07 (s, 6H), 1.01-0.94 (m, 3H), 0.62-0.58 (m, 2H). MS: 558.3 $(M + 1)^+$. |
| 17/368 | 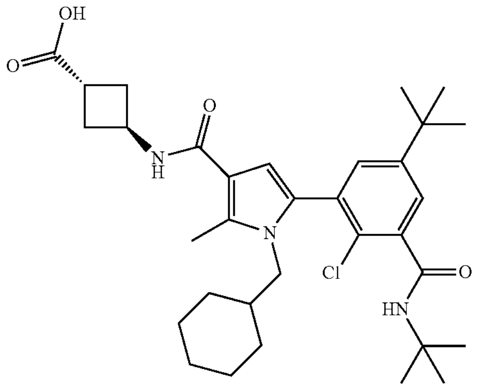 [SMILES: Cc1c(C(=O)N[C@H]2C[C@H](C(=O)O)C2)cc(-c2cc(C(C)(C)C)cc(C(=O)NC(C)(C)C)c2Cl)n1CC1CCCCC1] | $^1$H-NMR (400 MHz, DMSO-$d_6$) δ: 7.59 (d, 1H, J = 2.4 Hz), 7.37 (d, 1H, J = 2.4 Hz), 6.19 (s, 1H), 6.05 (d, 1H, J = 7.2 Hz), 5.86 (s, 1H), 4.77 (t, 1H, J = 5.2 Hz), 3.49 (s, 2H), 3.06 (t, 1H, J = 7.2 Hz), 2.77 (t, 2H, J = 9.2 Hz), 2.59 (s, 3H), 2.30 (t, 2H, J = 8.8 Hz), 1.57-1.25 (m, 24H), 1.01 (s, 3H), 0.65-0.60 (m, 2H). MS: 584.3 $(M + 1)^+$. |
| 17/369 | 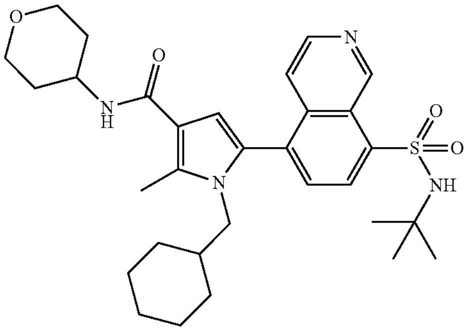 [SMILES: Cc1c(C(=O)NC2CCOCC2)cc(-c2ccc(S(=O)(=O)NC(C)(C)C)c3cnccc23)n1CC1CCCCC1] | $^1$H-NMR (400 MHz, $CDCl_3$) δ: 10.17 (s, 1H), 8.67 (d, J = 6.0 Hz, 1H), 8.41 (d, J = 7.6 Hz, 1H), 7.73-7.68 (m, 2H), 6.38 (s, 1H), 5.63 (d, J = 8.0 Hz, 1H), 5.21 (s, 1H), 4.19 (m, 1H), 4.02-3.95 (m, 2H), 3.77-3.70 (m, 1H), 3.54 (m, 2H), 3.37-3.30 (m, 1H), 2.69 (s, 3H), 2.03-1.97 (m, 2H), 1.59-1.42 (m, 5H), 1.29-1.19 (m, 12H), 0.95-0.85 (m, 3H), 0.55-0.46 (m, 2H). MS: 567.3 $(M + 1)^+$. |
| 17/370 | 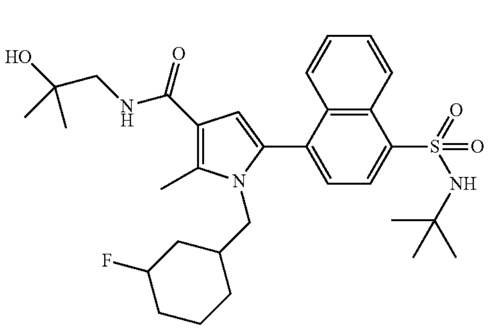 [SMILES: Cc1c(C(=O)NCC(C)(C)O)cc(-c2ccc(S(=O)(=O)NC(C)(C)C)c3ccccc23)n1CC1CCCC(F)C1] | $^1$H-NMR (300 MHz, $CDCl_3$) δ: 8.66 (d, J = 8.4 Hz, 1H), 8.34 (d, J = 8.4 Hz, 1H), 7.80-7.45 (m, 4H), 6.39 (s, 1H), 6.20 (t, J = 6.4 Hz, 1H), 4.70-4.52 (m, 1H), 3.75-3.60 (m, 1H), 3.41 (m, 2H), 3.36-3.27 (m, 1H), 2.66 (s, 3H), 1.86-1.73 (m, 2H), 1.40-1.01 (m, 21H), 0.95-0.46 (m, 3H). MS: 572.3 $[M + 1]^+$. |

-continued
| # | Structure | Analytical data |
| --- | --- | --- |
| 17/371 | 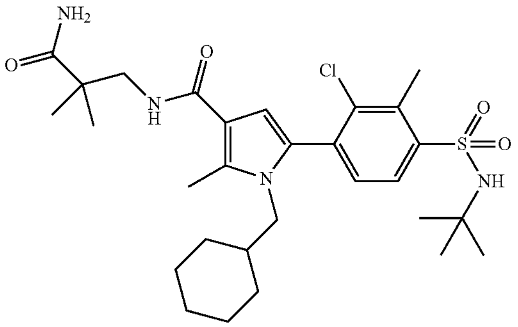 [SMILES: Cc1c(S(=O)(=O)NC(C)(C)C)ccc(-c2cc(C(=O)NCC(C)(C)C(N)=O)c(C)n2CC2CCCCC2)c1Cl] | $^1$H-NMR (300 MHz, $CDCl_3$) δ: 0.87-0.68 (m, 2H), 1.30-1.20 (m, 3H), 1.47 (s, 9H), 1.49 (s, 6H), 1.85-1.50 (m, 6H), 2.79 (s, 3H), 2.95 (s, 3H), 3.80-3.60 (m, 4H), 4.98 (s, 1H), 5.75 (br s, 1H), 6.44 (s, 1H), 6.49 (br s, 1H), 6.70 (t, J = 6.3 Hz, 1H), 7.47 (d, J = 8.4 Hz, 1H), 8.21 (d, J = 8.4 Hz, 1H). MS: 579.3 $[M + 1]^+$. |
| 17/372 | 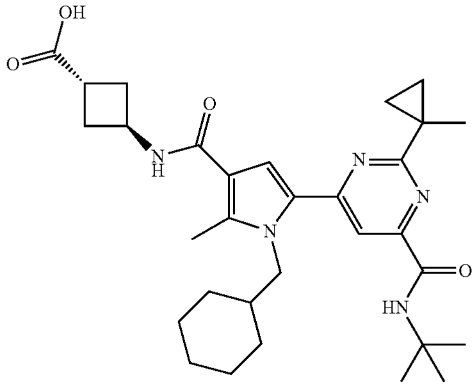 [SMILES: Cc1c(C(=O)N[C@H]2C[C@H](C(=O)O)C2)cc(-c2cc(C(=O)NC(C)(C)C)nc(C3(C)CC3)n2)n1CC1CCCCC1] | $^1$H-NMR (400 MHz, $CDCl_3$) δ: 8.08 (s, 1H), 7.20 (s, 1H), 6.22 (m, 1H), 4.75-4.69 (m, 1H), 4.51-4.47 (m, 2H), 3.23-3.18 (m, 1H), 2.83-2.81 (m, 2H), 2.61 (s, 3H), 2.43-2.36 (m, 2H), 1.70-1.60 (m, 6H), 1.54 (s, 9H), 1.44-1.25 (m, 5H), 1.10-0.81 (m, 7H). MS: 550.3 $(M + 1)^+$. |
| 17/373 | 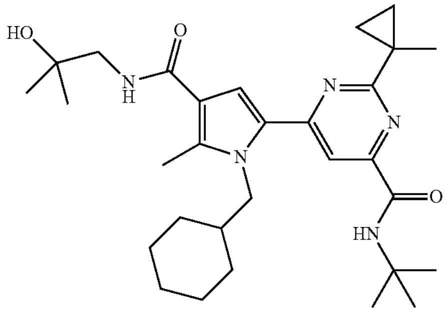 [SMILES: Cc1c(C(=O)NCC(C)(C)O)cc(-c2cc(C(=O)NC(C)(C)C)nc(C3(C)CC3)n2)n1CC1CCCCC1] | $^1$H-NMR (400 MHz, $CDCl_3$) δ: 8.04 (s, 1H), 7.96 (s, 1H), 7.05 (s, 1H), 6.29 (m, 1H), 4.51 (m, 1H), 3.41 (m, 2H), 2.61 (s, 3H), 1.70-1.60 (m, 6H), 1.56 (s, 9H), 1.54-1.34 (m, 5H), 1.28-1.22 (m, 6H), 1.09-0.80 (m, 7H). MS: 524.3 $(M + 1)^+$. |
| 17/374 | 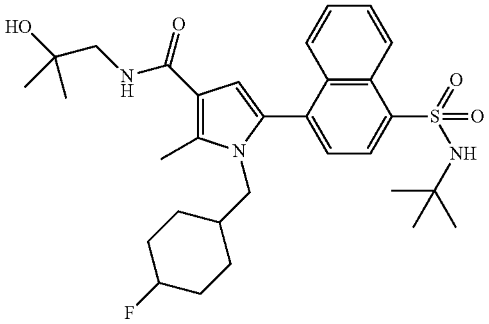 [SMILES: Cc1c(C(=O)NCC(C)(C)O)cc(-c2ccc(S(=O)(=O)NC(C)(C)C)c3ccccc23)n1CC1CCC(F)CC1] | $^1$H-NMR (300 MHz, $CDCl_3$) δ: 8.67 (d, J = 8.4 Hz, 1H), 8.35 (d, J = 8.4 Hz, 1H), 7.78-7.40 (m, 4H), 6.42 (s, 1H), 6.32 (br s, 1H), 4.71 (br s, 1H), 4.30-4.11 (m, 1H), 3.78-3.72 (m, 1H), 3.50-3.28 (m, 3H), 2.68 (s, 3H), 1.50-1.10 (m, 23H), 1.95-1.70 (m, 2H). MS: 572.3 $[M + 1]^+$. |

Example 18/1 to 18/5

The following Preparative Examples were prepared similar as described in WO2012/139775 according the depicted experimental number.

| # | Structure | educt | Analytical data |
|---|---|---|---|
| 18/1 | 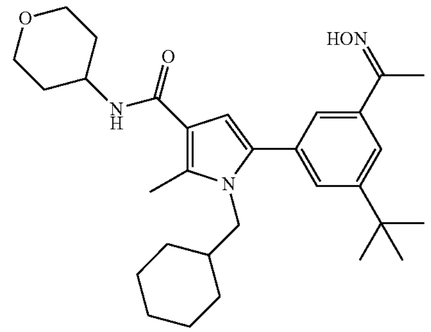 | 17/103 Ex. #6 | $^1$H-NMR ($CDCl_3$, 300 MHz) δ: 7.66 (t, 1H), 7.50 (s, 1H), 7.36 (t, 2H), 6.21 (s, 1H), 5.63 (d, 1H, J = 7.8 Hz), 4.14-4.19 (m, 1H), 3.98 (d, 2H, J = 12.6 Hz), 3.74 (d, 2H, J = 7.2 Hz), 3.53 (t, 2H, J = 9.9 Hz), 2.62 (s, 3H), 2.31 (s, 3H), 1.96-2.00 (m, 2H), 1.30-1.58 (m, 12H), 0.97-1.00 (m, 3H), 0.61-0.66 (m, 2H). MS: 494.3 $(M + 1)^+$. |
| 18/2 | 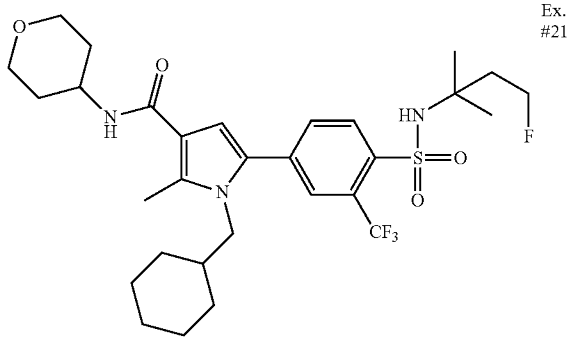 | 17/108 Ex. #21 | $^1$H-NMR ($CDCl_3$, 400 MHz) δ: 8.29 (d, 1H, J = 8.4 Hz), 7.81 (s, 1H), 7.62 (dd, 1H, J = 8.4, J = 1.6 Hz), 6.38 (s, 1H), 5.62 (d, 1H), 4.94 (br s, 1H), 4.69 (t, 1H), 4.57 (t, 1H), 4.13-4.20 (m, 1H), 3.98-4.00 (m, 2H), 3.81 (d, 2H), 3.53 (td, 2H), 2.63 (s, 3H), 2.07 (7, 1H), 1.97-2.01 (m, 3H), 1.48-1.57 (m, 5H), 1.28-1.38 (m, 3H), 1.25 (s, 6H), 1.00-1.24 (m, 3H), 0.61-0.67 (m, 2H). MS: 616.3 $(M + 1)^+$. |
| 18/3 | 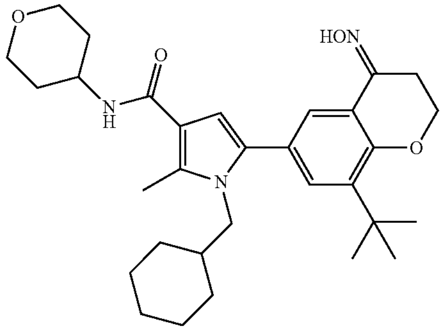 | 17/104 Ex. #6/1 | $^1$H-NMR ($CDCl_3$, 400 MHz) δ: 7.70 (d, 1H), 7.41 (s, 1H), 7.20 (d, 1H), 6.15 (s, 1H), 5.62 (d, 1H, J = 8.0 Hz), 4.27 (t, 2H, J = 6.0 Hz), 4.13-4.19 (m, 1H), 3.96-3.99 (m, 2H), 3.72 (d, 2H, J = 7.6 Hz), 3.50-3.55 (m, 2H), 3.02 (t, 2H, J = 6.0 Hz), 2.61 (s, 3H), 1.96-1.99 (m, 2H), 1.47-1.58 (m, 5H), 1.32-1.38 (m, 12H), 0.98-1.02 (m, 3H), 0.64-0.72 (m, 2H). MS: 522.3 $(M + 1)^+$. |
| 18/4 | 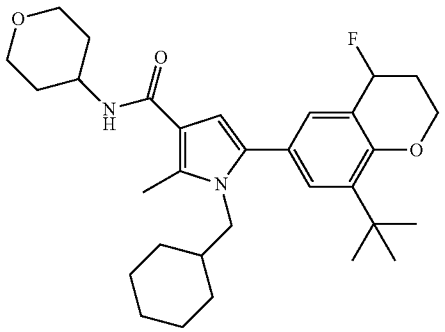 [SMILES: Cc1c(C(=O)NC2CCOCC2)cc(-c2cc3c(c(C(C)(C)C)c2)OCCC3F)n1CC1CCCCC1] | 17/105 Ex. #26 | $^1$H-NMR ($CDCl_3$, 400 MHz) δ: 7.21 (s, 1H), 7.15 (s, 1H), 6.13 (s, 1H), 5.44-5.61 (m, 2H), 4.41-4.44 (m, 1H), 4.14-4.27 (m, 2H), 3.97 (d, 2H, J = 12.0 Hz), 3.64-3.75 (m, 2H), 3.49-3.55 (m, 2H), 2.61 (s, 3H), 2.27-2.31 (m, 2H), 1.96-2.00 (m, 2H), 1.38-1.57 (m, 17H), 1.02-1.04 (m, 3H), 0.65-0.72 (m, 2H). $^{19}$F-NMR ($CDCl_3$, 376 MHz) δ: −149.97 (s). MS: 511.4 $(M + 1)^+$. |

-continued

| # | Structure | educt | Analytical data |
|---|---|---|---|
| 18/5 | 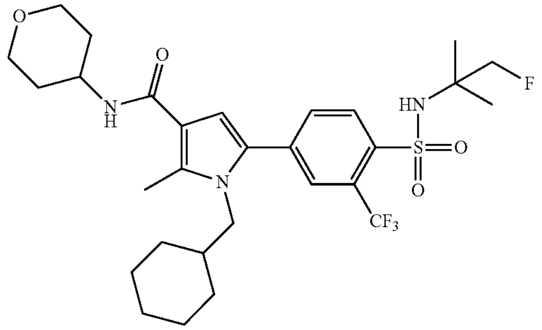 [SMILES: Cc1c(C(=O)NC2CCOCC2)cc(-c2ccc(S(=O)(=O)NC(C)(C)CF)c(C(F)(F)F)c2)n1CC1CCCCC1] | 17/107 Ex. #21 | $^1$H-NMR ($CDCl_3$, 400 MHz) δ: 8.20 (d, 1H, J = 8.0 Hz), 7.84 (s, 1H), 7.63 (d, 1H, J = 8.0 Hz), 6.37 (s, 1H), 5.63 (d, 1H, J = 8.0 Hz), 5.04 (t, J = 6.0 Hz, 1H), 4.13-4.19 (m, 1H), 3.98-4.01 (m, 2H), 3.81 (d, J = 7.2 Hz, 2H), 3.49-3.56 (m, 2H), (m, 3.12-3.18 (m, 2H), 2.64 (s 3H), 1.97-2.00 (m, 2H), 1.49-1.67 (m, 5H), 1.40 (s, 3H), 1.34 (s, 6H), 0.99-1.12 (m, 3H), 0.62-0.65 (m, 2H). MS: 602.3 (M + 1)$^+$. |

Example 19

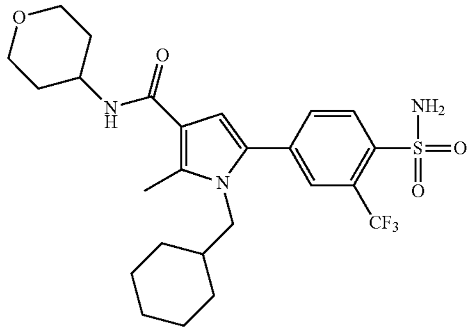

19

1-(Cyclohexylmethyl)-2-methyl-5-(4-sulfamoyl-3-(trifluoromethyl)phenyl)-N-(tetrahydro-2H-pyran-4-yl)-1H-pyrrole-3-carboxamide (19)

To a solution of compound 17/97 (150 mg, 0.26 mmol) in DCM (5 mL) was added TFA (5 mL) and the solution was stirred at 30° C. for 5 h, concentrated and purified by prep. HPLC to give compound 19 (108 mg, 82%) as a colorless solid. $^1$H-NMR (400 MHz, $CDCl_3$) δ: 0.62-0.66 (2H, m), 1.00-1.04 (3H, m), 1.26-1.57 (8H, m), 1.97-2.01 (2H, m), 2.63 (3H, s), 3.50-3.55 (2H, m), 3.81 (2H, d, J=7.6 Hz), 3.98-4.00 (2H, m), 4.14-4.17 (2H, m), 5.05-5.07 (2H, m), 5.60 (1H, d, J=8.0 Hz), 6.35 (1H, s), 7.64 (1H, dd, J=8.4, 1.6 Hz), 7.82 (1H, s), 8.30 (1H, d, J=8.0 Hz). MS: 528.2 [M+1]$^+$.

Example 19/1

Using a procedure similar as described in Example 19, the following compound was prepared.

| # | Structure | Analytical data |
|---|---|---|
| 19/1 | 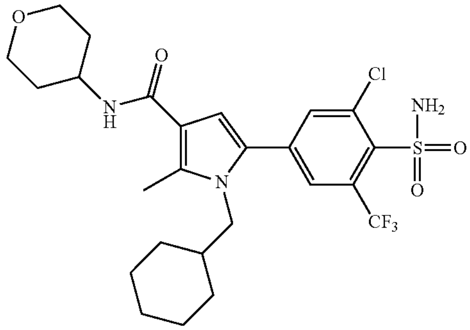 [SMILES: Cc1c(C(=O)NC2CCOCC2)cc(-c2cc(Cl)c(S(N)(=O)=O)c(C(F)(F)F)c2)n1CC1CCCCC1] | $^1$H-NMR (300 MHz, $CDCl_3$) δ: 0.66-0.77 (2H, m), 1.05-1.11 (3H, m), 1.27-1.60 (8H, m), 1.98-2.03 (2H, m), 2.64 (3H, s), 3.55 (2H, dt, J = 1.5, J = 11.4 Hz), 3.83 (2H, d, J = 7.2 Hz), 4.00 (2H, dd, J = 2.4, J = 10.2 Hz), 4.15-4.20 (1H, m), 5.53 (2H, d, J = 7.5 Hz), 5.63 (1H, d, J = 7.5 Hz), 6.41 (1H, s), 7.73 (1H, d, J = 1.8 Hz), 7.79 (1H, s). MS: 562.2 [M + 1]$^+$. |

Example 20

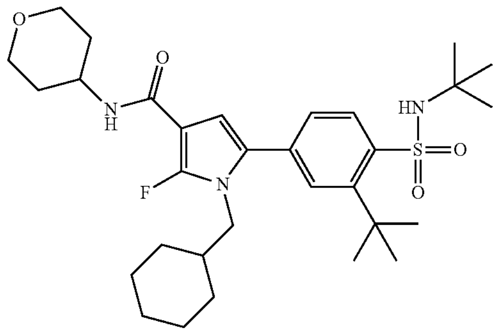

5-(3-(tert-Butyl)-4-(N-(tert-butyl)sulfamoyl)phenyl)-1-(cyclohexylmethyl)-2-fluoro-N-(tetrahydro-2H-pyran-4-yl)-1H-pyrrole-3-carboxamide (20)

To a solution of compound 17/116 (100 mg, 0.18 mmol) in MeCN (30 mL) at rt under $N_2$ was added Selectfluor (83 mg, 234 μmol) and the resulting solution was stirred at 55° C. overnight, diluted with water (50 mL) and extracted with EA (3×50 mL). The combined organic layer was concentrated and purified by prep. HPLC to give compound 20 (45 mg, 43%) as a colorless solid. $^1$H-NMR (400 MHz, $CDCl_3$) δ: 8.19 (d, J=8.4 Hz, 1H), 7.59 (d, J=1.2 Hz, 1H), 7.27 (t, 1H), 6.51 (d, J=5.6 Hz, 1H), 5.70 (br s, 1H), 4.48 (s, 1H), 4.02-3.95 (m, 1H), 4.00-3.97 (d, 2H), 3.75 (d, 2H), 3.54 (dd, J=10.0 Hz, 11.6 Hz, 2H), 2.02-1.99 (m, 2H), 1.61-1.38 (m, 17H), 1.31 (s, 9H), 1.05 (br s, 3H), 0.79-0.74 (m, 2H). MS: 576.3 [M+1]$^+$.

Example 20/1 to Example 20/9

Using a procedure similar as described in Example 20, the following compounds were prepared (and optionally subsequently saponified).

| # | Structure | Analytical data |
|---|---|---|
| 20/1 | 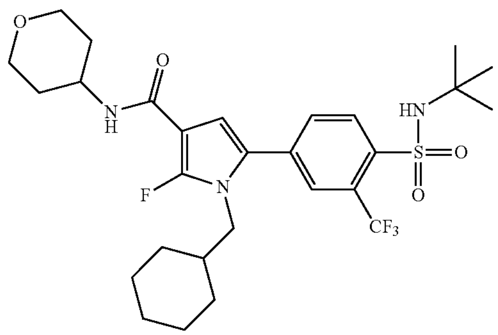 [SMILES: CC(C)(C)NS(=O)(=O)c1ccc(-c2cc(C(=O)NC3CCOCC3)c(F)n2CC2CCCCC2)cc1C(F)(F)F] | $^1$H-NMR ($CDCl_3$, 400 MHz) δ: 0.73-0.81 (m, 2H), 1.06-1.10 (m, 3H), 1.27 (s, 9H), 1.41-1.44 (m, 3H), 1.52-1.60 (m, 5H), 2.01 (d, J = 12.8 Hz, 2H), 3.54 (t, J = 11.2 Hz, 2H), 3.78 (d, J = 6.8 Hz, 2H), 3.99 (d, J = 11.2 Hz, 2H), 4.15-4.25 (m, 1H), 4.72 (s, 1H), 5.70 (br s, 1H), 6.62 (d, J = 5.6 Hz, 1H), 7.62 (d, J = 8.4 Hz, 1H), 7.80 (s, 1H) 8.32 (d, J = 8.4 Hz, 1H). $^{19}$F-NMR ($CDCl_3$, 376 MHz) δ: −57.70 (s), −127.80. MS: 588.2 (M + 1)$^+$. |
| 20/2 | 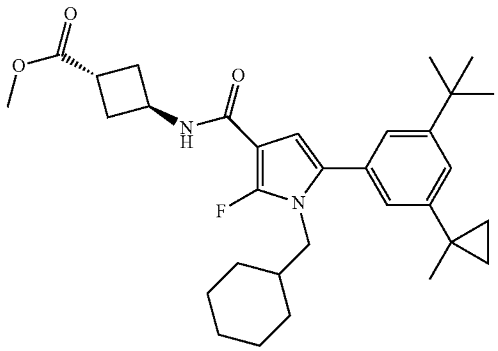 [SMILES: COC(=O)[C@H]1C[C@H](NC(=O)c2cc(-c3cc(C(C)(C)C)cc(C4(C)CC4)c3)n(CC3CCCCC3)c2F)C1] | $^1$H-NMR (DMSO-$d_6$, 400 MHz) δ: 0.72-0.78 (m, 4H), 0.86-0.88 (m, 2H), 0.97-1.02 (m, 3H), 1.30 (s, 12H), 1.35 (s, 3H), 1.50-1.55 (m, 3H), 2.30-2.47 (m, 4H), 3.01-3.06 (m, 1H), 3.65 (s, 3H), 3.73 (d, J = 6.4 Hz, 2H), 4.48-4.54 (m, 1H), 6.47 (d, J = 5.2 Hz, 1H), 7.02 (s, 1H), 7.19 (s, 1H), 7.22 (s, 1H), 7.94 (d, J = 7.6 Hz, 1H). MS: 523.3 (M + 1)$^+$. |

-continued

| # | Structure | Analytical data |
| --- | --- | --- |
| 20/3 | 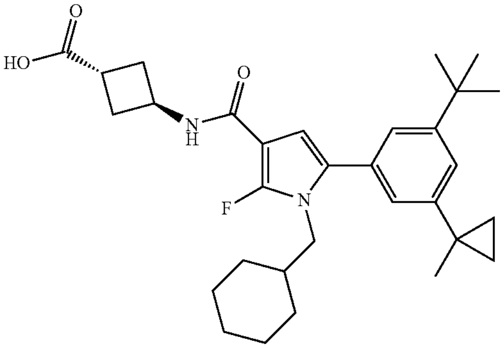 [SMILES: CC(C)(C)c1cc(-c2cc(C(=O)N[C@H]3C[C@H](C(=O)O)C3)c(F)n2CC2CCCCC2)cc(C2(C)CC2)c1] | $^1$H-NMR (DMSO-$d_6$, 400 MHz) δ: 0.76-0.78 (m, 4H), 0.86-0.88 (m, 2H), 0.98-1.03 (m, 3H), 1.30 (s, 12H), 1.40 (s, 3H), 1.50-1.55 (m, 3H), 2.28-2.42 (m, 4H), 2.91 (br s, 1H), 3.73 (d, J = 6.8 Hz, 2H), 4.47-4.53 (m, 1H), 6.48 (d, J = 5.6 Hz, 1H), 7.02 (s, 1H), 7.20 (d, J = 12.0 Hz, 2H), 7.91 (d, J = 8.0 Hz, 1H). $^{19}$F-NMR (DMSO-$d_6$, 376 MHz) δ: −129.55. MS: 509.3 $(M + 1)^+$. |
| 20/4 | 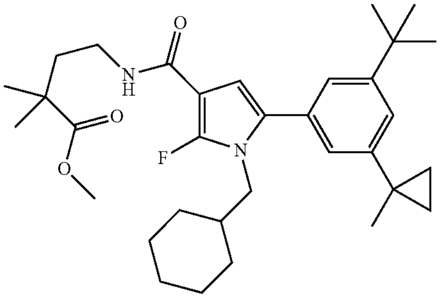 [SMILES: COC(=O)C(C)(C)CCNC(=O)c1cc(-c2cc(C(C)(C)C)cc(C3(C)CC3)c2)n(CC2CCCCC2)c1F] | $^1$H-NMR (DMSO-$d_6$, 400 MHz) δ: 0.75-0.78 (m, 4H), 0.84-0.87 (m, 2H), 1.00-1.04 (m, 3H), 1.16 (s, 6H), 1.30 (s, 12H), 1.40 (s, 3H), 1.50-1.55 (m, 3H), 1.72 (t, J = 8.0 Hz, 2H), 3.12-3.15 (m, 2H), 3.59 (s, 1H), 3.73 (d, J = 7.2 Hz, 2H), 6.42 (d, J = 5.2 Hz, 1H), 7.01 (s, 1H), 7.20 (d, J = 12.8 Hz, 2H), 7.63 (t, J = 5.2 Hz, 1H). MS: 539.4 $(M + 1)^+$. |
| 20/5 | 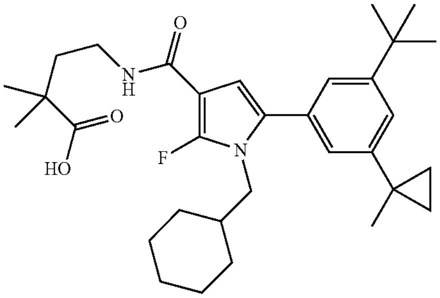 [SMILES: CC(C)(CCNC(=O)c1cc(-c2cc(C(C)(C)C)cc(C3(C)CC3)c2)n(CC2CCCCC2)c1F)C(=O)O] | $^1$H-NMR (DMSO-$d_6$, 400 MHz) δ: 0.74-0.78 (m, 4H), 0.84-0.87 (m, 2H), 0.97-1.03 (m, 3H), 1.13 (s, 6H), 1.24-1.35 (m, 12H), 1.42 (s, 3H), 1.50-1.55 (m, 3H), 1.67-1.71 (m, 2H), 3.13-3.19 (m, 2H), 3.73 (d, J = 7.2 Hz, 2H), 6.44 (d, J = 5.2 Hz, 1H), 7.01 (s, 1H), 7.19 (d, J = 11.6 Hz, 2H), 7.65 (t, J = 5.2 Hz, 1H), 12.17 (br s, 1H). $^{19}$F-NMR (DMSO-$d_6$, 376 MHz) δ: −130.03. MS: 525.3 $(M + 1)^+$. |
| 20/6 | 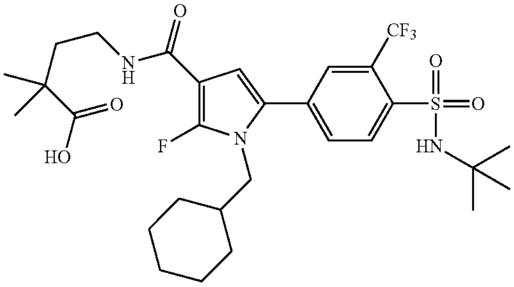 [SMILES: CC(C)(C)NS(=O)(=O)c1ccc(-c2cc(C(=O)NCCC(C)(C)C(=O)O)c(F)n2CC2CCCCC2)cc1C(F)(F)F] | $^1$H-NMR ($CD_3OD$, 400 MHz) δ: 0.77-0.83 (m, 2H), 1.03-1.08 (m, 3H), 1.24 (s, 15H), 1.38 (d, J = 10.8 Hz, 3H), 1.56-1.61 (m, 3H), 1.85 (t, J = 8.0 Hz, 2H), 3.37 (t, J = 8.0 Hz, 2H), 3.90 (d, J = 6.8 Hz, 2H), 6.62 (d, J = 5.6 Hz, 1H), 7.83 (dd, J = 8.4 Hz, 1.6 Hz, 1H), 7.91 (s, 1H), 8.31 (d, J = 8.4 Hz, 1H). $^{19}$F-NMR ($CD_3OD$, 376 MHz) δ: −57.70, −127.92. MS: 618.3 $(M + 1)^+$. |

-continued

| # | Structure | Analytical data |
|---|---|---|
| 20/7 | 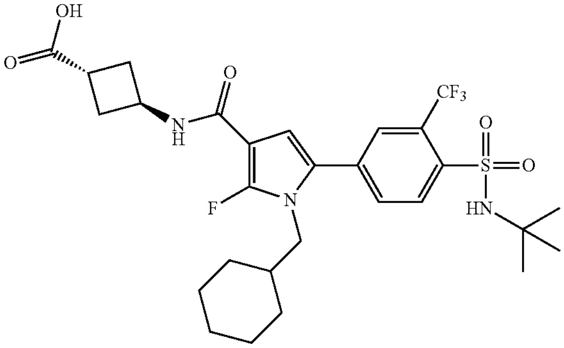 [SMILES: CC(C)(C)NS(=O)(=O)c1ccc(-c2cc(C(=O)N[C@H]3C[C@H](C(=O)O)C3)c(F)n2CC2CCCCC2)cc1C(F)(F)F] | $^1$H-NMR ($CD_3OD$, 400 MHz) δ: 0.76-0.85 (m, 2H), 1.03-1.08 (m, 3H), 1.24 (s, 9H), 1.38 (d, J = 10.0 Hz, 3H), 1.56-1.62 (m, 3H), 2.35-2.43 (m, 2H), 2.58-2.64 (m, 2H), 3.02-3.07 (m, 1H), 3.91 (d, J = 6.8 Hz, 2H), 4.64-4.68 (m, 1H), 6.69 (d, J = 6.0 Hz, 1H), 7.84 (dd, J = 8.4 Hz, 1.6 Hz, 1H), 7.92 (s, 1H) 8.32 (d, J = 8.4 Hz, 1H). MS: 602.2 $(M + 1)^+$. |
| 20/8 | 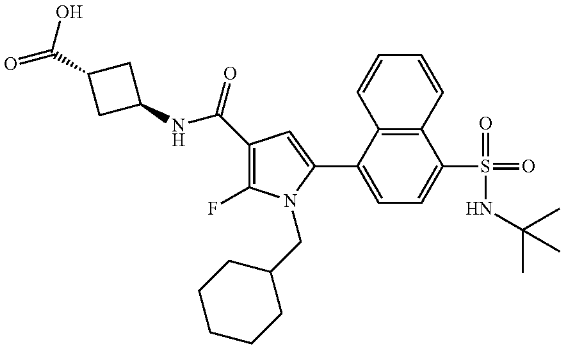 [SMILES: CC(C)(C)NS(=O)(=O)c1ccc(-c2cc(C(=O)N[C@H]3C[C@H](C(=O)O)C3)c(F)n2CC2CCCCC2)c2ccccc12] | $^1$H-NMR ($CDCl_3$, 400 MHz) δ: 0.58-0.63 (m, 2H), 0.93-0.96 (m, 3H), 1.19 (s, 9H), 1.26-1.29 (m, 3H), 1.52 (br s, 3H), 2.33-2.41 (m, 2H), 2.80-2.85 (m, 2H), 3.12-3.17 (m, 1H), 3.35 (br s, 1H), 3.55 (br s, 1H), 4.72-4.73 (m, 1H), 4.79-4.85 (m, 1H), 6.09-6.10 (m, 1H), 6.55 (d, J = 5.2 Hz, 1H), 7.48 (d, J = 7.6 Hz, 1H), 7.55 (t, J = 7.6 Hz, 1H), 7.69 (td, J = 7.6 Hz, 1.2 Hz, 1H), 7.84 (d, J = 8.8 Hz, 1H), 8.34 (d, J = 7.6 Hz, 1H), 8.66 (d, J = 8.8 Hz, 1H). MS: 584.3 $(M + 1)^+$. |
| 20/9 | 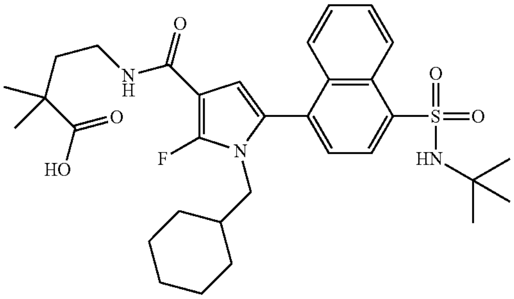 [SMILES: CC(C)(C)NS(=O)(=O)c1ccc(-c2cc(C(=O)NCCC(C)(C)C(=O)O)c(F)n2CC2CCCCC2)c2ccccc12] | $^1$H-NMR ($CDCl_3$, 400 MHz) δ: 0.54-0.61 (m, 2H), 0.91-0.94 (m, 3H), 1.19 (s, 9H), 1.21-1.25 (m, 3H), 1.29 (s, 6H), 1.51 (br s, 3H), 1.92 (t, J = 7.6 Hz, 1H), 3.30-3.65 (m, 4H), 4.69-4.70 (m, 1H), 6.03-6.04 (m, 1H), 6.52 (d, J = 5.6 Hz, 1H), 7.48 (d, J = 7.2 Hz, 1H), 7.56 (t, J = 7.6 Hz, 1H), 7.68 (t, J = 7.6 Hz, 1H), 7.85 (d, J = 8.4 Hz, 1H), 8.33 (d, J = 7.6 Hz, 1H), 8.65 (d, J = 8.4 Hz, 1H). MS: 600.3 $(M + 1)^+$. |

Example 21 and Example 22

21

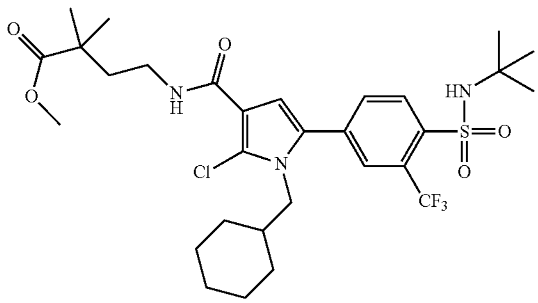

-continued

22

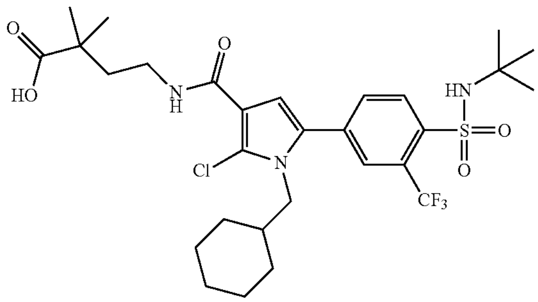

Step 1: Methyl 4-(5-(4-(N-(tert-butyl)sulfamoyl)-3-(trifluoromethyl)phenyl)-2-chloro-1-(cyclohexylmethyl)-1H-pyrrole-3-carboxamido)-2,2-dimethylbutanoate (21)

To a solution of methyl 4-(5-(4-(N-(tert-butyl)sulfamoyl)-3-(trifluoromethyl)phenyl)-1-(cyclohexylmethyl)-1H-pyrrole-3-carboxamido)-2,2-dimethylbutanoate (100 mg, 0.16 mmol) in dry THF (2 mL) was added a solution of NCS (21.6 mg, 0.16 mmol) in dry THF (1 mL) at −78° C. and the solution was stirred at −55° C. for 8 h, quenched with water and extracted with EA. The organic layer was washed with brine, dried over $Na_2SO_4$, filtered, concentrated and purified by CC (PE/EA=2/1) and then prep. TLC to give compound 21 (75 mg, 72%) as a colorless solid.

Step 2: 4-(5-(4-(N-(tert-Butyl)sulfamoyl)-3-(trifluoromethyl)phenyl)-2-chloro-1-(cyclohexylmethyl)-1H-pyrrole-3-carboxamido)-2,2-dimethylbutanoic acid (22)

To a solution of compound 21 (70 mg, 0.10 mmol) in a mixture of MeOH (4 mL) and $H_2O$ (0.5 mL) was added KOH (56 mg, 1.0 mmol) and the solution was stirred at 80° C. for 1 h, concentrated and adjusted with 1M HCl to pH=6. The aqueous phase was extracted with EA twice. The combined organic layers were washed with brine, dried over $Na_2SO_4$, filtered, concentrated and purified by prep. TLC to give compound 22 (41 mg, 60%) as a colorless solid. $^1$H-NMR ($CDCl_3$, 400 MHz) δ: 0.60-0.69 (m, 2H), 0.99-1.04 (m, 3H), 1.27 (s, 9H), 1.28-1.34 (s, 8H), 1.40-1.47 (m, 1H), 1.56 (br s, 3H), 1.91 (d, J=7.2 Hz, 2H), 3.47-3.53 (m, 2H), 3.89 (d, J=7.2 Hz, 2H), 4.75 (s, 1H), 6.39-6.41 (m, 1H), 6.76 (s, 1H), 7.64 (d, J=8.4 Hz, 1H), 7.80 (s, 1H), 8.33 (d, J=8.4 Hz, 1H). MS: 634.2 $(M+1)^+$.

Example 22/1 to Example 22/2

Using a procedure similar as described in Example 21, the following compound was prepared (and optionally subsequently saponified).

| # | Structure | Analytical data |
|---|---|---|
| 22/1 | 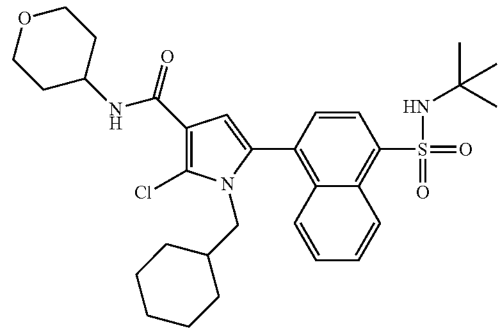 [SMILES: CC(C)(C)NS(=O)(=O)c1ccc(-c2cc(C(=O)NC3CCOCC3)c(Cl)n2CC2CCCCC2)c2ccccc12] | $^1$H-NMR ($CDCl_3$, 400 MHz) δ: 0.49-0.55 (m, 2H), 0.90-0.95 (m, 3H), 1.19 (s, 9H), 1.22 (s, 3H), 1.25-1.40 (m, 3H), 1.46-1.65 (m, 4H), 2.03-2.06 (m, 2H), 3.35-3.41 (m, 1H), 3.54 (td, J = 11.2 Hz, 1.6 Hz, 2H), 3.77-3.82 (m, 1H), 3.99-4.01 (m, 2H), 4.23-4.26 (m, 1H), 4.61 (s, 1H), 6.23 (d, J = 7.2 Hz, 1H), 6.74 (s, 1H), 7.50 (d, J = 7.2 Hz, 1H), 7.57 (t, J= 7.6 Hz, 1H), 7.70 (t, J = 7.6 Hz, 1H), 7.76 (d, J = 8.0 Hz, 1H), 8.35 (d, J = 7.6 Hz, 1H), 8.66 (d, J = 8.0 Hz, 1H). MS: 586.2 $(M + 1)^+$. |
| 22/2 | 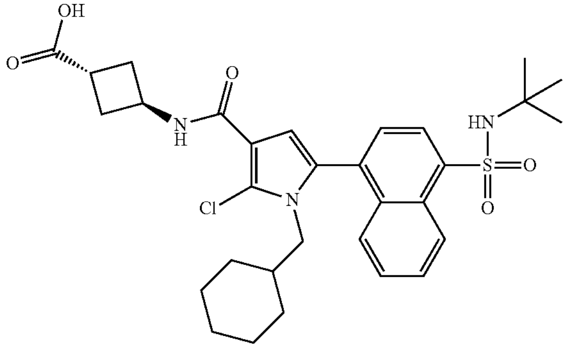 [SMILES: CC(C)(C)NS(=O)(=O)c1ccc(-c2cc(C(=O)N[C@H]3C[C@H](C(=O)O)C3)c(Cl)n2CC2CCCCC2)c2ccccc12] | $^1$H-NMR ($CDCl_3$, 400 MHz) δ: 0.51-0.55 (m, 2H), 0.90-0.91 (m, 3H), 1.14 (s, 9H), 1.19-1.37 (m, 3H), 1.49-1.50 (m, 3H), 2.34-2.44 (m, 2H), 2.81-2.84 (m, 2H), 3.15-3.17 (m, 1H), 3.36-3.42 (m, 1H), 3.77-3.82 (m, 1H), 4.64 (s, 1H), 4.79-4.82 (m, 1H), 6.55 (d, J = 6.8 Hz, 1H), 6.75 (s, 1H), 7.49 (d, J = 7.6 Hz, 1H), 7.57 (t, J = 7.2 Hz, 1H), 7.70 (t, J = 7.2 Hz, 1H), 7.75 (d, J = 8.8 Hz, 1H), 8.35 (d, J = 8.0 Hz, 1H), 8.66 (d, J = 8.4 Hz, 1H). MS: 600.2 $(M + 1)^+$. |

Example 23

23

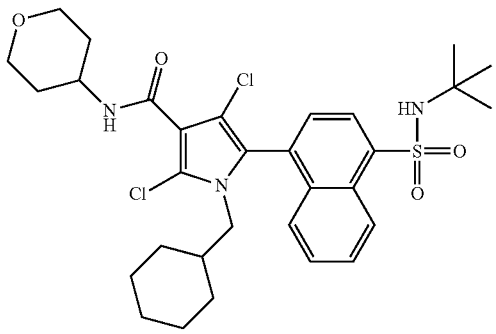

5-(4-(N-(tert-Butyl)sulfamoyl)naphthalen-1-yl)-2,4-dichloro-1-(cyclohexylmethyl)-N-(tetrahydro-2H-pyran-4-yl)-1H-pyrrole-3-carboxamide (23)

To a solution of compound 21/1 (100 mg, 0.17 mmol) in THF (3 mL) was added NCS (46 mg, 0.34 mmol) at rt and the solution was stirred overnight at 50° C., diluted with water and extracted with EA twice. The combined organic layers were washed with water and brine, dried over $Na_2SO_4$, filtered, concentrated and purified by prep. HPLC to give compound 23 (50 mg, 48%) as a colorless solid. $^1$H-NMR ($CDCl_3$, 400 MHz) δ: 0.55-0.58 (m, 2H), 0.87-0.92 (m, 3H), 1.19 (s, 9H), 1.25 (s, 3H), 1.47-1.52 (m, 2H), 1.58-1.62 (m, 2H), 2.03-2.06 (m, 2H), 3.34-3.40 (m, 1H), 3.56 (td, J=11.6 Hz, 2.0 Hz, 2H), 3.73-3.78 (m, 1H), 3.97-4.00 (m, 2H), 4.20-4.35 (m, 1H), 4.63 (s, 1H), 6.42 (d, J=7.2 Hz, 1H), 7.53 (d, J=7.6 Hz, 1H), 7.59-7.60 (m, 2H), 7.70-7.75 (m, 1H), 8.40 (d, J=7.6 Hz, 1H), 8.69 (d, J=8.4 Hz, 1H). MS: 620.2 $(M+1)^+$.

Example 24

24

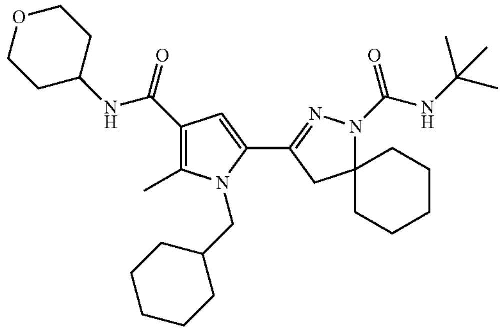

Step 1: Ethyl 5-(2-bromoacetyl)-1-(cyclohexylmethyl)-2-methyl-1H-pyrrole-3-carboxylate (24a)

To a suspension of $AlCl_3$ (12.0 g, 90.0 mmol) in dry DCM (100 mL) was added ethyl 1-(cyclohexylmethyl)-2-methyl-1H-pyrrole-3-carboxylate (prepared according to Example 1d, 10 g, 40.2 mmol) and 2-bromoacetyl bromide (16.0 g, 79.3 mmol) and the solution was stirred at rt for 2 h, poured into ice water and extracted with DCM (3×). The combined organic layers were dried over $Na_2SO_4$, filtered, concentrated and purified by CC (PE/EA=10:1) to afford intermediate 24a (7.0 g, 47%) as a yellow oil.

Step 2: Ethyl 1-(cyclohexylmethyl)-5-(2-(diethoxyphosphoryl)acetyl)-2-methyl-1H-pyrrole-3-carboxylate (24b)

A solution of intermediate 24a (7.0 g, 19 mmol) in triethyl phosphite (60 mL) was refluxed for 1 h and concentrated to afford crude intermediate 24b (10.1 g) as a yellow oil.

Step 3: Ethyl 5-(2-cyclohexylideneacetyl)-1-(cyclohexylmethyl)-2-methyl-1H-pyrrole-3-carboxylate (24c)

To a solution of crude intermediate 24b (10.1 g, 18.97 mmol) in dry THF (70 mL) at 0° C. was added NaH (1.86 g, 46.5 mmol). After stirring for 15 min, cyclohexanone (2.3 g, 23 mmol) was added and the solution was stirred overnight at rt, quenched with aq. $NH_4Cl$ and extracted with EA twice. The combined organic layers were washed with brine, dried over $Na_2SO_4$, filtered, concentrated and purified by CC (PE/EA=10/1) to give intermediate 24c (3.6 g, 51% in two steps) as yellow powder.

Step 4: Ethyl 1-(cyclohexylmethyl)-2-methyl-5-(1,2-diazaspiro[4.5]dec-2-en-3-yl)-1H-pyrrole-3-carboxylate (24d)

To a solution of intermediate 24c (3.6 g, 9.7 mmol) in a mixture of DMSO (20 mL) and water (ten drops) was added KO$^t$Bu (1.86 g, 19.4 mmol) and the solution was heated overnight at 85° C., cooled to rt, poured into water, adjusted to pH~3 with 1N HCl and then extracted with EA (3×). The combined organic layers were washed with brine, dried over $Na_2SO_4$, filtered, concentrated and purified by CC (PE/EA=1/1) to give intermediate 24d (3.0 g, 90%) as a pale yellow powder.

Step 5: 1-(Cyclohexylmethyl)-2-methyl-5-(1,2-diazaspiro[4.5]dec-2-en-3-yl)-1H-pyrrole-3-carboxylic acid (24e)

To a solution of intermediate 24d (1.0 g, 2.9 mmol) in MeOH (15 mL) was added hydrazine monohydrate (290 mg, 5.8 mmol) and the solution was stirred at reflux overnight, cooled to rt, concentrated and purified by CC (DCM/MeOH=10:1) to afford intermediate 24e (490 mg, 48%) as a colorless oil.

Step 6: 1-(Cyclohexylmethyl)-2-methyl-5-(1,2-diazaspiro[4.5]dec-2-en-3-yl)-N-(tetrahydro-2H-pyran-4-yl)-1H-pyrrole-3-carboxamide (24f)

A mixture of intermediate 24e (1.00 g, 2.8 mmol), tetrahydro-2H-pyran-4-amine (283 mg, 5.60 mmol), HATU (2.21 g, 5.60 mmol) and DIPEA (1.44 g, 11.2 mmol) in DMF (15 mL) was stirred at rt for 25 min, diluted with $H_2O$ and extracted with EA (3×). The combined organic layers were washed with $H_2O$ (3×) and brine consecutively, dried over $Na_2SO_4$, filtered, concentrated and purified by CC (DCM/MeOH=80/1) to afford intermediate 24f (881 mg, 71%) as a yellow solid.

Step 7: N-(tert-Butyl)-3-(1-(cyclohexylmethyl)-5-methyl-4-((tetrahydro-2H-pyran-4-yl)carbamoyl)-1H-pyrrol-2-yl)-1,2-diazaspiro[4.5]dec-2-ene-1-carboxamide (24)

To a solution of intermediate 24f (150 mg, 0.34 mmol) in dry DCM (3 mL) was added tert-butyl isocyanate (67 mg, 0.68 mmol) at 0° C. under $N_2$ and the solution was stirred overnight at rt, washed with 1M HCl and brine consecutively, dried over $Na_2SO_4$, filtered, concentrated and purified by prep. TLC (PE/EA=1/5) to give example 24 (54 mg, 29%) as a colorless solid. $^1$H-NMR ($CDCl_3$, 400 MHz) δ: 6.42 (s, 1H), 5.80 (s, 1H), 5.57 (d, 1H, J=7.2 Hz), 4.10-4.17 (m, 3H), 3.99 (dd, 1H, J=1.6, 11.2 Hz), 3.53 (dt, 1H, J=1.6, 11.2 Hz), 3.07 (s, 2H), 2.61-2.68 (m, 2H), 2.59 (s, 3H), 1.98 (dd, 1H, J=2.0, 12.0 Hz), 1.52-1.81 (m, 13H), 1.39 (s, 9H), 1.15-1.20 (m, 3H), 0.98-1.04 (m, 2H). MS: 540.2 $(M+1)^+$.

Example 24/1 to 24/2

Using a procedure similar as described in Example 24, the following compounds were prepared.

| # | Structure | Analytical data |
|---|---|---|
| 24/1 | 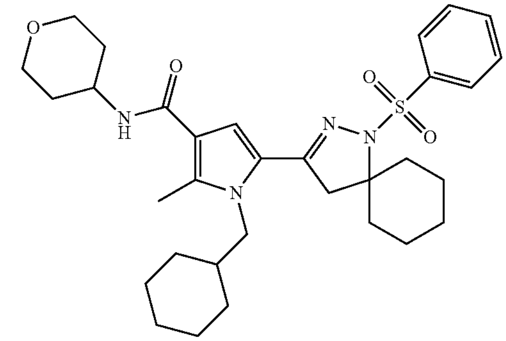 [SMILES: Cc1c(C(=O)NC2CCOCC2)cc(C2=NN(S(=O)(=O)c3ccccc3)C3(CCCCC3)C2)n1CC1CCCCC1] | $^1$H-NMR ($CDCl_3$, 400 MHz) δ: 7.98-8.00 (m, 2H), 7.47-7.56 (m, 3H), 6.40 (s, 1H), 5.52 (d, 1H, J = 8.0 Hz), 4.05-4.15 (m, 3H), 3.98 (m, 2H), 3.51 (m, 2H), 3.08 (s, 2H), 2.54 (s, 3H), 2.43-2.48 (m, 2H), 1.97 (m, 2H), 1.74-1.84 (m, 4H), 1.62-1.68 (m, 5H), 1.50-1.57 (m, 2H), 1.40-1.43 (m, 2H), 1.31-1.35 (m, 3H), 0.82-0.88 (m, 2H). MS: 581.2 $(M + 1)^+$. |
| 24/2 | 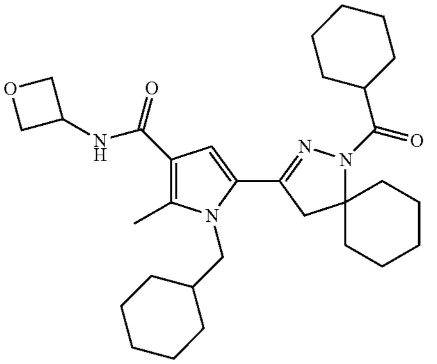 [SMILES: Cc1c(C(=O)NC2COC2)cc(C2=NN(C(=O)C3CCCCC3)C3(CCCCC3)C2)n1CC1CCCCC1] | $^1$H-NMR ($CDCl_3$, 400 MHz) δ: 6.54 (s, 1H), 6.17 (d, 1H, J = 7.6 Hz), 5.21 (m, 1H), 5.00 (m, 1H), 4.59 (m, 1H), 4.22 (m, 1H), 3.10 (s, 3H), 2.72-2.79 (m, 2H), 2.58 (s, 3H), 1.76-1.81 (m, 7H), 1.63-1.70 (m, 5H), 1.43-1.51 (m, 5H), 1.26-1.32 (m, 7H), 1.11-1.16 (m, 3H), 0.97-1.02 (m, 2H). MS: 523 $(M + 1)^+$. |

Example 25

25

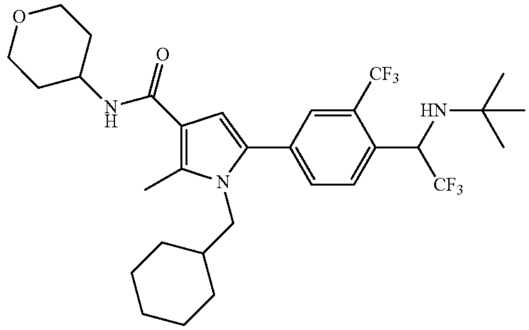

5-(4-(1-(tert-Butylamino)-2,2,2-trifluoroethyl)-3-(trifluoromethyl)phenyl)-1-(cyclohexylmethyl)-2-methyl-N-(tetrahydro-2H-pyran-4-O-1H-pyrrole-3-carboxamide (25)

To a mixture of crude compound 32 (1.34 mmol) and $KHF_2$ (105 mg, 1.34 mmol) in dry MeCN (5 mL) was added dry $CF_3CO_2H$ at 0° C. and the suspension was stirred for 5 min. $Me_3SiCF_3$ (382 mg, 2.7 mmol) was added, the cooling bath was removed and the mixture was stirred for 20 h at rt, diluted with sat. aq. $Na_2CO_3$ (0.5 mL) and stirred for an additional two min, diluted with water and extracted with EA (3×). The combined organic phases were dried over $Na_2SO_4$, filtered, concentrated and purified by CC (PE/EA=1/1) to afford example 25 (45 mg, 6%) as a colorless solid. $^1$H-NMR ($CDCl_3$, 300 MHz) δ: 7.82 (d, J=7.5 Hz, 1H), 7.66 (s, 1H), 7.57 (d, J=7.8 Hz, 1H), 6.30 (s, 1H), 5.63 (d, J=7.5 Hz, 1H), 4.83 (q, J=6.6 Hz, 1H), 4.20 (m, 1H), 3.99 (m, 2H), 3.78 (m, 2H), 3.54 (m, 2H), 2.63 (s, 3H), 2.00 (m, 2H), 1.59-1.48 (m, 5H), 1.34-1.29 (m, 3H), 1.04 (s, 9H), 1.00-0.98 (m, 3H), 0.65-0.61 (m, 2H). MS: 602.4 $(M+1)^+$.

Example 26

26

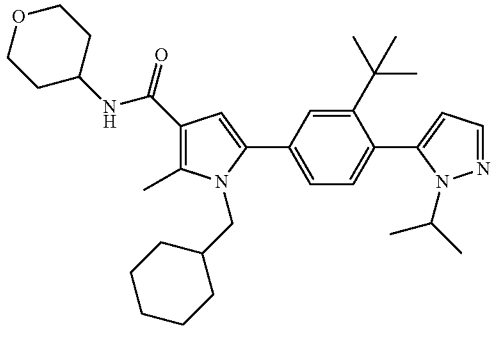

Step 1: 4-Bromo-2-(tert-butyl)phenol (26a)

To a solution of 2-(tert-butyl)phenol (5 g, 33 mmol) in DCM (200 mL) was added tetrabutyl-ammonium tribromide (16.5 mg, 33 mmol) and the mixture was stirred at rt for 12 h, diluted with $H_2O$ (50 mL) and extracted with DCM (150 mL). The organic layer was washed with brine and dried over $Na_2SO_4$, concentrated and purified by CC (PE/EA=5/1) to afford compound 26a (6.8 g, 89%) as a clear oil.

Step 2: 2-(tert-Butyl)-4-(4,4,5,5-tetramethyl-1,3,2-dioxaborolan-2-yl)phenol (26b)

To a solution of compound 26a (162 mg, 0.71 mmol) in 1,4-dioxane (20 mL) was added $B_2Pin_2$ (541 mg, 2.13 mmol) and KOAc (278 mg, 2.84 mmol), followed by $Pd(dppf)Cl_2$ (52 mg, 71 μmol) under Ar and the suspension was heated to 100° C. overnight, cooled, concentrated and purified by CC (PE/EA=50/1 to 10/1) to afford compound 26b (109 mg, 56%) as a colorless solid.

Step 3: 5-(3-(tert-Butyl)-4-hydroxyphenyl)-1-(cyclohexylmethyl)-2-methyl-N-(tetrahydro-2H-pyran-4-yl)-1H-pyrrole-3-carboxamide (26c)

A solution of 5-bromo-1-(cyclohexylmethyl)-2-methyl-N-(tetrahydro-2H-pyran-4-yl)-1H-pyrrole-3-carboxamide (382 mg, 1.0 mmol, prepared similar as described for intermediate 9b), compound 26b (331 mg, 1.2 mmol), $Cs_2CO_3$ (487 mg, 1.5 mmol) and $Pd(dppf)Cl_2$ (30 μmol) in 1,4-dioxane and water (10 mL; 20:1) was heated to 90° C. overnight, cooled to rt, evaporated, diluted with water and extracted with DCM. The organic layer was dried over $MgSO_4$, filtered, evaporated and purified by CC (hexane/EA=5/1) to give compound 26c (253 mg, 56%).

Step 4: 2-(tert-Butyl)-4-(1-(cyclohexylmethyl)-5-methyl-4-((tetrahydro-2H-pyran-4-yl)carbamoyl)-1H-pyrrol-2-yl)phenyl trifluoromethanesulfonate (26d)

To a solution of compound 26c (100 mg, 0.22 mmol) in DCM (20 mL) was added TEA (44 mg, 0.44 mmol) and catalytic amounts of DMAP, followed by $Tf_2O$ (74 mg, 0.26 mmol) and the resulting mixture was stirred at rt for 12 h, concentrated and purified by CC (PE/EA=3/1) to afford compound 26d (56 mg, 43%) as a brown solid.

Step 5: 5-(3-(tert-Butyl)-4-(1-isopropyl-1H-pyrazol-5-yl)phenyl)-1-(cyclohexylmethyl)-2-methyl-N-(tetrahydro-2H-pyran-4-yl)-1H-pyrrole-3-carboxamide (26)

A 20-ml microwave vial was charged with compound 26d (100 mg, 0.17 mmol), 1-isopropyl-5-(4,4,5,5-tetramethyl-1,3,2-dioxaborolan-2-yl)-1H-pyrazole (0.2 mmol, 1.2 eq) and $Cs_2CO_3$ (167 mg, 0.51 mmol) dissolved in 1,4-dioxane and water (10 mL, 20:1), followed by $Pd(dppf)Cl_2$ (0.03 eq) under $N_2$. The mixture was heated to 90° C. overnight, evaporated, diluted with water and extracted with DCM. The organic layer was separated, dried over $Na_2SO_4$, filtered, evaporated and purified by CC (hexane/EA=5/1) to give compound 26. $^1$H-NMR (400 MHz, $CDCl_3$) δ: 7.62 (s, 1H), 7.45 (s, 1H), 7.13 (m, 1H), 7.00 (m, 1H), 6.24-6.18 (m, 1H), 5.60 (br d, 1H, J=6.4 Hz), 4.20-4.15 (m, 1H), 4.01-3.89 (m, 3H), 3.73 (m, 2H), 3.46 (m, 2H), 2.55 (s, 3H), 1.94-1.91 (m, 2H), 1.50-1.43 (m, 8H), 1.39-1.30 (m, 6H), 1.15 (m, 9H), 1.05-0.90 (m, 3H), 0.70-0.57 (m, 2H). MS: 545.4 $(M+H)^+$.

Example 26/1 to 26/6

Using a procedure similar as described in Example 26, the following compounds were prepared.

| # | Structure | Analytical data |
|---|---|---|
| 26/1 | 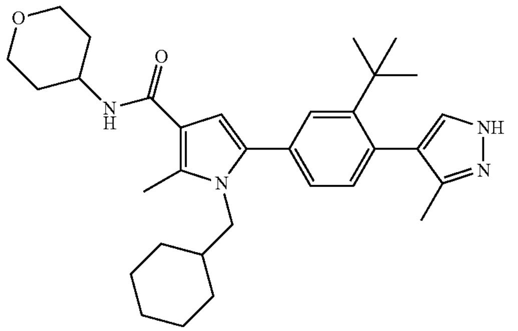 [SMILES: Cc1n[nH]cc1-c1ccc(-c2cc(C(=O)NC3CCOCC3)c(C)n2CC2CCCCC2)cc1C(C)(C)C] | $^1$H-NMR (400 MHz, $CDCl_3$) δ: 7.43-7.38 (m, 2H), 7.06 (m, 1H), 6.94-6.90 (m, 2H), 6.16 (s, 1H), 5.58 (m, 1H), 4.15-4.04 (m, 1H), 3.95-3.88 (m, 2H), 3.72 (m, 2H), 3.46 (m, 2H), 2.56 (s, 3H), 2.04 (s, 3H), 1.93-1.90 (m, 2H), 1.49-1.47 (m, 5H), 1.32-1.29 (m, 3H), 1.18 (s, 9H), 0.95 (m, 3H), 0.61 (m, 2H). MS: 517.3 $(M + H)^+$. |
| 26/2 | 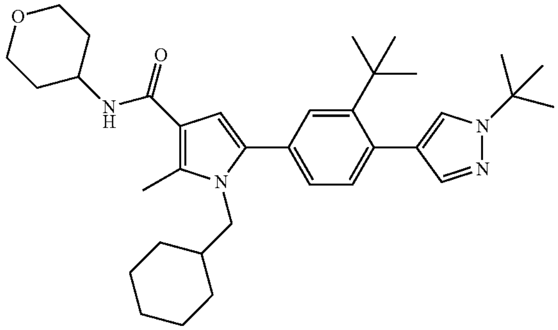 [SMILES: Cc1c(C(=O)NC2CCOCC2)cc(-c2ccc(-c3cnn(C(C)(C)C)c3)c(C(C)(C)C)c2)n1CC1CCCCC1] | $^1$H-NMR (400 MHz, $CDCl_3$) δ: 7.47 (s, 1H), 7.40 (s, 1H), 7.36 (s, 1H), 7.02 (s, 1H), 6.11 (s, 1H), 5.57 (d, 2H, J = 6.4 Hz), 4.13 (m, 1H), 3.92-3.89 (m, 2H), 3.71 (m, 2H), 3.46 (m, 2H), 2.55 (s, 3H), 1.94-1.90 (m, 2H), 1.58 (s, 9H), 1.51-1.50 (m, 5H), 1.34 (m, 3H), 1.91 (m, 9H), 0.97 (m, 3H), 0.61 (m, 2H). MS: 559.4 $(M + H)^+$. |

-continued

| # | Structure | Analytical data |
|---|---|---|
| 26/3 | 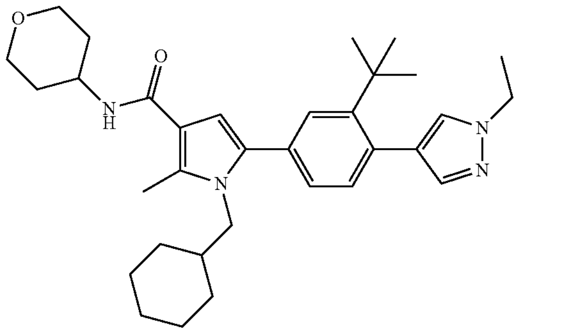 [SMILES: CCn1cc(-c2ccc(-c3cc(C(=O)NC4CCOCC4)c(C)n3CC3CCCCC3)cc2C(C)(C)C)cn1] | $^1$H-NMR (400 MHz, $CDCl_3$) δ: 7.40 (s, 1H), 7.36 (s, 1H), 7.29 (s, 1H), 7.19 (s, 1H), 7.01 (s, 2H), 6.12 (s, 1H), 5.56 (d, 2H, J = 6.4 Hz), 4.18-4.16 (m, 3H), 3.92 (m, 2H), 3.71 (m, 2H), 3.46-3.45 (m, 2H), 2.56 (s, 3H), 1.93-1.90 (m, 2H), 1.56-1.48 (m, 8H), 1.46 (m, 3H), 1.20 (s, 9H), 0.97 (m, 3H), 0.64 (m, 2H). MS: 531.4 $(M + H)^+$. |
| 26/4 | 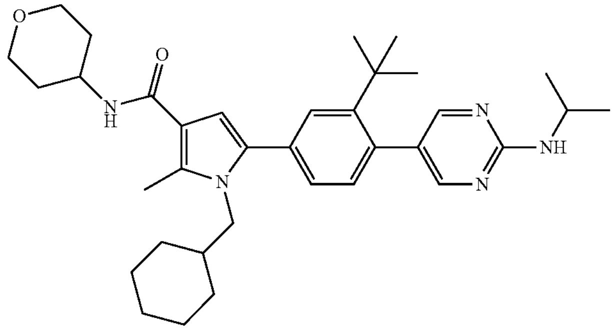 [SMILES: Cc1c(C(=O)NC2CCOCC2)cc(-c2ccc(-c3cnc(NC(C)C)nc3)c(C(C)(C)C)c2)n1CC1CCCCC1] | $^1$H-NMR (400 MHz, $CDCl_3$) δ: 8.13 (s, 2H), 7.41 (s, 1H), 7. 15 (m, 1H), 6.94 (d, 1H, J = 7.6 Hz), 6.14 (s, 1H), 5.54 (d, 1H, J = 7.6 Hz), 5.02 (m, 1H), 4.13-4.11 (m, 2H), 3.85 (m, 2H), 3.72 (m, 2H), 3.46 (m, 2H), 2.56 (s, 1H), 1.96-1.91 (m, 2H), 1.51-1.48 (m, 5H), 1.33-1.32 (m, 3H), 1.23 (d, 6H, J = 6.4 Hz), 1.19 (s, 9H), 0.97 (m, 3H), 0.62 (m, 2H). MS: 572.4 $(M + H)^+$. |
| 26/5 | 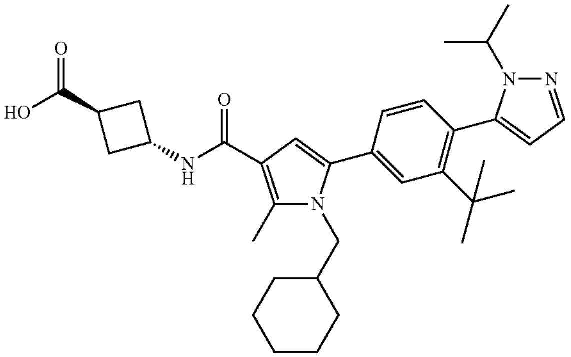 [SMILES: Cc1c(C(=O)N[C@H]2C[C@H](C(=O)O)C2)cc(-c2ccc(-c3ccnn3C(C)C)c(C(C)(C)C)c2)n1CC1CCCCC1] | $^1$H-NMR (400 MHz, $CDCl_3$) δ: 7.66 (s, 1H), 7.52 (s, 1H), 7.19-7.17 (m, 1H), 7.07-7.05 (m, 1H), 6.28 (s, 2H), 6.01 (m, 1H), 4.84-4.78 (m, 1H), 4.15-3.98 (m, 1H), 3.80 (m, 2H), 3.14-3.05 (m, 1H), 2.83-2.78 (m, 2H), 2.62 (s, 3H), 2.34-2.26 (m, 2H), 1.57-1.50 (m, 6H), 1.42-1.36 (m, 6H), 1.25 (s, 9H), 1.07-1.02 (m, 3H), 0.72-0.67 (m, 2H). MS: 559.3 $(M + H)^+$. |
| 26/6 | 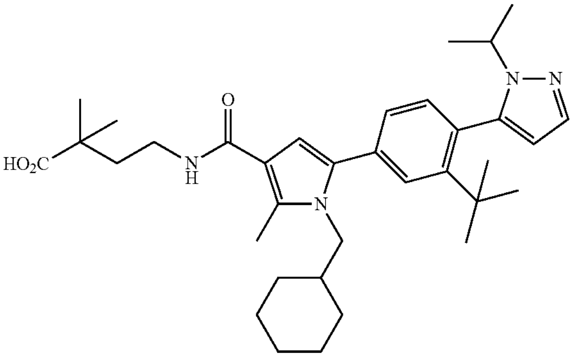 [SMILES: Cc1c(C(=O)NCCC(C)(C)C(=O)O)cc(-c2ccc(-c3ccnn3C(C)C)c(C(C)(C)C)c2)n1CC1CCCCC1] | $^1$H-NMR (400 MHz, $CDCl_3$) δ: 7.69 (s, 1H), 7.46 (s, 1H), 7.13-7.10 (m, 1H), 6.98-6.96 (m, 1H), 6.23-6.20 (m, 1H), 6.07 (br s, 1H), 4.03-4.00 (m, 1H), 3.72 (m, 2H), 3.42-3.38 (m, 2H), 2.53 (s, 3H), 1.83-1.80 (m, 2H), 1.52-1.41 (m, 6H), 1.36-1.29 (m, 6H), 1.20 (s, 6H), 1.15 (s, 9H), 0.98-0.90 (m, 3H), 0.68-0.57 (m, 2H). MS: 575.3 $(M + H)^+$. |

Example 27

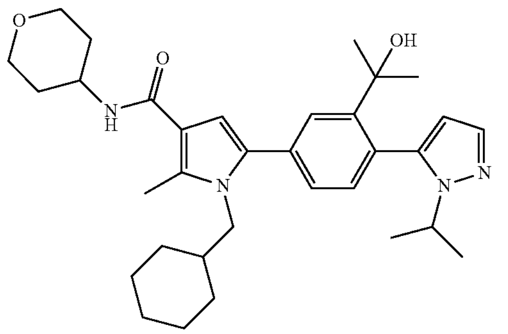

27

Step 1: 1-(2-Hydroxy-5-(4,4,5,5-tetramethyl-1,3,2-dioxaborolan-2-yl)phenyl)ethanone (27a)

To a solution of 1-(5-bromo-2-hydroxyphenyl)ethanone (152 mg, 0.71 mmol) in 1,4-dioxane (20 mL) was added $B_2Pin_2$ (541 mg, 2.13 mmol) and KOAc (278 mg, 2.84 mmol), followed by $Pd(dppf)Cl_2$ (52 mg, 71 μmol) under Ar and the resulting suspension was heated to 100° C. overnight, concentrated and purified by CC (PE/EA=50/1 to 10/1) to afford compound 27a (109 mg, 59%) as a colorless solid.

Step 2: Ethyl 5-(3-acetyl-4-hydroxyphenyl)-1-(cyclohexylmethyl)-2-methyl-1H-pyrrole-3-carboxylate (27b)

A solution of ethyl 5-bromo-1-(cyclohexylmethyl)-2-methyl-1H-pyrrole-3-carboxylate (328 mg, 1.0 mmol, prepared similar as described for compound 1e), compound 27a (314 mg, 1.2 mmol), $Cs_2CO_3$ (487 mg, 1.5 mmol) and $Pd(dppf)Cl_2$ (30 μmol) in 1,4-dioxane and water (10 mL, 20:1) was heated to 90° C. overnight, cooled to rt, evaporated, diluted with water and extracted with DCM. The organic layer was dried over $MgSO_4$, filtered, evaporated and purified by CC (hexane/EA=5/1) to give compound 27b (250 mg, 65%)

Step 3: Ethyl 5-(3-acetyl-4-(((trifluoromethyl)sulfonyl)oxy)phenyl)-1-(cyclohexylmethyl)-2-methyl-1H-pyrrole-3-carboxylate (27c)

To a solution of compound 27b (84 mg, 0.22 mmol) in DCM (20 mL) was added TEA (44 mg, 0.44 mmol) and DMAP, followed by $Tf_2O$ (75 mg, 0.26 mmol) and the resulting mixture was stirred at rt for 12 h, concentrated to dryness and purified by CC (PE/EA=3/1) to afford compound 27c (52 mg, 46%) as a brown solid.

Step 4: Ethyl 5-(3-acetyl-4-(1-isopropyl-1H-pyrazol-5-yl)phenyl)-1-(cyclohexylmethyl)-2-methyl-1H-pyrrole-3-carboxylate (27d)

A 20-ml microwave vial was charged with compound 27c (93 mg, 0.18 mmol), 1-isopropyl-5-(4,4,5,5-tetramethyl-1,3,2-dioxaborolan-2-yl)-1H-pyrazole (47 mg, 0.20 mmol) and $Cs_2CO_3$ (167 mg, 0.51 mmol) dissolved in 1,4-dioxane and water (10 mL, 20:1), followed by $Pd(dppf)Cl_2$ (0.03 eq) under $N_2$. The mixture was heated to 90° C. overnight, concentrated, diluted with water and extracted with DCM. The organic layer was dried over $Na_2SO_4$, filtered, concentrated and purified by CC (hexane/EA=5/1) to give compound 27d (62 mg, 73%).

Step 5: 5-(3-Acetyl-4-(1-isopropyl-1H-pyrazol-5-yl)phenyl)-1-(cyclohexylmethyl)-2-methyl-1H-pyrrole-3-carboxylic acid (27e)

To a solution of compound 27d (95 mg, 0.20 mmol) in EtOH was added 1M aq. KOH (8 mL) at rt. The mixture was stirred for 4 h at rt, concentrated, diluted with water (30 mL) and extracted with EA (150 mL). The organic layer was washed with brine, dried over $Na_2SO_4$, filtered, concentrated and purified by CC (hexane/EA=1/3) to give compound 27e (80 mg, 89%).

Step 6: 5-(3-Acetyl-4-(1-isopropyl-1H-pyrazol-5-yl)phenyl)-1-(cyclohexylmethyl)-2-methyl-N-(tetrahydro-2H-pyran-4-yl)-1H-pyrrole-3-carboxamide (27f)

To a solution of 27e (94 mg, 0.21 mmol) in DMF (2 mL) was added HATU (167 mg, 0.44 mmol), DIPEA (224 mg, 1.74 mmol) and tetrahydro-2H-pyran-4-amine (48 mg, 0.48 mmol). The mixture was stirred at rt overnight, then 5 mL $H_2O$ and 10 mL EA was added into the reaction. The organic layer was separated and the aq. layer was extracted with EA (3×). The combined organic layers were washed with brine, dried over $Na_2SO_4$, filtered, concentrated and purified by prep. HPLC to give product 27f (70 mg, 63%).

Step 7: 1-(Cyclohexylmethyl)-5-(3-(2-hydroxypropan-2-yl)-4-(1-isopropyl-1H-pyrazol-5-yl)phenyl)-2-methyl-N-(tetrahydro-2H-pyran-4-yl)-1H-pyrrole-3-carboxamide (27)

A solution of 27f (70 mg, 132 μmol) in THF (4 mL) was cooled to 0° C. and treated dropwise with MeMgBr (1M in $Et_2O$, 1 mmol). Upon completion of addition, the resulting suspension was allowed to warm to rt and was stirred for 5 h. Sat. aq. $NH_4Cl$ (20 mL) was added slowly and the mixture was diluted with EA (20 mL). The layers were separated and the aq. layer was extracted with EA (3×25 mL). The combined organic layers were dried over $MgSO_4$, filtered, concentrated and purified by prep. HPLC to afford 27 (20 mg, 28%). $^1H$-NMR (400 MHz, $CDCl_3$) δ: 7.61 (s, 1H), 7.26 (s, 1H), 7.15-7.09 (m, 1H), 6.29-6.22 (m, 2H), 5.65-5.58 (m, 1H), 4.30-4.11 (m, 2H), 4.01-3.92 (m, 2H), 3.84-3.79 (m, 2H), 3.60-3.59 (m, 2H), 2.63 (s, 3H), 2.02-1.95 (m, 2H), 1.59-1.54 (m, 8H), 1.53-1.48 (m, 6H), 1.46-1.39 (m, 3H), 1.06-1.00 (m, 3H), 0.72-0.67 (m, 2H). MS: 547.3 $(M+H)^+$.

Example 28

28

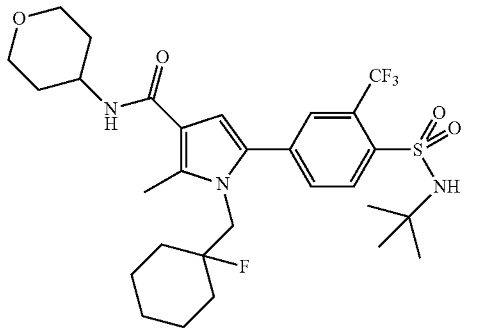

5-(4-(N-(tert-Butyl)sulfamoyl)-3-(trifluoromethyl) phenyl)-1-((1-fluorocyclohexyl)-methyl)-2-methyl-N-(tetrahydro-2H-pyran-4-yl)-1H-pyrrole-3-carboxamide (28)

To a solution of compound 17/255 (200 mg, 0.33 mmol) in DCM (10 mL) was added diethylaminosulfur trifluoride (0.13 mL, 0.65 mmol) in one portion at rt and the mixture was stirred at rt for 1 h, poured into water and extracted with DCM. The organic layer was concentrated and purified by prep. HPLC to give compound 28 (25 mg, 13%) as a colorless solid. $^1$H-NMR (300 MHz, $CDCl_3$) δ: 0.85-1.10 (m, 2H), 1.25 (s, 11H), 1.39-1.59 (m, 8H), 1.99 (m, 2H), 2.65 (s, 3H), 3.49-3.56 (m, 3H), 3.99 (m, 2H), 4.09-4.24 (m, 3H), 4.71 (s, 1H), 5.64 (d, J=7.5 Hz, 1H), 6.40 (s, 1H), 7.59 (d, J=8.1 Hz, 1H), 7.77 (s, 1H), 8.31 (d, J=8.1 Hz, 1H). MS: 602.2 $(M+1)^+$.

Example 29

29

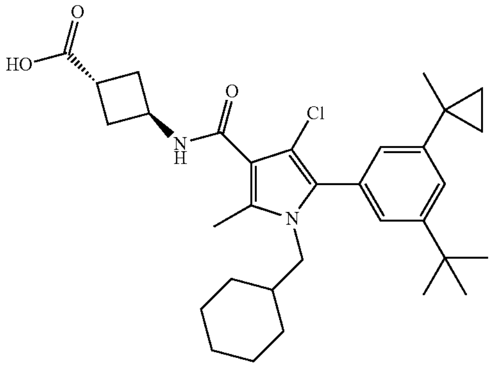

Step 1: Methyl 5-(3-(tert-butyl)-5-(1-methylcyclopropyl)phenyl)-4-chloro-1-(cyclohexylmethyl)-2-methyl-1H-pyrrole-3-carboxylate (29a)

To a solution of methyl 5-(3-(tert-butyl)-5-(1-methylcyclopropyl)phenyl)-1-(cyclohexylmethyl)-2-methyl-1H-pyrrole-3-carboxylate (368 mg, 0.85 mmol) in ACN (20 mL) was added NCS (113 mg, 0.85 mmol) and the mixture was stirred at rt for overnight, concentrated and purified by prep. TLC (PE/EA=50/1) to afford compound 29a (319 mg, 80%) as a pale yellow oil. $^1$H-NMR (400 MHz, $CDCl_3$) δ: 0.56-0.70 (2H, m), 0.73-0.76 (2H, m), 0.86-0.89 (2H, m), 0.97-1.03 (3H, m), 1.33 (12H, br s), 1.38 (3H, t, J=6.8 Hz), 1.42 (3H, s), 1.53-1.55 (3H, m), 2.55 (3H, s), 3.64 (2H, d, J=7.2 Hz), 4.33 (2H, q, J=6.8 Hz), 6.99 (1H, t, J=1.6 Hz), 7.13 (1H, t, J=1.6 Hz), 7.29 (1H, t, J=1.6 Hz).

Step 2: (trans)-3-(5-(3-(tert-Butyl)-5-(1-methylcyclopropyl)phenyl)-4-chloro-1-(cyclohexylmethyl)-2-methyl-1H-pyrrole-3-carboxamido)cyclobutanecarboxylic acid (29)

Compound 29a was saponified and coupled with the amino acid methyl ester and then finally saponified to obtain target compound 29 similar as described above. $^1$H-NMR (300 MHz, $CDCl_3$) δ: 0.53-0.67 (2H, m), 0.74-0.77 (2H, m), 0.86-0.90 (2H, m), 0.94-1.04 (3H, m), 1.26-1.34 (13H, m), 1.43 (3H, s), 1.54 (3H, d, J=6.3 Hz), 2.27-2.38 (2H, m), 2.60 (3H, s), 2.77-2.84 (2H, m), 3.06-3.17 (1H, m), 3.62 (2H, d, J=7.2 Hz), 4.75-4.88 (1H, m), 6.97 (1H, s), 7.02 (1H, d, J=7.8 Hz), 7.11 (1H, s), 7.31 (1H, s). MS: 539.3 $[M+1]^+$.

Example 29/1 to 29/2

Using a procedure similar as described in Example 29, the following compounds were prepared.

| # | Structure | Analytical data |
|---|---|---|
| 29/1 | 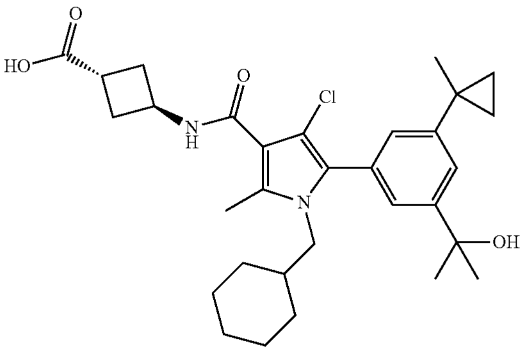 [SMILES: Cc1c(C(=O)N[C@H]2C[C@H](C(=O)O)C2)c(Cl)c(-c2cc(C(C)(C)O)cc(C3(C)CC3)c2)n1CC1CCCCC1] | $^1$H-NMR (300 MHz, $CDCl_3$) δ: 0.58-0.73 (2H, m), 0.75-0.81 (2H, m), 0.84-0.89 (2H, m), 0.95-1.04 (3H, m), 1.27-1.36 (5H, m), 1.43 (3H, s), 1.54 (7H, br s), 2.32-2.41 (2H, m), 2.43 (3H, s), 2.60-2.69 (2H, m), 3.05-3.09 (1H, m), 3.73 (2H, d, J = 7.2 Hz), 4.61-4.72 (1H, m), 7.06 (1H, d, J = 1.8 Hz), 7.20 (1H, d, J = 1.8 Hz), 7.48 (1H, d, J = 1.8 Hz). MS: 541.3 $[M + 1]^+$. |

-continued

| # | Structure | Analytical data |
|---|---|---|
| 29/2 | 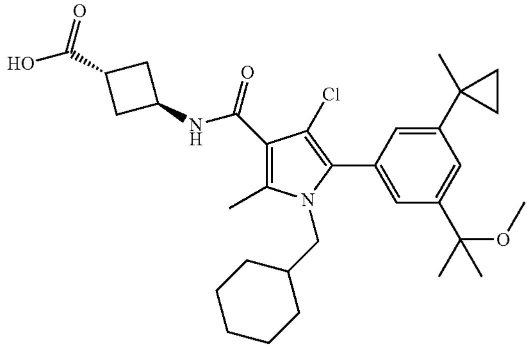 [SMILES: COC(C)(C)c1cc(-c2c(Cl)c(C(=O)N[C@H]3C[C@H](C(=O)O)C3)c(C)n2CC2CCCCC2)cc(C2(C)CC2)c1] | $^1$H-NMR (300 MHz, $CDCl_3$) δ: 0.58-0.66 (2H, m), 0.77-0.83 (2H, m), 0.85-0.91 (2H, m), 0.94-0.99 (3H, m), 1.25-1.36 (4H, m), 1.44 (3H, s), 1.52 (8H, s), 2.27-2.37 (2H, m), 2.60 (3H, s), 2.77-2.85 (2H, m), 3.07-3.15 (4H, m), 3.64 (2H, d, J = 7.2 Hz), 4.76-4.88 (1H, m), 7.00 (1H, d, J = 7.2 Hz), 7.04 (1H, t, J = 1.5 Hz), 7.15 (1H, t, J = 1.5 Hz), 7.31 (1H, t, J = 1.5 Hz). MS: 555.3 [M + 1]$^+$. |

Example 30 and Example 31

30

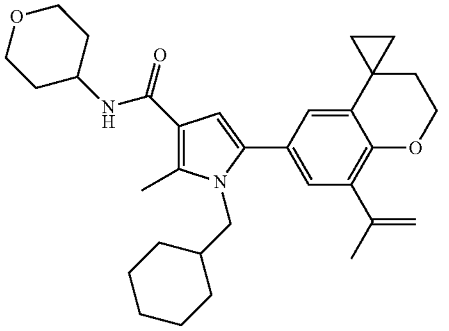

31

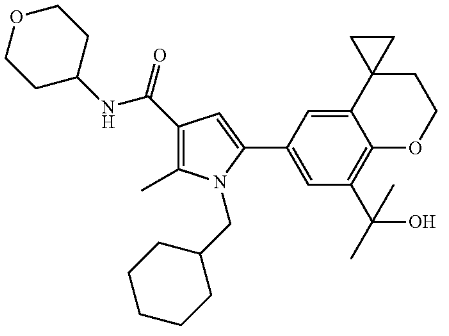

Step 1: 1-(Cyclohexylmethyl)-2-methyl-5-(8-(prop-1-en-2-yl)spiro[chroman-4,1'-cyclopropan]'-6-yl)-N-(tetrahydro-2H-pyran-4-yl)-1H-pyrrole-3-carboxamide (30)

To a solution of compound P97 (128 mg, 0.39 mmol) 5-bromo-1-(cyclohexylmethyl)-2-methyl-N-(tetrahydro-2H-pyran-4-yl)-1H-pyrrole-3-carboxamide (180 mg, 471 μmol), $K_2CO_3$ (135 mg, 981 μmol) and TBAB (10 mg) in a mixture of 1,4-dioxane (3 mL) and water (1.5 mL) was added $Pd(PPh_3)_2Cl_2$ (20 mg) under $N_2$. Under microwave conditions (120 W), the solution was heated at 105° C. for 1 h, cooled, poured into a mixture of water and EA and extracted with EA twice. The combined organic layers were washed with water and brine, concentrated and purified by CC (PE/EA=5/1) and then prep. HPLC to give compound 30 (109 mg, 56%) as a colorless solid.

Step 2: 1-(Cyclohexylmethyl)-5-(8-(2-hydroxypropan-2-yl)spiro[chroman-4,1'-cyclopropan]-6-yl)-2-methyl-N-(tetrahydro-2H-pyran-4-yl)-1H-pyrrole-3-carboxamide (31)

To a stirred mixture of compound 30 (109 mg, 0.22 mmol) and $OsO_4$ (4 mg) in 1,4-dioxane (5 mL) was added a solution of $NaIO_4$ (200 mg, 0.94 mmol) in water (2 mL). The solution was stirred at 30° C. for 2 h, quenched with water and extracted with EA twice. The combined organic layers were washed with brine, concentrated and purified by CC (PE/EA=5/1) to give an intermediate as a colorless solid. To a stirred solution of this intermediate in dry THF (3 mL) was added $CH_3MgBr$ (3M, 70 μL, 0.21 mmol) and the mixture was stirred at rt for 2 h, quenched with aq. $NH_4Cl$ at 0° C. and extracted with EA. The organic layer was concentrated and purified by CC (PE/EA=3/1) to give compound 31 (61 mg, 53%). $^1$H-NMR ($CDCl_3$+$D_2O$, 300 MHz) δ: 0.61-0.63 (2H, m), 0.72-0.75 (2H, m), 0.88-0.98 (5H, m), 1.32-1.35 (3H, m), 1.54-1.62 (7H, m), 1.94-1.99 (3H, m), 1.99-2.00 (1H, m), 2.63 (3H, s), 3.53 (2H, t, J=11.7 Hz), 3.65 (2H, d, J=7.2 Hz), 3.98 (2H, d, J=10.8 Hz), 4.13-4.21 (1H, m), 4.44-4.47 (2H, m), 4.86 (3H, m), 5.61 (1H, d, J=7.5 Hz), 6.08 (1H, s), 6.50 (1H, s), 6.99 (1H, s). MS: 521.4 (M+1)$^+$.

Example 32 and Example 33

32

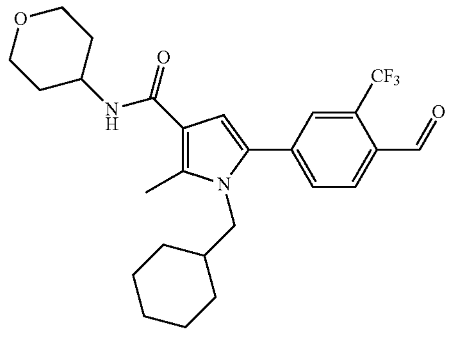

-continued

33

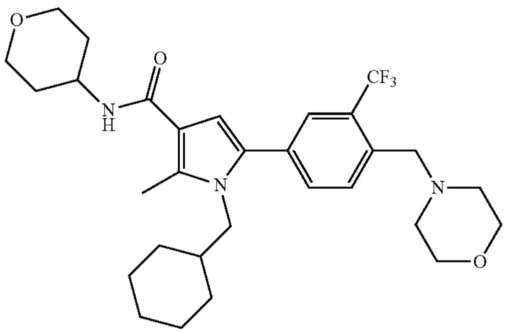

Step 1: 1-(Cyclohexylmethyl)-5-(4-formyl-3-(trifluoromethyl)phenyl)-2-methyl-N-(tetrahydro-2H-pyran-4-yl)-1H-pyrrole-3-carboxamide (32)

A solution of 5-bromo-1-(cyclohexylmethyl)-2-methyl-N-(tetrahydro-2H-pyran-4-yl)-1H-pyrrole-3-carboxamide (2.1 g, 5.5 mmol), (4-formyl-3-(trifluoromethyl)phenyl)boronic acid (1.0 g, 4.6 mmol), $K_2CO_3$ (1.0 g, 7.2 mmol), TBAB (50 mg) and $Pd(PPh_3)_2Cl_2$ (200 mg) in a mixture of 1,4-dioxane (10 mL) and water (5 mL) in a sealed tube was irradiated in a microwave at 100° C. for 2 h, concentrated and purified by CC (PE/EA=3/2) to give compound 32 (690 mg, 32%) as a yellow solid.

Step 2: 1-(Cyclohexylmethyl)-2-methyl-5-(4-(morpholinomethyl)-3-(trifluoromethyl)phenyl)-N-(tetrahydro-2H-pyran-4-yl)-1H-pyrrole-3-carboxamide (33)

To a solution of compound 32 (200 mg, 0.42 mmol) and morpholine (87 mg, 1.0 mmol) in DCM (3 mL) was added AcOH (one drop) and $NaBH(OAc)_3$ (212 mg, 1.0 mmol) and the solution was stirred overnight at rt and quenched with sat. $NaHCO_3$. The organic layer was washed with sat. $NaHCO_3$, water and brine, dried over $Na_2SO_4$, filtered, concentrated and purified by prep. HPLC to afford compound 33 (33 mg, 14%) as a colorless solid. $^1$H-NMR ($CDCl_3$, 400 MHz) δ: 7.83 (d, J=7.6 Hz, 1H), 7.59 (s, 1H), 7.47 (d, J=7.6 Hz, 1H), 6.22 (s, 1H), 5.60 (d, J=8.0 Hz, 1H), 4.12-4.18 (m, 1H), 3.97-4.00 (m, 2H), 3.74-3.77 (m, 6H), 3.70 (s, 2H), 3.52 (m, 2H), 2.62 (s, 3H), 2.50-2.56 (m, 4H), 1.96-2.05 (m, 2H), 1.47-1.51 (m, 3H), 1.32-1.42 (m, 4H), 1.24-1.28 (m, 1H), 0.97-1.02 (m, 3H), 0.58-0.70 (m, 2H). MS: 548.3 $(M+1)^+$.

Example 34

34

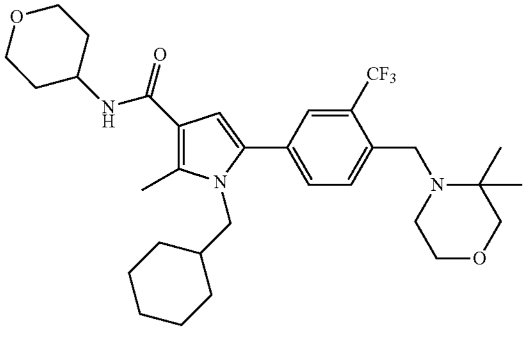

1-(Cyclohexylmethyl)-5-(4-((3,3-dimethylmorpholino)methyl)-3-(trifluoromethyl)phenyl)-2-methyl-N-(tetrahydro-2H-pyran-4-yl)-1H-pyrrole-3-carboxamide (34)

Using similar procedures as described in Example 33 compound 34 was prepared. $^1$H-NMR ($CDCl_3$, 400 MHz) δ: 7.97 (d, J=8.0 Hz, 1H), 7.56 (s, 1H), 7.46 (d, J=8.0 Hz, 1H), 6.21 (s, 1H), 5.60 (d, J=7.6 Hz, 1H), 4.11-4.18 (m, 1H), 3.98 (d, J=11.2 Hz, 2H), 3.69-3.77 (m, 6H), 3.52 (m, 2H), 3.42 (s, 2H), 2.62 (s, 3H), 2.46 (m, 2H), 1.98 (m, 2H), 1.47-1.56 (m, 6H), 1.34-1.43 (m, 3H), 1.13 (s, 6H), 0.96-1.05 (m, 3H), 0.61-0.68 (m, 2H). MS: 576.4 $(M+1)^+$.

Additional Examples

If one were to use the appropriate building blocks as described in the Examples above, one would obtain the following compounds:

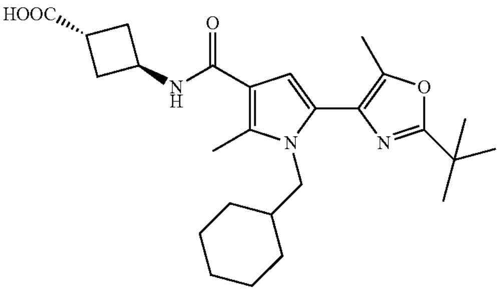

,

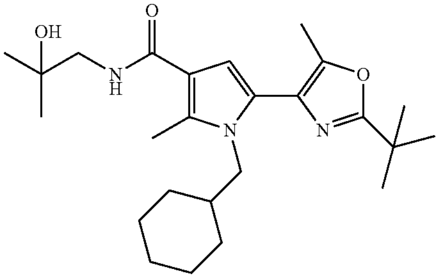

,

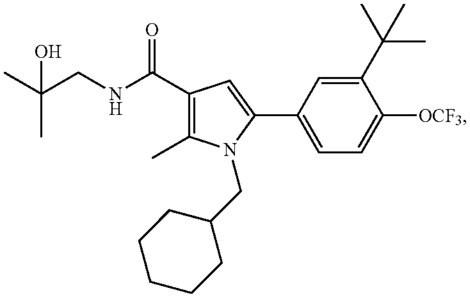

,

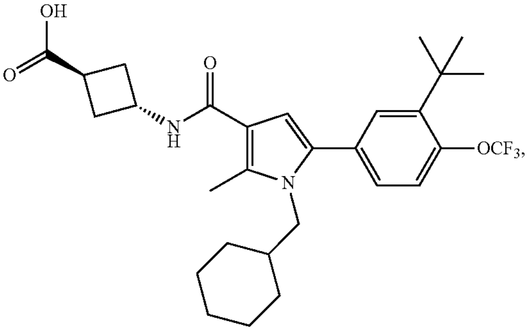

,

-continued
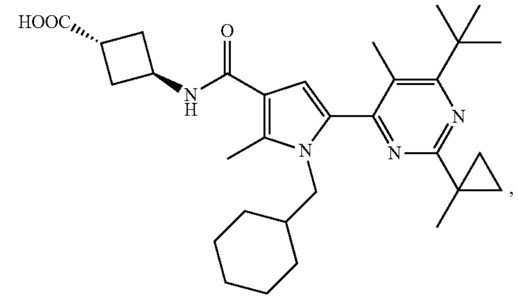
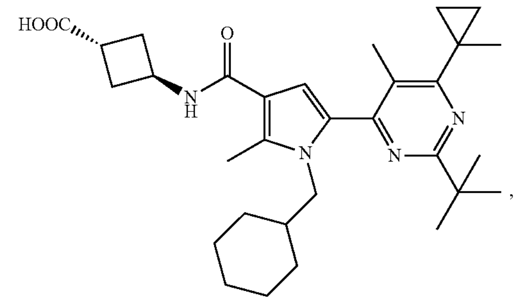
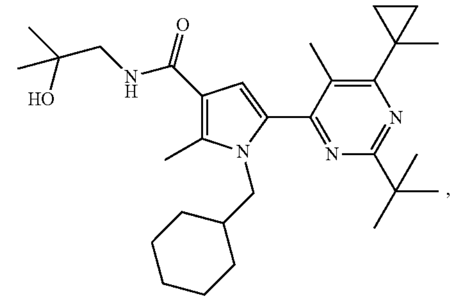
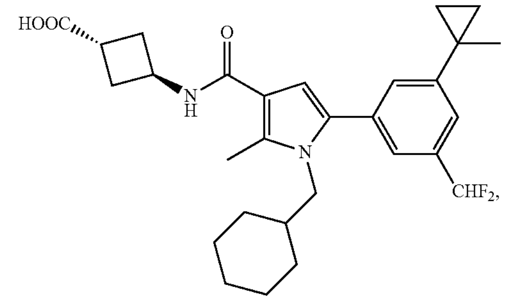
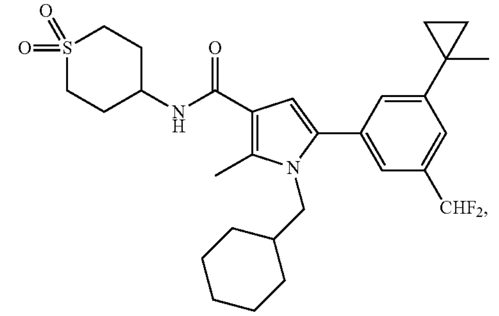
-continued
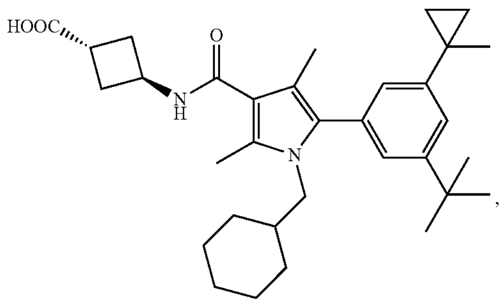
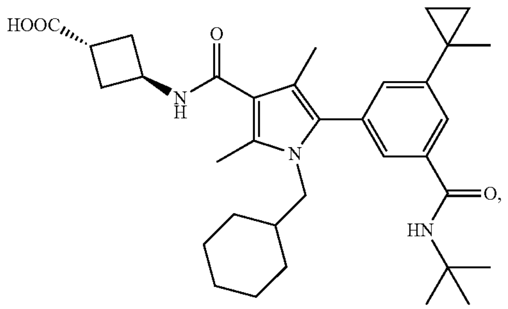
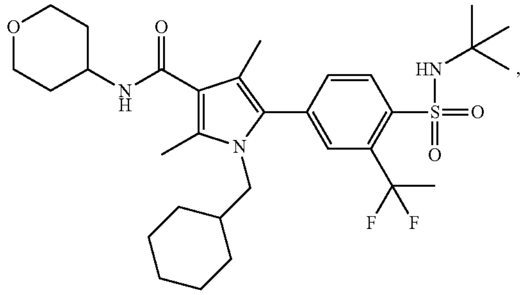
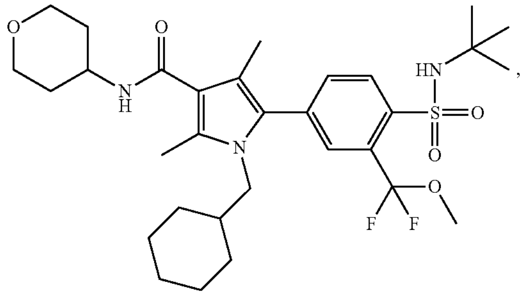
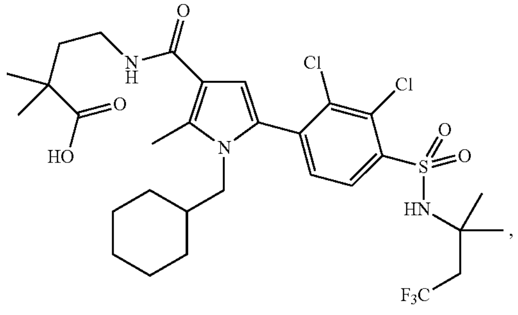

-continued
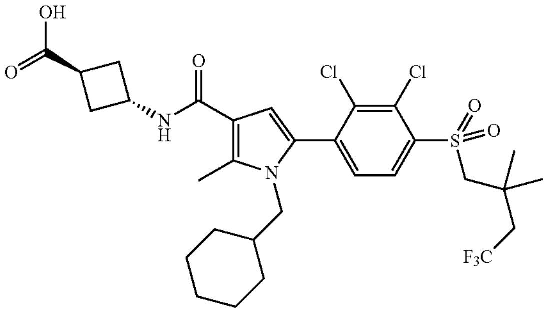
,
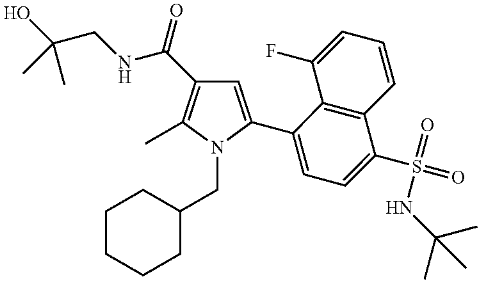
,
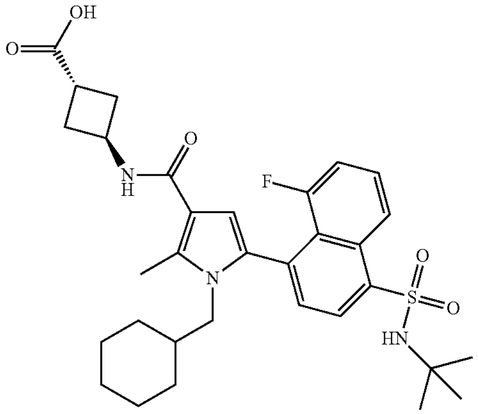
,
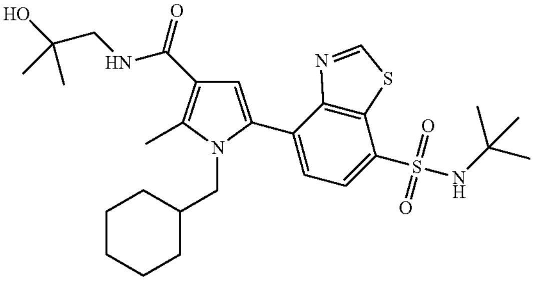
,
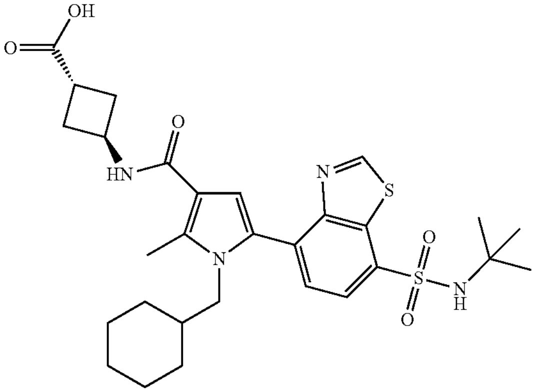
,
-continued
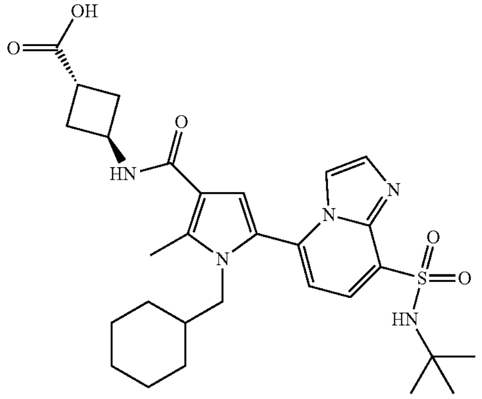
,
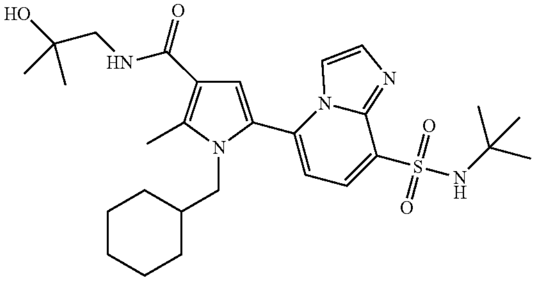
,
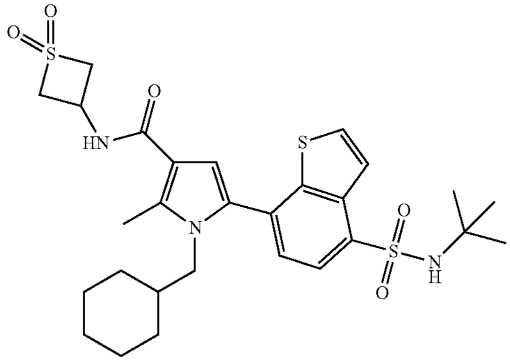
,
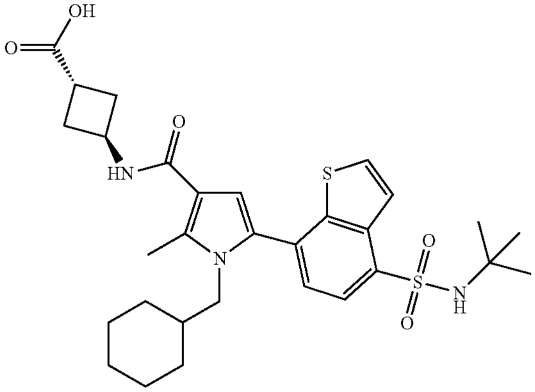
, -continued
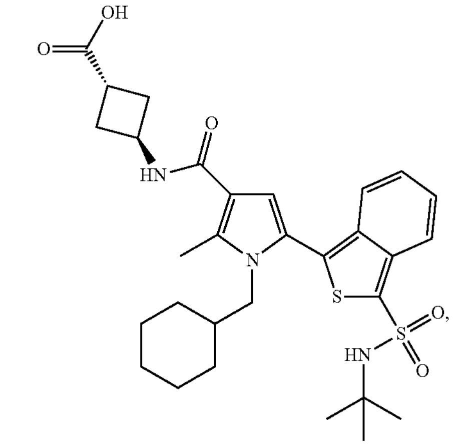,
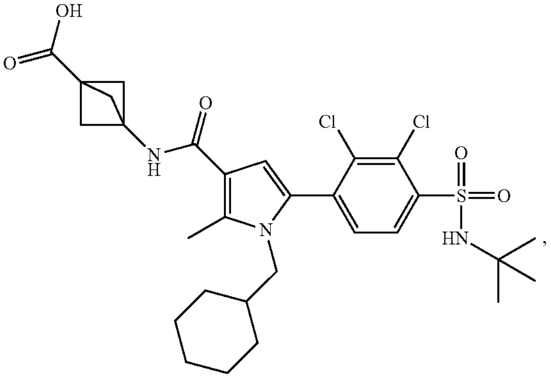,
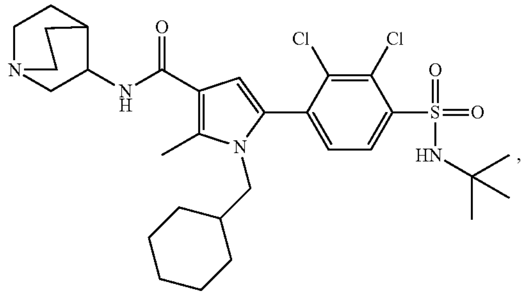,
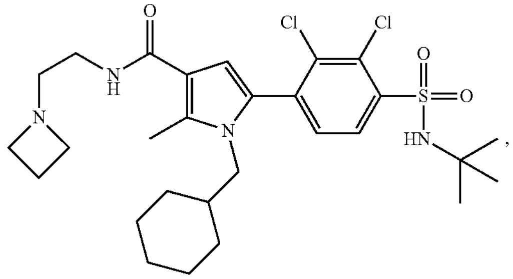,
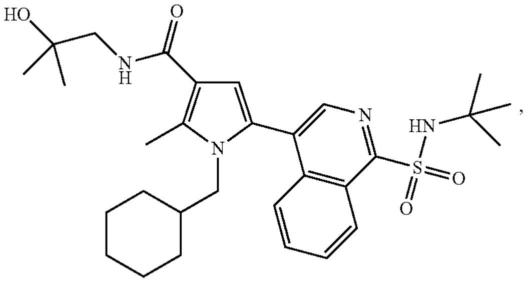,
-continued
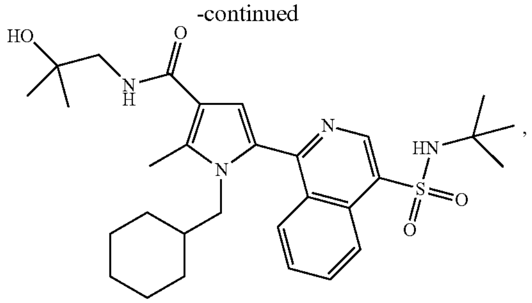,
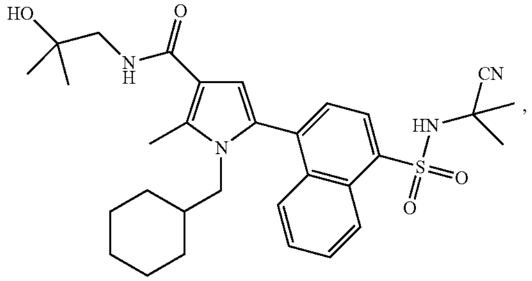,
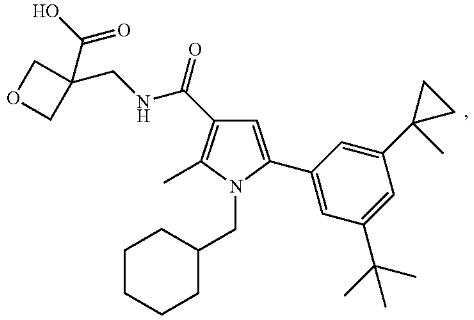,
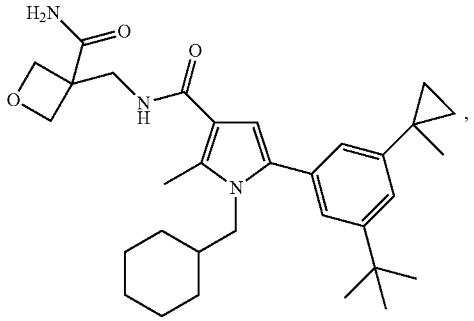,
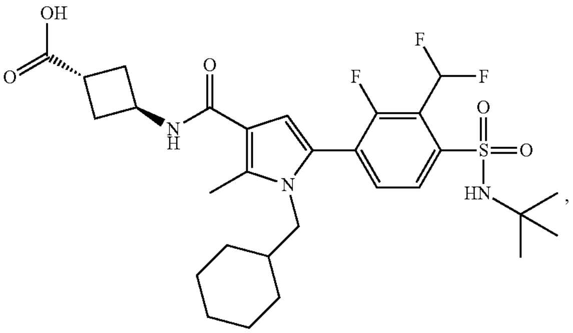, -continued
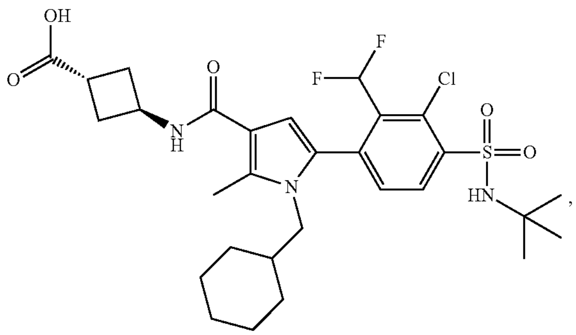
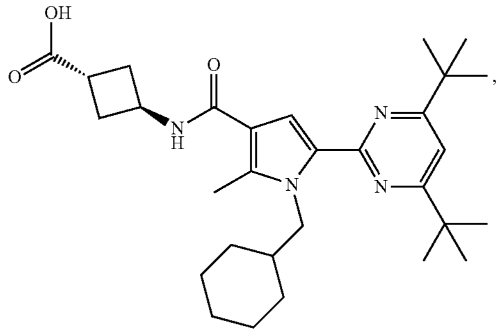
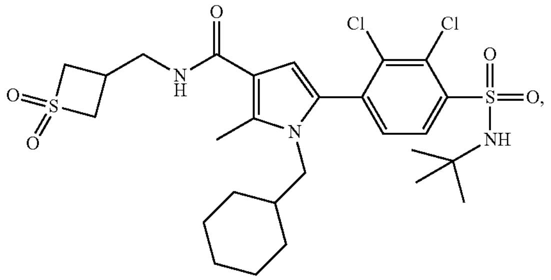
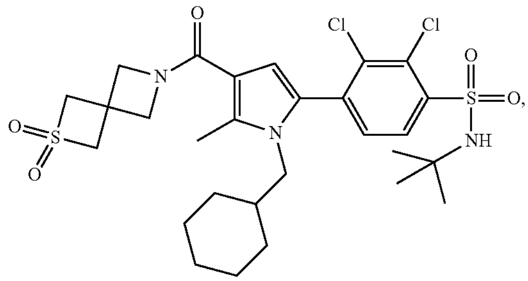
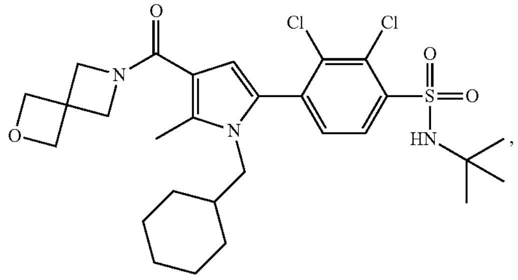
-continued
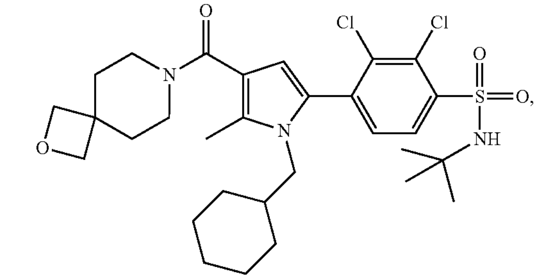
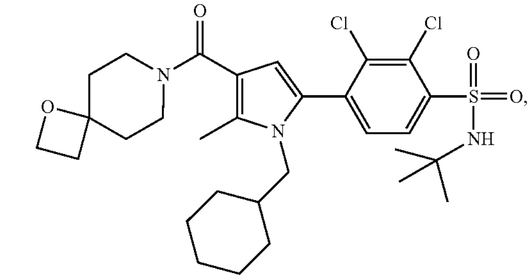
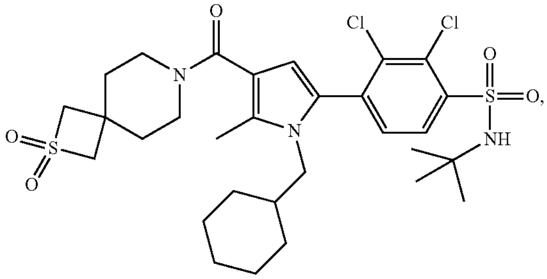
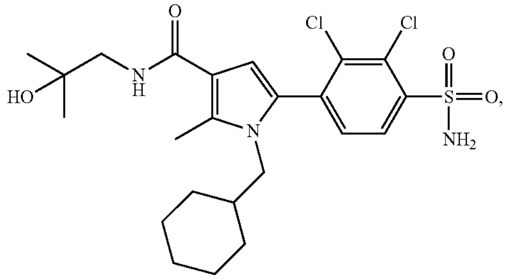
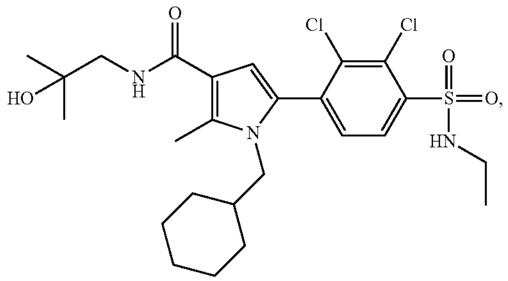
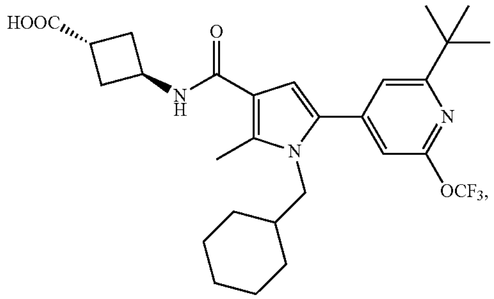

-continued
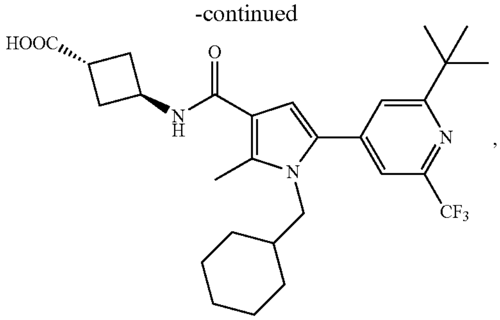
,
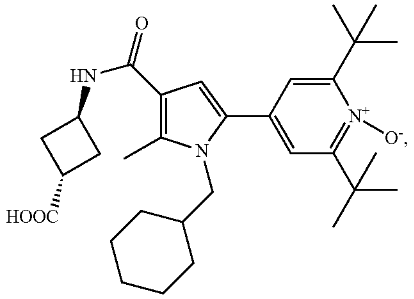
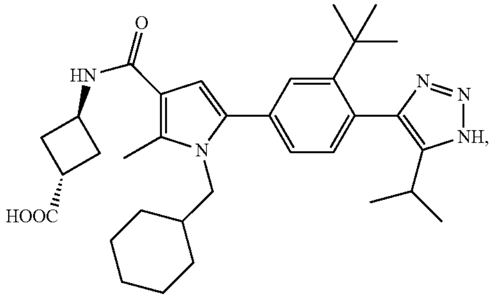
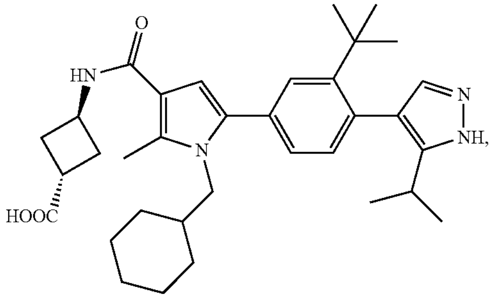
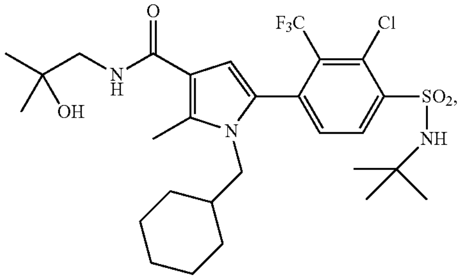
-continued
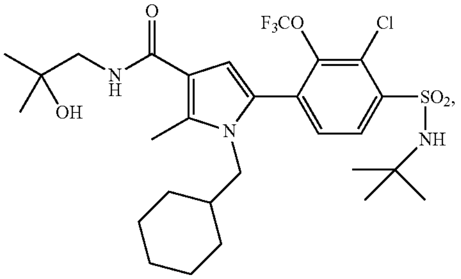
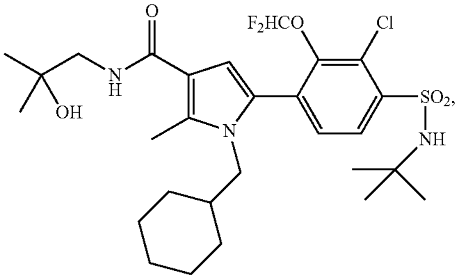
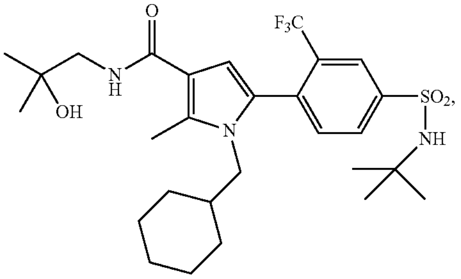
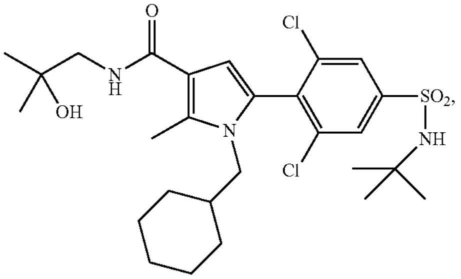
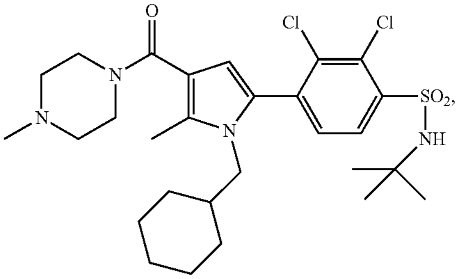
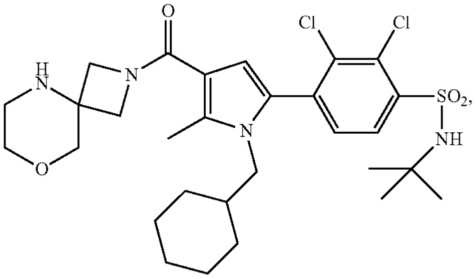

-continued
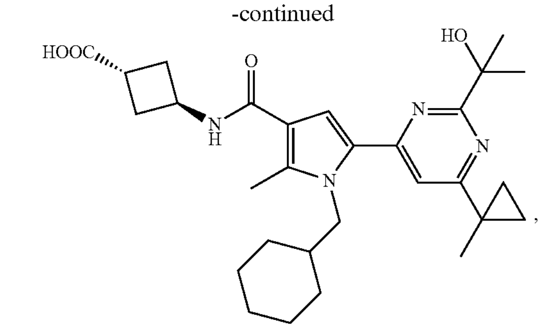
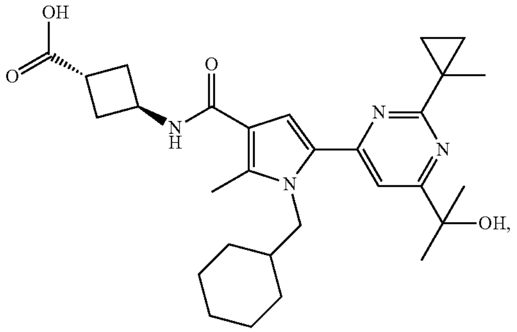
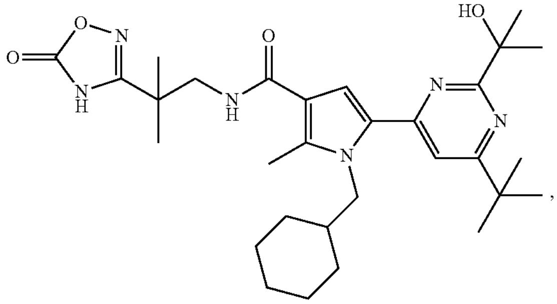
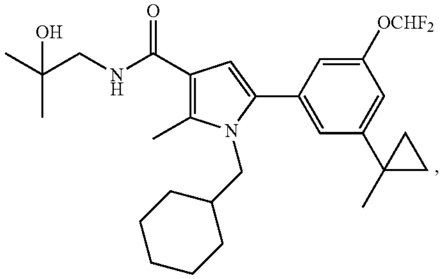
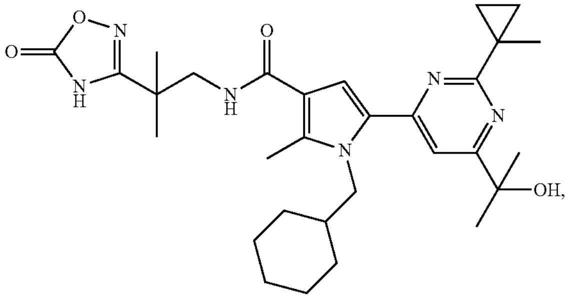
-continued
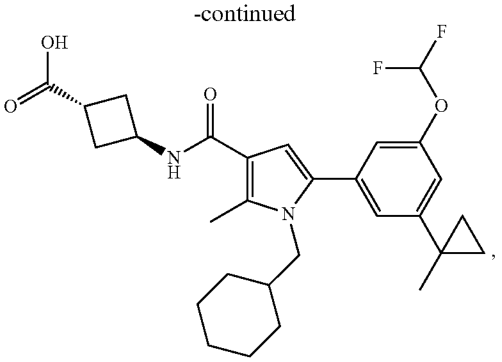
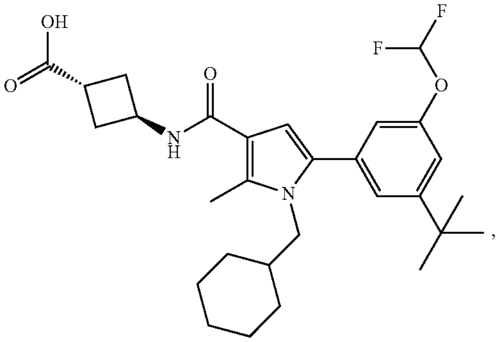
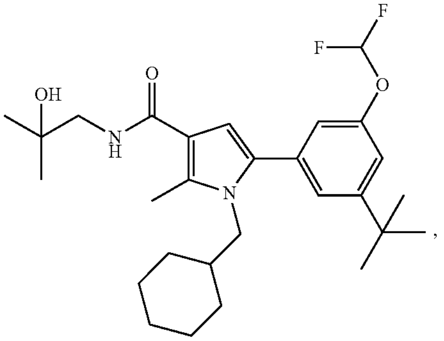
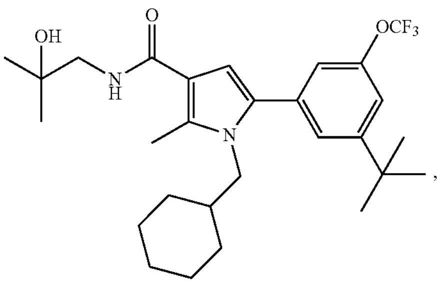
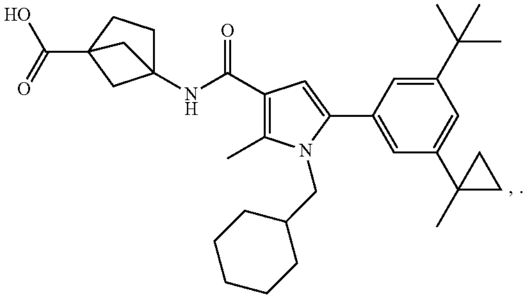

-continued

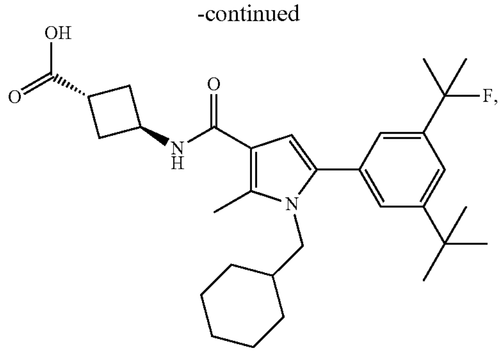

,

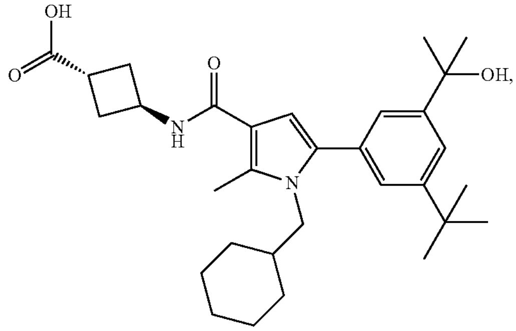

,

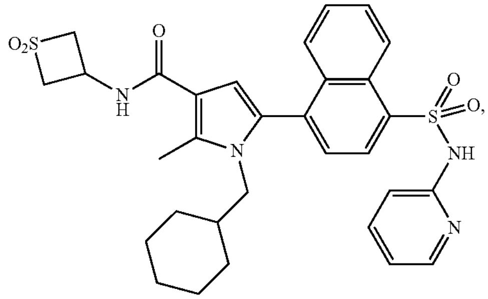

,

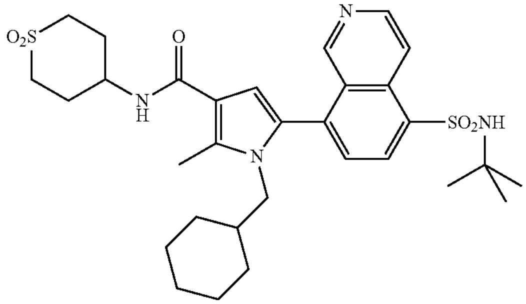

,

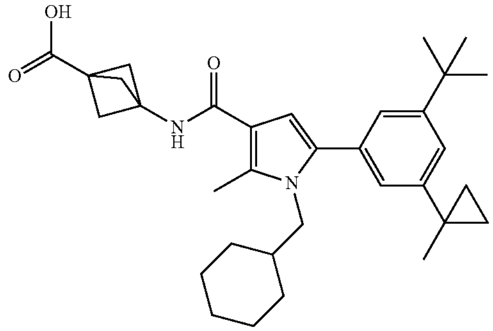

,

-continued

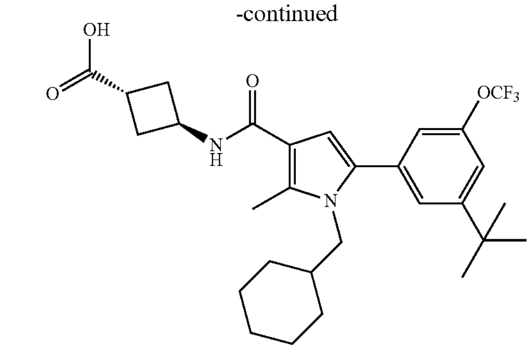

,

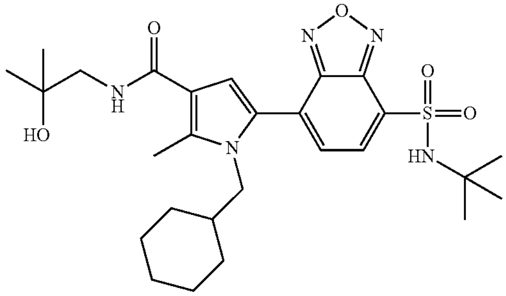

and

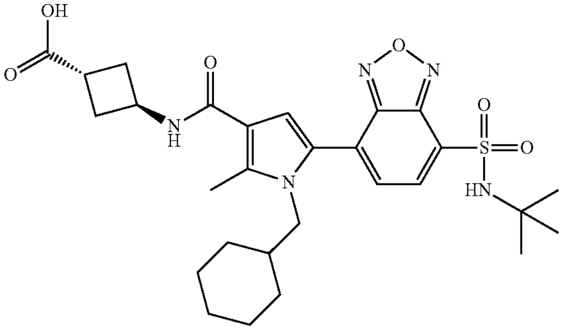

.

Protein Expression and Purification

Protein expression and purification was done as described in WO2010/049144.

TR-FRET Activity Assay

This method measures the ability of putative ligands to modulate the interaction between the purified bacterial expressed RORγ ligand binding domain (LBD) and synthetic N-terminally biotinylated peptides which are derived from nuclear receptor coactivator proteins such as but not limited to SRC1 (NcoA1), SRC2 (NcoA2, TIF2), SRC3 (NcoA3), PGC1α, PGC1β, CBP, GRIP1, TRAP220, RIP140. The peptides used are listed in Table 1 below:

TABLE 1

| Peptide Name (aa range) | DB entry Protein | DB entry DNA | Sequence |
|---|---|---|---|
| SRC1 (676-700) | NP_003734 | NM_003743.4 | $NH_2$—CPSSHSSL TERHKILHRLLQ EGSPS—COOH |
| TRAP220 (631-655) | NP_004765 | NM_004774.3 | $NH_2$—PVSSMAGN TKNHPMLMNLLK DNPAQ-COOH |
| TIF2 (628-651) | NP_006531 | NM_006540.2 | $NH_2$-GQSRLHDS KGQTKLLQLLTT KSDQ-COOH |

The ligand-binding domain (LBD) of RORγ was expressed as fusion protein with GST in BL-21 (BL3) cells using the vector pDEST15. Cells were lysed by lysozyme-treatment and sonication, and the fusion proteins purified over glutathione sepharose (Pharmacia) according to the manufacturers instructions. For screening of compounds for their influence on the RORγ-peptide interaction, the LANCE technology (Perkin Elmer) was applied. This method relies on the binding dependent energy transfer from a donor to an acceptor fluorophor attached to the binding partner of interest. For ease of handling and reduction of background from compound fluorescence LANCE technology makes use of generic fluorophore labels and time resolved detection assays were done in a final volume of 25 μL in a 384 well plate, in a Tris-based buffer system (20 mM Tris-HCl pH 6.8; 60 mM KCl, 1 mM DTT; 5 mM $MgCl_2$; 35 ng/μL BSA), containing 20-60 ng/well recombinantly expressed RORγ-LBD fused to GST, 200-600 nM N-terminally biotinylated peptide, 200 ng/well Streptavidin-xlAPC conjugate (Prozyme) and 6-10 ng/well Eu W1024-antiGST (Perkin Elmer). DMSO content of the samples was kept at 1%.

After generation of the Tris-based buffer system, the potentially RORγ modulating ligands were diluted. After this step, protein, peptide and fluorescent acceptor and donor solutions were mixed in the Tris-based buffer system and have been added to the compound dilutions, after this addition of 'detection mix', the assay was equilibrated for 1 h in the dark at rt in FIA-plates black 384 well (Corning). The LANCE signal was detected by a Perkin Elmer EnVision™ Multilabel Counter. The results were visualized by plotting the ratio between the emitted light at 665 nm and 615 nm. A basal level of RORγ-peptide formation is observed in the absence of added ligand. Ligands that promote the complex formation induce a concentration-dependent increase in time-resolved fluorescent signal. Compounds which bind equally well to both monomeric RORγ and to the RORγ-peptide complex would be expected to give no change in signal, whereas ligands, which bind preferentially to the monomeric receptor would be expected to induce a concentration-dependent decrease in the observed signal.

To assess the antagonistic potential of the compounds, $IC_{50}$ values were determined using a Ligand Sensing Assay based on Time-resolved Fluorescence Energy Transfer (TR-FRET) as described above. The normalised TR-FRET assay values, using the following equation: 1000*665 nm measurement value/615 nm measurement value, were transferred to the program GraphPad Prism to generate graphs and dose response curves using the following equation:

Equation: Sigmoidal dose-response (variable slope)

$$Y=\text{Bottom}+(\text{Top}-\text{Bottom})/(1+10\hat{\ }((\text{Log EC50}-X)*\text{HillSlope}))$$

X is the logarithm of the concentration. Y is the response. Y starts at Bottom and goes to Top with a sigmoidal shape.

This is identical to the "four parameter logistic equation". The $IC_{50}$ values are calculated using this equation. Examples listed below do reduce the signal in the TR-FRET assay in a dose dependent manner. The Examples of the present invention usually have an inhibition activity ($IC_{50}$ FRET) ranging from below 100 nM to about 20 μM and typically, from about 150 nM to about 2 μM. The RORγ modulating compounds of the invention desirably have an inhibition in the TR-FRET Activity Assay ranging from below 150 nM to about 2 μM. Table 2 lists the $pIC_{50}$-value of compounds of the invention (FRET). Is is understood that the data illustrated below may have reasonable variation depending on the specific conditions and procedures used by the person conducting the test. The efficacy was determined in comparison to the RORγt inhibitor T0901317 (equals 100%) and the $pIC_{50}$-value is underlined, when the efficacy of the compound is below 50% of the reference.

RORγ Gal4 Reporter Gene Assay

Determination of a ligand mediated Gal4 promoter driven transactivation to quantify ligand binding to RORγ was performed as follows: DNA encoding three different RORγ protein fragments was cloned into vector pCMV-BD (Stratagene). Expression was under control of a CMV promoter and as fusion to the DNA-binding domain of the yeast protein GAL4. The amino acid boundaries of the three proteins and the respective database entries are listed in Table 3. Other vectors used were pFR-Luc (Stratagene) as regulated reporter plasmid. pFR-Luc contains a synthetic promoter with five tandem repeats of the yeast GAL4 binding sites that control expression of the *Photinus pyralis* (American firefly) luciferase gene. In order to improve experimental accuracy the plasmid pRL-CMV was cotransfected. pRL-CMV contains the constitutive CMV promoter, controlling the expression of the *Renilla reniformis* luciferase.

TABLE 3

| construct name | aa borders (RefSeq) | Ref sequence ID |
|---|---|---|
| hRORγ-LBD | aa259-518 | NP_005051.2 |
| hRORγt | aa1-497 | NP_001001523 (RORγ, t isoform, 497aa) |
| mRORγ-LBD | aa264-516 | NP_035411 |

All Gal4 reporter gene assays were done in 293T cells (DSMZ (German Collection of Microorganisms and Cell Cultures), Braunschweig, Germany, ACC635) grown in Minimum Essential Medium (MEM) with Phenol Red. The medium is supplemented with 10% fetal bovine serum, 0.1 mM nonessential amino acids, 1 mM sodium pyruvate, 1% Glutamax and 100 units Penicillin/Streptavidin per mL at 37° C. in 5% $CO_2$.

For the assay, $5\times10^5$ cells were plated per well in 96 well plates in 100 μL per well, incubated over night at 37° C. in 5% $CO_2$. The following day, medium was discarded and the cells were transiently transfected using 20 μL per well of a OptiMEM-PEI-based transfection-reagent (Sigma-Aldrich, 408727) including the three plasmids described above. About 4 h after addition of the transfection solution, fresh MEM (same composition as used for plating cells, but without serum) was added. Then compound stocks, prediluted in MEM (same composition as used for plating cells) were added (final vehicle concentration not exceeding 0.1%).

Cells were incubated for additional 16 h before firefly (FF) and *renilla* (REN) luciferase activities were measured sequentially in the same cell extract using a Dual-Light-Luciferase-Assay system (Dyer et al., Anal. Biochem. 2000, 282:158). All experiments were done in triplicates.

Applying the Gal4 reporter gene assay as described above, the Examples of the present invention usually have an inhibition activity ($IC_{50}$ FF resp. $IC_{50}$ RENnorm) ranging from below 5 nM to about 20 μM and typically, from about 10 nM to about 2 μM. The RORγ modulating compounds of the invention desirably have an inhibition in the Gal4 reporter gene assay ranging from below 5 nM to about 1 μM. Table 2 list the $pIC_{50}$-value of typical examples of compounds of the invention that have an RORγ activity in the Gal4 reporter gene assay for firefly (FF) and renilla normalised (REN) luciferase measurements. Is is understood that the data illustrated below may have reasonable variation depending on the specific conditions and procedures used by the person conducting the test. The efficacy was determined in comparison to the RORγt inhibitor T0901317 (equals 100%) and the $pIC_{50}$-value is underlined, when the efficacy of the compound is below 50% of the reference.

TABLE 2

| Ex. # | $pIC_{50}$ (FRET/FF/REN) | Ex. # | $pIC_{50}$ (FRET/FF/REN) | Ex. # | $pIC_{50}$ (FRET/FF/REN) |
|---|---|---|---|---|---|
| 1 | 6.5/6.8/6.9 | 1/1 | 6.6/6.6/6.7 | 1/2 | 6.9/7.5/7.4 |
| 1/3 | 6.4/7.6/7.5 | 1/4 | 6.5/7.5/7.6 | 1/5 | 6.0/6.3/6.2 |
| 1/6 | 6.2/6.7/6.7 | 1/7 | 6.3/6.8/6.8 | 1/8 | 6.5/6.4/6.3 |
| 1/9 | 6.5/6.6/6.7 | 1/10 | 6.3/7.5/7.5 | 1/11 | 5.7/6.1/6.1 |
| 1/12 | 5.9/6.4/6.5 | 1/13 | 5.9/6.2/6.1 | 1/14 | 5.7/6.5/6.6 |
| 1/15 | 5.5/5.5/5.5 | 1/16 | 5.2/6.1/5.8 | 1/17 | 6.7/6.3/6.4 |
| 1/18 | 6.2/7.1/7.0 | 1/19 | 6.0/7.0/7.1 | 1/22 | 6.0/6.9/6.9 |
| 1/24 | 6.2/6.5/6.5 | 1/26 | 5.0/<4.7/<4.7 | 1/27 | 4.9/<4.7/<4.7 |
| 1/28 | 6.1/6.7/6.8 | 1/29 | 6.2/7.2/7.2 | 1/30 | 5.4/6.4/6.2 |
| 1/31 | 5.7/6.4/6.4 | 1/32 | 5.8/6.4/6.2 | 1/33 | 6.1/6.6/6.5 |
| 1/34 | 5.9/6.8/6.7 | 1/35 | 6.9/6.9/6.9 | 1/36 | 6.8/6.5/6.6 |
| 1/37 | 6.5/6.8/6.8 | 1/38 | 6.6/7.2/7.3 | 1/39 | 6.5/6.9/7.0 |
| 1/40 | 6.6/7.5/7.6 | 1/41 | 6.3/6.9/7.0 | 1/42 | 6.6/7.5/7.6 |
| 1/43 | 6.0/7.1/7.1 | 1/44 | 6.3/7.4/7.3 | 1/45 | 6.0/5.6/5.8 |
| 1/46 | 6.5/6.5/6.5 | 1/47 | 5.4/<4.7/<4.7 | 1/48 | 6.2/6.4/6.4 |
| 1/49 | 4.5/6.2/6.6 | 1/50 | 5.8/6.0/6.1 | 1/51 | 5.6/5.9/6.1 |
| 1/52 | 6.8/6.4/6.5 | 1/53 | 6.8/7.3/7.4 | 1/54 | 6.4/6.3/6.4 |
| 1/55 | 6.6/6.8/6.9 | 1/56 | 5.5/<4.7/<4.7 | 1/57 | 5.6/5.8/5.8 |
| 1/58 | 6.2/6.2/6.2 | 1/59 | 6.2/6.3/6.3 | 1/60 | 6.0/6.2/6.2 |
| 1/61 | 6.0/6.2/6.2 | 1/62 | 6.5/6.4/6.3 | 1/63 | 6.2/6.7/6.7 |
| 1/64 | 6.5/6.5/6.5 | 1/65 | 6.4/6.6/6.6 | 1/66 | 6.4/6.7/6.8 |
| 1/67 | 6.8/7.2/7.3 | 1/68 | 5.8/6.7/6.8 | 1/69 | 5.8/6.8/6.9 |
| 1/70 | 6.2/6.6/6.6 | 1/71 | 5.9/5.8/5.9 | 1/72 | 6.0/7.1/7.1 |
| 1/73 | 5.9/7.2/7.2 | 1/74 | 5.3/<4.7/<4.7 | 1/75 | 5.31/<4.7<4.7 |
| 1/76 | 5.9/5.9/5.8 | 1/77 | 6.7/6.9/7.0 | 1/78 | 6.5/7.1/7.1 |
| 1/79 | 6.4/7.2/7.2 | 1/80 | 6.7/7.5/7.5 | 1/81 | 6.7/7.4/7.4 |
| 1/82 | 6.8/7.4/7.4 | 1/83 | 6.5/6.9/7.0 | 1/84 | 6.8/7.6/7.6 |
| 1/85 | 6.5/7.7/7.7 | 1/86 | 6.8/7.6/7.6 | 1/87 | 6.5/7.2/7.2 |
| 1/88 | 6.4/6.5/6.5 | 1/89 | 6.6/6.3/6.2 | 1/90 | 5.7/7.0/6.9 |
| 1/91 | 5.7/7.4/7.4 | 1/92 | 6.7/7.0/6.9 | 1/93 | 6.7/7.4/7.4 |
| 1/94 | 6.3/7.4/7.3 | 1/95 | 6.8/7.0/7.1 | 1/96 | 6.7/6.7/6.8 |
| 1/97 | 6.6/7.1/7.0 | 1/98 | 6.2/7.3/7.3 | 1/99 | 6.4/7.1/7.2 |
| 1/100 | 6.6/7.2/7.2 | 1/101 | 6.6/7.2/7.2 | 1/102 | 6.3/6.4/6.4 |
| 1/103 | 6.4/7.3/7.3 | 1/104 | 6.3/6.8/6.8 | 1/105 | 6.6/6.5/6.5 |
| 1/106 | 6.1/7.0/7.1 | 1/107 | 6.1/7.2/7.2 | 1/108 | 5.1/7.2/7.3 |
| 1/109 | 4.9/<4.7/<4.7 | 1/110 | 6.1/7.3/7.4 | 1/111 | 6.4/7.4/7.4 |
| 1/112 | 6.3/7.1/7.1 | 1/113 | 5.4/<4.7/<4.7 | 1/114 | 6.6/6.7/6.8 |
| 1/115 | 6.6/7.3/7.3 | 1/116 | 6.9/6.9/6.9 | 1/117 | 6.3/6.8/7.0 |
| 1/118 | 6.2/6.5/6.6 | 1/119 | 6.7/7.4/7.3 | 1/120 | 6.9/7.1/7.3 |
| 1/121 | 6.9/7.0/7.2 | 1/122 | 6.8/7.0/7.0 | 1/123 | 6.3/6.8/6.8 |
| 1/124 | 6.2/7.5/7.5 | 1/125 | 6.1/7.4/7.4 | 1/126 | 6.2/7.1/7.0 |
| 1/127 | 6.3/7.5/7.4 | 1/128 | 6.3/7.2/7.2 | 1/129 | 5.8/7.3/7.3 |
| 1/130 | 6.1/6.8/6.8 | 1/131 | 6.3/7.8/7.8 | 1/132 | 6.2/6.8/6.8 |
| 2 | 6.6/7.0/7.0 | 2/1 | 6.1/6.5/6.5 | 2/2 | 6.6/7.0/7.0 |
| 2/3 | 5.8/6.5/6.7 | 3 | 6.6/7.4/7.4 | 4 | 6.2/6.4/6.4 |
| 5 | 6.3/7.0/7.2 | 6 | 6.2/6.3/6.4 | 6/1 | 5.7/6.7/6.7 |
| 6/2 | 5.5/6.5/6.4 | 6/3 | 5.1/5.9/5.7 | 6/4 | 5.0/<4.7/<4.7 |
| 6/5 | 5.6/6.5/6.4 | 6/6 | 6.2/6.8/6.7 | 6/7 | 6.0/6.5/6.4 |
| 6/8 | 5.0/6.8/7.3 | 6/9 | 5.0/6.4/6.2 | | |
| 7 | 6.5/6.8/6.9 | 7/1 | 6.5/6.7/6.8 | 7/2 | 6.6/7.0/7.0 |
| 7/3 | 6.6/6.6/6.7 | 7/4 | 6.7/7.1/7.1 | 7/5 | 6.5/6.3/6.4 |
| 7/6 | 6.4/6.6/6.5 | 7/7 | 6.4/6.5/6.6 | 7/8 | 6.3/6.0/6.2 |
| 8 | 5.4/7.2/7.2 | 8/1 | 5.3/6.8/6.9 | 8/1 | 5.6/6.7/6.8 |
| 9 | 6.1/7.1/7.2 | 9/1 | 6.3/7.5/7.5 | 9/2 | 6.2/7.4/7.5 |
| 9/3 | 6.5/7.1/7.1 | 9/4 | 6.2/7.1/7.2 | 9/5 | 6.5/7.2/7.2 |
| 9/6 | 6.6/7.7/7.8 | 9/7 | 6.3/7.5/7.5 | 9/8 | 6.2/7.0/7.1 |
| 9/9 | 6.3/7.2/7.3 | 9/10 | 6.5/7.7/7.2 | 9/11 | 6.3/7.7/7.8 |
| 9/12 | 5.8/6.3/6.5 | 9/13 | 6.0/6.0/6.1 | 9/14 | 5.1/6.3/6.2 |
| 9/15 | 6.5/6.5/6.5 | 10 | 5.8/6.9/6.9 | 10/1 | 4.8/6.7/6.6 |
| 11 | 6.6/6.5/6.5 | 11/1 | 6.6/7.3/7.3 | 11/2 | 6.6/6.9/6.9 |
| 11/3 | 6.0/6.5/6.5 | 11/4 | 6.4/6.9/7.0 | 11/5 | 6.5/7.3/7.4 |
| 11/6 | 6.6/8.0/8.2 | 11/7 | 6.6/7.1/7.2 | 12 | 6.0/6.1/6.2 |
| 15 | 6.3/6.9/6.9 | 15/1 | 5.7/6.6/6.7 | 15/2 | 6.0/6.3/6.3 |
| 15/3 | 6.4/7.0/7.1 | 15/4 | 5.8/7.3/7.3 | 15/5 | 6.1/7.6/7.7 |
| 15/6 | 5.9/7.4/7.4 | 15/7 | 5.9/7.2/7.2 | 15/8 | 6.0/7.3/7.4 |
| 15/9 | 6.0/6.9/7.0 | 16 | 6.8/6.4/6.5 | | |
| 17/1 | 5.9/8.0/7.9 | 17/2 | 6.0/6.6/6.5 | 17/3 | 6.4/6.9/6.9 |
| 17/4 | 6.2/6.7/6.7 | 17/5 | 6.5/6.4/6.4 | 17/6 | 6.6/6.4/6.5 |
| 17/7 | 5.5/<4.7/<4.7 | 17/8 | 6.1/7.2/7.2 | 17/9 | 6.2/6.8/6.8 |
| 17/10 | 6.4/7.6/7.6 | 17/11 | 6.7/7.2/7.2 | 17/12 | 6.7/7.2/7.4 |
| 17/13 | 6.2/6.8/6.9 | 17/14 | 5.9/5.9/5.7 | 17/15 | 6.1/7.2/7.1 |
| 17/16 | 5.4/6.1/6.0 | 17/17 | 6.1/6.3/6.4 | 17/18 | 6.0/6.1/6.1 |

TABLE 2-continued

| Ex. # | $pIC_{50}$ (FRET/FF/REN) | Ex. # | $pIC_{50}$ (FRET/FF/REN) | Ex. # | $pIC_{50}$ (FRET/FF/REN) |
|---|---|---|---|---|---|
| 17/19 | 6.1/7.5/7.5 | 17/20 | 6.4/7.1/7.1 | 17/21 | 6.2/7.0/6.9 |
| 17/22 | 6.0/6.5/6.6 | 17/23 | 5.9/6.6/6.6 | 17/24 | 5.5/5.8/5.7 |
| 17/25 | 6.5/6.9/7.0 | 17/26 | 5.8/7.3/7.3 | 17/27 | 5.6/6.3/6.5 |
| 17/28 | 6.6/7.4/7.4 | 17/29 | 5.9/6.8/6.7 | 17/30 | 6.6/7.7/7.7 |
| 17/31 | 6.0/7.3/7.3 | 17/32 | 6.7/7.2/7.2 | 17/33 | 6.2/7.1/7.2 |
| 17/34 | 5.8/7.0/6.9 | 17/35 | 5.8/6.4/6.3 | 17/36 | 6.1/6.9/6.9 |
| 17/37 | 5.9/7.1/7.1 | 17/38 | 6.0/6.7/6.7 | 17/39 | 6.4/6.9/6.8 |
| 17/40 | 5.9/6.9/6.8 | 17/41 | 6.4/8.1/8.2 | 17/42 | 5.7/7.5/7.6 |
| 17/43 | 6.7/7.4/7.4 | 17/44 | 6.2/6.1/6.1 | 17/45 | 6.0/6.5/6.4 |
| 17/46 | 6.5/6.5/6.5 | 17/47 | 6.7/7.3/7.4 | 17/48 | 6.0/7.6/7.5 |
| 17/49 | 5.7/7.0/7.1 | 17/50 | 5.5/6.5/6.5 | 17/51 | 5.8/6.7/6.7 |
| 17/52 | 5.8/6.7/6.7 | 17/53 | 5.8/6.9/6.9 | 17/54 | 5.8/7.1/7.2 |
| 17/55 | 5.7/7.5/7.6 | 17/56 | 4.9/6.4/6.4 | 17/57 | 6.1/7.4/7.5 |
| 17/58 | 5.8/6.7/6.7 | 17/59 | 5.7/6.6/6.6 | 17/60 | 5.8/7.6/7.6 |
| 17/61 | 6.0/7.4/7.5 | 17/62 | 6.5/8.3/8.3 | 17/63 | 6.7/7.7/7.6 |
| 17/64 | 6.5/7.8/7.7 | 17/65 | 6.7/7.7/7.7 | 17/66 | 6.8/7.4/7.4 |
| 17/67 | 6.6/7.7/7.5 | 17/68 | 6.8/7.4/7.5 | 17/69 | <4.7/7.2/7.4 |
| 17/70 | 5.9/7.9/7.9 | 17/71 | 5.8/6.9/6.8 | 17/72 | 5.2/6.1/6.1 |
| 17/73 | 6.0/7.2/7.3 | 17/74 | 6.3/7.3/7.2 | 17/75 | 5.2/5.8/5.8 |
| 17/76 | 5.7/6.9/6.9 | 17/77 | 6.1/8.0/8.1 | 17/78 | 6.3/7.3/7.3 |
| 17/79 | 5.8/6.4/6.3 | 17/80 | 6.3/6.9/7.0 | 17/81 | 6.2/7.1/7.1 |
| 17/82 | 6.1/6.7/6.7 | 17/83 | 6.9/8.2/8.3 | 17/84 | <4.7/7.2/7.2 |
| 17/85 | <4.7/7.4/7.5 | 17/86 | 6.5/7.1/7.1 | 17/87 | 6.3/6.9/6.9 |
| 17/88 | 6.2/7.7/7.7 | 17/89 | 5.8/6.9/6.9 | 17/90 | 5.8/7.9/8.0 |
| 17/91 | 6.2/7.1/7.0 | 17/92 | 6.0/7.3/7.1 | 17/93 | 6.0/6.8/6.9 |
| 17/94 | 5.9/6.8/6.7 | 17/95 | 6.2/7.8/7.7 | 17/96 | 5.5/6.9/7.0 |
| 17/97 | 6.9/8.0/8.0 | 17/98 | 6.5/6.8/6.9 | 17/99 | 6.6/6.9/7.0 |
| 17/100 | 6.1/6.9/6.9 | 17/101 | 6.1/7.7/7.7 | 17/102 | 6.6/6.8/6.9 |
| 17/103 | 6.1/6.7/6.8 | 17/104 | 6.3/6.5/6.7 | 17/105 | 5.7/6.1/6.3 |
| 17/106 | 6.3/7.3/7.3 | 17/107 | 6.0/6.9/6.9 | 17/108 | 6.0/6.9/7.1 |
| 17/109 | 6.2/7.2/7.3 | 17/110 | 5.7/6.3/6.5 | 17/111 | 6.5/7.2/7.3 |
| 17/112 | 6.5/7.4/7.5 | 17/113 | 6.3/6.8/6.8 | 17/114 | 6.2/6.5/6.4 |
| 17/115 | 6.5/7.9/8.0 | 17/116 | 6.2/7.3/7.3 | 17/117 | 6.0/7.6/7.7 |
| 17/118 | 5.0/6.3/6.5 | 17/119 | 6.3/7.6/7.7 | 17/120 | 5.6/6.1/6.0 |
| 17/121 | 6.5/7.6/7.7 | 17/122 | 6.4/7.6/7.5 | 17/123 | 5.5/7.0/7.0 |
| 17/124 | 6.1/7.4/7.5 | 17/125 | 7.1/6.4/6/ | 17/126 | 6.5/6.7/6.9 |
| 17/127 | 6.5/7.1/7.2 | 17/128 | 6.7/8.0/8.0 | 17/129 | 6.7/8.0/8.0 |
| 17/130 | 6.6/7.5/7.6 | 17/131 | 6.3/6.8/6.9 | 17/132 | 5.4/6.3/6.2 |
| 17/133 | 5.9/6.3/6.3 | 17/134 | 6.4/7.4/7.7 | 17/135 | 6.2/6.7/6.7 |
| 17/136 | 6.1/6.6/6.7 | 17/137 | 6.3/<4.7/<4.7 | 17/138 | 6.7/7.1/7.3 |
| 17/139 | 6.8/7.2/7.4 | 17/140 | 6.7/8.0/8.1 | 17/141 | 6.5/8.3/8.5 |
| 17/142 | 6.4/7.4/7.6 | 17/143 | 6.9/8.2/8.2 | 17/144 | 6.3/7.7/7.7 |
| 17/145 | 6.2/7.6/7.7 | 17/146 | 6.0/7.4/7.5 | 17/147 | 6.1/6.7/6.7 |
| 17/148 | 6.1/7.0/7.0 | 17/149 | 5.9/6.6/6.6 | 17/150 | 6.3/8.0/8.2 |
| 17/151 | 6.5/8.3/8.3 | 17/152 | 6.0/8.2/8.2 | 17/153 | 6.5/6.7/6.7 |
| 17/154 | 6.5/7.2/7.3 | 17/155 | 6.2/7.0/7.0 | 17/156 | 6.5/7.1/7.2 |
| 17/157 | 6.4/7.0/7.1 | 17/158 | 6.1/6.1/6.2 | 17/159 | 5.8/6.8/6.9 |
| 17/160 | 6.7/7.8/8.0 | 17/161 | 6.2/7.6/7.6 | 17/162 | 6.1/7.5/7.7 |
| 17/163 | 5.8/7.0/7.2 | 17/164 | 5.9/6.4/6.5 | 17/165 | 5.3/6.5/6.9 |
| 17/166 | 6.8/7.8/8.0 | 17/167 | 6.1/6.6/6.8 | 17/168 | 6.0/6.4/6.4 |
| 17/169 | 6.1/6.7/6.7 | 17/170 | 6.5/6.8/7.0 | 17/171 | 6.1/6.9/6.9 |
| 17/172 | 6.4/7.5/7.5 | 17/173 | 6.5/7.3/7.3 | 17/174 | 6.7/7.1/7.1 |
| 17/175 | 6.1/6.6/6.7 | 17/176 | 6.6/7.1/7.0 | 17/177 | 6.8/7.3/7.4 |
| 17/178 | 6.1/7.9/7.9 | 17/179 | 6.4/6.1/6.1 | 17/180 | 6.2/7.1/7.2 |
| 17/181 | 6.4/7.0/6.9 | 17/182 | 6.3/7.8/7.9 | 17/183 | 6.7/7.9/8.1 |
| 17/184 | 6.1/6.9/7.1 | 17/185 | 6.3/6.4/6.2 | 17/186 | 6.4/6.9/7.1 |
| 17/187 | 4.8/<4.7/<4.7 | 17/188 | 6.1/6.8/6.9 | 17/189 | 5.3/6.3/6.3 |
| 17/190 | 5.8/6.5/6.6 | 17/191 | 5.9/7.0/6.9 | 17/192 | 5.8/6.5/6.4 |
| 17/193 | 5.6/6.9/7.0 | 17/194 | 4.9/6.4/6.5 | 17/195 | 6.2/7.6/7.6 |
| 17/196 | 5.4/7.0/7.0 | 17/197 | 6.1/7.9/7.7 | 17/198 | 6.3/6.8/6.9 |
| 17/199 | 6.2/6.6/6.7 | 17/200 | 6.3/6.9/6.9 | 17/201 | 6.1/5.7/5.7 |
| 17/202 | 6.5/7.7/7.7 | 17/203 | 6.3/7.8/7.8 | 17/204 | 6.1/6.7/6.8 |
| 17/205 | 6.1/6.9/7.0 | 17/206 | 6.2/7.0/7.2 | 17/207 | 6.3/7.9/8.0 |
| 17/208 | 6.4/6.6/6.6 | 17/209 | 6.7/7.3/7.6 | 17/210 | 6.8/7.9/8.1 |
| 17/211 | 6.3/8.0/8.0 | 17/212 | 6.2/7.3/7.4 | 17/213 | 6.2/7.1/7.2 |
| 17/214 | 6.6/7.5/7.5 | 17/215 | 6.5/7.5/7.3 | 17/216 | 6.7/7.8/7.8 |
| 17/217 | 6.9/7.6/7.7 | 17/218 | 6.5/7.1/7.3 | 17/219 | 6.3/6.9/7.0 |
| 17/220 | 6.5/6.6/6.6 | 17/221 | 5.7/7.1/7.1 | 17/222 | 6.2/7.4/7.5 |
| 17/223 | 6.4/7.1/7.2 | 17/224 | 6.1/7.1/7.2 | 17/225 | 6.1/7.6/7.6 |
| 17/226 | 6.5/8.2/8.2 | 17/227 | 6.3/8.1/8.1 | 17/228 | 6.4/7.7/7.7 |
| 17/229 | 6.2/7.2/7.3 | 17/230 | 6.6/7.5/7.6 | 17/231 | 6.6/7.5/7.7 |
| 17/232 | 6.1/6.8/7.0 | 17/233 | 5.8/6.5/6.5 | 17/234 | 6.7/7.1/7.2 |
| 17/235 | 6.7/7.6/7.6 | 17/236 | 6.2/8.1/8.2 | 17/237 | 5.9/6.5/6.5 |
| 17/238 | 6.0/6.9/6.7 | 17/239 | 6.0/7.9/8.1 | 17/240 | 6.1/7.5/7.6 |
| 17/241 | 5.9/7.7/7.8 | 17/242 | 6.4/7.5/7.6 | 17/243 | 6.2/7.4/7.6 |
| 17/244 | 5.0/6.2/6.2 | 17/245 | <4.7/5.7/5.7 | 17/246 | 5.4/6.1/6.2 |
| 17/247 | 5.9/6.9/7.0 | 17/248 | 5.6/6.4/7.3 | 17/249 | 6.3/6.6/6.7 |
| 17/250 | 5.8/6.6/6.5 | 17/251 | 6.3/6.9/6.9 | 17/252 | 5.8/6.5/6.6 |

TABLE 2-continued

| Ex. # | $pIC_{50}$ (FRET/FF/REN) | Ex. # | $pIC_{50}$ (FRET/FF/REN) | Ex. # | $pIC_{50}$ (FRET/FF/REN) |
|---|---|---|---|---|---|
| 17/253 | 6.2/7.0/7.2 | 17/254 | 6.2/6.6/6.6 | 17/255 | 5.1/<4.7/<4.7 |
| 17/256 | 6.2/6.8/7.0 | 17/257 | 6.3/7.4/7.6 | 17/258 | 5.1/<4.7/<4.7 |
| 17/259 | 6.0/7.2/7.2 | 17/260 | 5.9/7.3/7.4 | 17/261 | 5.9/7.5/7.6 |
| 17/262 | 6.2/7.6/7.8 | 17/263 | 6.5/7.9/8.0 | 17/264 | 6.2/7.9/7.7 |
| 17/265 | 6.5/7.9/8.0 | 17/266 | 6.6/8.3/8.5 | 17/267 | 6.1/7.9/8.0 |
| 17/268 | 6.1/7.7/7.8 | 17/269 | 6.0/6.9/7.0 | 17/270 | 6.2/7.8/8.0 |
| 17/271 | 6.1/7.1/7.1 | 17/272 | 6.3/6.8/6.9 | 17/273 | 5.8/7.2/7.3 |
| 17/274 | 6.6/7.9/7.9 | 17/275 | 6.2/7.0/7.0 | 17/276 | 6.8/7.9/8.0 |
| 17/277 | 6.4/7.2/7.2 | 17/278 | 5.6/7.0/7.0 | 17/279 | 5.5/<4.7/<4.7 |
| 17/280 | 6.0/8.1/8.1 | 17/281 | 6.0/7.7/7.7 | 17/282 | 5.7/6.6/6.7 |
| 17/283 | 6.0/6.7/6.8 | 17/284 | 5.9/7.3/7.3 | 17/285 | 6.2/7.3/7.4 |
| 17/286 | 5.9/7.4/7.5 | 17/287 | 6.2/7.7/7.7 | 17/288 | 6.4/7.3/7.3 |
| 17/289 | 5.9/7.1/7.2 | 17/290 | 6.2/7.6/7.6 | 17/291 | 6.4/7.6/7.7 |
| 17/292 | 5.9/7.5/7.4 | 17/293 | 5.9/6.6/6.7 | 17/294 | 5.5/<4.7/<4.7 |
| 17/295 | 6.0/6.6/6.5 | 17/296 | 6.6/7.0/7.1 | 17/297 | 6.9/7.2/7.4 |
| 17/298 | 5.6/5.9/6.0 | 17/299 | 5.3/7.1/7.5 | 17/300 | 6.1/7.3/7.6 |
| 17/301 | 5.7/7.6/7.6 | 17/302 | 5.8/7.3/7.2 | 17/303 | 5.4/6.3/6.4 |
| 17/304 | 5.8/7.2/7.3 | 17/305 | 5.7/6.8/6.7 | 17/306 | 5.8/6.8/6.9 |
| 17/307 | 5.5/6.2/6.0 | 17/308 | 5.2/6.5/6.4 | 17/309 | 6.1/6.7/6.8 |
| 17/310 | 6.0/7.4/7.6 | 17/311 | 6.1/7.0/7.2 | 17/312 | 6.5/7.2/7.3 |
| 17/313 | 6.0/6.8/6.8 | 17/314 | 6.0/7.2/7.1 | 17/315 | 5.9/6.5/6.5 |
| 17/316 | 5.6/6.3/6.3 | 17/317 | 5.6/6.5/6.5 | 17/318 | 5.7/7.7/7.6 |
| 17/319 | 5.7/6.5/6.6 | 17/320 | 5.8/7.3/7.3 | 17/321 | 6.0/7.3/7.3 |
| 17/322 | 5.4/5.9/6.0 | 17/323 | 5.1/5.6/5.7 | 17/324 | 5.5/6.8/6.8 |
| 17/325 | 5.6/7.1/7.2 | 17/326 | 6.0/7.8/7.9 | 17/327 | 6.1/6.8/6.9 |
| 17/328 | 6.3/6.6/6.6 | 17/329 | 5.6/6.8/6.9 | 17/330 | 5.6/7.3/7.4 |
| 17/331 | 5.9/6.6/6.5 | 17/332 | 6.7/6.4/6.4 | 17/333 | 6.4/6.4/6.3 |
| 17/334 | 5.9/5.8/5.9 | 17/335 | 6.5/5.5/5.6 | 17/336 | 6.0/<4.7/<4.7 |
| 17/337 | 6.0/7.7/7.8 | 17/338 | 5.5/7.2/7.2 | 17/339 | 5.9/7.6/7.7 |
| 17/340 | 5.8/7.1/7.1 | 17/341 | 6.1/7.4/7.6 | 17/342 | 6.0/7.1/7.1 |
| 17/343 | 6.3/7.4/7.3 | 17/344 | 6.2/7.3/7.5 | 17/345 | 6.5/7.3/7.4 |
| 17/346 | 5.3/<4.7/<4.7 | 17/347 | 6.4/6.5/6.5 | 17/348 | 6.5/6.9/7.0 |
| 17/349 | 6.2/6.8/6.8 | 17/350 | 6.0/7.7/7.7 | 17/351 | 5.7/6.8/6.9 |
| 17/352 | 6.2/7.5/7.5 | 17/353 | 5.7/6.8/6.8 | 17/354 | 6.0/7.0/7.0 |
| 17/355 | 6.5/6.6/6.6 | 17/356 | 6.4/6.7/6.7 | 17/357 | 5.7/6.7/6.8 |
| 17/358 | 6.0/6.3/6.2 | 17/359 | 5.5/7.4/7.4 | 17/360 | 5.2/7.3/7.4 |
| 17/361 | 5.7/6.4/6.4 | 17/362 | 5.9/5.9/5.8 | 17/363 | 6.0/7.4/7.5 |
| 17/364 | 6.0/6.9/7.0 | 17/365 | 5.9/7.0/7.0 | 17/366 | 5.3/6.6/6.3 |
| 17/367 | 5.3/6.4/6.1 | 17/368 | 5.1/6.4/6.2 | 17/369 | 5.9/7.5/7.5 |
| 17/370 | 5.7/7.2/7.3 | 17/371 | 6.2/8.0/8.0 | 17/372 | 5.5/6.3/6.2 |
| 17/373 | 5.3/<4.7/<4.7 | 17/374 | 5.8/7.3/7.3 | | |
| 18/1 | 6.1/7.5/7.7 | 18/2 | 6.6/8.0/8.2 | 18/3 | 5.8/6.1/6.5 |
| 18/4 | 6.1/6.3/6.5 | 18/5 | 6.2/7.5/7.5 | 19 | 4.9/6.6/6.4 |
| 19/1 | 6.3/6.8/6.8 | 20 | 6.4/7.4/7.5 | 20/1 | 6.6/7.1/7.3 |
| 20/2 | 6.5/7.0/7.2 | 20/3 | 6.2/7.3/7.4 | 20/4 | 6.7/6.9/6.9 |
| 20/5 | 6.1/7.0/7.0 | 20/6 | 6.3/6.9/6.9 | 20/7 | 6.4/6.2/6.2 |
| 20/8 | 6.0/7.0/7.0 | 20/9 | 5.9/7.8/7.6 | 22 | 6.4/7.5/7.6 |
| 22/1 | 6.8/8.4/8.4 | 22/2 | 6.4/8.1/8.0 | 23 | 6.7/8.5/8.5 |
| 24 | 5.5/6.4/6.4 | 24/1 | 4.9/6.3/6.4 | 24/2 | 5.2/<4.7/<4.7 |
| 25 | 5.8/6.3/6.2 | 26 | 6.7/7.5/7.6 | 26/1 | 6.6/7.4/7.5 |
| 26/2 | 6.7/7.2/7.2 | 26/3 | 6.1/6.6/6.8 | 26/4 | 5.4/6.6/6.8 |
| 26/5 | 6.5/7.9/8.0 | 26/6 | 6.4/7.7/7.9 | 27 | 5.7/6.4/6.5 |
| 28 | 5.9/6.6/6.9 | 29 | 5.4/7.2/7.2 | 29/1 | 5.5/6.8/6.8 |
| 29/2 | 5.6/7.3/7.1 | 31 | 5.9/6.9/6.9 | 33 | 5.5/6.2/6.3 |
| 34 | 6.4/6.8/7.1 | | | | |

The invention claimed is:

1. A compound represented by Formula (1):

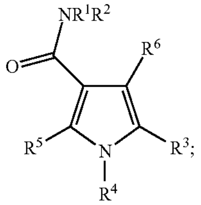

(1)

or an enantiomer, diastereomer, tautomer, N-oxide or solvate thereof, or a pharmaceutically acceptable salt thereof, wherein:

$R^1$ is selected from H, $C_{1-10}$-alkyl, $C_{2-10}$-alkenyl, $C_{2-10}$-alkynyl, $C_{3-6}$-cycloalkyl, $C_{3-6}$-heterocycloalkyl, $C_{1-10}$-alkylene-$C_{3-10}$-cycloalkyl, $C_{1-10}$-alkylene-$C_{3-10}$-heterocycloalkyl, $C_{1-10}$-alkylene-(5-membered monocyclic heteroaryl), $SO_2$—$C_{1-10}$-alkyl, wherein alkyl, alkenyl, alkynyl, alkylene, cycloalkyl, heterocycloalkyl and heteroaryl is unsubstituted or substituted with 1 to 7 substituents independently selected from oxo, CN, $OR^{11}$, O—$C_{2-6}$-alkylene-$OR^{11}$, $C_{1-6}$-alkyl, halo-$C_{1-6}$-alkyl, halogen, $CO_2R^{11}$, $CONR^{11}R^{12}$, $COR^{11}$, $SO_yR^{11}$, $SO_3H$, $SO_2NR^{11}R^{12}$, $NR_{11}COR^{11}$, $NR^{11}SO_2R^{11}$, $NR^{11}$—CO—$NR^{11}R^{12}$, $NR^{11}$—$SO_2$—$NR^{11}R^{12}$, $C_{3-6}$-cycloalkyl, O—$C_{3-6}$-cycloalkyl, $C_{3-6}$-heterocycloalkyl, O—$C_{3-6}$-heterocycloalkyl and $NR^{11}R^{12}$; and $R^3$ is pyridinone, a 6- to 10-membered mono- or bicyclic aryl, a 5- to 10-membered mono- or bicyclic heteroaryl containing 1 to 4 heteroatoms independently selected from the group consisting of N, O and S or a 6- to 12-membered partially saturated spiroheterocycle containing 1 to 4 heteroatoms independently selected from the group consisting of N, O and S, wherein pyridinone and spiroheterocycle is optionally substituted with 1 to 4 groups independently selected from halogen, $C_{1-6}$-alkyl, halo-$C_{1-6}$-alkyl, OH, O—$C_{1-6}$-alkyl, O-halo-$C_{1-6}$-alkyl, oxo, =N—$OR^{32}$, $N(R^{32})$, $C_{0-6}$-alkylene-$C_{3-10}$-cycloalkyl, $C_{0-6}$-alkylene-$C_{3-10}$-heterocycloalkyl, $C_{0-6}$-alkylene-(5- or 6-membered monocyclic heteroaryl), $C_{1-6}$-alkylene-O—$R^{31}$, $C_{0-6}$-alkylene-CN, O—$C_{3-10}$-cycloalkyl, O—$C_{1-6}$-alkylene-O—$R^{32}$, O—$C_{3-10}$-heterocycloalkyl, $C_{0-6}$-alkylene-$COOR^{31}$, $C_{0-6}$-alkylene-C(O)$R^{31}$, $C_{0-6}$-alkylene-C(O)$N(R^{31})_2$, $C_{0-6}$-alkylene-$N(R^{31})C(O)R^{31}$, $C_{0-6}$-alkylene-SO—$R^{31}$, $C_{0-6}$-alkylene-$SO_2$—$R^{31}$, $C_{0-6}$-alkylene-$SO_2$—$N(R^{31})_2$, $C_{0-6}$-alkylene-$N(R^{31})SO_2$—$R^{31}$, $C_{0-6}$-alkylene-$SO_2$—$C_{3-10}$-heterocycloalkyl and $C_{0-6}$-alkylene-$SO_2$—$C_{3-10}$-heterocycloalkyl, wherein alkylene, cycloalkyl, heterocycloalkyl and heteroaryl is optionally substituted by 1 to 4 substituents independently selected from the group consisting of halogen, CN, $C_{1-3}$-alkyl, halo-$C_{1-3}$-alkyl, OH, oxo, O—$C_{1-3}$-alkyl and O-halo-$C_{1-3}$-alkyl;

wherein aryl and heteroaryl are each optionally substituted by 1 to 4 substituents independently selected from the group consisting of halogen, CN, $C_{1-3}$-alkyl, halo-$C_{1-3}$-alkyl, OH, O—$C_{1-3}$-alkyl and O-halo-$C_{1-3}$-alkyl, and are each substituted with at least one group selected from $C_{3-10}$-cycloalkyl, a 4-membered heterocyclylalkyl group containing one heteroatom selected from the group consisting of N, O and S, $C_{1-4}$-alkylene-$C_{3-10}$-cycloalkyl, $C_{1-4}$-alkylene-($C_{3-10}$-heterocycloalkyl), carbon atom linked 5- or 6-membered monocyclic heteroaryl, $C_{1-6}$-alkylene-(5- or 6-membered monocyclic heteroaryl), $C_{1-4}$-alkylene-O—$R^{31}$, $C_{1-4}$-alkylene-CN, O—$C_{3-10}$-cycloalkyl, O—$C_{1-6}$-alkylene-O—$R^{32}$, O—$C_{3-10}$-heterocycloalkyl, $C_{0-6}$-alkylene-$COOR^{31}$, $C_{0-6}$-alkylene-C(O)$R^{31}$, $C_{0-6}$-alkylene-C(O)$N(R^{31})_2$, $C_{0-6}$-alkylene-$N(R^{31})C(O)R^{31}$, $C_{0-6}$-alkylene-SO—$R^{31}$, $C_{1-6}$-alkylene-$SO_2$—$R^{31}$, $C_{0-6}$-alkylene-$SO_2$—$N(R^{31})_2$, $C_{0-6}$-alkylene-$N(R^{31})SO_2$—$R^{31}$, $SO_2$—$C_{3-10}$-heterocycloalkyl, $SO_2$—$C_{3-10}$-cycloalkyl, $C_{0-6}$-alkylene-SO—$R^{31}$ and two adjacent substituents completing a 3- to 8-membered saturated or partially unsaturated ring containing carbon atoms and optionally containing 1 to 3 heteroatoms selected from O, S or N, wherein the ring is unsubstituted or substituted with 1 to 6 substituents independently selected from halogen, $C_{1-6}$-alkyl, halo-$C_{1-6}$-alkyl, $C_{3-6}$-cycloalkyl, $C_{3-6}$-heterocycloalkyl, oxo, =N—$OR^{32}$, OH, O—$C_{1-6}$-alkyl and O-halo-$C_{1-6}$-alkyl, wherein alkylene, cycloalkyl, heterocycloalkyl and the 5- or 6-membered monocyclic heteroaryl is optionally substituted by 1 to 4 substituents independently selected from the group consisting of halogen, CN, $C_{1-3}$-alkyl, halo-$C_{1-3}$-alkyl, OH, oxo, =N—$OR^{32}$, O—$C_{1-3}$-alkyl and O-halo-$C_{1-3}$-alkyl;

or $R^1$ is selected from:

a 4-membered heterocycloalkyl group containing one heteroatom selected from the group consisting of N, O and S, or $C_{1-10}$-alkyl substituted with a group selected from halogen, CN, $OR^{11}$, $SO_yR^{11}$, $SO_3H$, $NR^{11}SO_2R^{11}$, $SO_2NR^{11}R^{12}$, $CO_2R^{11}$, $CONR^{11}R^{12}$, $NR^{11}$—CO—$R^{11}$, $NR^{11}$—CO—$NR^{11}R^{12}$, $NR^{11}$—$SO_2$—$NR^{11}R^{12}$, $NR^{11}R^{12}$ and a 4-membered heterocycloalkyl group containing one heteroatom selected from the group consisting of N, O and S, or $C_{0-1}$-alkylene-$C_{3-10}$-cycloalkyl substituted with a group selected from halogen, CN, $SO_yR^{11}$, $NR^{11}SO_2R^{11}$, $SO_2NR^{11}R^{12}$, $CO_2R^{11}$, $CONR^{11}R^{12}$, $NR^{11}$—CO—$R^{11}$, $NR^{11}$—CO—$NR^{11}R^{12}$, $NR^{11}$—$SO_2$—$NR^{11}R^{12}$ and $NR^{11}R^{12}$, or $C_{2-10}$-alkylene-$C_{3-10}$-cycloalkyl, $C_{2-10}$-alkylene-O—$C_{3-10}$-cycloalkyl, $C_{2-10}$-alkylene-$C_{5-10}$-heterocycloalkyl, $C_{2-10}$-alkylene-O—$C_{5-10}$-heterocycloalkyl and $SO_2$—$C_{1-10}$-alkyl, wherein alkyl, alkylene, cycloalkyl and heterocycloalkyl are optionally substituted with 1 to 7 substituents independently selected from the group consisting of OH, oxo, CN, O—$C_{1-6}$-alkyl, O-halo-$C_{1-6}$-alkyl, $C_{1-6}$-alkyl, halo-$C_{1-6}$-alkyl, halogen, $CO_2R^{11}$, $CONR^{11}R^{12}$, $COR^{11}$, $SO_2R^{11}$, $SO_2NR^{11}R^{12}$, $NR^{11}COR^{11}$, $NR^{11}SO_2R^{11}$, $C_{3-6}$-cycloalkyl, O—$C_{3-6}$-cycloalkyl, $C_{3-6}$-heterocycloalkyl, O—$C_{3-6}$-heterocycloalkyl, O—$C_{2-6}$-alkylene-$OR^{11}$ and $NR^{11}R^{12}$; and $R^3$ is pyridinone, a 6- to 10-membered mono- or bicyclic aryl, a 5- to 10-membered mono- or bicyclic heteroaryl containing 1 to 4 heteroatoms independently selected from the group consisting of N, O and S or a 6- to 12-membered partially saturated spiroheterocycle containing 1 to 4 heteroatoms independently selected from the group consisting of N, O and S, wherein pyridinone, aryl and heteroaryl and spiroheterocycle is optionally substituted with 1 to 4 groups independently selected from halogen, $C_{1-6}$-alkyl, halo-$C_{1-6}$-alkyl, OH, O—$C_{1-6}$-alkyl, O-halo-$C_{1-6}$-alkyl, oxo, =N—$OR^{32}$, $N(R^{32})$, $C_{0-6}$-alkylene-$C_{3-10}$-cycloalkyl, $C_{0-6}$-alkylene-$C_{3-10}$-heterocycloalkyl, $C_{0-6}$-alkylene-(5- or 6-membered monocyclic heteroaryl), $C_{1-6}$-alkylene-O—$R^{31}$, $C_{0-6}$-alkylene-CN, O—$C_{3-10}$-cycloalkyl, O—$C_{1-6}$-alkylene-O—$R^{32}$, O—$C_{3-10}$-heterocycloalkyl, $C_{0-6}$-alkylene-$COOR^{31}$, $C_{0-6}$-alkylene-C(O)$R^{31}$, $C_{0-6}$-alkylene-C(O)$N(R^{31})_2$, $C_{0-6}$-alkylene-$N(R^{31})C(O)R^{31}$, $C_{0-6}$-alkylene-SO—$R^{31}$, $C_{0-6}$-alkylene-$SO_2$—$R^{31}$, $C_{0-6}$-alkylene-$SO_2$—$N(R^{31})_2$ and $C_{0-6}$-alkylene-$N(R^{31})SO_2$—$R^{31}$, and two adjacent substituents completing a 3- to 8-membered saturated or partially unsaturated ring containing carbon atoms and optionally containing 1 to 3 heteroatoms selected from O, S or N, wherein the ring is unsubstituted or substituted with 1 to 6 substituents independently selected from halogen, $C_{1-6}$-alkyl, halo-$C_{1-6}$-alkyl, $C_{3-6}$-cycloalkyl, $C_{3-6}$-heterocycloalkyl, oxo, =N—$OR^{32}$, OH, O—$C_{1-6}$-alkyl and O-halo-$C_{1-6}$-alkyl, wherein alkylene, cycloalkyl, heterocycloalkyl and the 5- or 6-membered monocyclic heteroaryl is optionally substituted by 1 to 4 substituents independently selected from the group consisting of halogen, CN, $C_{1-3}$-alkyl, halo-$C_{1-3}$-alkyl, OH, oxo, =N—$OR^{32}$, O—$C_{1-3}$-alkyl and O-halo-$C_{1-3}$-alkyl;

and $R^2$ is selected from the group consisting of H, $C_{1-6}$-alkyl, halo-$C_{1-6}$-alkyl and hydroxy-$C_{1-6}$-alkyl, or $R^1$ and $R^2$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from halogen, oxo, CN, $OR^{11}$, $SO_yR^{11}$, $SO_3H$, $NR^{11}SO_2R^{11}$, $SO_2NR^{11}R^{12}$, $C_{0-6}$-alkylene-$CO_2R^{11}$, $CONR^{11}R^{12}$, $COR^{11}$, $NR^{11}$—CO—$R^{11}$, $NR^{11}$—CO—$NR^{11}R^{12}$, $N^{11}SO_2$—$NR^{11}R^{12}$, $NR^{11},R^{12}$, $C_{1-6}$-alkyl, halo-$C_{1-6}$-alkyl, hydroxy-$C_{1-6}$-alkyl, $C_{3-6}$-cycloalkyl, O—$C_{3-6}$-cycloalkyl, $C_{3-6}$-heterocycloalkyl and O—$C_{3-6}$-heterocycloalkyl, wherein cycloalkyl and heterocycloalkyl are unsubstituted or substituted with 1 to 4 substitutents independently selected from halogen, $C_{1-3}$-alkyl, halo-$C_{1-3}$-alkyl and oxo;

$R^4$ is $SO_2$—$(CR^8R^8)_yR^7$, $SO_2$—$NR^{12}R^7$, $(CR^8R^8)_x$—$R^{10}$ or $C_{3-6}$-cycloalkyl, which is spirocyclic fused with $C_{3-10}$-cycloalkyl;

$R^5$ is selected from H, $C_{1-6}$-alkyl, halo-$C_{1-6}$-alkyl, CHO, $CON(R^{52})_2$ or halogen, wherein alkyl is unsubstituted or substituted with 1 to 3 substituents independently selected from the group consisting of O—$C_{1-6}$-alkyl, O-halo-$C_{1-6}$-alkyl and OH;

$R^6$ is selected from H, $C_{1-6}$-alkyl, halo-$C_{1-6}$-alkyl or halogen;

$R^7$ is selected from $C_{3-10}$-cycloalkyl and $C_{3-10}$-heterocycloalkyl, wherein cycloalkyl and heterocycloalkyl are unsubstituted or substituted with 1 to 3 substituents independently selected from the group consisting of halogen, OH, oxo, O—$C_{1-6}$-alkyl, O-halo-$C_{1-6}$-alkyl, $C_{1-6}$-alkyl, halo-$C_{1-6}$-alkyl, cycloalkyl and heterocycloalkyl;

$R^8$ is independently selected from H, F, $C_{1-3}$-alkyl, halo-$C_{1-3}$-alkyl or OH;

$R^{10}$ is $C_{3-10}$-cycloalkyl, wherein cycloalkyl is unsubstituted or substituted with 1 to 6 substituents independently selected from halogen, OH, oxo, O—$C_{1-6}$-alkyl, O-halo-$C_{1-6}$-alkyl, $C_{1-6}$-alkyl, halo-$C_{1-6}$-alkyl, cycloalkyl, heterocycloalkyl, and optionally two adjacent substituents together complete a 6-membered aryl ring wherein the ring is unsubstituted or substituted with 1 to 3 substituents independently selected from halogen, $C_{1-2}$-alkyl, halo-$C_{1-2}$-alkyl;

$R^{11}$ is independently selected from H, $C_{1-6}$-alkyl, $C_{0-6}$-alkylene-$C_{3-6}$-cycloalkyl, $C_{0-6}$-alkylene-$C_{3-6}$-heterocycloalkyl, wherein alkyl, alkylene, cycloalkyl and heterocycloalkyl are unsubstituted or substituted with 1 to 6 substituents independently selected from halogen, OH, oxo, $C_{1-3}$-alkyl, halo-$C_{1-3}$-alkyl, O—$C_{1-3}$-alkyl, O-halo-$C_{1-3}$-alkyl and $SO_2$—$C_{1-3}$-alkyl;

$R^{12}$ is independently selected from H, $C_{1-6}$-alkyl and halo-$C_{1-6}$-alkyl;

$R^{31}$ is independently selected from H, $C_{1-6}$-alkyl, halo-$C_{1-6}$-alkyl, $C_{0-6}$-alkylene-$C_{3-6}$-cycloalkyl, $C_{0-6}$-alkylene-$C_{3-6}$-heterocycloalkyl, 5- or 6-membered heteroaryl and 6-membered aryl, wherein alkyl, alkylene, cycloalkyl, heterocycloalkyl, aryl and heteroaryl are unsubstituted or substituted with 1 to 6 substituents independently selected from halogen, CN, OH, oxo, $C_{1-3}$-alkyl, halo-$C_{1-3}$-alkyl, O—$C_{1-3}$-alkyl, O-halo-$C_{1-3}$-alkyl and $SO_2$—$C_{1-3}$-alkyl;

and optionally wherein two $R^{31}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substituents independently selected from fluoro, OH, oxo, $C_{1-4}$-alkyl and halo-$C_{1-4}$-alkyl;

$R^{32}$ is independently selected from H, $C_{1-6}$-alkyl and halo-$C_{1-6}$-alkyl;

$R^{52}$ is independently selected from H, $C_{1-3}$-alkyl and halo-$C_{1-3}$-alkyl;

x is independently selected from 1 and 2;

y is independently selected from 0, 1 and 2;

with the proviso that $R^3$ is not an unsubstituted or substituted ring selected from

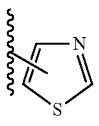, 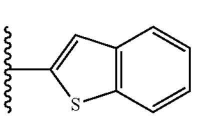, 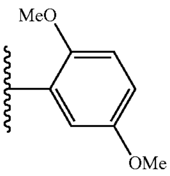,

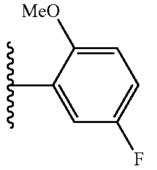, 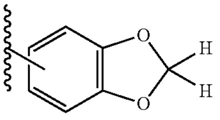,

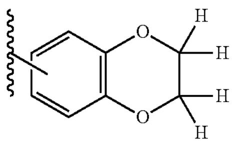, 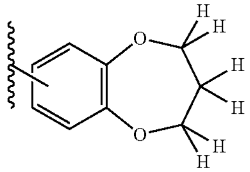,

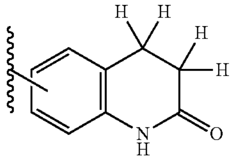 and 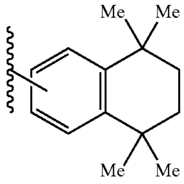.

2. The compound according to claim 1 wherein:

$R^1$ is selected from H, $C_{1-10}$-alkyl, $C_{2-10}$-alkenyl, $C_{2-10}$-alkynyl, $C_{3-6}$-cycloalkyl, $C_{3-6}$-heterocycloalkyl, $C_{1-10}$-alkylene-$C_{3-10}$-cycloalkyl, $C_{1-10}$-alkylene-$C_{3-10}$-heterocycloalkyl, $C_{1-10}$-alkylene-(5-membered monocyclic heteroaryl), $SO_2$—$C_{1-10}$-alkyl, wherein alkyl, alkenyl, alkynyl, alkylene, cycloalkyl, heterocycloalkyl and heteroaryl is unsubstituted or substituted with 1 to 7 substituents independently selected from oxo, CN, $OR^{11}$, O—$C_{2-6}$-alkylene-$OR^{11}$, $C_{1-6}$-alkyl, halo-$C_{1-6}$-alkyl, halogen, $CO_2R^{11}$, $CONR^{11}R^{12}$, $COR^{11}$, $SO_yR^{11}$, $SO_3H$, $SO_2NR^{11}R^{12}$, $NR^{11}COR^{11}$, $NR^{11}SO_2R^{11}$, $NR^{11}$—CO—$NR^{11}R^{12}$, $NR^{11}$—$SO_2$—$NR^{11}R^{12}$, $C_{3-6}$-cycloalkyl, O—$C_{3-6}$-cycloalkyl, $C_{3-6}$-heterocycloalkyl, O—$C_{3-6}$-heterocycloalkyl and $NR^{11}R^{12}$; and $R^3$ is pyridinone, a 6- to 10-membered mono- or bicyclic aryl, a 5- to 10-membered mono- or bicyclic heteroaryl containing 1 to 4 heteroatoms independently selected from the group consisting of N, O and S or a 6- to 12-membered partially saturated spiroheterocycle containing 1 to 4 heteroatoms independently selected from the group consisting of N, O and S, wherein pyridinone and spiroheterocycle is optionally substituted with a group selected from $C_{3-10}$-cycloalkyl, $C_4$-heterocycloalkyl, $C_{1-4}$-alkylene-$C_{3-10}$-cycloalkyl, $C_{1-4}$-alkylene-$C_{3-10}$-heterocycloalkyl, $C_{0-6}$-alkylene-(5-membered monocyclic heteroaryl), $C_{1-4}$-alkylene-O—$R^{31}$, $C_{1-4}$-alkylene-CN, O—$C_{3-10}$-cycloalkyl, O—$C_{1-6}$-alkylene-O—$R^{32}$, O—$C_{3-10}$-heterocycloalkyl, $C_{0-6}$-alkylene-$COOR^{31}$, $C_{0-6}$-alkylene-C(O)$R^{31}$, $C_{0-6}$-alkylene-C(O)N($R^{31}$)$_2$, $C_{0-6}$-alkylene-N($R^{31}$)C(O)$R^{31}$, $C_{0-6}$-alkylene-$SO_2$—N($R^{31}$)$_2$, $C_{0-6}$-alkylene-N($R^{31}$)$SO_2$—$R^{31}$, $C_{0-6}$-alkylene-$SO_2$—$C_{3-10}$-heterocycloalkyl and $C_{0-6}$-alkylene-SO—$R^{31}$, and wherein aryl and heteroaryl is substituted with at least one group selected from $C_{3-10}$-cycloalkyl, a 4-membered heterocyclylalkyl group containing one heteroatom selected from the group consisting of N, O and S, $C_{1-4}$-alkylene-$C_{3-10}$-cycloalkyl, $C_{1-4}$-alkylene-$C_{3-10}$-heterocycloalkyl, $C_{0-6}$-alkylene-(5-membered monocyclic heteroaryl), $C_{0-6}$-alkylene-(6-membered monocyclic heteroaryl), $C_{1-4}$-alkylene-O—$R^{31}$, $C_{1-4}$-alkylene-CN, O—$C_{3-10}$-cycloalkyl, O—$C_{1-6}$-alkylene-O—$R^{32}$, O—$C_{3-10}$-heterocycloalkyl, $C_{0-6}$-alkylene-$COOR^{31}$, $C_{0-6}$-alkylene-C(O)$R^{31}$, $C_{0-6}$-alkylene-C(O)N($R^{31}$)$_2$, $C_{0-6}$-alkylene-N($R^{31}$)C(O)$R^{31}$, $C_{0-6}$-alkylene-$SO_2$—N($R^{31}$)$_2$, $C_{0-6}$-alkylene-N($R^{31}$)$SO_2$—$R^{31}$, $C_{0-6}$-alkylene-$SO_2$—$C_{3-10}$-heterocycloalkyl, $C_{0-6}$-alkylene-SO—$R^{31}$ and two adjacent substituents completing a 3- to 8-membered saturated or partially unsaturated ring containing carbon atoms and optionally containing 1 to 3 heteroatoms selected from O, S or N, wherein the ring is unsubstituted or substituted with 1 to 6 substituents independently selected from halogen, $C_{1-6}$-alkyl, halo-$C_{1-6}$-alkyl, $C_{3-6}$-cycloalkyl, $C_{3-6}$-heterocycloalkyl, oxo, OH, O—$C_{1-6}$-alkyl and O-halo-$C_{1-6}$-alkyl, wherein pyridinone, aryl, heteroaryl, spiroheterocycle, alkyl, alkylene, cycloalkyl and heterocycloalkyl are optionally substituted by 1 to 4 substituents independently selected from the group consisting of halogen, CN, $C_{1-6}$-alkyl, halo-$C_{1-6}$-alkyl, $C_{3-6}$-cycloalkyl, $C_{3-6}$-heterocycloalkyl, OH, O—$C_{1-3}$-alkyl, O-halo-$C_{1-3}$-alkyl, O—$C_{3-6}$-cycloalkyl, O—$C_{3-6}$-heterocycloalkyl, oxo, N($R^{32}$)$_2$, COOH, CON($R^{32}$)$_2$, CN and $NR^{32}$—$COR^{32}$;

or $R^1$ is selected from:

a 4-membered heterocycloalkyl group containing one heteroatom selected from the group consisting of N, O and S, or $C_{1-10}$-alkyl substituted with a group selected from halogen, CN, $OR^{11}$, $SO_yR^{11}$, $SO_3H$, $NR^{11}SO_2R^{11}$, $SO_2NR^{11}R^{12}$, $CO_2R^{11}$, $CONR^{11}R^{12}$, $NR^{11}$—CO—$NR^{11}$, $NR^{11}$—CO—$NR^{11}R^{12}$, $NR^{11}$—$SO_2$—$NR^{11}R^{12}$, $NR^{11}R^{12}$ and a 4-membered heterocycloalkyl group containing one heteroatom selected from the group consisting of N, O and S, or $C_{0-1}$-alkylene-$C_{3-10}$-cycloalkyl substituted with a group selected from halogen, CN, $SO_yR^{11}$, $NR^{11}SO_2R^{11}$, $SO_2NR^{11}R^{12}$, $CO_2R^{11}$, $CONR^{11}R^{12}$, $NR^{11}$—CO—$R^{11}$, $NR^{11}$—CO—$NR^{11}R^{12}$, $NR^{11}$—$SO_2$—$NR^{11}R^{12}$ and $NR^{11}R^{12}$, or $C_{2-10}$-alkylene-$C_{3-10}$-cycloalkyl, $C_{2-10}$-alkylene-O—$C_{3-10}$-cycloalkyl, $C_{2-10}$-alkylene-$C_{5-10}$-heterocycloalkyl, $C_{2-10}$-alkylene-O—$C_{5-10}$-heterocycloalkyl and $SO_2$—$C_{1-10}$-alkyl, wherein alkyl, alkylene, cycloalkyl and heterocycloalkyl are optionally substituted with 1 to 7 substituents independently selected from the group consisting of OH, oxo, CN, O—$C_{1-6}$-alkyl, O-halo-$C_{1-6}$-alkyl, $C_{1-6}$-alkyl, halo-$C_{1-6}$-alkyl, halogen, $CO_2R^{11}$, $CONR^{11}R^{12}$, $COR^{11}$, $SO_2R^{11}$, $SO_2NR^{11}R^{12}$, $NR^{11}COR^{11}$, $NR^{11}SO_2R^{11}$, $C_{3-6}$-cycloalkyl, O—$C_{3-6}$-cycloalkyl, $C_{3-6}$-heterocycloalkyl, O—$C_{3-6}$-heterocycloalkyl, O—$C_{2-6}$-alkylene-$OR^{11}$ and $NR^{11}R^{12}$; and $R^3$ is pyridinone, a 6- to 10-membered mono- or bicyclic aryl, a 5- to 10-membered mono- or bicyclic heteroaryl containing 1 to 4 heteroatoms independently selected from the group consisting of N, O and S or a 6- to 12-membered partially saturated spiroheterocycle containing 1 to 4 heteroatoms independently selected from the group consisting of N, O and S, wherein pyridinone, aryl, heteroaryl and spiroheterocycle are unsubstituted or substituted with 1 to 4 substituents independently selected from halogen, CN, $C_{1-6}$-alkyl, $C_{3-10}$-cycloalkyl, $C_{3-10}$-heterocycloalkyl, $C_{0-6}$-alkylene-(5-membered monocyclic heteroaryl), $C_{0-6}$-alkylene-(6-membered monocyclic heteroaryl), $C_{1-6}$-alkylene-O—$R^{31}$, O—$C_{1-6}$-alkylene-O—$R^{32}$, $C_{0-6}$-alkylene-$COOR^{31}$, $C_{0-6}$-alkylene-C(O)$R^{31}$, $C_{0-6}$-alkylene-C(O)N($R^{31}$)$_2$, $C_{0-6}$-alkylene-N($R^{31}$)C(O)$R^{31}$, $C_{0-6}$-alkylene-$SO_2$—N($R^{31}$)$_2$, $C_{0-6}$-alkylene-N($R^{31}$)$SO_2$—$R^{31}$, $C_{0-6}$-alkylene-$SO_2$—$R^{31}$, $C_{0-6}$-alkylene-SO—$R^{31}$ and $C_{0-6}$-alkylene-N($R^{31}$)$_2$, wherein alkylene, cycloalkyl and heterocycloalkyl are unsubstituted or substituted by 1 to 4 substituents independently selected from the group consisting of halogen, CN, $C_{1-3}$-alkyl, halo-$C_{1-3}$-alkyl, OH, O—$C_{1-3}$-alkyl, O-halo-$C_{1-3}$-alkyl, and oxo, and wherein optionally two adjacent substituents complete a 3- to 8-membered saturated or partially unsaturated ring containing carbon atoms and optionally containing 1 to 3 heteroatoms selected from O, S or N, wherein the ring is unsubstituted or substituted with 1 to 6 substituents independently selected from halogen, $C_{1-6}$-alkyl, halo-$C_{1-6}$-alkyl, $C_{3-6}$-cycloalkyl, $C_{3-6}$-heterocycloalkyl, oxo, OH, O—$C_{1-6}$-alkyl and O-halo-$C_{1-6}$-alkyl;

and $R^2$ is selected from the group consisting of H, $C_{1-6}$-alkyl, halo-$C_{1-6}$-alkyl and hydroxy-$C_{1-6}$-alkyl, or $R^1$ and $R^2$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from halogen, oxo, CN, $OR^{11}$, $SO_yR^{11}$, $SO_3H$, $NR^{11}SO_2R^{11}$, $SO_2NR^{11}R^{12}$, $CO_2R^{11}$, $CONR^{11}R^{12}$, $COR^{11}$, $NR^{11}$—CO—$R^{11}$, $NR^{11}$—CO—$NR^{11}R^{12}$, $NR^{11}$—$SO_2$—$NR^{11}R^{12}$, $NR^{11}R^{12}$, $C_{1-6}$-alkyl, halo-$C_{1-6}$-alkyl, hydroxy-$C_{1-6}$-alkyl, $C_{3-6}$-cycloalkyl, O—$C_{3-6}$-cycloalkyl, $C_{3-6}$-heterocycloalkyl and O—$C_{3-6}$-heterocycloalkyl;

$R^4$ is $SO_2$—$(CR^8R^8)_yR^7$, $SO_2$—$NR^{12}R^7$ or $(CR^8R^8)_x$—$R^{10}$;

$R^5$ is selected from H, $C_{1-6}$-alkyl, halo-$C_{1-6}$-alkyl, CHO or halogen, wherein alkyl is unsubstituted or substituted with 1 to 3 substituents independently selected from the group consisting of O—$C_{1-6}$-alkyl, O-halo-$C_{1-6}$-alkyl and OH;

$R^6$ is selected from H, $C_{1-6}$-alkyl, halo-$C_{1-6}$-alkyl or halogen;

$R^7$ is selected from $C_{3-10}$-cycloalkyl and $C_{3-10}$-heterocycloalkyl, wherein cycloalkyl and heterocycloalkyl are unsubstituted or substituted with 1 to 3 substituents independently selected from the group consisting of halogen, OH, oxo, O—$C_{1-6}$-alkyl, O-halo-$C_{1-6}$-alkyl, $C_{1-6}$-alkyl, halo-$C_{1-6}$-alkyl, cycloalkyl and heterocycloalkyl;

$R^8$ is independently selected from H, F, $C_{1-3}$-alkyl, halo-$C_{1-3}$-alkyl or OH;

$R^{10}$ is $C_{3-10}$-cycloalkyl, wherein cycloalkyl is unsubstituted or substituted with 1 to 6 substituents independently selected from halogen, OH, oxo, O—$C_{1-6}$-alkyl, O-halo-$C_{1-6}$-alkyl, $C_{1-6}$-alkyl, halo-$C_{1-6}$-alkyl, cycloalkyl, heterocycloalkyl, and optionally two adjacent substituents together complete a 6-membered aryl ring wherein the ring is unsubstituted or substituted with 1 to 3 substituents independently selected from halogen, $C_{1-2}$-alkyl, halo-$C_{1-2}$-alkyl;

$R^{11}$ is independently selected from H, $C_{1-6}$-alkyl, $C_{0-6}$-alkylene-$C_{3-6}$-cycloalkyl, $C_{0-6}$-alkylene-$C_{3-6}$-heterocycloalkyl, wherein alkyl, alkylene, cycloalkyl and heterocycloalkyl are unsubstituted or substituted with 1 to 6 substituents independently selected from halogen, OH, oxo, $C_{1-3}$-alkyl, halo-$C_{1-3}$-alkyl, O—$C_{1-3}$-alkyl, O-halo-$C_{1-3}$-alkyl and $SO_2$—$C_{1-3}$-alkyl;

$R^{12}$ is independently selected from H, $C_{1-6}$-alkyl and halo-$C_{1-6}$-alkyl;

$R^{31}$ is independently selected from H, $C_{1-6}$-alkyl, $C_{0-6}$-alkylene-$C_{3-6}$-cycloalkyl, $C_{0-6}$-alkylene-$C_{3-6}$-heterocycloalkyl, a 6-membered aryl wherein alkyl, alkylene, cycloalkyl, heterocycloalkyl and aryl are unsubstituted or substituted with 1 to 6 substituents independently selected from halogen, OH, oxo, $C_{1-3}$-alkyl, halo-$C_{1-3}$-alkyl, O—$C_{1-3}$-alkyl, O-halo-$C_{1-3}$-alkyl and $SO_2$—$C_{1-3}$-alkyl;

$R^{32}$ is independently selected from H, $C_{1-6}$-alkyl and halo-$C_{1-6}$-alkyl;

x is independently selected from 1 and 2;

y is independently selected from 0, 1 and 2;

with the proviso that $R^3$ is not an unsubstituted or substituted ring selected from:

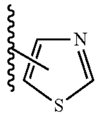 , 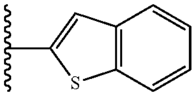 , 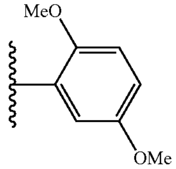 ,

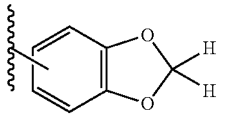 , 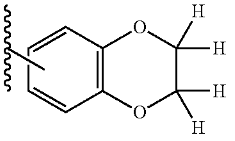 ,

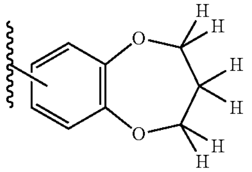 , 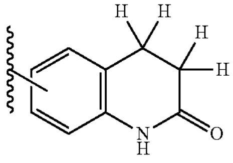 and

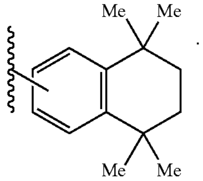 .

3. The compound according to claim 1 wherein:

$R^1$ is selected from H, $C_{1-10}$-alkyl, $C_{3-6}$-cycloalkyl, $C_{3-6}$-heterocycloalkyl, $C_{1-10}$-alkylene-$C_{3-10}$-cycloalkyl, $C_{1-10}$-alkylene-$C_{3-10}$-heterocycloalkyl, $C_{1-10}$-alkylene-(5-membered monocyclic heteroaryl), wherein alkyl, alkylene, cycloalkyl, heterocycloalkyl and heteroaryl is unsubstituted or substituted with 1 to 7 substituents independently selected from oxo, CN, $OR^{11}$, O—$C_{2-6}$-alkylene-$OR^{11}$, $C_{1-6}$-alkyl, halo-$C_{1-6}$-alkyl, halogen, $CO_2R^{11}$, $CONR^{11}R^{12}$, $COR^{11}$, $SO_yR^{11}$, $SO_3H$, $SO_2NR^{11}R^{12}$, $NR^{11}COR^{11}$, $NR^{11}SO_2R^{11}$, $NR^{11}$—CO—$NR^{11}R^{12}$, $NR^{11}$—$SO_2$—$NR^{11}R^{12}$, $C_{3-6}$-cycloalkyl, O—$C_{3-6}$-cycloalkyl, $C_{3-6}$-heterocycloalkyl, O—$C_{3-6}$-heterocycloalkyl and $NR^{11}R^{12}$;

$R^2$ is selected from the group consisting of H, $C_{1-6}$-alkyl, halo-$C_{1-6}$-alkyl and hydroxy-$C_{1-6}$-alkyl, or $R^1$ and $R^2$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from halogen, oxo, CN, $OR^{11}$, $SO_yR^{11}$, $SO_3H$, $NR^{11}SO_2R^{11}$, $SO_2NR^{11}R^{12}$, $C_{0-6}$-alkylene-$CO_2R^{11}$, $CONR^{11}R^{12}$, $COR^{11}$, $NR^{11}$—CO—$R^{11}$, $NR^{11}$—CO—$NR^{11}R^{12}$, $NR^{11}$—$SO_2$—$NR^{11}R^{12}$, $NR^{11}R^{12}$, $C_{1-6}$-alkyl, halo-$C_{1-6}$-alkyl, hydroxy-$C_{1-6}$-alkyl, $C_{3-6}$-cycloalkyl, O-$C_{3-6}$-cycloalkyl, $C_{3-6}$-heterocycloalkyl and O-$C_{3-6}$-heterocycloalkyl, wherein cycloalkyl and heterocycloalkyl are unsubstituted or substituted with 1 to 4 substitutents independently selected from halogen, $C_{1-3}$-alkyl, halo-$C_{1-3}$-alkyl and oxo; and $R^3$ is a 6- or 10-membered mono- or bicyclic aryl or a 6- to 10-membered mono- or bicyclic heteroaryl containing 1 or 2 heteroatoms selected from the group consisting of N, O and S, wherein aryl and heteroaryl are each optionally substituted by 1 to 4 substituents independently selected from the group consisting of halogen, CN, $C_{1-3}$-alkyl, halo-$C_{1-3}$-alkyl, OH, O-$C_{1-3}$-alkyl and O-halo-$C_{1-3}$-alkyl, and are each substituted with at least one group selected from $C_{3-6}$-cycloalkyl, a 4-membered heterocyclylalkyl group containing one heteroatom selected from the group consisting of N, O and S, $C_{1-4}$-alkylene-$C_{3-10}$cycloalkyl, carbon atom linked 5- or 6-membered monocyclic heteroaryl, $C_{1-4}$-alkylene-O-$R^{31}$, O-$C_{3-10}$-cycloalkyl, $C(O)R^{31}$, $C_{0-6}$-alkylene-$C(O)N(R^{31})_2$, $SO_2$-$N(R^{31})_2$, $N(R^{31})SO_2$-$R^{31}$, $SO_2$-$C_{3.10}$-heterocycloalkyl, SO-$R^{31}$ and two adjacent substituents completing a 3- to 8-membered saturated or partially unsaturated ring containing carbon atoms and optionally containing 1 to 3 heteroatoms selected from O, S or N, wherein the ring is unsubstituted or substituted with 1 to 6 substituents independently selected from halogen, $C_{1-6}$-alkyl, halo-$C_{1-6}$-alkyl, $C_{3-6}$-cycloalkyl, $C_{3-8}$-heterocycloalkyl, oxo, =N-$OR^{32}$, OH, O-$C_{1-6}$-alkyl and O-halo-$C_{1-6}$-alkyl, wherein alkylene, cycloalkyl, heterocycloalkyl and the carbon atom linked 5- or 6-membered monocyclic heteroaryl is optionally substituted by 1 to 4 substituents independently selected from the group consisting of halogen, CN, $C_{1-3}$-alkyl, halo-$C_{1-3}$-alkyl, OH, oxo, =N-$OR^{32}$, O-$C_{1-3}$-alkyl and O-halo-$_{1-3}$-alkyl.

4. The compound according to claim 3 wherein:

$R^1$ is selected from $C_{1-10}$-alkyl, $C_{3-6}$-cycloalkyl, $C_{3-6}$-heterocycloalkyl, $C_{1-10}$-alkylene-$C_{3-10}$-cycloalkyl, $C_{1-10}$-alkylene-$C_{3-10}$-heterocycloalkyl, wherein alkyl, alkylene, cycloalkyl and heterocycloalkyl is unsubstituted or substituted with 1 to 7 substituents independently selected from oxo, CN, $OR^{11}$, O-$C_{2-6}$-alkylene-$OR^{11}$, $C_{1-6}$-alkyl, halo-$C_{1-6}$-alkyl, halogen, $CO_2R^{11}$, $CONR^{11}R^{12}$, $COR^{11}$, $SO_yR^{11}$, $SO_3H$, $SO_2NR^{11}R^{12}$, $NR^{11}COR^{11}$, $NR^{11}SO_2R^{11}$, $NR^{11}$—CO—$NR^{11}R^{12}$, $NR^{11}$—$SO_2$—$NR^{11}R^{12}$, $C_{3-6}$-cycloalkyl, O—$C_{3-6}$-cycloalkyl, $C_{3-6}$-heterocycloalkyl, O—$C_{3-6}$-heterocycloalkyl and $NR^{11}R^{12}$; and $R^2$ is selected from the group consisting of H, $C_{1-6}$-alkyl and halo-$C_{1-6}$-alkyl, and or $R^1$ and $R^2$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from halogen, oxo, CN, $OR^{11}$, $SO_yR^{11}$, $SO_3H$, $NR^{11}SO_2R^{11}$, $SO_2NR^{11}R^{12}$, $C_{0-6}$-alkylene-$CO_2R^{11}$, $CONR^{11}R^{12}$, $COR^{11}$, $NR^{11}$—CO—$R^{11}$, $NR^{11}$—CO—$NR^{11}R^{12}$, $NR^{11}$—$SO_2$—$NR^{11}R^{12}$, $NR^{11}R^{12}$, $C_{1-6}$-alkyl, halo-$C_{1-6}$-alkyl, hydroxy-$C_{1-6}$-alkyl, $C_{3-6}$-cycloalkyl, O—$C_{3-6}$-cycloalkyl, $C_{3-6}$-heterocycloalkyl and O—$C_{3-6}$-heterocycloalkyl, wherein cycloalkyl and heterocycloalkyl are unsubstituted or substituted with 1 to 4 substituents independently selected from halogen, $C_{1-3}$-alkyl, halo-$C_{1-3}$-alkyl and oxo.

5. The compound according to claim 3 wherein:

$NR^1R^2$ is selected from:

$NH_2$, NHMe, NHEt, $NH^iPr$, $NH^tBu$, $NHCH_2CONH_2$, $NHCH_2CONMe_2$, $NHCH_2CH_2OH$, $NHCH_2CH(CF_3)OH$, $NHCH_2C(CF_3)_2OH$, $NHCH_2CH_2OMe$, $NHCH_2CH_2SO_2Me$, $NHCH_2CH_2SO_2NH_2$, $NH(CH_2)_3OH$, $NH(CH_2)_3OMe$, $NH(CH_2)_4OH$, $NH(CH_2)_4OMe$, $NH(CH_2)_5OH$, $NH(CH_2)_2CO_2H$, $NH(CH_2)_3CO_2H$, $NH(CH_2)_4CO_2H$, $NH(CH_2)_5CO_2H$, $NHCH_2CMe_2OH$, $NHCH(Me)CMe_2OH$, $NHCH_2CMe_2OMe$, $NHCH_2CMe_2CO_2H$, $NHCH_2CMe_2CONH_2$, $NHCH_2CMe_2CONHMe$, $NHCH_2CMe_2CONMe_2$, $NHCH_2CMe_2NHSO_2Me$, $NH(CH_2)_3SOMe$, $NH(CH_2)_5SO_2Me$, $NH(CH_2)_5SO_2NH_2$, $NH(CH_2)_3NHSO_2Me$, $NH(CH_2)_2O(CH_2)_2OH$, $NHCH_2CHMeOH$, $NH(CH_2)_5SOMe$, $NH(CH_2)_3SO_2Me$,

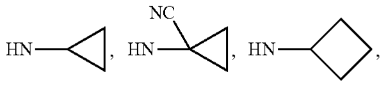

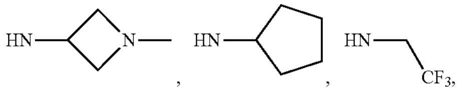

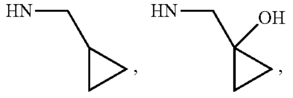

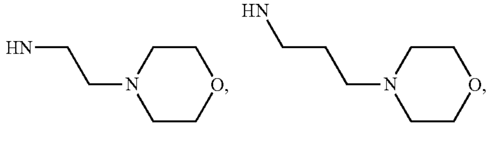

-continued

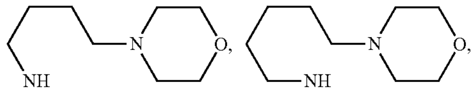

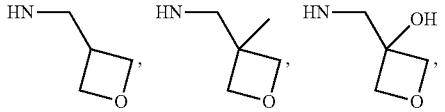

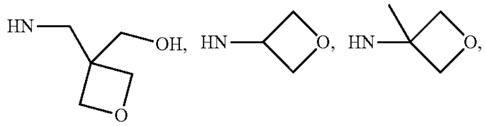

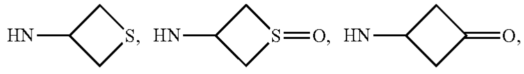

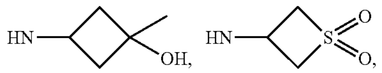

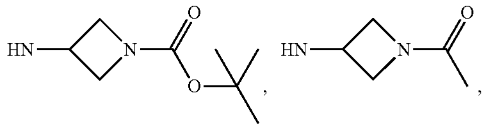

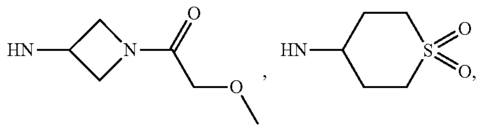

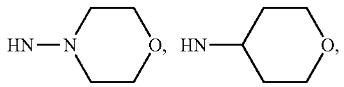

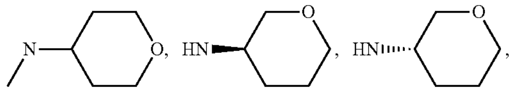

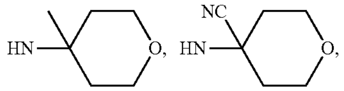

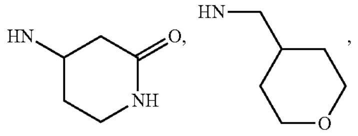

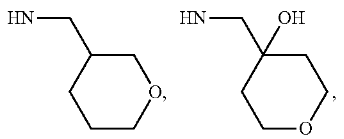

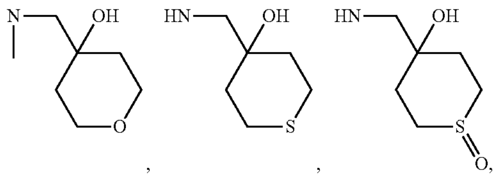

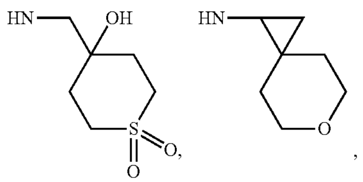

-continued
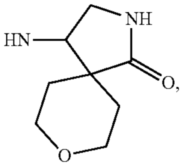 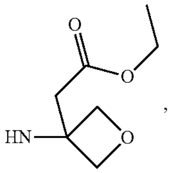
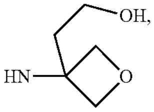 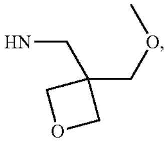
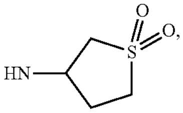 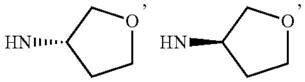
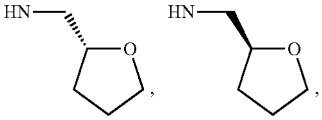
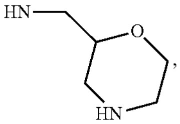 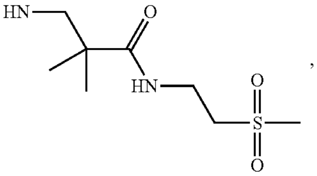
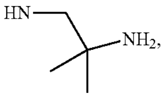 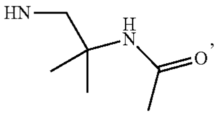
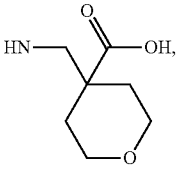 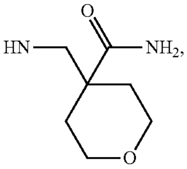
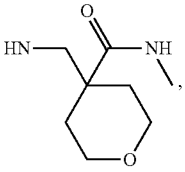 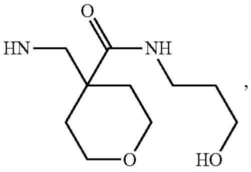
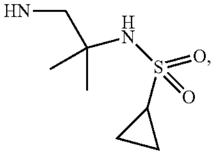 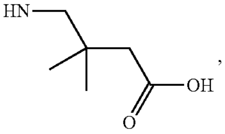
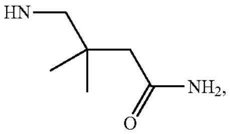 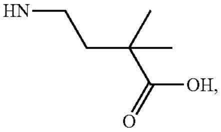
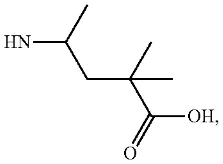 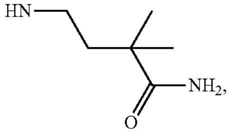
-continued
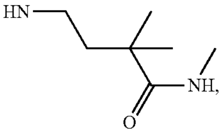 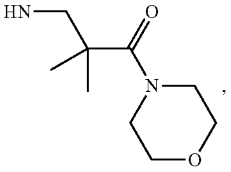
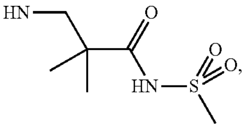 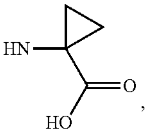
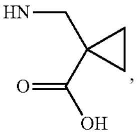 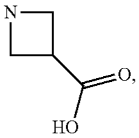 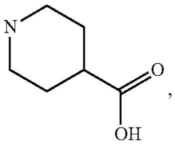
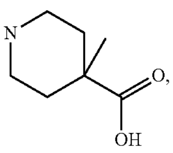 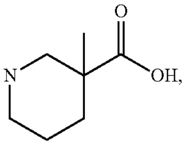
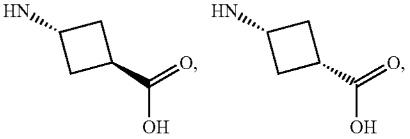
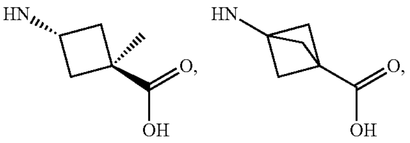
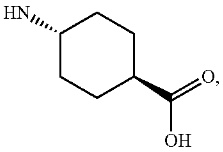 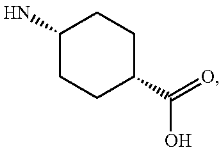
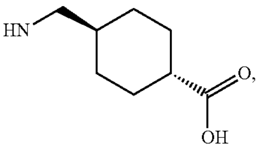
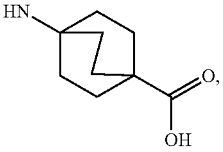 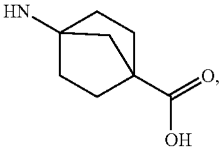
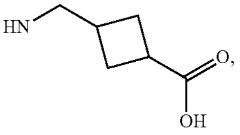 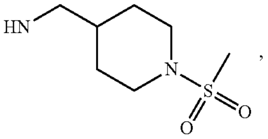
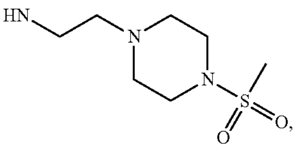

-continued
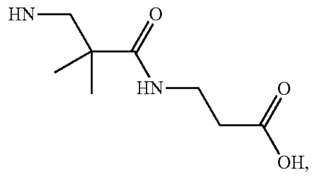
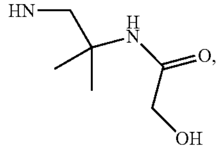 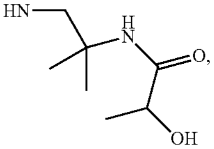
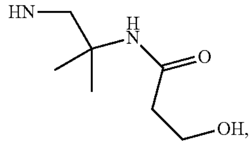 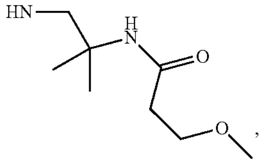
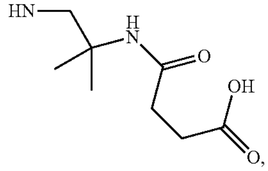
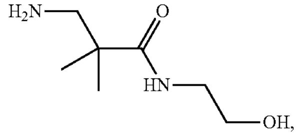
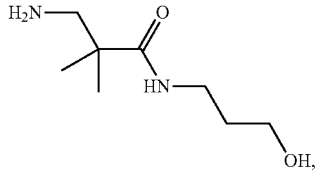
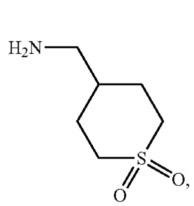 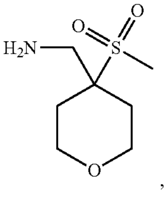
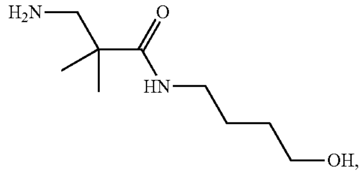
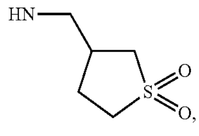 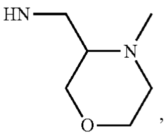
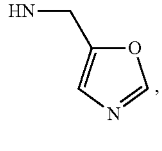 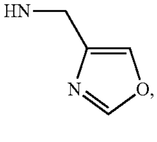 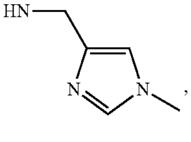
-continued
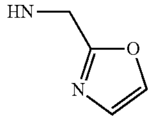 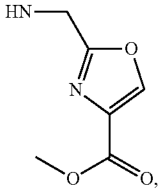
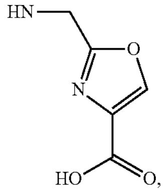 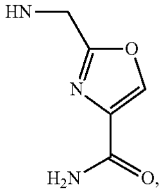 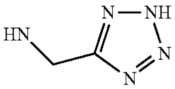
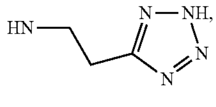 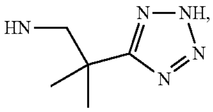
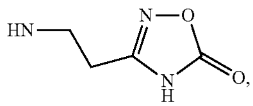 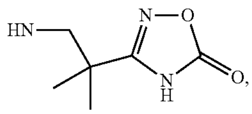
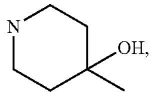 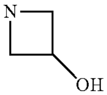 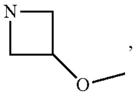
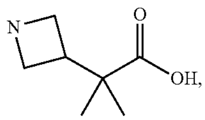 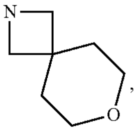
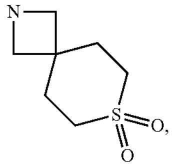 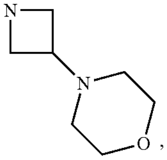
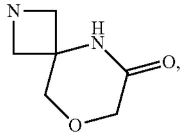 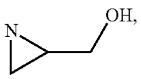
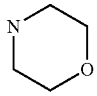 and 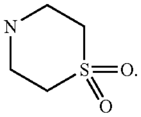
6. The compound according to claim 3, wherein: $R^3$ is selected from:
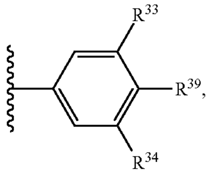 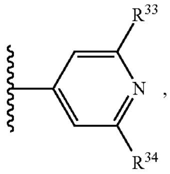

-continued

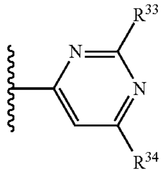 , 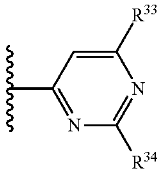 ,

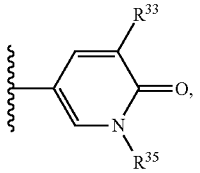 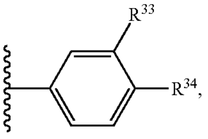

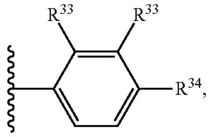 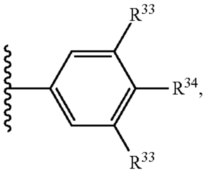

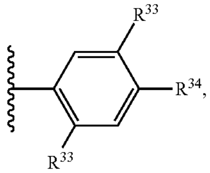 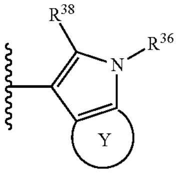 ,

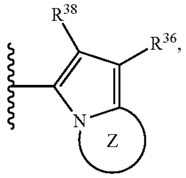 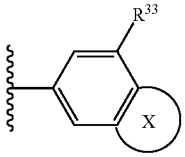 and

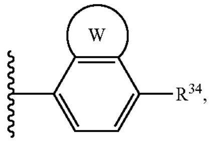

wherein:

$R^{33}$ is independently selected from H, halogen, CN, $C_{1-6}$-alkyl, fluoro-$C_{1-6}$-alkyl, $C_{1-4}$-alkylene-OH, $C_{1-4}$-alkylene-O—$C_{1-3}$-alkyl, $C_{1-4}$-alkylene-O-fluoro-$C_{1-3}$-alkyl, O—$C_{1-6}$-alkyl, O-fluoro-$C_{1-6}$-alkyl, NH—$C_{1-6}$-alkyl, NH-fluoro-$C_{1-6}$-alkyl, $C_{3-10}$-cycloalkyl, C(O)N$(R^{37})_2$, wherein alkylene is unsubstituted or substituted with 1 to 3 substituents selected from F and cycloalkyl is unsubstituted or substituted with 1 to 3 substituents independently selected from F, $C_{1-3}$-alkyl and fluoro-$C_{1-3}$-alkyl;

$R^{34}$ is selected from $C_{1-4}$-alkylene-OH, $C_{1-4}$-alkylene-O—$C_{1-3}$-alkyl, $C_{1-4}$-alkylene-O-fluoro-$C_{1-3}$-alkyl, $C_{3-10}$-cycloalkyl, C(O)N$(R^{37})_2$, $SO_2N(R^{37})_2$, wherein alkylene is unsubstituted or substituted with 1 to 3 substituents selected from F and cycloalkyl is unsubstituted or substituted with 1 to 3 substituents independently selected from F, $C_{1-3}$-alkyl and fluoro-$C_{1-3}$-alkyl;

$R^{35}$ is selected from $C_{1-6}$-alkyl and fluoro-$C_{1-6}$-alkyl;

$R^{36}$ is selected from $C_{1-6}$-alkyl, fluoro-$C_{1-6}$-alkyl, C(O)N$(R^{37})_2$, $SO_2N(R^{37})_2$, $R^{37}$ is independently selected from H, $C_{1-6}$-alkyl, halo-$C_{1-6}$-alkyl, $C_{0-4}$-alkylene-$C_{3-6}$-cycloalkyl, $C_{0-4}$-alkylene-$C_{3-6}$-heterocycloalkyl, wherein alkyl and alkylene is unsubstituted or substituted with a substituent selected from halogen, OH, O—$C_{1-3}$-alkyl, CN; and cycloalkyl or heterocycloalkyl is unsubstituted or substituted with 1 to 3 substituents independently selected from F, CN, OH, oxo, $C_{1-3}$-alkyl and fluoro-$C_{1-3}$-alkyl;

or wherein two $R^{37}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from fluoro, OH, oxo, $C_{1-4}$-alkyl and halo-$C_{1-4}$-alkyl;

$R^{38}$ is selected from H, $C_{1-3}$-alkyl and fluoro-$C_{1-3}$-alkyl;

$R^{39}$ is selected from H, F, OH, O—$C_{1-3}$-alkyl, O-halo-$C_{1-3}$-alkyl;

W is selected from an annelated $C_{5-8}$-cycloalkyl, an annelated 6-membered aryl or an annelated 5- to 6-membered heteroaryl, wherein cycloalkyl, aryl and heteroaryl is unsubstituted or substituted with 1 to 2 substituents selected from halogen, methyl or $CF_3$;

X is an annelated saturated heterocycle selected from the group consisting of:

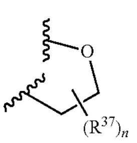 , 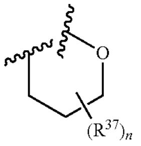 , 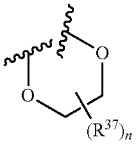 ,

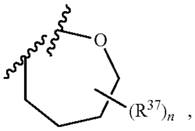 , 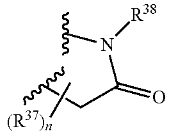 ,

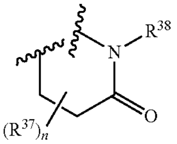 , 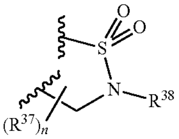 and

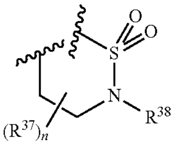 ;

Y is an annelated 5- or 6-membered carbocycle, an annelated 6-membered aryl or an annelated 6-membered heteroaryl containing 1 to 2 nitrogen atoms, wherein the carbocycle, aryl or heteroaryl is unsubstituted or substituted with 1 to 3 substituents selected from fluoro, $C_{1-3}$-alkyl and fluoro-$C_{1-3}$-alkyl;

Z is an annelated 6-membered cycle forming a heteroaryl containing 1 to 2 nitrogen atoms, wherein the heteroaryl is unsubstituted or substituted with 1 to 3 substituents selected from fluoro, $C_{1-3}$-alkyl and fluoro-$C_{1-3}$-alkyl; and n is selected from 1 to 4.

7. The compound according to claim 3 wherein:

$R^3$ is selected from:

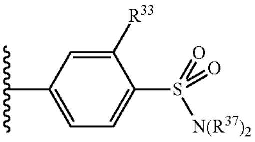 , 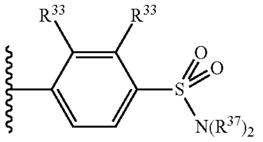 ,

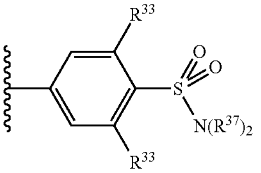 , 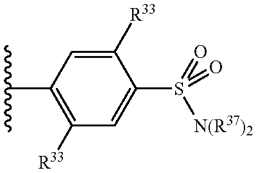 and

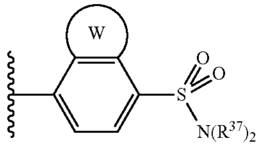 , wherein:

$R^{33}$ is independently selected from H, halogen, CN, $C_{1-6}$-alkyl, fluoro-$C_{1-6}$-alkyl, $C_{1-4}$-alkylene-OH, $C_{1-4}$-alkylene-O—$C_{1-3}$-alkyl, O—$C_{1-6}$-alkyl, O-fluoro-$C_{1-6}$-alkyl, $C_{3-6}$-cycloalkyl;

one $R^{37}$ is selected from H, $C_{1-6}$-alkyl, halo-$C_{1-6}$-alkyl and the other $R^{37}$ is selected from $C_{1-6}$-alkyl, halo-$C_{1-6}$-alkyl, $C_{0-4}$-alkylene-$C_{3-6}$-cycloalkyl, $C_{0-4}$-alkylene-$C_{3-6}$-heterocycloalkyl, wherein:

alkyl and alkylene is unsubstituted or substituted with a substituent selected from halogen, OH, O—$C_{1-3}$-alkyl, CN; and cycloalkyl or heterocycloalkyl is unsubstituted or substituted with 1 to 3 substituents independently selected from F, CN, OH, oxo, $C_{1-3}$-alkyl and fluoro-$C_{1-3}$-alkyl;

or wherein two $R^{37}$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from fluoro, OH, oxo, $C_{1-4}$-alkyl and halo-$C_{1-4}$-alkyl;

W is selected from an annelated $C_{5-8}$-cycloalkyl, an annelated 6-membered aryl or an annelated 5- to 6-membered heteroaryl, wherein cycloalkyl, aryl and heteroaryl is unsubstituted or substituted with 1 to 2 substituents selected from halogen, methyl or $CF_3$.

8. The compound according to claim 3 wherein:

$R^3$ is selected from:

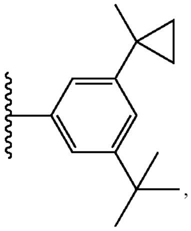 , 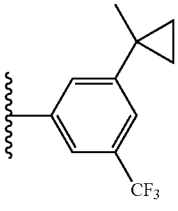 ,

-continued

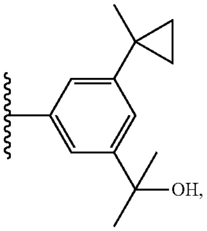 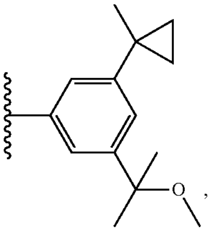 ,

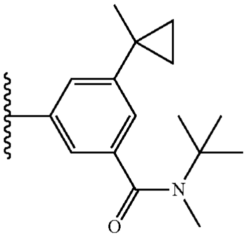 , 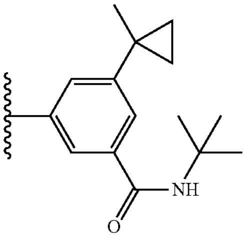 ,

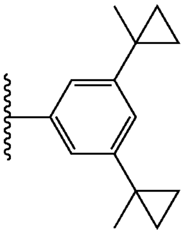 , 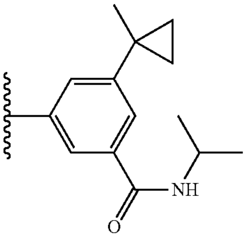 ,

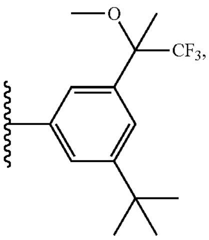 , 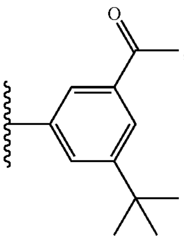 ,

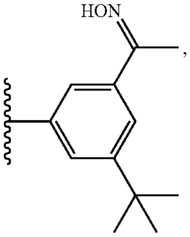 ,

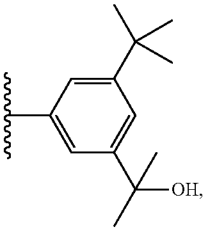 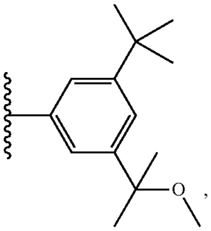 ,

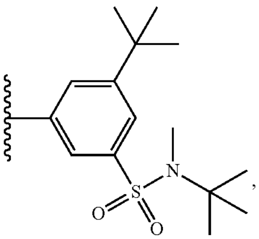 , 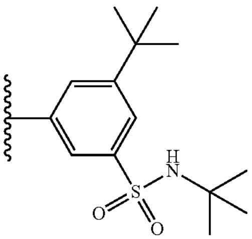 ,

-continued
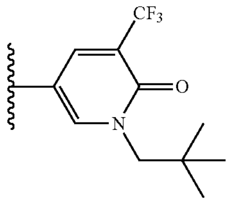,
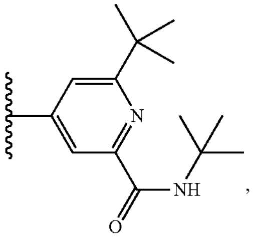,
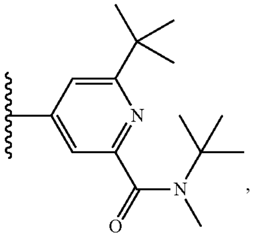,
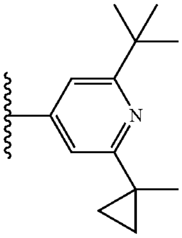,
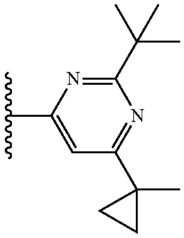,
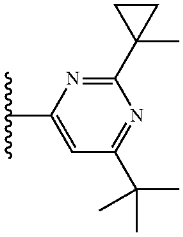,
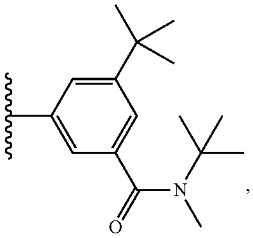,
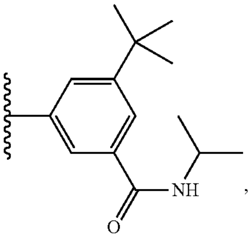,
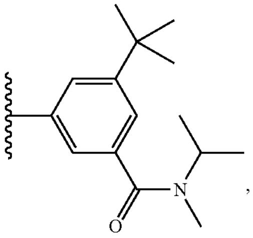,
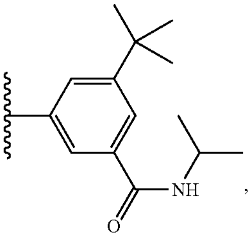,
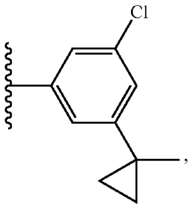,
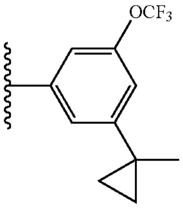,
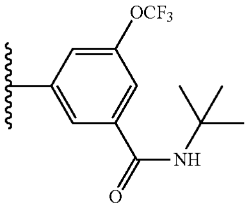,
-continued
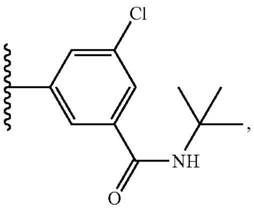,
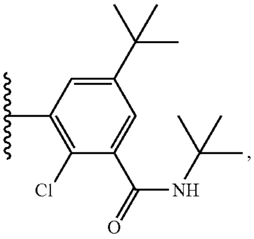,
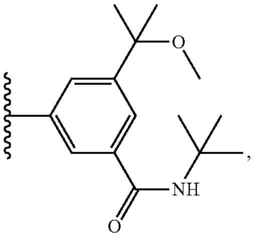,
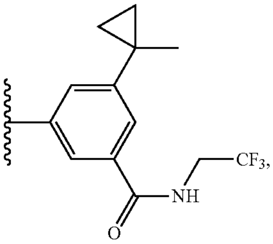
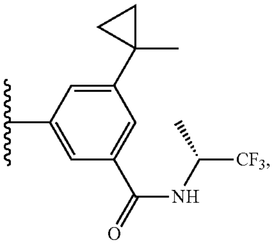
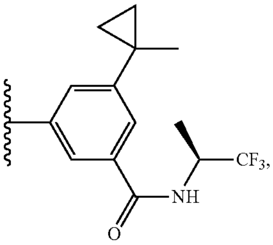
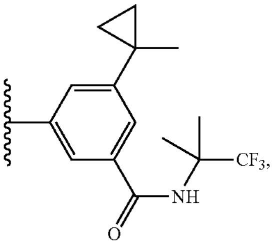
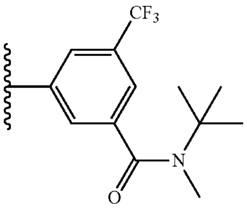, -continued
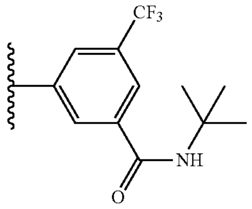,
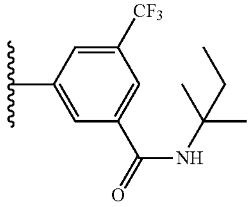,
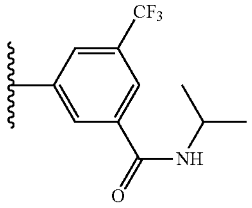,
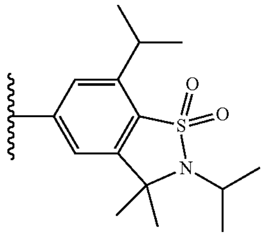,
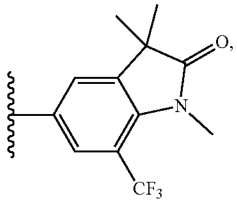,
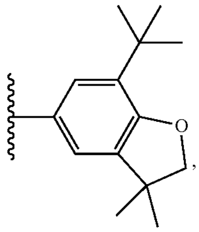,
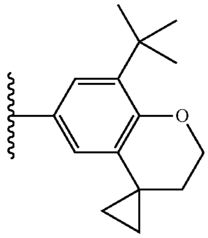, 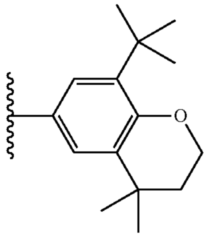,
-continued
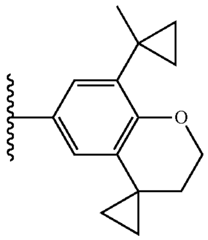, 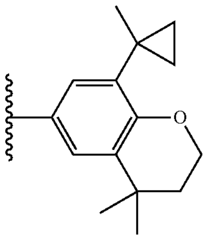,
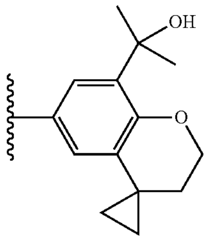, 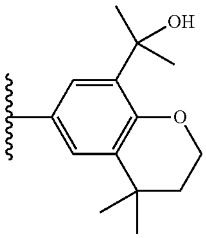,
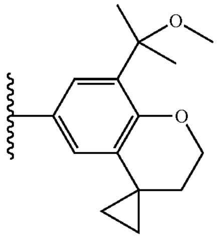, 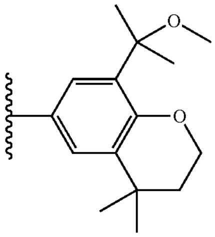,
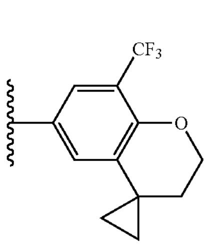, 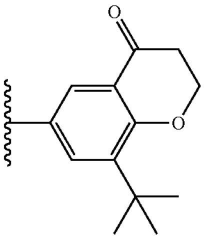,
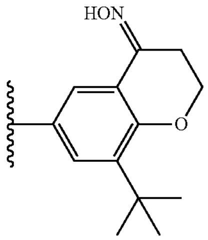, 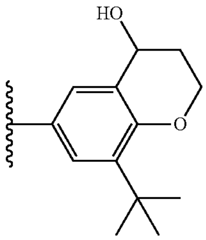,
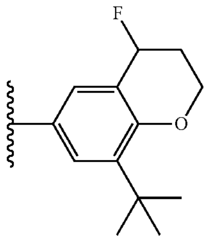, 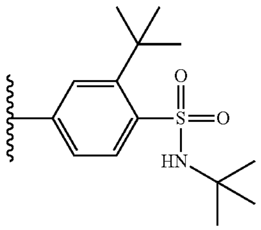,
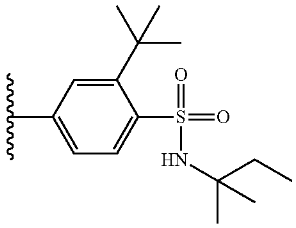, -continued
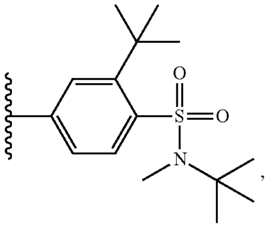
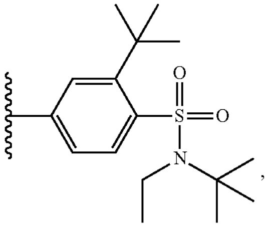
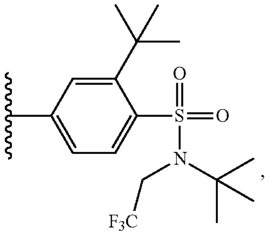
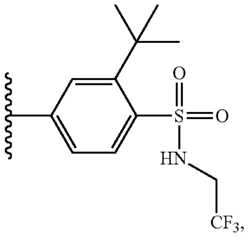
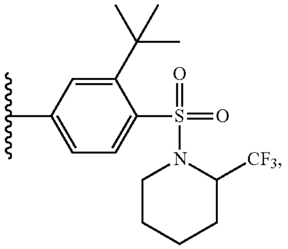
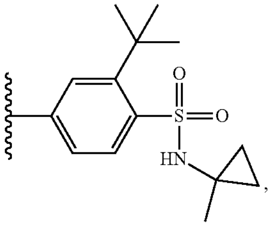
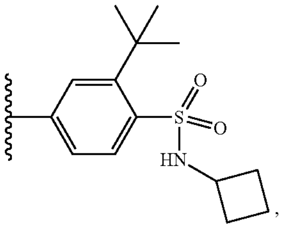
-continued
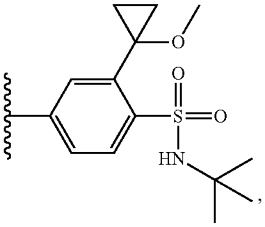
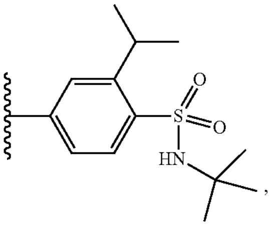
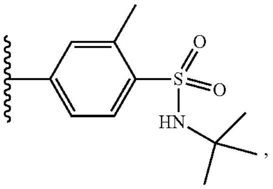
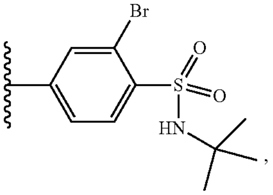
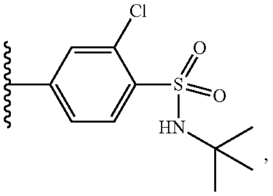
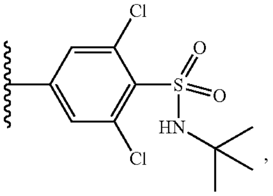
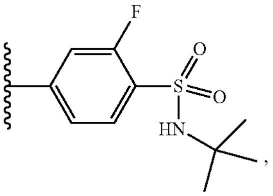
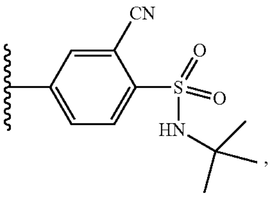

-continued
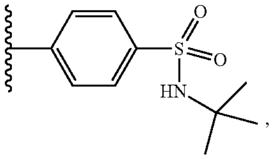
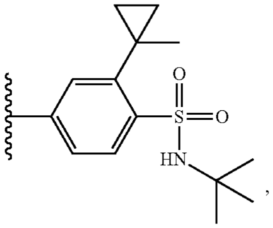
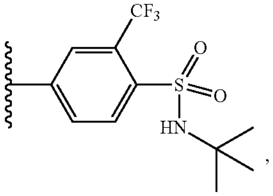
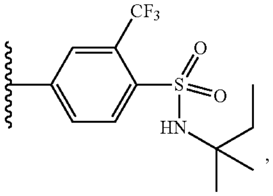
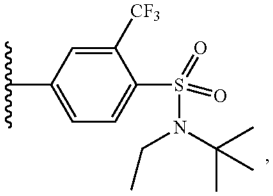
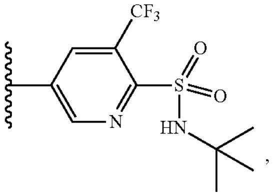
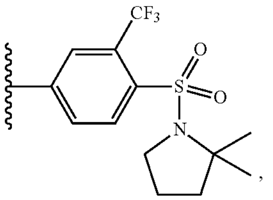
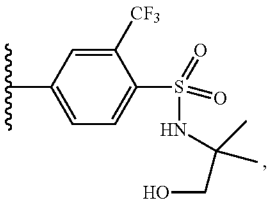
-continued
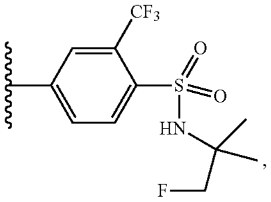
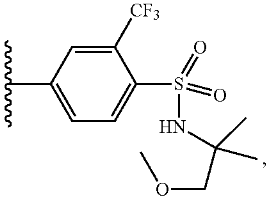
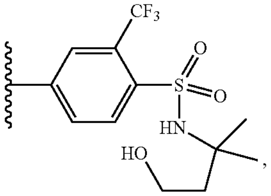
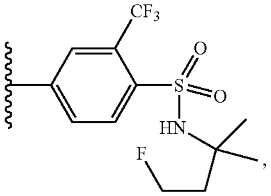
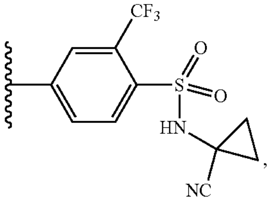
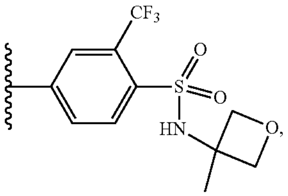 [SMILES: *c1ccc(S(=O)(=O)NC2(C)COC2)c(C(F)(F)F)c1]
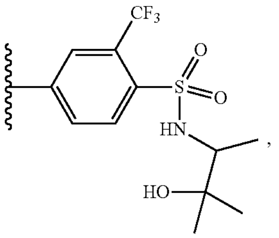
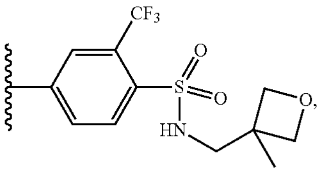

-continued
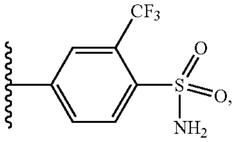
,
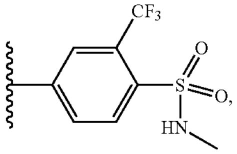
,
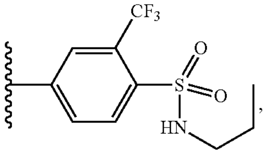
,
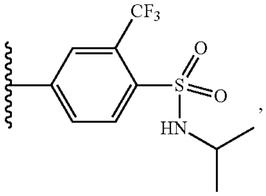
,
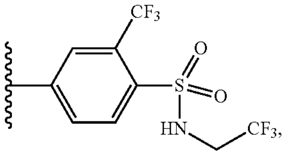
,
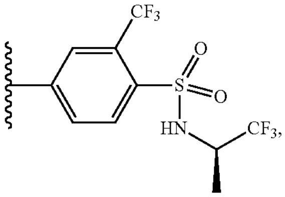
,
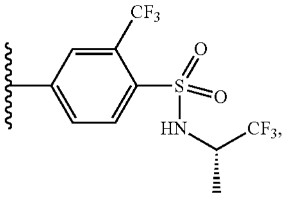
,
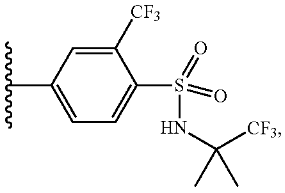
,
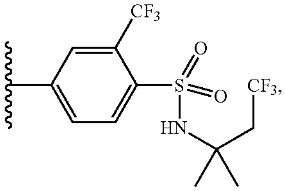
,
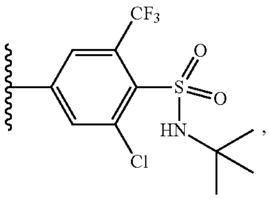
,
-continued
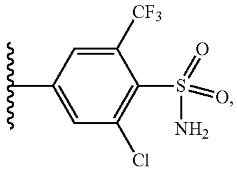
,
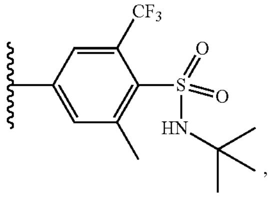
,
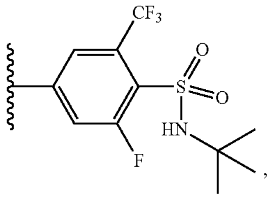
,
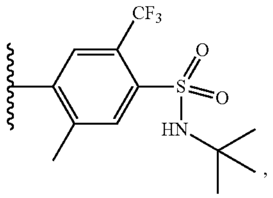
,
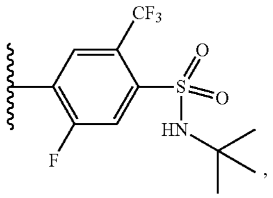
,
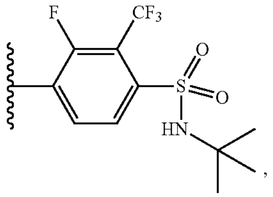
,
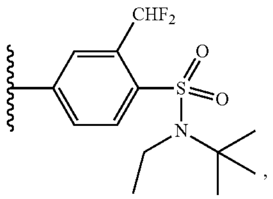
,
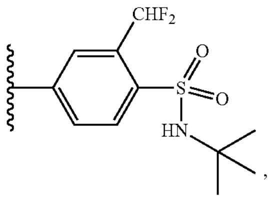
, -continued
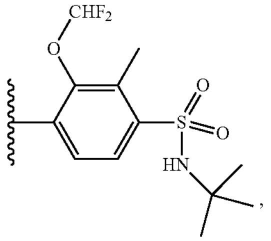
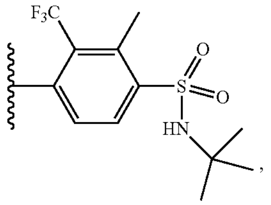
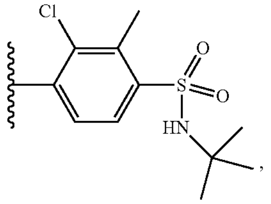
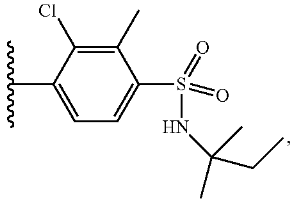
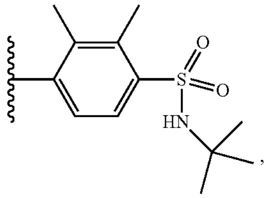
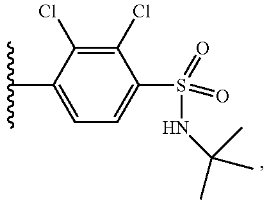
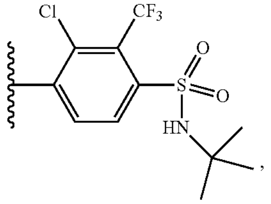
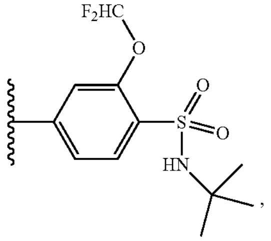
-continued
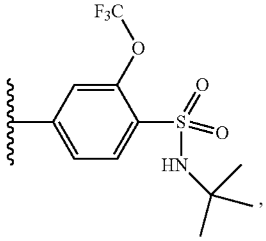
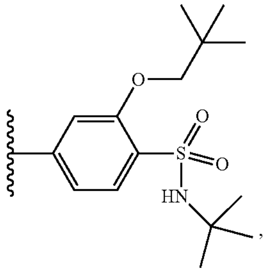
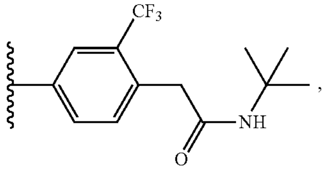
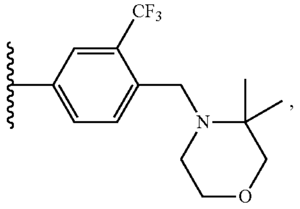
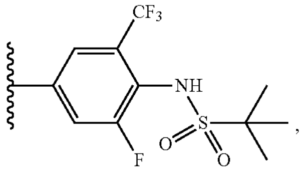
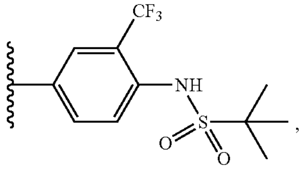
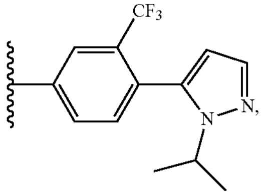
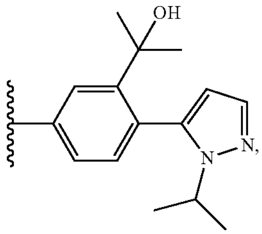

-continued
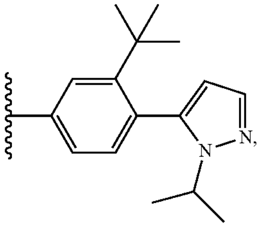
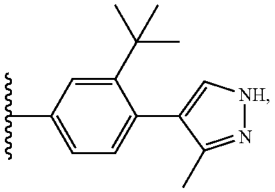
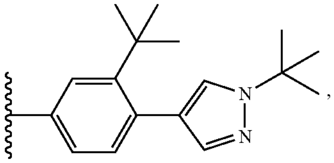
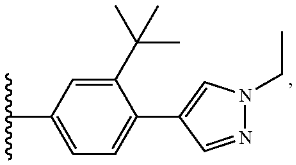
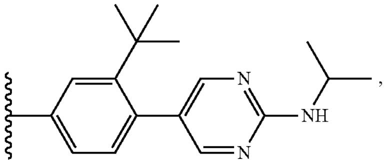
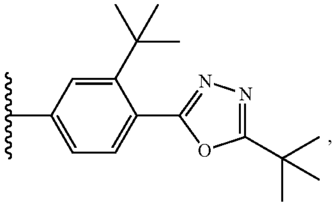
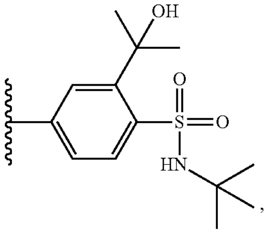
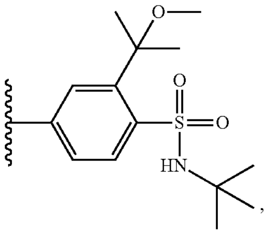
-continued
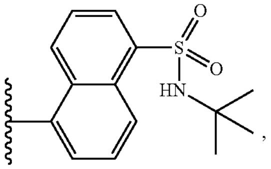
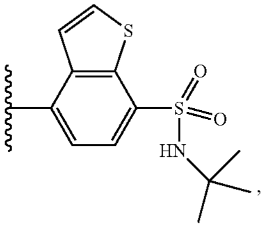
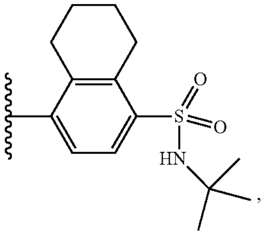
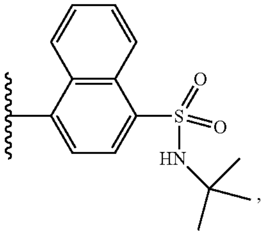
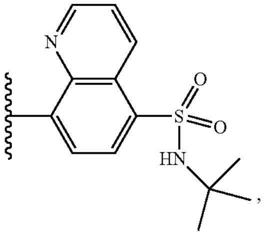
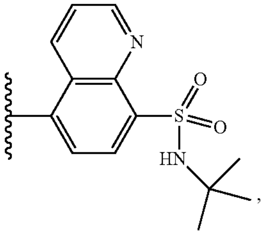
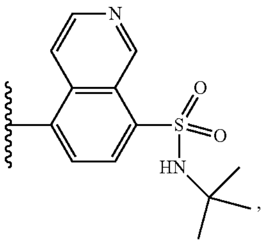

-continued
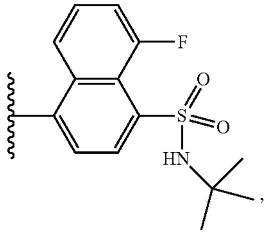
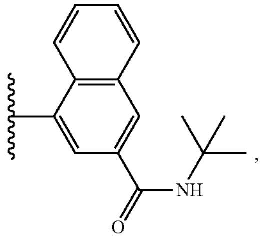
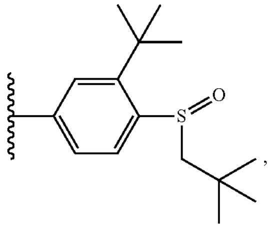
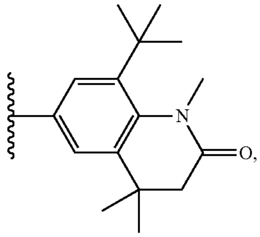
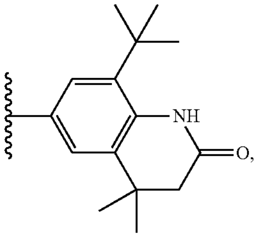
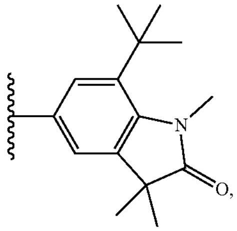
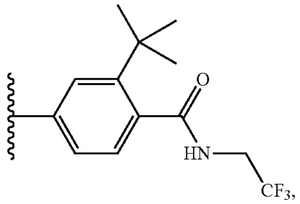
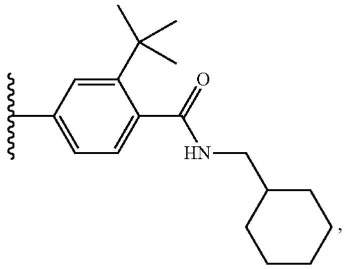
-continued
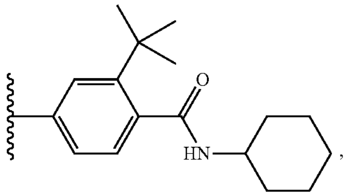
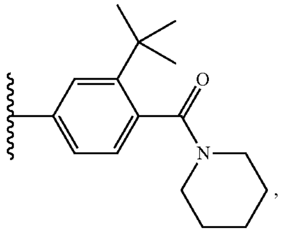
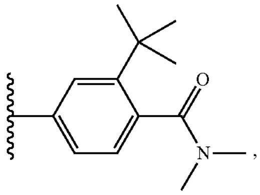
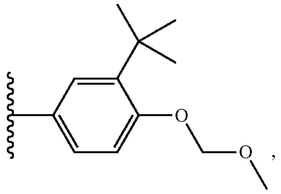
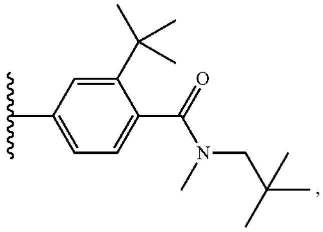
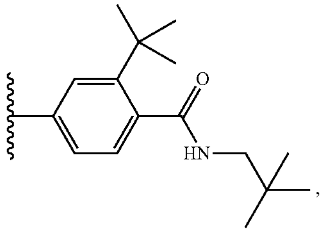
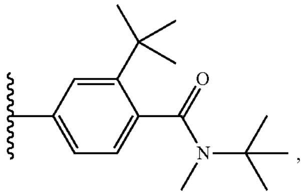
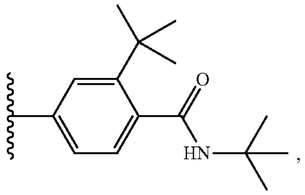

-continued

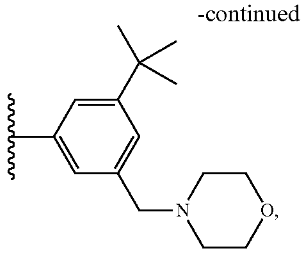

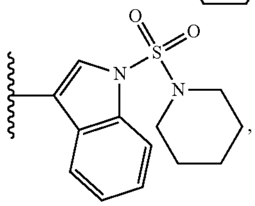,

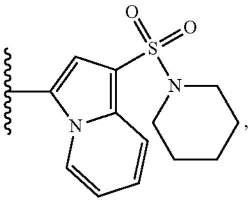,

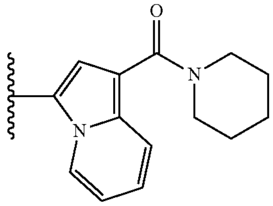

and

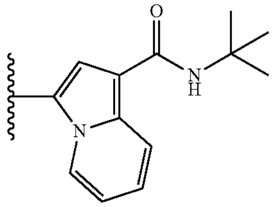.

9. The compound according to claim 3 wherein:

$R^5$ is selected from H, $C_{1-6}$-alkyl, halo-$C_{1-6}$-alkyl or halogen, wherein alkyl is unsubstituted or substituted with 1 to 3 substituents independently selected from the group consisting of O—$C_{1-6}$-alkyl, O-halo-$C_{1-6}$-alkyl and OH;

$R^6$ is selected from H or halogen.

10. The compound according to claim 3 wherein:

$R^4$ is $CR^8R^8$—$R^{10}$;

$R^8$ is independently selected from H, F, $C_{1-3}$-alkyl or halo-$C_{1-3}$-alkyl;

$R^{10}$ is $C_{3-10}$-cycloalkyl, wherein cycloalkyl is unsubstituted or substituted with 1 to 6 substituents independently selected from halogen, $C_{1-6}$-alkyl, halo-$C_{1-6}$-alkyl and cycloalkyl.

11. The compound according to claim 3 wherein:

$R^4$ is selected from:

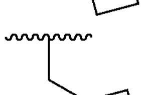,

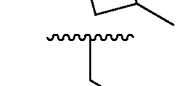,

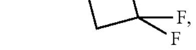

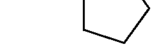,

-continued

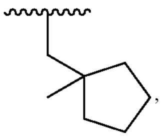,

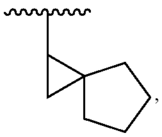,

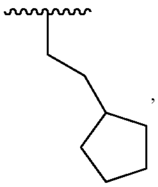,

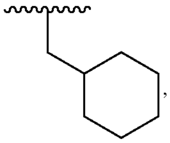,

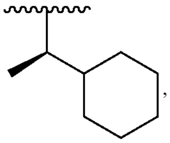,

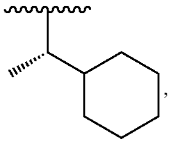,

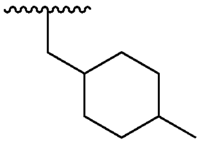,

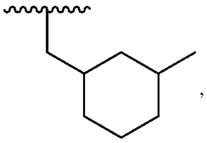,

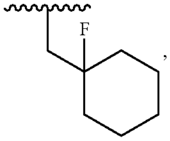,

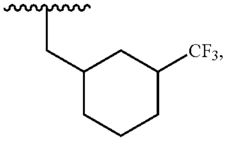

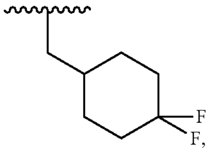

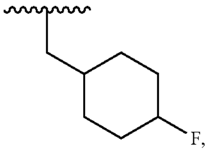

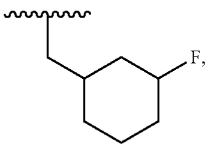

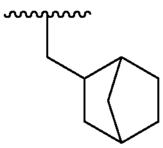

and

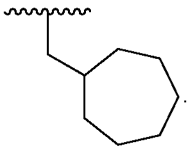.

12. The compound according to claim 3 selected from the group consisting of:

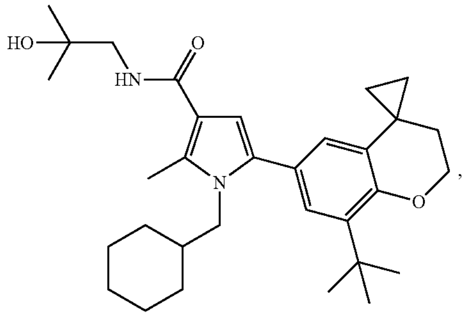,

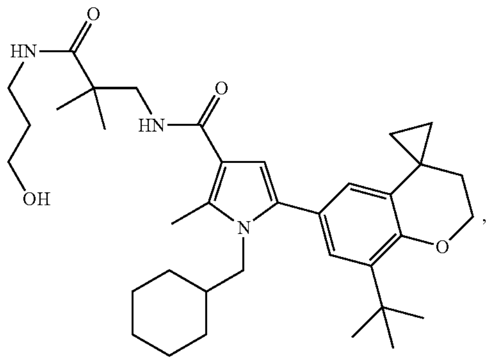
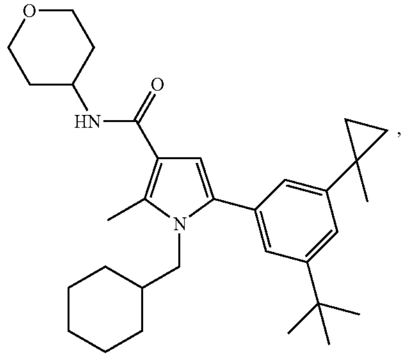
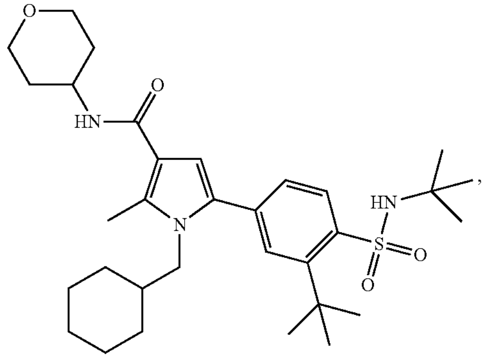
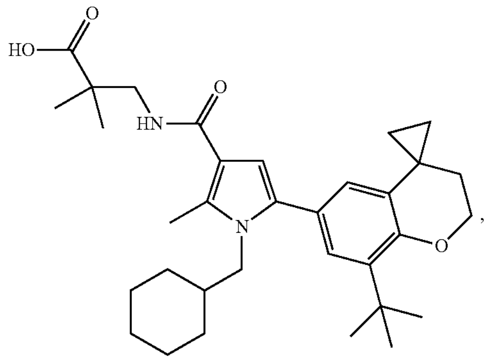
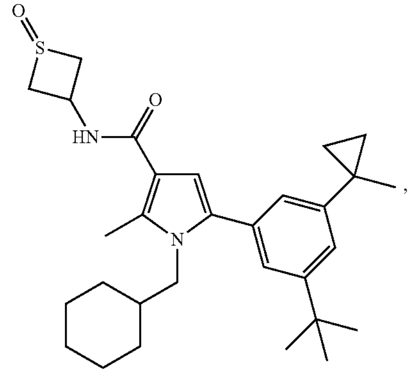
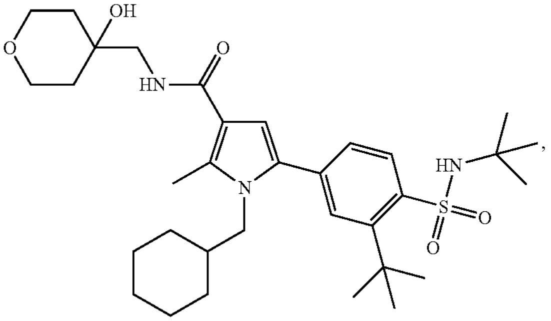
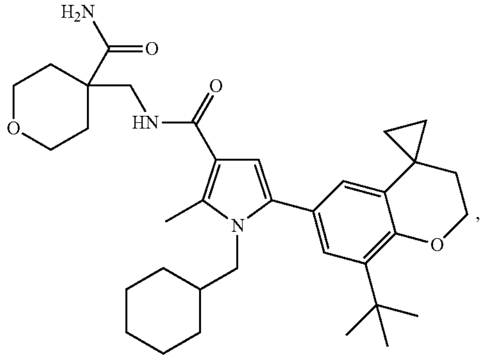
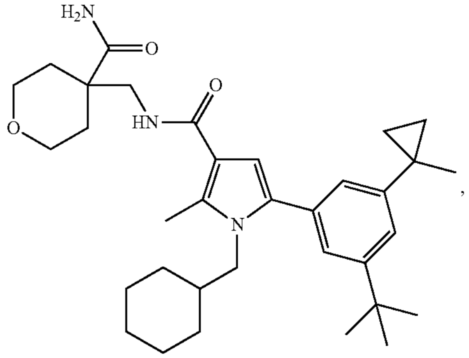

-continued
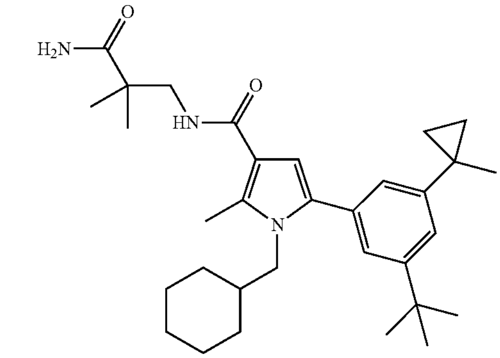
,
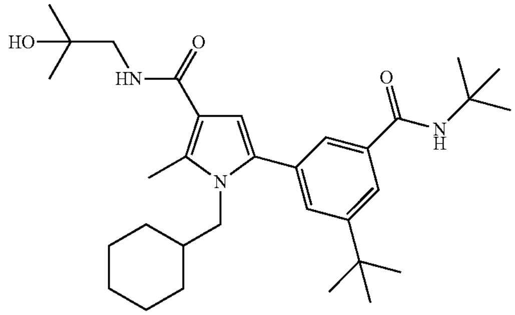
,
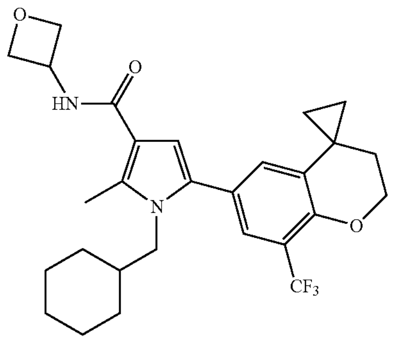
,
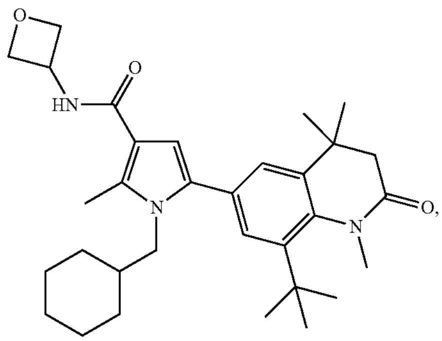
,
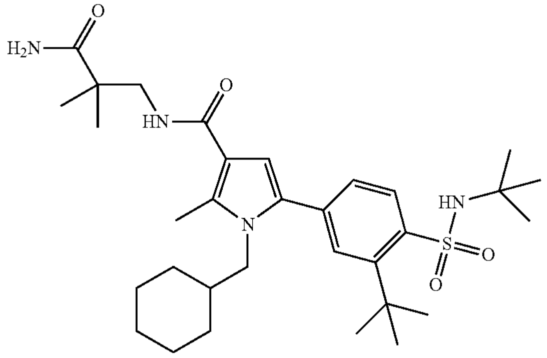
,
-continued
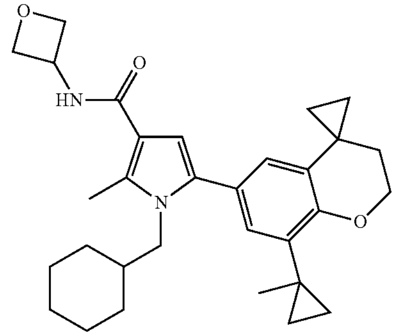
,
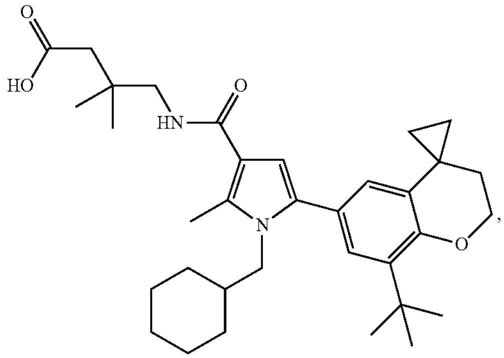
,
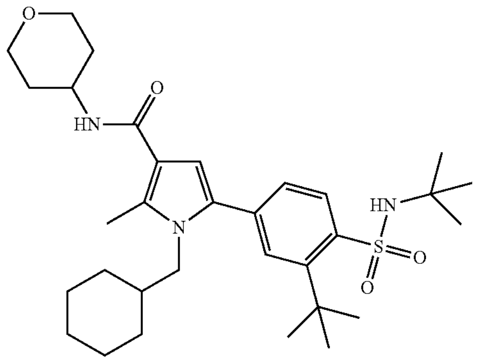
,
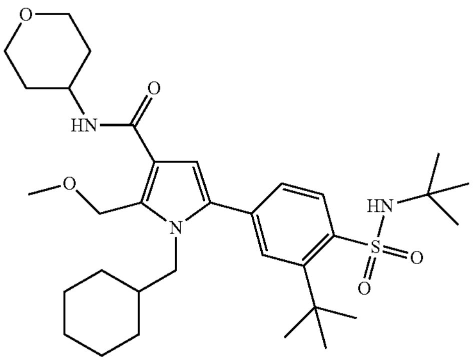
, -continued
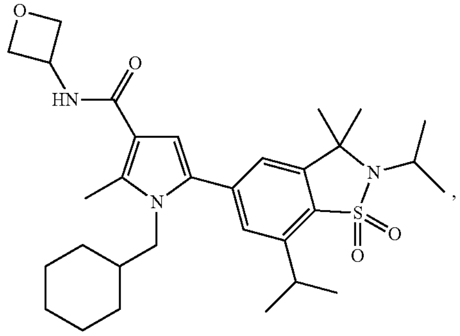
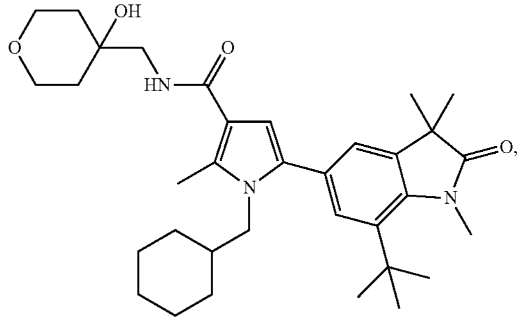
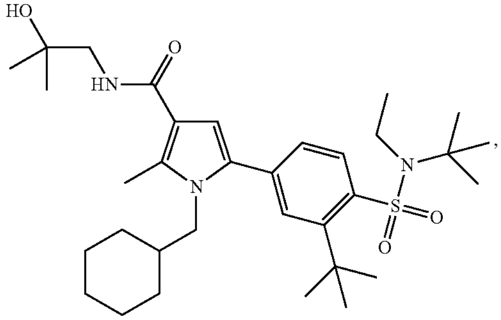
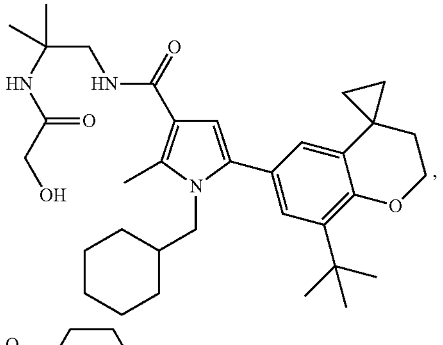
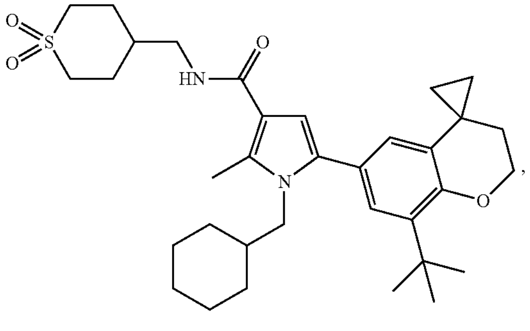
-continued
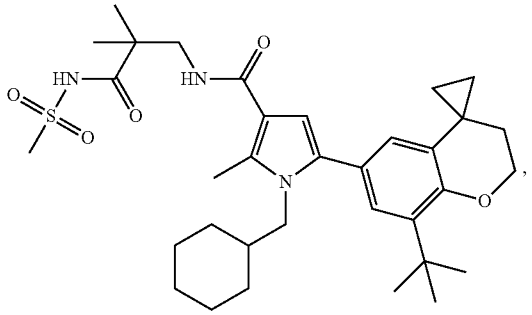
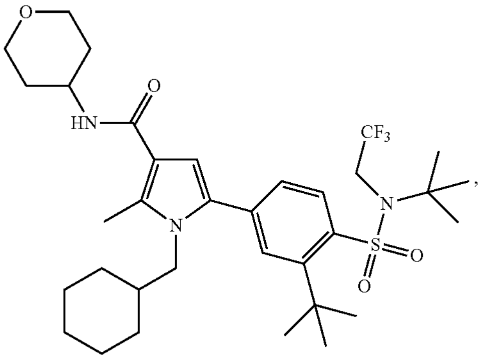
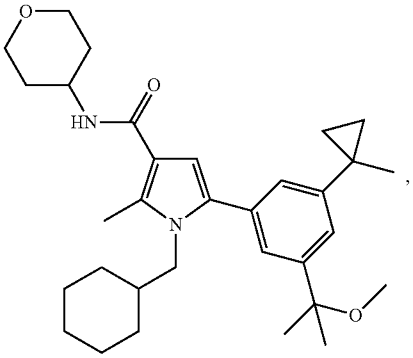
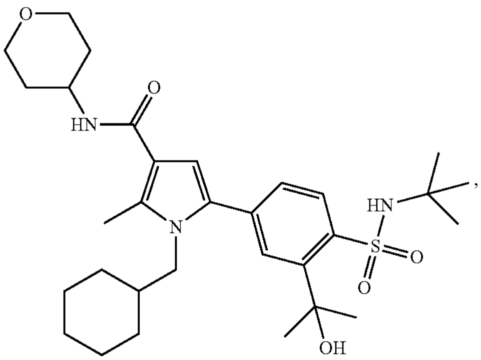

-continued
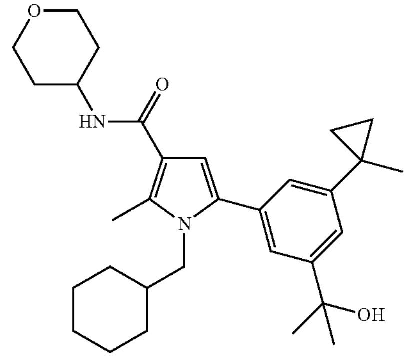
,
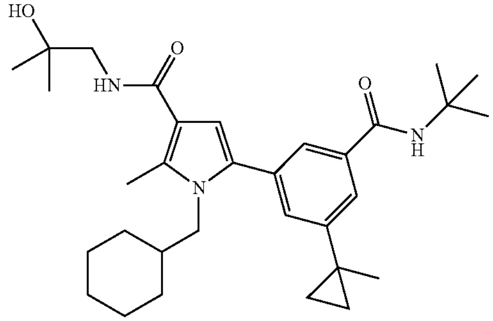
,
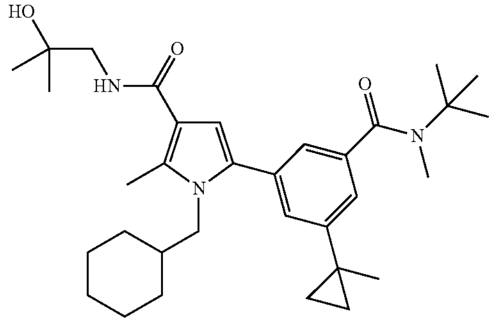
,
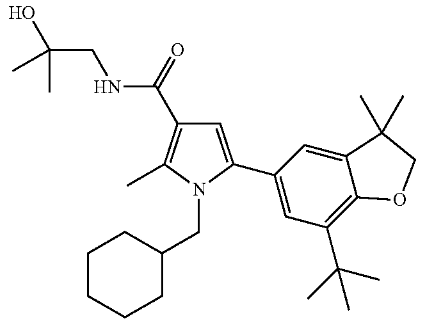
,
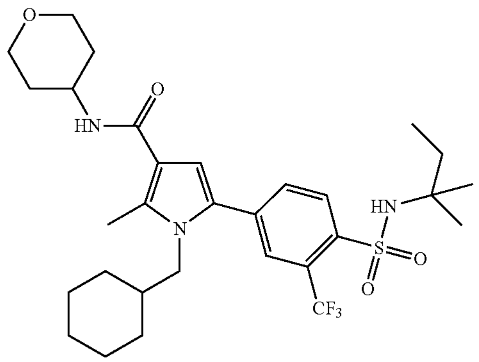
,
-continued
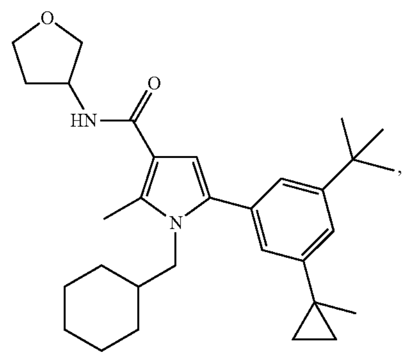
,
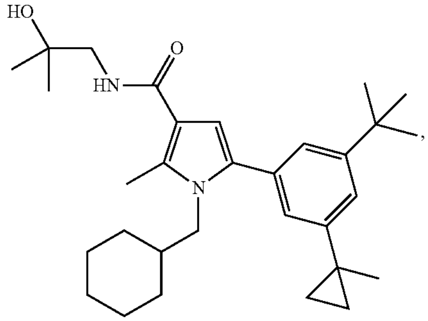
,
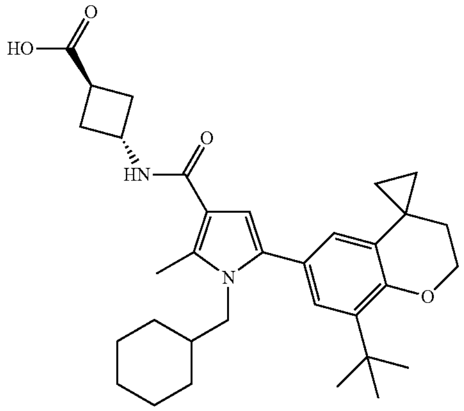
,
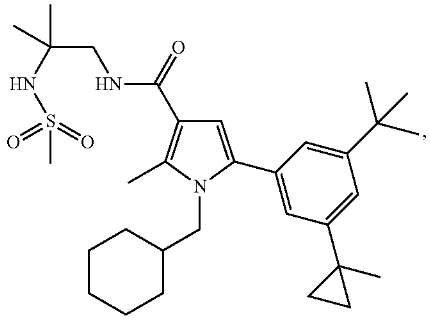
,
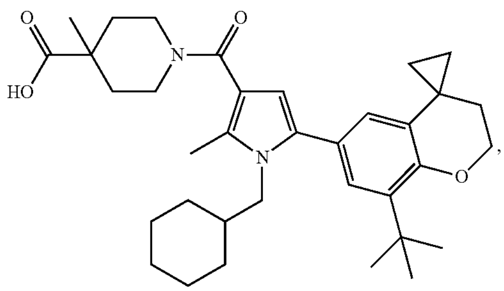
, -continued
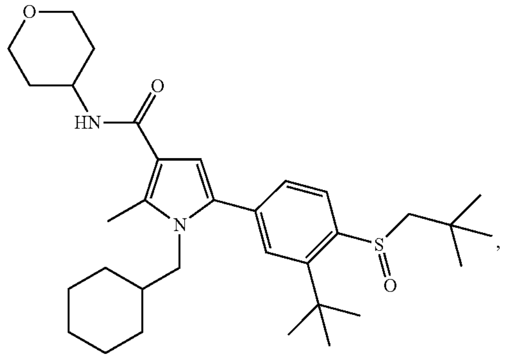
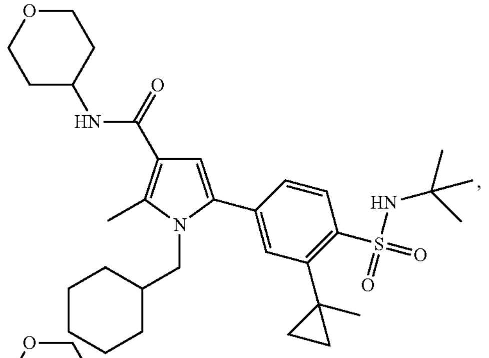
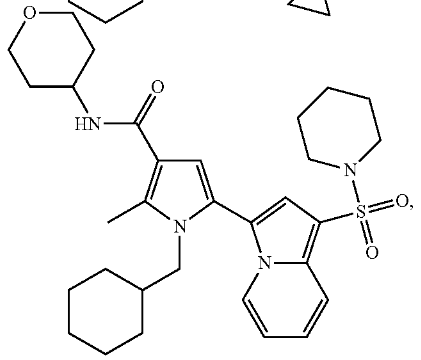
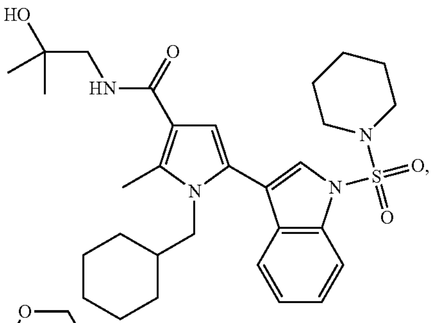
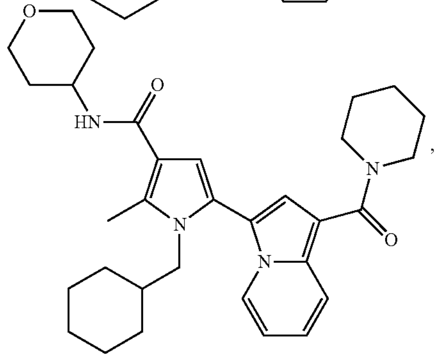
-continued
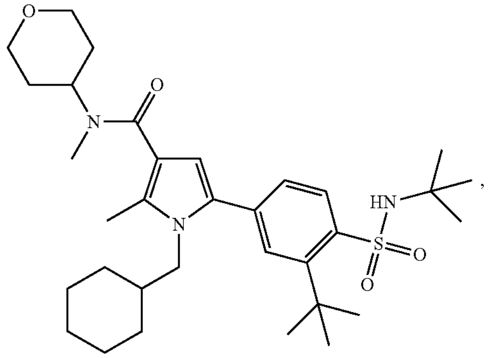
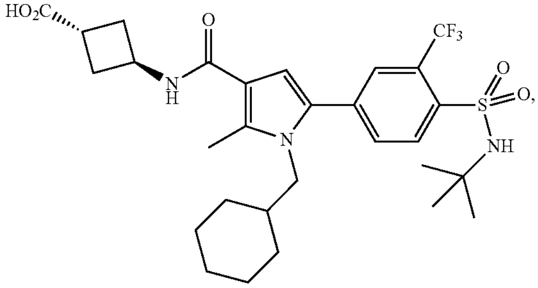
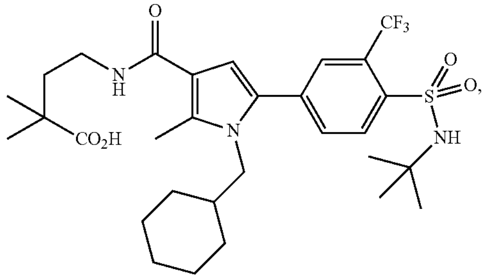
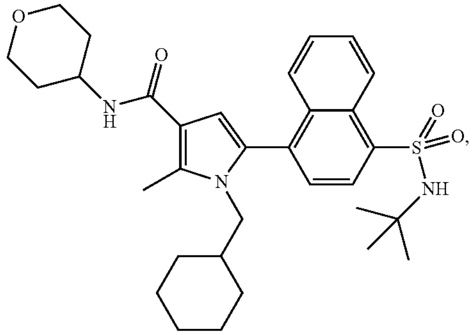
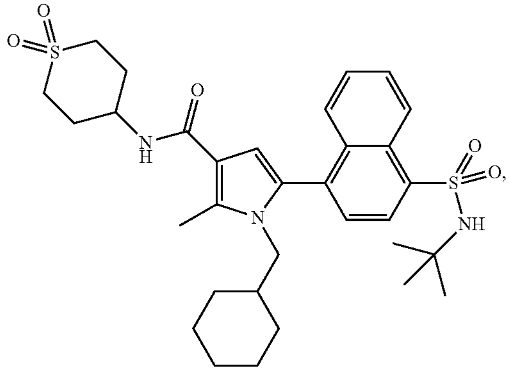

-continued
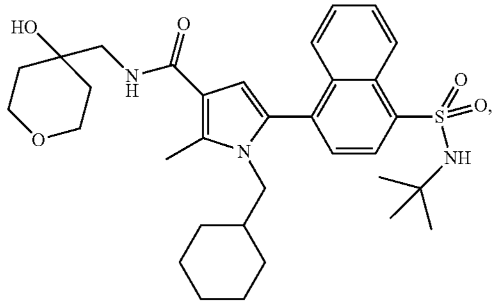
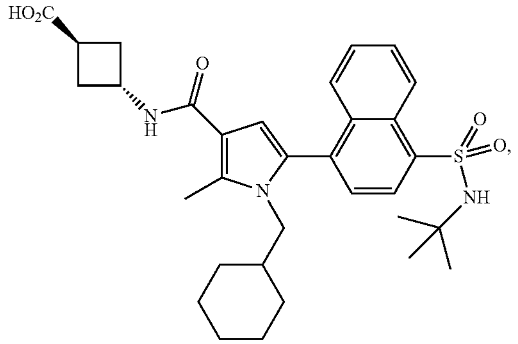
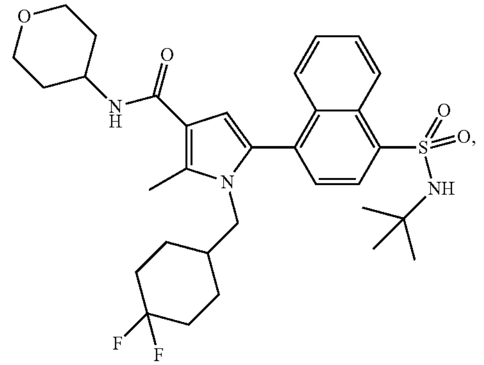
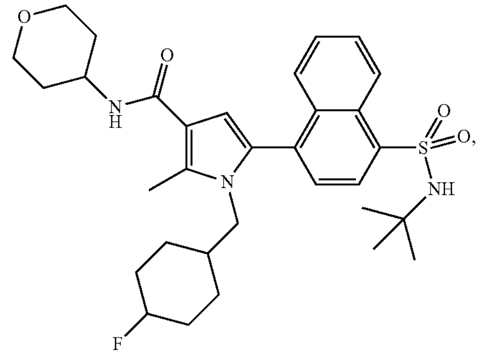
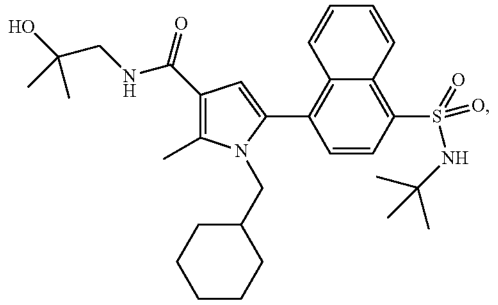
-continued
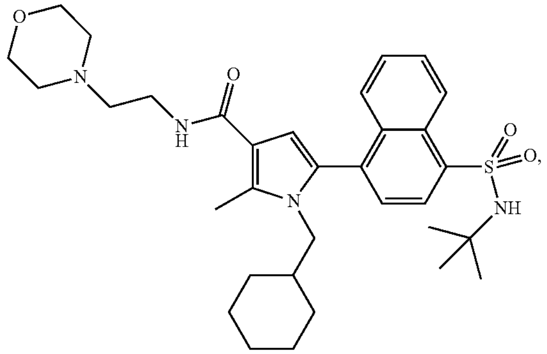
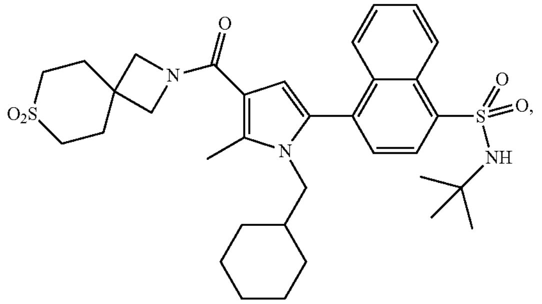
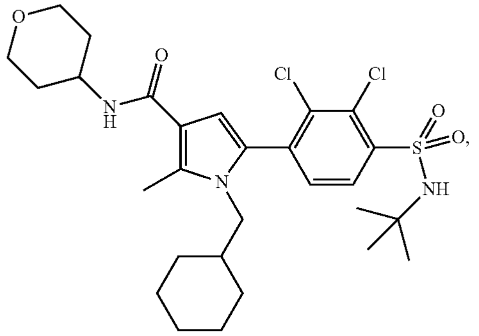
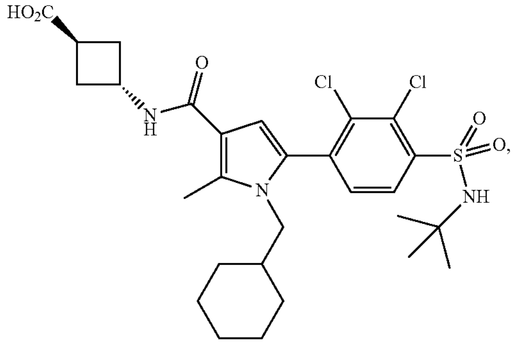
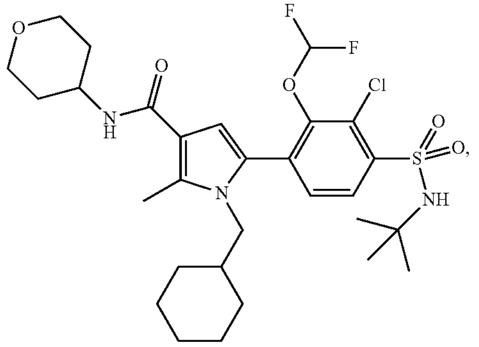

-continued
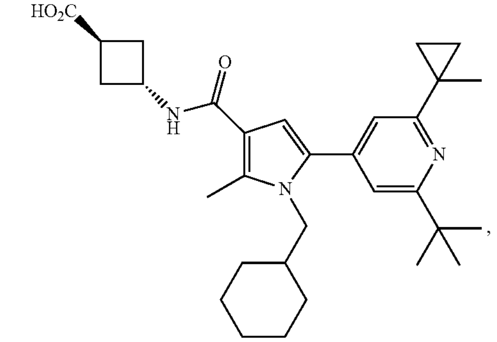
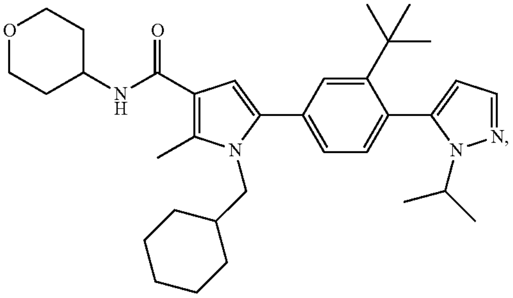
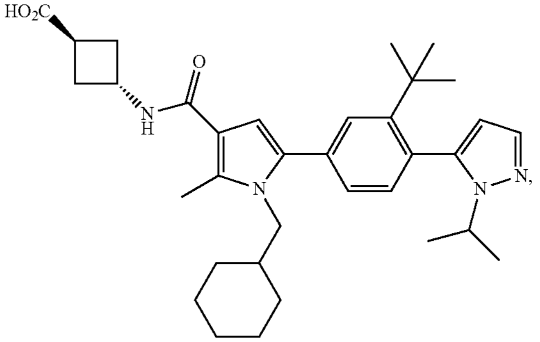
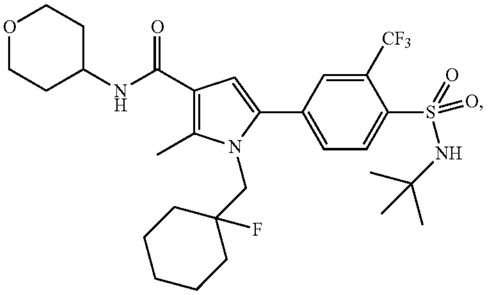
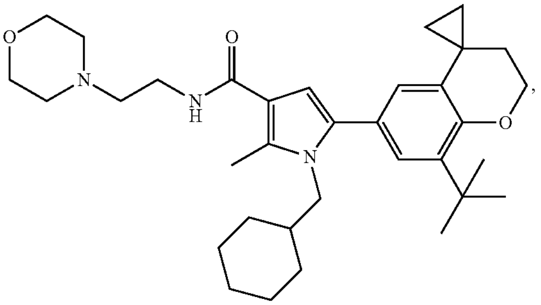
-continued
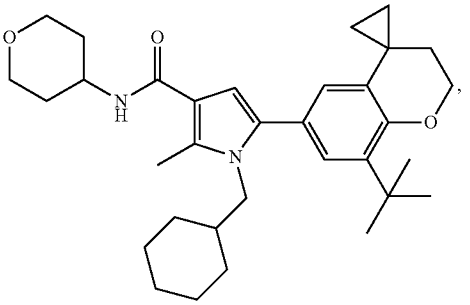
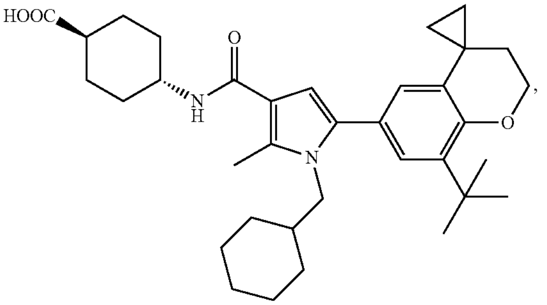
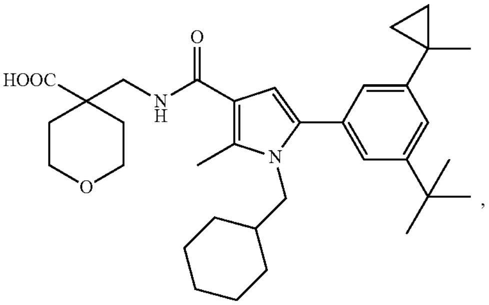
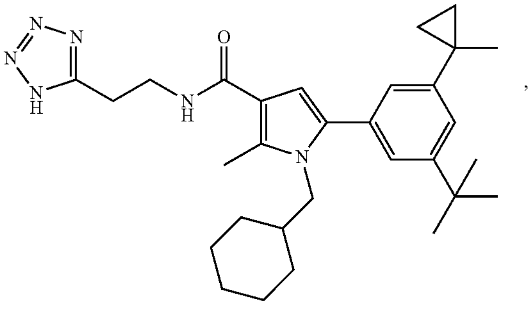
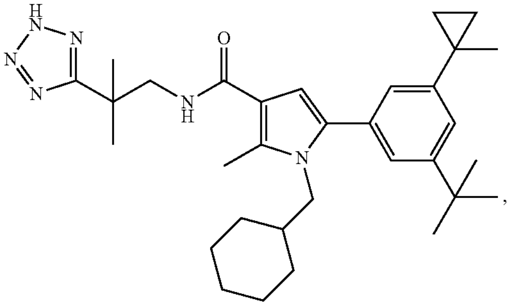

-continued
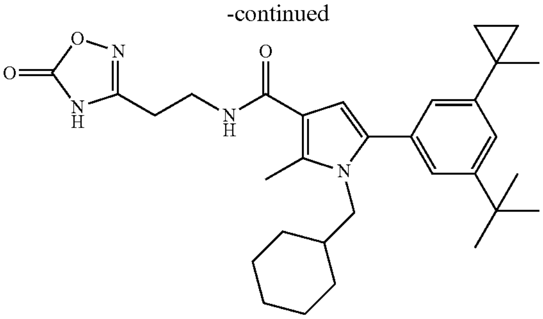
,
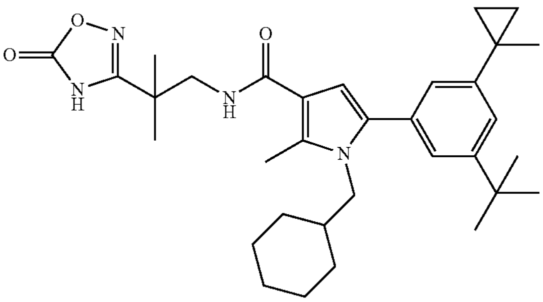
,
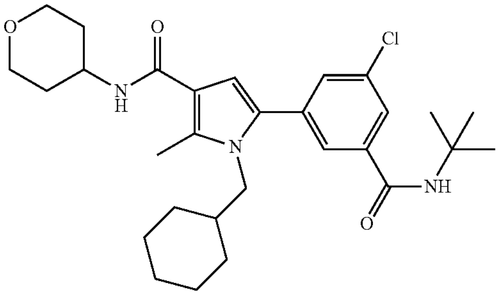
,
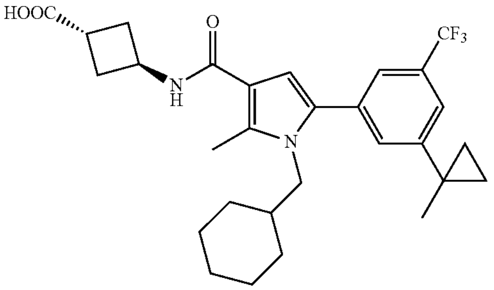
,
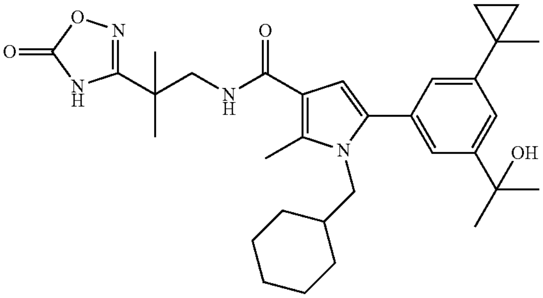
,
-continued
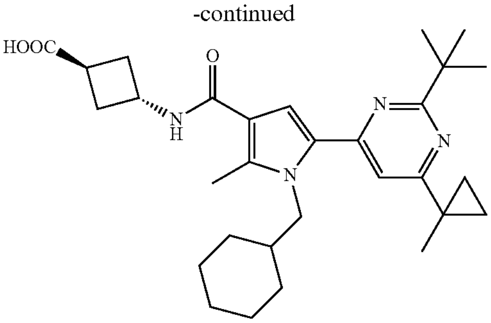
,
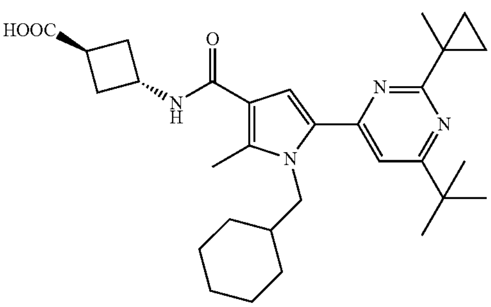
,
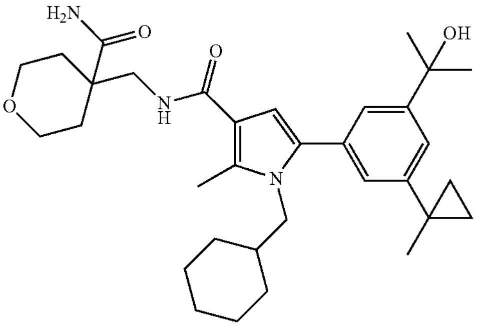
,
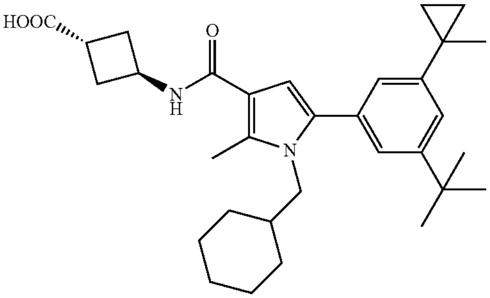
,
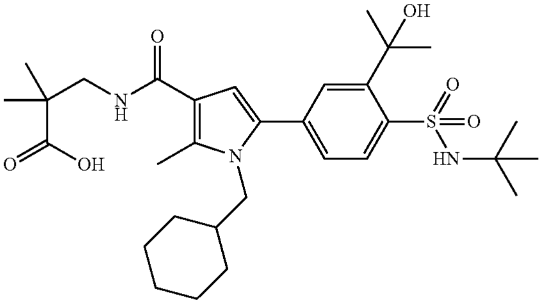
, -continued
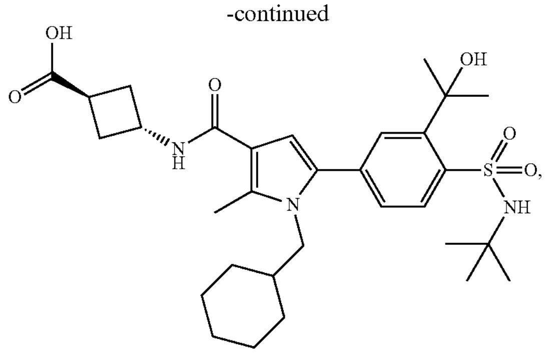
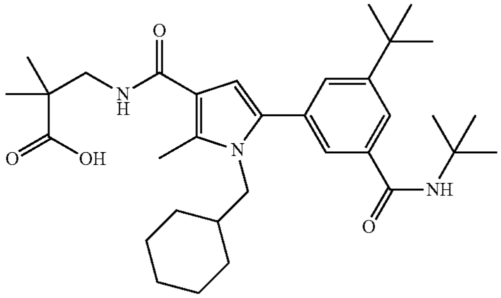
,
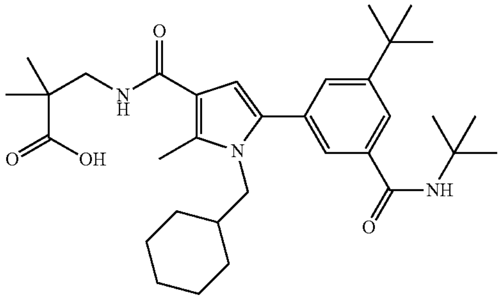
,
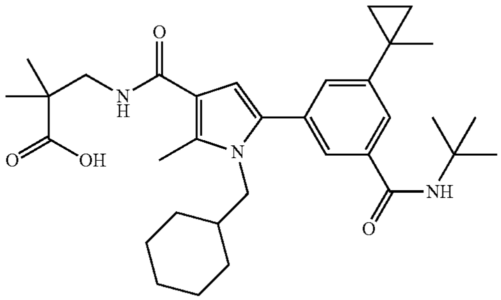
,
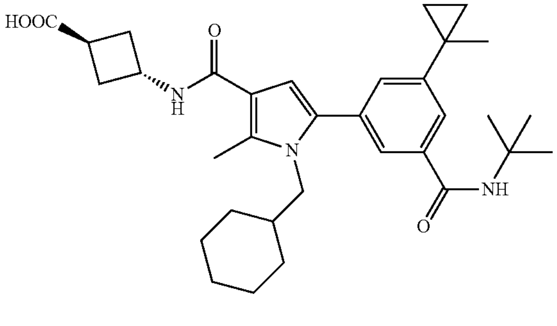
,
-continued
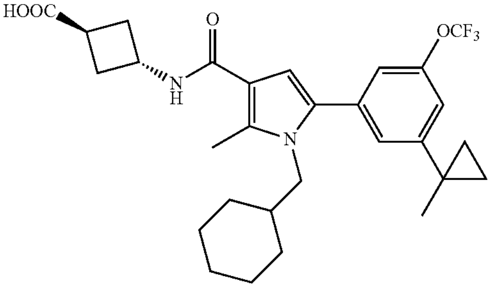
,
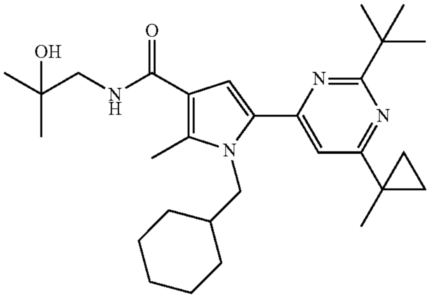
,
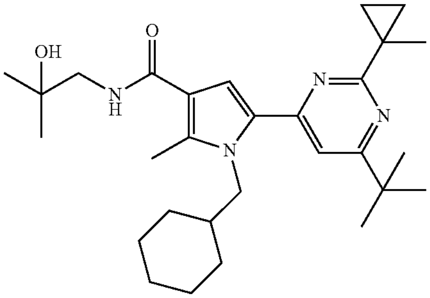
,
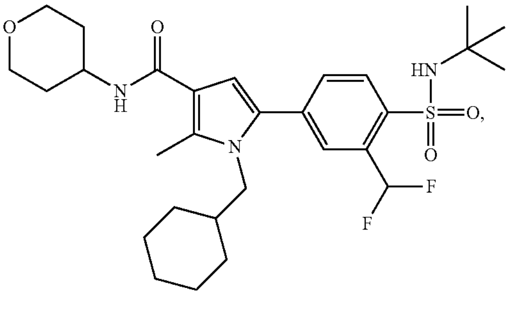
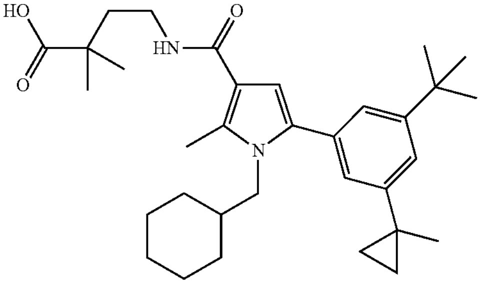
, -continued
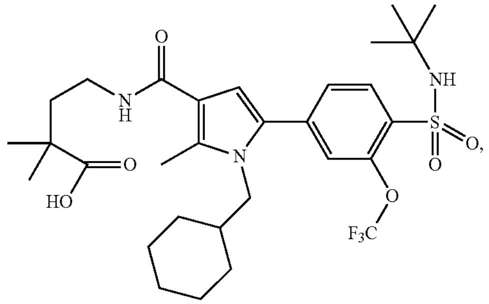
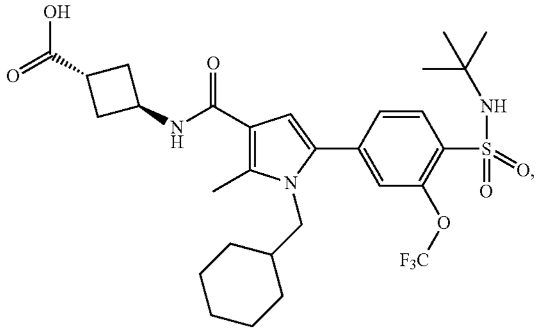
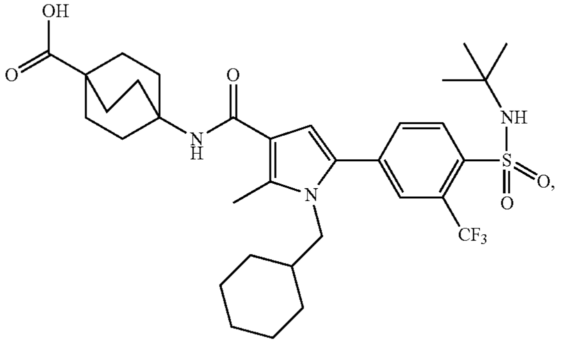
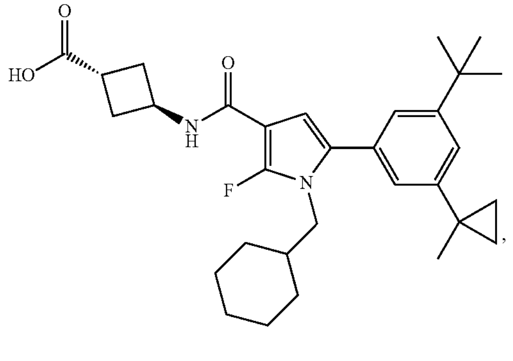
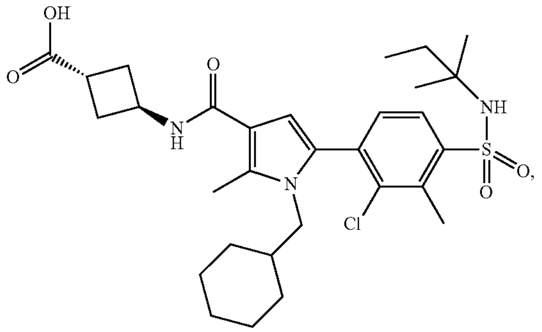
-continued
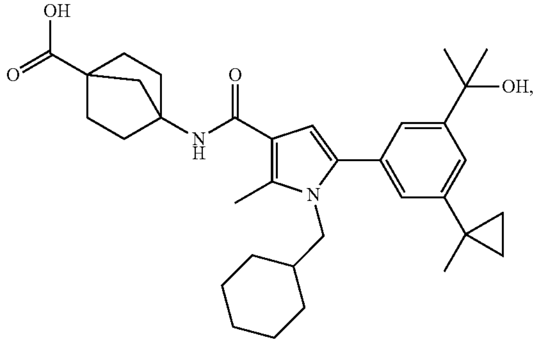
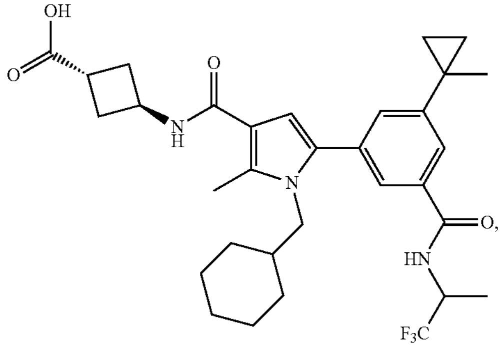
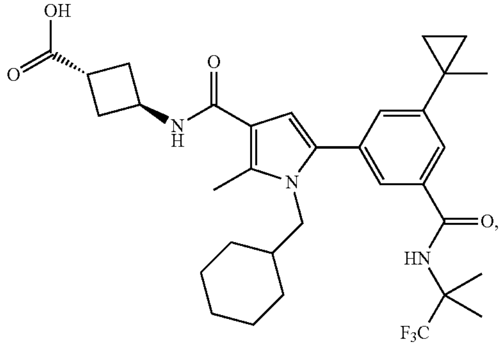
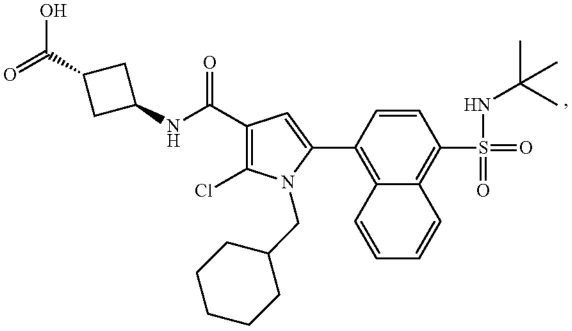
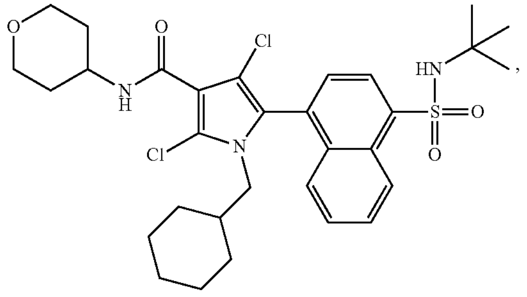
and -continued

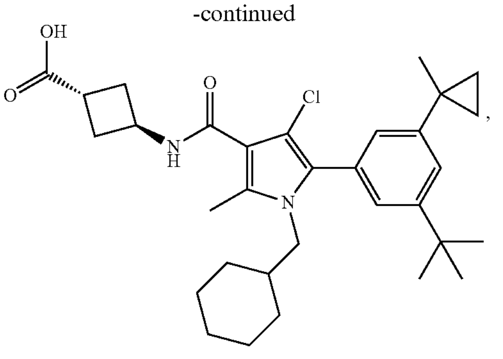, or an enantiomer, diastereomer, tautomer, N-oxide, or solvate thereof, or a pharmaceutically acceptable salt thereof.

13. The compound according to claim 1 wherein:

$R^1$ is selected from:

a 4-membered heterocycloalkyl group containing one heteroatom selected from the group consisting of N, O and S, or $C_{1-10}$-alkyl substituted with a group selected from halogen, CN, $OR^{11}$, $SO_yR^{11}$, $SO_3H$, $NR^{11}SO_2R^{11}$, $SO_2NR^{11}R^{12}$, $CO_2R^{11}$, $COR^{11}$, $CONR^{11}R^{12}$, $NR^{11}$—CO—$R^{11}$, $NR^{11}$—CO—$NR^{11}R^{12}$, $NR^{11}$—$SO_2$—$NR^{11}R^{12}$, $NR^{11}R^{12}$ and a 4-membered heterocycloalkyl group containing one heteroatom selected from the group consisting of N, O and S, or $C_{0-1}$-alkylene-$C_{3-10}$-cycloalkyl substituted with a group selected from halogen, CN, $SO_yR^{11}$, $NR^{11}SO_2R^{11}$, $SO_2NR^{11}R^{12}$, $CO_2R^{11}$, $CONR^{11}R^{12}$, $NR^{11}$—CO—$R^{11}$, $NR^{11}$—CO—$NR^{11}R^{12}$, $NR^{11}$—$SO_2$—$NR^{11}R^{12}$ and $NR^{11}R^{12}$, or $C_{2-10}$-alkylene-$C_{3-10}$-cycloalkyl, $C_{2-10}$-alkylene-O—$C_{3-10}$-cycloalkyl, $C_{2-10}$-alkylene-$C_{5-10}$-heterocycloalkyl and $C_{2-10}$-alkylene-O—$C_{5-10}$-heterocycloalkyl, wherein alkyl, alkylene, cycloalkyl and heterocycloalkyl are optionally substituted with 1 to 7 substituents independently selected from the group consisting of OH, oxo, CN, O—$C_{1-6}$-alkyl, O-halo-$C_{1-6}$-alkyl, $C_{1-6}$-alkyl, halo-$C_{1-6}$-alkyl, halogen, $CO_2R^{11}$, $CONR^{11}R^{12}$, $SO_2R^{11}$, $SO_2NR^{11}R^{12}$, $NR^{11}COR^{11}$, $NR^{11}SO_2R^{11}$, $C_{3-6}$-cycloalkyl, O—$C_{3-6}$-cycloalkyl, $C_{3-6}$-heterocycloalkyl, O—$C_{3-6}$-heterocycloalkyl, O—$C_{2-6}$-alkylene-$OR^{11}$ and $NR_{11}R^{12}$;

$R^2$ is selected from the group consisting of H, $C_{1-6}$-alkyl, halo-$C_{1-6}$-alkyl and hydroxy-$C_{1-6}$-alkyl;

or $R^1$ and $R^2$ when taken together with the nitrogen to which they are attached complete a 3- to 8-membered ring containing carbon atoms and optionally containing 1 or 2 heteroatoms selected from O, S or N, wherein the ring is unsubstituted or substituted with 1 to 4 substitutents independently selected from halogen, oxo, CN, $OR^{11}$, $SO_yR^{11}$, $SO_3H$, $NR^{11}SO_2R^{11}$, $SO_2NR^{11}R^{12}$, $C_{0-6}$-alkylene-$CO_2R^{11}$, $CONR^{11}R^{12}$, $COR^{11}$, $NR^{11}$—CO—$R^{11}$, $NR^{11}$—CO—$NR^{11}R^{12}$, $NR^{11}$—$SO_2$—$NR^{11}R^{12}$, $NR^{11}R^{12}$, $C_{1-6}$-alkyl, halo-$C_{1-6}$-alkyl, hydroxy-$C_{1-6}$-alkyl, $C_{3-6}$-cycloalkyl, O—$C_{3-6}$-cycloalkyl, $C_{3-6}$-heterocycloalkyl and O—$C_{3-6}$-heterocycloalkyl, wherein cycloalkyl and heterocycloalkyl are unsubstituted or substituted with 1 to 4 substitutents independently selected from halogen, $C_{1-3}$-alkyl, halo-$C_{1-3}$-alkyl and oxo;

$R^3$ is a 6- or 10-membered mono- or bicyclic aryl or a 6- to 10-membered mono- or bicyclic heteroaryl containing 1 or 2 heteroatom selected from the group consisting of N, O and S, wherein aryl and heteroaryl are unsubstituted or substituted with 1 to 4 substituents independently selected from halogen, CN, $C_{1-6}$-alkyl, $C_{3-10}$-cycloalkyl, $C_{0-6}$-alkylene-$C_{3-10}$-heterocycloalkyl, $C_{1-6}$-alkylene-O—$R^{31}$, $C_{0-6}$-alkylene-$COOR^{31}$, $C_{0-6}$-alkylene-C(O)$R^{31}$, $C_{0-6}$-alkylene-C(O)N($R^{31}$)$_2$, $C_{0-6}$-alkylene-N($R^{31}$)C(O)$R^{31}$, $C_{0-6}$-alkylene-$SO_2$—N($R^{31}$)$_2$, $C_{0-6}$-alkylene-N($R^{31}$)$SO_2$—$R^{31}$, $C_{0-6}$-alkylene-$SO_2$—$R^{31}$, $C_{0-6}$-alkylene-SO—$R^{31}$ and $C_{0-6}$-alkylene-N($R^{31}$)$_2$, wherein alkylene, cycloalkyl and heterocycloalkyl are unsubstituted or substituted by 1 to 4 substituents independently selected from the group consisting of halogen, CN, $C_{1-3}$-alkyl, halo-$C_{1-3}$-alkyl, OH, O—$C_{1-3}$-alkyl, O-halo-$C_{1-3}$-alkyl, and oxo, and wherein optionally two adjacent substituents complete a 3- to 8-membered saturated or partially unsaturated ring containing carbon atoms and optionally containing 1 to 3 heteroatoms selected from O, S or N, wherein the ring is unsubstituted or substituted with 1 to 6 substituents independently selected from halogen, $C_{1-6}$-alkyl, halo-$C_{1-6}$-alkyl, $C_{3-6}$-cycloalkyl, $C_{3-6}$-heterocycloalkyl, oxo, OH, O—$C_{1-6}$-alkyl and O-halo-$C_{1-6}$-alkyl.

14. The compound according to claim 13 wherein:

$NR^1R^2$ is selected from:

$NHCH_2CONH_2$, $NHCH_2CONMe_2$, $NHCH_2CH_2OH$, $NHCH_2CH(CF_3)OH$, $NHCH_2C(CF_3)_2OH$, $NHCH_2CH_2OMe$, $NHCH_2CH_2SO_2Me$, $NHCH_2CH_2SO_2NH_2$, $NH(CH_2)_3OH$, $NH(CH_2)_3OMe$, $NH(CH_2)_4OH$, $NH(CH_2)_4OMe$, $NH(CH_2)_5OH$, $NH(CH_2)_2CO_2H$, $NH(CH_2)_3CO_2H$, $NH(CH_2)_4CO_2H$, $NH(CH_2)_5CO_2H$, $NHCH_2CMe_2OH$, NHCH(Me)$CMe_2OH$, $NHCH_2CMe_2OMe$, $NHCH_2CMe_2CO_2H$, $NHCH_2CMe_2CONH_2$, $NHCH_2CMe_2CONHMe$, $NHCH_2CMe_2CONMe_2$, $NHCH_2CMe_2NHSO_2Me$, $NH(CH_2)_3SOMe$, $NH(CH_2)_5SO_2Me$, $NH(CH_2)_5SO_2NH_2$, $NH(CH_2)_3NHSO_2Me$, $NH(CH_2)_2O(CH_2)_2OH$, $NHCH_2CHMeOH$, $NH(CH_2)_5SOMe$, $NH(CH_2)_3SO_2Me$, 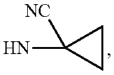, 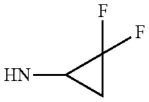,

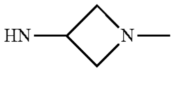, 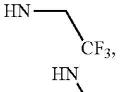,

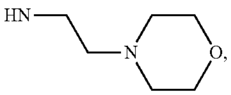, 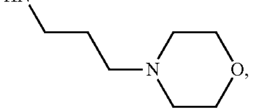,

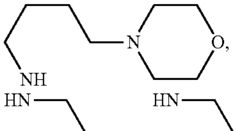, 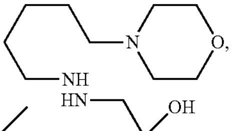,

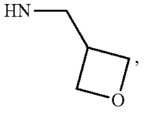, 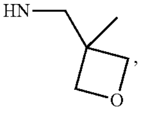, 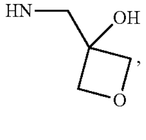,

-continued
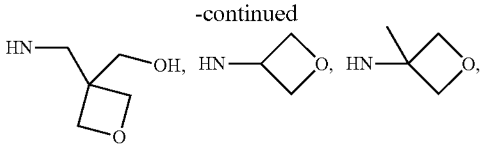
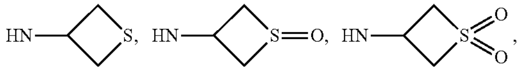
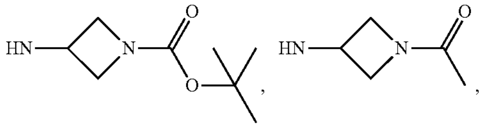
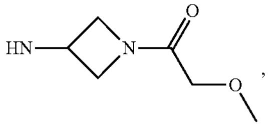
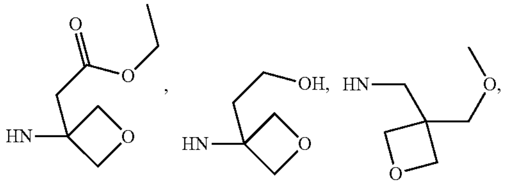
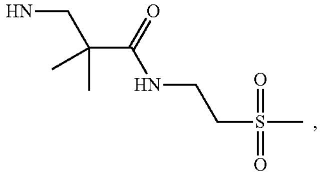
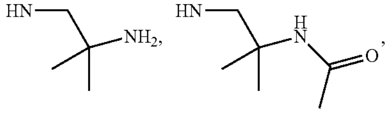
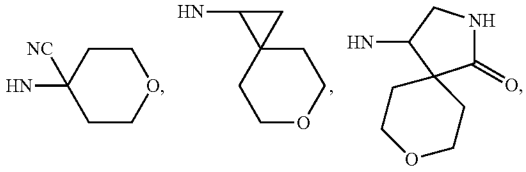
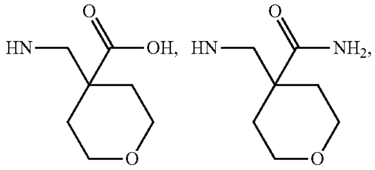
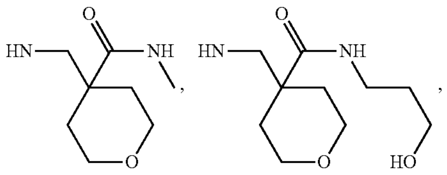
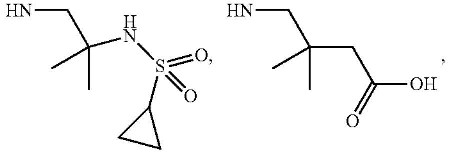
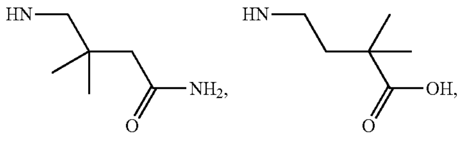
-continued
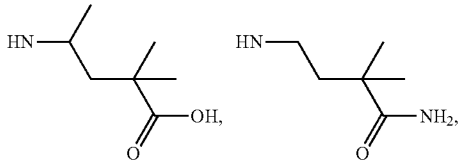
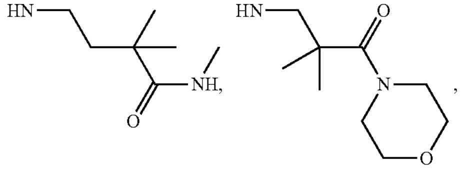
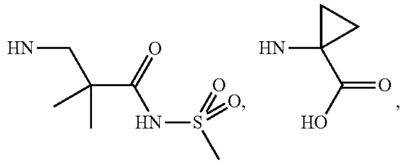
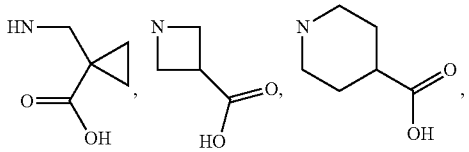
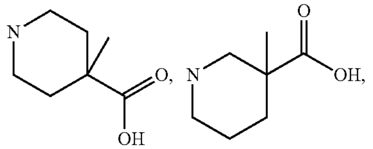
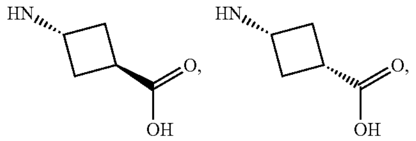
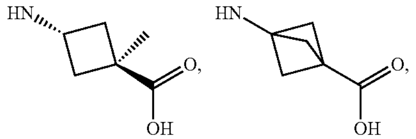
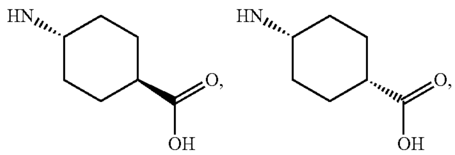
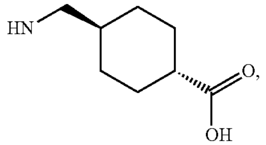
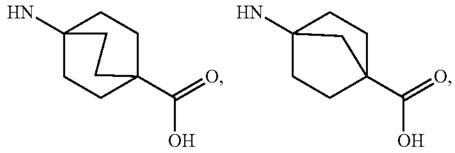
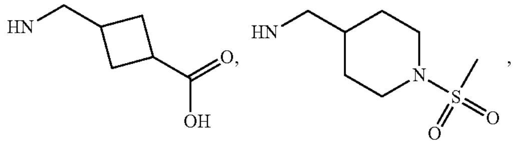

-continued

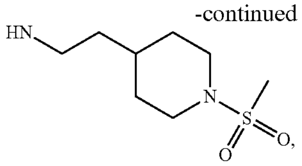
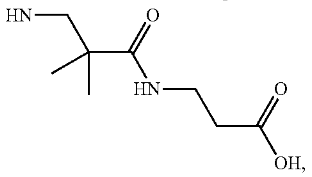
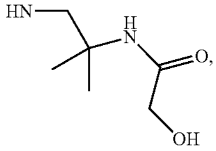
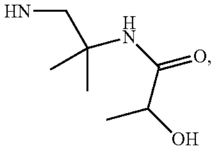
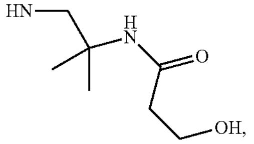
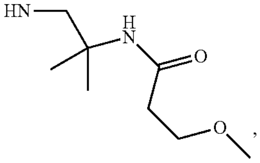
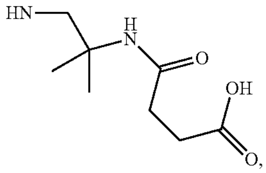
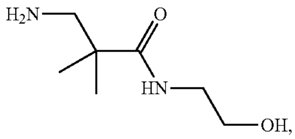
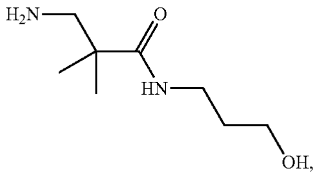
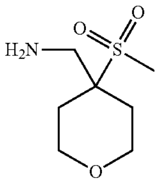
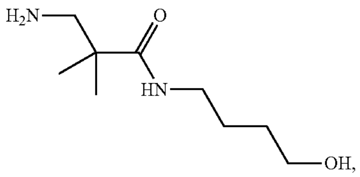
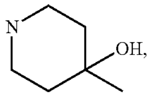
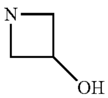
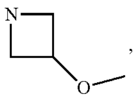
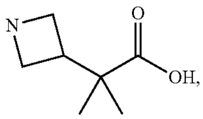
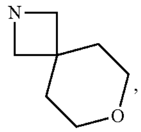
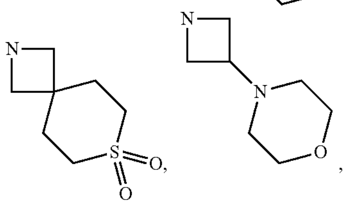

-continued

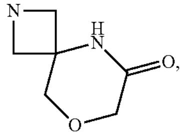
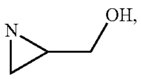
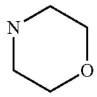
and
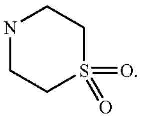

15. The compound according to claim 13 wherein: $R^3$ is selected from:

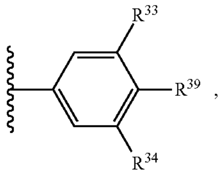
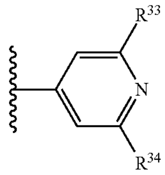
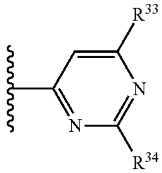
and
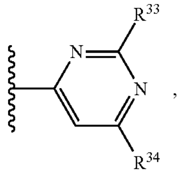

wherein $R^{33}$ is selected from $C_{1-6}$-alkyl and fluoro-$C_{1-6}$-alkyl;

$R^{34}$ is selected from halogen, $C_{1-6}$-alkyl, fluoro-$C_{1-6}$-alkyl, O—$C_{1-6}$-alkyl, O-fluoro-$C_{1-6}$-alkyl, NH—$C_{1-6}$-alkyl and NH-fluoro-$C_{1-6}$-alkyl;

$R^{39}$ is selected from H, F and OH.

16. The compound according to claim 13 wherein: $R^3$ is selected from:

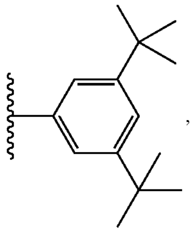
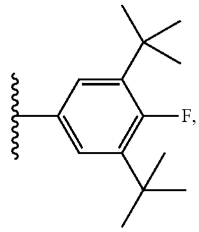
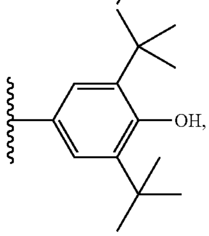
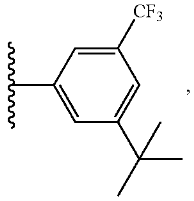
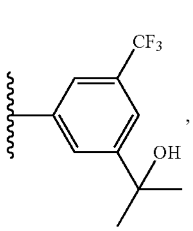
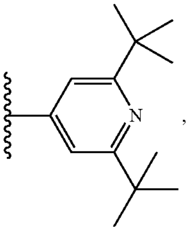

-continued

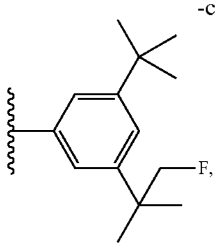 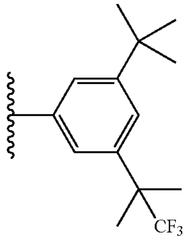 ,

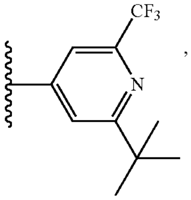 , 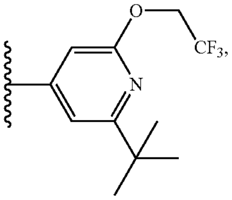

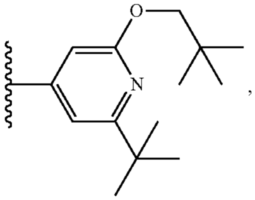 , 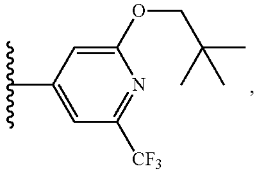 ,

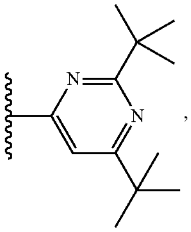 , 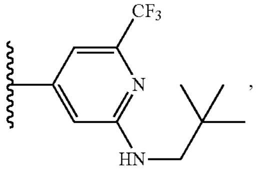 ,

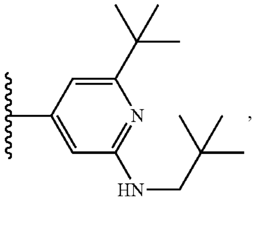 , 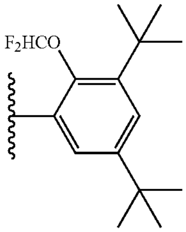 and

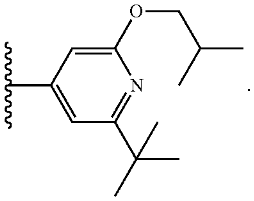 .

17. The compound according to claim 13 wherein:

$R^5$ is selected from H, $C_{1-6}$-alkyl, halo-$C_{1-6}$-alkyl or halogen, wherein alkyl is unsubstituted or substituted with 1 to 3 substituents independently selected from the group consisting of O—$C_{1-6}$-alkyl, O-halo-$C_{1-6}$-alkyl and OH;

$R^6$ is selected from H or halogen.

18. The compound according to claim 13 wherein:

$R^4$ is $SO_2$—$R^7$, $SO_2$—$NR^{12}R^7$, $CHR^8$—$R^{10}$ and $(CH)_2R^{10}$;

$R^7$ is selected from $C_{3-10}$-cycloalkyl and $C_{3-10}$-heterocycloalkyl, wherein cycloalkyl and heterocycloalkyl are unsubstituted or substituted with 1 to 3 substituents independently selected from the group consisting of fluoro, OH, $C_{1-6}$-alkyl, halo-$C_{1-6}$-alkyl and cycloalkyl;

$R^8$ is independently selected from H, F, $C_{1-3}$-alkyl or halo-$C_{1-3}$-alkyl;

$R^{10}$ is $C_{3-10}$-cycloalkyl, wherein cycloalkyl is unsubstituted or substituted with 1 to 6 substituents independently selected from halogen, $C_{1-6}$-alkyl, halo-$C_{1-6}$-alkyl and cycloalkyl.

19. The compound according to claim 13 wherein:

$R^4$ is selected from:

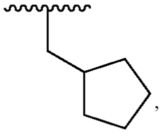 , 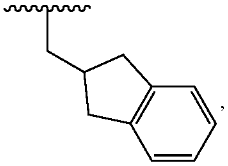 ,

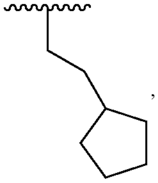 , 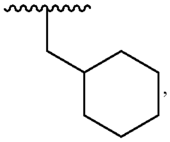 , 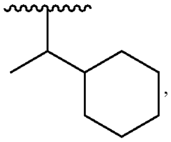 ,

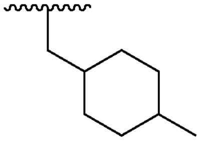 , 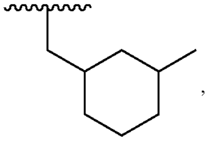 ,

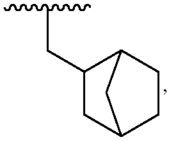 , 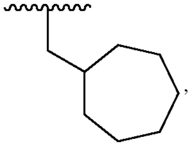 ,

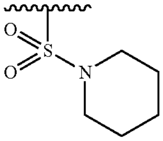 , 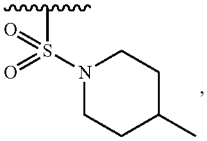 ,

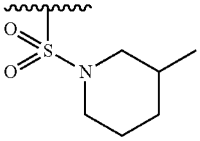 , 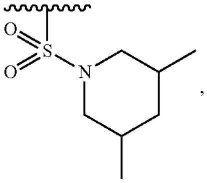 ,

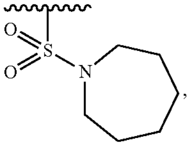 , 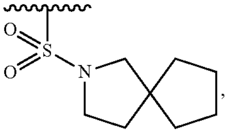 ,

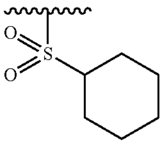 and 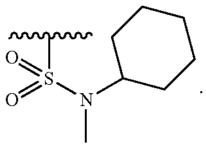 .

20. The compound according to claim 13 selected from the group consisting of:

-continued
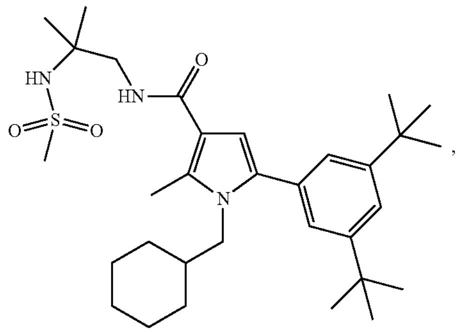
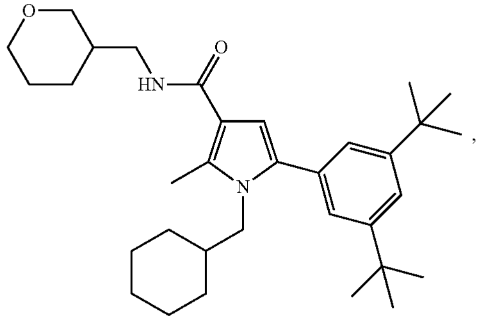
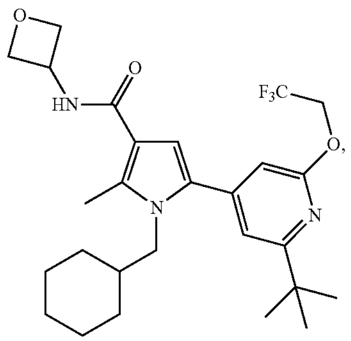
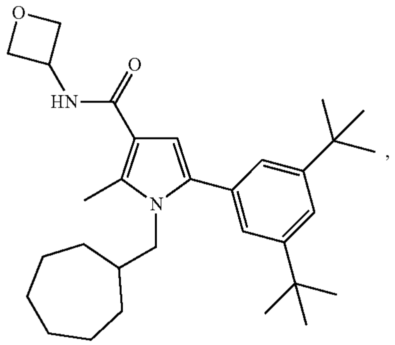
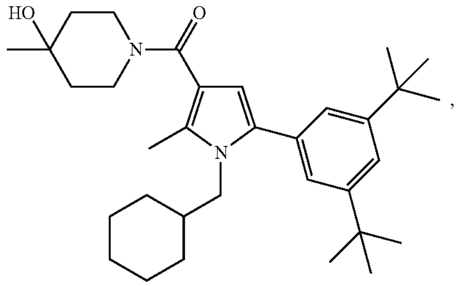
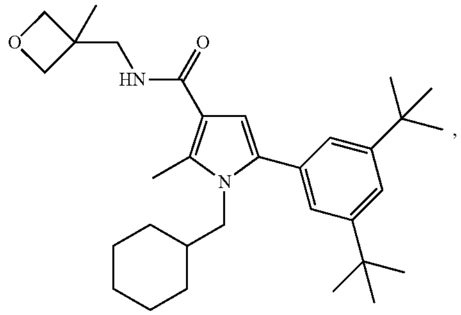
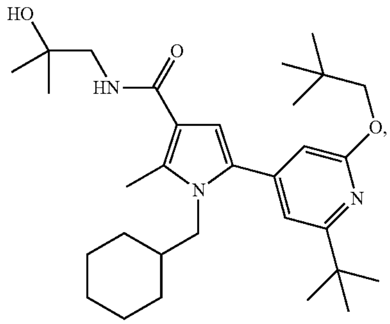
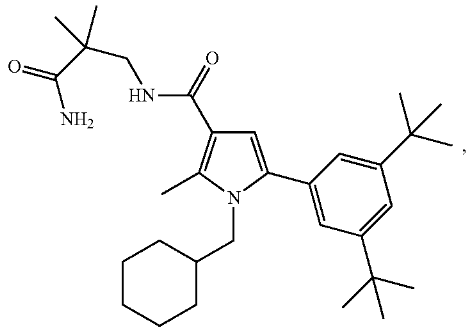
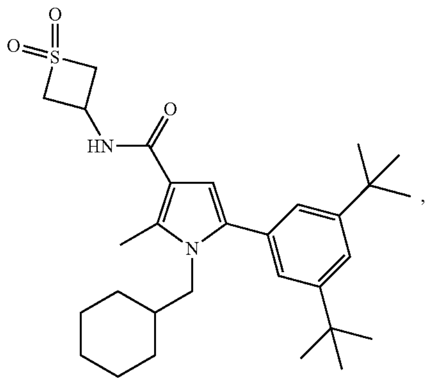
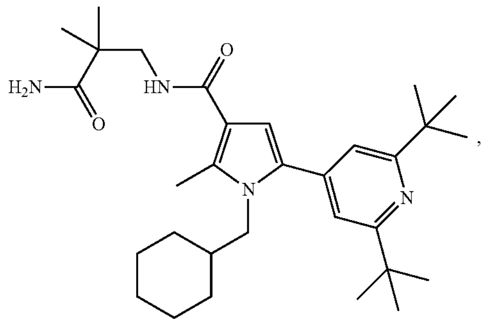

-continued
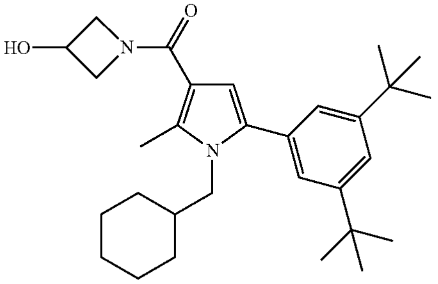
,
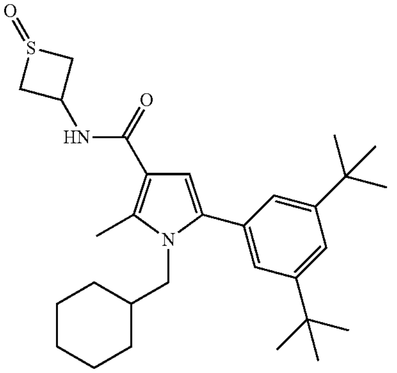
,
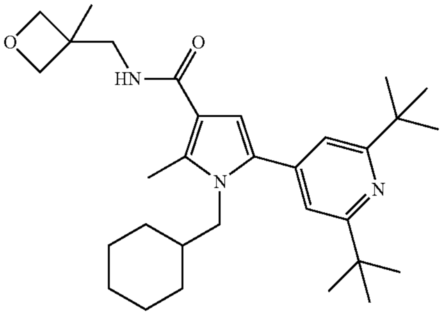
,
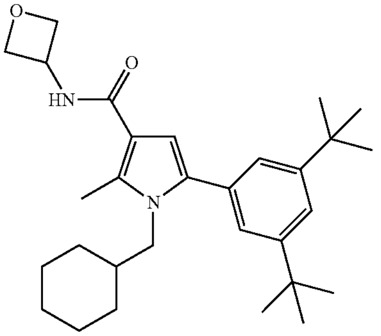
,
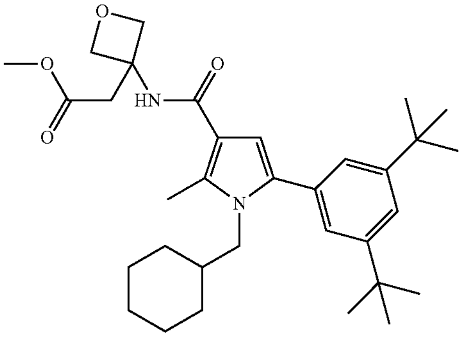
,
-continued
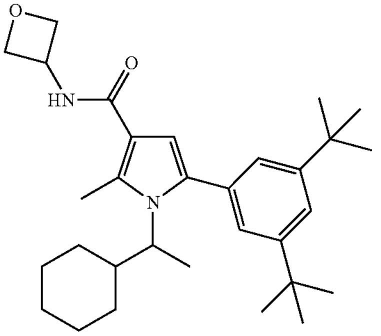
,
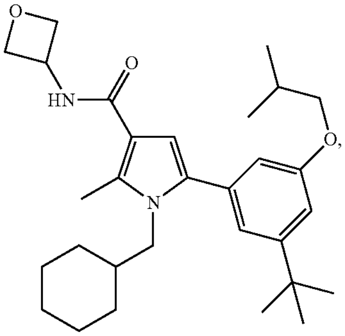
,
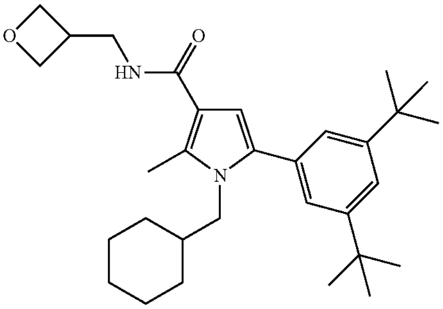
,
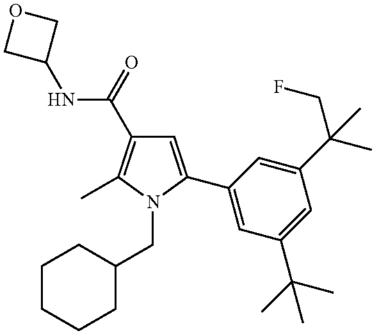
,
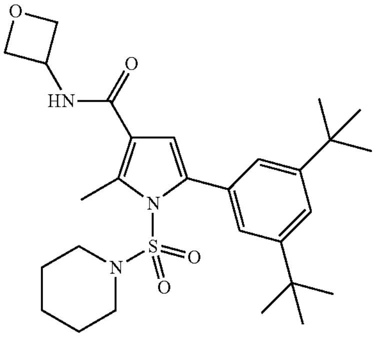
, -continued
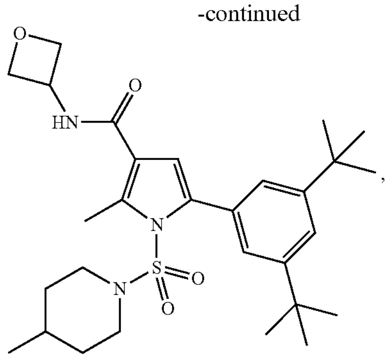
,
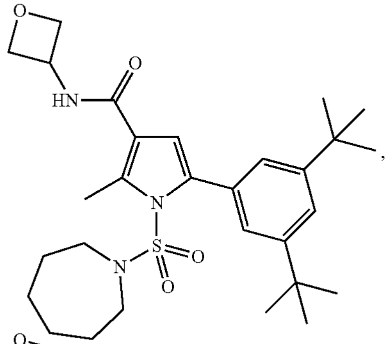
,
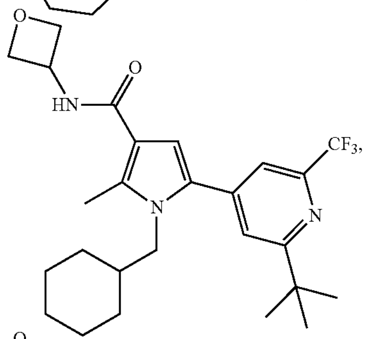
,
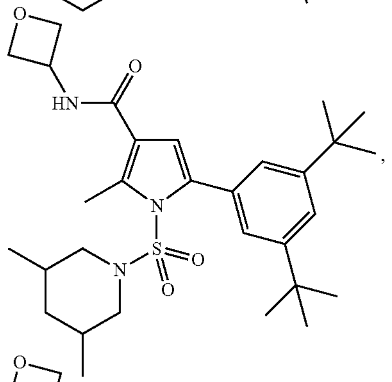
,
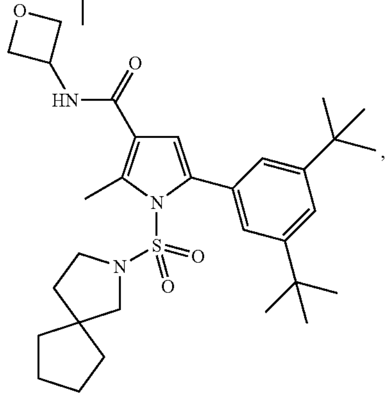
,
-continued
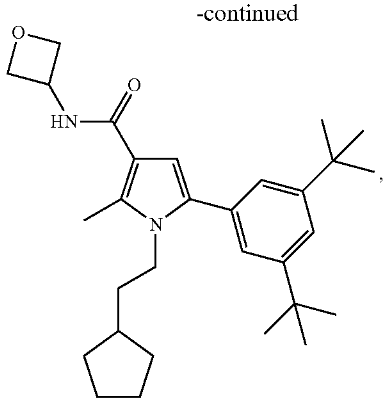
,
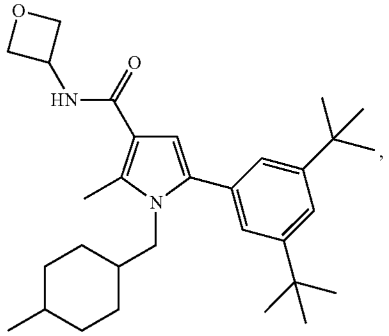
,
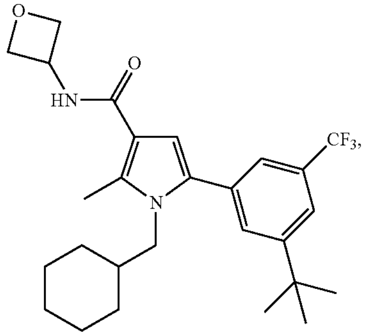
,
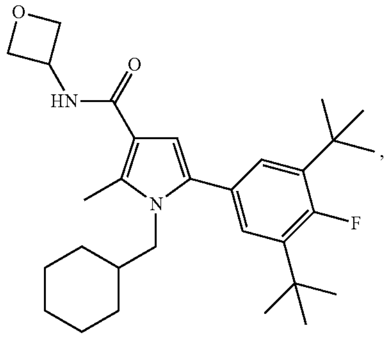
,
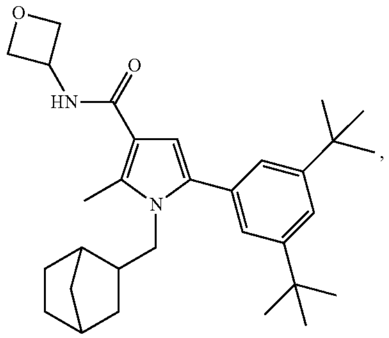
, -continued

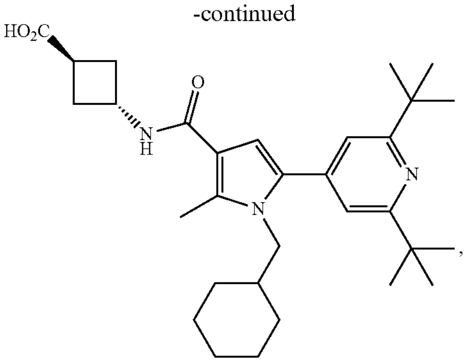

,

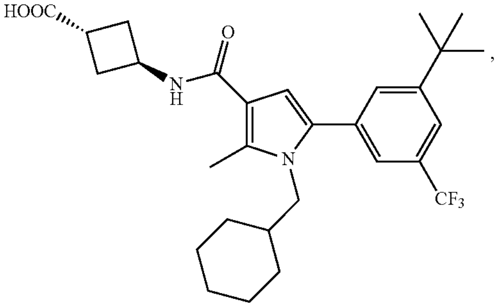

,

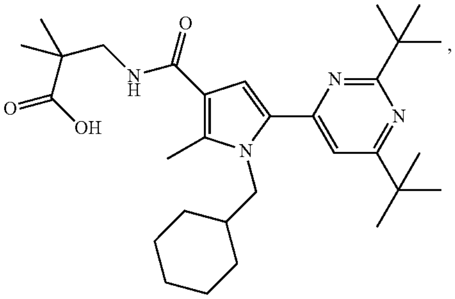

,

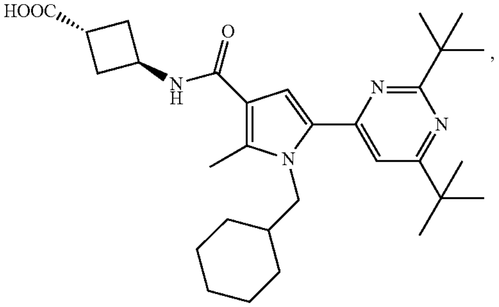

,

-continued

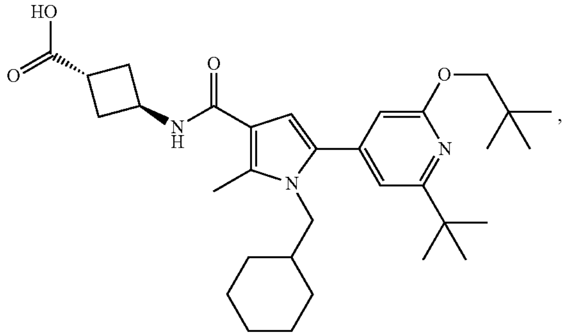

, or an enantiomer, diastereomer, tautomer, N-oxide, or solvate thereof, or a pharmaceutically acceptable salt thereof.

21. A method of treating a $ROR_{\gamma}$ mediated inflammatory or autoimmune disease in a mammal comprising administering a compound according to claim 1, or an enantiomer, diastereomer, tautomer, N-oxide, or solvate thereof, or a pharmaceutically acceptable salt thereof, to the mammal in need thereof, wherein the disease is selected from the group consisting of rheumatoid arthritis, ankylosing spondylitis, lupus erythematosus, psoriasis, psoriatic arthritis, atopic eczema, Crohn's disease, asthma, mucosal leishmaniasis, multiple sclerosis, systemic sclerosis, type 1 diabetes, Kawasaki disease, Hashimoto's thyroiditis, chronic graft-versus-host disease, acute graft-versus-host disease, Celiac Sprue, idiopathic thrombocytopenic thrombotic purpura, myasthenia gravis, Sjogren's syndrome, scleroderma, ulcerative colitis, epidermal hyperplasia, glomerulonephritis, chronic obstructive pulmonary disease and amyotrophic lateral sclerosis.

22. A pharmaceutical composition comprising a compound according to claim 1, or an enantiomer, diastereomer, tautomer, N-oxide, or solvate thereof, or a pharmaceutically acceptable salt thereof, and a pharmaceutically acceptable carrier.

* * * * *